(12) United States Patent
Wang et al.

(10) Patent No.: US 11,384,055 B2
(45) Date of Patent: Jul. 12, 2022

(54) GLYCOLATE OXIDASE INHIBITORS FOR THE TREATMENT OF DISEASE

(71) Applicant: BIOMARIN PHARMACEUTICAL INC., Novato, CA (US)

(72) Inventors: Bing Wang, San Jose, CA (US); Qi Chao, San Diego, CA (US)

(73) Assignee: BIOMARIN PHARMACEUTICAL INC., Novato, CA (US)

(*) Notice: Subject to any disclaimer, the term of this patent is extended or adjusted under 35 U.S.C. 154(b) by 0 days.

(21) Appl. No.: 16/958,511

(22) PCT Filed: Dec. 28, 2018

(86) PCT No.: PCT/US2018/067784
§ 371 (c)(1),
(2) Date: Jun. 26, 2020

(87) PCT Pub. No.: WO2019/133770
PCT Pub. Date: Jul. 4, 2019

(65) Prior Publication Data
US 2021/0171474 A1 Jun. 10, 2021

Related U.S. Application Data

(60) Provisional application No. 62/765,313, filed on Aug. 20, 2018, provisional application No. 62/611,995, filed on Dec. 29, 2017.

(51) Int. Cl.
| | | |
|---|---|---|
| *C07D 417/12* | (2006.01) | |
| *C07D 409/12* | (2006.01) | |
| *C07D 405/12* | (2006.01) | |
| *C07D 403/12* | (2006.01) | |
| *C07D 401/12* | (2006.01) | |
| *C07D 249/04* | (2006.01) | |
| *C07D 401/14* | (2006.01) | |

(52) U.S. Cl.
CPC ......... *C07D 249/04* (2013.01); *C07D 401/12* (2013.01); *C07D 401/14* (2013.01); *C07D 403/12* (2013.01); *C07D 405/12* (2013.01); *C07D 409/12* (2013.01); *C07D 417/12* (2013.01)

(58) Field of Classification Search
CPC .. C07D 471/12; C07D 401/12; C07D 403/12; C07D 409/12; C07D 405/12
USPC .................................................. 514/254.07
See application file for complete search history.

(56) References Cited

U.S. PATENT DOCUMENTS

| | | |
|---|---|---|
| 4,248,879 A | 2/1981 | Buckle et al. |
| 4,349,561 A | 9/1982 | Cragoe, Jr. et al. |
| 4,428,956 A | 1/1984 | Cragoe, Jr. et al. |
| 4,431,652 A | 2/1984 | Cragoe, Jr. et al. |
| 4,431,660 A | 2/1984 | Cragoe, Jr. et al. |
| 2005/0272789 A1 | 12/2005 | Hale et al. |
| 2015/0284343 A1 | 10/2015 | Campbell et al. |

FOREIGN PATENT DOCUMENTS

| | | |
|---|---|---|
| CN | 105541796 A | 5/2016 |
| CN | 105669569 A | 6/2016 |
| JP | 2003146974 A | 5/2003 |
| JP | 2017095366 A | 6/2017 |
| WO | WO 2017100266 A1 | 6/2017 |

OTHER PUBLICATIONS

Accession No. 2002:849604, 2002, "Triazole-derived protein kinase inhibitors, and therapeutic uses thereof," retrieved from STN Database CA [online] Chemical Abstracts Services (10 pages).
Accession No. 2003:389981, 2003, "Preparation of 4,5-disubstituted-1,2,3-triazole derivatives by cyclization of 3-halo-2-hydrazono-1-hydroxyiminopropane derivatives," retrieved from STN Database CA [online] Chemical Abstracts Services (2 pages).
Accession No. 55780 (XRN), 1912, retrieved from Reaxys Database [online] Elsevier Life Sciences IP Limited (1 page).
Accession Nos. 4567854, 4574239, 4587423, and 4698190 (XRNs), 1982, retrieved from Reaxys Database [online] Elsevier Life Sciences IP Limited (1 page).
Alimi et al., 2017, "Photochemical C—H Activation: Generation of Indole and Carbazole Libraries, and First Total Synthesis of Clausenawalline D," Eng. J. Org. Chem., 2017(22):3197-3210.
Augustine et al., 2014, "α-Haloacrylates as acceptors in the [3+2] cycloaddition reaction with NaN3: an expedient approach to N-unsubstituted 1,2,3-triazole-4-carboxylates," Org. Biomol. Chem., 12(14):2280-2288.
Buckle et al., 1982, "Studies on v-triazoles. Part V. Acylation, alkylation and sulphonation reactions of ethyl 5-(4-hydroxyphenoxy)-1H-v-triazole-4-carboxylate," J. Heterocyclic Chem., 19:1147-1152.
Buckle et al., 1984, "Studies on 1,2,3-triazoles. 10. Synthesis and antiallergic properties of 9-oxo-1H,9H-benzothiopyrano[2,3-d]-1,2,3-triazoles and their S-oxides," J. Med. Chem., 27(2):223-227.
Chai et al., 2015, "One-pot, three-component reaction using modified Julia reagents: a facile synthesis of 4,5-disubstituted 1,2,3-(NH)-triazoles in a wet organic solvent," ACS Comb. Sci., 17(3):147-151.
Chen et al., 2016, "Discovery and Structure-Activity Relationship Study of 4-Phenoxythiazol-5-carboxamides as Highly Potent TGR5 Agonists," Chem. Pharm. Bull. (Tokyo), 64(4):326-339.

(Continued)

*Primary Examiner* — Niloofar Rahmani
(74) *Attorney, Agent, or Firm* — Jones Day

(57) ABSTRACT

Described herein are compounds, methods of making such compounds, pharmaceutical compositions and medicaments containing such compounds, and methods of using such compounds to treat or prevent diseases or disorders associated with the enzyme glycolate oxidase (GO). Such diseases or disorders include, for example, disorders of glyoxylate metabolism, including primary hyperoxaluria, that are associated with production of excessive amounts of oxalate.

14 Claims, No Drawings

(56) References Cited

OTHER PUBLICATIONS

International Search Report and Written Opinion for International Patent Application No. PCT/US2018/067784 (Pub No. WO 2019133770) dated Jul. 5, 2019 (35 pages).
Khalaf et al., 2011, "A new flexible strategy for the synthesis of gem-difluoro-bisarylic derivatives and heterocyclic analogues," Tetrahedron, 67(21):3881-3886.
Li et al., 2017, "Catalytic Intermolecular Cross-Couplings of Azides and LUMO-Activated Unsaturated Acyl Azoliums," ACS Catal., 7(3):2139-2144.
Pippione et al., 2017, "Hydroxytriazole derivatives as potent and selective aldo-keto reductase 1C3 (AKR1C3) inhibitors discovered by bioisosteric scaffold hopping approach," Eur. J. Med. Chem., 139:936-946.
Smalley et al., 2015, "Novel heterocyclic scaffolds of GW4064 as farnesoid X receptor agonists," Bioorg. Med. Chem. Lett., 25(2):280-284 (Epub 2014).
Wamhoff et al., 1986, "Heterocyclic β-enamino esters 43†— Easy $^{13}$C NMR distinction between aryl-substituted dimroth isomers of the 1,2,3-triazole series," Magnetic Resonance in Chemistry, 24(9):809-811.
Wolff, 1912, "Anlagerung von Diazobenzolimid an Chinone," Justus Liebigs Annalen der Chemie, 394:68-85, in German (18 pages), with English machine translation (19 pages).
Wu et al., 2018, "Metal-Free Multicomponent Reaction for Synthesis of 4,5-Disubstituted 1,2,3-(NH)-Triazoles," Adv. Synth. Catal., 360(10):1949-1953.
Yuan et al., 2017, "Cycloadduct formation of α,β-unsaturated esters with azides catalyzed by NHC systems," Org. Biomol. Chem., 15(43):9066-9070.

GLYCOLATE OXIDASE INHIBITORS FOR THE TREATMENT OF DISEASE

CROSS REFERENCE

This application is a U.S. National Stage of International Application No. PCT/US2018/067784, filed Dec. 28, 2018, which claims the benefit of U.S. Provisional Patent Application No. 62/611,995, filed Dec. 29, 2017, and U.S. Provisional Patent Application No. 62/765,313, filed Aug. 20, 2018, the content of each of which is incorporated by reference herein in its entirety.

FIELD

Described herein are compounds, methods of making such compounds, pharmaceutical compositions and medicaments containing such compounds, and methods to treat or prevent diseases or disorders associated with the enzyme glycolate oxidase (GO). Also described herein is that such compounds are for use in said methods for treating or preventing diseases or disorders. Such diseases or disorders include, for example, disorders of glyoxylate metabolism, including primary hyperoxaluria, that are associated with production of excessive amounts of oxalate.

BACKGROUND

Primary hyperoxaluria ("PH") is an autosomal-recessive disorder of glyoxylate metabolism. PH type I (PH1) is caused by inherited mutations in the AGXT gene encoding liver peroxisomal alanine: glyoxylate aminotransferase (AGT) which is deficient or mistargeted to mitochondria (Danpure et al., *FEBS Lett.* 201(1):20-24 (1986)). AGT detoxifies glyoxylate to glycine. When AGT activity is deficient or mistargeted, excessive glyoxylate cannot be detoxified and is oxidized by intracellular lactate dehydrogenase ("LDH") to oxalate. Excessive amounts of oxalate lead to urolithiasis and nephrocalcinosis, and can result in renal failure, end stage renal disease and systemic oxalosis.

Glycolate oxidase (GO) is a key enzyme involved in the oxalate metabolic pathway. Glycolate from internal metabolism and from diet will be oxidized by GO to glyoxylate. This oxidation only occurs in the liver peroxisome (Holmes et al., *J. Urol.* 160(5):1617-1624). Under normal conditions, the glyoxylate generated by GO will be detoxified by AGT to glycine. However, in PH1 patients, where the glyoxylate to glycine pathway is blocked, the glyoxylate generated by GO is oxidized by LDH to produce excessive amounts of oxalate.

An approach to treatment of PH1 is to inhibit the GO enzyme to reduce the production of glyoxylate and ultimately reduce the production of excessive amounts of oxalate. It has been shown in HAO1 (GO)$^{-/-}$/AGXT$^{-/-}$ double knockout mouse that GO deficiency can correct overproduction of urine oxalate over production in AGXT$^{-/-}$ mouse (Martin-Higueras et al., *Mol Ther.* 24(4): 719-725). In both humans and mice, the HAO1$^{-/-}$ deficiency appears clinically/phenotypically normal except for the increased urine glycolate secretion (Martin-Higueras et al., *Mol Ther.* 24(4): 719-725). Inhibition of GO with Dicer-substrate siRNA has also been shown to reduce urine oxalate secretion and reduce kidney calcium oxylate deposition in the PH1 mouse model (Dutta et al., *Mol Ther.* 24(4): 770-778).

Accordingly, molecules that inhibit the activity of GO may be used to treat disorders of glyoxylate metabolism, including PH1, that are associated with production of excessive amounts of oxalate.

SUMMARY

In one aspect, provided herein is a compound of Formula (I):

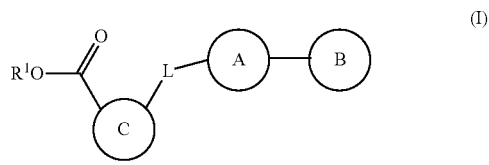

wherein:
ring C is selected from:

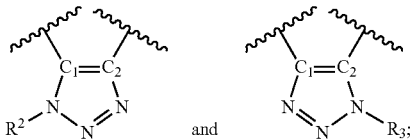

wherein the wavy lines ( ~~~ ) indicate the points of attachment of the $C_1$ carbon to the carbonyl of C(O)—$OR^1$, and the $C_2$ carbon to L;

L is a bond, $CH_2$, $CF_2$, O, $NR^L$, S, S(=O), C(=O), $CH_2$-Q, or Q-$CH_2$; wherein Q is O, $NR^L$, or S;

$R^L$ is hydrogen, $C_{1-4}$ alkyl, $C_{3-6}$ cycloalkyl, phenyl, or benzyl; wherein the $C_{1-4}$ alkyl is optionally substituted with hydroxycarbonyl, alkoxycarbonyl, hydroxycarbonylalkyl, or alkylcarbonyloxy; and the phenyl group alone or as a part of the benzyl group is optionally substituted with one or two groups selected from halo and haloalkoxy;

Ring A is $C_{3-8}$ cycloalkyl, $C_{8-11}$ spirocycloalkyl, 5-8 membered heterocycloalkyl, pyrazolyl, imidazolyl, triazolyl, thiazolyl, thienyl, phenyl, naphthyl, indanyl, tetrahydronaphthyl, dihydronaphthyl, pyridyl, indolyl, benzothiazolyl, quinolinyl, isoquinolinyl, indolinyl, isoindolinyl, tetrahydroquinolinyl, dihydroisoquinolinyl, tetrahydroisoquinolinyl, 2,3-dihydrobenzo[b][1,4]dioxinyl, or tetrahydro-methanonaphthalenyl;

Ring B is present or not present; wherein:
when Ring B is present, then Ring A is optionally substituted with one or two groups independently selected from halo, alkyl, alkoxy, cyano, hydroxy, haloalkoxy, (cycloalkyl)alkoxy, and cycloalkyl;

when Ring B is not present and Ring A is phenyl, then Ring A is substituted with:
(i) one or two $R^{AA}$ groups;
(ii) 2 halo groups when L is other than O;
(iii) 2 halo groups when L is O, and $R^2$ and $R^3$ are not hydrogen or alkyl;
(iv) one halo group when L is $CH_2NR^L$;
(v) one halo group and one group selected from the group consisting of haloalkoxy, cycloalkyloxy, (cycloalkyl)alkoxy, and (phenyl)alkoxy, when L is bond, O, S, or S(=O), wherein the phenyl is optionally substituted with halo, cyano, haloalkyl, or haloalkoxy; or (vi) one cyano group and one (phenyl)alkoxy group, when L is bond or O, wherein the phenyl as part of the (phenyl)alkoxy group is optionally substituted with halo or haloalkoxy;

when Ring B is not present and Ring A is other than phenyl, then
(i) Ring A is substituted with one or two $R^{AB}$ groups or
(ii) Ring A is unsubstituted, wherein:
1) when Ring A is unsubstituted tetrahydroquinolinyl, then L is a bond;
2) when Ring A is unsubstituted 2,3-dihydrobenzo[b][1,4]dioxinyl, then L is O;
3) when Ring A is unsubstituted tetrahydronaphthyl, then L is O, and $R^1$ is not hydrogen or ethyl; or
4) when Ring A is unsubstituted spirocycloalkyl, then L is O, S, or $CH_2S$;

each $R^{AA}$ is independently alkyl; haloalkyl; haloalkoxy; cycloalkyloxy; (cycloalkyl)alkoxy; phenoxy optionally substituted with one or two halo groups; or alkylcarbonylaminoalkoxy;

each $R^{AB}$ is independently halo; alkyl; hydroxy; alkoxy; haloalkyl; haloalkoxy; cycloalkyloxy; (cycloalkyl)alkoxy; or phenoxy optionally substituted with one or two halo groups;

Ring B, when present, is cycloalkyl, heterocycloalkyl, aryl, or heteroaryl; wherein each is optionally substituted with 1, 2, or 3 $R^B$ groups;

each $R^B$ is independently halo; cyano; alkyl; hydroxyalkyl; alkylsulfonyl; aminosulfonyl; alkylaminosulfonyl; dialkylaminosulfonyl; haloalkyl; alkoxy; aminoalkoxy; alkylaminoalkoxy; dialkylaminoalkoxy; hydroxyalkoxy; haloalkoxy; alkylcarbonyl; alkoxyalkoxy; aminocarbonyl; alkylaminocarbonyl; dialkylaminocarbonyl; alkylcarbonylaminoalkoxy; cycloalkyl; (cycloalkyl)alkyl; cycloalkyloxy; (cycloalkyl)alkoxy wherein the cycloalkyl group is optionally substituted with hydroxyalkyl; cycloalkylcarbonyl; cycloalkylcarbonyloxy; heterocycloalkyl optionally substituted with one or two groups independently selected from halo, alkyl, and alkylcarbonyl; (5-6-membered heterocycloalkyl-one)alkyl; 5-6-membered heterocycloalkyl-one; (heterocycloalkyl)alkyl; heterocycloalkylcarbonyl; or 5-6 membered heteroaryl optionally substituted with one group selected from alkyl, hydroxyalkyl, (hydroxycycloalkyl)alkyl, alkoxyalkyl, and hydroxycycloalkyl;

$R^1$ is hydrogen, alkyl, cycloalkyl, heterocycloalkyl, or W; wherein W is alkyl substituted with amino, alkylamino, dialkylamino, alkylcarbonyloxy, alkoxycarbonyl, phenylcarbonyloxy, aminocarbonyloxy, alkylaminocarbonyloxy, dialkylaminocarbonyloxy, alkoxycarbonyloxy, cycloalkylcarbonyloxy, —N($R^{1A}$)C(O)$R^{1B}$, —N($R^{1A}$)C(O)O$R^{1B}$, or —N($R^{1A}$)C(O)N$R^{1B}R^{1C}$, wherein $R^{1A}$, $R^{1B}$, and $R^{1C}$ are each independently hydrogen or $C_{1-6}$alkyl;

$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;

provided:
i. when L is S or $CH_2$, and Ring A is phenyl other than phenyl substituted with (cycloalkyl)alkoxy, then Ring B cannot be halo-substituted phenyl;
ii. when L is O, Ring A is phenyl, and Ring B is not present, then $R^{AA}$ cannot be alkyl;
iii. when L is O, Ring A is phenyl substituted with 1 $R^{AA}$, and Ring B is not present, then $R^{AA}$ cannot be meta-substituted trifluoromethyl;
iv. when L is O, Ring A is phenyl, Ring B is not present, and $R^1$ is ethyl, then $R^{AA}$ cannot be trifluoromethoxy;
v. when L is bond, Ring A is other than phenyl, Ring B is not present, and $R^1$ is H, then $R^{AB}$ cannot be methyl, and
vi. when L is NH, Ring A is pyridyl, indolyl, or indolinyl, and Ring B is not present, then $R^{AB}$ cannot be alkyl; and optionally a single stereoisomer or mixture of stereoisomers thereof and additionally optionally a pharmaceutically acceptable salt thereof.

In another aspect, provided herein is a pharmaceutical composition comprising a compound disclosed herein, for example, a compound of Formula (I), (II), (III), (IV), (V), (VI), (VII), (VIII), (IX), (X) or (XI) as disclosed herein, and a pharmaceutically acceptable excipient.

In a further aspect, provided herein is a method of treating a disease or disorder associated with a defect in glyoxylate metabolism with a compound disclosed herein. Thus, a compound disclosed herein is for use in a method of treating a disease or disorder associated with a defect in glyoxylate metabolism. Such a compound is, for example, a compound of Formula (I), (II), (III), (IV), (V), (VI), (VII), (VIII), (IX), (X) or (XI) as disclosed herein, or a pharmaceutical composition disclosed herein.

In certain embodiments, the disease or disorder is a primary hyperoxaluria. In certain embodiments, the disease or disorder is primary hyperoxaluria type I.

DETAILED DESCRIPTION

Abbreviations

| Abbreviation | Meaning |
| --- | --- |
| DME | Dimethoxyethane |
| DMF | Dimethylformamide |
| NBS | N-Bromosuccinimide |
| NIS | N-Iodosuccinimide |
| PMB | p-Methoxybenzyl |
| THF | Tetrahydrofuran |
| TFA | Trifluoroacetic acid |

Definitions

To facilitate understanding of the disclosure set forth herein, a number of terms are defined below. Generally, the nomenclature used herein and the laboratory procedures in organic chemistry, medicinal chemistry, and pharmacology described herein are those well-known and commonly employed in the art.

"About" preceding a numerical value refers to a range of values±10% of the value specified.

"Acceptable" with respect to a formulation, composition or ingredient, means having no persistent detrimental effect on the general health of the subject being treated.

Whenever a group is described as being "optionally substituted," it is meant that the referenced group can be "unsubstituted or substituted."

"Alkoxy" means a group of the formula —OR, wherein R is alkyl. In certain embodiments, alkoxy includes methoxy, ethoxy, propoxy, 2-propoxy, butoxy, tert-butoxy, pentyloxy, or hexyloxy.

"Alkoxyalkoxy" means a group of the formula —OR—OR', wherein R is alkylene as defined herein, and $R^1$ is alkyl as defined herein.

"Alkoxycarbonyl" means a group of the formula —C(O)R, wherein R is alkoxy, as defined herein.

"Alkoxycarbonyloxy" means a group of the formula —OC(O)R, wherein R is alkoxy, as defined herein.

"Alkylcarbonylaminoalkoxy" means a group of the formula —OR—NH—C(O)R', wherein R is alkylene, as defined herein, and $R^1$ is alkyl, as defined herein.

"Alkyl" means a straight or branched saturated hydrocarbon group containing from 1-10 carbon atoms, and in certain embodiments includes 1-6 carbon atoms. In certain embodiments, alkyl includes 1-4 carbon atoms ("$C_{1-4}$ alkyl"). In certain embodiments alkyl includes 1-3 carbon atoms ("$C_{1-3}$ alkyl"). In certain embodiments, alkyl includes methyl, ethyl, n-propyl, iso-propyl, n-butyl, sec-butyl, tert-butyl, n-pentyl, isopentyl, neopentyl, n-hexyl, 3-methylhexyl, 2,2-dimethylpentyl, 2,3-dimethylhexyl, n-heptyl, n-octyl, n-nonyl, or n-decyl.

"Alkylene" means a straight or branched saturated divalent hydrocarbon group containing from 1-10 carbon atoms, and in certain embodiments includes 1-6 carbon atoms.

"Alkylcarbonylamino" means a group of the formula —NHC(O)R, wherein R is alkyl, as defined herein.

"Amino" means an —NH$_2$ group.

"Aminoalkoxy" means a group of the formula —O—R—NH$_2$, wherein R is alkyl as defined herein. In one embodiment, (amino)alkoxy includes (amino)propyloxy.

"Alkylaminoalkoxy" means an —O—R—NHR$^1$ group, wherein R and $R^1$ are independently alkyl as defined herein. In one embodiment (dialkylamino)alkoxy includes (methylamino)propyloxy.

"Aminocarbonyl" means an —C(O)NH$_2$ group.

"Aminocarbonyloxy" means a group of the formula —OC(O)R, wherein R is amino, as defined herein.

"Alkylaminocarbonyloxy" means a group of the formula —OC(O)R, wherein R is alkylamino, as defined herein.

"Alkylamino" means a group of the formula —NHR, wherein R is alkyl as defined herein. In certain embodiments, alkylamino includes methylamino, ethylamino, n-propylamino, iso-propylamino, n-butylamino, iso-butylamino, or tert-butylamino.

"Alkylcarbonyl" means a group of the formula —C(O)R, wherein R is alkyl, as defined herein.

"Alkylcarbonyloxy" means a group of the formula —OC(O)R, wherein R is alkyl, as defined herein.

"Alkylsulfonyl" means a group of the formula —SO$_2$R, wherein R is alkyl, as defined herein.

"Aminosulfonyl" means a group of the formula —SO$_2$NH$_2$.

"Alkylaminosulfonyl" means a group of the formula —SO$_2$NHR, wherein R is alkyl, as defined herein.

"Dialkylaminoalkoxy" means an —O—R—NR'R" group, wherein R, R', and R" are independently alkyl as defined herein. In one embodiment (dialkylamino)alkoxy includes (dimethylamino)propyloxy.

"Dialkylaminosulfonyl" means a group of the formula —SO$_2$NRR', wherein R and $R^1$ are independently alkyl, as defined herein.

"Aryl" means a monovalent six- to fourteen-membered, mono-, bi-, or tri-carbocyclic ring, wherein the monocyclic ring is aromatic and at least one of the rings in the bicyclic or tricyclic ring is aromatic. In certain embodiments, aryl includes phenyl, naphthyl, tetrahydronaphthyl, dihydronaphthyl, indanyl, or anthracenyl.

"Carbonyl" means an —C=(O) group.

"Carboxyl" means an —C(O)OH group.

"Cyano" means an —CN group.

"Cycloalkyl" means a monocyclic or bicyclic, saturated or partially unsaturated (but not aromatic), hydrocarbon ring of three to ten carbon ring atoms. Cycloalkyl groups include fused and bridged bicyclic rings. For example, when fused, the cycloalkyl group may comprise two rings that share adjacent atoms (e.g., one covalent bond). When bridged, the cycloalkyl group may comprise two rings that share three or more atoms, separating the two bridgehead atoms by a bridge containing at least one atom. When a cycloalkyl group contains from x-y ring carbon atoms, it may be referred to herein as $C_{x-y}$ cycloalkyl. In certain embodiments, cycloalkyl is $C_{3-10}$ cycloalkyl, or is $C_{5-7}$ cycloalkyl, or is $C_{5-6}$ cycloalkyl, or is $C_{3-6}$ cycloalkyl, or is $C_{3-7}$ cycloalkyl. In certain embodiments, cycloalkyl is $C_{3-8}$ cycloalkyl. In certain embodiments, cycloalkyl groups include cyclopropyl, cyclobutyl, cyclopentyl, or cyclohexyl. In certain embodiments, the cycloalkyl group is

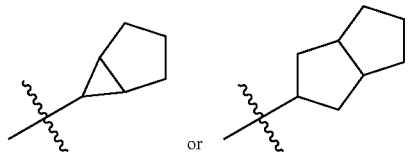

"(Cycloalkyl)alkyl" means an alkyl group, as defined herein, substituted with at least one cycloalkyl groups as defined herein. In certain embodiments, alkyl is substituted with 1 cycloalkyl group. In certain embodiments, alkyl is substituted with 1 or 2 cycloalkyl groups. In certain embodiments, (cycloalkyl)alkyl includes cyclobutylmethyl, cyclopentylmethyl, and cyclohexylmethyl.

"(Cycloalkyl)alkoxy" means a group of the formula —OR, wherein R is a (cycloalkyl)alkyl group as defined herein. In certain embodiments, (cycloalkyl)alkoxy includes cyclobutylmethoxy, cyclopentylmethoxy, and cyclohexylmethoxy.

"Cycloalkyloxy" means a group of the formula —OR, wherein R is cycloalkyl, as defined herein. In certain embodiments, cycloalkyloxy includes cyclobutyloxy, cyclopentyloxy, and cyclohexyloxy.

"Cycloalkylcarbonyl" means a group of the formula —C(O)R, wherein R is cycloalkyl, as defined herein.

"Cycloalkylcarbonyloxy" means a group of the formula —OC(O)R, wherein R is cycloalkyl, as defined herein.

"Dialkylamino" means a group of the formula —NRR', wherein R and $R^1$ are independently alkyl as defined herein. In certain embodiments, dialkylamino includes dimethylamino, diethylamino, N,N-methylpropylamino or N,N-methylethylamino.

"Dialkylaminocarbonyl" means a group of the formula —C(O)R, wherein R is dialkylamino, as defined herein.

"Dialkylaminocarbonyloxy" means a group of the formula —OC(O)R, wherein R is dialkylamino, as defined herein.

"Halo" means a fluoro, chloro, bromo, or iodo group.

"Haloalkoxy" means an alkoxy group, substituted with one or more halo atoms. In certain embodiments, all hydrogen atoms of the alkoxy group are replaced with halo atoms. In certain embodiments, the alkoxy is substituted with 1, 2, 3, 4, 5, or 6 halo atoms. In certain embodiments, the alkoxy is substituted with 1, 2, or 3 halo atoms. In certain other embodiments, the alkoxy is substituted with 2 halo atoms. In certain embodiments, the alkoxy is substituted with 1 halo atom. Certain embodiments of haloalkoxy include difluoromethoxy, trifluoromethoxy, or 1,1,1-trifluoroethoxy.

"Haloalkyl" means an alkyl group substituted with one or more halo atoms. In certain embodiments, all hydrogen atoms of the alkyl group are substituted with halo atoms. In certain embodiments, the alkyl group is substituted by 1, 2, 3, 4, 5, or 6 halo atoms. In certain embodiments, the alkyl group is substituted by 1, 2, or 3 halo atoms. In certain other embodiments, the alkyl group is substituted with 2 halo atoms. In certain embodiments, the alkyl group is substituted with 1 halo atom. In certain embodiments, haloalkyl includes trifluoromethyl, fluoromethyl, perfluoroethyl, or chloromethyl. Certain other embodiments of haloalkyl include chloromethyl, fluoromethyl, difluoromethyl, trifluoromethyl, or 1,1,1-trifluoroethanyl.

"Heteroaryl" means a monocyclic, bicyclic, or tricyclic ring of 5 to 14 ring atoms containing one or more ring heteroatoms independently selected from —O—, —S—, —N═ (trivalent nitrogen), and —N(H)—, and the remaining ring atoms being carbon atoms, wherein the monocyclic ring is aromatic and wherein at least one of the rings in the bicyclic or tricyclic rings is aromatic (but does not have to be a ring which contains a heteroatom, e.g.; tetrahydroquinolinyl, dihydroisoquinolinyl, dihydrobenzodioxinyl, 2,3-dihydrobenzo[b][1,4]dioxinyl, and the like). In certain embodiments, heteroaryl is a monocylic ring of 5 to 6 rings atoms. Unless stated otherwise, the valency may be located on any atom of any ring of the heteroaryl group, valency rules permitting.

In certain embodiments, heteroaryl includes, but is not limited to, triazolyl, tetrazolyl, pyrrolyl, imidazolyl, thienyl, furanyl, pyrazolyl, thiazolyl, oxazolyl, isooxazolyl, oxadiazolyl, thiadiazolyl, indolyl, indolinyl, isoindolinyl, indazolyl, benzimidazolyl, benzoxazolyl, benzofuranyl, benzothienyl, benzopyranyl, benzothiazolyl, pyridyl, pyrazinyl, pyrimidinyl, pyridazinyl, quinolinyl, isoquinolinyl, tetrahydroisoquinolinyl, dihydroisoquinolinyl, pyrrolo[3,2-c]pyridinyl, pyrrolo[1,2-b]pyridazinyl, imidazo[1,2-a]pyridinyl, benzo[d][1,3]dioxolyl, 2,3-dihydrobenzo[b][1,4]dioxinyl, furo[2,3-d]thiazolyl, thieno[2,3-d]oxazolyl, thieno[3,2-b]furanyl, furo[2,3-d]pyrimidinyl, furo[3,2-b]pyridinyl, furo[3,2-c]pyridinyl, 6,7-dihydro-5H-cyclopenta[b]pyridinyl, 7,8-dihydro-6H-cyclopenta[g]quinoxalinyl, dihydrobenzodioxinyl, or 2,3-dihydrobenzo[b][1,4]dioxinyl.

"Heterocycloalkyl" means a saturated or partially unsaturated (but not aromatic) monocyclic ring of 3 to 9 ring atoms, or a saturated or partially unsaturated (but not aromatic) bicyclic ring of 5 to 12 ring atoms in which one or more ring atoms is a heteroatom independently selected from —O—, —S—, —N═ (trivalent nitrogen), or —NH—, and the remaining ring atoms are carbon. In certain embodiments, heterocycloalkyl is a saturated or partially unsaturated monocyclic group of 4 to 7 rings atoms, or a saturated or partially unsaturated bicyclic group of 7 to 9 ring atoms. In certain embodiments, heterocycloalkyl is a saturated or partially unsaturated monocyclic group of 5 to 6 rings atoms or a saturated or partially unsaturated bicyclic group of 6 to 8 ring atoms.

In certain embodiments, the heterocycloalkyl group comprises one, two, three, or four ring heteroatoms, independently selected from —O—, —S—, —N═ (trivalent nitrogen), or —NH—, and the remaining ring atoms are carbon. In certain embodiments, the heterocycloalkyl group contains only one or two nitrogen atoms, and the remaining ring atoms are carbon. When a heterocycloalkyl group contains from x to y ring atoms, it may be referred to herein as "a x-y membered heterocycloalkyl". In certain embodiments, the heterocycloalkyl is a 4-7 membered heterocycloalkyl, or is a 5-6 membered heterocycloalkyl, or is a 7-9 membered heterocycloalkyl. In certain embodiments, the heterocycloalkyl is a 5-8 membered heterocycloalkyl.

Heterocycloalkyl groups include fused or bridged heterocycloalkyl bicyclic rings. For example, a fused heterocycloalkyl group may comprise two rings that share adjacent atoms (e.g., one covalent bond). When bridged, the heterocycloalkyl group may comprise two rings that share three or more atoms, separating the two bridgehead atoms by a bridge containing at least one atom. In certain embodiments, the heterocycloalkyl group is

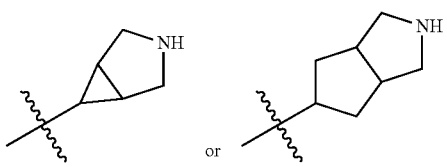

In certain embodiments, heterocycloalkyl includes, but is not limited to, azetidinyl, pyrrolidinyl, 2,5-dihydro-1H-pyrrolinyl, 2,5-dihydro-1H-pyrrolyl, piperidinyl, morpholinyl, piperazinyl, pyranyl, tetrahydropyranyl, tetrahydrothiopyranyl, 1,3-dioxinyl, 1,3-dioxanyl, 1,4-dioxinyl, 1,4-dioxanyl, thiomorpholinyl, thiamorpholinyl, perhydroazepinyl, pyrazolidinyl, imidazolinyl, imidazolidinyl, dihydropyridinyl, tetrahydropyridinyl, oxazolinyl, oxazolidinyl, isoxazolidinyl, thiazolinyl, thiazolidinyl, quinuclidinyl, isothiazolidinyl, octahydroindolyl, octahydroisoindolyl, octahydropyrrolo[3,4-c]pyrrolinyl, decahydroisoquinolyl, tetrahydrofuryl, 2-azaspiro[3.3]heptanyl, 4,7-diazaspiro[2.5]octanyl, 1,6-diazaspiro[3.3]heptanyl, 7-azabicyclo[2.2.1]heptanyl, 3-azabicyclo[3.2.1]octanyl, and 8-azabicyclo[3.2.1]octanyl.

"(Heterocycloalkyl)alkyl" means an alkyl group, as defined herein, substituted with at least one, in another example 1 or 2, heterocycloalkyl groups as defined herein. In certain embodiments, the alkyl is substituted with one heterocycloalkyl group.

"Heterocycloalkylcarbonyl" means a group of the formula —C(O)R, wherein R is heterocycloalkyl, as defined herein.

"Heterocycloalkylcarbonyloxy" means a group of the formula —OC(O)R, wherein R is heterocycloalkyl, as defined herein.

"Heterocycloalkyl-one" means a heterocycloalkyl group as defined herein and wherein one ring carbon atom of the heterocycloalkyl group forms a double bond with oxygen atom. In certain embodiments heterocycloalkyl-one group is

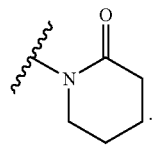

"Hydroxy" means an —OH group. The terms "hydroxy" and "hydroxyl" are used interchangeably and mean an —OH group.

"Hydroxyalkyl" means a group of formula —R—(OH)$_z$, where R is an alkyl as defined herein and z is 1 or 2. In one embodiment, hydroxyalkyl is —ROH. In one embodiment, hydroxyalkyl includes —CH₂OH. In one embodiment, hydroxyalkyl is —R(OH)₂.

"Hydroxyalkoxy" means a group of formula —O—R—(OH)$_z$, where R is an alkyl as defined herein and z is 1 or 2. In one embodiment, hydroxyalkoxy is —OR—(OH). In one embodiment, hydroxyalkoxy is —OR—(OH)₂. In one embodiment (hydroxy)alkoxy includes (hydroxy)propyloxy.

"Hydroxycarbonyl" means an —C(O)OH group. As used herein, the terms "hydroxycarbonyl" and "carboxyl" are used interchangeably and refer to the same group.

"Hydroxycarbonylalkyl" means a group of the formula —RC(O)OH, wherein R is alkylene as defined herein.

"Hydroxycycloalkyl" means a group of the formula —ROH, wherein R is cycloalkyl as defined herein. In certain embodiments, hydroxycycloalkyl is

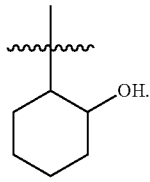 [SMILES: *C1CCCCC1O]

"(Hydroxycycloalkyl)alkyl" means a group of formula —RR¹ wherein R is alkyl and R¹ is hydroxycycloalkyl as defined herein. In certain embodiments (hydroxycycloalkyl)alkyl is

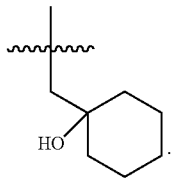 [SMILES: *CC1(O)CCCCC1]

"(Phenyl)alkyl" means an alkyl group, as defined herein, substituted with at least one phenyl group. In certain embodiments, the alkyl is substituted with one phenyl group. In certain embodiments, (phenyl)alkyl is benzyl.

"(Phenyl)alkoxy" means a group of the formula —OR, wherein R is (phenyl)alkyl as defined herein.

"Phenylcarbonyloxy" means a group of the formula —OC(O)R, wherein R is phenyl.

"Spirocycloalkyl" means a bicyclic cycloalkyl ring of 5 to 12 carbon ring atoms having one quaternary carbon ring atom common to both rings. In certain embodiments, the spirocycloalkyl is a C$_{5-12}$ spirocycloalkyl, or is a C$_{8-11}$ sirocycloalkyl.

In certain embodiments, spirocycloalkyl groups include spiro[2.5]octane, spiro[3.4]octane, spiro[3.5]nonane, spiro[4.4]nonane, spiro[4.5]decane, or spiro[5.5]undecane.

In certain embodiments, the spirocycloalkyl group is

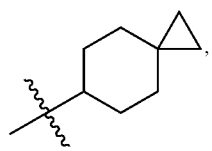 [SMILES: *C1CCC2(CC1)CC2]

or is

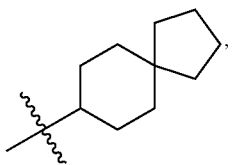 [SMILES: *C1CCC2(CCCC2)CC1]

or is

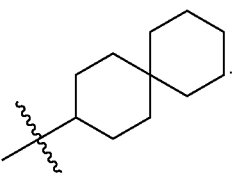 [SMILES: *C1CCC2(CCCCC2)CC1]

In some embodiments, compounds of the described herein exist as stereoisomers, wherein asymmetric or chiral centers are present. The term (R) and (S) used herein are configurations as defined in IUPAC 1974 Recommendations for Section E, Fundamental Stereochemistry, *Pure Appl. Chem.*, (1976), 45:13-30, hereby incorporated by reference. The embodiments described herein specifically includes the various stereoisomers and mixtures thereof.

"Stereoisomers" include (but are not limited to) geometric isomers, enantiomers, diastereomers, and mixtures of geometric isomers, enantiomers or diastereomers. In some embodiments, individual stereoisomers of compounds are prepared synthetically from commercially available starting materials which contain asymmetric or chiral centers or by preparation of racemic mixtures followed by resolution. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic column.

"Amelioration" of the symptoms of a particular disorder by administration of a particular compound or pharmaceutical composition refers to any lessening of severity, delay in onset, slowing of progression, or shortening of duration, whether permanent or temporary, lasting or transient that can be attributed to or associated with administration of the compound or composition.

The terms "effective amount" or "therapeutically effective amount," refer to a sufficient amount of an agent or a compound being administered which will relieve to some extent one or more of the symptoms of the disease or disorder being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is determined using any suitable technique, such as a dose escalation study.

"Excipient" or "pharmaceutically acceptable excipient" means a pharmaceutically-acceptable material, composition, or vehicle, such as a liquid or solid filler, diluent, solvent, or encapsulating material. Excipients include, for example, encapsulating materials or additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., Remington: The Science and Practice of Pharmacy, 21st ed.; Lippincott Williams & Wilkins: Philadelphia, Pa., 2005; Handbook of Pharmaceutical Excipients, 6th ed.; Rowe et al., Eds.; The Pharmaceutical Press and the American Pharmaceutical Association: 2009; Handbook of Pharmaceutical Additives, 3rd ed.; Ash and Ash Eds.; Gower Publishing Company: 2007; Pharmaceutical Preformulation and Formulation, 2nd ed.; Gibson Ed.; CRC Press LLC: Boca Raton, Fla., 2009.

"Pharmaceutically acceptable salt" refers to a formulation of a compound that does not cause significant irritation to an organism to which it is administered and does not abrogate the biological activity and properties of the compound. In certain instances, pharmaceutically acceptable salts are obtained by reacting a compound described herein, with acids such as hydrochloric acid, hydrobromic acid, hydroiodic acid, sulfuric acid, nitric acid, phosphoric acid, methanesulfonic acid, ethanesulfonic acid, p-toluenesulfonic acid, formic acid, acetic acid, trifluoroacetic acid, or salicylic acid. In some instances, pharmaceutically acceptable salts are obtained by reacting a compound described herein with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, or lysine, or by other methods previously determined. The pharmacologically acceptable salts are not specifically limited as far as it can be used in medicaments.

The term "pharmaceutical composition" refers to a mixture of a compound described herein with other chemical components, such as an excipient. The pharmaceutical composition facilitates administration of the compound to an organism. Multiple techniques of administering a compound exist in the art including, but not limited to, intravenous, oral, aerosol, parenteral, ophthalmic, pulmonary and topical administration.

"Subject" refers to an animal, including, but not limited to, a primate (e.g., human), monkey, cow, pig, sheep, goat, horse, dog, cat, rabbit, rat, or mouse. The terms "subject" and "patient" are used interchangeably. In certain embodiments, the subject is a mammal. In certain embodiments, the subject is a human. In certain embodiments, the subject is an adult human. In certain embodiments, the subject is a human child.

In certain embodiments, the subject is a mammal. In certain embodiments, the subject is a human. In certain embodiments, the subject is an adult human. In certain embodiments, the subject is a human child.

"Treat," "treating," and "treatment," in the context of treating a disease or disorder, are meant to include alleviating or abrogating a disorder, disease, or condition, or one or more of the symptoms associated with the disorder, disease, or condition; or to slowing the progression, spread or worsening of a disease, disorder or condition or of one or more symptoms thereof. Often, the beneficial effects that a subject derives from a therapeutic agent do not result in a complete cure of the disease, disorder or condition.

Embodiments

The following paragraphs present a number of embodiments of the compounds disclosed herein. In each instance the embodiment includes both the recited compound(s) as well as a single stereoisomer or mixture of stereoisomers thereof, as well as a pharmaceutically acceptable salt thereof.

In one aspect, provided herein is a compound of Formula (I):

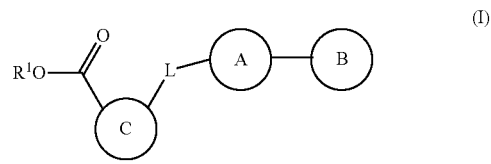

wherein:
Ring C is selected from:

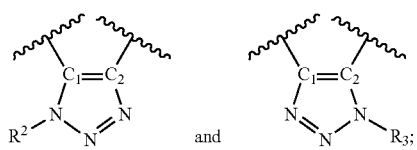

wherein the wavy lines ( ⁓⁓⁓ ) indicate the points of attachment of the $C_1$ carbon to the carbonyl of C(O)—$OR^1$, and the $C_2$ carbon to L;

L is a bond, $CH_2$, $CF_2$, O, $NR^L$, S, S(=O), C(=O), $CH_2$-Q, or Q-$CH_2$; wherein Q is O, $NR^L$, or S;

$R^L$ is hydrogen, $C_{1-4}$ alkyl, $C_{3-6}$ cycloalkyl, phenyl, or benzyl; wherein the $C_{1-4}$ alkyl is optionally substituted with hydroxycarbonyl, alkoxycarbonyl, hydroxycarbonylalkyl, or alkylcarbonyloxy; and the phenyl group alone or as a part of the benzyl group is optionally substituted with one or two groups selected from halo and haloalkoxy;

Ring A is $C_{3-8}$ cycloalkyl, $C_{8-11}$ spirocycloalkyl, 5-8 membered heterocycloalkyl, pyrazolyl, imidazolyl, triazolyl, thiazolyl, thienyl, phenyl, naphthyl, indanyl, tetrahydronaphthyl, dihydronaphthyl, pyridyl, indolyl, benzothiazolyl, quinolinyl, isoquinolinyl, indolinyl, isoindolinyl, tetrahydroquinolinyl, dihydroisoquinolinyl, tetrahydroisoquinolinyl, 2,3-dihydrobenzo[b][1,4]dioxinyl, or tetrahydro-methanonaphthalenyl;

Ring B is present or not present; wherein:
when Ring B is present, then Ring A is optionally substituted with one or two groups independently selected from halo, alkyl, alkoxy, cyano, hydroxy, haloalkoxy, (cycloalkyl)alkoxy, and cycloalkyl;
when Ring B is not present and Ring A is phenyl, then Ring A is substituted with:
  (i) one or two $R^{AA}$ groups;
  (ii) 2 halo groups when L is other than O;

(iii) 2 halo groups when L is O, and $R^2$ and $R^3$ are not hydrogen or alkyl;
(iv) one halo group when L is $CH_2NR^L$;
(v) one halo group and one group selected from the group consisting of haloalkoxy, cycloalkyloxy, (cycloalkyl) alkoxy, and (phenyl)alkoxy, when L is bond, O, S, or S(=O), wherein the phenyl is optionally substituted with halo, cyano, haloalkyl, or haloalkoxy; or
(vi) one cyano group and one (phenyl)alkoxy group, when L is bond or O, wherein the phenyl as part of the (phenyl)alkoxy group is optionally substituted with halo or haloalkoxy;

when Ring B is not present and Ring A is other than phenyl, then
(i) Ring A is substituted with one or two $R^{AB}$ groups or
(ii) Ring A is unsubstituted, wherein:
  1) when Ring A is unsubstituted tetrahydroquinolinyl, then L is bond;
  2) when Ring A is unsubstituted 2,3-dihydrobenzo[b][1,4]dioxinyl, then L is O;
  3) when Ring A is unsubstituted tetrahydronaphthyl, then L is O, and $R^1$ is not hydrogen or ethyl; or
  4) when Ring A is unsubstituted spirocycloalkyl, then L is O, S, or $CH_2S$;

each $R^{AA}$ is independently alkyl; haloalkyl; haloalkoxy; cycloalkyloxy; (cycloalkyl)alkoxy; phenoxy optionally substituted with one or two halo groups; or alkylcarbonylaminoalkoxy;

each $R^{AB}$ is independently halo; alkyl; hydroxy; alkoxy; haloalkyl; haloalkoxy; cycloalkyloxy; (cycloalkyl) alkoxy; or phenoxy optionally substituted with one or two halo groups;

Ring B, when present, is cycloalkyl, heterocycloalkyl, aryl, or heteroaryl; wherein each is optionally substituted with 1, 2, or 3 $R^B$ groups;

each $R^B$ is independently halo; cyano; alkyl; hydroxyalkyl; alkylsulfonyl; aminosulfonyl; alkylaminosulfonyl; dialkylaminosulfonyl; haloalkyl; alkoxy; aminoalkoxy; alkylaminoalkoxy; dialkylaminoalkoxy; hydroxyalkoxy; haloalkoxy; alkylcarbonyl; alkoxyalkoxy; aminocarbonyl; alkylaminocarbonyl; dialkylaminocarbonyl; alkylcarbonylaminoalkoxy; cycloalkyl; (cycloalkyl)alkyl; cycloalkyloxy; (cycloalkyl)alkoxy wherein cycloalkyl group is optionally substituted with hydroxyalkyl; cycloalkylcarbonyl; cycloalkylcarbonyloxy; heterocycloalkyl optionally substituted with one or two groups independently selected from halo, alkyl, and alkylcarbonyl; (5-6-membered heterocycloalkyl-one)alkyl; 5-6-membered heterocycloalkyl-one; (heterocycloalkyl)alkyl; heterocycloalkylcarbonyl; or 5-6 membered heteroaryl optionally substituted with one group selected from alkyl, hydroxyalkyl, (hydroxycycloalkyl)alkyl, alkoxyalkyl, and hydroxycycloalkyl;

$R^1$ is hydrogen, alkyl, cycloalkyl, heterocycloalkyl, or W; wherein W is alkyl substituted with amino, alkylamino, dialkylamino, alkylcarbonyloxy, alkoxycarbonyl, phenylcarbonyloxy, aminocarbonyloxy, alkylaminocarbonyloxy, dialkylaminocarbonyloxy, alkoxycarbonyloxy, cycloalkylcarbonyloxy, —N($R^{1A}$)C(O)$R^{1B}$, —N($R^{1A}$)C(O)O$R^{1B}$, or —N($R^{1A}$)C(O)N$R^{1B}R^{1C}$, wherein $R^{1A}$, $R^{1B}$, and $R^{1C}$ are each independently hydrogen or $C_{1-6}$ alkyl;

$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;

provided:
  i. when L is S or $CH_2$, and Ring A is phenyl other than phenyl substituted with (cycloalkyl)alkoxy, then Ring B cannot be halo-substituted phenyl;
  ii. when L is O, Ring A is phenyl, and Ring B is not present, then $R^{AA}$ cannot be alkyl;
  iii. when L is O, Ring A is phenyl substituted with 1 $R^{AA}$, and Ring B is not present, then $R^{AA}$ cannot be meta-substituted trifluoromethyl;
  iv. when L is O, Ring A is phenyl, Ring B is not present, and $R^1$ is ethyl, then $R^{AA}$ cannot be trifluoromethoxy;
  v. when L is bond, Ring A is other than phenyl, Ring B is not present, and $R^1$ is H, then $R^{AB}$ cannot be methyl, and
  vi. when L is NH, Ring A is pyridyl, indolyl, or indolinyl, and Ring B is not present, then $R^{AB}$ cannot be alkyl; and optionally a single stereoisomer or mixture of stereoisomers thereof and additionally optionally a pharmaceutically acceptable salt thereof.

In certain embodiments, Ring B cannot be mono or di-substituted halo.

In certain embodiments, Ring B cannot be unsubstituted phenyl or phenyl substituted with one or two groups independently selected from alkyl, halo, or haloalkyl.

In certain embodiments, Ring A cannot be unsubstituted phenyl or phenyl substituted with one or two groups independently selected from alkyl, halo, or haloalkyl, and Ring B cannot be unsubstituted phenyl or phenyl substituted with one or two groups independently selected from alkyl, halo, or haloalkyl.

In certain embodiments, when L is S or $CH_2$, Ring B cannot be mono or di-substituted halo.

In certain embodiments, when L is S or $CH_2$, Ring B cannot be unsubstituted phenyl or phenyl substituted with one or two groups independently selected from alkyl, halo, or haloalkyl.

In certain embodiments, when L is S or $CH_2$, Ring A cannot be unsubstituted phenyl or phenyl substituted with one or two groups independently selected from alkyl, halo, or haloalkyl, and Ring B cannot be unsubstituted phenyl or phenyl substituted with one or two groups independently selected from alkyl, halo, or haloalkyl.

In certain embodiments, the compound of Formula (I):

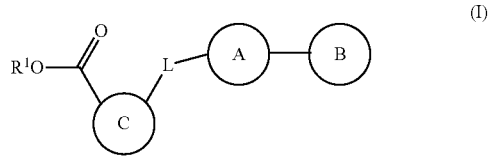

(I)

is that wherein:
ring C is selected from:

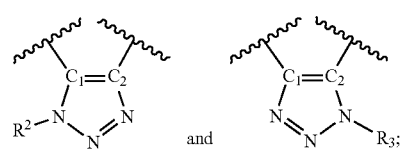

and wherein the wavy lines ( ~~~ ) indicate the points of attachment of the $C_1$ carbon to the carbonyl of C(O)—O$R^1$, and the $C_2$ carbon to L;

L is a bond, CH$_2$, CF$_2$, O, NR$^L$, S, S(=O), C(=O), CH$_2$-Q, or Q-CH$_2$; wherein Q is O, NR$^L$, or S;

R$^L$ is hydrogen, C$_{1-4}$ alkyl, C$_{3-6}$ cycloalkyl, phenyl, or benzyl; wherein the C$_{1-4}$ alkyl is optionally substituted with hydroxycarbonyl, alkoxycarbonyl, or alkylcarbonyloxy; and the phenyl group alone or as a part of the benzyl group is optionally substituted with one or two groups selected from halo and haloalkoxy;

Ring A is cycloalkyl, spirocycloalkyl, heterocycloalkyl, aryl, or heteroaryl, each is optionally substituted with 1 or 2 R$^{AA}$ groups;

when Ring B is present, then Ring A is optionally substituted with one or two groups selected from halo, alkyl, alkoxy, haloalkoxy, (cycloalkyl)alkoxy, and cycloalkyl;

each R$^{AA}$ is independently alkyl; halo; hydroxy; alkoxy; haloalkyl; haloalkoxy; cycloalkyloxy; (cycloalkyl)alkoxy; alkylcarbonylaminoalkoxy; phenoxy optionally substituted with one or two halo; or (phenyl)alkoxy wherein the phenyl is optionally substituted with halo, cyano, haloalkyl, or haloalkoxy;

Ring B, when present, is cycloalkyl, heterocycloalkyl, aryl, or heteroaryl; wherein each is optionally substituted with 1, 2, or 3 R$^B$ groups;

each R$^B$ is independently halo; cyano; alkyl; alkylsulfonyl; aminosulfonyl; alkylaminosulfonyl; dialkylaminosulfonyl; haloalkyl; alkoxy; haloalkoxy; alkylcarbonyl; alkoxyalkoxy; aminocarbonyl; alkylaminocarbonyl; dialkylaminocarbonyl; alkylcarbonylaminoalkoxy; cycloalkyl; (cycloalkyl)alkyl; cycloalkyloxy; (cycloalkyl)alkoxy; cycloalkylcarbonyl; cycloalkylcarbonyloxy; heterocycloalkyl optionally substituted with one or two groups independently selected from halo, alkyl, and alkylcarbonyl; (5-6-membered heterocycloalkyl-one)alkyl; 5-6-membered heterocycloalkyl-one; (heterocycloalkyl)alkyl; heterocycloalkylcarbonyl; or 5-6 membered heteroaryl;

R$^1$ is hydrogen, alkyl, cycloalkyl, heterocycloalkyl, or W; wherein W is alkyl substituted with amino, alkylamino, dialkylamino, alkylcarbonyloxy, alkoxycarbonyl, phenylcarbonyloxy, aminocarbonyloxy, alkylaminocarbonyloxy, dialkylaminocarbonyloxy, alkoxycarbonyloxy, cycloalkylcarbonyloxy, —N(R$^{1A}$)C(O)R$^{1B}$, —N(R$^{1A}$)C(O)OR$^{1B}$, or —N(R$^{1A}$)C(O)NR$^{1B}$R$^{1C}$; wherein R$^{1A}$, R$^{1B}$, and R$^{1C}$ are each independently hydrogen or C$_{1-6}$ alkyl;

R$^2$ and R$^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl; and optionally a single stereoisomer or mixture of stereoisomers thereof and additionally optionally a pharmaceutically acceptable salt thereof.

In certain embodiments, the compound of Formula (I):

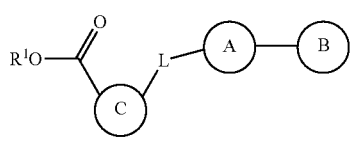

(I)

is that wherein:
ring C is selected from:

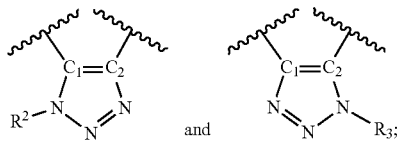

wherein the wavy lines ( ~~~ ) indicate the points of attachment of the C$_1$ carbon to the carbonyl of C(O)—OR$^1$, and the C$_2$ carbon to L;

L is a bond, CH$_2$, CF$_2$, O, NR$^L$, S, C(=O), CH$_2$-Q, or Q-CH$_2$; wherein Q is O, NR$^L$, or S;

R$^L$ is hydrogen or C$_{1-4}$ alkyl optionally substituted with hydroxycarbonyl, alkoxycarbonyl, or alkylcarbonyloxy;

Ring A is cycloalkyl, heterocycloalkyl, aryl, or heteroaryl, each is optionally substituted with 1 or 2 R$^{AA}$ groups;

each R$^{AA}$ is independently alkyl, haloalkyl, haloalkoxy, cycloalkyloxy, (cycloalkyl)alkoxy, alkylcarbonylaminoalkoxy, or phenoxy optionally substituted with one or two halo;

each R$^{AB}$ is independently halo, alkyl, hydroxy, alkoxy, haloalkyl, haloalkoxy, cycloalkyloxy, (cycloalkyl)alkoxy, or phenoxy optionally substituted with one or two halo;

Ring B, when present, is cycloalkyl, heterocycloalkyl, aryl, or heteroaryl; wherein each is optionally substituted with one or two R$^B$ groups;

each R$^B$ is independently halo, cyano, alkyl, haloalkyl, alkoxy, haloalkoxy, alkylcarbonyl, alkoxyalkoxy, alkylcarbonylaminoalkoxy, cycloalkyl, (cycloalkyl)alkyl, cycloalkyloxy, (cycloalkyl)alkoxy, cycloalkylcarbonyl, cycloalkylcarbonyloxy, heterocycloalkyl optionally substituted with alkyl or alkylcarbonyl, (5-6-membered heterocycloalkyl-one)alkyl, (heterocycloalkyl)alkyl, or heterocycloalkylcarbonyl;

R$^1$ is hydrogen, alkyl, cycloalkyl, heterocycloalkyl, or W; where W is alkyl substituted with amino, alkylamino, dialkylamino, alkylcarbonyloxy, alkoxycarbonyl, or phenylcarbonyloxy;

R$^2$ and R$^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl; and optionally a single stereoisomer or mixture of stereoisomers thereof and additionally optionally a pharmaceutically acceptable salt thereof.

In certain embodiments, the compound of Formula (I) is that wherein:
L is a bond, CH$_2$, CF$_2$, O, NR$^L$, S, S(=O), C(=O), CH$_2$-Q, or Q-CH$_2$; wherein Q is O, NR$^L$, or S;

R$^L$ is hydrogen, C$_{1-4}$ alkyl, C$_{3-6}$ cycloalkyl, phenyl, or benzyl; wherein the C$_{1-4}$ alkyl is optionally substituted with hydroxycarbonyl, alkoxycarbonyl, or alkylcarbonyloxy; and the phenyl group alone or as a part of the benzyl group is optionally substituted with one or two groups selected from halo and haloalkoxy;

when Ring B is present, then Ring A is optionally substituted with one or two groups selected from halo, alkyl, alkoxy, haloalkoxy, (cycloalkyl)alkoxy, and cycloalkyl;

Ring A is cycloalkyl, spirocycloalkyl, heterocycloalkyl, aryl, or heteroaryl, each is optionally substituted with 1 or 2 R$^{AA}$ groups;

each $R^{AA}$ is independently alkyl; halo; hydroxy; alkoxy; haloalkyl; haloalkoxy; cycloalkyloxy; (cycloalkyl)alkoxy; alkylcarbonylaminoalkoxy; phenoxy optionally substituted with one or two halo; or (phenyl)alkoxy wherein the phenyl is optionally substituted with halo, cyano, haloalkyl, or haloalkoxy;

Ring B, when present, is cycloalkyl, heterocycloalkyl, aryl, or heteroaryl; wherein each is optionally substituted with 1, 2, or 3 $R^B$ groups;

each $R^B$ is independently halo; cyano; alkyl; alkylsulfonyl; aminosulfonyl; alkylaminosulfonyl; dialkylaminosulfonyl; haloalkyl; alkoxy; haloalkoxy; alkylcarbonyl; alkoxyalkyl; aminocarbonyl; alkylaminocarbonyl; dialkylaminocarbonyl; alkylcarbonylaminoalkoxy; cycloalkyl; (cycloalkyl)alkyl; cycloalkyloxy; (cycloalkyl)alkoxy; cycloalkylcarbonyl; cycloalkylcarbonyloxy; heterocycloalkyl optionally substituted with one or two groups independently selected from halo, alkyl, and alkylcarbonyl; (5-6-membered heterocycloalkyl-one)alkyl; 5-6-membered heterocycloalkyl-one; (heterocycloalkyl)alkyl; heterocycloalkylcarbonyl; or 5-6 membered heteroaryl;

$R^1$ is W; wherein W is alkyl substituted with amino, alkylamino, dialkylamino, alkylcarbonyloxy, alkoxycarbonyl, phenylcarbonyloxy, aminocarbonyloxy, alkylaminocarbonyloxy, dialkylaminocarbonyloxy, alkoxycarbonyloxy, cycloalkylcarbonyloxy, —N($R^{1A}$)C(O)$R^{1B}$, —N($R^{1A}$)C(O)O$R^{1B}$, or —N($R^{1A}$)C(O)N$R^{1B}$$R^{1C}$; wherein $R^{1A}$, $R^{1B}$, and $R^{1C}$ are each independently hydrogen or $C_{1-6}$ alkyl;

$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;

optionally a single stereoisomer or mixture of stereoisomers thereof and additionally optionally a pharmaceutically acceptable salt thereof.

In certain embodiments, the compound of Formula (I) is that wherein:

L is a bond, $CH_2$, $CF_2$, O, $NR^L$, S, S(=O), C(=O), $CH_2$-Q, or Q-$CH_2$; wherein Q is O, $NR^L$, or S;

$R^L$ is hydrogen, $C_{1-4}$ alkyl, $C_{3-6}$ cycloalkyl, phenyl, or benzyl; wherein the $C_{1-4}$ alkyl is optionally substituted with hydroxycarbonyl, alkoxycarbonyl, hydroxycarbonylalkyl, or alkylcarbonyloxy; and the phenyl group alone or as a part of the benzyl group is optionally substituted with one or two groups selected from halo and haloalkoxy;

Ring A is $C_{3-7}$ cycloalkyl, $C_{8-11}$ spirocycloalkyl, 5-6 membered heterocycloalkyl, pyrazolyl, imidazolyl, triazolyl, thiazolyl, thienyl, phenyl, naphthyl, indanyl, tetrahydronaphthyl, dihydronaphthyl, pyridyl, indolyl, benzothiazolyl, quinolinyl, isoquinolinyl, indolinyl, isoindolinyl, tetrahydroquinolinyl, dihydroisoquinolinyl, tetrahydroisoquinolinyl, 2,3-dihydrobenzo[b][1,4]dioxinyl, or tetrahydro-methanonaphthalenyl;

Ring B is present or not present; wherein:

when Ring B is present, then Ring A is optionally substituted with one or two groups selected from halo, alkyl, alkoxy, haloalkoxy, (cycloalkyl)alkoxy, and cycloalkyl;

when Ring B is not present and Ring A is phenyl, then Ring A is substituted with:
(i) one or two R groups,
(ii) 2 halo groups when L is other than O,
(iii) 2 halo groups when L is O, and $R^2$ and $R^3$ are not hydrogen or alkyl,
(iv) one halo group when L is $CH_2NR^L$, or
(v) one halo group and one group selected from the group consisting of haloalkoxy, (cycloalkyl)alkoxy, and (phenyl)alkoxy, when L is bond, O or S, wherein the phenyl is optionally substituted with halo;

when Ring B is not present and Ring A is other than phenyl, then Ring A is optionally substituted with one or two $R^{AB}$ groups;

each $R^{AA}$ is independently alkyl; haloalkyl; haloalkoxy; cycloalkyloxy; (cycloalkyl)alkoxy; alkylcarbonylaminoalkoxy; or phenoxy optionally substituted with one or two halo;

each $R^{AB}$ is independently halo; alkyl; hydroxy; alkoxy; haloalkyl; haloalkoxy; cycloalkyloxy; (cycloalkyl)alkoxy; or phenoxy optionally substituted with one or two halo;

Ring B, when present, is cycloalkyl, heterocycloalkyl, aryl, or heteroaryl; wherein each is optionally substituted with 1, 2, or 3 $R^B$ groups;

each $R^B$ is independently halo; cyano; alkyl; alkylsulfonyl; aminosulfonyl; alkylaminosulfonyl; dialkylaminosulfonyl; haloalkyl; alkoxy; haloalkoxy; alkylcarbonyl; alkoxyalkyl; aminocarbonyl; alkylaminocarbonyl; dialkylaminocarbonyl; alkylcarbonylaminoalkoxy; cycloalkyl; (cycloalkyl)alkyl; cycloalkyloxy; (cycloalkyl)alkoxy; cycloalkylcarbonyl; cycloalkylcarbonyloxy; heterocycloalkyl optionally substituted with one or two groups independently selected from halo, alkyl, and alkylcarbonyl; (5-6-membered heterocycloalkyl-one)alkyl; 5-6-membered heterocycloalkyl-one; (heterocycloalkyl)alkyl; heterocycloalkylcarbonyl; or 5-6 membered heteroaryl;

$R^1$ is hydrogen, alkyl, cycloalkyl, heterocycloalkyl, or W; wherein W is alkyl substituted with amino, alkylamino, dialkylamino, alkylcarbonyloxy, alkoxycarbonyl, phenylcarbonyloxy, aminocarbonyloxy, alkylaminocarbonyloxy, dialkylaminocarbonyloxy, alkoxycarbonyloxy, cycloalkylcarbonyloxy, —N($R^{1A}$)C(O)$R^{1B}$, —N($R^{1A}$)C(O)O$R^{1B}$, or —N($R^{1A}$)C(O)N$R^{1B}$$R^{1C}$; wherein $R^{1A}$, $R^{1B}$, and $R^{1C}$ are each independently hydrogen or $C_{1-6}$ alkyl;

$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;

provided:
i. when L is S or $CH_2$, and Ring A is phenyl, then Ring B cannot be halo-substituted phenyl;
ii. when L is O, Ring A is phenyl, and Ring B is not present, then $R^{AA}$ cannot be alkyl;
iii. when L is O, Ring A is phenyl substituted with 1 $R^{AA}$, and Ring B is not present, then $R^{AA}$ cannot be meta-substituted trifluoromethyl;
iv. when L is O, Ring A is phenyl, Ring B is not present, and $R^1$ is ethyl, then $R^{AA}$ cannot be trifluoromethoxy;
v. when L is bond, Ring A is other than phenyl, Ring B is not present, and $R^1$ is H, then $R^{AB}$ cannot be methyl, and
vi. when L is NH, Ring A is pyridyl, indolyl, or indolinyl, and Ring B is not present, then $R^{AB}$ cannot be alkyl; and optionally a single stereoisomer or mixture of stereoisomers thereof and additionally optionally a pharmaceutically acceptable salt thereof.

In certain embodiments, the compound of Formula (I) is that wherein:

L is a bond, $CH_2$, $CF_2$, O, $NR^L$, S, S(=O), C(=O), $CH_2$-Q, or Q-$CH_2$; wherein Q is O, $NR^L$, or S;

$R^L$ is hydrogen, $C_{1-4}$ alkyl, $C_{3-6}$ cycloalkyl, phenyl, or benzyl; wherein the $C_{1-4}$ alkyl is optionally substituted with hydroxycarbonyl, alkoxycarbonyl, hydroxycarbonylalkyl, or alkylcarbonyloxy; and the phenyl group alone or as a part of the benzyl group is optionally substituted with one or two groups selected from halo and haloalkoxy;

Ring A is $C_{3-7}$ cycloalkyl, $C_{8-11}$ spirocycloalkyl, 5-8 membered heterocycloalkyl, pyrazolyl, imidazolyl, triazolyl, thiazolyl, thienyl, phenyl, naphthyl, indanyl, tetrahydronaphthyl, dihydronaphthyl, pyridyl, indolyl, benzothiazolyl, quinolinyl, isoquinolinyl, indolinyl, isoindolinyl, tetrahydroquinolinyl, dihydroisoquinolinyl, tetrahydroisoquinolinyl, 2,3-dihydrobenzo[b][1,4]dioxinyl, or tetrahydro-methanonaphthalenyl;

Ring B is present or not present; wherein:

when Ring B is present, then Ring A is optionally substituted with one or two groups selected from halo, alkyl, alkoxy, haloalkoxy, (cycloalkyl)alkoxy, and cycloalkyl;

when Ring B is not present and Ring A is phenyl, then Ring A is substituted with:
  (i) one or two $R^{AA}$ groups,
  (ii) 2 halo groups when L is other than O,
  (iii) 2 halo groups when L is O, and $R^2$ and $R^3$ are not hydrogen or alkyl,
  (iv) one halo group when L is $CH_2NR^L$, or
  (v) one halo group and one group selected from the group consisting of haloalkoxy, (cycloalkyl)alkoxy, and (phenyl)alkoxy, when L is bond, O or S, wherein the phenyl is optionally substituted with halo;

when Ring B is not present and Ring A is other than phenyl, then
  (i) Ring A is substituted with one or two $R^{AB}$ groups or
  (ii) Ring A is unsubstituted, wherein:
    1) when Ring A is unsubstituted tetrahydroquinolinyl, then L is bond;
    2) when Ring A is unsubstituted 2,3-dihydrobenzo[b][1,4]dioxinyl, then L is O;
    3) when Ring A is unsubstituted tetrahydronaphthyl, then L is O, and $R^1$ is not hydrogen or ethyl; or
    4) when Ring A is unsubstituted spirocycloalkyl, then L is O or S;

each $R^{AA}$ is independently alkyl; haloalkyl; haloalkoxy; cycloalkyloxy; (cycloalkyl)alkoxy; phenoxy optionally substituted with one or two halo; or alkylcarbonylaminoalkoxy;

each $R^{AB}$ is independently halo; alkyl; hydroxy; alkoxy; haloalkyl; haloalkoxy; cycloalkyloxy; (cycloalkyl)alkoxy; or phenoxy optionally substituted with one or two halo;

Ring B, when present, is cycloalkyl, heterocycloalkyl, aryl, or heteroaryl; wherein each is optionally substituted with 1, 2, or 3 $R^B$ groups;

each $R^B$ is independently halo; cyano; alkyl; alkylsulfonyl; aminosulfonyl; alkylaminosulfonyl; dialkylaminosulfonyl; haloalkyl; alkoxy; haloalkoxy; alkylcarbonyl; alkoxyalkoxy; aminocarbonyl; alkylaminocarbonyl; dialkylaminocarbonyl; alkylcarbonylaminoalkoxy; cycloalkyl; (cycloalkyl)alkyl; cycloalkyloxy; (cycloalkyl)alkoxy; cycloalkylcarbonyl; cycloalkylcarbonyloxy; heterocycloalkyl optionally substituted with one or two groups independently selected from halo, alkyl, and alkylcarbonyl; (5-6-membered heterocycloalkyl-one)alkyl; 5-6-membered heterocycloalkyl-one; (heterocycloalkyl)alkyl; heterocycloalkylcarbonyl; or 5-6 membered heteroaryl;

$R^1$ is hydrogen, alkyl, cycloalkyl, heterocycloalkyl, or W; wherein W is alkyl substituted with amino, alkylamino, dialkylamino, alkylcarbonyloxy, alkoxycarbonyl, phenylcarbonyloxy, aminocarbonyloxy, alkylaminocarbonyloxy, dialkylaminocarbonyloxy, alkoxycarbonyloxy, cycloalkylcarbonyloxy, —$N(R^{1A})C(O)R^{1B}$, —$N(R^{1A})C(O)OR^{1B}$, or —$N(R^{1A})C(O)NR^{1B}R^{1C}$; wherein $R^{1A}$, $R^{1B}$, and $R^{1C}$ are each independently hydrogen or $C_{1-6}$ alkyl;

$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;

provided:
  i. when L is S or $CH_2$, and Ring A is phenyl, then Ring B cannot be halo-substituted phenyl;
  ii. when L is O, Ring A is phenyl, and Ring B is not present, then $R^{AA}$ cannot be alkyl;
  iii. when L is O, Ring A is phenyl substituted with 1 $R^{AA}$, and Ring B is not present, then $R^{AA}$ cannot be meta-substituted trifluoromethyl;
  iv. when L is O, Ring A is phenyl, Ring B is not present, and $R^1$ is ethyl, then $R^{AA}$ cannot be trifluoromethoxy;
  v. when L is bond, Ring A is other than phenyl, Ring B is not present, and $R^1$ is H, then $R^{AB}$ cannot be methyl, and
  vi. when L is NH, Ring A is pyridyl, indolyl, or indolinyl, and Ring B is not present, then $R^{AB}$ cannot be alkyl; and optionally a single stereoisomer or mixture of stereoisomers thereof and additionally optionally a pharmaceutically acceptable salt thereof.

In certain embodiments, the compound of Formula (I) is that wherein:

L is a bond, $CH_2$, $CF_2$, O, $NR^L$, S, S(=O), C(=O), $CH_2$-Q, or Q-$CH_2$; wherein Q is O, $NR^L$, or S;

$R^L$ is hydrogen, $C_{1-4}$ alkyl, $C_{3-6}$ cycloalkyl, phenyl, or benzyl; wherein the $C_{1-4}$ alkyl is optionally substituted with hydroxycarbonyl, alkoxycarbonyl, hydroxycarbonylalkyl, or alkylcarbonyloxy; and the phenyl group alone or as a part of the benzyl group is optionally substituted with one or two groups selected from halo and haloalkoxy;

Ring A is $C_{3-7}$ cycloalkyl, $C_{8-11}$ spirocycloalkyl, 5-6 membered heterocycloalkyl, pyrazolyl, imidazolyl, triazolyl, thiazolyl, thienyl, phenyl, naphthyl, indanyl, tetrahydronaphthyl, dihydronaphthyl, pyridyl, indolyl, benzothiazolyl, quinolinyl, isoquinolinyl, indolinyl, isoindolinyl, tetrahydroquinolinyl, dihydroisoquinolinyl, tetrahydroisoquinolinyl, 2,3-dihydrobenzo[b][1,4]dioxinyl, or tetrahydro-methanonaphthalenyl;

Ring B is present or not present; wherein:

when Ring B is present, then Ring A is optionally substituted with one or two groups selected from halo, alkyl, alkoxy, haloalkoxy, (cycloalkyl)alkoxy, and cycloalkyl;

when Ring B is not present and Ring A is phenyl, then Ring A is substituted with:
  (i) one or two $R^{AA}$ groups,
  (ii) 2 halo groups when L is other than O,
  (iii) 2 halo groups when L is O, and $R^2$ and $R^3$ are not hydrogen or alkyl,
  (iv) one halo group when L is $CH_2NR^L$, or
  (v) one halo group and one group selected from the group consisting of haloalkoxy, (cycloalkyl)alkoxy, and (phenyl)alkoxy, when L is bond, O or S, wherein the phenyl is optionally substituted with halo;
when Ring B is not present and Ring A is other than phenyl, then
   (i) Ring A is substituted with one or two R groups or
   (ii) Ring A is unsubstituted, wherein:
      1) when Ring A is unsubstituted tetrahydroquinolinyl, then L is bond;
      2) when Ring A is unsubstituted 2,3-dihydrobenzo[b][1,4]dioxinyl, then L is O;
      3) when Ring A is unsubstituted tetrahydronaphthyl, then L is O, and $R^1$ is not hydrogen or ethyl; or
      4) when Ring A is unsubstituted spirocycloalkyl, then L is O or S;
each $R^{AA}$ is independently alkyl; haloalkyl; haloalkoxy; cycloalkyloxy; (cycloalkyl)alkoxy; phenoxy optionally substituted with one or two halo; or alkylcarbonylaminoalkoxy;
each $R^{AB}$ is independently halo; alkyl; hydroxy; alkoxy; haloalkyl; haloalkoxy; cycloalkyloxy; (cycloalkyl)alkoxy; or phenoxy optionally substituted with one or two halo;
Ring B, when present, is cycloalkyl, heterocycloalkyl, aryl, or heteroaryl; wherein each is optionally substituted with 1, 2, or 3 $R^B$ groups;
each $R^B$ is independently halo; cyano; alkyl; alkylsulfonyl; aminosulfonyl; alkylaminosulfonyl; dialkylaminosulfonyl; haloalkyl; alkoxy; haloalkoxy; alkylcarbonyl; alkoxyalkoxy; aminocarbonyl; alkylaminocarbonyl; dialkylaminocarbonyl; alkylcarbonylaminoalkoxy; cycloalkyl; (cycloalkyl)alkyl; cycloalkyloxy; (cycloalkyl)alkoxy; cycloalkylcarbonyl; cycloalkylcarbonyloxy; heterocycloalkyl optionally substituted with 1 or 2 groups independently selected from halo, alkyl, and alkylcarbonyl; (5-6-membered heterocycloalkyl-one)alkyl; 5-6-membered heterocycloalkyl-one; (heterocycloalkyl)alkyl; heterocycloalkylcarbonyl; or 5-6 membered heteroaryl;
$R^1$ is hydrogen, alkyl, cycloalkyl, heterocycloalkyl, or W; wherein W is alkyl substituted with amino, alkylamino, dialkylamino, alkylcarbonyloxy, alkoxycarbonyl, phenylcarbonyloxy, aminocarbonyloxy, alkylaminocarbonyloxy, dialkylaminocarbonyloxy, alkoxycarbonyloxy, cycloalkylcarbonyloxy, —N($R^{1A}$)C(O)$R^{1B}$, —N($R^{1A}$)C(O)O$R^{1B}$, or —N($R^{1A}$)C(O)N$R^{1B}R^{1C}$; wherein $R^{1A}$, $R^{1B}$, and $R^{1C}$ are each independently hydrogen or $C_{1-6}$ alkyl;
$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;
provided:
   i. when L is S or $CH_2$, and Ring A is phenyl, then Ring B cannot be halo-substituted phenyl;
   ii. when L is O, Ring A is phenyl, and Ring B is not present, then $R^{AA}$ cannot be alkyl;
   iii. when L is O, Ring A is phenyl substituted with 1 $R^{AA}$, and Ring B is not present, then $R^{AA}$ cannot be meta-substituted trifluoromethyl;
   iv. when L is O, Ring A is phenyl, Ring B is not present, and $R^1$ is ethyl, then $R^{AA}$ cannot be trifluoromethoxy;
   v. when L is bond, Ring A is other than phenyl, Ring B is not present, and $R^1$ is H, then $R^{AB}$ cannot be methyl, and
   vi. when L is NH, Ring A is pyridyl, indolyl, or indolinyl, and Ring B is not present, then $R^{AB}$ cannot be alkyl; and optionally a single stereoisomer or mixture of stereoisomers thereof and additionally optionally a pharmaceutically acceptable salt thereof. In a further embodiment, the compound of Formula (I) is that wherein: $R^L$ is hydrogen, $C_{1-4}$ alkyl, or benzyl; and the benzyl group is optionally substituted with one or two haloalkoxy groups; and Ring A is $C_{3-7}$ cycloalkyl, $C_{8-11}$ spirocycloalkyl, 5-8 membered heterocycloalkyl, phenyl, naphthyl, indanyl, tetrahydronaphthyl, 2,3-dihydrobenzo[b][1,4]dioxinyl, pyridyl, quinolinyl, isoquinolinyl, tetrahydroquinolinyl, or tetrahydroisoquinolinyl. In a further embodiment, the compound of Formula (I) is that wherein: $R^L$ is hydrogen, $C_{1-4}$ alkyl, or benzyl; and the benzyl group is optionally substituted with one or two haloalkoxy groups; and Ring B, when present, is cycloalkyl, heterocycloalkyl, phenyl, tetrahydronaphthyl, quinolinyl, isoquinolinyl, tetrahydroquinolinyl.

In certain embodiments, the compound of Formula (I) is that wherein:
L is a bond, $CH_2$, $CF_2$, O, $NR^L$, S, S(=O), C(=O), $CH_2$-Q, or Q-$CH_2$; wherein Q is O, $NR^L$, or S;
$R^L$ is hydrogen, $C_{1-4}$ alkyl, $C_{3-6}$ cycloalkyl, phenyl, or benzyl; wherein the $C_{1-4}$ alkyl is optionally substituted with hydroxycarbonyl, alkoxycarbonyl, hydroxycarbonylalkyl, or alkylcarbonyloxy; and the phenyl group alone or as a part of the benzyl group is optionally substituted with one or two groups selected from halo and haloalkoxy;
Ring A is $C_{3-7}$ cycloalkyl, $C_{8-11}$ spirocycloalkyl, 5-6 membered heterocycloalkyl, pyrazolyl, imidazolyl, triazolyl, thiazolyl, thienyl, phenyl, naphthyl, indanyl, tetrahydronaphthyl, dihydronaphthyl, pyridyl, indolyl, benzothiazolyl, quinolinyl, isoquinolinyl, indolinyl, isoindolinyl, tetrahydroquinolinyl, dihydroisoquinolinyl, tetrahydroisoquinolinyl, 2,3-dihydrobenzo[b][1,4]dioxinyl, or tetrahydro-methanonaphthalenyl;
Ring B is present or not present; wherein:
when Ring B is present, then Ring A is optionally substituted with one or two groups selected from halo, alkyl, alkoxy, haloalkoxy, (cycloalkyl)alkoxy, and cycloalkyl;
when Ring B is not present and Ring A is phenyl, then Ring A is substituted with:
   (i) one or two $R^{AA}$ groups,
   (ii) 2 halo groups when L is other than O,
   (iii) 2 halo groups when L is O, and $R^2$ and $R^3$ are not hydrogen or alkyl,
   (iv) one halo group when L is $CH_2NR^L$, or
   (v) one halo group and one group selected from the group consisting of haloalkoxy, (cycloalkyl)alkoxy, and (phenyl)alkoxy, when L is bond, O or S, wherein the phenyl is optionally substituted with halo;
when Ring B is not present and Ring A is other than phenyl, then Ring A is substituted with one or two $R^{AB}$ groups;
each $R^{AA}$ is independently alkyl; haloalkyl; haloalkoxy; cycloalkyloxy; (cycloalkyl)alkoxy; phenoxy optionally substituted with one or two halo; or alkylcarbonylaminoalkoxy;
each $R^{AB}$ is independently halo; alkyl; hydroxy; alkoxy; haloalkyl; haloalkoxy; cycloalkyloxy; (cycloalkyl)alkoxy; or phenoxy optionally substituted with one or two halo;
Ring B, when present, is cycloalkyl, heterocycloalkyl, aryl, or heteroaryl; wherein each is optionally substituted with 1, 2, or 3 $R^B$ groups;
each $R^B$ is independently halo; cyano; alkyl; alkylsulfonyl; aminosulfonyl; alkylaminosulfonyl; dialkylaminosulfonyl; haloalkyl; alkoxy; haloalkoxy; alkylcarbonyl; alkoxyalkoxy; aminocarbonyl; alkylaminocarbonyl; dialkylaminocarbonyl; alkylcarbonylaminoalkoxy; cycloalkyl; (cycloalkyl)alkyl; cycloalkyloxy; (cycloalkyl)alkoxy; cycloalkylcarbonyl; cycloalkylcarbonyloxy; heterocycloalkyl optionally substituted with 1 or 2 groups independently selected from halo, alkyl, and alkylcarbonyl; (5-6-membered heterocycloalkyl-one)alkyl; 5-6-membered heterocycloalkyl-one; (heterocycloalkyl)alkyl; heterocycloalkylcarbonyl; or 5-6 membered heteroaryl;

$R^1$ is hydrogen, alkyl, cycloalkyl, heterocycloalkyl, or W; wherein W is alkyl substituted with amino, alkylamino, dialkylamino, alkylcarbonyloxy, alkoxycarbonyl, phenylcarbonyloxy, aminocarbonyloxy, alkylaminocarbonyloxy, dialkylaminocarbonyloxy, alkoxycarbonyloxy, cycloalkylcarbonyloxy, $-N(R^{1A})C(O)R^{1B}$, $-N(R^{1A})C(O)OR^{1B}$, or $-N(R^{1A})C(O)NR^{1B}R^{1C}$; wherein $R^{1A}$, $R^{1B}$, and $R^{1C}$ are each independently hydrogen or $C_{1-6}$ alkyl;

$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;

provided:
i. when L is S or $CH_2$, and Ring A is phenyl, then Ring B cannot be halo-substituted phenyl;
ii. when L is O, Ring A is phenyl, and Ring B is not present, then $R^{AA}$ cannot be alkyl;
iii. when L is O, Ring A is phenyl substituted with 1 $R^{AA}$, and Ring B is not present, then $R^{AA}$ cannot be meta-substituted trifluoromethyl;
iv. when L is O, Ring A is phenyl, Ring B is not present, and $R^1$ is ethyl, then $R^{AA}$ cannot be trifluoromethoxy;
v. when L is bond, Ring A is other than phenyl, Ring B is not present, and $R^1$ is H, then $R^{AB}$ cannot be methyl, and
vi. when L is NH, Ring A is pyridyl, indolyl, or indolinyl, and Ring B is not present, then $R^{AB}$ cannot be alkyl; and optionally a single stereoisomer or mixture of stereoisomers thereof and additionally optionally a pharmaceutically acceptable salt thereof.

In certain embodiments, the compound of Formula (I) is that wherein:

L is a bond, $CH_2$, $CF_2$, O, $NR^L$, S, S(=O), C(=O), $CH_2$-Q, or Q-$CH_2$; wherein Q is O, $NR^L$, or S;

$R^L$ is hydrogen, $C_{1-4}$ alkyl, or benzyl; and the benzyl group is optionally substituted with one or two groups selected from halo and haloalkoxy;

Ring A is $C_{5-6}$ cycloalkyl, $C_{8-11}$ spirocycloalkyl, 5-6 membered heterocycloalkyl, phenyl, naphthyl, indanyl, tetrahydronaphthyl, 2,3-dihydrobenzo[b][1,4]dioxinyl, pyridyl, quinolinyl, isoquinolinyl, tetrahydroquinolinyl, or tetrahydroisoquinolinyl;

Ring B is present or not present; wherein:
when Ring B is present, then Ring A is optionally substituted with one or two groups selected from halo and haloalkoxy;
when Ring B is not present and Ring A is phenyl, then Ring A is substituted with:
(i) one or two $R^{AA}$ groups,
(ii) 2 halo groups when L is other than O,
(iii) 2 halo groups when L is O, and $R^2$ and $R^3$ are not hydrogen or alkyl,
(iv) one halo group when L is $CH_2NR^L$, or
(v) one halo group and one group selected from the group consisting of haloalkoxy, (cycloalkyl)alkoxy, and (phenyl)alkoxy, when L is bond, O or S, wherein the phenyl is optionally substituted with halo;

when Ring B is not present and Ring A is other than phenyl, then
(i) Ring A is substituted with one or two $R^{AB}$ groups; or
(ii) Ring A is unsubstituted, wherein:
1) when Ring A is unsubstituted tetrahydroquinolinyl, then L is bond;
2) when Ring A is unsubstituted 2,3-dihydrobenzo[b][1,4]dioxinyl, then L is O;
3) when Ring A is unsubstituted tetrahydronaphthyl, then L is O, and $R^1$ is not hydrogen or ethyl; or
4) when Ring A is unsubstituted spirocycloalkyl, then L is O or S;

each $R^{AA}$ is independently haloalkyl; cycloalkyloxy; (cycloalkyl)alkoxy; alkylcarbonylaminoalkoxy; or phenoxy optionally substituted with one or two halo;

each $R^{AB}$ is independently halo, alkyl, haloalkyl, or haloalkoxy;

Ring B, when present, cycloalkyl, heterocycloalkyl, phenyl, tetrahydronaphthyl, tetrahydroquinolinyl, quinolinyl, or isoquinolinyl; wherein each Ring B is optionally substituted with one or two $R^B$ groups;

each $R^B$ is independently halo; cyano; alkyl; haloalkyl; haloalkoxy; alkoxyalkoxy; aminocarbonyl; alkylcarbonylaminoalkoxy; cycloalkyl; (cycloalkyl)alkoxy; heterocycloalkyl optionally substituted with 1 or 2 alkyl, alkylcarbonyl or halo; or (5-6-membered heterocycloalkyl-one)alkyl;

$R^1$ is hydrogen, alkyl or W; wherein W is alkyl substituted with alkylcarbonyloxy, dialkylaminocarbonyloxy cycloalkylcarbonyloxy, or phenylcarbonyloxy;

$R^2$ and $R^3$ are independently hydrogen or alkyl; wherein the alkyl is optionally substituted with cycloalkylcarbonyloxy or heterocycloalkylcarbonyloxy, wherein the heterocycloalkylcarbonyloxy optionally substituted with alkoxycarbonyl;

provided:
(i) when L is S or $CH_2$, and Ring A is phenyl, then Ring B cannot be halo substituted phenyl;
(ii) when L is O, Ring A is phenyl, and Ring B is not present, then $R^{AA}$ cannot be alkyl;
(iii) when L is O, Ring A is phenyl substituted with 1 $R^{AA}$, and Ring B is not present, then $R^{AA}$ cannot be meta-substituted trifluoromethyl;
(iv) when L is O, Ring A is phenyl, Ring B is not present, and $R^1$ is ethyl, then $R^{AA}$ cannot be trifluoromethoxy;
(v) when L is bond, Ring A is other than phenyl, Ring B is not present, and $R^1$ is H, then $R^{AB}$ cannot be methyl, and
(vi) when L is NH, Ring A is pyridyl and Ring B is not present, then $R^{AB}$ cannot be alkyl; and optionally a single stereoisomer or mixture of stereoisomers thereof and additionally optionally a pharmaceutically acceptable salt thereof.

In certain embodiments, the compound of Formula (I) is that wherein:

L is a bond, $CH_2$, $CF_2$, O, $NR^L$, S, S(=O), C(=O), $CH_2$-Q, or Q-$CH_2$; wherein Q is O, $NR^L$, or S;

$R^L$ is H, $C_{1-4}$ alkyl, $C_{3-6}$ cycloalkyl, phenyl, or benzyl; wherein the $C_{1-4}$ alkyl is optionally substituted with hydroxycarbonyl, alkoxycarbonyl, hydroxycarbonylalkyl, or alkylcarbonyloxy; and the phenyl group alone or as a part of the benzyl group is optionally substituted with one or two groups selected from halo and haloalkoxy;

Ring A is cycloalkyl, spirocycloalkyl, heterocycloalkyl, aryl, or heteroaryl; wherein each is optionally substituted with one halo or alkyl;

Ring B, when present, is cycloalkyl, heterocycloalkyl, aryl, or heteroaryl; wherein each is optionally substituted with one or two $R^B$ groups;

each $R^B$ is independently cyano; alkyl; haloalkyl; alkoxy; haloalkoxy; alkylcarbonyl; alkoxyalkoxy; aminocarbonyl; alkylcarbonylaminoalkoxy; cycloalkyl; (cycloalkyl)alkyl; cycloalkyloxy; (cycloalkyl)alkoxy; cycloalkylcarbonyl; cycloalkylcarbonyloxy; heterocycloalkyl optionally substituted with 1 or 2 alkyl, alkylcarbonyl or halo; (5-6-membered heterocycloalkyl-one)alkyl, (heterocycloalkyl)alkyl, or heterocycloalkylcarbonyl;

$R^1$ is hydrogen, alkyl, cycloalkyl, heterocycloalkyl, or W; wherein W is alkyl substituted with amino, alkylamino, dialkylamino, alkylcarbonyloxy, alkoxycarbonyl, phenylcarbonyloxy, aminocarbonyloxy, alkylaminocarbonyloxy, dialkylaminocarbonyloxy, alkoxycarbonyloxy, cycloalkylcarbonyloxy, —N(R$^{1A}$)C(O)R$^{1B}$, —N(R$^{1A}$)C(O)OR$^{1B}$, or —N(R$^{1A}$)C(O)NR$^{1B}$R$^{1C}$; wherein R$^{1A}$, R$^{1B}$, and R$^{1C}$ are each independently hydrogen or $C_{1-6}$ alkyl;

$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;

provided that when L is S or CH$_2$, and Ring A is phenyl, then Ring B is not halo-substituted phenyl; and optionally a single stereoisomer or mixture of stereoisomers thereof and additionally optionally a pharmaceutically acceptable salt thereof.

In certain embodiments, the compound of Formula (I) is that wherein:

L is a bond, O, CF$_2$, NR$^L$, S, S(=O), C(=O), CH$_2$-Q, or Q-CH$_2$; wherein Q is O, NR$^L$, or S;

$R^L$ is H, $C_{1-4}$ alkyl, or benzyl; and the phenyl in the benzyl group is optionally substituted with one or two groups selected from halo and haloalkoxy;

Ring A is cycloalkyl, spirocycloalkyl, heterocycloalkyl, phenyl, or heteroaryl; wherein each is optionally substituted with one halo or alkyl;

Ring B, when present, is cycloalkyl, heterocycloalkyl, phenyl, or heteroaryl; wherein each is optionally substituted with one or two $R^B$ groups;

each $R^B$ is independently halo; cyano; alkyl; haloalkyl; haloalkoxy; alkoxyalkoxy; aminocarbonyl; alkylcarbonylaminoalkoxy; cycloalkyl; (cycloalkyl)alkyl; heterocycloalkyl optionally substituted with 1 or 2 alkyl, alkylcarbonyl or halo; or (5-6-membered heterocycloalkyl-one)alkyl;

$R^1$ is hydrogen, alkyl or W; wherein W is alkyl substituted with alkylcarbonyloxy, dialkylaminocarbonyloxy cycloalkylcarbonyloxy, or phenylcarbonyloxy;

$R^2$ and $R^3$ are independently hydrogen or alkyl; wherein the alkyl is optionally substituted with cycloalkylcarbonyloxy or heterocycloalkylcarbonyloxy, wherein the heterocycloalkylcarbonyloxy optionally substituted with alkoxycarbonyl;

provided that when L is S and Ring A is phenyl, then Ring B is not halo-substituted phenyl; and optionally a single stereoisomer or mixture of stereoisomers thereof and additionally optionally a pharmaceutically acceptable salt thereof.

In certain embodiments, the compound of Formula (I) is that wherein:

L is a bond, CH$_2$, CF$_2$, O, NR$^L$, S, C(=O), CH$_2$-Q, or Q-CH$_2$; wherein Q is O, NR$^L$, or S;

$R^L$ is hydrogen or $C_{1-4}$ alkyl optionally substituted with hydroxycarbonyl, alkoxycarbonyl, or alkylcarbonyloxy;

Ring A is cycloalkyl, heterocycloalkyl, aryl, or heteroaryl, each is optionally substituted with 1 or 2 $R^{AA}$ groups;

each $R^{AA}$ is independently alkyl, haloalkyl, haloalkoxy, cycloalkyloxy, (cycloalkyl)alkoxy, alkylcarbonylaminoalkoxy, or phenoxy optionally substituted with one or two halo;

each $R^{AB}$ is independently halo, alkyl, hydroxy, alkoxy, haloalkyl, haloalkoxy, cycloalkyloxy, (cycloalkyl)alkoxy, or phenoxy optionally substituted with one or two halo;

Ring B, when present, is cycloalkyl, heterocycloalkyl, aryl, or heteroaryl; wherein each is optionally substituted with one or two $R^B$ groups;

each $R^B$ is independently halo, cyano, alkyl, haloalkyl, alkoxy, haloalkoxy, alkylcarbonyl, alkoxyalkoxy, alkylcarbonylaminoalkoxy, cycloalkyl, (cycloalkyl)alkyl, cycloalkyloxy, (cycloalkyl)alkoxy, cycloalkylcarbonyl, cycloalkylcarbonyloxy, heterocycloalkyl optionally substituted with alkyl or alkylcarbonyl, (5-6-membered heterocycloalkyl-one)alkyl, (heterocycloalkyl)alkyl, or heterocycloalkylcarbonyl;

$R^1$ is W; where W is alkyl substituted with amino, alkylamino, dialkylamino, alkylcarbonyloxy, alkoxycarbonyl, or phenylcarbonyloxy;

$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;

optionally a single stereoisomer or mixture of stereoisomers thereof and additionally optionally a pharmaceutically acceptable salt thereof.

In certain embodiments, the compound of Formula (I) is that wherein:

L is a bond, CH$_2$, CF$_2$, O, NR$^L$, S, C(=O), CH$_2$-Q, or Q-CH$_2$; wherein Q is O, NR$^L$, or S;

$R^L$ is hydrogen or $C_{1-4}$ alkyl optionally substituted with hydroxycarbonyl, alkoxycarbonyl, hydroxycarbonylalkyl, or alkylcarbonyloxy;

Ring A is $C_{5-7}$ cycloalkyl, 5-6 membered heterocycloalkyl, pyrazolyl, imidazolyl, triazolyl, thiazolyl, thiophenyl, phenyl, naphthyl, indanyl, tetrahydronaphthalinyl, dihydronaphthalinyl, pyridyl, indolyl, benzothiazolyl, quinolinyl, isoquinolinyl, indolinyl, isoindolinyl, tetrahydroquinolinyl, dihydroisoquinolinyl, dihydrobenzodioxinyl, or tetrahydro-methanonaphthalenyl; Ring B is present or not present; wherein:

when Ring B is present, then Ring A is optionally substituted with one or two halo, alkyl, alkoxy, or haloalkoxy;

when Ring B is not present and Ring A is phenyl, then Ring A is substituted with:

(i) one or two $R^{AA}$ groups, or (ii) 2 halo groups when L is other than O;

when Ring B is not present and Ring A is other than phenyl, then Ring A is optionally substituted with one or two $R^{AB}$ groups;

each $R^{AA}$ is independently alkyl, haloalkyl, haloalkoxy, cycloalkyloxy, (cycloalkyl)alkoxy, or phenoxy optionally substituted with one or two halo;

each $R^{AB}$ is independently halo, alkyl, hydroxy, alkoxy, haloalkyl, haloalkoxy, cycloalkyloxy, (cycloalkyl)alkoxy, or phenoxy optionally substituted with one or two halo;

Ring B, when present, is cycloalkyl, heterocycloalkyl, aryl, or heteroaryl; wherein each is optionally substituted with one or two $R^B$ groups;

each $R^B$ is independently halo, cyano, alkyl, haloalkyl, alkoxy, haloalkoxy, alkylcarbonyl, alkoxyalkoxy, alkylcarbonylaminoalkoxy, cycloalkyl, (cycloalkyl)alkyl, cycloalkyloxy, (cycloalkyl)alkoxy, cycloalkylcarbonyl, cycloalkylcarbonyloxy, heterocycloalkyl optionally substituted with alkyl or alkylcarbonyl, (5-6-membered heterocycloalkyl-one)alkyl, (heterocycloalkyl)alkyl, or heterocycloalkylcarbonyl;

$R^1$ is hydrogen, alkyl, cycloalkyl, heterocycloalkyl, or W; where W is alkyl substituted with amino, alkylamino, dialkylamino, alkylcarbonyloxy, alkoxycarbonyl, or phenylcarbonyloxy;

$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;

provided:
  i. when L is S and Ring A is phenyl, then Ring B cannot be halo-substituted phenyl;
  ii. when L is O, Ring A is phenyl, and Ring B is not present, then $R^{AA}$ cannot be alkyl or trifluoromethyl;
  iii. when L is O, Ring A is phenyl, Ring B is not present, and $R^1$ is ethyl, then $R^{AA}$ cannot be trifluoromethoxy;
  iv. when L is NH, Ring A is pyridyl, indolyl, or indolinyl, and Ring B is not present, then $R^{AB}$ cannot be alkyl; and optionally a single stereoisomer or mixture of stereoisomers thereof and additionally optionally a pharmaceutically acceptable salt thereof.

In certain embodiments, the compound of Formula (I) is that wherein:

L is a bond, $CH_2$, $CF_2$, O, $NR^L$, S, C(=O), $CH_2$-Q, or Q-$CH_2$; wherein Q is O, $NR^L$, or S;

$R^L$ is hydrogen or $C_{1-4}$ alkyl optionally substituted with hydroxycarbonyl, alkoxycarbonyl, hydroxycarbonylalkyl, or alkylcarbonyloxy;

Ring A is $C_{5-7}$ cycloalkyl, 5-6 membered heterocycloalkyl, pyrazolyl, imidazolyl, triazolyl, thiazolyl, phenyl, naphthyl, indanyl, tetrahydronaphthalinyl, dihydronaphthalinyl, pyridyl, indolyl, benzothiazolyl, quinolinyl, isoquinolinyl, indolinyl, isoindolinyl, tetrahydroquinolinyl, dihydroisoquinolinyl, or tetrahydro-methanonaphthalenyl;

Ring B is present or not present; wherein:

when Ring B is present, then Ring A is optionally substituted with one or two halo, alkyl, alkoxy, or haloalkoxy;

when Ring B is not present and Ring A is phenyl, then Ring A is substituted with:
(i) one or two $R^{AA}$ groups, or (ii) 2 halo groups when L is other than O;

when Ring B is not present and Ring A is other than phenyl, then Ring A is substituted with one or two $R^{AB}$ groups;

each $R^{AA}$ is independently alkyl, haloalkyl, haloalkoxy, cycloalkyloxy, (cycloalkyl)alkoxy, or phenoxy optionally substituted with one or two halo;

each $R^{AB}$ is independently halo, alkyl, hydroxy, alkoxy, haloalkyl, haloalkoxy, cycloalkyloxy, (cycloalkyl)alkoxy, or phenoxy optionally substituted with one or two halo;

Ring B, when present, is cycloalkyl, heterocycloalkyl, aryl, or heteroaryl; wherein each is optionally substituted with one or two $R^B$ groups;

each $R^B$ is independently halo, cyano, alkyl, haloalkyl, alkoxy, haloalkoxy, alkylcarbonyl, alkoxyalkoxy, alkylcarbonylaminoalkoxy, cycloalkyl, (cycloalkyl)alkyl, cycloalkyloxy, (cycloalkyl)alkoxy, cycloalkylcarbonyl, cycloalkylcarbonyloxy, heterocycloalkyl optionally substituted with alkyl or alkylcarbonyl, (5-6-membered heterocycloalkyl-one)alkyl, (heterocycloalkyl)alkyl, or heterocycloalkylcarbonyl;

$R^1$ is hydrogen, alkyl, cycloalkyl, heterocycloalkyl, or W; where W is alkyl substituted with amino, alkylamino, dialkylamino, alkylcarbonyloxy, alkoxycarbonyl, or phenylcarbonyloxy; and $R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl; and optionally a single stereoisomer or mixture of stereoisomers thereof and additionally optionally a pharmaceutically acceptable salt thereof.

In certain embodiments, the compound of Formula (I) is that wherein:

Ring B is present; wherein Ring B is cycloalkyl, heterocycloalkyl, aryl, or heteroaryl; wherein each is optionally substituted with one or two $R^B$ groups;

each $R^B$ is independently halo, cyano, alkyl, haloalkyl, alkoxy, haloalkoxy, alkylcarbonyl, alkoxyalkoxy, alkylcarbonylaminoalkoxy, cycloalkyl, (cycloalkyl)alkyl, cycloalkyloxy, (cycloalkyl)alkoxy, cycloalkylcarbonyl, cycloalkylcarbonyloxy, heterocycloalkyl optionally substituted with alkyl or alkylcarbonyl, (5-6-membered heterocycloalkyl-one)alkyl, (heterocycloalkyl)alkyl, or heterocycloalkylcarbonyl; provided when L is S and Ring A is phenyl, then Ring B is not halo-substituted phenyl; and optionally a single stereoisomer or mixture of stereoisomers thereof and additionally optionally a pharmaceutically acceptable salt thereof.

In certain embodiments, the compound of Formula (I) is that wherein:

Ring A is $C_{3-7}$ cycloalkyl, $C_{8-11}$ spirocycloalkyl, 5-8 membered heterocycloalkyl, pyrazolyl, imidazolyl, triazolyl, thiazolyl, thienyl, phenyl, naphthyl, indanyl, tetrahydronaphthyl, dihydronaphthyl, pyridyl, indolyl, benzothiazolyl, quinolinyl, isoquinolinyl, indolinyl, isoindolinyl, tetrahydroquinolinyl, dihydroisoquinolinyl, tetrahydroisoquinolinyl, 2,3-dihydrobenzo[b][1,4]dioxinyl, or tetrahydro-methanonaphthalenyl;

Ring B is present or not present; wherein:

when Ring B is present, then Ring A is optionally substituted with one or two groups selected from halo, alkyl, alkoxy, haloalkoxy, (cycloalkyl)alkoxy, and cycloalkyl;

when Ring B is not present and Ring A is other than phenyl, then
(i) Ring A is substituted with one or two $R^{AB}$ groups or (ii) Ring A is unsubstituted, wherein:
  1) when Ring A is unsubstituted tetrahydroquinolinyl, then L is bond;
  2) when Ring A is unsubstituted 2,3-dihydrobenzo[b][1,4]dioxinyl, then L is O;
  3) when Ring A is unsubstituted tetrahydronaphthyl, then L is O, and $R^1$ is not hydrogen or ethyl; or
  4) when Ring A is unsubstituted spirocycloalkyl, then L is O or S;

each $R^B$ is independently halo; cyano; alkyl; alkylsulfonyl; aminosulfonyl; alkylaminosulfonyl; dialkylaminosulfonyl; haloalkyl; alkoxy; haloalkoxy; alkylcarbonyl; alkoxyalkoxy; aminocarbonyl; alkylaminocarbonyl; dialkylaminocarbonyl; alkylcarbonylaminoalkoxy; cycloalkyl; (cycloalkyl)alkyl; cycloalkyloxy; (cycloalkyl)alkoxy; cycloalkylcarbonyl; cycloalkylcarbonyloxy; heterocycloalkyl optionally substituted with one or two groups independently selected from halo, alkyl, and alkylcarbonyl; (5-6-membered heterocycloalkyl-one)alkyl; 5-6-membered heterocycloalkyl-one; (heterocycloalkyl)alkyl; heterocycloalkylcarbonyl; or 5-6 membered heteroaryl;

and optionally a single stereoisomer or mixture of stereoisomers thereof and additionally optionally a pharmaceutically acceptable salt thereof.

In certain embodiments, the compound of Formula (I) is that wherein: ring B is not present;

L is a bond, $CH_2$, $CF_2$, O, $NR^L$, S, $C(=O)$, $CH_2$-Q, or Q-$CH_2$; wherein Q is O, $NR^L$, or S;

$R^L$ is hydrogen or $C_{1-4}$ alkyl optionally substituted with hydroxycarbonyl, alkoxycarbonyl, hydroxycarbonylalkyl, or alkylcarbonyloxy;

Ring A is $C_{5-7}$ cycloalkyl, 5-6 membered heterocycloalkyl, pyrazolyl, imidazolyl, triazolyl, thiazolyl, phenyl, naphthyl, indanyl, tetrahydronaphthalinyl, dihydronaphthalinyl, pyridyl, indolyl, benzothiazolyl, quinolinyl, isoquinolinyl, indolinyl, isoindolinyl, tetrahydroquinolinyl, dihydroisoquinolinyl, or tetrahydro-methanonaphthalenyl;

wherein:

when Ring A is phenyl, then Ring A is substituted with:
(i) one or two $R^{AA}$ groups, or (ii) 2 halo groups when L is other than O;

when Ring A is other than phenyl, then Ring A is substituted with one or two $R^{AB}$ groups;

each $R^{AA}$ is independently alkyl, haloalkyl, haloalkoxy, cycloalkyloxy, (cycloalkyl)alkoxy, or phenoxy optionally substituted with one or two halo;

each $R^{AB}$ is independently halo, alkyl, hydroxy, alkoxy, haloalkyl, haloalkoxy, cycloalkyloxy, (cycloalkyl)alkoxy, or phenoxy optionally substituted with one or two halo;

$R^1$ is hydrogen, alkyl, cycloalkyl, heterocycloalkyl, or W; where W is alkyl substituted with amino, alkylamino, dialkylamino, alkylcarbonyloxy, alkoxycarbonyl, or phenylcarbonyloxy; and $R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl; and optionally a single stereoisomer or mixture of stereoisomers thereof and additionally optionally a pharmaceutically acceptable salt thereof.

In certain embodiments, the compound of Formula (I) is that wherein:

Ring A is phenyl, naphthyl, indanyl, tetrahydronaphthalinyl, dihydronaphthalinyl, pyridyl, benzothiazolyl, quinolinyl, isoquinolinyl, indolinyl, isoindolinyl, tetrahydroquinolinyl, or dihydroisoquinolinyl;

wherein:

when Ring A is phenyl, then Ring A is substituted with:
(i) one or two $R^{AA}$ groups, or (ii) 2 halo groups when L is other than O;

when Ring A is other than phenyl, then Ring A is substituted with one or two $R^{AB}$ groups;

each $R^{AA}$ is independently haloalkoxy, cycloalkyloxy, or phenoxy optionally substituted with one or two halo;

each $R^{AB}$ is independently halo, alkyl, alkoxy, or haloalkoxy;

$R^1$ is hydrogen, alkyl, cycloalkyl, or W; where W is alkyl substituted with alkylcarbonyloxy; and $R^2$ and $R^3$ are independently hydrogen or alkyl; wherein the alkyl is optionally substituted with alkylcarbonyloxy; and optionally a single stereoisomer or mixture of stereoisomers thereof and additionally optionally a pharmaceutically acceptable salt thereof.

In certain embodiments, the compound of Formula (I) is that wherein: ring B is not present;

Ring A is $C_{3-7}$ cycloalkyl, $C_{8-11}$ spirocycloalkyl, 5-6 membered heterocycloalkyl, pyrazolyl, imidazolyl, triazolyl, thiazolyl, phenyl, naphthyl, indanyl, tetrahydronaphthyl, dihydronaphthyl, pyridyl, indolyl, benzothiazolyl, quinolinyl, isoquinolinyl, indolinyl, isoindolinyl, tetrahydroquinolinyl, dihydroisoquinolinyl, tetrahydroisoquinolinyl, 2,3-dihydrobenzo[b][1,4]dioxinyl, or tetrahydromethanonaphthalenyl;

wherein:

when Ring A is phenyl, then Ring A is substituted with:
(i) one or two $R^{AA}$ groups,
(ii) 2 halo groups when L is other than O;
(iii) 2 halo groups when L is O, and $R^2$ and $R^3$ are not hydrogen or alkyl,
(iv) one halo group when L is $CH_2NR^L$, or
(v) one halo group and one group selected from the group consisting of haloalkoxy, (cycloalkyl)alkoxy, and (phenyl)alkoxy, when L is bond, O or S, wherein the phenyl is optionally substituted with halo;

when Ring A is other than phenyl, then
(i) Ring A is substituted with one or two $R^{AB}$ groups; or
(ii) Ring A is unsubstituted, wherein:
1) when Ring A is unsubstituted tetrahydroquinolinyl, then L is bond;
2) when Ring A is unsubstituted 2,3-dihydrobenzo[b][1,4]dioxinyl, then L is O;
3) when Ring A is unsubstituted tetrahydronaphthyl, then L is O, and $R^1$ is not hydrogen or ethyl; or
4) when Ring A is unsubstituted spirocycloalkyl, then L is O or S;

and optionally a single stereoisomer or mixture of stereoisomers thereof and additionally optionally a pharmaceutically acceptable salt thereof.

In certain embodiments, the compound of Formula (I) is that wherein:

Ring A is piperidinyl, phenyl, naphthyl, indanyl, tetrahydronaphthyl, 2,3-dihydrobenzo[b][1,4]dioxinyl, pyridyl, quinolinyl, isoquinolinyl, tetrahydroquinolinyl, tetrahydroisoquinolinyl, spiro[2.5]octane, spiro[4.5]decane, or spiro[5.5]undecane;

when Ring A is phenyl, then Ring A is substituted with:
(i) one or two $R^{AA}$ groups,
(ii) 2 halo groups when L is other than O;
(iii) 2 halo groups when L is O, and $R^2$ and $R^3$ are not hydrogen or alkyl,
(iv) one halo group when L is $CH_2NR^L$, or
(v) one halo group and one group selected from the group consisting of haloalkoxy and (cycloalkyl)alkoxy, when L is bond, O or S;

each $R^{AA}$ is independently haloalkyl, cycloalkyloxy, (cycloalkyl)alkoxy, or alkylcarbonylaminoalkoxy;

each $R^{AB}$ is independently halo, alkyl, haloalkyl, or haloalkoxy;

$R^1$ is hydrogen, alkyl or W; wherein W is alkyl substituted with alkylcarbonyloxy;

$R^2$ and $R^3$ are independently hydrogen or alkyl; wherein the alkyl is optionally substituted with cycloalkylcarbonyloxy or heterocycloalkylcarbonyloxy, wherein the heterocycloalkylcarbonyloxy optionally substituted with alkoxycarbonyl; and optionally a single stereoisomer or mixture of stereoisomers thereof and additionally optionally a pharmaceutically acceptable salt thereof.

In certain embodiments, the compound of Formula (I) is that wherein: ring B is present;

Ring A is $C_{3-7}$ cycloalkyl, $C_{8-11}$ spirocycloalkyl, 5-6 membered heterocycloalkyl, pyrazolyl, imidazolyl, triazolyl, thiazolyl, thienyl, phenyl, naphthyl, indanyl, tetrahydronaphthyl, dihydronaphthyl, pyridyl, indolyl, benzothiazolyl, quinolinyl, isoquinolinyl, indolinyl, isoindolinyl, tetrahydroquinolinyl, dihydroisoquinolinyl, tetrahydroisoquinolinyl, 2,3-dihydrobenzo[b][1,4]dioxinyl, or tetrahydro-methanonaphthalenyl; wherein Ring A is optionally substituted with one or two groups selected from halo, alkyl, alkoxy, and haloalkoxy;

Ring B is cycloalkyl, heterocycloalkyl, aryl, or heteroaryl; wherein each is optionally substituted with one or two $R^B$ groups;

each $R^B$ is independently halo; cyano; alkyl; haloalkyl; alkoxy; haloalkoxy; alkylcarbonyl; alkoxyalkoxy; aminocarbonyl; alkylcarbonylaminoalkoxy; cycloalkyl; (cycloalkyl)alkyl; cycloalkyloxy; (cycloalkyl)alkoxy; cycloalkylcarbonyl; cycloalkylcarbonyloxy; heterocycloalkyl optionally substituted with 1 or 2 alkyl, alkylcarbonyl or a halo; (5-6-membered heterocycloalkyl-one)alkyl; (heterocycloalkyl)alkyl; or heterocycloalkylcarbonyl; and optionally a single stereoisomer or mixture of stereoisomers thereof and additionally optionally a pharmaceutically acceptable salt thereof.

In certain embodiments, the compound of Formula (I) is that wherein: L is bond, $CH_2$, $CF_2$, O, $NR^L$, S, $CH_2$-Q, or Q-$CH_2$; wherein Q is O, $NR^L$, or S;

$R^L$ is hydrogen, $C_{1-4}$ alkyl, or benzyl, wherein the phenyl, as part of the benzyl group, is optionally substituted with haloalkoxy group;

Ring A is $C_{3-7}$ cycloalkyl, 5-6 membered heterocycloalkyl, phenyl, or naphthyl, wherein Ring A is optionally substituted with halo or haloalkoxy;

Ring B is cycloalkyl, heterocycloalkyl, phenyl, tetrahydronaphthyl, tetrahydroquinolinyl, quinolinyl, or, isoquinolinyl; wherein each Ring B is optionally substituted with one or two $R^B$ groups;

each $R^B$ is independently halo; cyano; haloalkyl; haloalkoxy; alkoxyalkoxy; aminocarbonyl; alkylcarbonylaminoalkoxy; cycloalkyl; (cycloalkyl)alkyl; heterocycloalkyl optionally substituted with 1 or 2 alkyl, alkylcarbonyl or halo; or (5-6-membered heterocycloalkyl-one)alkyl; and $R^1$ is hydrogen or W; wherein W is alkyl substituted with alkylcarbonyloxy, dialkylaminocarbonyloxy cycloalkylcarbonyloxy, or phenylcarbonyloxy; and optionally a single stereoisomer or mixture of stereoisomers thereof and additionally optionally a pharmaceutically acceptable salt thereof.

In certain embodiments, the compound of Formula (I) is that wherein L is bond, O, S, $NR^L$, $CH_2$-Q, or Q-$CH_2$; wherein Q is O, $NR^L$, or S, and optionally a single stereoisomer or mixture of stereoisomers thereof and additionally optionally a pharmaceutically acceptable salt thereof.

In certain embodiments, the compound of Formula (I) is that wherein L is O or S, and optionally a single stereoisomer or mixture of stereoisomers thereof and additionally optionally a pharmaceutically acceptable salt thereof.

In certain embodiments, the compound of Formula (I) is that wherein: ring C is selected from:

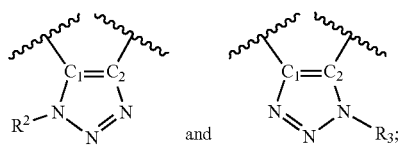

wherein the wavy lines ( ~~~ ) indicate the points of attachment of the $C_1$ carbon to the carbonyl of C(O)—$OR^1$, and the $C_2$ carbon to L; and Ring B is present.

In certain embodiments, the compound or Formula (I) is that wherein:

L is a bond, $CH_2$, $CF_2$, O, $NR^L$, S, S(=O), C(=O), $CH_2$-Q, or Q-$CH_2$; wherein Q is O, $NR^L$, or S;

$R^L$ is hydrogen, $C_{1-4}$ alkyl, $C_{3-6}$ cycloalkyl, phenyl, or benzyl; wherein the $C_{1-4}$ alkyl is optionally substituted with hydroxycarbonyl, alkoxycarbonyl, hydroxycarbonylalkyl, or alkylcarbonyloxy; and the phenyl group alone or as a part of the benzyl group is optionally substituted with one or two groups selected from halo and haloalkoxy;

Ring A is $C_{3-7}$ cycloalkyl, $C_{8-11}$ spirocycloalkyl, 5-6 membered heterocycloalkyl, pyrazolyl, imidazolyl, triazolyl, thiazolyl, thienyl, phenyl, naphthyl, indanyl, tetrahydronaphthyl, dihydronaphthyl, pyridyl, indolyl, benzothiazolyl, quinolinyl, isoquinolinyl, indolinyl, isoindolinyl, tetrahydroquinolinyl, dihydroisoquinolinyl, tetrahydroisoquinolinyl, 2,3-dihydrobenzo[b][1,4]dioxinyl, or tetrahydro-methanonaphthalenyl; wherein Ring A is optionally substituted with one or two groups selected from halo, alkyl, alkoxy, or haloalkoxy;

Ring B is cycloalkyl, heterocycloalkyl, aryl, or heteroaryl; wherein each is optionally substituted with one or two $R^B$ groups;

each $R^B$ is independently halo; cyano; alkyl; haloalkyl; alkoxy; haloalkoxy; alkylcarbonyl; alkoxyalkoxy; aminocarbonyl; alkylcarbonylaminoalkoxy; cycloalkyl; (cycloalkyl)alkyl; cycloalkyloxy; (cycloalkyl)alkoxy; cycloalkylcarbonyl; cycloalkylcarbonyloxy; heterocycloalkyl optionally substituted with 1 or 2 alkyl, alkylcarbonyl or halo; (5-6-membered heterocycloalkyl-one)alkyl; (heterocycloalkyl)alkyl; or heterocycloalkylcarbonyl;

$R^1$ is hydrogen, alkyl, cycloalkyl, heterocycloalkyl, or W; wherein W is alkyl substituted with amino, alkylamino, dialkylamino, alkylcarbonyloxy, alkoxycarbonyl, phenylcarbonyloxy, aminocarbonyloxy, alkylaminocarbonyloxy, dialkylaminocarbonyloxy, alkoxycarbonyloxy, cycloalkylcarbonyloxy, —N($R^{1A}$)C(O)$R^{1B}$, —N($R^{1A}$)C(O)O$R^{1B}$, or —N($R^{1A}$)C(O)N$R^{1B}R^{1C}$, wherein $R^{1A}$, $R^{1B}$, and $R^{1C}$ are each independently hydrogen or $C_{1-6}$ alkyl;

$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;

provided that when L is S or $CH_2$, and Ring A is phenyl, then Ring B cannot be halo-substituted phenyl; and optionally a single stereoisomer or mixture of stereoisomers thereof and additionally optionally a pharmaceutically acceptable salt thereof.

In certain embodiments, the compound of Formula (I) is that wherein:

L is bond, $CH_2$, $CF_2$, O, $NR^L$, S, $CH_2$-Q, or Q-$CH_2$; wherein Q is O, $NR^L$, or S;

$R^L$ is hydrogen, $C_{1-4}$ alkyl, or benzyl, wherein the phenyl in the benzyl group is optionally substituted with haloalkoxy group;

Ring A is $C_{3-7}$ cycloalkyl, 5-6 membered heterocycloalkyl, phenyl, or naphthyl, wherein Ring A is optionally substituted with halo or haloalkoxy;

Ring B is cycloalkyl, heterocycloalkyl, phenyl, tetrahydronaphthyl, tetrahydroquinolinyl, quinolinyl, or isoquinolinyl; wherein each Ring B is optionally substituted with one or two $R^B$ groups;

each $R^B$ is independently halo; cyano; haloalkyl; haloalkoxy; alkoxyalkoxy; aminocarbonyl; alkylcarbonylaminoalkoxy; cycloalkyl; (cycloalkyl)alkyl; heterocycloalkyl optionally substituted with 1 or 2 alkyl, alkylcarbonyl or halo; or (5-6-membered heterocycloalkyl-one)alkyl; and $R^1$ is hydrogen or W; wherein W is alkyl substituted with alkylcarbonyloxy, dialkylaminocarbonyloxy cycloalkylcarbonyloxy, or phenylcarbonyloxy;

provided that when L is S or $CH_2$, and Ring A is phenyl, then Ring B cannot be halo-substituted phenyl; and optionally a single stereoisomer or mixture of stereoisomers thereof and additionally optionally a pharmaceutically acceptable salt thereof.

In certain embodiments, the compound of Formula (I) is that wherein:

L is a bond, $CH_2$, $CF_2$, O, $NR^L$, S, C(=O), $CH_2$-Q, or Q-$CH_2$; wherein Q is O, $NR^L$, or S;

$R^L$ is hydrogen or $C_{1-4}$ alkyl optionally substituted with hydroxycarbonyl, alkoxycarbonyl, hydroxycarbonylalkyl, or alkylcarbonyloxy;

Ring A is $C_{5-7}$ cycloalkyl, 5-6 membered heterocycloalkyl, pyrazolyl, imidazolyl, triazolyl, thiazolyl, thiophenyl, phenyl, naphthyl, indanyl, tetrahydronaphthalinyl, dihydronaphthalinyl, pyridyl, indolyl, benzothiazolyl, quinolinyl, isoquinolinyl, indolinyl, isoindolinyl, tetrahydroquinolinyl, dihydroisoquinolinyl, dihydrobenzodioxinyl, or tetrahydro-methanonaphthalenyl; Ring B is present or not present; wherein:

when Ring B is present, then Ring A is optionally substituted with one or two halo, alkyl, alkoxy, or haloalkoxy;

when Ring B is not present and Ring A is phenyl, then Ring A is substituted with:
  (i) one or two $R^{AA}$ groups, or (ii) 2 halo groups when L is other than O;

when Ring B is not present and Ring A is other than phenyl, then Ring A is substituted with one or two $R^{AB}$ groups;

each $R^{AA}$ is independently alkyl, haloalkyl, haloalkoxy, cycloalkyloxy, (cycloalkyl)alkoxy, or phenoxy optionally substituted with one or two halo;

each $R^{AB}$ is independently halo, alkyl, hydroxy, alkoxy, haloalkyl, haloalkoxy, cycloalkyloxy, (cycloalkyl)alkoxy, or phenoxy optionally substituted with one or two halo;

Ring B, when present, is cycloalkyl, heterocycloalkyl, aryl, or heteroaryl; wherein each is optionally substituted with one or two $R^B$ groups;

each $R^B$ is independently halo, cyano, alkyl, haloalkyl, alkoxy, haloalkoxy, alkylcarbonyl, alkoxyalkoxy, alkylcarbonylaminoalkoxy, cycloalkyl, (cycloalkyl)alkyl, cycloalkyloxy, (cycloalkyl)alkoxy, cycloalkylcarbonyl, cycloalkylcarbonyloxy, heterocycloalkyl optionally substituted with alkyl or alkylcarbonyl, (5-6-membered heterocycloalkyl-one)alkyl, (heterocycloalkyl)alkyl, or heterocycloalkylcarbonyl;

$R^1$ is hydrogen, alkyl, cycloalkyl, heterocycloalkyl, or W; where W is alkyl substituted with amino, alkylamino, dialkylamino, alkylcarbonyloxy, alkoxycarbonyl, or phenylcarbonyloxy;

$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;

provided:
  i. when L is S and Ring A is phenyl, then Ring B cannot be halo-substituted phenyl;
  ii. when L is O, Ring A is phenyl, and Ring B is not present, then $R^{AA}$ cannot be alkyl or trifluoromethyl;
  iii. when L is O, Ring A is phenyl, Ring B is not present, and $R^1$ is ethyl, then $R^{AA}$ cannot be trifluoromethoxy;
  iv. when L is NH, Ring A is pyridyl, indolyl, or indolinyl, and Ring B is not present, then $R^{AB}$ cannot be alkyl; and optionally a single stereoisomer or mixture of stereoisomers thereof and additionally optionally a pharmaceutically acceptable salt thereof.

In certain embodiments, the compound of Formula (I) is that wherein:

L is a bond, $CH_2$, $CF_2$, O, $NR^L$, S, C(=O), $CH_2$-Q, or Q-$CH_2$; wherein Q is O, $NR^L$, or S;

$R^L$ is H or $C_{1-4}$ alkyl optionally substituted with hydroxycarbonylalkyl;

Ring A is 5-6 membered heterocycloalkyl, imidazolyl, triazolyl, thiazolyl, phenyl, naphthyl, indanyl, tetrahydronaphthalinyl, dihydronaphthalinyl, pyridyl, benzothiazolyl, quinolinyl, isoquinolinyl, indolinyl, isoindolinyl, tetrahydroquinolinyl, or dihydroisoquinolinyl;

wherein:
  when Ring B is present, then Ring A is optionally substituted with one or two halo, alkyl, alkoxy, or haloalkoxy;
  when Ring B is not present and Ring A is phenyl, then Ring A is substituted with:
    (i) one or two $R^{AA}$ groups, or (ii) 2 halo groups when L is other than O;
  when Ring B is not present and Ring A is other than phenyl, then Ring A is substituted with one or two $R^{AB}$ groups;

each $R^{AA}$ is independently haloalkoxy, cycloalkyloxy, (cycloalkyl)alkoxy, or phenoxy substituted with one or two halo;

each $R^{AB}$ is independently halo, alkyl, alkoxy, haloalkoxy, or phenoxy optionally substituted with one or two halo;

Ring B, when present, is heterocycloalkyl, aryl, or heteroaryl; wherein each is optionally substituted with one or two $R^B$ groups;

each $R^B$ is independently halo, alkyl, haloalkyl, alkoxy, haloalkoxy, cycloalkyloxy, heterocycloalkyl optionally substituted with alkyl or alkylcarbonyl, (heterocycloalkyl)alkyl, or heterocycloalkylcarbonyl;

$R^1$ is hydrogen, alkyl, cycloalkyl, heterocycloalkyl, or W; where W is alkyl substituted with amino, alkylamino, dialkylamino, alkylcarbonyloxy, alkoxycarbonyl, or phenylcarbonyloxy;

$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;

provided:
i. when L is S and Ring A is phenyl, then Ring B cannot be halo-substituted phenyl;
ii. when L is O, Ring A is phenyl, and Ring B is not present, then $R^{AA}$ cannot be alkyl or trifluoromethyl;
iii. when L is O, Ring A is phenyl, Ring B is not present, and $R^1$ is ethyl, then $R^{AA}$ cannot be trifluoromethoxy;
iv. when L is NH, Ring A is pyridyl, indolyl, or indolinyl, and Ring B is not present, then $R^{AB}$ cannot be alkyl; and optionally a single stereoisomer or mixture of stereoisomers thereof and additionally optionally a pharmaceutically acceptable salt thereof.

In certain embodiments, the compound of Formula (I) is that wherein:
L is a bond, $CH_2$, $CF_2$, O, $NR^L$, S, C(=O), $CH_2$-Q, or Q-$CH_2$; wherein Q is O, $NR^L$, or S;
$R^L$ is H or $C_{1-4}$ alkyl optionally substituted with hydroxycarbonyl, alkoxycarbonyl, hydroxycarbonylalkyl, or alkylcarbonyloxy;
Ring A is heterocycloalkyl, aryl, or heteroaryl; wherein each is optionally substituted with one halo or alkyl;
Ring B, when present, is cycloalkyl, heterocycloalkyl, aryl, or heteroaryl; wherein each is optionally substituted with one or two $R^B$ groups;
each $R^B$ is independently cyano, alkyl, haloalkyl, alkoxy, haloalkoxy, alkylcarbonyl, alkoxyalkoxy, alkylcarbonylaminoalkoxy, cycloalkyl, (cycloalkyl)alkyl, cycloalkyloxy, (cycloalkyl)alkoxy, cycloalkylcarbonyl, cycloalkylcarbonyloxy, heterocycloalkyl optionally substituted with alkyl or alkylcarbonyl, (5-6-membered heterocycloalkylone)alkyl, (heterocycloalkyl)alkyl, or heterocycloalkylcarbonyl;
$R^1$ is hydrogen, alkyl, cycloalkyl, heterocycloalkyl, or W; where W is alkyl substituted with amino, alkylamino, dialkylamino, alkylcarbonyloxy, alkoxycarbonyl, or phenylcarbonyloxy;
$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;
provided that when L is S and Ring A is phenyl, then Ring B is not halo-substituted phenyl; and
optionally a single stereoisomer or mixture of stereoisomers thereof and additionally optionally a pharmaceutically acceptable salt thereof.

In certain embodiments, the compound of Formula (I) is that wherein:
L is a bond, O, $NR^L$, S, C(=O), $CH_2$-Q, or Q-$CH_2$; wherein Q is O, $NR^L$, or S;
$R^L$ is H or $C_{1-4}$ alkyl optionally substituted with hydroxycarbonylalkyl;
Ring A is heterocycloalkyl, phenyl, or heteroaryl; wherein each is optionally substituted with one halo or alkyl;
Ring B, when present, is heterocycloalkyl, phenyl, or heteroaryl; wherein each is optionally substituted with one or two $R^B$ groups;
each $R^B$ is independently halo, alkyl, alkoxy, haloalkoxy, cycloalkyloxy, heterocycloalkyl, (heterocycloalkyl)alkyl, or heterocycloalkylcarbonyl;
$R^1$ is hydrogen, alkyl, cycloalkyl, heterocycloalkyl, or W; where W is alkyl substituted with amino, alkylamino, dialkylamino, or alkylcarbonyloxy;

$R^2$ and $R^3$ are each hydrogen or alkyl optionally substituted with alkylcarbonyloxy; provided that when L is S and Ring A is phenyl, then Ring B is not halo-substituted phenyl; and
optionally a single stereoisomer or mixture of stereoisomers thereof and additionally optionally a pharmaceutically acceptable salt thereof.

In certain embodiments, the compound of Formula (I) is that wherein:
L is a bond, O, $NR^L$, S, C(=O), $CH_2$-Q, or Q-$CH_2$; wherein Q is O, $NR^L$, or S;
$R^L$ is H or $C_{1-4}$ alkyl;
Ring A is phenyl or heteroaryl; wherein each is optionally substituted with one halo or alkyl;
Ring B, when present, is phenyl or heteroaryl; wherein each is optionally substituted with one or two $R^B$ groups;
each $R^B$ is independently halo, alkyl, haloalkyl, alkoxy, haloalkoxy, cycloalkyloxy, or heterocycloalkyl optionally substituted with alkyl or alkylcarbonyl;
$R^1$ is hydrogen, alkyl, cycloalkyl, heterocycloalkyl, or W; where W is alkyl substituted with amino, alkylamino, dialkylamino, or alkylcarbonyloxy;
$R^2$ and $R^3$ are independently hydrogen or alkyl;
provided that when L is S and Ring A is phenyl, then Ring B is not halo-substituted phenyl; and
optionally a single stereoisomer or mixture of stereoisomers thereof and additionally optionally a pharmaceutically acceptable salt thereof.

In certain embodiments, the compound of Formula (I) is according to Formula (II):

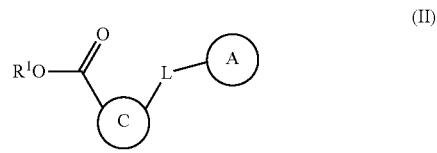

(II)

wherein:
ring C is selected from:

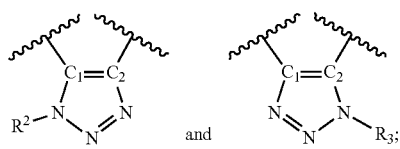

and wherein the wavy lines ( ∼∼∼ ) indicate the points of attachment of the $C_1$ carbon to the carbonyl of C(O)—$OR^1$, and the $C_2$ carbon to L.

In certain embodiments, the compound of Formula (II) is that wherein:
L is a bond, $CH_2$, $CF_2$, O, $NR^L$, S, S(=O), C(=O), $CH_2$-Q, or Q-$CH_2$; wherein Q is O, $NR^L$, or S;
$R^L$ is H, $C_{1-4}$ alkyl, $C_{3-6}$ cycloalkyl, phenyl, or benzyl; wherein the $C_{1-4}$ alkyl is optionally substituted with hydroxycarbonyl, alkoxycarbonyl, hydroxycarbonylalkyl, or alkylcarbonyloxy; and the phenyl group alone or as a part of the benzyl group is optionally substituted with one or two groups selected from halo and haloalkoxy;
Ring A is cycloalkyl, spirocycloalkyl, heterocycloalkyl, aryl, or heteroaryl; wherein each is optionally substituted with one halo or alkyl;

$R^1$ is hydrogen, alkyl, cycloalkyl, heterocycloalkyl, or W; wherein W is alkyl substituted with amino, alkylamino, dialkylamino, alkylcarbonyloxy, alkoxycarbonyl, phenylcarbonyloxy, aminocarbonyloxy, alkylaminocarbonyloxy, dialkylaminocarbonyloxy, alkoxycarbonyloxy, cycloalkylcarbonyloxy, —N($R^{1A}$)C(O)$R^{1B}$, —N($R^{1A}$)C(O)O$R^{1B}$, or —N($R^{1A}$)C(O)N$R^{1B}R^{1C}$; wherein $R^{1A}$, $R^{1B}$, and $R^{1C}$ are each independently hydrogen or $C_{1-6}$ alkyl;

$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;

provided that when L is S or $CH_2$, and Ring A is phenyl, then Ring B is not halo-substituted phenyl; and optionally a single stereoisomer or mixture of stereoisomers thereof and additionally optionally a pharmaceutically acceptable salt thereof.

In certain embodiments, the compound of Formula (II) is that wherein:

L is a bond, $CH_2$, $CF_2$, O, $NR^L$, S, S(=O), C(=O), $CH_2$-Q, or Q-$CH_2$; wherein Q is O, $NR^L$, or S;

$R^L$ is hydrogen, $C_{1-4}$ alkyl, $C_{3-6}$ cycloalkyl, phenyl, or benzyl; wherein the $C_{1-4}$ alkyl is optionally substituted with hydroxycarbonyl, alkoxycarbonyl, hydroxycarbonylalkyl, or alkylcarbonyloxy; and the phenyl group alone or as a part of the benzyl group is optionally substituted with one or two groups selected from halo and haloalkoxy;

Ring A is $C_{3-7}$ cycloalkyl, $C_{8-11}$ spirocycloalkyl, 5-6 membered heterocycloalkyl, pyrazolyl, imidazolyl, triazolyl, thiazolyl, phenyl, naphthyl, indanyl, tetrahydronaphthyl, dihydronaphthyl, pyridyl, indolyl, benzothiazolyl, quinolinyl, isoquinolinyl, indolinyl, isoindolinyl, tetrahydroquinolinyl, dihydroisoquinolinyl, tetrahydroisoquinolinyl, 2,3-dihydrobenzo[b][1,4]dioxinyl, or tetrahydromethanonaphthalenyl;

wherein:
when Ring A is phenyl, then Ring A is substituted with:
(i) one or two $R^{AA}$ groups,
(ii) 2 halo groups when L is other than O,
(iii) 2 halo groups when L is O, and $R^2$ and $R^3$ are not hydrogen or alkyl,
(iv) one halo group when L is $CH_2NR^L$, or
(v) one halo group and one group selected from the group consisting of haloalkoxy, (cycloalkyl)alkoxy, and (phenyl)alkoxy, when L is bond, O or S, wherein the phenyl is optionally substituted with halo;

when Ring A is other than phenyl, then
(i) Ring A is substituted with one or two $R^{AB}$ groups; or
(ii) Ring A is unsubstituted, wherein:
1) when Ring A is unsubstituted tetrahydroquinolinyl, then L is bond;
2) when Ring A is unsubstituted 2,3-dihydrobenzo[b][1,4]dioxinyl, then L is O;
3) when Ring A is unsubstituted tetrahydronaphthyl, then L is O, and $R^1$ is not hydrogen or ethyl, or
4) when Ring A is unsubstituted spirocycloalkyl, then L is O or S;

each $R^{AA}$ is independently alkyl, haloalkyl, haloalkoxy, cycloalkyloxy, (cycloalkyl)alkoxy, phenoxy optionally substituted with one or two halo, or alkylcarbonylaminoalkoxy;

each $R^{AB}$ is independently halo, alkyl, hydroxy, alkoxy, haloalkyl, haloalkoxy, cycloalkyloxy, (cycloalkyl)alkoxy, or phenoxy optionally substituted with one or two halo;

$R^1$ is hydrogen, alkyl, cycloalkyl, heterocycloalkyl, or W; wherein W is alkyl substituted with amino, alkylamino, dialkylamino, alkylcarbonyloxy, alkoxycarbonyl, phenylcarbonyloxy, aminocarbonyloxy, alkylaminocarbonyloxy, dialkylaminocarbonyloxy, alkoxycarbonyloxy, cycloalkylcarbonyloxy, —N($R^{1A}$)C(O)$R^{1B}$, —N($R^{1A}$)C(O)O$R^{1B}$, or —N($R^{1A}$)C(O)N$R^{1B}R^{1C}$; wherein $R^{1A}$, R', and $R^{1C}$ are each independently hydrogen or $C_{1-6}$ alkyl;

$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;

provided:
i. when L is O and Ring A is phenyl, then $R^{AA}$ cannot be alkyl;
ii. when L is O, Ring A is phenyl, and $R^1$ is ethyl, then $R^{AB}$ cannot be trifluoromethoxy;
ii. when L is O, Ring A is phenyl substituted with 1 $R^{AA}$, then $R^{AA}$ cannot be meta-substituted trifluoromethyl;
iv. when L is bond, Ring A is other than phenyl, and $R^1$ is H, then $R^{AB}$ cannot be methyl, and
v. when L is NH, Ring A is pyridyl, indolyl, or indolinyl, then $R^{AB}$ cannot be alkyl; and optionally a single stereoisomer or mixture of stereoisomers thereof and additionally optionally a pharmaceutically acceptable salt thereof.

In certain embodiments, the compound of Formula (II) is that wherein:

L is a bond, $CH_2$, $CF_2$, O, $NR^L$, S, S(=O), C(=O), $CH_2$-Q, or Q-$CH_2$; wherein Q is O, $NR^L$, or S;

$R^L$ is H, $C_{1-4}$ alkyl, $C_{3-6}$ cycloalkyl, phenyl, or benzyl; wherein the $C_{1-4}$ alkyl is optionally substituted with hydroxycarbonyl, alkoxycarbonyl, hydroxycarbonylalkyl, or alkylcarbonyloxy; and the phenyl group alone or as a part of the benzyl group is optionally substituted with one or two groups selected from halo and haloalkoxy;

Ring A is $C_{3-7}$ cycloalkyl, $C_{8-11}$ spirocycloalkyl, tetrahydronaphthyl, dihydronaphthyl, benzothiazolyl, isoquinolinyl, tetrahydroquinolinyl, dihydroisoquinolinyl, tetrahydroisoquinolinyl, 2,3-dihydrobenzo[b][1,4]dioxinyl, or tetrahydro-methanonaphthalenyl; provided that when L is $NR^L$ or O, then Ring A cannot be tetrahydronaphthyl;

$R^1$ is hydrogen, alkyl, cycloalkyl, heterocycloalkyl, or W; wherein W is alkyl substituted with amino, alkylamino, dialkylamino, alkylcarbonyloxy, alkoxycarbonyl, phenylcarbonyloxy, aminocarbonyloxy, alkylaminocarbonyloxy, dialkylaminocarbonyloxy, alkoxycarbonyloxy, cycloalkylcarbonyloxy, —N($R^{1A}$)C(O)$R^{1B}$, —N($R^{1A}$)C(O)O$R^{1B}$, or —N($R^{1A}$)C(O)N$R^{1B}R^{1C}$; wherein $R^{1A}$, $R^{1B}$, and $R^{1C}$ are each independently hydrogen or $C_{1-6}$ alkyl;

$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl; and optionally a single stereoisomer or mixture of stereoisomers thereof and additionally optionally a pharmaceutically acceptable salt thereof.

In certain embodiments, the compound of Formula (II) is that wherein:

L is a bond, $CH_2$, O, NH, S, S(=O), C(=O), $CH_2$-Q, or Q-$CH_2$; wherein Q is O, NH, or S;

Ring A is piperidinyl, phenyl, naphthyl, indanyl, tetrahydronaphthyl, 2,3-dihydrobenzo[b][1,4]dioxinyl, pyridyl, quinolinyl, isoquinolinyl, tetrahydroquinolinyl, tetrahydroisoquinolinyl, spiro[2.5]octane, spiro[4.5]decane, or spiro[5.5]undecane;

wherein:
when Ring A is phenyl, then Ring A is substituted with:
(i) one or two $R^{AA}$ groups,
(ii) 2 halo groups when L is other than O;
(iii) 2 halo groups when L is O, and $R^2$ and $R^3$ are not hydrogen or alkyl,
(iv) one halo group when L is $CH_2NR^L$, or
(v) one halo group and one group selected from the group consisting of haloalkoxy and (cycloalkyl)alkoxy, when L is bond, O or S;

when Ring A is other than phenyl, then
(i) Ring A is substituted with one or two $R^{AB}$ groups; or
(ii) Ring A is unsubstituted, wherein:
1) when Ring A is unsubstituted tetrahydroquinolinyl, then L is bond;
2) when Ring A is unsubstituted 2,3-dihydrobenzo[b][1,4]dioxinyl, then L is O;
3) when Ring A is unsubstituted tetrahydronaphthyl, then L is O, and $R^1$ is not hydrogen or ethyl, or
4) when Ring A is unsubstituted spirocycloalkyl, then L is O or S;

each $R^{AA}$ is independently haloalkyl, cycloalkyloxy, (cycloalkyl)alkoxy, or alkylcarbonylaminoalkoxy;
each $R^{AB}$ is independently halo, alkyl, haloalkyl, or haloalkoxy;
$R^1$ is hydrogen, alkyl, or W; wherein W is alkyl substituted with alkylcarbonyloxy;
$R^2$ and $R^3$ are independently hydrogen or alkyl; wherein the alkyl is optionally substituted with cycloalkylcarbonyloxy or heterocycloalkylcarbonyloxy, wherein the heterocycloalkylcarbonyloxy optionally substituted with alkoxycarbonyl;

provided:
i. when L is O, Ring A is phenyl, and $R^1$ is ethyl, then $R^{AB}$ cannot be trifluoromethoxy;
ii. when L is O, Ring A is phenyl substituted with 1 $R^{AA}$, then $R^{AA}$ cannot be meta-substituted trifluoromethyl;
iii. when L is O, Ring A is phenyl substituted with 1 $R^{AA}$, then $R^{AA}$ cannot be meta-substituted trifluoromethyl;
iv. when L is bond, Ring A is other than phenyl, and $R^1$ is H, then $R^{AB}$ cannot be methyl, and
v. when L is NH, Ring A is pyridyl, then R cannot be alkyl; and optionally a single stereoisomer or mixture of stereoisomers thereof and additionally optionally a pharmaceutically acceptable salt thereof.

In certain embodiments, the compound of Formula (I) is according to Formula (II):

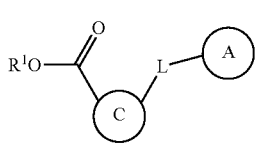

(II)

wherein:
ring C is selected from:

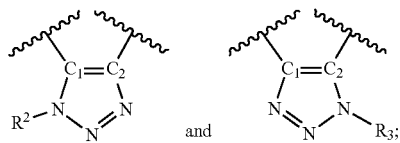

and wherein the wavy lines ( ~~~ ) indicate the points of attachment of the $C_1$ carbon to the carbonyl of C(O)—$OR^1$, and the $C_2$ carbon to L.

In certain embodiments, the compound of Formula (II) is that wherein:
L is a bond, $CH_2$, $CF_2$, O, $NR^L$, S, C(=O), $CH_2$-Q, or Q-$CH_2$; wherein Q is O, $NR^L$, or S;
$R^L$ is H or $C_{1-4}$ alkyl optionally substituted with hydroxycarbonyl, alkoxycarbonyl, hydroxycarbonylalkyl, or alkylcarbonyloxy;
Ring A is heterocycloalkyl, aryl, or heteroaryl; wherein each is optionally substituted with one halo or alkyl;
Ring B, when present, is cycloalkyl, heterocycloalkyl, aryl, or heteroaryl; wherein each is optionally substituted with one or two $R^B$ groups;
each $R^B$ is independently halo, cyano, alkyl, haloalkyl, alkoxy, haloalkoxy, alkylcarbonyl, alkoxyalkoxy, alkylcarbonylaminoalkoxy, cycloalkyl, (cycloalkyl)alkyl, cycloalkyloxy, (cycloalkyl)alkoxy, cycloalkylcarbonyl, cycloalkylcarbonyloxy, heterocycloalkyl optionally substituted with alkyl or alkylcarbonyl, (5-6-membered heterocycloalkyl-one)alkyl, (heterocycloalkyl)alkyl, or heterocycloalkylcarbonyl;
$R^1$ is hydrogen, alkyl, cycloalkyl, heterocycloalkyl, or W; where W is alkyl substituted with amino, alkylamino, dialkylamino, alkylcarbonyloxy, alkoxycarbonyl, or phenylcarbonyloxy;
$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;
provided that when L is S and Ring A is phenyl, then Ring B is not halo-substituted phenyl; and
optionally a single stereoisomer or mixture of stereoisomers thereof and additionally optionally a pharmaceutically acceptable salt thereof.

In certain embodiments, the compound of Formula (II) is that wherein:
L is a bond, $CH_2$, $CF_2$, O, $NR^L$, S, C(=O), $CH_2$-Q, or Q-$CH_2$; wherein Q is O, $NR^L$, or S;
$R^L$ is hydrogen or $C_{1-4}$ alkyl optionally substituted with hydroxycarbonyl, alkoxycarbonyl, hydroxycarbonylalkyl, or alkylcarbonyloxy;
Ring A is $C_{5-7}$ cycloalkyl, 5-6 membered heterocycloalkyl, pyrazolyl, imidazolyl, triazolyl, thiazolyl, phenyl, naphthyl, indanyl, tetrahydronaphthalinyl, dihydronaphthalinyl, pyridyl, indolyl, benzothiazolyl, quinolinyl, isoquinolinyl, indolinyl, isoindolinyl, tetrahydroquinolinyl, dihydroisoquinolinyl, or tetrahydro-methanonaphthalenyl;
wherein:
when Ring A is phenyl, then Ring A is substituted with: (i) one or two $R^{AA}$ groups, or (ii) 2 halo groups when L is other than O;
when Ring A is other than phenyl, then Ring A is substituted with one or two $R^{AB}$ groups;

each $R^{AA}$ is independently alkyl, haloalkyl, haloalkoxy, cycloalkyloxy, (cycloalkyl)alkoxy, or phenoxy optionally substituted with one or two halo;

each $R^{AB}$ is independently halo, alkyl, hydroxy, alkoxy, haloalkyl, haloalkoxy, cycloalkyloxy, (cycloalkyl)alkoxy, or phenoxy optionally substituted with one or two halo;

$R^1$ is hydrogen, alkyl, cycloalkyl, heterocycloalkyl, or W; where W is alkyl substituted with amino, alkylamino, dialkylamino, alkylcarbonyloxy, alkoxycarbonyl, or phenylcarbonyloxy;

$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;

provided:
  i. when L is O and Ring A is phenyl, then $R^{AA}$ cannot be alkyl or trifluoromethyl;
  ii. when L is O, Ring A is phenyl, and $R^1$ is ethyl, then $R^{AB}$ cannot be trifluoromethoxy;
  iii. when L is NH, Ring A is pyridyl, indolyl, or indolinyl, then $R^{AB}$ cannot be alkyl; and optionally a single stereoisomer or mixture of stereoisomers thereof and additionally optionally a pharmaceutically acceptable salt thereof.

In certain embodiments, the compound of Formula (II) is that wherein:

L is a bond, $CH_2$, $CF_2$, O, $NR^L$, S, C(=O), $CH_2$-Q, or Q-$CH_2$; wherein Q is O, $NR^L$, or S;

$R^L$ is H or $C_{1-4}$ alkyl optionally substituted with hydroxycarbonyl, alkoxycarbonyl, hydroxycarbonylalkyl, or alkylcarbonyloxy;

Ring A is $C_{5-7}$ cycloalkyl, tetrahydronaphthalinyl, dihydronaphthalinyl, benzothiazolyl, isoquinolinyl, tetrahydroquinolinyl, dihydroisoquinolinyl, or tetrahydro-methanonaphthalenyl; provided that when L is $NR^L$ or O, then Ring A cannot be tetrahydronaphthalinyl;

$R^1$ is hydrogen, alkyl, cycloalkyl, heterocycloalkyl, or W; where W is alkyl substituted with amino, alkylamino, dialkylamino, alkylcarbonyloxy, alkoxycarbonyl, or phenylcarbonyloxy;

$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl; and optionally a single stereoisomer or mixture of stereoisomers thereof and additionally optionally a pharmaceutically acceptable salt thereof.

In certain embodiments, the compound of Formula (II) is that wherein:

L is a bond, $CH_2$, O, NH, S, C(=O), $CH_2$-Q, or Q-$CH_2$; wherein Q is O, NH, or S;

Ring A is phenyl, naphthyl, indanyl, tetrahydronaphthalinyl, dihydronaphthalinyl, pyridyl, benzothiazolyl, quinolinyl, isoquinolinyl, indolinyl, isoindolinyl, tetrahydroquinolinyl, or dihydroisoquinolinyl;

wherein:
  when Ring A is phenyl, then Ring A is substituted with:
    (i) one or two $R^{AA}$ groups, or (ii) 2 halo groups when L is other than O;
  when Ring A is other than phenyl, then Ring A is substituted with one or two $R^{AB}$ groups;

each $R^{AA}$ is independently haloalkoxy, cycloalkyloxy, or phenoxy optionally substituted with one or two halo;

each R is independently halo, alkyl, alkoxy, or haloalkoxy;

$R^1$ is hydrogen, alkyl, cycloalkyl, or W; where W is alkyl substituted with alkylcarbonyloxy;

$R^2$ and $R^3$ are independently hydrogen or alkyl;

wherein the alkyl is optionally substituted with alkylcarbonyloxy;

provided:
  i. when L is O, Ring A is phenyl, and $R^1$ is ethyl, then R cannot be trifluoromethoxy;
  ii. when L is NH, Ring A is pyridyl or indolinyl, then $R^{AB}$ cannot be alkyl; and optionally a single stereoisomer or mixture of stereoisomers thereof and additionally optionally a pharmaceutically acceptable salt thereof.

In certain embodiments, the compound of Formula (I) is according to Formula (III):

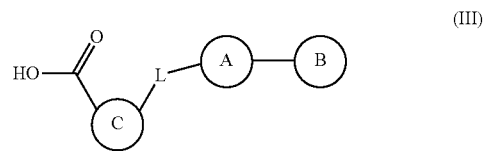

(III)

wherein:
ring C is selected from:

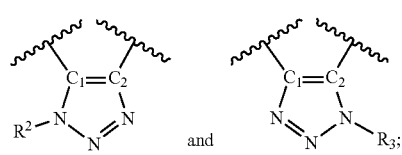

and wherein the wavy lines ( ～～～ ) indicate the points of attachment of the $C_1$ carbon to the carbonyl of C(O)—$OR^1$, and the $C_2$ carbon to L.

In certain embodiments, the compound of Formula (III) is that wherein:

L is a bond, $CH_2$, $CF_2$, O, $NR^L$, S, S(=O), C(=O), $CH_2$-Q, or Q-$CH_2$; wherein Q is O, $NR^L$, or S;

$R^L$ is hydrogen, $C_{1-4}$ alkyl, $C_{3-6}$ cycloalkyl, phenyl, or benzyl; wherein the $C_{1-4}$ alkyl is optionally substituted with hydroxycarbonyl, alkoxycarbonyl, hydroxycarbonylalkyl, or alkylcarbonyloxy; and the phenyl group alone or as a part of the benzyl group is optionally substituted with one or two groups selected from halo and haloalkoxy;

Ring A is $C_{3-7}$ cycloalkyl, $C_{8-11}$ spirocycloalkyl, 5-6 membered heterocycloalkyl, pyrazolyl, imidazolyl, triazolyl, thiazolyl, phenyl, naphthyl, indanyl, tetrahydronaphthyl, dihydronaphthyl, pyridyl, indolyl, benzothiazolyl, quinolinyl, isoquinolinyl, indolinyl, isoindolinyl, tetrahydroquinolinyl, dihydroisoquinolinyl, tetrahydroisoquinolinyl, 2,3-dihydrobenzo[b][1,4]dioxinyl, or tetrahydromethanonaphthalenyl;

Ring B is present or not present; wherein:
  when Ring B is present, then Ring A is optionally substituted with one or two groups selected from halo, alkyl, alkoxy, and haloalkoxy;
  when Ring B is not present and Ring A is phenyl, then Ring A is substituted with:
    (i) one or two $R^{AA}$ groups,
    (ii) 2 halo groups when L is other than O, (iii) 2 halo groups when L is O, and $R^2$ and $R^3$ are not hydrogen or alkyl,
(iv) one halo group when L is $CH_2NR^L$, or (v) one halo group and one group selected from the group consisting of haloalkoxy, (cycloalkyl)alkoxy, and (phenyl)alkoxy, when L is bond, O or S, wherein the phenyl is optionally substituted with halo;
when Ring B is not present and Ring A is other than phenyl, then
(i) Ring A is substituted with one or two $R^{AB}$ groups or
(ii) Ring A is unsubstituted, wherein:
  1) when Ring A is unsubstituted tetrahydroquinolinyl, then L is bond;
  2) when Ring A is unsubstituted 2,3-dihydrobenzo[b][1,4]dioxinyl, then L is O;
  3) when Ring A is unsubstituted tetrahydronaphthyl, then L is not O; or
  4) when Ring A is unsubstituted spirocycloalkyl, then L is O or S;
each $R^{AA}$ is independently alkyl; haloalkyl; haloalkoxy; cycloalkyloxy; (cycloalkyl)alkoxy; phenoxy optionally substituted with one or two halo; or alkylcarbonylaminoalkoxy;
each $R^{AB}$ is independently halo; alkyl; hydroxy; alkoxy; haloalkyl; haloalkoxy; cycloalkyloxy; (cycloalkyl)alkoxy; or phenoxy optionally substituted with one or two halo;
Ring B, when present, is cycloalkyl, heterocycloalkyl, aryl, or heteroaryl; wherein each is optionally substituted with one or two $R^B$ groups;
each $R^B$ is independently halo; cyano; alkyl; haloalkyl; alkoxy; haloalkoxy; alkylcarbonyl; alkoxyalkyl; aminocarbonyl; alkylcarbonylaminoalkyl; cycloalkyl; (cycloalkyl)alkyl; cycloalkyloxy; (cycloalkyl)alkoxy; cycloalkylcarbonyl; cycloalkylcarbonyloxy; heterocycloalkyl optionally substituted with 1 or 2 alkyl, alkylcarbonyl halo, (5-6-membered heterocycloalkyl-one)alkyl, (heterocycloalkyl)alkyl; or heterocycloalkylcarbonyl;
$R^2$ and $R^3$ are independently hydrogen, alkyl, phenyl, or benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;
provided:
  i. when L is S or $CH_2$, and Ring A is phenyl, then Ring B cannot be halo-substituted phenyl;
  ii. when L is O, Ring A is phenyl, and Ring B is not present, then $R^{AA}$ cannot be alkyl;
  iii. when L is O, Ring A is phenyl substituted with 1 $R^{AA}$, and Ring B is not present, then $R^{AA}$ cannot be meta-substituted trifluoromethyl;
  iv. when L is bond, Ring A is other than phenyl and Ring B is not present, then $R^{AB}$ cannot be methyl, and
  v. when L is NH, Ring A is pyridyl, indolyl, or indolinyl, and Ring B is not present, then $R^{AB}$ cannot be alkyl;
optionally a single stereoisomer or mixture of stereoisomers thereof and additionally optionally a pharmaceutically acceptable salt thereof.
In certain embodiments, the compound of Formula (III) is that wherein:
L is a bond, $CH_2$, $CF_2$, O, $NR^L$, S, S(=O), C(=O), $CH_2$-Q, or Q-$CH_2$; wherein Q is O, $NR^L$, or S;
$R^L$ is hydrogen, $C_{1-4}$ alkyl, or benzyl; and the phenyl in the benzyl group is optionally substituted with one or two groups selected from halo and haloalkoxy;

Ring A is $C_{5-6}$ cycloalkyl, $C_{8-11}$ spirocycloalkyl, 5-6 membered heterocycloalkyl, phenyl, naphthyl, indanyl, tetrahydronaphthyl, 2,3-dihydrobenzo[b][1,4]dioxinyl, pyridyl, quinolinyl, isoquinolinyl, tetrahydroquinolinyl, or tetrahydroisoquinolinyl;
Ring B is present or not present; wherein:
when Ring B is present, then Ring A is optionally substituted with one or two groups selected from halo and haloalkoxy;
when Ring B is not present and Ring A is phenyl, then Ring A is substituted with:
  (i) one or two $R^{AA}$ groups,
  (ii) 2 halo groups when L is other than O,
  (iii) 2 halo groups when L is O, and $R^2$ and $R^3$ are not hydrogen or alkyl,
  (iv) one halo group when L is $CH_2NR^L$, or
  (v) one halo group and one group selected from the group consisting of haloalkoxy, (cycloalkyl)alkoxy, and (phenyl)alkoxy, when L is bond, O or S, wherein the phenyl is optionally substituted with halo;
when Ring B is not present and Ring A is other than phenyl, then
  (i) Ring A is substituted with one or two $R^{AB}$ groups; or
  (ii) Ring A is unsubstituted, wherein:
    1) when Ring A is unsubstituted tetrahydroquinolinyl, then L is bond;
    2) when Ring A is unsubstituted 2,3-dihydrobenzo[b][1,4]dioxinyl, then L is O;
    3) when Ring A is unsubstituted tetrahydronaphthyl, then L is O, and $R^1$ is not hydrogen or ethyl; or
  4) when Ring A is unsubstituted spirocycloalkyl, then L is O or S;
each $R^{AA}$ is independently haloalkyl; cycloalkyloxy; (cycloalkyl)alkoxy; alkylcarbonylaminoalkoxy; or phenoxy optionally substituted with one or two halo;
each $R^{AB}$ is independently halo, alkyl, haloalkyl, or haloalkoxy;
Ring B, when present, cycloalkyl, heterocycloalkyl, phenyl, tetrahydronaphthyl, tetrahydroquinolinyl, quinolinyl, or isoquinolinyl; wherein each Ring B is optionally substituted with one or two $R^B$ groups;
each $R^B$ is independently halo; cyano; alkyl; haloalkyl; haloalkoxy; alkoxyalkoxy;
aminocarbonyl; alkylcarbonylaminoalkoxy; cycloalkyl; (cycloalkyl)alkoxy; heterocycloalkyl optionally substituted with 1 or 2 alkyl, alkylcarbonyl or halo; or (5-6-membered heterocycloalkyl-one)alkyl;
$R^2$ and $R^3$ are independently hydrogen or alkyl; wherein the alkyl is optionally substituted with cycloalkylcarbonyloxy or heterocycloalkylcarbonyloxy, wherein the heterocycloalkylcarbonyloxy optionally substituted with alkoxycarbonyl;
provided:
  (i) when L is S or $CH_2$, and Ring A is phenyl, then Ring B cannot be halo substituted phenyl;
  (ii) when L is O, Ring A is phenyl, and Ring B is not present, then $R^{AA}$ cannot be alkyl;
  (iii) when L is O, Ring A is phenyl substituted with 1 $R^{AA}$, and Ring B is not present, then $R^{AA}$ cannot be meta-substituted trifluoromethyl;
  (iv) when L is bond, Ring A is other than phenyl, Ring B is not present, then $R^{AB}$ cannot be methyl, and
  (v) when L is NH, Ring A is pyridyl and Ring B is not present, then R cannot be alkyl; and
optionally a single stereoisomer or mixture of stereoisomers thereof and additionally optionally a pharmaceutically acceptable salt thereof.

In certain embodiments, the compound of Formula (I) is according to Formula (III):

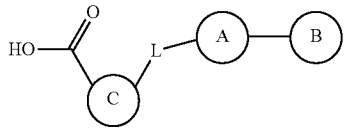

(III)

wherein:
ring C is selected from:

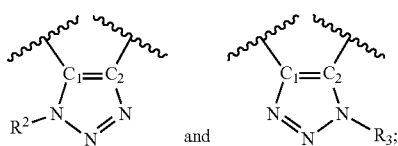

and wherein the wavy lines ( ～～～ ) indicate the points of attachment of the $C_1$ carbon to the carbonyl of C(O)—$OR^1$, and the $C_2$ carbon to L.

In certain embodiments, the compound of Formula (III) is that wherein:

L is a bond, $CH_2$, $CF_2$, O, $NR^L$, S, C(=O), $CH_2$-Q, or Q-$CH_2$; wherein Q is O, $NR^L$, or S;

$R^L$ is hydrogen or $C_{1-4}$ alkyl optionally substituted with hydroxycarbonyl, alkoxycarbonyl, hydroxycarbonylalkyl, or alkylcarbonyloxy;

Ring A is $C_{5-7}$ cycloalkyl, 5-6 membered heterocycloalkyl, pyrazolyl, imidazolyl, triazolyl, thiazolyl, phenyl, naphthyl, indanyl, tetrahydronaphthalinyl, dihydronaphthalinyl, pyridyl, indolyl, benzothiazolyl, quinolinyl, isoquinolinyl, indolinyl, isoindolinyl, tetrahydroquinolinyl, dihydroisoquinolinyl, or tetrahydro-methanonaphthalenyl;

Ring B is present or not present; wherein:
  when Ring B is present, then Ring A is optionally substituted with one or two halo, alkyl, alkoxy, or haloalkoxy;
  when Ring B is not present and Ring A is phenyl, then Ring A is substituted with:
    (i) one or two $R^{AA}$ groups, or (ii) 2 halo groups when L is other than O;
  when Ring B is not present and Ring A is other than phenyl, then Ring A is substituted with one or two $R^{AB}$ groups;

each $R^{AA}$ is independently alkyl, haloalkyl, haloalkoxy, cycloalkyloxy, (cycloalkyl)alkoxy, or phenoxy optionally substituted with one or two halo;

each $R^{AB}$ is independently halo, alkyl, hydroxy, alkoxy, haloalkyl, haloalkoxy, cycloalkyloxy, (cycloalkyl)alkoxy, or phenoxy optionally substituted with one or two halo;

Ring B, when present, is cycloalkyl, heterocycloalkyl, aryl, or heteroaryl; wherein each is optionally substituted with one or two $R^B$ groups;

each $R^B$ is independently halo, cyano, alkyl, haloalkyl, alkoxy, haloalkoxy, alkylcarbonyl, alkoxyalkoxy, alkylcarbonylaminoalkoxy, cycloalkyl, (cycloalkyl)alkyl, cycloalkyloxy, (cycloalkyl)alkoxy, cycloalkylcarbonyl, cycloalkylcarbonyloxy, heterocycloalkyl optionally substituted with alkyl or alkoxycarbonyl, (5-6-membered heterocycloalkyl-one)alkyl, (heterocycloalkyl)alkyl, or heterocycloalkylcarbonyl;

$R^2$ and $R^3$ are independently hydrogen, alkyl, phenyl, or benzyl;
  wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;
provided:
  i. when L is S and Ring A is phenyl, then Ring B cannot be halo-substituted phenyl;
  ii. when L is O, Ring A is phenyl, and Ring B is not present, then $R^{AA}$ cannot be alkyl or trifluoromethyl;
  iii. when L is NH, Ring A is pyridyl, indolyl, or indolinyl, and Ring B is not present, then $R^{AB}$ cannot be alkyl;
  iv. when L is S and Ring B is not present, then Ring A cannot be thienyl or benzothiophenyl; and
optionally a single stereoisomer or mixture of stereoisomers thereof and additionally optionally a pharmaceutically acceptable salt thereof.

In certain embodiments provided herein of the compound according to any one Formula (I), (II) or (III), or single stereoisomer or mixture of stereoisomers or pharmaceutically acceptable salt thereof, wherein L is a bond, $CH_2$, $CF_2$, O, $NR^L$, S, S(=O), or C(=O). In certain embodiments, L is $CH_2$, $CF_2$, O, $NR^L$, S, S(=O), $CH_2$-Q, or Q-$CH_2$; wherein Q is O, $NR^L$, or S. In certain embodiments, L is $CH_2$, $CF_2$, O, $NR^L$, or S. In certain embodiments, L is $CF_2$, O, $NR^L$, or S. In certain embodiments, L is $CF_2$, O, or $NR^L$. In certain embodiments, L is $CH_2$, O, $NR^L$, or S. In certain embodiments, L is O, $NR^L$, or S. In certain embodiments, L is $CH_2$, $CF_2$, or C(=O). In certain embodiments, L is $CH_2$, $CF_2$, $CH_2$-Q, or Q-$CH_2$; wherein Q is O, $NR^L$, or S. In certain embodiments, L is $CH_2$-Q, or Q-$CH_2$; wherein Q is O, $NR^L$, or S. In certain embodiments, L is bond, $CF_2$, O, $NR^L$, S, or S(=O). In certain embodiments, L is a bond, or L is $CH_2$, or L is $CF_2$. In certain embodiments, L is O. In certain embodiments, L is $NR^L$. In certain embodiments, L is S. In certain embodiments, L is S(=O). In certain embodiments, L is C(=O). In certain embodiments, L is $CH_2$-Q; wherein Q is O, $NR^L$, or S. In certain embodiments, L is $CH_2$—O, or L is $CH_2$—S, or L is $CH_2$—$NR^L$, or L is O—$CH_2$, or L is $NR^L$—$CH_2$.

In certain embodiments, $R^L$ is H. In certain embodiments, $R^L$ is $C_{1-4}$ alkyl optionally substituted with hydroxycarbonyl, alkoxycarbonyl, hydroxycarbonylalkyl, or alkylcarbonyloxy. In certain embodiments, $R^L$ is H or $C_{1-4}$ alkyl optionally substituted with hydroxycarbonyl. In certain embodiments, $R^L$ is $C_{1-4}$ alkyl optionally substituted with hydroxycarbonyl. In certain embodiments, $R^L$ is hydrogen, $C_{1-4}$ alkyl, $C_{3-6}$ cycloalkyl, phenyl, or benzyl; wherein the $C_{1-4}$ alkyl is substituted with hydroxycarbonyl, alkoxycarbonyl, hydroxycarbonylalkyl, or alkylcarbonyloxy; and the phenyl group alone or as a part of the benzyl group is substituted with one or two groups selected from halo and haloalkoxy. In certain embodiments, $R^L$ is $C_{3-6}$ cycloalkyl. In certain embodiments, $R^L$ is phenyl or benzyl; wherein the phenyl group alone or as a part of the benzyl group is optionally substituted with one or two groups selected from halo haloalkoxy. In certain embodiments, $R^L$ is benzyl optionally substituted with one or two groups selected from halo and haloalkoxy.

In certain embodiments, Ring A is cycloalkyl, spirocycloalkyl, heterocycloalkyl, aryl, or heteroaryl, each is optionally substituted with 1 or 2 $R^{AA}$ groups.

In certain embodiments, Ring A is $C_{3-7}$ cycloalkyl, $C_{8-11}$ spirocycloalkyl, 5-6 membered heterocycloalkyl, pyrazolyl, imidazolyl, triazolyl, thiazolyl, thienyl, pyridyl, phenyl, naphthyl, tetrahydronaphthyl, dihydronaphthyl, indanyl, indolyl, indolinyl, isoindolinyl, benzothiazolyl, quinolinyl, isoquinolinyl, tetrahydroquinolinyl, dihydroisoquinolinyl, tetrahydroisoquinolinyl, 2,3-dihydrobenzo[b][1,4]dioxinyl, or tetrahydro-methanonaphthalenyl.

In certain embodiments, Ring A is $C_{3-7}$ cycloalkyl, 5-6 membered heterocycloalkyl, phenyl, naphthyl, indanyl, tetrahydronaphthyl, 2,3-dihydrobenzo[b][1,4]dioxinyl, quinolinyl, isoquinolinyl, tetrahydroquinolinyl, or tetrahydroisoquinolinyl.

In certain embodiments, Ring A is cyclopentyl, cyclohexyl, spiro[2.5]octanyl, spiro[4.5]decanyl, spiro[5.5]undecanyl, piperidinyl, piperazinyl, phenyl, naphthyl, indanyl, tetrahydronaphthyl, 2,3-dihydrobenzo[b][1,4]dioxinyl, quinolinyl, isoquinolinyl, pyridyl, tetrahydroquinolinyl, tetrahydroisoquinolinyl, or 3-azabicyclo[3.1.0]hexanyl.

In certain embodiments, Ring A is cyclopentyl, cyclohexyl, bicycloheptanyl, spiro[2.5]octanyl, spiro[4.5]decanyl, or spiro[5.5]undecanyl, pyrrolidinyl, piperidinyl, piperazinyl, pyrazolyl, imidazolyl, triazolyl, phenyl, naphthyl, indanyl, tetrahydronaphthyl, dihydronaphthyl, pyridyl, indolyl, benzothiazolyl, quinolinyl, isoquinolinyl, indolinyl, isoindolinyl, tetrahydroquinolinyl, dihydroisoquinolinyl, tetrahydroisoquinolinyl, dihydrobenzodioxiny, or 3-azabicyclo[3.1.0]hexanyl.

In certain embodiments, Ring A is $C_{3-7}$ cycloalkyl, $C_{8-11}$ spirocycloalkyl, 5-6 membered heterocycloalkyl, phenyl, or naphthyl.

In certain embodiments, Ring A is cyclopentyl, cyclohexyl, spiro[2.5]octanyl, spiro[4.5]decanyl, or spiro[5.5]undecanyl, piperidinyl, piperazinyl, phenyl, or naphthyl.

In certain embodiments, Ring A is aryl. In certain embodiments, ring A is phenyl or naphthyl. In certain embodiments, ring A is phenyl.

In certain embodiments, Ring A is spirocycloalkyl, or is $C_{8-11}$ spirocycloalkyl. In certain embodiments, ring A is spiro[2.5]octanyl, spiro[4.5]decanyl, or spiro[5.5]undecanyl.

In certain embodiments, Ring A is $C_{3-7}$ cycloalkyl. In certain embodiments, Ring A is $C_{5-6}$ cycloalkyl. In certain embodiments, Ring A is cyclopentyl or cyclohexyl.

In certain embodiments, Ring A is 5-6 membered heterocycloalkyl. In certain embodiments, Ring A is piperidinyl or piperazinyl.

In certain embodiments, Ring A is $C_{3-7}$ cycloalkyl, $C_{8-11}$ spirocycloalkyl, 5-6 membered heterocycloalkyl, aryl, or heteroaryl, each is optionally substituted with 1 or 2 $R^{AA}$ or $R^{AB}$ groups. In certain embodiments, Ring A is $C_{3-7}$ cycloalkyl or $C_{8-11}$ spirocycloalkyl, each is optionally substituted with 1 or 2 $R^{AB}$ groups. In certain embodiments, Ring A is $C_{3-7}$ cycloalkyl, $C_{8-11}$ spirocycloalkyl, or 5-6 membered heterocycloalkyl, each is optionally substituted with 1 or 2 $R^{AB}$ groups. In certain embodiments, Ring A is $C_{3-7}$ cycloalkyl, $C_{8-11}$ spirocycloalkyl, aryl, or heteroaryl, each is optionally substituted with 1 or 2 $R^{AA}$ or $R^{AB}$ groups. In certain embodiments, Ring A is $C_{3-7}$ cycloalkyl, $C_{8-11}$ spirocycloalkyl, or aryl, each is optionally substituted with 1 or 2 $R^{AA}$ or $R^{AB}$ groups. In certain embodiments, Ring A is 5-6 membered heterocycloalkyl, aryl, or heteroaryl, each is optionally substituted with 1 or 2 $R^{AA}$ or $R^{AB}$ groups. In certain embodiments, Ring A is 5-6 membered heterocycloalkyl, aryl, or heteroaryl, each is optionally substituted with 1 or 2 $R^{AA}$ or $R^{AB}$ groups. In certain embodiments, Ring A is aryl or heteroaryl, each is optionally substituted with 1 or 2 $R^{AA}$ or $R^{AB}$ groups. In certain embodiments, Ring A is 5-6 membered heterocycloalkyl, phenyl, or heteroaryl, each is optionally substituted with 1 or 2 $R^{AA}$ or $R^{AB}$ groups. In certain embodiments, Ring A is 5-6 membered heterocycloalkyl, phenyl, or heteroaryl, each is optionally substituted with 1 or 2 $R^{AA}$ or $R^{AB}$ groups. In certain embodiments, Ring A is phenyl or heteroaryl, each is optionally substituted with 1 or 2 $R^{AA}$ or $R^{AB}$ groups. In certain embodiments, Ring A is $C_{3-7}$ cycloalkyl or $C_{8-11}$ spirocycloalkyl, each is optionally substituted with 1 or 2 $R^{AB}$ groups. In certain embodiments, Ring A is $C_{3-7}$ cycloalkyl optionally substituted with 1 or 2 $R^{AB}$ groups. In certain embodiments, Ring A does not include thienyl. In certain embodiments, Ring A does not include indolyl.

In certain embodiments, when Ring B is present, then Ring A is optionally substituted with one or two groups selected from halo, alkyl, alkoxy, or haloalkoxy.

In certain embodiments, when Ring B is not present and Ring A is phenyl, then Ring A is substituted with: (i) one or two $R^{AA}$ groups, or (ii) 2 halo groups when L is other than O.

In certain embodiments, when Ring B is not present and Ring A is phenyl, then Ring A is substituted with: (i) one or two $R^{AA}$ groups, (ii) 2 halo groups when L is other than O, (iii) 2 halo groups when L is O, and $R^2$ and $R^3$ are not hydrogen or alkyl, (iv), one halo group when L is $CH_2NR^L$, or (v) one halo group and one group selected from the group consisting of haloalkoxy, (cycloalkyl)alkoxy, and (phenyl)alkoxy, when L is bond, O or S, wherein the phenyl is optionally substituted with halo.

In certain embodiments, each $R^{AA}$ is independently alkyl, haloalkyl, haloalkoxy, cycloalkyloxy, (cycloalkyl)alkoxy, phenoxy optionally substituted with one or two groups selected from halo and alkylcarbonylaminoalkoxy. In certain embodiments, each $R^{AA}$ is independently alkyl, haloalkyl, haloalkoxy, cycloalkyloxy, (cycloalkyl)alkoxy, or alkylcarbonylaminoalkoxy. In certain embodiments, each $R^{AA}$ is independently haloalkyl, haloalkoxy, cycloalkyloxy, (cycloalkyl)alkoxy, or alkylcarbonylaminoalkoxy. In certain embodiments, each $R^{AA}$ is independently haloalkyl, cycloalkyloxy, (cycloalkyl)alkoxy, alkylcarbonylaminoalkoxy, (phenyl)alkoxy, wherein the phenyl is optionally substituted with halo, or alkylcarbonylaminoalkoxy. In certain embodiments, each $R^{AA}$ is independently haloalkyl or cycloalkyloxy, or is haloalkyl or (cycloalkyl)alkoxy, or is haloalkyl or (phenyl)alkoxy, wherein the phenyl is optionally substituted with halo.

In certain embodiments, each $R^{AA}$ is independently isopropyl, trifluoromethyl, propoxy, pentyloxy, trifluoromethoxy, cyclopropylmethoxy, cyclopentylmethoxy, or cyclohexylmethoxy. In certain embodiments, each $R^{AA}$ is independently isopropyl, trifluoromethyl, propoxy, pentyloxy, trifluoromethoxy, cyclopropylmethoxy, cyclopentylmethoxy, cyclohexylmethoxy, or halobenzyloxy.

In certain embodiments, when Ring B is not present and Ring A is phenyl, then Ring A is substituted with one halo group and one group selected from the group consisting of haloalkoxy, (cycloalkyl)alkoxy, and (phenyl)alkoxy, wherein the phenyl is optionally substituted with halo. In certain embodiments, when Ring B is not present and Ring A is phenyl, then Ring A is substituted with one halo and one haloalkoxy, or with one halo and one (cycloalkyl)alkoxy, or with one halo and one (phenyl)alkoxy, wherein the phenyl is optionally substituted with halo.

In certain embodiments, when Ring B is not present and Ring A is other than phenyl, then Ring A is substituted with one or two $R^{AB}$ groups. In certain embodiments, when Ring B is not present and Ring A is other than phenyl, then Ring A is unsubstituted: 1) when L is bond and Ring A is tetrahydroquinolinyl, 2) when L is O and Ring A is dihydroxybenzodioxynyl, 3) when L is O, Ring A is tetrahydronapthalene, and $R^1$ is hydrogen or ethyl, or 4) when L is O or S, and ring A is spirocycloalkyl.

In certain embodiments, each $R^{AB}$ is independently halo; alkyl; hydroxy; alkoxy; haloalkyl; haloalkoxy; cycloalkyloxy; (cycloalkyl)alkoxy; or phenoxy optionally substituted with one or two halo. In certain embodiments, each $R^{AB}$ is independently halo, alkyl, haloalkyl, or haloalkoxy. In certain embodiments, each $R^{AB}$ is independently chloro, bromo, fluoro, methyl, isopropyl, difluoromethyl, trifluoromethyl, trifluoromethoxy.

In certain embodiments, when Ring B is not present and Ring A is spiro[2.5]octanyl, spiro[4.5]decanyl, spiro[5.5]undecanyl, phenyl, naphthyl, indanyl, tetrahydronaphthyl, 2,3-dihydrobenzo[b][1,4]dioxinyl, pyridyl, quinolinyl, isoquinolinyl, pyridyl, tetrahydroquinolinyl, or tetrahydroisoquinolinyl; then ring A is substituted with one or two groups independently selected from the group consisting of haloalkyl, cycloalkyloxy, (cycloalkyl)alkoxy, alkylcarbonylaminoalkoxy, and (phenyl)alkoxy, wherein the phenyl as part of (phenyl)alkoxy is optionally substituted with halo, or with one or two groups independently selected from the group consisting of halo, alkyl, alkoxy, and haloalkoxy, or with difluoromethane, trifluoromethyl, cyclopropoxy, cyclopentyloxy, propylmethoxy, pentylmethoxy, hexylmethoxy, and fluorobenzyloxy, or with fluoro, chloro, bromo, methyl, isopropyl, and trifluoromethoxy.

In certain embodiments, Ring B, when present, is cycloalkyl, heterocycloalkyl, aryl, or heteroaryl; wherein each is optionally substituted with one or two $R^B$ groups. In certain embodiments, Ring B, when present, is cycloalkyl optionally substituted with one or two $R^B$ groups. In certain embodiments, Ring B, when present, is heterocycloalkyl optionally substituted with one or two $R^B$ groups. In certain embodiments, Ring B, when present, is aryl optionally substituted with one or two $R^B$ groups. In certain embodiments, Ring B, when present, is heteroaryl optionally substituted with one or two $R^B$ groups.

In certain embodiments, Ring B is $C_{4-6}$ cycloalkyl, heterocycloalkyl, aryl, or heteroaryl. In certain embodiments, Ring B is $C_{4-6}$ cycloalkyl, 5-6 membered heterocycloalkyl, aryl, or heteroaryl. In certain embodiments, Ring B is $C_{4-6}$ cycloalkyl, 5-6 membered heterocycloalkyl, phenyl, or heteroaryl. In certain embodiments, Ring B is 5-6 membered heterocycloalkyl, phenyl, tetrahydronaphthyl, tetrahydroquinolinyl, quinolinyl, or isoquinolinyl, tetrahydro-2H-pyranyl, cyclobutyl, cyclopentyl, cyclohexyl, or pyridyl. In certain embodiments, Ring B is piperidinyl, piperazinyl, phenyl, tetrahydronaphthyl, tetrahydroquinolinyl, quinolinyl, or isoquinolinyl, tetrahydro-2H-pyranyl, cyclobutyl, cyclopentyl, cyclohexyl, or pyridyl. In certain embodiments, Ring B is 5-6 membered heterocycloalkyl, phenyl, pyridyl, quinolinyl, or isoquinolinyl. In certain embodiments, Ring B is 5-6 membered heterocycloalkyl, phenyl, or quinolinyl. In certain embodiments, Ring B is piperidinyl, piperazinyl, phenyl, or heteroaryl. In certain embodiments, Ring B is cyclobutyl, cyclopentyl, cyclohexyl, piperidinyl, piperazinyl, phenyl, pyridyl, quinolinyl, or isoquinolinyl. In certain embodiments, Ring B is piperidinyl, piperazinyl, phenyl, or quinolinyl. In certain embodiments, Ring B is phenyl, pyridyl, quinolinyl, or isoquinolinyl. In certain embodiments, Ring B is phenyl or quinolinyl. In certain embodiments, Ring B is phenyl.

In certain embodiments, Ring B is cycloalkyl, heterocycloalkyl, aryl, or heteroaryl; each optionally substituted with one or two $R^B$ groups, wherein each $R^B$ is independently halo, cyano, alkyl, haloalkyl, haloalkoxy, alkoxyalkoxy, aminocarbonyl, alkylcarbonylaminoalkoxy, cycloalkyl, cycloalkyloxy, (cycloalkyl)alkoxy, heterocycloalkyl optionally substituted with alkyl, alkylcarbonyl or a halo, or (5-6-membered heterocycloalkyl-one)alkyl.

In certain embodiments, Ring B is cyclobutyl, cyclohexyl, piperidinyl, tetrahydropyranyl, phenyl, quinolinyl, isoquinolinyl, tetrahydronaphthyl, or tetrahydroquinolinyl; each substituted with one or two $R^B$ groups, wherein each $R^B$ is independently halo, cyano, alkyl, haloalkyl, haloalkoxy, alkoxyalkoxy, aminocarbonyl, alkylcarbonylaminoalkoxy, cycloalkyl, cycloalkyloxy, (cycloalkyl)alkoxy, (5-6-membered heterocycloalkyl-one)alkyl, or heterocycloalkyl optionally substituted with 1 or 2 alkyl, alkylcarbonyl or halo.

In certain embodiments, Ring B is cyclobutyl, cyclohexyl, piperidinyl, tetrahydropyranyl, phenyl, quinolinyl, isoquinolinyl, tetrahydronaphthyl, or tetrahydroquinolinyl; each substituted with one or two $R^B$ groups, wherein each $R^B$ is independently aminocarbonyl, cyano, chloro, bromo, fluoro, methyl, trifluoromethyl, trifluoromethoxy, methoxyethoxy, acetamidoethoxy, cyclopropoxy, cyclopropylmethoxy, cyclobutyl, cyclohexyl, tetrahydropyranyl, pyrrolidinyl, piperidinyl, methylpiperidinyl, difluoropiperidinyl, methylpiperazinyl, acetylpiperazinyl, or

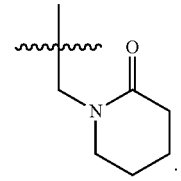 [SMILES: *CN1CCCCC1=O]

In certain embodiments, Ring B is phenyl optionally substituted with one or two $R^B$ groups, wherein each $R^B$ is independently aminocarbonyl, cyano, chloro, bromo, fluoro, trifluoromethyl, trifluoromethoxy, methoxyethoxy, acetamidoethoxy, cyclopropoxy, cyclopropylmethoxy, cyclobutyl, cyclohexyl, tetrahydropyranyl, pyrrolidinyl, piperidinyl, methylpiperidinyl, difluoropiperidinyl, methylpiperazinyl, acetylpiperazinyl, or

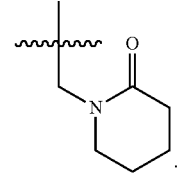 [SMILES: *CN1CCCCC1=O]

In certain embodiments, Ring B is cyclobutyl, cyclohexyl, piperidinyl, tetrahydropyranyl, quinolinyl, isoquinolinyl, tetrahydronaphthyl, or tetrahydroquinolinyl; each substituted with one or two $R^B$ groups, wherein each $R^B$ is independently chloro, bromo, fluoro, methyl, or piperidinyl.

In certain embodiments, when Ring B is not present and Ring A is phenyl, then Ring A is substituted with one or two $R^{AA}$ groups. In certain embodiments, when Ring B is not present and Ring A is phenyl, then Ring A is substituted with 2 halo groups when L is other than O. In certain embodiments, when Ring B is not present and Ring A is phenyl, then Ring A is substituted with one halo group when L is $CH_2NR^L$. In certain embodiments, when Ring B is not present and Ring A is phenyl, then Ring A is substituted with one halo group and one group selected from the group consisting of haloalkoxy, (cycloalkyl)alkoxy, and (phenyl)alkoxy, when L is bond, O or S, wherein the phenyl is optionally substituted with halo.

In certain embodiments, when Ring B is not present and Ring A is other than phenyl, then Ring A is substituted with one or two $R^{AB}$ groups. In certain embodiments, when Ring B is not present and Ring A is other than phenyl, then Ring A is unsubstituted tetrahydroquinolinyl when L is bond. In certain embodiments, when Ring B is not present and Ring A is other than phenyl, then Ring A is unsubstituted dihydroxybenzodioxynyl when L is O. In certain embodiments, when Ring B is not present and Ring A is other than phenyl, then Ring A is unsubstituted tetrahydronapthalene when L is O and $R^1$ is not hydrogen or ethyl. In certain embodiments, when Ring B is not present and Ring A is other than phenyl, then Ring A is unsubstituted spirocycloalkyl when L is O or S.

In certain embodiments, when L is S and Ring A is phenyl, then Ring B cannot be halo-substituted phenyl.

In certain embodiments, when L is S or $CH_2$, and Ring A is phenyl, then Ring B cannot be halo-substituted phenyl.

In certain embodiments, when L is $CH_2$ and Ring A is phenyl, then Ring B cannot be halo-substituted phenyl.

In certain embodiments, when L is O, Ring A is phenyl, and Ring B is not present, then $R^{AA}$ cannot be alkyl or trifluoromethyl;

In certain embodiments, when L is O, Ring A is phenyl, and Ring B is not present, then $R^{AA}$ cannot be alkyl.

In certain embodiments, when L is O, Ring A is phenyl substituted with 1 $R^{AA}$, and Ring B is not present, then $R^{AA}$ cannot be trifluoromethyl.

In certain embodiments, when L is O, Ring A is phenyl substituted with 1 $R^{AA}$, and Ring B is not present, then $R^{AA}$ cannot be meta-substituted trifluoromethyl.

In certain embodiments, when L is O, Ring A is phenyl, Ring B is not present, and $R^1$ is ethyl, then $R^{AA}$ cannot be trifluoromethoxy.

In certain embodiments, when L is NH, Ring A is pyridyl, indolyl, or indolinyl, and Ring B is not present, then $R^{AB}$ cannot be alkyl.

In certain embodiments, when L is bond, Ring A is other than phenyl, Ring B is not present, and $R^1$ is H, then $R^{AB}$ cannot be methyl.

In certain embodiments, $R^1$ is hydrogen, alkyl, cycloalkyl, heterocycloalkyl, or W; wherein W is alkyl substituted with amino, alkylamino, dialkylamino, alkylcarbonyloxy, alkoxycarbonyl, or phenylcarbonyloxy. In certain embodiments, $R^1$ is hydrogen, alkyl, cycloalkyl, heterocycloalkyl, or W; wherein W is alkyl substituted with amino, alkylamino, dialkylamino, alkylcarbonyloxy, alkoxycarbonyl, phenylcarbonyloxy, aminocarbonyloxy, alkylaminocarbonyloxy, dialkylaminocarbonyloxy, alkoxycarbonyloxy, cycloalkylcarbonyloxy, —N($R^{1A}$)C(O)$R^{1B}$, —N($R^{1A}$)C(O)O$R^{1B}$, or —N($R^{1A}$)C(O)N$R^{1B}$$R^{1C}$; wherein $R^{1A}$, $R^{1B}$, and $R^{1C}$ are each independently hydrogen or $C_{1-6}$ alkyl.

In certain embodiments, $R^1$ is hydrogen, alkyl, cycloalkyl, or heterocycloalkyl. In certain embodiments, $R^1$ is hydrogen or alkyl. In certain embodiments, $R^1$ is hydrogen. In certain embodiments, $R^1$ is alkyl. In certain embodiments, $R^1$ is hydrogen or W. In certain embodiments, $R^1$ is W. In certain embodiments, $R^1$ is W; wherein W is alkyl substituted with amino, alkylamino, dialkylamino, alkylcarbonyloxy, alkoxycarbonyl, or phenylcarbonyloxy, or W is substituted with dialkylamino or alkylcarbonyloxy, or W is substituted with alkylcarbonyloxy, dialkylaminocarbonyloxy cycloalkylcarbonyloxy, or phenylcarbonyloxy.

In certain embodiments, the compound of Formula (I) is according to Formula (IV):

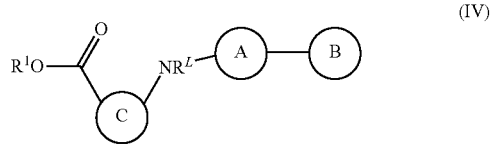

(IV)

wherein:
ring C is selected from:

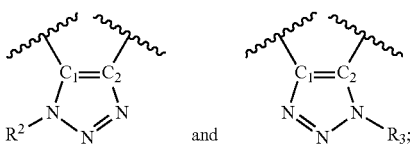

and wherein the wavy lines ( ~~~~ ) indicate the points of attachment of the $C_1$ carbon to the carbonyl of C(O)—O$R^1$, and the $C_2$ carbon to N of $NR^L$;

$R^L$ is hydrogen or $C_{1-4}$ alkyl optionally substituted with hydroxycarbonyl, alkoxycarbonyl, hydroxycarbonylalkyl, or alkylcarbonyloxy;

Ring A is $C_{5-7}$ cycloalkyl, 5-6 membered heterocycloalkyl, pyrazolyl, imidazolyl, triazolyl, thiazolyl, phenyl, naphthyl, indanyl, tetrahydronaphthalinyl, dihydronaphthalinyl, pyridyl, indolyl, benzothiazolyl, quinolinyl, isoquinolinyl, indolinyl, isoindolinyl, tetrahydroquinolinyl, dihydroisoquinolinyl, or tetrahydro-methanonaphthalenyl;

Ring B is present or not present; wherein:
when Ring B is present, then Ring A is optionally substituted with one or two halo, alkyl, alkoxy, or haloalkoxy;
when Ring B is not present and Ring A is phenyl, then Ring A is substituted with:
(i) one or two $R^{AA}$ groups, or (ii) 2 halo groups;
when Ring B is not present and Ring A is 5-6 membered heterocycloalkyl, pyrazolyl, imidazolyl, triazolyl, thiazolyl, naphthyl, indanyl, tetrahydronaphthalinyl, dihydronaphthalinyl, benzothiazolyl, quinolinyl, isoquinolinyl, isoindolinyl, tetrahydroquinolinyl, or dihydroisoquinolinyl, then Ring A is substituted with one or two $R^{AB}$ groups;
when Ring B is not present and Ring A is pyridyl, indolyl, or indolinyl, then Ring A is substituted with one or two $R^{AC}$ groups;
each $R^{AA}$ is independently alkyl, haloalkyl, haloalkoxy, cycloalkyloxy, (cycloalkyl)alkoxy, or phenoxy optionally substituted with one or two halo;
each $R^{AB}$ is independently halo, alkyl, hydroxy, alkoxy, haloalkyl, haloalkoxy, cycloalkyloxy, (cycloalkyl)alkoxy, or phenoxy optionally substituted with one or two halo;
each $R^{AC}$ is independently halo, hydroxy, alkoxy, haloalkyl, haloalkoxy, cycloalkyloxy, (cycloalkyl)alkoxy, or phenoxy optionally substituted with one or two halo;
Ring B, when present, is cycloalkyl, heterocycloalkyl, aryl, or heteroaryl; wherein each is optionally substituted with one or two $R^B$ groups;
each $R^B$ is independently halo, cyano, alkyl, haloalkyl, alkoxy, haloalkoxy, alkylcarbonyl, alkoxyalkoxy, alkylcarbonylaminoalkoxy, cycloalkyl, (cycloalkyl)alkyl, cycloalkyloxy, (cycloalkyl)alkoxy, cycloalkylcarbonyl, cycloalkylcarbonyloxy, heterocycloalkyl optionally substituted with alkyl or alkylcarbonyl, (5-6-membered heterocycloalkyl-one)alkyl, (heterocycloalkyl)alkyl, or heterocycloalkylcarbonyl;

$R^1$ is hydrogen, alkyl, cycloalkyl, heterocycloalkyl, or W; where W is alkyl substituted with amino, alkylamino, dialkylamino, alkylcarbonyloxy, alkoxycarbonyl, or phenylcarbonyloxy;

$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl; and optionally a single stereoisomer or mixture of stereoisomers thereof and additionally optionally a pharmaceutically acceptable salt thereof.

In certain embodiments, the compound of Formula (IV) is that wherein: ring C is selected from:

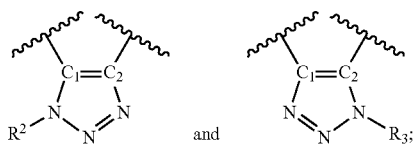

wherein the wavy lines ( ～～～ ) indicate the points of attachment of the $C_1$ carbon to the carbonyl of C(O)—$OR^1$, and the $C_2$ carbon to N of $NR^L$;

$R^L$ is hydrogen, $C_{1-4}$ alkyl, $C_{3-6}$ cycloalkyl, phenyl, or benzyl; wherein the $C_{1-4}$ alkyl is optionally substituted with hydroxycarbonyl, alkoxycarbonyl, hydroxycarbonylalkyl, or alkylcarbonyloxy; and the phenyl group alone or as a part of the benzyl group is optionally substituted with one or two groups selected from halo and haloalkoxy;

Ring A is $C_{3-7}$ cycloalkyl, $C_{8-11}$ spirocycloalkyl, 5-6 membered heterocycloalkyl, pyrazolyl, imidazolyl, triazolyl, thiazolyl, phenyl, naphthyl, indanyl, tetrahydronaphthyl, dihydronaphthyl, pyridyl, indolyl, benzothiazolyl, quinolinyl, isoquinolinyl, indolinyl, isoindolinyl, tetrahydroquinolinyl, dihydroisoquinolinyl, tetrahydroisoquinolinyl, 2,3-dihydrobenzo[b][1,4]dioxinyl, or tetrahydromethanonaphthalenyl;

Ring B is present or not present; wherein:
when Ring B is present, then Ring A is optionally substituted with one or two groups selected from halo, alkyl, alkoxy, and haloalkoxy;
when Ring B is not present and Ring A is phenyl, then Ring A is substituted with:
  (i) one or two $R^{AA}$ groups, or
  (ii) 2 halo groups;
when Ring B is not present and Ring A is 5-6 membered heterocycloalkyl, pyrazolyl, imidazolyl, triazolyl, thiazolyl, naphthyl, indanyl, tetrahydronaphthyl, dihydronaphthyl, benzothiazolyl, quinolinyl, isoquinolinyl, isoindolinyl, tetrahydroquinolinyl, dihydroisoquinolinyl, tetrahydroisoquinolinyl, or 2,3-dihydrobenzo[b][1,4]dioxinyl, then Ring A is substituted with one or two $R^{AB}$ groups;
when Ring B is not present and Ring A is $C_{3-7}$ cycloalkyl or $C_{8-11}$ spirocycloalkyl, then Ring A is optionally substituted with one or two $R^{AB}$ groups;

when Ring B is not present and Ring A is pyridyl, indolyl, or indolinyl, then Ring A is substituted with one or two $R^{AC}$ groups;

each $R^{AA}$ is independently alkyl; haloalkyl; haloalkoxy; cycloalkyloxy; (cycloalkyl)alkoxy; phenoxy optionally substituted with one or two halo; or alkylcarbonylaminoalkoxy;

each $R^{AB}$ is independently halo; alkyl; hydroxy; alkoxy; haloalkyl; haloalkoxy; cycloalkyloxy; (cycloalkyl)alkoxy; or phenoxy optionally substituted with one or two halo;

each $R^{AC}$ is independently halo; hydroxy; alkoxy; haloalkyl; haloalkoxy; cycloalkyloxy; (cycloalkyl)alkoxy; or phenoxy optionally substituted with one or two halo;

Ring B, when present, is cycloalkyl, heterocycloalkyl, aryl, or heteroaryl; wherein each is optionally substituted with one or two $R^B$ groups;

each $R^B$ is independently halo; cyano; alkyl; haloalkyl; alkoxy; haloalkoxy; alkylcarbonyl; alkoxyalkyl; aminocarbonyl; alkylcarbonylaminoalkoxy; cycloalkyl; (cycloalkyl)alkyl; cycloalkyloxy; (cycloalkyl)alkoxy; cycloalkylcarbonyl; cycloalkylcarbonyloxy; heterocycloalkyl optionally substituted with 1 or 2 alkyl, alkylcarbonyl or halo; (5-6-membered heterocycloalkyl-one)alkyl; (heterocycloalkyl)alkyl; or heterocycloalkylcarbonyl;

$R^1$ is hydrogen, alkyl, cycloalkyl, heterocycloalkyl, or W; wherein W is alkyl substituted with amino, alkylamino, dialkylamino, alkylcarbonyloxy, alkoxycarbonyl, phenylcarbonyloxy, aminocarbonyloxy, alkylaminocarbonyloxy, dialkylaminocarbonyloxy, alkoxycarbonyloxy, cycloalkylcarbonyloxy, —N($R^{1A}$)C(O)$R^{1B}$, —N($R^{1A}$)C(O)O$R^{1B}$, or —N($R^{1A}$)C(O)N$R^{1B}R^{1C}$, wherein $R^{1A}$, $R^{1B}$, and $R^{1C}$ are each independently hydrogen or $C_{1-6}$ alkyl;

$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl; and optionally a single stereoisomer or mixture of stereoisomers thereof and additionally optionally a pharmaceutically acceptable salt thereof.

In certain embodiments, the compound of Formula (IV) is that wherein $R^L$ is hydrogen or $C_{1-4}$ alkyl, and optionally a single stereoisomer or mixture of stereoisomers thereof and additionally optionally a pharmaceutically acceptable salt thereof.

In certain embodiments, the compound of Formula (IV) is that wherein $R^L$ is hydrogen, and optionally a single stereoisomer or mixture of stereoisomers thereof and additionally optionally a pharmaceutically acceptable salt thereof.

In certain embodiments, the compound of Formula (I) is according to Formula (IV):

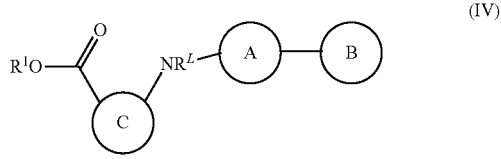

(IV)

wherein:
ring C is selected from:

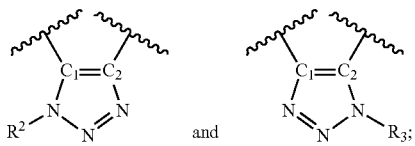

and

wherein the wavy lines ( ⌇⌇⌇ ) indicate the points of attachment of the $C_1$ carbon to the carbonyl of C(O)—$OR^1$, and the $C_2$ carbon to N of $NR^L$;

In certain embodiments, the compound of Formula (IV) is that wherein:

$R^L$ is hydrogen, $C_{1-4}$ alkyl, $C_{3-6}$ cycloalkyl, phenyl, or benzyl; wherein the $C_{1-4}$ alkyl is optionally substituted with hydroxycarbonyl, alkoxycarbonyl, hydroxycarbonylalkyl, or alkylcarbonyloxy; and the phenyl group alone or as a part of the benzyl group is optionally substituted with one or two groups selected from halo and haloalkoxy;

Ring A is $C_{3-7}$ cycloalkyl, $C_{8-11}$ spirocycloalkyl, 5-6 membered heterocycloalkyl, pyrazolyl, imidazolyl, triazolyl, thiazolyl, phenyl, naphthyl, indanyl, tetrahydronaphthyl, dihydronaphthyl, pyridyl, indolyl, benzothiazolyl, quinolinyl, isoquinolinyl, indolinyl, isoindolinyl, tetrahydroquinolinyl, dihydroisoquinolinyl, tetrahydroisoquinolinyl, 2,3-dihydrobenzo[b][1,4]dioxinyl, or tetrahydromethanonaphthalenyl;

Ring B is present or not present; wherein:
when Ring B is present, then Ring A is optionally substituted with one or two groups selected from halo, alkyl, alkoxy, or haloalkoxy;
when Ring B is not present and Ring A is phenyl, then Ring A is substituted with:
(i) one or two $R^{AA}$ groups, or (ii) 2 halo groups;
when Ring B is not present and Ring A is 5-6 membered heterocycloalkyl, pyrazolyl, imidazolyl, triazolyl, thiazolyl, naphthyl, indanyl, tetrahydronaphthyl, dihydronaphthyl, benzothiazolyl, quinolinyl, isoquinolinyl, isoindolinyl, tetrahydroquinolinyl, dihydroisoquinolinyl, tetrahydroisoquinolinyl, or 2,3-dihydrobenzo[b][1, 4]dioxinyl, then Ring A is substituted with one or two $R^{AB}$ groups;
when Ring B is not present and Ring A is $C_{3-7}$ cycloalkyl or $C_{8-11}$ spirocycloalkyl, then Ring A is optionally substituted with one or two $R^{AB}$ groups;
when Ring B is not present and Ring A is pyridyl, indolyl, or indolinyl, then Ring A is substituted with one or two $R^{AC}$ groups;

each $R^{AA}$ is independently alkyl; haloalkyl; haloalkoxy; cycloalkyloxy; (cycloalkyl)alkoxy; phenoxy optionally substituted with one or two halo; or alkylcarbonylaminoalkoxy;

each $R^{AB}$ is independently halo; alkyl; hydroxy; alkoxy; haloalkyl; haloalkoxy; cycloalkyloxy; (cycloalkyl)alkoxy; or phenoxy optionally substituted with one or two halo;

each $R^{AC}$ is independently halo; hydroxy; alkoxy; haloalkyl; haloalkoxy; cycloalkyloxy; (cycloalkyl)alkoxy; or phenoxy optionally substituted with one or two halo;

Ring B, when present, is cycloalkyl, heterocycloalkyl, aryl, or heteroaryl; wherein each is optionally substituted with one or two $R^B$ groups;

each $R^B$ is independently halo; cyano; alkyl; haloalkyl; alkoxy; haloalkoxy; alkylcarbonyl; alkoxyalkoxy; aminocarbonyl; alkylcarbonylaminoalkoxy; cycloalkyl; (cycloalkyl)alkyl; cycloalkyloxy; (cycloalkyl)alkoxy; cycloalkylcarbonyl; cycloalkylcarbonyloxy; heterocycloalkyl optionally substituted with 1 or 2 alkyl, alkylcarbonyl or halo; (5-6-membered heterocycloalkyl-one)alkyl; (heterocycloalkyl)alkyl; or heterocycloalkylcarbonyl;

$R^1$ is hydrogen, alkyl, cycloalkyl, heterocycloalkyl, or W; wherein W is alkyl substituted with amino, alkylamino, dialkylamino, alkylcarbonyloxy, alkoxycarbonyl, phenylcarbonyloxy, aminocarbonyloxy, alkylaminocarbonyloxy, dialkylaminocarbonyloxy, alkoxycarbonyloxy, cycloalkylcarbonyloxy, —N($R^{1A}$)C(O)$R^{1B}$, —N($R^{1A}$)C(O)OR$^{1B}$, or —N($R^{1A}$)C(O)NR$^{1B}$R$^{1C}$; wherein $R^{1A}$, R', and $R^{1C}$ are each independently hydrogen or $C_{1-6}$ alkyl;

$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl; and optionally a single stereoisomer or mixture of stereoisomers thereof and additionally optionally a pharmaceutically acceptable salt thereof.

In certain embodiments, the compound of Formula (I) is according to Formula (IV):

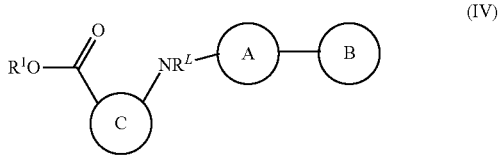

(IV)

wherein:
ring C is selected from:

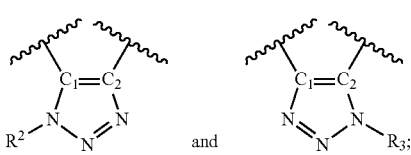

and

wherein the wavy lines ( ⌇⌇⌇ ) indicate the points of attachment of the $C_1$ carbon to the carbonyl of C(O)—$OR^1$, and the $C_2$ carbon to N of $NR^L$;

In certain embodiments, the compound of Formula (IV) is that wherein:

$R^L$ is hydrogen or $C_{1-4}$ alkyl optionally substituted with hydroxycarbonyl, alkoxycarbonyl, hydroxycarbonylalkyl, or alkylcarbonyloxy;

Ring A is $C_{5-7}$ cycloalkyl, 5-6 membered heterocycloalkyl, pyrazolyl, imidazolyl, triazolyl, thiazolyl, phenyl, naphthyl, indanyl, tetrahydronaphthalinyl, dihydronaphthalinyl, pyridyl, indolyl, benzothiazolyl, quinolinyl, isoquinolinyl, indolinyl, isoindolinyl, tetrahydroquinolinyl, dihydroisoquinolinyl, or tetrahydro-methanonaphthalenyl;

Ring B is present or not present; wherein:
when Ring B is present, then Ring A is optionally substituted with one or two halo, alkyl, alkoxy, or haloalkoxy;

when Ring B is not present and Ring A is phenyl, then Ring A is substituted with:
(i) one or two $R^{AA}$ groups, or (ii) 2 halo groups;
when Ring B is not present and Ring A is 5-6 membered heterocycloalkyl, pyrazolyl, imidazolyl, triazolyl, thiazolyl, naphthyl, indanyl, tetrahydronaphthalinyl, dihydronaphthalinyl, benzothiazolyl, quinolinyl, isoquinolinyl, isoindolinyl, tetrahydroquinolinyl, or dihydroisoquinolinyl, then Ring A is substituted with one or two $R^{AB}$ groups;
when Ring B is not present and Ring A is pyridyl, indolyl, or indolinyl, then Ring A is substituted with one or two $R^{AC}$ groups;
each $R^{AA}$ is independently alkyl, haloalkyl, haloalkoxy, cycloalkyloxy, (cycloalkyl)alkoxy, or phenoxy optionally substituted with one or two halo;
each $R^{AB}$ is independently halo, alkyl, hydroxy, alkoxy, haloalkyl, haloalkoxy, cycloalkyloxy, (cycloalkyl)alkoxy, or phenoxy optionally substituted with one or two halo;
each $R^{AC}$ is independently halo, hydroxy, alkoxy, haloalkyl, haloalkoxy, cycloalkyloxy, (cycloalkyl)alkoxy, or phenoxy optionally substituted with one or two halo;
Ring B, when present, is cycloalkyl, heterocycloalkyl, aryl, or heteroaryl; wherein each is optionally substituted with one or two $R^B$ groups;
each $R^B$ is independently halo, cyano, alkyl, haloalkyl, alkoxy, haloalkoxy, alkylcarbonyl, alkoxyalkoxy, alkylcarbonylaminoalkoxy, cycloalkyl, (cycloalkyl)alkyl, cycloalkyloxy, (cycloalkyl)alkoxy, cycloalkylcarbonyl, cycloalkylcarbonyloxy, heterocycloalkyl optionally substituted with alkyl or alkylcarbonyl, (5-6-membered heterocycloalkyl-one)alkyl, (heterocycloalkyl)alkyl, or heterocycloalkylcarbonyl;
$R^1$ is hydrogen, alkyl, cycloalkyl, heterocycloalkyl, or W; where W is alkyl substituted with amino, alkylamino, dialkylamino, alkylcarbonyloxy, alkoxycarbonyl, or phenylcarbonyloxy;
$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl; and
optionally a single stereoisomer or mixture of stereoisomers thereof and additionally optionally a pharmaceutically acceptable salt thereof.

In certain embodiments, the compound of Formula (I) is according to Formula (V):

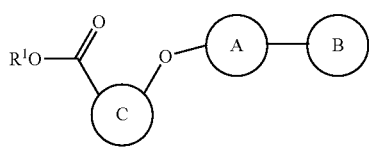

(V)

wherein:
ring C is selected from:

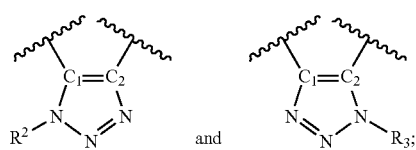

wherein the wavy lines ( ~~~ ) indicate the points of attachment of the $C_1$ carbon to the carbonyl of C(O)—OR$^1$, and the $C_2$ carbon to O;
Ring A is cycloalkyl, heterocycloalkyl, aryl, or heteroaryl; each is substituted with one or two $R^{AB}$ groups; provided
when Ring B is present, then Ring A is optionally substituted with one halo or alkyl;
when Ring B is not present and Ring A is phenyl, then Ring A is substituted with:
(i) one or two $R^{AD}$ groups, or (ii) two groups selected from chloro or bromo;
each $R^{AB}$ is independently halo, alkyl, hydroxy, alkoxy, haloalkyl, haloalkoxy, cycloalkyloxy, (cycloalkyl)alkoxy, or phenoxy optionally substituted with one or two halo;
each $R^{AD}$ is independently hydroxy, alkoxy, haloalkyl, cycloalkyloxy, (cycloalkyl)alkoxy, or phenoxy optionally substituted with one or two halo;
Ring B is present or not present; wherein:
Ring B, when present, is cycloalkyl, heterocycloalkyl, aryl, or heteroaryl; wherein each is optionally substituted with one or two $R^B$ groups;
each $R^B$ is independently halo, cyano, alkyl, haloalkyl, alkoxy, haloalkoxy, alkylcarbonyl, alkoxyalkoxy, alkylcarbonylaminoalkoxy, cycloalkyl, (cycloalkyl)alkyl, cycloalkyloxy, (cycloalkyl)alkoxy, cycloalkylcarbonyl, cycloalkylcarbonyloxy, heterocycloalkyl optionally substituted with alkyl or alkylcarbonyl, (5-6-membered heterocycloalkyl-one)alkyl, (heterocycloalkyl)alkyl, or heterocycloalkylcarbonyl;
$R^1$ is hydrogen, alkyl, cycloalkyl, heterocycloalkyl, or W; where W is alkyl substituted with amino, alkylamino, dialkylamino, alkylcarbonyloxy, alkoxycarbonyl, or phenylcarbonyloxy;
$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;
provided that when Ring A is phenyl, Ring B is not present, and $R^1$ is ethyl, then Ring A cannot be substituted with trifluoromethoxy; and
optionally a single stereoisomer or mixture of stereoisomers thereof and additionally optionally a pharmaceutically acceptable salt thereof.

In certain embodiments, the compound of Formula (V) is that wherein: ring C is selected from:

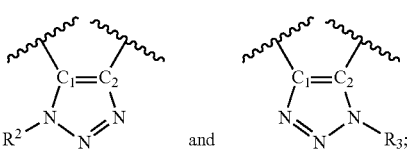

wherein the wavy lines ( ~~~ ) indicate the points of attachment of the $C_1$ carbon to the carbonyl of C(O)—OR$^1$, and the $C_2$ carbon to O;
Ring A is cycloalkyl, $C_{8-11}$ spirocycloalkyl, heterocycloalkyl, aryl, or heteroaryl; each is substituted with one or two $R^{AB}$ groups;
Ring B is present or not present; wherein
when Ring B is present, then Ring A is optionally substituted with a group selected from halo, alkyl, alkoxy, cyano, hydroxy, and (cycloalkyl)alkoxy;
when Ring B is not present and Ring A is phenyl, then Ring A is substituted with:
(i) one or two $R^{AD}$ groups;
(ii) two groups selected from chloro or bromo; or
(iii) one halo group and one group selected from the group consisting of haloalkoxy, (cycloalkyl)alkoxy, and (phenyl)alkoxy, wherein the phenyl is optionally substituted with halo;
(iv) one cyano group and one (phenyl)alkoxy group, wherein the phenyl as part of the (phenyl)alkoxy group is optionally substituted with halo or haloalkoxy;
or Ring A is unsubstituted $C_{8-11}$ spirocycloalkyl; unsubstituted dihydroxybenzodioxynyl; or unsubstituted tetrahydronaphthalene when $R^1$ is not hydrogen or ethyl;
each $R^{AB}$ is independently halo; alkyl; hydroxy; alkoxy; haloalkyl; haloalkoxy; cycloalkyloxy; (cycloalkyl)alkoxy; phenoxy optionally substituted with one or two halo; or (phenyl)alkoxy, wherein the phenyl is optionally substituted with halo;
each $R^{AD}$ is independently hydroxy; alkoxy; haloalkyl; cycloalkyloxy; (cycloalkyl)alkoxy; or phenoxy optionally substituted with one or two halo;
Ring B, when present, is cycloalkyl, heterocycloalkyl, aryl, or heteroaryl; wherein each is optionally substituted with one or two $R^B$ groups;
each $R^B$ is independently halo; cyano; alkyl; hydroxyalkyl; alkylsulfonyl; aminosulfonyl; alkylaminosulfonyl; dialkylaminosulfonyl; haloalkyl; alkoxy; aminoalkoxy; alkylaminoalkoxy; dialkylaminoalkoxy; hydroxyalkoxy; haloalkoxy; alkylcarbonyl; alkoxyalkoxy; aminocarbonyl; alkylcarbonylaminoalkoxy; cycloalkyl; (cycloalkyl)alkyl; cycloalkyloxy; (cycloalkyl)alkoxy wherein cycloalkyl group is optionally substituted with hydroxyalkyl; cycloalkylcarbonyl; cycloalkylcarbonyloxy; heterocycloalkyl optionally substituted with 1 or 2 alkyl, alkylcarbonyl or halo; (5-6-membered heterocycloalkyl-one)alkyl; (heterocycloalkyl)alkyl; or heterocycloalkylcarbonyl; or 5-6 membered heteroaryl optionally substituted with alkyl wherein alkyl is optionally substituted with 1 or 2 groups independently selected from cycloalkyl and hydroxy; alkoxyalkyl; hydroxyalkyl; or hydroxycycloalkyl;
$R^1$ is hydrogen, alkyl, cycloalkyl, heterocycloalkyl, or W; wherein W is alkyl substituted with amino, alkylamino, dialkylamino, alkylcarbonyloxy, alkoxycarbonyl, phenylcarbonyloxy, aminocarbonyloxy, alkylaminocarbonyloxy, dialkylaminocarbonyloxy, alkoxycarbonyloxy, cycloalkylcarbonyloxy, —N($R^{1A}$)C(O)R', —N($R^{1A}$)C(O)O$R^{1B}$, or —N($R^{1A}$)C(O)NR$^{1B}$R$^{1C}$, wherein $R^{1A}$, $R^{1B}$, and $R^{1C}$ are each independently hydrogen or $C_{1-6}$ alkyl;
$R^2$ and $R^3$ are independently hydrogen, alkyl, phenyl, benzyl, or alkoxy-substituted benzyl;
wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;
provided:
(i) when Ring A is phenyl, Ring B is not present, and $R^1$ is ethyl, then Ring A cannot be substituted with trifluoromethoxy; and
(ii) when Ring A is phenyl substituted with 1 $R^{AD}$, then $R^{AD}$ cannot be meta-substituted trifluoromethyl;
optionally a single stereoisomer or mixture of stereoisomers thereof and additionally optionally a pharmaceutically acceptable salt thereof.

In certain embodiments, the compound of Formula (I) is according to Formula (V):

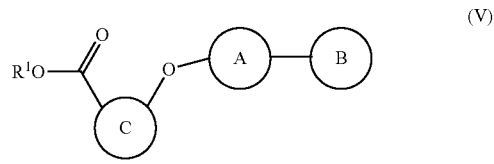

wherein:
ring C is selected from:

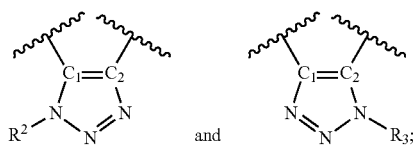

wherein the wavy lines ( ∿∿∿ ) indicate the points of attachment of the $C_1$ carbon to the carbonyl of C(O)—OR$^1$, and the $C_2$ carbon to O.

In certain embodiments, the compound of Formula (V) is that wherein:
Ring A is cycloalkyl, $C_{8-11}$ spirocycloalkyl, heterocycloalkyl, aryl, or heteroaryl; each is substituted with one or two $R^{AB}$ groups; provided:
when Ring B is present, then Ring A is optionally substituted with one halo or alkyl;
when Ring B is not present and Ring A is phenyl, then Ring A is substituted with:
(i) one or two $R^{AD}$ groups, (ii) two groups selected from chloro or bromo, or (iii) one halo group and one group selected from the group consisting of haloalkoxy, (cycloalkyl)alkoxy, and (phenyl)alkoxy, wherein the phenyl is optionally substituted with halo;
or Ring A is unsubstituted $C_{8-11}$ spirocycloalkyl; unsubstituted dihydroxybenzodioxynyl; or unsubstituted tetrahydronaphthalene when $R^1$ is not hydrogen or ethyl;
each $R^{AB}$ is independently halo; alkyl; hydroxy; alkoxy; haloalkyl; haloalkoxy; cycloalkyloxy; (cycloalkyl)alkoxy; phenoxy optionally substituted with one or two halo; or (phenyl)alkoxy, wherein the phenyl is optionally substituted with halo;
each $R^{AD}$ is independently hydroxy, alkoxy, haloalkyl, cycloalkyloxy, (cycloalkyl)alkoxy, or phenoxy optionally substituted with one or two halo;
Ring B is present or not present; wherein:
Ring B, when present, is cycloalkyl, heterocycloalkyl, aryl, or heteroaryl; wherein each is optionally substituted with one or two $R^B$ groups;
each $R^B$ is independently halo; cyano; alkyl; haloalkyl; alkoxy; haloalkoxy; alkylcarbonyl; alkoxyalkoxy; aminocarbonyl; alkylcarbonylaminoalkoxy; cycloalkyl; (cycloalkyl)alkyl; cycloalkyloxy; (cycloalkyl)alkoxy; cycloalkylcarbonyl; cycloalkylcarbonyloxy; heterocycloalkyl optionally substituted with 1 or 2 alkyl, alkylcarbonyl or halo; (5-6-membered heterocycloalkyl-one)alkyl; (heterocycloalkyl)alkyl; or heterocycloalkylcarbonyl;
$R^1$ is hydrogen, alkyl, cycloalkyl, heterocycloalkyl, or W; wherein W is alkyl substituted with amino, alkylamino, dialkylamino, alkylcarbonyloxy, alkoxycarbonyl, phenylcarbonyloxy, aminocarbonyloxy, alkylaminocarbonyloxy, dialkylaminocarbonyloxy, alkoxycarbonyloxy, cycloalkylcarbonyloxy, —N(R$^{1A}$)C(O)R$^{1B}$, —N(R$^{1A}$)C(O)OR$^{1B}$, or —N(R$^{1A}$)C(O)NR$^{1B}$R$^{1C}$; wherein R$^{1A}$, R$^{1B}$, and R$^{1C}$ are each independently hydrogen or C$_{1-6}$ alkyl;

R$^2$ and R$^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;

provided
(i) when Ring A is phenyl, Ring B is not present, and R$^1$ is ethyl, then Ring A cannot be substituted with trifluoromethoxy; and
(ii) when Ring A is phenyl substituted with 1 R$^{AD}$, then R$^{AD}$ cannot be meta-substituted trifluoromethyl; and optionally a single stereoisomer or mixture of stereoisomers thereof and additionally optionally a pharmaceutically acceptable salt thereof.

In certain embodiments, the compound of Formula (I) is according to Formula (V):

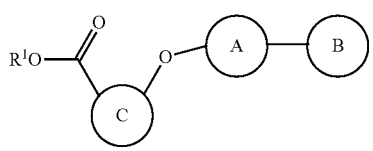

wherein:
ring C is selected from:

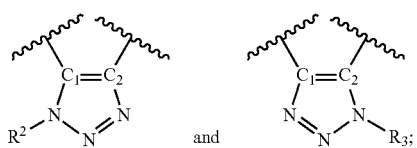

wherein the wavy lines ( ~~~ ) indicate the points of attachment of the C$_1$ carbon to the carbonyl of C(O)—OR$^1$, and the C$_2$ carbon to O.

In certain embodiments, the compound of Formula (V) is that wherein: Ring A is cycloalkyl, heterocycloalkyl, aryl, or heteroaryl; each is substituted with one or two R$^{AB}$ groups; provided:
when Ring B is present, then Ring A is optionally substituted with one halo or alkyl;
when Ring B is not present and Ring A is phenyl, then Ring A is substituted with:
(i) one or two R$^{AD}$ groups, or (ii) two groups selected from chloro or bromo;

each R$^{AB}$ is independently halo, alkyl, hydroxy, alkoxy, haloalkyl, haloalkoxy, cycloalkyloxy, (cycloalkyl)alkoxy, or phenoxy optionally substituted with one or two halo;

each R$^{AD}$ is independently hydroxy, alkoxy, haloalkyl, cycloalkyloxy, (cycloalkyl)alkoxy, or phenoxy optionally substituted with one or two halo;

Ring B is present or not present; wherein:
Ring B, when present, is cycloalkyl, heterocycloalkyl, aryl, or heteroaryl; wherein each is optionally substituted with one or two R$^B$ groups;

each R$^B$ is independently halo, cyano, alkyl, haloalkyl, alkoxy, haloalkoxy, alkylcarbonyl, alkoxyalkoxy, alkylcarbonylaminoalkoxy, cycloalkyl, (cycloalkyl)alkyl, cycloalkyloxy, (cycloalkyl)alkoxy, cycloalkylcarbonyl, cycloalkylcarbonyloxy, heterocycloalkyl optionally substituted with alkyl or alkylcarbonyl, (5-6-membered heterocycloalkyl-one)alkyl, (heterocycloalkyl)alkyl, or heterocycloalkylcarbonyl;

R$^1$ is hydrogen, alkyl, cycloalkyl, heterocycloalkyl, or W; where W is alkyl substituted with amino, alkylamino, dialkylamino, alkylcarbonyloxy, alkoxycarbonyl, or phenylcarbonyloxy;

R$^2$ and R$^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;

provided that when Ring A is phenyl, Ring B is not present, and R$^1$ is ethyl, then Ring A cannot be substituted with trifluoromethoxy; and optionally a single stereoisomer or mixture of stereoisomers thereof and additionally optionally a pharmaceutically acceptable salt thereof.

In certain embodiments, the compound of Formula (I) is according to Formula (VI):

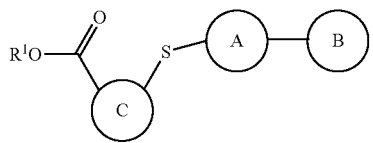

wherein:
ring C is selected from:

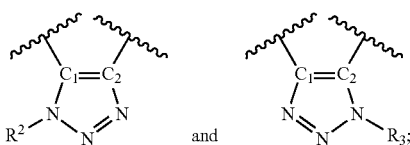

wherein the wavy lines ( ~~~ ) indicate the points of attachment of the C$_1$ carbon to the carbonyl of C(O)—OR$^1$, and the C$_2$ carbon to S; wherein:

Ring A is cycloalkyl, heterocycloalkyl, aryl, or heteroaryl other than thienyl or benzothiophenyl; each is substituted with one or two R$^{AB}$ groups;

provided when Ring A is phenyl and Ring B is not present, then Ring A is substituted with one or two R$^{AE}$;

each R$^{AB}$ is independently halo, alkyl, hydroxy, alkoxy, haloalkyl, haloalkoxy, cycloalkyloxy, (cycloalkyl)alkoxy, or phenoxy optionally substituted with one or two halo;

each R$^{AE}$ is independently halo, alkyl, haloalkyl, haloalkoxy, cycloalkyloxy, or (cycloalkyl)alkoxy;

Ring B is present or not present; wherein:
Ring B, when present, is cycloalkyl, heterocycloalkyl, aryl, or heteroaryl; wherein each is optionally substituted with one or two R$^B$ groups;

each R$^B$ is independently halo, cyano, alkyl, haloalkyl, alkoxy, haloalkoxy, alkylcarbonyl, alkoxyalkoxy, alkylcarbonylaminoalkoxy, cycloalkyl, (cycloalkyl)alkyl, cycloalkyloxy, (cycloalkyl)alkoxy, cycloalkylcarbonyl, cycloalkylcarbonyloxy, heterocycloalkyl optionally substituted with alkyl or alkylcarbonyl, (5-6-membered heterocycloalkyl-one)alkyl, (heterocycloalkyl)alkyl, or heterocycloalkylcarbonyl;

$R^1$ is hydrogen, alkyl, cycloalkyl, heterocycloalkyl, or W; where W is alkyl substituted with amino, alkylamino, dialkylamino, alkylcarbonyloxy, alkoxycarbonyl, or phenylcarbonyloxy;

$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;

provided that when Ring A is phenyl, then Ring B cannot be halo-substituted phenyl; and optionally a single stereoisomer or mixture of stereoisomers thereof and additionally optionally a pharmaceutically acceptable salt thereof.

In certain embodiments, the compound of Formula (VI) is that wherein: ring C is selected from:

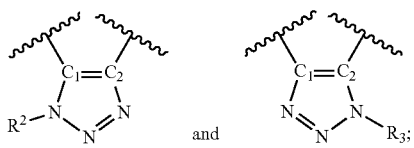

wherein the wavy lines ( ⌇⌇⌇ ) indicate the points of attachment of the $C_1$ carbon to the carbonyl of C(O)—$OR^1$, and the $C_2$ carbon to S;

Ring A is cycloalkyl, $C_{8-11}$ spirocycloalkyl, heterocycloalkyl, aryl, or heteroaryl other than thienyl or benzothiophenyl; each is substituted with one or two $R^{AB}$ groups; provided when Ring A is phenyl and Ring B is not present, then Ring A is substituted with one or two $R^{AE}$;

Ring B is present or not present; wherein:

each $R^{AB}$ is independently halo; alkyl; hydroxy; alkoxy; haloalkyl; haloalkoxy; cycloalkyloxy; (cycloalkyl)alkoxy; phenoxy optionally substituted with one or two halo; or (phenyl)alkoxy, wherein the phenyl is optionally substituted with halo;

each $R^{AE}$ is independently halo; haloalkyl; haloalkoxy; cycloalkyloxy; (cycloalkyl)alkoxy; or (phenyl)alkoxy, wherein the phenyl is optionally substituted with halo;

Ring B, when present, is cycloalkyl, heterocycloalkyl, aryl, or heteroaryl; wherein each is optionally substituted with one or two $R^B$ groups;

each $R^B$ is independently halo; cyano; alkyl; alkylsulfonyl; haloalkyl; alkoxy; haloalkoxy; alkylcarbonyl; alkoxyalkoxy; aminocarbonyl; alkylcarbonylaminoalkoxy; cycloalkyl; (cycloalkyl)alkyl; cycloalkyloxy; (cycloalkyl)alkoxy; cycloalkylcarbonyl; cycloalkylcarbonyloxy; heterocycloalkyl optionally substituted with 1 or 2 alkyl, alkylcarbonyl or halo; (5-6-membered heterocycloalkyl-one)alkyl; (heterocycloalkyl)alkyl; heterocycloalkylcarbonyl; or 5-6 membered heteroaryl;

$R^1$ is hydrogen, alkyl, cycloalkyl, heterocycloalkyl, or W; wherein W is alkyl substituted with amino, alkylamino, dialkylamino, alkylcarbonyloxy, alkoxycarbonyl, phenylcarbonyloxy, aminocarbonyloxy, alkylaminocarbonyloxy, dialkylaminocarbonyloxy, alkoxycarbonyloxy, cycloalkylcarbonyloxy, —N($R^{1A}$)C(O)$R^{1B}$, —N($R^{1A}$)C(O)$OR^{1B}$, or —N($R^{1A}$)C(O)NR$^{1B}R^{1C}$, wherein $R^{1A}$, $R^{1B}$, and $R^{1C}$ are each independently hydrogen or $C_{1-6}$ alkyl;

$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;

provided when Ring A is phenyl, then Ring B cannot be halo-substituted phenyl; and optionally a single stereoisomer or mixture of stereoisomers thereof and additionally optionally a pharmaceutically acceptable salt thereof.

In certain embodiments, the compound of Formula (I) is according to Formula (VI):

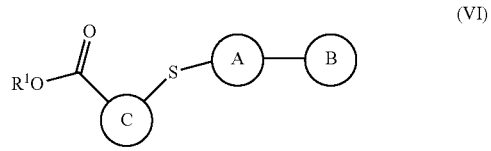

wherein:
ring C is selected from:

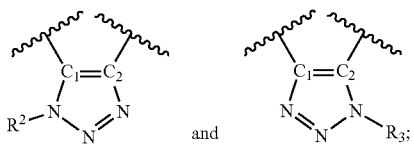

wherein the wavy lines ( ⌇⌇⌇ ) indicate the points of attachment of the $C_1$ carbon to the carbonyl of C(O)—$OR^1$, and the $C_2$ carbon to S.

In certain embodiments, the compound of Formula (VI) is that wherein:

Ring A is cycloalkyl, $C_{8-11}$ spirocycloalkyl, heterocycloalkyl, aryl, or heteroaryl other than thienyl or benzothiophenyl; each is substituted with one or two $R^{AB}$ groups; provided when Ring A is phenyl and Ring B is not present, then Ring A is substituted with one or two $R^{AE}$;

each $R^{AB}$ is independently halo; alkyl; hydroxy; alkoxy; haloalkyl; haloalkoxy; cycloalkyloxy; (cycloalkyl)alkoxy; phenoxy optionally substituted with one or two halo; (phenyl)alkoxy, wherein the phenyl is optionally substituted with halo;

each $R^{AE}$ is independently halo; alkyl; haloalkyl; haloalkoxy; cycloalkyloxy; (cycloalkyl)alkoxy; or (phenyl)alkoxy, wherein the phenyl is optionally substituted with halo;

Ring B is present or not present; wherein:

Ring B, when present, is cycloalkyl, heterocycloalkyl, aryl, or heteroaryl; wherein each is optionally substituted with one or two $R^B$ groups;

each $R^B$ is independently halo; cyano; alkyl; haloalkyl; alkoxy; haloalkoxy; alkylcarbonyl; alkoxyalkoxy; aminocarbonyl; alkylcarbonylaminoalkoxy; cycloalkyl; (cycloalkyl)alkyl; cycloalkyloxy; (cycloalkyl)alkoxy; cycloalkylcarbonyl; cycloalkylcarbonyloxy; heterocycloalkyl optionally substituted with 1 or 2 alkyl, alkylcarbonyl or halo; (5-6-membered heterocycloalkyl-one) alkyl; (heterocycloalkyl)alkyl; or heterocycloalkylcarbonyl;

R$^1$ is hydrogen, alkyl, cycloalkyl, heterocycloalkyl, or W; wherein W is alkyl substituted with amino, alkylamino, dialkylamino, alkylcarbonyloxy, alkoxycarbonyl, phenylcarbonyloxy, aminocarbonyloxy, alkylaminocarbonyloxy, dialkylaminocarbonyloxy, alkoxycarbonyloxy, cycloalkylcarbonyloxy, —N(R$^{1A}$)C(O)R$^{1B}$, —N(R$^{1A}$)C(O)OR$^{1B}$, or —N(R$^{1A}$)C(O)NR$^{1B}$R$^{1C}$; wherein R$^{1A}$, R$^{1B}$, and R$^{1C}$ are each independently hydrogen or C$_{1-6}$ alkyl;

R$^2$ and R$^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;

provided that when Ring A is phenyl, then Ring B cannot be halo-substituted phenyl; and optionally a single stereoisomer or mixture of stereoisomers thereof and additionally optionally a pharmaceutically acceptable salt thereof.

In certain embodiments, the compound of Formula (I) is according to Formula (VI):

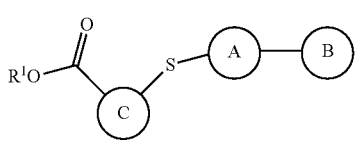

(VI)

wherein:
ring C is selected from:

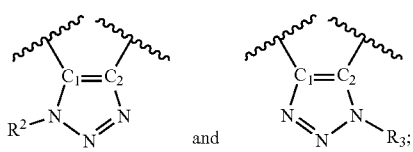

wherein the wavy lines ( ~~~ ) indicate the points of attachment of the C$_1$ carbon to the carbonyl of C(O)—OR$^1$, and the C$_2$ carbon to S.

In certain embodiments, the compound of Formula (VI) is that wherein:

Ring A is cycloalkyl, heterocycloalkyl, aryl, or heteroaryl other than thienyl or benzothiophenyl; each is substituted with one or two R$^{AB}$ groups;
  provided when Ring A is phenyl and Ring B is not present, then Ring A is substituted with one or two R$^{AE}$;
each R$^{AB}$ is independently halo, alkyl, hydroxy, alkoxy, haloalkyl, haloalkoxy, cycloalkyloxy, (cycloalkyl)alkoxy, or phenoxy optionally substituted with one or two halo;
each R$^{AE}$ is independently halo, alkyl, haloalkyl, haloalkoxy, cycloalkyloxy, or (cycloalkyl)alkoxy;

Ring B is present or not present; wherein:
Ring B, when present, is cycloalkyl, heterocycloalkyl, aryl, or heteroaryl; wherein each is optionally substituted with one or two R$^B$ groups;
each R$^B$ is independently halo, cyano, alkyl, haloalkyl, alkoxy, haloalkoxy, alkylcarbonyl, alkoxyalkoxy, alkylcarbonylaminoalkoxy, cycloalkyl, (cycloalkyl)alkyl, cycloalkyloxy, (cycloalkyl)alkoxy, cycloalkylcarbonyl, cycloalkylcarbonyloxy, heterocycloalkyl optionally substituted with alkyl or alkylcarbonyl, (5-6-membered heterocycloalkyl-one)alkyl, (heterocycloalkyl)alkyl, or heterocycloalkylcarbonyl;

R$^1$ is hydrogen, alkyl, cycloalkyl, heterocycloalkyl, or W; where W is alkyl substituted with amino, alkylamino, dialkylamino, alkylcarbonyloxy, alkoxycarbonyl, or phenylcarbonyloxy;

R$^2$ and R$^3$ are independently hydrogen, alkyl, phenyl, benzyl, or alkoxy-substituted benzyl;
  wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;

provided that when Ring A is phenyl, then Ring B cannot be halo-substituted phenyl; and optionally a single stereoisomer or mixture of stereoisomers thereof and additionally optionally a pharmaceutically acceptable salt thereof.

In another aspect, provided herein is a compound of Formula (VII):

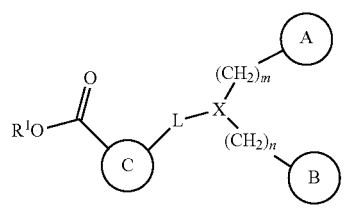

(VII)

wherein:
ring C is selected from:

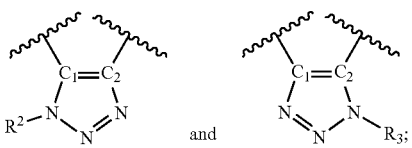

wherein the wavy lines ( ~~~ ) indicate the points of attachment of the C$_1$ carbon to the carbonyl of C(O)—OR$^1$, and the C$_2$ carbon to L;

R$^1$, R$^2$ and R$^3$ are as defined above.
L is a bond, CH$_2$, CH$_2$CH$_2$, O, or CH$_2$O;
X is N or CH;
m is 1, 2, or 3;
n is 0, 1, 2, or 3;
Ring A and Ring B are each independently C$_{3-7}$ cycloalkyl, 5-6 membered heterocycloalkyl, aryl or heteroaryl, optionally substituted with halo, haloalkyl or phenyl; wherein phenyl is optionally substituted with halo, haloalkyl, or haloalkoxy; and optionally a single stereoisomer or mixture of stereoisomers thereof and additionally optionally a pharmaceutically acceptable salt thereof.

In certain embodiments, the compound of Formula (VII) is that wherein:
L is a bond, CH$_2$, CH$_2$CH$_2$, O, or CH$_2$O;
X is N or CH;
m is 1, 2, or 3;
n is 0, 1, 2, or 3;
Ring A and Ring B are each independently aryl, optionally substituted with halo, haloalkyl or phenyl; wherein phenyl is optionally substituted with halo, haloalkyl, or haloalkoxy; and optionally a single stereoisomer or mixture of stereoisomers thereof and additionally optionally a pharmaceutically acceptable salt thereof.

In certain embodiments, the compound of Formula (VII) is that wherein:

L is a bond, $CH_2$, $CH_2CH_2$, O, or $CH_2O$;
X is N or CH;
m is 1 or 2;
n is 0, 1, or 2;
Ring A and Ring B are each independently phenyl, optionally substituted with halo, or phenyl substituted with halo or haloalkoxy; and optionally a single stereoisomer or mixture of stereoisomers thereof and additionally optionally a pharmaceutically acceptable salt thereof.

In certain embodiments, the compound of Formula (I) is according to Formula (VIII):

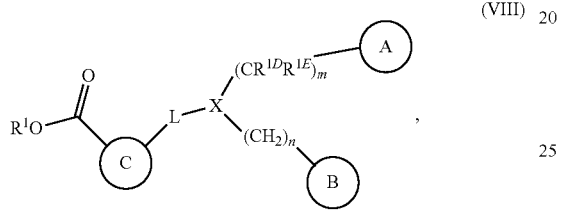

wherein:
ring C is selected from:

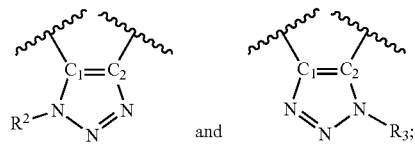

wherein the wavy lines ($\sim\!\sim\!\sim$) indicate the points of attachment of the $C_1$ carbon to the carbonyl of $C(O)-OR^1$, and the $C_2$ carbon to L;

$R^1$, $R^2$ and $R^3$ are as defined above;
L is a bond, $CH_2$, $CH_2CH_2$, O, or $CH_2O$;
X is N or CH;
$R^{1D}$ and $R^{1E}$ are each independently H or hydroxy;
m is 1, 2, or 3;
n is 0, 1, 2, or 3;
Ring A and Ring B are each independently $C_{3-7}$ cycloalkyl, 5-6 membered heterocycloalkyl, aryl or heteroaryl, optionally substituted with halo, haloalkyl or phenyl; wherein phenyl is optionally substituted with halo, haloalkyl, or haloalkoxy; and optionally a single stereoisomer or mixture of stereoisomers thereof and additionally optionally a pharmaceutically acceptable salt thereof.

In certain embodiments of any of the above formulas, Ring A is $C_{3-7}$ cycloalkyl, 5-6 membered heterocycloalkyl, or phenyl. In certain embodiments, Ring A is $C_{3-7}$ cycloalkyl. In certain embodiments, Ring A is 5-6 membered heterocycloalkyl. In certain embodiments, Ring A is phenyl.

In certain embodiments of any of the above formulas, $R^1$ is hydrogen or W. In certain embodiments, $R^1$ is hydrogen. In certain embodiments, $R^1$ is W.

In certain embodiments of any of the above formulas, $R^2$ and $R^3$ are independently hydrogen. In certain embodiments, $R^2$ is hydrogen. In certain embodiments, $R^3$ is hydrogen.

In certain embodiments of any of the above formulas, Ring C is:

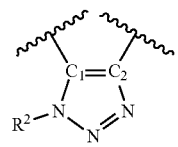

In certain embodiments of any of the above formulas, Ring C is:

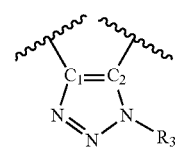

In certain embodiments of any of the above formulas where L is present, L is a bond, $CH_2$, $CF_2$, O, $NR^L$, S, $C(=O)$, $CH_2$-Q, or Q-$CH_2$; wherein Q is O, $NR^L$, or S.

In certain embodiments, L is $CH_2$, $CF_2$, O, $NR^L$, S, $C(=O)$, $CH_2$-Q, or Q-$CH_2$; wherein Q is O, $NR^L$, or S. In certain embodiments, L is $CH_2$, $CF_2$, O, $NR^L$, or S. In certain embodiments, L is $CH_2$, O, $NR^L$, or S. In certain embodiments, L is O, $NR^L$, or S. In certain embodiments, L is $CH_2$, $CF_2$, $C(=O)$, $CH_2$-Q, or Q-$CH_2$; wherein Q is O, $NR^L$, or S. In certain embodiments, L is $CH_2$, $CF_2$, or $C(=O)$. In certain embodiments, L is $CH_2$, $CF_2$, $CH_2$-Q, or Q-$CH_2$; wherein Q is O, $NR^L$, or S. In certain embodiments, L is $CH_2$-Q, or Q-$CH_2$; wherein Q is O, $NR^L$, or S.

In certain embodiments of any of the above formulas where $R^L$ is present, $R^L$ is H. In certain embodiments, $R^L$ is $C_{1-4}$ alkyl optionally substituted with hydroxycarbonyl, alkoxycarbonyl, hydroxycarbonylalkyl, or alkylcarbonyloxy. In certain embodiments, $R^L$ is H or $C_{1-4}$ alkyl optionally substituted with hydroxycarbonyl. In certain embodiments, $R^L$ is $C_{1-4}$ alkyl optionally substituted with hydroxycarbonyl. In certain embodiments, $R^L$ is H or $C_{1-4}$ alkyl substituted with hydroxycarbonyl, alkoxycarbonyl, hydroxycarbonylalkyl, or alkylcarbonyloxy. In certain embodiments, $R^L$ is $C_{1-4}$ alkyl substituted with hydroxycarbonyl, alkoxycarbonyl, hydroxycarbonylalkyl, or alkylcarbonyloxy. In certain embodiments, $R^L$ is H or $C_{1-4}$ alkyl substituted with hydroxycarbonyl.

In certain embodiments of any of the above formulas, Ring A is cycloalkyl, heterocycloalkyl, aryl, or heteroaryl, each is optionally substituted with 1 or 2 $R^{AA}$ groups;

In certain embodiments of any of the above formulas, Ring A is $C_{5-7}$ cycloalkyl, 5-6 membered heterocycloalkyl, pyrazolyl, imidazolyl, triazolyl, thiazolyl, thiophenyl, pyridyl, phenyl, naphthyl, tetrahydronaphthalinyl, dihydronaphthalinyl, indanyl, indolyl, indolinyl, isoindolinyl, benzothiazolyl, quinolinyl, isoquinolinyl, tetrahydroquinolinyl, dihydroisoquinolinyl, dihydrobenzodioxinyl, or tetrahydro-methanonaphthalenyl.

In certain embodiments of any of the above formulas, Ring A is $C_{5-7}$ cycloalkyl, 5-6 membered heterocycloalkyl, pyrazolyl, imidazolyl, triazolyl, thiazolyl, phenyl, naphthyl, indanyl, tetrahydronaphthalinyl, dihydronaphthalinyl, pyridyl, indolyl, benzothiazolyl, quinolinyl, isoquinolinyl, indolinyl, isoindolinyl, tetrahydroquinolinyl, dihydroisoquinolinyl, or tetrahydro-methanonaphthalenyl.

In certain embodiments of any of the above formulas, Ring A is heterocycloalkyl, pyrazolyl, triazolyl, thiazolyl, pyridyl, phenyl, naphthyl, tetrahydronaphthalinyl, dihydronaphthalinyl, indanyl, indolyl, isoindolinyl, benzothiazolyl, quinolinyl, isoquinolinyl, tetrahydroquinolinyl, dihydroisoquinolinyl, or dihydrobenzodioxinyl.

In certain embodiments of any of the above formulas, Ring A is heterocycloalkyl, imidazolyl, triazolyl, thiazolyl, phenyl, naphthyl, indanyl, tetrahydronaphthalinyl, dihydronaphthalinyl, pyridyl, benzothiazolyl, quinolinyl, isoquinolinyl, indolinyl, isoindolinyl, tetrahydroquinolinyl, or dihydroisoquinolinyl.

In certain embodiments of any of the above formulas, Ring A is $C_{5-7}$ cycloalkyl, 5-6 membered heterocycloalkyl, aryl, or heteroaryl, each is optionally substituted with 1 or 2 $R^{AA}$ groups. In certain embodiments, Ring A is 5-6 membered heterocycloalkyl, aryl, or heteroaryl, each is optionally substituted with 1 or 2 $R^{AA}$ groups. In certain embodiments, Ring A is heterocycloalkyl, aryl, or heteroaryl, each is optionally substituted with 1 or 2 $R^{AA}$ groups. In certain embodiments, Ring A is aryl or heteroaryl, each is optionally substituted with 1 or 2 $R^{AA}$ groups. In certain embodiments, Ring A is 5-6 membered heterocycloalkyl, phenyl, or heteroaryl, each is optionally substituted with 1 or 2 $R^{AA}$ groups. In certain embodiments, Ring A is heterocycloalkyl, phenyl, or heteroaryl, each is optionally substituted with 1 or 2 $R^{AA}$ groups. In certain embodiments, Ring A is phenyl or heteroaryl, each is optionally substituted with 1 or 2 $R^{AA}$ groups. In certain embodiments, Ring A does not include thienyl. In certain embodiments, Ring A does not include indolyl.

In certain embodiments, Ring A is $C_{5-7}$ cycloalkyl, 5-6 membered heterocycloalkyl, pyrazolyl, thienyl, imidazolyl, triazolyl, thiazolyl, phenyl, naphthyl, indanyl, tetrahydronaphthalinyl, dihydronaphthalinyl, pyridyl, indolyl, benzothiazolyl, quinolinyl, isoquinolinyl, indolinyl, isoindolinyl, tetrahydroquinolinyl, dihydroisoquinolinyl, or tetrahydro-methanonaphthalenyl. In certain embodiments, Ring A is pyrazolyl, thienyl, imidazolyl, triazolyl, thiazolyl, phenyl, naphthyl, indanyl, tetrahydronaphthalinyl, dihydronaphthalinyl, pyridyl, indolyl, benzothiazolyl, quinolinyl, isoquinolinyl, indolinyl, isoindolinyl, tetrahydroquinolinyl, dihydroisoquinolinyl, or tetrahydro-methanonaphthalenyl.

In certain embodiments, Ring A is cyclohexyl, bicycloheptanyl, pyrrolidinyl, piperidinyl, pyrazolyl, thienyl, imidazolyl, triazolyl, thiazolyl, phenyl, naphthyl, indanyl, tetrahydronaphthalinyl, dihydronaphthalinyl, pyridyl, indolyl, benzothiazolyl, quinolinyl, isoquinolinyl, indolinyl, isoindolinyl, tetrahydroquinolinyl, dihydroisoquinolinyl, or tetrahydro-methanonaphthalenyl.

In certain embodiments, Ring A is $C_{5-7}$ cycloalkyl, 5-6 membered heterocycloalkyl, pyrazolyl, thienyl, imidazolyl, triazolyl, thiazolyl, phenyl, naphthyl, indanyl, tetrahydronaphthalinyl, dihydronaphthalinyl, pyridyl, indolyl, benzothiazolyl, quinolinyl, isoquinolinyl, indolinyl, isoindolinyl, tetrahydroquinolinyl, or dihydroisoquinolinyl. In certain embodiments, Ring A is cyclohexyl, bicycloheptanyl, pyrrolidinyl, piperidinyl, pyrazolyl, thienyl, imidazolyl, triazolyl, thiazolyl, phenyl, naphthyl, indanyl, tetrahydronaphthalinyl, dihydronaphthalinyl, pyridyl, indolyl, benzothiazolyl, quinolinyl, isoquinolinyl, indolinyl, isoindolinyl, tetrahydroquinolinyl, or dihydroisoquinolinyl.

In certain embodiments, Ring A is cyclohexyl, bicycloheptanyl, pyrrolidinyl, piperidinyl, pyrazolyl, imidazolyl, triazolyl, thiazolyl, phenyl, naphthyl, indanyl, tetrahydronaphthalinyl, dihydronaphthalinyl, pyridyl, indolyl, benzothiazolyl, quinolinyl, isoquinolinyl, indolinyl, isoindolinyl, tetrahydroquinolinyl, dihydroisoquinolinyl, or tetrahydro-methanonaphthalenyl.

In certain embodiments, Ring A is cyclohexyl, bicycloheptanyl, pyrrolidinyl, piperidinyl, pyrazolyl, imidazolyl, triazolyl, thiazolyl, phenyl, naphthyl, indanyl, tetrahydronaphthalinyl, dihydronaphthalinyl, pyridyl, benzothiazolyl, quinolinyl, isoquinolinyl, indolinyl, isoindolinyl, tetrahydroquinolinyl, dihydroisoquinolinyl, or tetrahydro-methanonaphthalenyl.

In certain embodiments, Ring A is pyrazolyl, imidazolyl, triazolyl, thiazolyl, phenyl, naphthyl, indanyl, tetrahydronaphthalinyl, dihydronaphthalinyl, pyridyl, indolyl, benzothiazolyl, quinolinyl, isoquinolinyl, indolinyl, isoindolinyl, tetrahydroquinolinyl, dihydroisoquinolinyl, or tetrahydro-methanonaphthalenyl. In certain embodiments, Ring A is pyrazolyl, imidazolyl, triazolyl, thiazolyl, phenyl, naphthyl, indanyl, tetrahydronaphthalinyl, dihydronaphthalinyl, pyridyl, indolyl, benzothiazolyl, quinolinyl, isoquinolinyl, indolinyl, isoindolinyl, tetrahydroquinolinyl, dihydroisoquinolinyl, or tetrahydro-methanonaphthalenyl.

In certain embodiments, Ring A is pyrrolidinyl, piperidinyl, imidazolyl, triazolyl, thiazolyl, phenyl, pyridyl, or thienyl. In certain embodiments, Ring A is pyrrolidinyl, piperidinyl, imidazolyl, triazolyl, thiazolyl, phenyl, or pyridyl. In certain embodiments, Ring A is thiazolyl, phenyl, or pyridyl. In certain embodiments, Ring A is thiazolyl or phenyl. In certain embodiments, Ring A is phenyl.

In certain embodiments, Ring A is phenyl, naphthyl, indanyl, tetrahydronaphthalinyl, dihydronaphthalinyl, pyridyl, benzothiazolyl, quinolinyl, isoquinolinyl, indolinyl, isoindolinyl, tetrahydroquinolinyl, or dihydroisoquinolinyl. In certain embodiments, Ring A is phenyl, naphthyl, indanyl, tetrahydronaphthalinyl, pyridyl, benzothiazolyl, quinolinyl, indolinyl, tetrahydroquinolinyl, or dihydroisoquinolinyl. In certain embodiments, Ring A is tetrahydronaphthalinyl, dihydronaphthalinyl, benzothiazolyl, quinolinyl, isoquinolinyl, or tetrahydroquinolinyl.

In certain embodiments, Ring A is $C_{5-7}$ cycloalkyl, 5-6 membered heterocycloalkyl, pyrazolyl, imidazolyl, triazolyl, thiazolyl, phenyl, dihydronaphthalinyl, benzothiazolyl, isoquinolinyl, indolinyl, isoindolinyl, tetrahydroquinolinyl, dihydroisoquinolinyl, or tetrahydro-methanonaphthalenyl. In certain embodiments, Ring A is $C_{5-7}$ cycloalkyl, 5-6 membered heterocycloalkyl, pyrazolyl, imidazolyl, triazolyl, thiazolyl, phenyl, dihydronaphthalinyl, benzothiazolyl, isoquinolinyl, indolinyl, isoindolinyl, tetrahydroquinolinyl, or dihydroisoquinolinyl. In certain embodiments, Ring A is pyrazolyl, imidazolyl, triazolyl, thiazolyl, phenyl, dihydronaphthalinyl, benzothiazolyl, isoquinolinyl, indolinyl, isoindolinyl, tetrahydroquinolinyl, or dihydroisoquinolinyl. In certain embodiments, Ring A is pyrazolyl, imidazolyl, triazolyl, thiazolyl, phenyl, benzothiazolyl, or isoquinolinyl.

In certain embodiments of any of the above formulas, when Ring B is present, then Ring A is optionally substituted with one or two halo, alkyl, alkoxy, or haloalkoxy;

In certain embodiments of any of the above formulas, when Ring B is not present and Ring A is phenyl, then Ring A is substituted with: (i) one or two $R^{AA}$ groups, or (ii) 2 halo groups when L is other than O.

In certain embodiments, each $R^{AA}$ is independently alkyl, haloalkyl, haloalkoxy, cycloalkyloxy, (cycloalkyl)alkoxy, or phenoxy optionally substituted with one or two halo. In certain embodiments, when Ring B is not present and Ring A is other than phenyl, then Ring A is optionally substituted with one or two $R^{AB}$ groups.

In certain embodiments of any of the above formulas, when Ring B is not present and Ring A is other than phenyl, then Ring A is substituted with one or two $R^{AB}$ groups.

In certain embodiments, each $R^{AB}$ is independently halo, alkyl, hydroxy, alkoxy, haloalkyl, haloalkoxy, cycloalkyloxy, (cycloalkyl)alkoxy, or phenoxy optionally substituted with one or two halo.

In certain embodiments of any of the above formulas, when Ring B is not present, Ring A is pyrazolyl, imidazolyl, triazolyl, thiazolyl, phenyl, naphthyl, indanyl, tetrahydronaphthalinyl, dihydronaphthalinyl, pyridyl, indolyl, benzothiazolyl, quinolinyl, isoquinolinyl, isoindolinyl, tetrahydroquinolinyl, dihydroisoquinolinyl, or tetrahydromethanonaphthalenyl; wherein Ring A is substituted with one or two groups independently selected from halo, alkyl, alkoxy, haloalkyl, haloalkoxy, cycloalkyloxy, (cycloalkyl)alkoxy, and phenoxy substituted with one or two chloro groups. In certain embodiments, when Ring B is not present, Ring A is phenyl, naphthyl, indanyl, tetrahydronaphthalinyl, pyridyl, benzothiazolyl, quinolinyl, isoquinolinyl, isoindolinyl, tetrahydroquinolinyl, or dihydroisoquinolinyl; wherein Ring A is substituted with one or two groups independently selected from halo, alkyl, alkoxy, haloalkyl, haloalkoxy, cycloalkyloxy, (cycloalkyl)alkoxy, and phenoxy substituted with one or two chloro groups. In certain embodiments, when Ring B is not present, Ring A is phenyl, naphthyl, pyridyl, benzothiazolyl, quinolinyl, or isoquinolinyl; wherein Ring A is substituted with one or two groups independently selected from halo, alkyl, alkoxy, haloalkyl, haloalkoxy, cycloalkyloxy, (cycloalkyl)alkoxy, and phenoxy substituted with one or two chloro groups. In certain embodiments, when Ring B is not present, Ring A is phenyl substituted with one or two groups independently selected from halo, alkyl, alkoxy, haloalkyl, haloalkoxy, cycloalkyloxy, (cycloalkyl)alkoxy, and phenoxy substituted with one or two chloro groups. In certain embodiments, when Ring B is not present, Ring A is phenyl substituted with one or two groups independently selected from chloro, fluoro, trifluoromethoxy, cyclopentyloxy, and phenoxy substituted with one or two chloro groups.

In certain embodiments of any of the above formulas, Ring B, when present, is cycloalkyl, heterocycloalkyl, aryl, or heteroaryl; wherein each is optionally substituted with one or two $R^B$ groups.

In certain embodiments, each $R^B$ is independently halo, cyano, alkyl, haloalkyl, alkoxy, haloalkoxy, alkylcarbonyl, alkoxyalkoxy, alkylcarbonylaminoalkoxy, cycloalkyl, (cycloalkyl)alkyl, cycloalkyloxy, (cycloalkyl)alkoxy, cycloalkylcarbonyl, cycloalkylcarbonyloxy, heterocycloalkyl optionally substituted with alkyl or alkylcarbonyl, (5-6-membered heterocycloalkyl-one)alkyl, (heterocycloalkyl)alkyl, or heterocycloalkylcarbonyl.

In certain embodiments of any of the above formulas, Ring B is heterocycloalkyl, aryl, or heteroaryl. In certain embodiments, Ring B is 5-6 membered heterocycloalkyl, aryl, or heteroaryl. In certain embodiments, Ring B is 5-6 membered heterocycloalkyl, phenyl, or heteroaryl. In certain embodiments, Ring B is 5-6 membered heterocycloalkyl, phenyl, pyridyl, quinolinyl, or isoquinolinyl. In certain embodiments, Ring B is 5-6 membered heterocycloalkyl, phenyl, or quinolinyl. In certain embodiments, Ring B is piperidinyl, piperazinyl, phenyl, or heteroaryl. In certain embodiments, Ring B is piperidinyl, piperazinyl, phenyl, pyridyl, quinolinyl, or isoquinolinyl. In certain embodiments, Ring B is piperidinyl, piperazinyl, phenyl, or quinolinyl. In certain embodiments, Ring B is phenyl, pyridyl, quinolinyl, or isoquinolinyl. In certain embodiments, Ring B is phenyl or quinolinyl. In certain embodiments, Ring B is phenyl.

In certain embodiments, Ring B is heterocycloalkyl, aryl, or heteroaryl; each substituted with one or two $R^B$ groups, where each $R^B$ is independently halo, alkyl, haloalkyl, alkoxy, haloalkoxy, cycloalkyloxy, heterocycloalkyl, (heterocycloalkyl)alkyl, or heterocycloalkylcarbonyl. In certain embodiments, Ring B is piperidinyl, piperazinyl, phenyl, or quinolinyl; each substituted with one or two $R^B$ groups, where each $R^B$ is independently halo, alkyl, haloalkyl, alkoxy, haloalkoxy, cycloalkyloxy, heterocycloalkyl, (heterocycloalkyl)alkyl, or heterocycloalkylcarbonyl.

In certain embodiments of any of the above formulas, Ring B is piperidinyl, piperazinyl, phenyl, or quinolinyl; each substituted with one or two $R^B$ groups, where each $R^B$ is independently chloro, bromo, fluoro, methyl, trifluoromethyl, methoxy, isopropoxy, trifluoromethoxy, cyclopropoxy, cyclopentoxy, piperidinyl, piperidinylalkyl, or piperidinylcarbonyl. In certain embodiments, Ring B is phenyl or quinolinyl; each substituted with one or two $R^B$ groups, where each $R^B$ is independently chloro, bromo, fluoro, methyl, trifluoromethyl, methoxy, isopropoxy, trifluoromethoxy, cyclopropoxy, cyclopentoxy, piperidinyl, piperidinylalkyl, or piperidinylcarbonyl. In certain embodiments, Ring B is phenyl substituted with one or two $R^B$ groups, where each $R^B$ is independently chloro, bromo, fluoro, methyl, trifluoromethyl, methoxy, isopropoxy, trifluoromethoxy, cyclopropoxy, cyclopentoxy, piperidinyl, piperidinylalkyl, or piperidinylcarbonyl. In certain embodiments, Ring B is phenyl substituted with one or two $R^B$ groups, where each $R^B$ is independently chloro, bromo, trifluoromethyl, methoxy, isopropoxy, trifluoromethoxy, or cyclopropoxy. In certain embodiments, Ring B is phenyl substituted with one or two $R^B$ groups, where each $R^B$ is independently chloro, trifluoromethyl, methoxy, or trifluoromethoxy.

In certain embodiments, when L is S and Ring A is phenyl, then Ring B cannot be halo-substituted phenyl.

In certain embodiments, when L is O, Ring A is phenyl, and Ring B is not present, then $R^{AA}$ cannot be alkyl or trifluoromethyl;

In certain embodiments, when L is O, Ring A is phenyl, Ring B is not present, and $R^1$ is ethyl, then $R^{AA}$ cannot be trifluoromethoxy.

In certain embodiments, when L is NH, Ring A is pyridyl, indolyl, or indolinyl, and Ring B is not present, then $R^{AB}$ cannot be alkyl.

In certain embodiments, $R^1$ is hydrogen, alkyl, cycloalkyl, heterocycloalkyl, or W; where W is alkyl substituted with amino, alkylamino, dialkylamino, alkylcarbonyloxy, alkoxycarbonyl, or phenylcarbonyloxy.

In certain embodiments, $R^1$ is hydrogen, alkyl, cycloalkyl, or heterocycloalkyl. In certain embodiments, $R^1$ is hydrogen or alkyl. In certain embodiments, $R^1$ is hydrogen. In certain embodiments, $R^1$ is alkyl. In certain embodiments, $R^1$ is W; where W is alkyl substituted with amino, alkylamino, dialkylamino, alkylcarbonyloxy, alkoxycarbonyl, or phenylcarbonyloxy. In certain embodiments, $R^1$ is W; where W is alkyl substituted with dialkylamino or alkylcarbonyloxy.

In some embodiments provided herein is a compound or pharmaceutically acceptable salt thereof where the compound has Formula (IX), (X) or (XI):

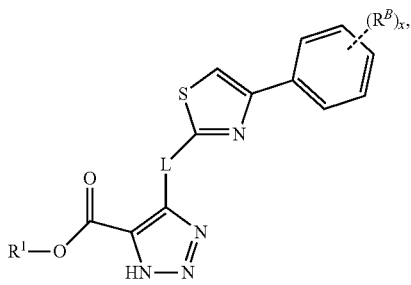

(IX)

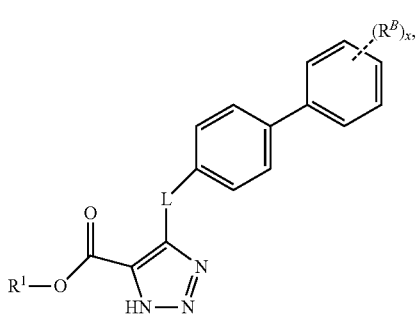

(X)

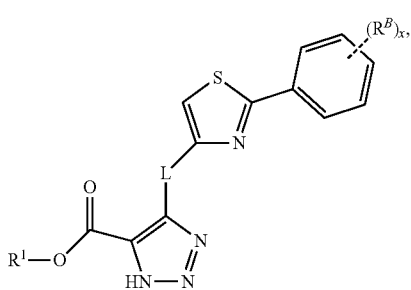

(XI)

wherein
R¹ and $R^B$ are as defined in any of the above formulas;
L is S, O, NH or $NR^L$;
$R^L$ is hydrogen, $C_{1-4}$ alkyl, $C_{3-6}$ cycloalkyl, phenyl, or benzyl; wherein the $C_{1-4}$ alkyl is optionally substituted with hydroxycarbonyl, alkoxycarbonyl, hydroxycarbonylalkyl, or alkylcarbonyloxy; and the phenyl group alone or as a part of the benzyl group is optionally substituted with one or two groups selected from halo and haloalkoxy; and
subscript x is 0, 1, 2 or 3.

In one aspect, provided herein is a compound of Formula I:

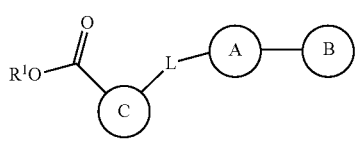

(I)

wherein:
ring C is selected from:

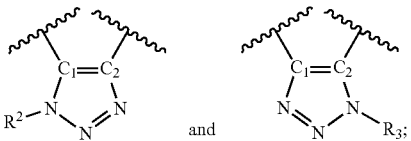

and wherein the wavy lines (⁓) indicate the points of attachment of the $C_1$ carbon to the carbonyl of C(O)—OR¹, and the $C_2$ carbon to L;
L is a bond, $CH_2$, $CF_2$, O, $NR^L$, S, C(=O), $CH_2$-Q, or Q-$CH_2$; wherein Q is O, $NR^L$, or S;
$R^L$ is hydrogen or $C_{1-4}$ alkyl optionally substituted with hydroxycarbonyl, alkoxycarbonyl, hydroxycarbonylalkyl, or alkylcarbonyloxy;
Ring A is $C_{5-7}$ cycloalkyl, 5-6 membered heterocycloalkyl, pyrazolyl, imidazolyl, triazolyl, thiazolyl, thiophenyl, pyridyl, phenyl, naphthyl, tetrahydronaphthalinyl, dihydronaphthalinyl, indanyl, indolyl, indolinyl, isoindolinyl, benzothiazolyl, quinolinyl, isoquinolinyl, tetrahydroquinolinyl, dihydroisoquinolinyl, dihydrobenzodioxinyl, or tetrahydro-methanonaphthalenyl;
Ring B is present or not present; wherein:
when Ring B is present, then Ring A is optionally substituted with one or two halo, alkyl, alkoxy, or haloalkoxy;
when Ring B is not present and Ring A is phenyl, then Ring A is substituted with:
(i) one or two $R^{AA}$ groups, or (ii) 2 halo groups when L is other than O;
when Ring B is not present and Ring A is other than phenyl, then Ring A is optionally substituted with one or two $R^{AB}$ groups;
each $R^{AA}$ is independently alkyl, haloalkyl, haloalkoxy, cycloalkyloxy, (cycloalkyl)alkoxy, alkylcarbonylaminoalkoxy, or phenoxy optionally substituted with one or two halo;
each $R^{AB}$ is independently halo, alkyl, hydroxy, alkoxy, haloalkyl, haloalkoxy, cycloalkyloxy, (cycloalkyl)alkoxy, or phenoxy optionally substituted with one or two halo;
Ring B, when present, is cycloalkyl, heterocycloalkyl, aryl, or heteroaryl; wherein each is optionally substituted with one or two $R^B$ groups;
each $R^B$ is independently halo, cyano, alkyl, haloalkyl, alkoxy, haloalkoxy, alkylcarbonyl, alkoxyalkoxy, alkylcarbonylaminoalkoxy, cycloalkyl, (cycloalkyl)alkyl, cycloalkyloxy, (cycloalkyl)alkoxy, cycloalkylcarbonyl, cycloalkylcarbonyloxy, heterocycloalkyl optionally substituted with alkyl or alkylcarbonyl, (5-6-membered heterocycloalkyl-one)alkyl, (heterocycloalkyl)alkyl, or heterocycloalkylcarbonyl;
R¹ is hydrogen, alkyl, cycloalkyl, heterocycloalkyl, or W; where W is alkyl substituted with amino, alkylamino, dialkylamino, alkylcarbonyloxy, alkoxycarbonyl, or phenylcarbonyloxy;
R² and R³ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;
provided:
i. when L is S and Ring A is phenyl, then Ring B cannot be halo-substituted phenyl;

ii. when L is O, Ring A is phenyl, and Ring B is not present, then $R^{AA}$ cannot be alkyl or trifluoromethyl;

iii. when L is O, Ring A is phenyl, Ring B is not present, and $R^1$ is ethyl, then $R^{AA}$ cannot be trifluoromethoxy;

iv. when L is NH, Ring A is pyridyl, indolyl, or indolinyl, and Ring B is not present, then $R^{AB}$ cannot be alkyl; and optionally a single stereoisomer or mixture of stereoisomers thereof and additionally optionally a pharmaceutically acceptable salt thereof.

In certain embodiments, the compound of Formula (I):

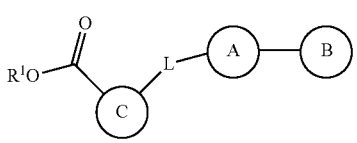

is that wherein:
ring C is selected from:

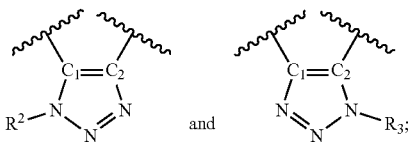

wherein the wavy lines ( ~~~ ) indicate the points of attachment of the $C_1$ carbon to the carbonyl of C(O)—$OR^1$, and the $C_2$ carbon to L;

L is a bond, $CH_2$, $CF_2$, O, $NR^L$, S, C(=O), $CH_2$-Q, or Q-$CH_2$; wherein Q is O, $NR^L$, or S;

$R^L$ is hydrogen or $C_{1-4}$ alkyl optionally substituted with hydroxycarbonyl, alkoxycarbonyl, or alkylcarbonyloxy;

Ring A is cycloalkyl, heterocycloalkyl, aryl, or heteroaryl, each is optionally substituted with 1 or 2 $R^{AA}$ groups;

each $R^{AA}$ is independently alkyl, haloalkyl, haloalkoxy, cycloalkyloxy, (cycloalkyl)alkoxy, alkylcarbonylaminoalkoxy, or phenoxy optionally substituted with one or two halo; each $R^{AB}$ is independently halo, alkyl, hydroxy, alkoxy, haloalkyl, haloalkoxy, cycloalkyloxy, (cycloalkyl)alkoxy, or phenoxy optionally substituted with one or two halo;

Ring B, when present, is cycloalkyl, heterocycloalkyl, aryl, or heteroaryl; wherein each is optionally substituted with one or two $R^B$ groups;

each $R^B$ is independently halo, cyano, alkyl, haloalkyl, alkoxy, haloalkoxy, alkylcarbonyl, alkoxyalkoxy, alkylcarbonylaminoalkoxy, cycloalkyl, (cycloalkyl)alkyl, cycloalkyloxy, (cycloalkyl)alkoxy, cycloalkylcarbonyl, cycloalkylcarbonyloxy, heterocycloalkyl optionally substituted with alkyl or alkylcarbonyl, (5-6-membered heterocycloalkyl-one)alkyl, (heterocycloalkyl)alkyl, or heterocycloalkylcarbonyl;

$R^1$ is hydrogen, alkyl, cycloalkyl, heterocycloalkyl, or W; where W is alkyl substituted with amino, alkylamino, dialkylamino, alkylcarbonyloxy, alkoxycarbonyl, or phenylcarbonyloxy;

$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl; and optionally a single stereoisomer or mixture of stereoisomers thereof and additionally optionally a pharmaceutically acceptable salt thereof.

In certain embodiments, the compound of Formula (I) is that wherein:

L is a bond, $CH_2$, $CF_2$, O, $NR^L$, S, C(=O), $CH_2$-Q, or Q-$CH_2$; wherein Q is O, $NR^L$, or S;

$R^L$ is hydrogen or $C_{1-4}$ alkyl optionally substituted with hydroxycarbonyl, alkoxycarbonyl, or alkylcarbonyloxy;

Ring A is cycloalkyl, heterocycloalkyl, aryl, or heteroaryl, each is optionally substituted with 1 or 2 $R^{AA}$ groups;

each $R^{AA}$ is independently alkyl, haloalkyl, haloalkoxy, cycloalkyloxy, (cycloalkyl)alkoxy, alkylcarbonylaminoalkoxy, or phenoxy optionally substituted with one or two halo; each $R^{AB}$ is independently halo, alkyl, hydroxy, alkoxy, haloalkyl, haloalkoxy, cycloalkyloxy, (cycloalkyl)alkoxy, or phenoxy optionally substituted with one or two halo;

Ring B, when present, is cycloalkyl, heterocycloalkyl, aryl, or heteroaryl; wherein each is optionally substituted with one or two $R^B$ groups;

each $R^B$ is independently halo, cyano, alkyl, haloalkyl, alkoxy, haloalkoxy, alkylcarbonyl, alkoxyalkoxy, alkylcarbonylaminoalkoxy, cycloalkyl, (cycloalkyl)alkyl, cycloalkyloxy, (cycloalkyl)alkoxy, cycloalkylcarbonyl, cycloalkylcarbonyloxy, heterocycloalkyl optionally substituted with alkyl or alkylcarbonyl, (5-6-membered heterocycloalkyl-one)alkyl, (heterocycloalkyl)alkyl, or heterocycloalkylcarbonyl;

$R^1$ is W; where W is alkyl substituted with amino, alkylamino, dialkylamino, alkylcarbonyloxy, alkoxycarbonyl, or phenylcarbonyloxy;

$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;

optionally a single stereoisomer or mixture of stereoisomers thereof and additionally optionally a pharmaceutically acceptable salt thereof.

In certain embodiments, the compound of Formula (I) is that wherein:

L is a bond, $CH_2$, $CF_2$, O, $NR^L$, S, C(=O), $CH_2$-Q, or Q-$CH_2$; wherein Q is O, $NR^L$, or S;

$R^L$ is hydrogen or $C_{1-4}$ alkyl optionally substituted with hydroxycarbonyl, alkoxycarbonyl, hydroxycarbonylalkyl, or alkylcarbonyloxy;

Ring A is $C_{5-7}$ cycloalkyl, 5-6 membered heterocycloalkyl, pyrazolyl, imidazolyl, triazolyl, thiazolyl, thiophenyl, phenyl, naphthyl, indanyl, tetrahydronaphthalinyl, dihydronaphthalinyl, pyridyl, indolyl, benzothiazolyl, quinolinyl, isoquinolinyl, indolinyl, isoindolinyl, tetrahydroquinolinyl, dihydroisoquinolinyl, dihydrobenzodioxinyl, or tetrahydro-methanonaphthalenyl; Ring B is present or not present; wherein:

when Ring B is present, then Ring A is optionally substituted with one or two halo, alkyl, alkoxy, or haloalkoxy;

when Ring B is not present and Ring A is phenyl, then Ring A is substituted with:
(i) one or two $R^{AA}$ groups, or (ii) 2 halo groups when L is other than O;

when Ring B is not present and Ring A is other than phenyl, then Ring A is optionally substituted with one or two $R^{AB}$ groups;

each $R^{AA}$ is independently alkyl, haloalkyl, haloalkoxy, cycloalkyloxy, (cycloalkyl)alkoxy, or phenoxy optionally substituted with one or two halo;

each $R^{AB}$ is independently halo, alkyl, hydroxy, alkoxy, haloalkyl, haloalkoxy, cycloalkyloxy, (cycloalkyl)alkoxy, or phenoxy optionally substituted with one or two halo;

Ring B, when present, is cycloalkyl, heterocycloalkyl, aryl, or heteroaryl; wherein each is optionally substituted with one or two $R^B$ groups;

each $R^B$ is independently halo, cyano, alkyl, haloalkyl, alkoxy, haloalkoxy, alkylcarbonyl, alkoxyalkoxy, alkylcarbonylaminoalkoxy, cycloalkyl, (cycloalkyl)alkyl, cycloalkyloxy, (cycloalkyl)alkoxy, cycloalkylcarbonyl, cycloalkylcarbonyloxy, heterocycloalkyl optionally substituted with alkyl or alkylcarbonyl, (5-6-membered heterocycloalkyl-one)alkyl, (heterocycloalkyl)alkyl, or heterocycloalkylcarbonyl;

$R^1$ is hydrogen, alkyl, cycloalkyl, heterocycloalkyl, or W; where W is alkyl substituted with amino, alkylamino, dialkylamino, alkylcarbonyloxy, alkoxycarbonyl, or phenylcarbonyloxy;

$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;

provided:
  i. when L is S and Ring A is phenyl, then Ring B cannot be halo-substituted phenyl;
  ii. when L is O, Ring A is phenyl, and Ring B is not present, then $R^{AA}$ cannot be alkyl or trifluoromethyl;
  iii. when L is O, Ring A is phenyl, Ring B is not present, and $R^1$ is ethyl, then $R^{AA}$ cannot be trifluoromethoxy;
  iv. when L is NH, Ring A is pyridyl, indolyl, or indolinyl, and Ring B is not present, then $R^{AB}$ cannot be alkyl; and optionally a single stereoisomer or mixture of stereoisomers thereof and additionally optionally a pharmaceutically acceptable salt thereof.

In certain embodiments, the compound of Formula (I) is that wherein:

L is a bond, $CH_2$, $CF_2$, O, $NR^L$, S, C(=O), $CH_2$-Q, or Q-$CH_2$; wherein Q is O, $NR^L$, or S;

$R^L$ is H or $C_{1-4}$ alkyl optionally substituted with hydroxycarbonylalkyl;

Ring A is 5-6 membered heterocycloalkyl, imidazolyl, triazolyl, thiazolyl, phenyl, naphthyl, indanyl, tetrahydronaphthalinyl, dihydronaphthalinyl, pyridyl, benzothiazolyl, quinolinyl, isoquinolinyl, indolinyl, isoindolinyl, tetrahydroquinolinyl, or dihydroisoquinolinyl;

wherein:
  when Ring B is present, then Ring A is optionally substituted with one or two halo, alkyl, alkoxy, or haloalkoxy;
  when Ring B is not present and Ring A is phenyl, then Ring A is substituted with:
    (i) one or two $R^{AA}$ groups, or (ii) 2 halo groups when L is other than O;
  when Ring B is not present and Ring A is other than phenyl, then Ring A is substituted with one or two $R^{AB}$ groups;

each $R^{AA}$ is independently haloalkoxy, cycloalkyloxy, (cycloalkyl)alkoxy, or phenoxy substituted with one or two halo;

each $R^{AB}$ is independently halo, alkyl, alkoxy, haloalkoxy, or phenoxy optionally substituted with one or two halo;

Ring B, when present, is heterocycloalkyl, aryl, or heteroaryl; wherein each is optionally substituted with one or two $R^B$ groups;

each $R^B$ is independently halo, alkyl, haloalkyl, alkoxy, haloalkoxy, cycloalkyloxy, heterocycloalkyl optionally substituted with alkyl or alkylcarbonyl, (heterocycloalkyl)alkyl, or heterocycloalkylcarbonyl;

$R^1$ is hydrogen, alkyl, cycloalkyl, heterocycloalkyl, or W; where W is alkyl substituted with amino, alkylamino, dialkylamino, alkylcarbonyloxy, alkoxycarbonyl, or phenylcarbonyloxy;

$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;

provided:
 i. when L is S and Ring A is phenyl, then Ring B cannot be halo-substituted phenyl;
 ii. when L is O, Ring A is phenyl, and Ring B is not present, then $R^{AA}$ cannot be alkyl or trifluoromethyl;
 iii. when L is O, Ring A is phenyl, Ring B is not present, and $R^1$ is ethyl, then $R^{AA}$ cannot be trifluoromethoxy;
 iv. when L is NH, Ring A is pyridyl, indolyl, or indolinyl, and Ring B is not present, then $R^{AB}$ cannot be alkyl; and optionally a single stereoisomer or mixture of stereoisomers thereof and additionally optionally a pharmaceutically acceptable salt thereof.

In certain embodiments, the compound of Formula (I) is that wherein:

L is a bond, $CH_2$, $CF_2$, O, $NR^L$, S, C(=O), $CH_2$-Q, or Q-$CH_2$; wherein Q is O, $NR^L$, or S;

$R^L$ is H or $C_{1-4}$ alkyl optionally substituted with hydroxycarbonyl, alkoxycarbonyl, hydroxycarbonylalkyl, or alkylcarbonyloxy;

Ring A is heterocycloalkyl, aryl, or heteroaryl; wherein each is optionally substituted with one halo or alkyl;

Ring B, when present, is cycloalkyl, heterocycloalkyl, aryl, or heteroaryl; wherein each is optionally substituted with one or two $R^B$ groups;

each $R^B$ is independently cyano, alkyl, haloalkyl, alkoxy, haloalkoxy, alkylcarbonyl, alkoxyalkoxy, alkylcarbonylaminoalkoxy, cycloalkyl, (cycloalkyl)alkyl, cycloalkyloxy, (cycloalkyl)alkoxy, cycloalkylcarbonyl, cycloalkylcarbonyloxy, heterocycloalkyl optionally substituted with alkyl or alkylcarbonyl, (5-6-membered heterocycloalkyl-one)alkyl, (heterocycloalkyl)alkyl, or heterocycloalkylcarbonyl;

$R^1$ is hydrogen, alkyl, cycloalkyl, heterocycloalkyl, or W; where W is alkyl substituted with amino, alkylamino, dialkylamino, alkylcarbonyloxy, alkoxycarbonyl, or phenylcarbonyloxy;

$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;

provided that when L is S and Ring A is phenyl, then Ring B is not halo-substituted phenyl; and optionally a single stereoisomer or mixture of stereoisomers thereof and additionally optionally a pharmaceutically acceptable salt thereof.

In certain embodiments, the compound of Formula (I) is that wherein:

L is a bond, O, $NR^L$, S, C(=O), $CH_2$-Q, or Q-$CH_2$; wherein Q is O, $NR^L$, or S;

$R^L$ is H or $C_{1-4}$ alkyl optionally substituted with hydroxycarbonylalkyl;

Ring A is heterocycloalkyl, phenyl, or heteroaryl; wherein each is optionally substituted with one halo or alkyl;

Ring B, when present, is heterocycloalkyl, phenyl, or heteroaryl; wherein each is optionally substituted with one or two $R^B$ groups;

each $R^B$ is independently halo, alkyl, alkoxy, haloalkoxy, cycloalkyloxy, heterocycloalkyl, (heterocycloalkyl)alkyl, or heterocycloalkylcarbonyl;

$R^1$ is hydrogen, alkyl, cycloalkyl, heterocycloalkyl, or W; where W is alkyl substituted with amino, alkylamino, dialkylamino, or alkylcarbonyloxy;

$R^2$ and $R^3$ are each hydrogen or alkyl optionally substituted with alkylcarbonyloxy;

provided that when L is S and Ring A is phenyl, then Ring B is not halo-substituted phenyl; and optionally a single stereoisomer or mixture of stereoisomers thereof and additionally optionally a pharmaceutically acceptable salt thereof.

In certain embodiments, the compound of Formula (I) is that wherein:

L is a bond, O, $NR^L$, S, C(=O), $CH_2$-Q, or Q-$CH_2$; wherein Q is O, $NR^L$, or S;

$R^L$ is H or $C_{1-4}$ alkyl;

Ring A is phenyl or heteroaryl; wherein each is optionally substituted with one halo or alkyl;

Ring B, when present, is phenyl or heteroaryl; wherein each is optionally substituted with one or two $R^B$ groups;

each $R^B$ is independently halo, alkyl, haloalkyl, alkoxy, haloalkoxy, cycloalkyloxy, or heterocycloalkyl optionally substituted with alkyl or alkylcarbonyl;

$R^1$ is hydrogen, alkyl, cycloalkyl, heterocycloalkyl, or W; where W is alkyl substituted with amino, alkylamino, dialkylamino, or alkylcarbonyloxy;

$R^2$ and $R^3$ are independently hydrogen or alkyl;

provided that when L is S and Ring A is phenyl, then Ring B is not halo-substituted phenyl; and optionally a single stereoisomer or mixture of stereoisomers thereof and additionally optionally a pharmaceutically acceptable salt thereof.

In certain embodiments, the compound of Formula (I) is according to Formula (II):

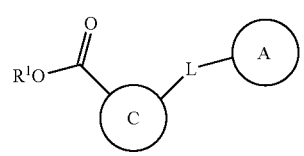

wherein:
ring C is selected from:

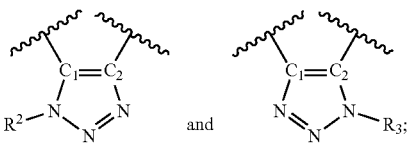

wherein the wavy lines ( ~~~ ) indicate the points of attachment of the $C_1$ carbon to the carbonyl of C(O)—$OR^1$, and the $C_2$ carbon to L.

In certain embodiments, the compound of Formula (II) is that wherein:

L is a bond, $CH_2$, $CF_2$, O, $NR^L$, S, C(=O), $CH_2$-Q, or Q-$CH_2$; wherein Q is O, $NR^L$, or S;

$R^L$ is H or $C_{1-4}$ alkyl optionally substituted with hydroxycarbonyl, alkoxycarbonyl, hydroxycarbonylalkyl, or alkylcarbonyloxy;

Ring A is heterocycloalkyl, aryl, or heteroaryl; wherein each is optionally substituted with one halo or alkyl;

Ring B, when present, is cycloalkyl, heterocycloalkyl, aryl, or heteroaryl; wherein each is optionally substituted with one or two $R^B$ groups;

each $R^B$ is independently halo, cyano, alkyl, haloalkyl, alkoxy, haloalkoxy, alkylcarbonyl, alkoxyalkoxy, alkylcarbonylaminoalkoxy, cycloalkyl, (cycloalkyl)alkyl, cycloalkyloxy, (cycloalkyl)alkoxy, cycloalkylcarbonyl, cycloalkylcarbonyloxy, heterocycloalkyl optionally substituted with alkyl or alkylcarbonyl, (5-6-membered heterocycloalkyl-one)alkyl, (heterocycloalkyl)alkyl, or heterocycloalkylcarbonyl;

$R^1$ is hydrogen, alkyl, cycloalkyl, heterocycloalkyl, or W; where W is alkyl substituted with amino, alkylamino, dialkylamino, alkylcarbonyloxy, alkoxycarbonyl, or phenylcarbonyloxy;

$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;

provided that when L is S and Ring A is phenyl, then Ring B is not halo-substituted phenyl; and optionally a single stereoisomer or mixture of stereoisomers thereof and additionally optionally a pharmaceutically acceptable salt thereof.

In certain embodiments, the compound of Formula (II) is that wherein:

L is a bond, $CH_2$, $CF_2$, O, $NR^L$, S, C(=O), $CH_2$-Q, or Q-$CH_2$; wherein Q is O, $NR^L$, or S;

$R^L$ is hydrogen or $C_{1-4}$ alkyl optionally substituted with hydroxycarbonyl, alkoxycarbonyl, hydroxycarbonylalkyl, or alkylcarbonyloxy;

Ring A is $C_{5-7}$ cycloalkyl, 5-6 membered heterocycloalkyl, pyrazolyl, imidazolyl, triazolyl, thiazolyl, phenyl, naphthyl, indanyl, tetrahydronaphthalinyl, dihydronaphthalinyl, pyridyl, indolyl, benzothiazolyl, quinolinyl, isoquinolinyl, indolinyl, isoindolinyl, tetrahydroquinolinyl, dihydroisoquinolinyl, or tetrahydro-methanonaphthalenyl;

wherein:
  when Ring A is phenyl, then Ring A is substituted with: (i) one or two $R^{AA}$ groups, or (ii) 2 halo groups when L is other than O;
  when Ring A is other than phenyl, then Ring A is substituted with one or two $R^{AB}$ groups;

each $R^{AA}$ is independently alkyl, haloalkyl, haloalkoxy, cycloalkyloxy, (cycloalkyl)alkoxy, or phenoxy optionally substituted with one or two halo;

each $R^{AB}$ is independently halo, alkyl, hydroxy, alkoxy, haloalkyl, haloalkoxy, cycloalkyloxy, (cycloalkyl)alkoxy, or phenoxy optionally substituted with one or two halo;

$R^1$ is hydrogen, alkyl, cycloalkyl, heterocycloalkyl, or W; where W is alkyl substituted with amino, alkylamino, dialkylamino, alkylcarbonyloxy, alkoxycarbonyl, or phenylcarbonyloxy;

$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;

provided:
  i. when L is O and Ring A is phenyl, then $R^{AA}$ cannot be alkyl or trifluoromethyl;
  ii. when L is O, Ring A is phenyl, and $R^1$ is ethyl, then $R^{AB}$ cannot be trifluoromethoxy;
  iii. when L is NH, Ring A is pyridyl, indolyl, or indolinyl, then $R^{AB}$ cannot be alkyl; and optionally a single stereoisomer or mixture of stereoisomers thereof and additionally optionally a pharmaceutically acceptable salt thereof.

In certain embodiments, the compound of Formula (II) is that wherein:

L is a bond, $CH_2$, $CF_2$, O, $NR^L$, S, C(=O), $CH_2$-Q, or Q-$CH_2$; wherein Q is O, $NR^L$, or S;

$R^L$ is H or $C_{1-4}$ alkyl optionally substituted with hydroxycarbonyl, alkoxycarbonyl, hydroxycarbonylalkyl, or alkylcarbonyloxy;

Ring A is $C_{5-7}$ cycloalkyl, tetrahydronaphthalinyl, dihydronaphthalinyl, benzothiazolyl, isoquinolinyl, tetrahydroquinolinyl, dihydroisoquinolinyl, or tetrahydro-methanonaphthalenyl; provided that when L is $NR^L$ or O, then Ring A cannot be tetrahydronaphthalinyl;

$R^1$ is hydrogen, alkyl, cycloalkyl, heterocycloalkyl, or W; where W is alkyl substituted with amino, alkylamino, dialkylamino, alkylcarbonyloxy, alkoxycarbonyl, or phenylcarbonyloxy;

$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl; and optionally a single stereoisomer or mixture of stereoisomers thereof and additionally optionally a pharmaceutically acceptable salt thereof.

In certain embodiments, the compound of Formula (II) is that wherein:

L is a bond, $CH_2$, O, NH, S, C(=O), $CH_2$-Q, or Q-$CH_2$; wherein Q is O, NH, or S;

Ring A is phenyl, naphthyl, indanyl, tetrahydronaphthalinyl, dihydronaphthalinyl, pyridyl, benzothiazolyl, quinolinyl, isoquinolinyl, indolinyl, isoindolinyl, tetrahydroquinolinyl, or dihydroisoquinolinyl;

wherein:
  when Ring A is phenyl, then Ring A is substituted with: (i) one or two $R^{AA}$ groups, or (ii) 2 halo groups when L is other than O;
  when Ring A is other than phenyl, then Ring A is substituted with one or two $R^{AB}$ groups;

each $R^{AA}$ is independently haloalkoxy, cycloalkyloxy, or phenoxy optionally substituted with one or two halo;

each $R^{AB}$ is independently halo, alkyl, alkoxy, or haloalkoxy;

$R^1$ is hydrogen, alkyl, cycloalkyl, or W; where W is alkyl substituted with alkylcarbonyloxy;

$R^2$ and $R^3$ are independently hydrogen or alkyl;

wherein the alkyl is optionally substituted with alkylcarbonyloxy; provided:
  i. when L is O, Ring A is phenyl, and $R^1$ is ethyl, then $R^{AB}$ cannot be trifluoromethoxy;
  ii. when L is NH, Ring A is pyridyl or indolinyl, then $R^{AB}$ cannot be alkyl; and optionally a single stereoisomer or mixture of stereoisomers thereof and additionally optionally a pharmaceutically acceptable salt thereof.

In certain embodiments, the compound of Formula (I) is according to Formula (III):

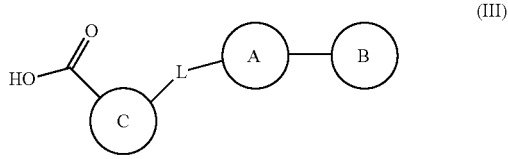

wherein:
ring C is selected from:

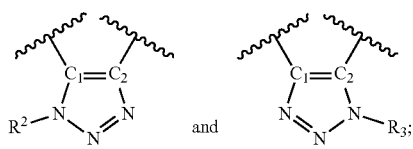

wherein the wavy lines (∿) indicate the points of attachment of the $C_1$ carbon to the carbonyl of C(O)—$OR^1$, and the $C_2$ carbon to L.

In certain embodiments, the compound of Formula (III) is that wherein:

L is a bond, $CH_2$, $CF_2$, O, $NR^L$, S, C(=O), $CH_2$-Q, or Q-$CH_2$; wherein Q is O, $NR^L$, or S;

$R^L$ is hydrogen or $C_{1-4}$ alkyl optionally substituted with hydroxycarbonyl, alkoxycarbonyl, hydroxycarbonylalkyl, or alkylcarbonyloxy;

Ring A is $C_{5-7}$ cycloalkyl, 5-6 membered heterocycloalkyl, pyrazolyl, imidazolyl, triazolyl, thiazolyl, phenyl, naphthyl, indanyl, tetrahydronaphthalinyl, dihydronaphthalinyl, pyridyl, indolyl, benzothiazolyl, quinolinyl, isoquinolinyl, indolinyl, isoindolinyl, tetrahydroquinolinyl, dihydroisoquinolinyl, or tetrahydro-methanonaphthalenyl;

Ring B is present or not present; wherein:
when Ring B is present, then Ring A is optionally substituted with one or two halo, alkyl, alkoxy, or haloalkoxy;
when Ring B is not present and Ring A is phenyl, then Ring A is substituted with:
(i) one or two $R^{AA}$ groups, or (ii) 2 halo groups when L is other than O;
when Ring B is not present and Ring A is other than phenyl, then Ring A is substituted with one or two $R^{AB}$ groups;

each $R^{AA}$ is independently alkyl, haloalkyl, haloalkoxy, cycloalkyloxy, (cycloalkyl)alkoxy, or phenoxy optionally substituted with one or two halo;

each $R^{AB}$ is independently halo, alkyl, hydroxy, alkoxy, haloalkyl, haloalkoxy, cycloalkyloxy, (cycloalkyl)alkoxy, or phenoxy optionally substituted with one or two halo;

Ring B, when present, is cycloalkyl, heterocycloalkyl, aryl, or heteroaryl; wherein each is optionally substituted with one or two $R^B$ groups;

each $R^B$ is independently halo, cyano, alkyl, haloalkyl, alkoxy, haloalkoxy, alkylcarbonyl, alkoxyalkoxy, alkylcarbonylaminoalkoxy, cycloalkyl, (cycloalkyl)alkyl, cycloalkyloxy, (cycloalkyl)alkoxy, cycloalkylcarbonyl, cycloalkylcarbonyloxy, heterocycloalkyl optionally substituted with alkyl or alkylcarbonyl, (5-6-membered heterocycloalkyl-one)alkyl, (heterocycloalkyl)alkyl, or heterocycloalkylcarbonyl;

$R^2$ and $R^3$ are independently hydrogen, alkyl, phenyl, or benzyl;
wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;

provided:
i. when L is S and Ring A is phenyl, then Ring B cannot be halo-substituted phenyl;
ii. when L is O, Ring A is phenyl, and Ring B is not present, then $R^{AA}$ cannot be alkyl or trifluoromethyl;
iii. when L is NH, Ring A is pyridyl, indolyl, or indolinyl, and Ring B is not present, then $R^{AB}$ cannot be alkyl;
iv. when L is S and Ring B is not present, then Ring A cannot be thienyl or benzothiophenyl; and optionally a single stereoisomer or mixture of stereoisomers thereof and additionally optionally a pharmaceutically acceptable salt thereof.

In certain embodiments, the compound of Formula (I) is according to Formula (IV):

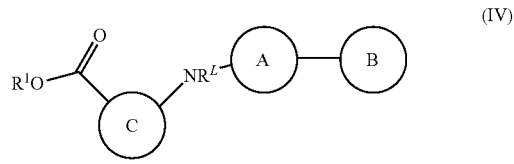

wherein:
ring C is selected from:

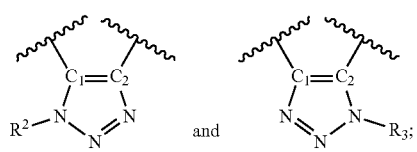

wherein the wavy lines (∿) indicate the points of attachment of the $C_1$ carbon to the carbonyl of C(O)—$OR^1$, and the $C_2$ carbon to L.

In certain embodiments, the compound of Formula (IV) is that wherein:

$R^L$ is hydrogen or $C_{1-4}$ alkyl optionally substituted with hydroxycarbonyl, alkoxycarbonyl, hydroxycarbonylalkyl, or alkylcarbonyloxy;

Ring A is $C_{5-7}$ cycloalkyl, 5-6 membered heterocycloalkyl, pyrazolyl, imidazolyl, triazolyl, thiazolyl, phenyl, naphthyl, indanyl, tetrahydronaphthalinyl, dihydronaphthalinyl, pyridyl, indolyl, benzothiazolyl, quinolinyl, isoquinolinyl, indolinyl, isoindolinyl, tetrahydroquinolinyl, dihydroisoquinolinyl, or tetrahydro-methanonaphthalenyl;

Ring B is present or not present; wherein:
when Ring B is present, then Ring A is optionally substituted with one or two halo, alkyl, alkoxy, or haloalkoxy;

when Ring B is not present and Ring A is phenyl, then Ring A is substituted with:
(i) one or two $R^{AA}$ groups, or (ii) 2 halo groups;

when Ring B is not present and Ring A is 5-6 membered heterocycloalkyl, pyrazolyl, imidazolyl, triazolyl, thiazolyl, naphthyl, indanyl, tetrahydronaphthalinyl, dihydronaphthalinyl, benzothiazolyl, quinolinyl, isoquinolinyl, isoindolinyl, tetrahydroquinolinyl, or dihydroisoquinolinyl, then Ring A is substituted with one or two $R^{AB}$ groups;

when Ring B is not present and Ring A is pyridyl, indolyl, or indolinyl, then Ring A is substituted with one or two $R^{AC}$ groups;

each $R^{AA}$ is independently alkyl, haloalkyl, haloalkoxy, cycloalkyloxy, (cycloalkyl)alkoxy, or phenoxy optionally substituted with one or two halo;

each $R^{AB}$ is independently halo, alkyl, hydroxy, alkoxy, haloalkyl, haloalkoxy, cycloalkyloxy, (cycloalkyl)alkoxy, or phenoxy optionally substituted with one or two halo;

each $R^{AC}$ is independently halo, hydroxy, alkoxy, haloalkyl, haloalkoxy, cycloalkyloxy, (cycloalkyl)alkoxy, or phenoxy optionally substituted with one or two halo;

Ring B, when present, is cycloalkyl, heterocycloalkyl, aryl, or heteroaryl; wherein each is optionally substituted with one or two $R^B$ groups;

each $R^B$ is independently halo, cyano, alkyl, haloalkyl, alkoxy, haloalkoxy, alkylcarbonyl, alkoxyalkoxy, alkylcarbonylaminoalkoxy, cycloalkyl, (cycloalkyl)alkyl, cycloalkyloxy, (cycloalkyl)alkoxy, cycloalkylcarbonyl, cycloalkylcarbonyloxy, heterocycloalkyl optionally substituted with alkyl or alkylcarbonyl, (5-6-membered heterocycloalkyl-one)alkyl, (heterocycloalkyl)alkyl, or heterocycloalkylcarbonyl;

$R^1$ is hydrogen, alkyl, cycloalkyl, heterocycloalkyl, or W; where W is alkyl substituted with amino, alkylamino, dialkylamino, alkylcarbonyloxy, alkoxycarbonyl, or phenylcarbonyloxy;

$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl; and optionally a single stereoisomer or mixture of stereoisomers thereof and additionally optionally a pharmaceutically acceptable salt thereof.

In certain embodiments, the compound of Formula (I) is according to Formula (V):

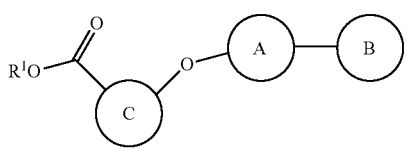

(V)

wherein:
ring C is selected from:

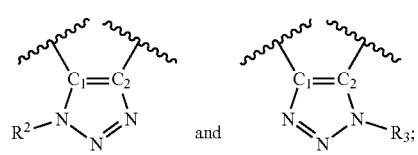

and wherein the wavy lines (∼) indicate the points of attachment of the $C_1$ carbon to the carbonyl of C(O)—$OR^1$, and the $C_2$ carbon to L.

In certain embodiments, the compound of Formula (V) is that wherein: Ring A is cycloalkyl, heterocycloalkyl, aryl, or heteroaryl; each is substituted with one or two $R^{AB}$ groups; provided:

when Ring B is present, then Ring A is optionally substituted with one halo or alkyl;

when Ring B is not present and Ring A is phenyl, then Ring A is substituted with:
(i) one or two $R^{AD}$ groups, or (ii) two groups selected from chloro or bromo;

each $R^{AB}$ is independently halo, alkyl, hydroxy, alkoxy, haloalkyl, haloalkoxy, cycloalkyloxy, (cycloalkyl)alkoxy, or phenoxy optionally substituted with one or two halo;

each $R^{AD}$ is independently hydroxy, alkoxy, haloalkyl, cycloalkyloxy, (cycloalkyl)alkoxy, or phenoxy optionally substituted with one or two halo;

Ring B is present or not present; wherein:

Ring B, when present, is cycloalkyl, heterocycloalkyl, aryl, or heteroaryl; wherein each is optionally substituted with one or two $R^B$ groups;

each $R^B$ is independently halo, cyano, alkyl, haloalkyl, alkoxy, haloalkoxy, alkylcarbonyl, alkoxyalkoxy, alkylcarbonylaminoalkoxy, cycloalkyl, (cycloalkyl)alkyl, cycloalkyloxy, (cycloalkyl)alkoxy, cycloalkylcarbonyl, cycloalkylcarbonyloxy, heterocycloalkyl optionally substituted with alkyl or alkylcarbonyl, (5-6-membered heterocycloalkyl-one)alkyl, (heterocycloalkyl)alkyl, or heterocycloalkylcarbonyl;

$R^1$ is hydrogen, alkyl, cycloalkyl, heterocycloalkyl, or W; where W is alkyl substituted with amino, alkylamino, dialkylamino, alkylcarbonyloxy, alkoxycarbonyl, or phenylcarbonyloxy;

$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;

provided that when Ring A is phenyl, Ring B is not present, and $R^1$ is ethyl, then Ring A cannot be substituted with trifluoromethoxy; and optionally a single stereoisomer or mixture of stereoisomers thereof and additionally optionally a pharmaceutically acceptable salt thereof.

In certain embodiments, the compound of Formula (I) is according to Formula (VI):

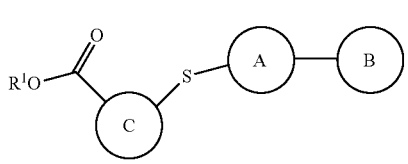

(VI)

wherein:
ring C is selected from:

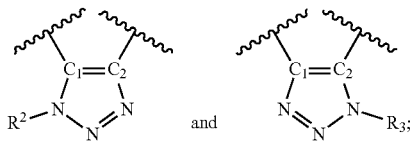

wherein the wavy lines (⁓) indicate the points of attachment of the $C_1$ carbon to the carbonyl of C(O)—OR$^1$, and the $C_2$ carbon to L.

In certain embodiments, the compound of Formula (VI) is that wherein:
Ring A is cycloalkyl, heterocycloalkyl, aryl, or heteroaryl other than thienyl or benzothiophenyl; each is substituted with one or two $R^{AB}$ groups;
provided when Ring A is phenyl and Ring B is not present, then Ring A is substituted with one or two $R^{AE}$;
each $R^{AB}$ is independently halo, alkyl, hydroxy, alkoxy, haloalkyl, haloalkoxy, cycloalkyloxy, (cycloalkyl)alkoxy, or phenoxy optionally substituted with one or two halo;
each $R^{AE}$ is independently halo, alkyl, haloalkyl, haloalkoxy, cycloalkyloxy, or (cycloalkyl)alkoxy;
Ring B is present or not present; wherein:
Ring B, when present, is cycloalkyl, heterocycloalkyl, aryl, or heteroaryl; wherein each is optionally substituted with one or two $R^B$ groups;
each $R^B$ is independently halo, cyano, alkyl, haloalkyl, alkoxy, haloalkoxy, alkylcarbonyl, alkoxyalkoxy, alkylcarbonylaminoalkoxy, cycloalkyl, (cycloalkyl)alkyl, cycloalkyloxy, (cycloalkyl)alkoxy, cycloalkylcarbonyl, cycloalkylcarbonyloxy, heterocycloalkyl optionally substituted with alkyl or alkylcarbonyl, (5-6-membered heterocycloalkyl-one)alkyl, (heterocycloalkyl)alkyl, or heterocycloalkylcarbonyl;
$R^1$ is hydrogen, alkyl, cycloalkyl, heterocycloalkyl, or W; where W is alkyl substituted with amino, alkylamino, dialkylamino, alkylcarbonyloxy, alkoxycarbonyl, or phenylcarbonyloxy;
$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;
provided that when Ring A is phenyl, then Ring B cannot be halo-substituted phenyl; and
optionally a single stereoisomer or mixture of stereoisomers thereof and additionally optionally a pharmaceutically acceptable salt thereof.

In certain embodiments, L is a bond, $CH_2$, $CF_2$, O, $NR^L$, S, C(=O), $CH_2$-Q, or Q-$CH_2$; wherein Q is O, $NR^L$, or S.
In certain embodiments, L is $CH_2$, $CF_2$, O, $NR^L$, S, C(=O), $CH_2$-Q, or Q-$CH_2$; wherein Q is O, $NR^L$, or S. In certain embodiments, L is $CH_2$, $CF_2$, O, $NR^L$, or S. In certain embodiments, L is $CH_2$, O, $NR^L$, or S. In certain embodiments, L is O, $NR^L$, or S. In certain embodiments, L is $CH_2$, $CF_2$, C(=O), $CH_2$-Q, or Q-$CH_2$; wherein Q is O, $NR^L$, or S. In certain embodiments, L is $CH_2$, $CF_2$, or C(=O). In certain embodiments, L is $CH_2$, $CF_2$, $CH_2$-Q, or Q-$CH_2$; wherein Q is O, $NR^L$, or S. In certain embodiments, L is $CH_2$-Q, or Q-$CH_2$; wherein Q is O, $NR^L$, or S.
In certain embodiments, $R^L$ is H. In certain embodiments, $R^L$ is $C_{1-4}$ alkyl optionally substituted with hydroxycarbonyl, alkoxycarbonyl, hydroxycarbonylalkyl, or alkylcarbonyloxy. In certain embodiments, $R^L$ is H or $C_{1-4}$ alkyl optionally substituted with hydroxycarbonyl. In certain embodiments, $R^L$ is $C_{1-4}$ alkyl optionally substituted with hydroxycarbonyl. In certain embodiments, $R^L$ is H or $C_{1-4}$ alkyl substituted with hydroxycarbonyl, alkoxycarbonyl, hydroxycarbonylalkyl, or alkylcarbonyloxy. In certain embodiments, $R^L$ is $C_{1-4}$ alkyl substituted with hydroxycarbonyl, alkoxycarbonyl, hydroxycarbonylalkyl, or alkylcarbonyloxy. In certain embodiments, $R^L$ is H or $C_{1-4}$ alkyl substituted with hydroxycarbonyl.

In certain embodiments, Ring A is cycloalkyl, heterocycloalkyl, aryl, or heteroaryl, each is optionally substituted with 1 or 2 $R^{AA}$ groups;
In certain embodiments, Ring A is $C_{5-7}$ cycloalkyl, 5-6 membered heterocycloalkyl, pyrazolyl, imidazolyl, triazolyl, thiazolyl, thiophenyl, pyridyl, phenyl, naphthyl, tetrahydronaphthalinyl, dihydronaphthalinyl, indanyl, indolyl, indolinyl, isoindolinyl, benzothiazolyl, quinolinyl, isoquinolinyl, tetrahydroquinolinyl, dihydroisoquinolinyl, dihydrobenzodioxinyl, or tetrahydro-methanonaphthalenyl.
In certain embodiments, Ring A is $C_{5-7}$ cycloalkyl, 5-6 membered heterocycloalkyl, pyrazolyl, imidazolyl, triazolyl, thiazolyl, phenyl, naphthyl, indanyl, tetrahydronaphthalinyl, dihydronaphthalinyl, pyridyl, indolyl, benzothiazolyl, quinolinyl, isoquinolinyl, indolinyl, isoindolinyl, tetrahydroquinolinyl, dihydroisoquinolinyl, or tetrahydromethanonaphthalenyl.
In certain embodiments, Ring A is heterocycloalkyl, pyrazolyl, triazolyl, thiazolyl, pyridyl, phenyl, naphthyl, tetrahydronaphthalinyl, dihydronaphthalinyl, indanyl, indolyl, isoindolinyl, benzothiazolyl, quinolinyl, isoquinolinyl, tetrahydroquinolinyl, dihydroisoquinolinyl, or dihydrobenzodioxinyl.
In certain embodiments, Ring A is heterocycloalkyl, imidazolyl, triazolyl, thiazolyl, phenyl, naphthyl, indanyl, tetrahydronaphthalinyl, dihydronaphthalinyl, pyridyl, benzothiazolyl, quinolinyl, isoquinolinyl, indolinyl, isoindolinyl, tetrahydroquinolinyl, or dihydroisoquinolinyl.
In certain embodiments, Ring A is $C_{5-7}$ cycloalkyl, 5-6 membered heterocycloalkyl, aryl, or heteroaryl, each is optionally substituted with 1 or 2 $R^{AA}$ groups. In certain embodiments, Ring A is 5-6 membered heterocycloalkyl, aryl, or heteroaryl, each is optionally substituted with 1 or 2 $R^{AA}$ groups. In certain embodiments, Ring A is heterocycloalkyl, aryl, or heteroaryl, each is optionally substituted with 1 or 2 $R^{AA}$ groups. In certain embodiments, Ring A is aryl or heteroaryl, each is optionally substituted with 1 or 2 $R^{AA}$ groups. In certain embodiments, Ring A is 5-6 membered heterocycloalkyl, phenyl, or heteroaryl, each is optionally substituted with 1 or 2 $R^{AA}$ groups. In certain embodiments, Ring A is heterocycloalkyl, phenyl, or heteroaryl, each is optionally substituted with 1 or 2 $R^{AA}$ groups. In certain embodiments, Ring A is phenyl or heteroaryl, each is optionally substituted with 1 or 2 $R^{AA}$ groups. In certain embodiments, Ring A does not include thienyl. In certain embodiments, Ring A does not include indolyl.
In certain embodiments, Ring A is $C_{5-7}$ cycloalkyl, 5-6 membered heterocycloalkyl, pyrazolyl, thienyl, imidazolyl, triazolyl, thiazolyl, phenyl, naphthyl, indanyl, tetrahydronaphthalinyl, dihydronaphthalinyl, pyridyl, indolyl, benzothiazolyl, quinolinyl, isoquinolinyl, indolinyl, isoindolinyl, tetrahydroquinolinyl, dihydroisoquinolinyl, or tetrahydro-methanonaphthalenyl. In certain embodiments, Ring A is pyrazolyl, thienyl, imidazolyl, triazolyl, thiazolyl, phenyl, naphthyl, indanyl, tetrahydronaphthalinyl, dihydronaphthalinyl, pyridyl, indolyl, benzothiazolyl, quinolinyl, isoquinolinyl, indolinyl, isoindolinyl, tetrahydroquinolinyl, dihydroisoquinolinyl, or tetrahydro-methanonaphthalenyl.

In certain embodiments, Ring A is cyclohexyl, bicycloheptanyl, pyrrolidinyl, piperidinyl, pyrazolyl, thienyl, imidazolyl, triazolyl, thiazolyl, phenyl, naphthyl, indanyl, tetrahydronaphthalinyl, dihydronaphthalinyl, pyridyl, indolyl, benzothiazolyl, quinolinyl, isoquinolinyl, indolinyl, isoindolinyl, tetrahydroquinolinyl, dihydroisoquinolinyl, or tetrahydro-methanonaphthalenyl.

In certain embodiments, Ring A is $C_{5-7}$ cycloalkyl, 5-6 membered heterocycloalkyl, pyrazolyl, thienyl, imidazolyl, triazolyl, thiazolyl, phenyl, naphthyl, indanyl, tetrahydronaphthalinyl, dihydronaphthalinyl, pyridyl, indolyl, benzothiazolyl, quinolinyl, isoquinolinyl, indolinyl, isoindolinyl, tetrahydroquinolinyl, or dihydroisoquinolinyl. In certain embodiments, Ring A is cyclohexyl, bicycloheptanyl, pyrrolidinyl, piperidinyl, pyrazolyl, thienyl, imidazolyl, triazolyl, thiazolyl, phenyl, naphthyl, indanyl, tetrahydronaphthalinyl, dihydronaphthalinyl, pyridyl, indolyl, benzothiazolyl, quinolinyl, isoquinolinyl, indolinyl, isoindolinyl, tetrahydroquinolinyl, or dihydroisoquinolinyl.

In certain embodiments, Ring A is cyclohexyl, bicycloheptanyl, pyrrolidinyl, piperidinyl, pyrazolyl, imidazolyl, triazolyl, thiazolyl, phenyl, naphthyl, indanyl, tetrahydronaphthalinyl, dihydronaphthalinyl, pyridyl, indolyl, benzothiazolyl, quinolinyl, isoquinolinyl, indolinyl, isoindolinyl, tetrahydroquinolinyl, dihydroisoquinolinyl, or tetrahydro-methanonaphthalenyl.

In certain embodiments, Ring A is cyclohexyl, bicycloheptanyl, pyrrolidinyl, piperidinyl, pyrazolyl, imidazolyl, triazolyl, thiazolyl, phenyl, naphthyl, indanyl, tetrahydronaphthalinyl, dihydronaphthalinyl, pyridyl, benzothiazolyl, quinolinyl, isoquinolinyl, indolinyl, isoindolinyl, tetrahydroquinolinyl, dihydroisoquinolinyl, or tetrahydro-methanonaphthalenyl.

In certain embodiments, Ring A is pyrazolyl, imidazolyl, triazolyl, thiazolyl, phenyl, naphthyl, indanyl, tetrahydronaphthalinyl, dihydronaphthalinyl, pyridyl, indolyl, benzothiazolyl, quinolinyl, isoquinolinyl, indolinyl, isoindolinyl, tetrahydroquinolinyl, dihydroisoquinolinyl, or tetrahydro-methanonaphthalenyl. In certain embodiments, Ring A is pyrazolyl, imidazolyl, triazolyl, thiazolyl, phenyl, naphthyl, indanyl, tetrahydronaphthalinyl, dihydronaphthalinyl, pyridyl, indolyl, benzothiazolyl, quinolinyl, isoquinolinyl, isoindolinyl, tetrahydroquinolinyl, dihydroisoquinolinyl, or tetrahydro-methanonaphthalenyl.

In certain embodiments, Ring A is pyrrolidinyl, piperidinyl, imidazolyl, triazolyl, thiazolyl, phenyl, pyridyl, or thienyl. In certain embodiments, Ring A is pyrrolidinyl, piperidinyl, imidazolyl, triazolyl, thiazolyl, phenyl, or pyridyl. In certain embodiments, Ring A is thiazolyl, phenyl, or pyridyl. In certain embodiments, Ring A is thiazolyl or phenyl. In certain embodiments, Ring A is phenyl.

In certain embodiments, Ring A is phenyl, naphthyl, indanyl, tetrahydronaphthalinyl, dihydronaphthalinyl, pyridyl, benzothiazolyl, quinolinyl, isoquinolinyl, indolinyl, isoindolinyl, tetrahydroquinolinyl, or dihydroisoquinolinyl. In certain embodiments, Ring A is phenyl, naphthyl, indanyl, tetrahydronaphthalinyl, pyridyl, benzothiazolyl, quinolinyl, indolinyl, tetrahydroquinolinyl, or dihydroisoquinolinyl. In certain embodiments, Ring A is tetrahydronaphthalinyl, dihydronaphthalinyl, benzothiazolyl, quinolinyl, isoquinolinyl, or tetrahydroquinolinyl.

In certain embodiments, Ring A is $C_{5-7}$ cycloalkyl, 5-6 membered heterocycloalkyl, pyrazolyl, imidazolyl, triazolyl, thiazolyl, phenyl, dihydronaphthalinyl, benzothiazolyl, isoquinolinyl, indolinyl, isoindolinyl, tetrahydroquinolinyl, dihydroisoquinolinyl, or tetrahydro-methanonaphthalenyl.

In certain embodiments, Ring A is $C_{5-7}$ cycloalkyl, 5-6 membered heterocycloalkyl, pyrazolyl, imidazolyl, triazolyl, thiazolyl, phenyl, dihydronaphthalinyl, benzothiazolyl, isoquinolinyl, indolinyl, isoindolinyl, tetrahydroquinolinyl, or dihydroisoquinolinyl. In certain embodiments, Ring A is pyrazolyl, imidazolyl, triazolyl, thiazolyl, phenyl, dihydronaphthalinyl, benzothiazolyl, isoquinolinyl, indolinyl, isoindolinyl, tetrahydroquinolinyl, or dihydroisoquinolinyl. In certain embodiments, Ring A is pyrazolyl, imidazolyl, triazolyl, thiazolyl, phenyl, benzothiazolyl, or isoquinolinyl.

In certain embodiments, when Ring B is present, then Ring A is optionally substituted with one or two halo, alkyl, alkoxy, or haloalkoxy;

In certain embodiments, when Ring B is not present and Ring A is phenyl, then Ring A is substituted with: (i) one or two $R^{AA}$ groups, or (ii) 2 halo groups when L is other than O.

In certain embodiments, each $R^{AA}$ is independently alkyl, haloalkyl, haloalkoxy, cycloalkyloxy, (cycloalkyl)alkoxy, or phenoxy optionally substituted with one or two halo. In certain embodiments, when Ring B is not present and Ring A is other than phenyl, then Ring A is optionally substituted with one or two $R^{AB}$ groups.

In certain embodiments, when Ring B is not present and Ring A is other than phenyl, then Ring A is substituted with one or two $R^{AB}$ groups.

In certain embodiments, each $R^{AB}$ is independently halo, alkyl, hydroxy, alkoxy, haloalkyl, haloalkoxy, cycloalkyloxy, (cycloalkyl)alkoxy, or phenoxy optionally substituted with one or two halo.

In certain embodiments, when Ring B is not present, Ring A is pyrazolyl, imidazolyl, triazolyl, thiazolyl, phenyl, naphthyl, indanyl, tetrahydronaphthalinyl, dihydronaphthalinyl, pyridyl, indolyl, benzothiazolyl, quinolinyl, isoquinolinyl, isoindolinyl, tetrahydroquinolinyl, dihydroisoquinolinyl, or tetrahydro-methanonaphthalenyl; wherein Ring A is substituted with one or two groups independently selected from halo, alkyl, alkoxy, haloalkyl, haloalkoxy, cycloalkyloxy, (cycloalkyl)alkoxy, and phenoxy substituted with one or two chloro groups. In certain embodiments, when Ring B is not present, Ring A is phenyl, naphthyl, indanyl, tetrahydronaphthalinyl, pyridyl, benzothiazolyl, quinolinyl, isoquinolinyl, isoindolinyl, tetrahydroquinolinyl, or dihydroisoquinolinyl; wherein Ring A is substituted with one or two groups independently selected from halo, alkyl, alkoxy, haloalkyl, haloalkoxy, cycloalkyloxy, (cycloalkyl)alkoxy, and phenoxy substituted with one or two chloro groups. In certain embodiments, when Ring B is not present, Ring A is phenyl, naphthyl, pyridyl, benzothiazolyl, quinolinyl, or isoquinolinyl; wherein Ring A is substituted with one or two groups independently selected from halo, alkyl, alkoxy, haloalkyl, haloalkoxy, cycloalkyloxy, (cycloalkyl)alkoxy, and phenoxy substituted with one or two chloro groups. In certain embodiments, when Ring B is not present, Ring A is phenyl substituted with one or two groups independently selected from halo, alkyl, alkoxy, haloalkyl, haloalkoxy, cycloalkyloxy, (cycloalkyl)alkoxy, and phenoxy substituted with one or two chloro groups. In certain embodiments, when Ring B is not present, Ring A is phenyl substituted with one or two groups independently selected from chloro, fluoro, trifluoromethoxy, cyclopentyloxy, and phenoxy substituted with one or two chloro groups.

In certain embodiments, Ring B, when present, is cycloalkyl, heterocycloalkyl, aryl, or heteroaryl; wherein each is optionally substituted with one or two $R^B$ groups.

In certain embodiments, each $R^B$ is independently halo, cyano, alkyl, haloalkyl, alkoxy, haloalkoxy, alkylcarbonyl, alkoxyalkoxy, alkylcarbonylaminoalkoxy, cycloalkyl, (cycloalkyl)alkyl, cycloalkyloxy, (cycloalkyl)alkoxy, cycloalkylcarbonyl, cycloalkylcarbonyloxy, heterocycloalkyl optionally substituted with alkyl or alkylcarbonyl, (5-6-membered heterocycloalkyl-one)alkyl, (heterocycloalkyl)alkyl, or heterocycloalkylcarbonyl.

In certain embodiments, Ring B is heterocycloalkyl, aryl, or heteroaryl. In certain embodiments, Ring B is 5-6 membered heterocycloalkyl, aryl, or heteroaryl. In certain embodiments, Ring B is 5-6 membered heterocycloalkyl, phenyl, or heteroaryl. In certain embodiments, Ring B is 5-6 membered heterocycloalkyl, phenyl, pyridyl, quinolinyl, or isoquinolinyl. In certain embodiments, Ring B is 5-6 membered heterocycloalkyl, phenyl, or quinolinyl. In certain embodiments, Ring B is piperidinyl, piperazinyl, phenyl, or heteroaryl. In certain embodiments, Ring B is piperidinyl, piperazinyl, phenyl, pyridyl, quinolinyl, or isoquinolinyl. In certain embodiments, Ring B is piperidinyl, piperazinyl, phenyl, or quinolinyl. In certain embodiments, Ring B is phenyl, pyridyl, quinolinyl, or isoquinolinyl. In certain embodiments, Ring B is phenyl or quinolinyl. In certain embodiments, Ring B is phenyl.

In certain embodiments, Ring B is heterocycloalkyl, aryl, or heteroaryl; each substituted with one or two $R^B$ groups, where each $R^B$ is independently halo, alkyl, haloalkyl, alkoxy, haloalkoxy, cycloalkyloxy, heterocycloalkyl, (heterocycloalkyl)alkyl, or heterocycloalkylcarbonyl. In certain embodiments, Ring B is piperidinyl, piperazinyl, phenyl, or quinolinyl; each substituted with one or two $R^B$ groups, where each $R^B$ is independently halo, alkyl, haloalkyl, alkoxy, haloalkoxy, cycloalkyloxy, heterocycloalkyl, (heterocycloalkyl)alkyl, or heterocycloalkylcarbonyl.

In certain embodiments, Ring B is piperidinyl, piperazinyl, phenyl, or quinolinyl; each substituted with one or two $R^B$ groups, where each $R^B$ is independently chloro, bromo, fluoro, methyl, trifluoromethyl, methoxy, isopropoxy, trifluoromethoxy, cyclopropoxy, cyclopentoxy, piperidinyl, piperidinylalkyl, or piperidinylcarbonyl. In certain embodiments, Ring B is phenyl or quinolinyl; each substituted with one or two $R^B$ groups, where each $R^B$ is independently chloro, bromo, fluoro, methyl, trifluoromethyl, methoxy, isopropoxy, trifluoromethoxy, cyclopropoxy, cyclopentoxy, piperidinyl, piperidinylalkyl, or piperidinylcarbonyl. In certain embodiments, Ring B is phenyl substituted with one or two $R^B$ groups, where each $R^B$ is independently chloro, bromo, fluoro, methyl, trifluoromethyl, methoxy, isopropoxy, trifluoromethoxy, cyclopropoxy, cyclopentoxy, piperidinyl, piperidinylalkyl, or piperidinylcarbonyl. In certain embodiments, Ring B is phenyl substituted with one or two $R^B$ groups, where each $R^B$ is independently chloro, bromo, trifluoromethyl, methoxy, isopropoxy, trifluoromethoxy, or cyclopropoxy. In certain embodiments, Ring B is phenyl substituted with one or two $R^B$ groups, where each $R^B$ is independently chloro, trifluoromethyl, methoxy, or trifluoromethoxy.

In certain embodiments, when L is S and Ring A is phenyl, then Ring B cannot be halo-substituted phenyl.

In certain embodiments, when L is O, Ring A is phenyl, and Ring B is not present, then $R^{AA}$ cannot be alkyl or trifluoromethyl;

In certain embodiments, when L is O, Ring A is phenyl, Ring B is not present, and $R^1$ is ethyl, then $R^{AA}$ cannot be trifluoromethoxy.

In certain embodiments, when L is NH, Ring A is pyridyl, indolyl, or indolinyl, and Ring B is not present, then $R^{AB}$ cannot be alkyl.

In certain embodiments, $R^1$ is hydrogen, alkyl, cycloalkyl, heterocycloalkyl, or W; where W is alkyl substituted with amino, alkylamino, dialkylamino, alkylcarbonyloxy, alkoxycarbonyl, or phenylcarbonyloxy.

In certain embodiments, $R^1$ is hydrogen, alkyl, cycloalkyl, or heterocycloalkyl. In certain embodiments, $R^1$ is hydrogen or alkyl. In certain embodiments, $R^1$ is hydrogen. In certain embodiments, $R^1$ is alkyl. In certain embodiments, $R^1$ is W; where W is alkyl substituted with amino, alkylamino, dialkylamino, alkylcarbonyloxy, alkoxycarbonyl, or phenylcarbonyloxy. In certain embodiments, $R^1$ is W; where W is alkyl substituted with dialkylamino or alkylcarbonyloxy.

In one aspect, provided herein is a compound of Formula (I):

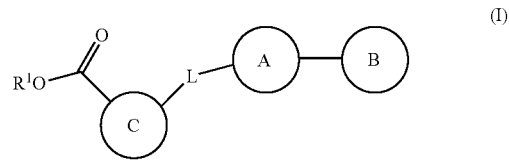

wherein:

ring C is selected from:

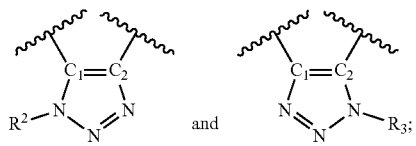

wherein the wavy lines (〜) indicate the points of attachment of the $C_1$ carbon to the carbonyl of C(O)—OR$^1$, and the $C_2$ carbon to L;

L is a bond, $CH_2$, $CF_2$, O, $NR^L$, S, S(=O), C(=O), $CH_2$-Q, or Q-$CH_2$; wherein Q is O, $NR^L$, or S;

$R^L$ is hydrogen, $C_{1-4}$ alkyl, $C_{3-6}$ cycloalkyl, phenyl, or benzyl; wherein the $C_{1-4}$ alkyl is optionally substituted with hydroxycarbonyl, alkoxycarbonyl, hydroxycarbonylalkyl, or alkylcarbonyloxy; and the phenyl group alone or as part of the benzyl group is optionally substituted with one or two groups selected from halo and haloalkoxy;

Ring A is $C_{3-7}$ cycloalkyl, $C_{8-11}$ spirocycloalkyl, 5-8 membered heterocycloalkyl, pyrazolyl, imidazolyl, triazolyl, thiazolyl, thienyl, phenyl, naphthyl, indanyl, tetrahydronaphthyl, dihydronaphthyl, pyridyl, indolyl, benzothiazolyl, quinolinyl, isoquinolinyl, indolinyl, isoindolinyl, tetrahydroquinolinyl, dihydroisoquinolinyl, tetrahydroisoquinolinyl, 2,3-dihydrobenzo[b][1,4]dioxinyl, or tetrahydro-methanonaphthalenyl;

Ring B is present or not present; wherein:

when Ring B is present, then Ring A is optionally substituted with one or two groups selected from halo, alkyl, alkoxy, haloalkoxy, (cycloalkyl)alkoxy, and cycloalkyl;

when Ring B is not present and Ring A is phenyl, then Ring A is substituted with:
(i) one or two R groups;
(ii) 2 halo groups when L is other than O;
(iii) 2 halo groups when L is O, and $R^2$ and $R^3$ are not hydrogen or alkyl;
(iv) one halo group when L is $CH_2NR^L$;
(v) one halo group and one group selected from the group consisting of haloalkoxy, cycloalkyloxy, (cycloalkyl)alkoxy, and (phenyl)alkoxy, when L is bond, O, S, or S(=O), wherein the phenyl as part of the (phenyl)alkoxy group is optionally substituted with halo, haloalkyl, haloalkoxy, or cyano; or
(vi) one cyano group and one (phenyl)alkoxy group, when L is bond, O, wherein the phenyl as part of the (phenyl)alkoxy group is optionally substituted with halo or haloalkoxy;
when Ring B is not present and Ring A is other than phenyl, then
(i) Ring A is substituted with one or two R groups or
(ii) Ring A is unsubstituted, wherein:
5) when Ring A is unsubstituted tetrahydroquinolinyl, then L is a bond;
6) when Ring A is unsubstituted 2,3-dihydrobenzo[b][1,4]dioxinyl, then L is O;
7) when Ring A is unsubstituted tetrahydronaphthyl, then L is O, and $R^1$ is not hydrogen or ethyl; or
8) when Ring A is unsubstituted spirocycloalkyl, then L is O or S;
each $R^{AA}$ is independently alkyl; haloalkyl; haloalkoxy; cycloalkyloxy; (cycloalkyl)alkoxy; or phenoxy optionally substituted with one or two halo groups; or alkylcarbonylaminoalkoxy;
each $R^{AB}$ is independently halo; alkyl; hydroxy; alkoxy; haloalkyl; haloalkoxy; cycloalkyloxy; (cycloalkyl)alkoxy; or phenoxy optionally substituted with one or two halo groups;
Ring B, when present, is cycloalkyl, heterocycloalkyl, aryl, or heteroaryl; wherein each is optionally substituted with 1, 2, or 3 $R^B$ groups;
each $R^B$ is independently halo; cyano; alkyl; alkylsulfonyl; aminosulfonyl; alkylaminosulfonyl; dialkylaminosulfonyl; haloalkyl; alkoxy; haloalkoxy; alkylcarbonyl; alkoxyalkoxy; aminocarbonyl; alkylaminocarbonyl; dialkylaminocarbonyl; alkylcarbonylaminoalkoxy; cycloalkyl; (cycloalkyl)alkyl; cycloalkyloxy; (cycloalkyl)alkoxy; cycloalkylcarbonyl; cycloalkylcarbonyloxy; heterocycloalkyl optionally substituted with one or two groups independently selected from halo, alkyl, and alkylcarbonyl; (5-6-membered heterocycloalkyl-one)alkyl; 5-6-membered heterocycloalkyl-one; (heterocycloalkyl)alkyl; heterocycloalkylcarbonyl; or 5-6 membered heteraminooaryl;
$R^1$ is hydrogen, alkyl, cycloalkyl, heterocycloalkyl, or W; wherein W is alkyl substituted with amino, alkylamino, dialkylamino, alkylcarbonyloxy, alkoxycarbonyl, phenylcarbonyloxy, aminocarbonyloxy, alkylaminocarbonyloxy, dialkylaminocarbonyloxy, alkoxycarbonyloxy, cycloalkylcarbonyloxy, —N($R^{1A}$)C(O)$R^{1B}$, —N($R^{1A}$)C(O)O$R^{1B}$, or —N($R^{1A}$)C(O)N$R^{1B}R^{1C}$; wherein $R^{1A}$, $R^{1B}$, and $R^{1C}$ are each independently hydrogen or $C_{1-6}$ alkyl;
$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;

provided:
i. when L is S or $CH_2$, and Ring A is phenyl, then Ring B cannot be halo-substituted phenyl;
ii. when L is O, Ring A is phenyl, and Ring B is not present, then $R^{AA}$ cannot be alkyl;
iii. when L is O, Ring A is phenyl substituted with 1 $R^{AA}$, and Ring B is not present, then $R^{AA}$ cannot be meta-substituted trifluoromethyl;
iv. when L is O, Ring A is phenyl, Ring B is not present, and $R^1$ is ethyl, then $R^{AA}$ cannot be trifluoromethoxy;
v. when L is bond, Ring A is other than phenyl, Ring B is not present, and $R^1$ is H, then $R^{AB}$ cannot be methyl, and
vi. when L is NH, Ring A is pyridyl, indolyl, or indolinyl, and Ring B is not present, then $R^{AB}$ cannot be alkyl; and
optionally a single stereoisomer or mixture of stereoisomers thereof and additionally optionally a pharmaceutically acceptable salt thereof.

In certain embodiments, the compound of Formula (I):

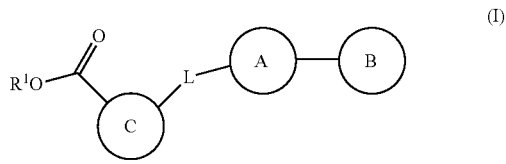

is that wherein:
ring C is selected from:

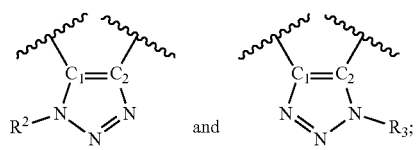

wherein the wavy lines (〰) indicate the points of attachment of the $C_1$ carbon to the carbonyl of C(O)—O$R^1$, and the $C_2$ carbon to L;
L is a bond, $CH_2$, $CF_2$, O, $NR^L$, S, S(=O), C(=O), $CH_2$-Q, or Q-$CH_2$; wherein Q is O, $NR^L$, or S;
$R^L$ is hydrogen, $C_{1-4}$ alkyl, $C_{3-6}$ cycloalkyl, phenyl, or benzyl; wherein the $C_{1-4}$ alkyl is optionally substituted with hydroxycarbonyl, alkoxycarbonyl, or alkylcarbonyloxy; and the phenyl group alone or as a part of the benzyl group is optionally substituted with one or two groups selected from halo and haloalkoxy;
Ring A is cycloalkyl, spirocycloalkyl, heterocycloalkyl, aryl, or heteroaryl, each is optionally substituted with 1 or 2 $R^{AA}$ groups;
when Ring B is present, then Ring A is optionally substituted with one or two groups selected from halo, alkyl, alkoxy, haloalkoxy, (cycloalkyl)alkoxy, and cycloalkyl;
each $R^{AA}$ is independently alkyl; halo; hydroxy; alkoxy; haloalkyl; haloalkoxy; cycloalkyloxy; (cycloalkyl)alkoxy; alkylcarbonylaminoalkoxy; phenoxy optionally substituted with one or two halo; or (phenyl)alkoxy wherein the phenyl is optionally substituted with halo, cyano, haloalkyl, or haloalkoxy;
Ring B, when present, is cycloalkyl, heterocycloalkyl, aryl, or heteroaryl; wherein each is optionally substituted with 1, 2, or 3 $R^B$ groups;

each $R^B$ is independently halo; cyano; alkyl; alkylsulfonyl; aminosulfonyl; alkylaminosulfonyl; dialkylaminosulfonyl; haloalkyl; alkoxy; haloalkoxy; alkylcarbonyl; alkoxyalkoxy; aminocarbonyl; alkylaminocarbonyl; dialkylaminocarbonyl; alkylcarbonylaminoalkoxy; cycloalkyl; (cycloalkyl)alkyl; cycloalkyloxy; (cycloalkyl)alkoxy; cycloalkylcarbonyl; cycloalkylcarbonyloxy; heterocycloalkyl optionally substituted with one or two groups independently selected from halo, alkyl, and alkylcarbonyl; (5-6-membered heterocycloalkyl-one)alkyl; 5-6-membered heterocycloalkyl-one; (heterocycloalkyl)alkyl; heterocycloalkylcarbonyl; or 5-6 membered heteroaryl;

$R^1$ is hydrogen, alkyl, cycloalkyl, heterocycloalkyl, or W; wherein W is alkyl substituted with amino, alkylamino, dialkylamino, alkylcarbonyloxy, alkoxycarbonyl, phenylcarbonyloxy, aminocarbonyloxy, alkylaminocarbonyloxy, dialkylaminocarbonyloxy, alkoxycarbonyloxy, cycloalkylcarbonyloxy, —N($R^{1A}$)C(O)$R^{1B}$, —N($R^{1A}$)C(O)OR$^{1B}$, or —N($R^{1A}$)C(O)NR$^{1B}$R$^{1C}$; wherein $R^{1A}$, $R^{1B}$, and $R^{1C}$ are each independently hydrogen or $C_{1-6}$ alkyl;

$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl; and optionally a single stereoisomer or mixture of stereoisomers thereof and additionally optionally a pharmaceutically acceptable salt thereof.

In certain embodiments, the compound of Formula (I) is that wherein:

L is a bond, $CH_2$, $CF_2$, O, $NR^L$, S, S(=O), C(=O), $CH_2$-Q, or Q-$CH_2$; wherein Q is O, $NR^L$, or S;

$R^L$ is hydrogen, $C_{1-4}$ alkyl, $C_{3-6}$ cycloalkyl, phenyl, or benzyl; wherein the $C_{1-4}$ alkyl is optionally substituted with hydroxycarbonyl, alkoxycarbonyl, or alkylcarbonyloxy; and the phenyl group alone or as a part of the benzyl group is optionally substituted with one or two groups selected from halo and haloalkoxy;

when Ring B is present, then Ring A is optionally substituted with one or two groups selected from halo, alkyl, alkoxy, haloalkoxy, (cycloalkyl)alkoxy, and cycloalkyl;

Ring A is cycloalkyl, spirocycloalkyl, heterocycloalkyl, aryl, or heteroaryl, each is optionally substituted with 1 or 2 $R^{AA}$ groups;

each $R^{AA}$ is independently alkyl; halo; hydroxy; alkoxy; haloalkyl; haloalkoxy; cycloalkyloxy; (cycloalkyl)alkoxy; alkylcarbonylaminoalkoxy; phenoxy optionally substituted with one or two halo; or (phenyl)alkoxy wherein the phenyl is optionally substituted with halo, cyano, haloalkyl, or haloalkoxy;

Ring B, when present, is cycloalkyl, heterocycloalkyl, aryl, or heteroaryl; wherein each is optionally substituted with 1, 2, or 3 $R^B$ groups;

each $R^B$ is independently halo; cyano; alkyl; alkylsulfonyl; aminosulfonyl; alkylaminosulfonyl; dialkylaminosulfonyl; haloalkyl; alkoxy; haloalkoxy; alkylcarbonyl; alkoxyalkoxy; aminocarbonyl; alkylaminocarbonyl; dialkylaminocarbonyl; alkylcarbonylaminoalkoxy; cycloalkyl; (cycloalkyl)alkyl; cycloalkyloxy; (cycloalkyl)alkoxy; cycloalkylcarbonyl; cycloalkylcarbonyloxy; heterocycloalkyl optionally substituted with one or two groups independently selected from halo, alkyl, and alkylcarbonyl; (5-6-membered heterocycloalkyl-one)alkyl; 5-6-membered heterocycloalkyl-one; (heterocycloalkyl)alkyl; heterocycloalkylcarbonyl; or 5-6 membered heteroaryl;

$R^1$ is W; wherein W is alkyl substituted with amino, alkylamino, dialkylamino, alkylcarbonyloxy, alkoxycarbonyl, phenylcarbonyloxy, aminocarbonyloxy, alkylaminocarbonyloxy, dialkylaminocarbonyloxy, alkoxycarbonyloxy, cycloalkylcarbonyloxy, —N($R^{1A}$)C(O)$R^{1B}$, —N($R^{1A}$)C(O)OR$^{1B}$, or —N($R^{1A}$)C(O)NR$^{1B}$R$^{1C}$; wherein $R^{1A}$, $R^{1B}$, and $R^{1C}$ are each independently hydrogen or $C_{1-6}$ alkyl;

$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;

optionally a single stereoisomer or mixture of stereoisomers thereof and additionally optionally a pharmaceutically acceptable salt thereof.

In certain embodiments, the compound of Formula (I) is that wherein:

L is a bond, $CH_2$, $CF_2$, O, $NR^L$, S, S(=O), C(=O), $CH_2$-Q, or Q-$CH_2$; wherein Q is O, $NR^L$, or S;

$R^L$ is hydrogen, $C_{1-4}$ alkyl, $C_{3-6}$ cycloalkyl, phenyl, or benzyl; wherein the $C_{1-4}$ alkyl is optionally substituted with hydroxycarbonyl, alkoxycarbonyl, hydroxycarbonylalkyl, or alkylcarbonyloxy; and the phenyl group alone or as a part of the benzyl group is optionally substituted with one or two groups selected from halo and haloalkoxy;

Ring A is $C_{3-7}$ cycloalkyl, $C_{8-11}$ spirocycloalkyl, 5-6 membered heterocycloalkyl, pyrazolyl, imidazolyl, triazolyl, thiazolyl, thienyl, phenyl, naphthyl, indanyl, tetrahydronaphthyl, dihydronaphthyl, pyridyl, indolyl, benzothiazolyl, quinolinyl, isoquinolinyl, indolinyl, isoindolinyl, tetrahydroquinolinyl, dihydroisoquinolinyl, tetrahydroisoquinolinyl, 2,3-dihydrobenzo[b][1,4]dioxinyl, or tetrahydro-methanonaphthalenyl;

Ring B is present or not present; wherein:

when Ring B is present, then Ring A is optionally substituted with one or two groups selected from halo, alkyl, alkoxy, haloalkoxy, (cycloalkyl)alkoxy, and cycloalkyl;

when Ring B is not present and Ring A is phenyl, then Ring A is substituted with:
  (i) one or two $R^{AA}$ groups,
  (ii) 2 halo groups when L is other than O,
  (iii) 2 halo groups when L is O, and $R^2$ and $R^3$ are not hydrogen or alkyl,
  (iv) one halo group when L is $CH_2NR^L$, or
  (v) one halo group and one group selected from the group consisting of haloalkoxy, (cycloalkyl)alkoxy, and (phenyl)alkoxy, when L is bond, O or S, wherein the phenyl is optionally substituted with halo;

when Ring B is not present and Ring A is other than phenyl, then Ring A is optionally substituted with one or two $R^{AB}$ groups;

each $R^{AA}$ is independently alkyl; haloalkyl; haloalkoxy; cycloalkyloxy; (cycloalkyl)alkoxy; alkylcarbonylaminoalkoxy; or phenoxy optionally substituted with one or two halo;

each $R^{AB}$ is independently halo; alkyl; hydroxy; alkoxy; haloalkyl; haloalkoxy; cycloalkyloxy; (cycloalkyl)alkoxy; or phenoxy optionally substituted with one or two halo;

Ring B, when present, is cycloalkyl, heterocycloalkyl, aryl, or heteroaryl; wherein each is optionally substituted with 1, 2, or 3 $R^B$ groups;

each $R^B$ is independently halo; cyano; alkyl; alkylsulfonyl; aminosulfonyl; alkylaminosulfonyl; dialkylaminosulfonyl; haloalkyl; alkoxy; haloalkoxy; alkylcarbonyl; alkoxyalkoxy; aminocarbonyl; alkylaminocarbonyl; dialkylaminocarbonyl; alkylcarbonylaminoalkoxy; cycloalkyl; (cycloalkyl)alkyl; cycloalkyloxy; (cycloalkyl)alkoxy; cycloalkylcarbonyl; cycloalkylcarbonyloxy; heterocycloalkyl optionally substituted with one or two groups independently selected from halo, alkyl, and alkylcarbonyl; (5-6-membered heterocycloalkyl-one)alkyl; 5-6-membered heterocycloalkyl-one; (heterocycloalkyl)alkyl; heterocycloalkylcarbonyl; or 5-6 membered heteroaryl;

$R^1$ is hydrogen, alkyl, cycloalkyl, heterocycloalkyl, or W; wherein W is alkyl substituted with amino, alkylamino, dialkylamino, alkylcarbonyloxy, alkoxycarbonyl, phenylcarbonyloxy, aminocarbonyloxy, alkylaminocarbonyloxy, dialkylaminocarbonyloxy, alkoxycarbonyloxy, cycloalkylcarbonyloxy, —N($R^{1A}$)C(O)$R^{1B}$, —N($R^{1A}$)C(O)O$R^{1B}$, or —N($R^{1A}$)C(O)N$R^{1B}R^{1C}$; wherein $R^{1A}$, $R^{1B}$, and $R^{1C}$ are each independently hydrogen or $C_{1-6}$ alkyl;

$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;

provided:
i. when L is S or $CH_2$, and Ring A is phenyl, then Ring B cannot be halo-substituted phenyl;
ii. when L is O, Ring A is phenyl, and Ring B is not present, then $R^{AA}$ cannot be alkyl;
iii. when L is O, Ring A is phenyl substituted with 1 $R^{AA}$, and Ring B is not present, then $R^{AA}$ cannot be meta-substituted trifluoromethyl;
iv. when L is O, Ring A is phenyl, Ring B is not present, and $R^1$ is ethyl, then $R^{AA}$ cannot be trifluoromethoxy;
v. when L is bond, Ring A is other than phenyl, Ring B is not present, and $R^1$ is H, then $R^{AB}$ cannot be methyl, and
vi. when L is NH, Ring A is pyridyl, indolyl, or indolinyl, and Ring B is not present, then $R^{AB}$ cannot be alkyl; and optionally a single stereoisomer or mixture of stereoisomers thereof and additionally optionally a pharmaceutically acceptable salt thereof.

In certain embodiments, the compound of Formula (I) is that wherein:

L is a bond, $CH_2$, $CF_2$, O, $NR^L$, S, S(=O), C(=O), $CH_2$-Q, or Q-$CH_2$; wherein Q is O, $NR^L$, or S;

$R^L$ is hydrogen, $C_{1-4}$ alkyl, $C_{3-6}$ cycloalkyl, phenyl, or benzyl; wherein the $C_{1-4}$ alkyl is optionally substituted with hydroxycarbonyl, alkoxycarbonyl, hydroxycarbonylalkyl, or alkylcarbonyloxy; and the phenyl group alone or as a part of the benzyl group is optionally substituted with one or two groups selected from halo and haloalkoxy;

Ring A is $C_{3-7}$ cycloalkyl, $C_{8-11}$ spirocycloalkyl, 5-8 membered heterocycloalkyl, pyrazolyl, imidazolyl, triazolyl, thiazolyl, thienyl, phenyl, naphthyl, indanyl, tetrahydronaphthyl, dihydronaphthyl, pyridyl, indolyl, benzothiazolyl, quinolinyl, isoquinolinyl, indolinyl, isoindolinyl, tetrahydroquinolinyl, dihydroisoquinolinyl, tetrahydroisoquinolinyl, 2,3-dihydrobenzo[b][1,4]dioxinyl, or tetrahydro-methanonaphthalenyl;

Ring B is present or not present; wherein:
when Ring B is present, then Ring A is optionally substituted with one or two groups selected from halo, alkyl, alkoxy, haloalkoxy, (cycloalkyl)alkoxy, and cycloalkyl;
when Ring B is not present and Ring A is phenyl, then Ring A is substituted with:
(i) one or two $R^{AA}$ groups,
(ii) 2 halo groups when L is other than O,
(iii) 2 halo groups when L is O, and $R^2$ and $R^3$ are not hydrogen or alkyl,
(iv) one halo group when L is $CH_2NR^L$, or
(v) one halo group and one group selected from the group consisting of haloalkoxy, (cycloalkyl)alkoxy, and (phenyl)alkoxy, when L is bond, O or S, wherein the phenyl is optionally substituted with halo;
when Ring B is not present and Ring A is other than phenyl, then
(i) Ring A is substituted with one or two $R^{AB}$ groups or
(ii) Ring A is unsubstituted, wherein:
1) when Ring A is unsubstituted tetrahydroquinolinyl, then L is bond;
2) when Ring A is unsubstituted 2,3-dihydrobenzo[b][1,4]dioxinyl, then L is O;
3) when Ring A is unsubstituted tetrahydronaphthyl, then L is O, and $R^1$ is not hydrogen or ethyl; or
4) when Ring A is unsubstituted spirocycloalkyl, then L is O or S;

each $R^{AA}$ is independently alkyl; haloalkyl; haloalkoxy; cycloalkyloxy; (cycloalkyl)alkoxy; phenoxy optionally substituted with one or two halo; or alkylcarbonylaminoalkoxy;

each $R^{AB}$ is independently halo; alkyl; hydroxy; alkoxy; haloalkyl; haloalkoxy; cycloalkyloxy; (cycloalkyl)alkoxy; or phenoxy optionally substituted with one or two halo;

Ring B, when present, is cycloalkyl, heterocycloalkyl, aryl, or heteroaryl; wherein each is optionally substituted with 1, 2, or 3 $R^B$ groups;

each $R^B$ is independently halo; cyano; alkyl; alkylsulfonyl; aminosulfonyl; alkylaminosulfonyl; dialkylaminosulfonyl; haloalkyl; alkoxy; haloalkoxy; alkylcarbonyl; alkoxyalkoxy; aminocarbonyl; alkylaminocarbonyl; dialkylaminocarbonyl; alkylcarbonylaminoalkoxy; cycloalkyl; (cycloalkyl)alkyl; cycloalkyloxy; (cycloalkyl)alkoxy; cycloalkylcarbonyl; cycloalkylcarbonyloxy; heterocycloalkyl optionally substituted with one or two groups independently selected from halo, alkyl, and alkylcarbonyl; (5-6-membered heterocycloalkyl-one)alkyl; 5-6-membered heterocycloalkyl-one; (heterocycloalkyl)alkyl; heterocycloalkylcarbonyl; or 5-6 membered heteroaryl;

$R^1$ is hydrogen, alkyl, cycloalkyl, heterocycloalkyl, or W; wherein W is alkyl substituted with amino, alkylamino, dialkylamino, alkylcarbonyloxy, alkoxycarbonyl, phenylcarbonyloxy, aminocarbonyloxy, alkylaminocarbonyloxy, dialkylaminocarbonyloxy, alkoxycarbonyloxy, cycloalkylcarbonyloxy, —N($R^{1A}$)C(O)$R^{1B}$, —N($R^{1A}$)C(O)O$R^{1B}$, or —N($R^{1A}$)C(O)N$R^{1B}R^{1C}$; wherein $R^{1A}$, $R^{1B}$, and $R^{1C}$ are each independently hydrogen or $C_{1-6}$ alkyl;

$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;

provided:
  i. when L is S or CH$_2$, and Ring A is phenyl, then Ring B cannot be halo-substituted phenyl;
  ii. when L is O, Ring A is phenyl, and Ring B is not present, then R$^{AA}$ cannot be alkyl;
  iii. when L is O, Ring A is phenyl substituted with 1 R$^{AA}$, and Ring B is not present, then R$^{AA}$ cannot be meta-substituted trifluoromethyl;
  iv. when L is O, Ring A is phenyl, Ring B is not present, and R$^1$ is ethyl, then R$^{AA}$ cannot be trifluoromethoxy;
  v. when L is bond, Ring A is other than phenyl, Ring B is not present, and R$^1$ is H, then R$^{AB}$ cannot be methyl, and
  vi. when L is NH, Ring A is pyridyl, indolyl, or indolinyl, and Ring B is not present, then R$^{AB}$ cannot be alkyl; and
optionally a single stereoisomer or mixture of stereoisomers thereof and additionally optionally a pharmaceutically acceptable salt thereof.

In certain embodiments, the compound of Formula (I) is that wherein:

L is a bond, CH$_2$, CF$_2$, O, NR$^L$, S, S(=O), C(=O), CH$_2$-Q, or Q-CH$_2$; wherein Q is O, NR$^L$, or S;

R$^L$ is hydrogen, C$_{1-4}$ alkyl, C$_{3-6}$ cycloalkyl, phenyl, or benzyl; wherein the C$_{1-4}$ alkyl is optionally substituted with hydroxycarbonyl, alkoxycarbonyl, hydroxycarbonylalkyl, or alkylcarbonyloxy; and the phenyl group alone or as a part of the benzyl group is optionally substituted with one or two groups selected from halo and haloalkoxy;

Ring A is C$_{3-7}$ cycloalkyl, C$_{8-11}$ spirocycloalkyl, 5-6 membered heterocycloalkyl, pyrazolyl, imidazolyl, triazolyl, thiazolyl, thienyl, phenyl, naphthyl, indanyl, tetrahydronaphthyl, dihydronaphthyl, pyridyl, indolyl, benzothiazolyl, quinolinyl, isoquinolinyl, indolinyl, isoindolinyl, tetrahydroquinolinyl, dihydroisoquinolinyl, tetrahydroisoquinolinyl, 2,3-dihydrobenzo[b][1,4]dioxinyl, or tetrahydro-methanonaphthalenyl;

Ring B is present or not present; wherein:
when Ring B is present, then Ring A is optionally substituted with one or two groups selected from halo, alkyl, alkoxy, haloalkoxy, (cycloalkyl)alkyl, and cycloalkyl;
when Ring B is not present and Ring A is phenyl, then Ring A is substituted with:
  (i) one or two R$^{AA}$ groups,
  (ii) 2 halo groups when L is other than O,
  (iii) 2 halo groups when L is O, and R$^2$ and R$^3$ are not hydrogen or alkyl,
  (iv) one halo group when L is CH$_2$NR$^L$, or
  (v) one halo group and one group selected from the group consisting of haloalkoxy, (cycloalkyl)alkoxy, and (phenyl)alkoxy, when L is bond, O or S, wherein the phenyl is optionally substituted with halo;
when Ring B is not present and Ring A is other than phenyl, then
  (i) Ring A is substituted with one or two R groups or
  (ii) Ring A is unsubstituted, wherein:
    1) when Ring A is unsubstituted tetrahydroquinolinyl, then L is bond;
    2) when Ring A is unsubstituted 2,3-dihydrobenzo[b][1,4]dioxinyl, then L is O;
    3) when Ring A is unsubstituted tetrahydronaphthyl, then L is O, and R$^1$ is not hydrogen or ethyl; or
    4) when Ring A is unsubstituted spirocycloalkyl, then L is O or S;

each R$^{AA}$ is independently alkyl; haloalkyl; haloalkoxy; cycloalkyloxy; (cycloalkyl)alkoxy; phenoxy optionally substituted with one or two halo; or alkylcarbonylaminoalkoxy;

each R$^{AB}$ is independently halo; alkyl; hydroxy; alkoxy; haloalkyl; haloalkoxy; cycloalkyloxy; (cycloalkyl)alkoxy; or phenoxy optionally substituted with one or two halo;

Ring B, when present, is cycloalkyl, heterocycloalkyl, aryl, or heteroaryl; wherein each is optionally substituted with 1, 2, or 3 R$^B$ groups;

each R$^B$ is independently halo; cyano; alkyl; alkylsulfonyl; aminosulfonyl; alkylaminosulfonyl; dialkylaminosulfonyl; haloalkyl; alkoxy; haloalkoxy; alkylcarbonyl; alkoxyalkoxy; aminocarbonyl; alkylaminocarbonyl; dialkylaminocarbonyl; alkylcarbonylaminoalkoxy; cycloalkyl; (cycloalkyl)alkyl; cycloalkyloxy; (cycloalkyl)alkoxy; cycloalkylcarbonyl; cycloalkylcarbonyloxy; heterocycloalkyl optionally substituted with 1 or 2 groups independently selected from halo, alkyl, and alkylcarbonyl; (5-6-membered heterocycloalkyl-one)alkyl; 5-6-membered heterocycloalkyl-one; (heterocycloalkyl)alkyl; heterocycloalkylcarbonyl; or 5-6 membered heteroaryl;

R$^1$ is hydrogen, alkyl, cycloalkyl, heterocycloalkyl, or W; wherein W is alkyl substituted with amino, alkylamino, dialkylamino, alkylcarbonyloxy, alkoxycarbonyl, phenylcarbonyloxy, aminocarbonyloxy, alkylaminocarbonyloxy, dialkylaminocarbonyloxy, alkoxycarbonyloxy, cycloalkylcarbonyloxy, —N(R$^{1A}$)C(O)R$^{1B}$, —N(R$^{1A}$)C(O)OR$^{1B}$, or —N(R$^{1A}$)C(O)NR$^{1B}$R$^{1C}$; wherein R$^{1A}$, R$^{1B}$, and R$^{1C}$ are each independently hydrogen or C$_{1-6}$ alkyl;

R$^2$ and R$^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;

provided:
  i. when L is S or CH$_2$, and Ring A is phenyl, then Ring B cannot be halo-substituted phenyl;
  ii. when L is O, Ring A is phenyl, and Ring B is not present, then R$^{AA}$ cannot be alkyl;
  iii. when L is O, Ring A is phenyl substituted with 1 R$^{AA}$, and Ring B is not present, then R$^{AA}$ cannot be meta-substituted trifluoromethyl;
  iv. when L is O, Ring A is phenyl, Ring B is not present, and R$^1$ is ethyl, then R$^{AA}$ cannot be trifluoromethoxy;
  v. when L is bond, Ring A is other than phenyl, Ring B is not present, and R$^1$ is H, then R$^{AB}$ cannot be methyl, and
  vi. when L is NH, Ring A is pyridyl, indolyl, or indolinyl, and Ring B is not present, then R$^{AB}$ cannot be alkyl; and
optionally a single stereoisomer or mixture of stereoisomers thereof and additionally optionally a pharmaceutically acceptable salt thereof. In a further embodiment, the compound of Formula (I) is that wherein: R$^L$ is hydrogen, C$_{1-4}$ alkyl, or benzyl; and the benzyl group is optionally substituted with one or two haloalkoxy groups; and Ring A is C$_{3-7}$ cycloalkyl, C$_{8-11}$ spirocycloalkyl, 5-8 membered heterocycloalkyl, phenyl, naphthyl, indanyl, tetrahydronaphthyl, 2,3-dihydrobenzo[b][1,4]dioxinyl, pyridyl, quinolinyl, isoquinolinyl, tetrahydroquinolinyl, or tetrahydroisoquinolinyl. In a further embodiment, the compound of Formula (I) is that wherein: R$^L$ is hydrogen, C$_{1-4}$ alkyl, or benzyl; and the benzyl group is optionally substituted with one or two haloalkoxy groups; and Ring B, when present, is cycloalkyl, heterocycloalkyl, phenyl, tetrahydronaphthyl, quinolinyl, isoquinolinyl, tetrahydroquinolinyl.

In certain embodiments, the compound of Formula (I) is that wherein:

L is a bond, $CH_2$, $CF_2$, O, $NR^L$, S, S(=O), C(=O), $CH_2$-Q, or Q-$CH_2$; wherein Q is O, $NR^L$, or S;

$R^L$ is hydrogen, $C_{1-4}$ alkyl, $C_{3-6}$ cycloalkyl, phenyl, or benzyl; wherein the $C_{1-4}$ alkyl is optionally substituted with hydroxycarbonyl, alkoxycarbonyl, hydroxycarbonylalkyl, or alkylcarbonyloxy; and the phenyl group alone or as a part of the benzyl group is optionally substituted with one or two groups selected from halo and haloalkoxy;

Ring A is $C_{3-7}$ cycloalkyl, $C_{8-11}$ spirocycloalkyl, 5-6 membered heterocycloalkyl, pyrazolyl, imidazolyl, triazolyl, thiazolyl, thienyl, phenyl, naphthyl, indanyl, tetrahydronaphthyl, dihydronaphthyl, pyridyl, indolyl, benzothiazolyl, quinolinyl, isoquinolinyl, indolinyl, isoindolinyl, tetrahydroquinolinyl, dihydroisoquinolinyl, tetrahydroisoquinolinyl, 2,3-dihydrobenzo[b][1,4]dioxinyl, or tetrahydro-methanonaphthalenyl;

Ring B is present or not present; wherein:

when Ring B is present, then Ring A is optionally substituted with one or two groups selected from halo, alkyl, alkoxy, haloalkoxy, (cycloalkyl)alkoxy, and cycloalkyl;

when Ring B is not present and Ring A is phenyl, then Ring A is substituted with:
  (i) one or two $R^{AA}$ groups,
  (ii) 2 halo groups when L is other than O,
  (iii) 2 halo groups when L is O, and $R^2$ and $R^3$ are not hydrogen or alkyl,
  (iv) one halo group when L is $CH_2NR^L$, or
  (vi) one halo group and one group selected from the group consisting of haloalkoxy, (cycloalkyl)alkoxy, and (phenyl)alkoxy, when L is bond, O or S, wherein the phenyl is optionally substituted with halo;

when Ring B is not present and Ring A is other than phenyl, then Ring A is substituted with one or two $R^{AB}$ groups;

each $R^{AA}$ is independently alkyl; haloalkyl; haloalkoxy; cycloalkyloxy; (cycloalkyl)alkoxy; phenoxy optionally substituted with one or two halo; or alkylcarbonylaminoalkoxy;

each $R^{AB}$ is independently halo; alkyl; hydroxy; alkoxy; haloalkyl; haloalkoxy; cycloalkyloxy; (cycloalkyl)alkoxy; or phenoxy optionally substituted with one or two halo;

Ring B, when present, is cycloalkyl, heterocycloalkyl, aryl, or heteroaryl; wherein each is optionally substituted with 1, 2, or 3 $R^B$ groups;

each $R^B$ is independently halo; cyano; alkyl; alkylsulfonyl; aminosulfonyl; alkylaminosulfonyl; dialkylaminosulfonyl; haloalkyl; alkoxy; haloalkoxy; alkylcarbonyl; alkoxyalkoxy; aminocarbonyl; alkylaminocarbonyl; dialkylaminocarbonyl; alkylcarbonylaminoalkoxy; cycloalkyl; (cycloalkyl)alkyl; cycloalkyloxy; (cycloalkyl)alkoxy; cycloalkylcarbonyl; cycloalkylcarbonyloxy; heterocycloalkyl optionally substituted with 1 or 2 groups independently selected from halo, alkyl, and alkylcarbonyl; (5-6-membered heterocycloalkyl-one)alkyl; 5-6-membered heterocycloalkyl-one; (heterocycloalkyl)alkyl; heterocycloalkylcarbonyl; or 5-6 membered heteroaryl;

$R^1$ is hydrogen, alkyl, cycloalkyl, heterocycloalkyl, or W; wherein W is alkyl substituted with amino, alkylamino, dialkylamino, alkylcarbonyloxy, alkoxycarbonyl, phenylcarbonyloxy, aminocarbonyloxy, alkylaminocarbonyloxy, dialkylaminocarbonyloxy, alkoxycarbonyloxy, cycloalkylcarbonyloxy, —N($R^{1A}$)C(O)$R^{1B}$, —N($R^{1A}$)C(O)OR$^{1B}$, or —N($R^{1A}$)C(O)NR$^{1B}R^{1C}$; wherein $R^{1A}$, $R^{1B}$, and $R^{1C}$ are each independently hydrogen or $C_{1-6}$ alkyl;

$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;

provided:
  i. when L is S or $CH_2$, and Ring A is phenyl, then Ring B cannot be halo-substituted phenyl;
  ii. when L is O, Ring A is phenyl, and Ring B is not present, then $R^{AA}$ cannot be alkyl;
  iii. when L is O, Ring A is phenyl substituted with 1 $R^{AA}$, and Ring B is not present, then $R^{AA}$ cannot be meta-substituted trifluoromethyl;
  iv. when L is O, Ring A is phenyl, Ring B is not present, and $R^1$ is ethyl, then $R^{AA}$ cannot be trifluoromethoxy;
  v. when L is bond, Ring A is other than phenyl, Ring B is not present, and $R^1$ is H, then $R^{AB}$ cannot be methyl, and
  vi. when L is NH, Ring A is pyridyl, indolyl, or indolinyl, and Ring B is not present, then $R^{AB}$ cannot be alkyl; and optionally a single stereoisomer or mixture of stereoisomers thereof and additionally optionally a pharmaceutically acceptable salt thereof.

In certain embodiments, the compound of Formula (I) is that wherein:

L is a bond, $CH_2$, $CF_2$, O, $NR^L$, S, S(=O), C(=O), $CH_2$-Q, or Q-$CH_2$; wherein Q is O, $NR^L$, or S;

$R^L$ is hydrogen, $C_{1-4}$ alkyl, or benzyl; and the benzyl group is optionally substituted with one or two groups selected from halo and haloalkoxy;

Ring A is $C_{5-6}$ cycloalkyl, $C_{8-11}$ spirocycloalkyl, 5-6 membered heterocycloalkyl, phenyl, naphthyl, indanyl, tetrahydronaphthyl, 2,3-dihydrobenzo[b][1,4]dioxinyl, pyridyl, quinolinyl, isoquinolinyl, tetrahydroquinolinyl, or tetrahydroisoquinolinyl;

Ring B is present or not present; wherein:

when Ring B is present, then Ring A is optionally substituted with one or two groups selected from halo and haloalkoxy;

when Ring B is not present and Ring A is phenyl, then Ring A is substituted with:
  (i) one or two $R^{AA}$ groups,
  (ii) 2 halo groups when L is other than O,
  (iii) 2 halo groups when L is O, and $R^2$ and $R^3$ are not hydrogen or alkyl,
  (iv) one halo group when L is $CH_2NR^L$, or
  (v) one halo group and one group selected from the group consisting of haloalkoxy, (cycloalkyl)alkoxy, and (phenyl)alkoxy, when L is bond, O or S, wherein the phenyl is optionally substituted with halo;

when Ring B is not present and Ring A is other than phenyl, then
  (i) Ring A is substituted with one or two $R^{AB}$ groups; or
  (ii) Ring A is unsubstituted, wherein:
    1) when Ring A is unsubstituted tetrahydroquinolinyl, then L is bond;
    2) when Ring A is unsubstituted 2,3-dihydrobenzo[b][1,4]dioxinyl, then L is O;
    3) when Ring A is unsubstituted tetrahydronaphthyl, then L is O, and $R^1$ is not hydrogen or ethyl; or
    4) when Ring A is unsubstituted spirocycloalkyl, then L is O or S;

each R$^{AA}$ is independently haloalkyl; cycloalkyloxy; (cycloalkyl)alkoxy; alkylcarbonylaminoalkoxy; or phenoxy optionally substituted with one or two halo;

each R$^{AB}$ is independently halo, alkyl, haloalkyl, or haloalkoxy;

Ring B, when present, cycloalkyl, heterocycloalkyl, phenyl, tetrahydronaphthyl, tetrahydroquinolinyl, quinolinyl, or isoquinolinyl; wherein each Ring B is optionally substituted with one or two R$^B$ groups;

each R$^B$ is independently halo; cyano; alkyl; haloalkyl; haloalkoxy; alkoxyalkoxy; aminocarbonyl; alkylcarbonylaminoalkoxy; cycloalkyl; (cycloalkyl)alkoxy; heterocycloalkyl optionally substituted with 1 or 2 alkyl, alkylcarbonyl or halo; or (5-6-membered heterocycloalkyl-one)alkyl;

R$^1$ is hydrogen, alkyl or W; wherein W is alkyl substituted with alkylcarbonyloxy, dialkylaminocarbonyloxy cycloalkylcarbonyloxy, or phenylcarbonyloxy;

R$^2$ and R$^3$ are independently hydrogen or alkyl; wherein the alkyl is optionally substituted with cycloalkylcarbonyloxy or heterocycloalkylcarbonyloxy, wherein the heterocycloalkylcarbonyloxy optionally substituted with alkoxycarbonyl;

provided:
(i) when L is S or CH$_2$, and Ring A is phenyl, then Ring B cannot be halo substituted phenyl;
(ii) when L is O, Ring A is phenyl, and Ring B is not present, then R$^{AA}$ cannot be alkyl;
(iii) when L is O, Ring A is phenyl substituted with 1 R$^{AA}$, and Ring B is not present, then R$^{AA}$ cannot be meta-substituted trifluoromethyl;
(iv) when L is O, Ring A is phenyl, Ring B is not present, and R$^1$ is ethyl, then R$^{AA}$ cannot be trifluoromethoxy;
(v) when L is bond, Ring A is other than phenyl, Ring B is not present, and R$^1$ is H, then R$^{AB}$ cannot be methyl, and
(vi) when L is NH, Ring A is pyridyl and Ring B is not present, then R$^{AB}$ cannot be alkyl; and optionally a single stereoisomer or mixture of stereoisomers thereof and additionally optionally a pharmaceutically acceptable salt thereof.

In certain embodiments, the compound of Formula (I) is that wherein:

L is a bond, CH$_2$, CF$_2$, O, NR$^L$, S, S(=O), C(=O), CH$_2$-Q, or Q-CH$_2$; wherein Q is O, NR$^L$, or S;

R$^L$ is H, C$_{1-4}$ alkyl, C$_{3-6}$ cycloalkyl, phenyl, or benzyl; wherein the C$_{1-4}$ alkyl is optionally substituted with hydroxycarbonyl, alkoxycarbonyl, hydroxycarbonylalkyl, or alkylcarbonyloxy; and the phenyl group alone or as a part of the benzyl group is optionally substituted with one or two groups selected from halo and haloalkoxy;

Ring A is cycloalkyl, spirocycloalkyl, heterocycloalkyl, aryl, or heteroaryl; wherein each is optionally substituted with one halo or alkyl;

Ring B, when present, is cycloalkyl, heterocycloalkyl, aryl, or heteroaryl; wherein each is optionally substituted with one or two R$^B$ groups;

each R$^B$ is independently cyano; alkyl; haloalkyl; alkoxy; haloalkoxy; alkylcarbonyl; alkoxyalkoxy; aminocarbonyl; alkylcarbonylaminoalkoxy; cycloalkyl; (cycloalkyl)alkyl; cycloalkyloxy; (cycloalkyl)alkoxy; cycloalkylcarbonyl; cycloalkylcarbonyloxy; heterocycloalkyl optionally substituted with 1 or 2 alkyl, alkylcarbonyl or halo; (5-6-membered heterocycloalkyl-one)alkyl, (heterocycloalkyl)alkyl, or heterocycloalkylcarbonyl;

R$^1$ is hydrogen, alkyl, cycloalkyl, heterocycloalkyl, or W; wherein W is alkyl substituted with amino, alkylamino, dialkylamino, alkylcarbonyloxy, alkoxycarbonyl, phenylcarbonyloxy, aminocarbonyloxy, alkylaminocarbonyloxy, dialkylaminocarbonyloxy, alkoxycarbonyloxy, cycloalkylcarbonyloxy, —N(R$^{1A}$)C(O)R$^{1B}$, —N(R$^{1A}$)C(O)OR$^{1B}$, or —N(R$^{1A}$)C(O)NR$^{1B}$R$^{1C}$; wherein R$^{1A}$, R$^{1B}$, and R$^{1C}$ are each independently hydrogen or C$_{1-6}$ alkyl;

R$^2$ and R$^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;

provided that when L is S or CH$_2$, and Ring A is phenyl, then Ring B is not halo-substituted phenyl; and optionally a single stereoisomer or mixture of stereoisomers thereof and additionally optionally a pharmaceutically acceptable salt thereof.

In certain embodiments, the compound of Formula (I) is that wherein:

L is a bond, O, CF$_2$, NR$^L$, S, S(=O), C(=O), CH$_2$-Q, or Q-CH$_2$; wherein Q is O, NR$^L$, or S;

R$^L$ is H, C$_{1-4}$ alkyl, or benzyl; and the phenyl in the benzyl group is optionally substituted with one or two groups selected from halo and haloalkoxy;

Ring A is cycloalkyl, spirocycloalkyl, heterocycloalkyl, phenyl, or heteroaryl; wherein each is optionally substituted with one halo or alkyl;

Ring B, when present, is cycloalkyl, heterocycloalkyl, phenyl, or heteroaryl; wherein each is optionally substituted with one or two R$^B$ groups;

each R$^B$ is independently halo; cyano; alkyl, haloalkyl; haloalkoxy; alkoxyalkoxy; aminocarbonyl; alkylcarbonylaminoalkoxy; cycloalkyl; (cycloalkyl)alkoxy; heterocycloalkyl optionally substituted with 1 or 2 alkyl, alkylcarbonyl or halo; or (5-6-membered heterocycloalkyl-one)alkyl;

R$^1$ is hydrogen, alkyl or W; wherein W is alkyl substituted with alkylcarbonyloxy, dialkylaminocarbonyloxy cycloalkylcarbonyloxy, or phenylcarbonyloxy;

R$^2$ and R$^3$ are independently hydrogen or alkyl; wherein the alkyl is optionally substituted with cycloalkylcarbonyloxy or heterocycloalkylcarbonyloxy, wherein the heterocycloalkylcarbonyloxy optionally substituted with alkoxycarbonyl;

provided that when L is S and Ring A is phenyl, then Ring B is not halo-substituted phenyl; and optionally a single stereoisomer or mixture of stereoisomers thereof and additionally optionally a pharmaceutically acceptable salt thereof.

In certain embodiments, the compound of Formula (I) is according to Formula (II):

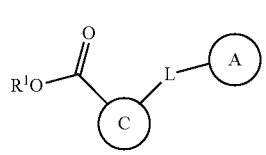

(II)

wherein:
ring C is selected from:

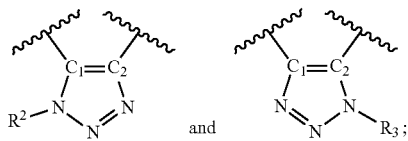

wherein the wavy lines (〰) indicate the points of attachment of the $C_1$ carbon to the carbonyl of C(O)—$OR^1$, and the $C_2$ carbon to L.

In certain embodiments, the compound of Formula (II) is that wherein:
L is a bond, $CH_2$, $CF_2$, O, $NR^L$, S, S(=O), C(=O), $CH_2$-Q, or Q-$CH_2$; wherein Q is O, $NR^L$, or S;
$R^L$ is H, $C_{1-4}$ alkyl, $C_{3-6}$ cycloalkyl, phenyl, or benzyl; wherein the $C_{1-4}$ alkyl is optionally substituted with hydroxycarbonyl, alkoxycarbonyl, hydroxycarbonylalkyl, or alkylcarbonyloxy; and the phenyl group alone or as a part of the benzyl group is optionally substituted with one or two groups selected from halo and haloalkoxy;
Ring A is cycloalkyl, spirocycloalkyl, heterocycloalkyl, aryl, or heteroaryl; wherein each is optionally substituted with one halo or alkyl;
$R^1$ is hydrogen, alkyl, cycloalkyl, heterocycloalkyl, or W; wherein W is alkyl substituted with amino, alkylamino, dialkylamino, alkylcarbonyloxy, alkoxycarbonyl, phenylcarbonyloxy, aminocarbonyloxy, alkylaminocarbonyloxy, dialkylaminocarbonyloxy, alkoxycarbonyloxy, cycloalkylcarbonyloxy, —N($R^{1A}$)C(O)$R^{1B}$, —N($R^{1A}$)C(O)O$R^{1B}$, or —N($R^{1A}$)C(O)N$R^{1B}R^{1C}$; wherein $R^{1A}$, $R^{1B}$, and $R^{1C}$ are each independently hydrogen or $C_{1-6}$ alkyl;
$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;
provided that when L is S or $CH_2$, and Ring A is phenyl, then Ring B is not halo-substituted phenyl; and
optionally a single stereoisomer or mixture of stereoisomers thereof and additionally optionally a pharmaceutically acceptable salt thereof.

In certain embodiments, the compound of Formula (II) is that wherein:
L is a bond, $CH_2$, $CF_2$, O, $NR^L$, S, S(=O), C(=O), $CH_2$-Q, or Q-$CH_2$; wherein Q is O, $NR^L$, or S;
$R^L$ is hydrogen, $C_{1-4}$ alkyl, $C_{3-6}$ cycloalkyl, phenyl, or benzyl; wherein the $C_{1-4}$ alkyl is optionally substituted with hydroxycarbonyl, alkoxycarbonyl, hydroxycarbonylalkyl, or alkylcarbonyloxy; and the phenyl group alone or as a part of the benzyl group is optionally substituted with one or two groups selected from halo and haloalkoxy;
Ring A is $C_{3-7}$ cycloalkyl, $C_{8-11}$ spirocycloalkyl, 5-6 membered heterocycloalkyl, pyrazolyl, imidazolyl, triazolyl, thiazolyl, phenyl, naphthyl, indanyl, tetrahydronaphthyl, dihydronaphthyl, pyridyl, indolyl, benzothiazolyl, quinolinyl, isoquinolinyl, indolinyl, isoindolinyl, tetrahydroquinolinyl, dihydroisoquinolinyl, tetrahydroisoquinolinyl, 2,3-dihydrobenzo[b][1,4]dioxinyl, or tetrahydromethanonaphthalenyl;

wherein:
when Ring A is phenyl, then Ring A is substituted with:
(i) one or two $R^{AA}$ groups,
(ii) 2 halo groups when L is other than O;
(iii) 2 halo groups when L is O, and $R^2$ and $R^3$ are not hydrogen or alkyl,
(iv) one halo group when L is $CH_2NR^L$, or
(v) one halo group and one group selected from the group consisting of haloalkoxy, (cycloalkyl)alkoxy, and (phenyl)alkoxy, when L is bond, O or S, wherein the phenyl is optionally substituted with halo;
when Ring A is other than phenyl, then
(i) Ring A is substituted with one or two $R^{AB}$ groups; or
(ii) Ring A is unsubstituted, wherein:
1) when Ring A is unsubstituted tetrahydroquinolinyl, then L is bond;
2) when Ring A is unsubstituted 2,3-dihydrobenzo[b][1,4]dioxinyl, then L is O;
3) when Ring A is unsubstituted tetrahydronaphthyl, then L is O, and $R^1$ is not hydrogen or ethyl, or
4) when Ring A is unsubstituted spirocycloalkyl, then L is O or S;
each $R^{AA}$ is independently alkyl, haloalkyl, haloalkoxy, cycloalkyloxy, (cycloalkyl)alkoxy, phenoxy optionally substituted with one or two halo, or alkylcarbonylaminoalkoxy;
each $R^{AB}$ is independently halo, alkyl, hydroxy, alkoxy, haloalkyl, haloalkoxy, cycloalkyloxy, (cycloalkyl)alkoxy, or phenoxy optionally substituted with one or two halo;
$R^1$ is hydrogen, alkyl, cycloalkyl, heterocycloalkyl, or W; wherein W is alkyl substituted with amino, alkylamino, dialkylamino, alkylcarbonyloxy, alkoxycarbonyl, phenylcarbonyloxy, aminocarbonyloxy, alkylaminocarbonyloxy, dialkylaminocarbonyloxy, alkoxycarbonyloxy, cycloalkylcarbonyloxy, —N($R^{1A}$)C(O)$R^{1B}$, —N($R^{1A}$)C(O)O$R^{1B}$, or —N($R^{1A}$)C(O)N$R^{1B}R^{1C}$; wherein $R^{1A}$, R', and $R^{1C}$ are each independently hydrogen or $C_{1-6}$ alkyl;
$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;
provided:
i. when L is O and Ring A is phenyl, then $R^{AA}$ cannot be alkyl;
ii. when L is O, Ring A is phenyl, and $R^1$ is ethyl, then $R^{AB}$ cannot be trifluoromethoxy;
ii. when L is O, Ring A is phenyl substituted with 1 $R^{AA}$, then $R^{AA}$ cannot be meta-substituted trifluoromethyl;
iv. when L is bond, Ring A is other than phenyl, and $R^1$ is H, then $R^{AB}$ cannot be methyl, and
v. when L is NH, Ring A is pyridyl, indolyl, or indolinyl, then $R^{AB}$ cannot be alkyl; and
optionally a single stereoisomer or mixture of stereoisomers thereof and additionally optionally a pharmaceutically acceptable salt thereof.

In certain embodiments, the compound of Formula (II) is that wherein:
L is a bond, $CH_2$, $CF_2$, O, $NR^L$, S, S(=O), C(=O), $CH_2$-Q, or Q-$CH_2$; wherein Q is O, $NR^L$, or S;
$R^L$ is H, $C_{1-4}$ alkyl, $C_{3-6}$ cycloalkyl, phenyl, or benzyl; wherein the $C_{1-4}$ alkyl is optionally substituted with hydroxycarbonyl, alkoxycarbonyl, hydroxycarbonylalkyl, or alkylcarbonyloxy; and the phenyl group alone or as a part of the benzyl group is optionally substituted with one or two groups selected from halo and haloalkoxy;
Ring A is $C_{3-7}$ cycloalkyl, $C_{8-11}$ spirocycloalkyl, tetrahydronaphthyl, dihydronaphthyl, benzothiazolyl, isoquinolinyl, tetrahydroquinolinyl, dihydroisoquinolinyl, tetrahydroisoquinolinyl, 2,3-dihydrobenzo[b][1,4]dioxinyl, or tetrahydro-methanonaphthalenyl; provided that when L is $NR^L$ or O, then Ring A cannot be tetrahydronaphthyl;

$R^1$ is hydrogen, alkyl, cycloalkyl, heterocycloalkyl, or W; wherein W is alkyl substituted with amino, alkylamino, dialkylamino, alkylcarbonyloxy, alkoxycarbonyl, phenylcarbonyloxy, aminocarbonyloxy, alkylaminocarbonyloxy, dialkylaminocarbonyloxy, alkoxycarbonyloxy, cycloalkylcarbonyloxy, —$N(R^{1A})C(O)R^{1B}$, —$N(R^{1A})C(O)OR^{1B}$, or —$N(R^{1A})C(O)NR^{1B}R^{1C}$; wherein $R^{1A}$, $R^{1B}$, and $R^{1C}$ are each independently hydrogen or $C_{1-6}$ alkyl;

$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl; and optionally a single stereoisomer or mixture of stereoisomers thereof and additionally optionally a pharmaceutically acceptable salt thereof.

In certain embodiments, the compound of Formula (II) is that wherein:

L is a bond, $CH_2$, O, NH, S, S(=O), C(=O), $CH_2$-Q, or Q-$CH_2$; wherein Q is O, NH, or S;

Ring A is piperidinyl, phenyl, naphthyl, indanyl, tetrahydronaphthyl, 2,3-dihydrobenzo[b][1,4]dioxinyl, pyridyl, quinolinyl, isoquinolinyl, tetrahydroquinolinyl, tetrahydroisoquinolinyl, spiro[2.5]octane, spiro[4.5]decane, or spiro[5.5]undecane;

wherein:
when Ring A is phenyl, then Ring A is substituted with:
(i) one or two $R^{AA}$ groups,
(ii) 2 halo groups when L is other than O;
(iii) 2 halo groups when L is O, and $R^2$ and $R^3$ are not hydrogen or alkyl,
(iv) one halo group when L is $CH_2NR^L$, or
(v) one halo group and one group selected from the group consisting of haloalkoxy and (cycloalkyl)alkoxy, when L is bond, O or S;
when Ring A is other than phenyl, then
(i) Ring A is substituted with one or two $R^{AB}$ groups; or
(ii) Ring A is unsubstituted, wherein:
1) when Ring A is unsubstituted tetrahydroquinolinyl, then L is bond;
2) when Ring A is unsubstituted 2,3-dihydrobenzo[b][1,4]dioxinyl, then L is O;
3) when Ring A is unsubstituted tetrahydronaphthyl, then L is O, and $R^1$ is not hydrogen or ethyl, or
4) when Ring A is unsubstituted spirocycloalkyl, then L is O or S;

each $R^{AA}$ is independently haloalkyl, cycloalkyloxy, (cycloalkyl)alkoxy, or alkylcarbonylaminoalkoxy;

each $R^{AB}$ is independently halo, alkyl, haloalkyl, or haloalkoxy;

$R^1$ is hydrogen, alkyl, or W; wherein W is alkyl substituted with alkylcarbonyloxy;

$R^2$ and $R^3$ are independently hydrogen or alkyl; wherein the alkyl is optionally substituted with cycloalkylcarbonyloxy or heterocycloalkylcarbonyloxy, wherein the heterocycloalkylcarbonyloxy optionally substituted with alkoxycarbonyl;

provided:
i. when L is O, Ring A is phenyl, and $R^1$ is ethyl, then $R^{AB}$ cannot be trifluoromethoxy;
ii. when L is O, Ring A is phenyl substituted with 1 $R^{AA}$, then $R^{AA}$ cannot be meta-substituted trifluoromethyl;
iii. when L is O, Ring A is phenyl substituted with 1 $R^{AA}$, then $R^{AA}$ cannot be meta-substituted trifluoromethyl;
iv. when L is bond, Ring A is other than phenyl, and $R^1$ is H, then $R^{AB}$ cannot be methyl, and
v. when L is NH, Ring A is pyridyl, then $R^{AB}$ cannot be alkyl; and optionally a single stereoisomer or mixture of stereoisomers thereof and additionally optionally a pharmaceutically acceptable salt thereof.

In certain embodiments, the compound of Formula (I) is according to Formula (III):

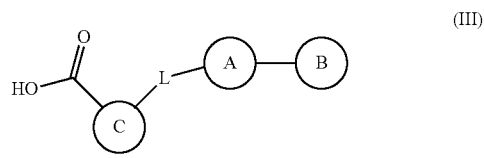

wherein:
ring C is selected from:

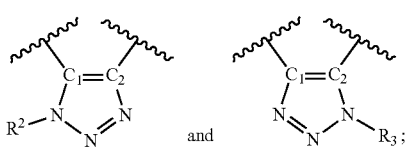

wherein the wavy lines ($\sim$) indicate the points of attachment of the $C_1$ carbon to the carbonyl of C(O)—$OR^1$, and the $C_2$ carbon to L.

In certain embodiments, the compound of Formula (III) is that wherein:

L is a bond, $CH_2$, $CF_2$, O, $NR^L$, S, S(=O), C(=O), $CH_2$-Q, or Q-$CH_2$; wherein Q is O, $NR^L$, or S;

$R^L$ is hydrogen, $C_{1-4}$ alkyl, $C_{3-6}$ cycloalkyl, phenyl, or benzyl; wherein the $C_{1-4}$ alkyl is optionally substituted with hydroxycarbonyl, alkoxycarbonyl, hydroxycarbonylalkyl, or alkylcarbonyloxy; and the phenyl group alone or as a part of the benzyl group is optionally substituted with one or two groups selected from halo and haloalkoxy;

Ring A is $C_{3-7}$ cycloalkyl, $C_{8-11}$ spirocycloalkyl, 5-6 membered heterocycloalkyl, pyrazolyl, imidazolyl, triazolyl, thiazolyl, phenyl, naphthyl, indanyl, tetrahydronaphthyl, dihydronaphthyl, pyridyl, indolyl, benzothiazolyl, quinolinyl, isoquinolinyl, indolinyl, isoindolinyl, tetrahydroquinolinyl, dihydroisoquinolinyl, tetrahydroisoquinolinyl, 2,3-dihydrobenzo[b][1,4]dioxinyl, or tetrahydromethanonaphthalenyl;

Ring B is present or not present; wherein:
when Ring B is present, then Ring A is optionally substituted with one or two groups selected from halo, alkyl, alkoxy, and haloalkoxy;
when Ring B is not present and Ring A is phenyl, then Ring A is substituted with:
(i) one or two $R^{AA}$ groups,
(ii) 2 halo groups when L is other than O,
(iii) 2 halo groups when L is O, and $R^2$ and $R^3$ are not hydrogen or alkyl,
(iv) one halo group when L is $CH_2NR^L$, or
(v) one halo group and one group selected from the group consisting of haloalkoxy, (cycloalkyl)alkoxy, and (phenyl)alkoxy, when L is bond, O or S, wherein the phenyl is optionally substituted with halo;

when Ring B is not present and Ring A is other than phenyl, then
  (i) Ring A is substituted with one or two $R^{AB}$ groups or
  (ii) Ring A is unsubstituted, wherein:
    1) when Ring A is unsubstituted tetrahydroquinolinyl, then L is bond;
    2) when Ring A is unsubstituted 2,3-dihydrobenzo[b][1,4]dioxinyl, then L is O;
    3) when Ring A is unsubstituted tetrahydronaphthyl, then L is not O; or
    4) when Ring A is unsubstituted spirocycloalkyl, then L is O or S;

each $R^{AA}$ is independently alkyl; haloalkyl; haloalkoxy; cycloalkyloxy; (cycloalkyl)alkoxy; phenoxy optionally substituted with one or two halo; or alkylcarbonylaminoalkoxy;

each $R^{AB}$ is independently halo; alkyl; hydroxy; alkoxy; haloalkyl; haloalkoxy; cycloalkyloxy; (cycloalkyl)alkoxy; or phenoxy optionally substituted with one or two halo;

Ring B, when present, is cycloalkyl, heterocycloalkyl, aryl, or heteroaryl; wherein each is optionally substituted with one or two $R^B$ groups;

each $R^B$ is independently halo; cyano; alkyl; haloalkyl; alkoxy; haloalkoxy; alkylcarbonyl; alkoxyalkoxy; aminocarbonyl; alkylcarbonylaminoalkoxy; cycloalkyl; (cycloalkyl)alkyl; cycloalkyloxy; (cycloalkyl)alkoxy; cycloalkylcarbonyl; cycloalkylcarbonyloxy; heterocycloalkyl optionally substituted with 1 or 2 alkyl, alkylcarbonyl halo, (5-6-membered heterocycloalkyl-one)alkyl, (heterocycloalkyl)alkyl; or heterocycloalkylcarbonyl;

$R^2$ and $R^3$ are independently hydrogen, alkyl, phenyl, or benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;

provided:
  i. when L is S or $CH_2$, and Ring A is phenyl, then Ring B cannot be halo-substituted phenyl;
  ii. when L is O, Ring A is phenyl, and Ring B is not present, then $R^{AA}$ cannot be alkyl;
  iii. when L is O, Ring A is phenyl substituted with 1 $R^{AA}$, and Ring B is not present, then $R^{AA}$ cannot be meta-substituted trifluoromethyl;
  iv. when L is bond, Ring A is other than phenyl and Ring B is not present, then $R^{AB}$ cannot be methyl, and
  v. when L is NH, Ring A is pyridyl, indolyl, or indolinyl, and Ring B is not present, then $R^{AB}$ cannot be alkyl;

optionally a single stereoisomer or mixture of stereoisomers thereof and additionally optionally a pharmaceutically acceptable salt thereof.

In certain embodiments, the compound of Formula (III) is that wherein:

L is a bond, $CH_2$, $CF_2$, O, $NR^L$, S, S(=O), C(=O), $CH_2$-Q, or Q-$CH_2$; wherein Q is O, $NR^L$, or S;

$R^L$ is hydrogen, $C_{1-4}$ alkyl, or benzyl; and the phenyl in the benzyl group is optionally substituted with one or two groups selected from halo and haloalkoxy;

Ring A is $C_{5-6}$ cycloalkyl, $C_{8-11}$ spirocycloalkyl, 5-6 membered heterocycloalkyl, phenyl, naphthyl, indanyl, tetrahydronaphthyl, 2,3-dihydrobenzo[b][1,4]dioxinyl, pyridyl, quinolinyl, isoquinolinyl, tetrahydroquinolinyl, or tetrahydroisoquinolinyl;

Ring B is present or not present; wherein:

when Ring B is present, then Ring A is optionally substituted with one or two groups selected from halo and haloalkoxy;

when Ring B is not present and Ring A is phenyl, then Ring A is substituted with:
  (i) one or two $R^{AA}$ groups,
  (ii) 2 halo groups when L is other than O,
  (iii) 2 halo groups when L is O, and $R^2$ and $R^3$ are not hydrogen or alkyl,
  (iv) one halo group when L is $CH_2NR^L$, or
  (v) one halo group and one group selected from the group consisting of haloalkoxy, (cycloalkyl)alkoxy, and (phenyl)alkoxy, when L is bond, O or S, wherein the phenyl is optionally substituted with halo;

when Ring B is not present and Ring A is other than phenyl, then
  (i) Ring A is substituted with one or two R groups; or
  (ii) Ring A is unsubstituted, wherein:
    1) when Ring A is unsubstituted tetrahydroquinolinyl, then L is bond;
    2) when Ring A is unsubstituted 2,3-dihydrobenzo[b][1,4]dioxinyl, then L is O;
    3) when Ring A is unsubstituted tetrahydronaphthyl, then L is O, and $R^1$ is not hydrogen or ethyl; or
    4) when Ring A is unsubstituted spirocycloalkyl, then L is O or S;

each $R^{AA}$ is independently haloalkyl; cycloalkyloxy; (cycloalkyl)alkoxy; alkylcarbonylaminoalkoxy; or phenoxy optionally substituted with one or two halo;

each $R^{AB}$ is independently halo, alkyl, haloalkyl, or haloalkoxy;

Ring B, when present, cycloalkyl, heterocycloalkyl, phenyl, tetrahydronaphthyl, tetrahydroquinolinyl, quinolinyl, or isoquinolinyl; wherein each Ring B is optionally substituted with one or two $R^B$ groups;

each $R^B$ is independently halo; cyano; alkyl; haloalkyl; haloalkoxy; alkoxyalkoxy; aminocarbonyl; alkylcarbonylaminoalkoxy; cycloalkyl; (cycloalkyl)alkoxy; heterocycloalkyl optionally substituted with 1 or 2 alkyl, alkylcarbonyl or halo; or (5-6-membered heterocycloalkyl-one)alkyl;

$R^2$ and $R^3$ are independently hydrogen or alkyl; wherein the alkyl is optionally substituted with cycloalkylcarbonyloxy or heterocycloalkylcarbonyloxy, wherein the heterocycloalkylcarbonyloxy optionally substituted with alkoxycarbonyl;

provided:
  (i) when L is S or $CH_2$, and Ring A is phenyl, then Ring B cannot be halo substituted phenyl;
  (ii) when L is O, Ring A is phenyl, and Ring B is not present, then $R^{AA}$ cannot be alkyl;
  (iii) when L is O, Ring A is phenyl substituted with 1 $R^{AA}$, and Ring B is not present, then $R^{AA}$ cannot be meta-substituted trifluoromethyl;
  (iv) when L is bond, Ring A is other than phenyl, Ring B is not present, then $R^{AB}$ cannot be methyl, and
  (v) when L is NH, Ring A is pyridyl and Ring B is not present, then $R^{AB}$ cannot be alkyl; and optionally a single stereoisomer or mixture of stereoisomers thereof and additionally optionally a pharmaceutically acceptable salt thereof.

In certain embodiments, the compound of Formula (I) is that wherein: ring C is selected from:

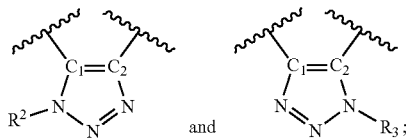

and;

wherein the wavy lines (⁓) indicate the points of attachment of the $C_1$ carbon to the carbonyl of C(O)—OR$^1$, and the $C_2$ carbon to L; and Ring B is present.

In certain embodiments, the compound or Formula (I) is that wherein:
L is a bond, CH$_2$, CF$_2$, O, NR$^L$, S, S(=O), C(=O), CH$_2$-Q, or Q-CH$_2$; wherein Q is O, NR$^L$, or S;
R$^L$ is hydrogen, C$_{1-4}$ alkyl, C$_{3-6}$ cycloalkyl, phenyl, or benzyl; wherein the C$_{1-4}$ alkyl is optionally substituted with hydroxycarbonyl, alkoxycarbonyl, hydroxycarbonylalkyl, or alkylcarbonyloxy; and the phenyl group alone or as a part of the benzyl group is optionally substituted with one or two groups selected from halo and haloalkoxy;
Ring A is C$_{3-7}$ cycloalkyl, C$_{8-11}$ spirocycloalkyl, 5-6 membered heterocycloalkyl, pyrazolyl, imidazolyl, triazolyl, thiazolyl, thienyl, phenyl, naphthyl, indanyl, tetrahydronaphthyl, dihydronaphthyl, pyridyl, indolyl, benzothiazolyl, quinolinyl, isoquinolinyl, indolinyl, isoindolinyl, tetrahydroquinolinyl, dihydroisoquinolinyl, tetrahydroisoquinolinyl, 2,3-dihydrobenzo[b][1,4]dioxinyl, or tetrahydro-methanonaphthalenyl; wherein Ring A is optionally substituted with one or two groups selected from halo, alkyl, alkoxy, or haloalkoxy;
Ring B is cycloalkyl, heterocycloalkyl, aryl, or heteroaryl; wherein each is optionally substituted with one or two R$^B$ groups;
each R$^B$ is independently halo; cyano; alkyl; haloalkyl; alkoxy; haloalkoxy; alkylcarbonyl; alkoxyalkoxy; aminocarbonyl; alkylcarbonylaminoalkoxy; cycloalkyl; (cycloalkyl)alkyl; cycloalkyloxy; (cycloalkyl)alkoxy; cycloalkylcarbonyl; cycloalkylcarbonyloxy; heterocycloalkyl optionally substituted with 1 or 2 alkyl, alkylcarbonyl or halo; (5-6-membered heterocycloalkyl-one)alkyl; (heterocycloalkyl)alkyl; or heterocycloalkylcarbonyl;
R$^1$ is hydrogen, alkyl, cycloalkyl, heterocycloalkyl, or W; wherein W is alkyl substituted with amino, alkylamino, dialkylamino, alkylcarbonyloxy, alkoxycarbonyl, phenylcarbonyloxy, aminocarbonyloxy, alkylaminocarbonyloxy, dialkylaminocarbonyloxy, alkoxycarbonyloxy, cycloalkylcarbonyloxy, —N(R$^{1A}$)C(O)R$^{1B}$, —N(R$^{1A}$)C(O)OR$^{1B}$, or —N(R$^{1A}$)C(O)NR$^{1B}$R$^{1C}$; wherein R$^{1A}$, R$^{1B}$, and R$^{1C}$ are each independently hydrogen or C$_{1-6}$ alkyl;
R$^2$ and R$^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;
provided that when L is S or CH$_2$, and Ring A is phenyl, then Ring B cannot be halo-substituted phenyl; and
optionally a single stereoisomer or mixture of stereoisomers thereof and additionally optionally a pharmaceutically acceptable salt thereof.

In certain embodiments, the compound of Formula (I) is that wherein:
mL is bond, CH$_2$, CF$_2$, O, NR$^L$, S, CH$_2$-Q, or Q-CH$_2$; wherein Q is O, NR$^L$, or S;
R$^L$ is hydrogen, C$_{1-4}$ alkyl, or benzyl, wherein the phenyl in the benzyl group is optionally substituted with haloalkoxy group;
Ring A is C$_{3-7}$ cycloalkyl, 5-6 membered heterocycloalkyl, phenyl, or naphthyl, wherein Ring A is optionally substituted with halo or haloalkoxy;
Ring B is cycloalkyl, heterocycloalkyl, phenyl, tetrahydronaphthyl, tetrahydroquinolinyl, quinolinyl, or isoquinolinyl; wherein each Ring B is optionally substituted with one or two R$^B$ groups;
each R$^B$ is independently halo; cyano; haloalkyl; haloalkoxy; alkoxyalkoxy; aminocarbonyl; alkylcarbonylaminoalkoxy; cycloalkyl; (cycloalkyl)alkoxy; heterocycloalkyl optionally substituted with 1 or 2 alkyl, alkylcarbonyl or halo; or (5-6-membered heterocycloalkyl-one)alkyl; and
R$^1$ is hydrogen or W; wherein W is alkyl substituted with alkylcarbonyloxy, dialkylaminocarbonyloxy cycloalkylcarbonyloxy, or phenylcarbonyloxy;
provided that when L is S or CH$_2$, and Ring A is phenyl, then Ring B cannot be halo-substituted phenyl; and
optionally a single stereoisomer or mixture of stereoisomers thereof and additionally optionally a pharmaceutically acceptable salt thereof.

In certain embodiments, the compound of Formula (I) is according to Formula (IV):

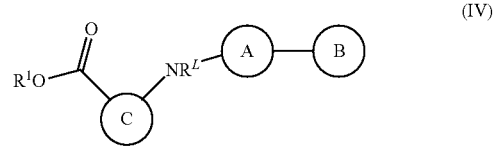

(IV)

wherein:
ring C is selected from:

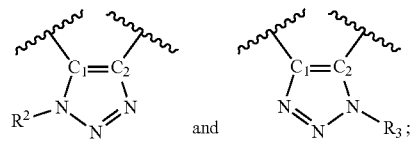

and;

wherein the wavy lines (⁓) indicate the points of attachment of the $C_1$ carbon to the carbonyl of C(O)—OR$^1$, and the $C_2$ carbon to L.

In certain embodiments, the compound of Formula (IV) is that wherein:
R$^L$ is hydrogen, C$_{1-4}$ alkyl, C$_{3-6}$ cycloalkyl, phenyl, or benzyl; wherein the C$_{1-4}$ alkyl is optionally substituted with hydroxycarbonyl, alkoxycarbonyl, hydroxycarbonylalkyl, or alkylcarbonyloxy; and the phenyl group alone or as a part of the benzyl group is optionally substituted with one or two groups selected from halo and haloalkoxy;
Ring A is C$_{3-7}$ cycloalkyl, C$_{8-11}$ spirocycloalkyl, 5-6 membered heterocycloalkyl, pyrazolyl, imidazolyl, triazolyl, thiazolyl, phenyl, naphthyl, indanyl, tetrahydronaphthyl, dihydronaphthyl, pyridyl, indolyl, benzothiazolyl, quinolinyl, isoquinolinyl, indolinyl, isoindolinyl, tetrahydroquinolinyl, dihydroisoquinolinyl, tetrahydroisoquinolinyl, 2,3-dihydrobenzo[b][1,4]dioxinyl, or tetrahydromethanonaphthalenyl;

Ring B is present or not present; wherein:
when Ring B is present, then Ring A is optionally substituted with one or two groups selected from halo, alkyl, alkoxy, or haloalkoxy;
when Ring B is not present and Ring A is phenyl, then Ring A is substituted with:
(i) one or two $R^{AA}$ groups, or (ii) 2 halo groups;
when Ring B is not present and Ring A is 5-6 membered heterocycloalkyl, pyrazolyl, imidazolyl, triazolyl, thiazolyl, naphthyl, indanyl, tetrahydronaphthyl, dihydronaphthyl, benzothiazolyl, quinolinyl, isoquinolinyl, isoindolinyl, tetrahydroquinolinyl, dihydroisoquinolinyl, tetrahydroisoquinolinyl, or
2,3-dihydrobenzo[b][1,4]dioxinyl, then Ring A is substituted with one or two $R^{AB}$ groups;
when Ring B is not present and Ring A is $C_{3-7}$ cycloalkyl or $C_{8-11}$ spirocycloalkyl, then Ring A is optionally substituted with one or two $R^{AB}$ groups;
when Ring B is not present and Ring A is pyridyl, indolyl, or indolinyl, then Ring A is substituted with one or two $R^{AC}$ groups;
each $R^{AA}$ is independently alkyl; haloalkyl; haloalkoxy; cycloalkyloxy; (cycloalkyl)alkoxy; phenoxy optionally substituted with one or two halo; or alkylcarbonylaminoalkoxy;
each $R^{AB}$ is independently halo; alkyl; hydroxy; alkoxy; haloalkyl; haloalkoxy; cycloalkyloxy; (cycloalkyl)alkoxy; or phenoxy optionally substituted with one or two halo;
each $R^{AC}$ is independently halo; hydroxy; alkoxy; haloalkyl; haloalkoxy; cycloalkyloxy; (cycloalkyl)alkoxy; or phenoxy optionally substituted with one or two halo;
Ring B, when present, is cycloalkyl, heterocycloalkyl, aryl, or heteroaryl; wherein each is optionally substituted with one or two $R^B$ groups;
each $R^B$ is independently halo; cyano; alkyl; haloalkyl; alkoxy; haloalkoxy; alkylcarbonyl; alkoxyalkoxy; aminocarbonyl; alkylcarbonylaminoalkoxy; cycloalkyl; (cycloalkyl)alkyl; cycloalkyloxy; (cycloalkyl)alkoxy; cycloalkylcarbonyl; cycloalkylcarbonyloxy; heterocycloalkyl optionally substituted with 1 or 2 alkyl, alkylcarbonyl or halo; (5-6-membered heterocycloalkyl-one)alkyl; (heterocycloalkyl)alkyl; or heterocycloalkylcarbonyl;
$R^1$ is hydrogen, alkyl, cycloalkyl, heterocycloalkyl, or W; wherein W is alkyl substituted with amino, alkylamino, dialkylamino, alkylcarbonyloxy, alkoxycarbonyl, phenylcarbonyloxy, aminocarbonyloxy, alkylaminocarbonyloxy, dialkylaminocarbonyloxy, alkoxycarbonyloxy, cycloalkylcarbonyloxy, —N($R^{1A}$)C(O)$R^{1B}$, —N($R^{1A}$)C(O)O$R^{1B}$, or —N($R^{1A}$)C(O)NR$^{1B}$R$^{1C}$; wherein $R^{1A}$, $R^{1B}$, and $R^{1C}$ are each independently hydrogen or $C_{1-6}$ alkyl;
$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl; and
optionally a single stereoisomer or mixture of stereoisomers thereof and additionally optionally a pharmaceutically acceptable salt thereof.

In certain embodiments, the compound of Formula (I) is according to Formula (V):

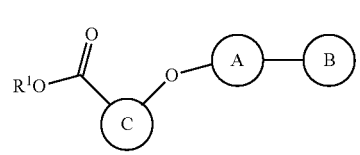

wherein:
ring C is selected from:

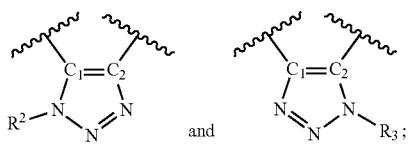

wherein the wavy lines (⁓) indicate the points of attachment of the $C_1$ carbon to the carbonyl of C(O)—OR$^1$, and the $C_2$ carbon to L.

In certain embodiments, the compound of Formula (V) is that wherein:
Ring A is cycloalkyl, $C_{8-11}$ spirocycloalkyl, heterocycloalkyl, aryl, or heteroaryl; each is substituted with one or two $R^{AB}$ groups; provided:
when Ring B is present, then Ring A is optionally substituted with one halo or alkyl;
when Ring B is not present and Ring A is phenyl, then Ring A is substituted with:
(i) one or two $R^{AD}$ groups, (ii) two groups selected from chloro or bromo, or (iii) one halo group and one group selected from the group consisting of haloalkoxy, (cycloalkyl)alkoxy, and (phenyl)alkoxy, wherein the phenyl is optionally substituted with halo;
or Ring A is unsubstituted $C_{8-11}$ spirocycloalkyl; unsubstituted dihydroxybenzodioxynyl; or unsubstituted tetrahydronaphthalene when $R^1$ is not hydrogen or ethyl;
each $R^{AB}$ is independently halo; alkyl; hydroxy; alkoxy; haloalkyl; haloalkoxy; cycloalkyloxy; (cycloalkyl)alkoxy; phenoxy optionally substituted with one or two halo; or (phenyl)alkoxy, wherein the phenyl is optionally substituted with halo;
each $R^{AD}$ is independently hydroxy, alkoxy, haloalkyl, cycloalkyloxy, (cycloalkyl)alkoxy, or phenoxy optionally substituted with one or two halo;
Ring B is present or not present; wherein:
Ring B, when present, is cycloalkyl, heterocycloalkyl, aryl, or heteroaryl; wherein each is optionally substituted with one or two $R^B$ groups;
each $R^B$ is independently halo; cyano; alkyl; haloalkyl; alkoxy; haloalkoxy; alkylcarbonyl; alkoxyalkoxy; aminocarbonyl; alkylcarbonylaminoalkoxy; cycloalkyl; (cycloalkyl)alkyl; cycloalkyloxy; (cycloalkyl)alkoxy; cycloalkylcarbonyl; cycloalkylcarbonyloxy; heterocycloalkyl optionally substituted with 1 or 2 alkyl, alkylcarbonyl or halo; (5-6-membered heterocycloalkyl-one)alkyl; (heterocycloalkyl)alkyl; or heterocycloalkylcarbonyl;
$R^1$ is hydrogen, alkyl, cycloalkyl, heterocycloalkyl, or W; wherein W is alkyl substituted with amino, alkylamino, dialkylamino, alkylcarbonyloxy, alkoxycarbonyl, phenylcarbonyloxy, aminocarbonyloxy, alkylaminocarbonyloxy, dialkylaminocarbonyloxy, alkoxycarbonyloxy, cycloalkylcarbonyloxy, —N($R^{1A}$)C(O)$R^{1B}$, —N($R^{1A}$)C(O)O$R^{1B}$, or —N($R^{1A}$)C(O)N$R^{1B}R^{1C}$; wherein $R^{1A}$, $R^{1B}$, and $R^{1C}$ are each independently hydrogen or $C_{1-6}$ alkyl;

$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;

provided
  (i) when Ring A is phenyl, Ring B is not present, and $R^1$ is ethyl, then Ring A cannot be substituted with trifluoromethoxy; and
  (ii) when Ring A is phenyl substituted with 1 $R^{AD}$, then $R^{AD}$ cannot be meta-substituted trifluoromethyl; and optionally a single stereoisomer or mixture of stereoisomers thereof and additionally optionally a pharmaceutically acceptable salt thereof.

In certain embodiments, the compound of Formula (I) is according to Formula (VI):

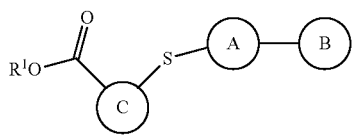

(VI)

wherein:
ring C is selected from:

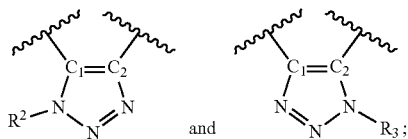

and wherein the wavy lines (⁓) indicate the points of attachment of the $C_1$ carbon to the carbonyl of C(O)—$OR^1$, and the $C_2$ carbon to L.

In certain embodiments, the compound of Formula (VI) is that wherein: Ring A is cycloalkyl, $C_{8-11}$ spirocycloalkyl, heterocycloalkyl, aryl, or heteroaryl other than thienyl or benzothiophenyl; each is substituted with one or two $R^{AB}$ groups; provided when Ring A is phenyl and Ring B is not present, then Ring A is substituted with one or two $R^{AE}$;

each $R^{AB}$ is independently halo; alkyl; hydroxy; alkoxy; haloalkyl; haloalkoxy; cycloalkyloxy; (cycloalkyl)alkoxy; phenoxy optionally substituted with one or two halo; (phenyl)alkoxy, wherein the phenyl is optionally substituted with halo;

each $R^{AE}$ is independently halo; alkyl; haloalkyl; haloalkoxy; cycloalkyloxy; (cycloalkyl)alkoxy; or (phenyl)alkoxy, wherein the phenyl is optionally substituted with halo;

Ring B is present or not present; wherein:
Ring B, when present, is cycloalkyl, heterocycloalkyl, aryl, or heteroaryl; wherein each is optionally substituted with one or two $R^B$ groups;

each $R^B$ is independently halo; cyano; alkyl; haloalkyl; alkoxy; haloalkoxy; alkylcarbonyl; alkoxyalkyl; aminocarbonyl; alkylcarbonylaminoalkoxy; cycloalkyl; (cycloalkyl)alkyl; cycloalkyloxy; (cycloalkyl)alkoxy; cycloalkylcarbonyl; cycloalkylcarbonyloxy; heterocycloalkyl optionally substituted with 1 or 2 alkyl, alkylcarbonyl or halo; (5-6-membered heterocycloalkyl-one) alkyl; (heterocycloalkyl)alkyl; or heterocycloalkylcarbonyl;

$R^1$ is hydrogen, alkyl, cycloalkyl, heterocycloalkyl, or W; wherein W is alkyl substituted with amino, alkylamino, dialkylamino, alkylcarbonyloxy, alkoxycarbonyl, phenylcarbonyloxy, aminocarbonyloxy, alkylaminocarbonyloxy, dialkylaminocarbonyloxy, alkoxycarbonyloxy, cycloalkylcarbonyloxy, —N($R^{1A}$)C(O)$R^{1B}$, —N($R^{1A}$)C(O)O$R^{1B}$, or —N($R^{1A}$)C(O)N$R^{1B}R^{1C}$; wherein $R^{1A}$, $R^{1B}$, and $R^{1C}$ are each independently hydrogen or $C_{1-6}$ alkyl;

$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;

provided that when Ring A is phenyl, then Ring B cannot be halo-substituted phenyl; and optionally a single stereoisomer or mixture of stereoisomers thereof and additionally optionally a pharmaceutically acceptable salt thereof.

In certain embodiments, L is a bond, $CH_2$, $CF_2$, O, $NR^L$, S, S(=O), or C(=O). In certain embodiments, L is $CH_2$, $CF_2$, O, $NR^L$, S, C(=O), $CH_2$-Q, or Q-$CH_2$; wherein Q is O, $NR^L$, or S. In certain embodiments, L is $CH_2$, $CF_2$, O, $NR^L$, or S. In certain embodiments, L is $CF_2$, O, $NR^L$, or S. In certain embodiments, L is $CF_2$, O, or $NR^L$. In certain embodiments, L is $CH_2$, O, $NR^L$, or S. In certain embodiments, L is O, $NR^L$, or S. In certain embodiments, L is $CH_2$, $CF_2$, or C(=O). In certain embodiments, L is $CH_2$, $CF_2$, $CH_2$-Q, or Q-$CH_2$; wherein Q is O, $NR^L$, or S. In certain embodiments, L is $CH_2$-Q, or Q-$CH_2$; wherein Q is O, $NR^L$, or S. In certain embodiments, L is bond, $CF_2$, O, $NR^L$, S, or S(=O). In certain embodiments, L is a bond, or L is $CH_2$, or L is $CF_2$. In certain embodiments, L is O. In certain embodiments, L is $NR^L$. In certain embodiments, L is S. In certain embodiments, L is S(=O). In certain embodiments, L is C(=O). In certain embodiments, L is $CH_2$-Q; wherein Q is O, $NR^L$, or S. In certain embodiments, L is $CH_2$—O, or L is $CH_2$—S, or L is $CH_2$—$NR^L$, or L is O—$CH_2$, or L is $NR^L$—$CH_2$.

In certain embodiments, $R^L$ is H. In certain embodiments, $R^L$ is $C_{1-4}$ alkyl optionally substituted with hydroxycarbonyl, alkoxycarbonyl, hydroxycarbonylalkyl, or alkylcarbonyloxy. In certain embodiments, $R^L$ is H or $C_{1-4}$ alkyl optionally substituted with hydroxycarbonyl. In certain embodiments, $R^L$ is $C_{1-4}$ alkyl optionally substituted with hydroxycarbonyl. In certain embodiments, $R^L$ is hydrogen, $C_{1-4}$ alkyl, $C_{3-6}$ cycloalkyl, phenyl, or benzyl; wherein the $C_{1-4}$ alkyl is substituted with hydroxycarbonyl, alkoxycarbonyl, hydroxycarbonylalkyl, or alkylcarbonyloxy; and the phenyl group alone or as a part of the benzyl group is substituted with one or two groups selected from halo and haloalkoxy. In certain embodiments, $R^L$ is $C_{3-6}$ cycloalkyl. In certain embodiments, $R^L$ is phenyl or benzyl; wherein the phenyl group alone or as a part of the benzyl group is optionally substituted with one or two groups selected from halo haloalkoxy. In certain embodiments, $R^L$ is benzyl optionally substituted with one or two groups selected from halo and haloalkoxy.

In certain embodiments, Ring A is cycloalkyl, spirocycloalkyl, heterocycloalkyl, aryl, or heteroaryl, each is optionally substituted with 1 or 2 $R^{AA}$ groups.

In certain embodiments, Ring A is $C_{3-7}$ cycloalkyl, $C_{8-11}$ spirocycloalkyl, 5-6 membered heterocycloalkyl, pyrazolyl, imidazolyl, triazolyl, thiazolyl, thienyl, pyridyl, phenyl, naphthyl, tetrahydronaphthyl, dihydronaphthyl, indanyl, indolyl, indolinyl, isoindolinyl, benzothiazolyl, quinolinyl, isoquinolinyl, tetrahydroquinolinyl, dihydroisoquinolinyl, tetrahydroisoquinolinyl, 2,3-dihydrobenzo[b][1,4]dioxinyl, or tetrahydro-methanonaphthalenyl.

In certain embodiments, Ring A is $C_{3-7}$ cycloalkyl, 5-6 membered heterocycloalkyl, phenyl, naphthyl, indanyl, tetrahydronaphthyl, 2,3-dihydrobenzo[b][1,4]dioxinyl, quinolinyl, isoquinolinyl, tetrahydroquinolinyl, or tetrahydroisoquinolinyl.

In certain embodiments, Ring A is cyclopentyl, cyclohexyl, spiro[2.5]octanyl, spiro[4.5]decanyl, spiro[5.5]undecanyl, piperidinyl, piperazinyl, phenyl, naphthyl, indanyl, tetrahydronaphthyl, 2,3-dihydrobenzo[b][1,4]dioxinyl, quinolinyl, isoquinolinyl, pyridyl, tetrahydroquinolinyl, tetrahydroisoquinolinyl, or 3-azabicyclo[3.1.0]hexanyl.

In certain embodiments, Ring A is cyclopentyl, cyclohexyl, bicycloheptanyl, spiro[2.5]octanyl, spiro[4.5]decanyl, or spiro[5.5]undecanyl, pyrrolidinyl, piperidinyl, piperazinyl, pyrazolyl, imidazolyl, triazolyl, phenyl, naphthyl, indanyl, tetrahydronaphthyl, dihydronaphthyl, pyridyl, indolyl, benzothiazolyl, quinolinyl, isoquinolinyl, indolinyl, isoindolinyl, tetrahydroquinolinyl, dihydroisoquinolinyl, tetrahydroisoquinolinyl, dihydrobenzodioxiny, or 3-azabicyclo[3.1.0]hexanyl.

In certain embodiments, Ring A is $C_{3-7}$ cycloalkyl, $C_{8-11}$ spirocycloalkyl, 5-6 membered heterocycloalkyl, phenyl, or naphthyl.

In certain embodiments, Ring A is cyclopentyl, cyclohexyl, spiro[2.5]octanyl, spiro[4.5]decanyl, or spiro[5.5]undecanyl, piperidinyl, piperazinyl, phenyl, or naphthyl.

In certain embodiments, Ring A is aryl. In certain embodiments, ring A is phenyl or naphthyl. In certain embodiments, ring A is phenyl.

In certain embodiments, Ring A is spirocycloalkyl, or is $C_{8-11}$ spirocycloalkyl. In certain embodiments, ring A is spiro[2.5]octanyl, spiro[4.5]decanyl, or spiro[5.5]undecanyl.

In certain embodiments, Ring A is $C_{3-7}$ cycloalkyl. In certain embodiments, Ring A is $C_{5-6}$ cycloalkyl. In certain embodiments, Ring A is cyclopentyl or cyclohexyl.

In certain embodiments, Ring A is 5-6 membered heterocycloalkyl. In certain embodiments, Ring A is piperidinyl or piperazinyl.

In certain embodiments, Ring A is $C_{3-7}$ cycloalkyl, $C_{8-11}$ spirocycloalkyl, 5-6 membered heterocycloalkyl, aryl, or heteroaryl, each is optionally substituted with 1 or 2 $R^{AA}$ or $R^{AB}$ groups. In certain embodiments, Ring A is $C_{3-7}$ cycloalkyl or $C_{8-11}$ spirocycloalkyl, each is optionally substituted with 1 or 2 $R^{AB}$ groups. In certain embodiments, Ring A is $C_{3-7}$ cycloalkyl, $C_{8-11}$ spirocycloalkyl, or 5-6 membered heterocycloalkyl, each is optionally substituted with 1 or 2 $R^{AB}$ groups. In certain embodiments, Ring A is $C_{3-7}$ cycloalkyl, $C_{8-11}$ spirocycloalkyl, aryl, or heteroaryl, each is optionally substituted with 1 or 2 $R^{AA}$ or $R^{AB}$ groups. In certain embodiments, Ring A is $C_{3-7}$ cycloalkyl, $C_{8-11}$ spirocycloalkyl, or aryl, each is optionally substituted with 1 or 2 $R^{AA}$ or $R^{AB}$ groups. In certain embodiments, Ring A is 5-6 membered heterocycloalkyl, aryl, or heteroaryl, each is optionally substituted with 1 or 2 $R^{AA}$ or $R^{AB}$ groups. In certain embodiments, Ring A is 5-6 membered heterocycloalkyl, aryl, or heteroaryl, each is optionally substituted with 1 or 2 $R^{AA}$ or $R^{AB}$ groups. In certain embodiments, Ring A is aryl or heteroaryl, each is optionally substituted with 1 or 2 $R^{AA}$ or $R^{AB}$ groups. In certain embodiments, Ring A is 5-6 membered heterocycloalkyl, phenyl, or heteroaryl, each is optionally substituted with 1 or 2 $R^{AA}$ or $R^{AB}$ groups. In certain embodiments, Ring A is 5-6 membered heterocycloalkyl, phenyl, or heteroaryl, each is optionally substituted with 1 or 2 $R^{AA}$ or $R^{AB}$ groups. In certain embodiments, Ring A is phenyl or heteroaryl, each is optionally substituted with 1 or 2 $R^{AA}$ or $R^{AB}$ groups. In certain embodiments, Ring A is $C_{3-7}$ cycloalkyl or $C_{8-11}$ spirocycloalkyl, each is optionally substituted with 1 or 2 $R^{AB}$ groups. In certain embodiments, Ring A is $C_{3-7}$ cycloalkyl optionally substituted with 1 or 2 $R^{AB}$ groups. In certain embodiments, Ring A does not include thienyl. In certain embodiments, Ring A does not include indolyl.

In certain embodiments, when Ring B is present, then Ring A is optionally substituted with one or two groups selected from halo, alkyl, alkoxy, or haloalkoxy.

In certain embodiments, when Ring B is not present and Ring A is phenyl, then Ring A is substituted with: (i) one or two $R^{AA}$ groups, or (ii) 2 halo groups when L is other than O.

In certain embodiments, when Ring B is not present and Ring A is phenyl, then Ring A is substituted with: (i) one or two $R^{AA}$ groups, (ii) 2 halo groups when L is other than O, (iii) 2 halo groups when L is O, and $R^2$ and $R^3$ are not hydrogen or alkyl, (iv), one halo group when L is $CH_2NR^L$, or (v) one halo group and one group selected from the group consisting of haloalkoxy, (cycloalkyl)alkoxy, and (phenyl)alkoxy, when L is bond, O or S, wherein the phenyl is optionally substituted with halo.

In certain embodiments, each $R^{AA}$ is independently alkyl, haloalkyl, haloalkoxy, cycloalkyloxy, (cycloalkyl)alkoxy, phenoxy optionally substituted with one or two groups selected from halo and alkylcarbonylaminoalkoxy. In certain embodiments, each $R^{AA}$ is independently alkyl, haloalkyl, haloalkoxy, cycloalkyloxy, (cycloalkyl)alkoxy, or alkylcarbonylaminoalkoxy. In certain embodiments, each $R^{AA}$ is independently haloalkyl, haloalkoxy, cycloalkyloxy, (cycloalkyl)alkoxy, or alkylcarbonylaminoalkoxy. In certain embodiments, each $R^{AA}$ is independently haloalkyl, cycloalkyloxy, (cycloalkyl)alkoxy, alkylcarbonylaminoalkoxy, (phenyl)alkoxy, wherein the phenyl is optionally substituted with halo, or alkylcarbonylaminoalkoxy. In certain embodiments, each $R^{AA}$ is independently haloalkyl or cycloalkyloxy, or is haloalkyl or (cycloalkyl)alkoxy, or is haloalkyl or (phenyl)alkoxy, wherein the phenyl is optionally substituted with halo.

In certain embodiments, each $R^{AA}$ is independently isopropyl, trifluoromethyl, propoxy, pentyloxy, trifluoromethoxy, cyclopropylmethoxy, cyclopentylmethoxy, or cyclohexylmethoxy. In certain embodiments, each $R^{AA}$ is independently isopropyl, trifluoromethyl, propoxy, pentyloxy, trifluoromethoxy, cyclopropylmethoxy, cyclopentylmethoxy, cyclohexylmethoxy, or halobenzyloxy.

In certain embodiments, when Ring B is not present and Ring A is phenyl, then Ring A is substituted with one halo group and one group selected from the group consisting of haloalkoxy, (cycloalkyl)alkoxy, and (phenyl)alkoxy, wherein the phenyl is optionally substituted with halo. In certain embodiments, when Ring B is not present and Ring A is phenyl, then Ring A is substituted with one halo and one haloalkoxy, or with one halo and one (cycloalkyl)alkoxy, or with one halo and one (phenyl)alkoxy, wherein the phenyl is optionally substituted with halo.

In certain embodiments, when Ring B is not present and Ring A is other than phenyl, then Ring A is substituted with one or two $R^{AB}$ groups. In certain embodiments, when Ring B is not present and Ring A is other than phenyl, then Ring A is unsubstituted: 1) when L is bond and Ring A is tetrahydroquinolinyl, 2) when L is O and Ring A is dihydroxybenzodioxynyl, 3) when L is O, Ring A is tetrahydronapthalene, and $R^1$ is not hydrogen or ethyl, or 4) when L is O or S, and ring A is spirocycloalkyl.

In certain embodiments, each R is independently halo; alkyl; hydroxy; alkoxy; haloalkyl; haloalkoxy; cycloalkyloxy; (cycloalkyl)alkoxy; or phenoxy optionally substituted with one or two halo. In certain embodiments, each $R^{AB}$ is independently halo, alkyl, haloalkyl, or haloalkoxy. In certain embodiments, each $R^{AB}$ is independently chloro, bromo, fluoro, methyl, isopropyl, difluoromethyl, trifluoromethyl, trifluoromethoxy.

In certain embodiments, when Ring B is not present and Ring A is spiro[2.5]octanyl, spiro[4.5]decanyl, spiro[5.5]undecanyl, phenyl, naphthyl, indanyl, tetrahydronaphthyl, 2,3-dihydrobenzo[b][1,4]dioxinyl, pyridyl, quinolinyl, isoquinolinyl, pyridyl, tetrahydroquinolinyl, or tetrahydroisoquinolinyl; then ring A is substituted with one or two groups independently selected from the group consisting of haloalkyl, cycloalkyloxy, (cycloalkyl)alkoxy, alkylcarbonylaminoalkoxy, and (phenyl)alkoxy, wherein the phenyl as part of (phenyl)alkoxy is optionally substituted with halo, or with one or two groups independently selected from the group consisting of halo, alkyl, alkoxy, and haloalkoxy, or with difluoromethane, trifluoromethyl, cyclopropoxy, cyclopentyloxy, propylmethoxy, pentylmethoxy, hexylmethoxy, and fluorobenzyloxy, or with fluoro, chloro, bromo, methyl, isopropyl, and trifluoromethoxy.

In certain embodiments, Ring B, when present, is cycloalkyl, heterocycloalkyl, aryl, or heteroaryl; wherein each is optionally substituted with one or two $R^B$ groups. In certain embodiments, Ring B, when present, is cycloalkyl optionally substituted with one or two $R^B$ groups. In certain embodiments, Ring B, when present, is heterocycloalkyl optionally substituted with one or two $R^B$ groups. In certain embodiments, Ring B, when present, is aryl optionally substituted with one or two $R^B$ groups. In certain embodiments, Ring B, when present, is heteroaryl optionally substituted with one or two $R^B$ groups.

In certain embodiments, Ring B is $C_{4-6}$ cycloalkyl, heterocycloalkyl, aryl, or heteroaryl. In certain embodiments, Ring B is $C_{4-6}$ cycloalkyl, 5-6 membered heterocycloalkyl, aryl, or heteroaryl. In certain embodiments, Ring B is $C_{4-6}$ cycloalkyl, 5-6 membered heterocycloalkyl, phenyl, or heteroaryl. In certain embodiments, Ring B is 5-6 membered heterocycloalkyl, phenyl, tetrahydronaphthyl, tetrahydroquinolinyl, quinolinyl, or isoquinolinyl, tetrahydro-2H-pyranyl, cyclobutyl, cyclopentyl, cyclohexyl, or pyridyl. In certain embodiments, Ring B is piperidinyl, piperazinyl, phenyl, tetrahydronaphthyl, tetrahydroquinolinyl, quinolinyl, or isoquinolinyl, tetrahydro-2H-pyranyl, cyclobutyl, cyclopentyl, cyclohexyl, or pyridyl. In certain embodiments, Ring B is 5-6 membered heterocycloalkyl, phenyl, pyridyl, quinolinyl, or isoquinolinyl. In certain embodiments, Ring B is 5-6 membered heterocycloalkyl, phenyl, or quinolinyl. In certain embodiments, Ring B is piperidinyl, piperazinyl, phenyl, or heteroaryl. In certain embodiments, Ring B is cyclobutyl, cyclopentyl, cyclohexyl, piperidinyl, piperazinyl, phenyl, pyridyl, quinolinyl, or isoquinolinyl. In certain embodiments, Ring B is piperidinyl, piperazinyl, phenyl, or quinolinyl. In certain embodiments, Ring B is phenyl, pyridyl, quinolinyl, or isoquinolinyl. In certain embodiments, Ring B is phenyl or quinolinyl. In certain embodiments, Ring B is phenyl.

In certain embodiments, Ring B is cycloalkyl, heterocycloalkyl, aryl, or heteroaryl; each optionally substituted with one or two $R^B$ groups, wherein each $R^B$ is independently halo, cyano, alkyl, haloalkyl, haloalkoxy, alkoxyalkoxy, aminocarbonyl, alkylcarbonylaminoalkoxy, cycloalkyl, cycloalkyloxy, (cycloalkyl)alkoxy, heterocycloalkyl optionally substituted with alkyl, alkylcarbonyl or a halo, or (5-6-membered heterocycloalkyl-one)alkyl.

In certain embodiments, Ring B is cyclobutyl, cyclohexyl, piperidinyl, tetrahydropyranyl, phenyl, quinolinyl, isoquinolinyl, tetrahydronaphthyl, or tetrahydroquinolinyl; each substituted with one or two $R^B$ groups, wherein each $R^B$ is independently halo, cyano, alkyl, haloalkyl, haloalkoxy, alkoxyalkoxy, aminocarbonyl, alkylcarbonylaminoalkoxy, cycloalkyl, cycloalkyloxy, (cycloalkyl)alkoxy, (5-6-membered heterocycloalkyl-one)alkyl, or heterocycloalkyl optionally substituted with 1 or 2 alkyl, alkylcarbonyl or halo.

In certain embodiments, Ring B is cyclobutyl, cyclohexyl, piperidinyl, tetrahydropyranyl, phenyl, quinolinyl, isoquinolinyl, tetrahydronaphthyl, or tetrahydroquinolinyl; each substituted with one or two $R^B$ groups, wherein each $R^B$ is independently aminocarbonyl, cyano, chloro, bromo, fluoro, methyl, trifluoromethyl, trifluoromethoxy, methoxyethoxy, acetamidoethoxy, cyclopropoxy, cyclopropylmethoxy, cyclobutyl, cyclohexyl, tetrahydropyranyl, pyrrolidinyl, piperidinyl, methylpiperidinyl, difluoropiperidinyl, methylpiperazinyl, acetylpiperazinyl, or

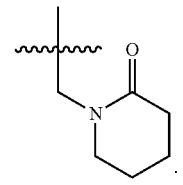

In certain embodiments, Ring B is phenyl optionally substituted with one or two $R^B$ groups, wherein each $R^B$ is independently aminocarbonyl, cyano, chloro, bromo, fluoro, trifluoromethyl, trifluoromethoxy, methoxyethoxy, acetamidoethoxy, cyclopropoxy, cyclopropylmethoxy, cyclobutyl, cyclohexyl, tetrahydropyranyl, pyrrolidinyl, piperidinyl, methylpiperidinyl, difluoropiperidinyl, methylpiperazinyl, acetylpiperazinyl, or

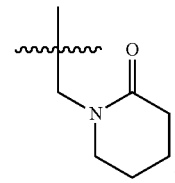

In certain embodiments, Ring B is cyclobutyl, cyclohexyl, piperidinyl, tetrahydropyranyl, quinolinyl, isoquinolinyl, tetrahydronaphthyl, or tetrahydroquinolinyl; each substituted with one or two $R^B$ groups, wherein each $R^B$ is independently chloro, bromo, fluoro, methyl, or piperidinyl.

In certain embodiments, when Ring B is not present and Ring A is phenyl, then Ring A is substituted with one or two $R^{AA}$ groups. In certain embodiments, when Ring B is not present and Ring A is phenyl, then Ring A is substituted with 2 halo groups when L is other than O. In certain embodiments, when Ring B is not present and Ring A is phenyl, then Ring A is substituted with one halo group when L is $CH_2NR^L$. In certain embodiments, when Ring B is not present and Ring A is phenyl, then Ring A is substituted with one halo group and one group selected from the group consisting of haloalkoxy, (cycloalkyl)alkoxy, and (phenyl) alkoxy, when L is bond, O or S, wherein the phenyl is optionally substituted with halo.

In certain embodiments, when Ring B is not present and Ring A is other than phenyl, then Ring A is substituted with one or two $R^{AB}$ groups. In certain embodiments, when Ring B is not present and Ring A is other than phenyl, then Ring A is unsubstituted tetrahydroquinolinyl when L is bond. In certain embodiments, when Ring B is not present and Ring A is other than phenyl, then Ring A is unsubstituted dihydroxybenzodioxynyl when L is O. In certain embodiments, when Ring B is not present and Ring A is other than phenyl, then Ring A is unsubstituted tetrahydronapthalene when L is O and $R^1$ is not hydrogen or ethyl. In certain embodiments, when Ring B is not present and Ring A is other than phenyl, then Ring A is unsubstituted spirocycloalkyl when L is O or S.

In certain embodiments, when L is S and Ring A is phenyl, then Ring B cannot be halo-substituted phenyl.

In certain embodiments, when L is S or $CH_2$, and Ring A is phenyl, then Ring B cannot be halo-substituted phenyl.

In certain embodiments, when L is $CH_2$ and Ring A is phenyl, then Ring B cannot be halo-substituted phenyl.

In certain embodiments, when L is O, Ring A is phenyl, and Ring B is not present, then $R^{AA}$ cannot be alkyl or trifluoromethyl;

In certain embodiments, when L is O, Ring A is phenyl, and Ring B is not present, then $R^{AA}$ cannot be alkyl.

In certain embodiments, when L is O, Ring A is phenyl substituted with 1 $R^{AA}$, and Ring B is not present, then $R^{AA}$ cannot be trifluoromethyl.

In certain embodiments, when L is O, Ring A is phenyl substituted with 1 $R^{AA}$, and Ring B is not present, then $R^{AA}$ cannot be meta-substituted trifluoromethyl.

In certain embodiments, when L is O, Ring A is phenyl, Ring B is not present, and $R^1$ is ethyl, then $R^{AA}$ cannot be trifluoromethoxy.

In certain embodiments, when L is NH, Ring A is pyridyl, indolyl, or indolinyl, and Ring B is not present, then $R^{AB}$ cannot be alkyl.

In certain embodiments, when L is bond, Ring A is other than phenyl, Ring B is not present, and $R^1$ is H, then $R^{AB}$ cannot be methyl.

In certain embodiments, $R^1$ is hydrogen, alkyl, cycloalkyl, heterocycloalkyl, or W; wherein W is alkyl substituted with amino, alkylamino, dialkylamino, alkylcarbonyloxy, alkoxycarbonyl, or phenylcarbonyloxy. In certain embodiments, $R^1$ is hydrogen, alkyl, cycloalkyl, heterocycloalkyl, or W; wherein W is alkyl substituted with amino, alkylamino, dialkylamino, alkylcarbonyloxy, alkoxycarbonyl, phenylcarbonyloxy, aminocarbonyloxy, alkylaminocarbonyloxy, dialkylaminocarbonyloxy, alkoxycarbonyloxy, cycloalkylcarbonyloxy, —$N(R^{1A})C(O)R^{1B}$, —$N(R^{1A})C(O)OR^{1B}$, or —$N(R^{1A})C(O)NR^{1B}R^{1C}$; wherein $R^{1A}$, $R^{1B}$, and $R^{1C}$ are each independently hydrogen or $C_{1-6}$ alkyl.

In certain embodiments, $R^1$ is hydrogen, alkyl, cycloalkyl, or heterocycloalkyl. In certain embodiments, $R^1$ is hydrogen or alkyl. In certain embodiments, $R^1$ is hydrogen. In certain embodiments, $R^1$ is alkyl. In certain embodiments, $R^1$ is hydrogen or W. In certain embodiments, $R^1$ is W. In certain embodiments, $R^1$ is W; wherein W is alkyl substituted with amino, alkylamino, dialkylamino, alkylcarbonyloxy, alkoxycarbonyl, or phenylcarbonyloxy, or W is substituted with dialkylamino or alkylcarbonyloxy, or W is substituted with alkylcarbonyloxy, dialkylaminocarbonyloxy cycloalkylcarbonyloxy, or phenylcarbonyloxy.

In another aspect, provided herein is a compound of Formula (VII):

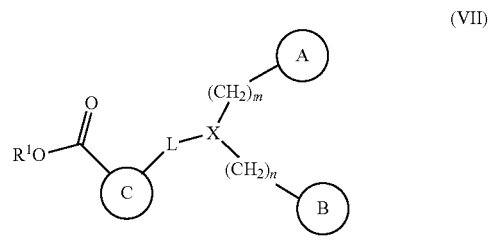

(VII)

wherein:
ring C is selected from:

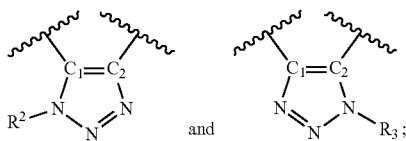

and wherein the wavy lines (~~~) indicate the points of attachment of the $C_1$ carbon to the carbonyl of C(O)—$OR^1$, and the $C_2$ carbon to L;
L is a bond, $CH_2$, $CH_2CH_2$, O, or $CH_2O$;
X is N or CH;
m is 1, 2, or 3;
n is 0, 1, 2, or 3;
Ring A and Ring B are each independently $C_{3-7}$ cycloalkyl, 5-6 membered heterocycloalkyl, aryl or heteroaryl, optionally substituted with halo, haloalkyl or phenyl; wherein phenyl is optionally substituted with halo, haloalkyl, or haloalkoxy; and
optionally a single stereoisomer or mixture of stereoisomers thereof and additionally optionally a pharmaceutically acceptable salt thereof.

In certain embodiments, the compound of Formula (VII) is that wherein:
L is a bond, $CH_2$, $CH_2CH_2$, O, or $CH_2O$;
X is N or CH;
m is 1, 2, or 3;
n is 0, 1, 2, or 3;
Ring A and Ring B are each independently aryl, optionally substituted with halo, haloalkyl or phenyl; wherein phenyl is optionally substituted with halo, haloalkyl, or haloalkoxy; and optionally a single stereoisomer or mixture of stereoisomers thereof and additionally optionally a pharmaceutically acceptable salt thereof.

In certain embodiments, the compound of Formula (VII) is that wherein:
L is a bond, $CH_2$, $CH_2CH_2$, O, or $CH_2O$;
X is N or CH;
m is 1 or 2;
n is 0, 1, or 2;
Ring A and Ring B are each independently phenyl, optionally substituted with halo, or phenyl substituted with halo or haloalkoxy; and
optionally a single stereoisomer or mixture of stereoisomers thereof and additionally optionally a pharmaceutically acceptable salt thereof.

In certain embodiments, the compound or pharmaceutically acceptable salt thereof is a compound from Table 1. In certain embodiments, the compound or pharmaceutically acceptable salt thereof is a compound selected from the compounds 1-168, or a single stereoisomer or mixture of stereoisomers thereof.

In certain embodiments, the compound or pharmaceutically acceptable salt thereof is a compound selected from the compounds 2, 3, 4, 5, 6, 7, 8, 9, 10, 11, 12, 13, 14, 15, 16, 17, 18, 19, 20, 21, 22, 23, 24, 25-1, 25-2, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58-1, 58-2, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 99, 100, 101, 102, 103, 104, 105, 106, 107, 108, 109, 111, 111-1, 111-2, 112, 113, 114, 115, 116, 117, 118, 119, 120, 121, 122, 124, 125, 126, 127, 128, 129, 130, 131, 132, 133, 134, 135, 136, 137, 138, 139, 140, 141, 143, 144, 145, 146, 147, 148, 149, 150, 152, 153, 154, 155, 156, 157, 158, 160, 161, 162, 163, 164, 165, 166, 167, and 168, or a single stereoisomer or mixture of stereoisomers thereof.

In certain embodiments, the compound or pharmaceutically acceptable salt thereof is a compound selected from the compounds 1, 2, 3, 4, 5, 6, 7, 8, 9, 10, 11, 12, 13, 14, 15, 16, 17, 18, 19, 20, 21, 22, 23, 24, 25-1, 25-2, 26, 27, 28, 29, 32, 33, 34, 35, 36, 37, 38, 39, 40, 41, 42, 43, 44, 45, 46, 47, 48, 49, 50, 51, 52, 53, 54, 55, 56, 57, 58-1, 58-2, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 99, 100, 101, 102, 103, 104, 105, 106, 107, 108, 109, 111, 111-1, 111-2, 112, 113, 114, 115, 116, 117, 118, 119, 120, 121, 122, 124, 125, 126, 127, 128, 129, 130, 131, 132, 133, 134, 135, 136, 137, 138, 139, 140, 141, 143, 144, 145, 146, 147, 148, 149, 150, 151, 152, 153, 154, 155, 156, 157, 158, 159, 160, 161, 162, 163, 164, 165, 166, 167, and 168, or a single stereoisomer or mixture of stereoisomers thereof.

In certain embodiments, the compound or pharmaceutically acceptable salt thereof is a compound selected from the compounds 1, 2, 3, 5, 6, 7, 8, 9, 10, 11, 12, 13, 14, 15, 16, 17, 18, 19, 20, 21, 22, 23, 24, 25-1, 25-2, 26, 27, 28, 29, 32, 33, 34, 35, 36, 37, 38, 39, 40, 41, 42, 43, 44, 45, 46, 47, 48, 49, 50, 51, 52, 53, 54, 55, 56, 57, 58-1, 58-2, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 99, 100, 101, 102, 103, 104, 105, 106, 107, 108, 109, 111, 111-1, 111-2, 112, 113, 114, 115, 116, 117, 118, 119, 120, 121, 122, 124, 125, 126, 127, 128, 129, 130, 131, 132, 133, 134, 135, 136, 137, 138, 139, 140, 141, 143, 144, 145, 146, 147, 148, 149, 150, 151, 152, 153, 154, 155, 156, 157, 158, 159, 160, 161, 162, 163, 164, 165, 166, 167, and 168, or a single stereoisomer or mixture of stereoisomers thereof.

In certain embodiments, the compound or pharmaceutically acceptable salt thereof is a compound selected from the compounds 1, 2, 3, 6, 7, 8, 9, 10, 11, 12, 13, 14, 15, 16, 17, 18, 19, 20, 23, 24, 25-1, 25-2, 26, 27, 28, 29, 32, 33, 34, 35, 36, 37, 38, 39, 40, 41, 42, 43, 44, 45, 46, 49, 50, 51, 52, 53, 54, 55, 56, 57, 58-1, 58-2, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 99, 100, 101, 102, 103, 104, 105, 106, 107, 108, 109, 111, 111-1, 111-2, 112, 113, 114, 115, 116, 117, 118, 119, 120, 121, 122, 124, 125, 126, 127, 128, 129, 130, 131, 132, 133, 134, 135, 136, 137, 138, 139, 140, 141, 143, 144, 145, 146, 147, 148, 149, 150, 151, 152, 153, 154, 155, 156, 157, 158, 159, 160, 161, 162, 163, 164, 165, 166, 167, and 168, or a single stereoisomer or mixture of stereoisomers thereof.

In certain embodiments, the compound or pharmaceutically acceptable salt thereof is a compound selected from the compounds 4-5, 14, 16, 21, 22, 30-33, 37, 38, 42, 45, 47, 51, 52, 54, 55, 58, 60, 62, 65-68, 72, 75, 81, 86, 87, 119, 126, 128-130, 139, 155-157, and 160-165, or a single stereoisomer or mixture of stereoisomers thereof.

In certain embodiments, the compound or pharmaceutically acceptable salt thereof is a compound selected from the compounds 1-3, 8, 9, 11, 15, 17-19, 23-27, 29, 34, 39, 40, 43, 44, 53, 59, 61, 63, 64, and 124, or a single stereoisomer or mixture of stereoisomers thereof.

In certain embodiments, the compound or pharmaceutically acceptable salt thereof is a compound selected from the compounds 12, 20, and 145, or a single stereoisomer or mixture of stereoisomers thereof.

In certain embodiments, the compound or pharmaceutically acceptable salt thereof is a compound selected from the compounds 73, 90, 146, 149, and 150, or a single stereoisomer or mixture of stereoisomers thereof.

In certain embodiments, the compound or pharmaceutically acceptable salt thereof is a compound selected from the compounds 70, 71, and 74, or a single stereoisomer or mixture of stereoisomers thereof.

In certain embodiments, the compound or pharmaceutically acceptable salt thereof is a compound selected from the compounds 1, 9, 11, 17, 19, 33, 37, 38, 40, 44, 45, 54, 55, 65, 72, 81, 93, 98, 107-110, 112, and 116, or a single stereoisomer or mixture of stereoisomers thereof.

In certain embodiments, the compound or pharmaceutically acceptable salt thereof is a compound selected from the compounds 54, 55, 37, 38, 81, and 107-109, or a single stereoisomer or mixture of stereoisomers thereof.

In certain embodiments, the compound or pharmaceutically acceptable salt thereof is a compound selected from the compounds 88, 91, 94, 95, 98, 100, 102-104, 112, and 131, or a single stereoisomer or mixture of stereoisomers thereof.

In certain embodiments, the compound or pharmaceutically acceptable salt thereof is a compound from Table 2. In certain embodiments, the compound or pharmaceutically acceptable salt thereof is a compound selected from the group consisting of compounds 169-375, or a single stereoisomer or mixture of stereoisomers thereof.

In certain embodiments, the compound or pharmaceutically acceptable salt thereof is a compound from Table 3. In certain embodiments, the compound or pharmaceutically acceptable salt thereof is a compound selected from the group consisting of compounds 294, 296, 366, 372 and 374, or a single stereoisomer or mixture of stereoisomers thereof.

In certain embodiments, the compound or pharmaceutically acceptable salt thereof is a compound selected from the group consisting of compounds 169, 170, 171, 172, 173, 174, 175, 176, 177, 178, 179, 180, 181, 182, 183, 185, 186, 187, 188, 189, 190, 194, 195, 196, 197, 198, 199, 200, 201, 203, 204, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 249, 250, 251, 252, 253, 254, 255, 256, 257, 258, 259, 260, 261, 262, 263, 264, 265, 266, 267, 268, 269, 270, 271, 272-1, 272-2, 273, 274, 275, 277, 278, 279, 280, 281, 282, 283, 284, 285, 286, 287, 288, 289, 290, 291, 292, 293, 295, 297, 298, 299, 300, 301, 303, 304, 305, 306, 307, 308-1, 308-2, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 367, 368, 369, 370, 373, and 375, or a single stereoisomer or mixture of stereoisomers thereof.

In certain embodiments, the compound or pharmaceutically acceptable salt thereof is a compound selected from the group consisting of compounds 169, 170, 171, 172, 172, 173, 174, 175, 176, 177, 178, 179, 180, 181, 183, 197, 198, 199, 200, 201, 203, 216, 217, 220, 221, 222, 223, 224, 225, 227, 228, 230, 231, 232, 233, 234, 235, 236, 237, 238, 241, 242, 243, 247, 250, 253, 254, 255, 257, 259, 262, 263, 264, 265, 266, 267, 268, 269, 270, 271, 272-1, 272-2, 273, 274, 275, 277, 279, 280, 282, 283, 284, 285, 286, 287, 289, 290, 291, 292, 293, 295, 297, 298, 299, 300, 304, 308-1, 308-2, 309, 310, 311, 312, 314, 315, 316, 318, 319, 320, 321, 322, 323, 324, 325, 326, 327, 328, 329, 330, 331, 332, 333, 334, 336, 337, 338, 339, 340, 341, 342, 343, 344, 345, 346, 347, 348, 349, 350, 352, 353, 354, 355, 356, 357, 358, 359, 360, 361, 362, 363, 364, 365, 367, 368, 369, 373, and 375, or a single stereoisomer or mixture of stereoisomers thereof.

In certain embodiments, the compound or pharmaceutically acceptable salt thereof is a compound selected from the group consisting of compounds 169, 170, 172, 173, 175, 244, 247, 277, 278, 311, 313, 314, 315, 317, 318, 319, 320, 321, 323, 324, 325, 326, 327, 330, 331, 332, 336, 337, 338, 339, 340, 341, 342, 343, 344, 345, 346, 347, 348, 349, 351, and 352, or a single stereoisomer or mixture of stereoisomers thereof.

In certain embodiments, the compound or pharmaceutically acceptable salt thereof is a compound selected from the compounds 1, 98, 110, 123, 142, 151, 159, 184, 191, 192, 193, 302, and 371, or a single stereoisomer or mixture of stereoisomers thereof.

In certain embodiments, the compound or pharmaceutically acceptable salt thereof is compound 335, or a single stereoisomer or mixture of stereoisomers thereof.

In certain embodiments, the compound or pharmaceutically acceptable salt thereof is a compound selected from the group consisting of compounds 171, 243, 312, 322, 328, 329, and 350, or a single stereoisomer or mixture of stereoisomers thereof.

In certain embodiments, the compound or pharmaceutically acceptable salt thereof is a compound selected from the group consisting of compounds 174, 176, 177, 316, and 373, or a single stereoisomer or mixture of stereoisomers thereof.

In certain embodiments, the compound or pharmaceutically acceptable salt thereof is a compound selected from the group consisting of compounds 220, 221, 222, 223, 224, 225, 226, 228, 229, 230, 231, 232, 233, 234, 235, 236, 237, 238, 239, 240, 241, 242, 245, 246, 249, 250, 251, 252, 253, 254, 255, 256, 257, 258, 259, 260, 261, 262, 263, 267, 268, 270, 271, 272-1, 272-2, 273, 275, 279, 280, 281, 282, 283, 284, 285, 286, 287, 288, 289, 290, 291, 292, 293, 295, 297, 301, 302, 303, 304, 305, 306, 307, 308-1, 308-2, 309, 310, 353, 354, 355, 356, 357, 358, 359, 360, 361, 362, 363, 364, 365, 367, 368, 370, 371, and 375, or a single stereoisomer or mixture of stereoisomers thereof.

In certain embodiments, the compound or pharmaceutically acceptable salt thereof is a compound selected from the group consisting of compounds 227, 269, 274, 298, and 369, or a single stereoisomer or mixture of stereoisomers thereof.

In certain embodiments, the compound or pharmaceutically acceptable salt thereof is a compound selected from the group consisting of compounds 264, 265, 266, 299, and 300, or a single stereoisomer or mixture of stereoisomers thereof.

In certain embodiments, the compound or pharmaceutically acceptable salt thereof is a compound selected from the group consisting of compounds 181, 183, 186, and 190, or a single stereoisomer or mixture of stereoisomers thereof.

In certain embodiments, the compound or pharmaceutically acceptable salt thereof is a compound selected from the group consisting of compounds 178, 179, 180, 184, 185, 187, 189, 193, 194, 195, 196, and 333, or a single stereoisomer or mixture of stereoisomers thereof.

In certain embodiments, the compound or pharmaceutically acceptable salt thereof is a compound selected from the group consisting of compounds 178, 179, 180, and 333, or a single stereoisomer or mixture of stereoisomers thereof.

In certain embodiments, the compound or pharmaceutically acceptable salt thereof is a compound 182, or a single stereoisomer or mixture of stereoisomers thereof.

In certain embodiments, the compound or pharmaceutically acceptable salt thereof is a compound selected from the group consisting of compounds 197, 198, 199, 200, and 201, or a single stereoisomer or mixture of stereoisomers thereof.

In certain embodiments, the compound or pharmaceutically acceptable salt thereof is a compound selected from the group consisting of compounds 203, 204, 206, 207, 208, 209, 210, 211, 212, 213, 214, 215, 216, 217, 218, 219, and 334, or a single stereoisomer or mixture of stereoisomers thereof.

In certain embodiments, the compound or pharmaceutically acceptable salt thereof is a compound selected from the group consisting of compound 188, 191, and 192, or a single stereoisomer or mixture of stereoisomers thereof.

In certain embodiments, the compound or pharmaceutically acceptable salt thereof is a compound from Table 4 or 5. In certain embodiments, the compound or pharmaceutically acceptable salt thereof is a compound selected from the compounds 376-486, or a single stereoisomer or mixture of stereoisomers thereof.

In certain embodiments, the compound or pharmaceutically acceptable salt thereof is a compound selected from the group consisting of compounds 376, 377, 379, 380, 381, 382, 383, 384, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442-1, 442-2, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, and 486, or a single stereoisomer or mixture of stereoisomers thereof.

In certain embodiments, the compound or pharmaceutically acceptable salt thereof is a compound selected from the group consisting of compounds 294, 296, 366, 372, 374, 378, and 385.

In certain embodiments, the compound or pharmaceutically acceptable salt thereof is a compound selected from the group consisting of compounds 4, 5, 21, 22, 30, 31, 47, 48, 276, and 376.

Pharmaceutical Compositions

In certain embodiments, optionally in combination with any or all of the above various embodiments, provided herein is a pharmaceutical composition comprising of a compound disclosed herein, for example, a compound of Formula (I), (II), (III), (IV), (V), (VI), (VII), (VIII), (IX), (X) or (XI), or a compound of Table 1, Table 2, Table 3, Table 4, Table 5, or Table 6, or stereoisomers thereof, or a pharmaceutically acceptable salt thereof, and one or more pharmaceutically acceptable excipients.

In certain embodiments, the pharmaceutical composition comprises a compound of Formula (I), (II), (III), (IV), (V), (VI), (VII), (VIII), (IX), (X) or (XI), or stereoisomers thereof, or a pharmaceutically acceptable salt thereof, and one or more pharmaceutically acceptable excipients. In certain embodiments, the pharmaceutical composition comprises a compound of Table 1, Table 2, Table 3, Table 4, Table 5, or Table 6, or stereoisomers thereof, or a pharmaceutically acceptable salt thereof, and one or more pharmaceutically acceptable excipients.

Excipients include, for example, encapsulating materials or additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof.

Suitable excipients are well known to those skilled in the art. Whether a particular excipient is suitable for incorporation into a pharmaceutical composition or dosage form depends on a variety of factors well known in the art, including, but not limited to, the method of administration. The suitability of a particular excipient may also depend on the specific active ingredients in the dosage form.

Formulation and Administration

All the compounds and pharmaceutical compositions provided herein can be used in all the methods provided herein. For example, the compounds and pharmaceutical compositions provided herein can be used in all the methods for treatment of all diseases or disorders provided herein. Thus, the compounds and pharmaceutical compositions provided herein are for use as a medicament. The compounds and pharmaceutical compositions provided herein are for use in a method for the treatment of a disease or disorder that is mediated by the enzyme GO. The compounds and pharmaceutical compositions provided herein are for use in a method for the treatment of a disease or disorder in which inhibition of the enzyme GO ameliorates or treats the disease or disorder. For example, a compound provided herein is a compound of Formula (I), (II), (III), (IV), (V), (VI), (VII), (VIII), (IX), (X) or (XI), or a compound of Table 1, Table 2, Table 3, Table 4, Table 5, or Table 6, or stereoisomers thereof, and additionally optionally a pharmaceutically acceptable salt thereof. In certain embodiments, provided is a method for treating any of the diseases or disorders described herein comprising administering to a subject in need of treatment thereof a compound according to any of the various embodiments described herein or a pharmaceutical composition according to any of the various embodiments described herein. The compounds and pharmaceutical compositions provided herein are for use in a method for the treatment of a disease or disorder that is mediated by the enzyme GO, or in which inhibition of the enzyme GO ameliorates or treats the disease or disorder. In certain embodiments, the compounds and pharmaceutical compositions provided herein are used in the preparation or manufacture of medicaments for the treatment of a disease or disorder that is mediated by the enzyme GO or in which inhibition of the enzyme GO ameliorates or treats the disease or disorder.

In certain embodiments, the method comprises administering to a subject in need thereof a therapeutically effective amount of a compound of Formula (I), (II), (III), (IV), (V), (VI), (VII), (VIII), (IX), (X) or (XI), or a compound of Table 1, Table 2, Table 3, Table 4, Table 5, or Table 6, or stereoisomers thereof, or a pharmaceutically acceptable salt thereof, and one or more pharmaceutically acceptable excipients.

In certain embodiments, the method comprises administering to a subject in need thereof a therapeutically effective amount of a pharmaceutical composition comprising a therapeutically effective amount of a compound of Formula (I), (II), (III), (IV), (V), (VI), (VII), (VIII), (IX), (X) or (XI), or a compound of Table 1, Table 2, Table 3, Table 4, Table 5, or Table 6, or stereoisomers thereof, and additionally optionally a pharmaceutically acceptable salt thereof, and one or more pharmaceutically acceptable excipients. In certain embodiments, the method comprises administering to a subject in need thereof a therapeutically effective amount of a pharmaceutical composition comprising a therapeutically effective amount of a compound of Table 1, or stereoisomers thereof, and additionally optionally a pharmaceutically acceptable salt thereof, and one or more pharmaceutically acceptable excipients. In certain embodiments, the method comprises administering to a subject in need thereof a therapeutically effective amount of a pharmaceutical composition comprising a therapeutically effective amount of a compound of Table 2, or stereoisomers thereof, and additionally optionally a pharmaceutically acceptable salt thereof, and one or more pharmaceutically acceptable excipients. In certain embodiments, the method comprises administering to a subject in need thereof a therapeutically effective amount of a pharmaceutical composition comprising a therapeutically effective amount of a compound of Table 4, or stereoisomers thereof, and additionally optionally a pharmaceutically acceptable salt thereof, and one or more pharmaceutically acceptable excipients.

In certain embodiments, the disease or disorder is a defect in glyoxylate metabolism. In certain embodiments, the disease or disorder is characterized by high oxalate content in the urine. In certain embodiments, the disease or disorder is a primary hyperoxaluria ("PH"). In certain embodiments, the disease or disorder is Primary hyperoxaluria type 1 ("PH1"). In certain embodiments, the disease or disorder is characterized by a deficiency in the enzyme alanine: glyoxylate aminotransferase (AGT).

The compounds or compositions disclosed herein can be administered in therapeutically effective amounts via any of the usual and acceptable modes known in the art, either singly or in combination with another therapeutic agent. The compounds are typically administered as pharmaceutical compositions by any route which makes the compound bioavailable. In certain embodiments, the composition is a solid formulation adapted for oral administration. In certain embodiments, the composition is a tablet, powder, or capsule; or the composition is a tablet. In certain embodiments, the composition is a liquid formulation adapted for oral administration. In certain embodiments, the composition is a liquid formulation adapted for parenteral administration. In certain embodiments, the composition is a solution, suspension, or emulsion; or the composition is a solution. In certain embodiments, solid form compositions can be converted, shortly before use, to liquid form compositions for either oral or parenteral administration. These particular solid form compositions are provided in unit dose form and as such are used to provide a single liquid dosage unit. These dosage forms can be prepared according to conventional methods and techniques known to those skilled in the art (See, *Remington: The Science and Practice of Pharmacy, supra; Modified-Release Drug Delivery Technology*, 2nd ed.; Rathbone et al., Eds.; Marcel Dekker, Inc.: New York, N.Y., 2008).

The dosages may be varied depending on the requirement of the patient, the severity of the disease or disorder being treating and the particular compound and/or composition being employed. Determination of the proper dosage can be determined by one skilled in the medical arts. The total daily dosage may be divided and administered in portions throughout the day or by means providing continuous delivery. In certain embodiments, the compounds are administered to a subject at a daily dosage of between 0.01 to about 50 mg/kg of body weight. In other embodiments, the dose is examples are illustrative and not limiting. All substituents, unless otherwise specified, are as previously defined. The reagents and starting materials are readily available to one of ordinary skill in the art. The specific synthetic steps for each of the routes described may be combined in different ways, or in conjunction with steps from different schemes, to prepare the compounds described herein.

General Scheme 1

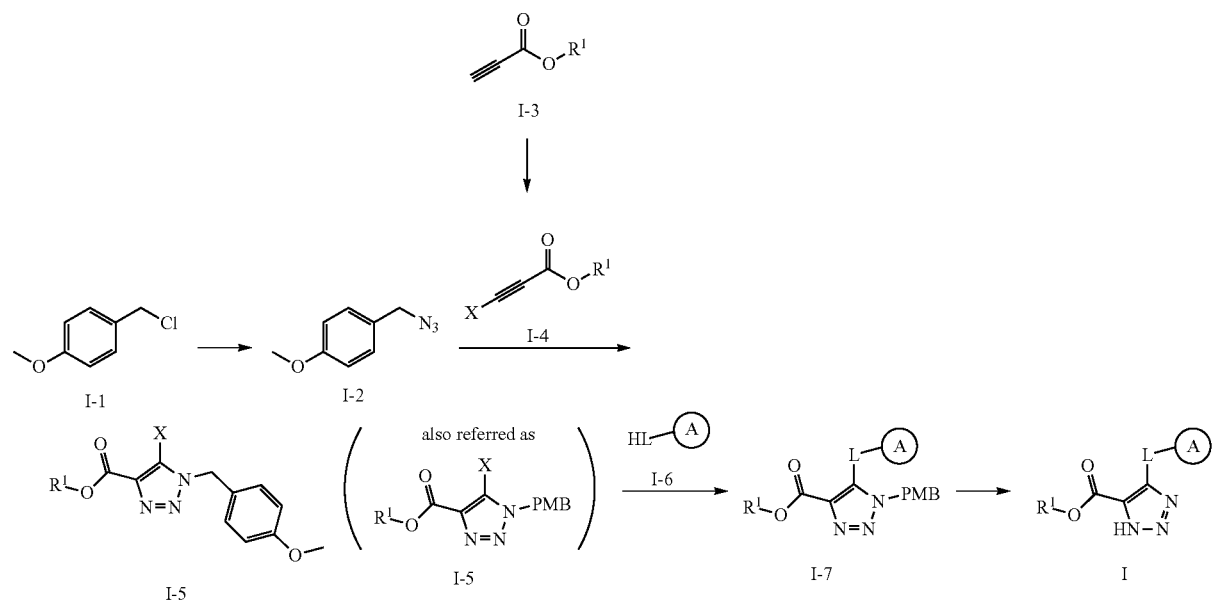

from 1 to 1000 mg/day. In certain embodiments, the daily dose is from 1 to 750 mg/day; or from 10 to 500 mg/day.

In certain embodiments, the pharmaceutical composition is in unit dosage form. The composition can be subdivided into unit doses containing appropriate quantities of the active component(s). The unit dosage form can be a tablet, capsule, or powder in a vial or ampule, or it may be the appropriate number of any of these in a packaged form. The unit dosage form can be a packaged form, the package containing discrete quantities of composition such as packeted tablets, capsules, or powders in vials or ampules. The quantity of active compound(s) in a unit dose of the composition may be varied or adjusted from about 1 mg to about 100 mg, or from about 1 mg to about 50 mg, or from about 1 mg to about 25 mg.

The compounds or pharmaceutical compositions disclosed herein can be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

Preparation of Compounds

The following are illustrative schemes and examples of how the compounds described herein can be prepared and tested. Although the examples can represent only some embodiments, it should be understood that the following A compound of Formula (I) can be prepared according to General Scheme 1, wherein $R^1$ can be, for example, alkyl or cycloalkyl group. In certain embodiments, $R^1$ is methyl, or ethyl.

Compound I-2 can be prepared from Compound I-1 using standard azide substitution conditions. More specifically, Compound I-1 can react with $NaN_3$ in a solvent such as DMF, or THF, and at ambient temperature or up to 50° C.

Compound I-4 can be prepared from corresponding unsubstituted acetylene 1-3 using standard halogenation conditions, wherein X is, for example, Cl, Br or I. More specifically, Compound I-3 can reaction with a halogenation reagent, such as NBS (N-Bromosuccinimide) or NIS (N-iodosuccinimide), in a solvent such as acetone or THF, in the presence of a silver salt such as $AgNO_3$, to yield Compound I-4.

Intermediate I-5 can be prepared from Compounds 1-2 and 1-4 using standard click reaction conditions. More specifically, Compound I-2 can reaction with Compound I-4 optionally in the presence of copper salts, for example, a mixture of Cu(I) and Cu(II) salts such as CuI and $Cu(OAc)_2$ in a solvent such as THF, to yield Intermediate I-5.

Compound I-7 can be prepared using standard substitution conditions. More specifically, Compound I-5 can reacted with Compound I-6, in a solvent such as DMF or THF, in the presence of a base such as $Na_2CO_3$ or $K_2CO_3$, to yield Compound I-7.

Compound I can be prepared using standard PMB (p-Methoxybenzyl) deprotection conditions. More specifically, Compound I-7 can be treated in acidic conditions, such as in TFA (trifluoroacetic acid) as the solvent, at ambient temperature or up to 50° C. to afford Compound I.

General Scheme 2

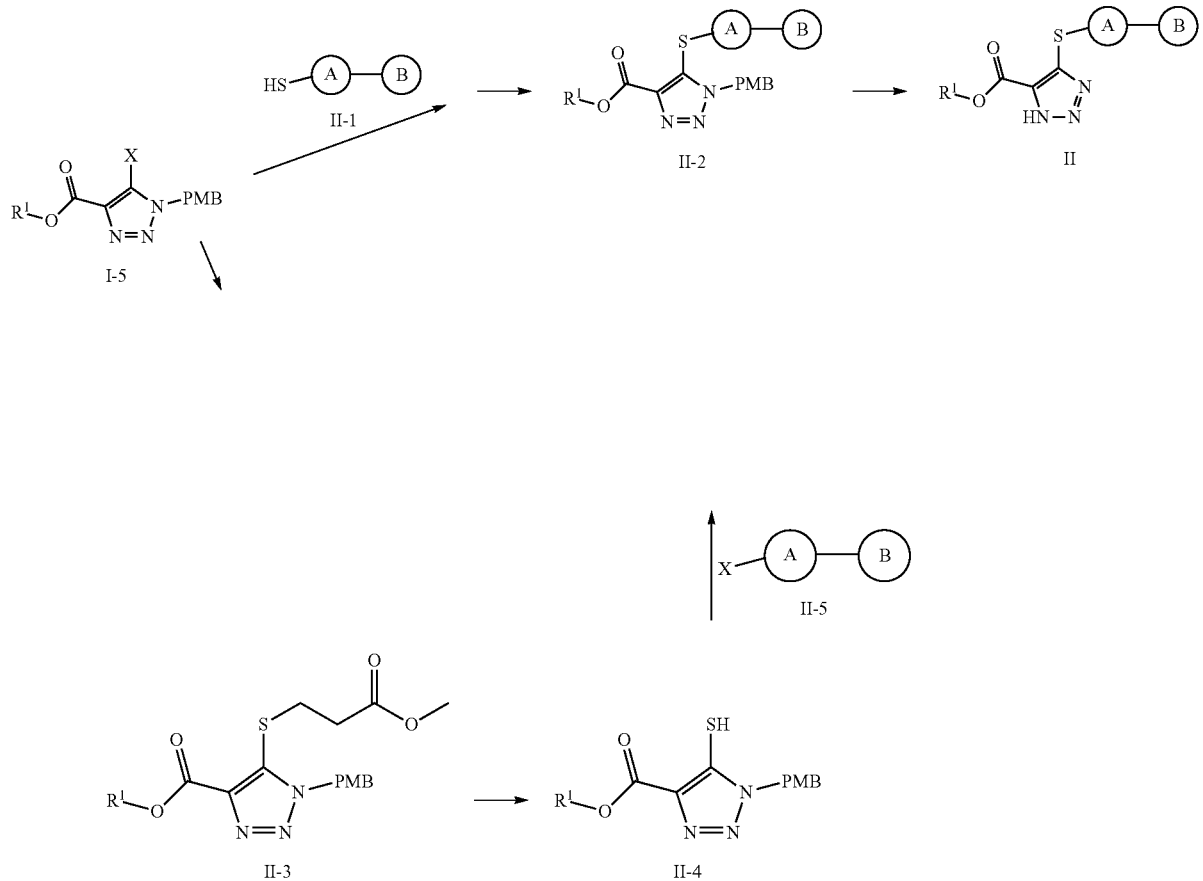

Compound I or II of Formula (I) can be also prepared using General Scheme 2.

Compound II-2 can be prepared using standard substitution conditions. More specifically, Intermediate I-5 can reacted with Compound II-1, in a solvent such as DMF or THF, in the presence of a base such as $Na_2CO_3$ or $K_2CO_3$, to yield Compound II-2.

Compound II-3 can be prepared using standard coupling conditions. More specifically, Intermediate I-5 can reacted with methyl 3-mercaptopropanoate, in a solvent such as 1,4-dioxane or THF, in the presence of a base such as DIPEA (N,N-diisopropylethylamine), a palladium salt such as $Pd_2(dba)_3$, and a phosphine such as Xantphos, and to yield Compound II-3.

Compound II-3 can be treated in basic condition to afford Compound II-4. More specification, Compound II-3 can reacted with potassium tert-butoxide, in a solvent such as THF at −78° C. and warmed up to ambient temperature, and to yield Compound II-4.

Compound II-2 can also be prepared using standard substitution conditions. More specifically, Compound II-4 can reacted with Compound II-5, in a solvent such as DMF or THF, in the presence of a base such as $Na_2CO_3$ or $K_2CO_3$, to yield Compound II-2.

Compound II can be prepared using standard PMB (p-Methoxybenzyl) deprotection conditions. More specifically, Compound II-2 can be treated in acidic conditions, such as in TFA (trifluoroacetic acid) as the solvent, at ambient temperature or up to 50° C. to afford Compound II.

General Scheme 3

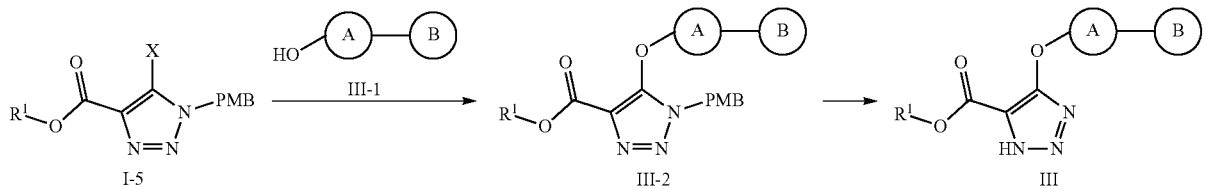

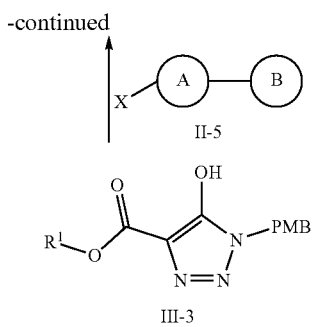
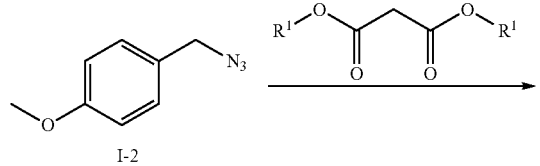

Compound III of Formula (I) can be also prepared using General Scheme 3.

Compound III-2 can be prepared using standard substitution conditions. More specifically, Intermediate I-5 can reacted with Compound III-1, in a solvent such as DMF or THF, in the presence of a base such as Na₂CO₃ or K₂CO₃, to yield Compound III-2.

Compound III-3 can be prepared using standard click reaction conditions. More specifically, Compound I-2 can reacted with dialkyl malonate, in a solvent such as 1,4-dioxane or THF, optionally in the presence of copper salts, for example, a mixture of Cu(I) and Cu(II) salts such as CuI and Cu(OAc)₂ in a solvent such as THF, to yield Intermediate III-3.

Compound III-2 can also be prepared using standard substitution conditions. More specifically, Compound III-3 can reacted with Compound II-5, in a solvent such as DMF or THF, in the presence of a base such as Na₂CO₃ or K₂CO₃, to yield Compound III-2.

Compound III can be prepared using standard PMB (p-Methoxybenzyl) deprotection conditions. More specifically, Compound III-2 can be treated in acidic conditions, such as in TFA (trifluoroacetic acid) as the solvent, at ambient temperature or up to 50° C. to afford Compound III.

General Scheme 4

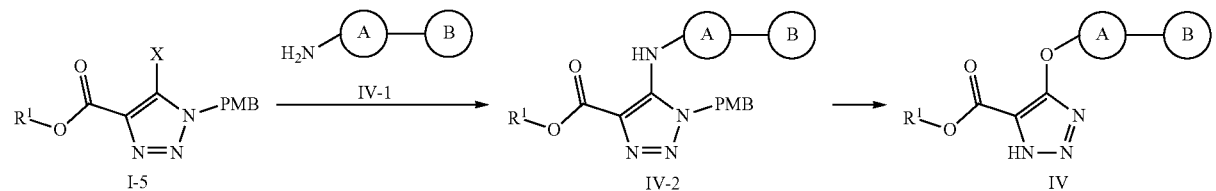

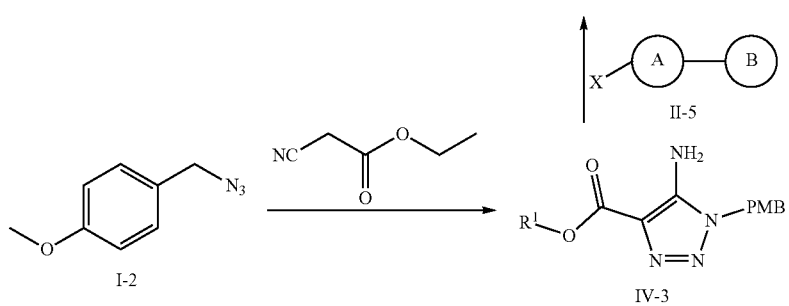

Compound IV of Formula (I) can be also prepared using General Scheme 4.

Compound IV-2 can be prepared using standard substitution conditions. More specifically, Intermediate I-5 can reacted with Compound IV-1, in a solvent such as DMF or THF, in the presence of a base such as $Na_2CO_3$ or $K_2CO_3$, to yield Compound IV-2.

Compound IV-3 can be prepared using standard click reaction conditions. More specifically, Compound I-2 can reacted with ethyl 2-cyanoacetate, in a solvent such as 1,4-dioxane or THF, optionally in the presence of copper salts, for example, a mixture of Cu(I) and Cu(II) salts such as CuI and $Cu(OAc)_2$ in a solvent such as THF, to yield Intermediate IV-3.

Compound IV-2 can also be prepared using standard substitution conditions. More specifically, Compound IV-3 can reacted with Compound II-5, in a solvent such as DMF or THF, in the presence of a base such as $Na_2CO_3$ or $K_2CO_3$, to yield Compound IV-2.

Compound IV can be prepared using standard PMB (p-Methoxybenzyl) deprotection conditions. More specifically, Compound IV-2 can be treated in acidic conditions, such as in TFA (trifluoroacetic acid) as the solvent, at ambient temperature or up to 50° C. to afford Compound IV.

reacted with Compound V-1, in a solvent such as DMF or THF, in the presence of a base such as $Na_2CO_3$ or $K_2CO_3$, to yield Compound V-2.

Compound V-4 can be prepared using standard Suzuki-Miyaura coupling reaction conditions. More specifically, Compound V-2 can reacted with boronic acid Compound V-3, in a solvent such as toluene/EtOH/$H_2O$ or toluene/$H_2O$, in the presence of a palladium salt such as $Pd(PPh_3)_4$ and a base such as $Na_2CO_3$ or $K_3PO_4.7H_2O$, to yield Intermediate V-4.

Compound V can be prepared using standard PMB (p-Methoxybenzyl) deprotection conditions. More specifically, Compound V-4 can be treated in acidic conditions, such as in TFA (trifluoroacetic acid) as the solvent, at ambient temperature or up to 50° C. to afford Compound V.

General Scheme 5

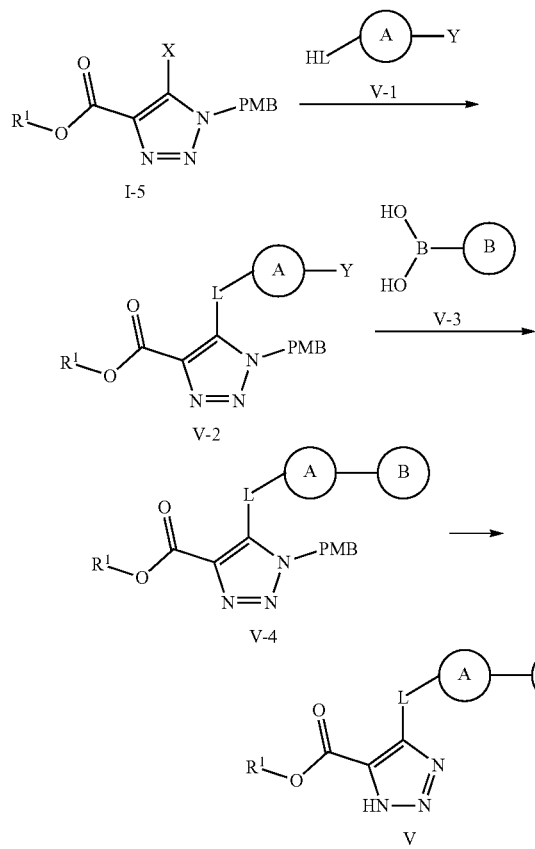

Compound V of Formula (I) can be also prepared using General Scheme 5, wherein Y is a halo group for example, Cl, Br, or I.

Compound V-2 can be prepared using standard substitution conditions. More specifically, Intermediate I-5 can General Scheme 6

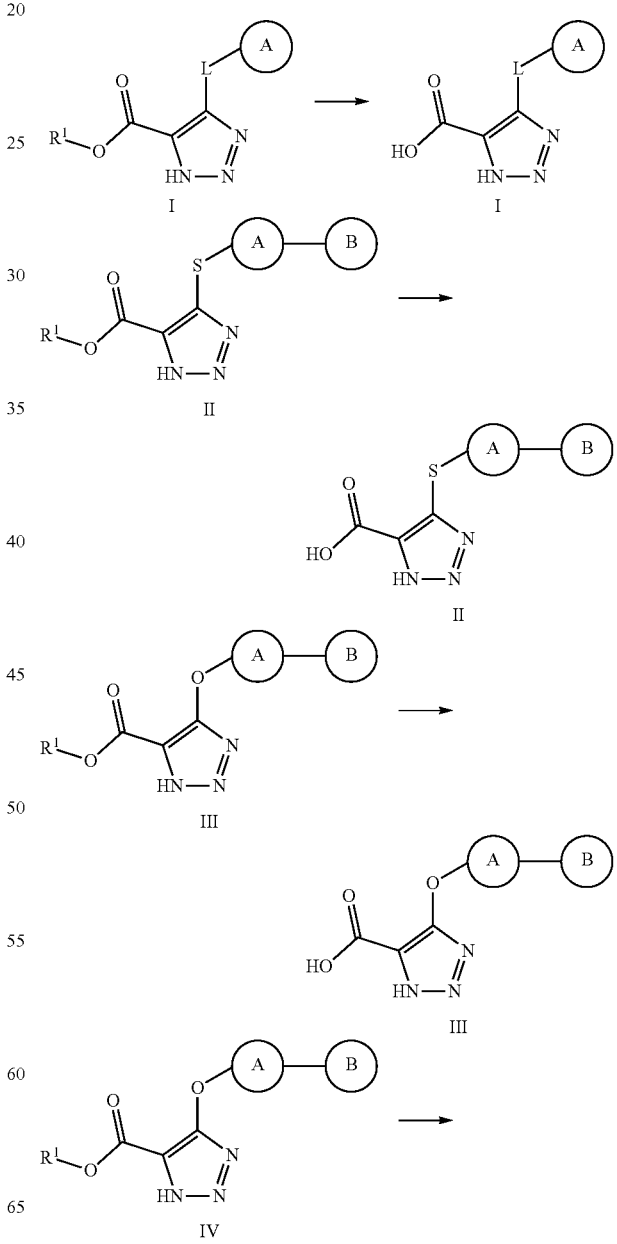

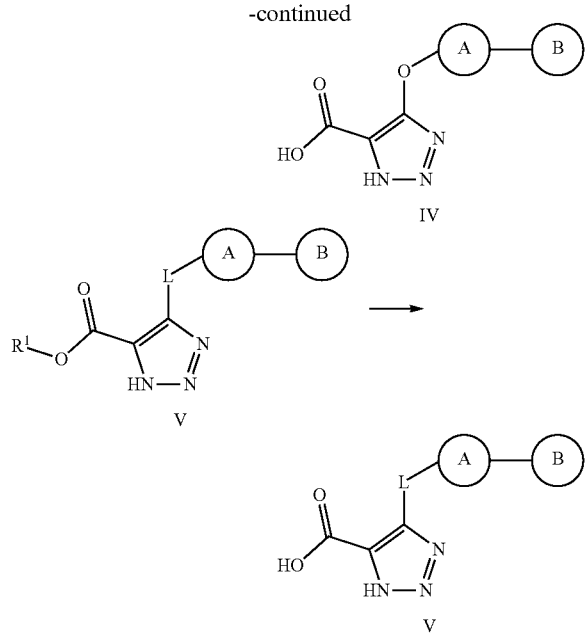

Compounds of Formula (I) can be also prepared using General Scheme 6. Compounds I, II, III, IV, or V can be prepared using standard hydrolysis conditions. More specifically, Compounds I, II, III, IV, or V, respectively, can be treated in basic conditions, such as in the presence of NaOH or LiOH H$_2$O in a solvent such as THF, at ambient temperature to afford the corresponding hydrolyzed Compound I, II, III, IV, or V, respectively.

Intermediate A

Synthesis of ethyl 5-bromo-1-(4-methoxybenzyl)-1H-1,2,3-triazole-4-carboxylate

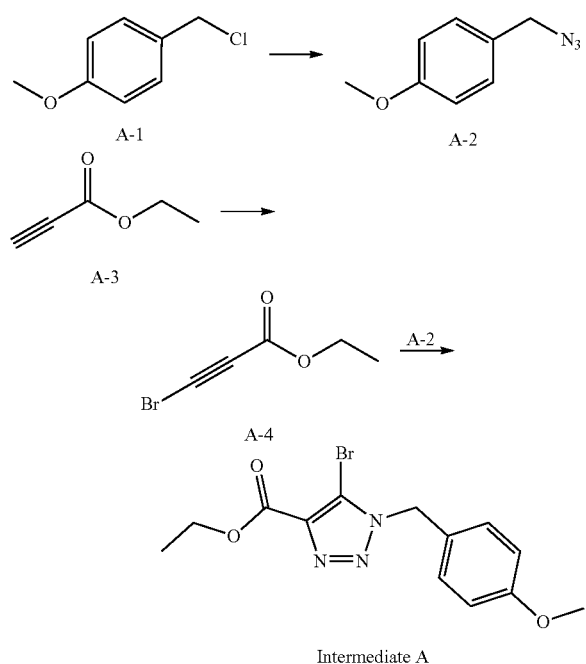

To a solution of NaN$_3$ (25.0 g, 0.38 mol) in DMF (300 mL) was slowly added 1-(chloromethyl)-4-methoxybenzene (A-1) (49.7 mL, 0.37 mol) and stirred at 50° C. overnight. After cooling down to room temperature, the mixture was diluted with water (1000 mL) and extracted with ethyl acetate (500 mL×3). The combined extracts were washed with water (500 mL×4) and brine (500 mL), dried over anhydrous sodium sulfate, filtered, and concentrated to afford Intermediate A-2. LC-MS (ESI) m/z: non-ionizable compound under routine conditions used; $^1$H-NMR (CDCl$_3$, 400 MHz): δ (ppm) 3.82 (s, 3H), 4.27 (s, 2H), 6.92 (d, J=8.4 Hz, 2H), 7.25 (d, J=8.4 Hz, 2H).

To a solution of ethyl propionate (A-3) (26.3 g, 0.268 mol) and AgNO$_3$ (4.56 g, 26.8 mmol) in anhydrous acetone (300 mL) was added NBS (52.6 g, 0.295 mol) in several small portions at 0° C. and stirred at room temperature overnight. The mixture was filtered. The filtrate was diluted with H$_2$O (500 mL) and extracted with n-hexane (500 mL×3). The combined extracts were washed with an aqueous HCl solution (10%, 500 mL×2) and brine (500 mL), dried over anhydrous sodium sulfate, filtered, and concentrated under reduced pressure at room temperature (<20° C.) to furnish Intermediate A-4 as a white solid. LC-MS (ESI) m/z: non-ionizable compound under routine conditions used; $^1$H-NMR (CDCl$_3$, 400 MHz): δ (ppm) 1.32 (t, J=7.2 Hz, 3H), 4.25 (q, J=7.2 Hz, 2H).

A mixture of Intermediate A-2 (23.0 g, 0.14 mol), Intermediate A-4 (27.4 g, 0.155 mol), CuI (1.34 g, 7 mmol), and Cu(OAc)$_2$ (1.27 g, 7 mmol) in anhydrous THF (500 mL) was stirred at 50° C. for 16 hours. After cooling down to room temperature, the mixture was filtered, the filtrate was concentrated under reduced pressure, and the residue was diluted with H$_2$O (500 mL) and extracted with dichloromethane (500 mL×2). The combined extracts were washed with saturated aqueous NaHCO$_3$ solution (500 mL×2) and brine (500 mL), dried over anhydrous sodium sulfate, filtered, and concentrated to give a product. The product was slurred in petroleum ether (300 mL), filtered, and dried under vacuum to afford Intermediate A. LC-MS (ESI) m/z: 701 [2M+Na]$^+$; $^1$H-NMR (CDCl$_3$, 400 MHz): δ (ppm) 1.42 (t, J=7.2 Hz, 3H), 3.80 (s, 3H), 4.44 (q, J=7.2 Hz, 2H), 5.55 (s, 2H), 6.87 (d, J=8.8 Hz, 2H), 7.27 (d, J=8.8 Hz, 2H).

Intermediate B

Synthesis of ethyl 5-iodo-1-(4-methoxybenzyl)-1H-1,2,3-triazole-4-carboxylate

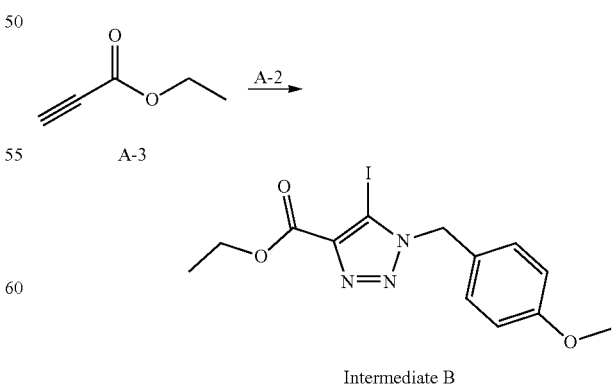

Intermediate B

A mixture of Intermediate A-2 (840 mg, 5.1 mmol), ethyl propiolate (A-3) (402 mg, 5.1 mmol), CuI (970 mg, 5.1 mmol), NIS (908 mg, 5.1 mmol), and N,N-diisopropylethylamine (658 mg, 5.1 mmol) in THF (10 mL) was stirred at room temperature for 16 hours. The mixture was concentrated and purified with flash column chromatography on silica gel (ethyl acetate in petroleum ether, 17% v/v) to afford Intermediate B. LC-MS (ESI) m/z: 388 [M+H]$^+$; $^1$H-NMR (CDCl$_3$, 400 MHz): δ (ppm) 1.43 (t, J=6.8 Hz, 3H), 3.79 (s, 3H), 4.43 (q, J=6.8 Hz, 2H), 5.60 (s, 2H), 6.86 (d, J=8.8 Hz, 2H), 7.26 (d, J=8.8 Hz, 2H).

Intermediate C

Synthesis of methyl 5-iodo-1-(4-methoxybenzyl)-1H-1,2,3-triazole-4-carboxylate

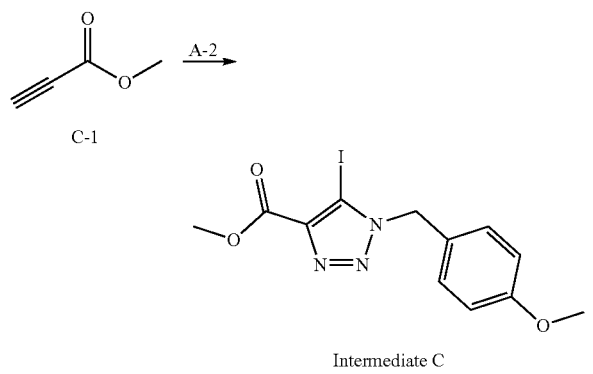

Intermediate C

Intermediate C was synthesized by employing the procedure described for Intermediate B using Intermediate C-1 in lieu of Intermediate A-3, LC-MS (ESI) m/z: 374 [M+H]$^+$.

Intermediate D

Synthesis of ethyl 5-mercapto-1-(4-methoxybenzyl)-1H-1,2,3-triazole-4-carboxylate

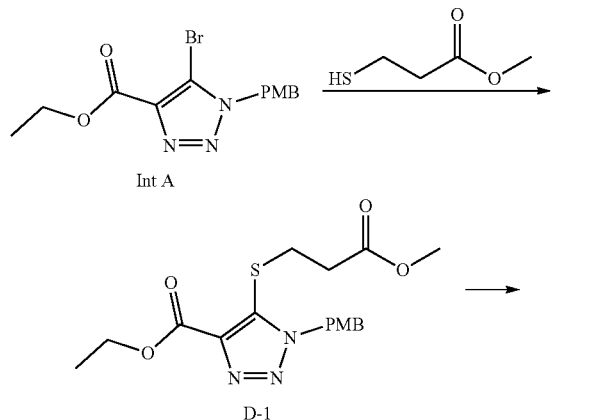

To a solution of Intermediate A (1 g, 2.9 mmol) and methyl 3-mercaptopropanoate (418 mg, 3.48 mmol) in 1,4-dioxane (8 mL) was added N,N-diisopropylethylamine (748 mg, 5.8 mmol), Pd$_2$(dba)$_3$ (133 mg, 0.145 mmol), and Xantphos (168 mg, 0.29 mmol). The mixture was purged with nitrogen for 2 minutes and heated in a microwave oven at 120° C. for 30 minutes. The reaction mixture was concentrated and purified with flash column chromatography on silica gel (ethyl acetate in petroleum ether from 0% to 60% v/v) to yield Intermediate D-1. LC-MS (ESI) m/z: 380 [M+H]$^+$; $^1$H-NMR (CDCl$_3$, 400 MHz): δ (ppm) 1.42 (t, J=7.2 Hz, 3H), 2.43 (t, J=7.2 Hz, 2H), 3.17 (t, J=6.8 Hz, 2H), 3.65 (s, 3H), 3.77 (s, 3H), 4.34 (q, J=7.2 Hz, 2H), 5.59 (s, 2H), 6.84 (d, J=8.8 Hz, 2H), 7.24 (d, J=8.8 Hz, 2H).

To a solution of Intermediate D-1 (0.8 g, 2.1 mmol) in dry THF (10 mL) was added potassium tert-butoxide (235 mg, 2.1 mmol) at −78° C. The mixture was stirred at −78° C. under nitrogen for 30 minutes. After slowly warming to room temperature, the mixture was diluted with water (4 mL), acidified to pH 6 with a concentrated HCl solution, and concentrated under reduced pressure. The residue was purified with reverse phase chromatography using eluents (methanol in H$_2$O, from 0% to 60% v/v) to afford Intermediate D. LC-MS (ESI) m/z: 294 [M+H]$^+$.

Intermediate E

Synthesis of methyl 5-((4-bromophenyl)thio)-1-(4-methoxybenzyl)-1H-1,2,3-triazole-4-carboxylate

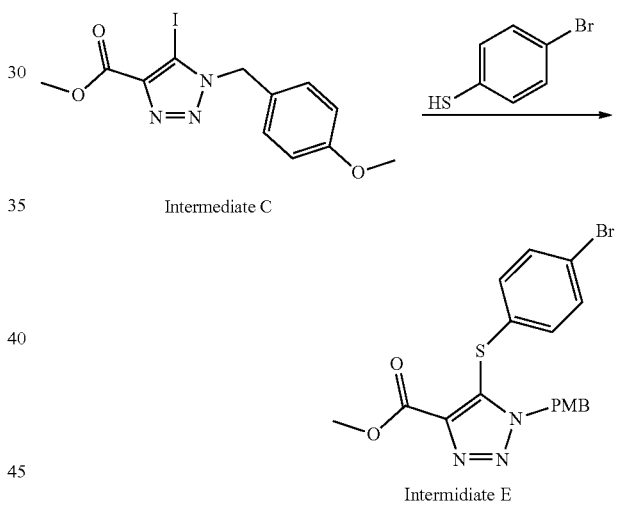

Intermediate E was synthesized by employing the procedure described for Compound 1E using 4-bromobenzenethiol and Intermediate C in lieu of Compound 1D and Intermediate B, LC-MS (ESI) m/z: 434 [M+H]$^+$.

Intermediate F

Synthesis of ethyl 5-((4-bromophenyl)thio)-1-(4-methoxybenzyl)-1H-1,2,3-triazole-4-carboxylate

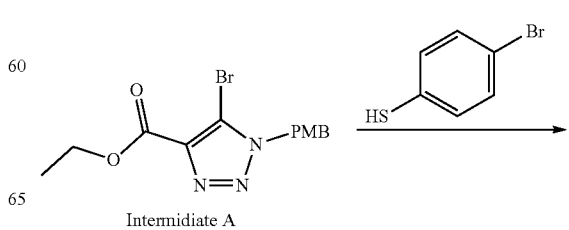

Intermidiate A

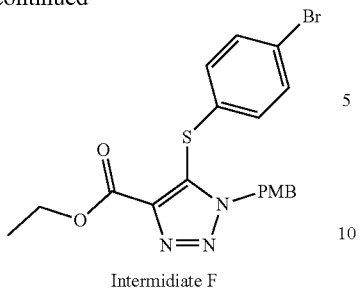

Intermidiate F

Intermediate F was synthesized by employing the procedure described for Compound 1E using 4-bromobenzenethiol and Intermediate A in lieu of Compound 1D and Intermediate B, LC-MS (ESI) m/z: 448 [M+H]$^+$.

Intermediate G

Synthesis of ethyl 5-amino-1-(4-methoxybenzyl)-1H-1,2,3-triazole-4-carboxylate

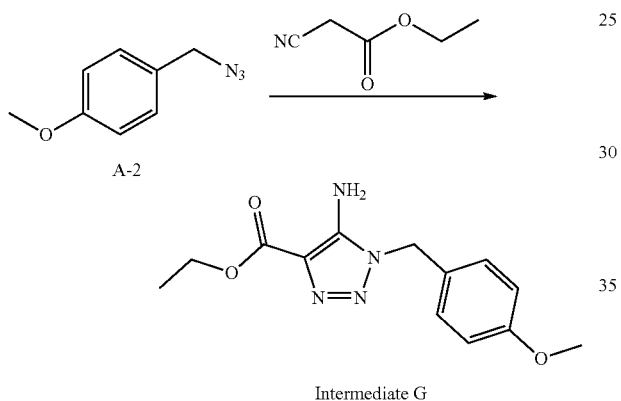

Intermediate G

A mixture of ethyl 2-cyanoacetate (2.4 ml, 22.3 mmol), Intermediate A-2 (3.64 g, 22.3 mmol), and EtONa (1.5 g, 22.3 mmol) in EtOH (50 mL) was stirred at 80° C. for 5.5 hours. The mixture was concentrated under reduced pressure. The residue was diluted with water (300 mL) and filtered. The cake was washed with water (100 mL×2) and slurred in petroleum ether (20 mL) for 15 minutes. The resulting solid was collected and dried under vacuum to afford Intermediate G. LC-MS (ESI) m/z: 277 [M+H]$^+$; $^1$H-NMR (DMSO-d$_6$, 400 MHz): δ (ppm) 1.27 (t, J=7.2 Hz, 3H), 3.72 (s, 3H), 4.25 (q, J=7.2 Hz, 2H), 5.35 (s, 2H), 6.57 (s, 2H), 6.91 (d, J=8.8 Hz, 2H), 7.19 (d, J=8.8 Hz, 2H).

Intermediate H

Synthesis of ethyl 5-hydroxy-1-(4-methoxybenzyl)-1H-1,2,3-triazole-4-carboxylate

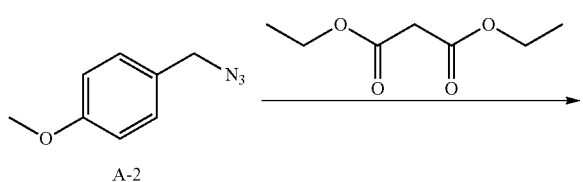

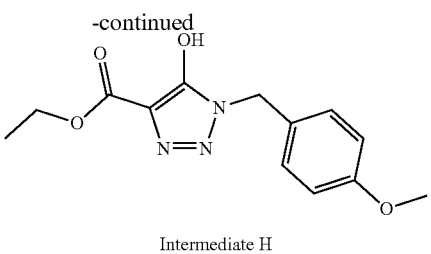

Intermediate H

To anhydrous EtOH (45 mL) at room temperature was added sodium (600 mg, 26 mmol) in small pieces and stirred at room temperature until sodium was dissolved. To the solution was added diethyl malonate (2.08 g, 1.98 mL, 13 mmol) and stirred at room temperature for 30 minutes. To the mixture was dropped a solution of Intermediate A-2 (2.12 g, 13 mmol) in EtOH (5 mL) and heated at reflux for 18 hours. The reaction mixture was cooled down to room temperature and concentrated under reduced pressure. The residue was diluted with H$_2$O (100 mL) and washed with ethyl acetate (50 mL×2). The aqueous layer was adjusted to pH 3-4 with a diluted HCl solution (2 N) and extracted with ethyl acetate (50 mL×3). The combined extracts were washed with brine (100 mL), dried over anhydrous sodium sulfate, filtered, and concentrated to afford Intermediate H. LC-MS (ESI) m/z: 278 [M+H]$^+$; $^1$H-NMR (CDCl$_3$, 400 MHz): δ (ppm) 1.40 (t, J=7.2 Hz, 3H), 3.79 (s, 3H), 4.42 (q, J=7.2 Hz, 2H), 5.31 (s, 2H), 6.85-6.88 (m, 2H), 7.29-7.31 (m, 2H).

Intermediate I

Synthesis of ethyl 5-(4-bromophenoxy)-1-(4-methoxybenzyl)-1H-1,2,3-triazole-4-carboxylate

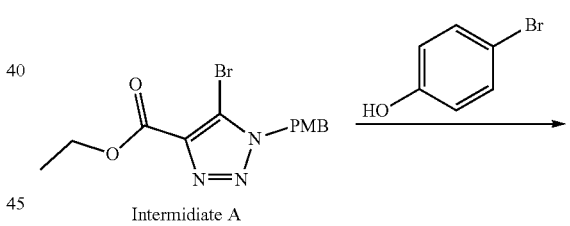

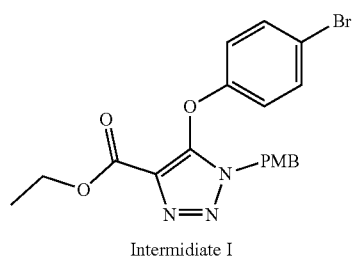

Intermidiate I

A mixture of 4-bromophenol (610 mg, 3.53 mmol), Intermediate A (1 g, 2.94 mmol), and K$_2$CO$_3$ (608 mg, 4.41 mmol) in DMF (20 mL) was stirred at 90° C. for 4 hours. The reaction mixture was cooled down to room temperature, diluted with water (50 mL), and extracted with EtOAc (50 mL×3). The combined extracts were washed with water (100 mL), dried over anhydrous Na$_2$SO$_4$, filtered, and concentrated. The residue was purified by column chromatography on silica gel (ethyl acetate in petroleum ether, 40% v/v) to afford Intermediate I LC-MS (ESI) m/z: 432 [M+H]$^+$.

Intermediate J

Synthesis of a mixture of 4-(ethoxycarbonyl)-1-(4-methoxybenzyl)-1H-1,2,3-triazole-5-carboxylic acid and 5-(ethoxycarbonyl)-1-(4-methoxybenzyl)-1H-1,2,3-triazole-4-carboxylic acid

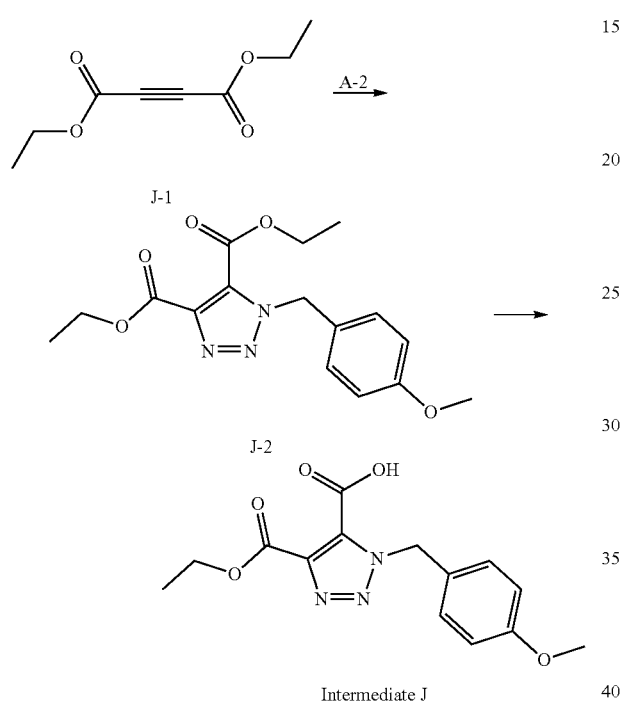

A mixture of Intermediate J-1, diethyl but-2-ynedioate, (1.0 g, 5.9 mmol), CuI (2.25 g, 11.8 mmol), and Intermediate A-2 (963 mg, 5.9 mmol) in DMSO (20 mL) was stirred at room temperature under nitrogen overnight. The mixture was diluted with EtOAc (50 mL), washed with brine (15 mL×3), dried over anhydrous sodium sulfate, filtered, and concentrated. The residue was purified with flash column chromatography on silica gel (ethyl acetate in petroleum ether, 10% v/v) to give Intermediate J-2. LC-MS (ESI) m/z: 334 [M+H]$^+$; $^1$H-NMR (CDCl$_3$, 400 MHz): δ (ppm) 1.31 (t, J=7.2 Hz, 3H), 1.60 (t, J=7.2 Hz, 3H), 3.79 (s, 3H), 4.33 (q, J=7.2 Hz, 2H), 4.42 (q, J=7.2 Hz, 2H), 5.73 (s, 2H), 6.85 (d, J=8.4 Hz, 2H), 7.23 (d, J=8.4 Hz, 2H).

A mixture of Intermediate J-2 (5 g, 15 mmol) and potassium hydroxide (840 mg, 15 mmol) in water (25 mL) and EtOH (25 mL) was stirred at room temperature for 16 hours. The mixture was adjusted to pH 6 with a diluted aqueous HCl solution (1 N) and a solid was precipitated. The solid was collected by filtration and dried under vacuum to give Intermediate J. LC-MS (ESI) m/z: 328 [M+Na]$^+$; $^1$H-NMR (CDCl$_3$, 400 MHz): δ (ppm) 1.49 (t, J=7.2 Hz, 3H), 3.76 (s, 3H), 4.57-4.59 (m, 2H), 6.00 (s, 2H), 6.82 (d, J=8.8 Hz, 2H), 7.39 (d, J=8.8 Hz, 2H).

Intermediate K

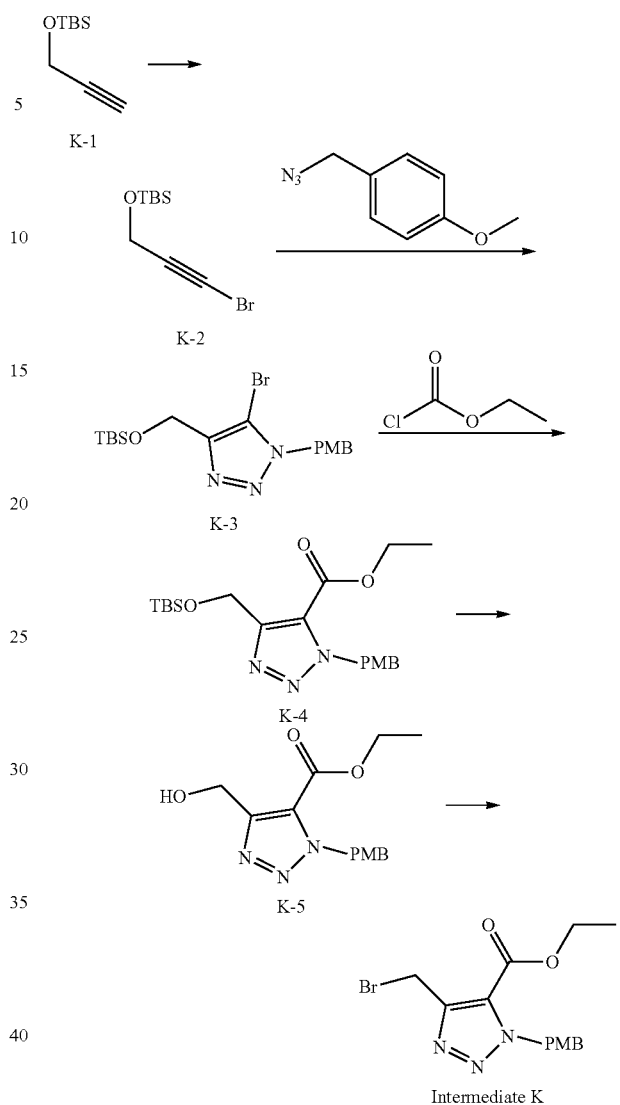

Intermediates K-2 and K-3 were synthesized by employing the procedures described for Intermediates A-4 and A using Intermediates K-1 and K-2 in lieu of Intermediates A-3 and A-4. Intermediate K-2: LC-MS (m/z): Non-ionzable compound under routine conditions used; $^1$H-NMR (CDCl$_3$, 400 MHz): δ (ppm) 0.05 (s, 6H), 0.84 (s 9H), 4.27 (s, 2H). Intermediate K-3: LC-MS (m/z): 412 [M+H]$^+$; $^1$H-NMR (CDCl$_3$, 400 MHz): δ (ppm) 0.09 (s, 6H), 0.89 (s 9H), 3.79 (s, 3H), 4.74 (s, 2H), 5.47 (s, 2H), 6.86 (d, J=8.8 Hz, 2H), 7.26 (d, J=8.8 Hz, 2H).

To a solution of Intermediate K-3 (14.02 g, 33.4 mmol) in dry THF (250 mL) at −78° C. under nitrogen was dropped a solution of n-BuLi in n-hexane (2.5 N, 15 mL, 37.4 mmol) and stirred at −78° C. for 0.5 hour, followed by addition of ethyl carbonochloridate (11 mL, 112.2 mmol). The mixture was stirred at −78° C. for 0.5 hour, quenched with saturated aqueous NH$_4$Cl solution (150 mL), and extracted with ethyl acetate (250 mL×2). The combined organic layers was washed with brine (500 mL), dried over anhydrous sodium sulfate, filtered, and concentrated to furnish Intermediate K-4. LC-MS (m/z): 406 [M+H]$^+$.

To a solution of Intermediate K-4 (13.5 g, 33.4 mmol) in dry THF (20 mL) was dropped a solution of Bu$_4$NF in THF (1 N, 16.7 mL, 16.7 mmol) and stirred at room temperature overnight. The reaction mixture was concentrated under reduced pressure and the residue was purified with flash column chromatography on silica gel (ethyl acetate in petroleum ether, from 0% to 50% v/v) to give Intermediate K-5. LC-MS (m/z): 292 [M+H]$^+$; $^1$H-NMR (CDCl$_3$, 500 MHz): δ (ppm) 1.38 (t, J=7.0 Hz, 3H), 3.78 (s, 3H), 4.39 (q, J=7.0 Hz, 2H), 4.91 (s, 2H), 5.82 (s, 2H), 6.84 (d, J=9.0 Hz, 2H), 7.26 (d, J=9.0 Hz, 2H).

To a solution of Intermediate K-5 (1.0 g, 3.44 mmol) in THF (40 mL) was added PBr$_3$ (1.38 g, 5.16 mmol). The mixture was stirred at room temperature for 4 hours, quenched with water (10 mL), and extracted with ethyl acetate (50 mL×3). The combined organic layers was washed with water (10 mL) and brine (10 mL), dried over anhydrous sodium sulfate, concentrated, and purified with flash column chromatography on silica gel (ethyl acetate in petroleum ether, 10% v/v) to afford Intermediate K. LC-MS (ESI) m/z: 354 [M+H]$^+$.

Example 1

Synthesis of ethyl 4-((4-(3,4-dichlorophenyl)thiazol-2-yl)thio)-1H-1,2,3-triazole-5-carboxylate (1)

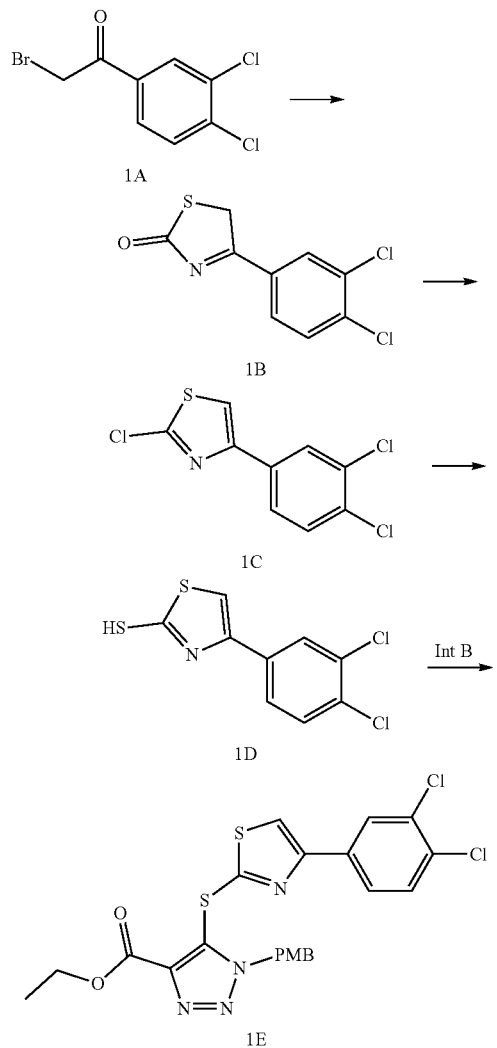

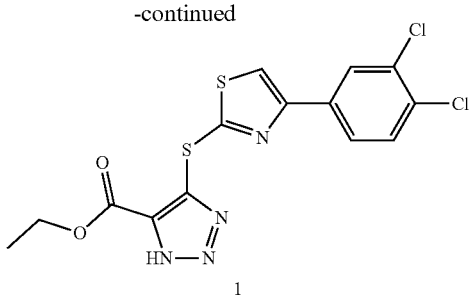

A mixture of 2-bromo-1-(3,4-dichlorophenyl)ethanone (Compound 1A) (1.5 g, 5.6 mmol) and carbamodithioic acid ammonia salt (677 mg, 6.1 mmol) in EtOH (5 mL) was stirred at 60° C. for 10 minutes. The reaction mixture was concentrated. The residue was washed with water (20 mL) and dried under vacuum to give Compound 1B. LC-MS (ESI) m/z: 246 [M+H]$^+$; $^1$H-NMR (CDCl$_3$, 400 MHz): δ (ppm) 4.66 (s, 2H), 7.63 (d, J=8.0 Hz, 1H), 7.75-7.78 (m, 1H), 8.03 (d, J=2.0 Hz, 1H).

A mixture of Compound 1B (1150 mg, 4.7 mmol) and POCl$_3$ (5 mL) was stirred at 100° C. for 1 hour. The mixture was concentrated to give Compound 1C. LC-MS (ESI) m/z: 264 [M+H]$^+$.

A mixture of Compound 1C (1.2 g, 4.5 mmol) and thiourea (686 mg, 9.0 mmol) in EtOH (10 mL) was stirred at 80° C. for 16 hours. After cooling down to room temperature, the mixture was diluted with water (60 mL) and filtered. The cake was dried under vacuum to afford Compound 1D. LC-MS (ESI) m/z: 262 [M+H]$^+$; $^1$H-NMR (DMSO-d$_6$, 400 MHz): δ (ppm) 7.63 (s, 1H), 7.69-7.78 (m, 2H), 8.11 (s, 1H), 13.75 (brs, 1H).

A mixture of Compound 1D (300 mg, 0.77 mmol), Intermediate B (407 mg, 1.55 mmol), and K$_2$CO$_3$ (214 mg, 1.55 mmol) or Na$_2$CO$_3$ in DMF (5 mL) was stirred at 50° C. for 16 hours. The mixture was concentrated and purified with flash column chromatography on silica gel (ethyl acetate in petroleum ether, 17% v/v) to afford Compound 1E. LC-MS (ESI) m/z: 521 [M+H]$^+$.

A mixture of Compound 1E (300 mg, 0.58 mmol) in TFA (5 mL) was stirred at 50° C. for 16 hours. The mixture was concentrated and purified with flash column chromatography on silica gel (ethyl acetate in petroleum ether, 33% v/v) to afford Compound 1. LC-MS (ESI) m/z: 401 [M+H]$^+$.

Example 2

Synthesis of 4-((4-(3,4-dichlorophenyl)thiazol-2-yl)thio)-1H-1,2,3-triazole-5-carboxylic acid (2)

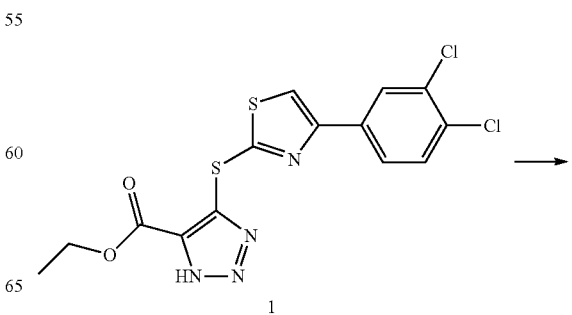

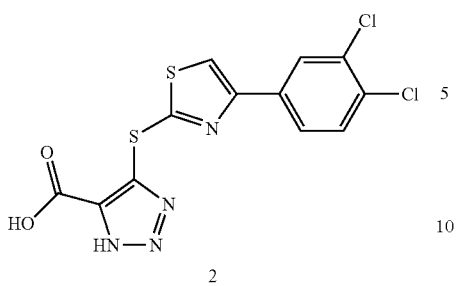

2

A mixture of Compound 1 (100 mg, 0.25 mmol) and NaOH (100 mg, 2.5 mmol) in THF (20 mL) and H$_2$O (2 mL) was stirred at room temperature for 16 hours. The mixture was concentrated and the residue was purified with preparative HPLC to afford Compound 2. LC-MS (ESI) m/z: 373 [M+H]$^+$. $^1$H-NMR (DMSO-d$_6$, 400 MHz): δ (ppm) 7.14 (brs, 2H), 7.68-7.71 (m, 1H), 7.89-7.92 (m, 1H), 8.15-8.18 (m, 2H).

Example 3

Synthesis of 4-((5-(3,4-dichlorophenyl)thiazol-2-yl)thio)-1H-1,2,3-triazole-5-carboxylic acid (3)

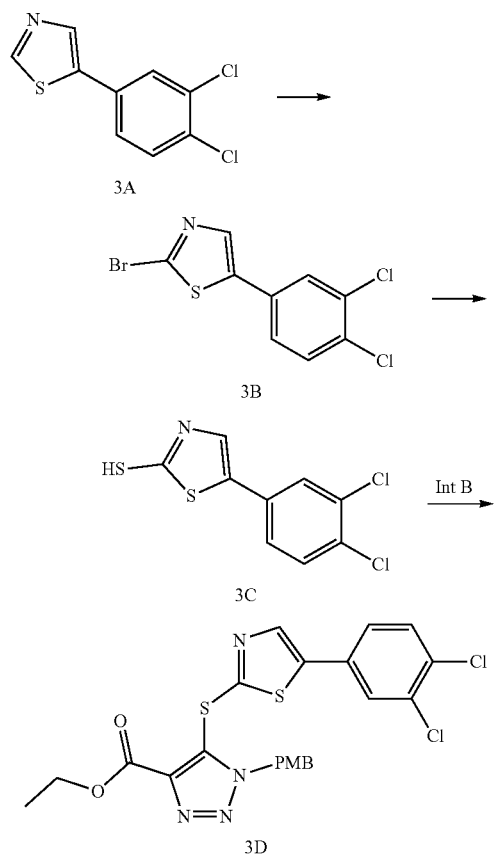

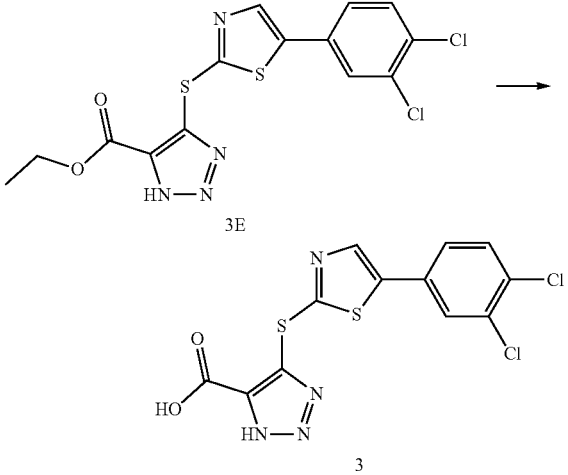

To a solution of 5-(3,4-dichlorophenyl)thiazole (Compound 3A) (2.3 g, 10 mmol) in anhydrous THF (20 mL) was dropped n-BuLi solution (2.5 Min n-hexane, 12 mL, 30 mmol) at −78° C. under nitrogen. After stirring at −78° C. for 30 minutes, to the mixture was added Br$_2$ (3.2 g, 20 mmol) and stirred at −78° C. for 30 minutes. The reaction mixture was quenched with water (2 mL), concentrated, and purified with flash column chromatography on silica gel (ethyl acetate in petroleum ether, 17% v/v) to give Compound 3B. LC-MS (ESI) m/z: 308 [M+H]$^+$.

Compounds 3C, 3D, 3E, and 3 were synthesized by employing the procedures described for Compounds 1D, 1E, 1, and 2 using Compounds 3B, 3C, 3D, and 3E in lieu of Compounds 1C, 1D, 1E, and 1. Compound 3C: LC-MS (ESI) m/z: 262 [M+H]$^+$; $^1$H-NMR (DMSO-d$_6$, 400 MHz): δ (ppm) 7.43-7.46 (m, 1H), 7.66 (d, J=8.4 Hz, 1H), 7.86 (d, J=2.0 Hz, 1H), 7.99 (s, 1H), 13.50 (brs, 1H). Compound 3D: LC-MS (ESI) m/z: 521 [M+H]$^+$. Compound 3E: LC-MS (ESI) m/z: 401 [M+H]$^+$. Compound 3: LC-MS (ESI) m/z: 373 [M+H]$^+$; $^1$H-NMR (DMSO-d$_6$, 400 MHz): δ (ppm) 7.13 (brs, 2H), 7.51-7.55 (m, 1H), 7.62-7.64 (m, 1H), 7.91 (d, J=2.0 Hz, 1H), 8.20 (s, 1H).

Reference Example 4

Synthesis of 4-((4'-bromo-[1,1'-biphenyl]-4-yl)thio)-1H-1,2,3-triazole-5-carboxylic acid (4)

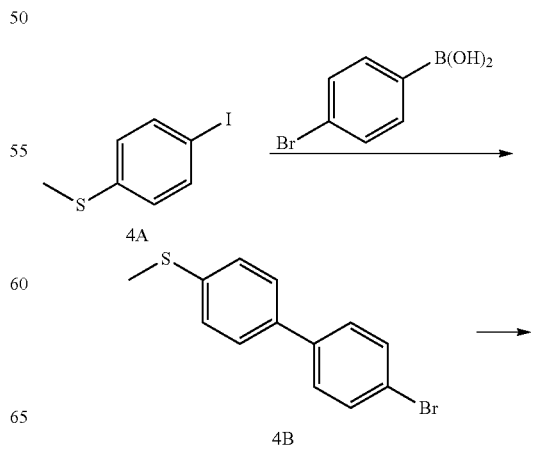

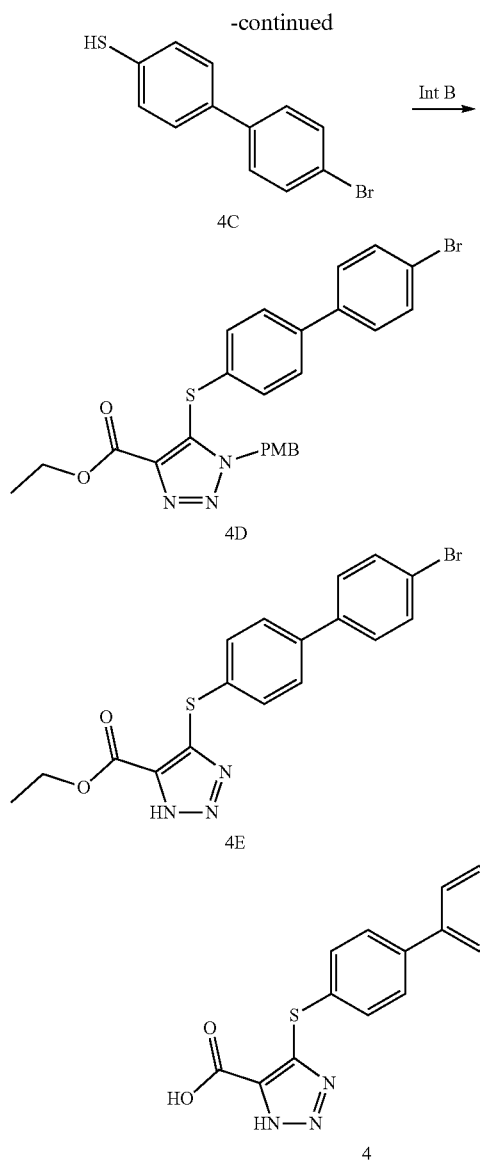

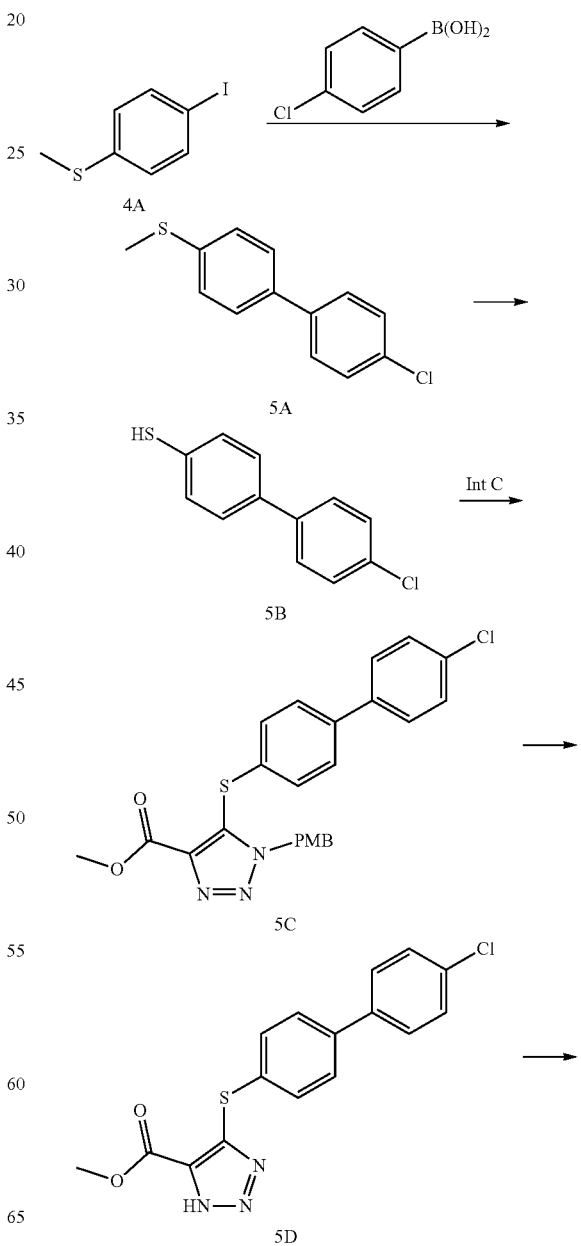

on silica gel (ethyl acetate in petroleum ether, 10% v/v) to afford Compound 4C. LC-MS (ESI) m/z: 263 [M−H]; $^1$H-NMR (CDCl$_3$, 400 MHz): δ (ppm) 5.64 (s, 1H), 7.41-7.55 (m, 8H).

Compounds 4D, 4E, and 4 were synthesized by employing the procedures described for Compounds 1E, 1, and 2 using Compounds 4C, 4D, and 4E in lieu of Compounds 1D, 1E, and 1. Compound 4D: LC-MS (ESI) m/z: 524 [M+H]$^+$. Compound 4E: LC-MS (ESI) m/z: 404 [M+H]$^+$. Compound 4: LC-MS (ESI) m/z: 376 [M+H]$^+$; $^1$H-NMR (CD$_3$OD, 400 MHz): δ (ppm) 7.18-7.50 (m, 2H), 7.56-7.60 (m, 6H).

Example 5

Synthesis of 4-((4'-chloro-[1,1'-biphenyl]-4-yl)thio)-1H-1,2,3-triazole-5-carboxylic acid (5)

A mixture of (4-iodophenyl)(methyl)sulfane (Compound 4A) (500 mg, 2 mmol), 4-bromophenylboronic acid (400 mg, 2 mmol), Na$_2$CO$_3$ (636 mg, 6 mmol), and Pd(PPh$_3$)$_4$ (115 mg, 0.1 mmol) in toluene/EtOH/H$_2$O (20/10/4 mL) was stirred at 80° C. under nitrogen overnight. The mixture was concentrated under reduced pressure. The residue was purified with flash column chromatography on silica gel (ethyl acetate in petroleum ether, 10% v/v) to afford Compound 4B. LC-MS (ESI) m/z: non-ionizable compound under routine conditions used. $^1$H-NMR (CDCl$_3$, 500 MHz): δ (ppm) 2.52 (s, 3H), 7.32 (d, J=8.5 Hz, 2H), 7.43 (d, J=8.5 Hz, 2H), 7.48 (d, J=8.5 Hz, 2H), 7.55 (d, J=8.5 Hz, 2H).

To a solution of Compound 4B (278 mg, 1 mmol) in dichloromethane (10 mL) was added m-CPBA (258 mg, 1.5 mmol) at 0° C., After the mixture was stirred at room temperature for 30 minutes, Ca(OH)$_2$ (238 mg, 1.7 mmol) was added. The mixture was stirred at room temperature for 5 minutes and filtered. To the filtrate was added trifluoroaceticanhydride (440 mg, 2.1 mmol) and heated at reflux for 1 hour. The mixture was evaporated under reduced pressure. The residue was purified with flash column chromatography

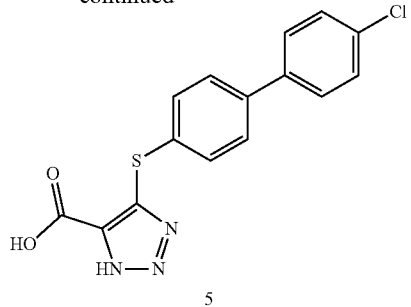

5

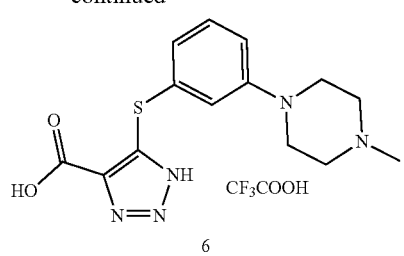

6

Compounds 5A, 5B, 5C, 5D, and 5 were synthesized by employing the procedures described for Compounds 4B, 4C, 1E, 1, and 2 using 4-chlorophenylboronic acid, Compounds 5A, 5B, Intermediate C, 5C, and 5D in lieu of 4-bromophenylboronic acid, Compounds 4B, 1D, Intermediate B, 1E, and 1. Compound 5A: LC-MS (ESI) m/z: non-ionizable compound under routine conditions used. $^1$H-NMR (CDCl$_3$, 400 MHz): δ (ppm) 2.52 (s, 3H), 7.31-7.33 (m, 2H), 7.38-7.40 (m, 2H), 7.47-7.50 (m, 4H). Compound 5B: LC-MS (ESI) m/z: 219 [M−H]; $^1$H-NMR (DMSO-d$_6$, 500 MHz): δ (ppm) 5.96 (s, 1H), 7.58-7.73 (m, 8H). Compound 5C: LC-MS (ESI) m/z: 466 [M+H]$^+$. Compound 5D: LC-MS (ESI) m/z: 346 [M+H]$^+$. Compound 5: LC-MS (ESI) m/z: 332 [M+H]$^+$; $^1$H-NMR (CD$_3$OD, 400 MHz): δ (ppm) 7.42-7.48 (m, 4H), 7.56-7.62 (m, 4H).

Example 6

Synthesis of 5-((3-(4-methylpiperazin-1-yl)phenyl)thio)-1H-1,2,3-triazole-4-carboxylic acid 2,2,2-trifluoroacetate (6)

Compound 6A was synthesized by employing the procedure described for Compound 1E using 3-bromobenzenethiol and Intermediate C in lieu of Compound 1D and Intermediate B, LC-MS (ESI) m/z: 434 [M+H]$^+$.

To a solution of Compound 6A (138 mg, 0.32 mmol) in toluene (4 mL) was added N-methylpiperazine (160 mg, 1.6 mmol), t-BuONa (61 mg, 0.64 mmol), Pd$_2$(dba)$_3$ (29 mg, 0.032 mmol), and Xantphos (37 mg, 0.064 mmol) and heated in a microwave oven at 120° C. for 2 hours. The mixture was concentrated and purified by reverse phase column chromatography to afford Compound 6B. LC-MS (ESI) m/z: 440 [M+H]$^+$.

Compound 6 was synthesized by employing the procedure described for Compound 1 using Compound 6B in lieu of Compound 1E, LC-MS (ESI) m/z: 320 [M+H]$^+$; $^1$H-NMR (CD$_3$OD, 400 MHz): δ (ppm) 2.85 (s, 3H), 3.00-3.20 (br, 2H), 3.24-3.95 (br, 6H), 6.92-6.94 (m, 2H), 7.07 (s, 1H), 7.17-7.21 (m, 1H).

Example 7

Synthesis of 4-((4-(piperidin-1-yl)phenyl)thio)-1H-1,2,3-triazole-5-carboxylic acid 2,2,2-trifluoroacetate (7)

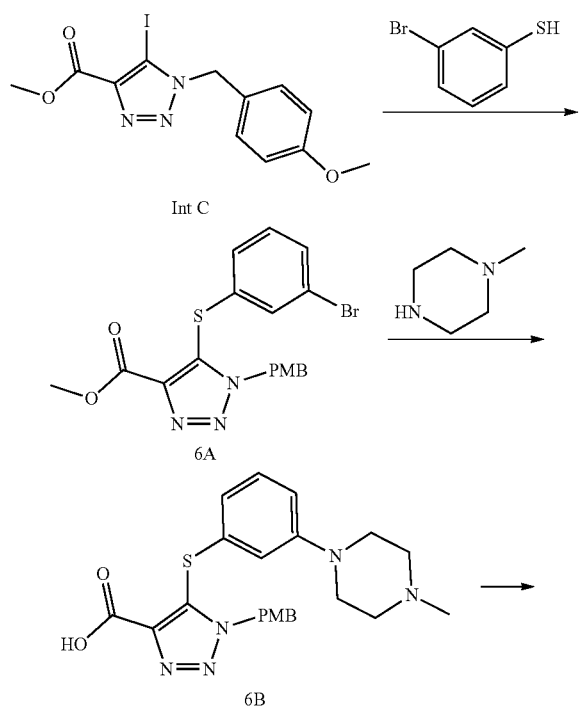

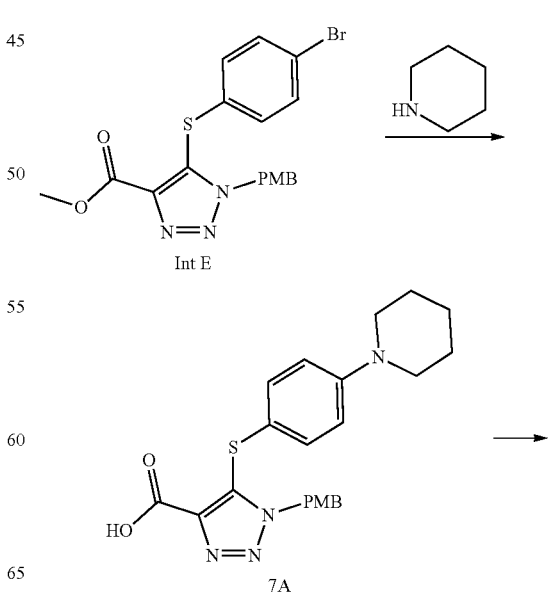

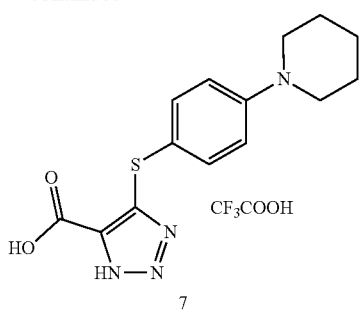

Compounds 7A and 7 were synthesized by employing the procedures described for Compounds 6B and 1 using Intermediate E, piperidine, and Compound 7A in lieu of Compounds 6A, 1-methylpiperazine, and 1E. Compound 7A: LC-MS (ESI) m/z: 425 [M+H]⁺. Compound 7: LC-MS (ESI) m/z: 305 [M+H]⁺; ¹H-NMR (CD₃OD, 400 MHz): δ (ppm) 1.75-1.76 (m, 2H), 1.91-1.94 (m, 4H), 3.49-3.52 (m, 4H), 7.40-7.42 (m, 2H), 7.57-7.59 (m, 2H).

Example 8

Synthesis of 4-((2-(3,4-dichlorophenyl)thiazol-4-yl)thio)-1H-1,2,3-triazole-5-carboxylic acid (8)

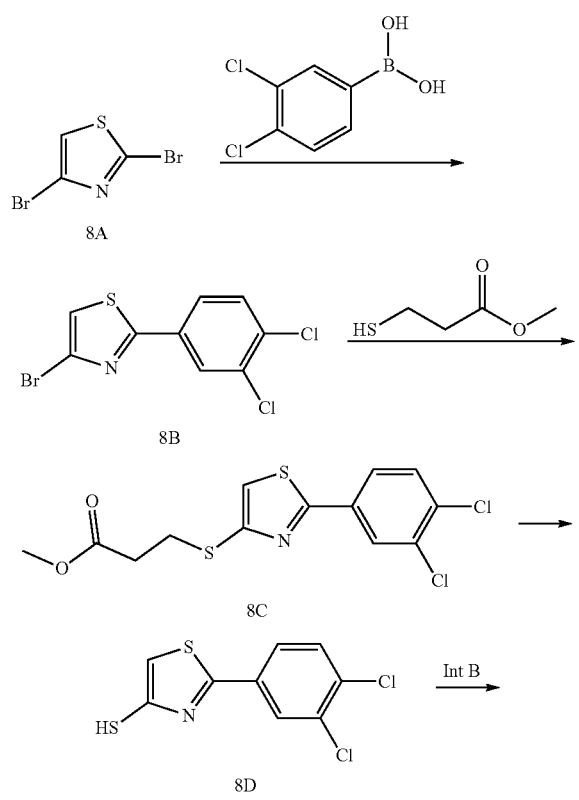

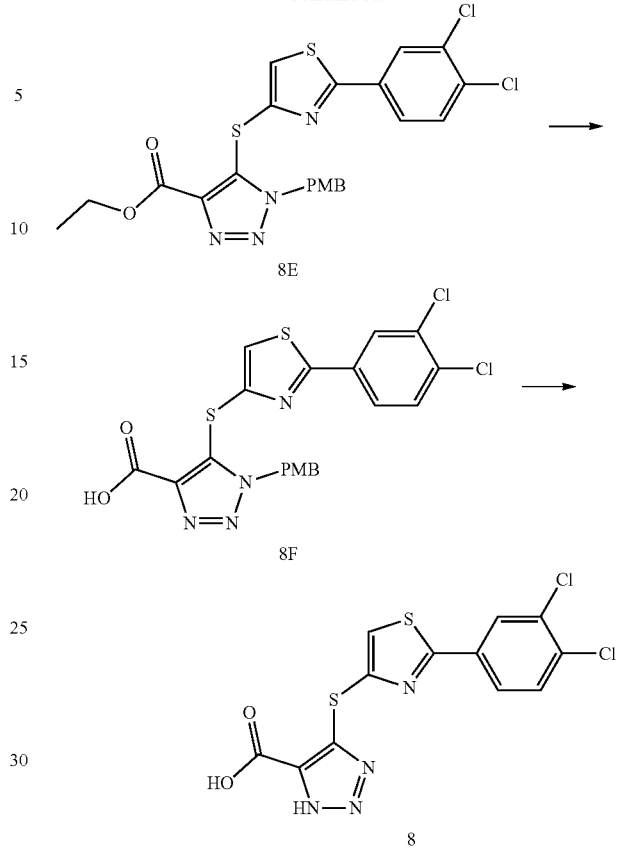

A mixture of 2,4-dibromothiazole (Compound 8A) (3.9 g, 16 mmol), 3,4-dichlorophenylboronic acid (3.05 g, 16 mol), Pd(dppf)Cl₂ (0.7 g, 0.87 mmol), and cesium carbonate (15 g, 46 mmol) in DME (120 mL) and water (10 mL) was heated at reflux under nitrogen overnight. The reaction mixture was diluted with water (100 mL) and extracted with ethyl acetate (200 mL×2). The combined extracts were washed with water (200 mL) and brine (200 mL), dried over anhydrous sodium sulfate, filtered, and concentrated. The residue was purified with flash column chromatography on silica gel (ethyl acetate in petroleum ether, from 0% to 10% v/v) to yield Compound 8B. LC-MS (ESI) m/z: 308 [M+H]⁺.

Compounds 8C, 8D, and 8E were synthesized by employing the procedures described for Intermediates D-1, D, and Compound 1E using Compounds 8B, 8C, and 8D in lieu of Intermediates A, D-1, and Compound 1D. Compound 8C: LC-MS (ESI) m/z: 348 [M+H]⁺. Compound 8D: LC-MS (ESI) m/z: 262 [M+H]⁺. Compound 8E: LC-MS (ESI) m/z: 521 [M+H]⁺.

To a solution of Compound 8E (220 mg, 0.42 mmol) in THF (40 mL) and water (8 mL) was added LiOH.H₂O (110 mg, 2.62 mmol). The mixture was stirred at room temperature for 2 hours and concentrated to furnish Compound 8F, which was used directly for next step without further purification. LC-MS (ESI) m/z: 493.

Compound 8 was synthesized by employing the procedure described for Compound 1 using Compound 8F in lieu of Compound 1E, LC-MS (ESI) m/z: 373 [M+H]⁺; ¹H-NMR (DMSO-d₆, 400 MHz): δ (ppm) 7.65 (d, J=8.4 Hz, 1H), 7.85-7.88 (m, 2H). 8.13 (d, J=2.0 Hz, 1H).

Example 9

Synthesis of cyclobutyl 4-((4-(3,4-dichlorophenyl)thiazol-2-yl)thio)-1H-1,2,3-triazole-5-carboxylate (9)

Compound 9A was synthesized by employing the procedure described for Compound 2 using Compound 1E in lieu of Compound 1, LC-MS (ESI) m/z: 493 [M+H]$^+$.

A mixture of Compound 9A (200 mg, 0.4 mmol), cyclobutanol (86 mg, 1.2 mmol), and HBTU (456 mg, 1.2 mmol) in dichloromethane (10 mL) was stirred at room temperature for 16 hours. The mixture was evaporated under reduced pressure and the residue was purified with flash column chromatography on silica gel (ethyl acetate in petroleum ether, 50% v/v) to afford Compound 9B. LC-MS (ESI) m/z: 547 [M+H]$^+$.

Compound 9 was synthesized by employing the procedure described for Compound 1 using Compound 9B in lieu of Compound 1E, LC-MS (ESI) m/z: 427 [M+H]$^+$; $^1$H-NMR (DMSO-d$_6$, 400 MHz): δ (ppm) 1.59-1.73 (m, 2H), 1.99-2.05 (m, 2H), 2.26-2.33 (m, 2H), 50.3-5.07 (m, 1H), 7.71 (d, J=8.0 Hz, 1H), 7.89-7.92 (m, 1H), 8.15 (d, J=2.0 Hz, 1H), 8.24 (s, 1H).

Example 10

Synthesis of 4-((4-(4-methylpiperazin-1-yl)phenyl)thio)-1H-1,2,3-triazole-5-carboxylic acid (10)

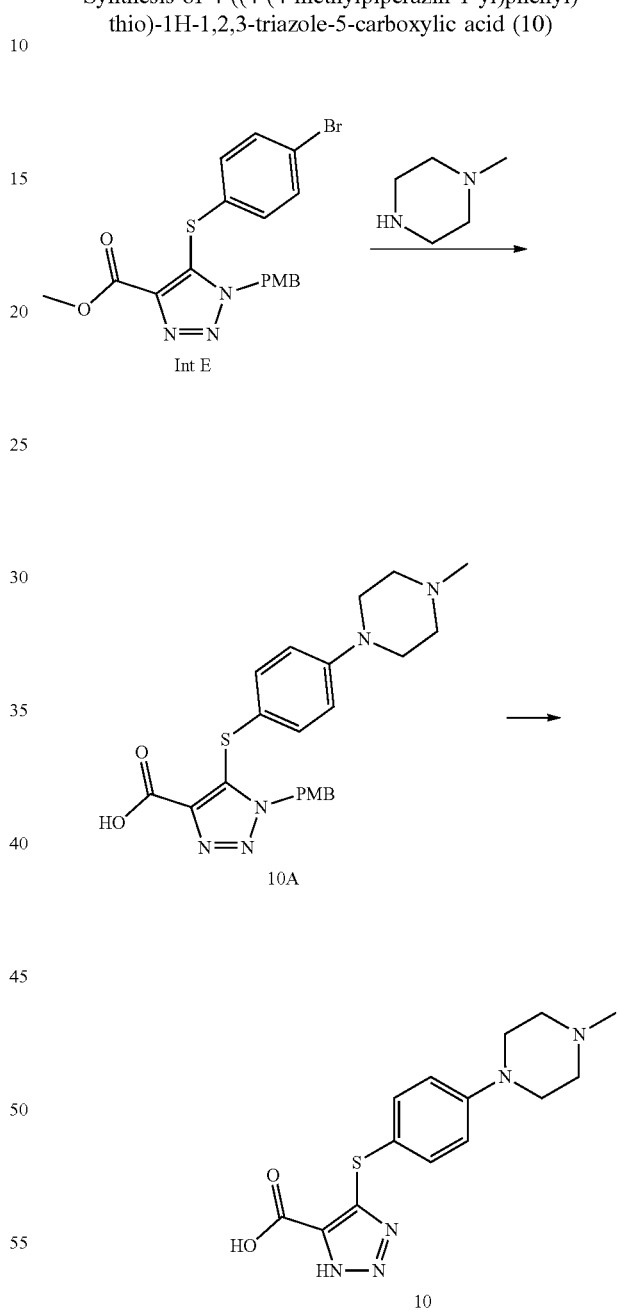

Compounds 10A and 10 were synthesized by employing the procedures described for Compounds 6B and 1 using N-methylpiperazine, Intermediate E, and Compound 10A in lieu of 1-methylpiperazine, Compounds 6A, and 1E. Compound 10A: LC-MS (ESI) m/z: 440 [M+H]$^+$. Compound 10: LC-MS (ESI) m/z: 320 [M+H]$^+$; $^1$H-NMR (400 MHz, DMSO-d$_6$): δ (ppm) 2.27 (s, 3H), 2.48-2.50 (m, 4H), 3.17-3.19 (m, 4H), 6.92 (d, J=8.8 Hz, 2H), 7.31 (d, J=8.8 Hz, 2H).

Example 11

Synthesis of isopropyl 4-((4-(3,4-dichlorophenyl)thiazol-2-yl)thio)-1H-1,2,3-triazole-5-carboxylate (11)

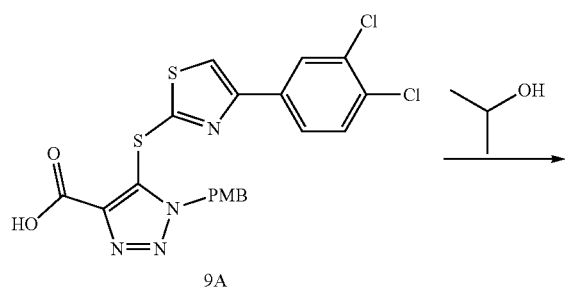

9A

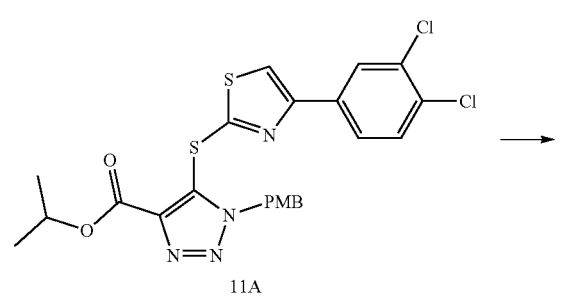

11A

11

A mixture of Compound 9A (400 mg, 0.8 mmol) and SOCl$_2$ (960 mg, 8.0 mmol) in propan-2-ol (5 mL) was stirred at 60° C. for 16 hours. The mixture was concentrated and purified with flash column chromatography on silica gel (ethyl acetate in petroleum ether, 50% v/v) to afford Compound 11A. LC-MS (ESI) m/z: 535 [M+H]$^+$.

Compound 11 was synthesized by employing the procedure described for Compound 1 using Compound 11A in lieu of Compound 1E, LC-MS (ESI) m/z: 415 [M+H]$^+$; $^1$H-NMR (DMSO-d$_6$, 500 MHz): δ (ppm) 1.18 (d, J=6.0 Hz, 6H), 4.97-5.00 (m, 1H), 7.69 (d, J=9.0 Hz, 1H), 7.89-7.91 (m, 1H), 8.09 (s, 1H), 8.14 (d, J=2.0 Hz, 1H).

Example 12

Synthesis of 4-((5-(4-bromophenyl)pyridin-2-yl)thio)-1H-1,2,3-triazole-5-carboxylic acid 2,2,2-trifluoroacetate (12)

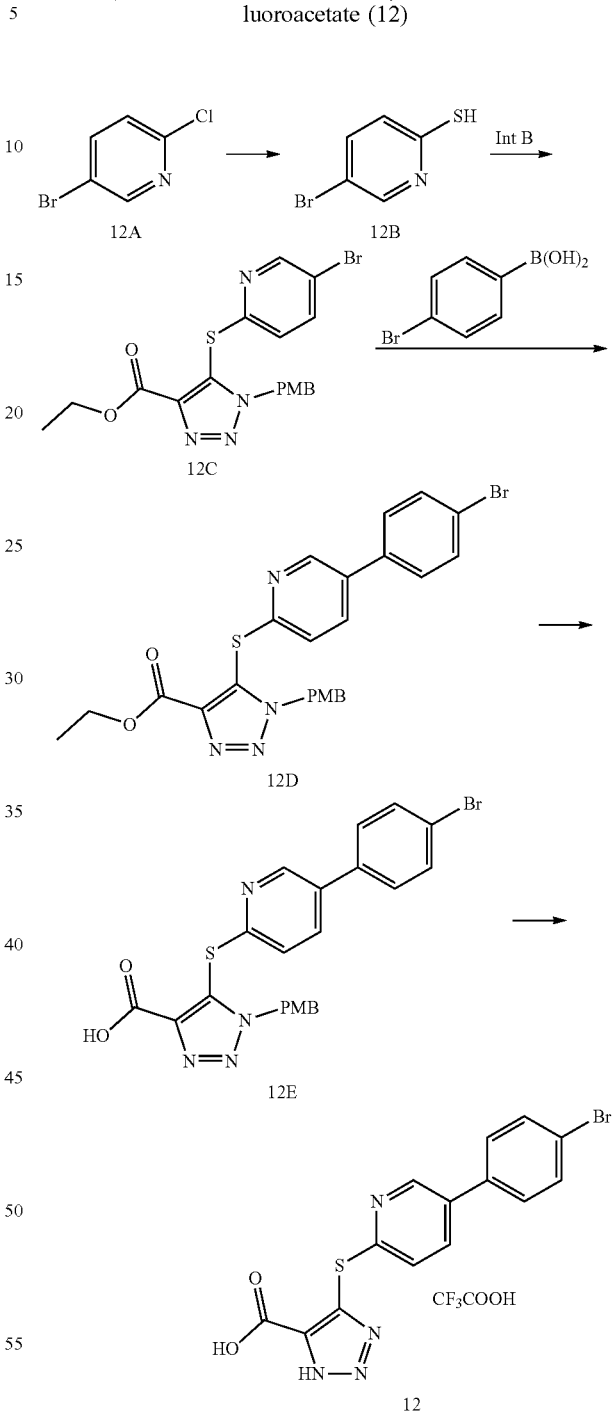

To a solution of Compound 12A (1.92 g, 10 mmol) in DMF (20 mL) was added NaHS (560 mg, 10.0 mmol). The reaction mixture was stirred at 70° C. under nitrogen for 14 hours. The mixture was diluted with water (50 mL) and extracted with ethyl acetate (50 mL×3). The combined extracts were washed with brine (100 mL×2), dried over anhydrous sodium sulfate, filtered, and concentrated to give Compound 12B. LC-MS (ESI) m/z: 190 [M+H]$^+$.

Compounds 12C, 12D, 12E, and 12 were synthesized by employing the procedures described for Compounds 1E, 4B, 8F, and 1 using Compounds 12B, 12C, 12D, and 12E in lieu of Compounds 1D, 4A, 8E, and 1E. Compound 12C: LC-MS (ESI) m/z: 449 [M+H]+. Compound 12D: LC-MS (ESI) m/z: 525 [M+H]+. Compound 12E: LC-MS (ESI) m/z: 497 [M+H]+. Compound 12: LC-MS (ESI) m/z: 377 [M+H]+; $^1$H-NMR (CD$_3$OD, 400 MHz): δ (ppm) 7.36 (d, J=8.4 Hz, 1H), 7.58 (d, J=8.4 Hz, 2H), 7.64 (d, J=8.4 Hz, 2H), 7.97 (dd, J$_1$=8.4 Hz, J$_2$=2.0 Hz, 1H), 8.66 (d, J=2.0 Hz, 1H).

Example 13

Synthesis of 4-((5-(3,4-dichlorophenyl)-4H-1,2,4-triazol-3-yl)thio)-1H-1,2,3-triazole-5-carboxylic acid (13)

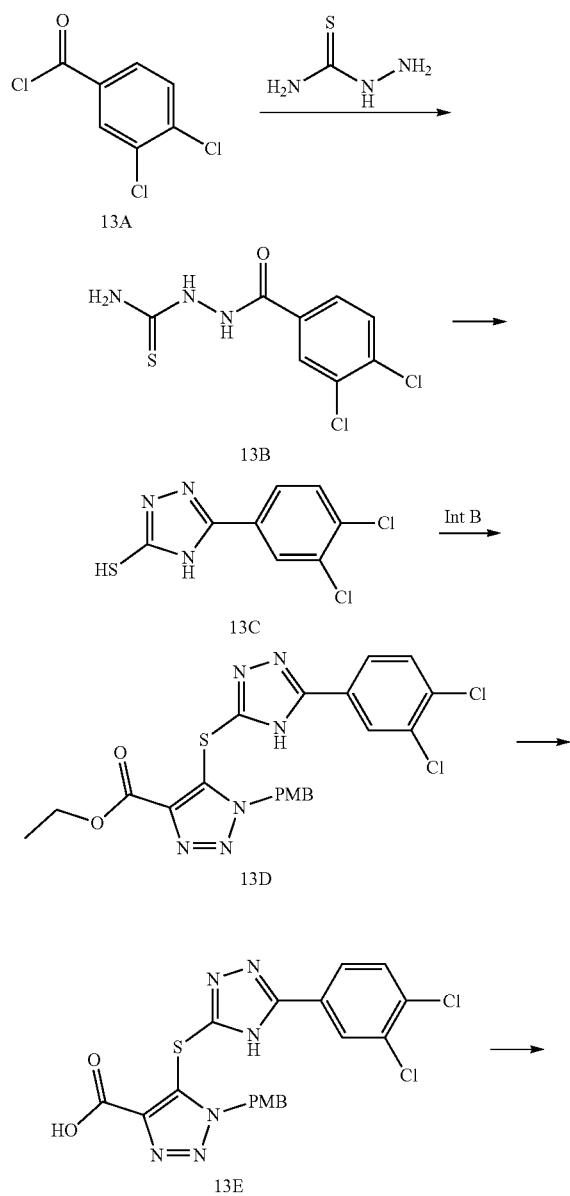

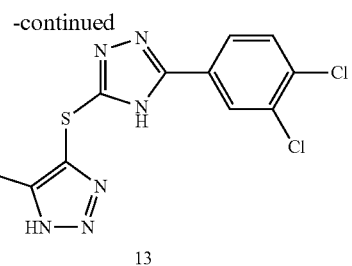

A mixture of 3,4-dichlorobenzoyl chloride (Compound 13A) (832 mg, 4 mmol) and hydrazinecarbothioamide (910 mg, 10 mmol) in THF (50 mL) was stirred at room temperature overnight. The mixture was diluted with H$_2$O (30 mL) and extracted with ethyl acetate (30 mL×3). The combined extracts were dried over anhydrous sodium sulfate, filtered, and concentrated to give Compound 13B. LC-MS (ESI) m/z: 264 [M+H]+.

To a mixture of Compound 13B (526 mg, 2 mmol) in ethanol (10 mL) was added aqueous NaOH solution (4 N, 10 mL). The mixture was stirred at 80° C. overnight. The mixture was adjusted to pH 4 with acetic acid (20 mL) and a solid was precipitated. The resulting solid was filtered and dried under vacuum to afford Compound 13C. LC-MS (ESI) m/z: 246 [M+H]+; $^1$H-NMR (DMSO-d$_6$, 400 MHz): δ (ppm) 7.79-7.89 (m, 2H), 8.14-8.15 (m, 1H), 13.84 (brs, 1H).

A mixture of Compound 13C (369 mg, 1.5 mmol), Intermediate B (388 mg, 1 mmol), t-BuONa (144 mg, 1.5 mmol), 2,9-dimethyl-1,10-phenanthroline (21 mg, 0.1 mmol), and CuI (20 mg, 0.1 mmol) in DMF (20 mL) was stirred at 110° C. under nitrogen overnight. The mixture was concentrated under reduced pressure. The residue was purified with flash column chromatography on silica gel (ethyl acetate in petroleum ether, 50% v/v) to afford Compound 13D. LC-MS (ESI) m/z: 505 [M+H]+.

Compounds 13E and 13 were synthesized by employing the procedures described for Compounds 2 and 1 using Compounds 13D and 13E in lieu of Compounds 1 and 1E. Compound 13E: LC-MS (ESI) m/z: 477 [M+H]+. Compound 13: LC-MS (ESI) m/z: 357 [M+H]+; $^1$H-NMR (CD$_3$OD, 400 MHz): δ (ppm) 7.66 (d, J=8.8 Hz, 1H), 7.91 (dd, J=8.8, 2.0 Hz, 1H), 8.15 (d, J=2.0 Hz, 1H).

Example 14

Synthesis of 4-((4'-methoxy-[1,1'-biphenyl]-4-yl)thio)-1H-1,2,3-triazole-5-carboxylic acid (14)

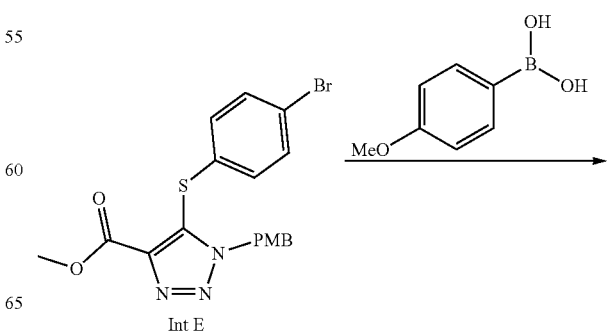

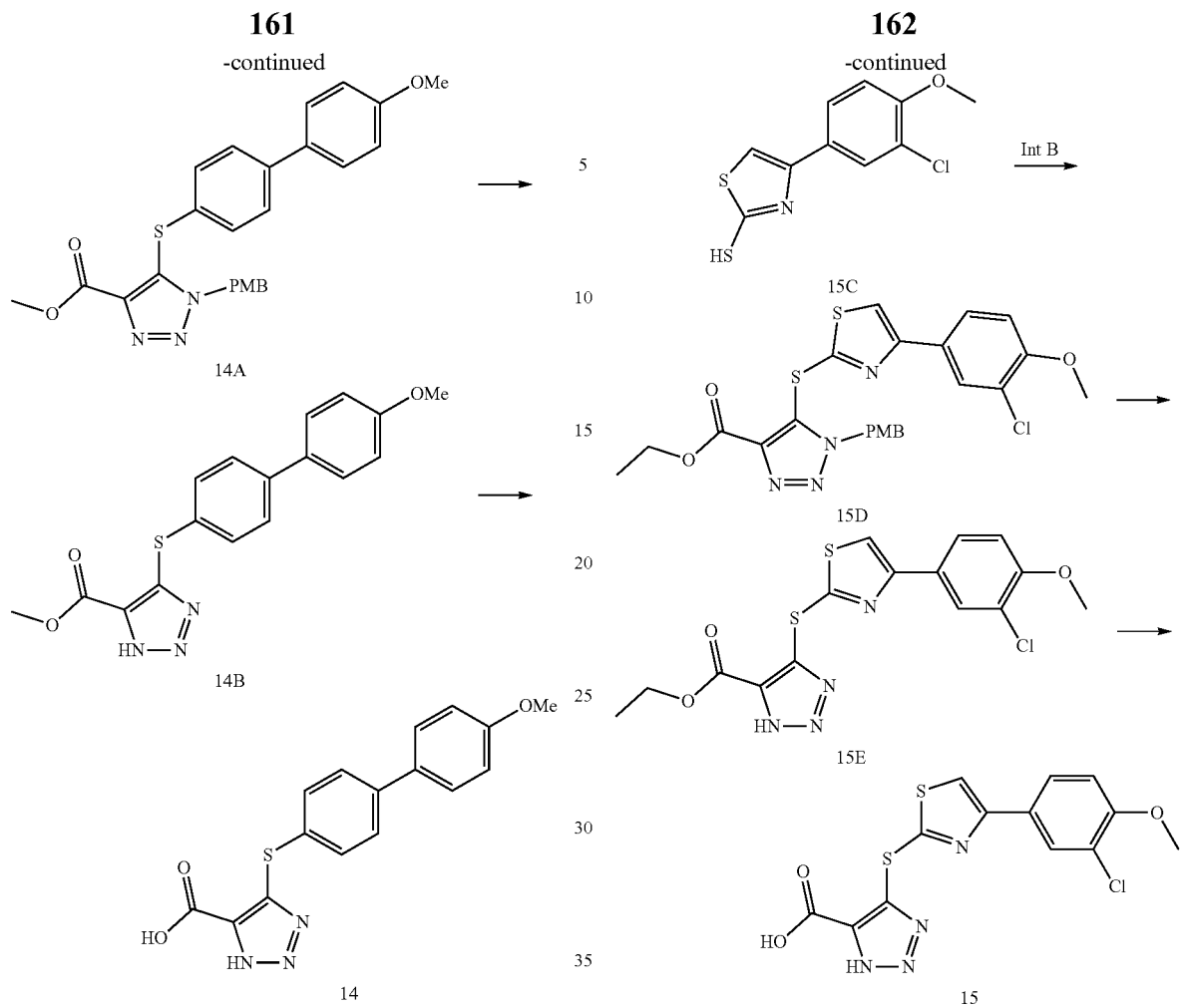

Compounds 14A, 14B, and 14 were synthesized by employing the procedures described for Compounds 4B, 1, and 8F using 4-methoxyphenylboronic acid, Intermediate E, Compounds 14A, and 14B in lieu of (4-bromophenyl) boronic acid, Compounds 4A, 1E, and 8E. Compound 14A: LC-MS (ESI) m/z: 462 [M+H]+. Compound 14B: LC-MS (ESI) m/z: 342 [M+H]+. Compound 14: LC-MS (ESI) m/z: 328 [M+H]+. $^1$H-NMR (DMSO-$d_6$, 400 MHz): δ (ppm) 3.80 (s, 3H), 7.01-7.06 (m, 2H), 7.48-7.52 (m, 2H), 7.61-7.66 (m, 4H).

Example 15

Synthesis of 4-((4-(3-chloro-4-methoxyphenyl)thi-azol-2-yl)thio)-1H-1,2,3-triazole-5-carboxylic acid (15)

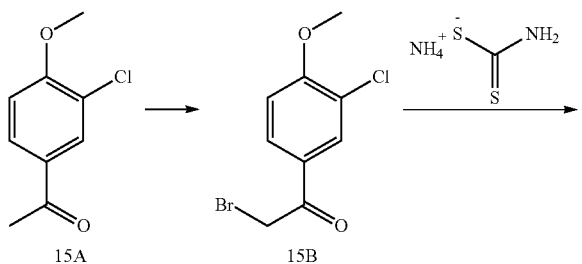

To a solution of 1-(3-chloro-4-methoxyphenyl)ethanone (Compound 15A) (500 mg, 2.7 mmol) and N-bromosuccinimide (482 mg, 2.7 mmol) in acetonitrile (10 mL) was added trimethylsilyl trifluoromethanesulfonate (600 mg, 2.7 mmol). The mixture was stirred at 40° C. overnight, diluted with ethyl acetate (30 mL), washed with H$_2$O (10 mL×3), dried over anhydrous sodium sulfate, filtered, and concentrated to give Compound 15B, which was used directly in the next step without further purification. LC-MS (ESI) m/z: 263 [M+H]+; $^1$H-NMR (CDCl$_3$, 400 MHz): δ (ppm) 4.00 (s, 3H), 4.39 (s, 2H), 7.01 (d, J=8.4 Hz, 1H), 7.92 (dd, J=8.4, 2.0 Hz, 1H), 8.04 (d, J=2.0 Hz, 1H).

A mixture of Compound 15B (700 mg, 1.90 mmol) and ammonium carbamodithioate (209 mg, 1.90 mmol) in ethanol (20 mL) was stirred at 80° C. for 3 hours. The mixture was concentrated under reduced pressure. The residue was slurred in mixed solvents (petroleum ether/EtOAc, 1/2, v/v, 15 mL) and filtered. The solid was dried under vacuum to give Compound 15C. LC-MS (ESI) m/z: 258 [M+H]+.

Compounds 15D, 15E, and 15 were synthesized by employing the procedures described for Compounds 1E, 1, and 8F using Compounds 15C, 15D, and 15E in lieu of Compounds 1D, 1E, and 8E. Compound 15D: LC-MS (ESI) m/z: 517 [M+H]+; $^1$H-NMR (CDCl$_3$, 400 MHz): δ (ppm) 1.36 (t, J=6.8 Hz, 3H), 3.70 (s, 3H), 3.95 (s, 3H), 4.41 (q, J=6.8 Hz, 2H), 5.72 (s, 2H), 6.74 (d, J=8.8 Hz, 2H), 6.95 (d, J=8.8 Hz, 1H), 7.24 (d, J=5.6 Hz, 3H), 7.63 (dd, J=5.6, 2.0 Hz, 1H), 7.78 (d, J=2.0 Hz, 1H). Compound 15E: LC-MS (ESI) m/z: 397 [M+H]+. Compound 15: LC-MS (ESI) m/z: 369 [M+H]+; 1H-NMR (CD3OD, 400 MHz): δ (ppm) 3.92 (s, 3H), 7.13 (d, J=8.4 Hz, 1H), 7.77 (s, 1H), 7.92 (dd, J=8.4, 2.4 Hz, 1H), 8.04 (d, J=2.4 Hz, 1H).

Example 16

Synthesis of 4-((4'-(trifluoromethoxy)-[1,1'-biphenyl]-4-yl)thio)-1H-1,2,3-triazole-5-carboxylic acid (16)

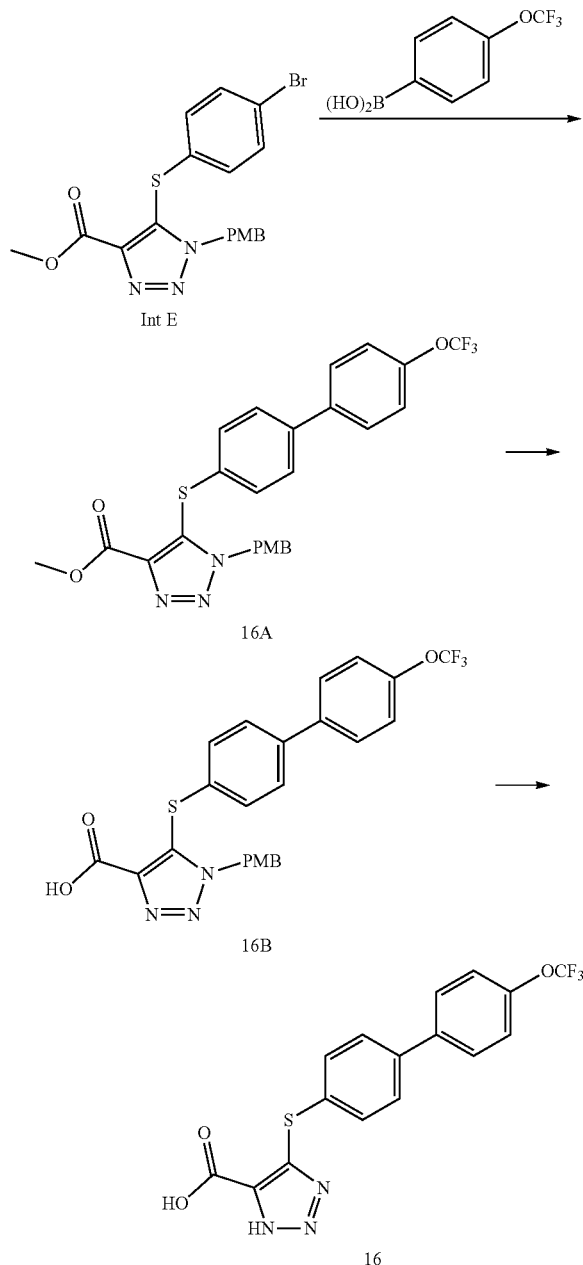

Compounds 16A, 16B, and 16 were synthesized by employing the procedures described for Compounds 4B, 8F, and 1 using 4-(trifluoromethoxy)phenylboronic acid, Intermediate E, Compounds 16A, and 16B in lieu of (4-bromophenyl)boronic acid, Compounds 4A, 8E, and 1E. Compound 16A: LC-MS (ESI) m/z: 516 [M+H]+. Compound 16B: LC-MS (ESI) m/z: 502. Compound 16: LC-MS (ESI) m/z: 382 [M+H]+; 1H-NMR (CD3OD, 400 MHz): δ (ppm) 7.35 (s, 1H), 7.38 (s, 1H), 7.57 (d, J=8.4 Hz, 2H), 7.66 (d, J=8.4 Hz, 2H), 7.73 (s, 1H), 7.75 (s, 1H).

Example 17

Synthesis of methyl 4-((4-(3,4-dichlorophenyl)thiazol-2-yl)thio)-1H-1,2,3-triazole-5-carboxylate (17)

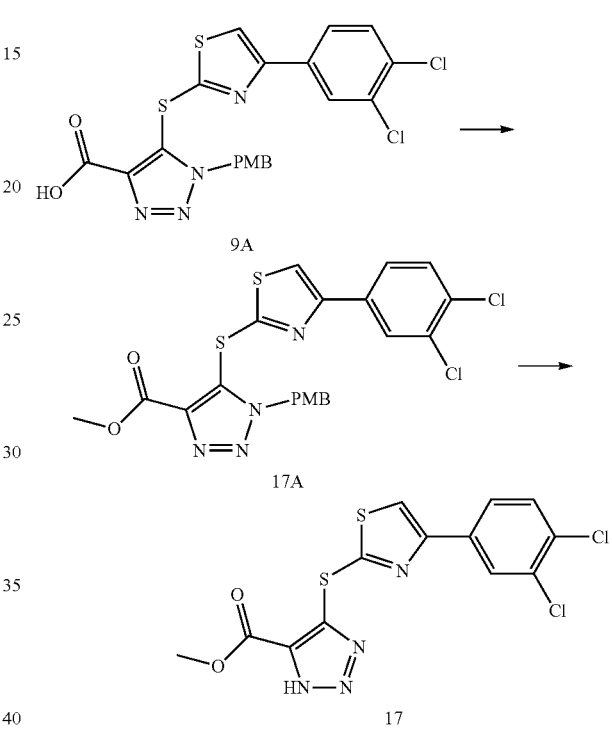

Compounds 17A and 17 were synthesized by employing the procedures described for Compounds 11A and 1 using methanol and Compound 17A in lieu of isopropanol and Compound 1E. Compound 17A: LC-MS (ESI) m/z: 507 [M+H]+. Compound 17: LC-MS (ESI) m/z: 387 [M+H]+; 1H-NMR (DMSO-d6, 400 MHz): δ (ppm) 3.85 (s, 3H), 7.72 (d, J=8.0 Hz, 1H), 7.91 (d, J=8.0 Hz, 1H), 8.16 (d, J=1.6 Hz, 1H), 8.39 (s, 1H).

Example 18

Synthesis of 4-((4-(3-chloro-4-cyclopropoxyphenyl)thiazol-2-yl)thio)-1H-1,2,3-triazole-5-carboxylic acid (18)

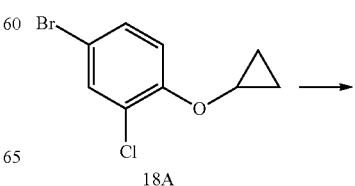

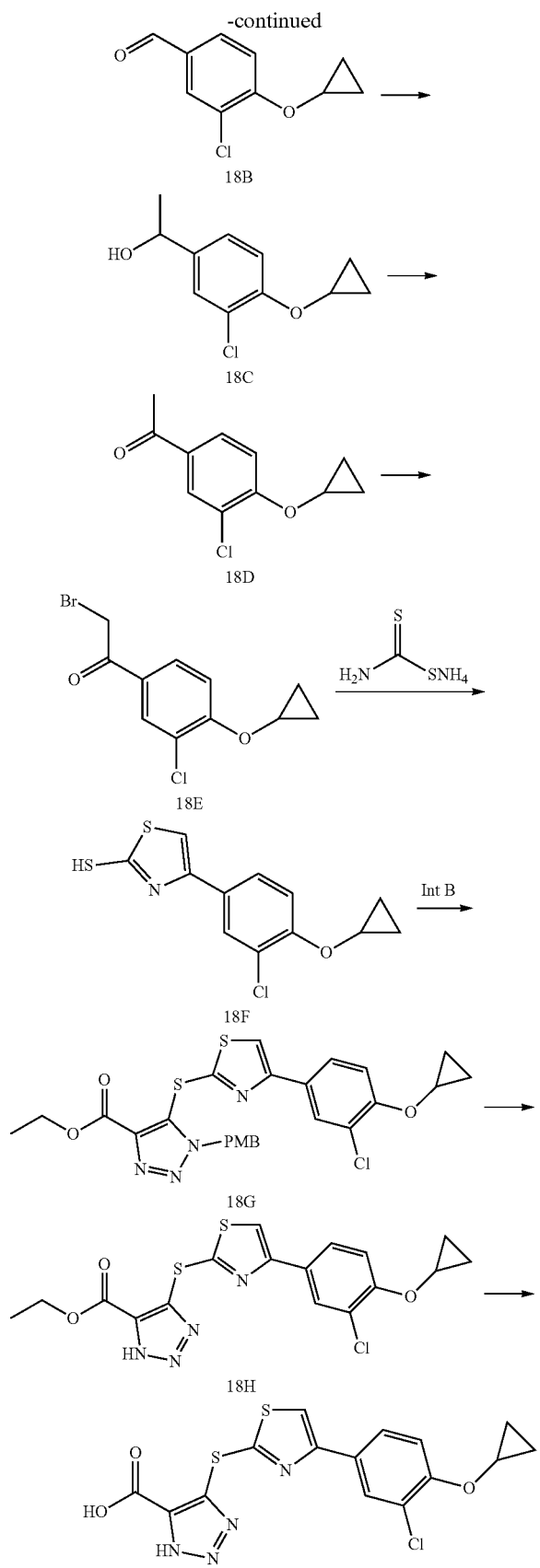

To a solution of 4-bromo-2-chloro-1-cyclopropoxybenzene (Compound 18A) (7.42 g, 30 mmol) in anhydrous THF (50 mL) was dropped a solution of n-BuLi in n-hexane (2.5 M, 13.2 mL, 33 mmol) over 15 minutes at −78° C. under nitrogen and stirred at −78° C. for 30 minutes. To the mixture was added anhydrous DMF (2.78 mL, 36 mmol), stirred at −78° C. for 30 minutes, quenched with saturated NH$_4$Cl solution (50 mL), and extracted with ethyl acetate (100 mL). The extract was washed with brine (100 mL), dried over anhydrous sodium sulfate, filtered, and concentrated. The residue was purified with flash column chromatography on silica gel (ethyl acetate in petroleum ether, 10% v/v) to give Compound 18B. LC-MS (ESI) m/z: 197 [M+H]$^+$; (CDCl$_3$, 400 MHz): δ (ppm) 0.90-0.92 (m, 4H), 3.88-3.92 (m, 1H), 7.44 (d, J=8.4 Hz, 1H), 7.78 (dd, J=8.4, 2.4 Hz, 1H), 7.89 (d, J=2.4 Hz, 1H), 9.87 (s, 1H).

To a solution of Compound 18B (5.21 g, 26.5 mmol) in anhydrous THF (50 mL) was dropped a MeMgBr solution (3 Min ether, 9.72 mL, 29.2 mmol) over 10 minutes at −20° C. and stirred at −20° C. for 30 minutes and at room temperature for 3 hours. The reaction mixture was quenched with a saturated NH$_4$Cl aqueous solution (100 mL) and extracted with ethyl acetate (100 mL×3). The combined extracts were washed with brine (100 mL), dried over anhydrous sodium sulfate, filtered, and concentrated to give Compound 18C. LC-MS (ESI) m/z: 195 [M−OH]$^+$.

To a solution of Compound 18C (5.52 g, 26.0 mmol) in dichloromethane (100 mL) was added Dess-Martin periodinane (13.2 g, 31.2 mmol) in several portions at 0° C. and stirred at room temperature for 30 minutes. The mixture was quenched with a saturated Na$_2$S$_2$O$_3$ aqueous solution (150 mL), stirred at room temperature for 15 minutes, and extracted with dichloromethane (100 mL×2). The combined extracts were washed with saturated NaHCO$_3$ solution (100 mL×2) and brine (100 mL), dried over anhydrous sodium sulfate, filtered, and concentrated. The residue was purified with flash column chromatography on silica gel (ethyl acetate in petroleum ether, 10% v/v) to furnish Compound 18D. LC-MS (ESI) m/z: 211 [M+H]$^+$; $^1$H-NMR (CDCl$_3$, 400 MHz): δ (ppm) 0.88-0.89 (m, 4H), 2.56 (s, 3H), 3.85-3.89 (m, 1H), 7.35 (d, J=8.4 Hz, 1H), 7.87 (dd, J=8.4, 2.4 Hz, 1H), 7.97 (d, J=2.4 Hz, 1H).

Compounds 18E, 18F, 18G, 18H, and 18 were synthesized by employing the procedures described for Compounds 15B, 15C, 1E, 1, and 8F using Compounds 18D, 18E, 18F, 18G, and 18H in lieu of Compounds 15A, 15B, 1D, 1E, and 8E. Compound 18E: LC-MS (ESI) m/z: 289 [M+H]$^+$. Compound 18F: LC-MS (ESI) m/z: 284 [M+H]$^+$; $^1$H-NMR (DMSO-d$_6$, 400 MHz): δ (ppm) 0.71-0.75 (m, 2H), 0.83-0.89 (m, 2H), 4.00-4.03 (m, 1H), 7.31 (s, 1H), 7.46 (d, J=8.8 Hz, 1H), 7.73-7.76 (m, 1H), 7.89 (s, 1H), 13.61 (s, 1H). Compound 18G: LC-MS (ESI) m/z: 543 [M+H]$^+$. Compound 18H: LC-MS (ESI) m/z: 423 [M+H]$^+$. Compound 18: LC-MS (ESI) m/z: 395 [M+H]$^+$; $^1$H-NMR (CD$_3$OD, 400 MHz): δ (ppm) 0.77-0.80 (m, 2H), 0.82-0.87 (m, 2H), 3.91-3.92 (m, 1H), 7.44 (d, J=8.8 Hz, 1H), 7.78 (s, 1H), 7.81 (dd, J=8.8, 2.0 Hz, 1H), 7.90 (d, J=2.0 Hz, 1H).

Example 19

Synthesis of cyclopropyl 4-((4-(3,4-dichlorophenyl)thiazol-2-yl)thio)-1H-1,2,3-triazole-5-carboxylate (19)

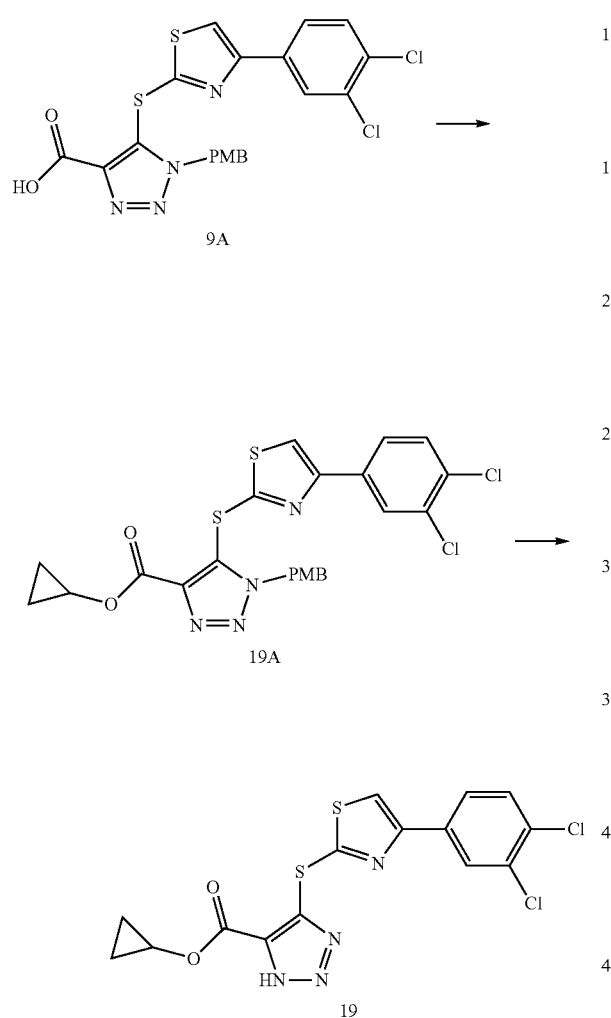

A mixture of Compound 9A (20 mg, 0.04 mmol), cyclopropanol (23 mg, 0.4 mmol), HATU (23 mg, 0.06 mmol), and DIPEA (10 mg, 0.08 mmol) in DMF (5 mL) was stirred at room temperature for 16 hours. The mixture was diluted with water (20 mL) and extracted with ethyl acetate (20 mL×3). The combined extracts were washed with water (20 mL×3), dried over anhydrous sodium sulfate, filtered, and concentrated to give Compound 19A. LC-MS (ESI) m/z: 533 [M+H]$^+$.

Compound 19 was synthesized by employing the procedure described for Compound 1 using Compound 19A in lieu of Compound 1E, LC-MS (ESI) m/z: 413 [M+H]$^+$; $^1$H-NMR (CD$_3$OD, 400 MHz): δ (ppm) 0.75-0.79 (m, 4H), 4.35-4.40 (m, 1H), 7.58 (d, J=8.0 Hz, 1H), 7.83 (d, J=8 Hz, 1H), 7.99 (s, 1H), 8.08 (s, 1H).

Example 20

Synthesis of 4-((6-(3,4-dichlorophenyl)pyridin-2-yl)thio)-1H-1,2,3-triazole-5-carboxylic acid (20)

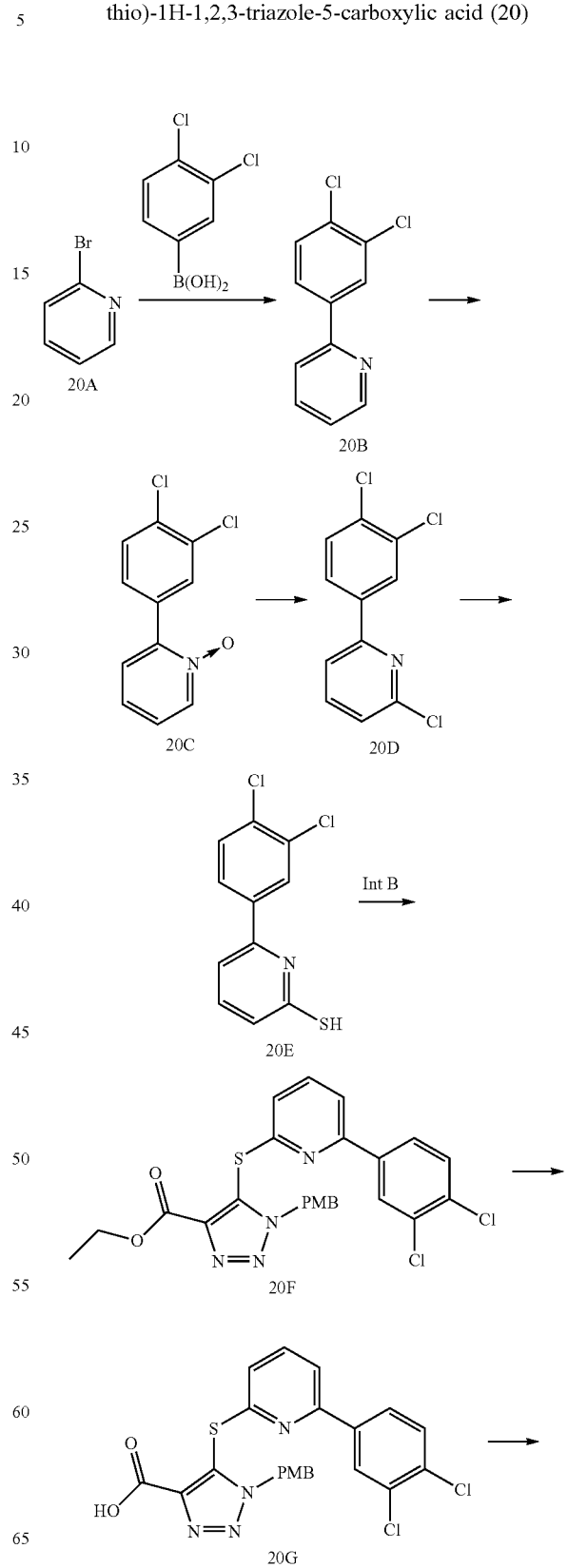

169
-continued

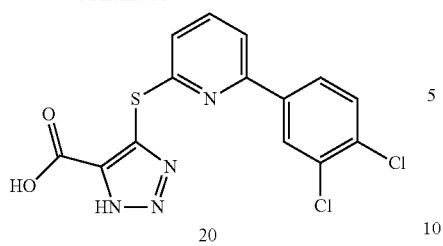
20

Compound 20B was synthesized by employing the procedure described for Compound 4B using (3,4-dichlorophenyl)boronic acid and Compound 20A in lieu of (4-bromophenyl)boronic acid and Compound 4A, LC-MS (ESI) m/z: 224 [M+H]$^+$. $^1$H-NMR (CDCl$_3$, 400 MHz): δ (ppm) 7.25-7.29 (m, 1H), 7.51-7.54 (m, 1H), 7.67-7.70 (m, 1H), 7.74-7.79 (m, 1H), 7.81-7.84 (m, 1H), 8.13 (d, J=2.0 Hz, 1H), 8.68 (d, J=4.4 Hz, 1H).

A mixture of Compound 20B (1.12 g, 5 mmol) and m-CPBA (1.3 g, 6.5 mmol) in dichloromethane (15 mL) was stirred at 20° C. for 5 hours. The mixture was poured into a saturated NaHCO$_3$ solution (100 mL) and extracted with dichloromethane (50 mL×2). The combined extracts were washed with water (50 mL×2) and brine (50 mL), dried over anhydrous sodium sulfate, filtered, and concentrated to give Compound 20C. LC-MS (ESI) m/z: 240 [M+H]$^+$.

A mixture of Compound 20C (840 mg, 3.5 mmol) and POCl$_3$ (9 mL) was stirred at 80° C. for 15 hour. The mixture was concentrated under reduced pressure. The residue was diluted with NaOH solution (6 N, 100 mL) and extracted with dichloromethane (50 mL×2). The combined extracts were washed with water (50 mL×2) and brine (50 mL), dried over anhydrous sodium sulfate, filtered, and concentrated. The residue was purified with flash column chromatography on silica gel (ethyl acetate in petroleum ether, 17% v/v) to afford Compound 20D. LC-MS (ESI) m/z: 258 [M+H]$^+$.

Compounds 20E, 20F, 20G, and 20 were synthesized by employing the procedures described for Compounds 12B, 1E, 8F, and 1 using Compounds 20D, 20E, 20F, and 20G in lieu of Compounds 12A, 1D, 8E, and 1E. Compound 20E: LC-MS (ESI) m/z: 256 [M+H]$^+$. Compound 20F: LC-MS (ESI) m/z: 515 [M+H]$^+$. Compound 20G: LC-MS (ESI) m/z: 487 [M+H]$^+$. Compound 20: LC-MS (ESI) m/z: 367 [M+H]$^+$. $^1$H-NMR (DMSO-d$_6$, 400 MHz): δ (ppm) 7.17 (brs, 1H), 7.75 (d, J=8.8 Hz, 1H), 8.05-8.08 (m, 2H), 8.32 (d, J=2 Hz, 1H), 8.53 (d, J=5.2 Hz, 1H).

Example 21

Synthesis of 4-((3',4'-dichloro-[1,1'-biphenyl]-4-yl)thio)-1H-1,2,3-triazole-5-carboxylic acid (21)

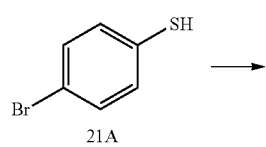

170
-continued

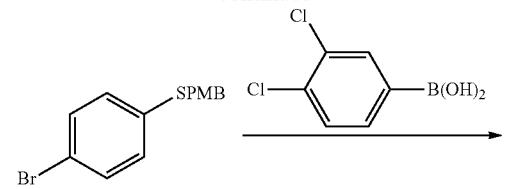
21B

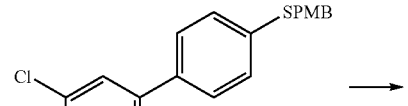
21C

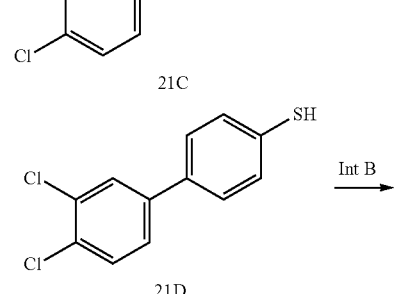
21D

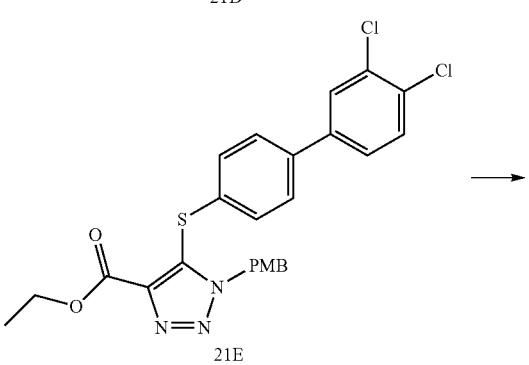
21E

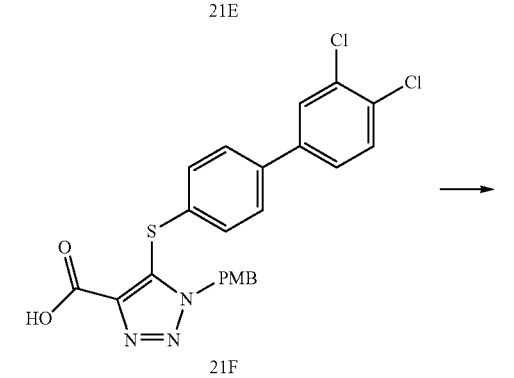
21F

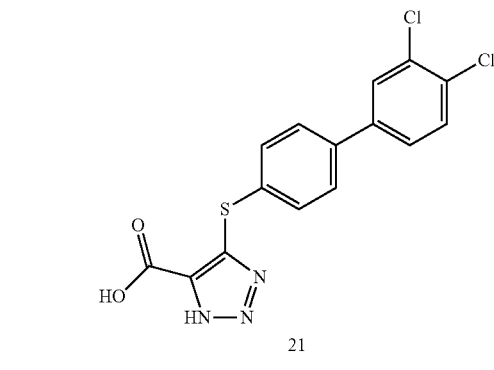
21

To a degassed solution of Compound 21A (1.89 g, 10 mmol) in DMF (15 mL) was added K₂CO₃ (1.38 g, 10 mmol). The mixture was stirred under nitrogen for 10 minutes, followed by addition of 1-(chloromethyl)-4-methoxybenzene (1.56 g, 10 mmol) dropwise. The mixture was stirred at room temperature for 12 hours and at 100° C. for 1 hour. The reaction was slowly quenched with water (25 mL) and a solid precipitated gradually. The solid was collected by filtration and recrystallized from methanol to give Compound 21B. LC-MS (ESI) m/z: non-ionizable compound under routine conditions used; ¹H-NMR (CDCl₃, 400 MHz): δ (ppm) 3.78 (s, 3H), 4.04 (s, 2H), 6.80-6.83 (m, 2H), 7.13-7.15 (m, 2H), 7.17-7.19 (m, 2H), 7.35-7.37 (m, 2H).

Compound 21C was synthesized by employing the procedure described for Compound 4B using (3,4-dichlorophenyl)boronic acid and Compound 21B in lieu of (4-bromophenyl)boronic acid and Compound 4A, LC-MS (ESI) m/z: non-ionizable compound under routine conditions used; ¹H-NMR (CDCl₃, 400 MHz): δ (ppm) 3.79 (s, 3H), 4.12 (s, 2H), 6.82-6.84 (m, 2H), 7.23-7.25 (m, 2H), 7.34-7.38 (m, 3H), 7.42-7.44 (m, 2H), 7.47-7.50 (m, 1H), 7.64 (d, J=2.4 Hz, 1H).

A mixture of compound 21C (188 mg, 0.5 mmol) and TFA (3 mL) was stirred at 80° C. for 4 hours and concentrated under reduced pressure. The residue was partitioned between CH₂Cl₂ (5 mL) and water (5 mL). The organic phase was dried over anhydrous sodium sulfate, filtered, and concentrated to furnish compound 21D. LC-MS (ESI) m/z: 253 [M−H]⁻.

Compounds 21E, 21F, and 21 were synthesized by employing the procedures described for Compounds 13D, 8F, and 1 using Compounds 21D, 21E, and 21F in lieu of Compounds 13C, 8E, and 1E. Compound 21E: LC-MS (ESI) m/z: 514 [M+H]⁺; ¹H-NMR (CDCl₃, 400 MHz): δ (ppm) 1.32 (t, J=5.6 Hz, 3H), 3.79 (s, 3H), 4.37 (q, J=5.6 Hz, 2H), 5.58 (s, 2H), 6.71-6.73 (m, 2H), 7.00-7.02 (m, 2H), 7.13-7.15 (m, 2H), 7.31-7.33 (m, 3H), 7.49 (d, J=6.8 Hz, 1H), 7.57 (d, J=1.6 Hz, 1H). Compound 21F: LC-MS (ESI) m/z: 486 [M+H]⁺. Compound 21: LC-MS (ESI) m/z: 366 [M+H]⁺; ¹H-NMR (CD₃OD, 400 MHz): δ (ppm) 7.45-7.47 (m, 2H), 7.56-7.59 (m, 4H), 7.79 (d, J=1.2 Hz, 1H).

Example 22

Synthesis of 4-((2',4'-dichloro-[1,1'-biphenyl]-4-yl)thio)-1H-1,2,3-triazole-5-carboxylic acid (22)

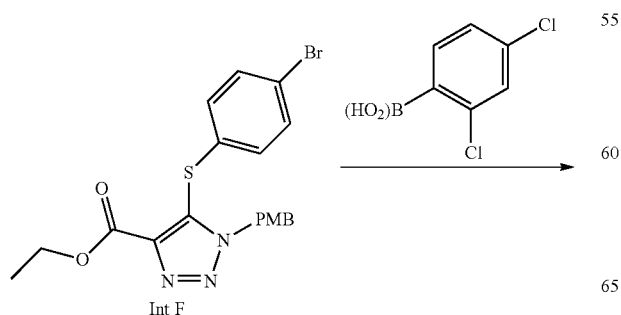

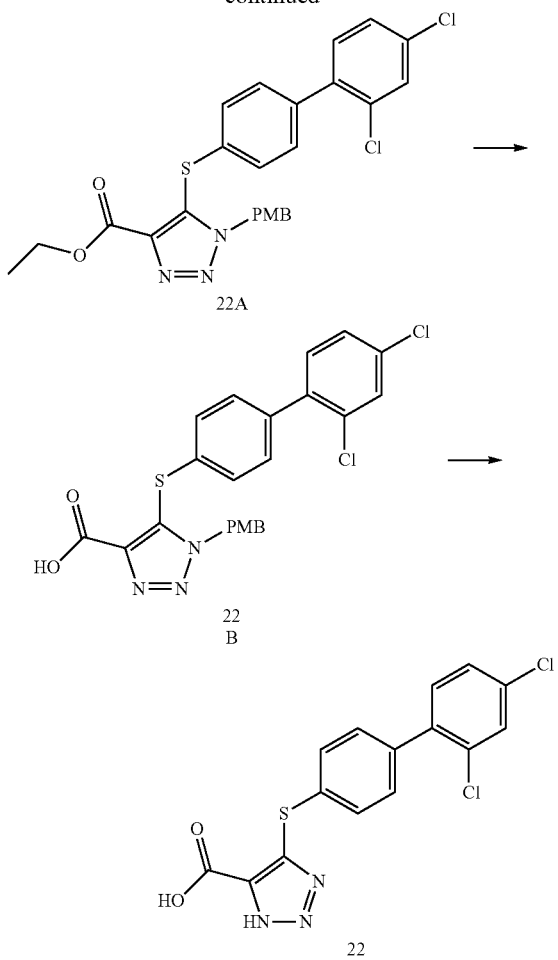

Compounds 22A, 22B, and 22 were synthesized by employing the procedures described for Compounds 4B, 8F, and 1 using Intermediate F, 2,4-dichlorophenylboronic acid, Compounds 22A, and 22B in lieu of Compounds 4A, (4-bromophenyl)boronic acid, 8E, and 1E. Compound 22A: LC-MS (ESI) m/z: 514 [M+H]⁺. Compound 22B: LC-MS (ESI) m/z: 486 [M+H]⁺. Compound 22: LC-MS (ESI) m/z: 366 [M+H]⁺; ¹H-NMR (DMSO-d₆, 400 MHz): δ (ppm) 7.43-7.47 (m, 3H), 7.52 (d, J=8.4 Hz, 3H), 7.75 (s, 1H).

Example 23

Synthesis of 4-((2-(4-chloro-3-methoxyphenyl)thiazol-4-yl)thio)-1H-1,2,3-triazole-5-carboxylic acid (23)

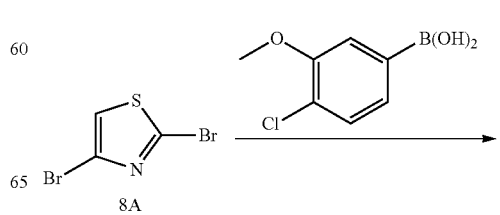

-continued

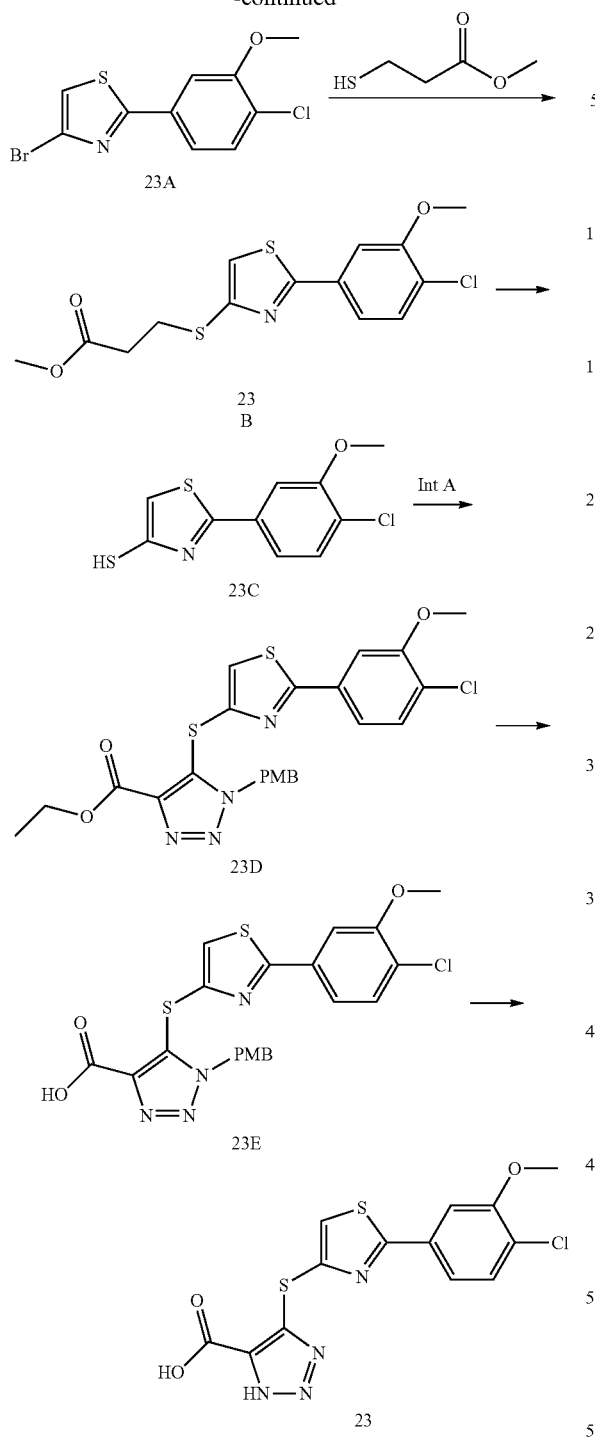

Compounds 23A, 23B, 23C, 23D, 23E, and 23 were synthesized by employing the procedures described for Compounds 8B, Intermediates D-1, D, 1E, 8F, and 1 using 4-chloro-3-methoxyphenylboronic acid, Compounds 23A, 23B, 23C, Intermediate A, 23D, and 23E in lieu of (3,4-dichlorophenyl)boronic acid, Intermediates A, D-1, Compounds 1D, Intermediate B, 8E, and 1E. Compound 23A: LC-MS (ESI) m/z: 304 [M+H]$^+$. Compound 23B: LC-MS (ESI) m/z: 344 [M+H]$^+$. Compound 23C: LC-MS (ESI) m/z: 258 [M+H]$^+$. Compound 23D: LC-MS (ESI) m/z: 517 [M+H]$^+$. Compound 23E: LC-MS (ESI) m/z: 489 [M+H]$^+$.

Compound 23: LC-MS (ESI) m/z: 369 [M+H]$^+$; $^1$H-NMR (CD$_3$OD, 400 MHz): δ (ppm) 3.97 (s, 3H), 7.48 (s, 2H), 7.67 (s, 1H), 7.86 (s, 1H).

Example 24

Synthesis of 4-((2-(4-chloro-3-isopropoxyphenyl)thiazol-4-yl)thio)-1H-1,2,3-triazole-5-carboxylic acid (24)

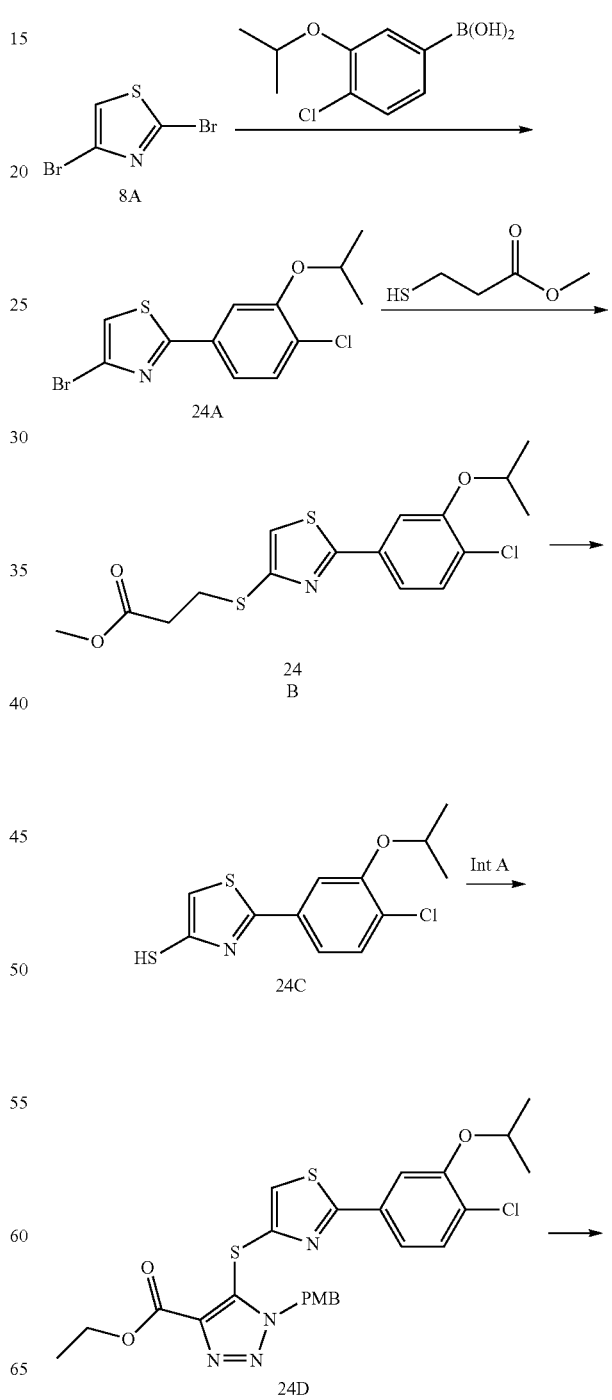

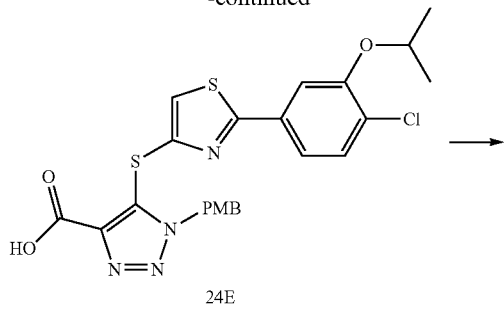

24E

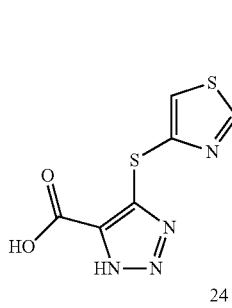

24

Compounds 24A, 24B, 24C, 24D, 24E, and 24 were synthesized by employing the procedures described for Compounds 8B, Intermediates D-1, D, 1E, 8F, and 1 using 4-chloro-3-methoxyphenylboronic acid, Compounds 24A, 24B, 24C, Intermediate A, 24D, and 24E in lieu of (3,4-dichlorophenyl)boronic acid, Intermediates A, D-1, Compounds 1D, Intermediate B, 8E, and 1E. Compound 24A: LC-MS (ESI) m/z: 332 [M+H]⁺. Compound 24B: LC-MS (ESI) m/z: 372 [M+H]⁺. Compound 24C: LC-MS (ESI) m/z: 286 [M+H]⁺. Compound 24D: LC-MS (ESI) m/z: 545 [M+H]⁺. Compound 24E: LC-MS (ESI) m/z: 517 [M+H]⁺. Compound 24: LC-MS (ESI) m/z: 397 [M+H]⁺; ¹H-NMR (CD₃OD, 400 MHz): δ (ppm) 1.38 (d, J=6.4 Hz, 6H), 4.75 (m, 1H), 7.47 (m, 2H), 7.66 (s, 1H), 7.85 (s, 1H).

Example 25

Synthesis of 5-((2-(3-chloro-4-methoxyphenyl)thiazol-4-yl)thio)-1-(4-methoxybenzyl)-1H-1,2,3-triazole-4-carboxylic acid (25-1) and 4-((2-(3-chloro-4-methoxyphenyl)thiazol-4-yl)thio)-1H-1,2,3-triazole-5-carboxylic acid (25-2)

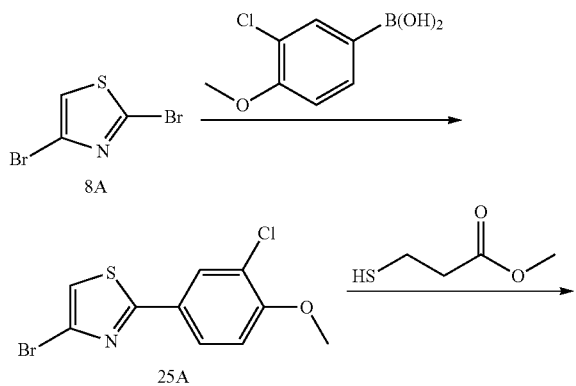

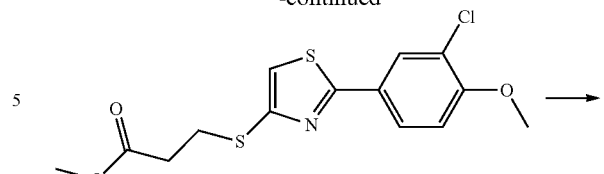

25B

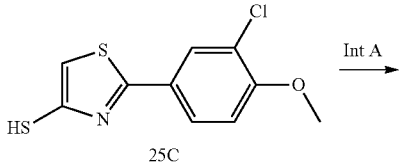

25C

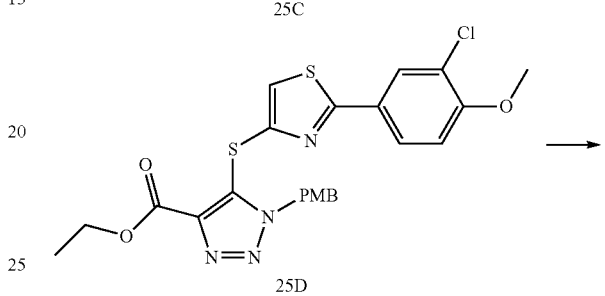

25D

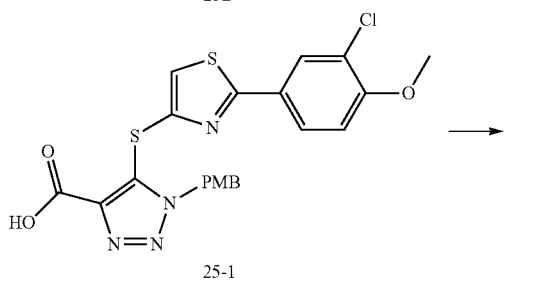

25-1

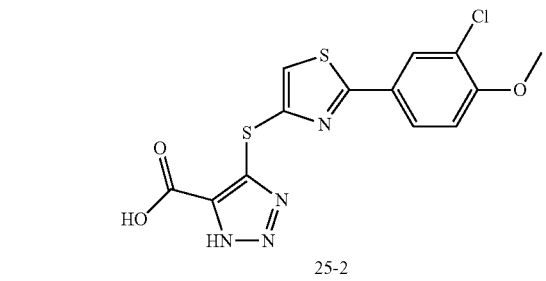

25-2

Compounds 25A, 25B, 25C, 25D, 25-1, and 25-2 were synthesized by employing the procedures described for Compounds 8B, Intermediates D-1, D, 1E, 8F, and 1 using 4-chloro-3-methoxyphenylboronic acid, Compounds 25A, 25B, 25C, Intermediate A, 25D, and 25-1 in lieu of (3,4-dichlorophenyl)boronic acid, Intermediates A, D-1, Compounds 1D, Intermediate B, 8E, and 1E. Compound 25A: LC-MS (ESI) m/z: 304 [M+H]; ¹H-NMR (CDCl₃, 400 MHz): δ (ppm) 3.96 (s, 3H), 6.97 (d, J=8.8 Hz, 1H), 7.17 (s, 1H), 7.80 (dd, J₁=8.4 Hz, J₂=2.4 Hz, 1H), 7.98 (d, J=2.4 Hz, 1H). Compound 25B: LC-MS (ESI) m/z: 344 [M+H]⁺; ¹H-NMR (CDCl₃, 400 MHz): δ (ppm) 2.77 (t, J=7.2 Hz, 2H), 3.33 (t, J=7.2 Hz, 2H), 3.71 (s, 3H), 3.97 (s, 3H), 6.98 (d, J=8.8 Hz, 1H), 7.07 (s, 1H), 7.81 (dd, J₁=8.8 Hz, K₂=2.0 Hz, 1H), 8.00 (d, J=2.0 Hz, 1H). Compound 25C: LC-MS (ESI) m/z: 258 [M+H]⁺. Compound 25D: LC-MS (ESI) m/z: 517 [M+H]⁺. Compound 25-1: LC-MS (ESI) m/z: 489 [M+H]⁺; ¹H-NMR (CDCl₃, 400 MHz): δ (ppm) 3.76 (s, 3H), 3.97 (s, 3H), 5.76 (s, 2H), 6.80-6.82 (m, 2H), 6.97 (d, J=8.8 Hz, 1H), 7.14 (s, 1H), 7.25 (d, J=8.8 Hz, 2H), 7.69 (dd, J$_1$=8.4 Hz, J$_2$=2.0 Hz, 1H), 7.79 (d, J=2.0 Hz, 1H). Compound 25-2: LC-MS (ESI) m/z: 369 [M+H]$^+$; $^1$H-NMR (CDCl$_3$, 400 MHz): δ (ppm) 3.92 (s, 3H), 7.27 (d, J=8.8 Hz, 1H), 7.86 (dd, J$_1$=8.4 Hz, J$_2$=2.4 Hz, 1H), 7.92 (d, J=2.0 Hz, 1H), 7.94 (s, 1H).

Example 26

Synthesis of 4-((2-(2,4-dichlorophenyl)thiazol-4-yl)thio)-1H-1,2,3-triazole-5-carboxylic acid (26)

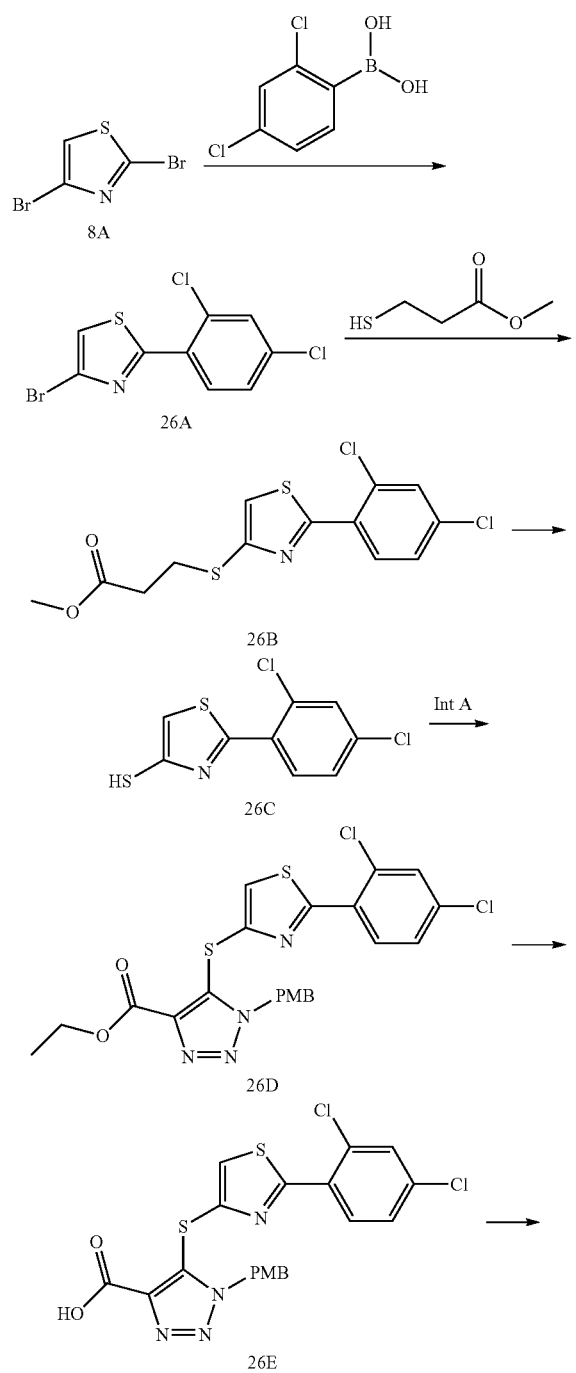

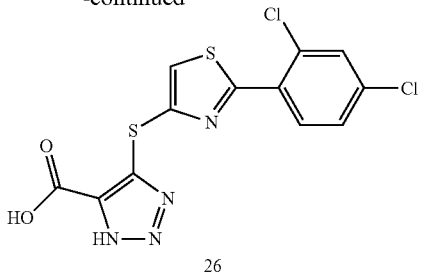

Compounds 26A, 26B, 26C, 26D, 26E, and 26 were synthesized by employing the procedures described for Compounds 8B, Intermediates D-1, D, 1E, 8F, and 1 using 4-chloro-3-methoxyphenylboronic acid, Compounds 26A, 26B, 26C, Intermediate A, 26D, and 26E in lieu of (3,4-dichlorophenyl)boronic acid, Intermediates A, D-1, Compounds 1D, Intermediate B, 8E, and 1E. Compound 26A: LC-MS (ESI) m/z: 308 [M+H]$^+$. $^1$H-NMR (CDCl$_3$, 400 MHz): δ (ppm) 7.35-7.39 (m, 2H), 7.51 (d, J=1.6 Hz, 1H), 8.28 (d, J=8.8 Hz, 1H). Compound 26B: LC-MS (ESI) m/z: 348 [M+H]$^+$. $^1$H-NMR (CDCl$_3$, 400 MHz): δ 2.77 (t, J=7.2 Hz, 2H), 3.35 (t, J=7.2 Hz, 2H), 3.70 (s, 3H), 7.26 (s, 1H), 7.36 (dd, J=2.0, 8.8 Hz, 1H), 7.51 (d, J=2.0 Hz, 1H), 8.25 (d, J=8.8 Hz, 1H). Compound 26C: LC-MS (ESI) m/z: 262 [M+H]$^+$. Compound 26D: LC-MS (ESI) m/z: 521. $^1$H-NMR (CDCl$_3$, 400 MHz): δ 1.35 (t, J=7.2 Hz, 3H), 3.72 (s, 3H), 4.39 (q, J=7.2 Hz, 2H), 5.73 (s, 2H), 6.74 (d, J=8.8 Hz, 2H), 7.18 (s, 1H), 7.23 (d, J=8.8 Hz, 2H), 7.31 (dd, J=2.0, 8.8 Hz, 1H), 7.49 (d, J=2.0 Hz, 1H), 7.96 (d, J=8.4 Hz, 1H). Compound 26E: LC-MS (ESI) m/z: 493 [M+H]$^+$. Compound 26: LC-MS (ESI) m/z: 373 [M+H]$^+$; $^1$H-NMR (DMSO-d$_6$, 400 MHz): δ (ppm) 7.60 (dd, J=2.0, 8.4 Hz, 1H), 7.87 (d, J=2.0 Hz, 1H), 8.16-8.18 (m, 2H).

Example 27

Synthesis of 4-((2-(3-chloro-4-isopropoxyphenyl)thiazol-4-yl)thio)-1H-1,2,3-triazole-5-carboxylic acid (27)

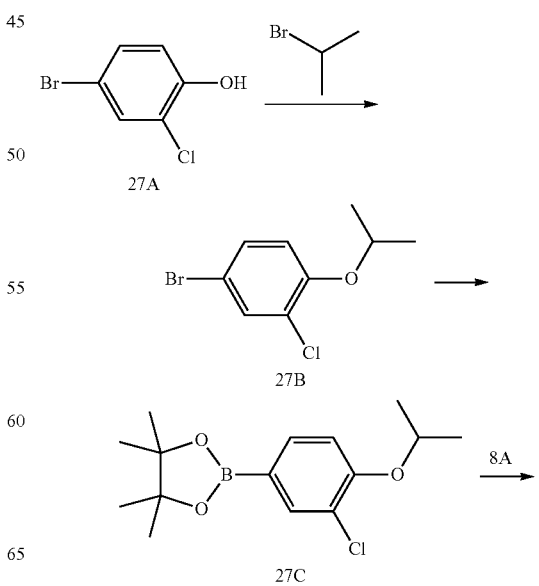

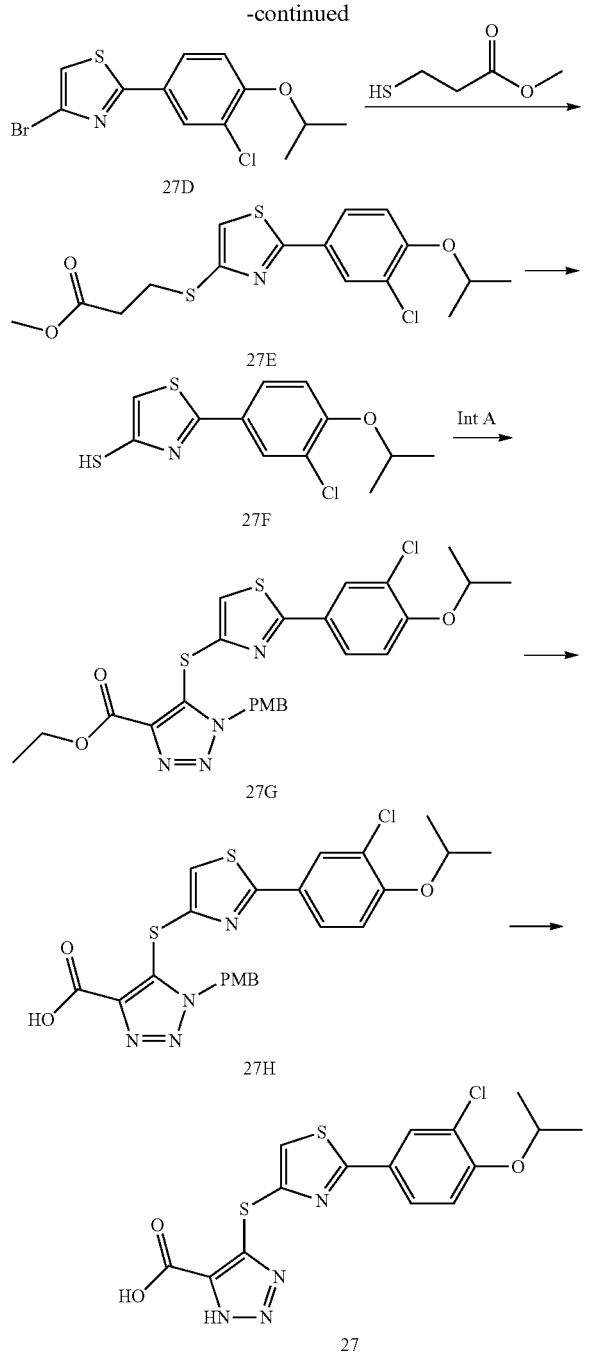

ethyl-2,2'-bi(1,3,2-dioxaborolane) (2.09 g, 8.22 mmol), and potassium acetate (1.62 g, 16.5 mmol) in 1,4-dioxane (50 ml) was heated at 80° C. for 16 hours. The mixture was diluted with water (200 mL) and extracted with ethyl acetate (200 mL×2). The combined extracts were washed with water (200 mL) and brine (200 mL), dried over anhydrous sodium sulfate, filtered, and concentrated. The residue was purified with flash column chromatography on silica gel (ethyl acetate in petroleum ether, from 0% to 10% v/v) to furnish Compound 27C. LC-MS (ESI) m/z: non-ionizable compound under routine conditions used.

Compounds 27D, 27E, 27F, 27G, 27H, and 27 were synthesized by employing the procedures described for Compounds 8B, Intermediates D-1, D, 1E, 8F, and 1 using Compounds 27C, 27D, 27E, 27F, Intermediate A, 27G, and 27H in lieu of (3,4-dichlorophenyl)boronic acid, Intermediates A, D-1, Compounds 1D, Intermediate B, 8E, and 1E. Compound 27D: LC-MS (ESI) m/z: 332. Compound 27E: LC-MS (ESI) m/z: 372 [M+H]$^+$. Compound 27F: LC-MS (ESI) m/z: 286 [M+H]$^+$. Compound 27G: LC-MS (ESI) m/z: 545 [M+H]$^+$. Compound 27H: LC-MS (ESI) m/z: 517 [M+H]$^+$. Compound 27: LC-MS (ESI) m/z: 397 [M+H]$^+$; $^1$H-NMR (DMSO-$d_6$, 400 MHz): δ (ppm) 1.33 (d, J=6.0 Hz, 6H), 4.77-4.80 (m, 1H), 7.29 (d, J=9.2 Hz, 1H), 7.82 (dd, $J_1$=2.0 Hz, $J_2$=8.4 Hz, 1H), 7.92-7.94 (m, 2H).

Example 28

Synthesis of 4-((5-(3,4-dichlorophenyl)-4-methyl-4H-1,2,4-triazol-3-yl)thio)-1H-1,2,3-triazole-5-carboxylic acid 2,2,2-trifluoroacetate (28)

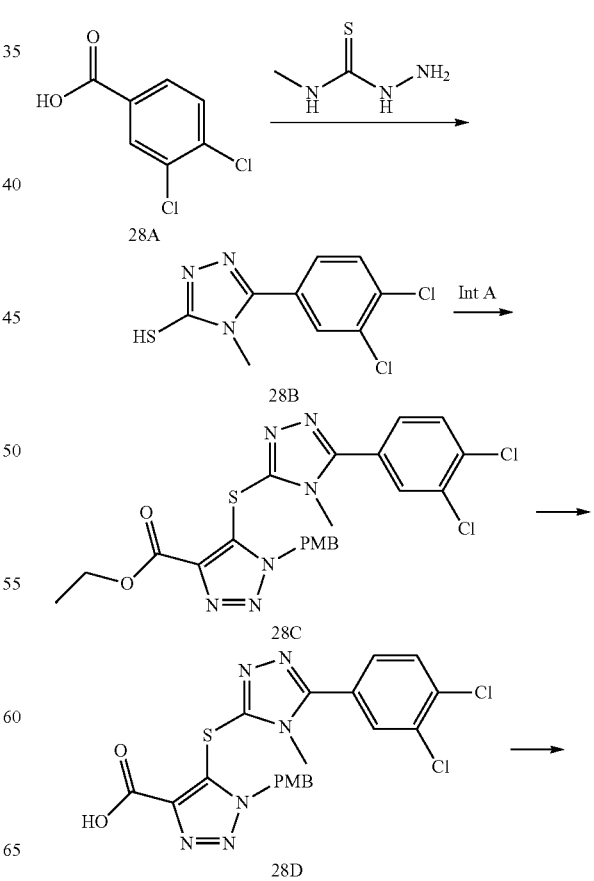

To a solution of 4-bromo-2-chlorophenol (Compound 27A) (5.0 g, 24.1 mmol) in DMF (100 mL) was added K$_2$CO$_3$ (10.0 g, 72.5 mmol) and 2-bromopropane (7.5 g, 61.5 mmol) and stirred at 100° C. for 16 hours. The mixture was diluted with water (400 mL) and extracted with a mixture of ethyl acetate in petroleum ether (15% v/v, 300 mL×3). The combined extracts were washed with bine (300 mL×4), dried over anhydrous sodium sulfate, filtered, and concentrated. The residue was purified with flash column chromatography on silica gel (petroleum ether) to furnish Compound 27B. LC-MS (ESI) m/z: non-ionizable compound under routine conditions used.

A mixture of Compound 27B (1.35 g, 5.4 mmol), Pd(dppf)Cl$_2$ (0.35 g, 0.43 mmol), 4,4,4',4',5,5,5',5'-octam-

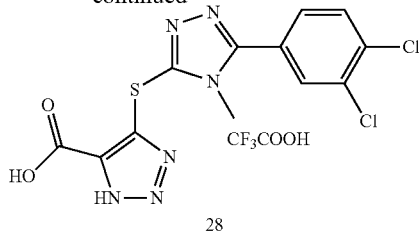

28

To a solution of 3,4-dichlorobenzoic acid (28A) (500 mg, 2.62 mmol), N-methylhydrazinecarbothioamide (302 mg, 2.88 mmoL), and DIPEA (606 mg, 4.7 mmoL) in DMF (5 mL) was added 2,4,6-tripropyl-1,3,5,2,4,6-trioxatriphosphorinane-2,4,6-trioxide ($T_3P$, 1.25 g, 3.93 mmol) and stirred at room temperature for 30 minutes. The reaction mixture was diluted with water (30 mL) and extracted with ethyl acetate (20 mL×3). The combined extracts were concentrated under reduced pressure. The residue was diluted with a mixture of water (10 mL) and DMF (2 mL), adjusted to pH 8 with aqueous NaOH solution (4 M) and heated to 70° C. for 16 hours. The mixture was acidified to pH 5 with concentrated HCl solution. The resulting solid was collected and purified with flash column chromatography on silica gel (ethyl acetate in petroleum ether from 0% to 100% v/v) to furnish Compound 28B. LC-MS (ESI) m/z: 260 [M+H]$^+$.

Compounds 28C, 28D, and 28 were synthesized by employing the procedures described for Compounds 1E, 8F, and 1 using Intermediate A, Compounds 28B, 28C, and 28D in lieu of Intermediate B, Compounds 1D, 8E, and 1E. Compound 28C: LC-MS (ESI) m/z: 519 [M+H]$^+$; $^1$H-NMR (CD$_3$OD, 400 MHz): δ (ppm) 1.35 (t, J=7.2 Hz, 3H), 3.70 (s, 3H), 3.72 (s, 3H), 4.37 (q, J=7.2 Hz, 2H), 5.84 (s, 2H), 6.84 (d, J=8.4 Hz, 2H), 7.16 (d, J=8.8 Hz, 2H), 7.55 (dd, J=8.0, 2.0 Hz, 1H), 7.74 (d, J=8.0 Hz, 1H), 7.81 (d, J=2.0 Hz, 1H). Compound 28D: LC-MS (ESI) m/z: 491 [M+H]$^+$. Compound 28: LC-MS (ESI) m/z: 371 [M+H]$^+$; $^1$H-NMR (DMSO-d$_6$, 400 MHz): δ (ppm) 3.70 (s, 3H), 7.78 (dd, J=8.0, 2.0 Hz, 1H), 7.87 (d, J=8.0 Hz, 1H), 8.05 (d J=2.0 Hz, 1H).

Example 29

Synthesis of 4-((5-ethoxybenzo[d]thiazol-2-yl)thio)-1H-1,2,3-triazole-5-carboxylic acid (29)

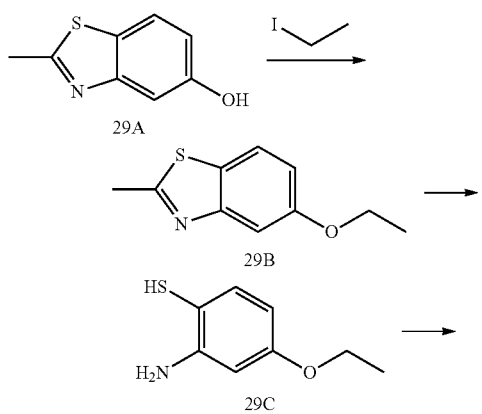

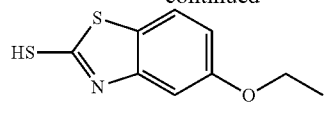

29D

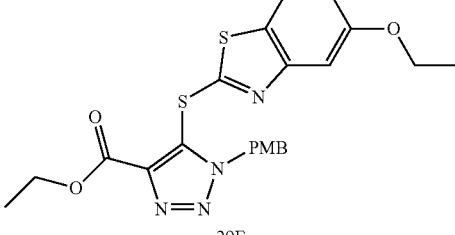

29E

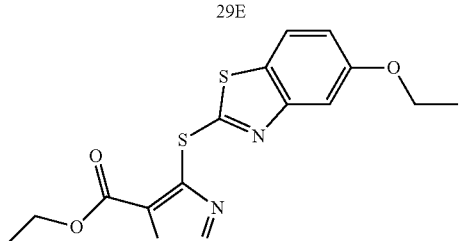

29F

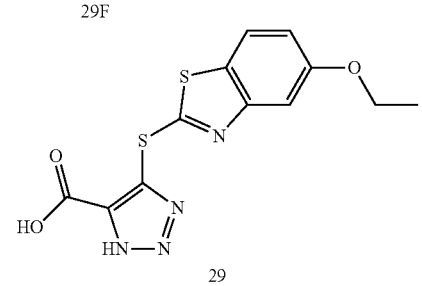

29

A mixture of 2-methylbenzo[d]thiazol-5-ol (Compound 29A) (2 g, 12.1 mmol), iodoethane (2.8 g, 18.2 mmol), and potassium carbonate (3.4 g, 24.2 mmol) in acetonitrile (40 mL) was stirred at 70° C. overnight. The mixture was concentrated under reduced pressure. The residue was diluted with ethyl acetate (50 mL), washed with H$_2$O (10 mL×3), dried over anhydrous Na$_2$SO$_4$, filtered, and concentrated. The residue was purified with flash column chromatography on silica gel (ethyl acetate in petroleum ether, 9% v/v) to give Compound 29B. LC-MS (ESI) m/z: 194 [M+H]$^+$.

To a solution of Compound 29B (500 mg, 2.59 mmol) in ethylene glycol (3 mL) was added an aqueous sodium hydroxide solution (50% w/w, 6 g, 75 mmol) and stirred at 140° C. for 3 hours. The mixture was poured into ice-water (50 mL), acidified to pH 3 with an aqueous hydrochloric acid solution (2 N), and extracted with dichloromethane (20 mL×4). The combined extracts were dried over anhydrous Na$_2$SO$_4$, filtered, and concentrated to give Compound 29C, which was used directly in next step without further purification. LC-MS (ESI) m/z: 170 [M+H]$^+$.

A mixture of Compound 29C (400 mg, 2.36 mmol), carbon disulfide (450 mg, 5.9 mmol), and sodium hydroxide (236 mg, 5.9 mmol) in ethanol (10 mL) was heated at reflux for 2 hours. After cooled to room temperature, the mixture was filtered. The filtrate was diluted with ice-water (30 mL) and acidified to pH 3 with an aqueous hydrochloric acid solution (2 N). The resulting solid was collected and dried under vacuum to give Compound 29D. LC-MS (ESI) m/z: 212 [M+H]$^+$.

Compounds 29E, 29F, and 29 were synthesized by employing the procedures described for Compounds 1E, 1, and 8F using Intermediate A, Compounds 29D, 29E, and 29F in lieu of Intermediate B, Compounds 1D, 1E, and 8E. Compound 29E: LC-MS (ESI) m/z: 471 [M+H]+; 1H-NMR (CDCl3, 400 MHz): δ (ppm) 1.33 (t, J=7.2 Hz, 3H), 1.47 (t, J=7.2 Hz, 3H), 3.63 (s, 3H), 4.09 (q, J=7.2 Hz, 2H), 4.39 (q, J=7.2 Hz, 2H), 5.67 (s, 2H), 6.67 (d, J=8.4 Hz, 2H), 6.97 (dd, J=8.8, 2.4 Hz, 1H), 7.22 (d, J=8.4 Hz, 2H), 7.31 (d, J=2.8 Hz, 1H), 7.50 (d, J=8.8 Hz, 1H). Compound 29F: LC-MS (ESI) m/z: 351 [M+H]+. Compound 29: LC-MS (ESI) m/z: 323 [M+H]+; 1H-NMR (DMSO-d6, 400 MHz): δ (ppm) 1.34 (t, J=7.2 Hz, 3H), 4.08 (q, J=7.2 Hz, 2H), 7.01 (dd, J=8.8, 2.4 Hz, 1H), 7.41 (d, J=2.4 Hz, 1H), 7.84 (d, J=8.4 Hz, 1H).

Example 30

Synthesis of 4-((4'-chloro-3'-(trifluoromethoxy)-[1,1'-biphenyl]-4-yl)thio)-1H-1,2,3-triazole-5-carboxylic acid (30)

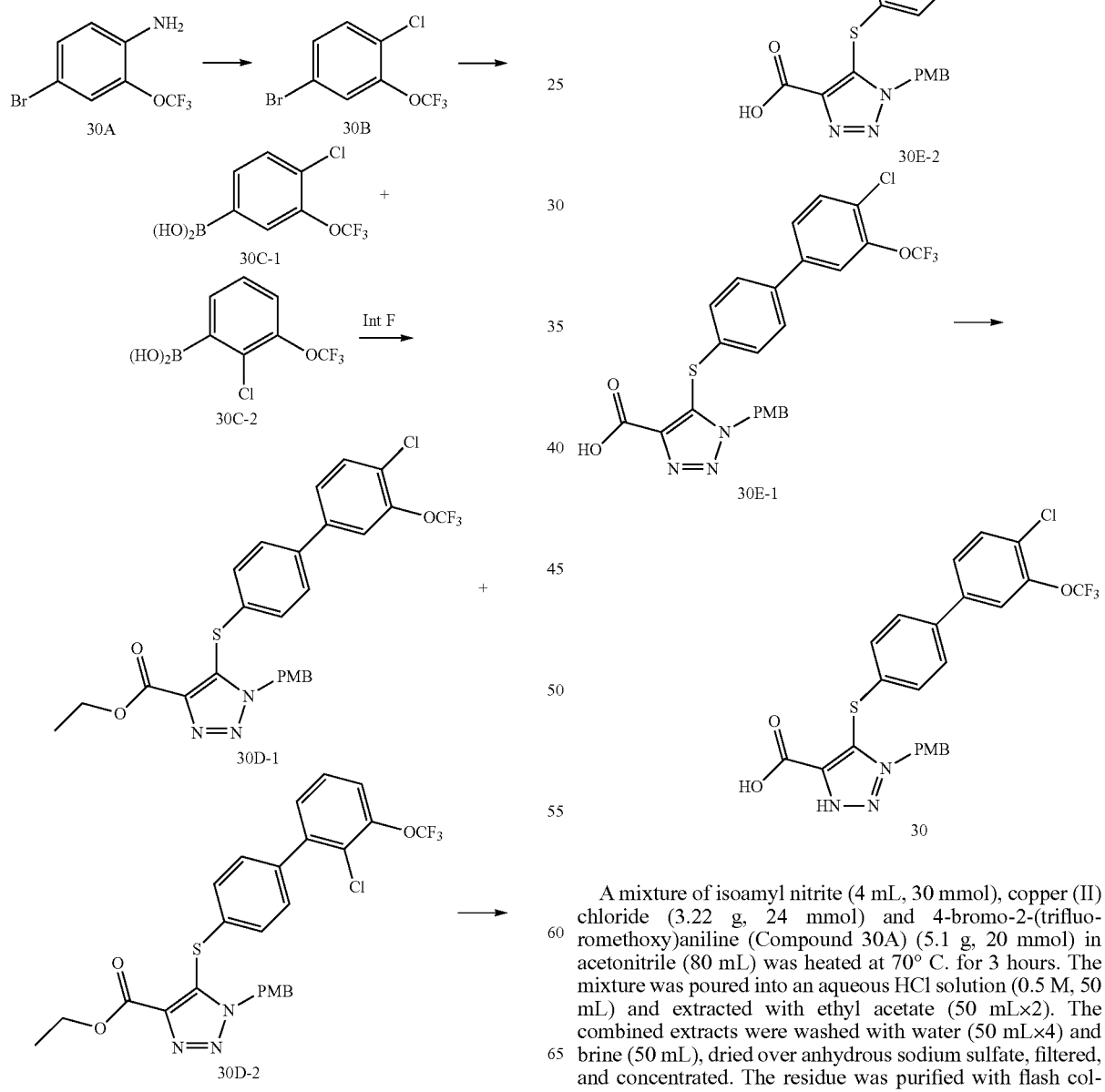

A mixture of isoamyl nitrite (4 mL, 30 mmol), copper (II) chloride (3.22 g, 24 mmol) and 4-bromo-2-(trifluoromethoxy)aniline (Compound 30A) (5.1 g, 20 mmol) in acetonitrile (80 mL) was heated at 70° C. for 3 hours. The mixture was poured into an aqueous HCl solution (0.5 M, 50 mL) and extracted with ethyl acetate (50 mL×2). The combined extracts were washed with water (50 mL×4) and brine (50 mL), dried over anhydrous sodium sulfate, filtered, and concentrated. The residue was purified with flash column chromatography on silica gel (petroleum ether) to afford Compound 30B. LC-MS (ESI) m/z: non-ionizable compound under routine conditions used. ¹H-NMR (DMSO-d₆, 400 MHz): δ (ppm) 7.33-7.35 (m, 1H), 7.37-7.40 (m, 1H), 7.48 (t, J=1.6 Hz, 1H).

To Compound 30B (1.7 g, 6.2 mmol) in anhydrous THF (30 mL) at −78° C. was dripped n-BuLi solution (2.5 M in hexanes, 3.15 mL, 6.25 mmol) and stirred at −78° C. for 30 minutes. To the mixture was added triisopropyl borate (1.44 mL, 6.25 mmol) and was gradually allowed to warm to room temperature and stirred at room temperature for 2 hours. The mixture was poured into water (100 mL), acidified to pH 4 with aqueous HCl solution (1 M), and extracted with ethyl acetate (100 mL×2). The combined extracts were washed with brine (100 mL), dried over anhydrous sodium sulfate, filtered, and concentrated to yield a mixture of Compound 30C-1 and 30C-2. LC-MS (ESI) m/z: non-ionizable compound under routine conditions used.

Mixture of 30D-1 and 30D-2, Compounds 30E-1, 30E-2, and 30 were synthesized by employing the procedures described for Compounds 4B, 8F, and 1 using Intermediate F, Mixtures of 30C-1 and 30C-2, 30D-1 and 30D-2, and Compound 30E-1 in lieu of Intermediate B, Compounds 4A, 8E, and 1E. Mixture of 30D-1 and 30D-2: LC-MS (ESI) m/z: 564 [M+H]⁺. Compound 30E-1: LC-MS (ESI) m/z: 536 [M+H]⁺. ¹H-NMR (DMSO-d₆, 400 MHz): δ (ppm) 3.62 (s, 3H), 5.62 (s, 2H), 6.78 (d, J=8.8 Hz, 2H), 7.10 (d, J=8.4 Hz, 4H), 7.58 (d, J=8.8 Hz, 2H), 7.69-7.78 (m, 3H), 13.36 (s, 1H). Compound 30E-2: LC-MS (ESI) m/z: 536 [M+H]⁺. ¹H-NMR (DMSO-d₆, 400 MHz): δ (ppm) 3.66 (s, 3H), 5.63 (d, J=14 Hz, 2H), 6.80 (d, J=8.8 Hz, 2H), 7.10-7.16 (m, 4H), 7.32-7.71 (m, 5H), 13.39 (s, 1H). Compound 30: LC-MS (ESI) m/z: 416 [M+H]⁺; ¹H-NMR (DMSO-d₆, 400 MHz): δ (ppm) 7.53 (d, J=8.4 Hz, 2H), 7.75 (d, J=8.4 Hz, 2H), 7.79 (s, 2H), 7.86 (s, 1H).

Example 31

Synthesis of 4-((2'-chloro-3'-(trifluoromethoxy)-[1,1'-biphenyl]-4-yl)thio)-1H-1,2,3-triazole-5-carboxylic acid (31)

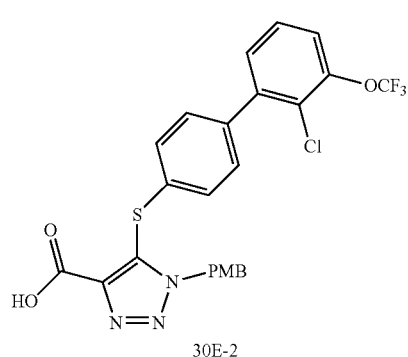

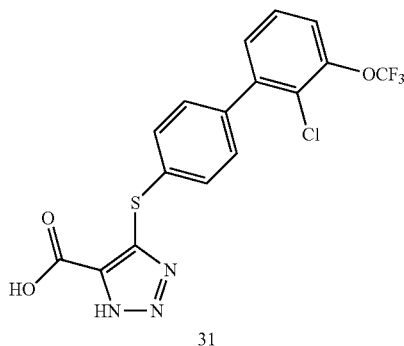

Compound 31 was synthesized by employing the procedure described for Compound 1 using Compound 30E-2 in lieu of Compound 1E, LC-MS (ESI) m/z: 416 [M+H]⁺; ¹H-NMR (DMSO-d₆, 400 MHz): δ (ppm) 7.45-7.71 (m, 7H).

Example 32

Synthesis of 4-((3'-chloro-4'-(trifluoromethoxy)-[1,1'-biphenyl]-4-yl)thio)-1H-1,2,3-triazole-5-carboxylic acid (32)

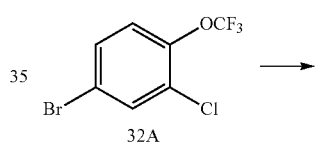

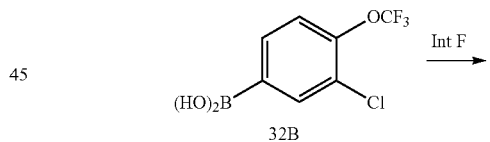

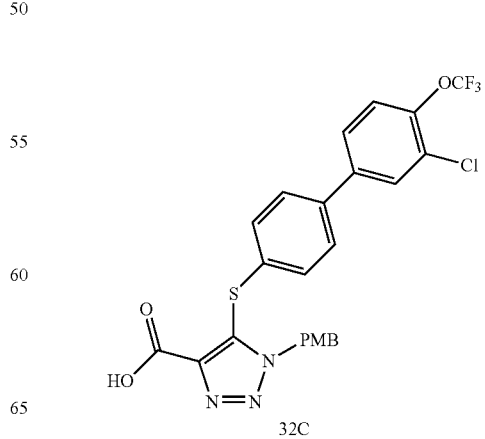

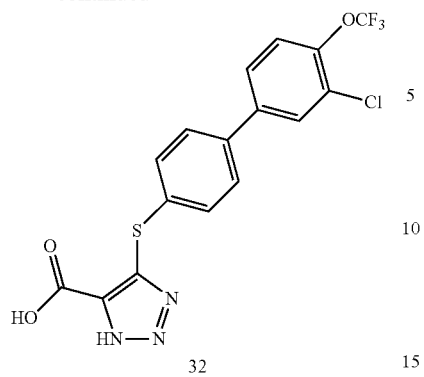

32

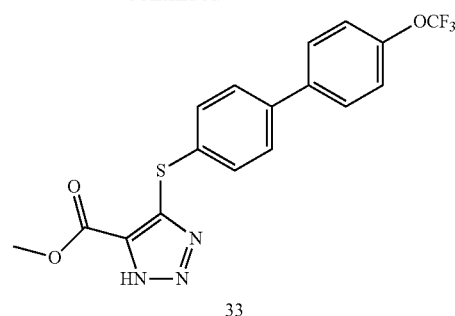

33

Compound 32B was synthesized by employing the procedure described for Compound 30C-1 using Compound 32A in lieu of Compound 30B, LC-MS: (ESI) m/z: 239 [M−H]⁻; ¹H-NMR (CDCl₃, 400 MHz): δ (ppm) 7.47-7.49 (m, 1H), 8.11-8.14 (m, 1H), 8.26 (d, J=1.6 Hz, 1H).

A mixture of Compound 32B (150 mg, 0.34 mmol), Intermediate F (129 mg, 0.54 mmol), Pd(PPh₃)₄ (39 mg, 0.03 mmol), and K₂CO₃ (187 mg, 1.36 mmol) in 1,4-dioxane (5 mL) and H₂O (1 mL) was stirred at 90° C. under nitrogen for 4 hours. After the mixture was cooled down to room temperature, a solution of LiOH.H₂O (21 mg, 053 mmol) in H₂O (1 mL) was added and stirred at 40° C. for 2 hours. The reaction mixture was concentrated and purified with reverse phase chromatography using eluents (acetonitrile in water, form 0% to 90% v/v) to furnish Compound 32C. LC-MS: (ESI) m/z: 536 [M+H]⁺.

Compound 32 was synthesized by employing the procedure described for Compound 1 using Compound 32C in lieu of Compound 1E, LC-MS (ESI) m/z: 416 [M+H]⁺; ¹H-NMR (DMSO-d₆, 400 MHz): δ (ppm) 77.53 (d, J=8.4 Hz, 2H), 7.64-7.67 (m, 1H), 7.74-7.78 (m, 2H), 7.79-7.81 (m, 1H), 8.02 (d, J=2.4 Hz, 1H).

Example 33

Synthesis of methyl 4-((4'-(trifluoromethoxy)-[1,1'-biphenyl]-4-yl)thio)-1H-1,2,3-triazole-5-carboxylate (33)

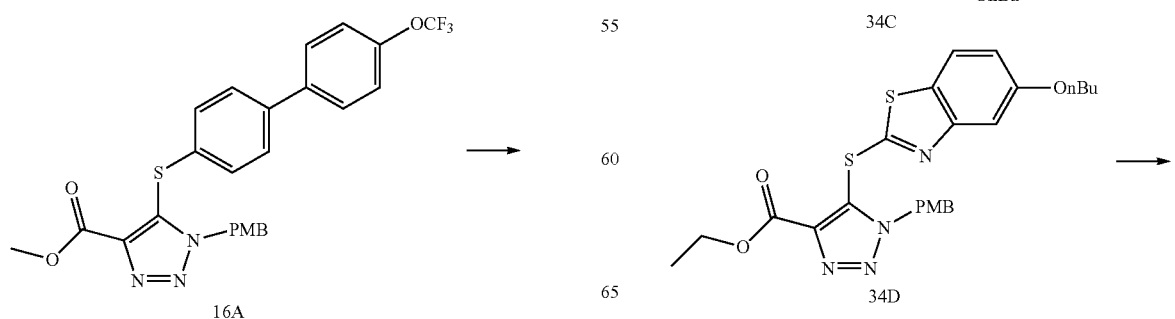

Compound 33 was synthesized by employing the procedure described for Compound 1 using Compound 16A in lieu of Compound 1E, LC-MS (ESI) m/z: 396 [M+H]⁺; ¹H-NMR (DMSO-d₆, 400 MHz): δ (ppm) 3.85 (s, 3H), 7.47 (d, J=8.0 Hz, 2H), 7.56 (d, J=8.4 Hz, 2H), 7.72 (d, J=8.0 Hz, 2H), 7.82 (d, J=8.8 Hz, 2H).

Example 34

Synthesis of 4-((5-butoxybenzo[d]thiazol-2-yl)thio)-1H-1,2,3-triazole-5-carboxylic acid (34)

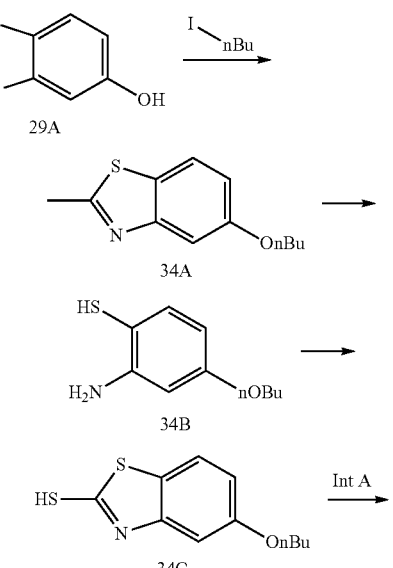

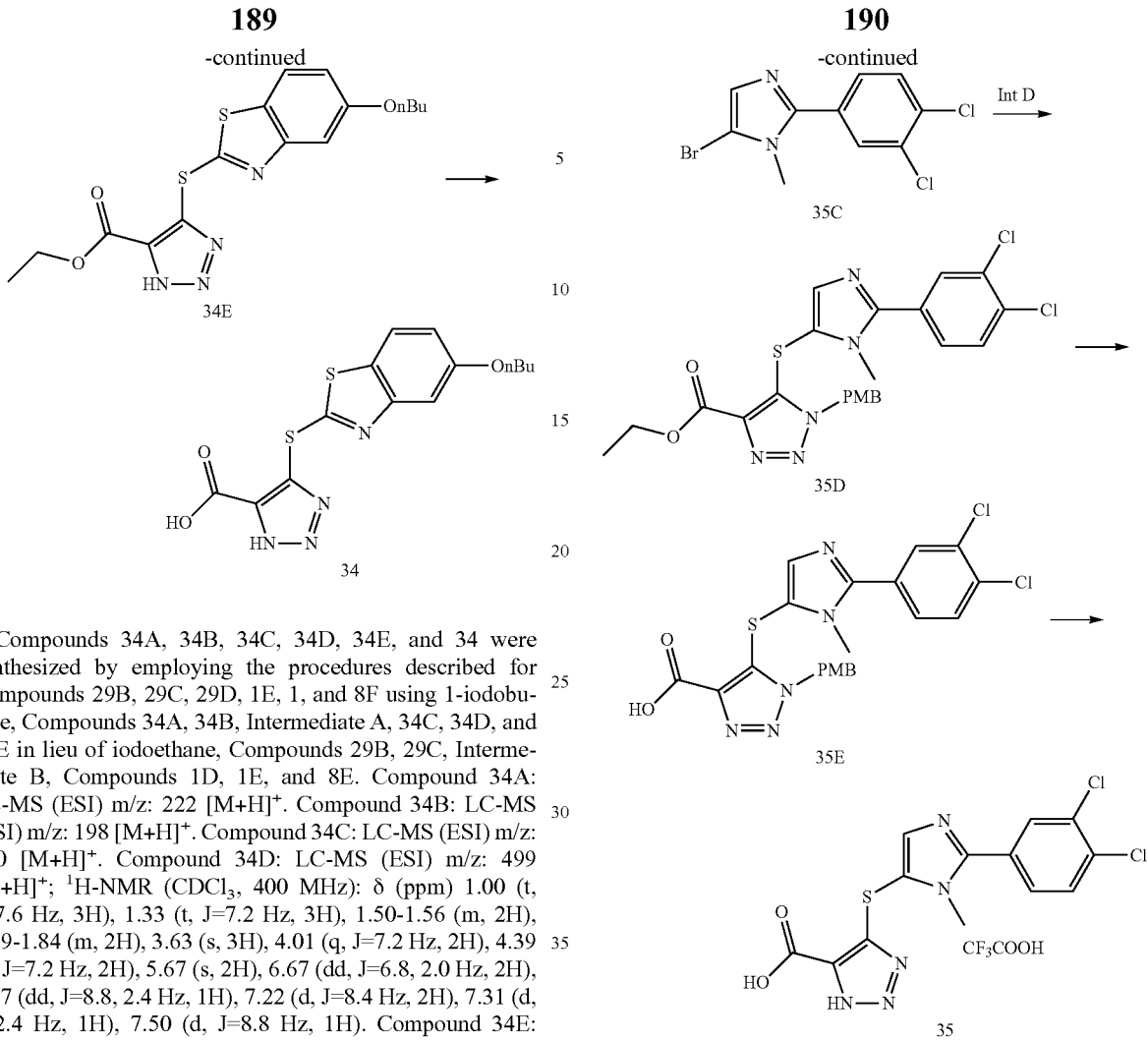

Compounds 34A, 34B, 34C, 34D, 34E, and 34 were synthesized by employing the procedures described for Compounds 29B, 29C, 29D, 1E, 1, and 8F using 1-iodobutane, Compounds 34A, 34B, Intermediate A, 34C, 34D, and 34E in lieu of iodoethane, Compounds 29B, 29C, Intermediate B, Compounds 1D, 1E, and 8E. Compound 34A: LC-MS (ESI) m/z: 222 [M+H]$^+$. Compound 34B: LC-MS (ESI) m/z: 198 [M+H]$^+$. Compound 34C: LC-MS (ESI) m/z: 240 [M+H]$^+$. Compound 34D: LC-MS (ESI) m/z: 499 [M+H]$^+$; $^1$H-NMR (CDCl$_3$, 400 MHz): δ (ppm) 1.00 (t, J=7.6 Hz, 3H), 1.33 (t, J=7.2 Hz, 3H), 1.50-1.56 (m, 2H), 1.79-1.84 (m, 2H), 3.63 (s, 3H), 4.01 (q, J=7.2 Hz, 2H), 4.39 (q, J=7.2 Hz, 2H), 5.67 (s, 2H), 6.67 (dd, J=6.8, 2.0 Hz, 2H), 6.97 (dd, J=8.8, 2.4 Hz, 1H), 7.22 (d, J=8.4 Hz, 2H), 7.31 (d, J=2.4 Hz, 1H), 7.50 (d, J=8.8 Hz, 1H). Compound 34E: LC-MS (ESI) m/z: 379 [M+H]$^+$. Compound 34: LC-MS (ESI) m/z: 351 [M+H]$^+$; $^1$H-NMR (DMSO-d$_6$, 400 MHz): δ (ppm) 0.93 (t, J=7.6 Hz, 3H), 1.44 (m, 2H), 1.71 (m, 2H), 4.03 (t, J=6.4 Hz, 2H), 7.01 (dd, J=8.8, J=2.4 Hz, 1H), 7.42 (d, J=2.4 Hz, 1H), 7.84 (d, J=8.8 Hz, 1H).

Example 35

Synthesis of 4-((2-(3,4-dichlorophenyl)-1-methyl-1H-imidazol-5-yl)thio)-1H-1,2,3-triazole-5-carboxylic acid 2,2,2-trifluoroacetate (35)

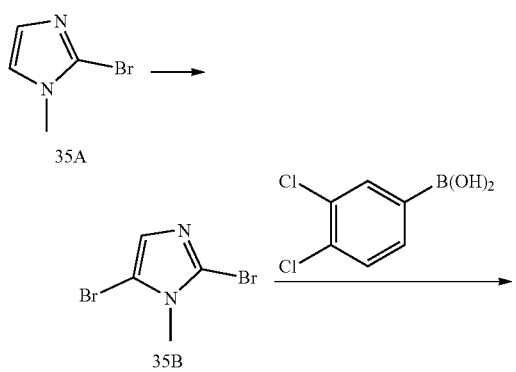

To a solution of 2-bromo-1-methyl-1H-imidazole 35A (5 g, 31.05 mmol) in chloroform (50 mL) was added NBS (5.53 g, 31.05 mmol) in several portions at 65° C. and stirred for 2 hours. The mixture was cooled down to room temperature, diluted with water (50 mL), and extracted with dichloromethane (30 mL). The organic phase was washed with water (20 mL) and brine (20 mL), dried over anhydrous sodium sulfate, filtered, and concentrated to give a product, which was slurred in dichloromethane/petroleum (50 mL, 2:3 in volume) to furnish Compound 35B. LC-MS (ESI) m/z: 239 [M+H]$^+$; $^1$H-NMR (CDCl$_3$, 400 MHz): δ (ppm) 3.60 (s, 3H), 7.00 (s, 1H).

Compound 35C was synthesized by employing the procedure described for Compound 8B using Compound 35B in lieu of Compound 8A, LC-MS (ESI) m/z: 305 [M+H]$^+$; $^1$H-NMR (CD$_3$OD, 400 MHz): δ (ppm) 3.72 (s, 3H), 7.13 (s, 1H), 7.56 (dd, J=8.4, 1.6 Hz, 1H), 7.69 (d, J=8.4 Hz, 1H), 7.82 (d, J=1.6 Hz, 1H).

To a solution of Intermediate D (380 mg, 1.29 mmol) and Compound 35C (395 mg, 1.29 mmol) in 1,4-dioxane (6 mL) was added N,N-diisopropylethylamine (333 mg, 2.58 mmol), Pd$_2$(dba)$_3$ (110 mg, 0.12 mmol), and Xantphos (133 mg, 0.23 mmol). The mixture was purged with nitrogen for 2 minutes and heated in a microwave oven at 120° C. for 70 minutes. After cooling down to room temperature, the mixture was filtered. The filtrate was concentrated and purified with reverse phase chromatography using eluents (methanol in H₂O, from 20% to 100% v/v) to yield Compound 35D. LC-MS (ESI) m/z: 518 [M+H]⁺.

Compounds 35E and 35 were synthesized by employing the procedures described for Compounds 8F and 1 using Compounds 35D and 35E in lieu of Compounds 8E and 1E. Compound 35E: LC-MS (ESI) m/z: 490 [M+H]⁺. Compound 35: LC-MS (ESI) m/z: 370 [M+H]⁺; ¹H-NMR (DMSO-d₆, 400 MHz): δ (ppm) 3.70 (s, 3H), 7.77-7.79 (m, 2H), 7.85 (d, J=8.4 Hz, 1H), 8.05 (d, J=2.0 Hz, 1H).

Example 36

Synthesis of 4-((5-(3,4-dichlorophenyl)thiophen-3-yl)thio)-1H-1,2,3-triazole-5-carboxylic acid (36)

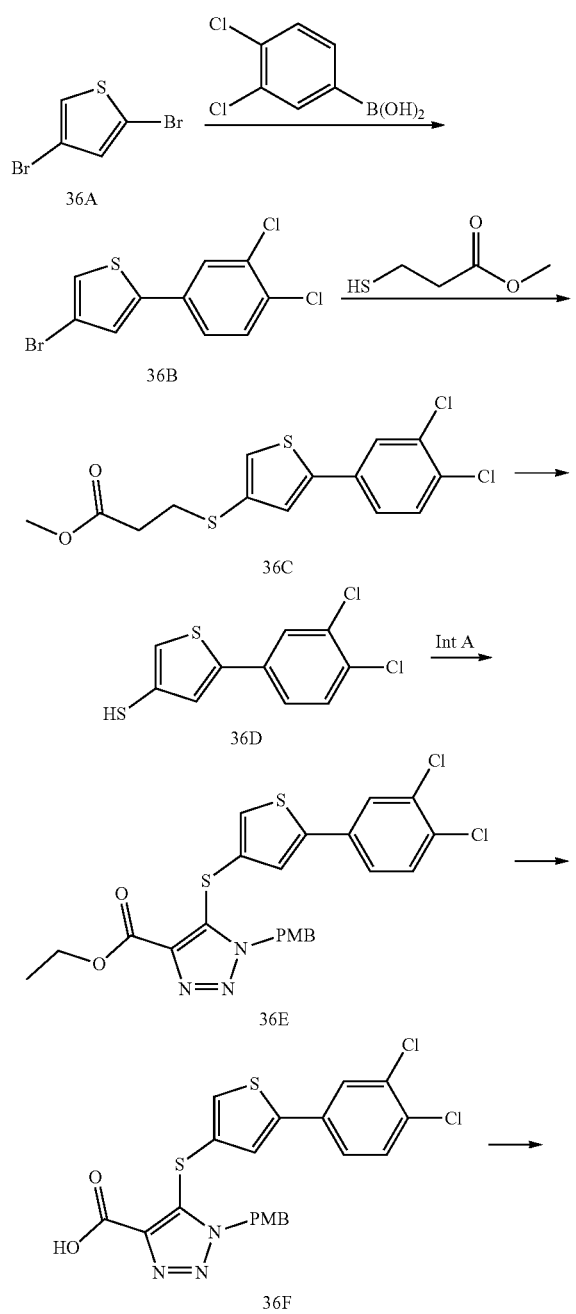

Compounds 36B, 36C, 36D, 36E, 36F, and 36 were synthesized by employing the procedures described for Compounds 8B, Intermediates D-1, D, 1E, 2, and 1 using Compounds 36A, 36B, 36C, Intermediate A, 36D, 36E, and 36F in lieu of Compounds 8A, Intermediates A, D-1, B, 1D, 1, and 1E. Compound 36B: LC-MS (ESI) m/z: no ionizable compound under routine conditions used. ¹H-NMR (CDCl₃, 400 MHz): δ (ppm) 7.21-7.23 (m, 2H), 7.36-7.39 (m, 1H), 7.45-7.47 (m, 1H), 7.62-7.64 (m, 1H). Compound 36C: LC-MS (ESI) m/z: 347 [M+H]⁺. Compound 36D: LC-MS (ESI) m/z: no ionizable compound under routine conditions used. Compound 36E: LC-MS (ESI) m/z: 520 [M+H]⁺. Compound 36F: LC-MS (ESI) m/z: 492 [M+H]⁺. Compound 36: LC-MS (ESI) m/z: 372 [M+H]⁺; ¹H-NMR (CD₃OD, 400 MHz): δ (ppm) 7.55-7.60 (m, 3H), 7.74 (s, 1H), 7.82 (d, J=1.6 Hz, 1H).

Example 37

Synthesis of 2-(dimethylamino)ethyl 4-((4'-(trifluoromethoxy)-[1,1'-biphenyl]-4-yl)thio)-1H-1,2,3-triazole-5-carboxylate (37)

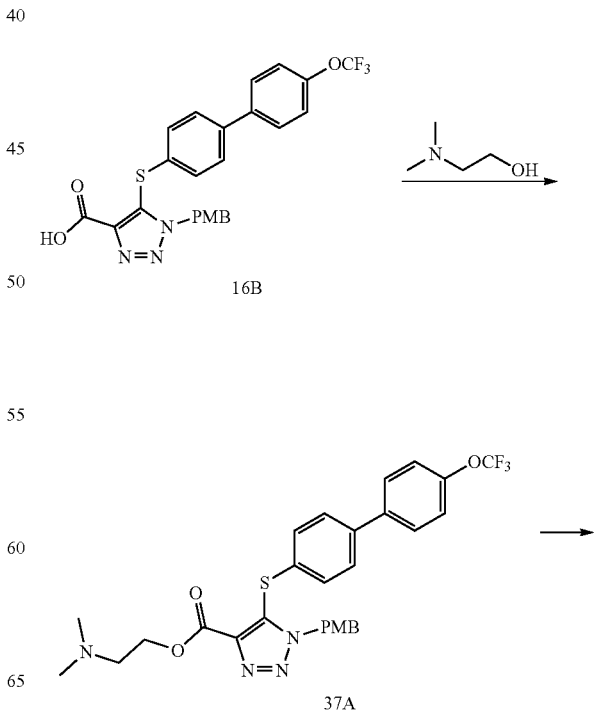

-continued

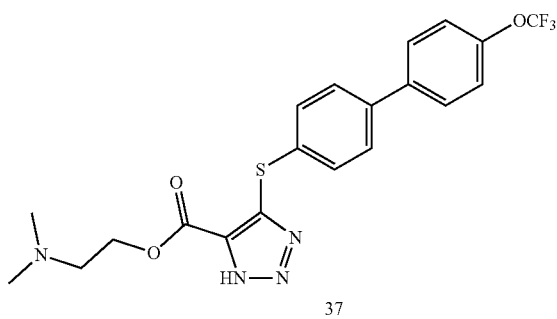

37

Compounds 37A and 37 were synthesized by employing the procedures described for Compounds 19A and 1 using 2-(dimethylamino)ethanol, Compounds 16B using TEA as base and dichloromethane as solvent, and 37A in lieu of cyclopropanol, Compounds 9A using DIPEA as base and DMF as solvent, and 1E. Compound 37A: LC-MS (ESI) m/z: 573 [M+H]$^+$. Compound 37: LC-MS (ESI) m/z: 453 [M+H]$^+$; $^1$H-NMR (DMSO-d$_6$, 400 MHz): δ (ppm) 2.87 (s, 6H), 3.50 (t, J=4.8 Hz, 2H), 4.62 (t, J=4.8 Hz, 2H), 7.48 (d, J=8.4 Hz, 2H), 7.57 (d, J=8.4 Hz, 2H), 7.73 (d, J=8.0 Hz, 2H), 7.82 (d, J=8.8 Hz, 2H).

Example 38

Synthesis of N,N,N-trimethyl-2-((4-((4'-(trifluoromethoxy)-[1,1'-biphenyl]-4-yl)thio)-1H-1,2,3-triazole-5-carbonyl)oxy)ethan-1-aminium iodide (38)

-continued

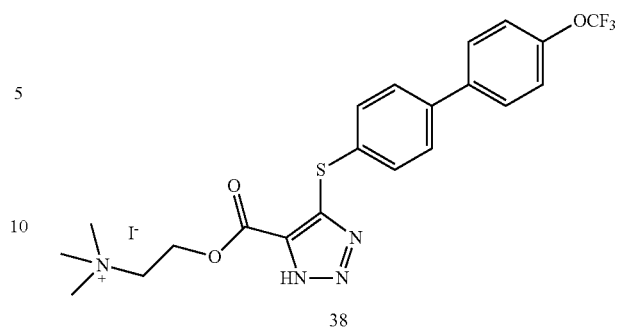

38

A mixture of Compound 37A (200 mg, 0.349 mmol) and iodomethane (495 mg, 3.49 mmol) in acetonitrile (5 mL) was stirred at 50° C. for 4 hours. The mixture was concentrated under reduced pressure to furnish Compound 38A. LC-MS (ESI) m/z: 587 [M]$^+$.

Compound 38 was synthesized by employing the procedure described for Compound 1 using Compound 38A in lieu of Compound 1E, LC-MS (ESI) m/z: 467 [M]$^+$; $^1$H-NMR (DMSO-d$_6$, 400 MHz): δ (ppm) 3.14 (s, 9H), 3.67-3.69 (m, 2H), 4.56-4.57 (m, 2H), 7.24 (d, J=8.8 Hz, 2H), 7.43 (d, J=8.4 Hz, 2H), 7.56 (d, J=8.4 Hz, 2H), 7.75 (d, J=8.8 Hz, 2H).

Example 39

Synthesis of 4-((2-(3-chloro-4-(trifluoromethoxy)phenyl)thiazol-4-yl)thio)-1H-1,2,3-triazole-5-carboxylic acid (39)

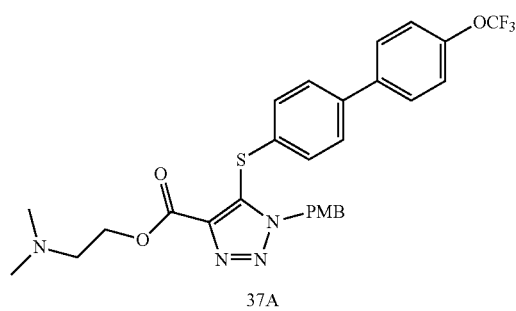

37A

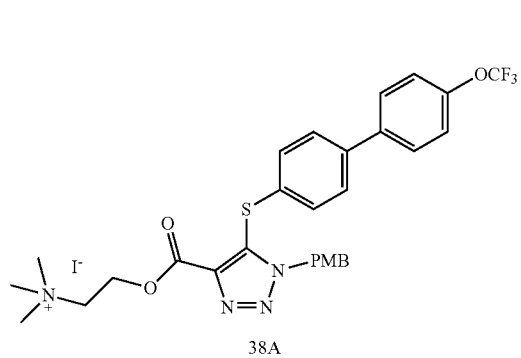

38A

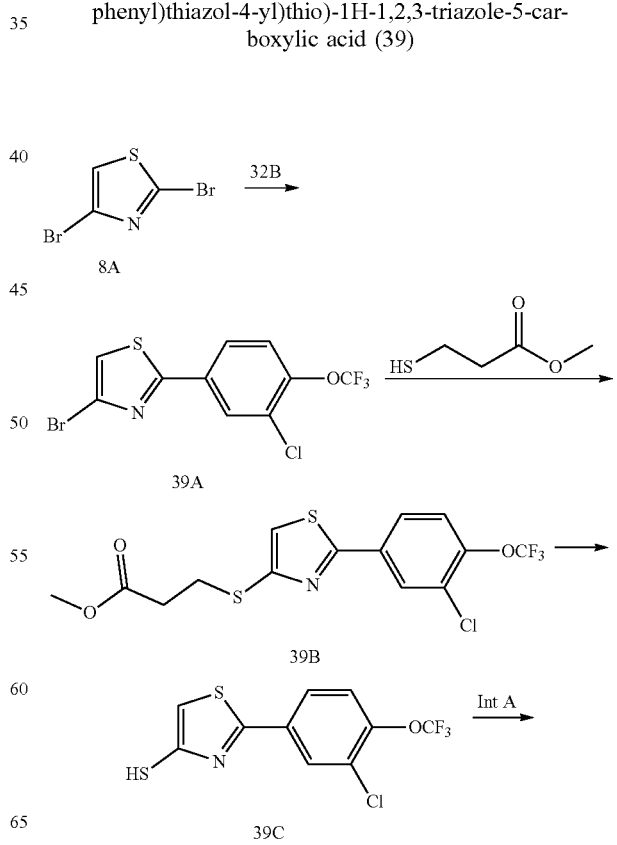

195

-continued

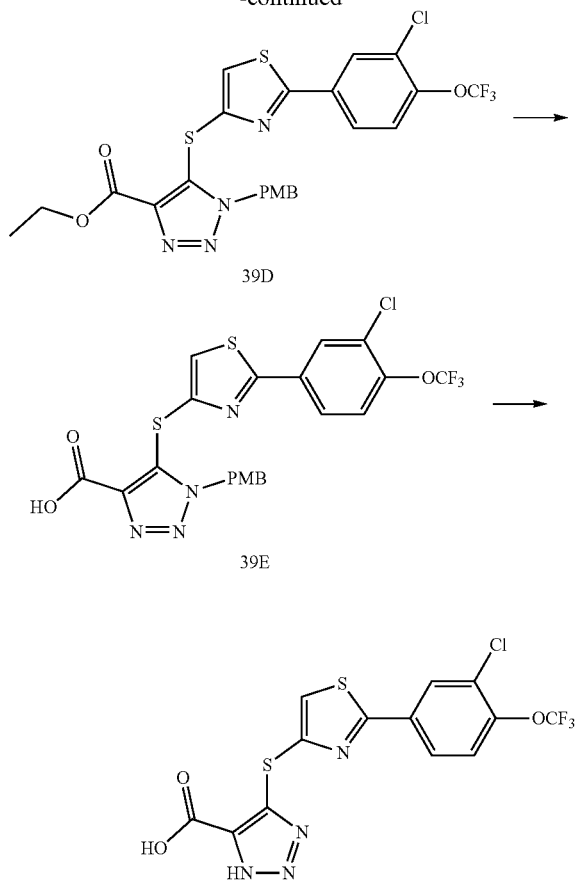

196

Example 40

Synthesis of methyl 4-((2-(3-chloro-4-(trifluoromethoxy)phenyl)thiazol-4-yl)thio)-1H-1,2,3-triazole-5-carboxylate (40)

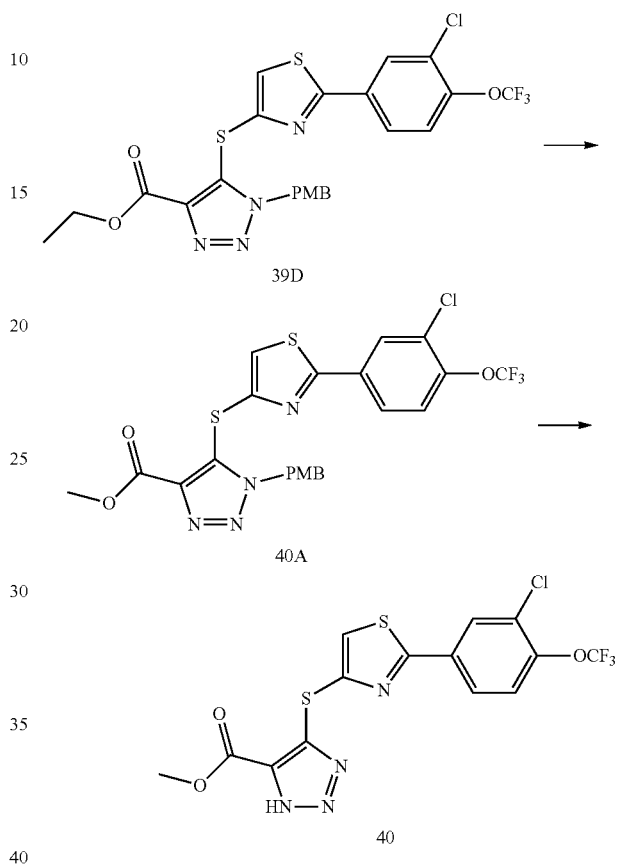

Compounds 39A, 39B, 39C, 39D, 39E, and 39 were synthesized by employing the procedures described for Compounds 8B, Intermediates D-1, D, 1E, 8F, and 1 using Compounds 32B, 39A, 39B, Intermediate A, 39C, 39D, and 39E in lieu of (3,4-dichlorophenyl)boronic acid, Intermediates A, D-1, B, Compounds 1D, 8E, and 1E. Compound 39A: LC-MS (ESI) m/z: 358 [M+H]$^+$; $^1$H-NMR (CDCl$_3$, 400 MHz): δ (ppm) 7.28 (s, 1H), 7.38-7.42 (m, 1H), 7.82 (d, J=8.0 Hz, 1H), 8.10 (d, J=2.0 Hz, 1H). Compound 39B: LC-MS (ESI) m/z: 398 [M+H]$^+$; $^1$H-NMR (CDCl$_3$, 400 MHz): δ (ppm) 2.78 (t, J=6.8 Hz, 2H), 3.35 (t, J=6.8 Hz, 2H), 3.71 (s, 3H), 7.15 (s, 1H), 7.37-7.40 (m, 1H), 7.83 (d, J=8.4 Hz, 1H), 8.09 (d, J=2.4 Hz, 1H). Compound 39C: LC-MS (ESI) m/z: 312 [M+H]$^+$. Compound 39D: LC-MS (ESI) m/z: 571 [M+H]$^+$; $^1$H-NMR (CDCl$_3$, 400 MHz): δ (ppm) 1.36 (t, J=7.2 Hz, 3H), 3.70 (s, 3H), 4.36-4.42 (m, 2H), 5.75 (s, 2H), 6.74 (d, J=9.2 Hz, 2H), 7.10 (s, 1H), 7.25 (d, J=8.8 Hz, 2H), 7.35 (d, J=10.4 Hz, 1H), 7.66 (d, J=8.8 Hz, 1H), 7.90 (d, J=2.4 Hz, 1H). Compound 39E: LC-MS (ESI) m/z: 543 [M+H]$^+$; $^1$H-NMR (CDCl$_3$, 400 MHz): δ (ppm) 3.55 (s, 3H), 5.53 (s, 2H), 6.59 (brs, 2H), 7.16 (brs, 2H), 7.19 (s, 1H), 7.34 (brs, 1H), 7.70 (brs, 2H). Compound 39: LC-MS (ESI) m/z: 423 [M+H]$^+$; $^1$H-NMR (DMSO-d$_6$, 400 MHz): δ (ppm) 7.70 (d, J=8.4 Hz, 1H), 8.01 (d, J=8.4 Hz, 1H), 8.07 (s, 1H), 8.19 (d, J=2.0 Hz, 1H).

A solution of Compound 39D (110 mg, 0.19 mmol) and concentrated H$_2$SO$_4$ (0.1 mL) in MeOH (5 mL) was stirred at 60° C. for 16 hours. The mixture was cooled down to room temperature, concentrated, and purified with reverse phase chromatography using eluents (acetonitrile in water, from 0% to 100% v/v) to afford Compound 40A. LC-MS (ESI) m/z: 557 [M+H]$^+$.

Compound 40 was synthesized by employing the procedure described for Compound 1 using Compound 40A in lieu of Compound 1E. LC-MS (ESI) m/z: 437 [M+H]$^+$; $^1$H-NMR (DMSO-d$_6$, 400 MHz): δ (ppm) 3.86 (s, 3H), 7.70 (d, J=8.4 Hz, 1H), 8.01 (d, J=8.4 Hz, 1H), 8.12 (s, 1H), 8.19 (d, J=2.4 Hz, 1H).

Example 41

Synthesis of 4-((3,4-dichlorophenyl)thio)-1H-1,2,3-triazole-5-carboxylic acid (41)

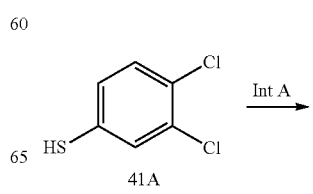

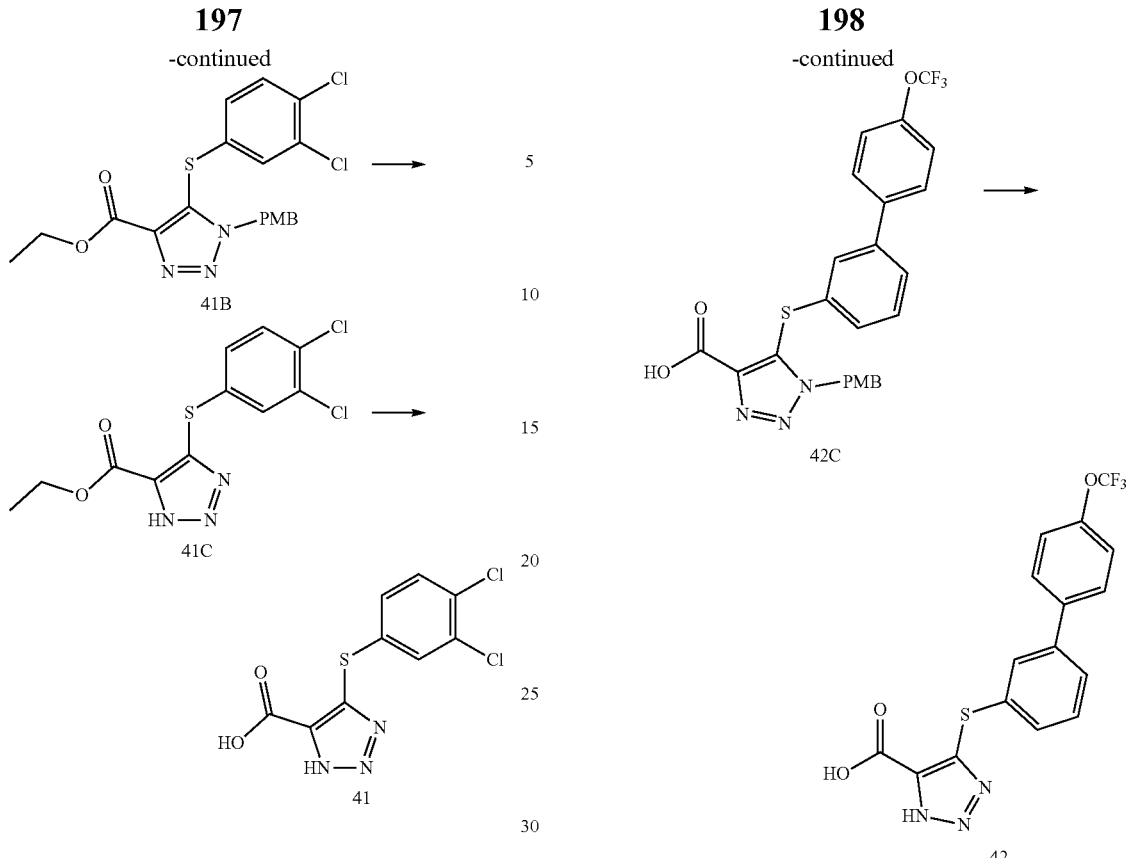

Compounds 41B, 41C, and 41 were synthesized by employing the procedures described for Compounds 1E, 1, and 8F using Intermediate A, Compounds 41A using NMP as solvent at 100° C., 41B, and 41C in lieu of Intermediates B, Compounds 1D using DMF as solvent at 50° C., 1E, and 8E. Compound 41B: LC-MS (ESI) m/z: 438 [M+H]$^+$. Compound 41C: LC-MS (ESI) m/z: 318 [M+H]$^+$. Compound 41: LC-MS (ESI) m/z: 290 [M+H]$^+$; $^1$H-NMR (CD$_3$OD, 400 MHz): δ (ppm) 7.40 (dd, J=8.4, 2.0 Hz, 1H), 7.53 (d, J=8.0 Hz, 1H), 7.67 (d, J=2.0 Hz, 1H).

Example 42

Synthesis of 4-((4'-(trifluoromethoxy)-[1,1'-biphenyl]-3-yl)thio)-1H-1,2,3-triazole-5-carboxylic acid (42)

Compounds 42B, 42C, and 42 were synthesized by employing the procedures described for Compounds 1E, 8B, and 1 using Intermediate A, Compounds 42A using NMP as solvent at 100° C., 42B, 4-(trifluoromethoxy)phenylboronic acid, and 42C in lieu of Intermediates B, Compounds 1D using DMF as solvent at 50° C., 8A, (3,4-dichlorophenyl)boronic acid, and 8E. Compound 42B: LC-MS (ESI) m/z: 448 [M+H]$^+$. Compound 42C: LC-MS (ESI) m/z: 502 [M+H]$^+$. Compound 42: LC-MS (ESI) m/z: 382 [M+H]$^+$; $^1$H-NMR (CD$_3$OD, 400 MHz): δ (ppm) 7.37 (d, J=8.4 Hz, 2H), 7.51-7.80 (m, 6H).

Example 43

Synthesis of 4-((4-(3-chloro-4-(trifluoromethoxy)phenyl)thiazol-2-yl)thio)-1H-1,2,3-triazole-5-carboxylic acid (43)

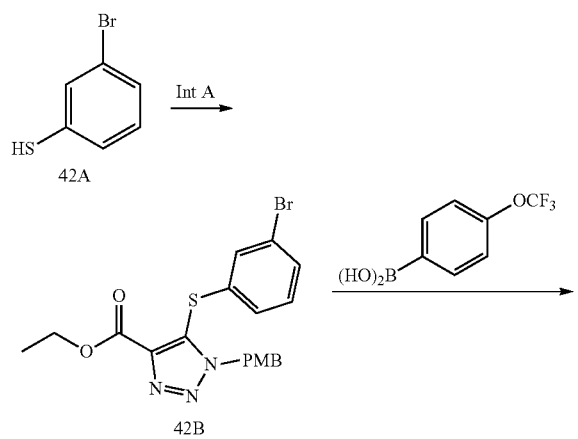

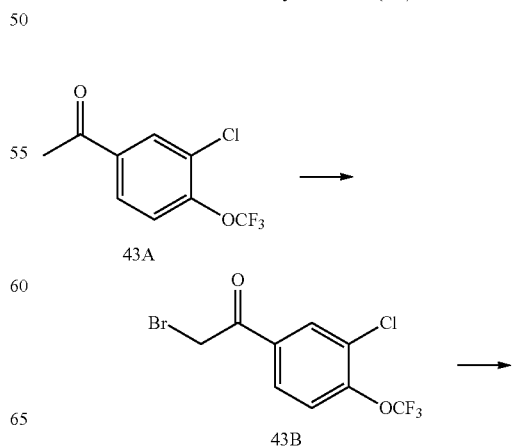

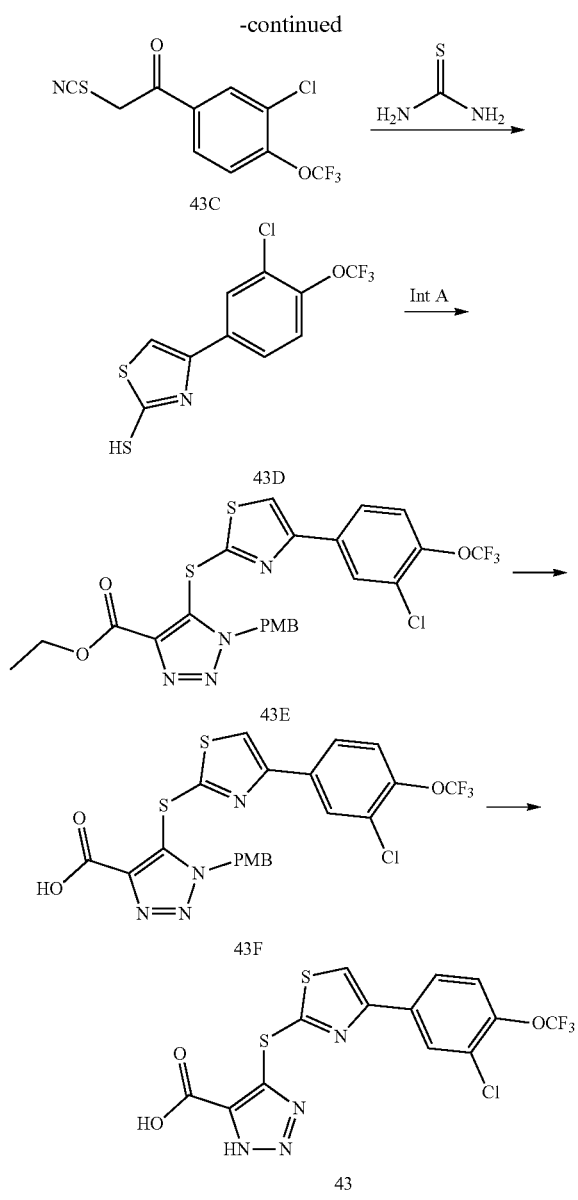

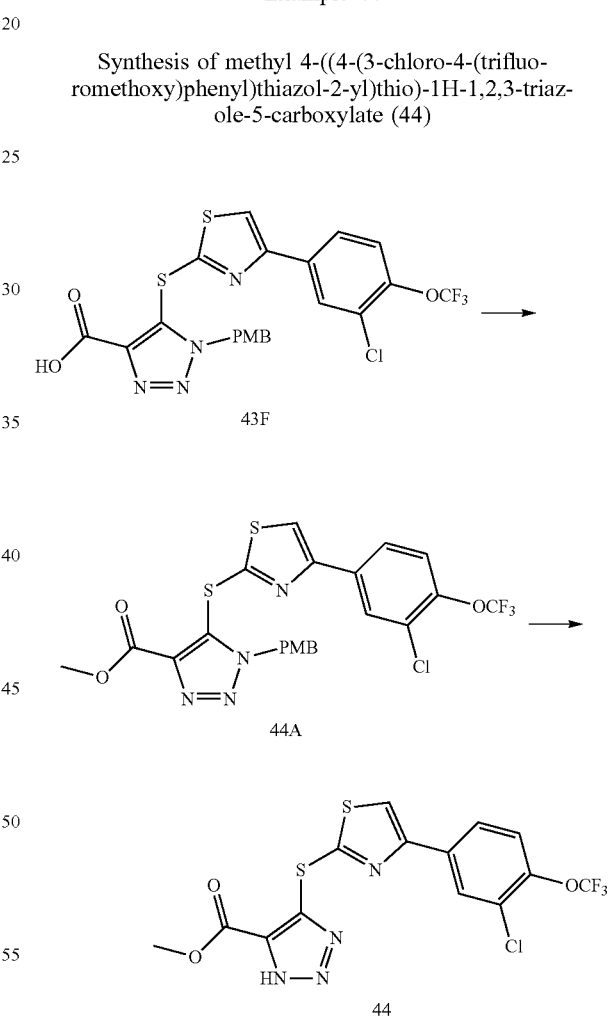

centrated and purified by flash column chromatography on silica gel (ethyl acetate in petroleum ether, 12% v/v) to furnish Compound 43D. LC-MS (ESI) m/z: 312 [M+H]$^+$; $^1$H-NMR (CDCl$_3$, 400 MHz): δ (ppm) 6.77 (s, 1H), 7.45-7.48 (m, 2H), 7.68 (d, J=2.4 Hz, 1H), 11.6 (br, 1H).

Compounds 43E, 43F, and 43 were synthesized by employing the procedures described for Compounds 1E, 8F, and 1 using Intermediate A, Compounds 43D using NMP as solvent at 90° C., 43E, and 43F in lieu of Intermediates B, Compounds 1D using DMF as solvent at 50° C., 8E, and 1E. Compound 43E: LC-MS (ESI) m/z: 571 [M+H]$^+$. Compound 43F: LC-MS (ESI) m/z: 543 [M+H]$^+$. Compound 43: LC-MS (ESI) m/z: 423 [M+H]$^+$; $^1$H-NMR (DMSO-d$_6$, 400 MHz): δ (ppm) 7.64 (dd, J$_1$=8.8 Hz, J$_2$=1.2 Hz, 1H), 8.01 (dd, J$_1$=8.4 Hz, J$_2$=1.6 Hz, 1H), 8.21 (d, J=2.0 Hz, 1H), 8.37 (s, 1H).

Example 44

Synthesis of methyl 4-((4-(3-chloro-4-(trifluoromethoxy)phenyl)thiazol-2-yl)thio)-1H-1,2,3-triazole-5-carboxylate (44)

To a solution of Compound 43A (2.38 g, 10.0 mmol) in Et$_2$O (15 mL) was dropped Br$_2$ (1.60 g, 10.0 mmol) and stirred at room temperature for 2 hours. The mixture was washed with saturated NaHSO$_3$ solution (20 mL) and brine (20 mL), dried over anhydrous sodium sulfate, filtered, and concentrated to give Compound 43B. LC-MS (ESI) m/z: 317 [M+H]$^+$.

To a solution of Compound 43B (3.17 g, 10.0 mmol) in EtOH (50 mL) was added KSCN (970 mg, 10.0 mmol). After the mixture was stirred at room temperature for 1 hour, it was concentrated under reduced pressure. The residue was diluted with ethyl acetate (50 mL), washed with H$_2$O (30 mL), dried over anhydrous sodium sulfate, filtered, and evaporated to give Compound 43C. LC-MS (ESI) m/z: 296 [M+H]$^+$.

To a solution of Compound 43C (1.9 g, 6.4 mmol) in EtOH (30%, 60 mL) was added thiourea (975 mg, 12.8 mmol) and concentrated HCl solution (10 mL). The mixture was stirred at 90° C. under nitrogen overnight. After cooling down to room temperature, the reaction mixture was con- Compounds 44A and 44 were synthesized by employing the procedures described for Compounds 11A and 1 using methanol, Compounds 43F, and 44A in lieu of propan-2-ol, Compounds 9A, and 1E. Compound 44A: LC-MS (ESI) m/z: 557 [M+H]$^+$. Compound 44: LC-MS (ESI) m/z: 437 [M+H]$^+$; $^1$H-NMR (DMSO-d$_6$, 400 MHz): δ (ppm) 3.85 (s, 3H), 7.65 (dd, J$_1$=8.4 Hz, J$_2$=1.2 Hz, 1H), 8.00 (dd, J$_1$=8.4 Hz, J$_2$=2.4 Hz, 1H), 8.20 (d, J=2.4 Hz, 1H), 8.40 (s, 1H).

Example 45

Synthesis of oxetan-3-yl 4-((4'-(trifluoromethoxy)-[1,1'-biphenyl]-4-yl)thio)-1H-1,2,3-triazole-5-carboxylate (45)

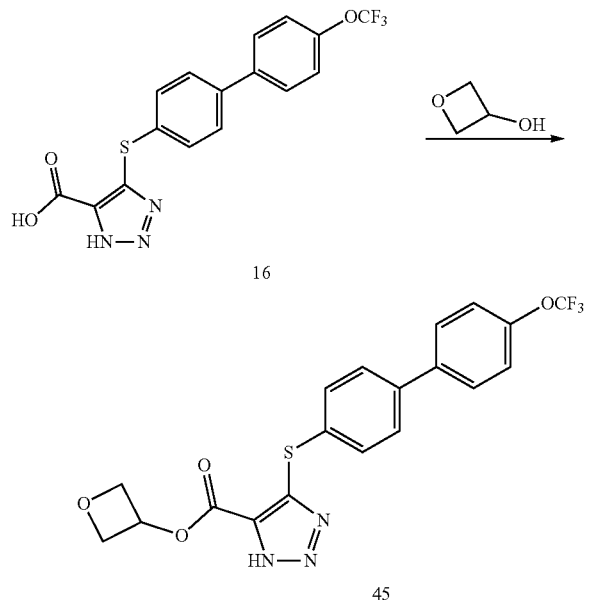

Compound 45 was synthesized by employing the procedure described for Compound 19A using oxetan-3-ol and Compound 16 using TEA as base and dichloromethane as solvent in lieu of cyclopropanol and Compound 9A using DIPEA as base and DMF as solvent, LC-MS (ESI) m/z: 438 [M+H]$^+$; $^1$H-NMR (DMSO-d$_6$, 400 MHz): δ (ppm) 4.52-4.55 (m, 2H), 4.81-4.85 (m, 2H), 5.53-5.59 (m, 1H), 7.45-7.48 (m, 4H), 7.68 (d, J=8.0 Hz, 2H), 7.80 (d, J=8.8 Hz, 2H).

Example 46

Synthesis of 4-((6-chloroquinolin-2-yl)thio)-1H-1,2,3-triazole-5-carboxylic acid (46)

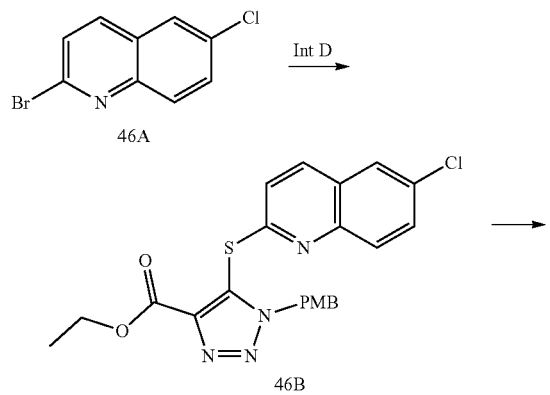

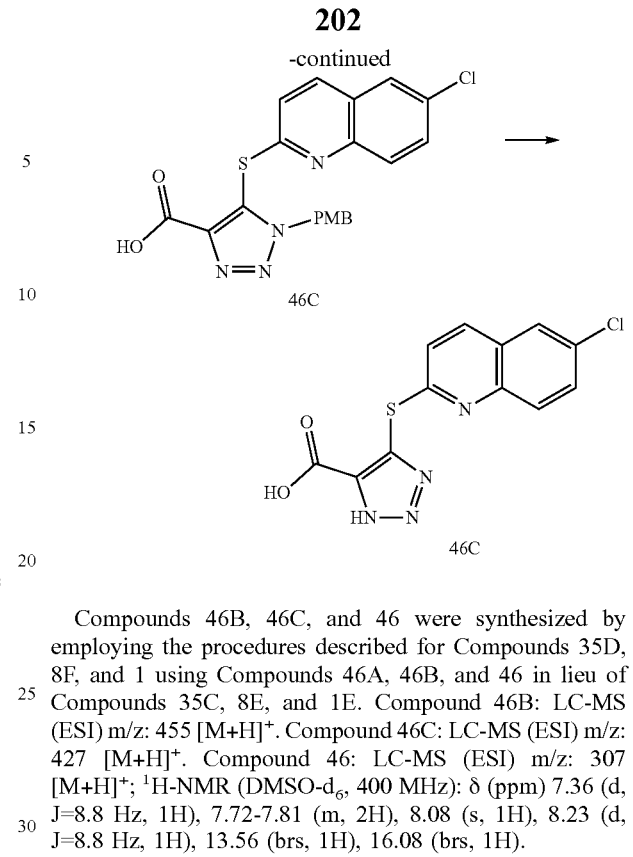

Compounds 46B, 46C, and 46 were synthesized by employing the procedures described for Compounds 35D, 8F, and 1 using Compounds 46A, 46B, and 46 in lieu of Compounds 35C, 8E, and 1E. Compound 46B: LC-MS (ESI) m/z: 455 [M+H]$^+$. Compound 46C: LC-MS (ESI) m/z: 427 [M+H]$^+$. Compound 46: LC-MS (ESI) m/z: 307 [M+H]$^+$; $^1$H-NMR (DMSO-d$_6$, 400 MHz): δ (ppm) 7.36 (d, J=8.8 Hz, 1H), 7.72-7.81 (m, 2H), 8.08 (s, 1H), 8.23 (d, J=8.8 Hz, 1H), 13.56 (brs, 1H), 16.08 (brs, 1H).

Example 47

Synthesis of 4-((2,4'-dichloro-[1,1'-biphenyl]-4-yl)thio)-1H-1,2,3-triazole-5-carboxylic acid (47)

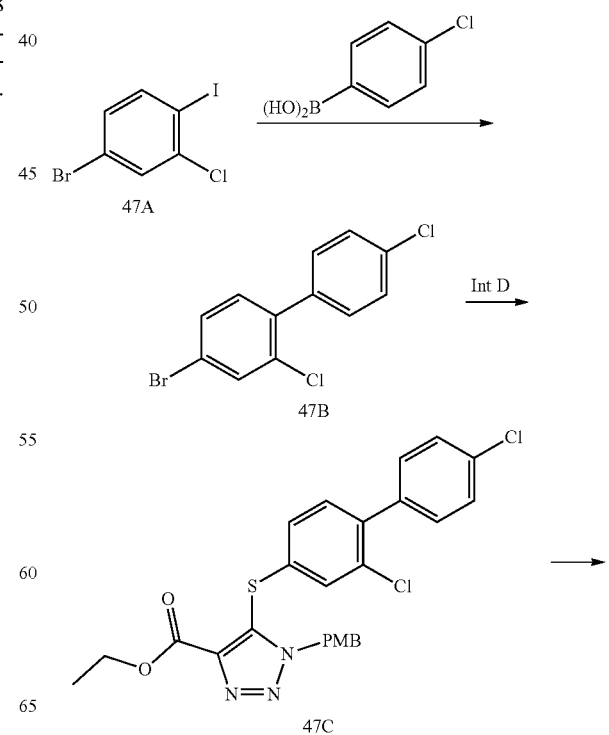

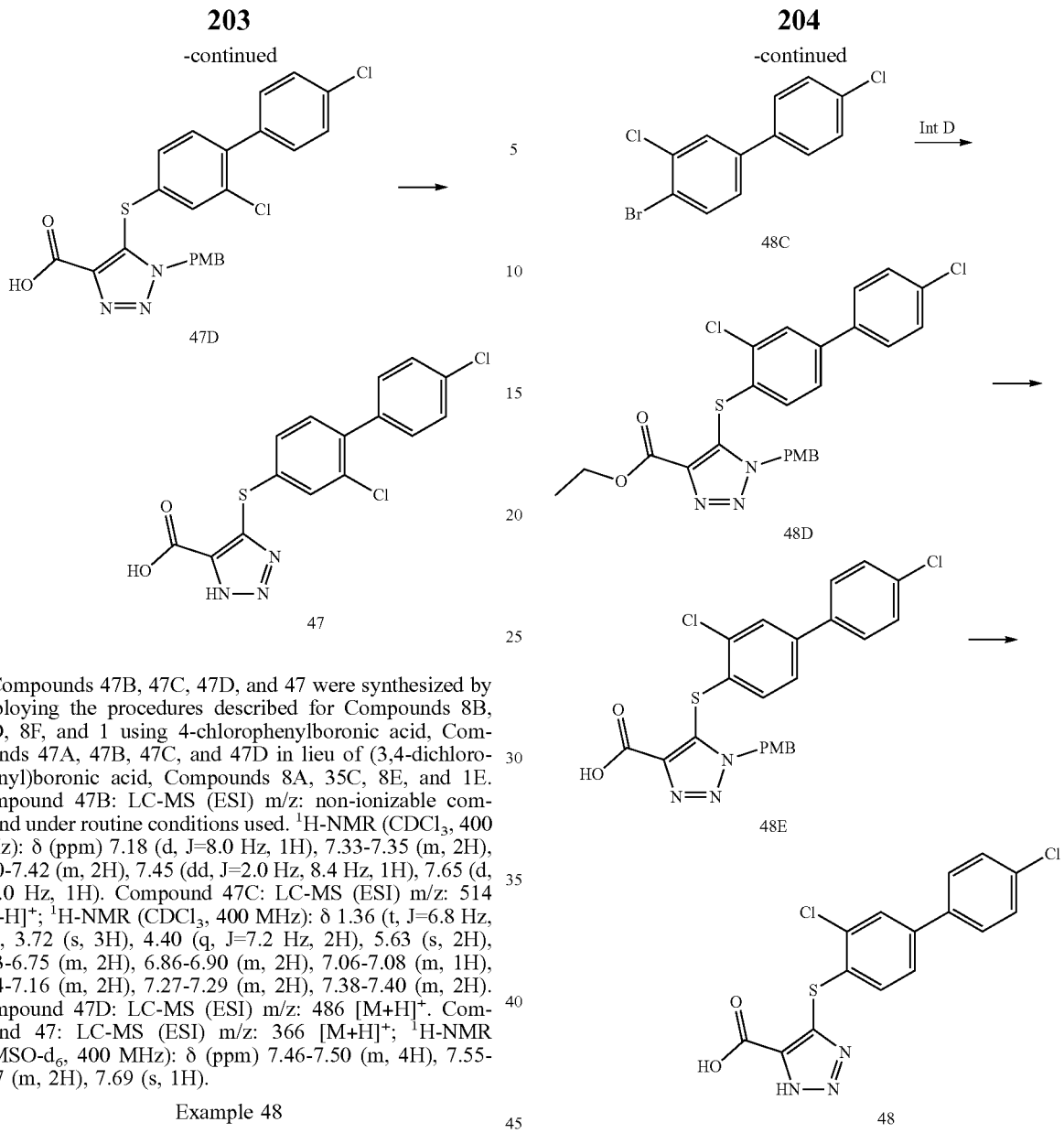

Compounds 47B, 47C, 47D, and 47 were synthesized by employing the procedures described for Compounds 8B, 35D, 8F, and 1 using 4-chlorophenylboronic acid, Compounds 47A, 47B, 47C, and 47D in lieu of (3,4-dichlorophenyl)boronic acid, Compounds 8A, 35C, 8E, and 1E. Compound 47B: LC-MS (ESI) m/z: non-ionizable compound under routine conditions used. $^1$H-NMR (CDCl$_3$, 400 MHz): δ (ppm) 7.18 (d, J=8.0 Hz, 1H), 7.33-7.35 (m, 2H), 7.40-7.42 (m, 2H), 7.45 (dd, J=2.0 Hz, 8.4 Hz, 1H), 7.65 (d, J=2.0 Hz, 1H). Compound 47C: LC-MS (ESI) m/z: 514 [M+H]$^+$; $^1$H-NMR (CDCl$_3$, 400 MHz): δ 1.36 (t, J=6.8 Hz, 3H), 3.72 (s, 3H), 4.40 (q, J=7.2 Hz, 2H), 5.63 (s, 2H), 6.73-6.75 (m, 2H), 6.86-6.90 (m, 2H), 7.06-7.08 (m, 1H), 7.14-7.16 (m, 2H), 7.27-7.29 (m, 2H), 7.38-7.40 (m, 2H). Compound 47D: LC-MS (ESI) m/z: 486 [M+H]$^+$. Compound 47: LC-MS (ESI) m/z: 366 [M+H]$^+$; $^1$H-NMR (DMSO-d$_6$, 400 MHz): δ (ppm) 7.46-7.50 (m, 4H), 7.55-7.57 (m, 2H), 7.69 (s, 1H).

Example 48

Synthesis of 4-((3,4'-dichloro-[1,1'-biphenyl]-4-yl)thio)-1H-1,2,3-triazole-5-carboxylic acid (48)

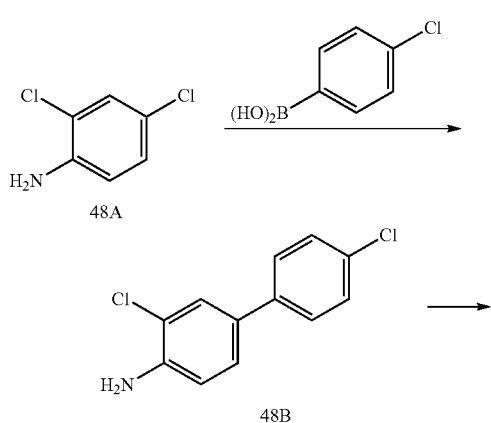

Compounds 48B, 48C, 48D, 48E, and 48 were synthesized by employing the procedures described for Compounds 8B, 30B, 35D, 8F, and 1 using 4-chlorophenylboronic acid, Compounds 48A using Na$_2$CO$_3$ as base and 1,4-dioxane as solvent, 48B using t-butyl nitrite and CuBr, 48C, 48D, and 48E in lieu of (3,4-dichlorophenyl)boronic acid, Compounds 8A using Cs$_2$CO$_3$ as base and DME as solvent, 30A using isoamyl nitrite and CuCl$_2$, 35C, 8E, and 1E. Compound 48B: LC-MS (ESI) m/z: 238 [M+H]$^+$. Compound 48C: LC-MS (ESI) m/z: non-ionizable compound under routine conditions used. Compound 48D: LC-MS (ESI) m/z: 514 [M+H]$^+$. Compound 48E: LC-MS (ESI) m/z: 486 [M+H]$^+$. Compound 48: LC-MS (ESI) m/z: 366 [M+H]$^+$; $^1$H-NMR (DMSO-d$_6$, 400 MHz): δ (ppm) 7.40 (d, J=6.8 Hz, 1H), 7.54 (d, J=8.8 Hz, 2H), 7.63-7.66 (m, 1H), 7.76 (d, J=8.8 Hz, 2H), 7.91 (d, J=2.0 Hz, 1H), 13.55 (br, 1H), 14.75 (br, 1H).

Example 49

Synthesis of 4-((3,4-difluorophenyl)thio)-1H-1,2,3-triazole-5-carboxylic acid (49)

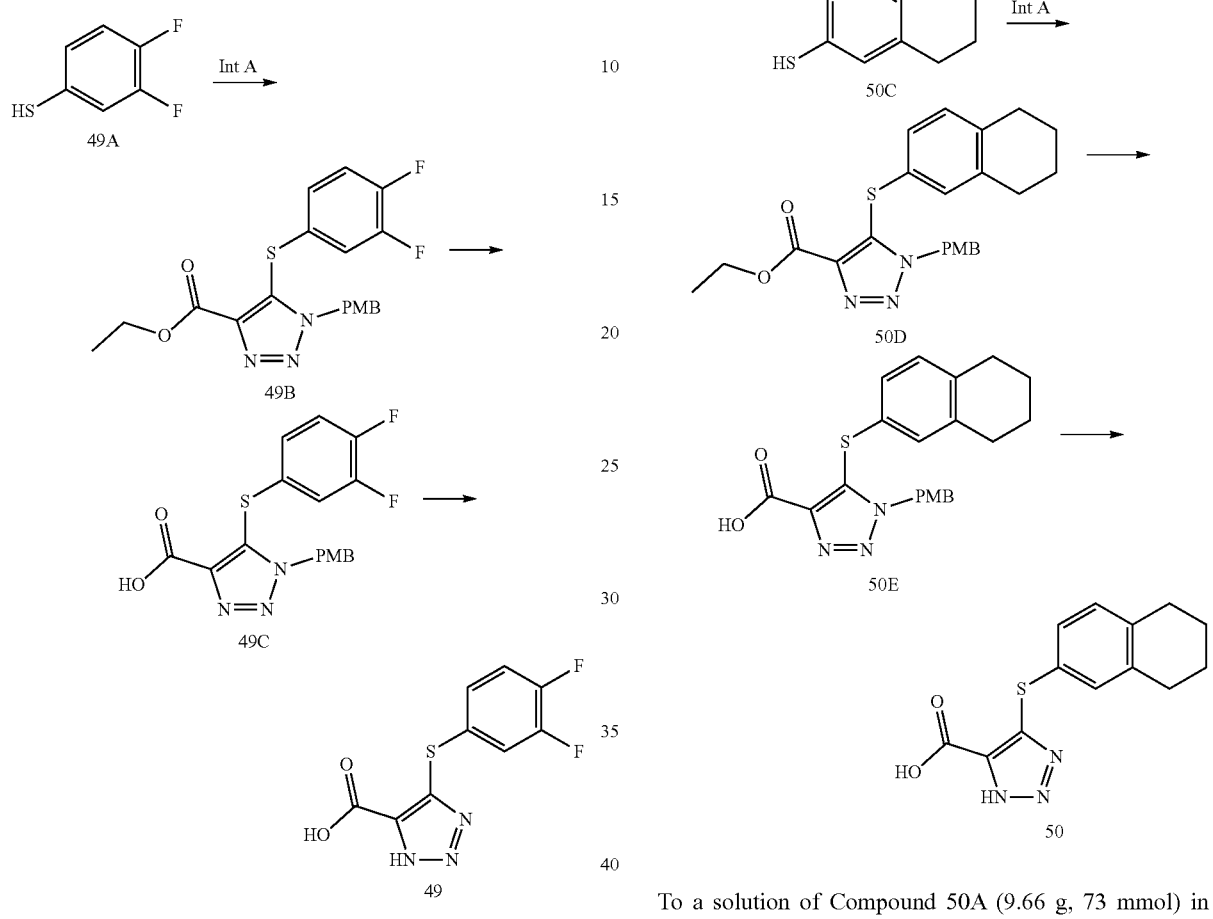

Compounds 49B, 49C, and 49 were synthesized by employing the procedures described for Compounds 1E, 8F, and 1 using Intermediate A, Compounds 49A, 49B, and 49C in lieu of Intermediates B, Compounds 1D, 8E, and 1E. Compound 49B: LC-MS: (ESI) m/z: 406 [M+H]⁺. Compound 49C: LC-MS (ESI) m/z: 400 [M+Na]⁺. Compound 49: LC-MS (ESI) m/z: 258 [M+H]⁺; ¹H-NMR (DMSO-$d_6$, 400 MHz): δ (ppm) 7.36 (s, 1H), 7.45-7.52 (m, 1H), 7.66 (t, J=8.4 Hz, 1H).

Example 50

Synthesis of 4-((5,6,7,8-tetrahydronaphthalen-2-yl)thio)-1H-1,2,3-triazole-5-carboxylic acid (50)

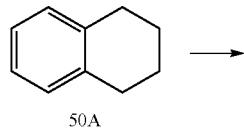

To a solution of Compound 50A (9.66 g, 73 mmol) in CHCl₃ (22 mL) was dropped ClSO₃H (26 g, 0.223 mol) at −10° C. The mixture was stirred at room temperature for 1 hour, poured into ice-water (100 mL), and extracted with dichloromethane (100 mL×2). The combined extracts were dried over anhydrous sodium sulfate, filtered, and concentrated. The residue was purified with flash column chromatography on silica gel (ethyl acetate in petroleum ether, 10% v/v) to yield Compound 50B. LC-MS (ESI) m/z: non-ionizable compound under routine conditions used. ¹H-NMR (CDCl₃, 400 MHz): δ (ppm) 1.83-1.86 (m, 4H), 2.85-2.88 (m, 4H), 7.27-7.29 (m, 1H), 7.71-7.73 (m, 2H).

To a mixture of Compound 50B (1.5 g, 6.5 mmol) and Zn powder (2.5 g, 38.2 mmol) in ethanol (10 mL) was dropped concentrated HCl (10 mL) over a period of 30 minutes. After the mixture was stirred at 80° C. for 1 hour and cooled down to room temperature, it was filtered. The filtration was diluted with ethyl acetate (200 mL). The organic phase was washed with brine (200 mL), dried over anhydrous sodium sulfate, filtered, and concentrated to yield Compound 50C. LC-MS (ESI) m/z: 163 [M−H]¹ H-NMR (CDCl₃, 400 MHz): δ (ppm) 1.75-1.78 (m, 4H), 2.68-2.72 (m, 4H), 3.34 (s, 1H), 6.92-6.94 (m, 1H), 7.00-7.02 (m, 2H).

Compounds 50D, 50E, and 50 were synthesized by employing the procedures described for Compounds 1E, 8F, and 1 using Intermediate A, Compounds 50C, 50D, and 50E in lieu of Intermediates B, Compounds 1D, 8E, and 1E. Compound 50D: LC-MS (ESI) m/z: 424 [M+H]⁺; ¹H-NMR (CDCl₃, 400 MHz): δ 1.34 (t, J=6.8 Hz, 3H), 1.72-1.73 (m, 4H), 2.53-2.56 (m, 2H), 2.66-2.68 (m, 2H), 3.76 (s, 3H), 4.37 (q, J=7.2 Hz, 2H), 5.51 (s, 2H), 6.63 (s, 1H), 6.75-6.78 (m, 2H), 6.83-6.91 (m, 2H), 7.12-7.15 (m, 2H). Compound 50E: LC-MS (ESI) m/z: 396 [M+H]⁺. Compound 50: LC-MS (ESI) m/z: 276 [M+H]⁺; ¹H-NMR (DMSO-d₆, 400 MHz): δ (ppm) 1.71-1.74 (m, 4H), 2.69-2.71 (m, 4H), 7.07-7.09 (m, 1H), 7.16-7.20 (m, 2H).

Example 51

Synthesis of 1-((pivaloyloxy)methyl)-4-((4'-(trifluoromethoxy)-[1,1'-biphenyl]-4-yl)thio)-1H-1,2,3-triazole-5-carboxylic acid (51)

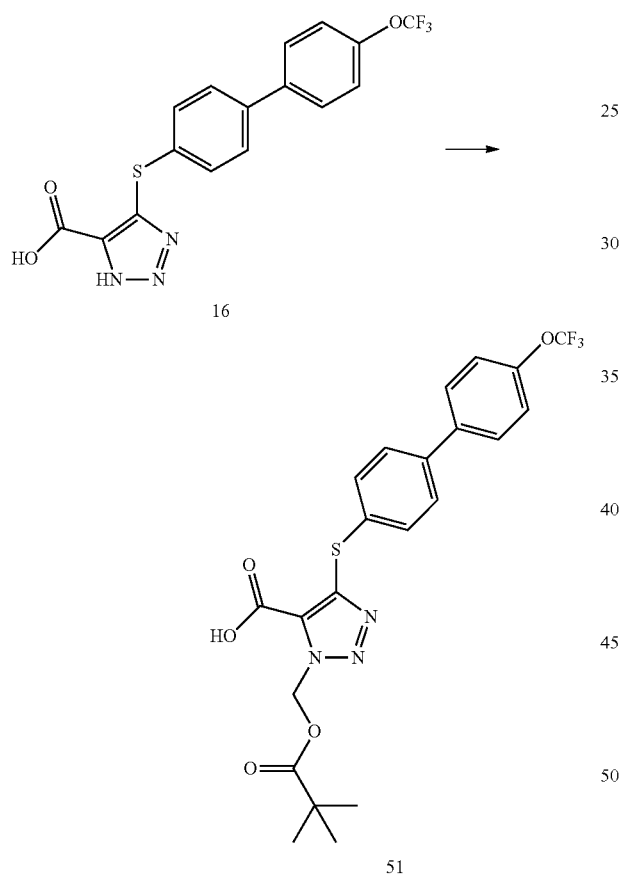

To a solution of Compound 16 (50 mg, 0.13 mmol) in 1,4-dioxane (2 mL) was added chloromethyl pivalate (21 mg, 0.143 mmol), triethylamine (59 mg, 0.26 mmol), and NaI (2 mg). The mixture was stirred at 50° C. for 1 hour and concentrated under vacuum. The residue was purified by preparative HPLC to furnish Compound 51. LC-MS (ESI) m/z: 496 [M+H]⁺. ¹H-NMR (DMSO-d₆, 400 MHz): δ (ppm) 1.11 (s, 9H), 6.15 (s, 2H), 7.46 (d, J=6.8 Hz, 2H), 7.58 (d, J=6.8 Hz, 2H), 7.68 (d, J=6.8 Hz, 2H), 7.82 (d, J=6.8 Hz, 2H).

Example 52

Synthesis of 1-((isobutyryloxy)methyl)-4-((4'-(trifluoromethoxy)-[1,1'-biphenyl]-4-yl)thio)-1H-1,2,3-triazole-5-carboxylic acid (52)

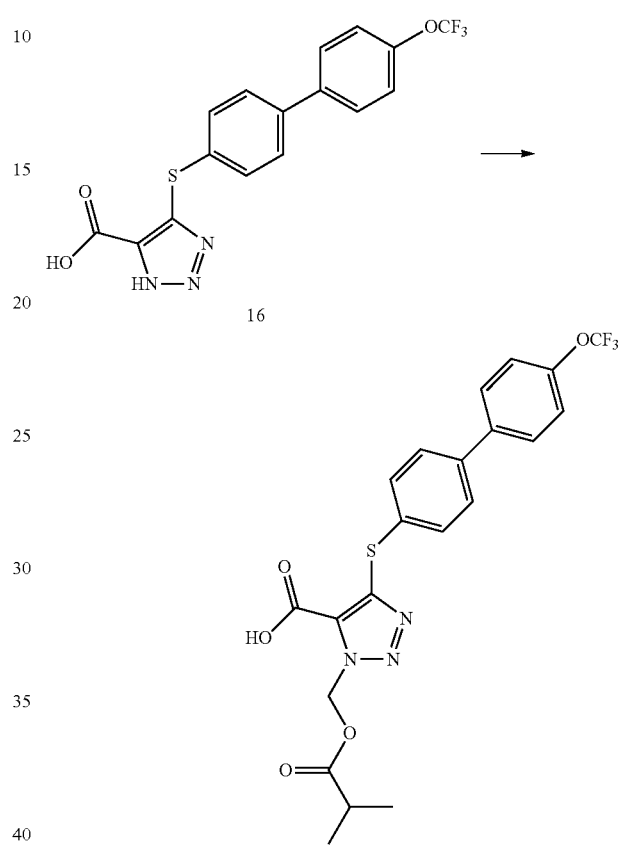

Compound 52 was synthesized by employing the procedure described for Compound 51 using chloromethyl isobutyrate in lieu of chloromethyl pivalate, LC-MS (ESI) m/z: 482 [M+H]⁺. ¹H-NMR (DMSO-d₆, 400 MHz): δ (ppm) 1.03 (s, 3H), 1.05 (s, 3H), 2.55-2.57 (m, 1H), 6.15 (s, 2H), 7.46 (d, J=6.8 Hz, 2H), 7.58 (d, J=6.8 Hz, 2H), 7.68 (d, J=6.8 Hz, 2H), 7.82 (d, J=6.8 Hz, 2H).

Example 53

Synthesis of 4-(benzo[d]thiazol-6-ylthio)-1H-1,2,3-triazole-5-carboxylic acid 2,2,2-trifluoroacetate (53)

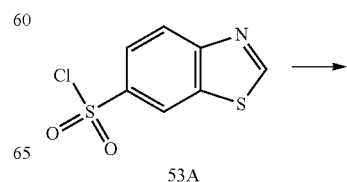

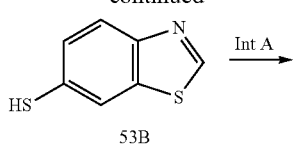

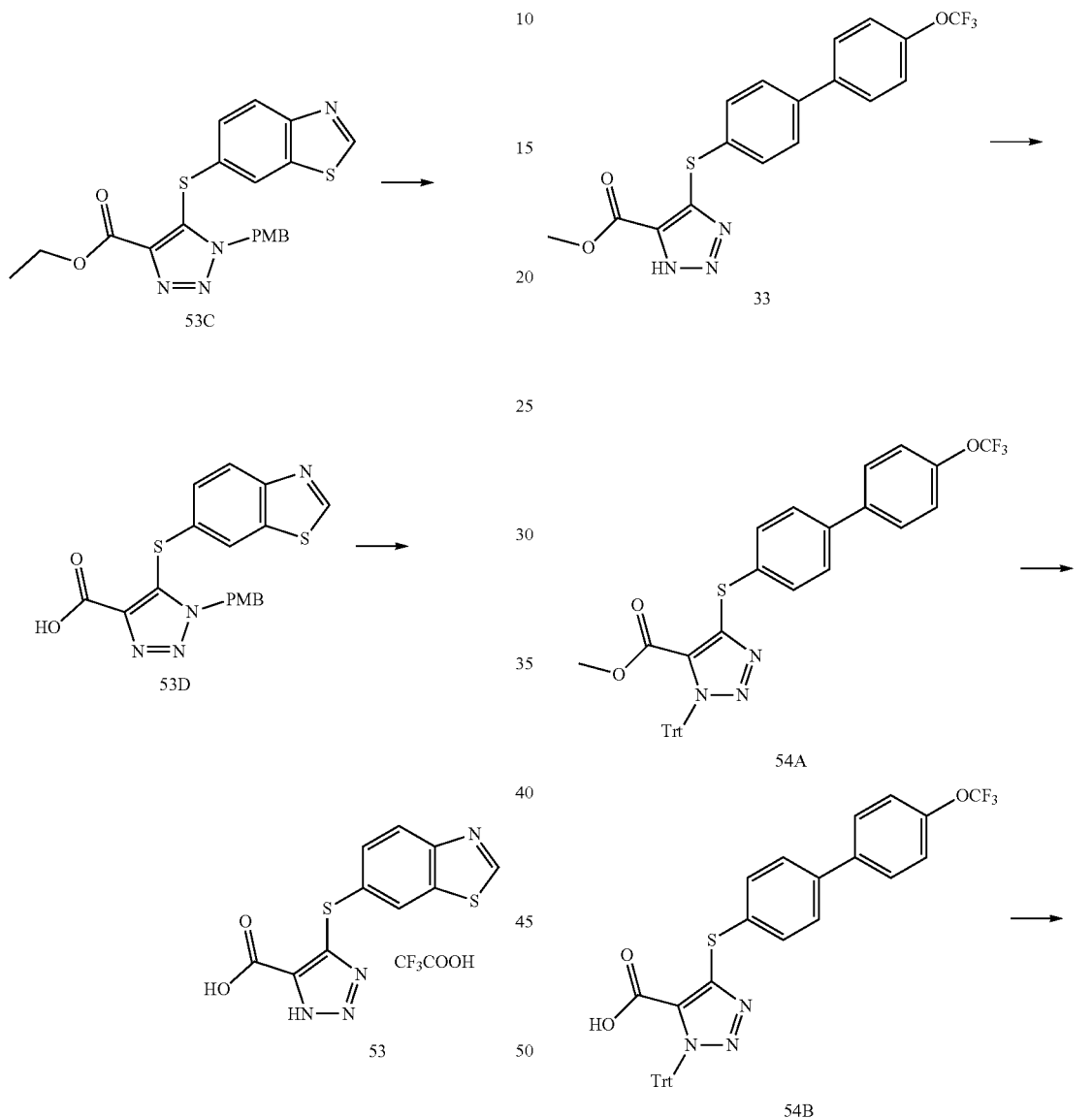

Example 54

Synthesis of (pivaloyloxy)methyl 4-((4'-(trifluoromethoxy)-[1,1'-biphenyl]-4-yl)thio)-1H-1,2,3-triazole-5-carboxylate (54)

Compounds 53B, 53C, 53D, and 53 were synthesized by employing the procedures described for Compounds 50C, 1E, 8F, and 1 using Compounds 53A, Intermediate A, 53B using NMP as solvent at 100° C., 53C, and 53D in lieu of Compounds 50B, Intermediates B, Compounds 1D using DMF as solvent at 50° C., 8E, and 1E. Compound 53B: LC-MS (ESI) m/z: 168 [M+H]$^+$. Compound 53C: LC-MS (ESI) m/z: 427 [M+H]$^+$. Compound 53D: LC-MS (ESI) m/z: 399 [M+H]$^+$. Compound 53: LC-MS (ESI) m/z: 279 [M+H]$^+$; $^1$H-NMR (DMSO-d$_6$, 400 MHz): δ (ppm) 7.60 (dd, $J_1$=8.8 Hz, $J_2$=2.0 Hz, 1H), 8.08 (d, J=8.4 Hz, 1H), 8.34 (d, J=1.2 Hz, 1H), 9.43 (s, 1H).

211

-continued

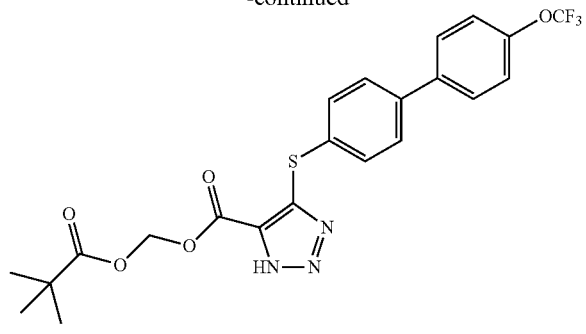

54

To a solution of Compound 33 (280 mg, 0.71 mmol) in CH₃CN (20 mL) was added (chloromethanetriyl)tribenzene (198 mg, 0.71 mmol) and triethylamine (143 mg, 1.42 mmol) and stirred at room temperature overnight. The reaction mixture was diluted with water (50 mL) and extracted with ethyl acetate (20 mL×3). The combined extracts were washed with brine (50 mL), dried over anhydrous sodium sulfate, filtered, and concentrated. The residue was purified by flash column chromatography on silica gel (ethyl acetate in petroleum ether, 20% v/v) to afford Compound 54A. LC-MS (ESI) m/z: 638 [M+H]⁺.

Compound 54B was synthesized by employing the procedure described for Compound 8F using Compound 54A in lieu of Compound 8E, LC-MS (ESI) m/z: 622. [M–H]⁻.

To a solution of Compound 54B (150 mg, 0.24 mmol) in DMF (10 mL) was added chloromethyl isobutyrate (36 mg, 0.24 mmol) and Na₂CO₃ (50 mg, 0.48 mmol). The reaction mixture was stirred at 50° C. for 3 hour. After cooling down to room temperature, the mixture was diluted with water (50 mL) and extracted with ethyl acetate (20 mL×3). The combined extracts were washed with brine (50 mL), dried over anhydrous sodium sulfate, filtered, and concentrated to furnish Compound 54C. LC-MS (ESI) m/z: non-ionizable compound under routine conditions used.

To a solution of Compound 54C (110 mg, 0.16 mmol) in dichloromethane (4 mL) was added 2,2,2-trifluoroacetic acid (1 mL) and stirred at room temperature for 3 hours. The mixture was concentrated under reduced pressure. The residue was purified by preparative HPLC to afford Compound 54. LC-MS (ESI) m/z: 496 [M+H]⁺; ¹H-NMR (CD₃OD, 400 MHz): δ (ppm) 1.19 (s, 9H), 5.99 (s, 2H), 7.35 (d, J=6.8 Hz, 2H), 7.56 (d, J=6.8 Hz, 2H), 7.65 (d, J=6.8 Hz, 2H), 7.73 (d, J=6.8 Hz, 2H).

212

Example 55

Synthesis of (isobutyryloxy)methyl 4-((4'-(trifluoromethoxy)-[1,1'-biphenyl]-4-yl)thio)-1H-1,2,3-triazole-5-carboxylate (55)

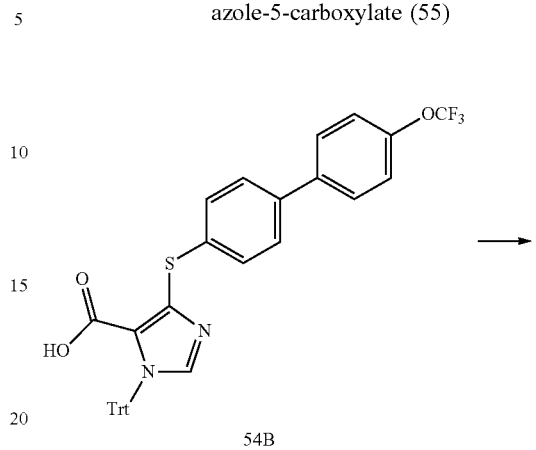

54B

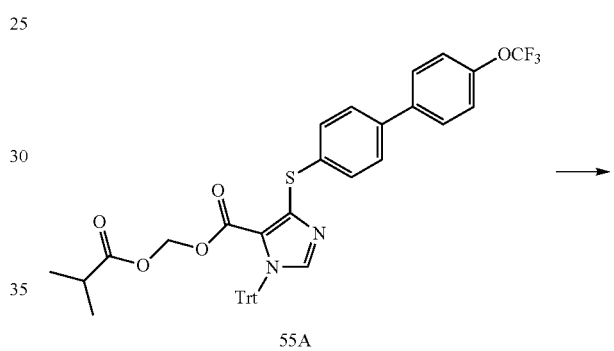

55A

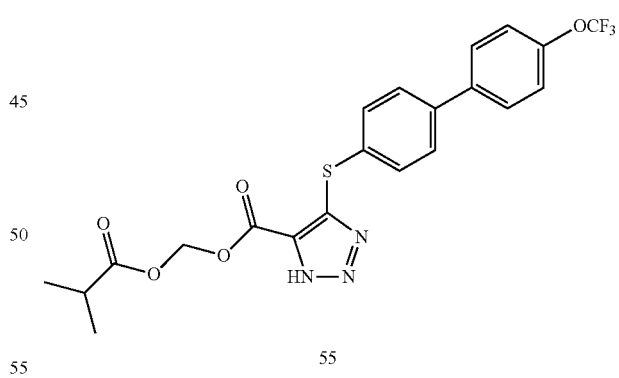

55

Compounds 55A and 55 were synthesized by employing the procedures described for Compounds 54C and 1 using chloromethyl isobutyrate and 55A in lieu of chloromethyl pivalate and 1E. Compound 55A: LC-MS (ESI) m/z: non-ionizable compound under routine conditions used. Compound 55: LC-MS (ESI) m/z: 482 [M–H]⁺; ¹H-NMR (CD₃OD, 400 MHz): δ (ppm) 1.13 (s, 3H), 1.15 (s, 3H), 2.57-2.60 (m, 1H), 5.97 (s, 2H), 7.34 (d, J=6.8 Hz, 2H), 7.51 (d, J=6.8 Hz, 2H), 7.61 (d, J=6.8 Hz, 2H), 7.71 (d, J=6.8 Hz, 2H).

Example 56

Synthesis of 4-((6-chloronaphthalen-2-yl)thio)-1H-1,2,3-triazole-5-carboxylic acid (56)

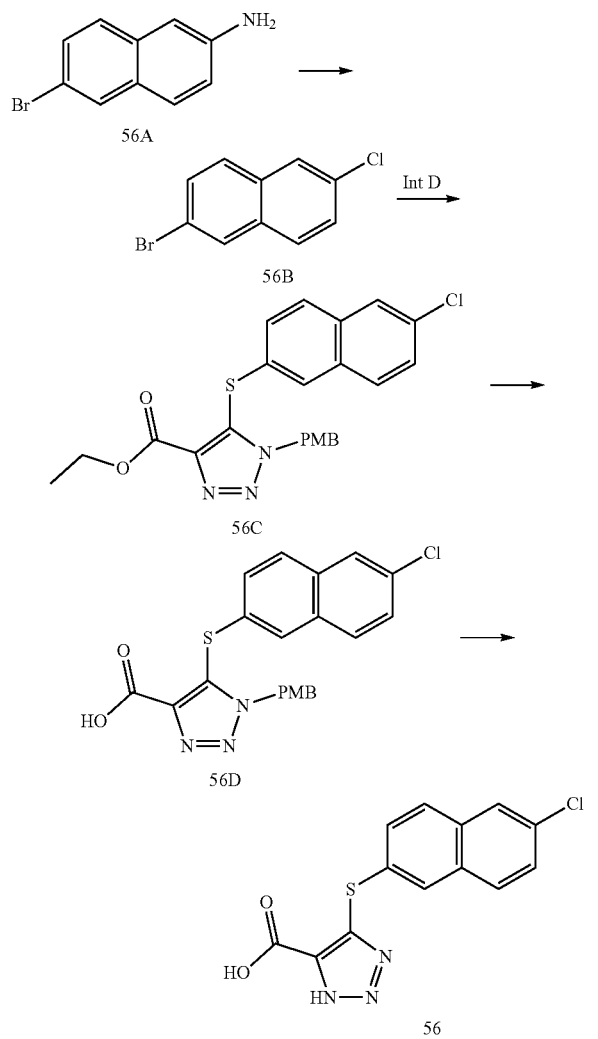

To a solution of 6-bromonaphthalen-2-amine (Compound 56A) (1 g, 4.52 mmol) in $H_2O$ (5 mL) and HCl (6 N, 10 mL) was added $NaNO_2$ (350 mg, 4.97 mmol). After the mixture was stirred at room temperature for 1 hour, to it was added a solution of CuCl (2.27 g, 20.73 mmol) in HCl (6 N, 5 mL) and stirred at room temperature for 3 hours. The reaction mixture was poured into ice water (50 mL). A solid was precipitated, filtered, and dried under vacuum to give Compound 56B. LC-MS (ESI) m/z: Non-ionizable compound under routine conditions used.

Compounds 56C, 56D, and 56 were synthesized by employing the procedures described for Compounds 35D, 8F, and 1 using Compounds 56B, 568C, and 56D in lieu of Compounds 35C, 8E, and 1E. Compound 56C: LC-MS (ESI) m/z: 454 [M+H]$^+$; $^1$H-NMR (DMSO-d$_6$, 400 MHz): δ (ppm) 1.08 (t, J=6.8 Hz, 3H), 3.59 (s, 3H), 4.13-4.20 (m, 2H), 5.66 (s, 2H), 6.72 (d, J=8.8 Hz, 2H), 7.10 (d, J=8.8 Hz, 2H), 7.20 (d, J=8.8 Hz, 1H), 7.49-7.53 (m, 1H), 7.56-7.57 (m, 1H), 7.76-7.79 (m, 2H), 7.99 (d, J=2.0 Hz, 1H). Compound 56D: LC-MS (ESI) m/z: 426 [M+H]$^+$; $^1$H-NMR (DMSO-d$_6$, 400 MHz): δ (ppm) 3.55 (s, 3H), 5.50 (s, 2H), 6.63 (d, J=9.2 Hz, 2H), 7.00 (d, J=8.8 Hz, 2H), 7.30 (d, J=8.8 Hz, 1H), 7.43-7.49 (m, 2H), 7.69-7.75 (m, 2H), 7.96 (d, J=1.6 Hz, 1H). Compound 56: LC-MS (ESI) m/z: 306 [M+H]$^+$; $^1$H-NMR (DMSO-d$_6$, 400 MHz): δ (ppm) 7.56 (d, J=8.8 Hz, 2H), 7.91-7.98 (m, 2H), 8.10 (d, J=8.8 Hz, 2H).

Example 57

Synthesis of 4-((5,6-dichloro-2,3-dihydro-1H-inden-2-yl)thio)-1H-1,2,3-triazole-5-carboxylic 2,2,2-trifluoroacetate (57)

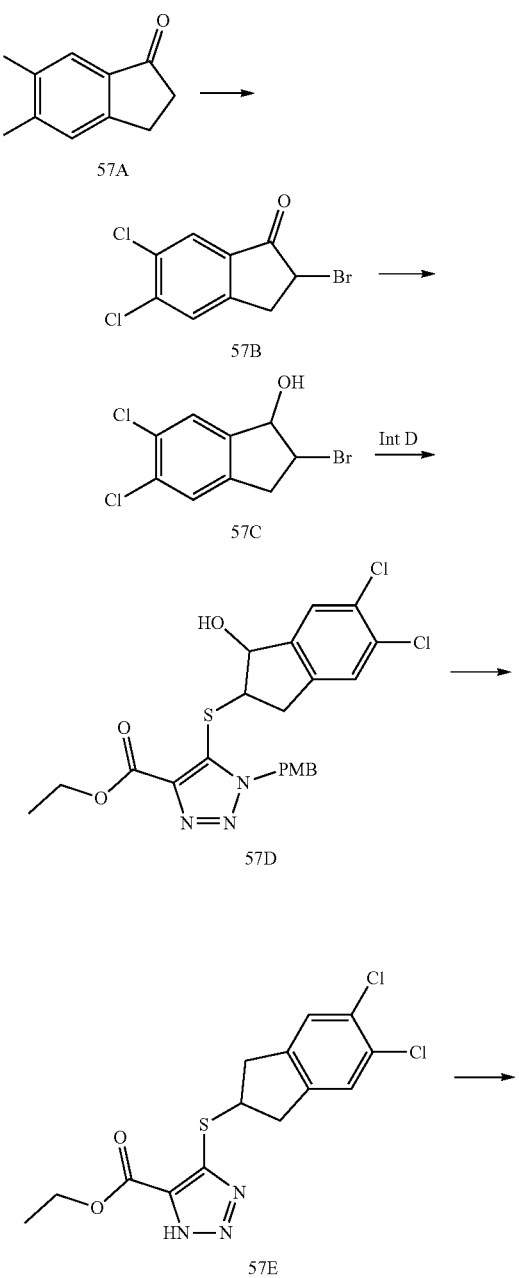

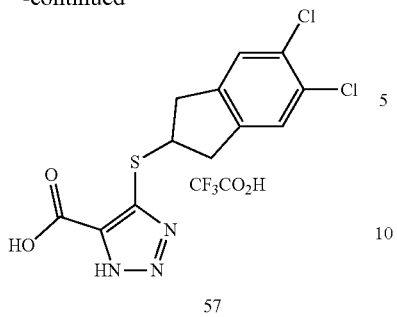

To a solution of 5,6-dichloro-2,3-dihydro-1H-inden-1-one (Compound 57A) (6.03 g, 30 mmol) in dichloromethane (100 mL) was added pyridinium bromide perbromide (10.5 g, 33 mmol) at 0° C. and stirred at room temperature overnight. The mixture was diluted with EtOAc (50 mL) and washed with brine (15 mL×3). The organic layer was dried over anhydrous sodium sulfate, filtered, and concentrated. The residue was purified with flash column chromatography on silica gel (ethyl acetate in petroleum ether, 5% v/v) to afford Compound 57B. LC-MS (ESI) m/z: 279 [M+H]$^+$; $^1$H-NMR (CDCl$_3$, 400 MHz): δ (ppm) 3.36-3.41 (m, 1H), 3.78-3.85 (m, 1H), 4.67 (dd, J=7.2, 2.8 Hz, 1H), 7.60 (s, 1H), 7.92 (s, 1H).

To a solution of Compound 57B (500 mg, 1.79 mmol) in methanol (15 mL) was added sodium borohydride (102 mg, 2.68 mmol) and stirred at room temperature for 2 hours. The reaction mixture was concentrated under reduced pressure. The residue was diluted with EtOAc (50 mL) and washed with brine (15 mL×3). The organic layer was dried over anhydrous sodium sulfate, filtered, concentrated, and purified with flash column chromatography on silica gel (ethyl acetate in petroleum ether, 20% v/v) to afford Compound 57C. LC-MS (ESI) m/z: 281 [M+H]$^+$.

A mixture of Compound 57C (200 mg, 0.71 mmol), Intermediate D (208 mg, 0.71 mmol), and sodium carbonate (159 mg, 1.5 mmol) in 1-methylpyrrolidin-2-one (8 mL) was stirred at 80° C. overnight. The mixture was diluted with EtOAc (50 mL) and washed with brine (15 mL×3). The organic layer was dried over anhydrous sodium sulfate, filtered, concentrated, and purified with flash column chromatography on silica gel (ethyl acetate in petroleum ether, 20% v/v) to afford Compound 57D. LC-MS (ESI) m/z: 494 [M+H]$^+$.

A mixture of Compound 57D (140 mg, 0.28 mmol) and triethylsilane (326 mg, 2.8 mmol) in TFA (2 mL) was stirred at 60° C. for 3 hours. The mixture was concentrated under reduced pressure. The residue was purified with preparative TLC (ethyl acetate in dichloromethane, 20% v/v) to afford Compound 57E. LC-MS (ESI) m/z: 358 [M+H]$^+$; $^1$H-NMR (CDCl$_3$, 400 MHz): δ (ppm) 1.42 (t, J=7.2 Hz, 3H), 3.00 (dd, J=16.8, 5.2 Hz, 2H), 3.52 (dd, J=16.8, 7.6 Hz, 2H), 4.44 (q, J=7.2 Hz, 2H), 4.46-4.50 (m, 1H), 7.30 (s, 2H).

Compound 57 was synthesized by employing the procedure described for Compound 8F using Compound 57E in lieu of Compound 8E. LC-MS (ESI) m/z: 330 [M+H]$^+$; $^1$H-NMR (CD$_3$OD, 400 MHz): δ (ppm) 3.00 (dd, J=16.8, 5.2 Hz, 2H), 3.52 (dd, J=16.8, 7.6 Hz, 2H), 4.46-4.50 (m, 1H), 7.38 (s, 2H).

Example 58

Synthesis of ethyl 4-((4'-chloro-[1,1'-biphenyl]-4-yl) amino)-1H-1,2,3-triazole-5-carboxylate (58-1) and 4-((4'-chloro-[1,1'-biphenyl]-4-yl)amino)-1H-1,2,3-triazole-5-carboxylic acid (58-2)

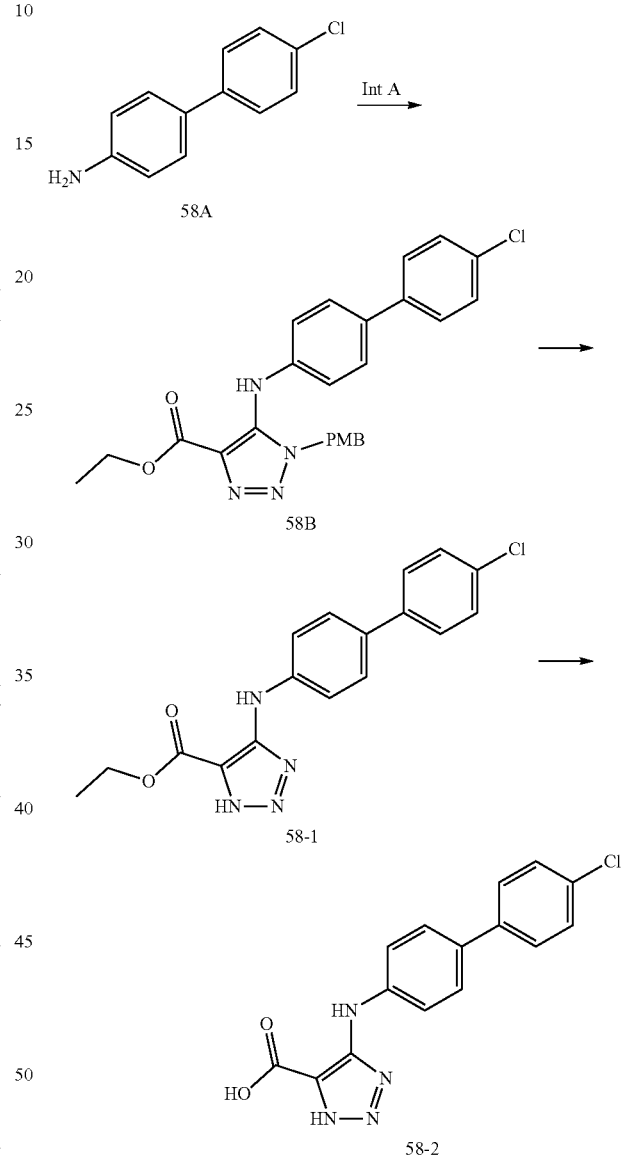

Compounds 58B, 58-1, and 58-2 were synthesized by employing the procedures described for Compounds 6B, 1, and 8F using Intermediate A, Compounds 58A using K$_3$PO$_4$ as base, 58B, and 58-1 in lieu of Compounds 6A, 1-methylpiperazine using t-BuONa as base, 1E, and 8E. Compound 58B: LC-MS (ESI) m/z: 463 [M+H]$^+$. Compound 58-1: LC-MS (ESI) m/z: 343. $^1$H-NMR (DMSO-d$_6$, 400 MHz): δ (ppm) 1.41 (t, J=7.2 Hz, 3H), 4.44 (q, J=7.2 Hz, 2H), 7.45-7.47 (m, 2H), 7.64-7.69 (s, 4H), 7.77-7.79 (s, 2H), 8.19 (brs, 1H). Compound 58-2: LC-MS (ESI) m/z: 315. $^1$H-NMR (DMSO-d$_6$, 400 MHz): δ (ppm) 7.45-7.47 (m, 2H), 7.54-7.63 (s, 4H), 7.65-7.67 (s, 2H), 9.13 (brs, 1H).

Example 59

Synthesis of 4-((4-(3,4-dichlorophenyl)thiazol-2-yl)amino)-1H-1,2,3-triazole-5-carboxylic acid (59)

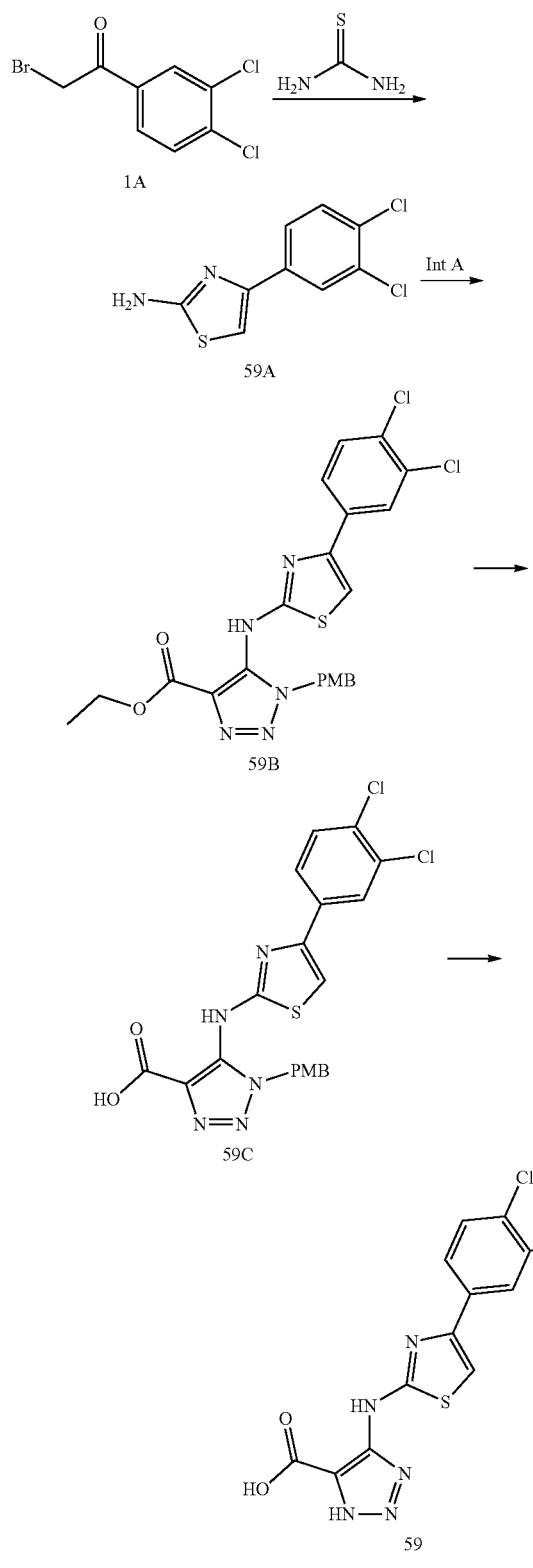

A suspension of 2-bromo-1-(3,4-dichlorophenyl)ethanone (1A) (2.68 g, 10 mmol) and thiourea (912 mg, 12.0 mmol) in EtOH (20 mL) was heated at reflux for 2 hours. The mixture was concentrated and the residue was partitioned between water (50 mL) and ethyl acetate (50 mL). The organic phase was separated, dried over anhydrous sodium sulfate, filtered, and concentrated to yield Compound 59A. LC-MS (ESI) m/z: 245 [M+H]$^+$; $^1$H-NMR (CDCl$_3$, 400 MHz): δ (ppm) 5.01 (br, 2H), 6.75 (s, 1H), 7.43 (d, J=8.4 Hz, 1H), 7.59 (dd, J$_1$=8.4 Hz, J$_2$=2.4 Hz, 1H), 7.89 (d, J=2.0 Hz, 1H)

Compounds 59B, 59C, and 59 were synthesized by employing the procedures described for Compounds 6B, 8F, and 1 using Intermediate A, Compounds 59A using K$_3$PO$_4$ as base, 59B, and 59C in lieu of Compounds 6A, 1-methylpiperazine using t-BuONa as base, 8E, and 1E. Compound 59B: LC-MS (ESI) m/z: 504 [M+H]$^+$. Compound 59C: LC-MS (ESI) m/z: 476 [M+H]$^+$. Compound 59: LC-MS (ESI) m/z: 356 [M+H]$^+$; $^1$H-NMR (DMSO-d$_6$, 400 MHz): δ (ppm) 4.02 (br, 1H), 7.67 (d, J=8.8 Hz, 1H), 7.76 (s, 1H), 7.93 (d, J=6.8 Hz, 1H), 8.19 (s, 1H), 9.57 (br, 1H).

Example 60

Synthesis of 4-((3',4'-dichloro-[1,1'-biphenyl]-4-yl)amino)-1H-1,2,3-triazole-5-carboxylic acid (60)

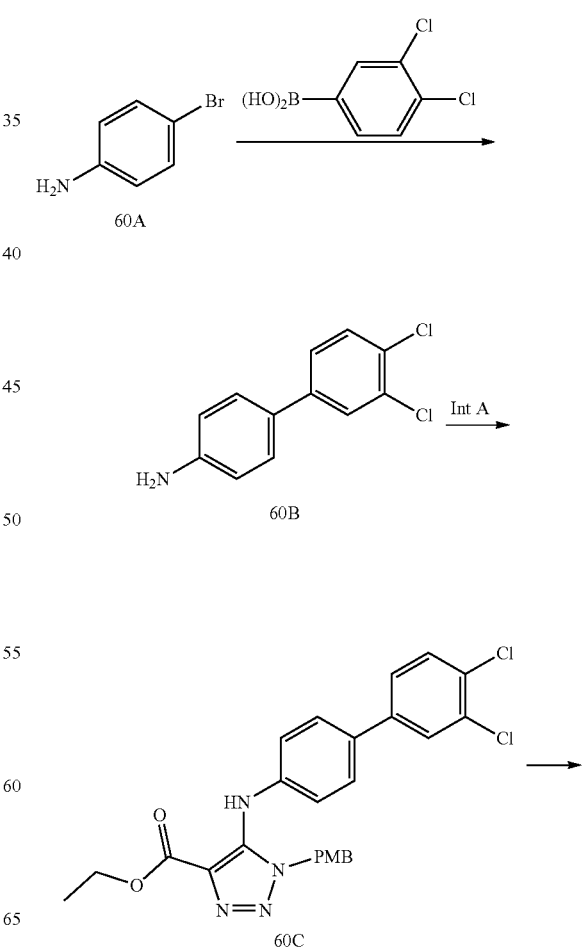

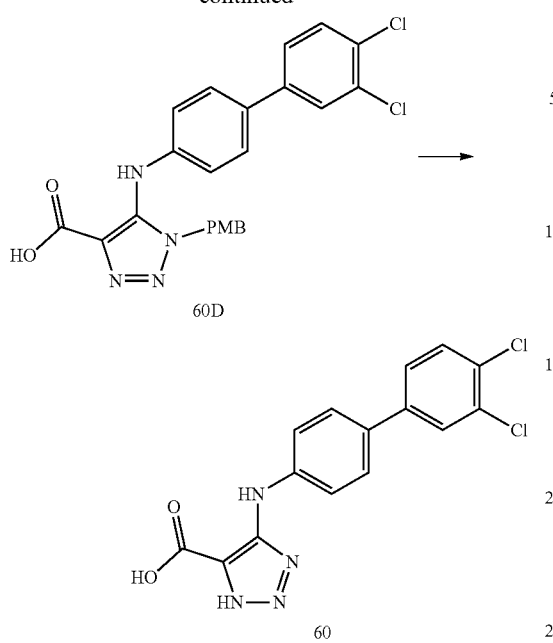

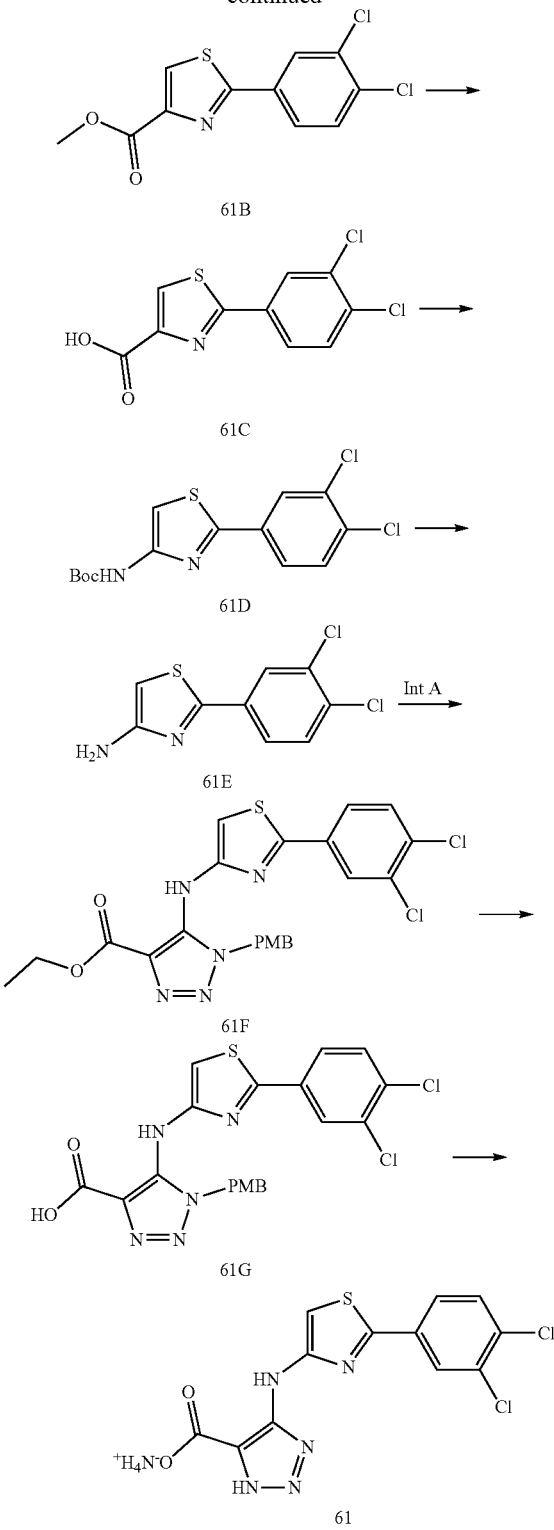

Compounds 60B, 60C, 60D, and 60 were synthesized by employing the procedures described for Compounds 8B, 6B, 8F, and 1 using Compounds 60A using Na$_2$CO$_3$ as base, Intermediate A, 60B using K$_3$PO$_4$ as base, 60C, and 60D in lieu of Compounds 8A using Cs$_2$CO$_3$ as base, 6A, 1-methylpiperazine using t-BuONa as base, 8E, and 1E. Compound 60B: LC-MS (ESI) m/z: 238 [M+H]$^+$. Compound 60C: LC-MS (ESI) m/z: 497 [M+H]$^+$. $^1$H-NMR (CDCl$_3$, 400 MHz): δ (ppm) 1.40 (t, J=6.8 Hz, 3H), 3.75 (s, 3H), 4.41 (q, J=7.6 Hz, 2H), 5.22 (s, 2H), 6.73 (dd, J=2.4, 6.8 Hz, 2H), 6.82-6.89 (m, 4H), 7.16 (s, 1H), 7.38 (dd, J=2.4, 8.8 Hz, 1H), 7.46 (dd, J=1.6, 6.8 Hz, 2H), 7.51 (d, J=8.4 Hz, 1H), 7.65 (d, J=2.0 Hz, 1H). Compound 60D: LC-MS (ESI) m/z: 469 [M+H]$^+$. Compound 60: LC-MS (ESI) m/z: 349 [M+H]$^+$; $^1$H-NMR (DMSO-d$_6$, 400 MHz): δ (ppm) 7.65-7.68 (m, 7H), 7.90 (s, 1H), 8.33 (s, 1H), 14.95 (s, 1H).

Example 61

Synthesis of ammonium 4-((2-(3,4-dichlorophenyl)thiazol-4-yl)amino)-1H-1,2,3-triazole-5-carboxylate (61)

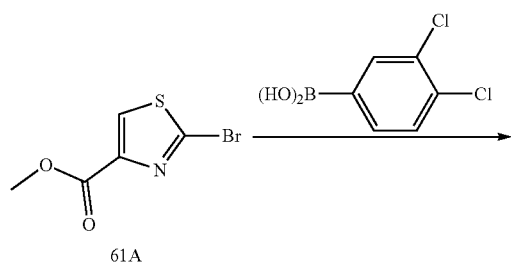

Compounds 61B and 61C were synthesized by employing the procedures described for Compounds 8B and 8F using Compounds 61A using KF as base and THF as solvent, and 61B in lieu of Compounds 8A using Cs$_2$CO$_3$ as base and DME as solvent, and 8E. Compound 61B: LC-MS (ESI) m/z: 288 [M+H]$^+$; $^1$H-NMR (CDCl$_3$, 400 MHz): δ (ppm) 4.00 (s, 3H), 7.55 (d, J=8.0 Hz, 1H), 7.83 (dd, J$_1$=8.8 Hz, $J_2$=2.0 Hz, 1H), 8.15 (d, J=2.4 Hz, 1H), 8.22 (s, 1H). Compound 61C: LC-MS (ESI) m/z: 274 [M+H]$^+$.

To a solution of Compound 61C (2.1 g, 7.66 mmol) in t-BuOH (100 mL) was added Et$_3$N (851 mg, 8.43 mmol) and DPPA (2.32 g, 8.43 mmol) at 0° C. The mixture was heated at reflux overnight and evaporated under reduced pressure. The residue was diluted with CH$_2$Cl$_2$ (50 mL), washed with brine (50 mL), dried over anhydrous sodium sulfate, filtered, and concentrated. The residue was purified by column chromatography on silica gel (ethyl acetate in petroleum ether, 5% v/v) to yield Compound 61D. LC-MS (ESI) m/z: 367 [M+Na]$^+$.

Compound 61D (400 mg, 1.6 mmol) was dissolved in a solution of HCl/1,4-dioxane (4 N, 5 mL) and stirred at room temperature overnight. The mixture was concentrated to yield Compound 61E. LC-MS (ESI) m/z: 245 [M+H]$^+$.

Compounds 61F, 61G, and 61 were synthesized by employing the procedures described for Compounds 6B, 8F, and 1 using Intermediate A, Compounds 61E using K$_3$PO$_4$ as base, 61F, and 61G in lieu of Compounds 6A, 1-methylpiperazine using t-BuONa as base, 8E, and 1E. Compound 61F: LC-MS (ESI) m/z: 504 [M+H]$^+$. Compound 61G: LC-MS (ESI) m/z: 476 [M+H]$^+$. Compound 61: LC-MS (ESI) m/z: 356 [M+H]$^+$; $^1$H-NMR (DMSO-d$_6$, 400 MHz): δ (ppm) 3.98 (br, 4H), 6.07 (s, 1H), 7.29 (s, 1H), 7.23 (d, J=8.8 Hz, 1H), 7.88 (dd, J$_1$=8.4 Hz, J$_2$=2.4 Hz, 1H), 8.12 (d, J=2.0 Hz, 1H).

Example 62

Synthesis of 4-((4'-(trifluoromethoxy)-[1,1'-biphenyl]-4-yl)amino)-1H-1,2,3-triazole-5-carboxylic acid 2,2,2-trifluoroacetate (62)

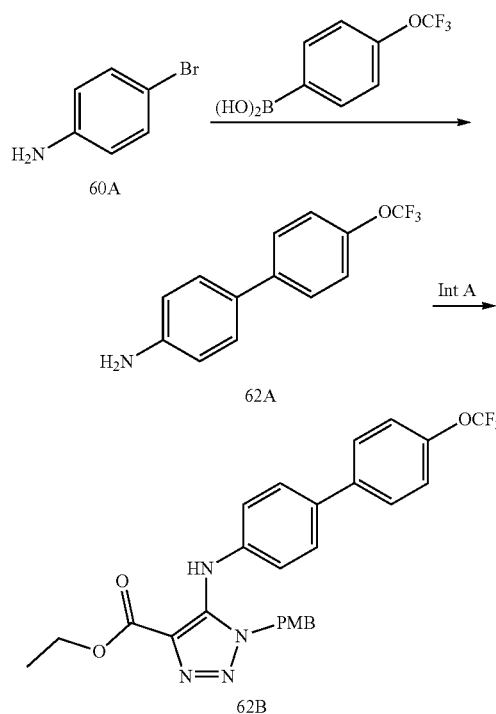

-continued

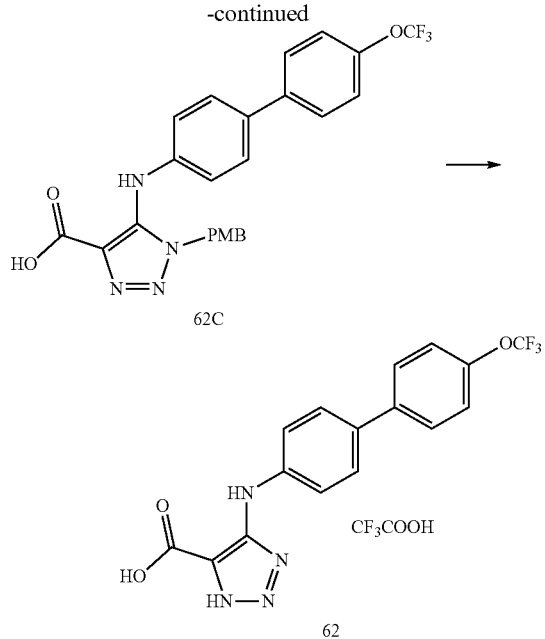

Compounds 62A, 62B, 62C, and 62 were synthesized by employing the procedures described for Compounds 8B, 6B, 2, and 1 using Compounds 60A using K$_2$CO$_3$ as base, Intermediate A, 62A using K$_3$PO$_4$ as base, 62B, and 62C in lieu of Compounds 8A using Cs$_2$CO$_3$ as base, 6A, 1-methylpiperazine using t-BuONa as base, 1, and 1E. Compound 62A: LC-MS (ESI) m/z: 254 [M+H]$^+$. Compound 62B: LC-MS (ESI) m/z: 513 [M+H]$^+$. Compound 62C: LC-MS (ESI) m/z: 485 [M+H]$^+$. Compound 62: LC-MS (ESI) m/z: 365 [M+H]$^+$; $^1$H-NMR (CD$_3$OD, 400 MHz): δ (ppm) 7.31 (d, J=8.4 Hz, 2H), 7.59-7.70 (m, 6H).

Example 63

Synthesis of 4-((2-(3,4-dichlorophenyl)thiazol-4-yl)(methyl)amino)-1H-1,2,3-triazole-5-carboxylic acid (63)

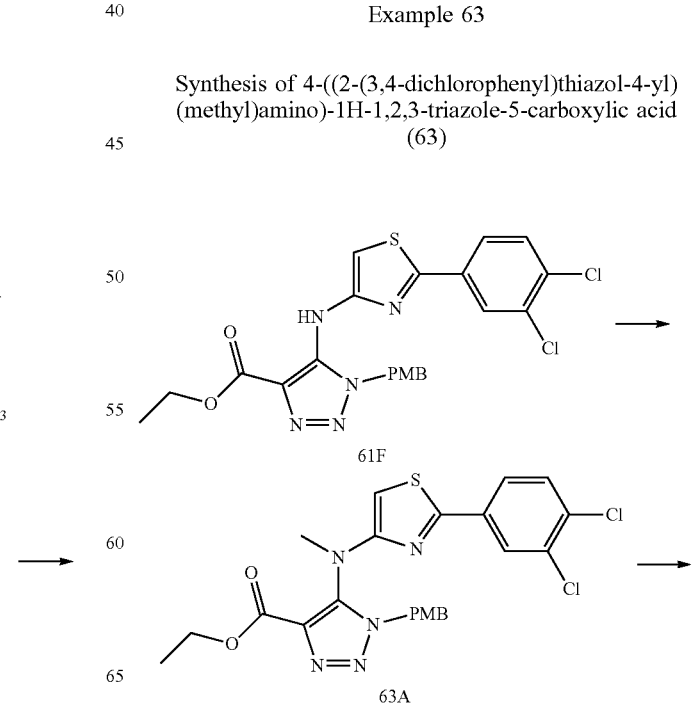

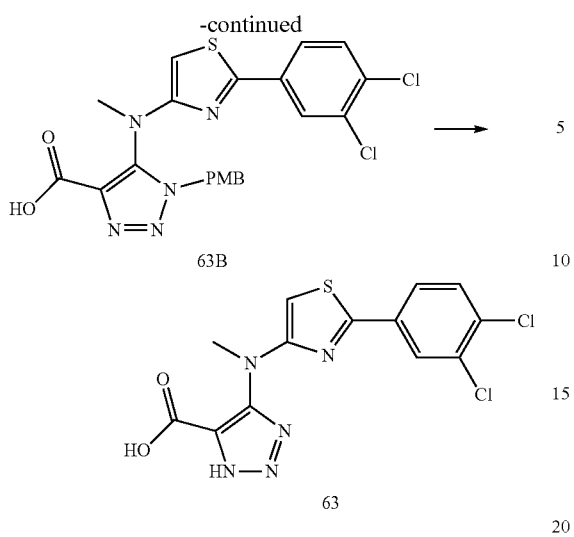

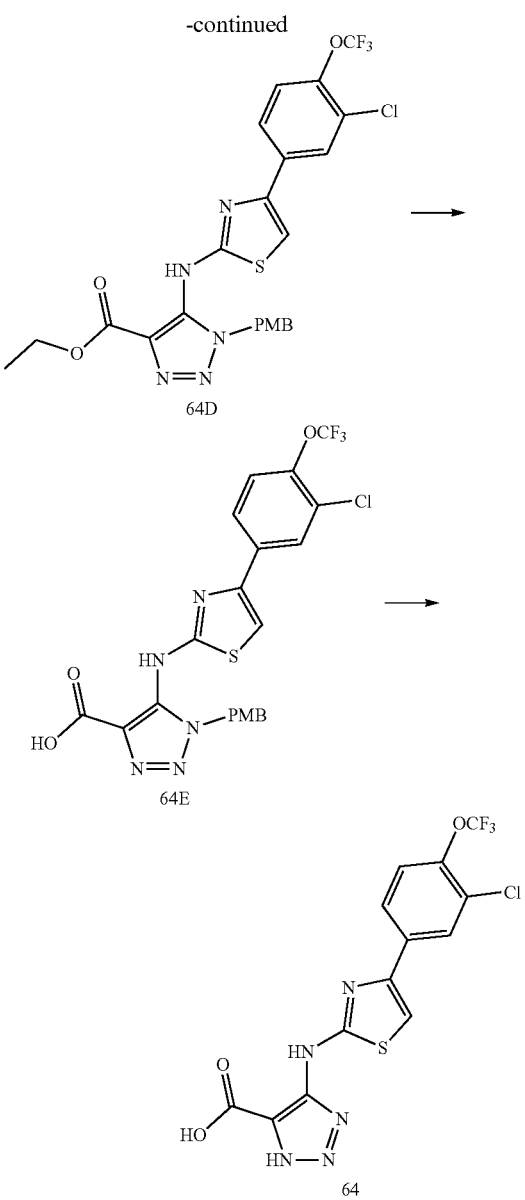

To a mixture of Compound 61F (250 mg, 0.5 mmol) and Cs$_2$CO$_3$ (326 mg, 1 mmol) in DMF (20 mL) was added MeI (142 mg, 1 mmol) and stirred at 60° C. for 3 hours. The reaction mixture was concentrated under reduced pressure. The residue was purified with flash column chromatography on silica gel (ethyl acetate in petroleum ether, 50% v/v) to afford Compound 63A. LC-MS (ESI) m/z: 518 [M+H]$^+$.

Compounds 63B and 63 were synthesized by employing the procedures described for Compounds 8F and 1 using Compounds 63A and 63B in lieu of Compounds 8E and 1E. Compound 63B: LC-MS (ESI) m/z: 490 [M+H]$^+$. Compound 63: LC-MS (ESI) m/z: 370 [M+H]$^+$; $^1$H-NMR (DMSO-d$_6$, 400 MHz): δ (ppm) 3.48 (s, 3H), 6.64 (s, 1H), 7.73-7.75 (m, 2H), 7.98 (s, 1H).

Example 64

Synthesis of 4-((4-(3-chloro-4-(trifluoromethoxy)phenyl)thiazol-2-yl)amino)-1H-1,2,3-triazole-5-carboxylic acid (64)

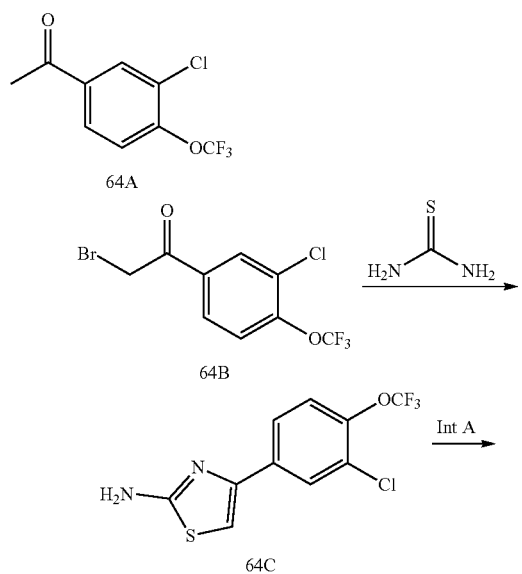

Compounds 64B, 64C, 64D, 64E, and 64 were synthesized by employing the procedures described for Compounds 15B, 58A, 6B, 8F, and 1 using Compounds 64A, 64B, Intermediate A, 64C using K$_3$PO$_4$ as base at 160° C. in a microwave oven, 64D, and 64E in lieu of Compounds 15A, 1A, 6A, 1-methylpiperazine using t-BuONa as base at 120° C., 8E, and 1E. Compound 64B: LC-MS (ESI) m/z: 317 [M+H]$^+$; $^1$H-NMR (CDCl$_3$, 400 MHz): δ (ppm) 4.39 (s, 2H), 7.45 (d, J=8.4 Hz, 1H), 7.92 (d, J=8.4 Hz, 1H), 8.11 (d, J=2.4 Hz, 1H). Compound 64C: LC-MS (ESI) m/z: 295 [M+H]$^+$; $^1$H-NMR (CDCl$_3$, 400 MHz): δ (ppm) 6.70 (s, 1H), 7.43 (d, J=8.4 Hz, 1H), 7.72 (d, J=8.4 Hz, 1H), 7.83 (d, J=2.4 Hz, 1H), 8.86 (s, 2H). Compound 64D: LC-MS (ESI) m/z: 554 [M+H]$^+$; (CDCl$_3$, 400 MHz): δ (ppm) 1.42 (t, J=8.8 Hz, 3H), 3.74 (s, 3H), 4.40-4.46 (m, 2H), 5.73 (s, 2H), 6.72 (d, J=8.4 Hz, 2H), 6.85 (d, J=8.4 Hz, 2H), 7.10 (s, 1H), 7.36 (d, J=8.4 Hz, 1H), 7.68-72 (m, 1H), 7.89 (d, J=2.0 Hz, 1H), 8.23 (s, 1H). Compound 64E: LC-MS (ESI) m/z: 526 [M+H]$^+$; $^1$H-NMR (DMSO-d$_6$, 400 MHz): δ (ppm) 3.68 (s, 3H), 5.55 (s, 2H), 6.81 (d, J=8.8 Hz, 2H), 6.99 (d, J=8.8 Hz, 2H), 7.42

(s, 1H), 7.56 (d, J=8.8 Hz, 1H), 7.82 (d, J=8.8 Hz, 1H), 8.02 (d, J=2.4 Hz, 1H). Compound 64: LC-MS (ESI) m/z: 406 [M+H]+; 1H-NMR (DMSO-d6, 400 MHz): δ (ppm) 7.61 (d, J=8.0 Hz, 1H), 7.79 (s, 1H), 8.01 (d, J=6.4 Hz, 1H), 8.20 (s, 1H), 9.57 (s, 1H), 13.76 (brs, 1H), 15.32 (brs, 1H).

Example 65

Synthesis of methyl 4-((4'-(trifluoromethoxy)-[1,1'-biphenyl]-4-yl)amino)-1H-1,2,3-triazole-5-carboxylate (65)

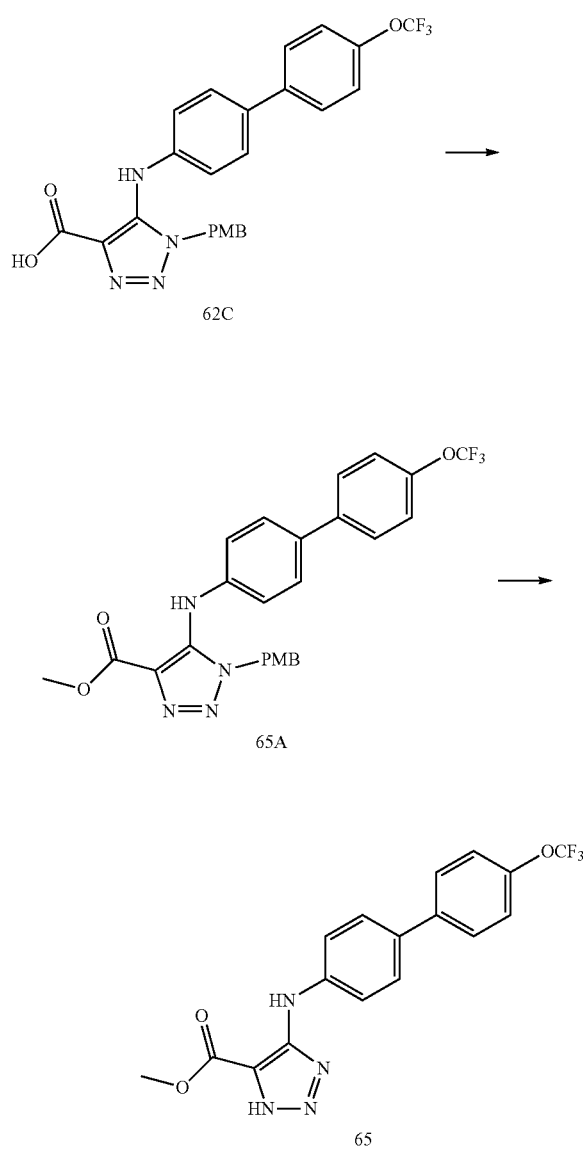

Compounds 65A and 65 were synthesized by employing the procedures described for Compounds 11A and 1 using Compounds 62C using methanol and 65A in lieu of Compounds 9A using propan-2-ol and 1E. Compound 65A: LC-MS (ESI) m/z: 499 [M+H]+. Compound 65: LC-MS (ESI) m/z: 379 [M+H]+; 1H-NMR (CD3OD, 400 MHz): δ (ppm) 3.98 (s, 3H), 7.32 (d, J=8.0 Hz, 2H), 7.60 (d, J=8.4 Hz, 2H), 7.69-7.71 (m, 4H).

Example 66

Synthesis of 4-((carboxymethyl)(4'-chloro-[1,1'-biphenyl]-4-yl)amino)-1H-1,2,3-triazole-5-carboxylic acid 2,2,2-trifluoroacetate (66)

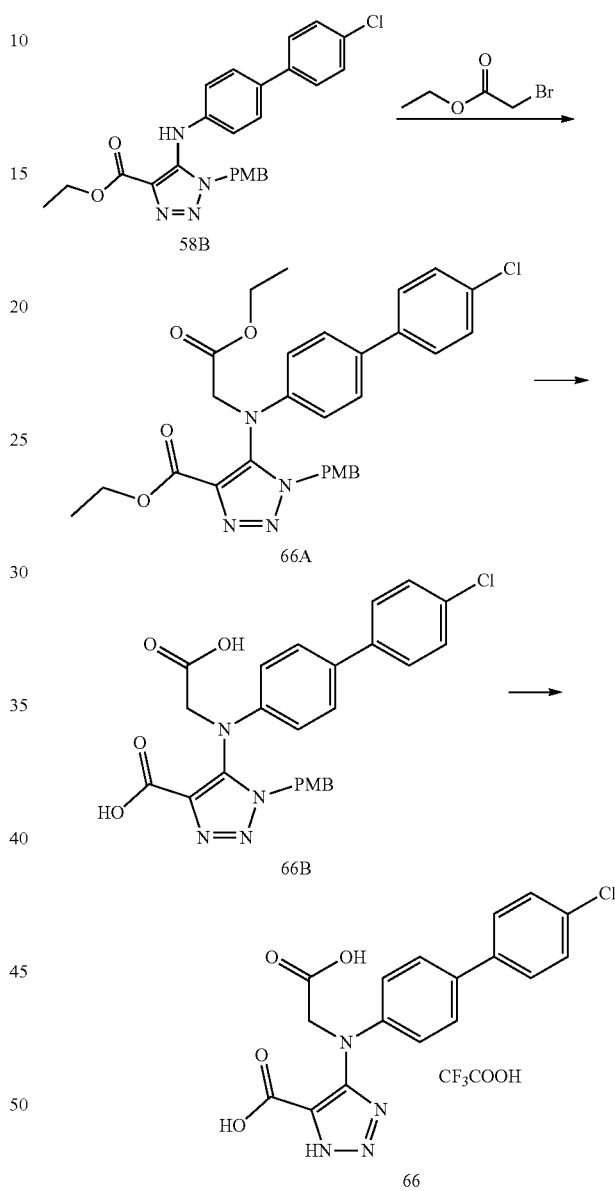

A mixture of Compound 58B (462 mg, 1 mmol), ethyl 2-bromoacetate (250 mg, 1.5 mmol) and Na2CO3 (160 mg, 1.5 mmol) in DMF (10 mL) was stirred at 70° C. overnight. The mixture was concentrated under reduced pressure. The residue was purified with flash column chromatography on silica gel (ethyl acetate in petroleum ether, 50% v/v) to afford Compound 66A. LC-MS (ESI) m/z: 549 [M+H]+.

Compounds 66B and 66 were synthesized by employing the procedures described for Compounds 8F and 1 using Compounds 66A and 66B in lieu of Compounds 8E and 1E. Compound 66B: LC-MS (ESI) m/z: 493 [M+H]+. Compound 66: LC-MS (ESI) m/z: 373 [M+H]+; 1H-NMR (DMSO-d$_6$, 400 MHz): δ (ppm) 4.52 (s, 2H), 6.83 (s, 2H), 7.46-7.53 (m, 4H), 7.62-7.64 (m, 2H), 12.87 (s, 1H), 15.13 (s, 1H).

Example 67

Synthesis of 4-(((3',4'-dichloro-[1,1'-biphenyl]-3-yl)methyl)amino)-1H-1,2,3-triazole-5-carboxylic acid (67)

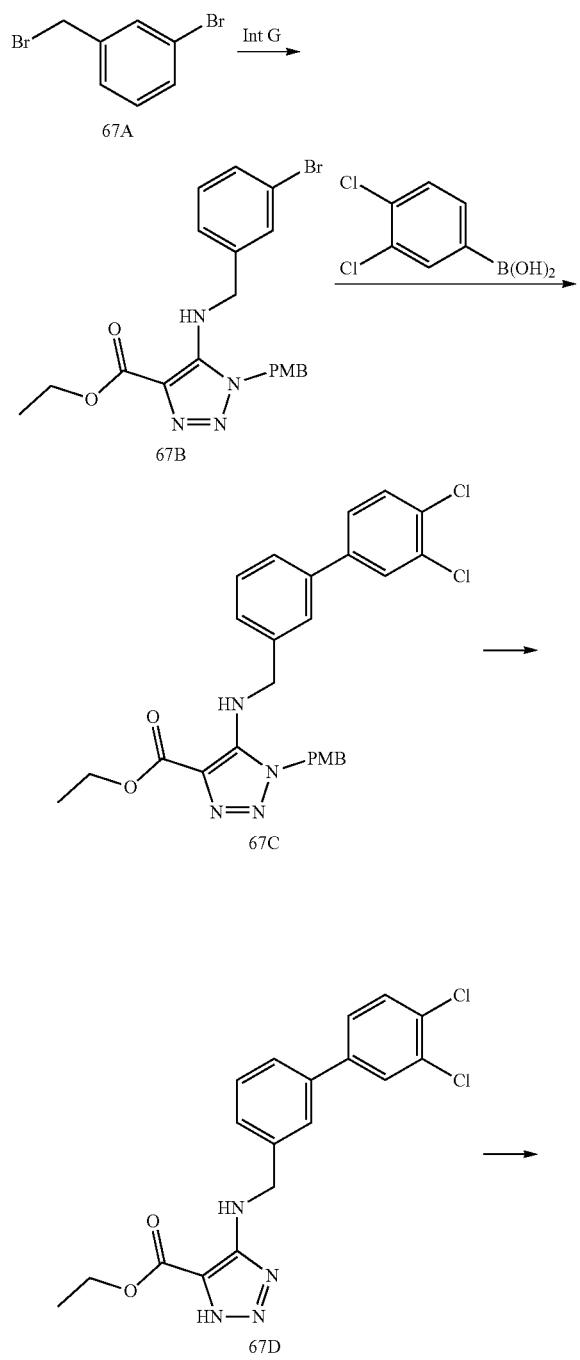

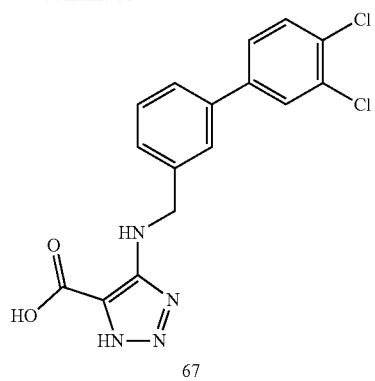

A mixture of Intermediate G (500 mg, 1.8 mmol) and NaH (60% suspension in oil, 216 mg, 5.4 mmol) in DMF (5 mL) was stirred at room temperature for 30 minutes. To the mixture was added 1-bromo-3-(bromomethyl)benzene (67A) (500 mg, 2.0 mmol) and was stirred at room temperature for 3 hours. The reaction mixture was quenched with water (50 mL) and extracted with ethyl acetate (30 mL×3). The combined extracts were concentrated and purified with flash column chromatography on silica gel (ethyl acetate in petroleum ether, 33% v/v) to afford Compound 67B. LC-MS (ESI) m/z: 445 [M+H]$^+$; $^1$H-NMR (DMSO-d$_6$, 400 MHz): δ (ppm) 1.25 (t, J=6.8 Hz, 3H), 3.74 (s, 3H), 4.20-4.26 (m, 2H), 4.59 (d, J=6.8 Hz, 2H), 5.42 (s, 2H), 6.88-6.94 (m, 3H), 7.07-7.09 (m, 3H), 7.19 (t, J=8.0 Hz, 1H), 7.29 (s, 1H), 7.39 (d, J=8.4 Hz, 1H).

Compounds 67C, 67D, and 67 were synthesized by employing the procedures described for Compounds 4B, 1, and 8F using 3,4-dichlorophenylboronic acid, Compounds 67B using 1,4-dioxane and H$_2$O as solvent, 67C, and 67D in lieu of (4-bromophenyl)boronic acid, Compounds 4A using toluene/EtOH/H$_2$O as solvent, 1E, and 8E. Compound 67C: LC-MS (ESI) m/z: 511 [M+H]$^+$. Compound 67D: LC-MS (ESI) m/z: 391 [M+H]$^+$. Compound 67: LC-MS (ESI) m/z: 363 [M+H]$^+$; $^1$H-NMR (CD$_3$OD, 400 MHz): δ (ppm) 4.57 (s, 2H), 7.40-7.65 (m, 6H), 7.78 (s, 1H).

Example 68

Synthesis of 4-(((3',4'-dichloro-[1,1'-biphenyl]-4-yl)methyl)amino)-1H-1,2,3-triazole-5-carboxylic acid (68)

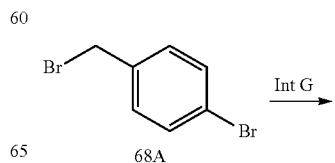

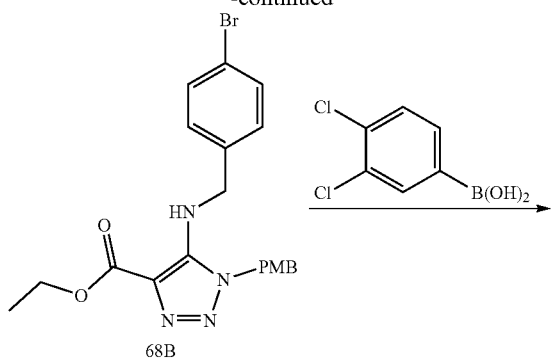

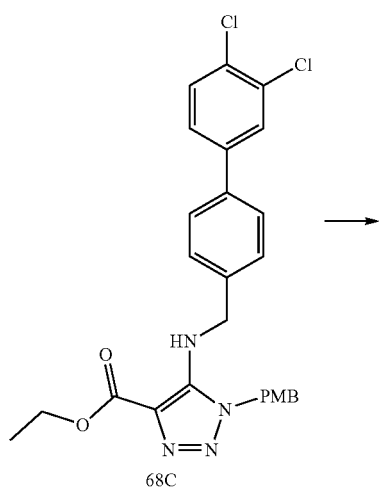

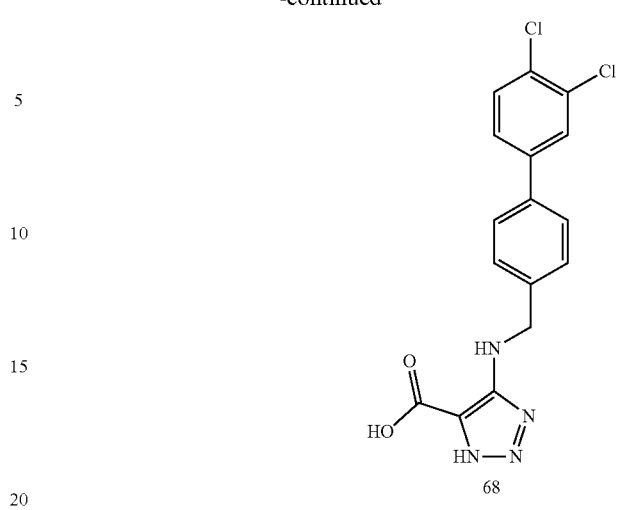

Compounds 68B, 68C, 68D, and 68 were synthesized by employing the procedures described for Compounds 67B, 4B, 1, and 8F using Compounds 68A, 3,4-dichlorophenylboronic acid, 68B using 1,4-dioxane and $H_2O$ as solvent, 68C, and 68D in lieu of Compounds 67A, (4-bromophenyl) boronic acid, 4A using toluene/EtOH/$H_2O$ as solvent, 1E, and 8E. Compound 68B: LC-MS (ESI) m/z: 445 [M+H]$^+$; $^1$H-NMR (DMSO-d$_6$, 400 MHz): δ (ppm) 1.25 (t, J=7.2 Hz, 3H), 3.74 (s, 3H), 4.21-4.24 (m, 2H), 4.56 (d, J=6.8 Hz, 2H), 5.40 (s, 2H), 6.88-6.91 (m, 3H), 7.02-7.07 (m, 4H), 7.40-7.42 (m, 2H). Compound 68C: LC-MS (ESI) m/z: 511 [M+H]$^+$. Compound 68D: LC-MS (ESI) m/z: 391 [M+H]$^+$. Compound 68: LC-MS (ESI) m/z: 363 [M+H]$^+$; $^1$H-NMR (CD$_3$OD, 400 MHz): δ (ppm) 4.54 (s, 2H), 7.48-7.56 (m, 6H), 7.77 (s, 1H).

Example 69

Synthesis of 4-((3,4-dichlorophenyl)amino)-1H-1,2,3-triazole-5-carboxylic acid (69)

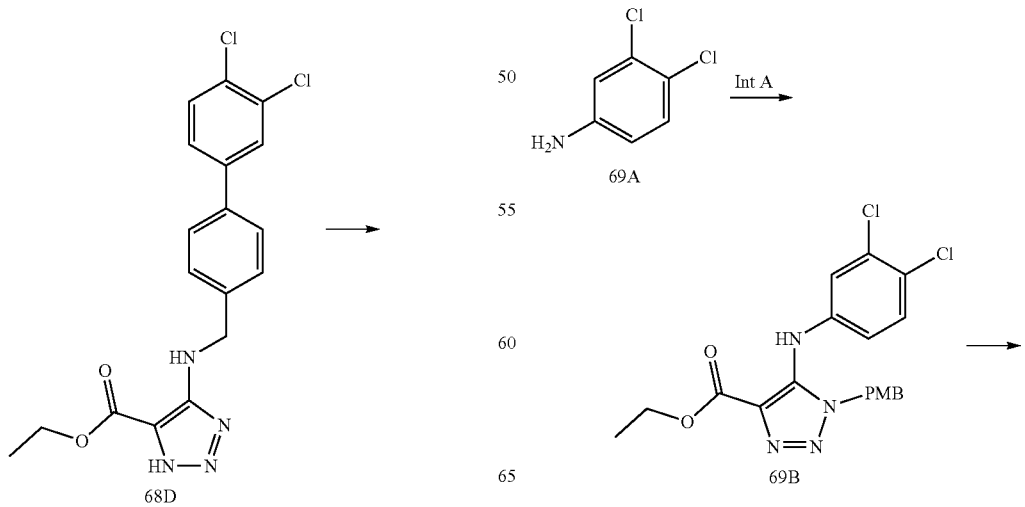

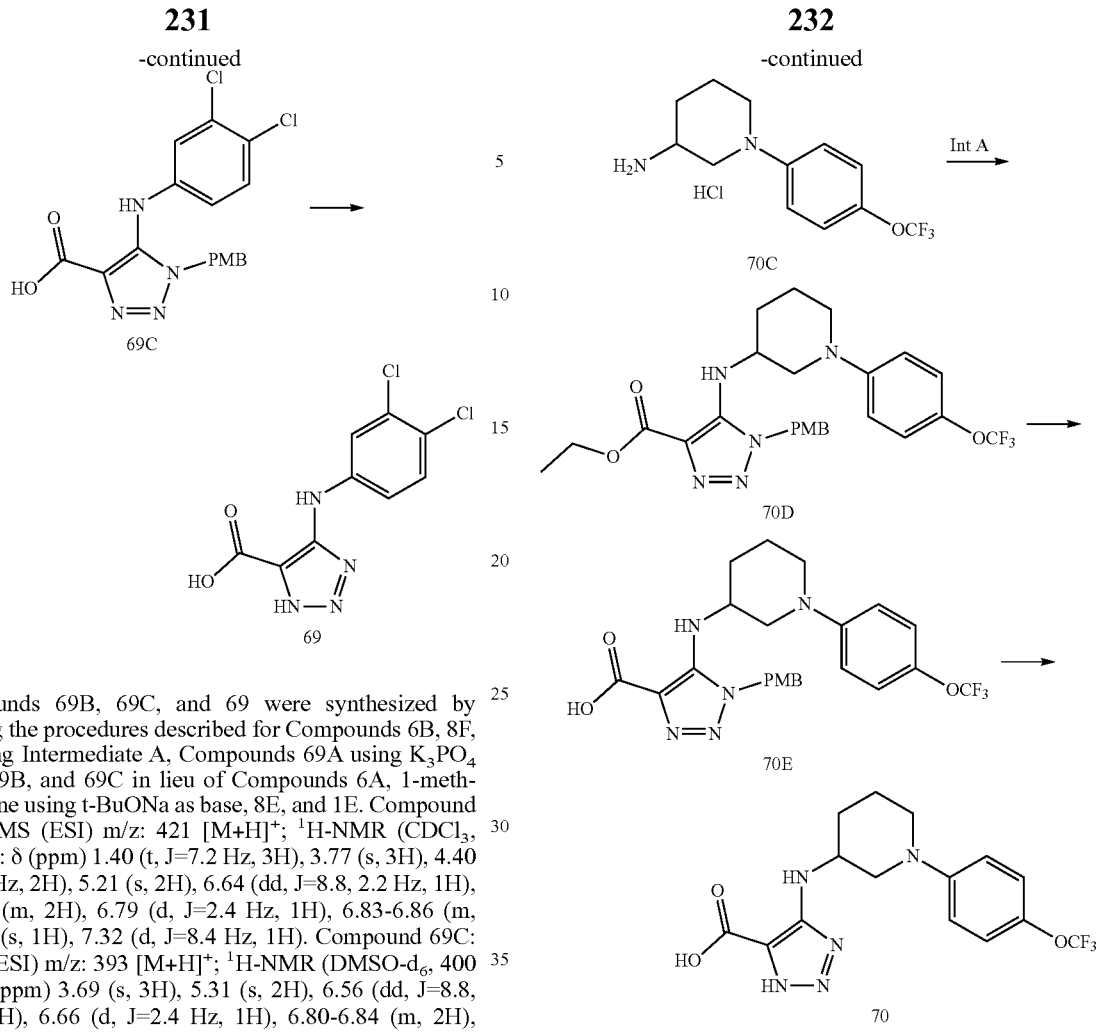

Compounds 69B, 69C, and 69 were synthesized by employing the procedures described for Compounds 6B, 8F, and 1 using Intermediate A, Compounds 69A using $K_3PO_4$ as base, 69B, and 69C in lieu of Compounds 6A, 1-methylpiperazine using t-BuONa as base, 8E, and 1E. Compound 69B: LC-MS (ESI) m/z: 421 [M+H]$^+$; $^1$H-NMR (CDCl$_3$, 400 MHz): δ (ppm) 1.40 (t, J=7.2 Hz, 3H), 3.77 (s, 3H), 4.40 (q, J=7.2 Hz, 2H), 5.21 (s, 2H), 6.64 (dd, J=8.8, 2.2 Hz, 1H), 6.74-6.77 (m, 2H), 6.79 (d, J=2.4 Hz, 1H), 6.83-6.86 (m, 2H), 6.94 (s, 1H), 7.32 (d, J=8.4 Hz, 1H). Compound 69C: LC-MS: (ESI) m/z: 393 [M+H]$^+$; $^1$H-NMR (DMSO-d$_6$, 400 MHz): δ (ppm) 3.69 (s, 3H), 5.31 (s, 2H), 6.56 (dd, J=8.8, 2.4 Hz, 1H), 6.66 (d, J=2.4 Hz, 1H), 6.80-6.84 (m, 2H), 7.05-7.07 (m, 2H), 7.33 (d, J=8.8 Hz, 1H), 8.73 (brs, 1H). Compound 69: LC-MS (ESI) m/z: 273 [M+H]$^+$; $^1$H-NMR (DMSO-d$_6$, 400 MHz): δ (ppm) 7.50 (d, J=8.8 Hz, 1H), 7.59 (dd, J=8.8, 2.4 Hz, 1H), 7.98 (d, J=2.4 Hz, 1H), 8.50 (s, 1H), 13.47 (brs, 1H), 15.06 (brs, 1H).

Example 70

Synthesis of 4-((1-(4-(trifluoromethoxy)phenyl)piperidin-3-yl)amino)-1H-1,2,3-triazole-5-carboxylic acid (70)

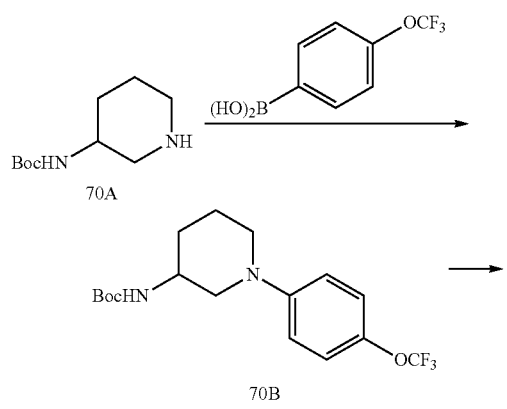

A mixture of tert-butyl piperidin-3-ylcarbamate (70A) (1.5 g, 7.29 mmol), 4-(trifluoromethoxy)phenylboronic acid (1.5 g, 7.29 mmol), Cu(OAc)$_2$ (1.57 g, 8.75 mmol), and $K_3PO_4$ (3.09 g, 14.58 mmol) in DMSO (30 mL) was stirred at 80° C. overnight. The mixture was cooled down to room temperature, diluted with water (100 mL), and extracted with EtOAc (50 mL×3). The combined extracts were concentrated under reduced pressure. The residue was purified with column chromatography on silica gel (ethyl acetate in petroleum ether, 10% v/v) to furnish Compound 70B. LC-MS (ESI) m/z: 361 [M+H]$^+$.

A mixture of Compound 70B (432 mg, 1.2 mmol) and a solution of HCl in 1,4-dioxane (4 M, 10 mL) was stirred at room temperature for 2 hours. The mixture was concentrated to give Compound 70C. LC-MS (ESI) m/z: 261 [M+H]$^+$.

Compounds 70D, 70E, and 70 were synthesized by employing the procedures described for Compounds 6B, 8F, and 1 using Intermediate A, Compounds 70C using $K_3PO_4$ as base, 70D, and 70E in lieu of Compounds 6A, 1-methylpiperazine using t-BuONa as base, 8E, and 1E. Compound 70D: LC-MS (ESI) m/z: 520 [M+H]$^+$. Compound 70E: LC-MS (ESI) m/z: 492 [M+H]$^+$. Compound 70: LC-MS (ESI) m/z: 372 [M+H]$^+$; $^1$H-NMR (DMSO-d$_6$, 400 MHz): δ (ppm) 1.58-1.60 (m, 2H), 1.71-1.73 (m, 1H), 2.31-2.33 (m, 1H), 2.89-2.94 (m, 2H), 3.33-3.51 (m, 3H), 7.99 (d, J=8.8 Hz, 2H), 7.16 (d, J=8.8 Hz, 2H).

Example 71

Synthesis of 4-((1-(4-chlorophenyl)piperidin-4-yl)amino)-1H-1,2,3-triazole-5-carboxylic acid 2,2,2-trifluoroacetate (71)

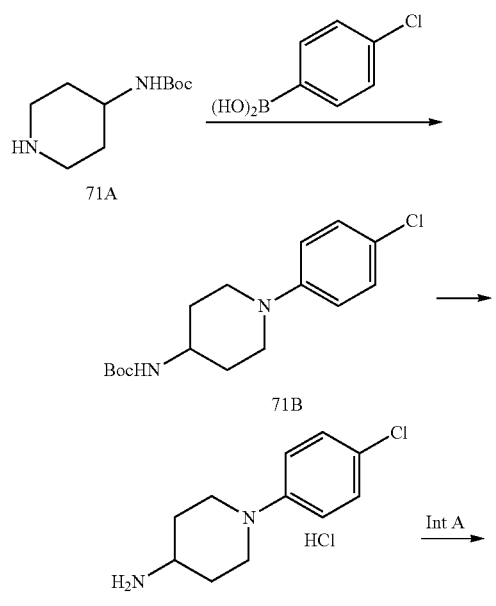

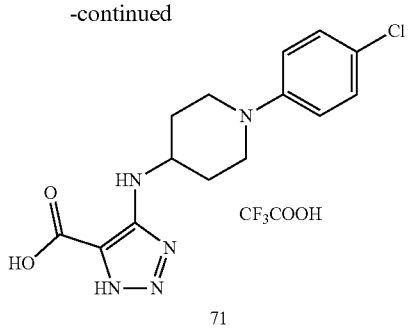

Compounds 71B, 71C, 71D, 71E, and 71 were synthesized by employing the procedures described for Compounds 70B, 70C, 6B, 8F, and 1 using 4-chlorophenylboronic acid, Compounds 71A using dichloromethane as solvent, 71B using EtOAc as solvent, Intermediate A, 71C using K$_3$PO$_4$ as base, 71D, and 71E in lieu of 4-(trifluoromethoxy)phenylboronic acid, Compounds 70A using DMSO as solvent, 70B using 1,4-dioxane as solvent, 6A, 1-methylpiperazine using t-BuONa as base, 8E, and 1E. Compound 71B: LC-MS (ESI) m/z: 311 [M+H]$^+$; $^1$H-NMR (CDCl$_3$, 400 MHz): δ (ppm) 1.46 (s, 9H), 1.51-1.59 (m, 2H), 2.03-2.06 (m, 2H), 2.79-2.86 (m, 2H), 3.54-3.61 (m, 3H), 4.47 (br, 1H), 6.82-6.86 (m, 2H), 7.17-7.21 (m, 2H). Compound 71C: LC-MS (ESI) m/z: 211 [M+H]$^+$. Compound 71D: LC-MS (ESI) m/z: 470 [M+H]$^+$. Compound 71E: LC-MS (ESI) m/z: 442 [M+H]$^+$. Compound 71: LC-MS (ESI) m/z: 322 [M+H]$^+$; $^1$H-NMR (DMSO-d$_6$, 400 MHz): δ (ppm) 1.59-1.62 (m, 2H), 1.97-2.00 (m, 2H), 2.80-2.86 (m, 2H), 3.51 (br, 1H), 3.62-3.66 (m, 2H), 6.96-6.99 (m, 2H), 7.20-7.23 (m, 2H).

Example 72

Synthesis of cyclopropyl 4-((4'-(trifluoromethoxy)-[1,1'-biphenyl]-4-yl)amino)-1H-1,2,3-triazole-5-carboxylate 2,2,2-trifluoroacetate (72)

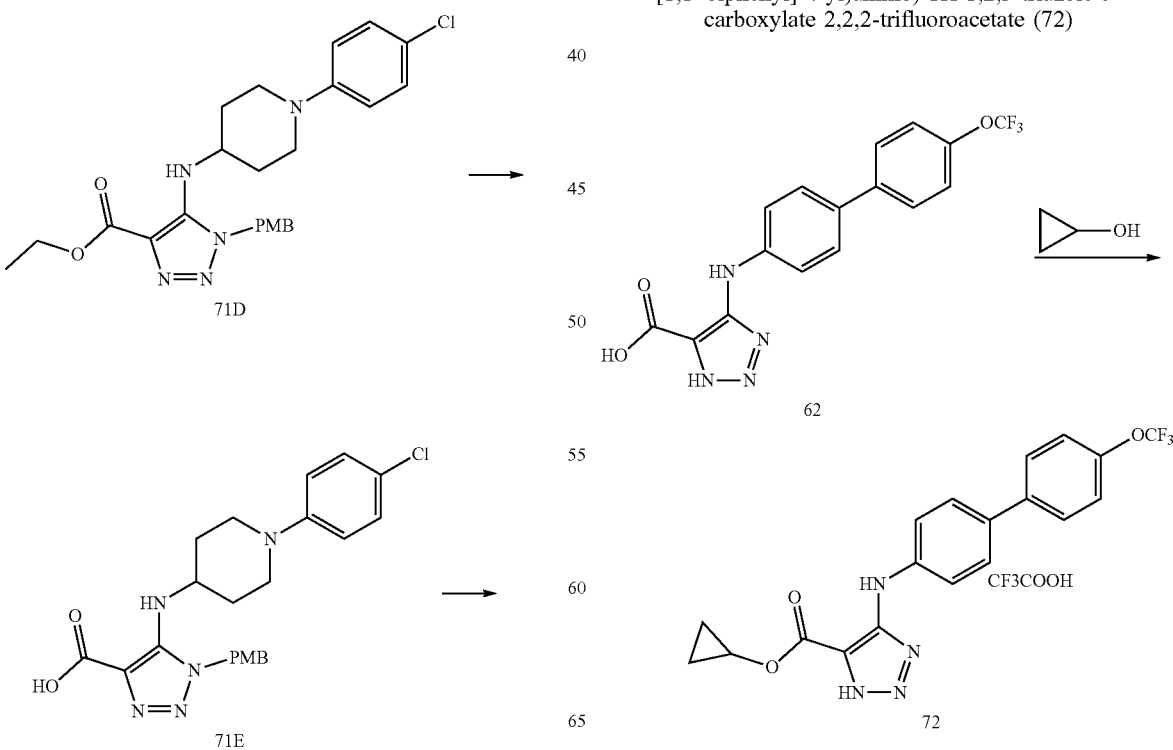

Compound 72 was synthesized by employing the procedure described for Compound 19A using Compound 62 in lieu of Compound 9A, LC-MS (ESI) m/z: 405 [M+H]+; 1H-NMR (CD3OD, 400 MHz): δ (ppm) 0.82-0.89 (m, 4H), 4.42-4.44 (m, 1H), 7.32 (d, J=8.0 Hz, 2H), 7.60-7.71 (m, 6H).

Example 73

Synthesis of 4-((4-(trifluoromethoxy)phenyl)pyrrolidin-3-yl)amino)-1H-1,2,3-triazole-5-carboxylic acid (73)

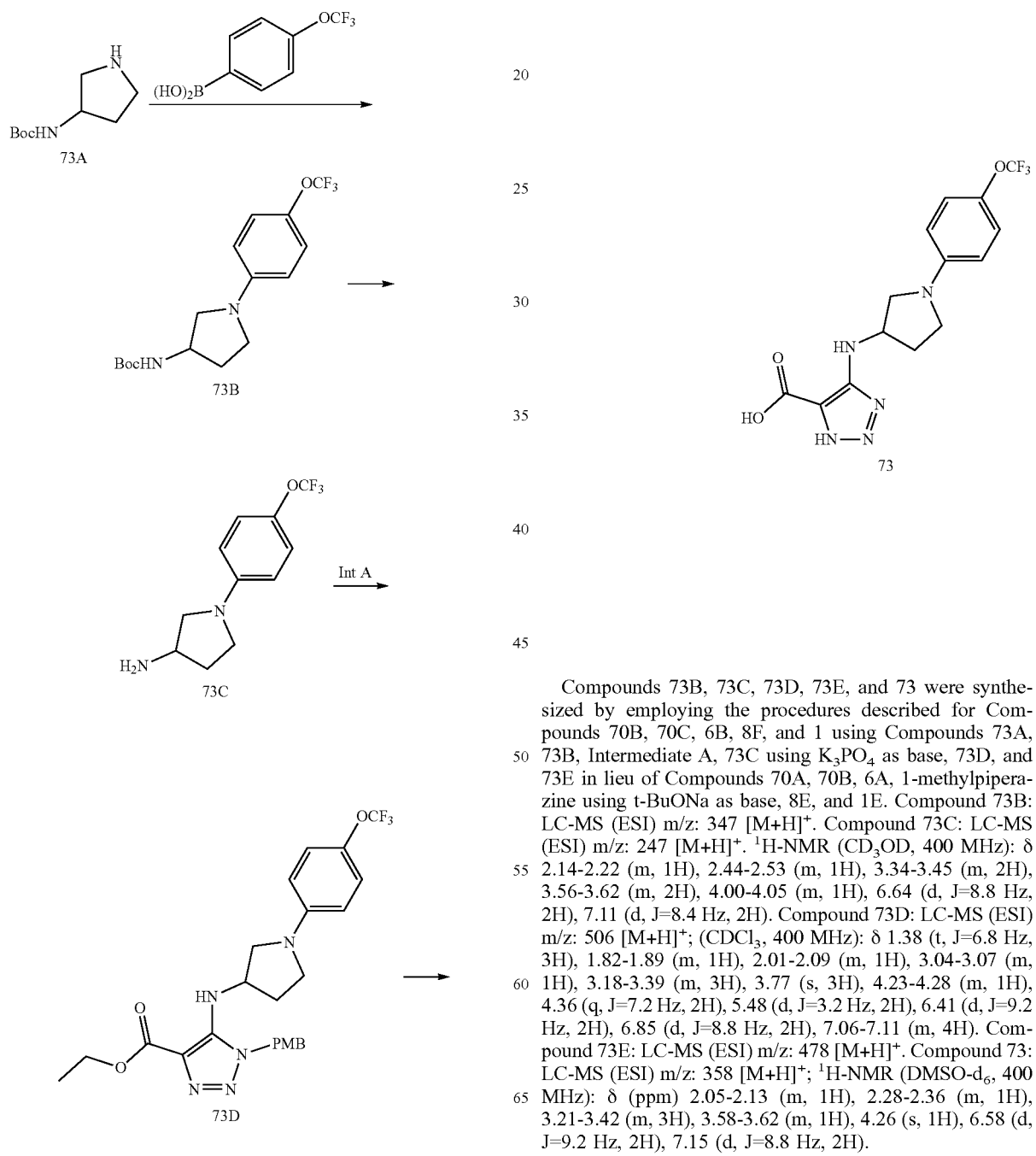

Compounds 73B, 73C, 73D, 73E, and 73 were synthesized by employing the procedures described for Compounds 70B, 70C, 6B, 8F, and 1 using Compounds 73A, 73B, Intermediate A, 73C using $K_3PO_4$ as base, 73D, and 73E in lieu of Compounds 70A, 70B, 6A, 1-methylpiperazine using t-BuONa as base, 8E, and 1E. Compound 73B: LC-MS (ESI) m/z: 347 [M+H]+. Compound 73C: LC-MS (ESI) m/z: 247 [M+H]+. 1H-NMR (CD3OD, 400 MHz): δ 2.14-2.22 (m, 1H), 2.44-2.53 (m, 1H), 3.34-3.45 (m, 2H), 3.56-3.62 (m, 2H), 4.00-4.05 (m, 1H), 6.64 (d, J=8.8 Hz, 2H), 7.11 (d, J=8.4 Hz, 2H). Compound 73D: LC-MS (ESI) m/z: 506 [M+H]+; (CDCl3, 400 MHz): δ 1.38 (t, J=6.8 Hz, 3H), 1.82-1.89 (m, 1H), 2.01-2.09 (m, 1H), 3.04-3.07 (m, 1H), 3.18-3.39 (m, 3H), 3.77 (s, 3H), 4.23-4.28 (m, 1H), 4.36 (q, J=7.2 Hz, 2H), 5.48 (d, J=3.2 Hz, 2H), 6.41 (d, J=9.2 Hz, 2H), 6.85 (d, J=8.8 Hz, 2H), 7.06-7.11 (m, 4H). Compound 73E: LC-MS (ESI) m/z: 478 [M+H]+. Compound 73: LC-MS (ESI) m/z: 358 [M+H]+; 1H-NMR (DMSO-d6, 400 MHz): δ (ppm) 2.05-2.13 (m, 1H), 2.28-2.36 (m, 1H), 3.21-3.42 (m, 3H), 3.58-3.62 (m, 1H), 4.26 (s, 1H), 6.58 (d, J=9.2 Hz, 2H), 7.15 (d, J=8.8 Hz, 2H).

Example 74

Synthesis of 4-((1-(4-(trifluoromethoxy)phenyl)piperidin-4-yl)amino)-1H-1,2,3-triazole-5-carboxylic acid (74)

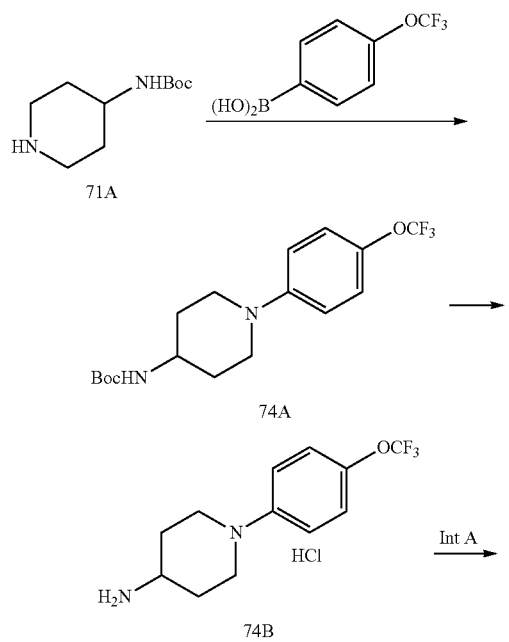

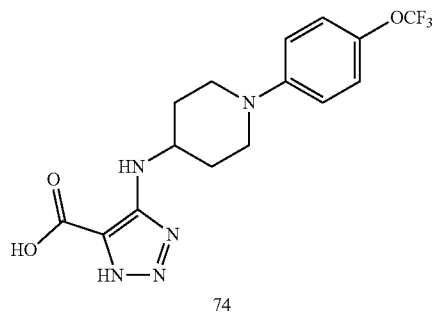

Compounds 74A, 74B, 74C, 74D, and 74 were synthesized by employing the procedures described for Compounds 70B, 70C, 6B, 1, and 8F using Compounds 71A, 74A using dichloromethane as solvent, Intermediate A, 74B using $K_3PO_4$ as base, 74C, and 74D in lieu of Compounds 70A, 70B using 1,4-dioxane as solvent, 6A, 1-methylpiperazine using t-BuONa as base, 1E, and 8E. Compound 74A: LC-MS (ESI) m/z: 361 [M+H]$^+$. Compound 74B: LC-MS (ESI) m/z: 261 [M+H]$^+$. Compound 74C: LC-MS (ESI) m/z: 520 [M+H]$^+$. Compound 74D: LC-MS (ESI) m/z: 400 [M+H]$^+$. Compound 74: LC-MS (ESI) m/z: 372 [M+H]$^+$; $^1$H-NMR (DMSO-d$_6$, 400 MHz): δ (ppm) 1.53-1.56 (m, 2H), 1.99-2.02 (m, 2H), 2.82-2.88 (m, 2H), 3.51-3.53 (m, 1H), 3.63-3.66 (m, 2H), 7.01-7.03 (m, 2H), 7.16-7.18 (m, 2H).

Example 75

Synthesis of 4-((4'-chloro-[1,1'-biphenyl]-4-yl)(methyl)amino)-1H-1,2,3-triazole-5-carboxylic acid 2,2,2-trifluoroacetate (75)

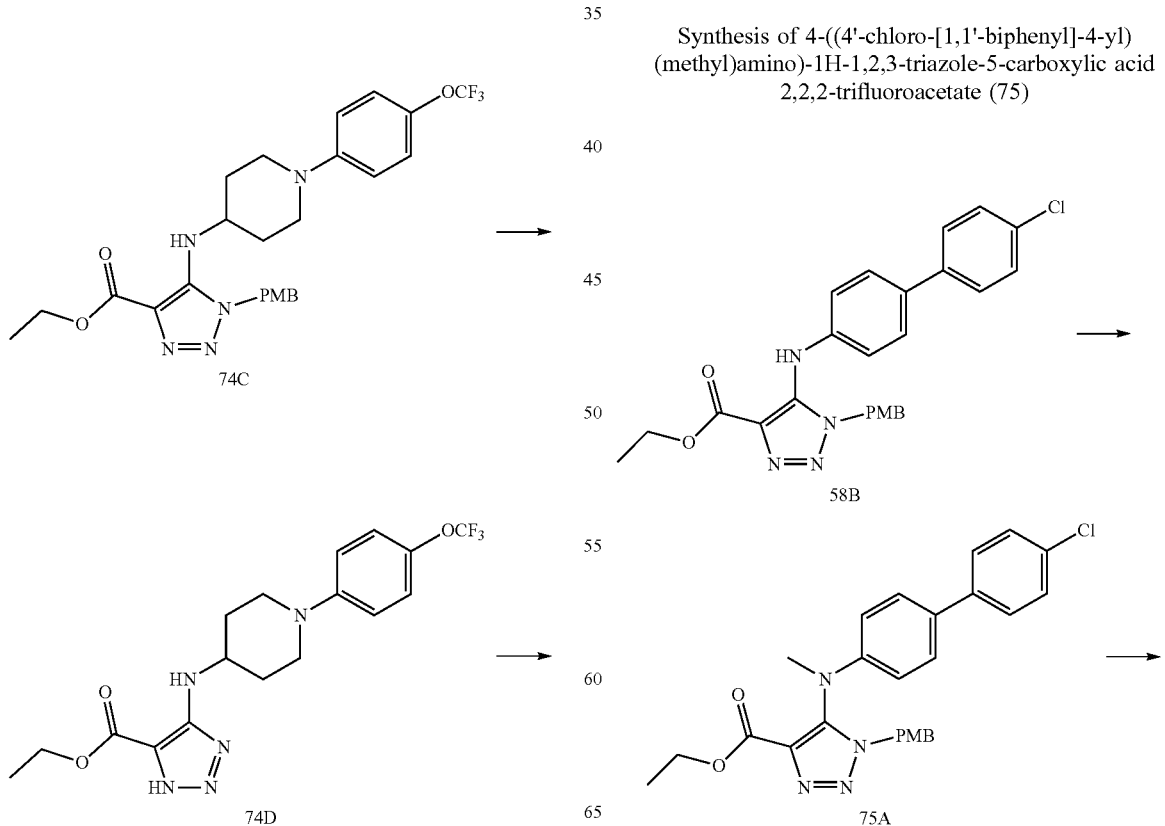

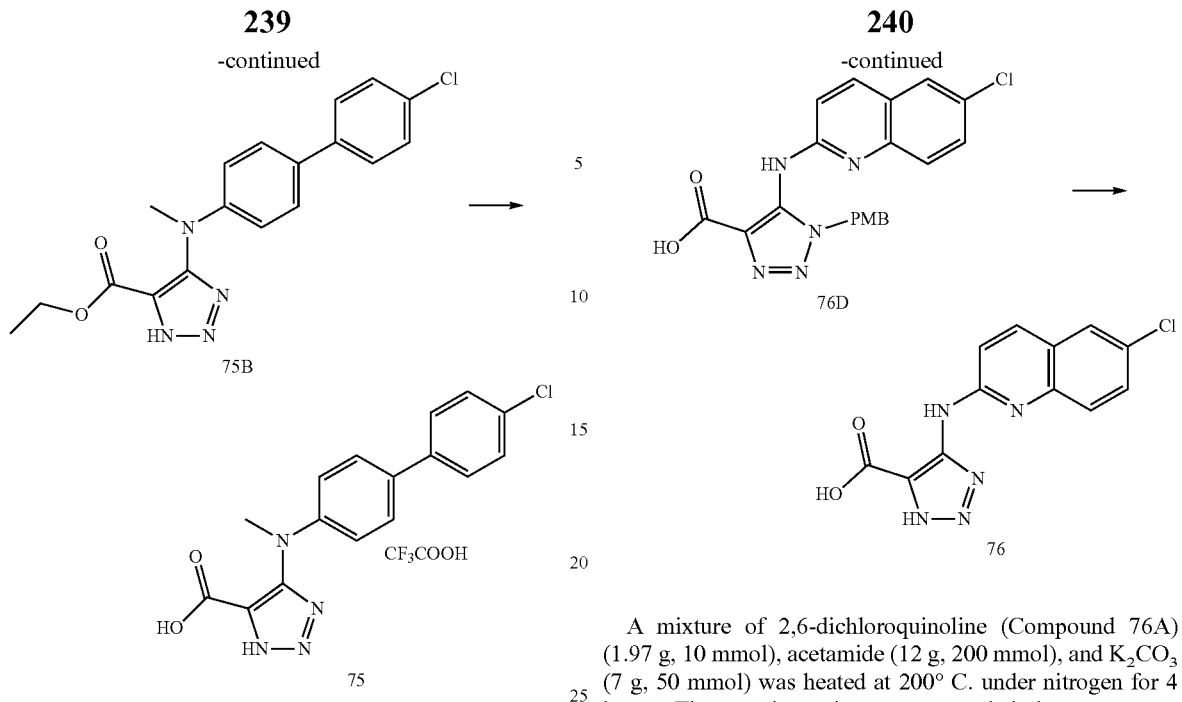

Compounds 75A, 75B, and 75 were synthesized by employing the procedures described for Compounds 63A, 1, and 8F using Compounds 58B using $K_2CO_3$ as base, 75A, and 75B in lieu of Compounds 61F using $Cs_2CO_3$ as base, 1E, and 8E. Compound 75A: LC-MS (ESI) m/z: 477 [M+H]$^+$. Compound 75B: LC-MS (ESI) m/z: 357 [M+H]$^+$. Compound 75: LC-MS (ESI) m/z: 329 [M+H]$^+$. $^1$H-NMR (DMSO-d$_6$, 400 MHz): δ (ppm) 3.28 (s, 3H), 6.77-6.79 (m, 2H), 7.44-7.46 (m, 2H), 7.51-7.53 (m, 2H), 7.61-7.63 (m, 2H).

Example 76

Synthesis of 4-((6-chloroquinolin-2-yl)amino)-1H-1,2,3-triazole-5-carboxylic acid (76)

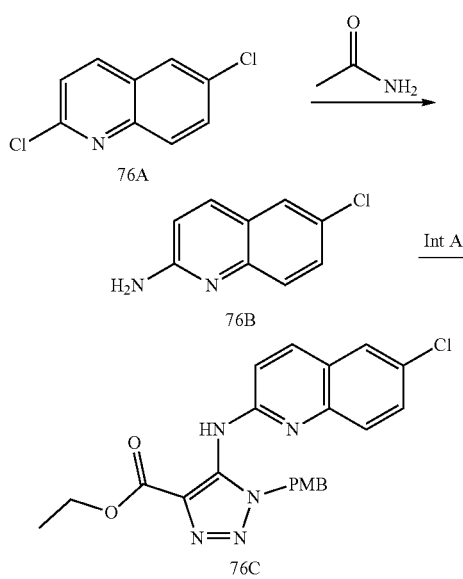

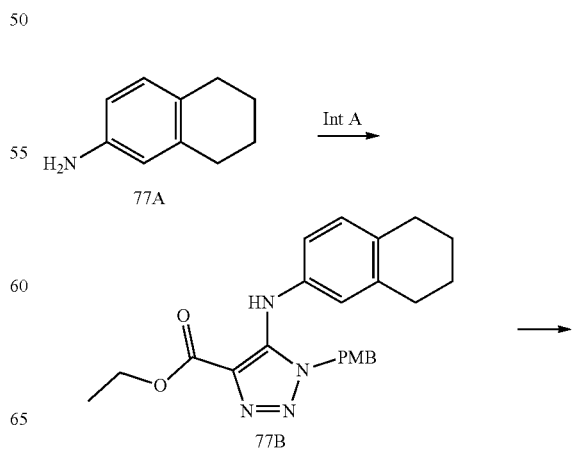

A mixture of 2,6-dichloroquinoline (Compound 76A) (1.97 g, 10 mmol), acetamide (12 g, 200 mmol), and $K_2CO_3$ (7 g, 50 mmol) was heated at 200° C. under nitrogen for 4 hours. The reaction mixture was cooled down to room temperature, diluted with $H_2O$ (200 mL), and extracted with ethyl acetate (50 mL×2). The combined extracts were dried over anhydrous sodium sulfate, filtered, and concentrated. The residue was purified with flash column chromatography on silica gel (ethyl acetate in petroleum ether, 30% v/v) to afford Compound 76B. LC-MS (ESI) m/z: 179 [M+H]$^+$.

Compounds 76C, 76D, and 76 were synthesized by employing the procedures described for Compounds 6B, 8F, and 1 using Intermediate A, Compounds 76B using $K_3PO_4$ as base, 76C, and 76D in lieu of Compounds 6A, 1-methylpiperazine using t-BuONa as base, 8E, and 1E. Compound 76C: LC-MS (ESI) m/z: 438 [M+H]$^+$. Compound 76D: LC-MS (ESI) m/z: 410 [M+H]$^+$. Compound 76: LC-MS (ESI) m/z: 290 [M+H]$^+$; $^1$H-NMR (DMSO-d$_6$, 400 MHz): δ (ppm) 7.61-7.64 (m, 1H), 7.85 (brs, 1H), 7.92 (d, J=2.4 Hz, 1H), 8.18-8.25 (m, 2H), 10.13 (brs, 1H).

Example 77

Synthesis of 4-((5,6,7,8-tetrahydronaphthalen-2-yl)amino)-1H-1,2,3-triazole-5-carboxylic acid (77)

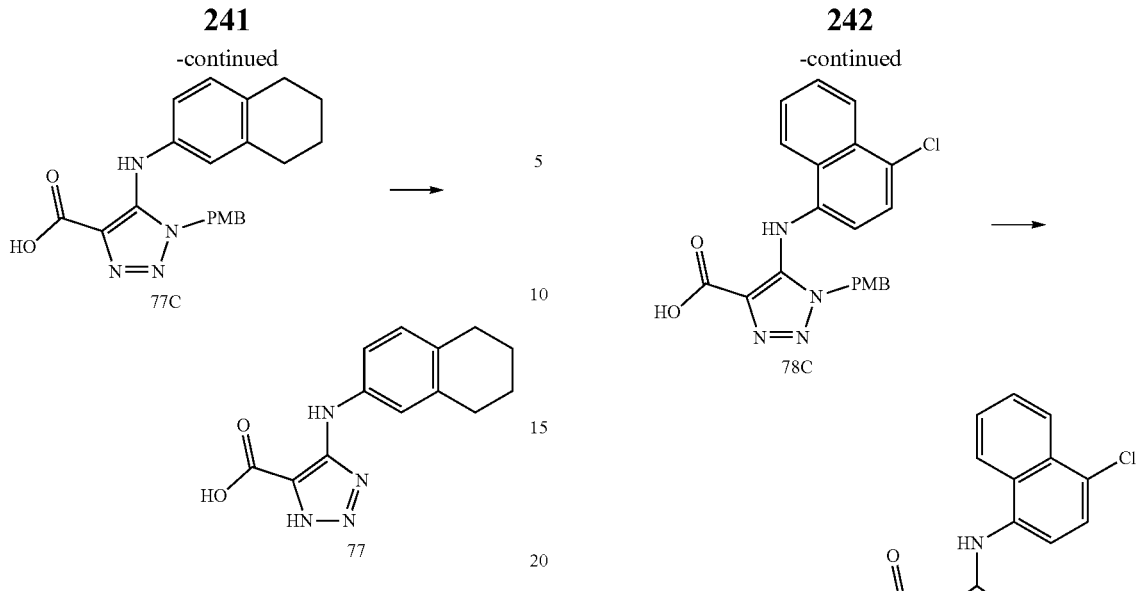

Compounds 77B, 77C, and 77 were synthesized by employing the procedures described for Compounds 6B, 8F, and 1 using Intermediate A, Compounds 77A using K$_3$PO$_4$ as base, 77B, and 77C in lieu of Compounds 6A, 1-methylpiperazine using t-BuONa as base, 8E, and 1E. Compound 77B: LC-MS (ESI) m/z: 407 [M+H]$^+$. Compound 77C: LC-MS (ESI) m/z: 379 [M+H]$^+$. Compound 77: LC-MS (ESI) m/z: 259 [M+H]$^+$; $^1$H-NMR (DMSO-d$_6$, 400 MHz): δ (ppm) 1.71-1.69 (m, 4H), 2.68-2.62 (m, 4H), 6.90 (d, J=8.4 Hz, 1H), 7.15 (d, J=10.4 Hz, 1H), 7.21 (s, 1H), 8.79 (s, 1H).

Example 78

Synthesis of 4-((4-chloronaphthalen-1-yl)amino)-1H-1,2,3-triazole-5-carboxylic acid (78)

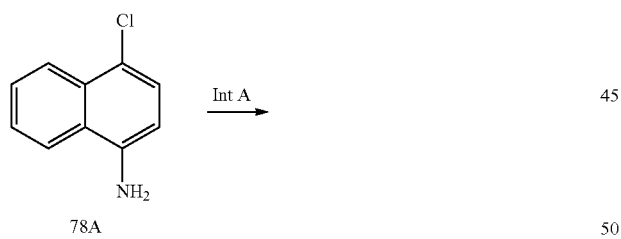

Compounds 78B, 78C, and 78 were synthesized by employing the procedures described for Compounds 6B, 8F, and 1 using Intermediate A, Compounds 78A using K$_3$PO$_4$ as base, 78B, and 78C in lieu of Compounds 6A, 1-methylpiperazine using t-BuONa as base, 8E, and 1E. Compound 78B: LC-MS (ESI) m/z: 437 [M+H]$^+$; $^1$H-NMR (CDCl$_3$, 400 MHz): δ 1.44 (t, J=7.2 Hz, 3H), 3.67 (s, 3H), 4.45 (q, J=7.2 Hz, 2H), 5.03 (s, 2H), 6.38-6.47 (m, 4H), 6.80 (d, J=7.6 Hz, 1H), 7.42 (d, J=8.0 Hz, 1H), 7.50-7.53 (m, 1H), 7.61-7.68 (m, 2H), 7.81 (d, J=8.0 Hz, 1H), 8.30 (d, J=8.8 Hz, 1H). Compound 78C: LC-MS (ESI) m/z: 409 [M+H]$^+$. Compound 78: LC-MS (ESI) m/z: 289 [M+H]$^+$; $^1$H-NMR (DMSO-d$_6$, 400 MHz): δ (ppm) 7.71 (d, J=8.4 Hz, 1H), 7.74-7.79 (m, 2H), 8.04-8.07 (m, 1H), 8.13-8.14 (m, 1H), 8.22-8.25 (m, 1H), 9.05 (s, 1H), 13.68 (s, 1H), 15.06 (s, 1H).

Example 79

Synthesis of 4-(benzo[d]thiazol-6-ylamino)-1H-1,2,3-triazole-5-carboxylic acid (79)

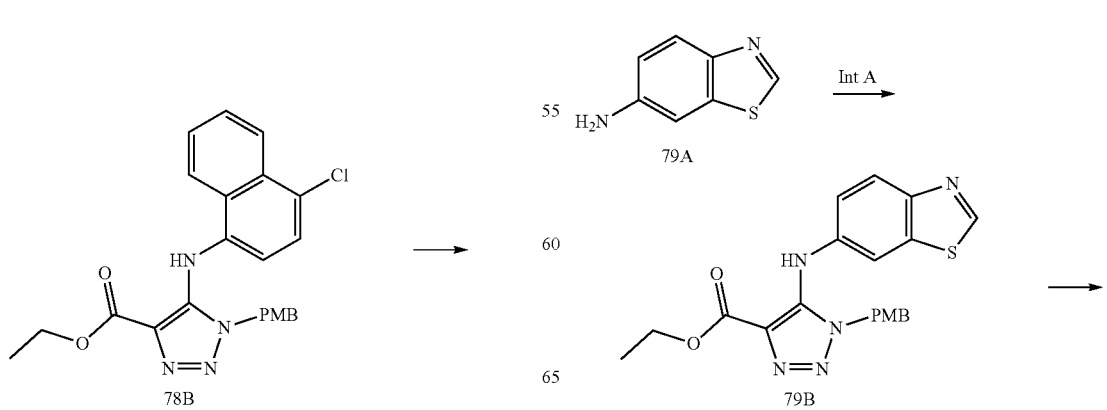

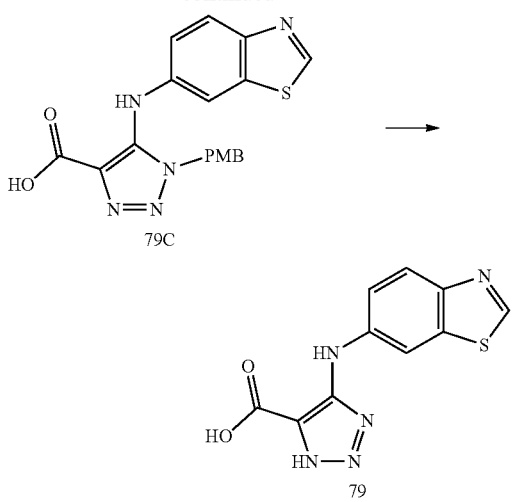

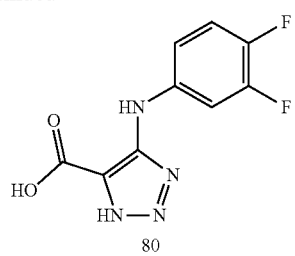

Compounds 79B, 79C, and 79 were synthesized by employing the procedures described for Compounds 6B, 8F, and 1 using Intermediate A, Compounds 79A using K₃PO₄ as base, 79B, and 79C in lieu of Compounds 6A, 1-methylpiperazine using t-BuONa as base, 8E, and 1E. Compound 79B: LC-MS: (ESI) m/z: 410 [M+H]⁺. Compound 79C: LC-MS (ESI) m/z: 382 [M+H]⁺. Compound 79: LC-MS (ESI) m/z: 262 [M+H]⁺; ¹H-NMR (DMSO-d₆, 400 MHz): δ (ppm) 7.67 (d, J=10.7 Hz, 1H), 7.97 (d, J=8.8 Hz, 1H), 8.43 (d, J=11.3 Hz, 2H), 9.16 (s, 1H), 13.52 (s, 1H), 14.96 (s, 1H).

Example 80

Synthesis of 4-((3,4-difluorophenyl)amino)-1H-1,2,3-triazole-5-carboxylic acid (80)

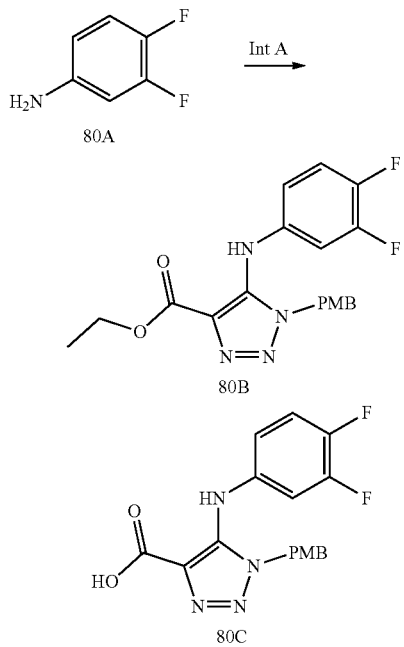

Compounds 80B, 80C, and 80 were synthesized by employing the procedures described for Compounds 6B, 8F, and 1 using Intermediate A, Compounds 80A using K₃PO₄ as base, 80B, and 80C in lieu of Compounds 6A, 1-methylpiperazine using t-BuONa as base, 8E, and 1E. Compound 80B: LC-MS: (ESI) m/z: 389 [M+H]⁺. Compound 80C: LC-MS (ESI) m/z: 361 [M+H]⁺. Compound 80: LC-MS (ESI) m/z: 241 [M+H]⁺; ¹H-NMR (DMSO-d₆, 400 MHz): δ (ppm) 7.28-7.41 (m, 2H), 7.71-7.76 (m, 1H), 8.34 (s, 1H), 13.37 (s, 1H), 14.96 (s, 1H).

Example 81

Synthesis of (pivaloyloxy)methyl 4-((4'-chloro-[1,1'-biphenyl]-4-yl)amino)-1H-1,2,3-triazole-5-carboxylate (81)

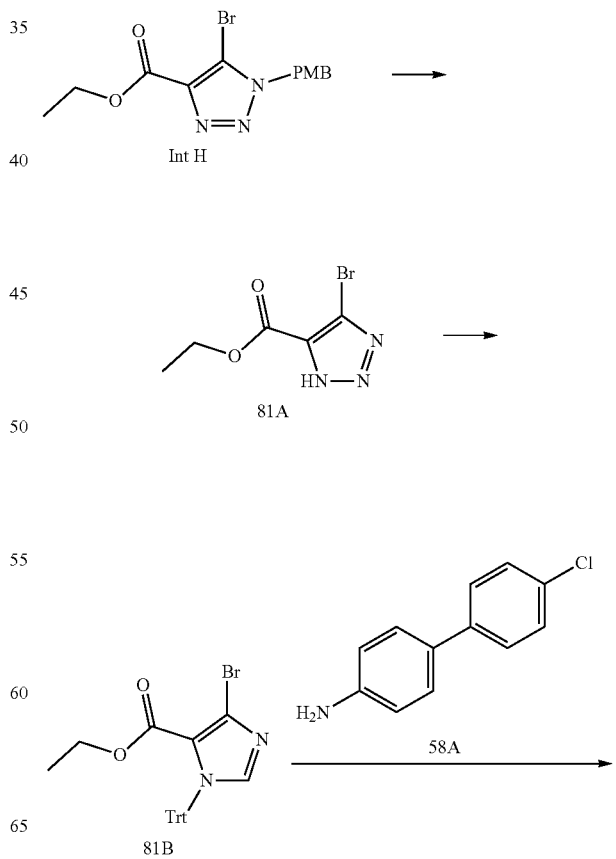

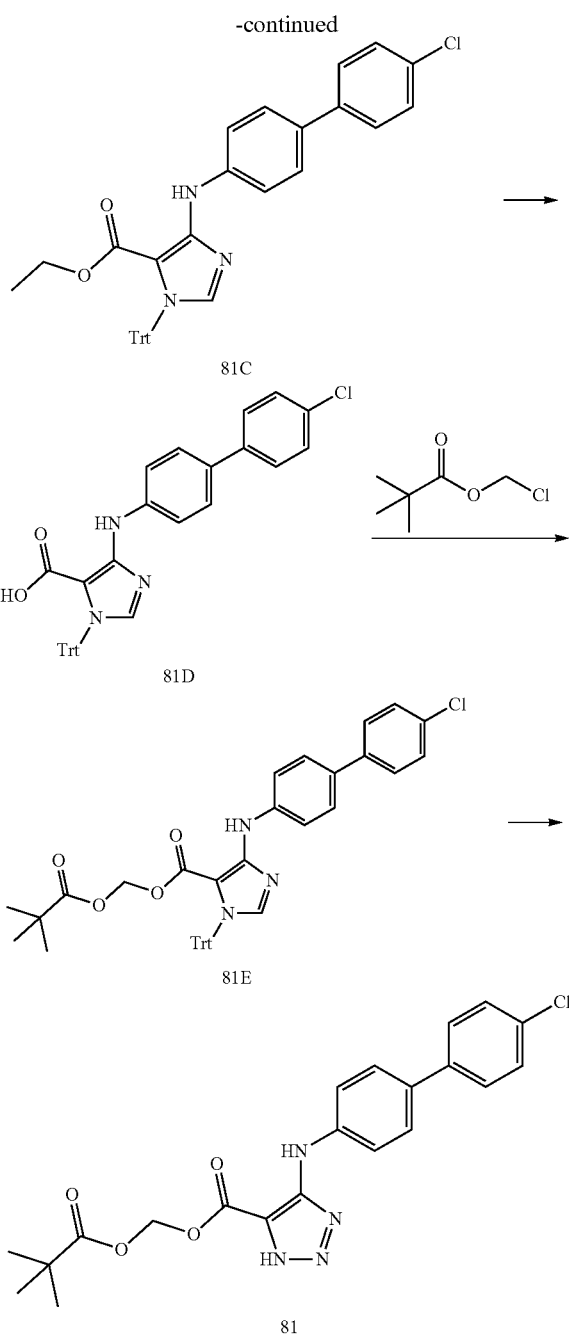

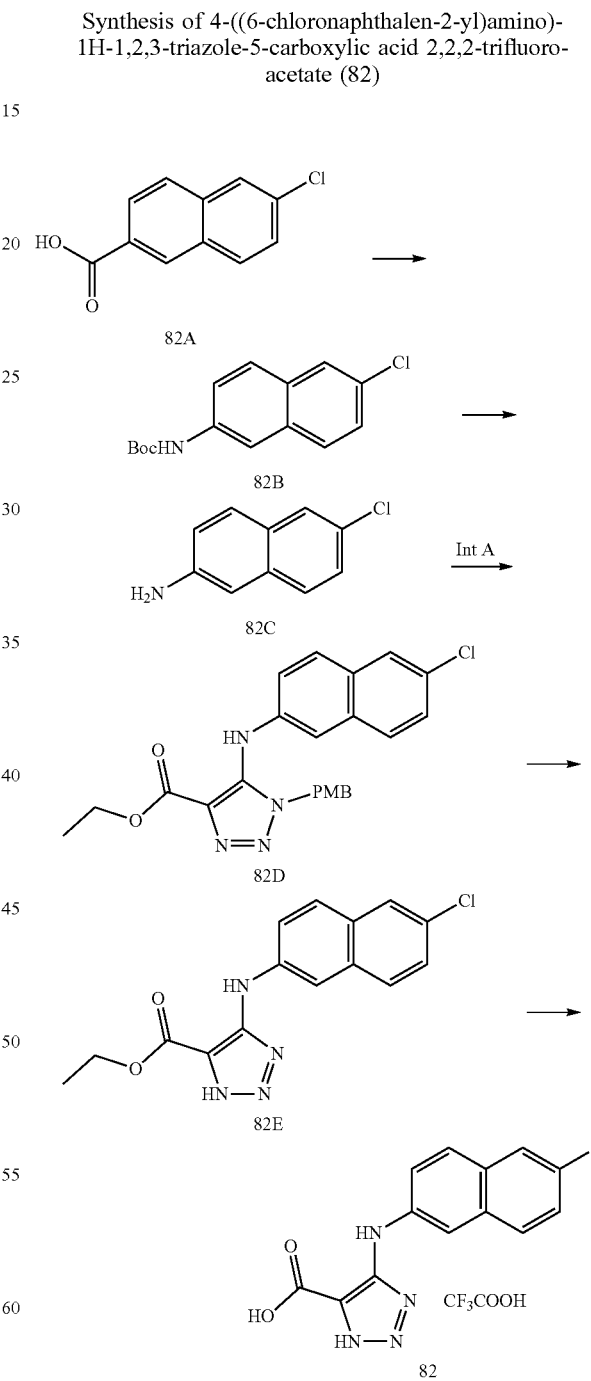

ylpiperazine using t-BuONa as base, 8E, 54B, and 1E. Compound 81C: LC-MS (ESI) m/z: 607 [M+Na]⁺. Compound 81D: LC-MS (ESI) m/z: 555. [M–H]⁺. Compound 81E: LC-MS (ESI) m/z: 669 [M–H]⁻. Compound 81: LC-MS (ESI) m/z: 429 [M+H]⁺; ¹H-NMR (DMSO-d$_6$, 400 MHz): δ (ppm) 1.16 (s, 9H), 5.97 (s, 2H), 7.47 (d, J=6.8 Hz, 2H), 7.62 (d, J=6.8 Hz, 2H), 7.67 (d, J=6.8 Hz, 2H), 7.71 (d, J=6.8 Hz, 2H), 8.18 (s, 1H).

Example 82

Synthesis of 4-((6-chloronaphthalen-2-yl)amino)-1H-1,2,3-triazole-5-carboxylic acid 2,2,2-trifluoroacetate (82)

Compound 81A was synthesized by employing the procedure described for Compound 1 using Intermediate A in lieu of Compound 1E, LC-MS (ESI) m/z: 220 [M+H]⁺.

To a solution of Compound 81A (2.3 g, 10.4 mmol) in CH$_3$CN (8 mL) was added TrtCl (2.9 g, 10.4 mmol) and Et$_3$N (2.17 g, 15.7 mmol). The mixture was stirred at room temperature for 18 hours and concentrated under reduced pressure. The residue was purified by flash column chromatography on silica gel (ethyl acetate in petroleum ether, 10% v/v) to afford Compound 81B. LC-MS (ESI) m/z: Non-ionizable compound under routine conditions used.

Compounds 81C, 81D, 81E, and 81 were synthesized by employing the procedures described for Compounds 6B, 8F, 54C, and 1 using Compounds 81B, 58A using K$_3$PO$_4$ as base, 81C, 81D, and 81E in lieu of Compounds 6A, 1-meth- Compounds 82B, 82C, 82D, 82E, and 82 were synthesized by employing the procedures described for Compounds 61D, 61E, 6B, 1, and 8F using Compounds 82A, 82B, Intermediate A, 82C using $K_3PO_4$ as base, 82D, and 82E in lieu of Compounds 61C, 61E, 6A, 1-methylpiperazine using t-BuONa as base, 1E, and 8E. Compound 82B: LC-MS (ESI) m/z: 276 [M–H]; $^1$H-NMR (DMSO-$d_6$, 400 MHz): δ (ppm) 1.51 (s, 9H), 7.43 (d, J=8.8 Hz, 1H), 7.54 (d, J=8.8 Hz, 1H), 7.81 (t, J=8.4 Hz, 2H), 7.91 (s, 1H), 8.13 (s, 1H), 9.64 (s, 1H). Compound 82C: LC-MS (ESI) m/z: 178 [M+H]$^+$; $^1$H-NMR (DMSO-$d_6$, 400 MHz): δ (ppm) 5.49 (s, 2H), 6.82 (d, J=2.0 Hz, 1H), 6.96 (d, J=8.8 Hz, 1H), 7.23 (s, J=8.8 Hz, 1H), 7.51-7.59 (m, 2H), 7.71 (d, J=2.0 Hz, 1H). Compound 82D: LC-MS (ESI) m/z: 437 [M+H]$^+$; (CDCl$_3$, 400 MHz): δ (ppm) 1.40 (t, J=8.8 Hz, 3H), 3.72 (s, 3H), 4.38-4.43 (m, 2H), 5.18 (s, 2H), 6.64 (d, J=8.8 Hz, 2H), 6.72 (d, J=8.8 Hz, 2H), 6.99 (s, 1H), 7.10 (d, J=8.4 Hz, 1H), 7.23 (s, 1H), 7.39 (d, J=8.8 Hz, 1H), 7.49 (d, J=8.8 Hz, 1H), 7.72 (d, J=8.8 Hz, 1H), 7.80 (s, 1H). Compound 82E: LC-MS (ESI) m/z: 317 [M+H]$^+$; $^1$H-NMR (DMSO-$d_6$, 400 MHz): δ (ppm) 1.35 (t, J=7.2 Hz, 3H), 4.34-4.42 (m, 2H), 7.42 (d, J=8.4 Hz, 1H), 7.70 (d, J=8.8 Hz, 1H), 7.80-7.85 (m, 2H), 7.92 (s, 1H), 8.22 (s, 1H), 8.40 (s, 1H), 15.12 (s, 1H). Compound 82: LC-MS (ESI) m/z: 289 [M+H]$^+$; $^1$H-NMR (DMSO-$d_6$, 400 MHz): δ (ppm) 7.42 (d, J=8.8 Hz, 1H), 7.68 (d, J=8.8 Hz, 1H), 7.82 (t, J=8.8 Hz, 2H), 7.92 (d, J=2.0 Hz, 1H), 8.21 (s, 1H), 8.47 (s, 1H).

Example 83

Synthesis of 4-((4-(trifluoromethoxy)phenyl)amino)-1H-1,2,3-triazole-5-carboxylic acid (83)

Compounds 83B, 83C, and 83 were synthesized by employing the procedures described for Compounds 6B, 8F, and 1 using Intermediate A, Compounds 83A using $K_3PO_4$ as base, 83B, and 83C in lieu of Compounds 6A, 1-methylpiperazine using t-BuONa as base, 8E, and 1E. Compound 83B: LC-MS (ESI) m/z: 437 [M+H]$^+$; $^1$H-NMR (DMSO-$d_6$, 400 MHz): δ (ppm) 0.96 (t, J=7.2 Hz, 3H), 3.69 (s, 3H), 4.02-4.07 (m, 2H), 5.40 (s, 2H), 6.69 (d, J=8.8 Hz, 2H), 6.84 (d, J=8.8 Hz, 2H), 7.09-7.16 (m, 4H), 8.67 (s, 1H). Compound 83C: LC-MS (ESI) m/z: 409 [M+H]$^+$; (CDCl$_3$, 400 MHz): δ (ppm) 3.67 (s, 3H), 5.18 (s, 2H), 6.70 (d, J=8.4 Hz, 2H), 6.78 (d, J=8.8 Hz, 2H), 6.95 (d, J=8.4 Hz, 2H), 7.12 (d, J=8.0 Hz, 2H). Compound 83: LC-MS (ESI) m/z: 289 [M+H]$^+$; $^1$H-NMR (DMSO-$d_6$, 400 MHz): δ (ppm) 7.28 (d, J=8.4 Hz, 2H), 7.68 (d, J=8.8 Hz, 2H), 8.34 (s, 1H), 13.42 (s, 1H), 15.01 (s, 1H).

Example 84

Synthesis of 4-(3,4-dihydroisoquinolin-2(1H)-yl)-1H-1,2,3-triazole-5-carboxylic acid 2,2,2-trifluoroacetate (84)

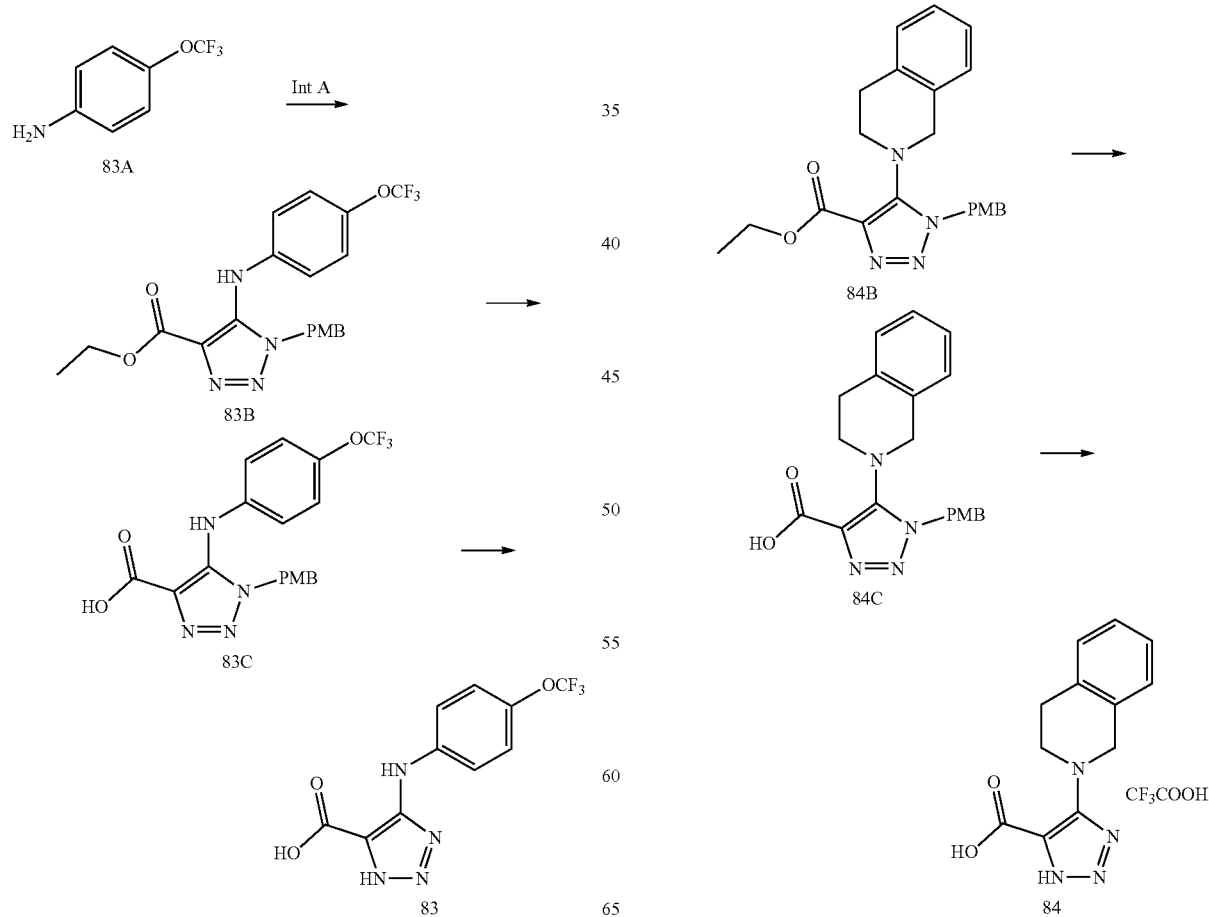

Compounds 84B, 84C, and 84 were synthesized by employing the procedures described for Compounds 6B, 8F, and 1 using Intermediate A, Compounds 84A using $Cs_2CO_2$ as base and 1,4-dioxane as solvent, 84B, and 84C in lieu of Compounds 6A, 1-methylpiperazine using t-BuONa as base and toluene as solvent, 8E, and 1E. Compound 84B: LC-MS (ESI) m/z: 393 [M+H]$^+$. Compound 84C: LC-MS (ESI) m/z: 365 [M+H]$^+$. Compound 84: LC-MS (ESI) m/z: 245 [M+H]$^+$; $^1$H-NMR (DMSO-d$_6$, 400 MHz): δ (ppm) 2.86-2.91 (m, 2H), 3.53-3.71 (m, 2H), 4.38-4.59 (m, 2H), 7.09-7.30 (m, 4H), 12.83 (brs, 1H), 14.78 (brs, 1H).

Example 85

Synthesis of 4-((6-bromonaphthalen-2-yl)amino)-1H-1,2,3-triazole-5-carboxylic acid 2,2,2-trifluoro-acetate (85)

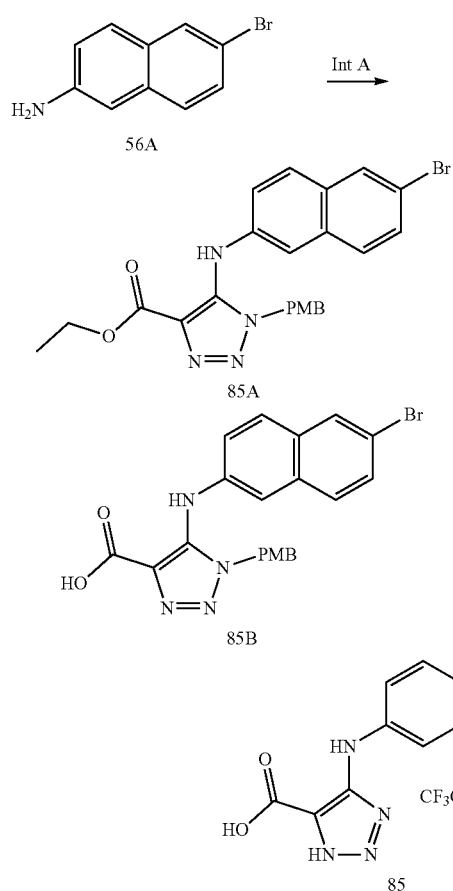

Compounds 85A, 85B, and 85 were synthesized by employing the procedures described for Compounds 6B, 8F, and 1 using Intermediate A, Compounds 56A using $K_3PO_4$ as base and DMF as solvent, 85A, and 85B in lieu of Compounds 6A, 1-methylpiperazine using t-BuONa as base and toluene as solvent, 8E, and 1E. Compound 85A: LC-MS (ESI) m/z: 481 [M+H]$^+$; $^1$H-NMR (CDCl$_3$, 400 MHz): δ (ppm) 1.40 (t, J=7.6 Hz, 3H), 3.72 (s, 3H), 4.38-4.43 (m, 2H), 5.19 (s, 2H), 6.64 (d, J=8.8 Hz, 2H), 6.73 (d, J=8.8 Hz, 2H), 6.98 (s, 1H), 7.07-7.10 (m, 1H), 7.42 (d, J=8.8 Hz, 1H), 7.52 (d, J=8.8 Hz, 1H), 7.71 (d, J=8.8 Hz, 1H), 7.97 (d, J=1.6 Hz, 1H). Compound 85B: LC-MS (ESI) m/z: 453 [M+H]$^+$; $^1$H-NMR (CDCl$_3$, 400 MHz): δ (ppm) 3.30 (s, 3H), 5.20 (s, 2H), 6.77 (d, J=8.4 Hz, 2H), 6.83 (s, 1H), 6.95 (d, J=8.4 Hz, 2H), 7.21 (d, J=8.8 Hz, 1H), 7.46 (d, J=6.8 Hz, 1H), 7.56 (d, J=8.8 Hz, 1H), 7.77 (d, J=8.8 Hz, 1H), 8.05 (d, J=1.6 Hz, 1H). Compound 85: LC-MS (ESI) m/z: 333 [M+H]$^+$; $^1$H-NMR (DMSO-d$_6$, 400 MHz): δ (ppm) 7.53 (d, J=8.8 Hz, 1H), 7.68 (d, J=8.8 Hz, 1H), 7.71 (d, J=8.8 Hz, 1H), 7.83 (d, J=8.8 Hz, 1H), 8.07 (s, 1H), 8.20 (s, 1H), 8.46 (s, 1H), 13.39 (s, 1H), 15.01 (s, 1H).

Example 86

Synthesis of 4-((4'-chloro-[1,1'-biphenyl]-4-yl)oxy)-1H-1,2,3-triazole-5-carboxylic acid (86)

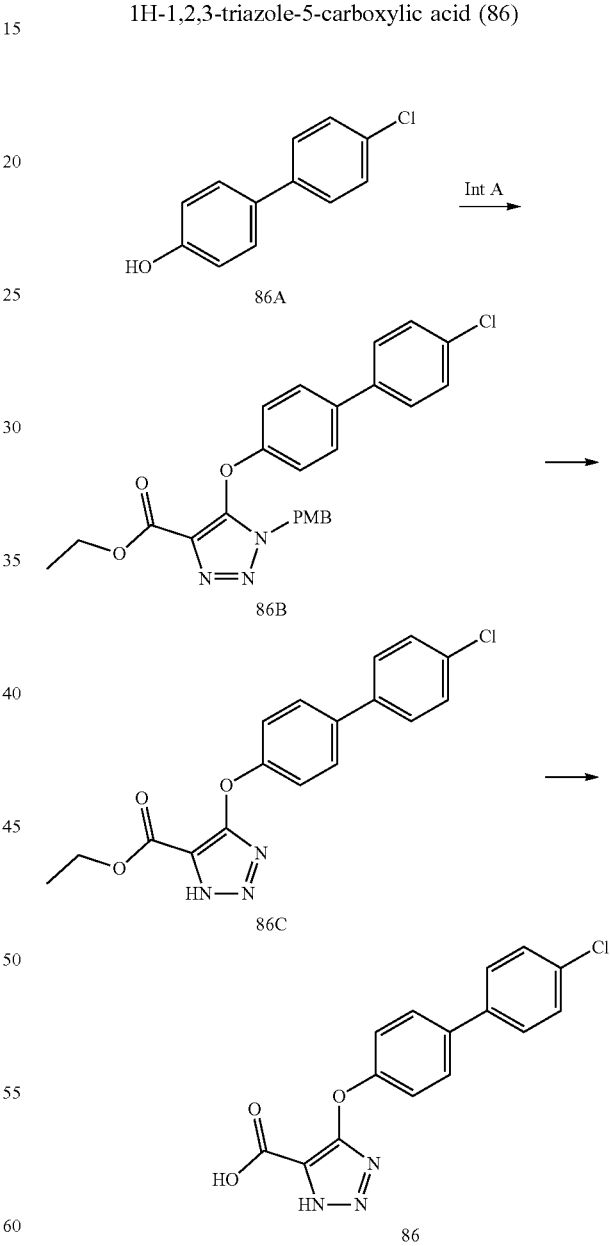

To a solution of 4'-chlorobiphenyl-4-ol (86A) (200 mg, 1 mmol) in DMF (100 mL) was added sodium hydride (60% in mineral oil, 40 mg, 1 mmol) under N$_2$ at 0° C. and stirred at for 30 minutes. To the mixture was added Intermediate A (340 mg, 1 mmol) and stirred at 90° C. for 16 hours. The mixture was cooled down to room temperature, diluted with ethyl acetate (50 mL), washed with water (50 mL) and brine (50 mL×3), dried over anhydrous sodium sulfate, filtered, and concentrated. The residue was purified with flash column chromatography on silica gel (ethyl acetate in petroleum ether, from 0% to 27% v/v) to give Compound 86B. LC-MS (ESI) m/z: 464 [M+H]+.

Compounds 86C and 86 were synthesized by employing the procedures described for Compounds 1 and 8F using Compounds 86B and 86C in lieu of Compounds 1E and 8E. Compound 86C: LC-MS (ESI) m/z: 344 [M+H]+. Compound 86: LC-MS (ESI) m/z: 316 [M+H]+; $^1$H-NMR (DMSO-d$_6$, 400 MHz): δ (ppm) 7.15 (d, J=8.8 Hz, 2H), 7.50 (d, J=8.4 Hz, 2H), 7.66 (dd, J=8.8, 2.4 Hz, 4H).

Example 87

Synthesis of 4-((4'-(trifluoromethoxy)-[1,1'-biphenyl]-4-yl)oxy)-1H-1,2,3-triazole-5-carboxylic acid (87)

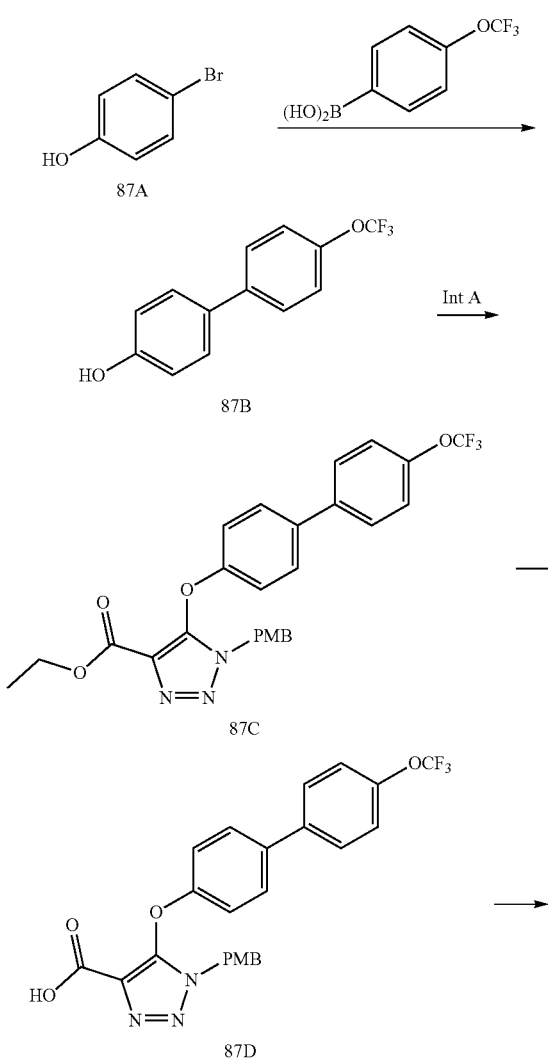

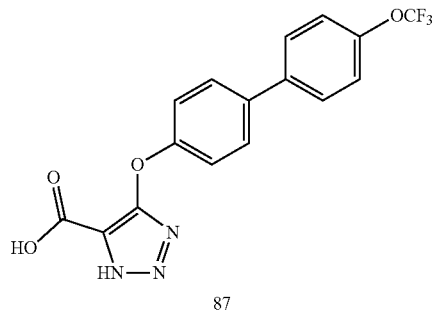

Compounds 87B, 87C, 87D, and 87 were synthesized by employing the procedures described for Compounds 4B, 86B, 8F, and 1 using (4-(trifluoromethoxy)phenyl)boronic acid, Compounds 87A using DME and H$_2$O as solvent, 87B, 87C, and 87D in lieu of (4-bromophenyl)boronic acid, Compounds 4A using toluene/EtOH/H$_2$O as solvent, 86A, 8E, and 1E. Compound 87B: LC-MS (ESI) m/z: 255 [M+H]+; $^1$H-NMR (CDCl$_3$, 400 MHz): δ (ppm) 4.82 (s, 1H), 6.90-6.92 (m, 2H), 7.25-7.27 (m, 2H), 7.43-7.46 (m, 2H), 7.52-7.55 (m, 2H). Compound 87C: LC-MS (ESI) m/z: 514 [M+H]+; $^1$H-NMR (CDCl$_3$, 400 MHz): δ (ppm) 1.12 (t, J=7.2 Hz, 3H), 3.73 (s, 3H), 4.21 (q, J=7.2 Hz, 2H), 5.38 (s, 2H), 6.76-6.79 (m, 2H), 6.81-6.84 (m, 2H), 7.20-7.23 (m, 2H), 7.26-7.30 (m, 2H), 7.41-7.45 (m, 2H), 7.51-7.54 (m, 2H). Compound 87D: LC-MS: (ESI) m/z: 486 [M+H]+; $^1$H-NMR (DMSO-d$_6$, 400 MHz): δ (ppm) 3.68 (s, 3H), 5.40 (s, 2H), 6.83-6.85 (m, 2H), 6.95-6.97 (m, 2H), 7.16-7.18 (m, 2H), 7.43-7.47 (m, 2H), 7.60-7.63 (m, 2H), 7.73-7.75 (m, 2H). Compound 87: LC-MS (ESI) m/z: 366 [M+H]+; $^1$H-NMR (DMSO-d$_6$, 400 MHz): δ (ppm) 7.14-7.18 (m, 2H), 7.44 (d, J=8.0 Hz, 2H), 7.66-7.70 (m, 2H), 7.75-7.79 (m, 2H).

Example 88

Synthesis of 4-(3,4-dichlorophenoxy)-1H-1,2,3-triazole-5-carboxylic acid (88)

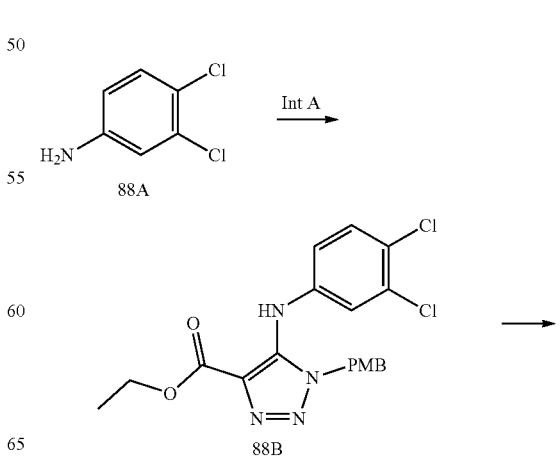

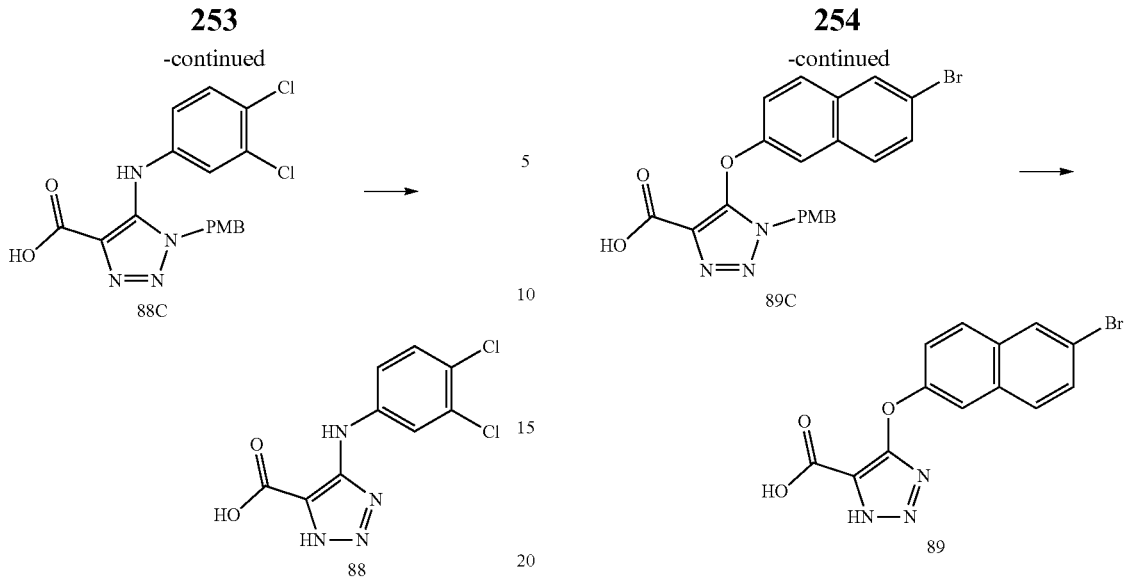

Compounds 88B, 88C, and 88 were synthesized by employing the procedures described for Compounds 86B, 8F, and 1 using Compounds 88A, 88B, and 88C in lieu of Compounds 86A, 8E, and 1E. Compound 88B: LC-MS (ESI) m/z: 422 [M+H]$^+$; $^1$H-NMR (CDCl$_3$, 400 MHz): δ (ppm) 1.17 (t, J=7.2 Hz, 3H), 3.76 (s, 3H), 4.23 (q, J=7.2 Hz, 2H), 5.38 (s, 2H), 6.58 (dd, J=8.8, 2.8 Hz, 1H), 6.70 (d, J=2.8 Hz, 1H), 6.75-6.77 (m, 2H), 7.15-7.17 (m, 2H), 7.28 (d, J=8.8 Hz, 1H). Compound 88C: LC-MS: (ESI) m/z: 394 [M+H]$^+$; $^1$H-NMR (DMSO-d$_6$, 400 MHz): δ (ppm) 3.70 (s, 3H), 5.43 (s, 2H), 6.81-6.83 (m, 2H), 7.10-7.12 (m, 1H), 7.15-7.17 (m, 2H), 7.37 (d, J=2.8 Hz, 1H), 7.64 (d, J=8.8 Hz, 1H), 13.24 (brs, 1H). Compound 88: LC-MS (ESI) m/z: 274 [M+H]$^+$; $^1$H-NMR (DMSO-d$_6$, 400 MHz): δ (ppm) 7.11 (dd, J=8.8, 2.8 Hz, 1H), 7.46 (d, J=2.8 Hz, 1H), 7.62 (d, J=8.8 Hz, 1H).

Compounds 89B, 89C, and 89 were synthesized by employing the procedures described for Compounds 86B, 8F, and 1 using Compounds 89A, 89B, and 89C in lieu of Compounds 86A, 8E, and 1E. Compound 89B: LC-MS (ESI) m/z: 482 [M+H]$^+$; $^1$H-NMR (CDCl$_3$, 400 MHz): δ (ppm) 1.03 (t, J=7.2 Hz, 3H), 3.65 (s, 3H), 4.14 (q, J=7.2 Hz, 2H), 5.39 (s, 2H), 6.67-6.69 (m, 2H), 6.76 (d, J=2.8 Hz, 1H), 7.14-7.26 (m, 3H), 7.40 (d, J=8.8 Hz, 1H), 7.52 (dd, J=8.8 Hz, 2.0 Hz, 1H), 7.70 (d, J=8.8 Hz, 1H), 7.96 (d, J=2.0 Hz, 1H). Compound 89C: LC-MS: (ESI) m/z: 454 [M+H]$^+$; $^1$H-NMR (DMSO-d$_6$, 400 MHz): δ (ppm) 3.62 (s, 3H), 5.43 (s, 2H), 6.76-6.78 (m, 2H), 7.14-7.17 (m, 3H), 7.34 (dd, J=8.8, 2.4 Hz, 1H), 7.60 (dd, J=8.8, 2.0 Hz, 1H), 7.73 (d, J=8.8 Hz, 1H), 7.92 (d, J=8.8 Hz, 1H), 8.20 (d, J=2.0 Hz, 1H). Compound 89: LC-MS (ESI) m/z: 334 [M+H]$^+$; $^1$H-NMR (DMSO-d$_6$, 400 MHz): δ (ppm) 7.43 (dd, J=8.8, 2.4 Hz, 1H), 7.49 (d, J=2.0 Hz, 1H), 7.62 (dd, J=8.8, 2.0 Hz, 1H), 7.83 (d, J=8.8 Hz, 1H), 7.96 (d, J=8.8 Hz, 1H), 8.21 (d, J=2.0 Hz, 1H).

Example 89

Synthesis of 4-((6-bromonaphthalen-2-yl)oxy)-1H-1,2,3-triazole-5-carboxylic acid (89)

Example 90

Synthesis of 4-((1-(4-(trifluoromethoxy)phenyl)pyrrolidin-3-yl)oxy)-1H-1,2,3-triazole-5-carboxylic acid (90)

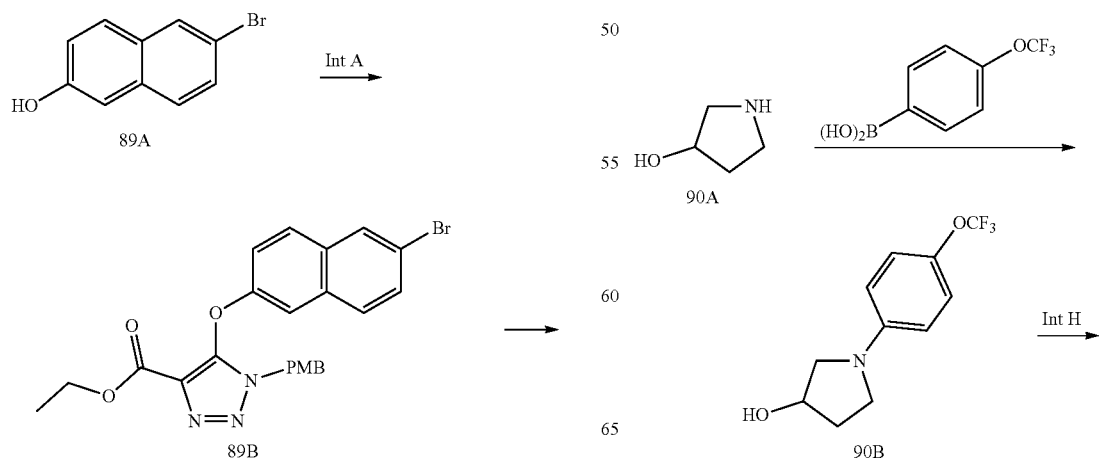

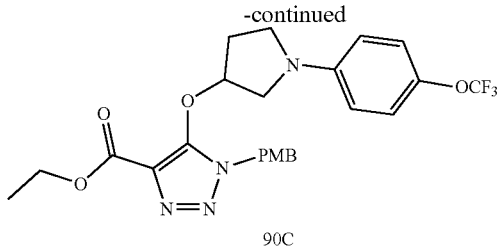

90C

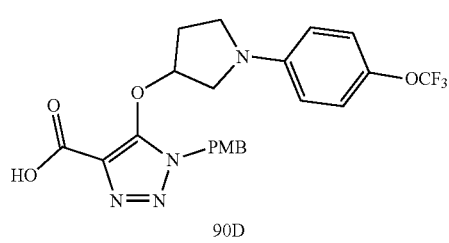

90D

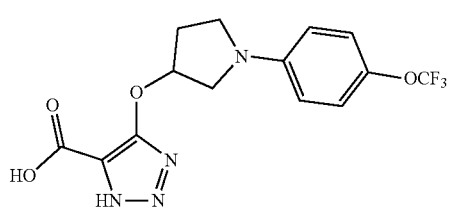

90

The mixture of 4-(trifluoromethoxy)phenylboronic acid (1.5 g, 7.28 mmol), pyrrolidin-3-ol (Compound 90A) (0.63 g, 7.28 mmol), Cu(OAc)$_2$ (1.57 g, 8.75 mmol), and K$_3$PO$_4$ (3.09 g, 14.58 mmol) in DMSO (20 mL) was stirred at 90° C. overnight. The reaction mixture was cooled down to room temperature, diluted with water (50 mL), and extracted with EtOAc (50 mL×3). The combined extracts were dried over anhydrous sodium sulfate, filtered, and concentrated. The residue was purified by column chromatography on silica gel (ethyl acetate in petroleum ether, 40% v/v) to furnish Compound 90B. LC-MS (ESI) m/z: 248 [M+H]$^+$.

A mixture of Compound 90B (100 mg, 0.40 mmol), Intermediate 11 (93 mg, 0.34 mmol), and PPh$_3$ (132 mg, 0.51 mmol) in dry THF (5 mL) was dropped DIAD (103 mg, 0.51 mmol) at 0° C. and stirred at room temperature overnight. The mixture was concentrated to give a product, which was purified by column chromatography on silica gel (ethyl acetate in petroleum ether, 30% v/v) to furnish Compound 90C. LC-MS (ESI) m/z: 507 [M+H]$^+$.

Compounds 90D and 90 were synthesized by employing the procedures described for Compounds 8F and 1 using Compounds 90C and 90D in lieu of Compounds 8E and 1E. Compound 90D: LC-MS (ESI) m/z: 479 [M+H]$^+$. Compound 90: LC-MS (ESI) m/z: 359 [M+H]$^+$; $^1$H-NMR (DMSO-d$_6$, 400 MHz): δ (ppm) 2.27-2.35 (m, 2H), 3.38-3.45 (m, 3H), 3.64-3.68 (m, 1H), 5.35 (s, 1H), 6.59 (d, J=6.8 Hz, 2H), 7.15 (d, J=8.4 Hz, 2H), 12.82 (s, 1H), 14.81 (s, 1H).

Example 91

Synthesis of 4-(3,5-dichlorophenoxy)-1H-1,2,3-triazole-5-carboxylic acid (91)

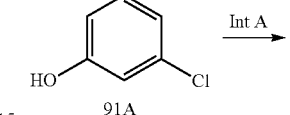

91A

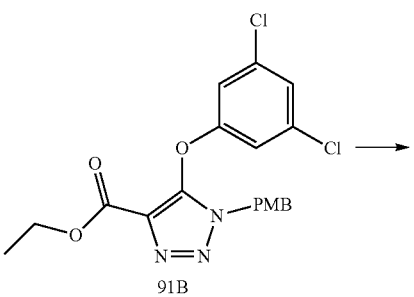

91B

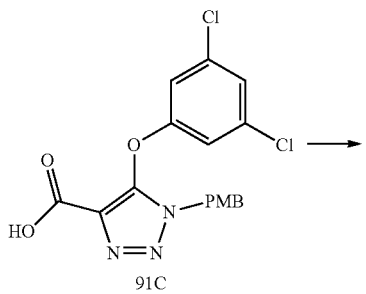

91C

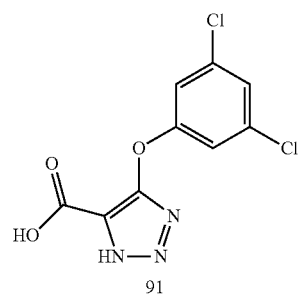

91

Compounds 91B, 91C, and 91 were synthesized by employing the procedures described for Compounds 86B, 8F, and 1 using Compounds 91A, 91B, and 91C in lieu of Compounds 86A, 8E, and 1E. Compound 91B: LC-MS (ESI) m/z: 422 [M+H]$^+$. Compound 91C: LC-MS (ESI) m/z: 392 [M−H]$^+$. Compound 91: LC-MS (ESI) m/z: 272 [M−H]$^−$; $^1$H-NMR (DMSO-d$_6$, 400 MHz): δ (ppm) 7.23 (d, J=1.6 Hz, 2H), 7.42 (d, J=1.6 Hz, 1H).

Example 92

Synthesis of 4-((4-chloronaphthalen-1-yl)oxy)-1H-1,2,3-triazole-5-carboxylic acid (92)

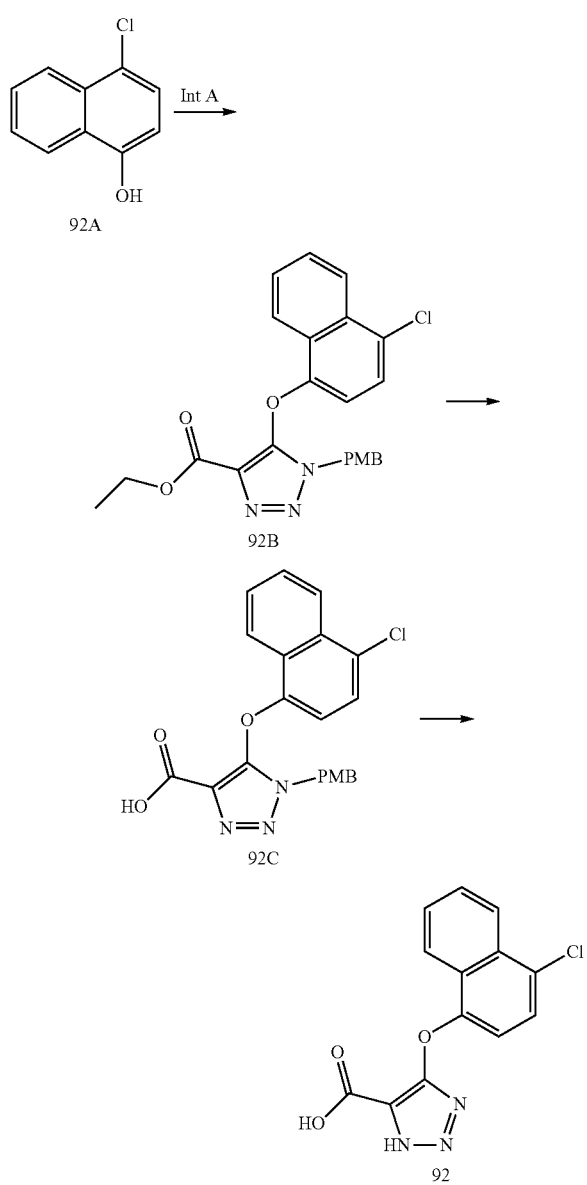

Compounds 92B, 92C, and 92 were synthesized by employing the procedures described for Compounds 86B, 8F, and 1 using Compounds 92A, 92B, and 92C in lieu of Compounds 86A, 8E, and 1E. Compound 92B: LC-MS (ESI) m/z: 438 [M+H]$^+$. Compound 92C: LC-MS (ESI) m/z: 410 [M+H]$^+$. Compound 92: LC-MS (ESI) m/z: 290 [M+H]$^+$. $^1$H-NMR (400 MHz, DMSO-d$_6$): δ (ppm) 7.11 (d, J=8.4 Hz, 1H), 7.64 (d, J=8.0 Hz, 1H), 7.73 (t, J=8.0 Hz, 1H), 7.79 (t, J=8.0 Hz, 1H), 8.21 (d, J=8.0 Hz, 1H), 8.29 (d, J=8.4 Hz, 1H).

Example 93

Synthesis of methyl 4-((6-bromonaphthalen-2-yl)oxy)-1H-1,2,3-triazole-5-carboxylate (93)

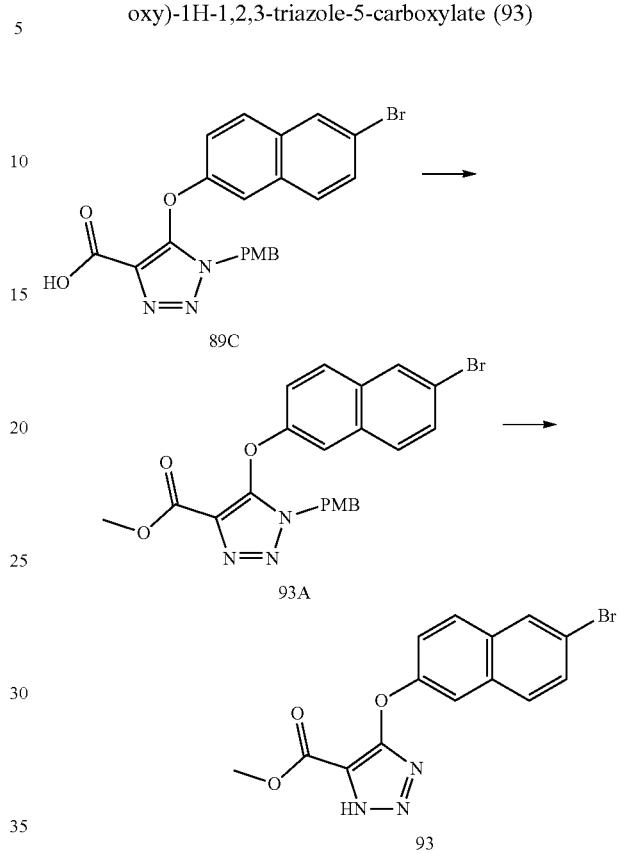

To a solution of Compound 89C (60 mg, 0.132 mmol) in CH$_3$CN (10 mL) and MeOH (10 mL) was added a solution of TMSCHN$_2$ in hexane (2 M, 0.2 mL, 0.41 mmol) at 0° C. and stirred at room temperature for 3 hours. The reaction mixture was concentrated under reduced pressure. The residue was used directly for next step without further purification. LC-MS (ESI) m/z: 468 [M+H]$^+$.

Compound 93 was synthesized by employing the procedure described for Compound 1 using Compound 93A in lieu of Compound 1E, LC-MS (ESI) m/z: 348 [M+H]$^+$; $^1$H-NMR (DMSO-d$_6$, 400 MHz): δ (ppm) 3.76 (s, 3H), 7.44 (dd, J=8.8, 2.4 Hz, 1H), 7.55 (d, J=2.8 Hz, 1H), 7.63 (dd, J=8.8, 2.0 Hz, 1H), 7.83 (d, J=8.8 Hz, 1H), 7.96 (d, J=8.8 Hz, 1H), 8.23 (d, J=1.6 Hz, 1H).

Example 94

Synthesis of 4-(3,4-difluorophenoxy)-1H-1,2,3-triazole-5-carboxylic acid (94)

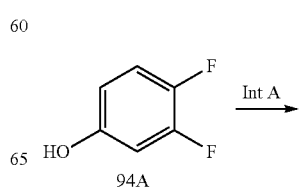

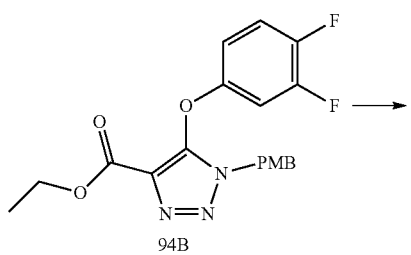

94B

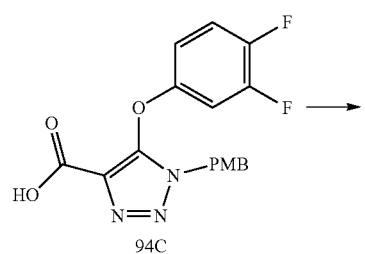

94C

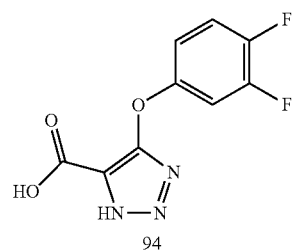

94

Compounds 94B, 94C, and 94 were synthesized by employing the procedures described for Compounds 86B, 8F, and 1 using Compounds 94A, 94B, and 94C in lieu of Compounds 86A, 8E, and 1E. Compound 94B: LC-MS: (ESI) m/z: 801 [2M+Na]$^+$. Compound 94C: LC-MS (ESI) m/z: 745 [2M+Na]$^+$. Compound 94: LC-MS (ESI) m/z: 242 [M+H]$^+$; $^1$H-NMR (DMSO-d$_6$, 400 MHz): δ (ppm) 6.92-6.97 (m, 1H), 7.30-7.36 (m, 1H), 7.40-7.47 (m, 1H).

Example 95

Synthesis of 4-(2,4-dichlorophenoxy)-1H-1,2,3-triazole-5-carboxylic acid (95)

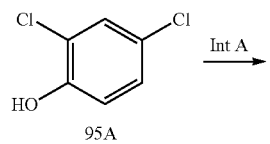

95A

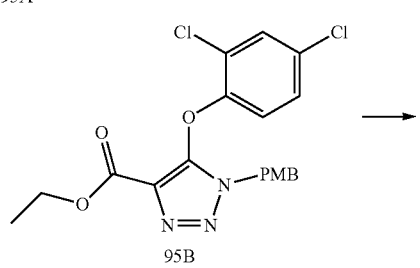

95B

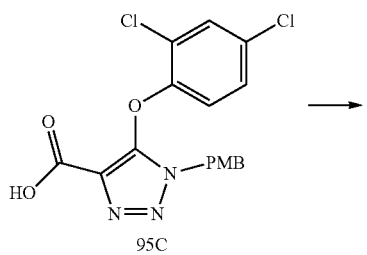

95C

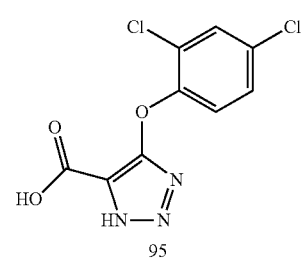

95

Compounds 95B, 95C, and 95 were synthesized by employing the procedures described for Intermediate I, Compounds 8F, and 1 using Compounds 95A, 95B, and 95C in lieu of 4-bromophenol, Compounds 8E, and 1E. Compound 95B: LC-MS (ESI) m/z: 422 [M+H]$^+$. Compound 95C: LC-MS (ESI) m/z: 392 [M−H]$^-$. Compound 95: LC-MS (ESI) m/z: 272 [M−H]$^-$; $^1$H-NMR (DMSO-d$_6$, 400 MHz): δ (ppm) 7.20 (d, J=9.2 Hz, 1H), 7.41 (dd, J=9.2, 2.4 Hz, 1H), 7.77 (d, J=2.4 Hz, 1H).

Example 96

Synthesis of 4-(4-(trifluoromethoxy)phenoxy)-1H-1,2,3-triazole-5-carboxylic acid (96)

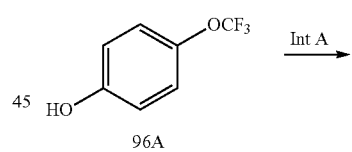

96A

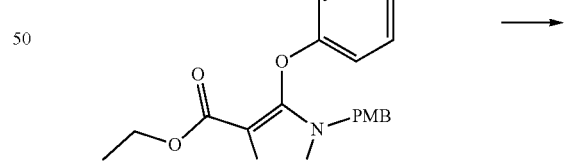

96B

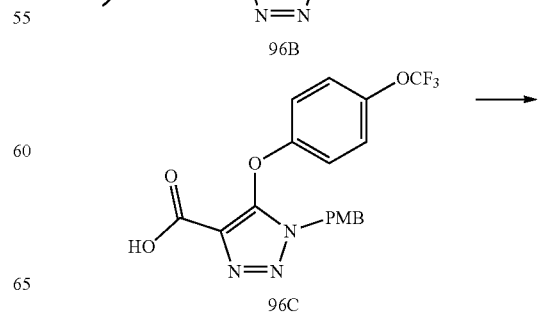

96C

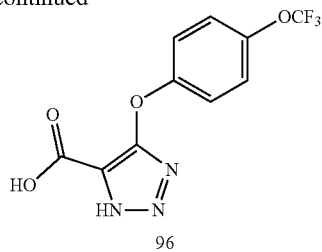

Compounds 96B, 96C, and 96 were synthesized by employing the procedures described for Compounds 86B, 8F, and 1 using Compounds 96A, 96B, and 96C in lieu of Compounds 86A, 8E, and 1E. Compound 96B: LC-MS: (ESI) m/z: 438 [M+H]$^+$. Compound 96C: LC-MS (ESI) m/z: 432 [M+Na]t Compound 96: LC-MS (ESI) m/z: 290 [M+H]$^+$; $^1$H-NMR (DMSO-d$_6$, 400 MHz): δ (ppm) 7.17-7.19 (m, 2H), 7.38 (d, J=8.4 Hz, 2H).

Example 97

Synthesis of 4-((5,6,7,8-tetrahydronaphthalen-2-yl)oxy)-1H-1,2,3-triazole-5-carboxylic acid (97)

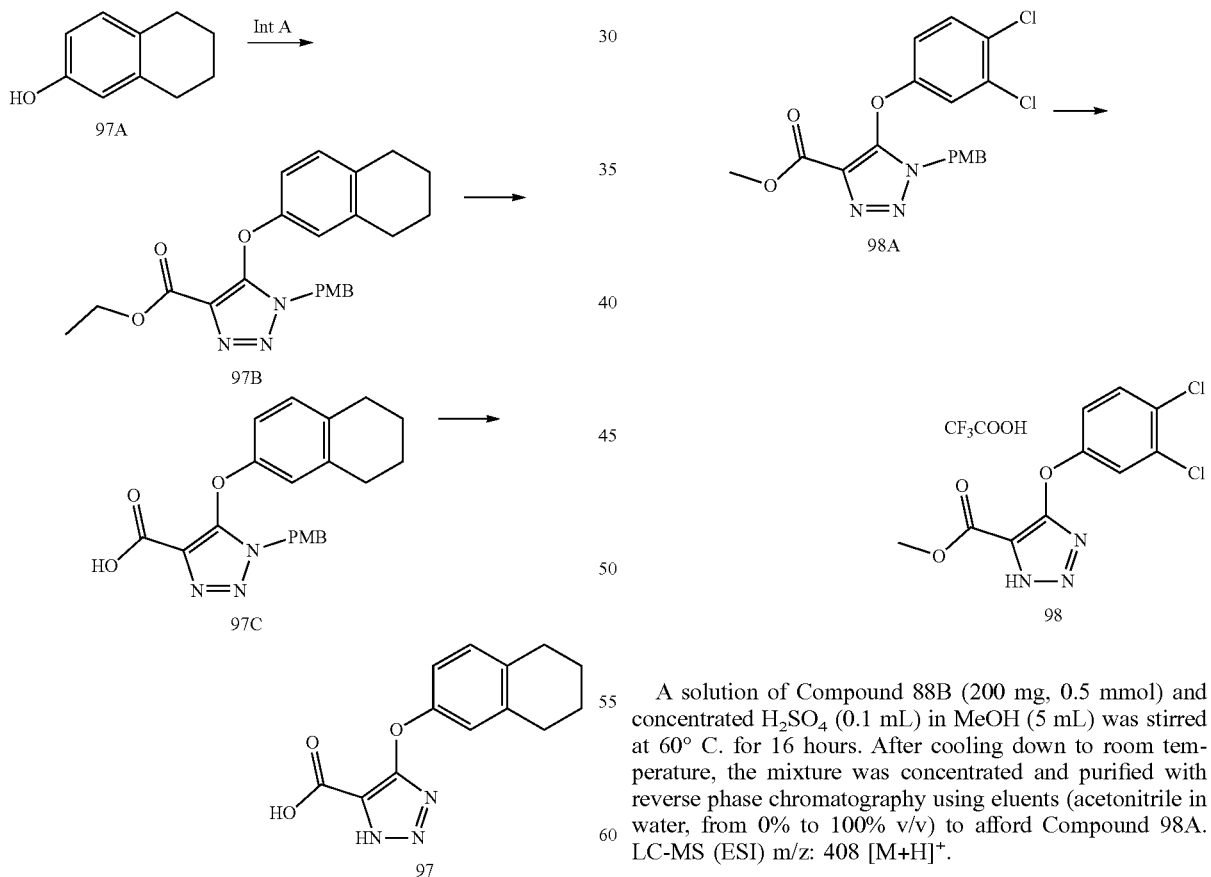

Compounds 97B, 97C, and 97 were synthesized by employing the procedures described for Compounds 86B, 8F, and 1 using Compounds 97A, 97B, and 97C in lieu of Compounds 86A, 8E, and 1E. Compound 97B: LC-MS (ESI) m/z: 408 [M+H]$^+$. Compound 97C: LC-MS (ESI) m/z: 380 [M+H]$^+$. Compound 97: LC-MS (ESI) m/z: 260 [M+H]$^+$. $^1$H-NMR (DMSO-d$_6$, 400 MHz): δ (ppm) 1.69-1.70 (m, 4H), 2.64 (s, 4H), 6.62 (s, 1H). 6.69 (d, J=8.4 Hz, 1H). 6.97 (d, J=8.4 Hz, 1H).

Example 98

Synthesis of methyl 4-(3,4-dichlorophenoxy)-1H-1,2,3-triazole-5-carboxylate 2,2,2-trifluoroacetate (98)

A solution of Compound 88B (200 mg, 0.5 mmol) and concentrated H$_2$SO$_4$ (0.1 mL) in MeOH (5 mL) was stirred at 60° C. for 16 hours. After cooling down to room temperature, the mixture was concentrated and purified with reverse phase chromatography using eluents (acetonitrile in water, from 0% to 100% v/v) to afford Compound 98A. LC-MS (ESI) m/z: 408 [M+H]$^+$.

Compound 98 was synthesized by employing the procedure described for Compound 1 using Compound 98A in lieu of Compound 1E, LC-MS (ESI) m/z: 288 [M+H]$^+$; $^1$H-NMR (CD$_3$OD, 400 MHz): δ (ppm) 3.87 (s, 3H), 7.10 (dd, J=8.8, 2.8 Hz, 1H), 7.37 (d, J=2.8 Hz, 1H), 7.52 (d, J=8.8 Hz, 1H).

Example 99

Synthesis of 4-(benzo[d]thiazol-6-yloxy)-1H-1,2,3-triazole-5-carboxylic acid 2,2,2-trifluoroacetate (99)

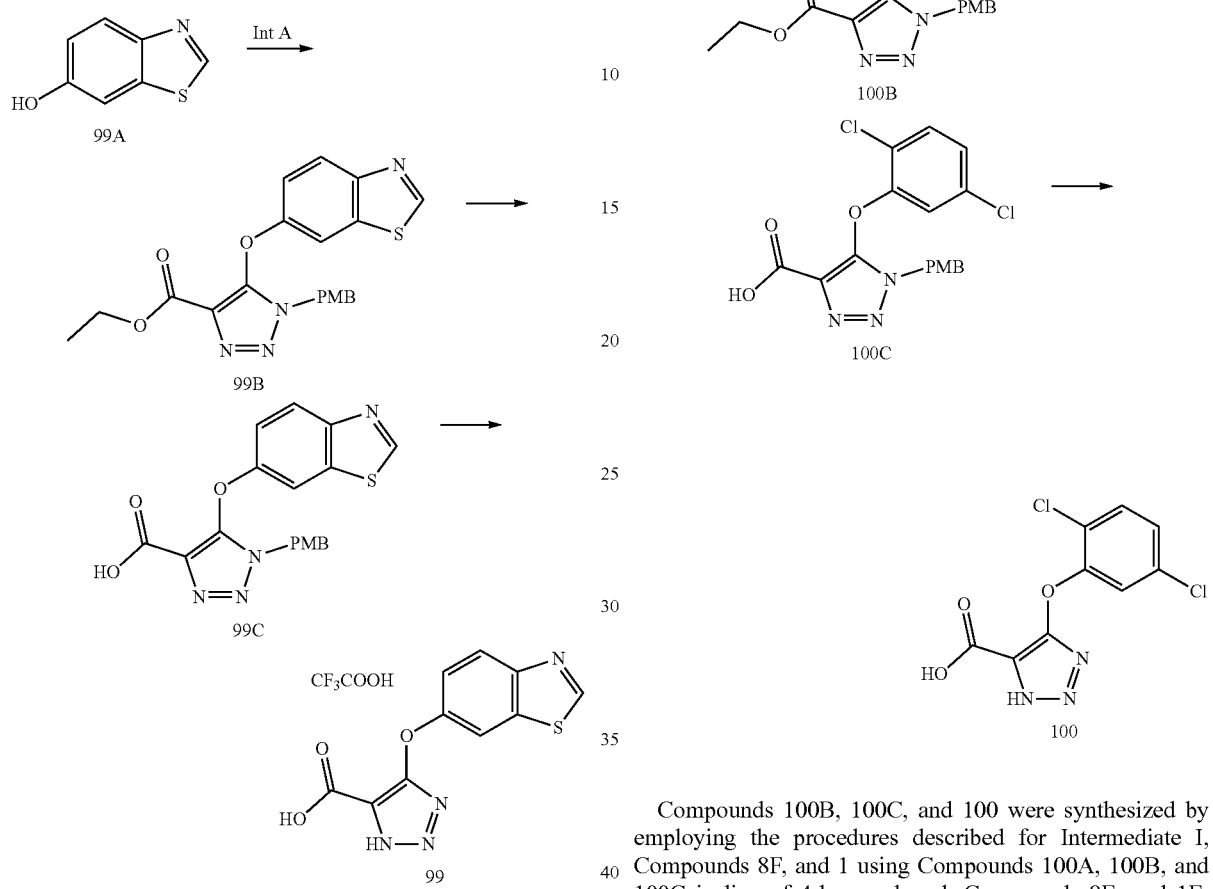

Compounds 99B, 99C, and 99 were synthesized by employing the procedures described for Intermediate I, Compounds 8F, and 1 using Compounds 99A using NMP as solvent, 99B, and 99C in lieu of 4-bromophenol using DMF as solvent, Compounds 8E, and 1E. Compound 99B: LC-MS (ESI) m/z: 411 [M+H]+. Compound 99C: LC-MS (ESI) m/z: 383 [M+H]+. Compound 99: LC-MS (ESI) m/z: 263 [M+H]+; $^1$H-NMR (DMSO-$d_6$, 400 MHz): δ (ppm) 7.31 (dd, $J_1$=8.4 Hz, $J_2$=2.0 Hz, 1H), 7.86 (d, J=2.0 Hz, 1H), 8.05 (d, J=8.8 Hz, 1H), 9.30 (s, 1H).

Example 100

Synthesis of 4-(2,5-dichlorophenoxy)-1H-1,2,3-triazole-5-carboxylic acid (100)

Compounds 100B, 100C, and 100 were synthesized by employing the procedures described for Intermediate I, Compounds 8F, and 1 using Compounds 100A, 100B, and 100C in lieu of 4-bromophenol, Compounds 8E, and 1E. Compound 100B: LC-MS (ESI) m/z: 422 [M+H]+. Compound 100C: LC-MS (ESI) m/z: 392 [M−H]−. Compound 100: LC-MS (ESI) m/z: 274 [M+H]+; $^1$H-NMR (DMSO-$d_6$, 400 MHz): δ (ppm) 7.31 (d, J=8.8 Hz, 2H), 7.63 (d, J=8.8 Hz, 1H).

Example 101

Synthesis of 1-(acetoxymethyl)-4-((6-bromonaphthalen-2-yl)oxy)-1H-1,2,3-triazole-5-carboxylic acid (101)

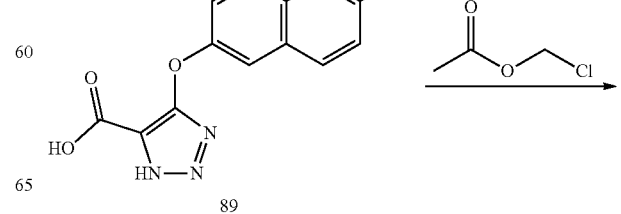

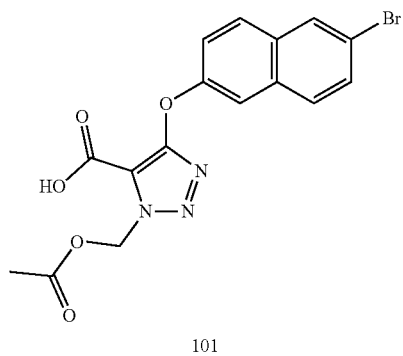

101

Compound 101 was synthesized by employing the procedure described for Compound 51 using chloromethyl acetate and Compound 89 in lieu of chloromethyl pivalate and Compound 16, LC-MS (ESI) m/z: 406 [M+H]+. 1H-NMR (DMSO-d6, 400 MHz): δ (ppm) 2.09 (s, 3H), 6.15 (s, 2H), 7.37 (dd, J=2.4, 8.8 Hz, 1H), 7.41 (d, J=5.2 Hz, 1H), 7.60 (dd, J=2.0, 8.8 Hz, 1H), 7.79 (d, J=8.8 Hz, 1H), 7.93 (d, J=9.2 Hz, 1H), 8.20 (d, J=2 Hz, 1H).

Example 102

Synthesis of 4-(3,4-dichlorophenoxy)-1-((pivaloyloxy)methyl)-1H-1,2,3-triazole-5-carboxylic acid (102)

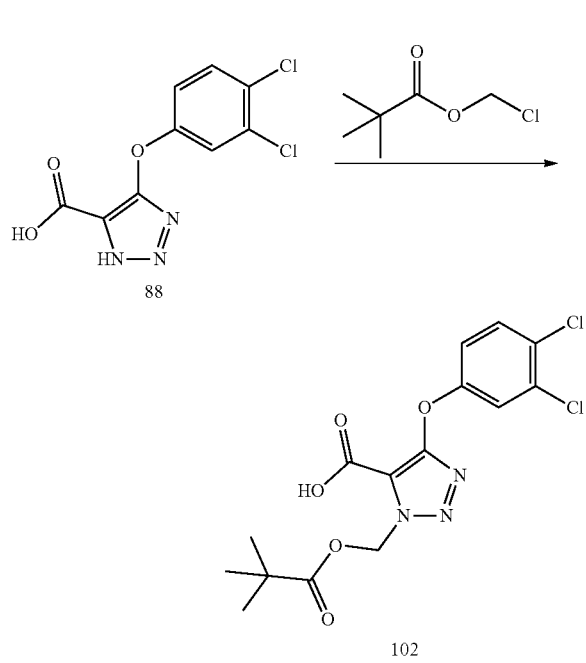

Compound 102 was synthesized by employing the procedure described for Compound 51 using Compound 88 in lieu of Compound 16, LC-MS (ESI) m/z: 405 [M+18]+; 1H-NMR (DMSO-d6, 400 MHz): δ (ppm) 1.04 (s, 9H), 5.72 (s, 2H), 6.88 (dd, J=9.2, 2.8 Hz, 1H), 7.06 (d, J=2.4 Hz, 1H), 7.50 (d, J=8.8 Hz, 1H).

Example 103

Synthesis of 4-(3,4-dichlorophenoxy)-1-((isobutyryloxy)methyl)-1H-1,2,3-triazole-5-carboxylic acid (103)

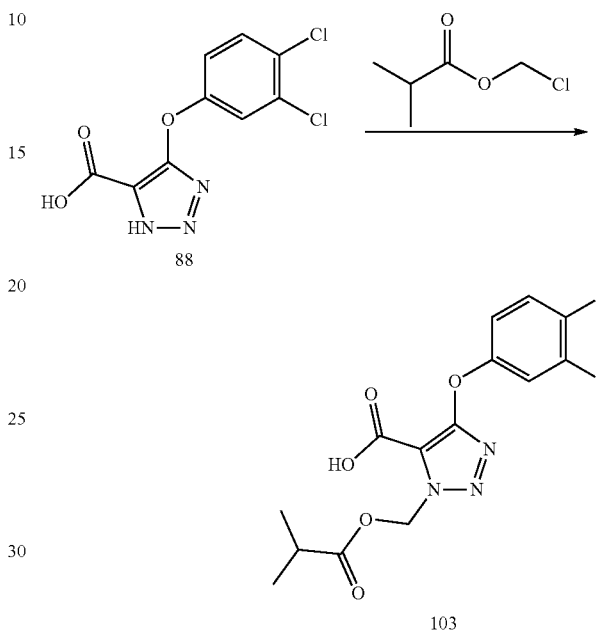

Compound 103 was synthesized by employing the procedure described for Compound 51 using chloromethyl isobutyrate and Compound 88 in lieu of chloromethyl pivalate and Compound 16, LC-MS (ESI) m/z: 391 [M+18]+; 1H-NMR (DMSO-d6, 400 MHz): δ (ppm) 1.07 (d, J=6.8 Hz, 6H), 2.58-2.59 (m, 1H), 6.18 (s, 2H), 7.03 (dd, J=8.8, 2.8 Hz, 1H), 7.28 (d, J=2.8 Hz, 1H), 7.60 (d, J=8.8 Hz, 1H).

Example 104

Synthesis of 1-(acetoxymethyl)-4-(3,4-dichlorophenoxy)-1H-1,2,3-triazole-5-carboxylic acid (104)

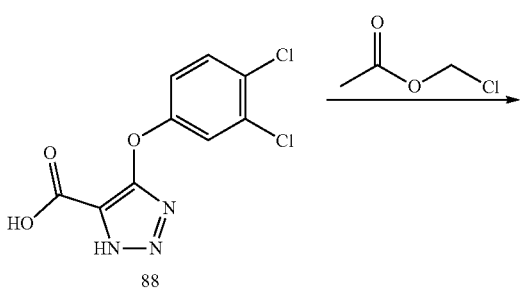

-continued

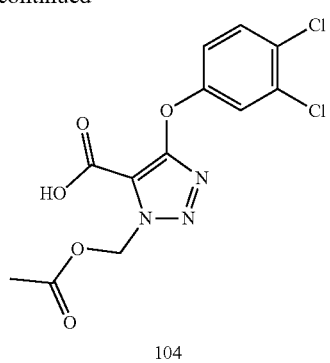

104

Compound 104 was synthesized by employing the procedure described for Compound 51 using chloromethyl acetate and Compound 88 in lieu of chloromethyl pivalate and Compound 16, LC-MS (ESI) m/z: 363 [M+18]+; 1H-NMR (DMSO-d6, 400 MHz): δ (ppm) 2.08 (s, 3H), 6.15 (s, 2H), 7.05 (dd, J=8.4, 2.8 Hz, 1H), 7.35 (d, J=3.2 Hz, 1H), 7.60 (d, J=9.2 Hz, 1H).

Example 105

Synthesis of acetoxymethyl 4-((6-bromonaphthalen-2-yl)oxy)-1H-1,2,3-triazole-5-carboxylate (105)

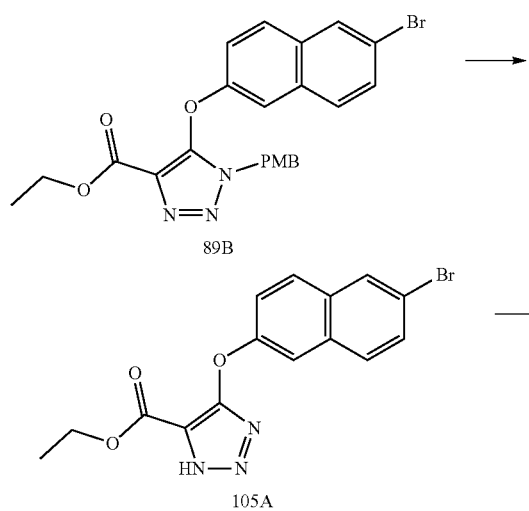

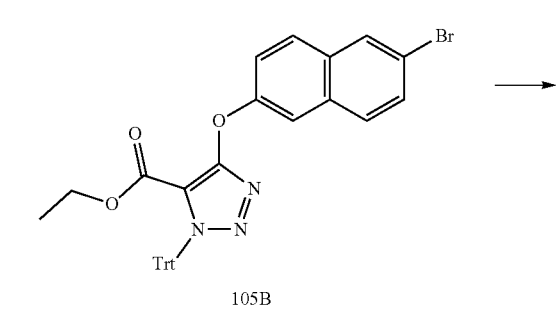

-continued

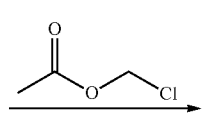

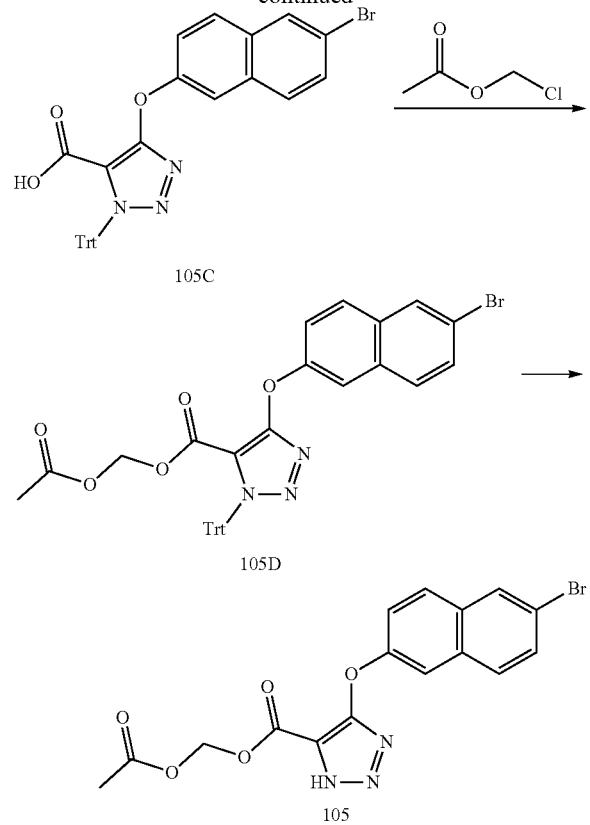

Compounds 105A, 105B, 105C, 105D, and 105 were synthesized by employing the procedures described for Compounds 1, 54A, 8F, 54C, and 54 using Compounds 89B, 105A, 105B, 105C, chloromethyl acetate, and 105D in lieu of Compounds 1E, 33, 8E, 54B, chloromethyl pivalate, and 54C. Compound 105A: LC-MS (ESI) m/z: 362 [M+H]+. Compound 105B: LC-MS (ESI) m/z: non-ionizable compound under routine conditions used; 1H-NMR (CDCl3, 400 MHz): δ 1.21 (t, J=6.8 Hz, 3H), 4.27 (q, J=6.8 Hz, 2H), 7.17-7.20 (m, 6H), 7.29-7.35 (m, 11H), 7.45-7.53 (m, 2H), 7.66-7.63 (m, 1H), 7.94-7.95 (m, 1H). Compound 105C: LC-MS (ESI) m/z: 243 [M−Trt]+. Compound 105D: LC-MS (ESI) m/z: non-ionizable compound under routine conditions used. Compound 105: LC-MS (ESI) m/z: 406 [M+H]+; 1H-NMR (DMSO-d6, 400 MHz): δ (ppm) 1.96 (s, 3H), 5.83 (s, 2H), 7.45 (dd, J=2.4 Hz, 8.8 Hz, 1H), 7.56 (d, J=2.0 Hz, 1H), 7.64 (dd, J=2.0 Hz, 8.8 Hz, 1H), 7.84 (d, J=9.2 Hz, 1H), 7.98 (d, J=9.2 Hz, 1H), 8.23 (d, J=1.6 Hz, 1H).

Example 106

Synthesis of 4-((6-chloronaphthalen-2-yl)oxy)-1H-1,2,3-triazole-5-carboxylic acid 2,2,2-trifluoroacetate (106)

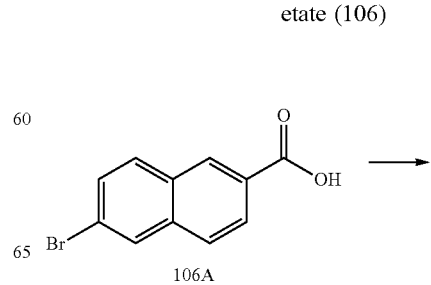

106A

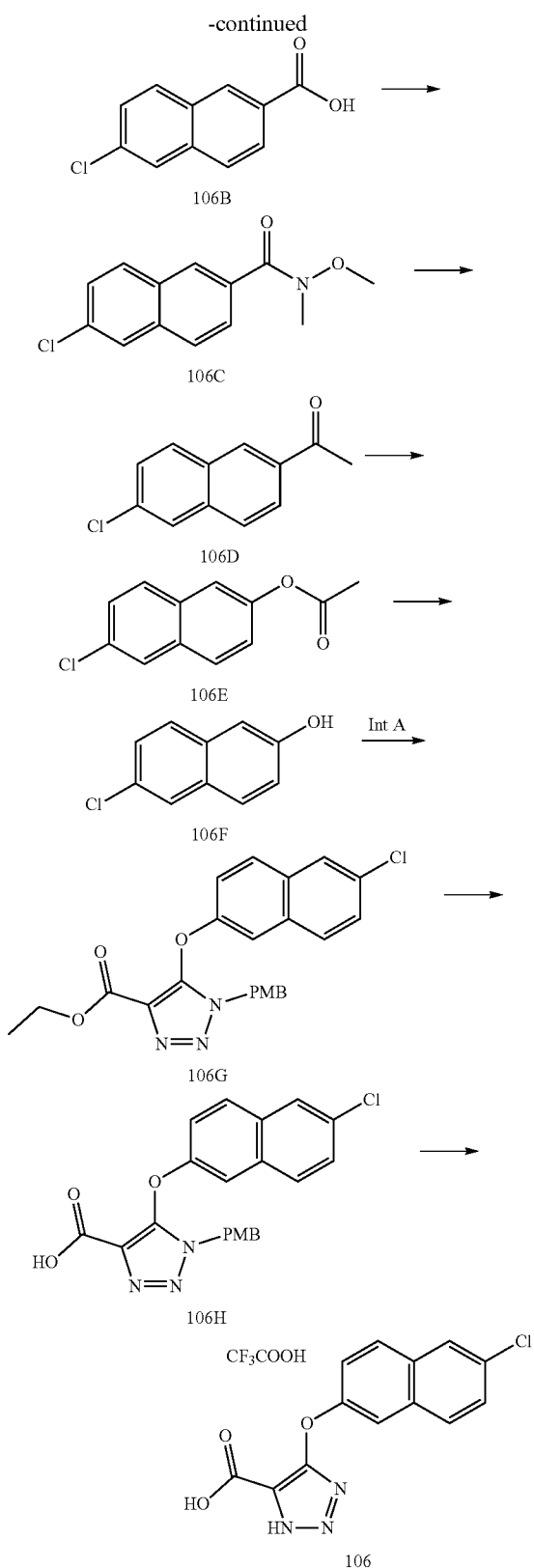

A mixture of 6-bromo-2-naphthoic acid (Compound 106A) (3.00 g, 11.47 mmol), CuI (2.19 g, 11.50 mmol), and CuCl (11.70 g, 114.64 mmol) in DMF (20 mL) was stirred at 150° C. under nitrogen for 3 hours. The mixture was cooled down to room temperature and diluted with an aqueous HCl solution (3 M, 100 mL). A solid was formed, filtered, and washed with water (100 mL). It was suspended in THF (100 mL), filtered, and washed with THF (100 mL). The combined filtrates were concentrated under reduced pressure. The residue was suspended in an aqueous HCl solution (3 M, 100 mL), stirred at room temperature for 10 minutes, and filtered. The cake was washed with water (50 mL) and CH$_3$CN (50 mL) and dried under vacuum to yield Compound 106B. LC-MS (ESI) m/z: 205 [M–H]; $^1$H-NMR (DMSO-d$_6$, 400 MHz): δ (ppm) 7.61-7.64 (m, 1H), 7.99-8.05 (m, 2H), 8.15-8.19 (m, 2H), 8.65 (s, 1H), 13.18 (s, 1H).

A mixture of Compound 106B (3.00 g, 14.56 mmol), N,O-dimethylhydroxylamine hydrochloride (1.71 g, 17.47 mmol), Et$_3$N (4.41 g, 43.68 mmol), and HATU (8.30 g, 21.84 mmol) in dichloromethane (30 mL) was stirred at room temperature for 4 hours. The mixture was diluted with ethyl acetate (160 mL), washed with water (100 mL) and brine (100 mL), and concentrated. The residue was purified with flash column chromatography on silica gel (ethyl acetate in petroleum ether from 0% to 80% v/v) to yield Compound 106C. LC-MS (ESI) m/z: 250 [M+H]$^+$; $^1$H-NMR (DMSO-d$_6$, 400 MHz): δ (ppm) 3.31 (s, 3H), 3.56 (s, 3H), 7.59-7.62 (m, 1H), 7.71-7.74 (m, 1H), 7.97 (d, J=8.8 Hz, 1H), 8.08-8.12 (m, 2H), 8.24 (s, 1H).

To a solution of Compound 106C (3.00 g, 12.05 mmol) in dry THF (20 mL) was added a solution of MeMgBr in Et$_2$O (3 M, 6.4 mL, 19.28 mmol) at 0° C. and stirred at room temperature under nitrogen for 16 hours. The reaction mixture was quenched with methanol (10 mL) and an aqueous HCl solution (3M, 50 mL), and extracted with ethyl acetate (160 mL). The extract was washed with water (100 mL) and brine (100 mL), dried over anhydrous sodium sulfate, filtered, and concentrated. The residue was purified with flash column chromatography on silica gel (ethyl acetate in petroleum ether from 0% to 10% v/v) to yield Compound 106D. LC-MS (ESI) m/z: 205 [M+H]$^+$; $^1$H-NMR (DMSO-d$_6$, 400 MHz): δ (ppm) 2.70 (s, 3H), 7.65 (d, J=8.8 Hz, 1H), 7.99-8.05 (m, 2H), 8.14-8.20 (m, 2H), 8.71 (s, 1H).

To a solution of Compound 106D (2.38 g, 11.67 mmol) in 1,2-dichloroethane (30 mL) was added m-CPBA (3.00 g, 17.50 mmol) at room temperature and stirred at 80° C. for 4 hours. Another portion of m-CPBA (3.00 g, 17.50 mmol) was added and stirred at 80° C. for 16 hours. The mixture was concentrated under reduced pressure. The residue was purified with flash column chromatography on silica gel (ethyl acetate in petroleum ether from 0% to 20% v/v) to yield Compound 106E. LC-MS (ESI) m/z: 221 [M+H]$^+$.

Compounds 106F, 106G, 106H, and 106 were synthesized by employing the procedures described for Compounds 8F, 86B, 8F, and 1 using Compounds 106E, 106F, 106G, and 106H in lieu of Compounds 8E, 86A, 8E, and 1E. Compound 106F: LC-MS (ESI) m/z: 179 [M+H]$^+$; $^1$H-NMR (DMSO-d$_6$, 400 MHz): δ (ppm) 7.11-7.14 (m, 2H), 7.38 (d, J=8.8 Hz, 1H), 7.71-7.77 (m, 2H), 7.88 (d, J=2.0 Hz, 1H), 9.87 (s, 1H). Compound 106G: LC-MS (ESI) m/z: 438 [M+H]$^+$; $^1$H-NMR (DMSO-d$_6$, 400 MHz): δ (ppm) 0.82 (t, J=7.2 Hz, 3H), 3.63 (s, 3H), 3.97 (q, J=7.2 Hz, 2H), 5.48 (s, 2H), 6.78 (d, J=8.8 Hz, 2H), 7.18-7.25 (m, 2H), 7.30-7.35 (m, 1H), 7.37-7.40 (m, 1H), 7.48-7.52 (m, 1H), 7.81 (d, J=8.8 Hz, 1H), 7.90-7.95 (m, 1H), 8.05 (d, J=2.4 Hz, 1H). Compound 106H: LC-MS (ESI) m/z: 410 [M+H]$^+$; $^1$H-NMR (DMSO-d$_6$, 400 MHz): δ (ppm) 3.61 (s, 3H), 5.30 (s, 2H), 6.74 (d, J=8.8 Hz, 2H), 7.04 (s, 1H), 7.10 (d, J=8.8 Hz, 2H), 7.26 (d, J=8.8 Hz, 1H), 7.46 (d, J=8.8 Hz, 1H), 7.73 (d, J=8.8 Hz, 1H), 7.86 (d, J=8.8 Hz. 1H), 8.01 (s, 1H). Compound 106: LC-MS (ESI) m/z: 290 [M+H]$^+$; $^1$H-NMR (DMSO-d$_6$, 400 MHz): δ (ppm) 7.42 (d, J=8.8 Hz, 1H), 7.19-7.52 (m, 2H), 7.90 (d, J=8.8 Hz, 1H), 7.95 (d, J=8.8 Hz, 1H), 8.06 (s, 1H).

Example 107

Synthesis of (pivaloyloxy)methyl 4-(3,4-dichlorophenoxy)-1H-1,2,3-triazole-5-carboxylate (107)

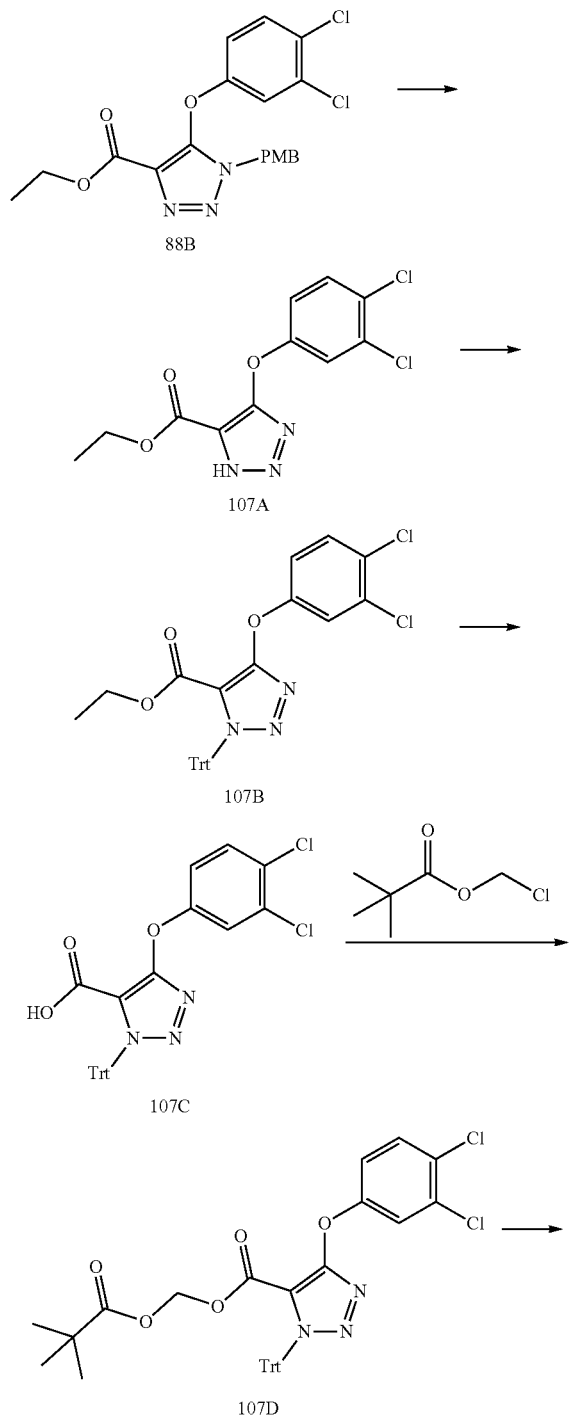

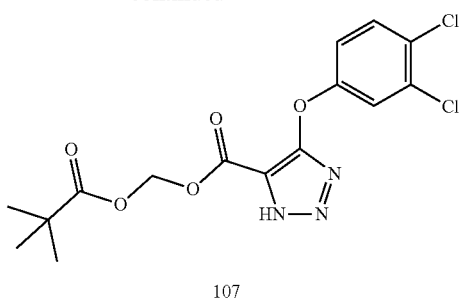

Compounds 107A, 107B, 107C, 107D, and 107 were synthesized by employing the procedures described for Compounds 1, 54A, 8F, 51, and 1 using Compounds 88B, 107A, 107B, 107C, and 107D in lieu of Compounds 1E, 33, 8E, 16, and 1E. Compound 107A: LC-MS (ESI) m/z: 302 [M+H]$^+$. Compound 107B: LC-MS (ESI) m/z: 566 [M+Na]$^+$. Compound 107C: LC-MS (ESI) m/z: 538 [M+Na]$^+$; $^1$H-NMR (DMSO-d$_6$, 400 MHz): δ (ppm) 7.08-7.12 (m, 7H), 7.37-7.43 (m, 10H), 7.58-7.60 (m, 1H), 13.50 (s, 1H). Compound 107D: LC-MS (ESI) m/z: 652 [M+Na]$^+$. Compound 107: LC-MS (ESI) m/z: 405 [M+H$_2$O]$^+$; (CD$_3$OD, 400 MHz): δ (ppm) 1.17 (s, 9H), 5.93 (s, 2H), 7.07-7.10 (m, 1H), 7.33 (s, 1H), 7.50-7.52 (m, 1H).

Example 108

Synthesis of (isobutyryloxy)methyl 4-(3,4-dichlorophenoxy)-1H-1,2,3-triazole-5-carboxylate (108)

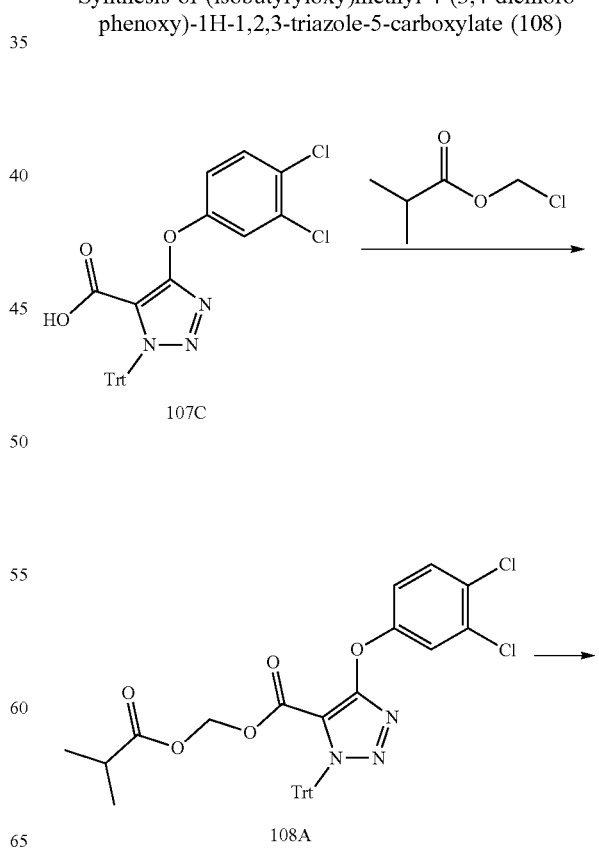

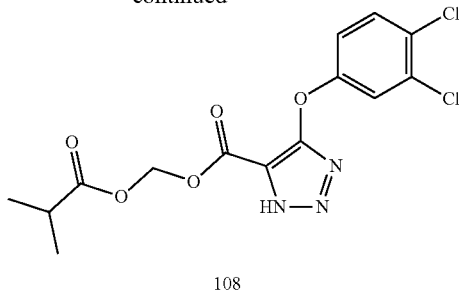

108

Compounds 108A and 108 were synthesized by employing the procedures described for Compounds 51 and 1 using chloromethyl isobutyrate, Compounds 107C, and 108A in lieu of chloromethyl pivalate, Compounds 16, and 1E. Compound 108A: LC-MS (ESI) m/z: 633 [M+H$_2$O]$^+$. Compound 108: LC-MS (ESI) m/z: 391 [M+H$_2$O]$^+$; $^1$H-NMR (CD$_3$OD, 400 MHz): δ (ppm) 1.10 (d, J=7.2 Hz, 6H), 2.46-2.54 (m, 1H), 5.84 (s, 2H), 6.87-6.90 (m, 1H), 7.06-7.07 (m, 1H), 7.41-7.43 (m, 1H).

Example 109

Synthesis of acetoxymethyl 4-(3,4-dichlorophenoxy)-1H-1,2,3-triazole-5-carboxylate (109)

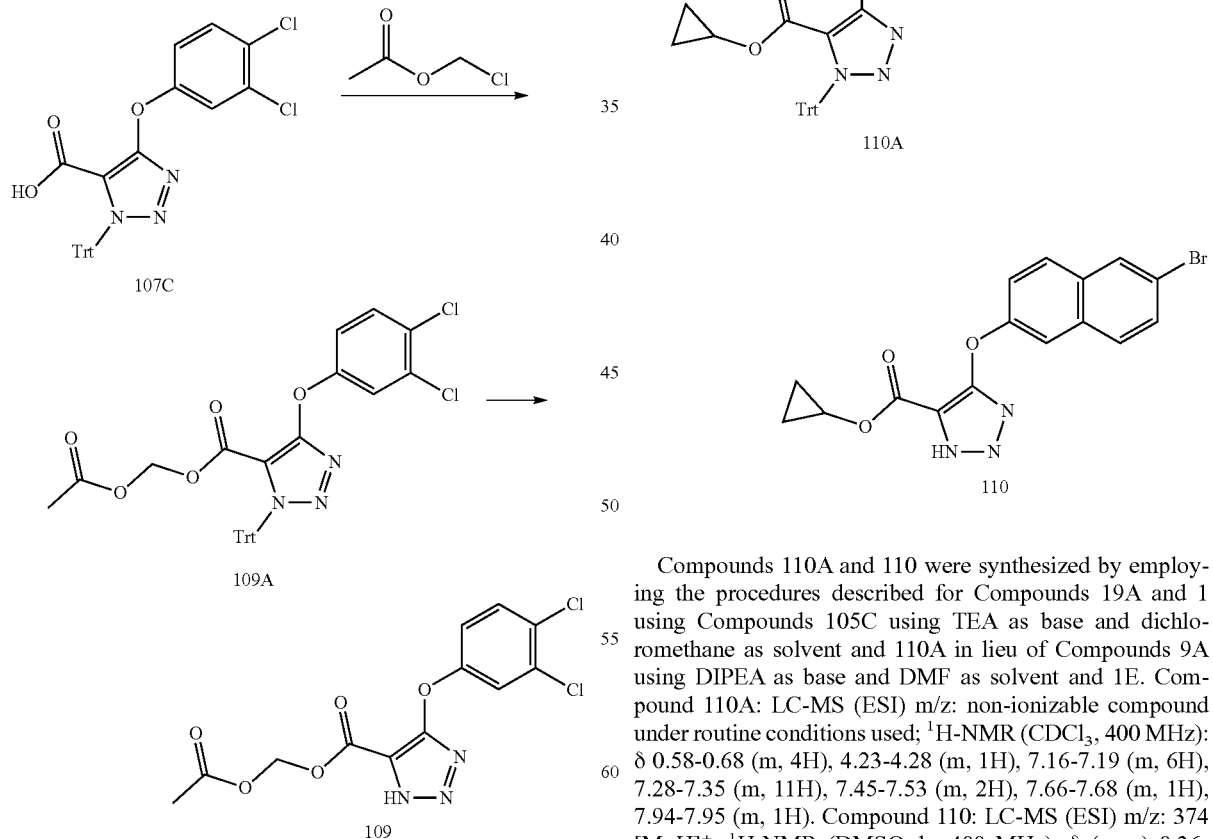

Compounds 109A and 109 were synthesized by employing the procedures described for Compounds 51 and 1 using chloromethyl acetate, Compounds 107C, and 109A in lieu of chloromethyl pivalate, Compounds 16, and 1E. Compound 109A: LC-MS (ESI) m/z: 605 [M+H$_2$O]$^+$. Compound 109: LC-MS (ESI) m/z: 346 [M+H]$^+$; $^1$H-NMR (CD$_3$OD, 400 MHz): δ (ppm) 2.01 (s, 3H), 5.82 (s, 2H), 6.87-6.90 (m, 1H), 7.07-7.08 (m, 1H), 7.41-7.43 (m, 1H).

Example 110

Synthesis of cyclopropyl 4-((6-bromonaphthalen-2-yl)oxy)-1H-1,2,3-triazole-5-carboxylate (110)

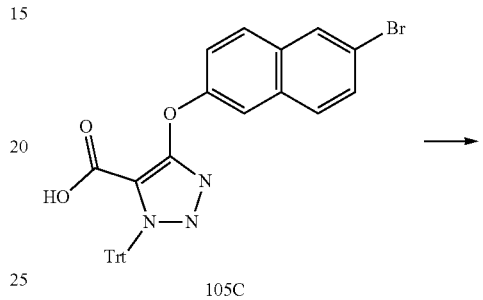

105C

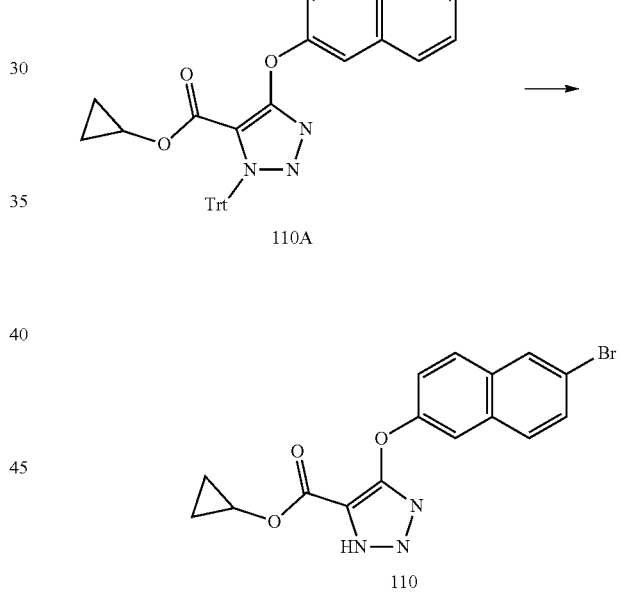

Compounds 110A and 110 were synthesized by employing the procedures described for Compounds 19A and 1 using Compounds 105C using TEA as base and dichloromethane as solvent and 110A in lieu of Compounds 9A using DIPEA as base and DMF as solvent and 1E. Compound 110A: LC-MS (ESI) m/z: non-ionizable compound under routine conditions used; $^1$H-NMR (CDCl$_3$, 400 MHz): δ 0.58-0.68 (m, 4H), 4.23-4.28 (m, 1H), 7.16-7.19 (m, 6H), 7.28-7.35 (m, 11H), 7.45-7.53 (m, 2H), 7.66-7.68 (m, 1H), 7.94-7.95 (m, 1H). Compound 110: LC-MS (ESI) m/z: 374 [M+H]$^+$; $^1$H-NMR (DMSO-d$_6$, 400 MHz): δ (ppm) 0.36-0.40 (m, 2H), 0.58-0.63 (m, 2H), 4.15-4.19 (m, 1H), 7.40 (dd, J=2.4 Hz, 8.8 Hz, 1H), 7.45 (d, J=1.6 Hz, 1H), 7.64 (dd, J=2.0 Hz, 8.8 Hz, 1H), 7.81 (d, J=8.8 Hz, 1H), 7.95 (d, J=8.8 Hz, 1H), 8.21 (d, J=1.6 Hz, 1H).

Example 111

Synthesis of 4-((6,7-dichloro-1,2,3,4-tetrahydronaphthalen-2-yl)oxy)-1H-1,2,3-triazole-5-carboxylic acid 2,2,2-trifluoroacetate (111)

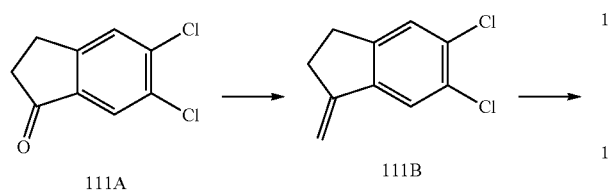

111A → 111B

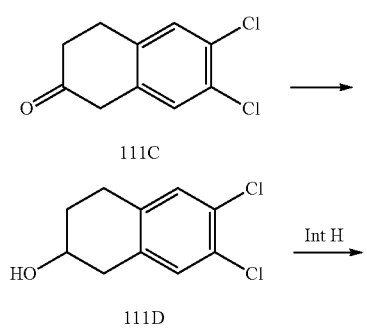

111C

111D

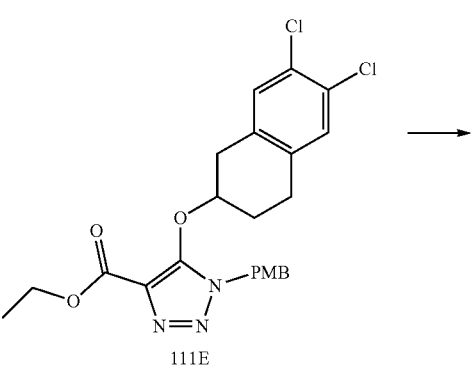

111E

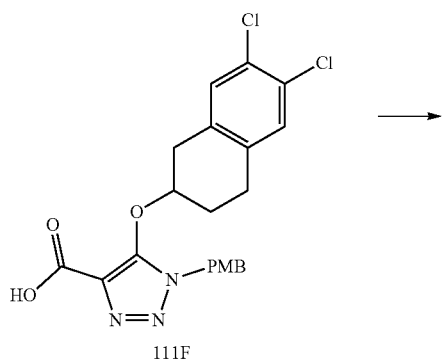

111F

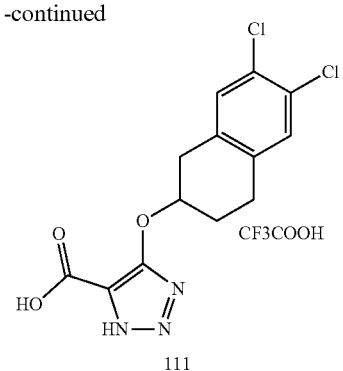

111

To a suspend of methyltriphenylphosphonium bromide (10.7 g, 30 mmol) in dry THF (150 mL) was added t-BuOK (3.37 g, 30 mmol) and stirred at 0° C. for 15 minutes. To the mixture was added a solution of 5,6-dichloro-2,3-dihydro-1H-inden-1-one (Compound 111A) (3.0 g, 15.0 mmol) in dry THF (60 mL) in one portion at 0° C. After stirring at 0° C. for 5 hours, to the mixture was added more methyltriphenylphosphonium bromide (10.7 g, 30 mmol) and t-BuOK (3.37 g, 30 mmol) at 0° C. and stirred at room temperature for 58 hours. The reaction mixture was filtered and the filtrate was concentrated to dryness. The residue was diluted with n-hexane (100 mL) and passed through a short silica gel column. The eluent was concentrated to give Compound 111B. LC-MS (ESI) m/z: Non-ionizable Compound under routine conditions used; $^1$H-NMR (CDCl$_3$, 400 MHz): δ (ppm) 2.78-2.84 (m, 2H), 2.89-2.94 (m, 2H), 5.08 (t, J=2.0 Hz, 1H), 5.42 (t, J=2.0 Hz, 1H), 7.32 (s, 1H), 7.51 (s, 1H).

To a solution of Compound 111B (907 mg, 4.56 mmol) in 95% MeOH (20 mL) at 0° C. was added hydroxy(tosyloxy)iodobenzene (1.8 g, 4.56 mmol) and stirred at 0° C. for 30 minutes. The mixture was concentrated under reduced pressure. The residue was diluted with dichloromethane (120 mL), washed with saturated aqueous NaHCO$_3$ solution (50 mL×2) and brine (50 mL), dried over anhydrous sodium sulfate, filtered, and concentrated to give Compound 111C. The product was used directly in next step without further purification. LC-MS (ESI) m/z: 215 [M+H]$^+$; $^1$H-NMR (CDCl$_3$, 400 MHz): δ (ppm) 2.55 (t, J=6.4 Hz, 2H), 3.03 (t, J=6.4 Hz, 2H), 3.54 (s, 2H), 7.23 (s, 1H), 7.34 (s, 1H).

Compounds 111D, 111E, 111F, and 111 were synthesized by employing the procedures described for Compounds 57C, 90C, 8F, and 1 using Compounds 111C, 111D, 111E, and 111F in lieu of Compounds 57B, 90B, 8E, and 1E. Compound 111D: LC-MS (ESI) m/z: 199 [M−OH]$^+$; $^1$H-NMR (CDCl$_3$, 400 MHz): δ (ppm) 1.77-1.86 (m, 1H), 1.97-2.04 (m, 1H), 2.67-2.73 (m, 1H), 2.76-2.79 (m, 1H), 2.88-2.95 (m, 1H), 2.98-3.03 (m, 1H), 4.13-4.19 (m, 1H), 7.16 (s, 1H), 7.18 (s, 1H). Compound 111E: LC-MS (ESI) m/z: 476 [M+H]$^+$; $^1$H-NMR (CDCl$_3$, 400 MHz): δ (ppm) 1.42 (t, J=7.2 Hz, 3H), 1.94-2.13 (m, 2H), 2.69-2.84 (m, 3H), 2.94-2.99 (m, 1H), 3.77 (s, 3H), 4.41 (q, J=7.2 Hz, 2H), 5.02-5.16 (m, 2H), 5.66-5.71 (m, 1H), 6.74-6.76 (m, 2H), 6.96-6.98 (m, 2H), 7.06 (s, 1H), 7.19 (s, 1H). Compound 111F: LC-MS (ESI) m/z: 448 [M+H]$^+$. Compound 111: LC-MS (ESI) m/z: 328 [M+H]$^+$; $^1$H-NMR (CD$_3$OD, 400 MHz): δ (ppm) 2.12-2.21 (m, 2H), 2.78-2.85 (m, 1H), 2.97-3.08 (m, 2H), 3.20-3.25 (m, 1H), 5.17 (t, J=4.0 Hz, 1H), 7.25 (s, 1H), 7.27 (s, 1H).

Example 111-1 and 111-2

Synthesis of (R)-4-((6,7-dichloro-1,2,3,4-tetrahydronaphthalen-2-yl)oxy)-1H-1,2,3-triazole-5-carboxylic acid (111-1) and (S)-4-((6,7-dichloro-1,2,3,4-tetrahydronaphthalen-2-yl)oxy)-1H-1,2,3-triazole-5-carboxylic acid (111-2)

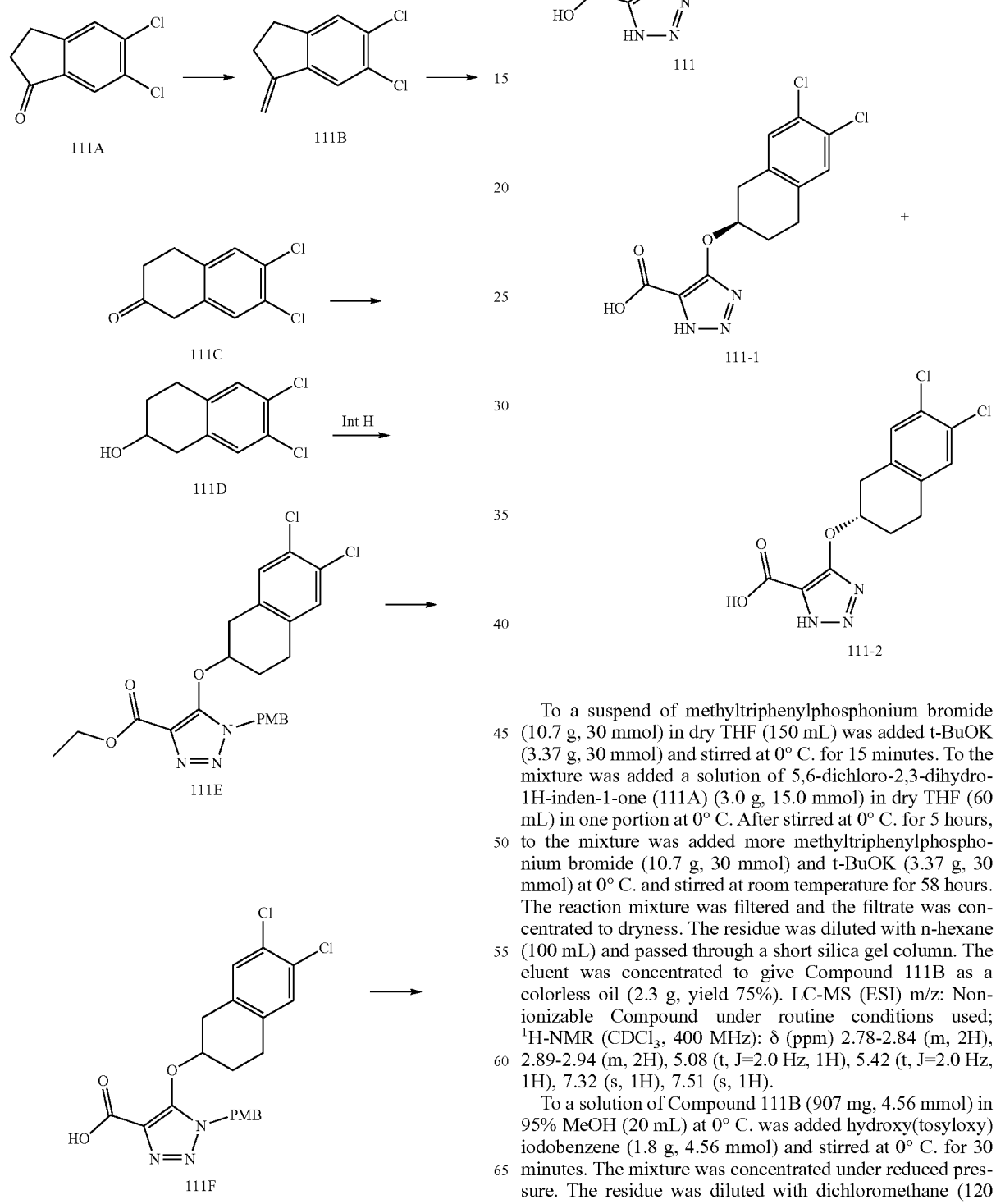

To a suspend of methyltriphenylphosphonium bromide (10.7 g, 30 mmol) in dry THF (150 mL) was added t-BuOK (3.37 g, 30 mmol) and stirred at 0° C. for 15 minutes. To the mixture was added a solution of 5,6-dichloro-2,3-dihydro-1H-inden-1-one (111A) (3.0 g, 15.0 mmol) in dry THF (60 mL) in one portion at 0° C. After stirred at 0° C. for 5 hours, to the mixture was added more methyltriphenylphosphonium bromide (10.7 g, 30 mmol) and t-BuOK (3.37 g, 30 mmol) at 0° C. and stirred at room temperature for 58 hours. The reaction mixture was filtered and the filtrate was concentrated to dryness. The residue was diluted with n-hexane (100 mL) and passed through a short silica gel column. The eluent was concentrated to give Compound 111B as a colorless oil (2.3 g, yield 75%). LC-MS (ESI) m/z: Non-ionizable Compound under routine conditions used; $^1$H-NMR (CDCl$_3$, 400 MHz): δ (ppm) 2.78-2.84 (m, 2H), 2.89-2.94 (m, 2H), 5.08 (t, J=2.0 Hz, 1H), 5.42 (t, J=2.0 Hz, 1H), 7.32 (s, 1H), 7.51 (s, 1H).

To a solution of Compound 111B (907 mg, 4.56 mmol) in 95% MeOH (20 mL) at 0° C. was added hydroxy(tosyloxy)iodobenzene (1.8 g, 4.56 mmol) and stirred at 0° C. for 30 minutes. The mixture was concentrated under reduced pressure. The residue was diluted with dichloromethane (120 mL), washed with saturated aqueous NaHCO$_3$ solution (50 mL×2) and brine (50 mL), dried over anhydrous sodium sulfate, filtered, and concentrated to give a crude Compound 111C as a yellow solid (980 mg, yield 100%). The crude product was used directly in next step without further purification. LC-MS (ESI) m/z: 215 [M+H]$^+$; $^1$H-NMR (CDCl$_3$, 400 MHz): δ (ppm) 2.55 (t, J=6.4 Hz, 2H), 3.03 (t, J=6.4 Hz, 2H), 3.54 (s, 2H), 7.23 (s, 1H), 7.34 (s, 1H).

Compounds 111D, 111E, 111F, and 111 were synthesized by employing the procedures described for Compounds 57C, 90C, 8F, and 1 using Compounds 111C, 111D, 111E, and 111F in lieu of Compounds 57B, 90B, 8E, and 1E. Compound 111D: LC-MS (ESI) m/z: 199 [M−OH]$^+$; $^1$H-NMR (CDCl$_3$, 400 MHz): δ (ppm) 1.77-1.86 (m, 1H), 1.97-2.04 (m, 1H), 2.67-2.73 (m, 1H), 2.76-2.79 (m, 1H), 2.88-2.95 (m, 1H), 2.98-3.03 (m, 1H), 4.13-4.19 (m, 1H), 7.16 (s, 1H), 7.18 (s, 1H). Compound 111E: LC-MS (ESI) m/z: 476 [M+H]$^+$; $^1$H-NMR (CDCl$_3$, 400 MHz): δ (ppm) 1.42 (t, J=7.2 Hz, 3H), 1.94-2.13 (m, 2H), 2.69-2.84 (m, 3H), 2.94-2.99 (m, 1H), 3.77 (s, 3H), 4.41 (q, J=7.2 Hz, 2H), 5.02-5.16 (m, 2H), 5.66-5.71 (m, 1H), 6.74-6.76 (m, 2H), 6.96-6.98 (m, 2H), 7.06 (s, 1H), 7.19 (s, 1H). Compound 111F: LC-MS (ESI) m/z: 448 [M+H]$^+$. Compound 111: LC-MS (ESI) m/z: 328 [M+H]$^+$; $^1$H-NMR (CD$_3$OD, 400 MHz): δ (ppm) 2.12-2.21 (m, 2H), 2.78-2.85 (m, 1H), 2.97-3.08 (m, 2H), 3.20-3.25 (m, 1H), 5.17 (t, J=4.0 Hz, 1H), 7.25 (s, 1H), 7.27 (s, 1H).

Compound 111 (130 mg) was separated with preparative chiral-HPLC and HPLC to furnish Compound III-1 as a white solid (29 mg, yield 22%) and Compound III-2 as a white solid (29 mg, yield 22%). Compound III-1: LC-MS (ESI) m/z: 328 [M+H]$^+$; $^1$H-NMR (CD$_3$OD, 400 MHz): δ (ppm) 2.14-2.19 (m, 2H), 2.78-2.86 (m, 1H), 2.98-3.09 (m, 2H), 3.20-3.26 (m, 1H), 5.17 (brs, 1H), 7.26 (s, 1H), 7.28 (s, 1H). Chiral separation condition: n-hexane/EtOH contained 0.1% diethylamine (30/70); IE (4.6×250 mm, 5 μm), retention time: 7.69 min. It is a mixture as mobile phase; Compound III-2: LC-MS (ESI) m/z: 328 [M+H]$^+$; $^1$H-NMR (CD$_3$OD, 400 MHz): δ (ppm) 2.16-2.21 (m, 2H), 2.80-2.88 (m, 1H), 3.00-3.11 (m, 2H), 3.23-3.28 (m, 1H), 5.19 (brs, 1H), 7.28 (s, 1H), 7.30 (s, 1H). Chiral separation condition: n-hexane/EtOH contained 0.1% diethylamine (30/70); IE (4.6×250 mm, 5 μm), retention time: 12.62 min.

Example 112

Synthesis of cyclopropyl 4-(3,4-dichlorophenoxy)-1H-1,2,3-triazole-5-carboxylate (112)

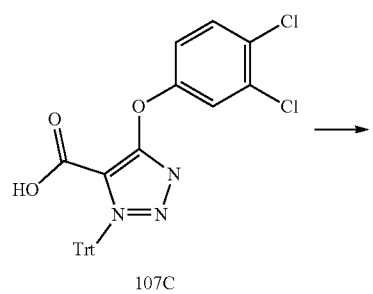

107C

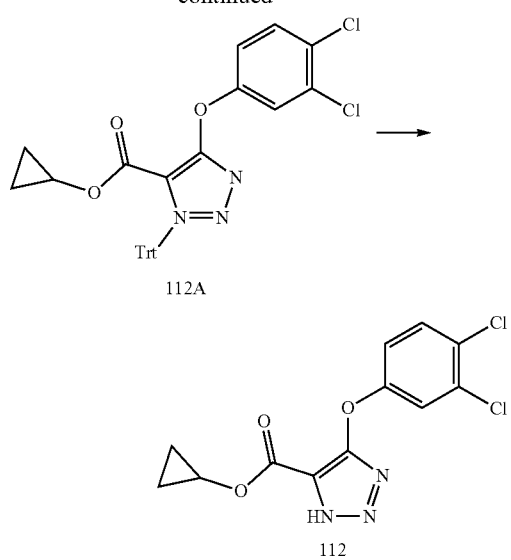

Compounds 112A and 112 were synthesized by employing the procedures described for Compounds 19A and 1 using Compounds 107C using dichloromethane as solvent and 112A in lieu of Compounds 9A using DMF as solvent and 1E. Compound 112A: LC-MS (ESI) m/z: 578 [M+Na]$^+$. Compound 112: LC-MS (ESI) m/z: 314 [M+H]$^+$; $^1$H-NMR (CD$_3$OD, 400 MHz): δ (ppm) 0.64-0.65 (m, 2H), 0.75-0.77 (m, 2H), 4.31-4.33 (m, 1H), 7.03-7.06 (m, 1H), 7.31-7.32 (m, 1H), 7.51-7.53 (m, 1H).

Example 113

Synthesis of 4-(quinolin-7-yloxy)-1H-1,2,3-triazole-5-carboxylic acid 2,2,2-trifluoroacetate (113)

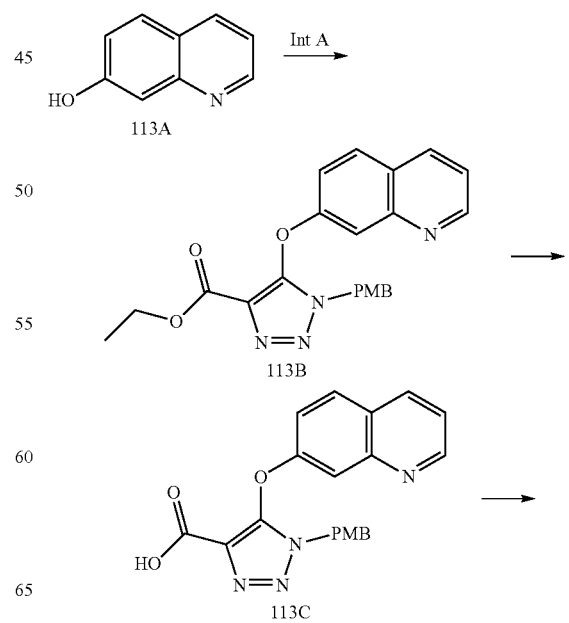

-continued

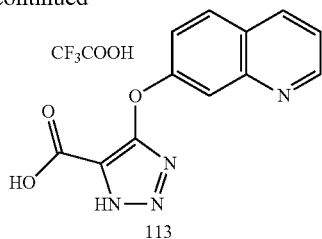
113

Compounds 113B, 113C, and 113 were synthesized by employing the procedures described for Intermediate I, Compounds 8F, and 1 using Compounds 113A, 113B, and 113C in lieu of 4-bromophenol, Compounds 8E, and 1E. Compound 113B: LC-MS (ESI) m/z: 405 [M+H]$^+$. Compound 113C: LC-MS (ESI) m/z: 377 [M+H]$^+$. Compound 113: LC-MS (ESI) m/z: 257 [M+H]$^+$; $^1$H-NMR (DMSO-d$_6$, 400 MHz): δ (ppm) 7.52 (s, 1H), 7.53-7.62 (m, 1H), 7.65-7.68 (m, 1H), 8.16 (d, J=9.2 Hz, 1H), 8.64 (d, J=8.0 Hz, 1H), 9.00 (d, J=4.4 Hz, 1H).

Example 114

Synthesis of 4-(3-(trifluoromethoxy)phenoxy)-1H-1,2,3-triazole-5-carboxylic acid (114)

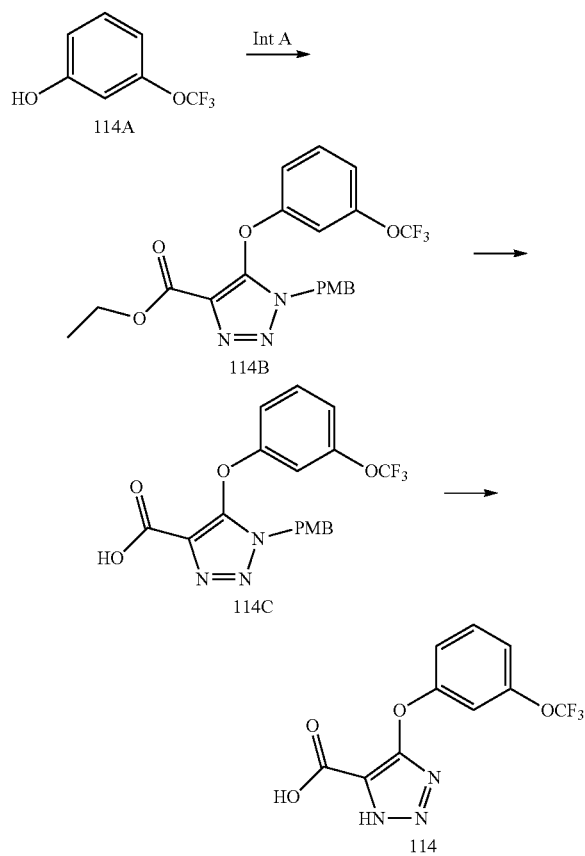

Compounds 114B, 114C, and 114 were synthesized by employing the procedures described for Compounds 86B, 8F, and 1 using Compounds 114A, 114B, and 114C in lieu of Compounds 86A, 8E, and 1E. Compound 114B: LC-MS (ESI) m/z: 438 [M+H]$^+$. Compound 114C: LC-MS (ESI) m/z: 410 [M+H]$^+$; $^1$H-NMR (DMSO-d$_6$, 400 MHz): δ (ppm) 3.32 (s, 3H), 5.28 (s, 2H), 6.74-6.82 (m, 4H), 7.01-7.03 (m, 1H), 7.06-7.09 (m, 2H), 7.35 (t, J=8.4 Hz, 1H). Compound 114: LC-MS (ESI) m/z: 290 [M+H]$^+$; $^1$H-NMR (DMSO-d$_6$, 400 MHz): δ (ppm) 7.09-7.17 (m, 3H), 7.50 (t, J=8.4 Hz, 1H).

Example 115

Synthesis of 4-(quinolin-3-yloxy)-1H-1,2,3-triazole-5-carboxylic acid 2,2,2-trifluoroacetate (115)

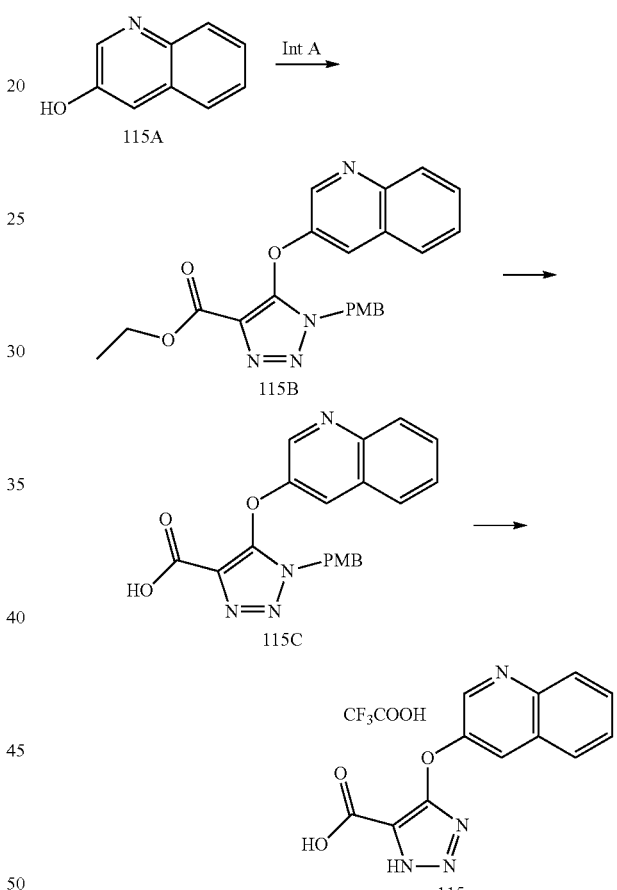

Compounds 115B, 115C, and 115 were synthesized by employing the procedures described for Intermediate I, Compounds 8F, and 1 using Compounds 115A, 115B, and 115C in lieu of 4-bromophenol, Compounds 8E, and 1E. Compound 115B: LC-MS (ESI) m/z: 405 [M+H]$^+$. Compound 115C: LC-MS (ESI) m/z: 377 [M+H]$^+$; $^1$H-NMR (DMSO-d$_6$, 400 MHz): δ (ppm) 3.56 (s, 3H), 5.41 (s, 2H), 6.73 (d, J=8.8 Hz, 2H), 7.15 (d, J=8.4 Hz, 2H), 7.33 (s, 1H), 7.54 (t, J=6.8 Hz, 1H), 7.65 (t, J=6.0 Hz, 1H), 7.75 (d, J=8.4 Hz, 1H), 7.98 (d, J=8.4 Hz, 1H), 8.71 (d, J=2.8 Hz, 1H). Compound 115: LC-MS (ESI) m/z: 257 [M+H]$^+$; $^1$H-NMR (DMSO-d$_6$, 400 MHz): δ (ppm) 7.62 (t, J=8.4 Hz, 1H), 7.72 (t, J=8.4 Hz, 1H), 7.95 (d, J=7.6 Hz, 1H), 7.99 (d, J=2.4 Hz, 1H), 8.04 (d, J=8.0 Hz, 1H), 8.90 (d, J=2.8 Hz, 1H).

Example 116

Synthesis of cyclopropyl 4-((5,6,7,8-tetrahydronaphthalen-2-yl)oxy)-1H-1,2,3-triazole-5-carboxylate (116)

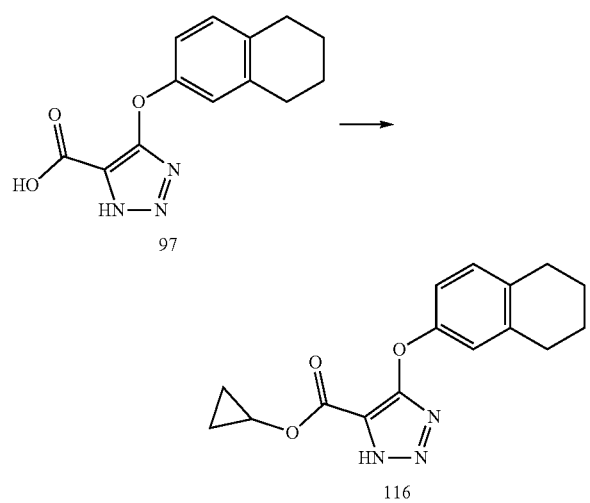

Compound 116 was synthesized by employing the procedure described for Compound 19A using Compound 97 in lieu of Compound 9A, LC-MS (ESI) m/z: 300 [M+H]$^+$; $^1$H-NMR (CD$_3$OD, 400 MHz): δ (ppm) 1.52-1.54 (m, 2H), 1.65-1.67 (m, 2H), 1.77-1.80 (m, 4H), 2.71-2.72 (m, 4H), 4.21-4.23 (m, 1H), 6.63-6.68 (m, 2H), 6.96-6.98 (m, 1H).

Example 117

Synthesis of 4-((1,2,3,4-tetrahydronaphthalen-2-yl)oxy)-1H-1,2,3-triazole-5-carboxylic acid 2,2,2-trifluoroacetate (117)

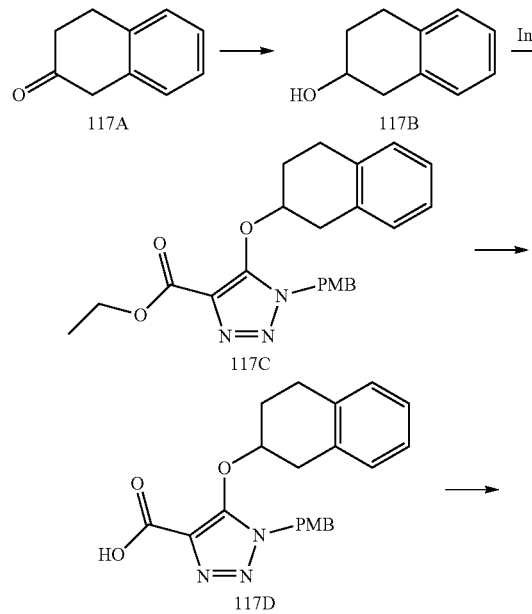

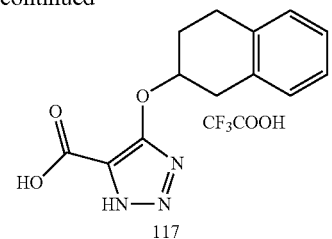

Compounds 117B, 117C, 117D, and 117 were synthesized by employing the procedures described for Compounds 57C, 90C, 8F, and 1 using Compounds 117A, 117B, 117C, and 117D in lieu of Compounds 57B, 90B, 8E, and 1E. Compound 117B: LC-MS (ESI) m/z: 131 [M−OH]$^+$; (CDCl$_3$, 400 MHz): δ (ppm) 1.75-1.80 (m, 1H), 2.01-2.15 (m, 1H), 2.80-2.94 (m, 2H), 2.95-2.98 (m, 1H), 3.03-3.18 (m, 1H), 4.15-4.21 (m, 1H), 7.07-7.13 (m, 4H). Compound 117C: LC-MS (ESI) m/z: 408 [M+H]$^+$. Compound 117D: LC-MS (ESI) m/z: 380 [M+H]$^+$. Compound 117: LC-MS (ESI) m/z: 260 [M+H]$^+$; $^1$H-NMR (DMSO-d$_6$, 400 MHz): δ (ppm) 1.99-2.03 (m, 1H), 2.08-2.15 (m, 1H), 2.73-2.80 (m, 1H), 2.91-2.98 (m, 2H), 3.19-3.25 (m, 1H), 5.06-5.07 (m, 1H), 7.09-7.11 (m, 4H).

Example 118

Synthesis of 4-(isoquinolin-7-yloxy)-1H-1,2,3-triazole-5-carboxylic acid 2,2,2-trifluoroacetate (118)

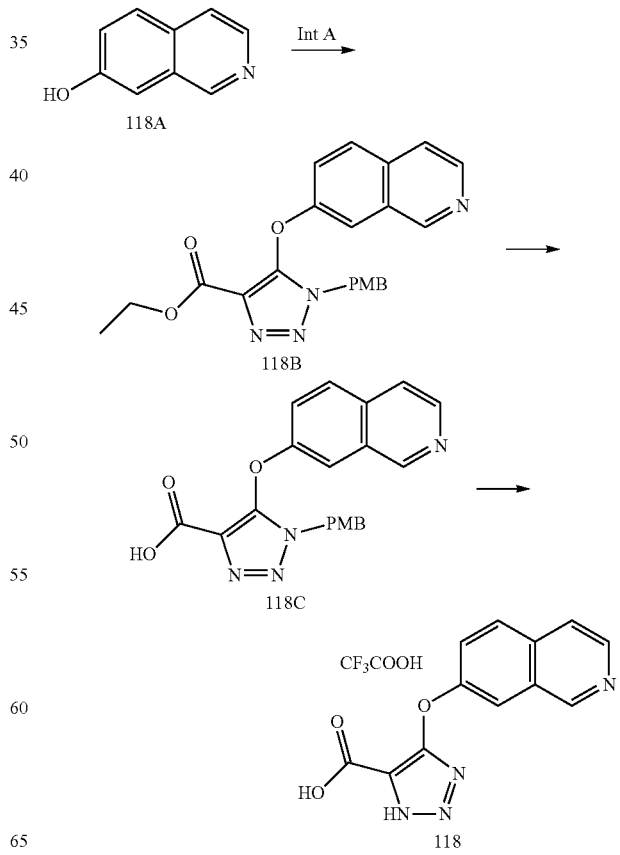

Compounds 118B, 118C, and 118 were synthesized by employing the procedures described for Intermediate I, Compounds 8F, and 1 using Compounds 118A, 118B, and 118C in lieu of 4-bromophenol, Compounds 8E, and 1E. Compound 118B: LC-MS: (ESI) m/z: 405 [M+H]+. Compound 118C: LC-MS (ESI) m/z: 377 [M+H]+. Compound 118: LC-MS (ESI) m/z: 257 [M+H]+; ¹H-NMR (DMSO-d₆, 400 MHz): δ (ppm) 7.56 (s, 1H), 7.68 (d, J=7.9 Hz, 1H), 8.01 (s, 1H), 8.35 (d, J=8.5 Hz, 1H), 8.52 (d, J=6.1 Hz, 1H), 9.50 (s, 1H).

Example 119

Synthesis of 4-((2-chloro-4'-(trifluoromethoxy)-[1,1'-biphenyl]-4-yl)oxy)-1H-1,2,3-triazole-5-carboxylic acid (119)

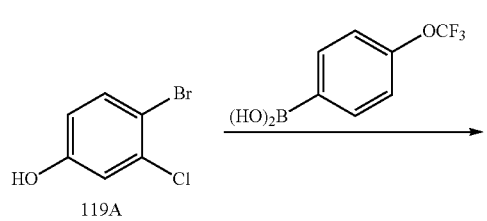

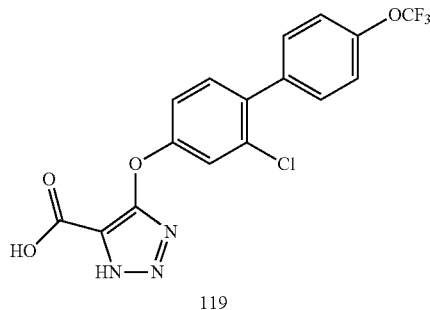

Compounds 119B, 119C, 119D, and 119 were synthesized by employing the procedures described for Compounds 4B, 86B, 8F, and 1 using (4-(trifluoromethoxy)phenyl)boronic acid, Compounds 119A using 1,4-dioxane and H₂O as solvent, 119B, 119C, and 119D in lieu of (4-bromophenyl)boronic acid, Compounds 4A using toluene/EtOH/H₂O as solvent, 86A, 8E, and 1E. Compound 119B: LC-MS (ESI) m/z: 287 [M–H]⁻. Compound 119C: LC-MS (ESI) m/z: 548 [M+H]+. Compound 119D: LC-MS (ESI) m/z: 1061 [2M+Na]t Compound 119: LC-MS (ESI) m/z: 400 [M+H]+; ¹H-NMR (DMSO-d₆, 400 MHz): δ (ppm) 7.13 (dd, J=8.4, 2.4 Hz, 1H), 7.34 (d, J=2.4 Hz, 1H), 7.43-7.48 (m, 3H), 7.55-7.59 (m, 2H).

Example 120

Synthesis of 4-(quinolin-6-yloxy)-1H-1,2,3-triazole-5-carboxylic acid 2,2,2-trifluoroacetate (120)

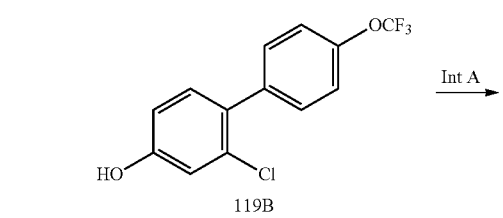

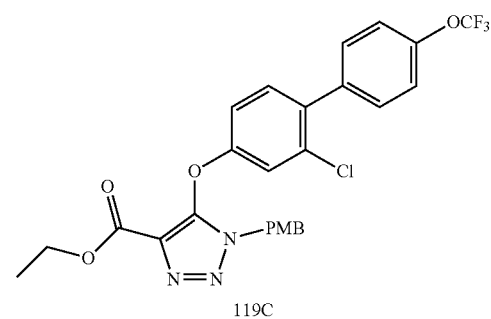

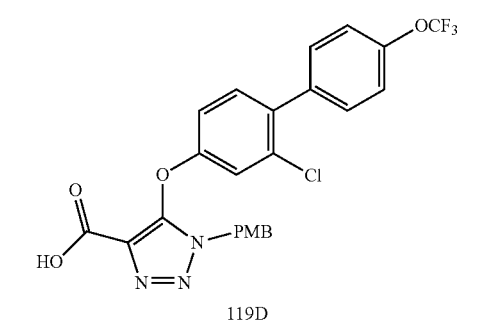

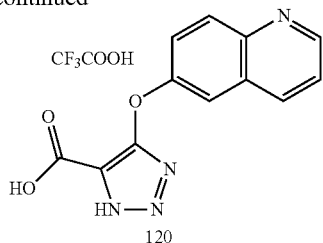

Compounds 120B, 120C, and 120 were synthesized by employing the procedures described for Intermediate I, Compounds 8F, and 1 using Compounds 120A, 120B, and 120C in lieu of 4-bromophenol, Compounds 8E, and 1E. Compound 120B: LC-MS: (ESI) m/z: 405 [M+H]$^+$; $^1$H-NMR (CDCl$_3$, 400 MHz): δ (ppm) 1.05 (t, J=7.1 Hz, 3H), 3.61 (s, 3H), 4.09-4.21 (m, 2H), 5.41 (s, 2H), 6.63-6.68 (m, 2H), 6.72 (d, J=2.4 Hz, 1H), 7.13-7.19 (m, 2H), 7.24 (dd, J=9.0, 2.5 Hz, 1H), 7.36 (d, J=5.8 Hz, 1H), 7.94 (d, J=9.0 Hz, 1H), 8.47 (d, J=5.8 Hz, 1H), 9.19 (s, 1H). Compound 120C: LC-MS (ESI) m/z: 377 [M+H]$^+$. Compound 120: LC-MS (ESI) m/z: 257 [M+H]$^+$; $^1$H-NMR (DMSO-d$_6$, 400 MHz): δ (ppm) 7.55-7.64 (m, 2H), 7.69 (dd, J=8.8, 2.4 Hz, 1H), 8.09 (d, J=9.2 Hz, 1H), 8.43 (d, J=7.7 Hz, 1H), 8.91 (d, J=2.6 Hz, 1H).

Example 121

Synthesis of 4-(isoquinolin-6-yloxy)-1H-1,2,3-triazole-5-carboxylic acid 2,2,2-trifluoroacetate (121)

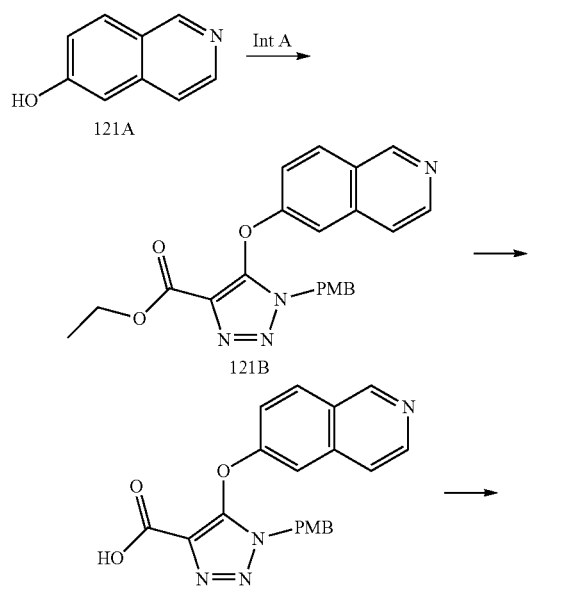

Compounds 121B, 121C, and 121 were synthesized by employing the procedures described for Compounds 86B, 8F, and 1 using Compounds 121A, 121B, and 121C in lieu of Compounds 86A, 8E, and 1E. Compound 121B: LC-MS: (ESI) m/z: 405 [M+H]$^+$; $^1$H-NMR (CDCl$_3$, 400 MHz): δ (ppm) 1.05 (t, J=7.1 Hz, 3H), 3.61 (s, 3H), 4.02-4.27 (m, 2H), 5.42 (s, 2H), 6.60-6.69 (m, 2H), 6.72 (d, J=2.4 Hz, 1H), 7.16 (d, J=8.7 Hz, 2H), 7.24 (dd, J=8.8, 2.4 Hz, 1H), 7.36 (d, J=5.8 Hz, 1H), 7.94 (d, J=9.0 Hz, 1H), 8.47 (d, J=5.8 Hz, 1H), 9.19 (s, 1H). Compound 121C: LC-MS (ESI) m/z: 377 [M+H]$^+$; $^1$H-NMR (DMSO-d$_6$, 400 MHz): δ (ppm) 3.55 (s, 3H), 5.51 (s, 2H), 6.69 (d, J=8.7 Hz, 2H), 7.14 (d, J=8.7 Hz, 2H), 7.42 (d, J=2.2 Hz, 1H), 7.75 (dd, J=8.8, 2.4 Hz, 1H), 8.19 (t, J=7.2 Hz, 1H), 8.50 (d, J=9.1 Hz, 1H), 8.58 (d, J=6.4 Hz, 1H), 9.75 (s, 1H). Compound 121: LC-MS (ESI) m/z: 257 [M+H]$^+$; $^1$H-NMR (DMSO-d$_6$, 400 MHz): δ (ppm) 7.62 (s, 1H), 7.74 (d, J=9.0 Hz, 1H), 8.11 (d, J=6.1 Hz, 1H), 8.41 (d, J=9.0 Hz, 1H), 8.55 (d, J=6.2 Hz, 1H), 9.58 (s, 1H).

Example 122

Synthesis of 5-(4-(quinolin-6-yl)phenoxy)-1H-1,2,3-triazole-4-carboxylic acid (122)

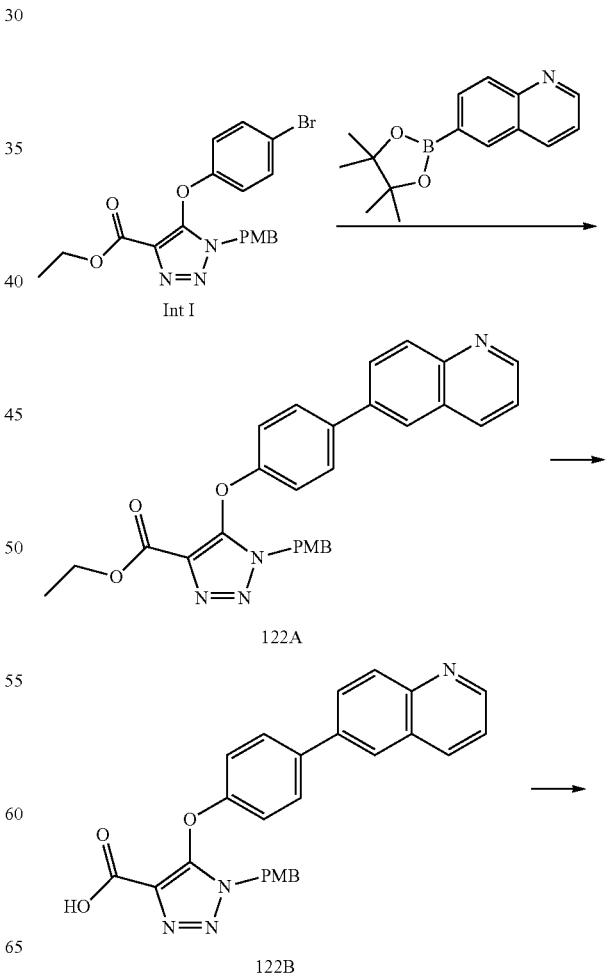

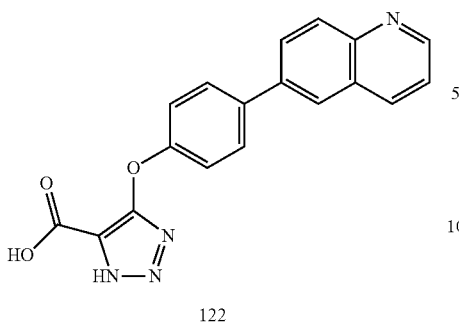

122

Compounds 122A, 122B, and 122 were synthesized by employing the procedures described for Compounds 8B, 8F, and 1 using 6-(4,4,5,5-tetramethyl-1,3,2-dioxaborolan-2-yl)quinolone, Intermediate I using $Na_2CO_3$ as base and 1,4-dioxane/$H_2O$ as solvent, Compounds 122A, and 122B in lieu of (3,4-dichlorophenyl)boronic acid, Compounds 8A using $Cs_2CO_3$ as base and DME/$H_2O$ as solvent, 8E, and 1E. Compound 122A: LC-MS (ESI) m/z: 481 [M+H]$^+$. Compound 122B: LC-MS (ESI) m/z: 453 [M+H]$^+$. Compound 122: LC-MS (ESI) m/z: 333 [M+H]$^+$; $^1$H-NMR (DMSO-$d_6$, 400 MHz): δ (ppm) 7.23 (dd, J=2.0, 6.8 Hz, 2H), 7.66 (dd, J=2.0, 6.8 Hz, 1H), 7.85 (dd, J=1.6, 6.4 Hz, 2H), 8.11-8.15 (m, 2H), 8.34 (s, 1H), 8.55 (d, J=8.4 Hz, 1H), 8.96 (d, J=4.8 Hz, 1H).

Example 123

Synthesis of 4-((2-isopropyl-1,2,3,4-tetrahydroisoquinolin-6-yl)oxy)-1H-1,2,3-triazole-5-carboxylic acid 2,2,2-trifluoroacetate (123)

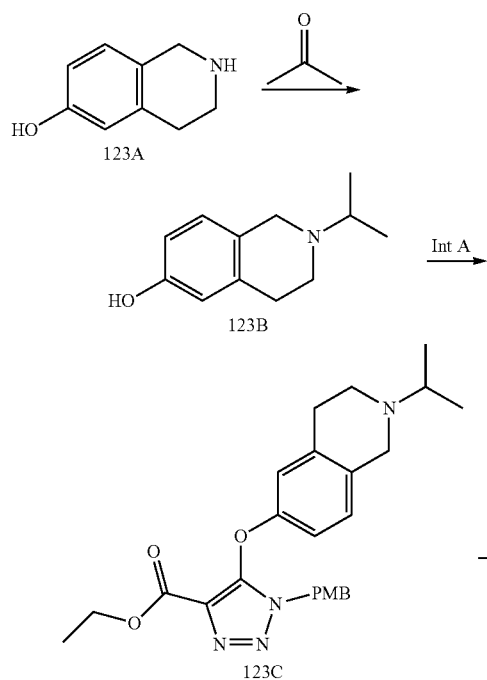

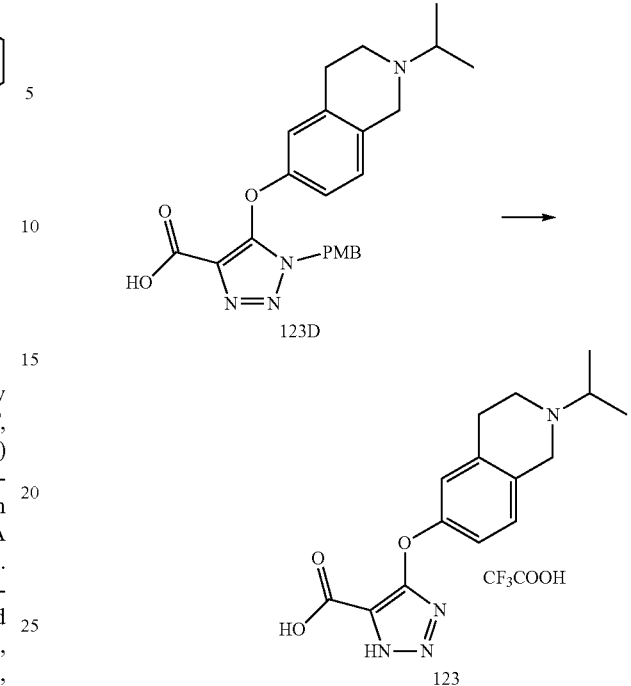

To a mixture of 1,2,3,4-tetrahydroisoquinolin-6-ol (Compound 123A) (1.49 g, 10.0 mmol), acetone (3 mL, 50 mmol), and sodium cyanoborohydride (1.26 g, 20 mmol) in methanol (100 mL) was added 60 drops of acetic acid and stirred at room temperature for 16 hours. The mixture was concentrated under reduced pressure. The residue was diluted with water (100 mL) and extracted with ethyl acetate (100 mL×2). The combined extracts were dried over anhydrous sodium sulfate, filtered, and concentrated to give Compound 123B. LC-MS (ESI) m/z: 192.

Compounds 123C, 123D, and 123 were synthesized by employing the procedures described for Intermediate I, Compounds 8F, and 1 using Compounds 123B using NMP as solvent, 123C, and 123D in lieu of 4-bromophenol using DMF as solvent, Compounds 8E, and 1E. Compound 123C: LC-MS (ESI) m/z: 451. Compound 123D: LC-MS (ESI) m/z: 423. Compound 123: LC-MS (ESI) m/z: 303 [M+H]$^+$; $^1$H-NMR (DMSO-$d_6$, 400 MHz): δ (ppm) 1.32 (s, 3H), 1.33 (s, 3H), 3.06 (d, J=2.4 Hz, 2H), 3.30 (s, 1H), 3.62-3.66 (m, 2H), 4.37 (s, 1H), 6.96-7.03 (m, 2H), 7.24 (d, J=8.0 Hz, 1H), 9.64 (s, 1H).

Example 124

Synthesis of 4-(2-(3,4-dichlorophenyl)thiazol-4-yl)-1H-1,2,3-triazole-5-carboxylic acid (124)

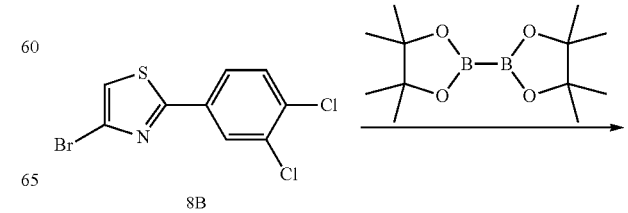

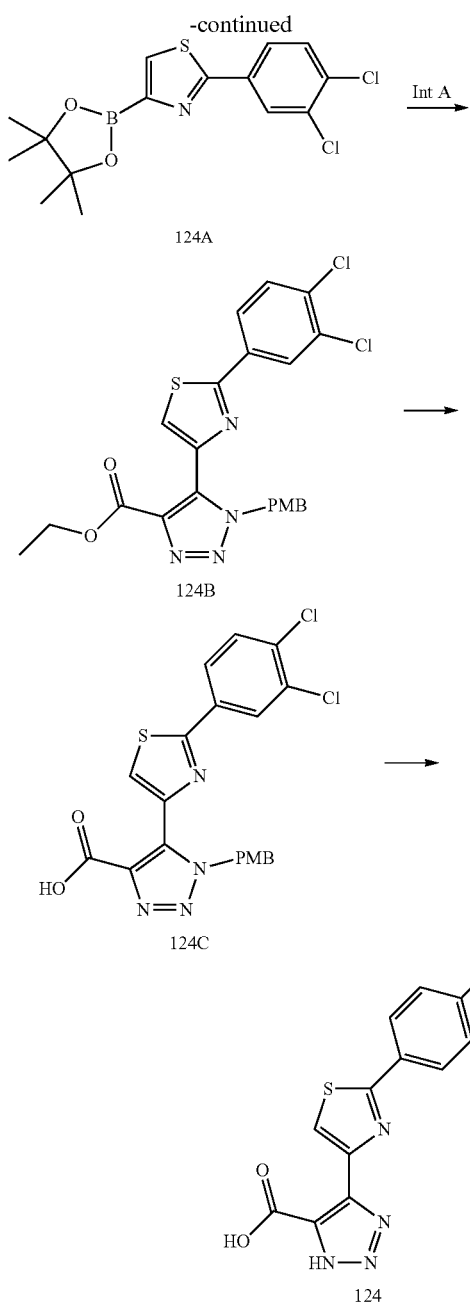

To a solution of Compound 8B (309 mg, 1.0 mmol) and 4,4,4',4',5,5,5',5'-octamethyl-2,2'-bi(1,3,2-dioxaborolane) (254 mg, 1.0 mmol) in 1,4-dioxane (5 mL) were successively added Pd$_2$(dba)$_3$ (92 mg, 0.1 mmol), tricyclohexyl phosphine (56 mg, 0.2 mmol) and potassium acetate (196 mg, 2.0 mmol). The mixture was heated at 145° C. in a microwave reactor under nitrogen for 50 minutes. The mixture was allowed to cool down to room temperature and filtered through Celite. The filtrate was concentrated under reduced pressure and the residue was partitioned between ethyl acetate (50 mL) and water (50 mL). The aqueous phase was extracted with ethyl acetate (50 mL×2). The combined extracts were washed with brine (100 mL), dried over anhydrous sodium sulfate, filtered, and concentrated to give Compound 124A, which was used directly for the next step. LC-MS (ESI) m/z: 274 [M−82+H]$^+$.

Compounds 124B, 124C, and 124 were synthesized by employing the procedures described for Compounds 4B, 8F, and 1 using Intermediate A, Compounds 124A using K$_3$PO$_4$ as base and DMF/H$_2$O as solvent, 124B, and 124C in lieu of Compounds 4A using Na$_2$CO$_3$ as base and toluene/EtOH/H$_2$O as solvent, 8E, and 1E. Compound 124B: LC-MS (ESI) m/z: 489 [M+H]$^+$. Compound 124C: LC-MS (ESI) m/z: 461 [M+H]$^+$. Compound 124: LC-MS (ESI) m/z: 341 [M+H]$^+$; $^1$H-NMR (DMSO-d$_6$, 400 MHz): δ (ppm) 7.83 (d, J=8.4 Hz, 1H), 8.02 (d, J=8.4 Hz, 1H), 8.37 (s, 1H), 8.77 (s, 1H).

Example 125

Synthesis of 4-(3,4-dichlorophenyl)-1H-1,2,3-triazole-5-carboxylic acid (125)

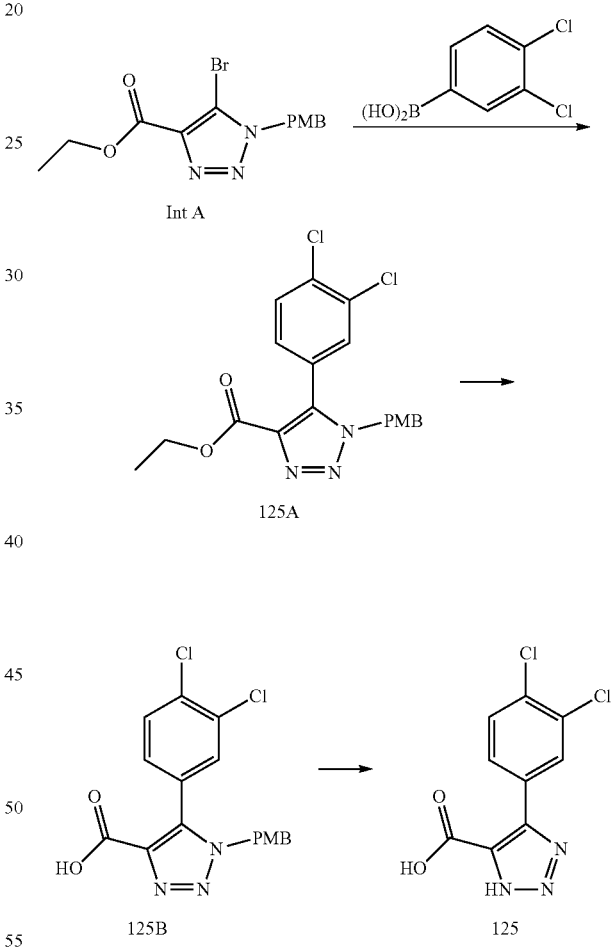

Compounds 125A, 125B, and 125 were synthesized by employing the procedures described for Compounds 8B, 8F, and 1 using Intermediate A using Na$_2$CO$_3$ as base and 1,4-dioxane/H$_2$O as solvent, Compounds 125A, and 125B in lieu of Compounds 8A using Cs$_2$CO$_3$ as base and DME/H$_2$O as solvent, 8E, and 1E. Compound 125A: LC-MS (ESI) m/z: 406 [M+H]$^+$. Compound 125B: LC-MS (ESI) m/z: 378 [M+H]$^+$. Compound 125: LC-MS (ESI) m/z: 258 [M+H]$^+$; $^1$H-NMR (DMSO-d$_6$, 400 MHz): δ (ppm) 7.73 (d, J=8.4 Hz, 1H), 7.97 (s, 1H), 8.31 (s, 1H).

Example 126

Synthesis of 4-(4'-chloro-[1,1'-biphenyl]-4-yl)-1H-1,2,3-triazole-5-carboxylic acid 2,2,2-trifluoroacetate (126)

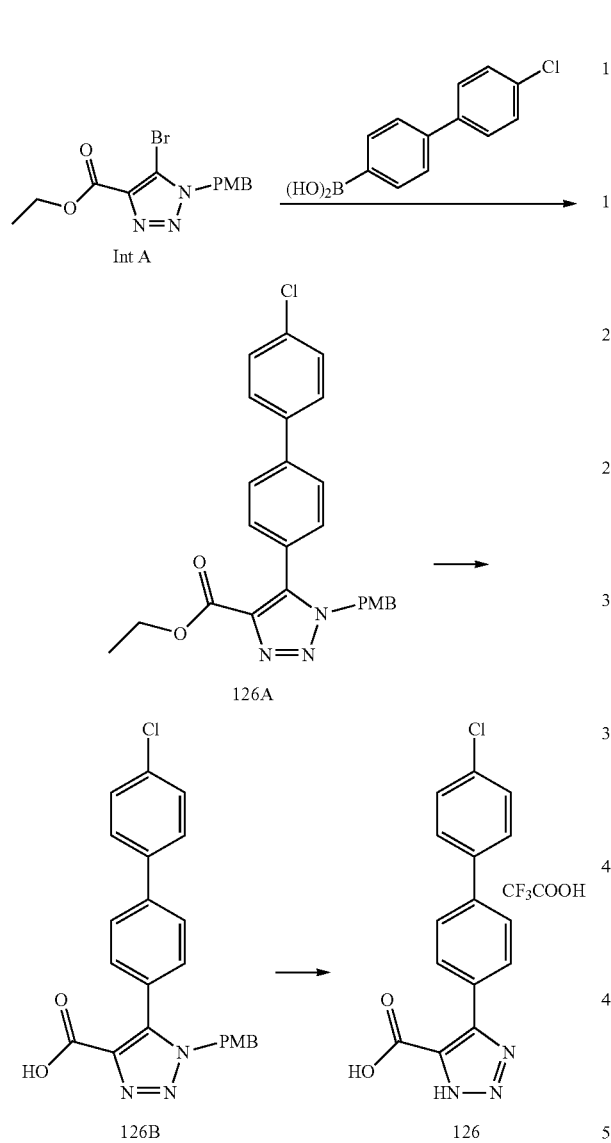

Compounds 126A, 126B, and 126 were synthesized by employing the procedures described for Compounds 8B, 8F, and 1 using 4'-chlorobiphenyl-4-ylboronic acid using Na$_2$CO$_3$ as base and 1,4-dioxane/H$_2$O as solvent, Compounds 126A, and 126B in lieu of Compounds 8A using Cs$_2$CO$_3$ as base and DME/H$_2$O as solvent, 8E, and 1E. Compound 126A: LC-MS (ESI) m/z: 448 [M+H]$^+$. Compound 126B: LC-MS (ESI) m/z: 420 [M+H]+. Compound 126: LC-MS (ESI) m/z: 300 [M+H]$^+$. $^1$H-NMR (DMSO-d$_6$, 400 MHz): δ (ppm) 7.54 (d, J=8.8 Hz, 4H). 7.78 (d, J=8.4 Hz, 4H), 7.85-7.91 (m, 3H).

Example 127

Synthesis of 4-(4-(4-chlorophenoxy)phenyl)-1H-1,2,3-triazole-5-carboxylic acid (127)

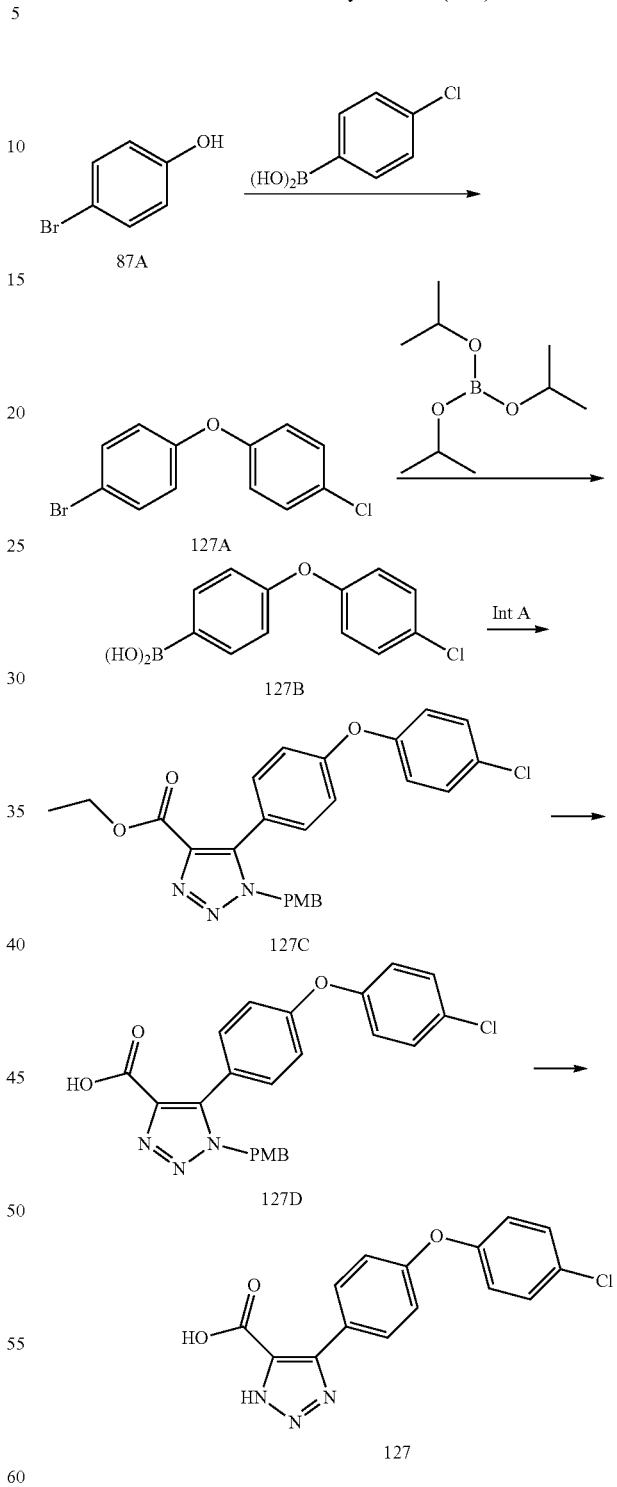

To a suspension of 4-bromophenol (Compound 87A) (5.0 g, 29 mmol), 4-chlorophenylboronic acid (6.8 g, 43.5 mmol), and 4 Å molecular sieves (2.0 g) in dichloromethane (200 mL) was added Cu(OAc)$_2$ (5.26 g, 29 mmol), pyridine (11.5 g, 145 mmol), and DIPEA (18.7 g, 145 mmol), stirred at room temperature for 12 hours, and filtered. The filtrate was concentrated and purified with flash column chromatography on silica gel (ethyl acetate in petroleum ether, 10% v/v) to give Compound 127A. LC-MS (ESI) m/z: non-ionizable compound under routine conditions used. $^1$H-NMR (CDCl$_3$, 400 MHz): δ (ppm) 6.86-6.88 (m, 2H), 6.91-6.94 (m, 2H), 7.28-7.30 (m, 2H), 7.42-7.44 (m, 2H).

To a solution of Compound 127A (660 mg, 2.3 mmol) in anhydrous THF (20 mL) at −78° C. under nitrogen was added a solution of n-BuLi in n-hexane (2.5 M, 1.1 mL, 2.76 mmol) and stirred at −78° C. for 30 minutes. To the solution was added triisopropyl borate (526 mg, 2.76 mmol) and stirred at −78° C. for 2 hours. The mixture was quenched with H$_2$O (10 mL), diluted with 10% aqueous HCl solution (10 mL), stirred at room temperature for additional 30 minutes, and extracted with ethyl acetate (50 mL×3). The combined extracts were dried over anhydrous Na$_2$SO$_4$, filtered, and concentrated to give Compound 127B, which was used directly in the next step. LC-MS (ESI) m/z: non-ionizable compound under routine conditions used.

Compounds 127C, 127D, and 127 were synthesized by employing the procedures described for Compounds 8B, 8F, and 1 using Intermediate A, Compounds 127B using toluene/DMF as solvent, 127C, and 127D in lieu of Compounds 8A, (3,4-dichlorophenyl)boronic acid using DME/H$_2$O as solvent, 8E, and 1E. Compound 127C: LC-MS (ESI) m/z: 464 [M+H]$^+$; $^1$H-NMR (CDCl$_3$, 400 MHz): δ (ppm) 1.30 (t, J=7.2 Hz, 3H), 3.77 (s, 3H), 4.31 (q, J=7.2 Hz, 2H), 5.38 (s, 2H), 6.78 (m, 2H), 6.94-6.97 (m, 2H), 7.01-7.04 (m, 4H), 7.16-7.18 (m, 2H), 7.34-7.36 (m, 2H). Compound 127D: LC-MS (ESI) m/z: 436 [M+H]$^+$; $^1$H-NMR (CDCl$_3$, 400 MHz): δ (ppm) 3.77 (s, 3H), 5.39 (s, 2H), 6.78-6.81 (m, 2H), 6.97-7.05 (m, 6H), 7.19-7.21 (m, 2H), 7.35-7.37 (m, 2H). Compound 127: LC-MS (ESI) m/z: 316 [M+H]$^+$; $^1$H-NMR (DMSO-d$_6$, 400 MHz): δ (ppm) 7.10-7.13 (m, 4H), 7.46-7.48 (m, 2H), 7.84-7.87 (m, 2H), 13.10 (s, 1H), 15.80 (s, 1H).

Example 128

Synthesis of 4-(4'-(trifluoromethoxy)-[1,1'-biphenyl]-4-yl)-1H-1,2,3-triazole-5-carboxylic acid (128)

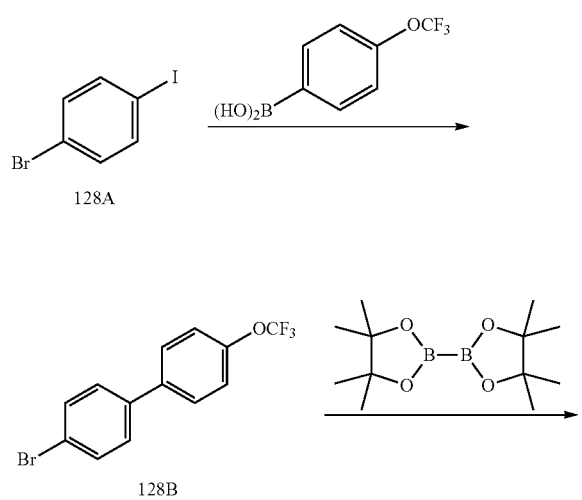

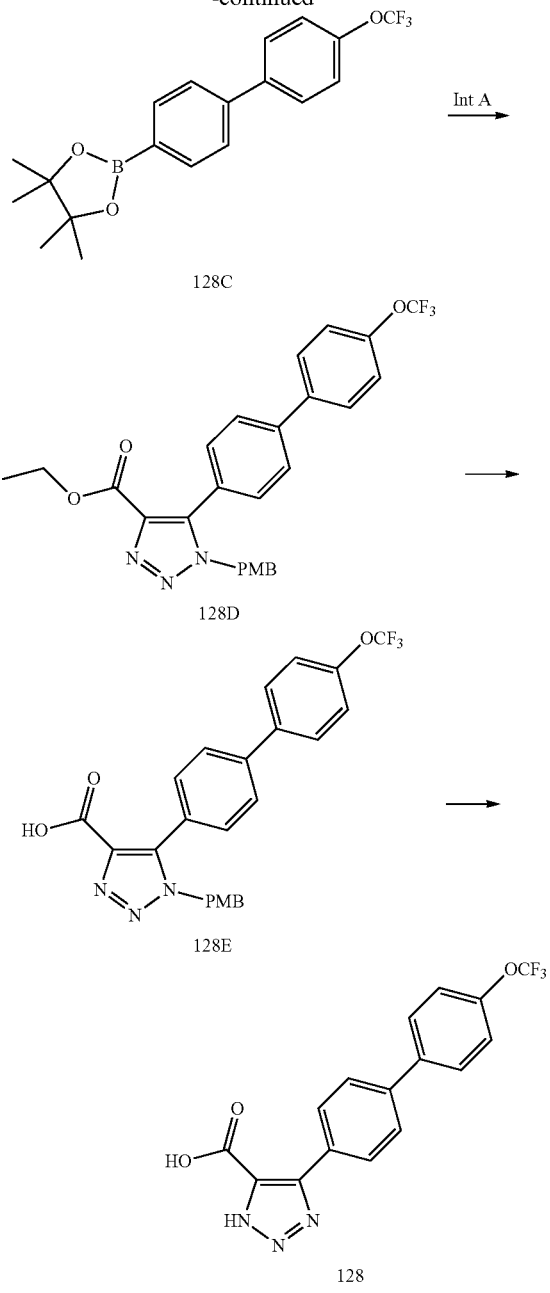

Compounds 128B, 128C, 128D, 128E, and 128 were synthesized by employing the procedures described for Compounds 8B, 27C, 8B, 8F, and 1 using Compounds 128A, 4-(trifluoromethoxy)phenylboronic acid using Na$_2$CO$_3$ as base and toluene/DMF as solvent, 128B, Intermediate A, 128C using Na$_2$CO$_3$ as base and toluene/DMF as solvent, 128D, and 128E in lieu of Compounds 8A, (3,4-dichlorophenyl)boronic acid using Cs$_2$CO$_3$ as base and DME/H$_2$O as solvent, 27B, 8A, (3,4-dichlorophenyl)boronic acid using Cs$_2$CO$_3$ as base and DME/H$_2$O as solvent, 8E, and 1E. Compound 128B: LC-MS (ESI) m/z: Non-ionizable compound under routine conditions used; $^1$H-NMR (CDCl$_3$, 400 MHz): δ (ppm) 7.30 (dd, J=8.8, 1.2 Hz, 2H), 7.43 (dd, J=6.4, 2.0 Hz, 2H), 7.56-7.60 (m, 4H). Compound 128C: LC-MS (ESI) m/z: Non-ionizable compound under routine conditions used; $^1$H-NMR (CDCl$_3$, 400

MHz): δ (ppm), 1.38 (s, 12H), 7.30 (d, J=8.0 Hz, 2H), 7.58 (d, J=8.4 Hz, 2H), 7.63 (d, J=8.8 Hz, 2H), 7.91 (d, J=8.0 Hz, 2H). Compound 128D: LC-MS (ESI) m/z: 498 [M+H]+. Compound 128E: LC-MS (ESI) m/z: 378 [M+H]+. Compound 128: LC-MS (ESI) m/z: 350 [M+H]+; 1H-NMR (CD3OD, 400 MHz): δ (ppm) 7.39 (d, J=8.0 Hz, 2H), 7.75-7.82 (m, 4H), 7.97 (d, J=8.0 Hz, 2H).

Example 129

Synthesis of 4-(3',4'-dichloro-[1,1'-biphenyl]-3-yl)-1H-1,2,3-triazole-5-carboxylic acid (129)

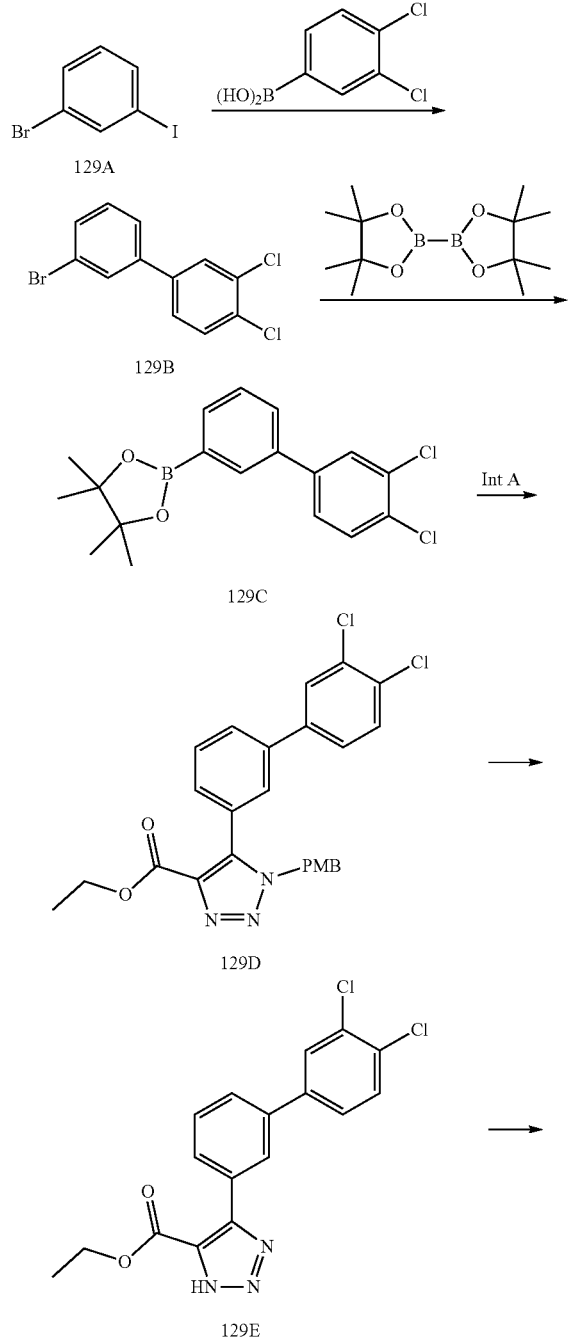

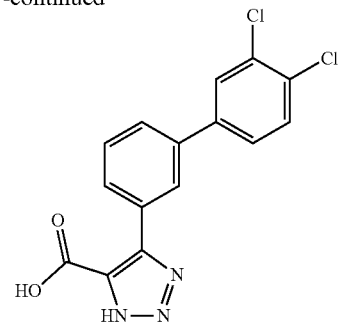

Compounds 129B, 129C, 129D, 129E, and 129 were synthesized by employing the procedures described for Compounds 8B, 27C, 8B, 1, and 8F using Compounds 129A using Na2CO3 as base and toluene/DMF as solvent, 129B, Intermediate A, 129C using Na2CO3 as base and toluene/DMF as solvent, 129D, and 129E in lieu of Compounds 8A using Cs2CO3 as base and DME/H2O as solvent, 27B, 8A, 4-dichlorophenyl)boronic acid using Cs2CO3 as base and DME/H2O as solvent, 1E, and 8E. Compound 129B: LC-MS (ESI) m/z: Non-ionizable compound under routine conditions used; 1H-NMR (CDCl3, 400 MHz): δ (ppm) 7.33 (t, J=8.0 Hz, 1H), 7.39 (dd, J=8.4, 2.0 Hz, 1H), 7.46-7.49 (m, 1H), 7.53 (dd, J=8.0, 1.6 Hz, 2H), 7.65 (d, J=2.0 Hz, 1H), 7.69 (t, J=1.6 Hz, 1H). Compound 129C: LC-MS (ESI) m/z: Non-ionizable compound under routine conditions used; 1H-NMR (CDCl3, 400 MHz): δ (ppm), 1.42 (s, 12H), 7.45-7.51 (m, 3H), 7.64 (d, J=8.0 Hz, 1H), 7.72 (d, J=2.0 Hz, 1H), 7.84 (d, J=7.2 Hz, 1H), 8.00 (s, 1H). Compound 129D: LC-MS (ESI) m/z: 482 [M+H]+. Compound 129E: LC-MS (ESI) m/z: 362 [M+H]+. Compound 129: LC-MS (ESI) m/z: 334 [M+H]+; 1H-NMR (CD3OD, 400 MHz): δ (ppm) 7.57-7.63 (m, 3H), 7.74 (d, J=8.0 Hz, 1H), 7.87-7.90 (m, 2H), 8.18 (s, 1H).

Example 130

Synthesis of 4-(2',4'-dichloro-[1,1'-biphenyl]-4-yl)-1H-1,2,3-triazole-5-carboxylic acid 2,2,2-trifluoroacetate (130)

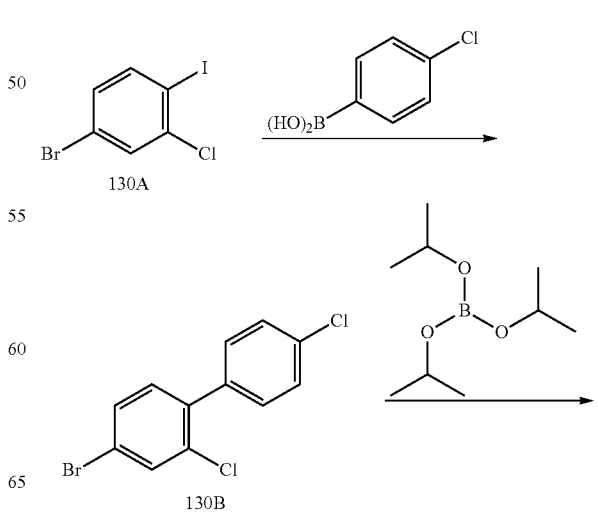

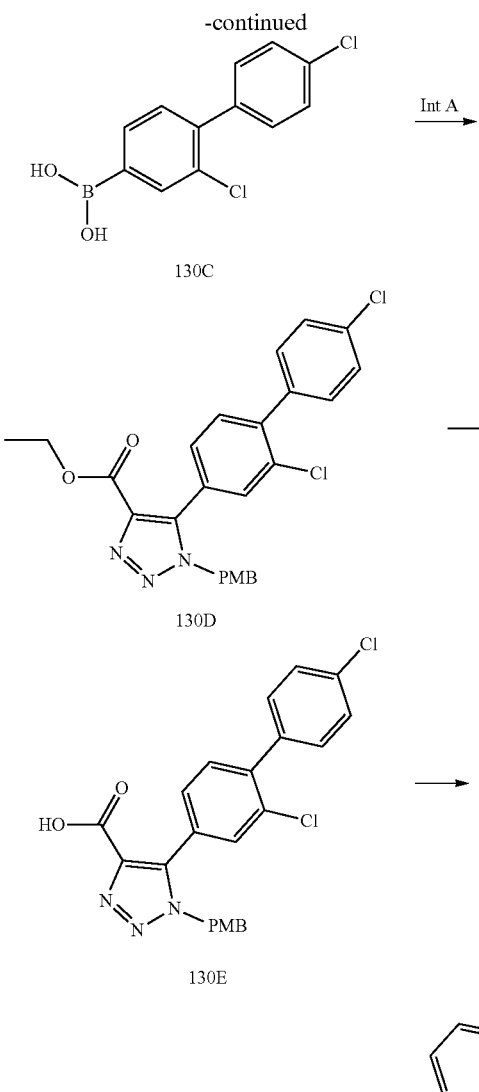

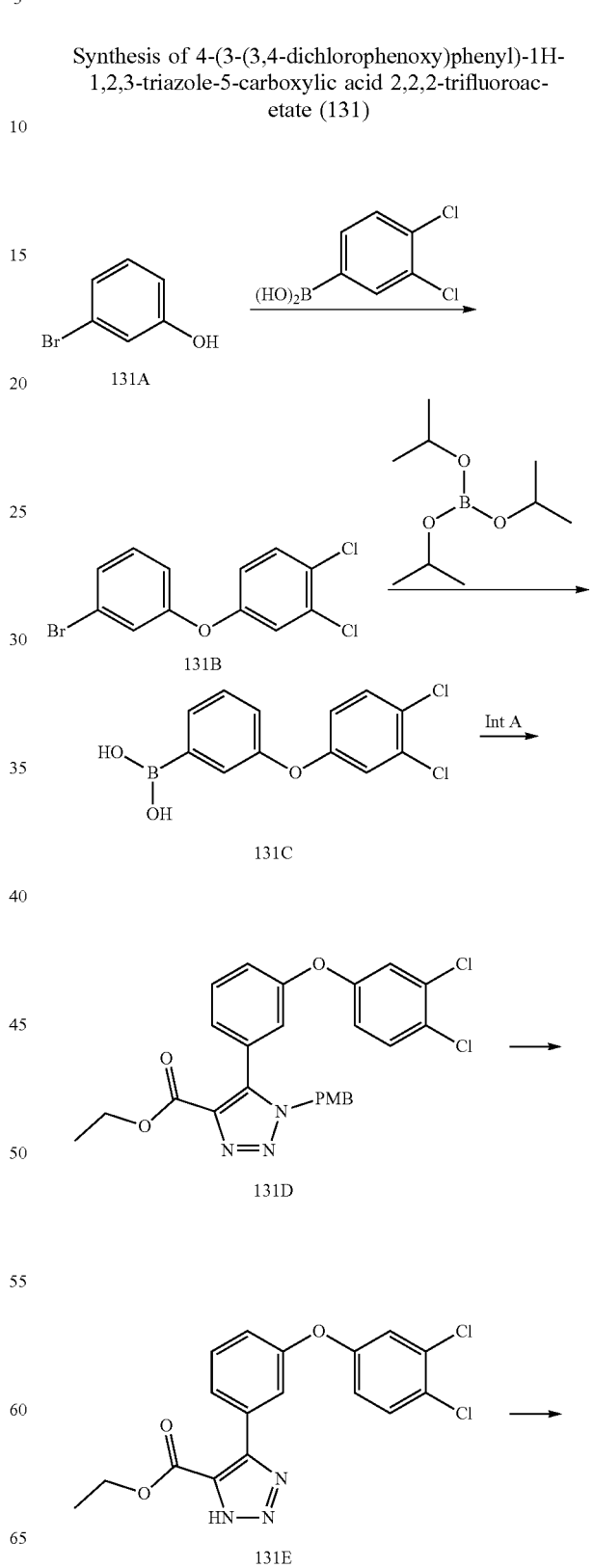

Compounds 130B, 130C, 130D, 130E, and 130 were synthesized by employing the procedures described for Compounds 8B, 127C, 8B, 8F, and 1 using Compounds 130A using $K_2CO_3$ as base and DMF/$H_2O$ as solvent, 130B, Intermediate A, 130C using $Na_2CO_3$ as base and toluene/DMF as solvent, 130D, and 130E in lieu of Compounds 8A using $Cs_2CO_3$ as base and DME/$H_2O$ as solvent, 127B, 8A, (3,4-dichlorophenyl)boronic acid using $Cs_2CO_3$ as base and DME/$H_2O$ as solvent, 8E, and 1E. Compound 130B: $^1$H-NMR (CDCl$_3$, 400 MHz): δ (ppm) 7.15-7.17 (d, J=8.0 Hz, 1H), 7.31-7.33 (m, 2H), 7.38-7.40 (m, 2H), 7.45 (dd, J=8.0, 2.0 Hz, 1H), 7.65 (d, J=2.0 Hz, 1H). Compound 130C: LC-MS (ESI) m/z: 267 [M+H]$^+$. Compound 130D: LC-MS (ESI) m/z: 482 [M+H]$^+$. Compound 130E: LC-MS (ESI) m/z: 454 [M+H]$^+$. Compound 130: LC-MS (ESI) m/z: 334 [M+H]$^+$; $^1$H-NMR (CD$_3$OD, 500 MHz): δ (ppm) 7.48-7.49 (m, 5H), 7.94-7.96 (m, 1H), 8.14 (s, 1H).

Example 131

Synthesis of 4-(3-(3,4-dichlorophenoxy)phenyl)-1H-1,2,3-triazole-5-carboxylic acid 2,2,2-trifluoroacetate (131)

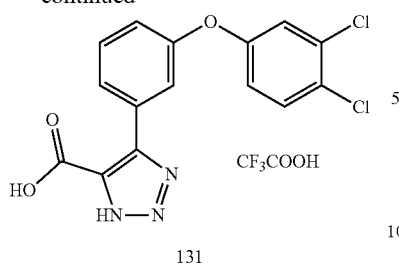

131

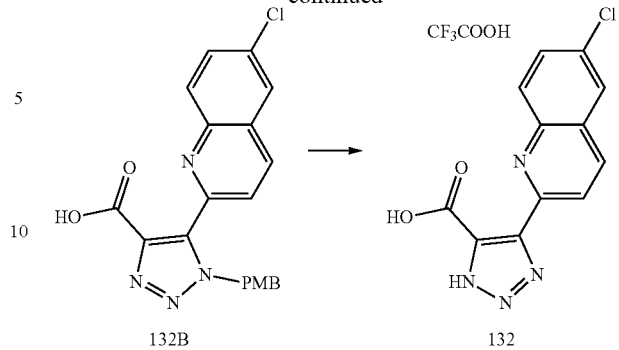

Compounds 131B, 131C, 131D, 131E, and 131 were synthesized by employing the procedures described for Compounds 127B, 127C, 8B, 8F, and 1 using 3,4-dichlorophenylboronic acid, Compounds 131A, 131B, Intermediate A, 131C using toluene/DMF as solvent, 131D, and 131E in lieu of 4-chlorophenylboronic acid, Compounds 127A, 127B, 8A, (3,4-dichlorophenyl)boronic acid using DME/H$_2$O as solvent, 8E, and 1E. Compound 131B: LC-MS (ESI) m/z: Non-ionizable compound under routine conditions used. Compound 131C: LC-MS (ESI) m/z: 283 [M+H]$^+$. Compound 131D: LC-MS (ESI) m/z: 498 [M+H]$^+$. Compound 131E: LC-MS (ESI) m/z: 470 [M+H]$^+$. Compound 131: LC-MS (ESI) m/z: 350 [M+H]$^+$; $^1$H-NMR (CD$_3$OD, 400 MHz): δ (ppm) 6.89 (dd, J=8.8, 2.8 Hz, 1H), 7.05 (dd, J=8.0, 2.0 Hz, 1H), 7.10 (d, J=3.2 Hz, 1H), 7.38-7.41 (m, 2H), 7.50-7.51 (m, 1H), 7.57-7.59 (m, 1H).

Example 132

Synthesis of 4-(6-chloroquinolin-2-yl)-1H-1,2,3-triazole-5-carboxylic acid 2,2,2-trifluoroacetate (132)

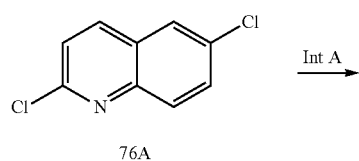

76A

To a mixture of Compound 76A (198 mg, 1.0 mmol) and tetrakis(triphenylphosphine)palladium (58 mg, 0.05 mmol) in xylene (10 mL) was added tributyltin hydride (582 mg, 2.0 mmol) and stirred at 135° C. under nitrogen for 2 hours. After the mixture was cooled down to room temperature, to it was added ethyl 5-bromo-1-(4-methoxybenzyl)-1H-1,2,3-triazole-4-carboxylate (340 mg, 1.0 mmol) and tetrakis(triphenylphosphine)palladium (58 mg, 0.05 mmol) and stirred at 120° C. under nitrogen for 4 hours. The mixture was cooled down to room temperature, quenched with water (50 mL), and extracted with ethyl acetate (50 mL×3). The combined extracts were washed with water (50 mL) and brine (50 mL), dried over anhydrous sodium sulfate, filtered, and concentrated. The residue was purified with flash column chromatography on silica gel (ethyl acetate in petroleum ether, from 10% to 25% v/v) to afford Compound 132A. LC-MS (ESI) m/z: 423 [M+H]$^+$.

Compounds 132B and 132 were synthesized by employing the procedures described for Compounds 8F and 1 using Compounds 132A and 131B in lieu of 8E and 1E. Compound 132B: LC-MS (ESI) m/z: 393 [M−H]$^-$. Compound 132: LC-MS (ESI) m/z: 275 [M+H]$^+$; $^1$H-NMR (DMSO-d$_6$, 400 MHz): δ (ppm) 7.92 (d, J=8.8, 2.0 Hz, 1H), 7.99 (d, J=8.8 Hz, 1H), 8.29 (d, J=2.0 Hz, 1H), 8.53 (d, J=8.8 Hz, 1H), 8.67 (d, J=8.8 Hz, 1H).

Example 133

Synthesis of 4-(6-chloronaphthalen-2-yl)-1H-1,2,3-triazole-5-carboxylic acid (133)

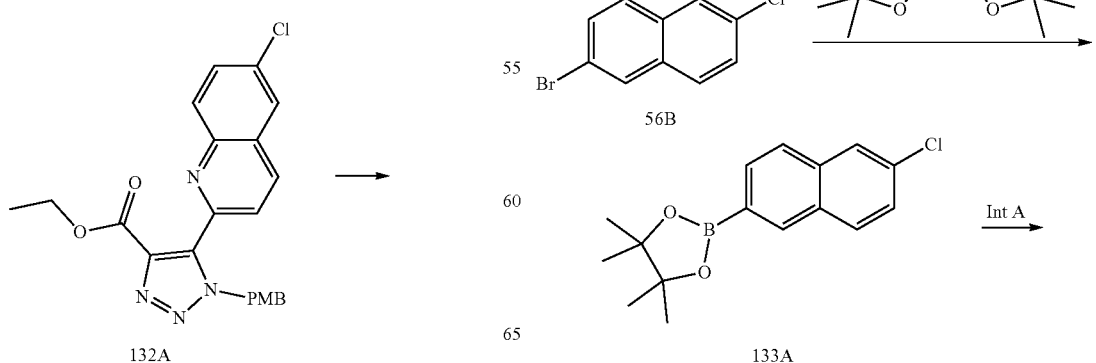

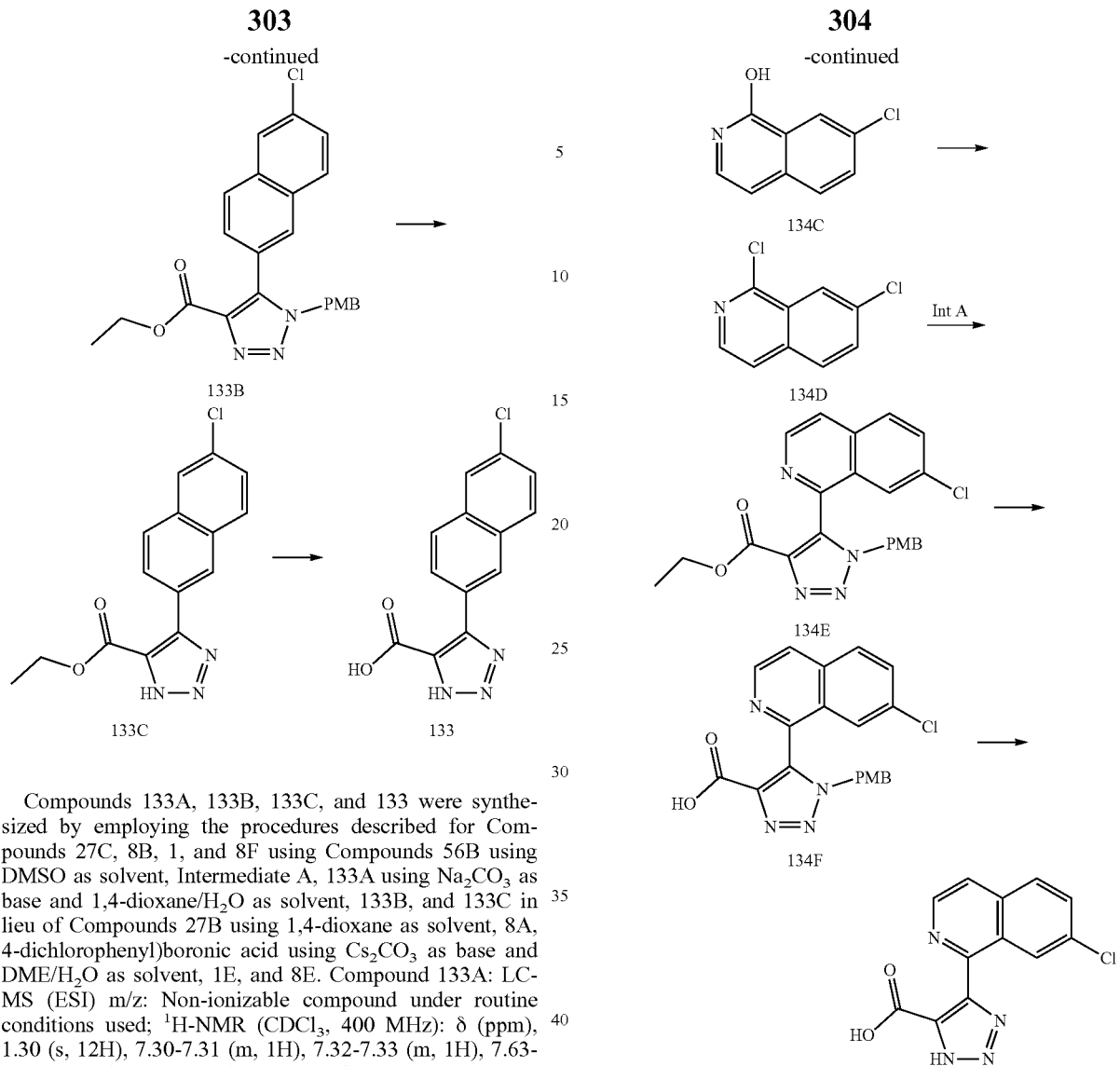

Compounds 133A, 133B, 133C, and 133 were synthesized by employing the procedures described for Compounds 27C, 8B, 1, and 8F using Compounds 56B using DMSO as solvent, Intermediate A, 133A using Na$_2$CO$_3$ as base and 1,4-dioxane/H$_2$O as solvent, 133B, and 133C in lieu of Compounds 27B using 1,4-dioxane as solvent, 8A, 4-dichlorophenyl)boronic acid using Cs$_2$CO$_3$ as base and DME/H$_2$O as solvent, 1E, and 8E. Compound 133A: LC-MS (ESI) m/z: Non-ionizable compound under routine conditions used; $^1$H-NMR (CDCl$_3$, 400 MHz): δ (ppm), 1.30 (s, 12H), 7.30-7.31 (m, 1H), 7.32-7.33 (m, 1H), 7.63-7.79 (m, 3H), 8.25 (s, 1H). Compound 133B: LC-MS (ESI) m/z: 422 [M+H]$^+$. Compound 133C: LC-MS (ESI) m/z: 302 [M+H]$^+$. Compound 133: LC-MS (ESI) m/z: 274 [M+H]$^+$; $^1$H-NMR (DMSO-d$_6$, 400 MHz): δ (ppm) 7.56-7.59 (m, 1H), 7.99-7.81 (m, 4H), 8.44 (s, 1H).

Example 134

Synthesis of 4-(7-chloroisoquinolin-1-yl)-1H-1,2,3-triazole-5-carboxylic acid (134)

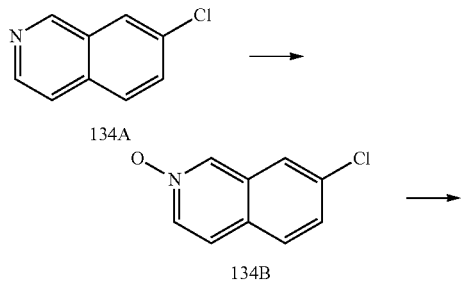

Compound 134B was synthesized by employing the procedure described for Compound 20C using Compound 134A in lieu of 20B, LC-MS (ESI) m/z: 180 [M+H]$^+$.

To a solution of Compound 134B (562 mg, 3.12 mmol) in dry DMF (10 mL) was added 4-methylbenzene-1-sulfonyl chloride (3.57 g, 18.73 mmol) and stirred at 80° C. overnight. The mixture was cooled down to room temperature, poured into a saturated aqueous NaHCO$_3$ solution (150 mL), stirred at room temperature for 0.5 hour, and extracted with EtOAc (60 mL×3). The combined extracts were washed with H$_2$O (100 mL) and brine (100 mL), dried over anhydrous sodium sulfate, filtered, and concentrated. The residue was purified with flash column chromatography on silica gel (ethyl acetate in petroleum ether, from 10% to 30% v/v) to afford Compound 134C. LC-MS (ESI) m/z: 180 [M+H]$^+$; $^1$H-NMR (CDCl$_3$, 400 MHz): δ (ppm) 6.51 (d, J=6.8 Hz, 1H), 7.13 (d, J=6.8 Hz, 1H), 7.50 (d, J=8.4 Hz, 1H), 7.61 (d, J=2 Hz, 1H), 8.38 (d, J=2.4 Hz, 1H), 10.48 (s, 1H).

To a solution of Compound 134C (280 mg, 3.12 mmol) in dry toluene (10 mL) was added DMF (1 mL) and SOCl$_2$ (1 mL) and stirred at 80° C. for 3 hours. The reaction mixture was cooled down to room temperature and concentrated under reduced pressure. The residue was purified with flash column chromatography on silica gel (ethyl acetate in petroleum ether, from 10% to 30% v/v) to afford Compound 134D. LC-MS (ESI) m/z: 198 [M+H]+. 1H-NMR (CDCl3, 400 MHz): δ (ppm) 7.59 (d, J=5.6 Hz, 1H), 7.70 (dd, J=2.4, 8.8 Hz, 1H), 7.81 (d, J=8.8 Hz, 1H), 8.29 (d, J=5.6 Hz, 1H), 8.34 (d, J=1.2 Hz, 1H).

Compounds 134E, 134F, and 134 were synthesized by employing the procedures described for Compounds 132A, 8F, and 1 using Compounds 134D, 134E, and 134F in lieu of Compounds 76A, 8E, and 1E. Compound 134E: LC-MS (ESI) m/z: 423 [M+H]+. Compound 134F: LC-MS (ESI) m/z: 395 [M+H]+. Compound 134: LC-MS (ESI) m/z: 275 [M+H]+; 1H-NMR (DMSO-d6, 400 MHz): δ (ppm) 7.93 (dd, J=1.6, 8.8 Hz, 1H), 8.08 (d, J=5.6 Hz, 1H), 8.18 (d, J=8.8 Hz, 1H), 8.64 (d, J=5.6 Hz, 1H), 8.98 (s, 1H).

Example 135

Synthesis of 4-(3-(trifluoromethoxy)phenyl)-1H-1,2,3-triazole-5-carboxylic acid (135)

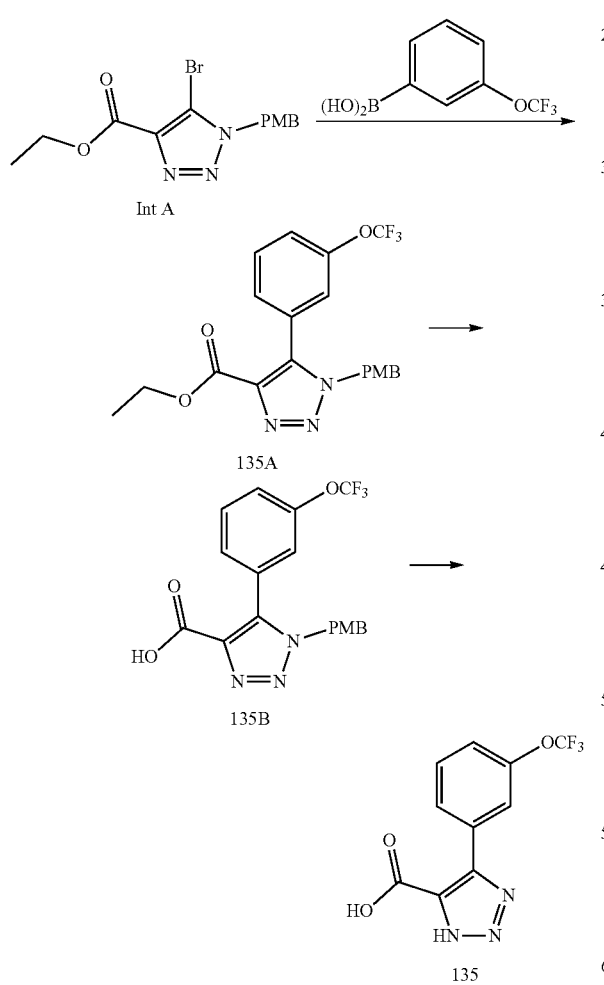

Compounds 135A, 135B, and 135 were synthesized by employing the procedures described for Compounds 4B, 8F, and 1 using 3-(trifluoromethoxy)phenylboronic acid, Intermediate A using 1,4-dioxane/H2O as solvent, Compounds 135A, and 135B in lieu of (4-bromophenyl)boronic acid, Compounds 4A using toluene/EtOH/H2O as solvent, 8E, and 1E. Compound 135A: LC-MS (ESI) m/z: 422 [M+H]+. Compound 135B: LC-MS (ESI) m/z: 394 [M+H]+. Compound 135: LC-MS (ESI) m/z: 274 [M+H]+; 1H-NMR (DMSO-d6, 400 MHz): δ (ppm) 7.45 (d, J=8 Hz, 1H), 7.61 (d, J=8.8 Hz, 1H), 7.90 (b, 2H).

Example 136

Synthesis of 4-(4-(trifluoromethoxy)phenyl)-1H-1,2,3-triazole-5-carboxylic acid (136)

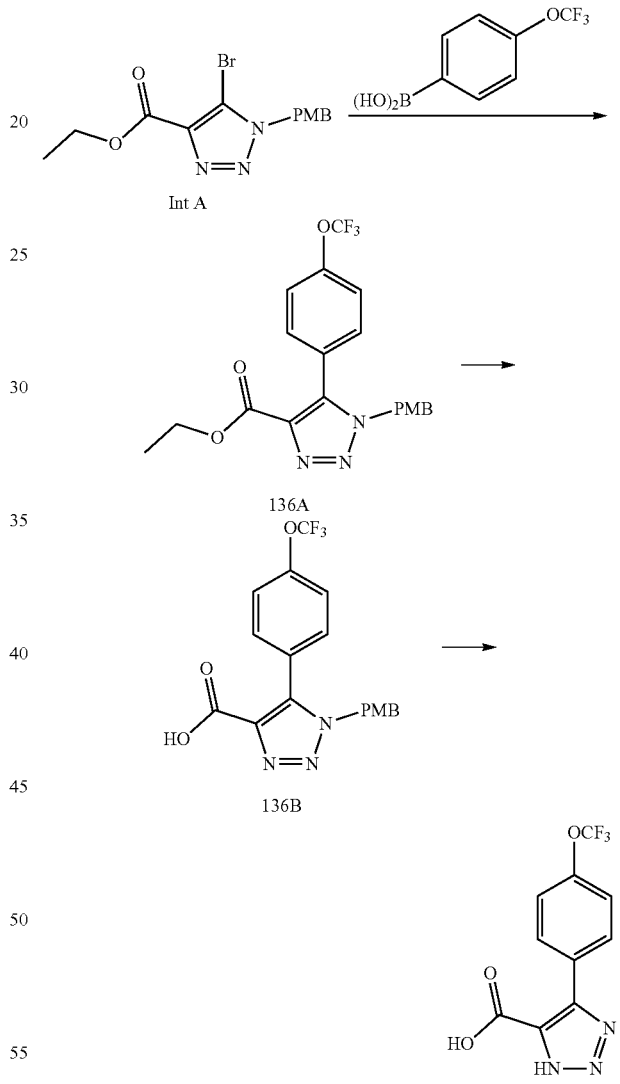

Compounds 136A, 136B, and 136 were synthesized by employing the procedures described for Compounds 4B, 8F, and 1 using 3-(trifluoromethoxy)phenylboronic acid, Intermediate A using 1,4-dioxane/H2O as solvent, Compounds 136A, and 136B in lieu of (4-bromophenyl)boronic acid, Compounds 4A using toluene/EtOH/H2O as solvent, 8E, and 1E. Compound 136A: LC-MS (ESI) m/z: 422 [M+H]+. Compound 136B: LC-MS (ESI) m/z: 394 [M+H]+. Compound 136: LC-MS (ESI) m/z: 274 [M+H]⁺. ¹H-NMR (DMSO-d₆, 400 MHz): δ (ppm) 7.48 (d, J=8.8 Hz, 2H), 7.95 (s, 2H).

Example 137

Synthesis of 4-(4-(cyclopentylmethoxy)phenyl)-1H-1,2,3-triazole-5-carboxylic acid (137)

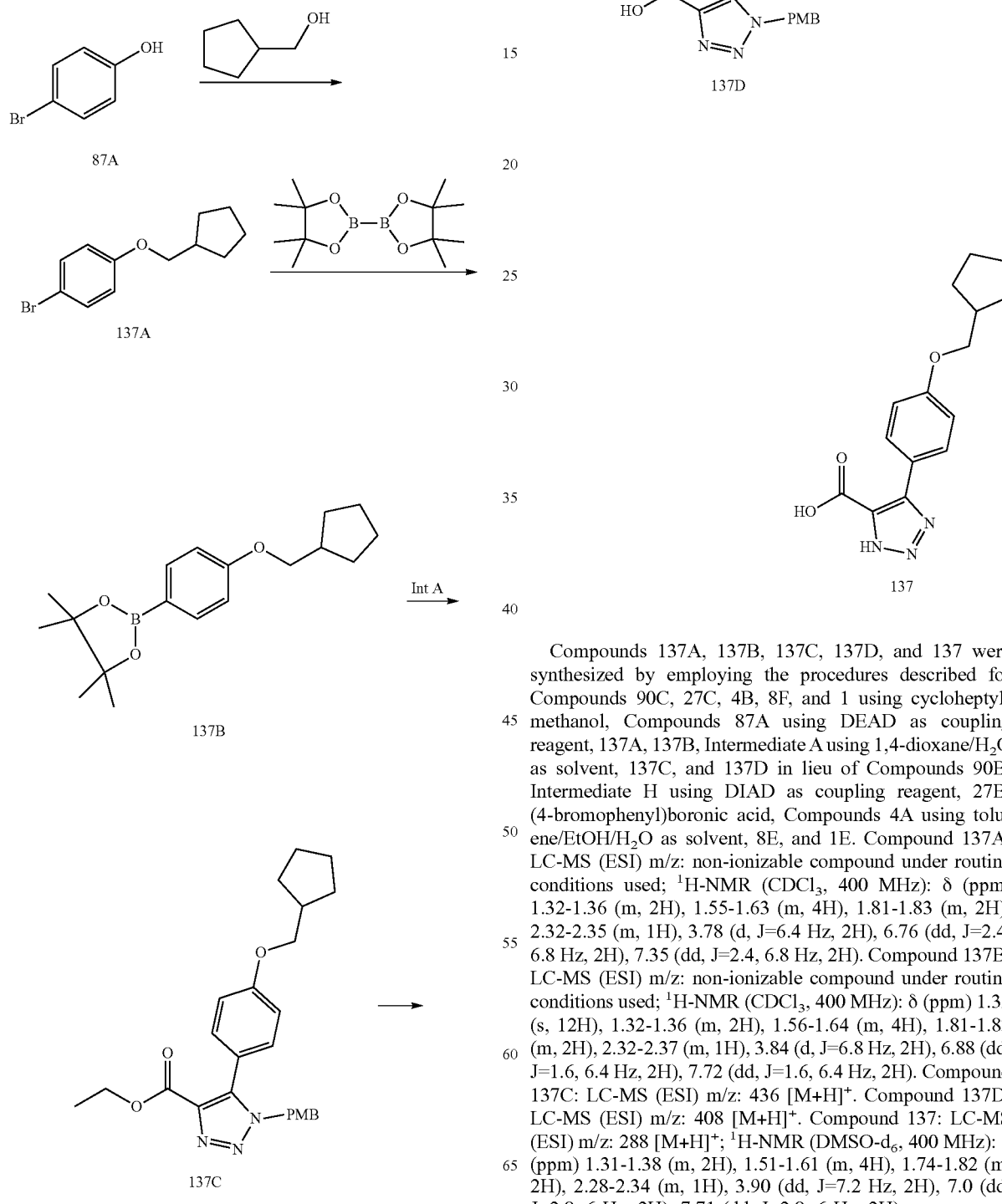

Compounds 137A, 137B, 137C, 137D, and 137 were synthesized by employing the procedures described for Compounds 90C, 27C, 4B, 8F, and 1 using cycloheptylmethanol, Compounds 87A using DEAD as coupling reagent, 137A, 137B, Intermediate A using 1,4-dioxane/H₂O as solvent, 137C, and 137D in lieu of Compounds 90B, Intermediate H using DIAD as coupling reagent, 27B, (4-bromophenyl)boronic acid, Compounds 4A using toluene/EtOH/H₂O as solvent, 8E, and 1E. Compound 137A: LC-MS (ESI) m/z: non-ionizable compound under routine conditions used; ¹H-NMR (CDCl₃, 400 MHz): δ (ppm) 1.32-1.36 (m, 2H), 1.55-1.63 (m, 4H), 1.81-1.83 (m, 2H), 2.32-2.35 (m, 1H), 3.78 (d, J=6.4 Hz, 2H), 6.76 (dd, J=2.4, 6.8 Hz, 2H), 7.35 (dd, J=2.4, 6.8 Hz, 2H). Compound 137B: LC-MS (ESI) m/z: non-ionizable compound under routine conditions used; ¹H-NMR (CDCl₃, 400 MHz): δ (ppm) 1.32 (s, 12H), 1.32-1.36 (m, 2H), 1.56-1.64 (m, 4H), 1.81-1.83 (m, 2H), 2.32-2.37 (m, 1H), 3.84 (d, J=6.8 Hz, 2H), 6.88 (dd, J=1.6, 6.4 Hz, 2H), 7.72 (dd, J=1.6, 6.4 Hz, 2H). Compound 137C: LC-MS (ESI) m/z: 436 [M+H]⁺. Compound 137D: LC-MS (ESI) m/z: 408 [M+H]⁺. Compound 137: LC-MS (ESI) m/z: 288 [M+H]⁺; ¹H-NMR (DMSO-d₆, 400 MHz): δ (ppm) 1.31-1.38 (m, 2H), 1.51-1.61 (m, 4H), 1.74-1.82 (m, 2H), 2.28-2.34 (m, 1H), 3.90 (dd, J=7.2 Hz, 2H), 7.0 (dd, J=2.8, 6 Hz, 2H), 7.71 (dd, J=2.8, 6 Hz, 2H).

Example 138

Synthesis of 4-(4-(cyclopentyloxy)phenyl)-1H-1,2,3-triazole-5-carboxylic acid (138)

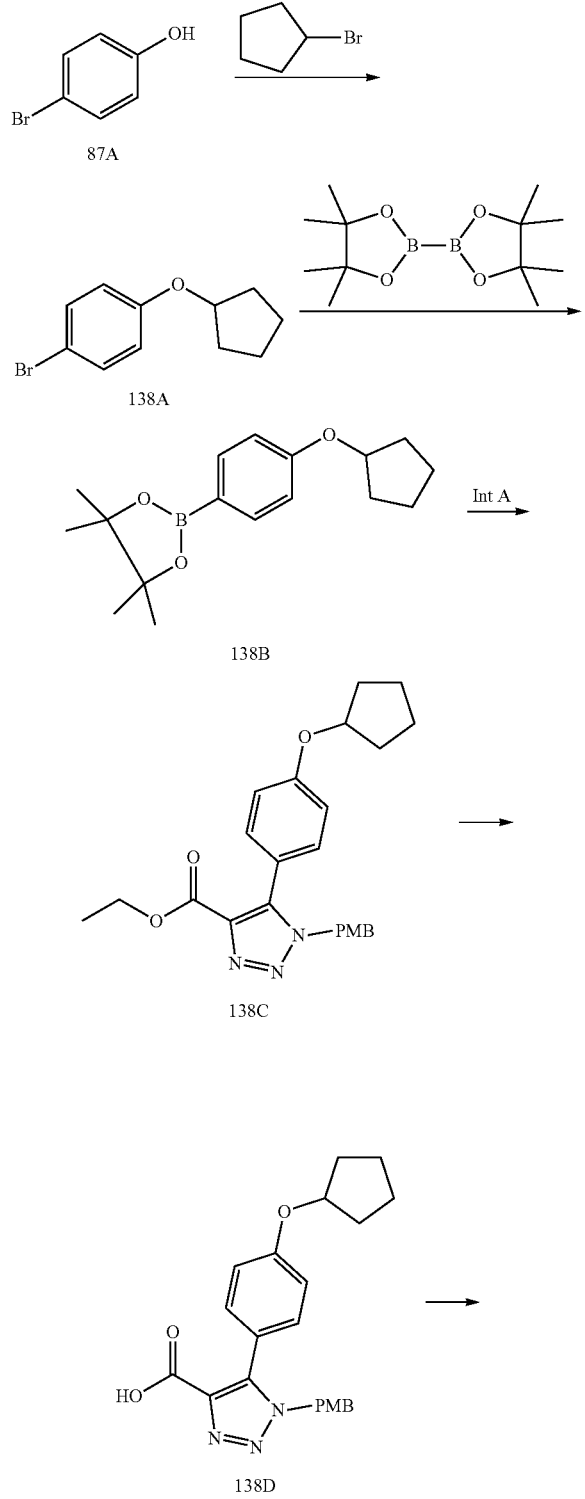

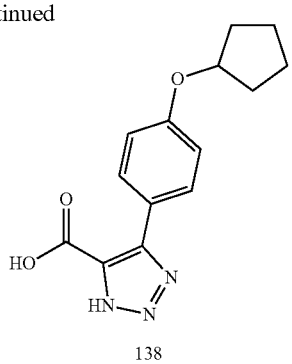

Compounds 138A, 138B, 138C, 138D, and 138 were synthesized by employing the procedures described for Compounds 27B, 27C, 4B, 8F, and 1 using bromocyclopentane at room temperature, Compounds 87A, 138A, 138B, Intermediate A using 1,4-dioxane/H$_2$O as solvent, 138C, and 138D in lieu of 2-bromopropane at 90° C., Compounds 27A, 27B, (4-bromophenyl)boronic acid, 4A using toluene/EtOH/H$_2$O as solvent, 8E, and 1E. Compound 138A: LC-MS (ESI) m/z: 241 [M+H]$^+$, Compound 138B: LC-MS (ESI) m/z: 289 [M+H]$^+$. Compound 138C: LC-MS (ESI) m/z: 422 [M+H]$^+$. Compound 138D: LC-MS (ESI) m/z: 394 [M+H]$^+$. Compound 138: LC-MS (ESI) m/z: 274 [M+H]$^+$. $^1$H-NMR (DMSO-d$_6$, 400 MHz): δ (ppm) 1.57-1.62 (m, 2H). 1.70-1.74 (m, 4H), 1.91-1.96 (m, 2H), 4.84-4.87 (m, 1H), 6.92 (d, J=8.8 Hz, 2H), 8.05 (s, 2H).

Example 139

Synthesis of 4-(2-chloro-4'-(trifluoromethoxy)-[1,1'-biphenyl]-4-yl)-1H-1,2,3-triazole-5-carboxylic acid 2,2,2-trifluoroacetate (139)

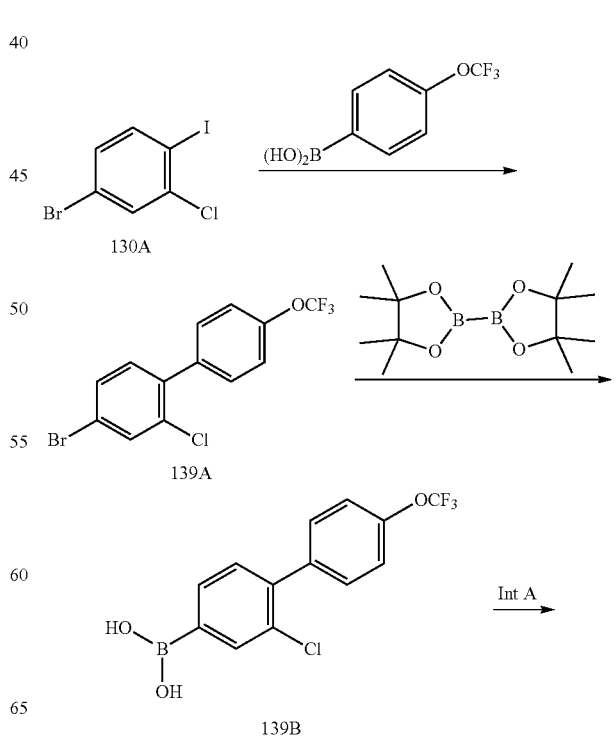

311
-continued

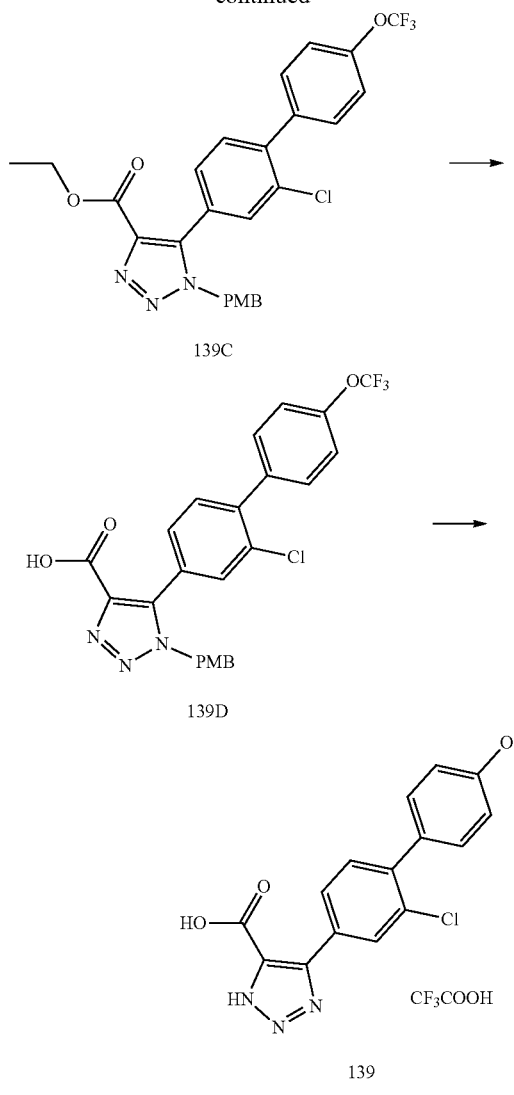

Compounds 139A, 139B, 139C, 139D, and 139 were synthesized by employing the procedures described for Compounds 8B, 27C, 4B, 8F, and 1 using 4-(trifluoromethoxy)phenylboronic acid, Compounds 130A using $K_2CO_3$ as base and 1,4-dioxane/$H_2O$ as solvent, 139A, Intermediate A, 139B using 1,4-dioxane/$H_2O$ as solvent, 139C, and 139D in lieu of (3,4-dichlorophenyl)boronic acid, Compounds 8A using $Cs_2CO_3$ as base and DME/$H_2O$ as solvent, 27B, 4A, (4-bromophenyl)boronic acid using toluene/EtOH/$H_2O$ as solvent, 8E, and 1E. Compound 139A: LC-MS (ESI) m/z: non-ionizable compound under routine conditions used. $^1$H-NMR (CDCl$_3$, 400 MHz): δ (ppm) 7.28-7.31 (m, 3H), 7.55 (d, J=8.0 Hz, 2H), 7.63 (s, 1H), 7.68 (d, J=8.4 Hz, 1H). Compound 139B: LC-MS (ESI) m/z: non-ionizable compound under routine conditions used. Compound 139C: LC-MS (ESI) m/z: 532 [M+H]$^+$. Compound 139D: LC-MS (ESI) m/z: 504 [M+H]$^+$. Compound 139: LC-MS (ESI) m/z: 384 [M+H]$^+$; $^1$H-NMR (DMSO-d$_6$, 400 MHz): δ (ppm) 7.49 (d, J=8.4 Hz, 2H), 7.59 (d, J=8.0 Hz, 1H), 7.75 (d, J=5.6 Hz, 1H), 7.92 (d, J=8.8 Hz, 3H).

312
Example 140

Synthesis of 4-(3,4-dihydronaphthalen-2-yl)-1H-1,2,3-triazole-5-carboxylic acid 2,2,2-trifluoroacetate (140)

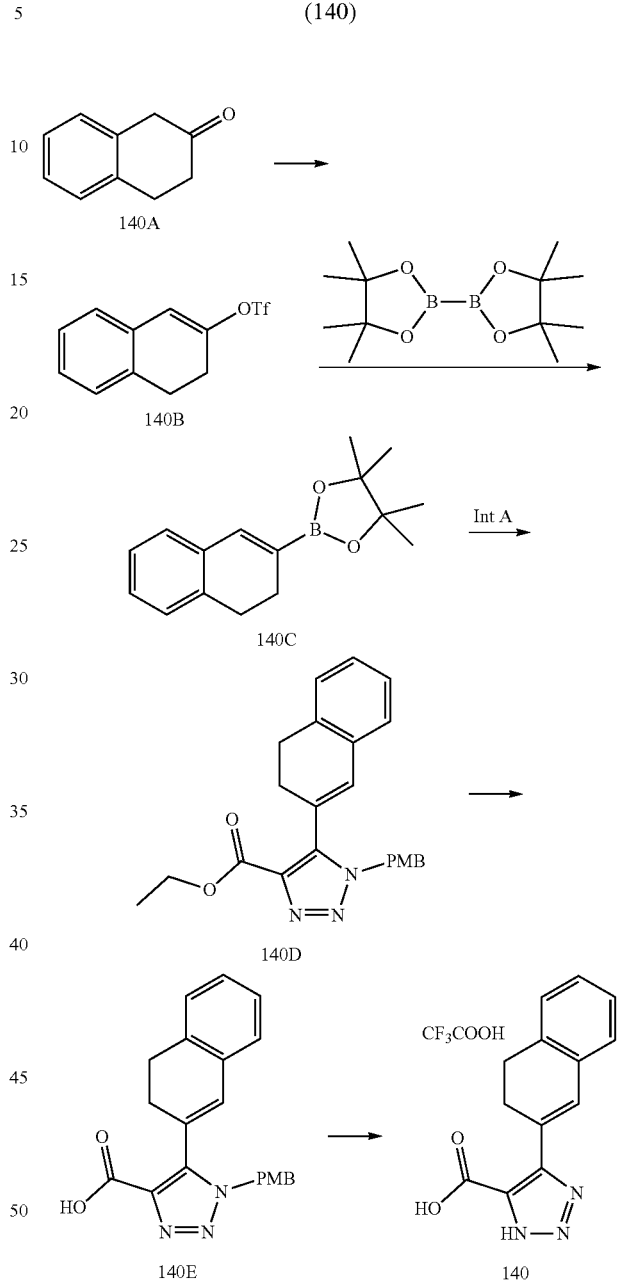

To a mixture of 3,4-dihydronaphthalen-2(1H)-one (Compound 140A) (1.5 g, 10.3 mmol) in THF (100 mL) was added t-BuOK (2.31 g, 20.6 mmol) at −20° C. under nitrogen and stirred at room temperature for 1 hour. To the mixture was added a solution of 1,1,1-trifluoro-N-phenyl-N-(trifluoromethylsulfonyl)methanesulfonamide (5.52 g, 15.5 mmol) in dry THF (10 mL) in one portion at −20° C. and stirred at room temperature for 4 hours. It was quenched with a saturated aqueous NH$_4$Cl solution (20 mL) and extracted with ethyl acetate (30 mL×3). The combined extracts were washed with water (50 mL) and brine (50 mL), dried over anhydrous Na$_2$SO$_4$, filtered, and concentrated. The residue was purified with flash column chromatography on silica gel (petroleum ether, 100% v/v) to give Compound 140B. LC-MS (ESI) m/z: 279 [M+H]⁺; ¹H-NMR (CDCl₃, 400 MHz): δ (ppm) 2.71 (t, J=7.2 Hz, 2H), 3.07 (t, J=7.2 Hz, 2H), 6.49 (s, 1H), 7.08-7.10 (m, 1H), 7.14-7.16 (m, 1H), 7.20-7.22 (m, 2H).

Compounds 140C, 140D, 140E, and 140 were synthesized by employing the procedures described for Compounds 27C, 8B, 8F, and 1 using Compounds 140B using DMSO as solvent, Intermediate A, 140C using 1,4-dioxane/H₂O as solvent, 140D, and 140E in lieu of Compounds 27B using 1,4-dioxane/H₂O as solvent, 8A, (4-bromophenyl)boronic acid using toluene/EtOH/H₂O as solvent, 8E, and 1E. Compound 140C: LC-MS (ESI) m/z: 257 [M+H]⁺; ¹H-NMR (CDCl₃, 400 MHz): δ (ppm) 1.22 (s, 12H), 2.41 (t, J=7.2 Hz, 2H), 2.76 (t, J=7.2 Hz, 2H), 7.12-7.13 (m, 2H), 7.15-7.18 (m, 3H). Compound 140D: LC-MS (ESI) m/z: 390 [M+H]⁺; ¹H-NMR (CDCl₃, 400 MHz): δ (ppm) 1.38 (t, J=7.2 Hz, 3H), 2.36 (t, J=7.2 Hz, 2H), 2.88 (t, J=7.2 Hz, 2H), 3.79 (s, 3H), 4.39 (q, J=7.2 Hz, 2H), 5.51 (s, 2H), 6.42 (s, 1H), 6.81-6.83 (m, 2H), 7.01-7.04 (m, 1H), 7.12-7.15 (m, 2H), 7.17-7.23 (m, 3H). Compound 140E: LC-MS (ESI) m/z: 362 [M+H]⁺. Compound 140: LC-MS (ESI) m/z: 242 [M+H]⁺; ¹H-NMR (DMSO-d₆, 400 MHz): δ (ppm) 2.70-2.71 (m, 2H), 2.86-2.90 (m, 2H), 7.18-7.30 (m, 5H), 13.13 (s, 1H), 15.60 (s, 1H).

Example 141

Synthesis of 4-(1,2,3,4-tetrahydronaphthalen-2-yl)-1H-1,2,3-triazole-5-carboxylic acid 2,2,2-trifluoroacetate (141)

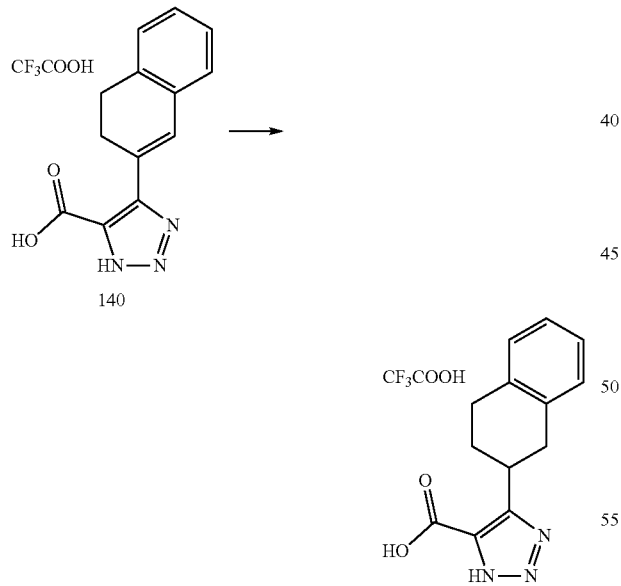

To a mixture of Compound 140 (40 mg, 0.17 mmol) in ethyl acetate (20 mL) was added 10% Pd/C (20 mg) and stirred at room temperature under hydrogen (1 atm) overnight. The mixture was filtered and filtration was concentrated. The residue was purified with preparative HPLC to afford Compound 141. LC-MS (ESI) m/z: 244 [M+H]⁺; ¹H-NMR (DMSO-d₆, 400 MHz): δ (ppm) 1.94-1.99 (m, 1H), 2.08-2.10 (m, 1H), 2.89-2.92 (m, 2H), 2.92-3.04 (m, 2H), 3.60-3.62 (m, 1H), 7.08-7.12 (m, 4H), 13.12 (s, 1H), 15.22 (s, 1H).

Example 142

Synthesis of 4-(1-isopropyl-1,2,3,4-tetrahydroquinolin-7-yl)-1H-1,2,3-triazole-5-carboxylic acid (142)

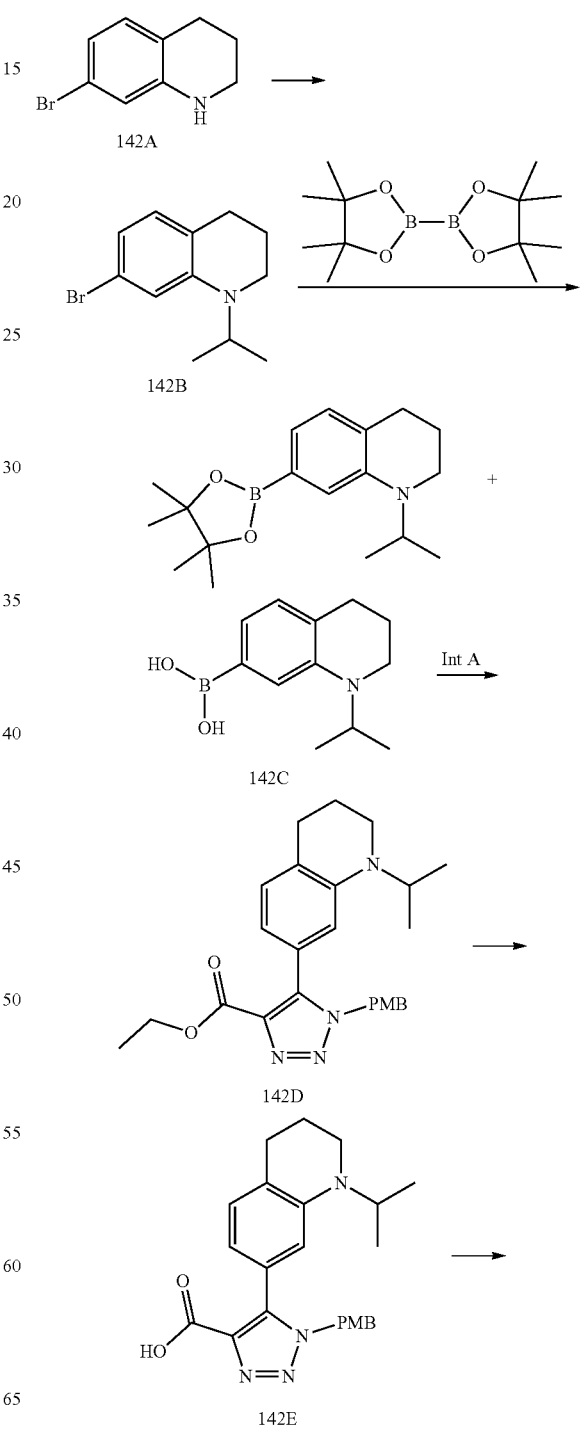

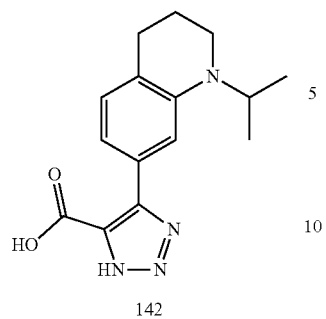

142

Compounds 142B, 142C, 142D, 142E, and 142 were synthesized by employing the procedures described for Compounds 63A, 27C, 8B, 8F, and 1 using 2-iodopropane, Compounds 142A using K$_2$CO$_3$ as base, 142B, Intermediate A, 142C using 1,4-dioxane/H$_2$O as solvent, 142D, and 142E in lieu of iodomethane, Compounds 61F using Cs$_2$CO$_3$ as base, 27B, 8A, (4-bromophenyl)boronic acid using toluene/EtOH/H$_2$O as solvent, 8E, and 1E. Compound 142B: LC-MS (ESI) m/z: 254 [M+H]$^+$. Compound 142C: LC-MS (ESI) m/z: 302 [M+H]$^+$; 260 [M+CH$_3$CN]$^+$. Compound 142D: LC-MS (ESI) m/z: 435 [M+H]$^+$. Compound 142E: LC-MS (ESI) m/z: 407 [M+H]$^+$. Compound 142: LC-MS (ESI) m/z: 287 [M+H]$^+$; $^1$H-NMR (DMSO-d$_6$, 400 MHz): δ (ppm) 1.14 (d, J=6.4 Hz, 6H), 1.82-1.85 (m, 2H), 2.69 (t, J=6 Hz, 2H), 3.15 (t, J=6 Hz, 2H), 4.06-4.10 (m, 1H), 6.89 (d, J=7.6 Hz, 1H), 6.97 (d, J=7.6 Hz, 1H), 7.17 (s, 1H).

Example 143

Synthesis of 4-(2-isopropyl-1,2,3,4-tetrahydroisoquinolin-6-yl)-1H-1,2,3-triazole-5-carboxylic acid 2,2,2-trifluoroacetate (143)

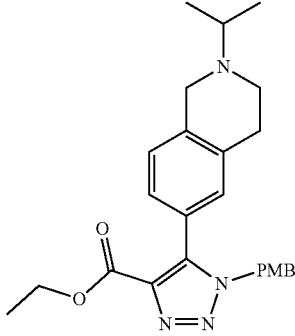

143D

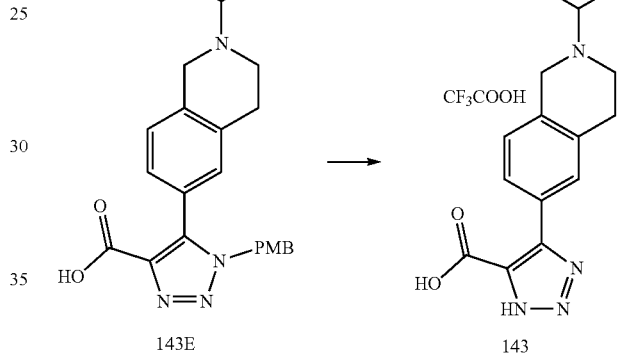

143E     143

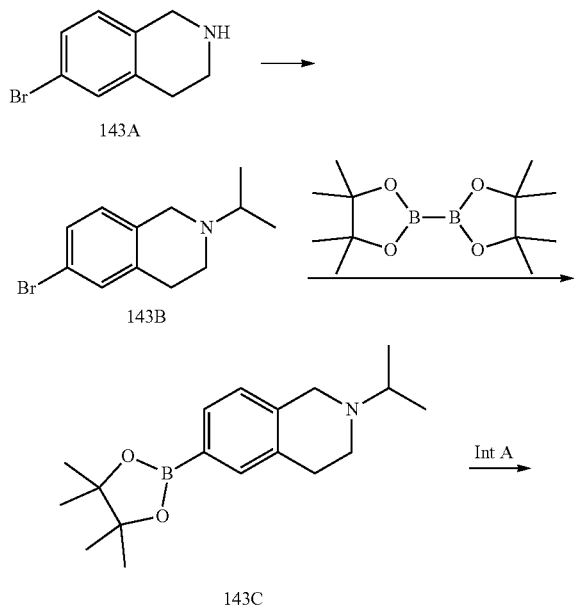

Compounds 143B, 143C, 143D, 143E, and 143 were synthesized by employing the procedures described for Compounds 63A, 27C, 8B, 8F, and 1 using 2-iodopropane, Compounds 143A using K$_2$CO$_3$ as base and acetonitrile as solvent, 143B, Intermediate A, 143C using 1,4-dioxane/H$_2$O as solvent, 143D, and 143E in lieu of iodomethane, Compounds 61F using Cs$_2$CO$_3$ as base, 27B, 8A, (4-bromophenyl)boronic acid using toluene/EtOH/H$_2$O as solvent, 8E, and 1E. Compound 143B: LC-MS (ESI) m/z: 254 [M+H]$^+$; $^1$H-NMR (CDCl$_3$, 400 MHz): δ 1.13 (d, J=6.4 Hz, 6H), 2.74 (t, J=6.4 Hz, 2H), 2.85-2.93 (m, 3H), 3.65 (s, 2H), 6.99 (d, J=8.0 Hz, 1H), 7.20-7.23 (m, 2H). Compound 143C: LC-MS (ESI) m/z: 302 [M+H]$^+$. Compound 143D: LC-MS (ESI) m/z: 435 [M+H]$^+$; $^1$H-NMR (CDCl$_3$, 400 MHz): δ 1.17 (d, J=6.8 Hz, 6H), 1.28 (t, J=6.8 Hz, 3H), 2.80 (t, J=5.6 Hz, 2H), 2.87 (t, J=5.6 Hz, 2H), 2.91-2.97 (m, 1H), 3.7-3.79 (m, 5H), 4.30 (q, J=6.8 Hz, 2H), 5.31 (s, 2H), 6.77-6.79 (m, 2H), 6.89 (s, 1H), 6.95-6.99 (m, 3H), 7.12 (d, J=8.0 Hz, 1H). Compound 143E: LC-MS (ESI) m/z: 407 [M+H]$^+$. Compound 143: LC-MS (ESI) m/z: 287 [M+H]$^+$; $^1$H-NMR (DMSO-d$_6$, 400 MHz): δ (ppm) 1.35 (d, J=8.4 Hz, 6H), 3.10-3.37 (m, 3H), 3.65-3.71 (m, 2H), 4.46-4.47 (m, 2H), 7.33 (d, J=8.4 Hz, 1H), 7.60-7.70 (m, 2H), 9.72 (bs, 1H).

Example 144

Synthesis of 4-(2-isopropyl-1,2,3,4-tetrahydroiso-quinolin-7-yl)-1H-1,2,3-triazole-5-carboxylic acid 2,2,2-trifluoroacetate (144)

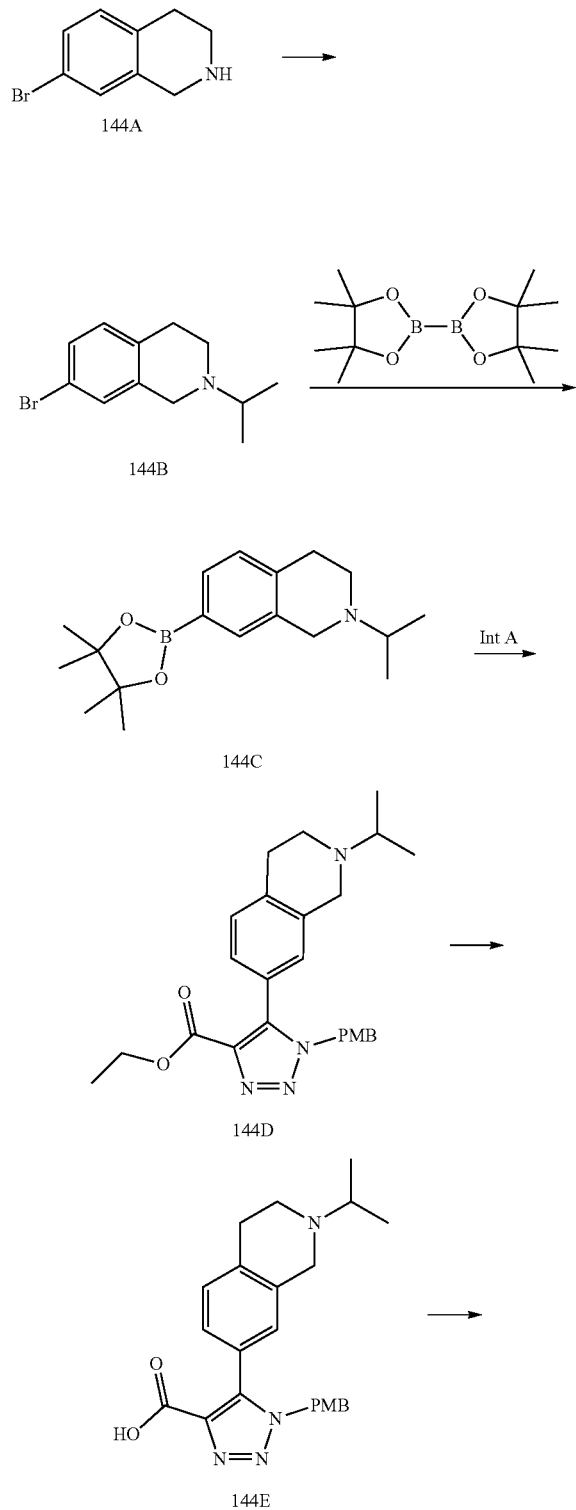

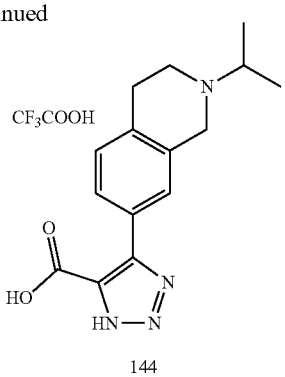

Compounds 144B, 144C, 144D, 144E, and 144 were synthesized by employing the procedures described for Compounds 63A, 27C, 8B, 8F, and 1 using 2-iodopropane, Compounds 144A using $K_2CO_3$ as base and acetonitrile as solvent, 144B, Intermediate A, 144C using $K_2CO_3$ as base and 1,4-dioxane/$H_2O$ as solvent, 144D, and 144E in lieu of iodomethane, Compounds 61F using $Cs_2CO_3$ as base, 27B, 8A, (4-bromophenyl)boronic acid using $Cs_2CO_3$ as base and toluene/EtOH/$H_2O$ as solvent, 8E, and 1E. Compound 144B: LC-MS (ESI) m/z: 254 [M+H]$^+$; $^1$H-NMR (CDCl$_3$, 400 MHz): δ 1.13 (d, J=6.8 Hz, 6H), 2.74-2.77 (m, 2H), 2.81-2.84 (m, 2H), 2.86-2.93 (m, 1H), 3.68 (s, 2H), 6.96 (d, J=8.0 Hz, 1H), 7.18-7.23 (m, 2H). Compound 144C: LC-MS (ESI) m/z: 302 [M+H]$^+$. Compound 144D: LC-MS (ESI) m/z: 435 [M+H]$^+$; $^1$H-NMR (CDCl$_3$, 400 MHz): δ 1.15 (d, J=6.8 Hz, 6H), 1.28 (t, J=7.2 Hz, 3H), 2.81 (t, J=6.0 Hz, 2H), 2.89-2.98 (m, 3H), 3.68 (s, 2H), 3.78 (s, 3H), 4.30 (q, J=7.2 Hz, 2H), 5.31 (s, 2H), 6.77-6.82 (m, 3H), 6.96-7.00 (m, 3H), 7.18 (d, J=8.0 Hz, 1H). Compound 144E: LC-MS (ESI) m/z: 407 [M+H]$^+$. Compound 144: LC-MS (ESI) m/z: 287 [M+H]$^+$; $^1$H-NMR (DMSO-d$_6$, 400 MHz): δ (ppm) 1.35 (d, J=8.4 Hz, 6H), 3.10-3.24 (m, 2H), 3.34-3.38 (m, 1H), 3.64-3.71 (m, 2H), 4.46 (s, 2H), 7.37 (d, J=8.4 Hz, 1H), 7.69-7.74 (m, 2H), 10.02 (bs, 1H).

Example 145

Synthesis of 4-(5-(trifluoromethoxy)pyridin-2-yl)-1H-1,2,3-triazole-5-carboxylic acid 2,2,2-trifluoro-acetate (145)

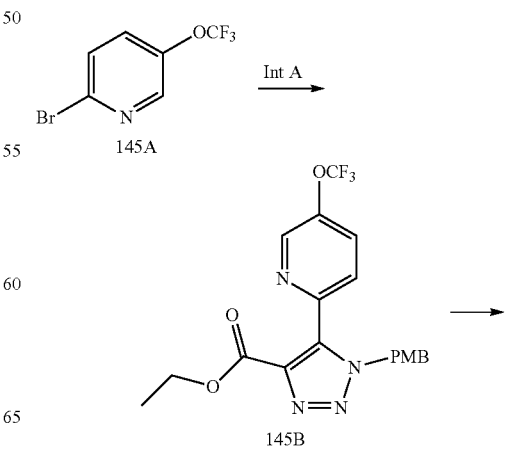

-continued

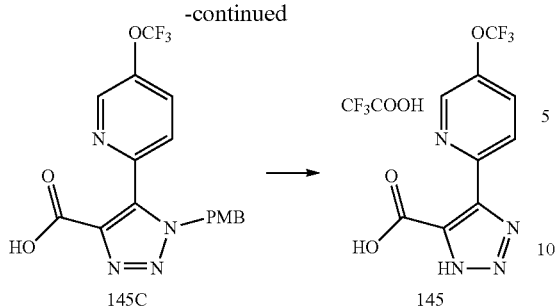

Compounds 145B, 145C, and 145 were synthesized by employing the procedures described for Compounds 132A, 8F, and 1 using Compounds 145A, 145B, and 145C in lieu of Compounds 76A, 8E, and 1E. Compound 145B: LC-MS (ESI) m/z: 423 [M+H]$^+$. Compound 145C: LC-MS (ESI) m/z: 395 [M+H]$^+$. Compound 145: LC-MS (ESI) m/z: 275 [M+H]$^+$; $^1$H-NMR (DMSO-d$_6$, 400 MHz): δ (ppm) 8.21 (d, J=8.0 Hz, 1H), 8.39 (d, J=8.0 Hz, 1H), 8.67 (s, 1H).

Example 146

Synthesis of 4-(3-(4-chlorophenyl)pyrrolidine-1-carbonyl)-1H-1,2,3-triazole-5-carboxylic acid (146)

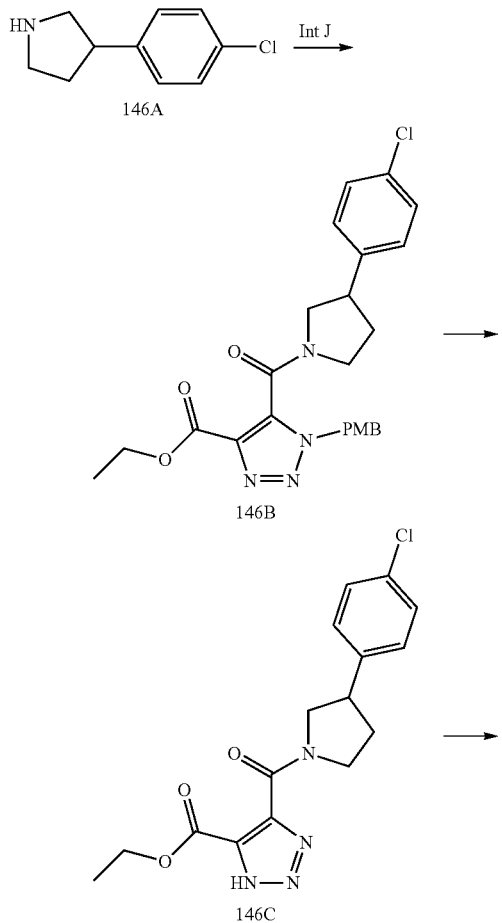

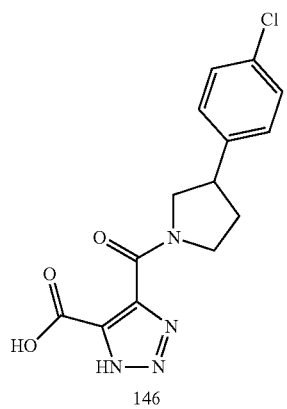

A mixture of Intermediate J (200 mg, 0.66 mmol), Compound 146A, 3-(4-chlorophenyl)pyrrolidine, (143 mg, 0.79 mmol), HATU (380 mg, 1 mmol), and DIPEA (258 mg, 2 mmol) in DMF (5 mL) was stirred at room temperature overnight. The mixture was diluted with EtOAc (50 mL), washed with brine (15 mL×3), dried over anhydrous sodium sulfate, filtered, and concentrated. The residue was purified with preparative HPLC give Compound 146B. LC-MS (ESI) m/z: 469 [M+H]$^+$.

Compounds 146C and 146 were synthesized by employing the procedures described for Compounds 1 and 2 using Compounds 146B and Compound 146C in lieu of Compounds 1E and 1. Compound 146C: LC-MS (ESI) m/z: 349 [M+H]$^+$. Compound 146: LC-MS (ESI) m/z: 321 [M+H]$^+$; $^1$H-NMR (CD$_3$OD, 400 MHz): δ (ppm) 2.10-2.20 (m, 1H), 2.38-2.47 (m, 1H), 3.53-3.63 (m, 1H), 3.66-3.81 (m, 2H), 3.99-4.44 (m, 2H), 7.32-7.37 (m, 4H).

Example 147

Synthesis of 4-(5-chloroisoindoline-2-carbonyl)-1H-1,2,3-triazole-5-carboxylic acid (147)

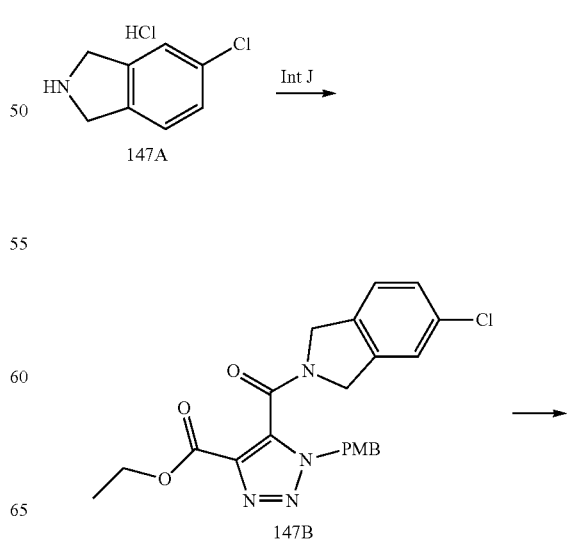

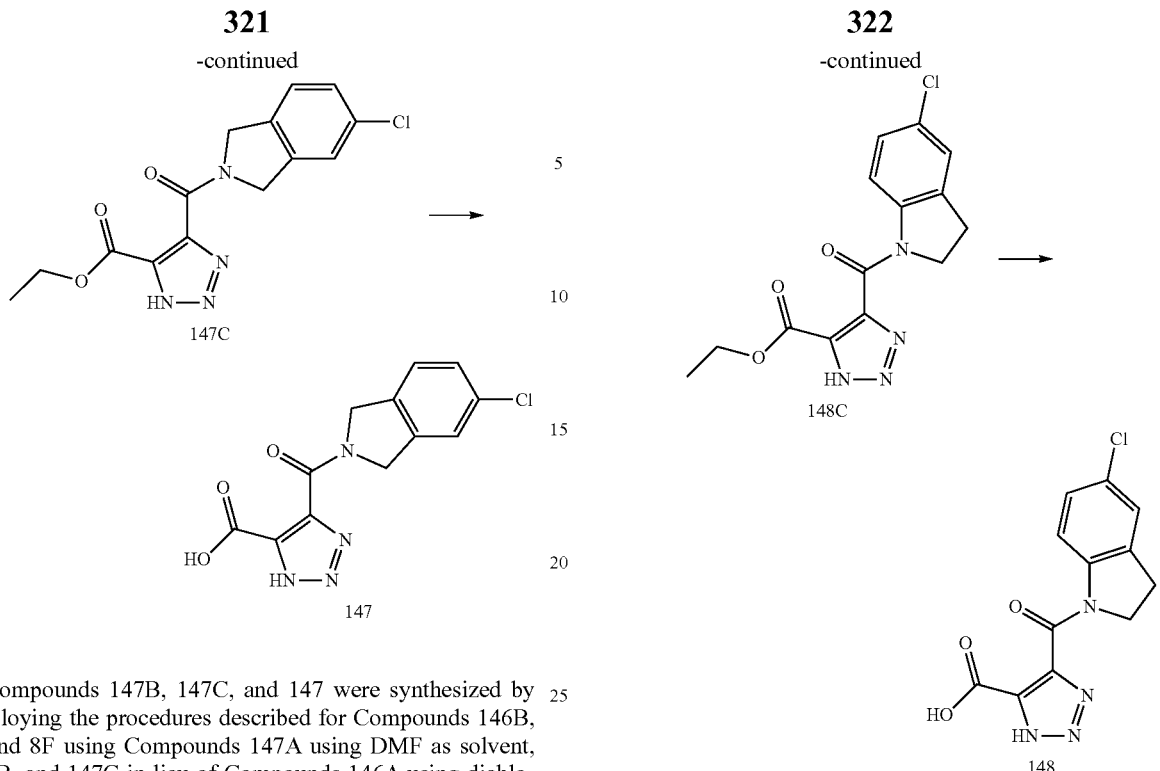

Compounds 147B, 147C, and 147 were synthesized by employing the procedures described for Compounds 146B, 1, and 8F using Compounds 147A using DMF as solvent, 147B, and 147C in lieu of Compounds 146A using dichloromethane as solvent, 1E, and 8E. Compound 147B: LC-MS (ESI) m/z: 441 [M+H]+. Compound 147C: LC-MS (ESI) m/z: 321 [M+H]+. Compound 147: LC-MS (ESI) m/z: 293 [M+H]+; 1H-NMR (DMSO-d6, 400 MHz): δ (ppm) 4.91-4.93 (m, 2H), 5.37-5.40 (m, 2H), 7.36-7.39 (m, 1H), 7.43-7.47 (m, 1H), 7.52-7.54 (m, 1H).

Example 148

Synthesis of 4-(5-chloroindoline-1-carbonyl)-1H-1,2,3-triazole-5-carboxylic acid (148)

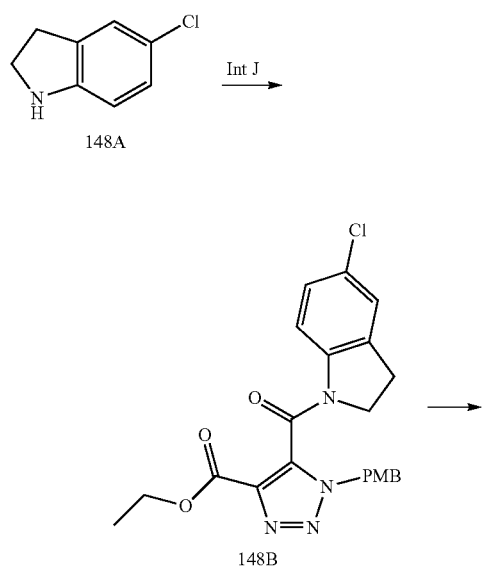

Compounds 148B, 148C, and 148 were synthesized by employing the procedures described for Compounds 146B, 1, and 8F using Compounds 148A, 148B, and 148C in lieu of Compounds 146A, 1E, and 8E. Compound 147B: LC-MS (ESI) m/z: 441 [M+H]+. Compound 148C: LC-MS (ESI) m/z: 321 [M+H]+. Compound 148: LC-MS (ESI) m/z: 293 [M+H]+; 1H-NMR (DMSO-d6, 400 MHz): δ (ppm) 3.11 (t, J=8.0 Hz, 2H), 4.23-4.25 (m, 2H), 7.27 (d, J=8.4 Hz, 1H), 7.35 (s, 1H), 8.15 (d, J=8.4 Hz, 1H).

Example 149

Synthesis of 4-(3-(2,4-dichlorophenyl)pyrrolidine-1-carbonyl)-1H-1,2,3-triazole-5-carboxylic acid (149)

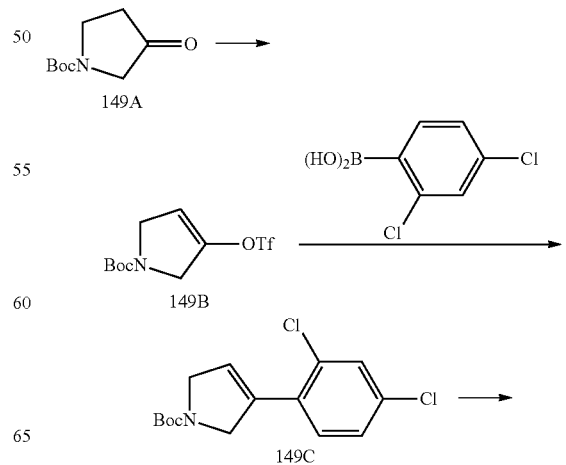

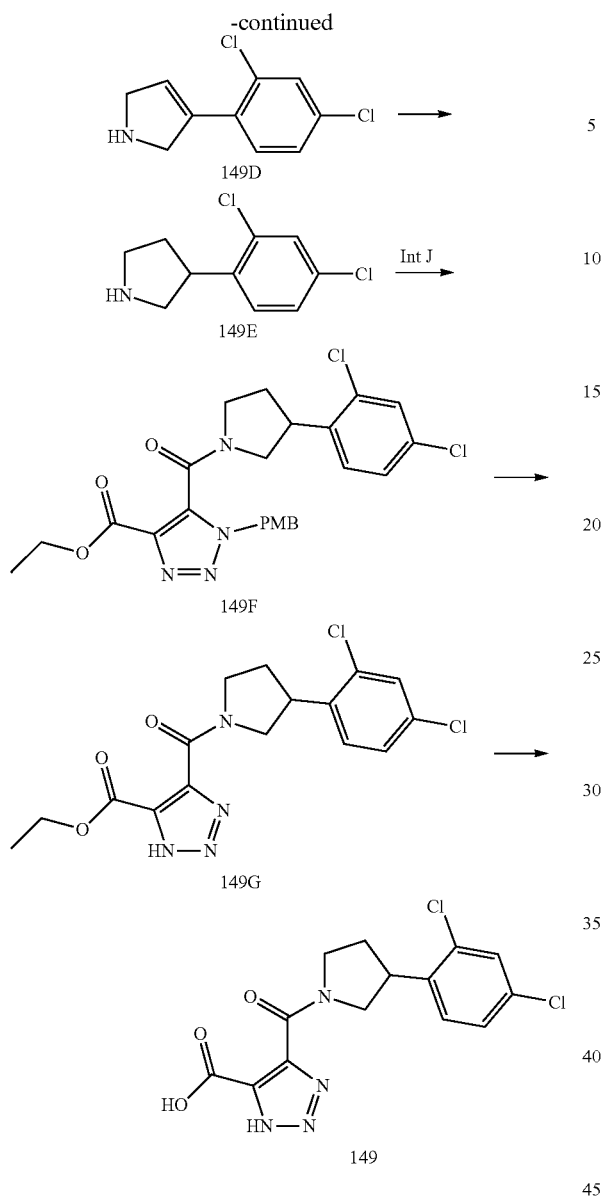

was filtered and the filtrate was concentrated to give Compound 149E. LC-MS (ESI) m/z: 216 [M+H]⁺.

Compounds 149F, 149G, and 149 were synthesized by employing the procedures described for Compounds 146B, 1, and 8F using Compounds 149E using dichloromethane as solvent, 149F, and 149G in lieu of Compounds 146A using DMF as solvent, 1E, and 8E. Compound 149F: LC-MS (ESI) m/z: 503 [M+H]⁺. Compounds 149G: LC-MS (ESI) m/z: 383 [M+H]⁺. Compounds 149: LC-MS (ESI) m/z: 355 [M+H]⁺; $^1$H-NMR (CD$_3$OD, 400 MHz): δ (ppm) 2.00-2.40 (m, 2H), 3.62-4.15 (m, 5H), 7.32-7.40 (m, 1H), 7.45-7.51 (m, 2H).

Example 150

Synthesis of 4-(3-(3,4-dichlorophenyl)pyrrolidine-1-carbonyl)-1H-1,2,3-triazole-5-carboxylic acid (150)

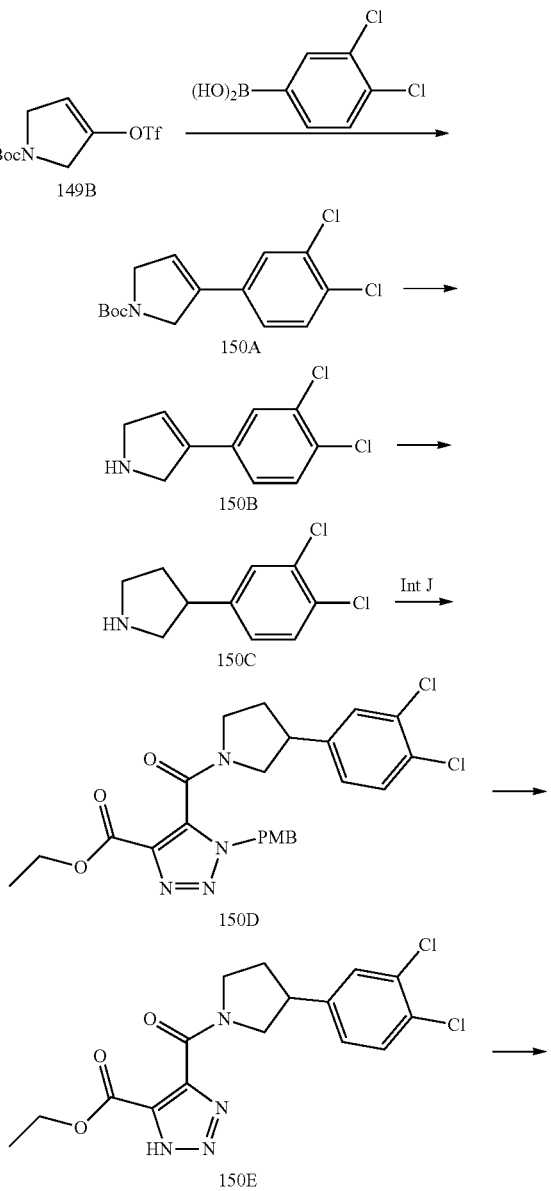

Compounds 149B and 149C were synthesized by employing the procedures described for Compounds 140B and 4B using Compound 149A using LiHMDS as base at −78° C., 149B using Et$_3$N as base and DMF as solvent, and 2,4-dichlorophenylboronic acid in lieu of Compound 140A using tBuOK as base at −20° C., 4A using Na$_2$CO$_3$ as base and toluene/EtOH/H$_2$O as solvent, and (4-bromophenyl)boronic acid. Compound 149B: LC-MS (ESI) m/z: 262 [M−55]⁺; $^1$H-NMR (CDCl$_3$, 400 MHz): δ (ppm) 1.42 (s, 9H), 2.85-3.00 (m, 2H), 3.78-3.90 (m, 2H), 6.66-6.81 (m, 1H). Compound 149C: LC-MS (ESI) m/z: 258 [M−55]⁺.

A mixture of Compound 149C (300 mg, 1 mmol) and HCl solution in EtOAc (3 M, 5 mL) was stirred at room temperature for 16 hours. The mixture was concentrated and purified with flash column chromatography on silica gel (methanol in ethyl acetate, 10% v/v) to afford Compound 149D. LC-MS (ESI) m/z: Non-ionizable compound under routine conditions used.

A mixture of Compound 149D (100 mg, 1 mmol) and PtO$_2$ (50 mg) in MeOH (5 mL) was stirred at room temperature under hydrogen (1 atm.) for 16 hours. The mixture

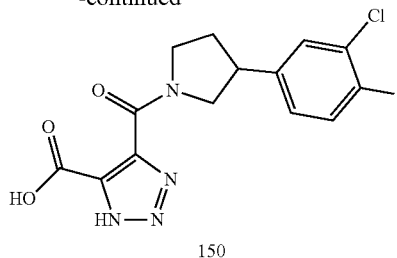

150

Compounds 150A, 150B, 150C, 150D, 150E, and 150 were synthesized by employing the procedures described for Compounds 4B, 149D, 149E, 146B, 1, and 8F using 3,4-dichlorophenylboronic acid, Compounds 149B using Et₃N as base and DMF as solvent, 150A, 150B, 150C using dichloromethane as solvent, 150D, and 150E in lieu of (4-bromophenyl)boronic acid, Compounds 4A using Na₂CO₃ as base and toluene/EtOH/H₂O as solvent, 149C, 149D, 146A using DMF as solvent, 1E, and 8E. Compound 150A: LC-MS (ESI) m/z: 258 [M−55]⁺. Compound 150B: LC-MS (ESI) m/z: 214 [M+H]⁺; ¹H-NMR (CD₃OD, 400 MHz): δ (ppm) 4.28-4.30 (m, 2H), 4.45-4.47 (m, 2H), 6.47 (s, 1H), 7.47 (d, J=2.0 Hz, 1H), 7.57 (d, J=8.0 Hz, 1H), 7.71 (d, J=2.0 Hz, 1H). Compound 150C: LC-MS (ESI) m/z: 216 [M+H]⁺. Compound 150D: LC-MS (ESI) m/z: 503 [M+H]⁺. Compound 150E: LC-MS (ESI) m/z: 383 [M+H]⁺. Compound 150: LC-MS (ESI) m/z: 355 [M+H]⁺; ¹H-NMR (CD₃OD, 400 MHz): δ (ppm) 2.00-2.11 (m, 1H), 2.27-2.44 (m, 1H), 3.54-4.17 (m, 5H), 7.25-7.34 (m, 1H), 7.45-7.56 (m, 2H).

Example 151

Synthesis of 4-((5-chloroisoindolin-2-yl)methyl)-1H-1,2,3-triazole-5-carboxylic acid (151)

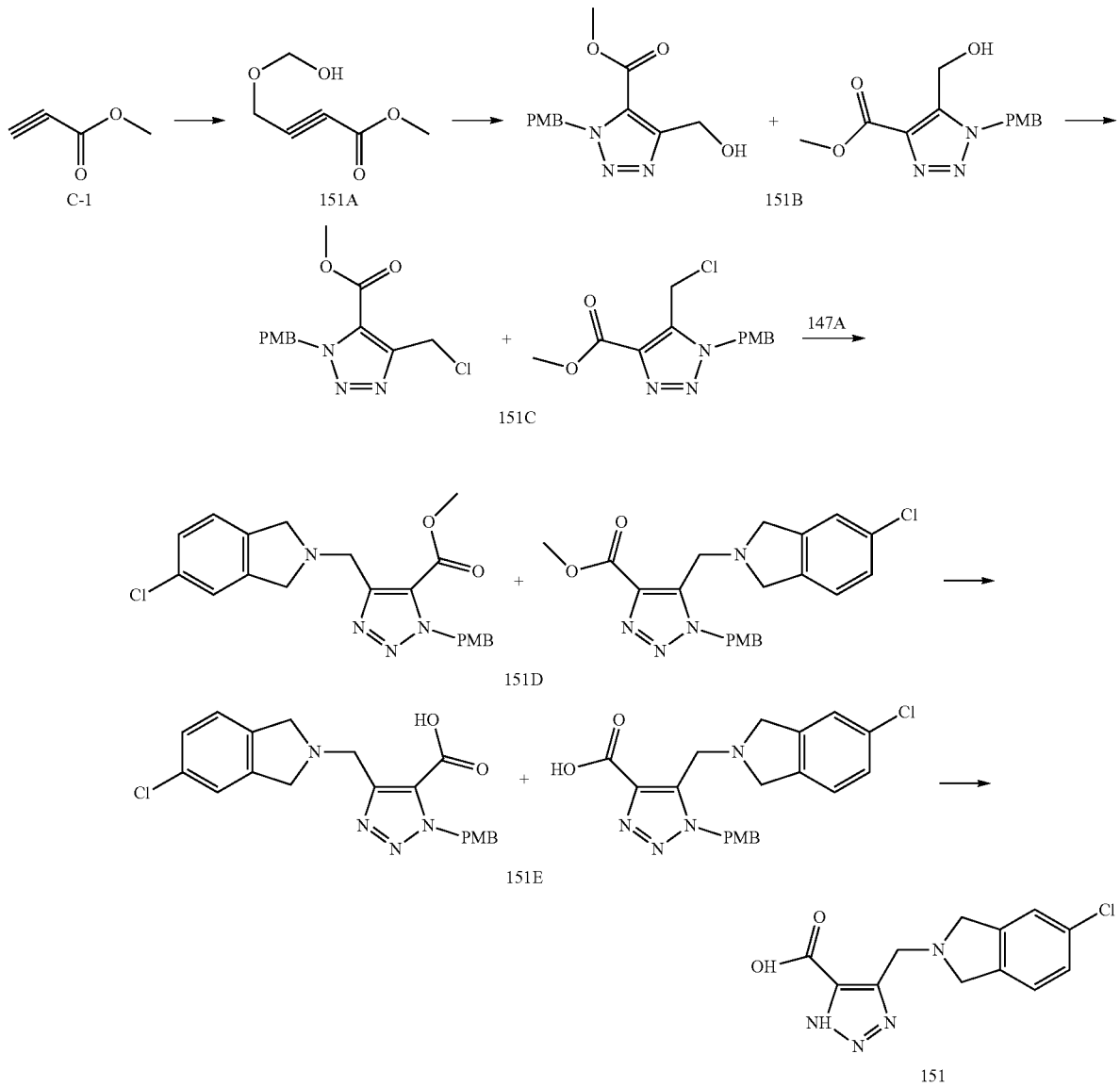

To a solution of Intermediate C-1 (3.34 g, 40 mmol) and paraformaldehyde (1.44 g, 48 mmol) in DMSO (20 mL) was added a solution of trimethylbenzylammonium hydroxide (0.668 g, 4 mmol) in DMSO (20 mL) over 10 minutes. The reaction mixture was stirred at room temperature for 3 hours. The reaction mixture was diluted with water (100 mL) and extracted with ethylacetate/hexane (1:3 in volume, 100 mL×3). The combined extracts were dried over anhydrous $Na_2SO_4$, filtered, and concentrated. The residue was purified by column chromatography on silica gel using ethyl acetate-hexane eluent to afford Compound 151A. LC-MS (ESI) m/z: 145 [M+H]$^+$. $^1$H-NMR (CDCl$_3$, 400 MHz): δ (ppm) 5.49 (s, 2H), 4.97 (t, J=1.6 Hz, 1H), 4.56 (d, J=1.2 Hz, 2H), 3.72 (s, 3H).

A mixture of Compound 151A (340 mg, 2.36 mmol) and 1-(azidomethyl)-4-methoxybenzene (500 mg, 3.07 mmol) in toluene (15 mL) was stirred at 110° C. for 48 hours. The reaction mixture was concentrated and purified by column chromatography on silica gel using ethyl acetate-hexane as eluent to afford a Mixture 151B. LC-MS (ESI) m/z: 278 [M+H]$^+$.

A Mixture 151B (60 mg, 0.217 mmol) and thionyl chloride (0.45 mL) in methylene chloride (10 mL) was stirred at 50° C. for 5 hours. The reaction mixture was concentrated to give 151C, which was used directly in the next step without further purification. LC-MS (ESI) m/z: 296 [M+H]$^+$.

A Mixture 151C (74 mg, 0.217 mmol), 5-chloroisoindoline (38 mg, 0.248 mmol), and $K_2CO_3$ (60 mg, 0.435 mmol) in DMF (6 mL) was stirred at 60° C. for 5 hours. The mixture was poured into water (100 mL) and extracted with ethyl acetate (100 mL×3). The combined extracts were washed with brine (200 mL), dried over anhydrous sodium sulfate, filtered, and concentrated. The residue was purified with preparative HPLC to afford a Mixture 151D. LC-MS (ESI) m/z: 413 [M+H]$^+$.

Mixture 151E and Compound 151 were synthesized by employing the procedures described for Compounds 8F and 1 using Mixtures 151D and 151E in lieu of Compounds 8E and 1E. Mixture 151E: LC-MS (ESI) m/z: 399. Compound 151: LC-MS (ESI) m/z: 279 [M+H]$^+$; $^1$H-NMR (CD$_3$OD, 400 MHz): δ (ppm) 4.80 (s, 2H), 4.81 (s, 2H), 4.97 (s, 2H), 7.38-7.40 (m, 1H), 7.42-7.46 (m, 2H).

Example 152

Synthesis of 4-(((4-chloronaphthalen-1-yl)methyl) thio)-1H-1,2,3-triazole-5-carboxylic acid 2,2,2-trifluoroacetate (152)

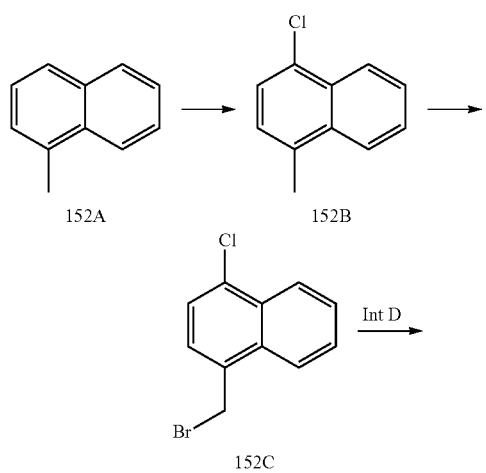

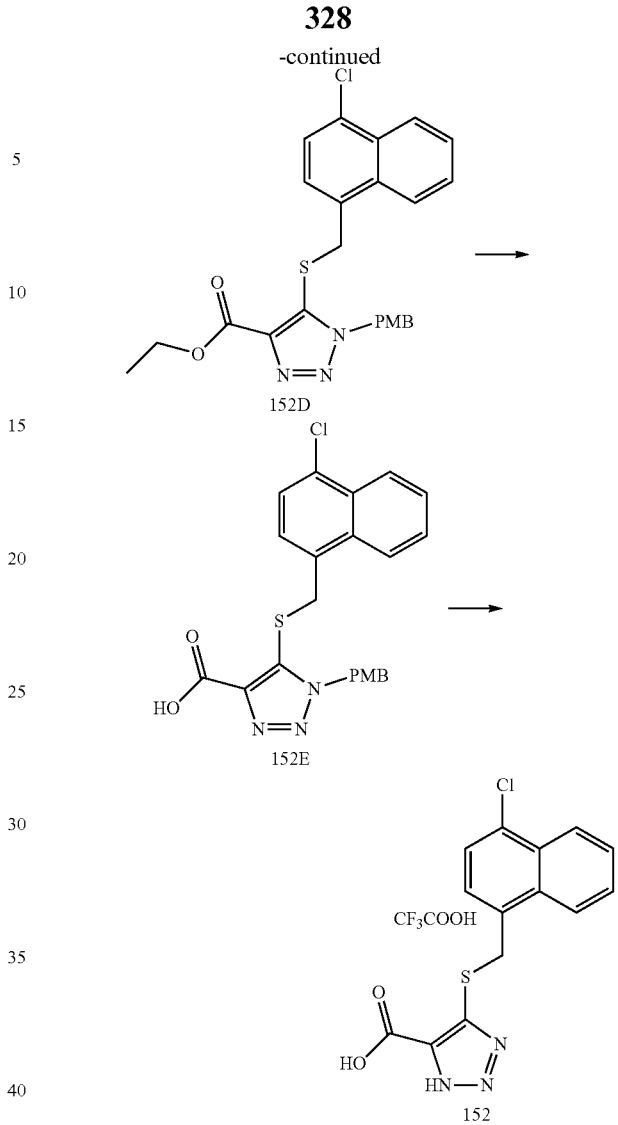

To a mixture of 1-methylnaphthalene (Compound 152A) (1.46 g, 10 mmol) and SnCl$_4$ (5.2 g, 20 mmol) in dichloromethane (40 mL) was added Pb(OAc)$_4$ (4.4 g, 10 mmol) at 0° C. and stirred at room temperature overnight. The mixture was diluted with Et$_2$O (80 mL) and filtered. The filtrate was concentrated under reduced pressure. The residue was purified with reverse phase chromatography using eluent (methanol in water, 60% v/v) to afford Compound 152B. LC-MS (ESI) m/z: Non-ionizable compound under routine conditions used; $^1$H-NMR (CDCl$_3$, 400 MHz): δ (ppm) 2.66 (s, 3H), 7.20-7.24 (m, 1H), 7.44 (d, J=8.0 Hz, 1H), 7.56-7.60 (m, 2H), 7.98 (d, J=7.6 Hz, 1H), 8.26 (d, J=8.0 Hz, 1H).

To a mixture of Compound 152B (1.76 g, 10 mmol) and N-Bromosuccinimide (1.94 g, 11 mmol) in carbon tetrachloride (40 mL) was added BPO (50 mg) at 0° C. and heated at reflux overnight. The mixture was concentrated under reduced pressure. The residue was purified with flash column chromatography on silica gel (ethyl acetate in petroleum ether, 30% v/v) to afford Compound 152C. LC-MS (ESI) m/z: Non-ionizable compound under routine conditions used; $^1$H-NMR (CDCl$_3$, 400 MHz): δ (ppm) 4.93 (s, 2H), 7.45-7.51 (m, 2H), 7.65-7.69 (m, 2H), 8.16 (d, J=8.0 Hz, 1H), 8.35 (d, J=8.0 Hz, 1H).

Compounds 152D, 152E, and 152 were synthesized by employing the procedures described for Compounds 35D, 8F, and 1 using Compounds 152C, 152D, and 152E in lieu of Compounds 35C, 8E, and 1E. Compound 152D: LC-MS (ESI) m/z: 468 [M+H]$^+$. Compound 152E: LC-MS (ESI) m/z: 440 [M+H]$^+$. Compound 152: LC-MS (ESI) m/z: 320 [M+H]$^+$; $^1$H-NMR (DMSO-d$_6$, 400 MHz): δ (ppm) 4.85 (s, 2H), 7.58-7.65 (m, 2H), 7.71-7.74 (m, 2H), 8.23-8.29 (m, 2H).

Example 153

Synthesis of 4-((3,5-dichlorophenyl)amino)-1H-1,2,3-triazole-5-carboxylic acid (153)

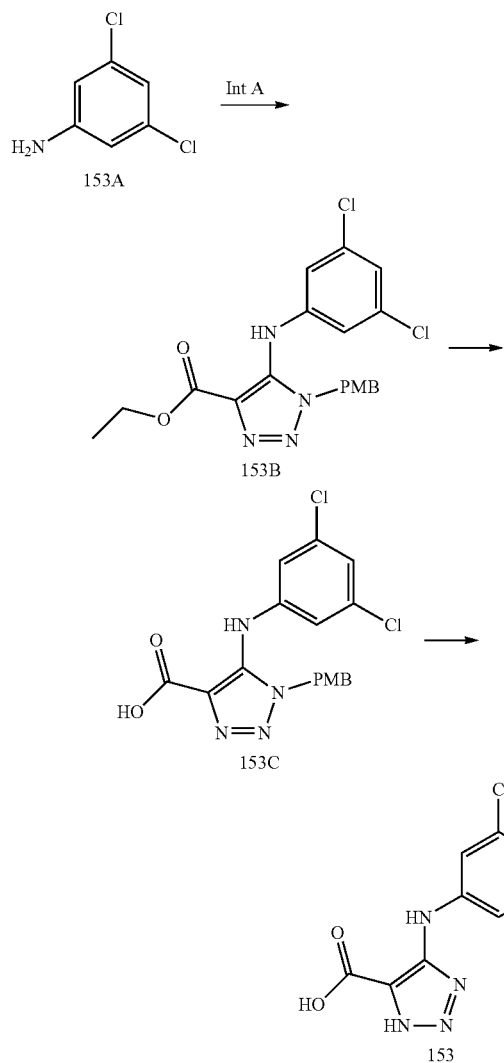

Compounds 153B, 153C, and 153 were synthesized by employing the procedures described for Compounds 6B, 8F, and 1 using Intermediate A, Compounds 153A using K$_3$PO$_4$ as base, 153B, and 153C in lieu of Compounds 6A, 1-methylpiperazine using t-BuONa as base, 8E, and 1E. Compound 153B: LC-MS (ESI) m/z: 421 [M+H]$^+$. Compound 153C: LC-MS (ESI) m/z: 301 [M+H]$^+$. Compound 153: LC-MS (ESI) m/z: 273 [M+H]$^+$; $^1$H-NMR (DMSO-d$_6$, 400 MHz): δ (ppm) 6.93-6.94 (m, 1H), 7.64-7.65 (m, 2H), 9.26 (brs, 1H).

Example 154

Synthesis of 4-((2,5-dichlorophenyl)amino)-1H-1,2,3-triazole-5-carboxylic acid 2,2,2-trifluoroacetate (154)

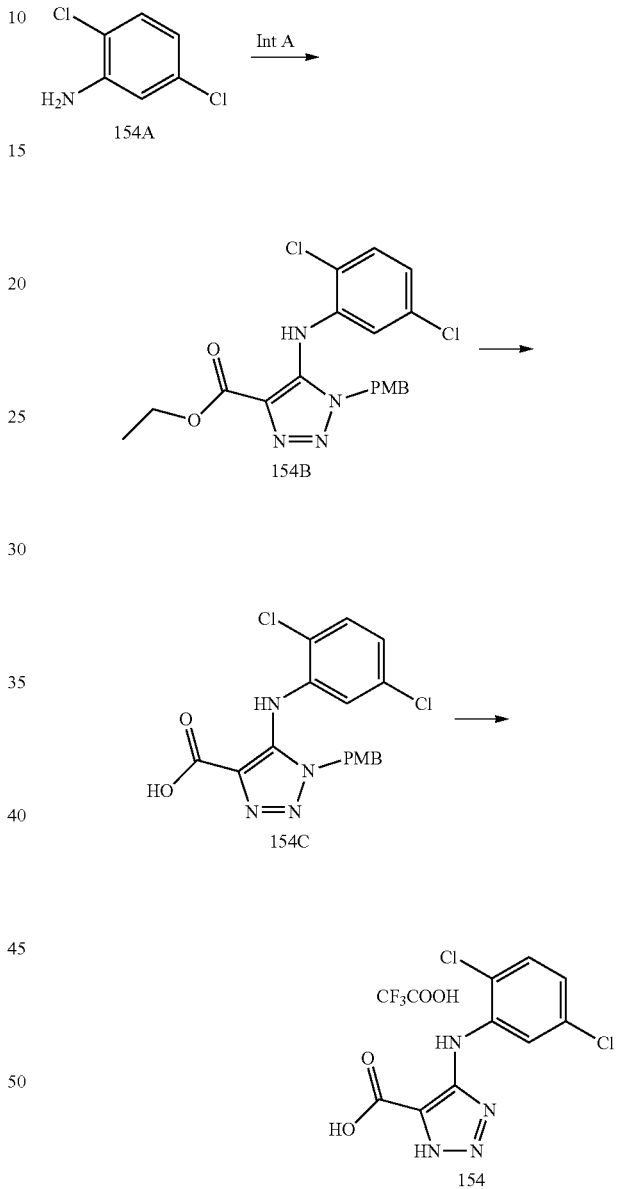

Compounds 154B, 154C, and 154 were synthesized by employing the procedures described for Compounds 6B, 8F, and 1 using Intermediate A, Compounds 154A using K$_3$PO$_4$ as base, 154B, and 154C in lieu of Compounds 6A, 1-methylpiperazine using t-BuONa as base, 8E, and 1E. Compound 154B: LC-MS (ESI) m/z: 421 [M+H]$^+$. Compound 154C: LC-MS (ESI) m/z: 301 [M+H]$^+$. Compound 154: LC-MS (ESI) m/z: 273 [M+H]$^+$; $^1$H-NMR (DMSO-d$_6$, 400 MHz): δ (ppm) 7.01 (dd, J$_1$=4.0 Hz, J$_2$=8.4 Hz, 1H), 7.53 (d, J=8.4 Hz, 1H), 8.38 (s, 1H), 8.85 (s, 1H).

Example 155

Synthesis of 4-((3'-chloro-4'-(trifluoromethoxy)-[1,1'-biphenyl]-4-yl)amino)-1H-1,2,3-triazole-5-carboxylic acid (155)

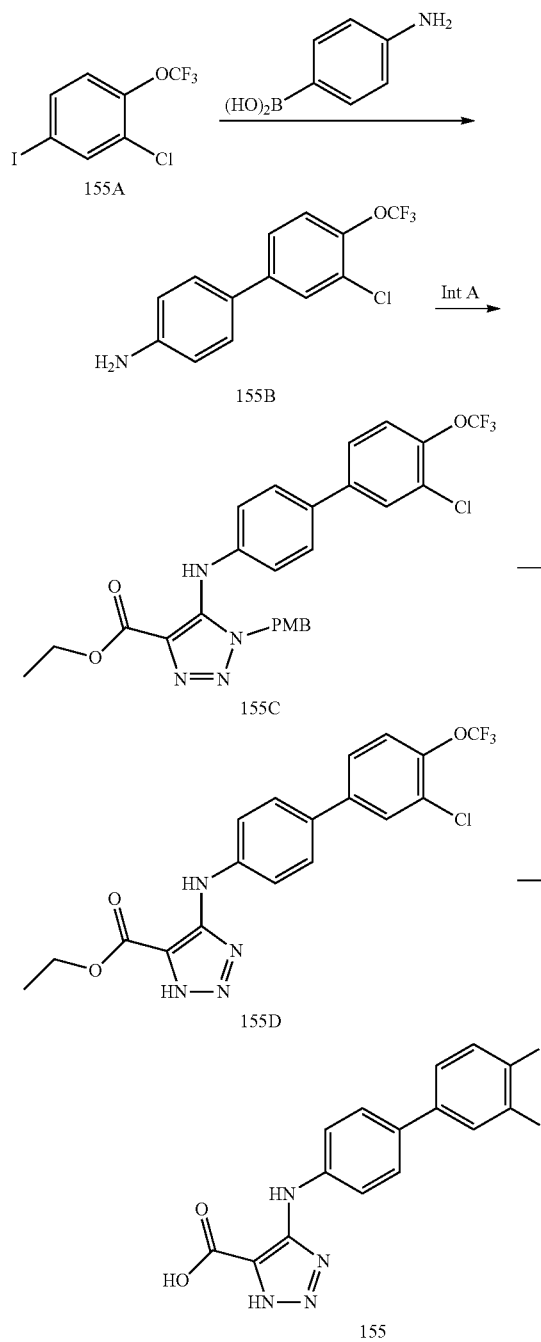

Example 156

Synthesis of 4-((3'-chloro-4'-(trifluoromethoxy)-[1,1'-biphenyl]-4-yl)oxy)-1H-1,2,3-triazole-5-carboxylic acid (156)

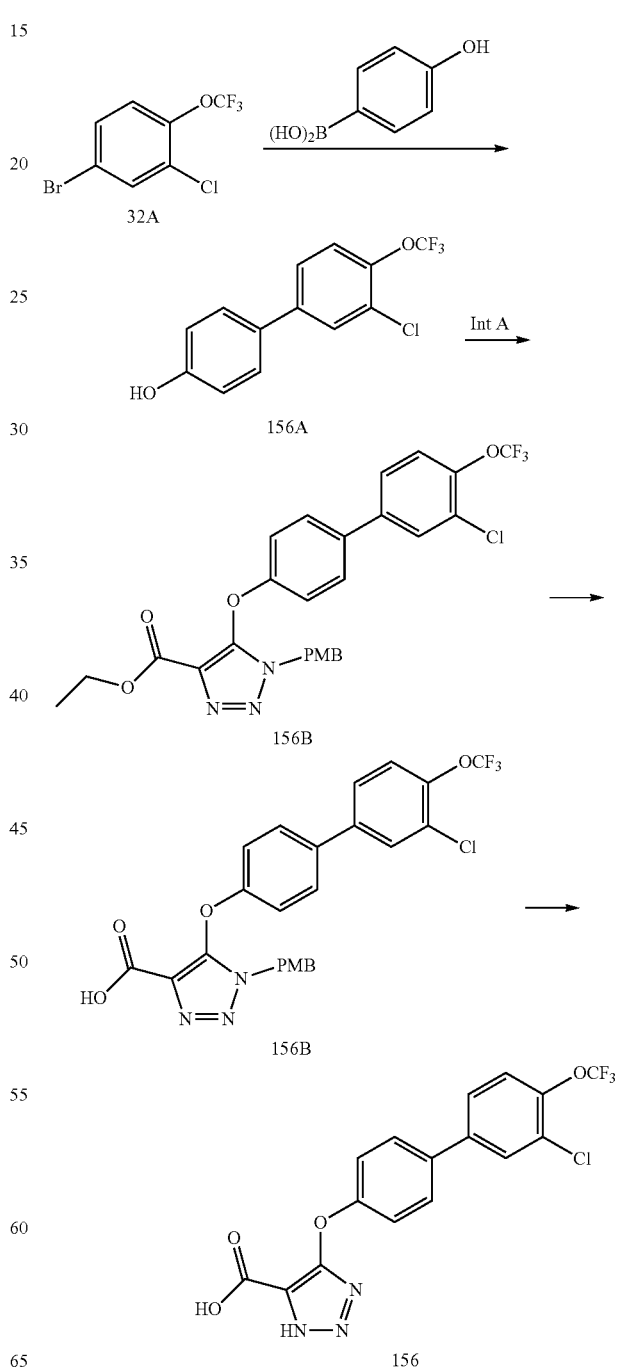

Compounds 155B, 155C, 155D, and 155 were synthesized by employing the procedures described for Compounds 4B, 6B, 1, and 8F using 4-aminophenylboronic acid, Compounds 155A, Intermediate A, 155B using $K_3PO_4$ as base, 155C, and 155D in lieu of (4-bromophenyl)boronic acid, Compounds 4A, 6A, 1-methylpiperazine using t-BuONa as base, 1E, and 8E. Compound 155B: LC-MS (ESI) m/z: 288 [M+H]$^+$. Compound 155C: LC-MS (ESI) m/z: 547 [M+H]$^+$. Compound 155D: LC-MS (ESI) m/z: 427 [M+H]$^+$. Compound 155: LC-MS (ESI) m/z: 399 [M+H]$^+$; $^1$H-NMR (DMSO-d$_6$, 400 MHz): δ (ppm) 7.59-7.61 (m, 1H), 7.70-7.71 (m, 5H), 7.95-7.96 (m, 1H), 8.36 (brs, 1H), 13.40 (brs, 1H), 14.97 (brs, 1H).

Compounds 156B, 156C, 156D, and 156 were synthesized by employing the procedures described for Compounds 8B, Intermediate I, 8F, and 1 using 4-hydroxyphenylboronic acid, Compounds 32A using $K_2CO_3$ as base and 1,4-dioxane/$H_2O$ as solvent, 156A, 156B, and 156C in lieu of (3,4-dichlorophenyl)boronic acid, Compounds 8A using $Cs_2CO_3$ as base and DME/$H_2O$ as solvent, 4-bromophenol, 8E, and 1E. Compound 156B: LC-MS (ESI) m/z: 287 $[M-H]^+$. Compound 156C: LC-MS (ESI) m/z: 548 $[M+H]^+$; $^1$H-NMR (CDCl$_3$, 400 MHz): δ (ppm) 1.13, 1.41 (t, J=7.2 Hz, 3H), 3.73, 3.75 (s, 3H), 4.20, 4.43 (q, J=7.2 Hz, 2H), 5.38, 5.54 (s, 2H), 6.75-6.88 (m, 4H), 7.19-7.27 (m, 3H), 7.38-7.60 (m, 4H). Compound 156D: LC-MS (ESI) m/z: 518 $[M-H]^-$. Compound 156: LC-MS (ESI) m/z: 400 $[M+H]^+$; $^1$H-NMR (DMSO-d$_6$, 400 MHz): δ (ppm) 7.15-7.19 (m, 2H), 7.63 (dd, J=1.2, 8.8 Hz, 1H), 7.72-7.77 (m, 3H), 7.98 (d, J=2 Hz, 1H), 13.34 (b, 1H), 15.32 (b, 1H).

Example 157

Synthesis of 4-((3'-(piperidine-1-carbonyl)-[1,1'-biphenyl]-4-yl)oxy)-1H-1,2,3-triazole-5-carboxylic acid 2,2,2-trifluoroacetate (157)

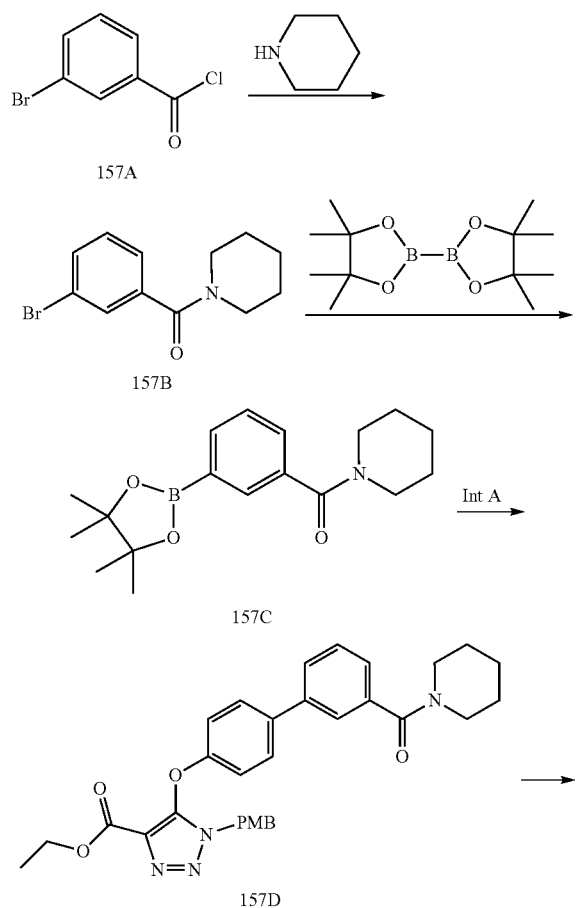

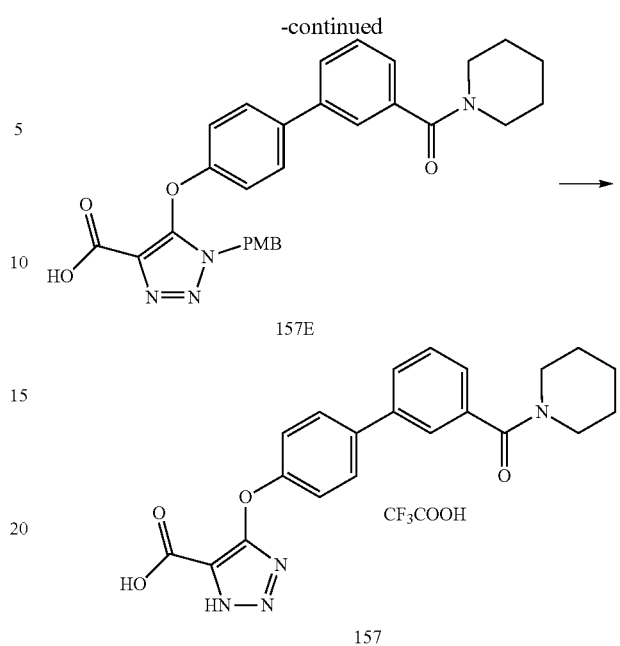

To a mixture of 3-bromobenzoyl chloride (Compound 157A) (1.09 g, 5 mmol) and DIPEA (3.22 g, 25 mol) in dichloromethane (10 mL) was added piperidine (2.12 g, 25 mmol) at −10° C. and stirred at room temperature for 2 hours. The mixture was washed successively with an aqueous HCl solution (1N, 20 mL), water (10 mL) and brine (20 mL), dried over anhydrous sodium sulfate, filtered, and concentrated to give Compound 157B. LC-MS (ESI) m/z: 268 $[M+H]^+$.

Compounds 157C, 157D, 157E, and 157 were synthesized by employing the procedures described for Compounds 27C, 4B, 8F, and 1 using Compounds 157B, Intermediate I, 157C using 1,4-dioxane/$H_2O$ as solvent, 157D, and 157E in lieu of Compounds 27B, 4A, (4-bromophenyl)boronic acid using toluene/EtOH/$H_2O$ as solvent, 8E, and 1E. Compound 157C: LC-MS (ESI) m/z: 316 $[M+H]^+$. Compound 157D: LC-MS (ESI) m/z: 541 $[M+H]^+$. Compound 157E: LC-MS (ESI) m/z: 513 $[M+H]^+$. Compound 157: LC-MS (ESI) m/z: 393 $[M+H]^+$; $^1$H-NMR (DMSO-d$_6$, 400 MHz): δ (ppm) 1.47-1.60 (m, 6H), 3.29 (s, 2H), 3.59 (s, 2H), 7.15 (d, J=4.4 Hz, 2H), 7.32 (d, J=7.6 Hz, 1H), 7.50 (t, J=7.6 Hz, 1H), 7.58 (s, 1H), 7.68-7.72 (m, 3H), 13.21 (s, 1H), 15.30 (s, 1H).

Example 158

Synthesis of 4-(((6-chloronaphthalen-2-yl)oxy)methyl)-1H-1,2,3-triazole-5-carboxylic acid 2,2,2-trifluoroacetate (158)

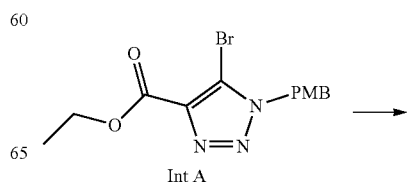

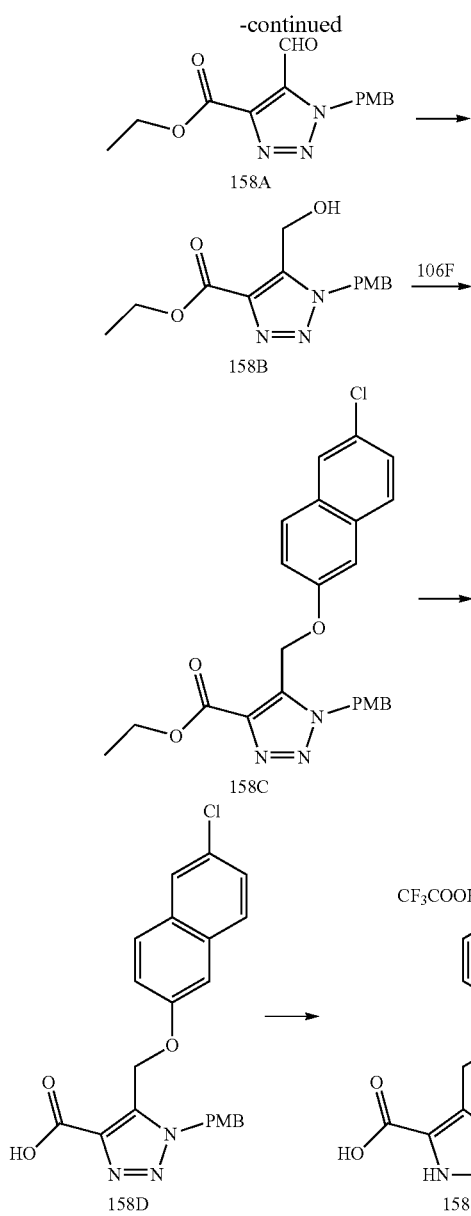

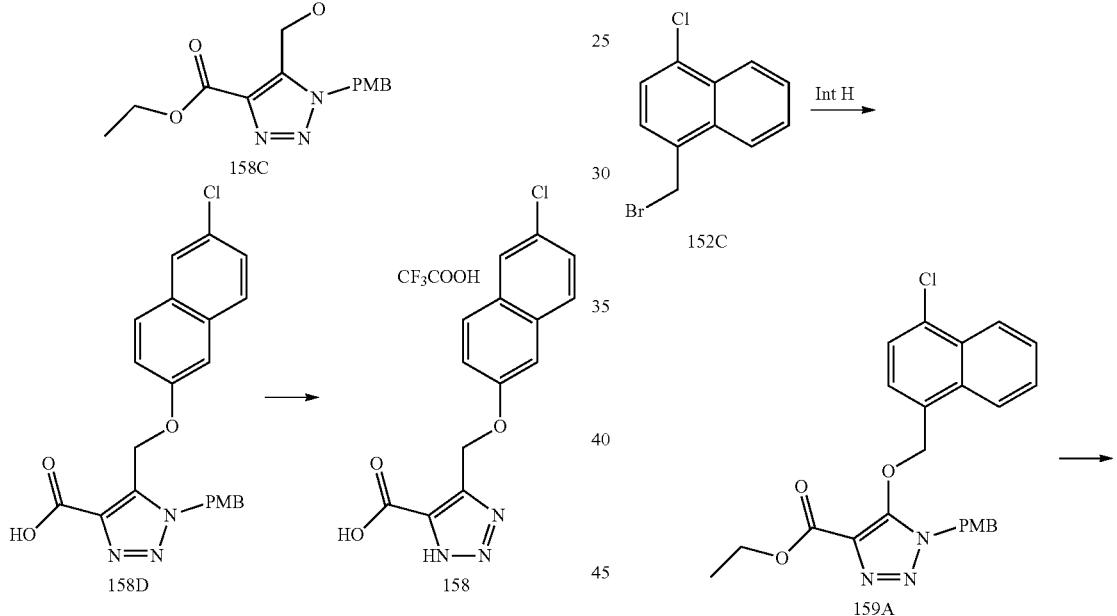

EtOAc as solvent, 158B using DEAD, 106F, 158C, and 158D in lieu of Compounds 57B using MeOH as solvent, 90B using DIAD, Intermediate H, 8E, and 1E. Compound 158B: LC-MS (ESI) m/z: 292 [M+H]⁺; (CDCl₃, 400 MHz): δ (ppm) 1.45 (t, J=7.2 Hz, 3H), 3.80-3.84 (m, 4H), 4.47 (q, J=7.2 Hz, 2H), 4.79 (d, J=6.8 Hz, 2H), 5.58 (s, 2H), 6.87 (d, J=8.8 Hz, 2H), 7.17 (t, J=8.8 Hz, 2H). Compound 158C: LC-MS (ESI) m/z: 452 [M+H]⁺. Compound 158D: LC-MS (ESI) m/z: 424 [M+H]⁺. Compound 158: LC-MS (ESI) m/z: 304 [M+H]⁺; ¹H-NMR (DMSO-d₆, 400 MHz): δ (ppm) 5.49 (s, 2H), 7.28 (dd, J=8.8, 2.4 Hz, 1H), 7.49 (dd, J=8.8, 2.4 Hz, 1H), 7.54 (d, J=2.0 Hz, 1H), 7.86 (dd, J=8.8, 2.4 Hz, 2H), 7.98 (d, J=2.0 Hz, 1H).

Example 159

Synthesis of 4-((4-chloronaphthalen-1-yl)methoxy)-1H-1,2,3-triazole-5-carboxylic acid formate (159)

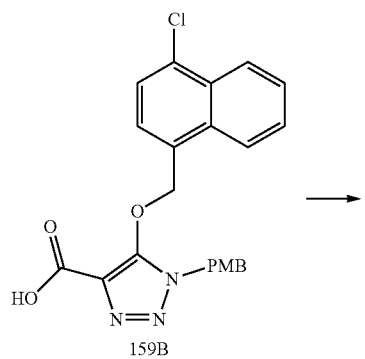

To a mixture of Intermediate A (3.39 g, 10 mmol) in anhydrous THF (100 mL) was added a solution of n-BuLi in hexane (2.5 M, 4.0 mL, 10 mmol) at −78° C. under nitrogen and stirred at −78° C. for 10 minutes. To the mixture was added DMF (730 mg, 100 mmol) and stirred at −78° C. for 1 hour. It was quenched with a saturated aqueous NH₄Cl solution (50 mL) and extracted with ethyl acetate (50 mL×3). The combined extracts were washed with water (100 mL) and brine (100 mL), dried over anhydrous Na₂SO₄, filtered, and concentrated. The residue was purified with flash column chromatography on silica gel (ethyl acetate in petroleum ether, 30% v/v) to give Compound 158A. LC-MS (ESI) m/z: 290 [M+H]⁺; (CDCl₃, 400 MHz): δ (ppm) 1.45 (t, J=7.2 Hz, 3H), 3.78 (s, 3H), 4.50 (q, J=7.2 Hz, 2H), 5.86 (s, 2H), 6.84 (d, J=8.8 Hz, 2H), 7.34 (t, J=8.8 Hz, 2H), 10.48 (s, 1H).

Compounds 158B, 158C, 158D, and 158 were synthesized by employing the procedures described for Compounds 57C, 90C, 8F, and 1 using Compounds 158A using -continued

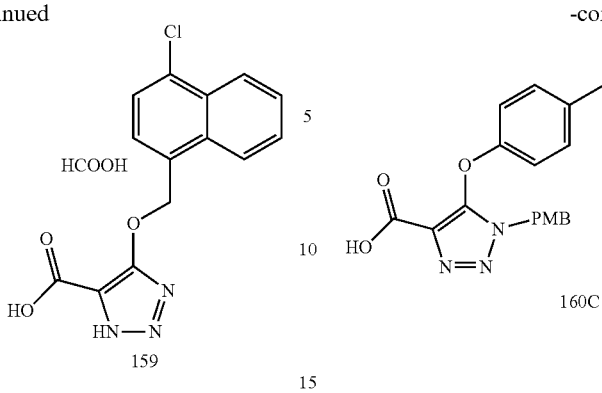

159

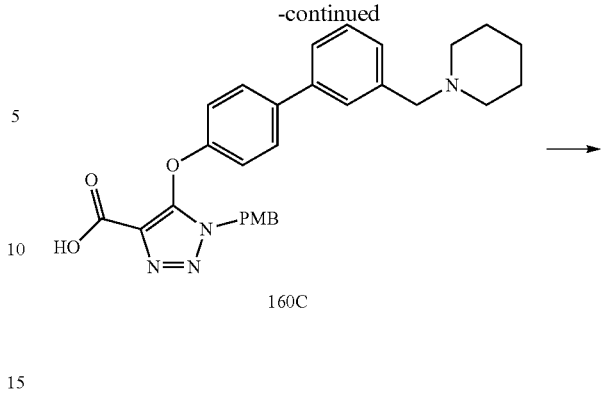

160C

Compounds 159A, 159B, and 159 were synthesized by employing the procedures described for Intermediate I, Compounds 8F, and 1 using Compounds 152C, 159A, and 159B in lieu of 4-bromophenol, Compounds 8E, and 1E. Compound 159A: LC-MS (ESI) m/z: 452 [M+H]$^+$. Compound 159B: LC-MS (ESI) m/z: 424 [M+H]$^+$. Compound 159: LC-MS (ESI) m/z: 302 [M−H]; $^1$H-NMR (DMSO-d$_6$, 400 MHz): δ (ppm) 6.20 (s, 2H), 7.00-7.07 (m, 1H), 7.61-7.80 (m, 3H), 8.12 (s, 1H), 8.24-8.27 (m, 1H), 8.35-8.41 (m, 1H).

Example 160

Synthesis of 4-((3'-(piperidin-1-ylmethyl)-[1,1'-biphenyl]-4-yl)oxy)-1H-1,2,3-triazole-5-carboxylic acid 2,2,2-trifluoroacetate (160)

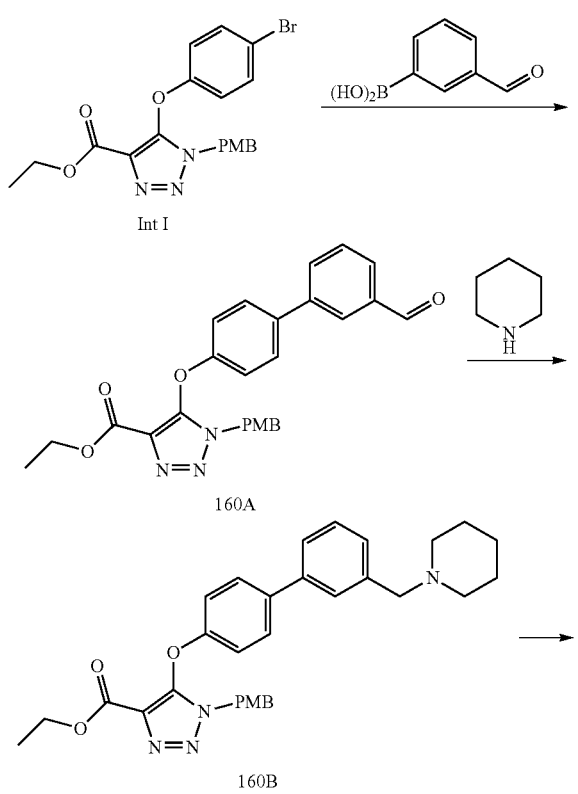

Compound 160A was synthesized by employing the procedure described for Compound 4B using 3-formylphenylboronic acid and Intermediate I in lieu of (4-bromophenyl)boronic acid and Compound 4A, LC-MS (ESI) m/z: 458 [M+H]$^+$. $^1$H-NMR (DMSO-d$_6$, 400 MHz): δ (ppm) 0.93 (t, J=7.2 Hz, 3H), 3.67 (s, 3H), 4.01-4.07 (m, 2H), 5.47 (s, 2H), 6.85 (d, J=8.8 Hz, 2H), 7.03 (d, J=8.4 Hz, 2H), 7.20 (d, J=8.4 Hz, 2H), 7.66-7.71 (m, 3H), 7.88 (d, J=7.2 Hz, 1H), 7.97 (d, J=7.6 Hz, 1H), 8.14 (s, 1H), 10.08 (s, 1H).

A mixture of Compound 160A (160 mg, 0.35 mmol), piperidine (36 mg, 0.42 mol) and anhydrous magnesium sulfate (500 mg) in dichloromethane (10 mL) was stirred at 20° C. under nitrogen for 0.5 hour. To the mixture was added NaBH$_3$CN (26 mg, 0.42 mol) and stirred at 20° C. for 15 hours. It was filtered and the filtrate was concentrated. The residue was purified with flash column chromatography on silica gel (ethyl acetate in petroleum ether, 60% v/v) to give Compound 160B. LC-MS (ESI) m/z: 527 [M+H]$^+$.

Compounds 160C and 160 were synthesized by employing the procedures described for Compounds 8F and 1 using Compounds 160B and 160C in lieu of Compounds 8E and 1E. Compound 160C: LC-MS (ESI) m/z: 499 [M+H]$^+$. Compound 160: LC-MS (ESI) m/z: 379 [M+H]$^+$; $^1$H-NMR (DMSO-d$_6$, 400 MHz): δ (ppm) 1.33-1.42 (m, 1H), 1.57-1.70 (m, 3H), 1.81-1.84 (m, 2H), 2.87 (s, 2H), 3.34-3.37 (m, 2H), 4.34 (s, 2H), 7.20 (d, J=8.8 Hz, 2H), 7.46 (d, J=7.2 Hz, 1H), 7.55 (t, J=7.6 Hz, 1H), 7.70 (d, J=8.4 Hz, 2H), 7.75 (d, J=8.4 Hz, 1H), 7.80 (s, 1H), 9.45 (s, 1H), 13.23 (s, 1H), 15.30 (s, 1H).

Example 161

Synthesis of 4-((4'-(trifluoromethyl)-[1,1'-biphenyl]-4-yl)oxy)-1H-1,2,3-triazole-5-carboxylic acid (161)

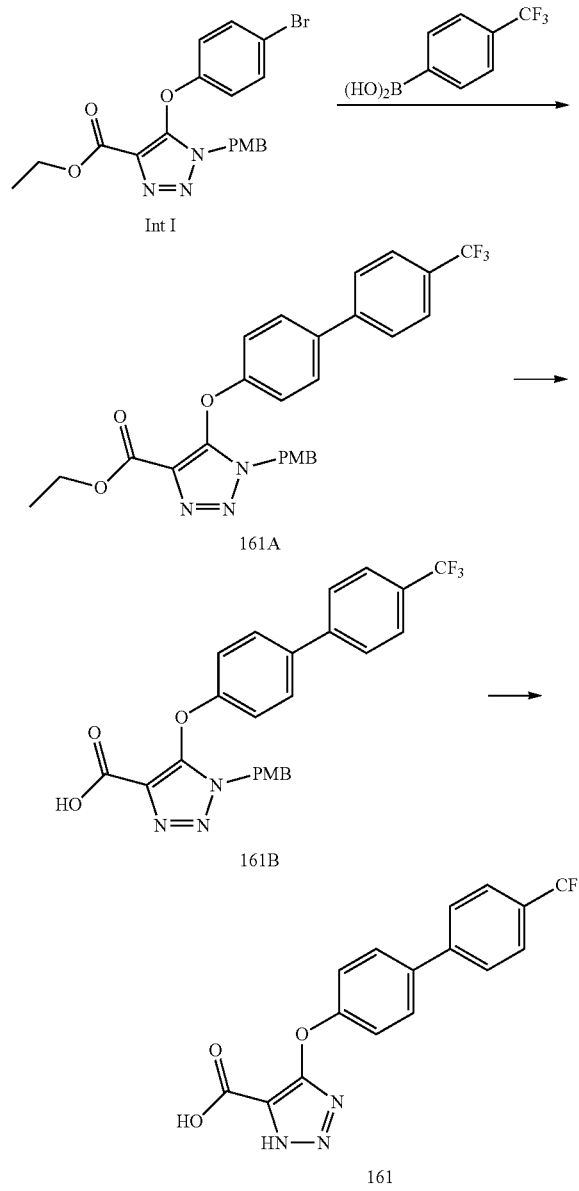

Compounds 161A, 161B, and 161 were synthesized by employing the procedures described for Compounds 4B, 8F, and 1 using 4-(trifluoromethyl)phenylboronic acid, Intermediate I using $K_2CO_3$ as base and 1,4-dioxane/$H_2O$ as solvent, Compounds 161A, and 161B in lieu of (4-bromophenyl) boronic acid, Compounds 4A using $Na_2CO_3$ as base and toluene/EtOH/$H_2O$ as solvent, 8E, and 1E. Compound 161A: LC-MS (ESI) m/z: 498 [M+H]$^+$; $^1$H-NMR (CDCl$_3$, 400 MHz): δ (ppm) 1.13 (t, J=7.2 Hz, 3H), 3.73 (s, 3H), 4.21 (q, J=7.2 Hz, 2H), 5.39 (s, 2H), 6.77 (d, J=8.4 Hz, 2H), 6.85 (d, J=8.4 Hz, 2H), 7.21 (d, J=8.4 Hz, 2H), 7.48 (d, J=8.4 Hz, 2H), 7.62 (d, J=8.4 Hz, 2H), 7.69 (d, J=8.4 Hz, 2H). Compound 161B: LC-MS (ESI) m/z: 492 [M+Na]$^+$. Compound 161: LC-MS (ESI) m/z: 350 [M+H]$^+$; $^1$H-NMR (DMSO-d$_6$, 400 MHz): δ (ppm) 7.20 (d, J=8.8 Hz, 2H), 7.75 (d, J=8.8 Hz, 2H), 7.81 (d, J=8.8 Hz, 2H), 7.88 (d, J=8.8 Hz, 2H).

Example 162

Synthesis of 4-((3'-(cyclopentyloxy)-[1,1'-biphenyl]-4-yl)oxy)-1H-1,2,3-triazole-5-carboxylic acid (162)

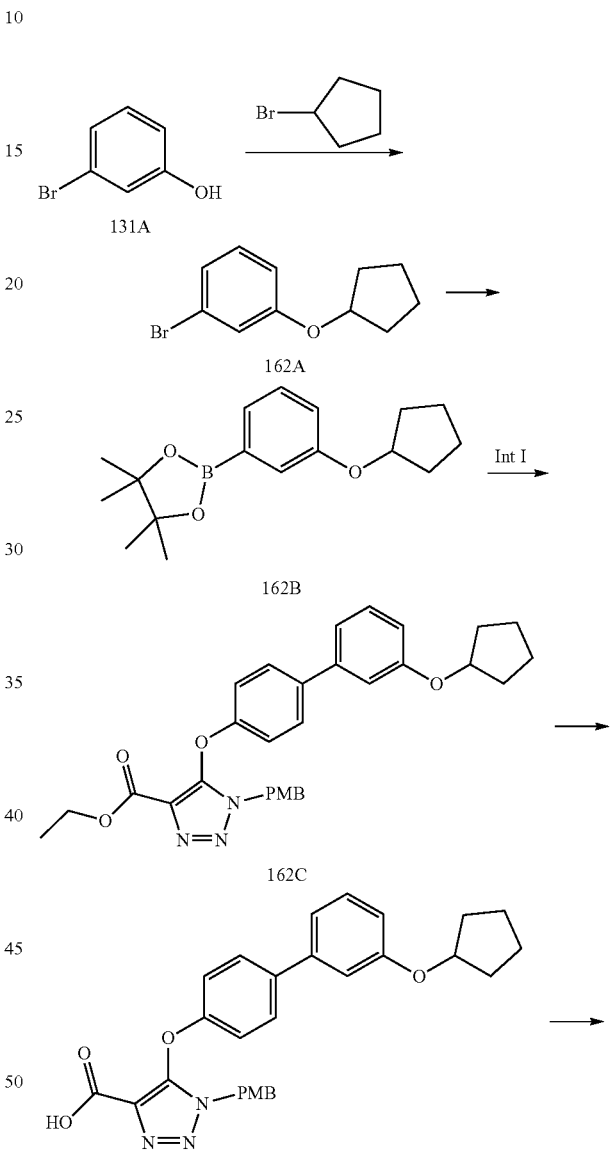

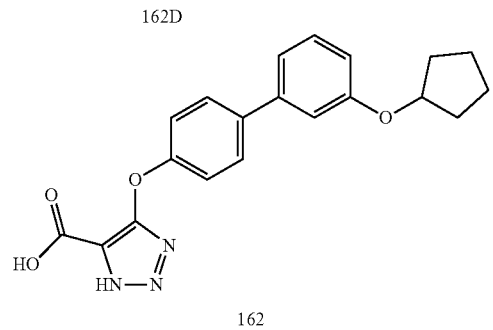

Compounds 162A, 162B, 162C, 162D, and 162 were synthesized by employing the procedures described for Compounds 27B, 27C, 8B, 8F, and 1 using bromocyclopentane, Compounds 131A, 162A, 162B, Intermediate I using Na$_2$CO$_3$ as base and 1,4-dioxane/H$_2$O as solvent, 162C, and 162D in lieu of 2-bromopropane, Compounds 27A, 27B, (4-bromophenyl)boronic acid, 8A using Cs$_2$CO$_3$ as base and DME/H$_2$O as solvent, 8E, and 1E. Compound 162A: LC-MS (ESI) m/z: non-ionizable compound under routine conditions used. Compound 162B: LC-MS (ESI) m/z: 289 [M+H]$^+$. Compound 162C: LC-MS (ESI) m/z: 514 [M+H]$^+$. Compound 162D: LC-MS (ESI) m/z: 486 [M+H]$^+$. Compound 162: LC-MS (ESI) m/z: 366 [M+H]$^+$; $^1$H-NMR (DMSO-d$_6$, 400 MHz): δ (ppm) 1.59-1.75 (m, 6H), 1.92-1.95 (m, 2H), 4.90-4.91 (m, 1H), 6.88 (dd, J$_1$=8.0 Hz, J$_2$=2.0 Hz, 1H), 7.10-7.18 (m, 4H), 7.34 (t, J=8.0 Hz, 1H), 7.65 (d, J=8.8 Hz, 2H).

Example 163

Synthesis of 4-((4'-chloro-3'-(trifluoromethoxy)-[1,1'-biphenyl]-4-yl)oxy)-1H-1,2,3-triazole-5-carboxylic acid (163)

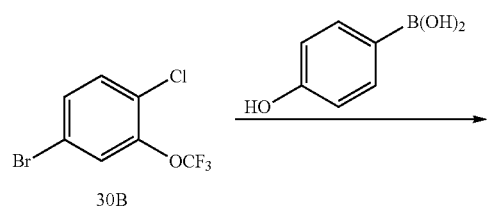

30B

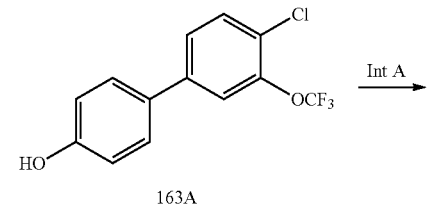

163A

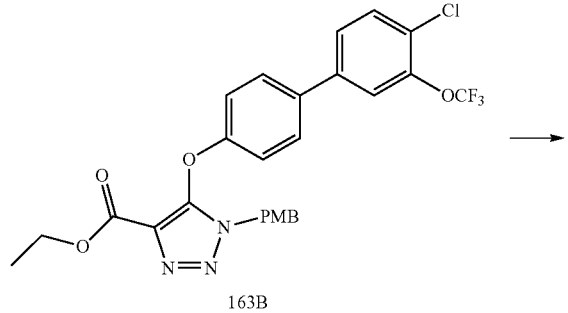

163B

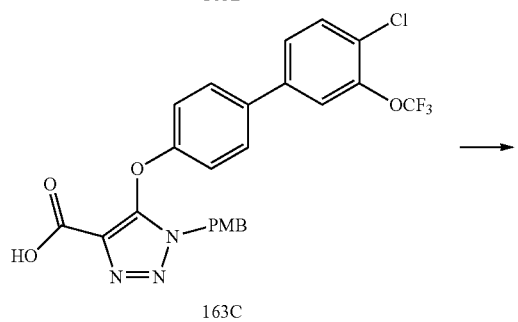

163C

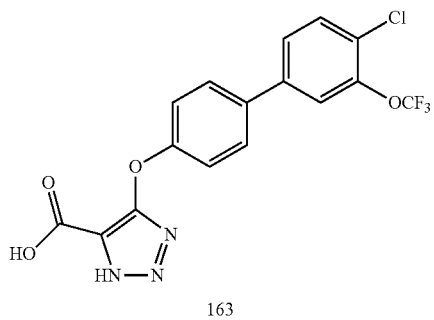

163

Compounds 163A, 163B, 163C, and 163 were synthesized by employing the procedures described for Compounds 8B, Intermediate I, 8F, and 1 using 4-hydroxyphenylboronic acid, Compounds 30B using K$_2$CO$_3$ as base and 1,4-dioxane/H$_2$O as solvent, 163A, 163B, and 163C in lieu of (3,4-dichlorophenyl)boronic acid, Compounds 8A using Cs$_2$CO$_3$ as base and DME/H$_2$O as solvent, 4-bromophenol, 8E, and 1E. Compound 163A: LC-MS (ESI) m/z: 287 [M−H]$^+$. Compound 163B: LC-MS (ESI) m/z: 548 [M+H]$^+$; $^1$H-NMR (CDCl$_3$, 400 MHz): δ 1.15 (t, J=7.2 Hz, 3H), 3.73 (s, 3H), 4.21 (q, J=7.2 Hz, 2H), 5.38 (s, 2H), 6.77 (d, J=8.8 Hz, 2H), 6.83 (d, J=8.8 Hz, 2H), 7.21 (d, J=8.4 Hz, 2H), 7.37-7.45 (m, 4H), 7.53 (d, J=8.4 Hz, 1H). Compound 163C: LC-MS (ESI) m/z: 518 [M−H]$^-$. Compound 163: LC-MS (ESI) m/z: 400 [M+H]$^+$; $^1$H-NMR (DMSO-d$_6$, 400 MHz): δ (ppm) 7.18 (d, J=8.8 Hz, 2H), 7.73-7.76 (m, 4H), 7.82 (s, 1H).

Example 164

Synthesis of 4-((3'-(piperidin-1-yl)-[1,1'-biphenyl]-4-yl)thio)-1H-1,2,3-triazole-5-carboxylic acid 2,2,2-trifluoroacetate (164)

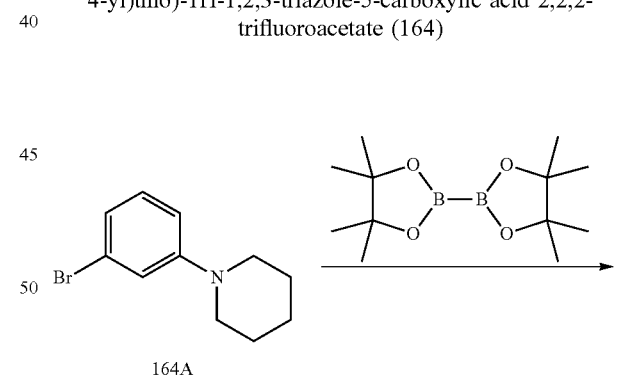

164A

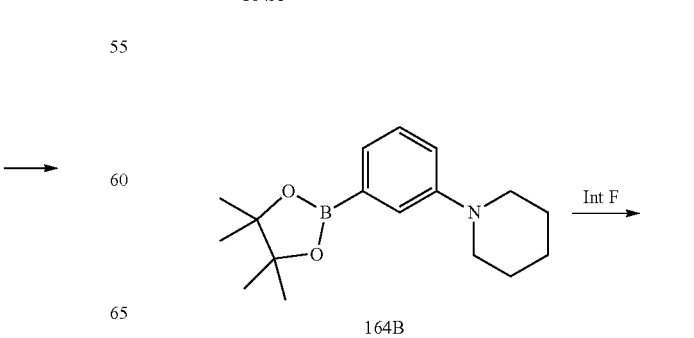

164B

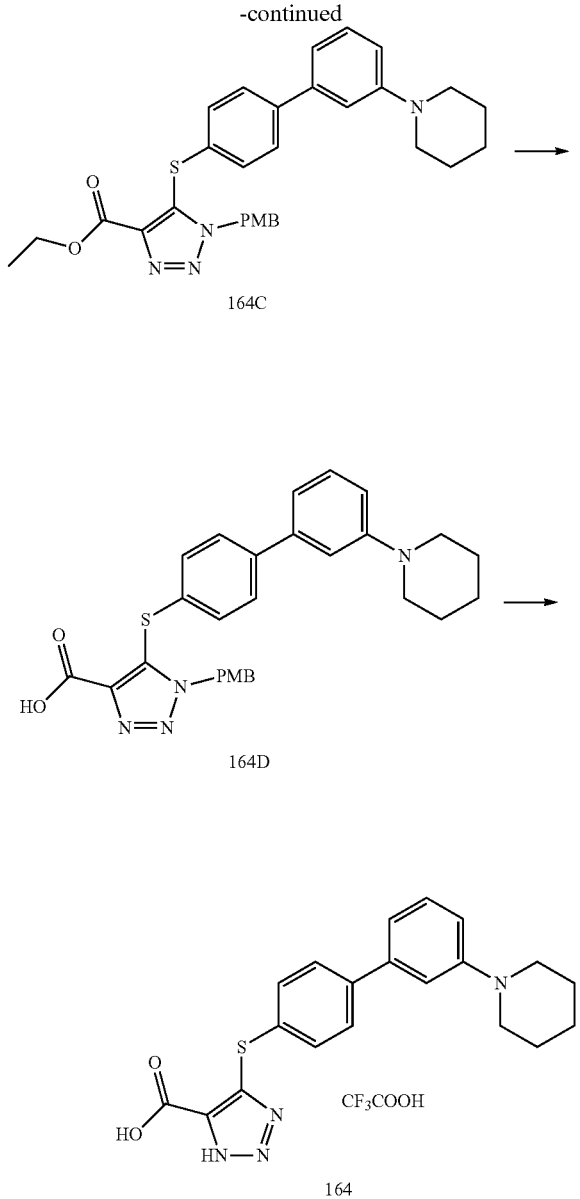

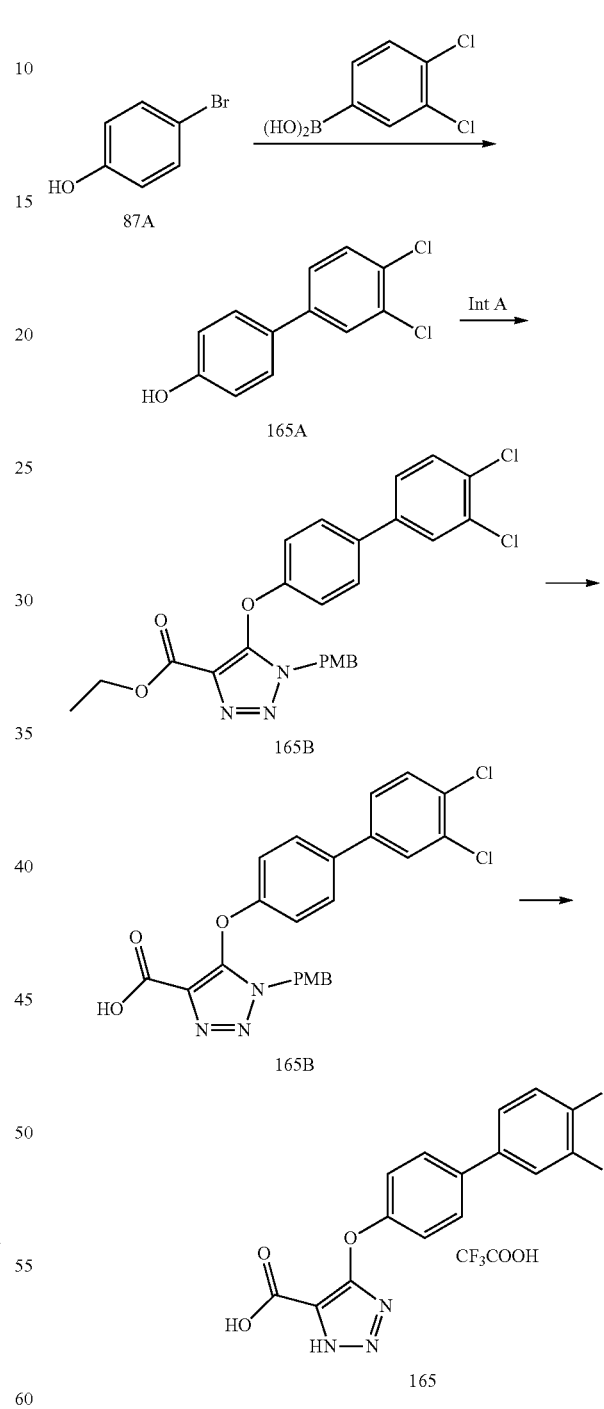

Example 165

Synthesis of 4-((3',4'-dichloro-[1,1'-biphenyl]-4-yl)oxy)-1H-1,2,3-triazole-5-carboxylic acid 2,2,2-trifluoroacetate (165)

Compounds 164B, 164C, 164D, and 164 were synthesized by employing the procedures described for Compounds 27C, 4B, 8F, and 1 using Compounds 164A, 164B, Intermediate F using $K_3PO_4$ as base and DME/$H_2O$ as solvent, 164C, and 164D in lieu of Compounds 27B, (4-bromophenyl)boronic acid, 4A using $Na_2CO_3$ as base and toluene/EtOH/$H_2O$ as solvent, 8E, and 1E. Compound 164B: LC-MS (ESI) m/z: 288 [M+H]$^+$. Compound 164C: LC-MS (ESI) m/z: 529 [M+H]$^+$; $^1$H-NMR (CDCl$_3$, 400 MHz): δ 1.24-1.28 (m, 2H), 1.32 (t, J=7.2 Hz, 3H), 1.70-1.74 (m, 4H), 3.19-3.22 (m, 4H), 3.71 (s, 3H), 4.37 (q, J=7.2 Hz, 2H), 5.56 (s, 2H), 6.75 (d, J=8.8 Hz, 2H), 6.92-6.96 (m, 2H), 7.04-7.07 (m, 3H), 7.15 (d, J=8.8 Hz, 2H), 7.28-7.31 (m, 1H), 7.40 (d, J=8.4 Hz, 2H). Compound 164D: LC-MS (ESI) m/z: 499 [M−H]$^-$. Compound 164: LC-MS (ESI) m/z: 381 [M+H]$^+$; $^1$H-NMR (DMSO-d$_6$, 400 MHz): δ (ppm) 1.54-1.57 (m, 2H), 1.64-1.66 (m, 4H), 3.23-3.25 (m, 4H), 7.01-7.10 (m, 2H), 7.20-7.23 (m, 1H), 7.32 (t, J=7.2 Hz, 1H), 7.53 (d, J=8.0 Hz, 2H), 7.68 (d, J=8.0 Hz, 2H), 13.53 (bs, 1H), 15.81 (bs, 1H).

Compounds 165A, 165B, 165C, and 165 were synthesized by employing the procedures described for Compounds 8B, Intermediate I, 8F, and 1 using Compounds 87A using $Na_2CO_3$ as base and 1,4-dioxane/$H_2O$ as solvent, 165A, 165B, and 165C in lieu of Compounds 8A using $Cs_2CO_3$ as base and DME/$H_2O$ as solvent, 4-bromophenol, 8E, and 1E. Compound 165A: LC-MS (ESI) m/z: non-ionizable compound under routine conditions used. ¹H-NMR (CDCl₃, 400 MHz): δ (ppm) 6.89-6.92 (m, 2H), 7.33-7.36 (m, 1H), 7.41-7.47 (m, 3H), 7.61 (d, J=2.4 Hz, 1H). Compound 165B: LC-MS (ESI) m/z: 498 [M+H]⁺. Compound 163C: LC-MS (ESI) m/z: 470 [M+H]⁺. Compound 165: LC-MS (ESI) m/z: 350 [M+H]⁺; ¹H-NMR (DMSO-d₆, 400 MHz): δ (ppm) 7.14 (d, J=8.8 Hz, 2H), 7.63-7.66 (m, 1H), 7.68-7.73 (m, 3H), 7.91 (d, J=2.0 Hz, 1H).

Example 166

Synthesis of 4-((3,4-dichlorophenyl)difluoromethyl)-1H-1,2,3-triazole-5-carboxylic acid (166)

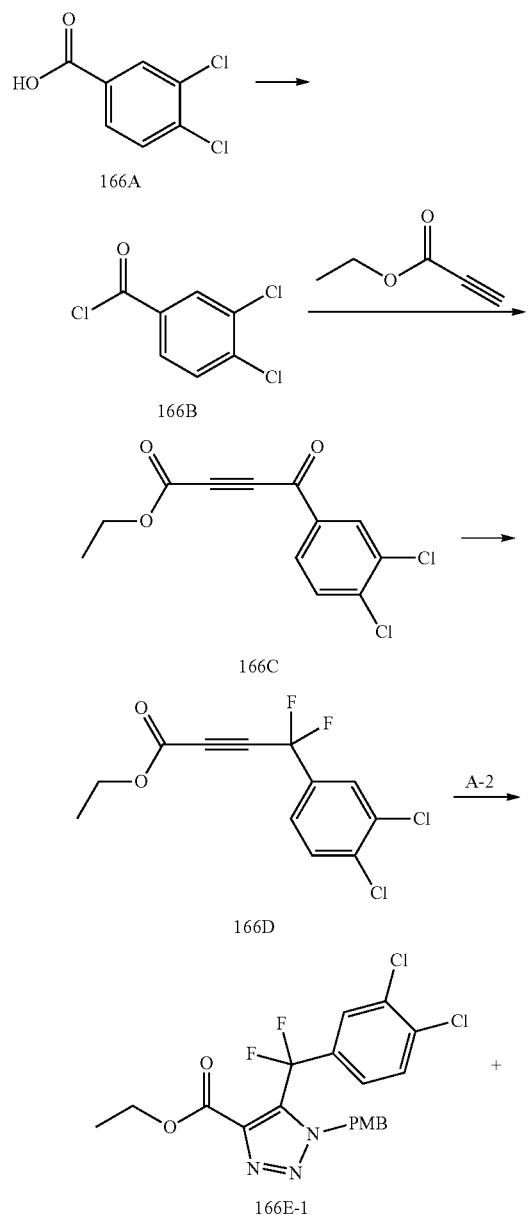

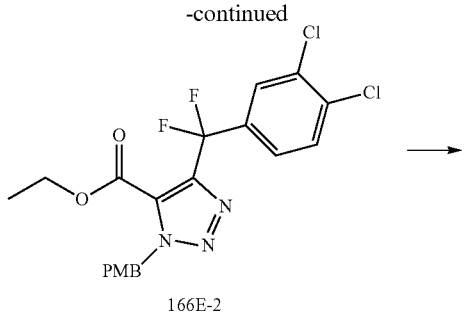

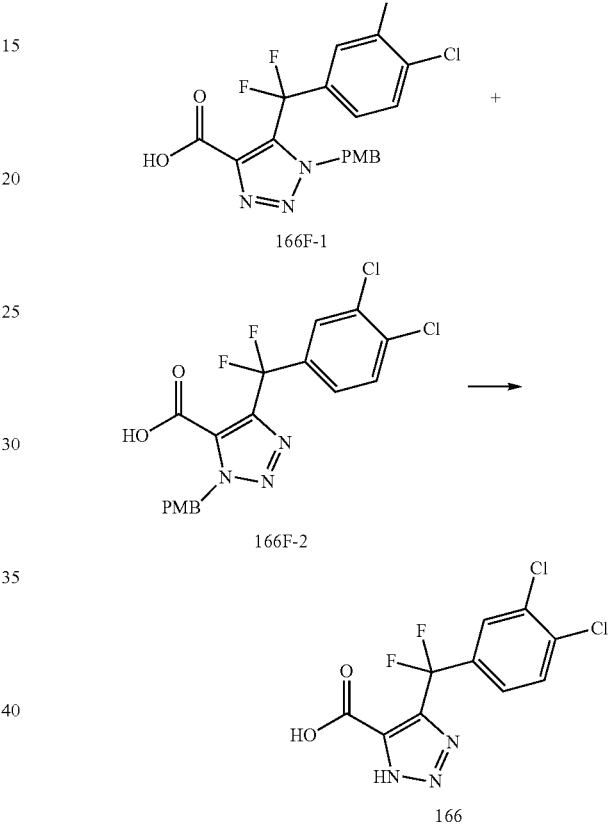

A mixture of 3,4-dichlorobenzoic acid (Compound 166A) (6.0 g, 28.7 mmol) and sulfurous dichloride (100 mL) was heated at 80° C. for 4 hours. The reaction mixture was concentrated to give a crude Compound 166B, which was used directly for next step without further purification.

A mixture of ethyl propiolate (2.82 g, 28.8 mmol), CuI (5.97 g, 31.4 mmol), DIPEA (4.2 g, 32.6 mmol), and Compound 166B (6.0 g, 28.8 mmol) in THF (70 mL) was stirred at room temperature for 16 hours. The reaction mixture was filtered through Celite and the filtrate was concentrated under the reduced pressure. The residue was purified be column chromatography (silica gel, eluted with petroleum ether/ethyl acetate: 1/0 to 20/1) to give Compound 166C. LC-MS (ESI) m/z: 271 [M+H]⁺.

To Compound 166C (900 mg, 3.33 mmol) was added DAST (5 mL) and two drops of ethanol (95%). The reaction mixture was stirred at 60° C. for 16 hours. After cooled down to room temperature, to the mixture was added pentane (50 mL), followed by slowly addition of HCl solution (1%, 50 mL). The organic layers were separated, washed with water (100 mL×2), dried over anhydrous sodium sulfate, filtered, and concentrated to give a crude Compound 166D, which was used directly for next step without further purification. LC-MS (ESI) m/z: non-ionizable compound under routine conditions used.

A mixture of Compound 166D (850 mg, 2.9 mmol) and Intermediate A-2 (608 mg, 3.73 mmol) in THF (10 mL) was stirred at 60° C. for 8 hours. The reaction mixture was concentrated and purified with preparative HPLC to afford a Mixture of 166E-1 and 166E-2. LC-MS (ESI) m/z: 456 [M+H]$^+$.

Mixture of 166F-1 and 166F-2, and Compound 166 were synthesized by employing the procedures described for Compounds 8F and 1 using Mixtures of 166E-1 and 166E-2, and 166F-1 and 166F-2 in lieu of Compounds 8E and 1E. Mixture of 166F-1 and 166F-2: which was used directly for next step without further purification. LC-MS (ESI) m/z: 877 [2M+Na]t Compound 166: LC-MS (ESI) m/z: 308 [M+H]$^+$; $^1$H-NMR (DMSO-d$_6$, 400 MHz): δ (ppm) 7.50 (dd, J$_1$=2.4 Hz, J$_2$=8.8 Hz, 1H), 7.76 (d, J=8.4 Hz, 1H), 7.80 (d, J=1.6 Hz, 1H).

Example 167

Synthesis of 4-((4,4-difluorocyclohexyl)oxy)-1H-1,2,3-triazole-5-carboxylic acid 2,2,2-trifluoroacetate (167)

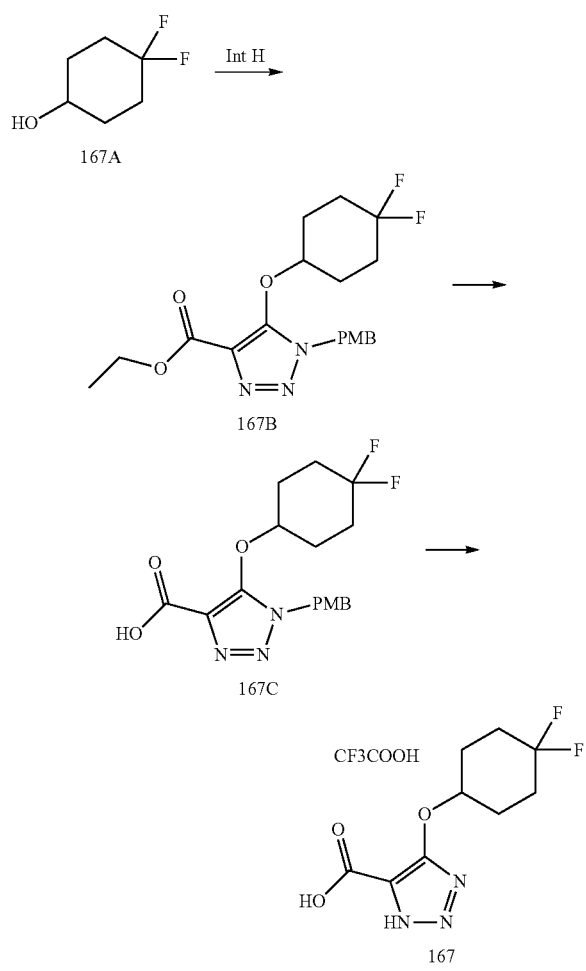

Compounds 167B, 167C, and 167 were synthesized by employing the procedures described for Compounds 90C, 8F, and 1 using Compounds 167A, 167B, and 167C in lieu of Compounds 90B, 8E, and 1E. Compound 167B: LC-MS (ESI) m/z: 396 [M+H]$^+$. Compound 167C: LC-MS (ESI) m/z: 368 [M+H]$^+$. Compound 167: LC-MS (ESI) m/z: 248 [M+H]$^+$; NMR (DMSO-d$_6$, 400 MHz): δ (ppm) 1.91-2.11 (m, 8H), 4.85 (s, 1H), 12.89 (s, 1H), 14.78 (s, 1H).

Example 168

Synthesis of 4-(bicyclo[2.2.1]heptan-2-yloxy)-1H-1,2,3-triazole-5-carboxylic acid (168)

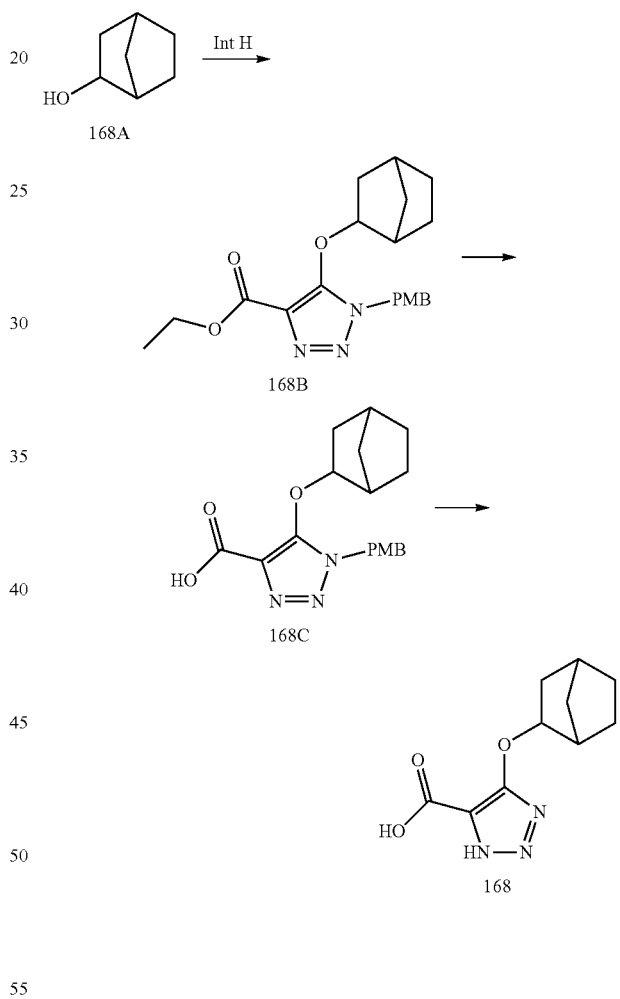

Compounds 168B, 168C, and 168 were synthesized by employing the procedures described for Compounds 90C, 8F, and 1 using Compounds 168A, 168B, and 168C in lieu of Compounds 90B, 8E, and 1E. Compound 168B: LC-MS (ESI) m/z: 372 [M+H]$^+$. Compound 168C: LC-MS (ESI) m/z: 344 [M+H]$^+$. Compound 168: LC-MS (ESI) m/z: 224 [M+H]$^+$; $^1$H-NMR (DMSO-d$_6$, 400 MHz): δ (ppm) 1.03 (dt, J=13.2 Hz, 1H), 1.31 (t, J=9.8 Hz, 3H), 1.42 (d, J=9.9 Hz, 1H), 1.54 (dd, J=8.3 Hz, 1H), 1.85 (t, J=13.0 Hz, 1H), 2.02 (dd, J=8.8 Hz, 1H), 2.21 (s, 1H), 2.57 (s, 1H), 4.90 (d, J=9.6 Hz, 1H).

Example 169

Synthesis of 4-((4'-(piperidin-1-yl)-[1,1'-biphenyl]-4-yl)thio)-1H-1,2,3 triazole-5-carboxylic acid 2,2,2-trifluoroacetate (169)

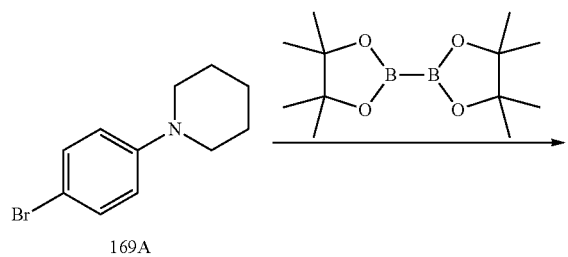

169A

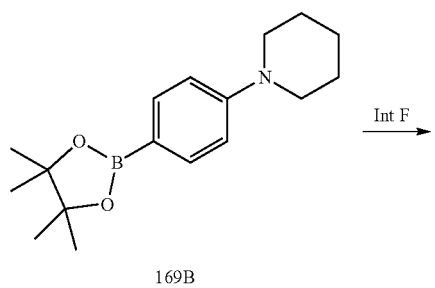

169B

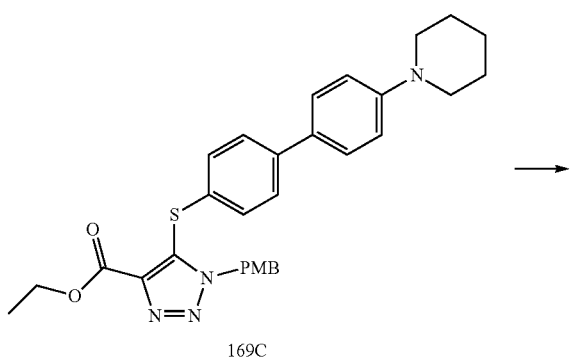

169C

169D

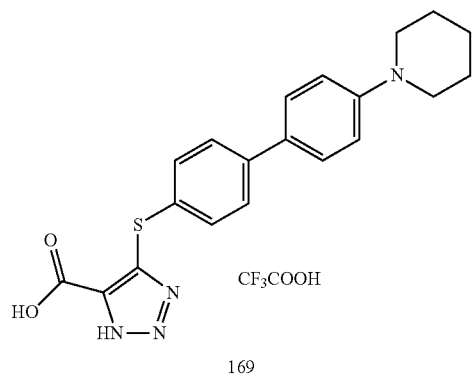

169

Compounds 169B, 169C, 169D, and 169 were synthesized by employing the procedures described for Compounds 27C, 4B, 1, and 8F using Compounds 169A, 169B, Intermediate F with $K_3CO_3$ as base and 1,4-dioxane/$H_2O$ as solvent, 169C, and 169D in lieu of Compounds 27B, (4-bromophenyl)boronic acid, 4A with $Na_2CO_3$ as base and toluene/EtOH/$H_2O$ as solvent, 1E, and 8E. Compound 169B: LC-MS (ESI) m/z: Non-ionizable compound under routine conditions used; $^1$H-NMR (CDCl$_3$, 400 MHz): δ (ppm) 1.33 (s, 12H), 1.61-1.63 (m, 2H), 1.66-1.72 (m, 4H), 3.24-3.28 (m, 4H), 6.90 (d, J=8.4 Hz, 2H), 7.70 (d, J=8.4 Hz, 2H). Compound 169C: LC-MS (ESI) m/z: 529 [M+H]$^+$; $^1$H-NMR (CDCl$_3$, 400 MHz): δ (ppm) 1.33 (t, J=7.2 Hz, 3H), 1.60-1.65 (m, 2H), 1.70-1.74 (m, 4H), 3.21-3.24 (m, 4H), 3.72 (s, 3H), 4.38 (q, J=7.2 Hz, 2H), 5.56 (s, 2H), 6.76 (d, J=8.8 Hz, 2H), 6.98 (d, J=8.8 Hz, 2H), 7.06 (d, J=8.4 Hz, 2H), 7.15 (d, J=8.8 Hz, 2H), 7.37-7.44 (m, 4H). Compound 169D: LC-MS (ESI) m/z: 409 [M+H]$^+$. Compound 169: LC-MS (ESI) m/z: 381 [M+H]$^+$; $^1$H-NMR (CD$_3$OD, 400 MHz): δ (ppm) 1.81-1.84 (m, 2H), 2.02-2.08 (m, 4H), 2.64-2.68 (m, 4H), 7.60 (d, J=8.4 Hz, 2H), 7.68-7.71 (m, 4H), 7.87 (d, J=8.4 Hz, 2H).

Example 170

Synthesis of 4-((3'-(cyclopropylmethoxy)-[1,1'-biphenyl]-4-yl)thio)-1H-1,2,3-triazole-5-carboxylic acid 2,2,2-trifluoroacetate (170)

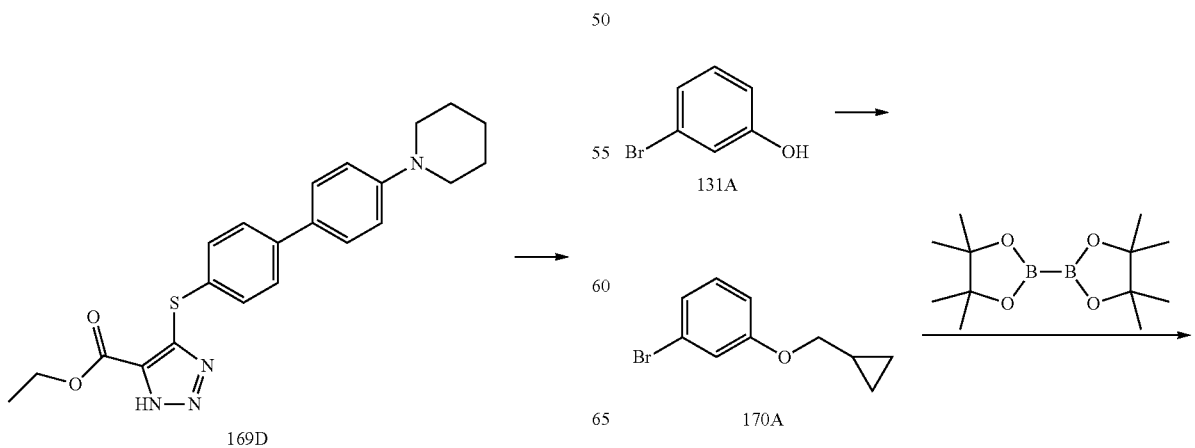

131A

170A

Example 171

Synthesis of 4-(((6-chloronaphthalen-2-yl)thio)methyl)-1H-1,2,3-triazole-5-carboxylic acid 2,2,2-trifluoroacetate (171)

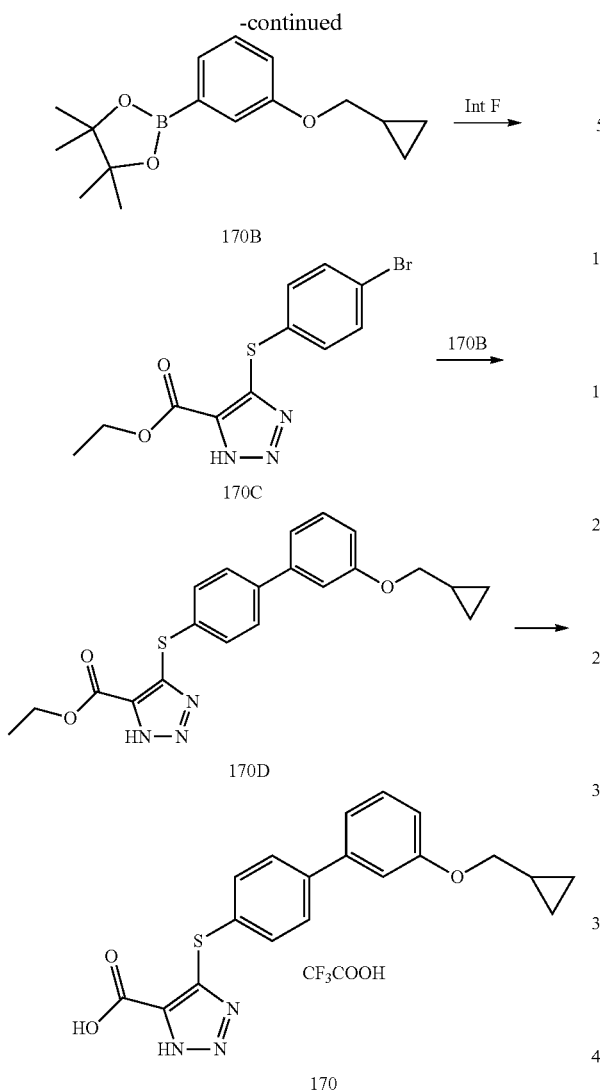

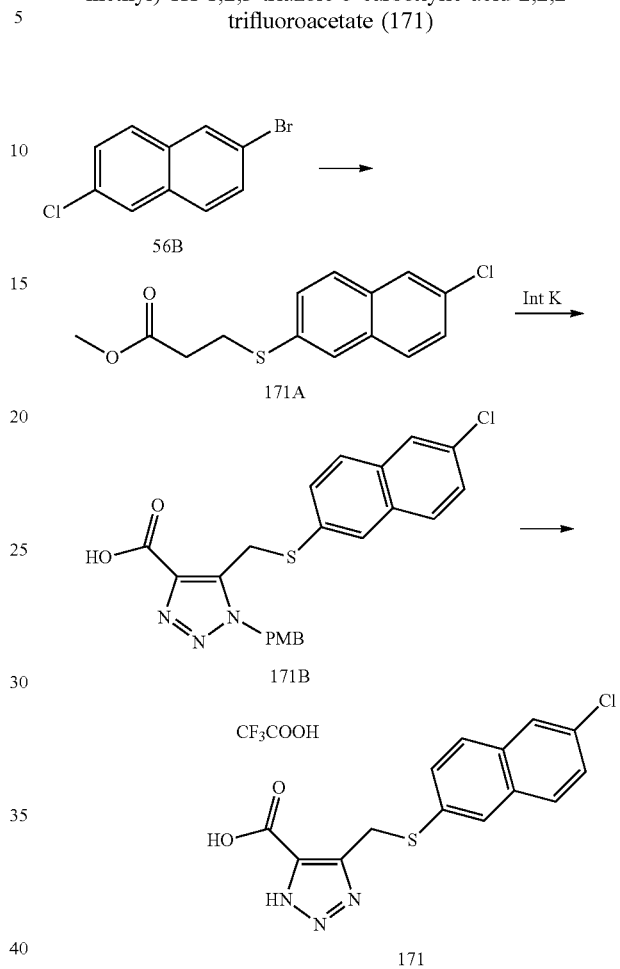

Compounds 170A, 170B, 170C, 170D, and 170 were synthesized by employing the procedures described for Compounds 29B, 27C, 1, 4B, and 8F using (bromomethyl)cyclopropane, Compounds 131A, 170A, Intermediate F, 170B, 170C with $K_3CO_3$ as base and 1,4-dioxane/$H_2O$ as solvent, and 170D in lieu of iodoethane, Compounds 29A, 27B, 1E, (4-bromophenyl)boronic acid, 4A with $Na_2CO_3$ as base and toluene/EtOH/$H_2O$ as solvent, and 8E. Compound 170A: LC-MS (ESI) m/z: Non-ionizable compound under routine conditions used. Compound 170B: LC-MS (ESI) m/z: 275 [M+H]$^+$; $^1$H-NMR (CDCl$_3$, 400 MHz): δ (ppm) 0.33-0.37 (m, 2H), 0.61-0.65 (m, 2H), 1.26-1.30 (m, 1H), 1.36 (s, 12H), 3.85 (d, J=6.8 Hz, 2H), 7.02-7.05 (m, 1H), 7.29-7.33 (m, 2H), 7.40 (d, J=7.6 Hz, 1H). Compound 170C: LC-MS (ESI) m/z: 328 [M+H]$^+$. Compound 170D: LC-MS (ESI) m/z: 396 [M+H]$^+$. Compound 170: LC-MS (ESI) m/z: 368 [M+H]$^+$; $^1$H-NMR (CD$_3$OD, 400 MHz): δ (ppm) 0.35-0.40 (m, 2H), 0.61-0.66 (m, 2H), 1.28-1.31 (m, 1H), 3.89 (d, J=6.4 Hz, 2H), 6.92 (dd, J=8.0 Hz, 2.0 Hz, 1H), 7.15 (t, J=2.0 Hz, 1H), 7.19 (d, J=8.0 Hz, 1H), 7.35 (t, J=8.0 Hz, 1H), 7.56 (d, J=8.4 Hz, 2H), 7.64 (d, J=8.4 Hz, 2H).

Compound 171A was synthesized by employing the procedure described for Intermediate D-1 using Compounds 56B in lieu of Intermediate A, LC-MS (ESI) m/z: non-ionizable compound under routine conditions used. $^1$H-NMR (CDCl$_3$, 400 MHz): δ (ppm) 2.69 (t, J=7.2 Hz, 2H), 3.28 (t, J=7.2 Hz, 2H), 3.69 (s, 3H), 7.41-7.48 (m, 2H), 7.69 (dd, J=8.8 Hz, 2.4 Hz, 2H), 7.77 (d, J=10.4 Hz, 2H).

To a solution of Compound 171A (70 mg, 0.25 mmol) in dry THF (10 mL) at −78° C. and under nitrogen was added potassium tert-butoxide (56 mg, 0.5 mmol) and stirred at −78° C. for 30 minutes, and then stirred at room temperature for 1 hour. A solution of Intermediate K (88 mg, 0.25 mmol) in dry THF (2 mL) was added. The resulting mixture was stirred at room temperature overnight and concentrated under vacuum. The residue was diluted with water (50 mL) and extracted with ethyl acetate (50 mL×3). The combined organic layers was washed with water (100 mL) and brine (100 mL), dried over anhydrous sodium sulfate, concentrated, and purified with flash column chromatography on silica gel (methanol in CH$_2$Cl$_2$, 20% v/v) to afford Compound 171B. LC-MS (ESI) m/z: 440 [M+H]$^+$.

Compound 171 was synthesized by employing the procedure described for Compound 1 using Compound 171B in lieu of Compound 1E, LC-MS (ESI) m/z: 320 [M+H]$^+$;

¹H-NMR (DMSO-d₆, 400 MHz): δ (ppm) 4.60 (s, 2H), 7.50-7.54 (m, 2H), 7.33 (dd, J=8.8, 3.2 Hz, 2H), 7.94 (s, 1H), 8.01 (d, J=2.0 Hz, 1H).

Example 172

Synthesis of 4-((6,7-difluoro-1,2,3,4-tetrahydronaphthalen-2-yl)thio)-1H-1,2,3-triazole-5-carboxylic acid (172)

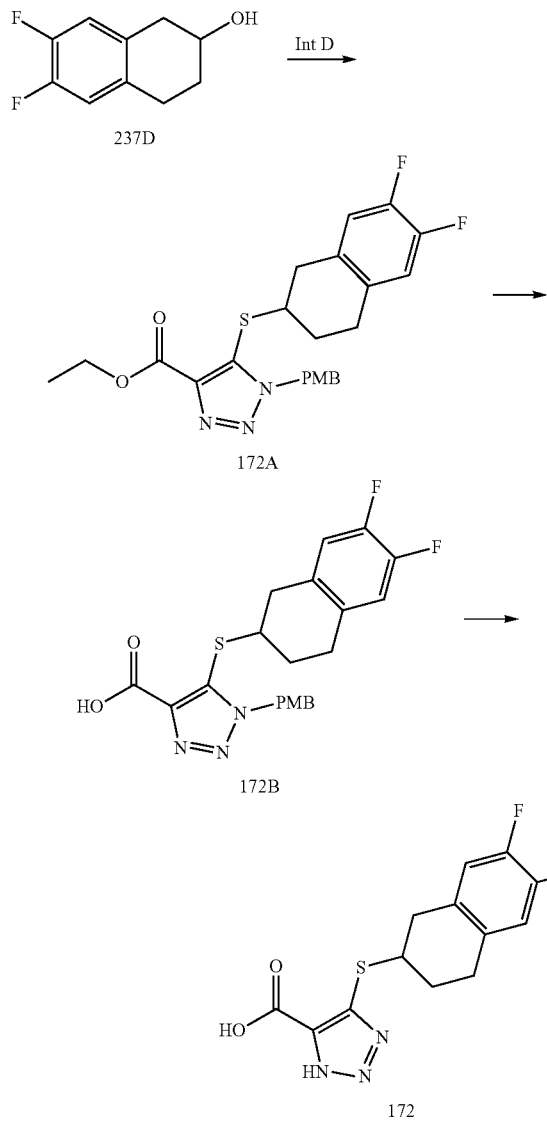

Compounds 172A, 172B, and 172 were synthesized by employing the procedures described for Compounds 90C, 8F, and 1 using Intermediate D, Compounds 237D with DEAD, 172A, and 172B in lieu of Intermediate H, Compounds 90B with DIAD, 8E, and 1E. Compound 172A: LC-MS (ESI) m/z: 460 [M+H]⁺; ¹H-NMR (CDCl₃, 400 MHz): δ (ppm) 1.25 (t, J=7.6 Hz, 3H), 1.70-1.75 (m, 1H), 1.94-1.98 (m, 1H), 2.47-2.54 (m, 1H), 2.65-2.69 (m, 1H), 2.75-2.80 (m, 2H), 3.75 (s, 3H), 3.79-3.84 (m, 1H), 4.44 (q, J=7.2 Hz, 2H), 5.5 (d, J=14.8 Hz, 2H), 6.66 (q, J=2.8, 8 Hz, 1H), 6.81-6.86 (m, 3H), 7.20 (d, J=8.8 Hz, 2H). Compound 172B: LC-MS (ESI) m/z: 432 [M+H]⁺. Compound 172: LC-MS (ESI) m/z: 312 [M+H]⁺; ¹H-NMR (DMSO-d₆, 400 MHz): δ (ppm) 1.84-1.89 (m, 1H), 2.16-2.19 (m, 1H), 2.82-2.85 (m, 3H), 3.21-3.22 (m, 1H), 3.97-3.99 (m, 1H), 7.14-7.19 (m, 2H), 13.24 (s, 1H), 15.60 (s, 1H).

Example 173

Synthesis of 4-((5,6-difluoro-2,3-dihydro-1H-inden-2-yl)thio)-1H-1,2,3-triazole-5-carboxylic acid (173)

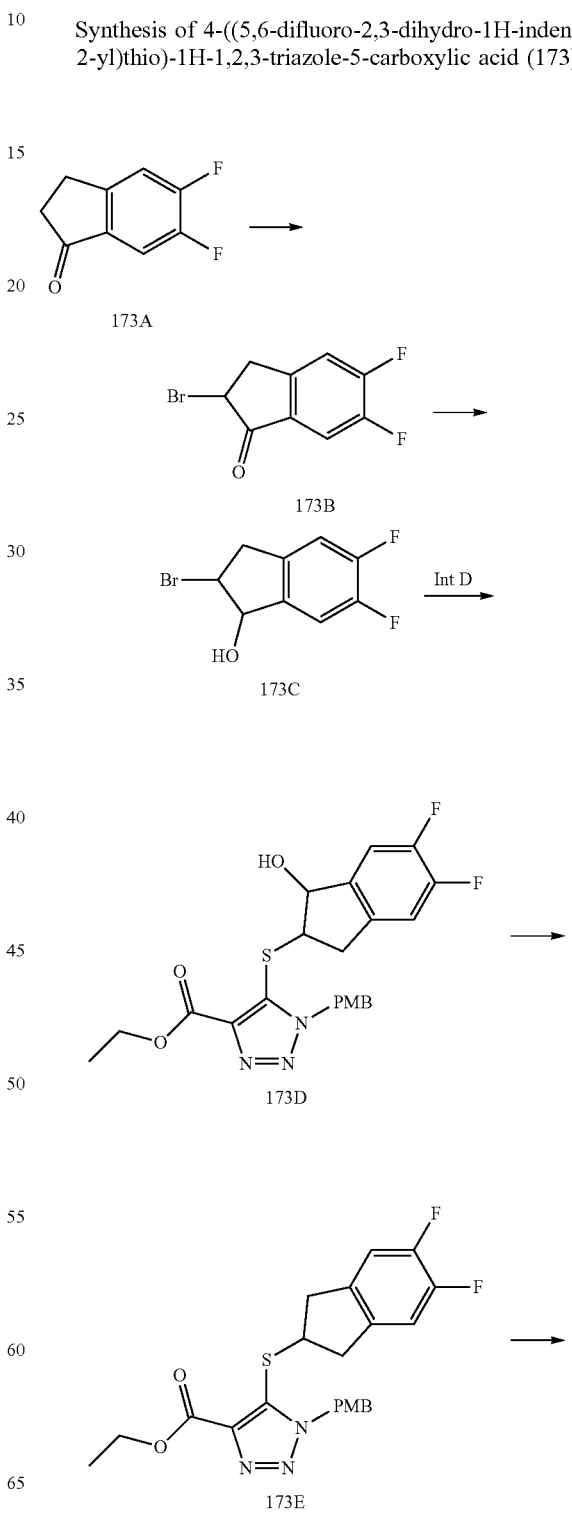

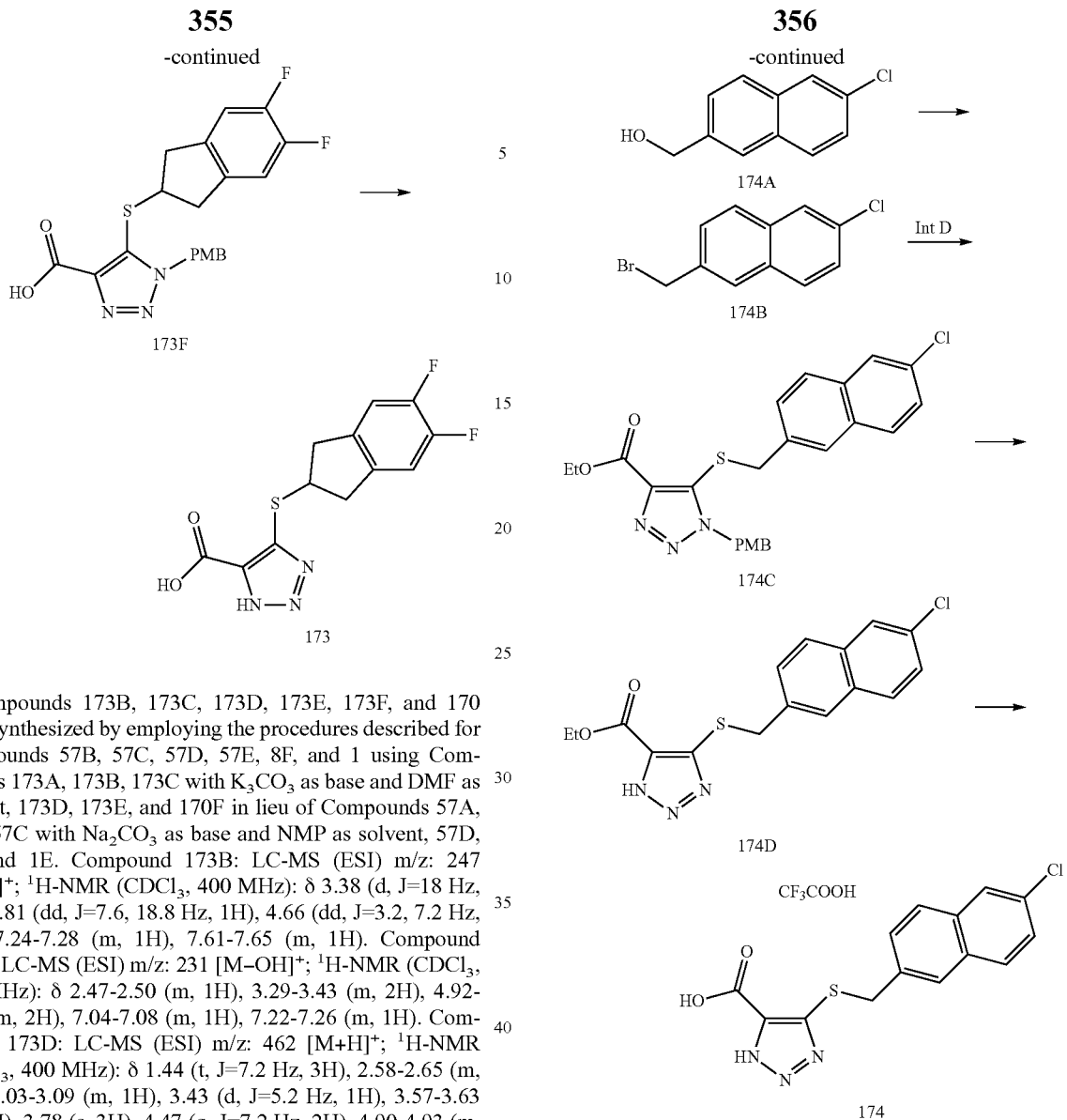

Compounds 173B, 173C, 173D, 173E, 173F, and 170 were synthesized by employing the procedures described for Compounds 57B, 57C, 57D, 57E, 8F, and 1 using Compounds 173A, 173B, 173C with $K_3CO_3$ as base and DMF as solvent, 173D, 173E, and 170F in lieu of Compounds 57A, 57B, 57C with $Na_2CO_3$ as base and NMP as solvent, 57D, 8E, and 1E. Compound 173B: LC-MS (ESI) m/z: 247 [M+H]$^+$; $^1$H-NMR (CDCl$_3$, 400 MHz): δ 3.38 (d, J=18 Hz, 1H), 3.81 (dd, J=7.6, 18.8 Hz, 1H), 4.66 (dd, J=3.2, 7.2 Hz, 1H), 7.24-7.28 (m, 1H), 7.61-7.65 (m, 1H). Compound 173C: LC-MS (ESI) m/z: 231 [M−OH]$^+$; $^1$H-NMR (CDCl$_3$, 400 MHz): δ 2.47-2.50 (m, 1H), 3.29-3.43 (m, 2H), 4.92-4.93 (m, 2H), 7.04-7.08 (m, 1H), 7.22-7.26 (m, 1H). Compound 173D: LC-MS (ESI) m/z: 462 [M+H]$^+$; $^1$H-NMR (CDCl$_3$, 400 MHz): δ 1.44 (t, J=7.2 Hz, 3H), 2.58-2.65 (m, 1H), 3.03-3.09 (m, 1H), 3.43 (d, J=5.2 Hz, 1H), 3.57-3.63 (m, 1H), 3.78 (s, 3H), 4.47 (q, J=7.2 Hz, 2H), 4.90-4.93 (m, 1H), 5.64 (s, 2H), 6.84-6.91 (m, 3H), 7.08-7.12 (m, 1H), 7.23-7.25 (m, 2H). Compound 173E: LC-MS (ESI) m/z: 446 [M+H]$^+$. Compound 173F: LC-MS (ESI) m/z: 418 [M+H]$^+$. Compound 173: LC-MS (ESI) m/z: 298 [M+H]$^+$; $^1$H-NMR (DMSO-d$_6$, 400 MHz): δ (ppm) 2.89-2.94 (m, 2H), 3.45-3.51 (m, 2H), 4.41-4.44 (m, 1H), 7.29-7.34 (m, 2H).

Example 174

Synthesis of 4-(((6-chloronaphthalen-2-yl)methyl) thio)-1H-1,2,3-triazole-5-carboxylic acid 2,2,2-trifluoroacetate (174)

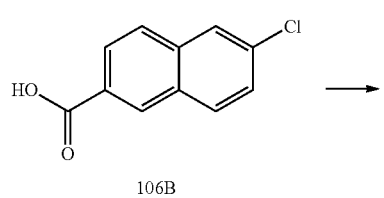

To a solution of 6-chloro-2-naphthoic acid (106B) (1.00 g, 10.00 mmol) in THF (20 mL) was added LiAlH$_4$ (295 mg, 2.77 mmol) in several portions. The mixture was stirred at room temperature for 16 hours, quenched with water (0.3 mL), NaOH solution (15% in water, 0.3 mL), and water (0.9 mL), and filtered through Celite. The filtrate was concentrated under reduced pressure and purified with flash column chromatography on silica gel (ethyl acetate in petroleum ether, from 0% to 40% v/v) to afford Compound 174A. LC-MS (ESI) m/z: 175 [M−OH]$^+$; $^1$H-NMR (DMSO-d$_6$, 400 MHz): δ (ppm) 4.66 (d, J=6.0 Hz, 2H), 5.35 (t, J=6.0 Hz, 1H), 7.48-7.53 (m, 2H), 7.86-7.89 (m, 2H), 7.94 (d, J=8.4 Hz, 1H), 8.01 (d, J=2.4 Hz, 1H).

To a solution of Compound 174A (190 mg, 0.99 mmol) and PPh$_3$ (337 mg, 1.29 mmol) in dichloromethane (5 mL) was added NBS (230 mg, 1.29 mmol). The mixture was stirred at room temperature under nitrogen for 16 hours and concentrated under reduced pressure. The residue was purified with flash column chromatography on silica gel (tetrahydrofuran in petroleum ether, from 0% to 20% v/v) to give Compound 174B. LC-MS (ESI) m/z: non-ionizable compound under routine conditions used; $^1$H-NMR CDCl$_3$, 400

MHz): δ (ppm) 4.64 (s, 2H), 7.43 (d, J=8.8 Hz, 1H), 7.53 (d, J=8.4 Hz, 1H), 7.75 (d, J=8.4 Hz, 2H), 7.81 (s, 2H).

Compounds 174C, 174D, and 174 were synthesized by employing the procedures described for Compounds 57D, 1, and 8F using Compounds 174B with $K_3CO_3$ as base and DMF as solvent, 174C, and 174D in lieu of Compounds 57C with $Na_2CO_3$ as base and NMP as solvent, 1E, and 8E. Compound 174C: LC-MS (ESI) m/z: 468 [M+H]$^+$; $^1$H-NMR (DMSO-d$_6$, 400 MHz): δ (ppm) 1.31 (t, J=7.2 Hz, 3H), 3.68 (s, 3H), 4.27-4.32 (m, 2H), 4.34 (s, 2H), 5.33 (s, 2H), 6.72 (d, J=8.8 Hz, 2H), 6.93 (d, J=8.8 Hz, 2H), 7.38 (d, J=8.4 Hz, 1H), 7.49-7.52 (m, 2H), 7.82 (d, J=8.8 Hz, 2H), 8.01 (s, 1H). Compound 174D: LC-MS (ESI) m/z: 348 [M+H]$^+$; $^1$H-NMR (CDCl$_3$, 400 MHz): δ (ppm) 1.40 (t, J=7.2 Hz, 3H), 4.39-4.45 (m, 2H), 4.53 (s, 2H), 7.41 (d, J=8.8 Hz, 1H), 7.56 (d, J=8.8 Hz, 1H), 7.70-7.73 (m, 2H), 7.79 (s, 1H), 7.83 (s, 1H). Compound 174: LC-MS (ESI) m/z: 320 [M+H]$^+$; $^1$H-NMR (DMSO-d$_6$, 400 MHz): δ (ppm) 4.52 (s, 2H), 7.51 (d, J=8.4 Hz, 1H), 7.62 (d, J=8.4 Hz, 1H), 7.88 (d, J=8.8 Hz, 1H), 7.91 (d, J=8.8 Hz, 1H), 7.95 (s, 1H), 8.01 (s, 1H).

Example 175

Synthesis of 4-((4-(1-methyl-1,2,3,4-tetrahydroquinolin-6-yl)phenyl)thio)-1H-1,2,3-triazole-5-carboxylic acid 2,2,2-trifluoroacetate (175)

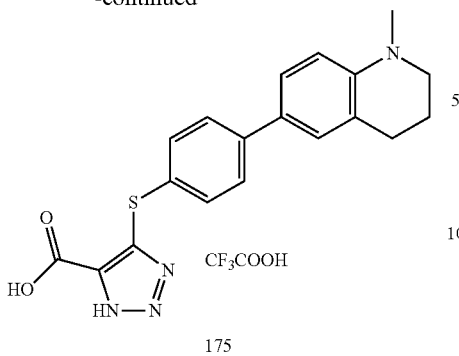

175

To a solution of 6-bromo-1,2,3,4-tetrahydroquinoline (175A) (1.3 g, 6.1 mmol) in toluene (20 mL) was added Boc$_2$O (1.6 g, 7.4 mmol). The reaction mixture was stirred at 110° C. overnight and concentrated under reduced pressure. The residue was purified by column chromatography on silica gel (ethyl acetate in petroleum ether, 20% v/v) to furnish Compound 175B. LC-MS (ESI) m/z: 255 [M−56]$^+$.

Compounds 175C and 175D were synthesized by employing the procedures described for Compounds 27C and 4B using Compounds 175B, Intermediate F, and 175C with K$_3$PO$_4$ as base and 1,4-dioxane as solvent in lieu of Compounds 27B and 4A, (4-bromophenyl)boronic acid with Na$_2$CO$_3$ as base and toluene/EtOH/H$_2$O as solvent. Compound 175C: LC-MS (ESI) m/z: 382 [M+Na]$^+$. Compound 175D: LC-MS (ESI) m/z: 601 [M+H]$^+$; NMR (CDCl$_3$, 400 MHz): δ (ppm) 1.33 (t, J=7.2 Hz, 3H), 1.55 (s, 9H), 1.93-2.00 (m, 2H), 2.80-2.85 (m, 2H), 3.72-3.77 (m, 5H), 4.35-4.40 (m, 2H), 5.55 (d, J=4.0 Hz, 2H), 6.76 (d, J=14.4 Hz, 2H), 7.04-7.17 (m, 4H), 7.23 (d, J=5.6 Hz, 1H), 7.28-7.31 (m, 1H), 7.37-7.40 (m, 2H), 7.74-7.78 (m, 1H).

A mixture of Compound 175D (560 mg, 0.93 mmol) and TFA (1 mL) in dichloromethane (4 mL) was stirred at 20° C. for 3 hours. The mixture was concentrated and purified by column chromatography on silica gel (ethyl acetate in petroleum ether, 30% v/v) to give Compound 175E. LC-MS (ESI) m/z: 501 [M+H]$^+$.

To a mixture of Compound 175E (300 mg, 0.6 mmol) and (CH$_2$O)n (180 mg, 6 mmol) in dichloromethane (10 mL) was added TFA (0.43 mL, 3 mmol) and TES (0.74 mL, 10 mmol) and stirred at room temperature under nitrogen overnight. The mixture was concentrated under reduced pressure. The residue was purified by column chromatography on silica gel (ethyl acetate in petroleum ether, 20% to 30% v/v) to furnish Compound 175F. LC-MS (ESI) m/z: 515 [M+H]$^+$; $^1$H-NMR (CDCl$_3$, 400 MHz): δ (ppm) 1.32 (t, J=7.2 Hz, 3H), 2.12-2.18 (m, 2H), 2.93 (t, J=6.4 Hz, 2H), 3.11 (s, 3H), 3.46 (t, J=5.6 Hz, 2H), 3.72 (s, 3H), 4.34-4.39 (m, 2H), 5.57 (s, 2H), 6.75 (d, J=8.4 Hz, 2H), 7.05 (d, J=8.0 Hz, 2H), 7.14-7.27 (m, 4H), 7.33-7.37 (m, 3H).

Compounds 175G and 175 were synthesized by employing the procedures described for Compounds 8F and 1 using Compounds 175F and 175G in lieu of Compounds 8E and 1E. Compound 175G: LC-MS (ESI) m/z: 487 [M+H]$^+$. Compound 175: LC-MS (ESI) m/z: 367 [M+H]$^+$; $^1$H-NMR (DMSO-d$_6$, 400 MHz): δ (ppm) 1.90 (t, J=6.4 Hz, 2H), 2.76 (t, J=6.4 Hz, 2H), 2.87 (s, 3H), 3.23 (t, J=5.6 Hz, 2H), 6.65 (d, J=8.8 Hz, 1H), 7.26 (s, 1H), 7.34 (dd, J$_1$=1.6 Hz, J$_2$=8.4 Hz, 1H), 7.46 (d, J=8.0 Hz, 2H), 7.58 (d, J=8.8 Hz, 2H).

Example 176

Synthesis of 4-((3,4-dichlorobenzyl)thio)-1H-1,2,3-triazole-5-carboxylic acid (176)

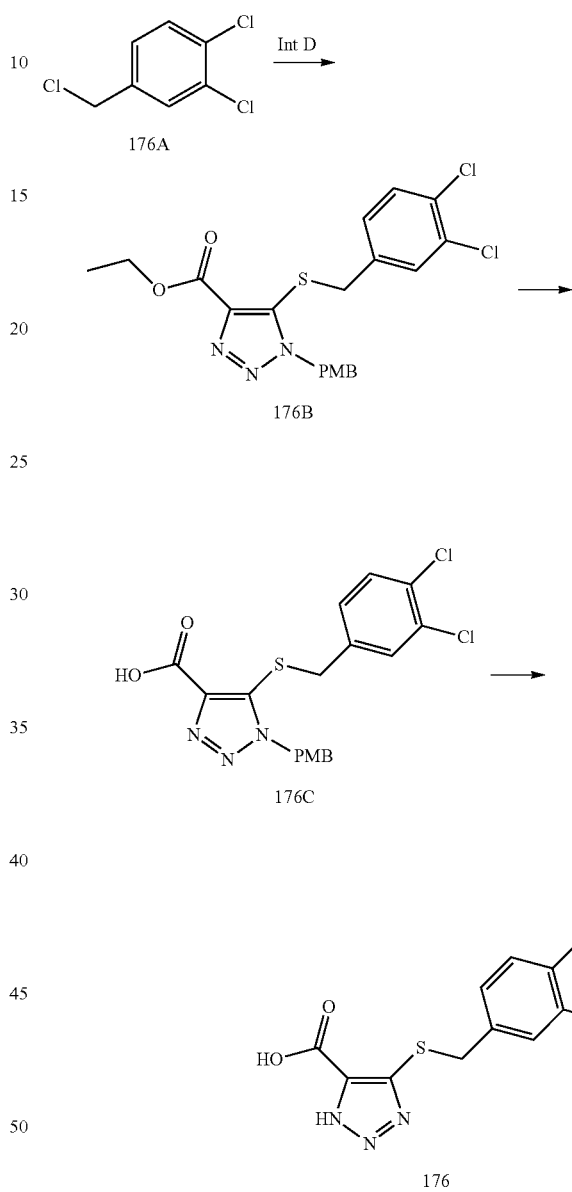

Compounds 176B, 176C, and 176 were synthesized by employing the procedures described for Compounds 57D, 8F, and 57E using Compounds 176A with K$_2$CO$_3$ as base and DMF as solvent, 176B, and 176C in lieu of Compounds 57C with Na$_2$CO$_3$ as base and NMP as solvent, 8E, and 57D. Compound 176B: LC-MS (ESI) m/z: 452 [M+H]$^+$; $^1$H-NMR (CDCl$_3$, 400 MHz): δ (ppm) 1.47 (t, J=6.8 Hz, 3H), 3.80 (s, 3H), 4.03 (s, 2H), 4.48 (q, J=7.2 Hz, 2H), 5.39 (s, 2H), 6.82-6.85 (m, 3H), 7.13-7.27 (m, 4H). Compound 176C: LC-MS (ESI) m/z: 424 [M+H]$^+$. Compound 176: LC-MS (ESI) m/z: 304 [M+H]$^+$; $^1$H-NMR (DMSO-d$_6$, 400 MHz): δ (ppm) 4.34 (s, 2H), 7.39 (dd, J=8.4, 1.6 Hz, 1H), 7.55 (d, J=8.4 Hz, 1H), 7.68 (d, J=2.0 Hz, 1H).

Example 177

Synthesis of 4-4(4'-(trifluoromethoxy)-[1,1'-biphenyl]-4-yl)methyl)thio)-1H-1,2,3-triazole-5-carboxylic acid (177)

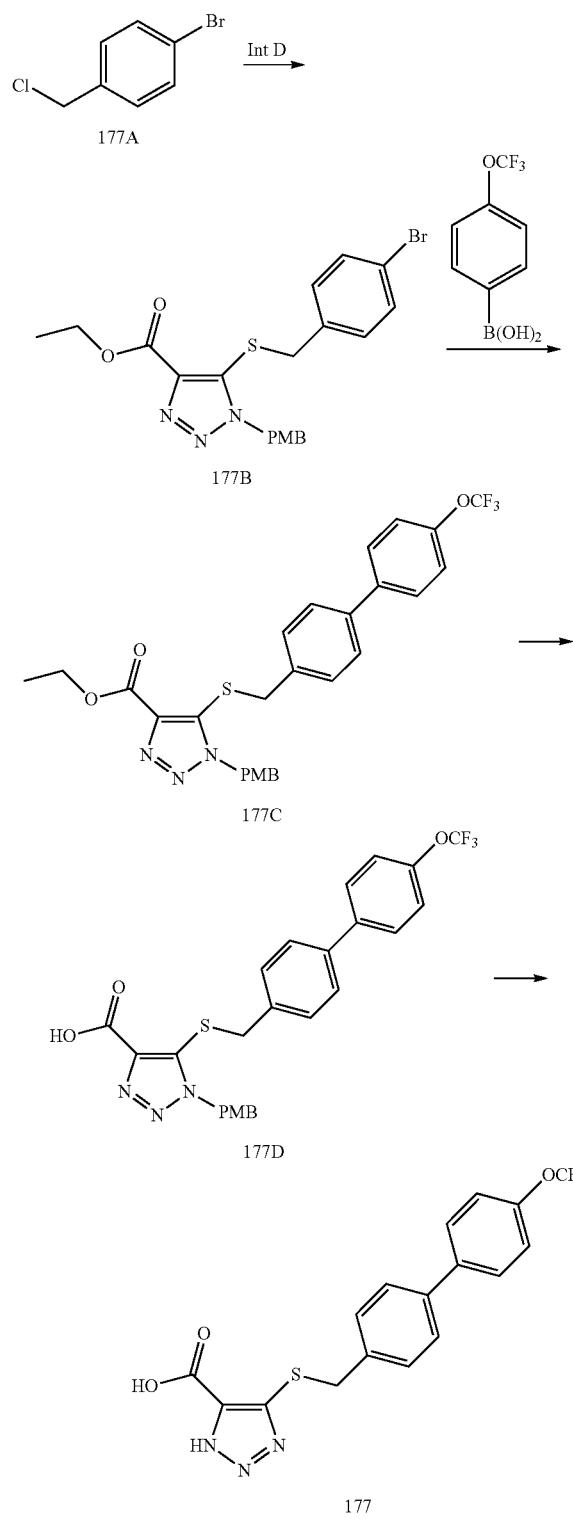

Compounds 177B, 177C, 177D, and 177 were synthesized by employing the procedures described for Compounds 57D, 4B, 8F, and 57E using Compounds 177A with $K_2CO_3$ as base and DMF as solvent, 177B with $K_2CO_3$ as base and 1,4-dioxane/$H_2O$ as solvent, 177C, and 177D in lieu of Compounds 57C with $Na_2CO_3$ as base and NMP as solvent, 4A with $Na_2CO_3$ as base and toluene/EtOH/$H_2O$ as solvent, 8E and 57D. Compound 177B: LC-MS (ESI) m/z: 462 [M+H]$^+$; $^1$H-NMR (CDCl$_3$, 400 MHz): δ (ppm) 1.46 (t, J=6.8 Hz, 3H), 3.79 (s, 3H), 4.05 (s, 2H), 4.47 (q, J=6.8 Hz, 2H), 5.30 (s, 2H), 6.81-6.83 (m, 2H), 6.89-6.92 (m, 2H), 7.11 (d, J=8.8 Hz, 2H), 7.34 (d, J=6.8 Hz, 2H). Compound 177C: LC-MS (ESI) m/z: 544 [M+H]$^+$. Compound 177D: LC-MS (ESI) m/z: 516 [M+H]$^+$. Compound 177: LC-MS (ESI) m/z: 396 [M+H]$^+$; $^1$H-NMR (DMSO-d$_6$, 400 MHz): δ (ppm) 4.38 (s, 2H), 7.42 (dd, J=8.4 Hz, 2H), 7.49 (d, J=8.4 Hz, 2H), 7.61 (d, J=7.6 Hz, 2H), 7.76 (d, J=8.4 Hz, 2H),

Example 178

Synthesis of 4-(((6-chloronaphthalen-2-yl)amino)methyl)-1H-1,2,3-triazole-5-carboxylic acid 2,2,2-trifluoroacetate (178)

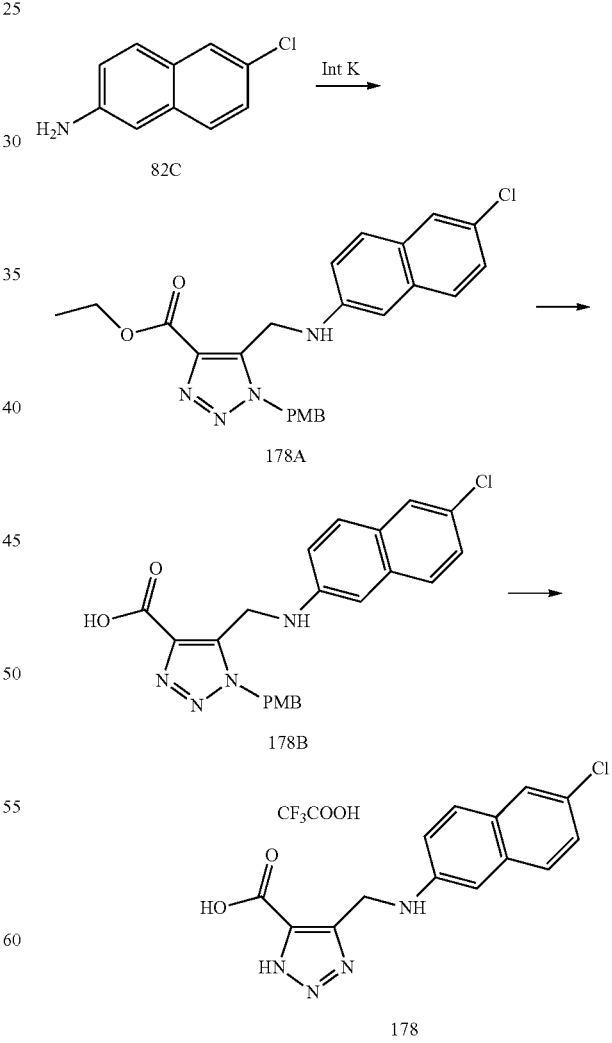

To a mixture of Intermediate K (950 mg, 2.69 mmol) in anhydrous DMF (30 mL) was added $K_2CO_3$ (557 mg, 4.04 mmol) and Compound 82C (476 mg, 2.69 mmol). The mixture was stirred at room temperature under nitrogen overnight, diluted with water (50 mL), and extracted with ethyl acetate (50 mL×3). The combined organic layers was washed with water (100 mL) and brine (100 mL), dried over anhydrous sodium sulfate, concentrated, and purified with flash column chromatography on silica gel (ethyl acetate in petroleum ether, 40% v/v) to furnish Compound 178A. LC-MS (ESI) m/z: 451 [M+H]$^+$; $^1$H-NMR (CDCl$_3$, 400 MHz): δ (ppm) 1.44 (t, J=7.2 Hz, 3H), 3.80 (s, 3H), 4.28-4.32 (m, 1H), 4.48 (q, J=7.2 Hz, 2H), 4.64 (d, J=7.2 Hz, 2H), 5.65 (s, 2H), 6.76-6.86 (m, 4H), 7.14 (d, J=8.8 Hz, 2H), 7.31-7.34 (m, 1H), 7.49 (d, J=8.8 Hz, 1H), 7.54 (d, J=8.8 Hz, 1H), 7.67 (s, 1H).

Compounds 178B and 178 were synthesized by employing the procedures described for Compounds 8F and 1 using Compounds 178A and 178B in lieu of Compounds 8E and 1E. Compound 178B: LC-MS (ESI) m/z: 423 [M+H]$^+$. Compound 178: LC-MS (ESI) m/z: 303 [M+H]$^+$; $^1$H-NMR (DMSO-d$_6$, 400 MHz): δ (ppm) 4.72 (s, 2H), 6.61 (s, 1H), 6.90 (s, 1H), 7.17 (dd, J=8.8, 2.0 Hz, 1H), 7.37 (dd, J=8.8, 2.0 Hz, 1H), 7.65 (d, J=8.8 Hz, 1H), 7.69 (d, J=8.8 Hz, 1H), 7.83 (s, 1H), 13.33 (s, 1H), 15.63 (s, 1H).

Example 179

Synthesis of 4-(((3,4-dichlorophenyl)(methyl)amino)methyl)-1H-1,2,3-triazole-5-carboxylic acid 2,2,2-trifluoroacetate (179)

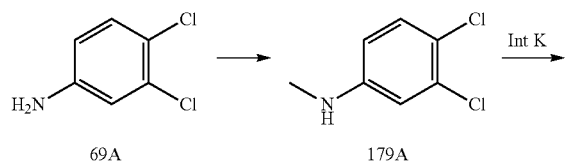

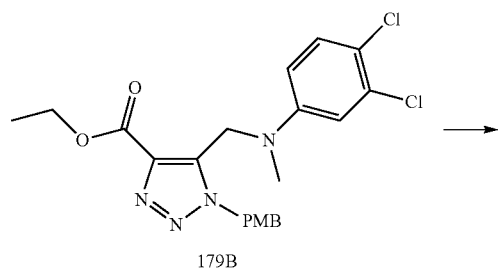

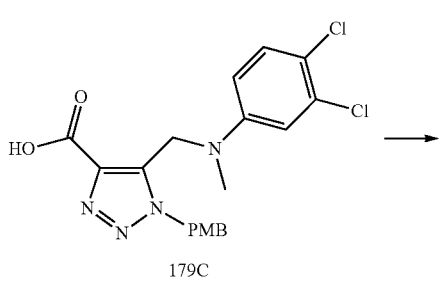

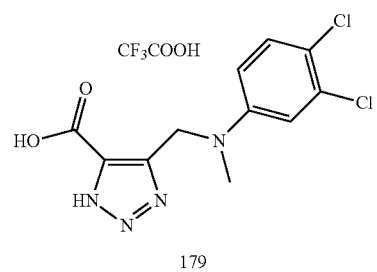

To a solution of 3,4-dichloroaniline (69A) (324 mg, 2.0 mmol) in MeOH (5 mL) was added MeONa (540 mg, 10.0 mmol), paraformaldehyde (120 mg, 4.0 mmol), and Molecular sieves (4 Angstroms, 200 mg). The mixture was stirred at room temperature under nitrogen overnight, and then sodium borohydride (151 mg, 4 mmol) was added. The mixture was heated at reflux for 1 hour, cooled down to room temperature, filtered through Celite, and concentrated under reduced pressure. The residue was diluted with ethyl acetate (50 mL), washed with water (50 mL) and brine (50 mL), dried over anhydrous sodium sulfate, concentrated, and purified with flash column chromatography on silica gel (ethyl acetate in petroleum ether, 20% v/v) to afford Compound 179A. LC-MS (ESI) m/z: 176 [M+H]$^+$; $^1$H-NMR (CDCl$_3$, 400 MHz): δ (ppm) 2.82 (s, 3H), 3.80 (s, 1H), 6.44 (dd, J=8.8, 2.8 Hz, 1H), 6.66 (d, J=2.8 Hz, 1H), 7.19 (d, J=8.8 Hz, 1H).

Compounds 179B, 179C, and 179 were synthesized by employing the procedures described for Compounds 178A, 8F, and 1 using Compounds 179A, 179B, and 179C in lieu of Compounds 82C, 8E and 1E. Compound 179B: LC-MS (ESI) m/z: 449 [M+H]$^+$. Compound 179C: LC-MS (ESI) m/z: 421 [M+H]$^+$. Compound 179: LC-MS (ESI) m/z: 301 [M+H]$^+$; $^1$H-NMR (DMSO-d$_6$, 400 MHz): δ (ppm) 3.05 (s, 3H), 4.86 (s, 2H), 6.74 (s, 1H), 6.96 (s, 1H), 7.32 (d, J=8.8 Hz, 1H), 13.38 (s, 1H), 15.38 (s, 1H).

Example 180

Synthesis of 4-(((6-chloronaphthalen-2-yl)(methyl)amino)methyl)-1H-1,2,3-triazole-5-carboxylic acid 2,2,2-trifluoroacetate (180)

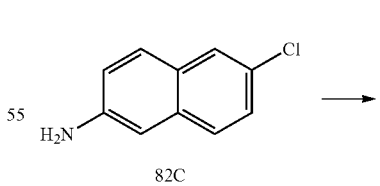

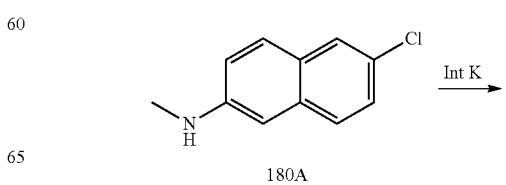

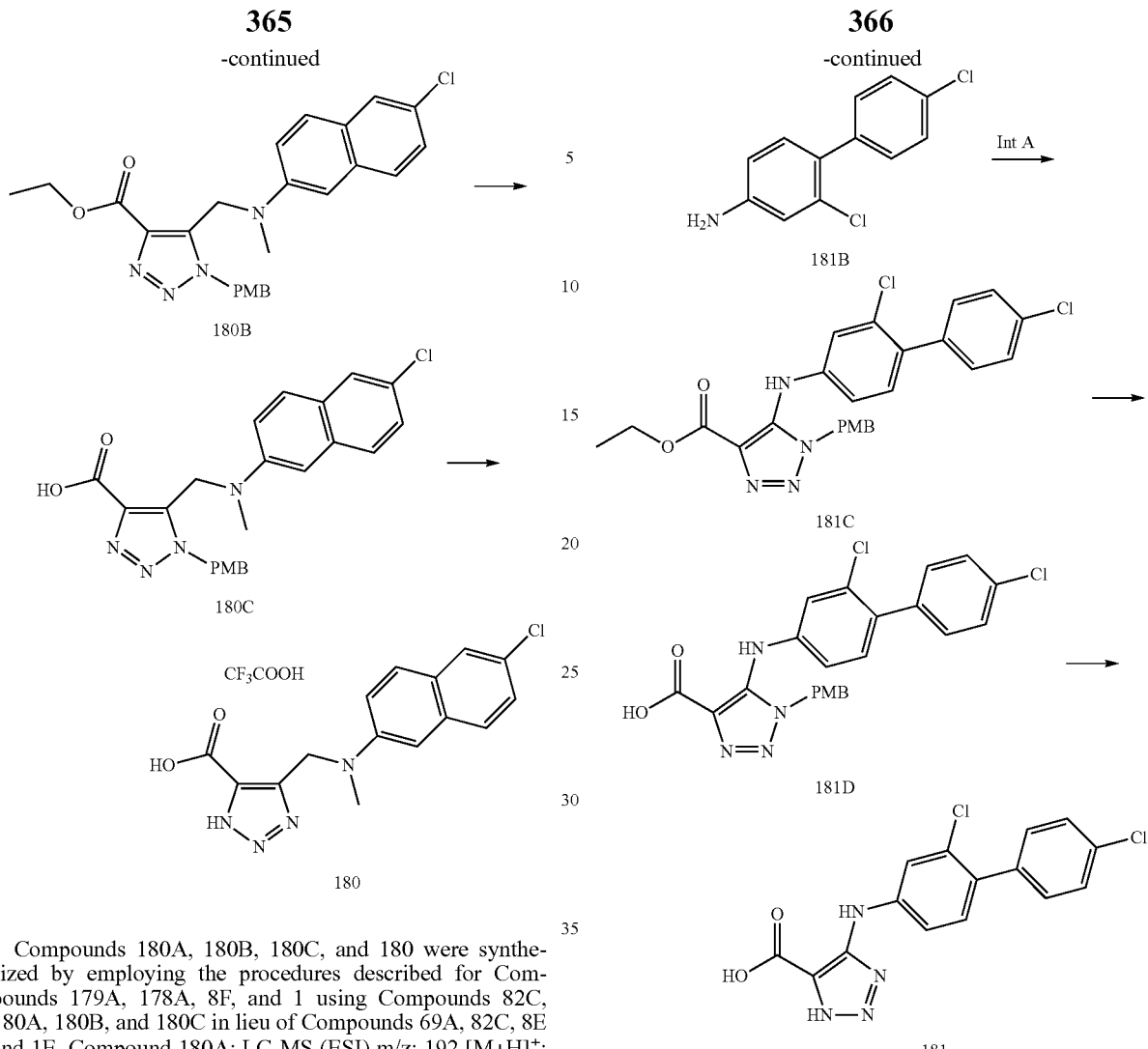

Compounds 180A, 180B, 180C, and 180 were synthesized by employing the procedures described for Compounds 179C, 178A, 8F, and 1 using Compounds 82C, 180A, 180B, and 180C in lieu of Compounds 69A, 82C, 8E and 1E. Compound 180A: LC-MS (ESI) m/z: 192 [M+H]$^+$; $^1$H-NMR (CDCl$_3$, 400 MHz): δ (ppm) 2.94 (s, 3H), 3.95 (s, 1H), 6.76 (d, J=2.0 Hz, 1H), 6.91 (dd, J=8.8, 2.0 Hz, 1H), 7.30 (dd, J=8.8, 2.4 Hz, 1H), 7.56 (dd, J=8.4, 2.0 Hz, 2H), 7.65 (d, J=2.4 Hz, 1H). Compound 180B: LC-MS (ESI) m/z: 465 [M+H]$^+$. Compound 180C: LC-MS (ESI) m/z: 437 [M+H]$^+$. Compound 180: LC-MS (ESI) m/z: 317 [M+H]$^+$; $^1$H-NMR (DMSO-d$_6$, 400 MHz): δ (ppm) 3.14 (s, 3H), 4.97 (s, 2H), 7.03 (d, J=2.0 Hz, 1H), 7.33 (dd, J=8.8, 2.0 Hz, 2H), 7.65-7.72 (m, 2H), 7.80 (s, 1H), 13.39 (s, 1H), 15.29 (s, 1H).

Example 181

Synthesis of 4-((2,4'-dichloro-[1,1'-biphenyl]-4-yl)amino)-1H-1,2,3-triazole-5-carboxylic acid (181)

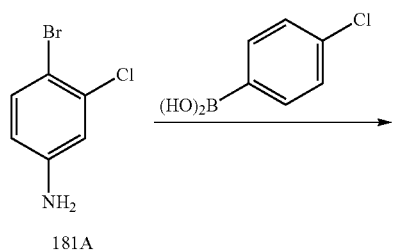

Compounds 181B, 181C, 181D, and 181 were synthesized by employing the procedures described for Compounds 8B, 6B, 8F, and 1 using (4-chlorophenyl)boronic acid, Compounds 181A with Na$_2$CO$_3$ as base and 1,4-dioxane/H$_2$O as solvent, Intermediate A, 181B with K$_3$PO$_4$ as base, 181C, and 181D in lieu of (3,4-dichlorophenyl)boronic acid, Compounds 8A with Cs$_2$CO$_3$ as base and DME/H$_2$O as solvent, 6A, 1-methylpiperazine with t-BuONa as base, 8E and 1E. Compound 181B: LC-MS (ESI) m/z: 238 [M+H]$^+$. Compound 181C: LC-MS (ESI) m/z: 497 [M+H]$^+$; $^1$H-NMR (DMSO-d$_6$, 400 MHz): δ (ppm) 1.05 (t, J=14.4 Hz, 3H), 3.7 (s, 3H), 4.12 (q, J=7.2 Hz, 2H), 5.44 (s, 2H), 6.66-6.63 (m, 1H), 6.70 (d, J=2.4 Hz, 1H), 6.86 (t, J=8.8 Hz, 2H), 7.14 (d, J=8.8 Hz, 2H), 7.20 (d, J=8.4 Hz, 1H), 7.39 (q, J=1.6 Hz, 2H), 7.49 (q, J=2 Hz, 2H), 8.8 (s, 1H). Compound 181D: LC-MS (ESI) m/z: 469 [M+H]$^+$. Compound 181: LC-MS (ESI) m/z: 349 [M+H]$^+$; $^1$H-NMR (DMSO-d$_6$, 400 MHz): δ (ppm) 7.33 (d, J=8.4 Hz, 1H), 7.5 (q, J=8.4 Hz, 4H), 7.63 (q, J=1.6 Hz, 1H), 7.94 (s, 1H), 8.46 (s, 1H), 13.44 (s, 1H), 15.01 (s, 1H).

Example 182

Synthesis of 4-(((6-chloronaphthalen-2-yl)methyl)amino)-1H-1,2,3-triazole-5-carboxylic acid (182)

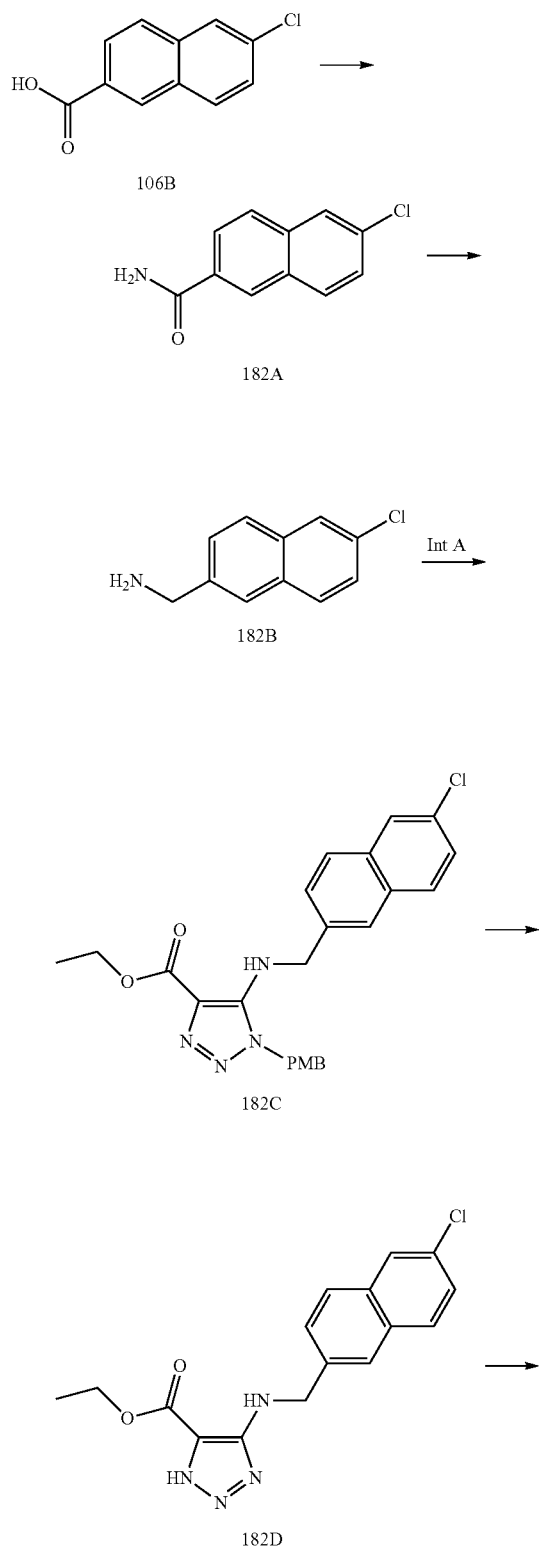

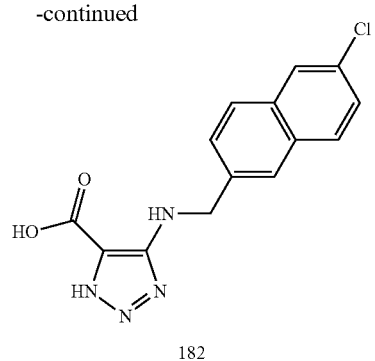

Compound 182A was synthesized by employing the procedure described for Compound 106C using NH$_4$Cl with DMF as solvent in lieu of N,O-dimethylhydroxylamine hydrochloride with dichloromethane as solvent, LC-MS (ESI) m/z: 206 [M+H]$^+$.

To a solution of Compound 182A (2.00 g, 9.75 mmol) in THF (10 mL) at room temperature was dropped a solution of BH$_3$ in THF (1M, 49 mL, 48.78 mmol) and stirred at 65° C. for 16 hours. After cooled down to room temperature, the mixture was quenched with water (10 mL) and methanol (10 mL), concentrated under reduced pressure. The residue was purified with reverse phase chromatography using eluent (acetonitrile in water, from 0% to 100% v/v) to afford Compound 182B. LC-MS (ESI) m/z: 175 [M–NH$_2$]$^+$; $^1$H-NMR (CDCl$_3$, 400 MHz): δ (ppm) 4.03 (s, 2H), 7.41 (d, J=8.8 Hz, 1H), 6.46 (d, J=8.8 Hz, 1H), 7.72-7.81 (m, 4H).

Compounds 182C, 182D, and 182 were synthesized by employing the procedures described for Compounds 6B, 1, and 8F using Intermediate A, Compounds 182B with K$_3$PO$_4$ as base and DMF as solvent, 182C, and 182D in lieu of Compounds 6A, 1-methylpiperazine with t-BuONa as base and toluene as solvent, 1E and 8E. Compound 182C: LC-MS (ESI) m/z: 451 [M+H]$^+$; $^1$H-NMR (DMSO-d$_6$, 400 MHz): δ (ppm) 1.23 (t, J=7.2 Hz, 3H), 3.72 (s, 3H), 4.20-4.26 (m, 2H), 4.75 (d, J=6.8 Hz, 2H), 5.43 (s, 2H), 6.86 (d, J=8.8 Hz, 2H), 7.07 (d, J=8.4 Hz, 2H), 7.32 (d, J=8.4 Hz, 1H), 7.48 (d, J=8.8 Hz, 1H), 7.54 (s, 1H), 7.76-7.79 (m, 2H), 7.98 (s, 1H). Compound 182D: LC-MS (ESI) m/z: 331 [M+H]$^+$; $^1$H-NMR (CDCl$_3$, 400 MHz): δ (ppm) 1.35 (t, J=7.2 Hz, 3H), 4.39-4.44 (m, 2H), 4.68 (s, 2H), 7.42 (d, J=8.4 Hz, 1H), 7.49 (d, J=8.8 Hz, 1H), 7.72-7.80 (m, 4H). Compound 182: LC-MS (ESI) m/z: 303 [M+H]$^+$; $^1$H-NMR (CD$_3$OD, 400 MHz): δ (ppm) 4.65 (s, 2H), 7.41 (d, J=8.8 Hz, 1H), 7.56 (d, J=8.8 Hz, 1H), 7.77-7.85 (m, 4H).

Example 183

Synthesis of 4-((4'-(trifluoromethyl)-[1,1'-biphenyl]-4-yl)amino)-1H-1,2,3-triazole-5-carboxylic acid (183)

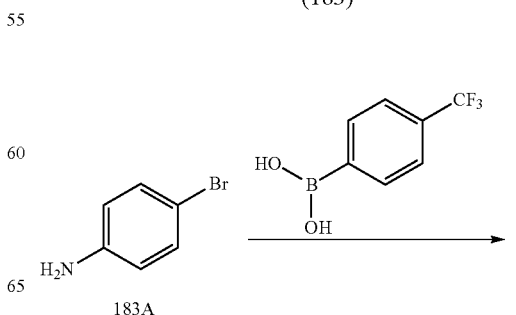

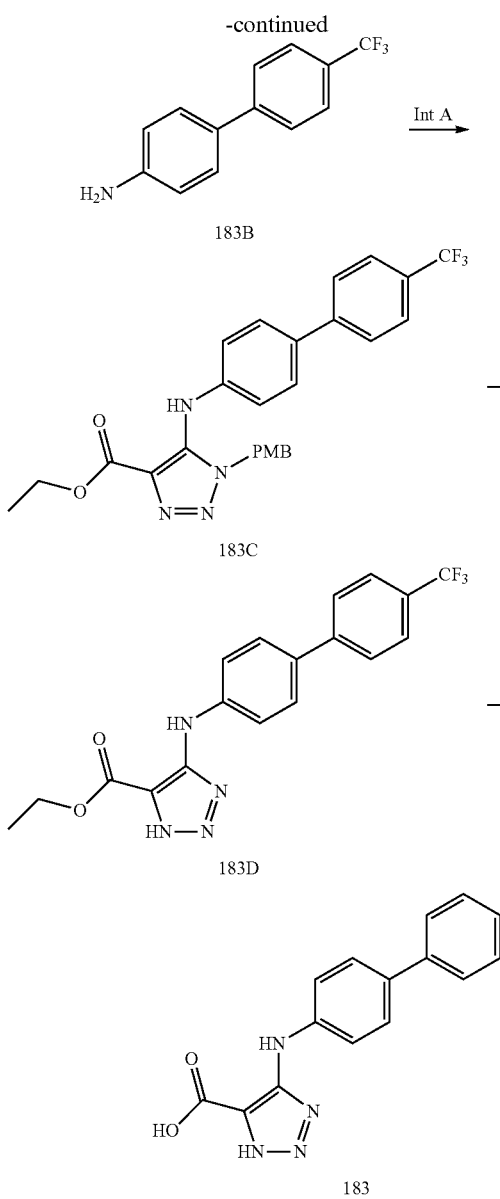

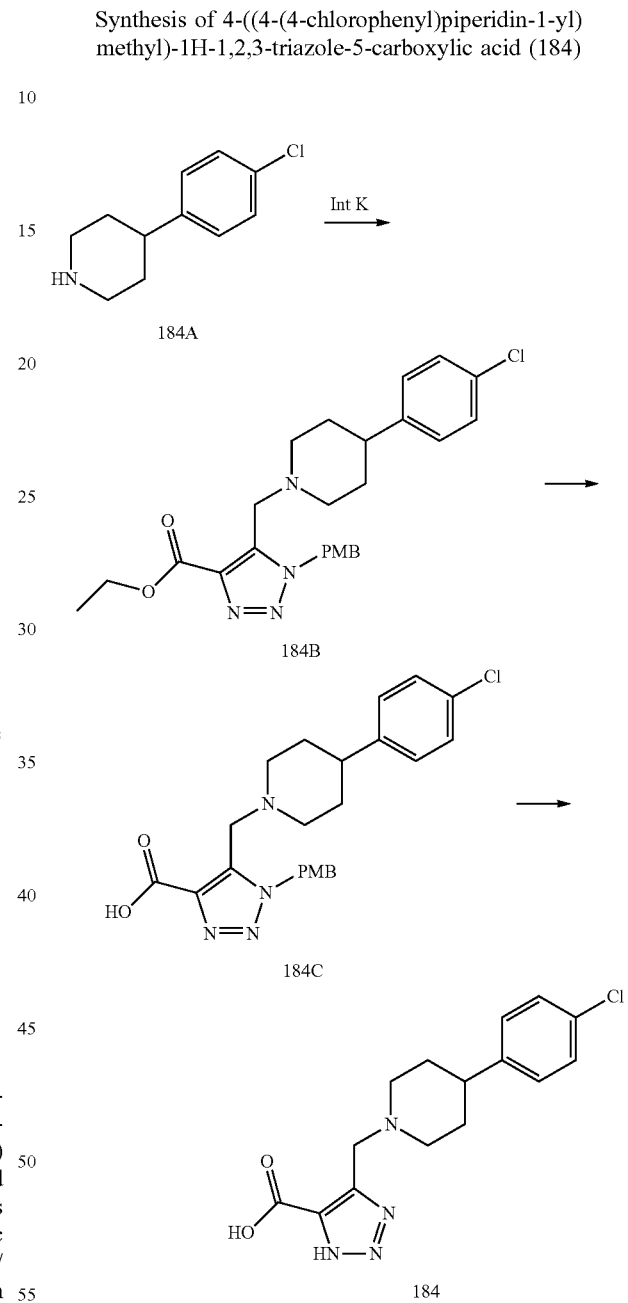

Compounds 183B, 183C, 183D, and 183 were synthesized by employing the procedures described for Compounds 4B, 6B, 1, and 8F using (4-(trifluoromethyl)phenyl) boronic acid, Compounds 183A with K$_2$CO$_3$ as base and DMF/H$_2$O as solvent, Intermediate A, 183B with K$_3$PO$_4$ as base, 183C, and 183D in lieu of (4-bromophenyl)boronic acid, Compounds 4A with Na$_2$CO$_3$ as base and toluene/EtOH/H$_2$O as solvent, 6A, 1-methylpiperazine with t-BuONa as base, 1E and 8E. Compound 183B: LC-MS: (ESI) m/z: 238 [M+H]$^+$; $^1$H-NMR (CDCl$_3$, 400 MHz): δ (ppm) 6.77-6.79 (m, 2H), 7.43-7.45 (m, 2H), 7.64 (s, 4H). Compound 183C: LC-MS (ESI) m/z: 497 [M+H]$^+$; $^1$H-NMR (CDCl$_3$, 400 MHz): δ (ppm) 1.42 (t, J=7.2 Hz, 3H), 3.76 (s, 3H), 4.42 (q, J=7.2 Hz, 2H), 5.24 (s, 2H), 6.74 (J=8.7 Hz, 2H), 6.86 (J=8.7 Hz, 2H), 6.92 (J=8.4 Hz, 2H), 7.18 (s, 1H), 7.55 (J=8.4 Hz, 2H), 7.67-7.73 (m, 4H). Compound 183D: LC-MS (ESI) m/z: 377 [M+H]$^+$; $^1$H-NMR (DMSO-d$_6$, 400 MHz): δ (ppm) 1.34 (t, J=7.2 Hz, 3H), 4.35 (q, J=7.2 Hz, 2H), 7.68-7.73 (m, 4H), 7.76 (d, J=8.4 Hz, 2H), 7.86 (d, J=8.2 Hz, 2H), 8.30 (s, 1H). Compound 183: LC-MS (ESI) m/z: 349 [M+H]$^+$; $^1$H-NMR (DMSO-d$_6$, 400 MHz): δ (ppm) 7.62-7.68 (m, 4H), 7.73 (d, J=8.4 Hz, 2H), 7.85 (d, J=8.2 Hz, 2H).

Example 184

Synthesis of 4-((4-(4-chlorophenyl)piperidin-1-yl)methyl)-1H-1,2,3-triazole-5-carboxylic acid (184)

Compounds 184B, 184C, and 184 were synthesized by employing the procedures described for Compounds 178A, 8F, and 1 using Compounds 184A, 184B, and 184C in lieu of Compounds 82C, 8E and 1E. Compound 184B: LC-MS (ESI) m/z: 469 [M+H]$^+$. Compound 184C: LC-MS (ESI) m/z: 441 [M+H]$^+$. Compound 184: LC-MS (ESI) m/z: 321 [M+H]$^+$; $^1$H-NMR (DMSO-d$_6$, 400 MHz): δ (ppm) 1.55-1.70 (m, 4H), 2.13-2.19 (m, 2H), 2.46-2.49 (m, 1H), 2.99-3.02 (m, 2H), 3.86 (s, 2H), 7.23-7.25 (m, 2H), 7.31-7.33 (m, 2H).

Example 185

Synthesis of 4-(((3,4-dichlorophenyl)(ethyl)amino) methyl)-1H-1,2,3-triazole-5-carboxylic acid (185)

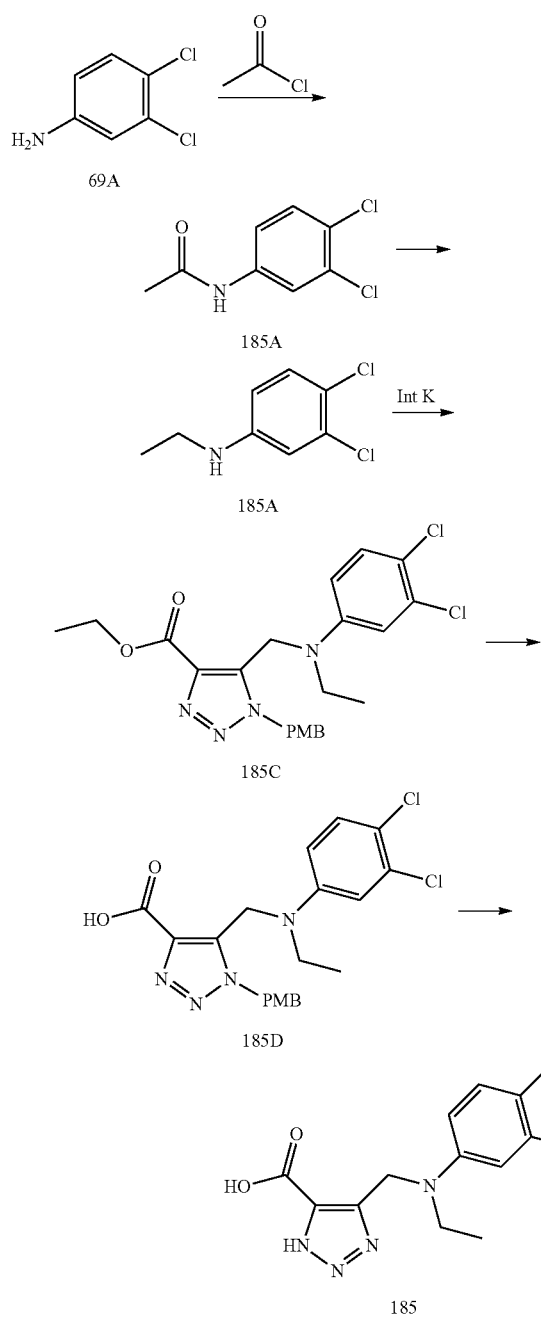

To a solution of 3,4-dichloroaniline (69A) (1.62 g, 10.0 mmol) in acetone (100 mL) was added $K_2CO_3$ (4.14 g, 30.0 mmol) and acetyl chloride (1.18 g, 15.0 mmol). The mixture was stirred at room temperature overnight and filtered. The filtrate was concentrated under reduced pressure. The residue was diluted with water (50 mL) and extracted with ethyl acetate (50 mL×3). The combined organic layers was washed with water (100 mL) and brine (100 mL), dried over anhydrous sodium sulfate, concentrated, and purified with flash column chromatography on silica gel (ethyl acetate in petroleum ether, 10% v/v) to afford Compound 185A. LC-MS (ESI) m/z: 204 [M+H]$^+$; $^1$H-NMR (CDCl$_3$, 400 MHz): δ (ppm) 2.20 (s, 3H), 7.33 (dd, J=8.8, 2.4 Hz, 1H), 7.37 (d, J=8.8 Hz, 1H), 7.76 (d, J=2.4 Hz, 1H).

To a solution of Compound 185A (612 mg, 3.0 mmol) in anhydrous THF (30 mL) was added LiAlH$_4$ (456 mg, 12 mmol) and stirred at 30° C. for 3 hours. The reaction mixture was quenched with Na$_2$SO$_4$.10H$_2$O and stirred at room temperature for 30 minutes. The resulting suspension was filtered through Celite and the cake was washed with ethyl acetate (50 mL×3). The combined filtrates was washed with brine (100 mL), dried over anhydrous sodium sulfate, concentrated, and purified with flash column chromatography on silica gel (ethyl acetate in petroleum ether, 40% v/v) to furnish Compound 185B. LC-MS (ESI) m/z: 190 [M+H]$^+$; $^1$H-NMR (CDCl$_3$, 400 MHz): δ (ppm) 1.26 (t, J=7.2 Hz, 3H), 3.12 (q, J=7.2 Hz, 2H), 3.64 (s, 1H), 6.43 (dd, J=8.8, 1.8 Hz, 1H), 6.66 (d, J=1.8 Hz, 1H), 7.18 (d, J=8.8 Hz, 1H).

Compounds 185C, 185D, and 185 were synthesized by employing the procedures described for Compounds 178A, 8F, and 1 using Compounds 185B, 185C, and 185D in lieu of Compounds 82C, 8E and 1E. Compound 185C: LC-MS (ESI) m/z: 463 [M+H]$^+$. Compound 185D: LC-MS (ESI) m/z: 435 [M+H]$^+$. Compound 185: LC-MS (ESI) m/z: 315 [M+H]$^+$; $^1$H-NMR (DMSO-d$_6$, 400 MHz): δ (ppm) 1.09 (t, J=7.2 Hz, 3H), 3.49 (q, J=7.2 Hz, 2H), 4.79 (s, 2H), 6.67 (d, J=8.0 Hz, 1H), 6.91 (d, J=2.8 Hz, 1H), 7.32 (d, J=8.0 Hz, 1H).

Example 186

Synthesis of 4-((7-chloroquinolin-3-yl)amino)-1H-1,2,3-triazole-5-carboxylic acid (186)

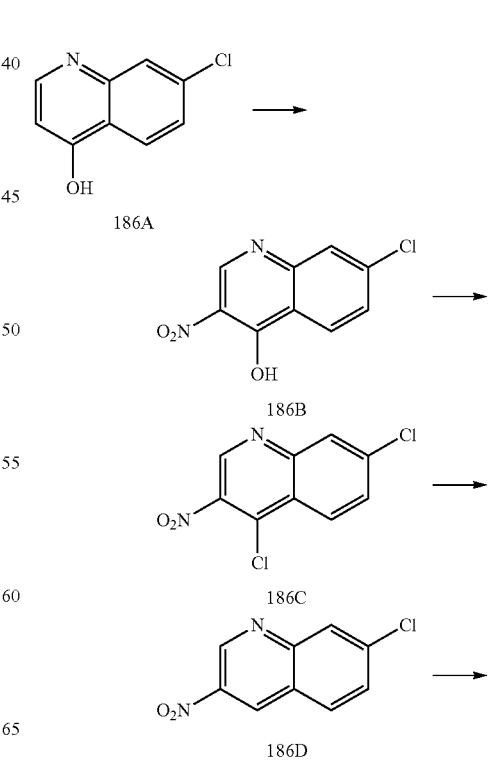

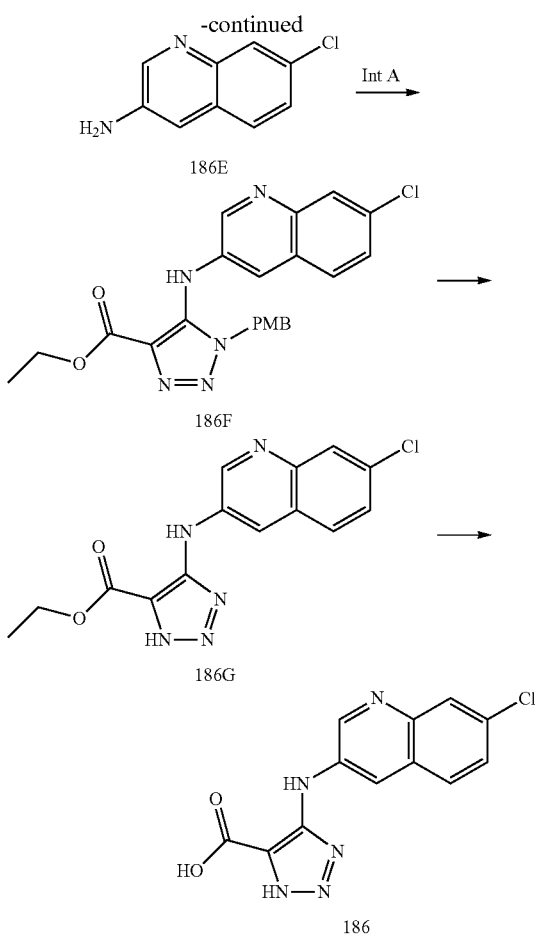

To a stirred solution of 7-chloroquinolin-4-ol (186A) (5 g, 27.9 mmol) in HOAc (100 mL) was added HNO₃ (63%, 5.41 g, 55.8 mmol) and stirred at 125° C. overnight. After cooled down to room temperature, the mixture was concentrated under reduced pressure, the residue was diluted with EtOH (20 mL), the resulting solid was collected and dried under vacuum to afford Compound 186B. LC-MS: (ESI) m/z: 225 [M+H]⁺; ¹H-NMR (DMSO-d₆, 400 MHz): δ (ppm) 7.53 (dd, J=8.8, 2.0 Hz, 1H), 7.74 (d, J=2.0 Hz, 1H), 8.22 (d, J=8.8 Hz, 1H), 9.23 (s, 1H), 12.99 (s, 1H).

A mixture of Compound 186B (5 g, 22.32 mmol) and POCl₃ (50 mL) was stirred at 115° C. overnight. The mixture was evaporated under reduced pressure and the residue was diluted with dichloromethane (50 mL) and washed with brine (30 mL×2). The organic layer wash dried over anhydrous Na₂SO₄, filtered and concentrated to give a crude Compound 186C, which was used directly in next step without further purification. LC-MS (ESI) m/z: 243 [M+H]⁺; ¹H-NMR (CDCl₃, 400 MHz): δ (ppm) 7.78 (dd, J=8.8, 2.0 Hz, 1H), 8.24 (d, J=2.0 Hz, 1H), 8.39 (d, J=8.8 Hz, 1H), 9.29 (s, 1H).

A solution of Compound 186C (4 g, 16.5 mmol) and p-toluenesulfonylhydrazine (6.1 g, 33 mmol) in CHCl₃ (100 mL) was stirred at room temperature for 24 hours. The mixture was filtered. The solid was washed with cold CHCl₃ and dried under vacuum to afford the hydrazino intermediate as solid. The intermediate was mixed with aqueous NaOH solution (0.5 N, 50 mL) and heated at 80° C. for 1 hour. After cooled down to room temperature, the resulting mixture was extracted with dichloromethane (30 mL×3). The combined organic layer was washed with brine (50 mL×2), dried over anhydrous Na₂SO₄, concentrated, and purified with flash column chromatography on silica gel (ethyl acetate in petroleum ether, 10% v/v) to afford Compound 186D. LC-MS (ESI) m/z: 209 [M+H]⁺; ¹H-NMR (CDCl₃, 400 MHz): δ (ppm) 7.71 (dd, J=8.8, 2.0 Hz, 1H), 8.00 (d, J=8.8 Hz, 1H), 8.26 (d, J=2.0 Hz, 1H), 9.04 (d, J=2.4 Hz, 1H), 9.67 (d, J=2.4 Hz, 1H).

To a solution of Compound 186D (200 mg, 0.96 mmol) in MeOH (10 mL) was added SnCl₂·2H₂O (1.25 g, 4.8 mmol) and stirred at 100° C. overnight. The reaction mixture was concentrated under reduced pressure. The residue was purified with flash column chromatography on silica gel (ethyl acetate in petroleum ether, 50% v/v) to leave a crude product, which was further purified with reverse phase chromatography using eluent (acetonitrile in water, from 0% to 20% v/v) afford Compound 186E. LC-MS (ESI) m/z: 179 [M+H]⁺; ¹H-NMR (DMSO-d₆, 400 MHz): δ (ppm) 7.28 (s, 1H), 7.43 (d, J=8.8 Hz, 1H), 7.70-7.73 (m, 1H), 7.82 (s, 1H), 8.50 (s, 1H).

Compounds 186F, 186G, and 186 were synthesized by employing the procedures described for Compounds 6B, 1, and 8F using Intermediate A, Compounds 186E with as Cs₂CO₃ base and DMF as solvent at 150° C. in a microwave reactor, 186F, and 186G in lieu of Compounds 6A, 1-methylpiperazine with as t-BuONa base and toluene as solvent at 120° C., 1E and 8E. Compound 186F: LC-MS (ESI) m/z: 438 [M+H]⁺; ¹H-NMR (DMSO-d₆, 400 MHz): δ (ppm) 0.87 (t, J=7.2 Hz, 3H), 3.60 (s, 3H), 4.01 (q, J=7.2 Hz, 2H), 5.48 (s, 2H), 6.77 (d, J=8.8 Hz, 2H), 7.11 (d, J=8.8 Hz, 2H), 7.15 (d, J=2.6 Hz, 1H), 7.46-7.49 (m, 1H), 7.73 (d, J=8.8 Hz, 1H), 7.91 (d, J=2.0 Hz, 1H), 8.60 (d, J=2.6 Hz, 1H), 9.13 (s, 1H). Compound 186G: LC-MS (ESI) m/z: 318 [M+H]⁺. Compound 186: LC-MS (ESI) m/z: 290 [M+H]⁺; ¹H-NMR (DMSO-d₆, 400 MHz): δ (ppm) 7.50 (d, J=8.8 Hz, 1H), 7.87-7.90 (m, 2H), 8.63 (s, 1H), 8.87 (s, 1H), 9.74 (s, 1H).

Example 187

Synthesis of 4-(((6-chloronaphthalen-2-yl)(ethyl)amino)methyl)-1H-1,2,3-triazole-5-carboxylic acid (187)

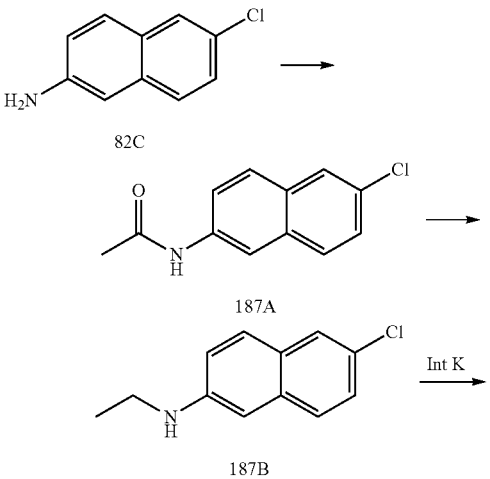

-continued

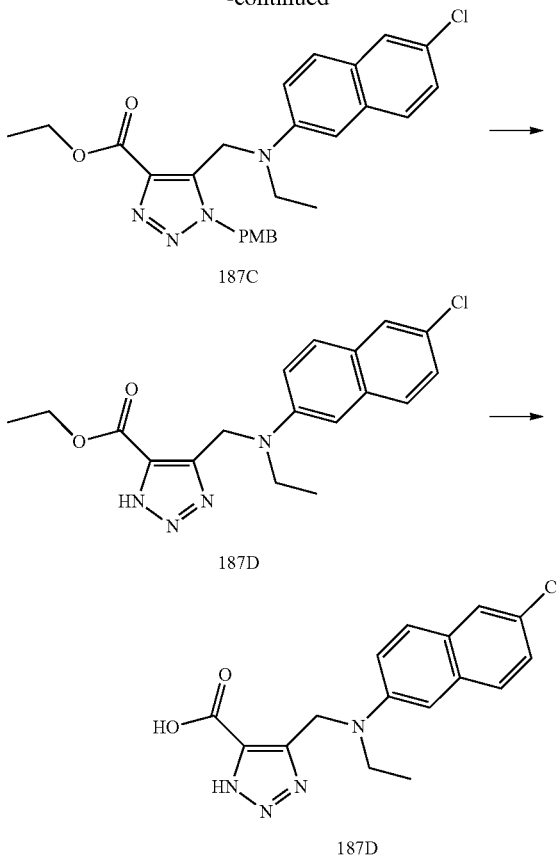

To a solution of 6-chloronaphthalen-2-amine (82C) (1.00 g, 4.69 mmol) and Et₃N (1.18 g, 11.73 mmol) in THF (10 mL) was dropped neat AcCl (439 mg, 5.63 mmol) at room temperature. The mixture was stirred at room temperature for 3 hours, diluted with ethyl acetate (160 mL), washed with water (100 mL) and brine (100 mL), dried over anhydrous sodium sulfate, concentrated, and purified with flash column chromatography on silica gel (tetrahydrofuran in petroleum ether, from 0% to 80% v/v) to afford Compound 187A. MS (ESI) m/z: 220 [M+H]⁺; ¹H-NMR (DMSO-d₆, 400 MHz): δ (ppm) 2.10 (s, 3H), 7.43-7.47 (m, 1H), 7.59-7.62 (m, 1H), 7.83-7.86 (m, 2H), 7.94 (s, 1H), 8.32 (s, 1H), 10.20 (s, 1H).

Compounds 187B, 187C, 187D, and 187 were synthesized by employing the procedures described for Compounds 182B, 178A, 1, and 8F using Compounds 187A, 187B, 187C, and 187D in lieu of Compounds 182A, 82C, 1E, and 8E. Compound 187B: LC-MS (ESI) m/z: 206 [M+H]⁺; ¹H-NMR (DMSO-d₆, 400 MHz): δ (ppm) 1.22 (t, J=7.6 Hz, 3H), 3.08-3.15 (m, 2H), 5.99 (t. J=5.2 Hz, 1H), 6.70 (s, 1H), 7.00 (d, J=8.8 Hz, 1H), 7.26 (d, J=8.8 Hz, 1H), 7.55-7.60 (m, 2H), 7.70 (s, 1H). Compound 187C: LC-MS (ESI) m/z: 479 [M+H]⁺; ¹H-NMR (CDCl₃, 400 MHz): δ (ppm) 0.96 (t, J=7.2 Hz, 3H), 1.46 (t, J=7.2 Hz, 3H), 3.18 (q, J=7.2 Hz, 2H), 3.73 (s, 3H), 4.48 (q, J=7.2 Hz, 2H), 4.73 (s, 2H), 5.53 (s, 2H), 6.68-6.71 (m, 2H), 6.85-6.89 (m, 2H), 7.00 (s, 1H), 7.14-7.18 (m, 1H), 7.33-7.36 (m, 1H), 7.50-7.54 (m, 2H), 7.71 (s, 1H). Compound 187D: LC-MS (ESI) m/z: 359 [M+H]⁺; ¹H-NMR (CDCl₃, 400 MHz): δ (ppm) 1.24 (t, J=7.2 Hz, 3H), 1.36 (t, J=7.2 Hz, 3H), 3.68 (q, J=7.2 Hz, 2H), 4.36 (q, J=7.2 Hz, 2H), 5.13 (s, 2H), 7.28-7.46 (m, 2H), 7.60 (d, J=1.6 Hz, 1H), 7.68-7.77 (m, 3H). Compound 187: LC-MS (ESI) m/z: 331 [M+H]⁺; ¹H-NMR (CD₃OD, 400 MHz): δ (ppm) 1.25 (t, J=7.2 Hz, 3H), 3.69 (q, J=7.2 Hz, 2H), 4.96 (s, 2H), 7.05 (d, J=2.4 Hz, 1H), 7.22 (d, J=8.8 Hz, 1H), 7.28 (d, J=8.8 Hz, 1H), 7.55-7.62 (m, 3H).

Example 188

Synthesis of 4-((6-chloro-3,4-dihydroquinolin-1 (2¹H)-yl)methyl)-1H-1,2,3-triazole-5-carboxylic acid (188)

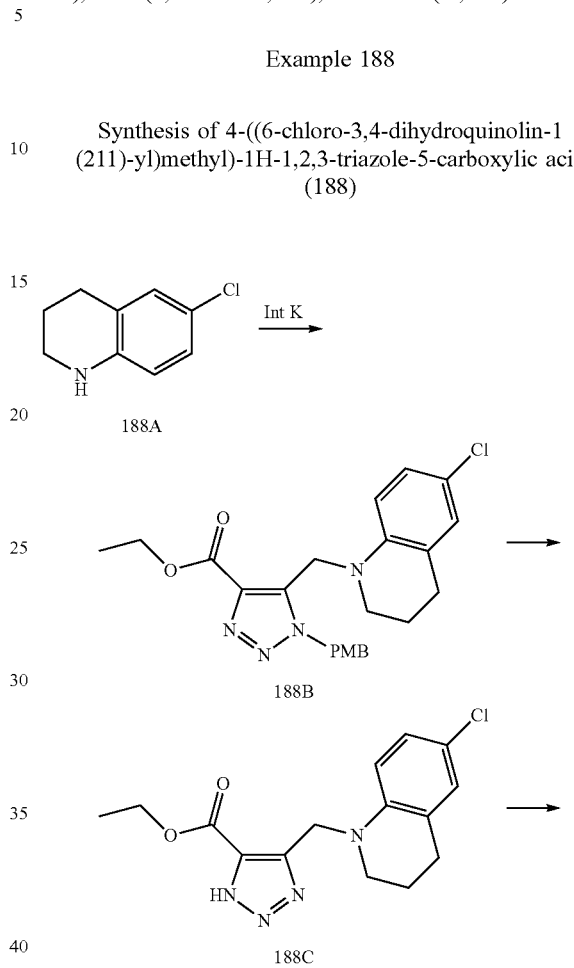

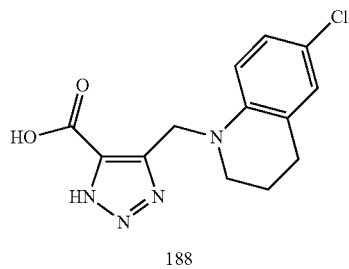

Compounds 188B, 188C, and 188 were synthesized by employing the procedures described for Compounds 178A, 1, and 8F using Compounds 188A, 188B, and 188C in lieu of Compounds 82C, 1E, and 8E. Compound 188B: LC-MS (ESI) m/z: 441 [M+H]⁺. Compound 188C: LC-MS (ESI) m/z: 321 [M+H]⁺. Compound 188: LC-MS (ESI) m/z: 293 [M+H]⁺; ¹H-NMR (DMSO-d₆, 400 MHz): δ (ppm) 1.87-1.88 (m, 2H), 2.67-2.68 (m, 2H), 3.34-3.41 (m, 2H), 4.73 (m, 2H), 6.54 (brs, 1H), 6.87-6.91 (m, 2H).

Example 189

Synthesis of 4-((ethyl(4'-(trifluoromethoxy)-[1,1'-biphenyl]-4-yl)amino)methyl)-1H-1,2,3-triazole-5-carboxylic acid 2,2,2-trifluoroacetate (189)

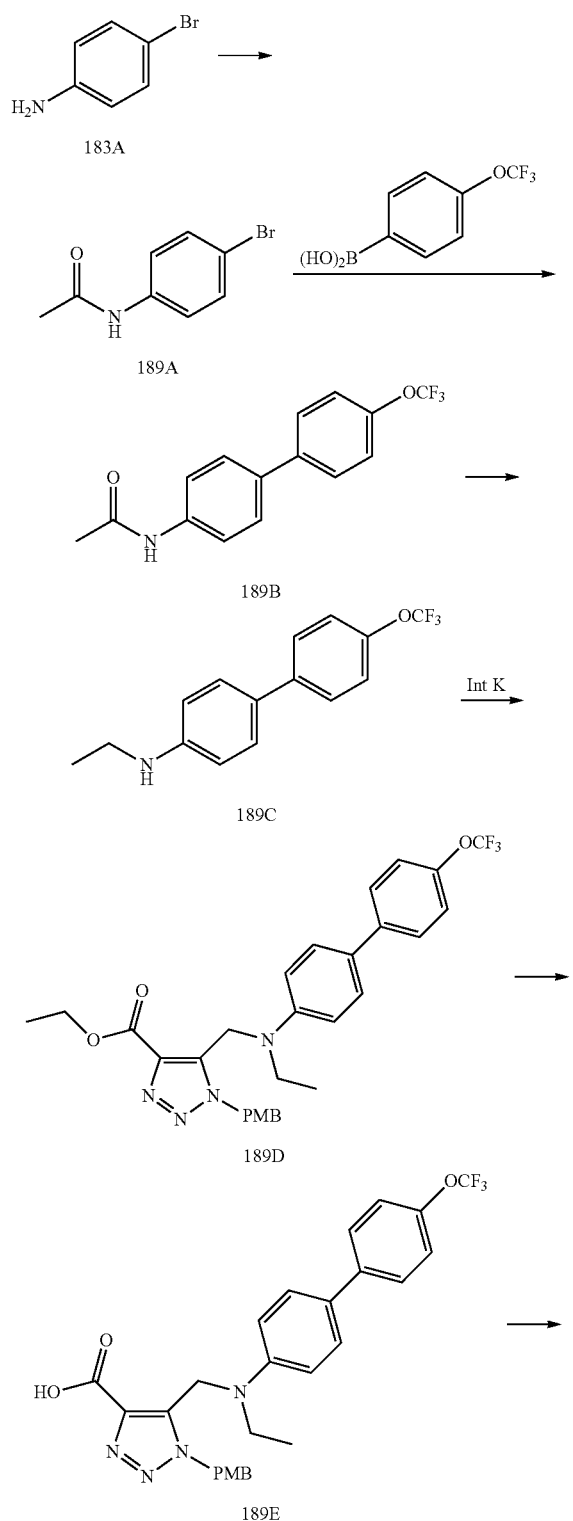

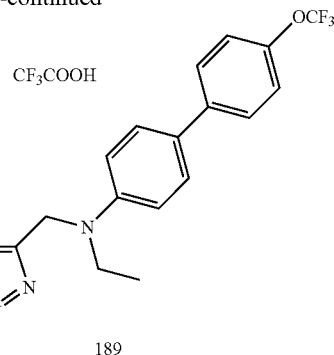

Compounds 189A, 189B, 189C, 189D, 189E, and 189 were synthesized by employing the procedures described for Compounds 185A, 4B, 185B, 178A, 8F, and 1 using Compounds 183A, (4-(trifluoromethoxy)phenyl)boronic acid, 189A with $K_2CO_3$ as base and as 1,4-dioxane/$H_2O$ solvent, 189B, 189C, 189D, and 189E in lieu of Compounds 69A, (4-bromophenyl)boronic acid, 4A with $Na_2CO_3$ as base and as toluene/EtOH/$H_2O$ solvent, 185A, 82C, 8E, and 1E. Compound 189A: LC-MS (ESI) m/z: 214 [M+H]$^+$; $^1$H-NMR (CDCl$_3$, 400 MHz): δ (ppm) 2.18 (s, 3H), 7.24 (s, 1H), 7.39-7.45 (m, 4H). Compound 189B: LC-MS (ESI) m/z: 296 [M+H]$^+$; $^1$H-NMR (CDCl$_3$, 400 MHz): δ (ppm) 2.21 (s, 3H), 7.28 (d, J=8.4 Hz, 2H), 7.37 (s, 1H), 7.52 (d, J=8.1 Hz, 2H), 7.56-7.61 (m, 4H). Compound 189C: LC-MS (ESI) m/z: 282 [M+H]$^+$; $^1$H-NMR (CDCl$_3$, 400 MHz): δ (ppm) 1.30 (t, J=7.2 Hz, 3H), 3.21 (q, J=7.2 Hz, 2H), 3.69 (s, 1H), 6.68 (d, J=8.4 Hz, 2H), 7.24 (d, J=8.0 Hz, 2H), 7.41 (d, J=8.8 Hz, 2H), 7.54 (d, J=8.8 Hz, 2H). Compound 189D: LC-MS (ESI) m/z: 555 [M+H]$^+$. Compound 189E: LC-MS (ESI) m/z: 527 [M+H]$^+$. Compound 189: LC-MS (ESI) m/z: 407 [M+H]$^+$; $^1$H-NMR (CD$_3$OD, 400 MHz): δ (ppm) 1.13 (t, J=7.2 Hz, 3H), 3.57 (q, J=7.2 Hz, 2H), 4.87 (s, 2H), 6.88 (d, J=8.0 Hz, 2H), 7.18 (d, J=8.4 Hz, 2H), 7.44 (d, J=8.8 Hz, 2H), 7.54 (d, J=8.8 Hz, 2H).

Example 190

Synthesis of 4-((5,6-dichloro-2,3-dihydro-1H-inden-2-yl)amino)-1H-1,2,3-triazole-5-carboxylic acid 2,2,2-trifluoroacetate (190)

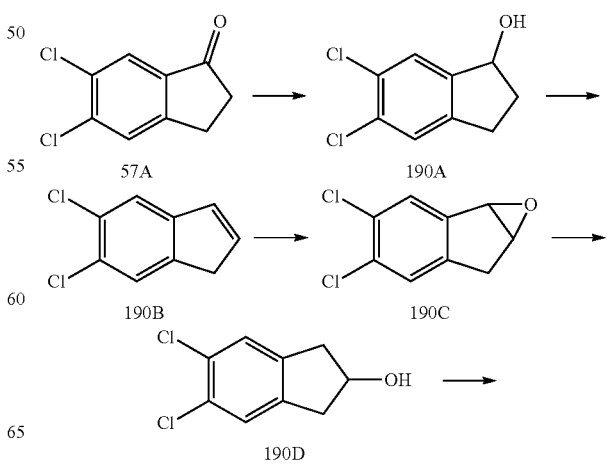

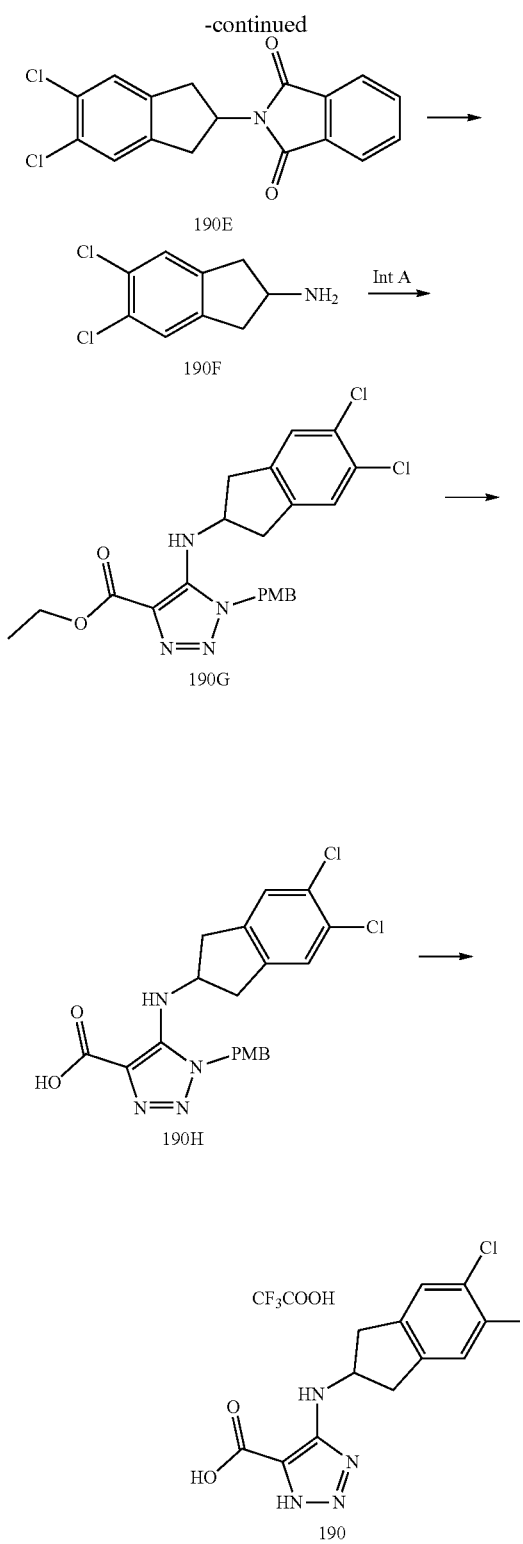

Compound 190A was synthesized by employing the procedure described for Compound 57C using Compound 57A and EtOH as solvent in lieu of Compound 57B and MeOH as solvent, LC-MS (ESI) m/z: 185 [M−OH]+; 1H-NMR (CDCl3, 400 MHz): δ (ppm) 1.93-2.00 (m, 1H), 2.49-2.57 (m, 1H), 2.75-2.83 (m, 1H), 2.98-3.05 (m, 1H), 5.21 (t, J=6.0 Hz, 1H), 7.34 (s, 1H), 7.48 (s, 1H).

To a mixture of Compound 190A (4.3 g, 21.3 mmol) in toluene (100 mL) was added MgSO4 (5.11 g, 42.6 mmol) and p-TsOH (366 mg, 2.13 mmol). The mixture was heated at reflux for 2 hours. After cooled down to room temperature, the mixture was filtered, diluted with water (50 mL), and extracted with ethyl acetate (50 mL×3). The combined organic layers was washed with water (100 mL) and brine (100 mL), dried over anhydrous Na2SO4, concentrated, and purified with flash column chromatography on silica gel (ethyl acetate in petroleum ether, 5% v/v) to give Compound 190B. LC-MS (ESI) m/z: 185 [M+H]+; 1H-NMR (CDCl3, 400 MHz): δ (ppm) 3.39-3.40 (m, 2H), 6.62 (d, J=8.8 Hz, 1H), 6.80 (d, J=8.8 Hz, 1H), 7.46 (s, 1H), 7.53 (s, 1H).

To a mixture of Compound 190B (1.0 g, 5.43 mmol) in dichloromethane (60 mL) was added m-CPBA (1.40 g, 8.15 mmol) and NaHCO3 (685 mg, 8.15 mmol). The resulting mixture was stirred at room temperature under nitrogen for 16 hours, quenched with water (100 mL), and extracted with dichloromethane (50 mL×3). The combined organic layers was washed with water (200 mL) and brine (200 mL), dried over anhydrous Na2SO4, concentrated, and purified with flash column chromatography on silica gel (ethyl acetate in petroleum ether, 20% v/v) to give Compound 190C. LC-MS (ESI) m/z: 201 [M+H]+; 1H-NMR (CDCl3, 400 MHz): δ (ppm) 2.95 (dd, J=18, 2.8 Hz, 1H), 3.18 (d, J=18 Hz, 1H), 4.15 (t, J=2.8 Hz, 1H), 4.22 (t, J=2.8 Hz, 1H), 7.32 (s, 1H), 7.57 (s, 1H).

To a solution of Compound 190C (400 mg, 2 mmol) in 1,4-dioxane (100 mL) was added InCl3 (443 mg, 2 mmol) and stirred at 60° C. for 2 hours, followed by addition of NaCNBH3 (378 mg, 6 mmol). The mixture was heated at reflux for 2 hours. After cooled down to room temperature, the mixture was quenched with water (100 mL) and extracted with ethyl acetate (50 mL×3). The combined organic layers was washed with water (200 mL) and brine (200 mL), dried over anhydrous Na2SO4, concentrated, and purified with flash column chromatography on silica gel (ethyl acetate in petroleum ether, 30% v/v) to give Compound 190D. LC-MS (ESI) m/z: 185 [M−OH]+; 1H-NMR (CDCl3, 400 MHz): δ (ppm) 2.89 (dd, J=18, 2.8 Hz, 2H), 3.17 (dd, J=18, 2.8 Hz, 2H), 4.72-4.76 (m, 1H), 7.32 (s, 2H).

Compound 190E was synthesized by employing the procedure described for Compound 90C using O-phthalimide and Compound 190D with DEAD in lieu of Intermediate H and Compound 90B with DIAD, LC-MS (ESI) m/z: 332 [M+H]+; 1H-NMR (CDCl3, 400 MHz): δ (ppm) 3.15-3.22 (m, 2H), 3.53-3.59 (m, 2H), 5.13-5.22 (m, 1H), 7.32 (s, 2H), 7.74 (d, J=8.4 Hz, 2H), 7.86 (d, J=8.4 Hz, 2H).

To a mixture of Compound 190E (570 mg, 1.72 mmol) in methanol (50 mL) was added 85% N2H4 (5 mL), stirred at reflux for 16 hours, and concentrated under reduced pressure. The residue was purified with reverse phase chromatography using eluent (methanol in water (include 0.5% NH4HCO3), 80% v/v) to furnish Compound 190F. LC-MS (ESI) m/z: 202 [M+H]+.

Compounds 190G, 190H, and 190 were synthesized by employing the procedures described for Compounds 6B, 8F, and 1 using Intermediate A, Compounds 190F with t-BuONa as base and DMF as solvent, 190G, and 190H in lieu of Compounds 6A, 1-methylpiperazine with K3PO4 as base and toluene as solvent, 8E, and 1E. Compound 190G: LC-MS (ESI) m/z: 461 [M+H]+. Compound 190H: LC-MS (ESI) m/z: 433 [M+H]+. Compound 190: LC-MS (ESI) m/z: 313 [M+H]+; 1H-NMR (DMSO-d6, 400 MHz): δ (ppm) 2.91-2.97 (m, 2H), 3.23-3.29 (m, 2H), 4.37 (s, 1H), 5.36 (s, 1H), 7.51 (s, 2H).

Example 191

Synthesis of 4-((6-chloro-3,4-dihydroisoquinolin-2(1H)-yl)methyl)-1H-1,2,3-triazole-5-carboxylic acid 2,2,2-trifluoroacetate (191)

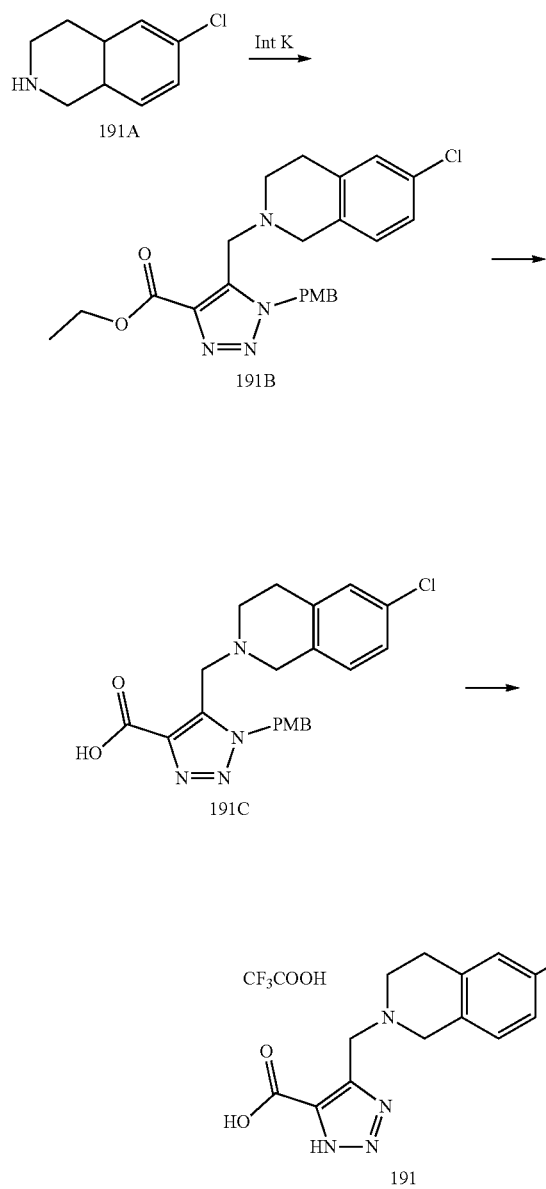

Compounds 191B, 191C, and 191 were synthesized by employing the procedures described for Compounds 178A, 8F, and 1 using Compounds 191A, 191B, and 191C in lieu of Compounds 82C, 8E, and 1E. Compound 191B: LC-MS (ESI) m/z: 441 [M+H]$^+$; $^1$H-NMR (CDCl$_3$, 400 MHz): δ (ppm) 1.42 (t, J=7.2 Hz, 3H), 2.67-2.70 (m, 2H), 2.82-2.85 (m, 2H), 3.50 (s, 2H), 3.77 (s, 3H), 3.91 (s, 2H), 4.45 (q, J=7.2 Hz, 2H), 5.69 (s, 2H), 6.78-6.80 (m, 2H), 6.88-6.90 (m, 1H), 7.09-7.13 (m, 4H). Compound 191C: LC-MS (ESI) m/z: 413 [M+H]$^+$; $^1$H-NMR (DMSO-d$_6$, 400 MHz): δ (ppm) 2.60-2.61 (m, 2H), 2.68-2.69 (m, 2H), 3.49 (s, 2H), 3.66 (s, 3H), 4.05 (s, 2H), 5.51 (s, 2H), 6.76 (d, J=8.6 Hz, 2H), 6.97 (d, J=8.0 Hz, 1H), 7.11 (d, J=8.7 Hz, 4H). Compound 191: LC-MS (ESI) m/z: 293 [M+H]$^+$; $^1$H-NMR (DMSO-d$_6$, 400 MHz): δ (ppm) 3.05-3.08 (m, 2H), 3.49 (s, 2H), 4.37 (s, 2H), 4.64 (s, 2H), 7.23 (d, J=8.4 Hz, 1H), 7.29-7.31 (m, 1H), 7.34 (s, 1H).

Example 192

Synthesis of 4-((4-(4-chlorophenyl)piperazin-1-yl)methyl)-1H-1,2,3-triazole-5-carboxylic acid (192)

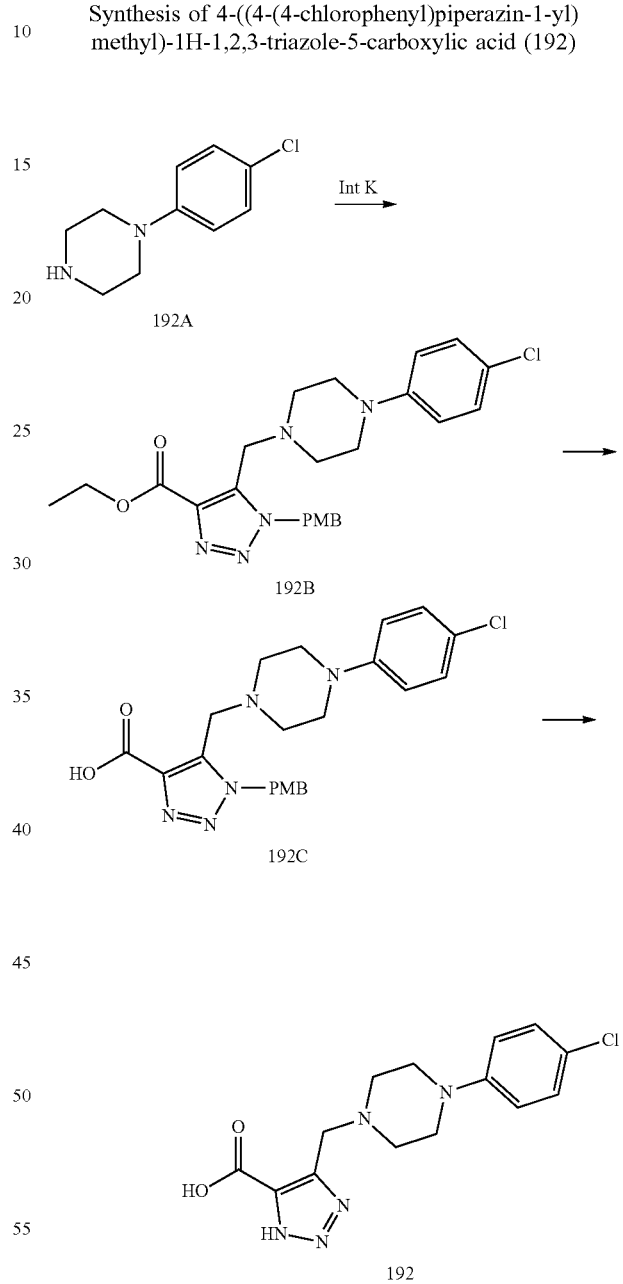

Compounds 192B, 192C, and 192 were synthesized by employing the procedures described for Compounds 178A, 8F, and 1 using Compounds 192A, 192B, and 192C in lieu of Compounds 82C, 8E, and 1E. Compound 192B: LC-MS (m/z): 470 [M+H]$^+$. Compound 192C: LC-MS (m/z): 442 [M+H]$^+$. Compound 192: LC-MS (m/z): 322 [M+H]$^+$; $^1$H-NMR (CD$_3$OD, 400 MHz): δ (ppm) 3.36-3.82 (m, 8H), 4.78 (s, 2H), 7.01 (d, J=8.8 Hz, 2H), 7.27 (d, J=8.8 Hz, 2H).

Example 193

Synthesis of 4-((benzyl(1-(4-chlorophenyl)piperidin-4-yl)amino)methyl)-1H-1,2,3-triazole-5-carboxylic acid 2,2,2-trifluoroacetate (193)

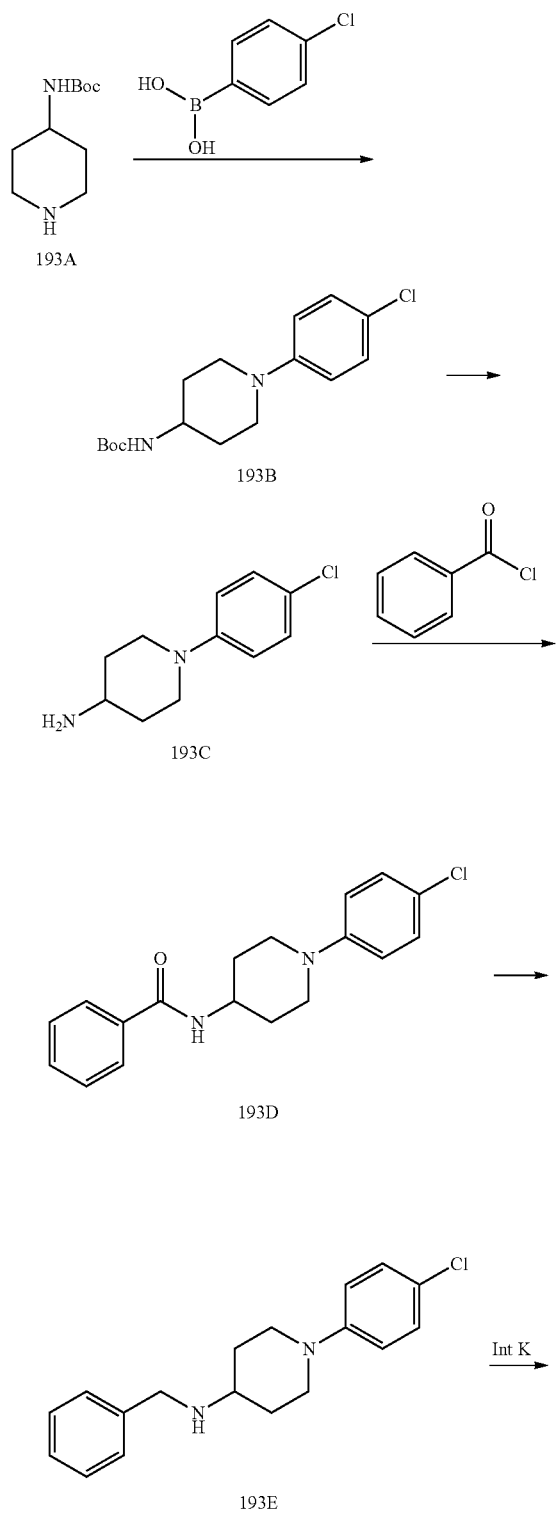

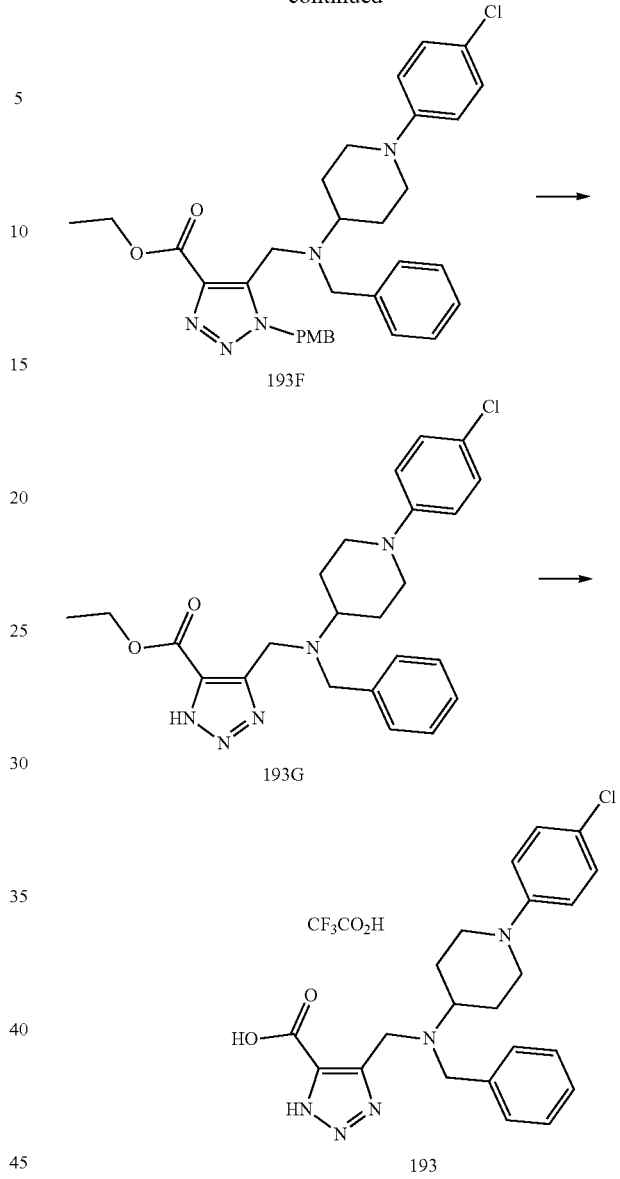

Compounds 193B and 193C were synthesized by employing the procedures described for Compounds 70B and 175E using (4-chlorophenyl)boronic acid, Compounds 193A with pyridine as base, and 192B in lieu of (4-(trifluoromethoxy)phenyl)boronic acid, Compounds 70A with $K_3PO_4$ as base, and 175D. Compound 193B: LC-MS (ESI) m/z: 311 [M+H]$^+$; $^1$H-NMR (CDCl$_3$, 400 MHz): δ (ppm) 1.46 (s, 9H), 1.49-1.55 (m, 2H), 2.03-2.07 (m, 2H), 2.79-2.86 (m, 2H), 3.54-3.61 (m, 3H), 4.48-4.49 (m, 1H), 6.85 (d, J=8.8 Hz, 2H), 7.20 (d, J=8.8 Hz, 2H). Compound 193C: LC-MS (ESI) m/z: 211 [M+H]$^+$; (CDCl$_3$, 400 MHz): δ (ppm) 1.47-1.55 (m, 4H), 1.90-1.94 (m, 2H), 2.74-2.80 (m, 3H), 3.58-3.62 (m, 2H), 6.86 (d, J=8.8 Hz, 2H), 7.19 (d, J=8.8 Hz, 2H).

A mixture of Compound 193C (278 mg, 1.32 mmol), benzoyl chloride (228 mg, 1.62 mmol), DMAP (36 mg, 0.294 mmol) and triethylamine (297 mg, 2.94 mmol) in dichloromethane (30 mL) was stirred at room temperature for 4 hours. The mixture was washed with water (50 mL) and brine (50 mL), dried over anhydrous Na$_2$SO$_4$, concentrated, and purified with flash column chromatography on silica gel (ethyl acetate in petroleum ether, 20% v/v) to give compound 193D. LC-MS (ESI) m/z: 315 [M+H]⁺; ¹H-NMR (CD₃OD, 400 MHz): δ (ppm) 1.73-1.83 (m, 2H), 2.03-2.06 (m, 2H), 2.83-2.89 (m, 2H), 3.71-3.75 (m, 2H), 4.03-4.07 (m, 1H), 6.96-7.01 (m, 2H), 7.20 (d, J=8.8 Hz, 2H), 7.44-7.48 (m, 2H), 7.51-7.56 (m, 1H), 7.83 (m, J=7.6 Hz, 2H).

Compounds 193E, 193F, 193G, and 193 were synthesized by employing the procedures described for Compounds 182B, 178A, 1, and 8F using Compounds 193D, 193E, 193F, and 192G in lieu of Compounds 182A, 82C, 1E, and 8E. Compound 193E: LC-MS (ESI) m/z: 301 [M+H]⁺; ¹H-NMR (CDCl₃, 400 MHz): δ (ppm) 1.59-1.62 (m, 2H), 2.02-2.05 (m, 2H), 2.69-2.78 (m, 3H), 3.59-3.63 (m, 2H), 3.88 (s, 2H), 6.85 (d, J=9.2 Hz, 2H), 7.17-7.20 (m, 2H), 7.28-7.39 (m, 5H). Compound 193F: LC-MS (ESI) m/z: 574 [M+H]⁺; ¹H-NMR (CDCl₃, 400 MHz): δ (ppm) 1.24 (t, J=7.2 Hz, 3H), 1.71-1.81 (m, 2H), 1.94-1.97 (m, 2H), 2.64-2.70 (m, 2H), 2.84-2.90 (m, 1H), 3.65-3.68 (m, 2H), 3.78 (s, 3H), 3.80 (s, 2H), 4.05 (s, 2H), 4.22 (q, J=7.2 Hz, 2H), 5.76 (s, 2H), 6.80-6.85 (m, 4H), 7.14-7.27 (m, 9H). Compound 193G: LC-MS (ESI) m/z: 454 [M+H]⁺. Compound 193: LC-MS (ESI) m/z: 426 [M+H]⁺; ¹H-NMR (CD₃OD, 400 MHz): δ (ppm) 2.07-2.17 (m, 2H), 2.26-2.29 (m, 2H), 2.75-2.81 (m, 2H), 3.61-3.67 (m, 1H), 3.85-3.89 (m, 2H), 4.57 (s, 2H), 4.78 (s, 2H), 6.98 (d, J=9.2 Hz, 2H), 7.20-7.24 (m, 2H), 7.41-7.52 (m, 5H).

Example 194

Synthesis of 4-((benzyl(4-cyclohexylphenyl)amino)methyl)-1H-1,2,3-triazole-5-carboxylic acid (194)

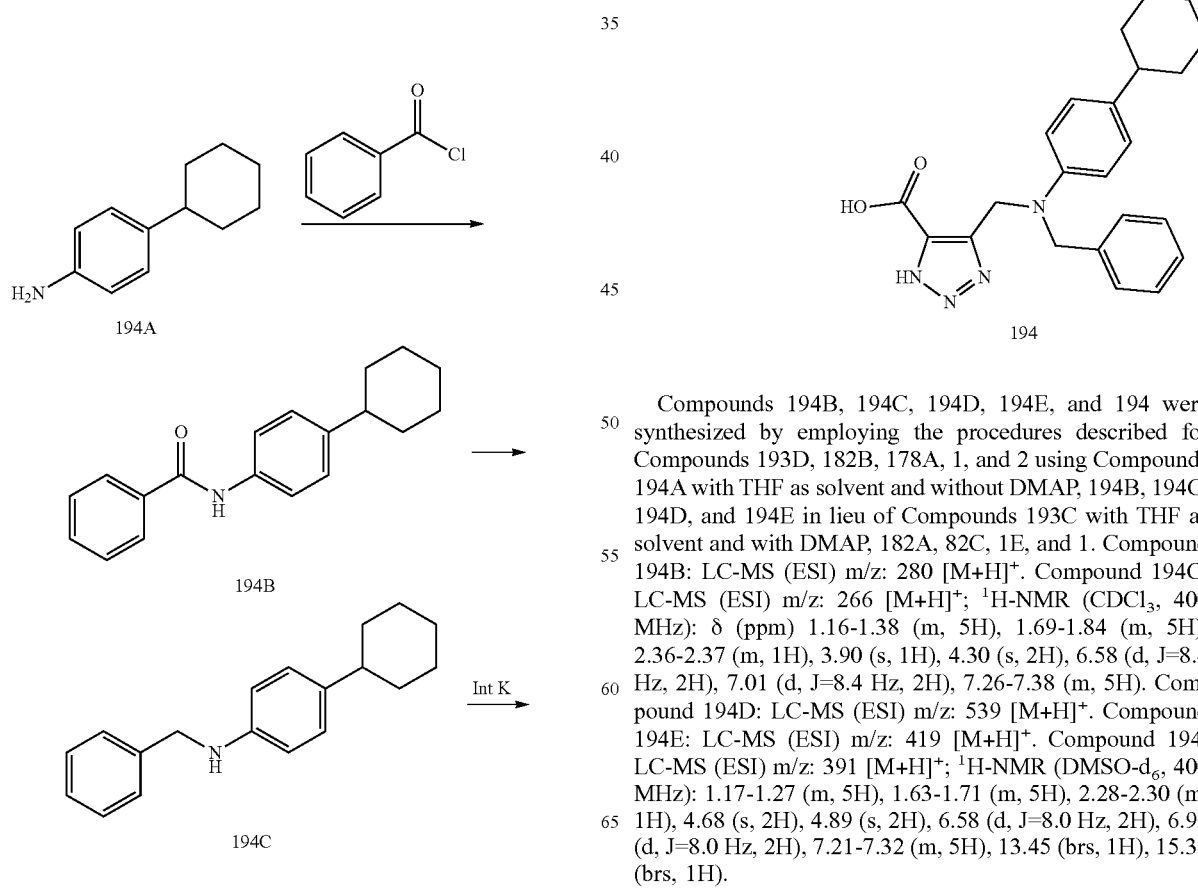

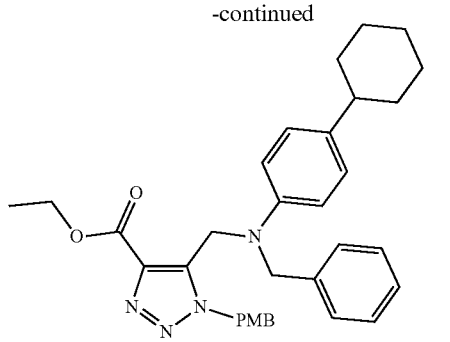

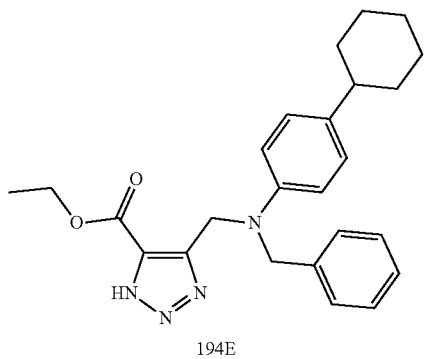

Compounds 194B, 194C, 194D, 194E, and 194 were synthesized by employing the procedures described for Compounds 193D, 182B, 178A, 1, and 2 using Compounds 194A with THF as solvent and without DMAP, 194B, 194C, 194D, and 194E in lieu of Compounds 193C with THF as solvent and with DMAP, 182A, 82C, 1E, and 1. Compound 194B: LC-MS (ESI) m/z: 280 [M+H]⁺. Compound 194C: LC-MS (ESI) m/z: 266 [M+H]⁺; ¹H-NMR (CDCl₃, 400 MHz): δ (ppm) 1.16-1.38 (m, 5H), 1.69-1.84 (m, 5H), 2.36-2.37 (m, 1H), 3.90 (s, 1H), 4.30 (s, 2H), 6.58 (d, J=8.4 Hz, 2H), 7.01 (d, J=8.4 Hz, 2H), 7.26-7.38 (m, 5H). Compound 194D: LC-MS (ESI) m/z: 539 [M+H]⁺. Compound 194E: LC-MS (ESI) m/z: 419 [M+H]⁺. Compound 194: LC-MS (ESI) m/z: 391 [M+H]⁺; ¹H-NMR (DMSO-d₆, 400 MHz): 1.17-1.27 (m, 5H), 1.63-1.71 (m, 5H), 2.28-2.30 (m, 1H), 4.68 (s, 2H), 4.89 (s, 2H), 6.58 (d, J=8.0 Hz, 2H), 6.91 (d, J=8.0 Hz, 2H), 7.21-7.32 (m, 5H), 13.45 (brs, 1H), 15.38 (brs, 1H).

Example 195

Synthesis of 4-(((4-chlorophenyl)(4-(trifluoromethoxy)benzyl)amino)methyl)-1H-1,2,3-triazole-5-carboxylic acid (195)

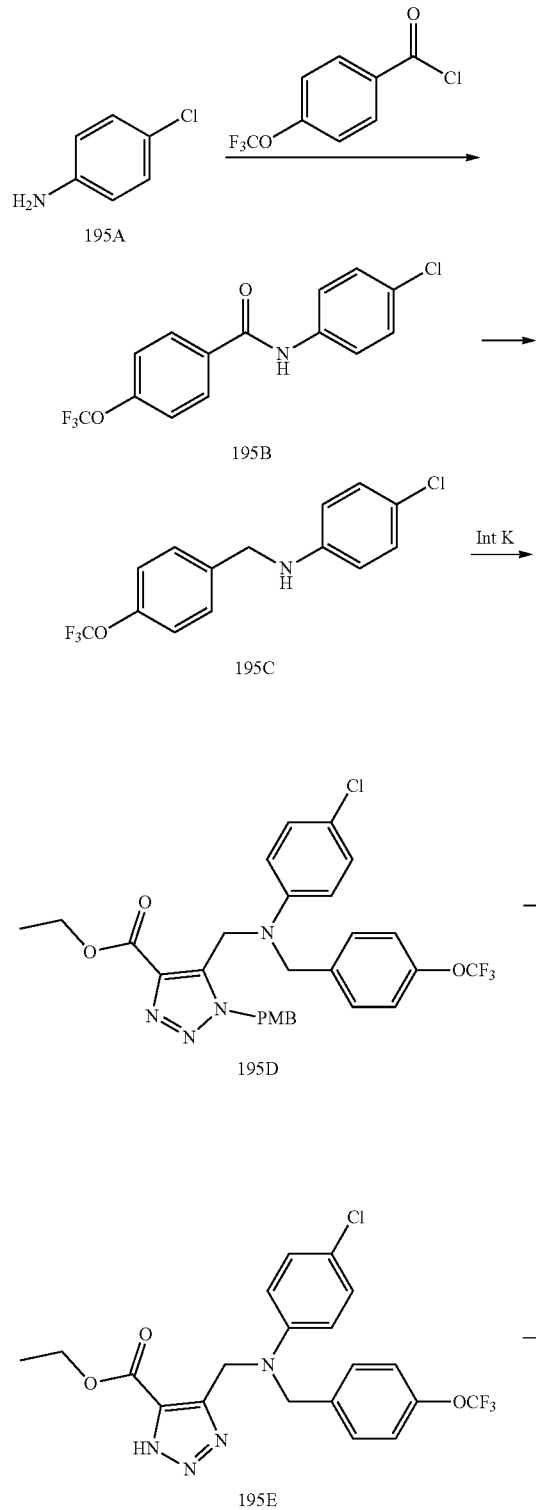

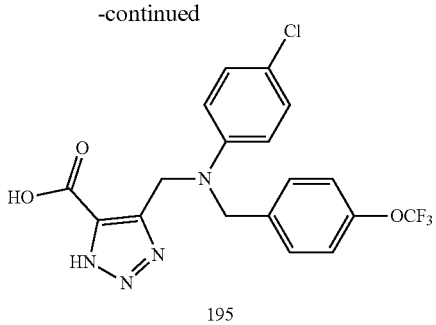

Compounds 195B, 195C, 195D, 195E, and 195 were synthesized by employing the procedures described for Compounds 193D, 182B, 178A, 1, and 8F using 4-(trifluoromethoxy)benzoyl chloride, Compounds 195A without DMAP, 195B with $BH_3 \cdot Me_2S$ as reducing agent, 195C, 195D, and 195E in lieu of benzoyl chloride, Compounds 193C with DMAP, 182A with $BH_3 \cdot THF$ as reducing agent, 82C, 1E, and 8E. Compound 195B: LC-MS (ESI) m/z: 316 $[M+H]^+$. Compound 195C: $^1$H-NMR (CDCl$_3$, 400 MHz): δ (ppm) 4.11 (s, 1H), 4.33 (s, 2H), 6.52-6.56 (m, 2H), 7.11-7.14 (m, 2H), 7.20 (d, J=8.1 Hz, 2H), 7.38 (d, J=8.6 Hz, 2H). Compound 195D: LC-MS (ESI) m/z: 575 $[M+H]^+$; $^1$H-NMR (CDCl$_3$, 400 MHz): 1.27 (t, J=7.2 Hz, 3H), 3.79 (s, 3H), 4.30 (q, J=7.2 Hz, 2H), 4.72 (s, 2H), 4.81 (s, 2H), 5.78 (s, 2H), 6.72-6.74 (m, 2H), 6.82-6.85 (m, 2H), 7.10-7.12 (m, 4H), 7.21-7.24 (m, 4H). Compound 195E: LC-MS (ESI) m/z: 455 $[M+H]^+$; $^1$H-NMR (CDCl$_3$, 400 MHz): 1.35 (t, J=7.2 Hz, 3H), 4.42 (q, J=7.2 Hz, 2H), 4.70 (s, 2H), 4.94 (s, 2H), 6.69 (d, J=8.6 Hz, 2H), 7.12-7.17 (m, 4H), 7.26 (m, 2H). Compound 195: LC-MS (ESI) m/z: 427 $[M+H]^+$; $^1$H-NMR (DMSO-d$_6$, 400 MHz): 4.74 (s, 2H), 4.93 (s, 2H), 6.65 (d, J=8.7 Hz, 2H), 7.10 (d, J=8.9 Hz, 2H), 7.28-7.35 (m, 4H).

Example 196

Synthesis of 4-((benzyl(4'-(trifluoromethoxy)-[1,1'-biphenyl]-4-yl)amino)methyl)-1H-1,2,3-triazole-5-carboxylic acid 2,2,2-trifluoroacetate (196)

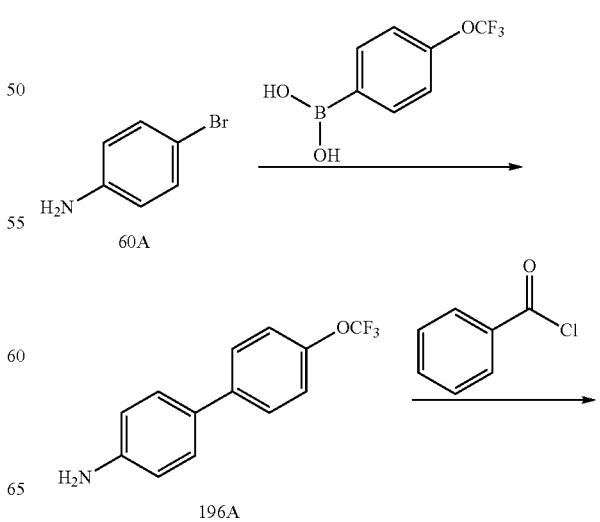

389
-continued

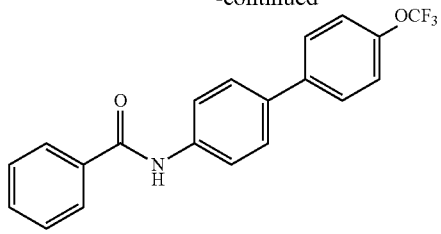

196B

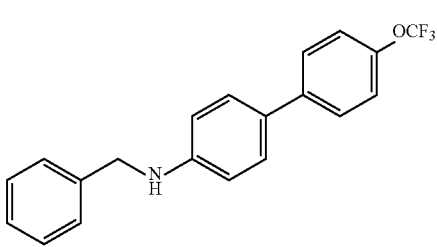

196C

Int K →

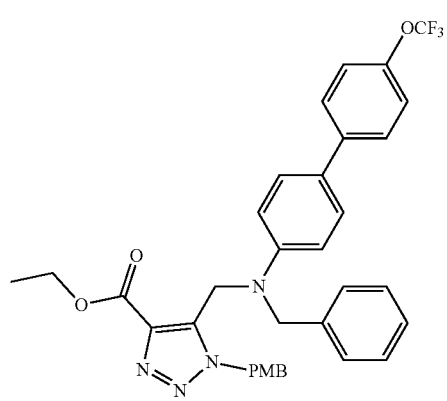

196D

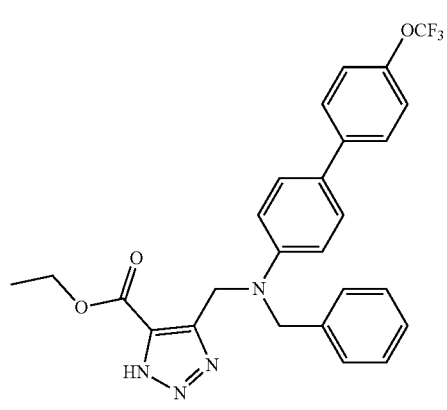

196E

390
-continued

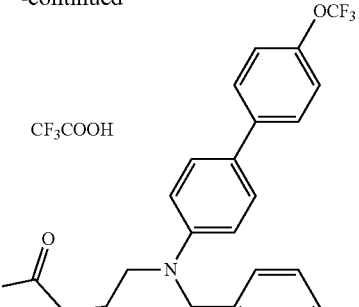

196

Compounds 196A, 196B, 196C, 196D, 196E, and 196 were synthesized by employing the procedures described for Compounds 8B, 193D, 182B, 178A, 1, and 8F using 4-(trifluoromethoxy)phenylboronic acid, Compounds 60A with $K_2CO_3$ as base and 1,4-dioxane/$H_2O$ as solvent, 196A without DMAP, 196B, 196C, 196D, and 196E in lieu of (3,4-dichlorophenyl)boronic acid, Compounds 8A with $Cs_2CO_3$ as base and toluene as solvent, 193C with DMAP, 182A, 82C, 1E, and 8E. Compound 196A: LC-MS (ESI) m/z: 254 [M+H]⁺. Compound 196B: LC-MS (ESI) m/z: 358 [M+H]⁺. Compound 196C: LC-MS (ESI) m/z: 344 [M+H]⁺; ¹H-NMR: ($CDCl_3$, 400 MHz): δ (ppm) 4.19 (s, 1H), 4.38 (s, 2H), 6.69-6.71 (m, 2H), 7.21-7.27 (m, 3H), 7.29-7.40 (m, 6H), 7.50-7.52 (m, 2H). Compound 196D: LC-MS (ESI) m/z: 617 [M+H]⁺. Compound 196E: LC-MS (ESI) m/z: 497 [M+H]⁺. Compound 196: LC-MS (ESI) m/z: 469 [M+H]⁺; ¹H-NMR ($CDCl_3$, 400 MHz): δ (ppm) 4.54 (s, 2H), 4.86 (s, 2H), 6.94-6.96 (m, 2H), 7.08-7.27 (m, 7H), 7.30-7.32 (m, 4H).

Example 197

Synthesis of 4-((2,4'-dichloro-[1,1'-biphenyl]-4-yl)difluoromethyl)-1H-1,2,3-triazole-5-carboxylic acid 2,2,2-trifluoroacetate (197)

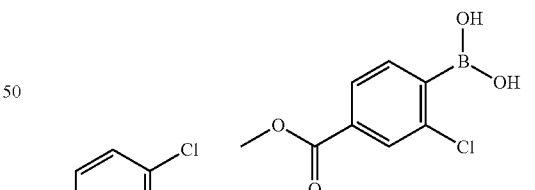

197A

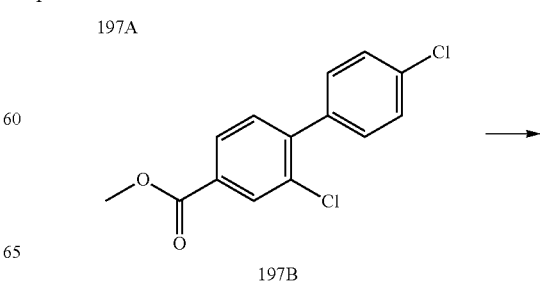

197B

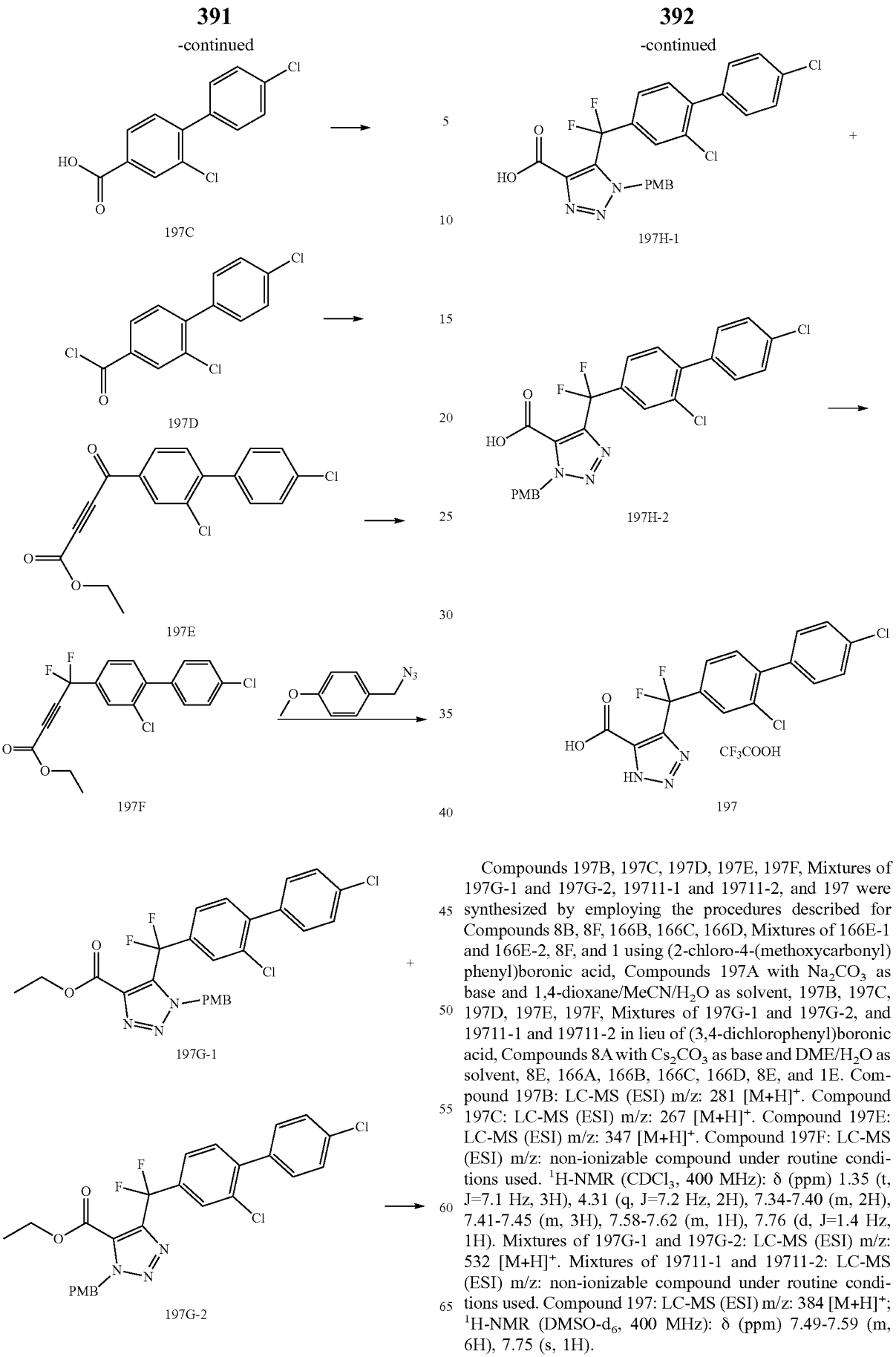

Compounds 197B, 197C, 197D, 197E, 197F, Mixtures of 197G-1 and 197G-2, 197H-1 and 197H-2, and 197 were synthesized by employing the procedures described for Compounds 8B, 8F, 166B, 166C, 166D, Mixtures of 166E-1 and 166E-2, 8F, and 1 using (2-chloro-4-(methoxycarbonyl)phenyl)boronic acid, Compounds 197A with $Na_2CO_3$ as base and 1,4-dioxane/MeCN/$H_2O$ as solvent, 197B, 197C, 197D, 197E, 197F, Mixtures of 197G-1 and 197G-2, and 197H-1 and 197H-2 in lieu of (3,4-dichlorophenyl)boronic acid, Compounds 8A with $Cs_2CO_3$ as base and DME/$H_2O$ as solvent, 8E, 166A, 166B, 166C, 166D, 8E, and 1E. Compound 197B: LC-MS (ESI) m/z: 281 [M+H]$^+$. Compound 197C: LC-MS (ESI) m/z: 267 [M+H]$^+$. Compound 197E: LC-MS (ESI) m/z: 347 [M+H]$^+$. Compound 197F: LC-MS (ESI) m/z: non-ionizable compound under routine conditions used. $^1$H-NMR (CDCl$_3$, 400 MHz): δ (ppm) 1.35 (t, J=7.1 Hz, 3H), 4.31 (q, J=7.2 Hz, 2H), 7.34-7.40 (m, 2H), 7.41-7.45 (m, 3H), 7.58-7.62 (m, 1H), 7.76 (d, J=1.4 Hz, 1H). Mixtures of 197G-1 and 197G-2: LC-MS (ESI) m/z: 532 [M+H]$^+$. Mixtures of 197H-1 and 197H-2: LC-MS (ESI) m/z: non-ionizable compound under routine conditions used. Compound 197: LC-MS (ESI) m/z: 384 [M+H]$^+$; $^1$H-NMR (DMSO-d$_6$, 400 MHz): δ (ppm) 7.49-7.59 (m, 6H), 7.75 (s, 1H).

Example 198

Synthesis of 4-(difluoro(4'-(trifluoromethoxy)-[1,1'-biphenyl]-4-yl)methyl)-1H-1,2,3-triazole-5-carboxylic acid 2,2,2-trifluoroacetate (198)

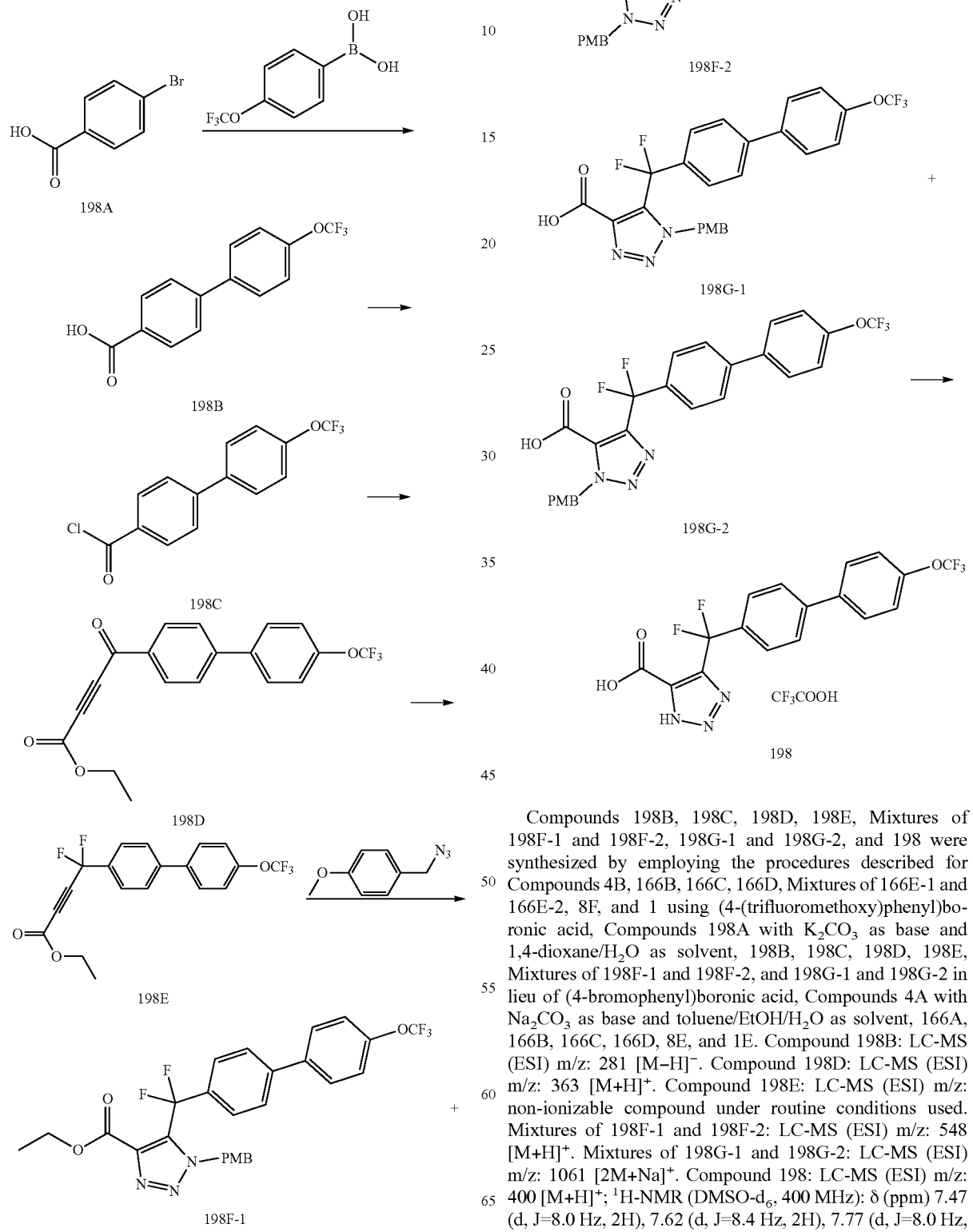

Compounds 198B, 198C, 198D, 198E, Mixtures of 198F-1 and 198F-2, 198G-1 and 198G-2, and 198 were synthesized by employing the procedures described for Compounds 4B, 166B, 166C, 166D, Mixtures of 166E-1 and 166E-2, 8F, and 1 using (4-(trifluoromethoxy)phenyl)boronic acid, Compounds 198A with $K_2CO_3$ as base and 1,4-dioxane/$H_2O$ as solvent, 198B, 198C, 198D, 198E, Mixtures of 198F-1 and 198F-2, and 198G-1 and 198G-2 in lieu of (4-bromophenyl)boronic acid, Compounds 4A with $Na_2CO_3$ as base and toluene/EtOH/$H_2O$ as solvent, 166A, 166B, 166C, 166D, 8E, and 1E. Compound 198B: LC-MS (ESI) m/z: 281 [M−H]−. Compound 198D: LC-MS (ESI) m/z: 363 [M+H]+. Compound 198E: LC-MS (ESI) m/z: non-ionizable compound under routine conditions used. Mixtures of 198F-1 and 198F-2: LC-MS (ESI) m/z: 548 [M+H]+. Mixtures of 198G-1 and 198G-2: LC-MS (ESI) m/z: 1061 [2M+Na]+. Compound 198: LC-MS (ESI) m/z: 400 [M+H]+; $^1$H-NMR (DMSO-$d_6$, 400 MHz): δ (ppm) 7.47 (d, J=8.0 Hz, 2H), 7.62 (d, J=8.4 Hz, 2H), 7.77 (d, J=8.0 Hz, 2H), 7.82 (d, J=8.4 Hz, 2H).

Example 199

Synthesis of 4-((6-chloronaphthalen-2-yl)difluoromethyl)-1H-1,2,3-triazole-5-carboxylic acid (199)

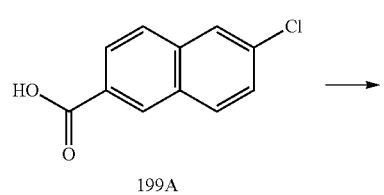

199A

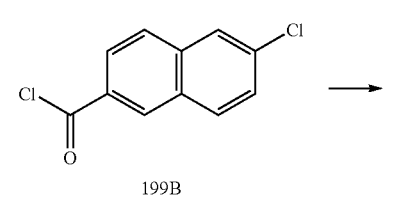

199B

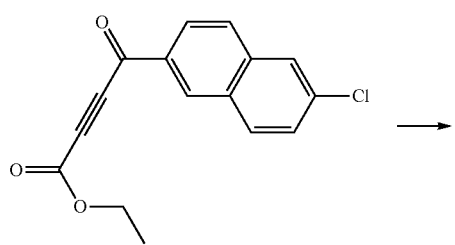

199C

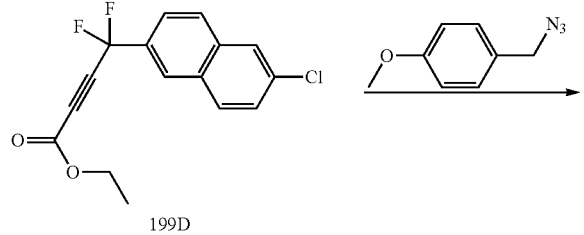

199D

199E-1

-continued 199E-1 →

199F

199

Compounds 199B, 199C, 199D, 199E-1 and 199E-2, 199F, and 199 were synthesized by employing the procedures described for Compounds 166B, 166C, 166D, Mixtures of 166E-1 and 166E-2, 8F, and 1 using Compounds 199A, 199B, 199C, 199D, 199E-1, and 199F in lieu of Compounds 166A, 166B, 166C, 166D, 8E, and 1E. Compound 199C: LC-MS (ESI) m/z: 287 [M+H]$^+$; $^1$H-NMR (CDCl$_3$, 400 MHz): δ (ppm) 1.40 (t, J=7.2 Hz, 3H), 4.39 (q, J=6.8 Hz, 2H), 7.55 (dd, J=2, 8.8 Hz, 1H), 7.84 (d, J=8.8 Hz, 1H), 7.90 (d, J=2 Hz, 1H), 7.98 (d, J=8.8 Hz, 1H), 8.12 (dd, J=2, 8.8 Hz, 1H), 8.66 (s, 1H). Compound 199D: LC-MS (ESI) m/z: non-ionizable compound under routine conditions used. $^1$H-NMR (CDCl$_3$, 400 MHz): δ (ppm) 1.32 (t, J=7.2 Hz, 3H), 4.30 (q, J=7.6 Hz, 2H), 7.52 (d, J=8.8 Hz, 1H), 7.86 (d, J=6.8 Hz, 1H), 7.87-7.89 (m, 3H), 8.14 (s, 1H). Compound 199E-1: LC-MS (ESI) m/z: 472 [M+H]$^+$; $^1$H-NMR (CDCl$_3$, 400 MHz): δ (ppm) 1.18 (t, J=6.8 Hz, 3H), 3.58 (s, 3H), 4.22 (q, J=7.2 Hz, 2H), 5.73 (s, 2H), 6.60 (dd, J=2, 6.4 Hz, 2H), 7.07 (d, J=8.8 Hz, 2H), 7.25-7.26 (m, 1H), 7.44 (dd, J=2, 8.4 Hz, 1H), 7.48-7.50 (m, 2H), 7.70 (d, J=8.4 Hz, 1H), 7.80 (d, J=2.0 Hz, 1H). Compound 199E-2: LC-MS (ESI) m/z: 472 [M+H]$^+$; $^1$H-NMR (CDCl$_3$, 400 MHz): δ (ppm) 1.26 (t, J=7.2 Hz, 3H), 3.78 (s, 3H), 4.25 (q, J=7.2 Hz, 2H), 5.82 (s, 2H), 6.84 (d, J=8.4 Hz, 2H), 7.28 (d, J=8.8 Hz, 2H), 7.48 (dd, J=2, 8.4 Hz, 1H), 7.68 (dd, J=2, 8.4 Hz, 1H), 7.79-7.86 (m, 3H), 8.02 (s, 1H). Compound 199F: LC-MS (ESI) m/z: 466 [M+Na]$^+$. Compound 199: LC-MS (ESI) m/z: 324 [M+H]$^+$; $^1$H-NMR (DMSO-d$_6$, 400 MHz): δ (ppm) 7.61 (dd, J=2.8, 8.0 Hz, 1H), 7.67 (d, J=8.4 Hz, 1H), 8.03 (d, J=9.2 Hz, 1H), 8.11 (d, J=8.8 Hz, 1H), 8.15 (d, J=2.8 Hz, 2H).

Example 200

Synthesis of 4-((4'-chloro-[1,1'-biphenyl]-4-yl)difluoromethyl)-1H-1,2,3-triazole-5-carboxylic acid 2,2,2-trifluoroacetate (200)

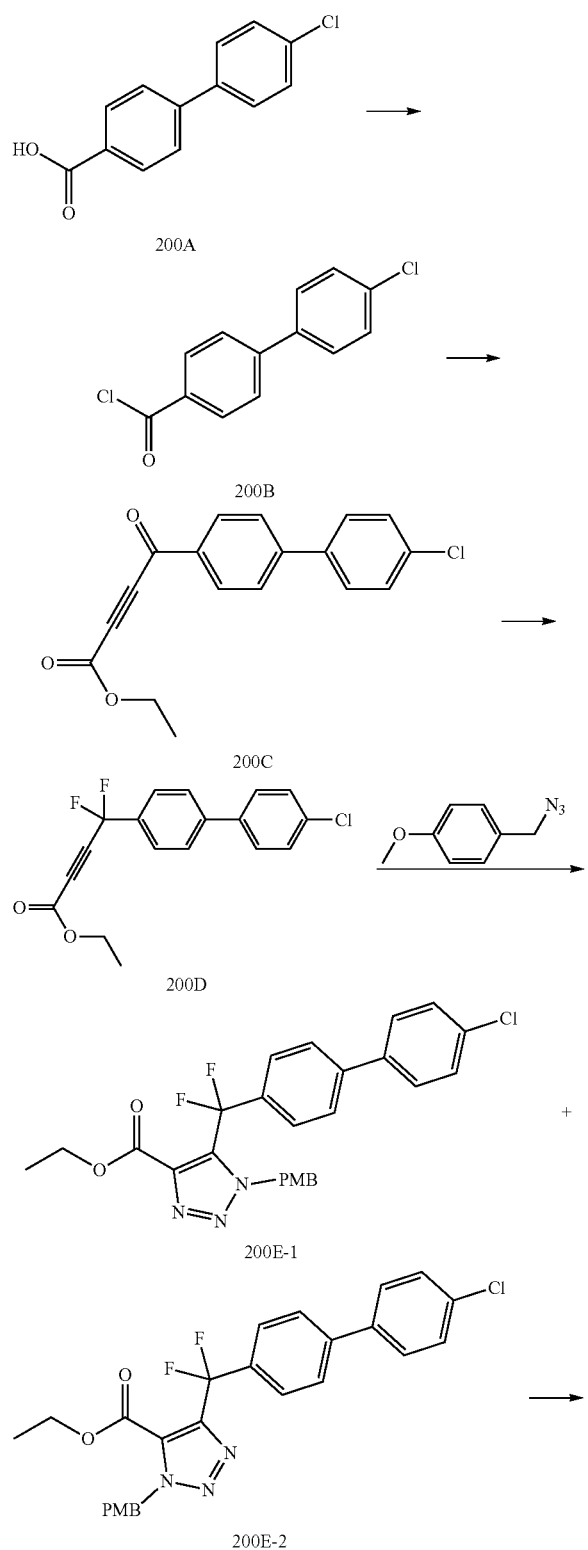

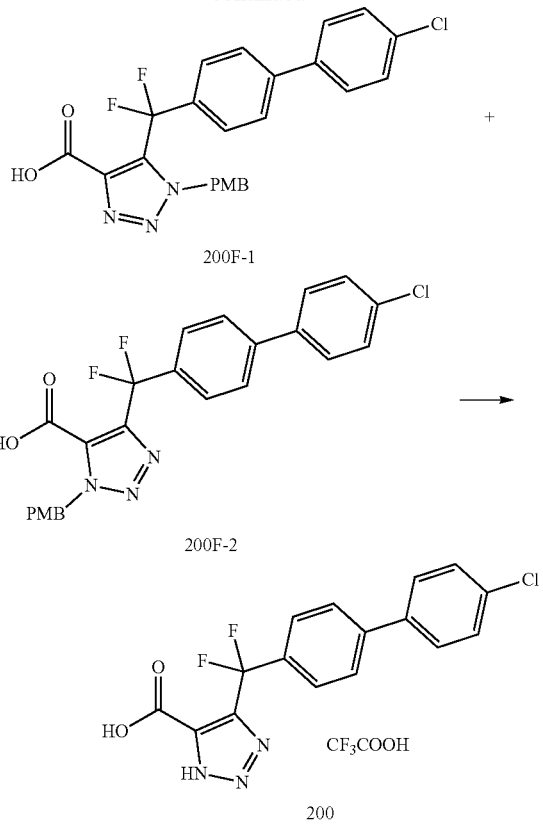

Compounds 200B, 200C, 200D, Mixtures of 200E-1 and 200E-2, 200E-1 and 200E-2, and 200 were synthesized by employing the procedures described for Compounds 166B, 166C, 166D, Mixtures of 166E-1 and 166E-2, 8F, and 1 using Compounds 200A, 200B, 200C, 200D, Mixtures of 200E-1 and 200E-2, and 200E-1 and 200E-2 in lieu of Compounds 166A, 166B, 166C, 166D, 8E, and 1E. Compound 200C: LC-MS (ESI) m/z: 313 [M+H]$^+$. Compound 200D: LC-MS (ESI) m/z: non-ionizable compound under routine conditions used. Mixtures of 200E-1 and 200E-2: LC-MS (ESI) m/z: 498 [M+H]$^+$. Mixtures of 200E-1 and 200E-2: LC-MS (ESI) m/z: 961 [2M+Na]$^+$. Compound 200: LC-MS (ESI) m/z: 350 [M+H]$^+$; $^1$H-NMR (DMSO-d$_6$, 400 MHz): δ (ppm) 7.53 (d, J=8.0 Hz, 2H), 7.60 (d, J=8.4 Hz, 2H), 7.72 (d, J=8.4 Hz, 2H), 7.77 (d, J=8.4 Hz, 2H).

Example 201

Synthesis of 4-((3',4'-dichloro-[1,1'-biphenyl]-4-yl)difluoromethyl)-1H-1,2,3-triazole-5-carboxylic acid 2,2,2-trifluoroacetate (201)

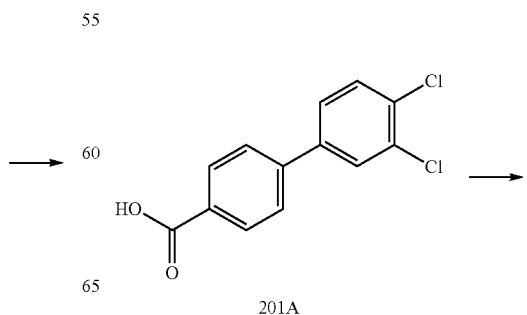

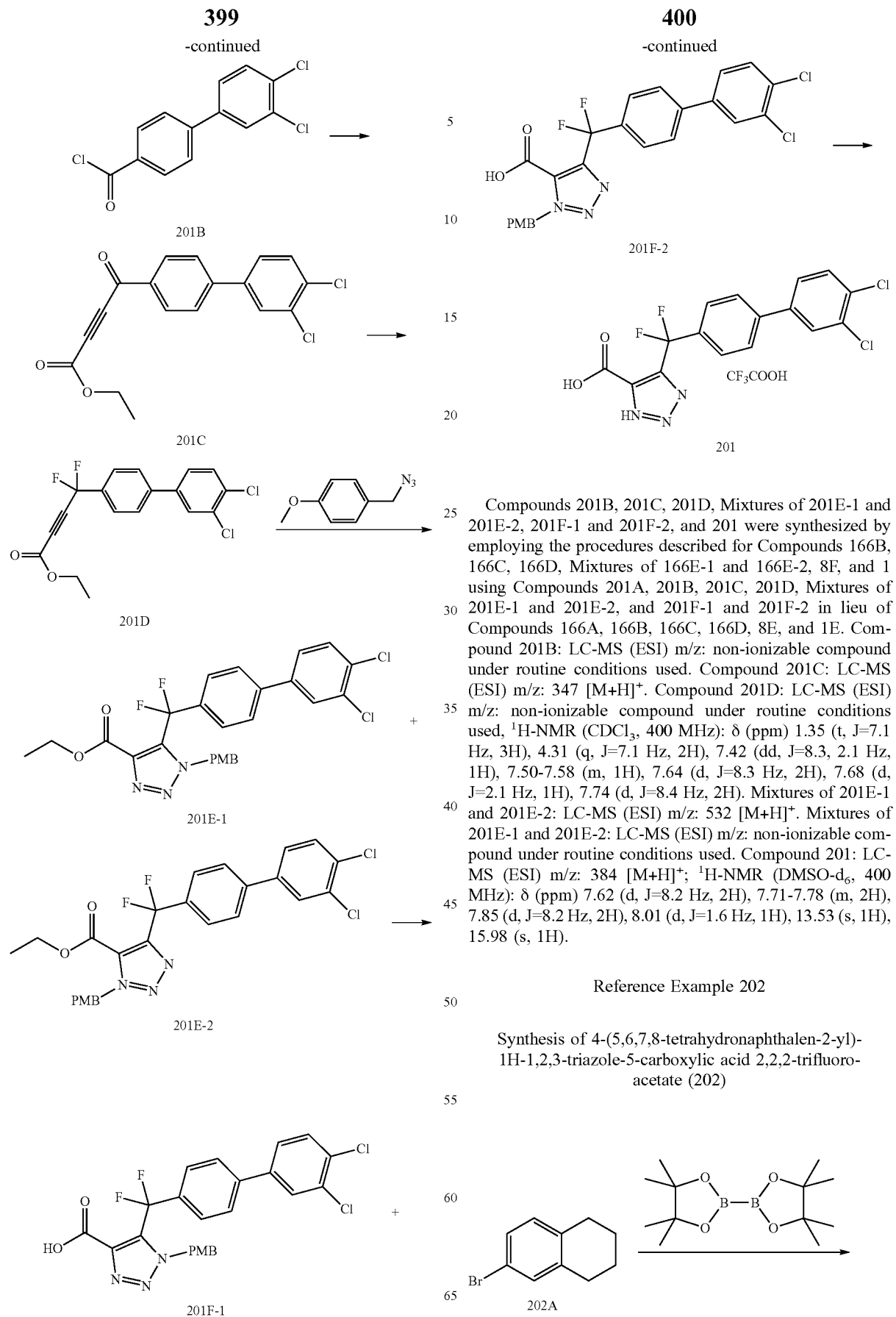

Compounds 201B, 201C, 201D, Mixtures of 201E-1 and 201E-2, 201F-1 and 201F-2, and 201 were synthesized by employing the procedures described for Compounds 166B, 166C, 166D, Mixtures of 166E-1 and 166E-2, 8F, and 1 using Compounds 201A, 201B, 201C, 201D, Mixtures of 201E-1 and 201E-2, and 201F-1 and 201F-2 in lieu of Compounds 166A, 166B, 166C, 166D, 8E, and 1E. Compound 201B: LC-MS (ESI) m/z: non-ionizable compound under routine conditions used. Compound 201C: LC-MS (ESI) m/z: 347 [M+H]$^+$. Compound 201D: LC-MS (ESI) m/z: non-ionizable compound under routine conditions used, $^1$H-NMR (CDCl$_3$, 400 MHz): δ (ppm) 1.35 (t, J=7.1 Hz, 3H), 4.31 (q, J=7.1 Hz, 2H), 7.42 (dd, J=8.3, 2.1 Hz, 1H), 7.50-7.58 (m, 1H), 7.64 (d, J=8.3 Hz, 2H), 7.68 (d, J=2.1 Hz, 1H), 7.74 (d, J=8.4 Hz, 2H). Mixtures of 201E-1 and 201E-2: LC-MS (ESI) m/z: 532 [M+H]$^+$. Mixtures of 201E-1 and 201E-2: LC-MS (ESI) m/z: non-ionizable compound under routine conditions used. Compound 201: LC-MS (ESI) m/z: 384 [M+H]$^+$; $^1$H-NMR (DMSO-d$_6$, 400 MHz): δ (ppm) 7.62 (d, J=8.2 Hz, 2H), 7.71-7.78 (m, 2H), 7.85 (d, J=8.2 Hz, 2H), 8.01 (d, J=1.6 Hz, 1H), 13.53 (s, 1H), 15.98 (s, 1H).

Reference Example 202

Synthesis of 4-(5,6,7,8-tetrahydronaphthalen-2-yl)-1H-1,2,3-triazole-5-carboxylic acid 2,2,2-trifluoroacetate (202)

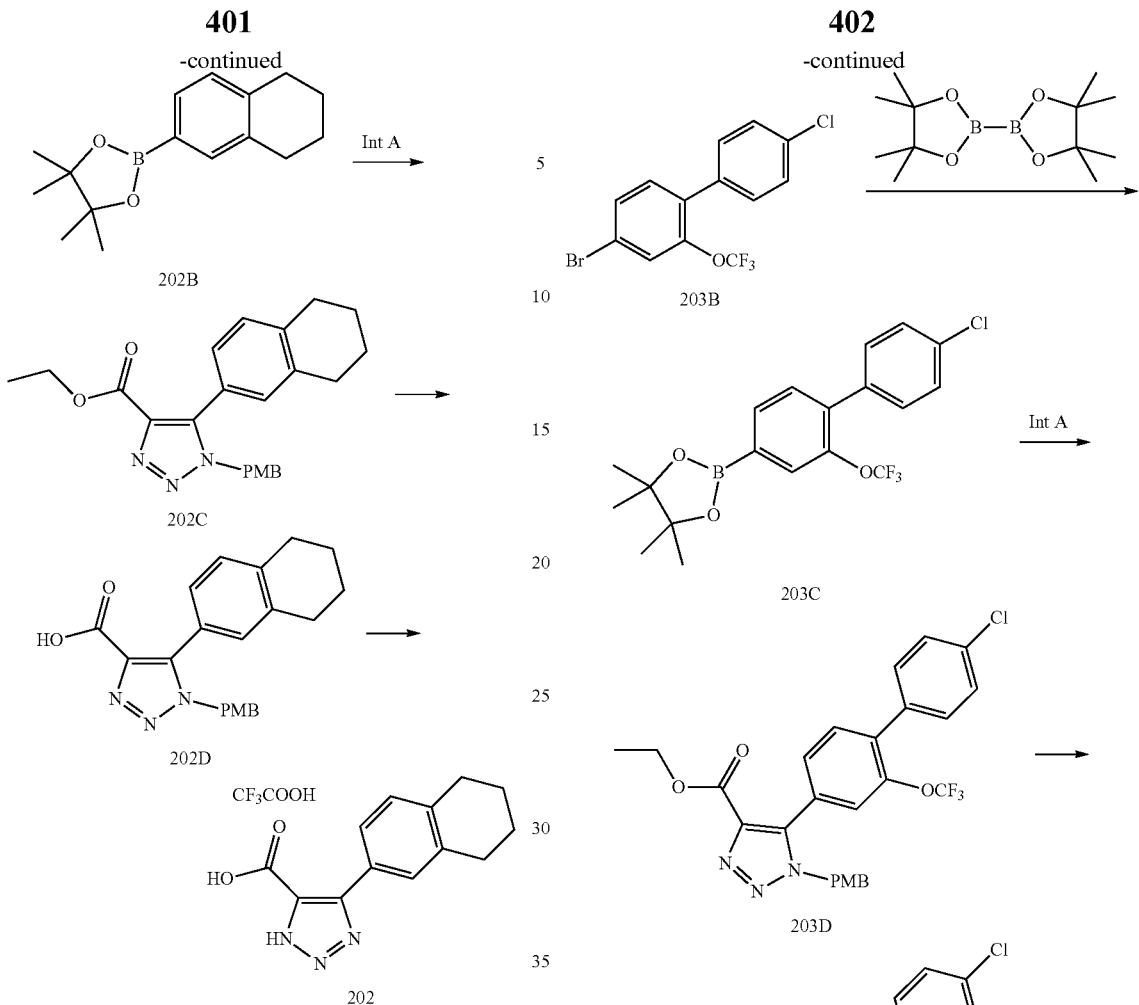

Compounds 202B, 202C, 202D, and 202 were synthesized by employing the procedures described for Compounds 27C, 8B, 8F, and 1 using Compounds 202A, 202B, 202C, and 202D in lieu of Compounds 27B, 8A, 8E, and 1E. Compound 202C: LC-MS (ESI) m/z: 392 [M+H]⁺. Compound 202D: LC-MS (ESI) m/z: 364 [M+H]⁺. Compound 202: LC-MS (ESI) m/z: 244 [M+H]⁺; $^1$H-NMR (DMSO-$d_6$, 400 MHz): δ (ppm) 1.74 (s, 4H), 2.74 (s, 4H), 7.12 (d, J=7.2 Hz, 1H), 7.46 (s, 2H), 13.03 (s, 1H), 15.63 (s, 1H).

Example 203

Synthesis of 4-(4'-chloro-2-(trifluoromethoxy)-[1,1'-biphenyl]-4-yl)-1H-1,2,3-triazole-5-carboxylic acid (203)

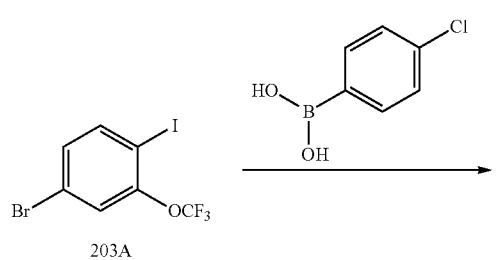

Compounds 203B, 203C, 203D, 203E, and 203 were synthesized by employing the procedures described for Compounds 4B, 27C, 4B, 1, and 8F using (4-chlorophenyl) boronic acid, Compounds 203A with $K_2CO_3$ as base and 1,4-dioxane as solvent, 203B with DMSO as solvent, 203C, Intermediate A with 1,4-dioxane/$H_2O$ as solvent, 203D, and 203E in lieu of (4-bromophenyl)boronic acid, Compounds 4A with Na₂CO₃ as base and toluene/EtOH/H₂O as solvent, 27B with 1,4-dioxane as solvent, (4-bromophenyl)boronic acid, 4A with toluene/EtOH/H₂O as solvent, 1E, and 8E. Compound 203B: LC-MS (ESI) m/z: non-ionizable compound under routine conditions used; ¹H-NMR (CDCl₃, 400 MHz): δ (ppm) 7.34-7.42 (m, 4H), 7.50-7.52 (m, 2H), 7.71-7.73 (m, 1H). Compound 203C: LC-MS (ESI) m/z: non-ionizable compound under routine conditions used. Compound 203D: LC-MS (ESI) m/z: 532 [M+H]⁺. Compound 203E: LC-MS (ESI) m/z: 412 [M+H]⁺. Compound 203: LC-MS (ESI) m/z: 384 [M+H]⁺; ¹H-NMR (CD₃OD, 400 MHz): δ (ppm) 7.47-7.57 (m, 5H), 8.12-8.14 (m, 1H), 8.21 (s, 1H).

Example 204

Synthesis of (isobutyryloxy)methyl 4-(6-chloroquinolin-2-yl)-1H-1,2,3-triazole-5-carboxylate (204)

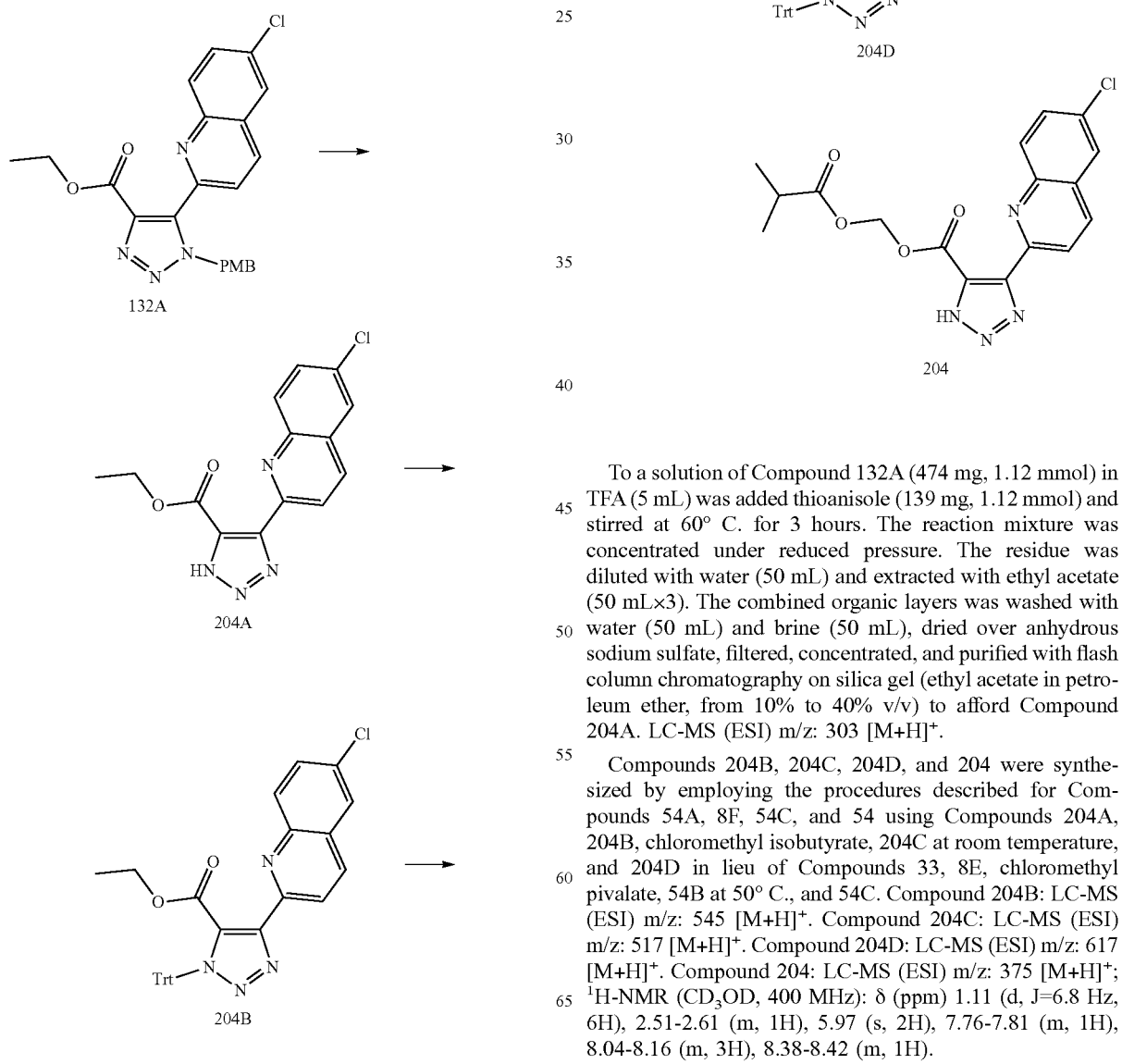

To a solution of Compound 132A (474 mg, 1.12 mmol) in TFA (5 mL) was added thioanisole (139 mg, 1.12 mmol) and stirred at 60° C. for 3 hours. The reaction mixture was concentrated under reduced pressure. The residue was diluted with water (50 mL) and extracted with ethyl acetate (50 mL×3). The combined organic layers was washed with water (50 mL) and brine (50 mL), dried over anhydrous sodium sulfate, filtered, concentrated, and purified with flash column chromatography on silica gel (ethyl acetate in petroleum ether, from 10% to 40% v/v) to afford Compound 204A. LC-MS (ESI) m/z: 303 [M+H]⁺.

Compounds 204B, 204C, 204D, and 204 were synthesized by employing the procedures described for Compounds 54A, 8F, 54C, and 54 using Compounds 204A, 204B, chloromethyl isobutyrate, 204C at room temperature, and 204D in lieu of Compounds 33, 8E, chloromethyl pivalate, 54B at 50° C., and 54C. Compound 204B: LC-MS (ESI) m/z: 545 [M+H]⁺. Compound 204C: LC-MS (ESI) m/z: 517 [M+H]⁺. Compound 204D: LC-MS (ESI) m/z: 617 [M+H]⁺. Compound 204: LC-MS (ESI) m/z: 375 [M+H]⁺; ¹H-NMR (CD₃OD, 400 MHz): δ (ppm) 1.11 (d, J=6.8 Hz, 6H), 2.51-2.61 (m, 1H), 5.97 (s, 2H), 7.76-7.81 (m, 1H), 8.04-8.16 (m, 3H), 8.38-8.42 (m, 1H).

Reference Example 205

Synthesis of 4-(2,3-dihydrobenzo[b][1,4]dioxin-6-yl)-1H-1,2,3-triazole-5-carboxylic acid 2,2,2-trifluoroacetate (205)

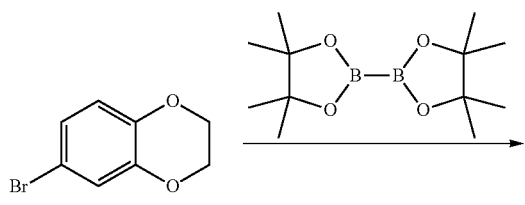
205A

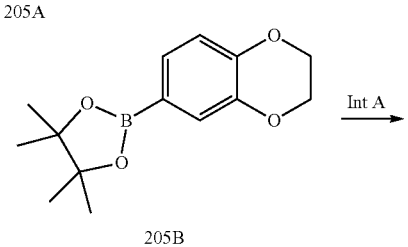
205B

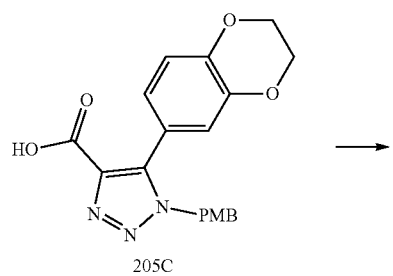
205C

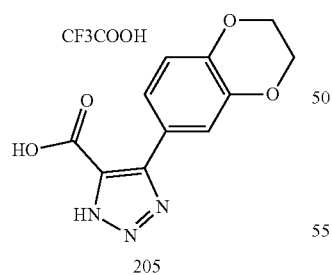
205

Compounds 205B, 205C, and 205 were synthesized by employing the procedures described for Compounds 27C, 4B, and 1 using Compounds 205A, Intermediate A, 205B with K₂CO₃ as base and 1,4-dioxane as solvent, and 205C in lieu of Compounds 27B, 4A, (4-bromophenyl)boronic acid with Na₂CO₃ as base and toluene/EtOH/H₂O as solvent, and 1E. Compound 205B: LC-MS: (ESI) m/z: 263 [M+H]⁺; ¹H-NMR (CDCl₃, 400 MHz): δ (ppm) 1.33 (s, 12H), 4.24-4.29 (m, 4H), 6.87 (d, J=8.0 Hz, 1H), 7.27-7.33 (m, 2H). Compound 205C: LC-MS (ESI) m/z: 368 [M+H]⁺; ¹H-NMR (DMSO-d₆, 400 MHz): δ (ppm) 3.69 (s, 3H), 4.26-4.30 (m, 4H), 5.36 (s, 2H), 6.78-6.84 (m, 3H), 6.88-6.95 (m, 4H), 12.82 (s, 1H). Compound 205: LC-MS (ESI) m/z: 248 [M+H]⁺; ¹H-NMR (DMSO-d₆, 400 MHz): δ (ppm) 4.23 (s, 4H), 6.81 (d, J=8.4 Hz, 1H), 7.74-7.76 (m, 1H), 7.96 (s, 1H).

Example 206

Synthesis of 4-(1-isopropyl-1,2,3,4-tetrahydroquinolin-6-yl)-1H-1,2,3-triazole-5-carboxylic acid 2,2,2-trifluoroacetate (206)

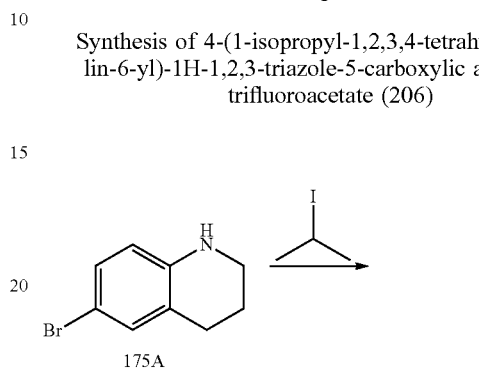
175A

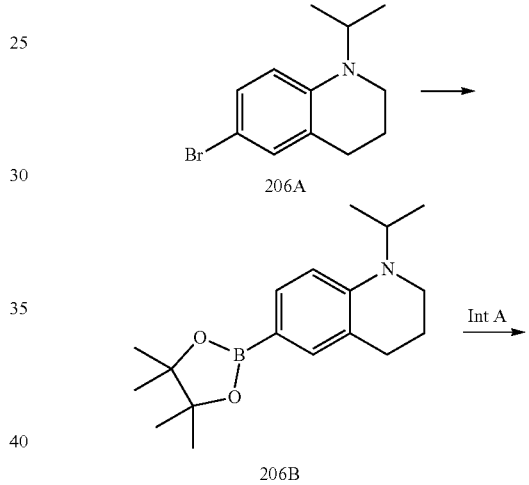
206A

206B

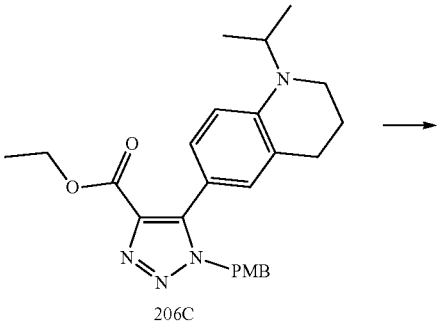
206C

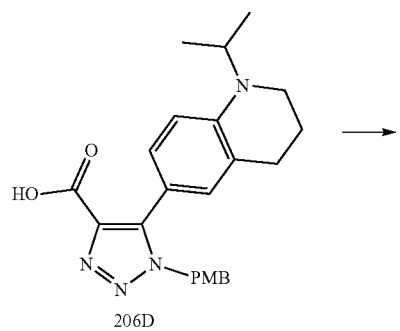
206D

-continued

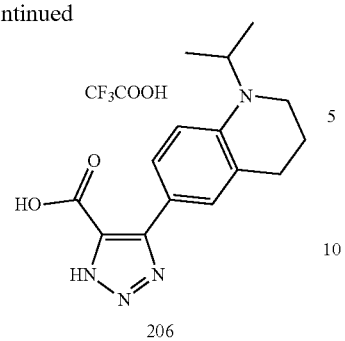

206

To a solution of 6-bromo-1,2,3,4-tetrahydroquinoline 175A (1.4 g, 6.6 mmol) in DMF (30 mL) was added Cs$_2$CO$_3$ (3.8 g, 11.7 mmol) and 2-iodopropane (7.5 g, 17.6 mmol). The mixture was stirred at 55° C. for 16 hours. After cooled down to room temperature, the mixture was diluted with water (200 mL) and extracted with ethyl acetate in petroleum ether (15% v/v) (200 mL×3). The combined organic phase was washed with bine (150 mL×4), dried over anhydrous sodium sulfate, concentrated, and purified with flash column chromatography on silica gel (petroleum ether) to furnish Compound 206A. LC-MS (ESI) m/z: 254 [M+H]$^+$.

Compound 206B was synthesized by employing the procedure described for Compound 27C using Compound 206A in lieu of Compound 27B, LC-MS (ESI) m/z: 302 [M+H]$^+$.

A mixture of Intermediate A (575 mg, 1.69 mmol), Pd(PPh$_3$)$_2$Cl$_2$ (387 mg, 0.55 mmol), Compound 206B (450 mg, 1.49 mmol), and Na$_2$CO$_3$ (473 mg, 4.46 mmol) in water (5 mL) and 1,4-dioxane (20 mL) was heated to 90° C. for 16 hours. The mixture was cooled down to room temperature, diluted with water (100 mL), and extracted with ethyl acetate (100 mL×2). The combined organic phases were dried over anhydrous sodium sulfate, concentrated, and purified with preparative HPLC to afford Compound 206C. LC-MS (ESI) m/z: 435 [M+H]$^+$.

Compounds 206D and 206 were synthesized by employing the procedures described for Compounds 8F and 1 using Compounds 206C and 206D in lieu of Compounds 8E and 1E. Compound 206D: LC-MS (ESI) m/z: 407 [M+H]$^+$. Compound 206: LC-MS (ESI) m/z: 287 [M+H]$^+$; $^1$H-NMR (DMSO-d$_6$, 400 MHz): δ (ppm) 1.26 (s, 3H), 1.28 (s, 3H), 1.98-2.04 (m, 2H), 2.84 (s, 2H), 3.39 (s, 2H), 4.21 (s, 1H), 7.05 (s, 1H), 7.59 (s, 1H), 7.67 (d, J=8.0 Hz, 1H).

Example 207

Synthesis of 4-(4,5-dichloropyridin-2-yl)-1H-1,2,3-triazole-5-carboxylic acid (207)

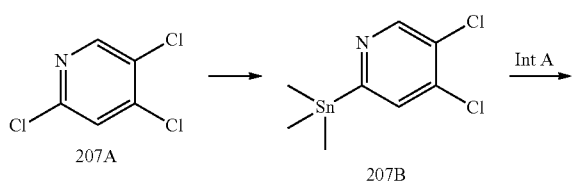

-continued

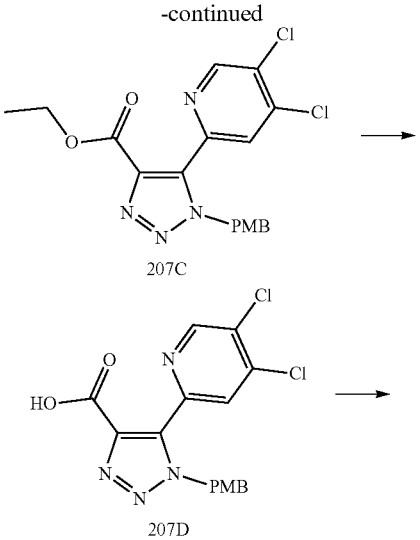

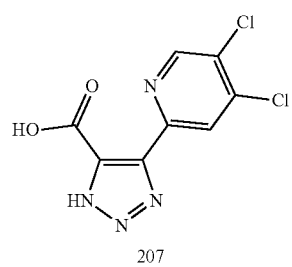

207

A mixture of 2,4,5-trichloropyridine 207A (600 mg, 3.28 mmol), 1,1,1,2,2,2-hexamethyldistannane (1.18 g, 3.61 mmol), and tetrakis(triphenylphosphine)palladium (379 mg, 0.328 mmol) in 1,4-dioxane (10 mL) was degassed with nitrogen, and then heated at 100° C. under nitrogen for 3 hours. The reaction mixture was concentrated to give a crude Compound 207B, which was used directly for next step without purification. LC-MS (ESI) m/z: 312 [M+H]$^+$.

To a solution of the crude Compound 207B in DMA (5 mL) was added Intermediate A (1.11 g, 3.28 mmol) and tetrakis(triphenylphosphine)palladium (379 mg, 0.328 mmol) and degassed with nitrogen, and then heated in a microwave reactor at 140° C. for 1 hour. The reaction mixture was quenched with a saturated KF solution (50 mL) and extracted with ethyl acetate (50 mL×3). The combined organic layers was washed with water (100 mL) and brine (100 mL), dried over anhydrous sodium sulfate, concentrated, and purified with flash column chromatography on silica gel (ethyl acetate in petroleum ether, 30% v/v) to afford Compound 207C. LC-MS (ESI) m/z: 407 [M+H]$^+$.

Compounds 207D and 207 were synthesized by employing the procedures described for Compounds 8F and 1 using Compounds 207C and 207D in lieu of Compounds 8E and 1E. Compound 207D: LC-MS (ESI) m/z: 379 [M+H]$^+$. Compound 207: LC-MS (ESI) m/z: 259 [M+H]$^+$; $^1$H-NMR (DMSO-d$_6$, 400 MHz): δ (ppm) 8.49 (s, 1H), 8.98 (s, 1H).

Example 208

Synthesis of 4-(5-chloropyridin-2-yl)-1H-1,2,3-triazole-5-carboxylic acid 2,2,2-trifluoroacetate (208)

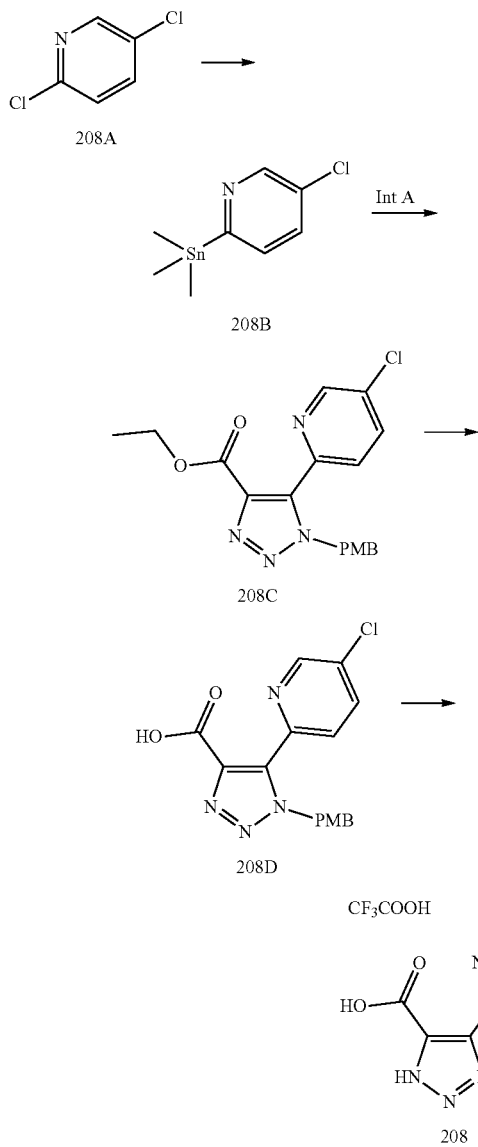

Example 209

Synthesis of 4-(4-(2-acetamidoethoxy)phenyl)-1H-1,2,3-triazole-5-carboxylic acid (209)

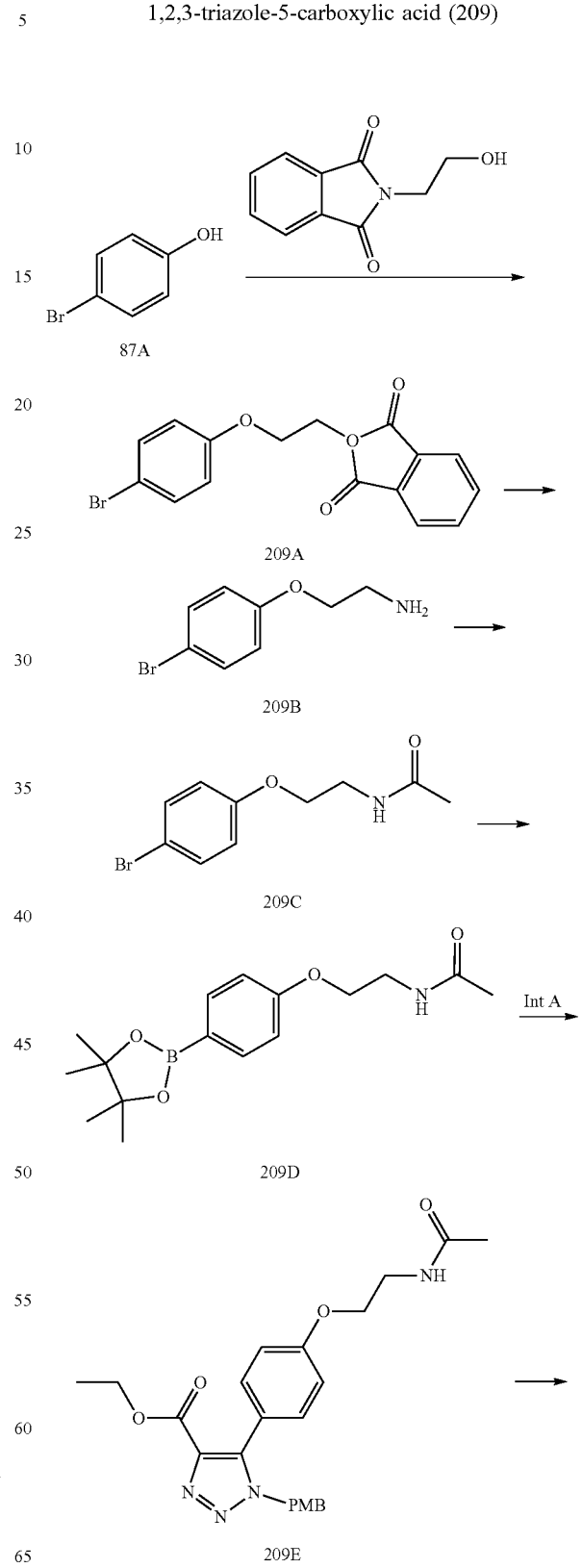

Compounds 208B, 208C, 208D, and 208 were synthesized by employing the procedures described for Compounds 207B, 207C, 8F, and 1 using Compounds 208A, 208B with 1,4-dioxane as solvent, 208C, and 208D in lieu of Compounds 207A, 207B with DMA as solvent, 8E, and 1E. Compound 208C: LC-MS (ESI) m/z: 373 [M+H]⁺. Compound 208D: LC-MS (ESI) m/z: 345 [M+H]⁺. Compound 208: LC-MS (ESI) m/z: 225 [M+H]⁺; ¹H-NMR (DMSO-d₆, 400 MHz): δ (ppm) 8.22-8.32 (m, 2H), 8.87 (s, 1H).

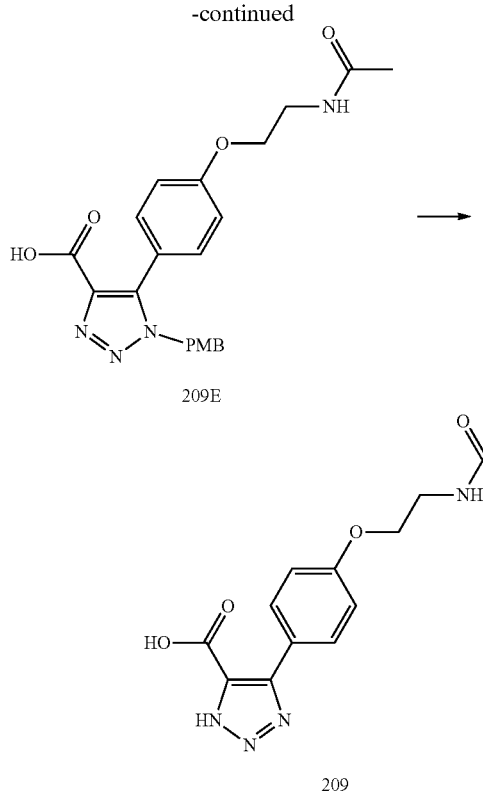

209E

209

Compounds 209A and 209B were synthesized by employing the procedures described for Compounds 90C and 190F using 2-(2-hydroxyethyl)isoindoline-1,3-dione, Compounds 87A with DEAD as coupling reagent, and 209A with EtOH as solvent in lieu of Compounds 90B, Intermediate H with DIAD as coupling reagent, and 190E with MeOH/H₂O as solvent. Compound 209A: LC-MS (ESI) m/z: 346 [M+H]⁺; ¹H-NMR (CDCl₃, 400 MHz): δ (ppm) 4.07-4.13 (m, 2H), 4.18-4.21 (m, 2H), 6.73-6.76 (m, 2H), 7.31-7.34 (m, 2H), 7.72-7.74 (m, 2H), 7.85-7.87 (m, 2H). Compound 209B: LC-MS (ESI) m/z: 216 [M+H]⁺.

To a solution of Compound 209B (541 mg, 2.65 mmol) in dichloromethane (20 mL) was added Et₃N (802 mg, 7.95 mmol) and acetic anhydride (541 mg, 5.3 mmol) and stirred at room temperature for 16 hours. The reaction mixture was concentrated under reduced pressure. The residue was diluted with EtOAc (50 mL), washed with diluted HCl solution (1N, 30 mL) and saturated NaHCO₃ solution (50 mL) and brine (50 mL), dried over anhydrous sodium sulfate, filtered, and concentrated to give Compound 209C. LC-MS (ESI) m/z: 258 [M+H]⁺; ¹H-NMR (CDCl₃, 400 MHz): δ (ppm) 2.04 (s, 3H), 3.65 (t, J=4.8 Hz, 2H), 4.00 (t, J=4.8 Hz, 2H), 5.97 (b, 1H), 6.75-6.79 (m, 2H), 7.35-7.39 (m, 2H).

Compounds 209D, 209E, 209F, and 209 were synthesized by employing the procedures described for Compounds 27C, 4B, 8F, and 1 using Compounds 209C, Intermediate A, 209D with K₂CO₃ as base and 1,4-dioxane as solvent, 209E, and 209F in lieu of Compounds 27B, 4A, (4-bromophenyl)boronic acid with Na₂CO₃ as base and toluene/EtOH/H₂O as solvent, 8E, and 1E. Compound 209D: LC-MS (ESI) m/z: 306 [M+H]⁺. Compound 209E: LC-MS (ESI) m/z: 439 [M+H]⁺. Compound 209F: LC-MS (ESI) m/z: 411 [M+H]⁺. Compound 209: LC-MS (ESI) m/z: 291 [M+H]⁺; ¹H-NMR (DMSO-d₆, 400 MHz): δ (ppm) 1.83 (s, 3H), 3.42 (q, J=5.6 Hz, 2H), 4.04 (t, J=5.7 Hz, 2H), 7.04 (d, J=8.5 Hz, 2H), 7.77 (s, 2H), 8.12 (s, 1H), 12.97 (s, 1H), 15.69 (s, 1H).

Example 210

Synthesis of 4-(7-fluoroisoquinolin-3-yl)-1H-1,2,3-triazole-5-carboxylic acid 2,2,2-trifluoroacetate (210)

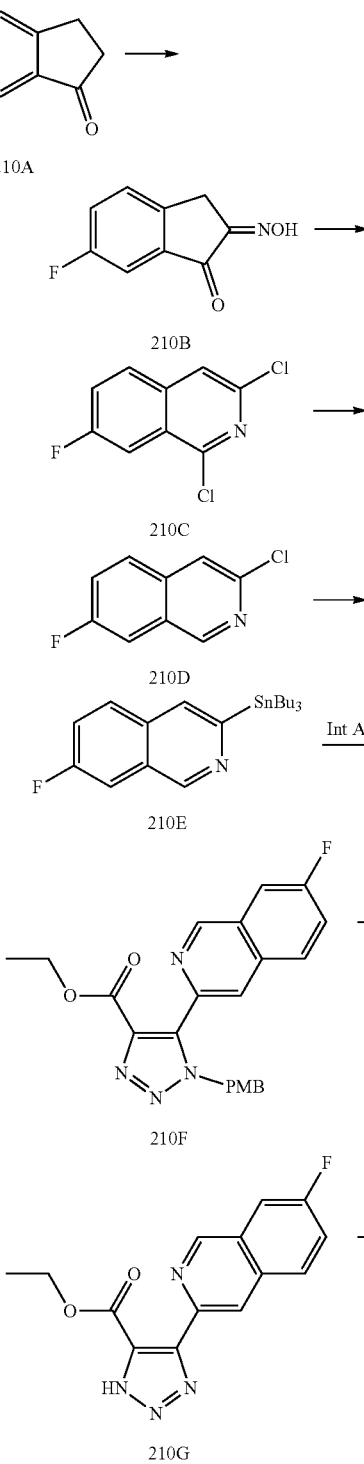

413
-continued

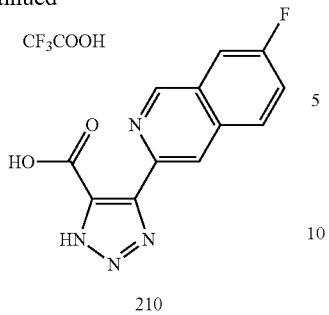

210

To a solution of 6-fluoro-2,3-dihydro-1H-inden-1-one (210A) (3.0 g, 20 mmol) in ether (20 mL) was added a solution of HCl in 1,4-dioxane (4M, 7.5 ml, 30 mmol), followed by dropping isopentyl nitrite (3.5 g, 30 mmol) at 0° C. The mixture was stirred at room temperature for 3 hours and concentrated under reduced pressure. The residue was washed with petroleum ether (50 ml) to afford Compound 210B. LC-MS (ESI) m/z: 180 [M+H]$^+$. $^1$H-NMR (DMSO-d$_6$, 400 MHz): δ (ppm) 3.76 (s, 2H), 7.50 (s, 1H), 7.51-7.68 (m, 2H), 12.74 (s, 1H).

A mixture of Compound 210B (2.5 g, 14 mmol) and PCl$_5$ (4.3 g, 21 mmol) in POCl$_3$ (20 mL) was stirred at 80° C. overnight. After cooled down to room temperature, the mixture was concentrated under reduced pressure to give a crude Compound 210C. LC-MS (ESI) m/z: 216 [M+H]$^+$.

To a solution of Compound 210C (3.0 g, 14 mmol) in acetic acid (10 mL) was added 55% aqueous HI solution (5 mL) and stirred at 100° C. for 16 hours. The mixture was concentrated under reduced pressure. The residue was diluted with saturated NaHCO$_3$ solution (100 mL), extracted with ethyl acetate (50 mL×3), washed with water (50 mL) and brine (50 mL), dried over anhydrous sodium sulfate, concentrated, and purified with flash column chromatography on silica gel (ethyl acetate in petroleum ether, from 0% to 10% v/v) to afford Compound 210D. LC-MS (ESI) m/z: 182 [M+H]$^+$; $^1$H-NMR (CDCl$_3$, 400 MHz): δ (ppm) 7.52-7.55 (m, 1H), 7.58-7.61 (m, 1H), 7.75 (s, 1H), 7.78-7.82 (m, 1H), 9.05 (s, 1H).

Compounds 210E, 210F, 210G, and 210 were synthesized by employing the procedures described for Compounds 207B, 207C, 1, and 8F using tributyltin hydride, Compounds 210D with xylene as solvent at 135° C., 210E with xylene as solvent, 210F, and 210G in lieu of 1,1,1,2,2,2-hexamethyldistannane, Compounds 207A with 1,4-dioxane as solvent at 100° C., 207B with DMA as solvent, 1E, and 8E. Compound 210E: LC-MS (ESI) m/z: 438 [M+H]$^+$. Compound 210F: LC-MS (ESI) m/z: 407 [M+H]$^+$; $^1$H-NMR (CDCl$_3$, 400 MHz): δ (ppm) 1.33 (t, J=7.2 Hz, 3H), 3.67 (s, 3H), 4.36 (q, J=7.2 Hz, 2H), 5.81 (s, 2H), 6.61-6.64 (m, 2H), 6.92 (d, J=8.8 Hz, 2H), 7.55-7.57 (m, 1H), 7.67-7.69 (m, 1H), 7.87-7.90 (m, 1H), 8.03 (s, 1H), 9.34 (s, 1H). Compound 210G: LC-MS (ESI) m/z: 287 [M+H]$^+$. Compound 210: LC-MS (ESI) m/z: 259 [M+H]$^+$; $^1$H-NMR (DMSO-d$_6$, 400 MHz): δ (ppm) 7.92-7.94 (m, 1H), 8.10-8.13 (m, 1H), 8.39 (s, 1H), 8.95 (s, 1H), 9.57 (s, 1H).

414

Example 211

Synthesis of 4-(6-(trifluoromethoxy)isoquinolin-3-yl)-1H-1,2,3-triazole-carboxylic acid (211)

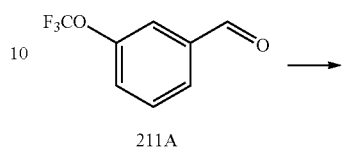
211A

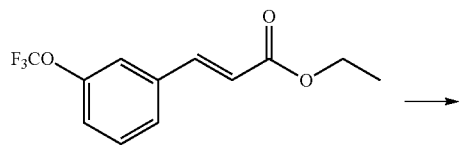
211B

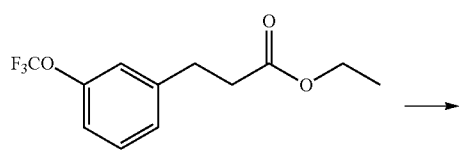
211C

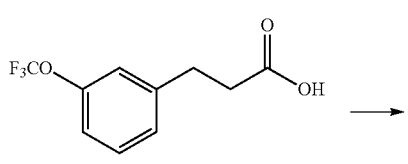
211D

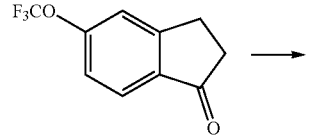
211E

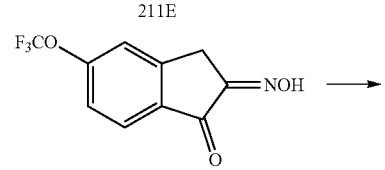
211F

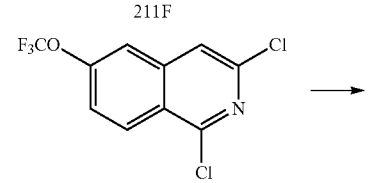
211G

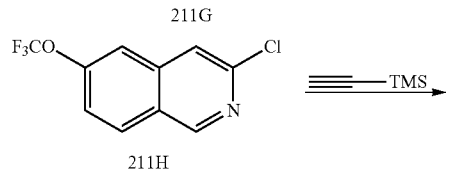
211H

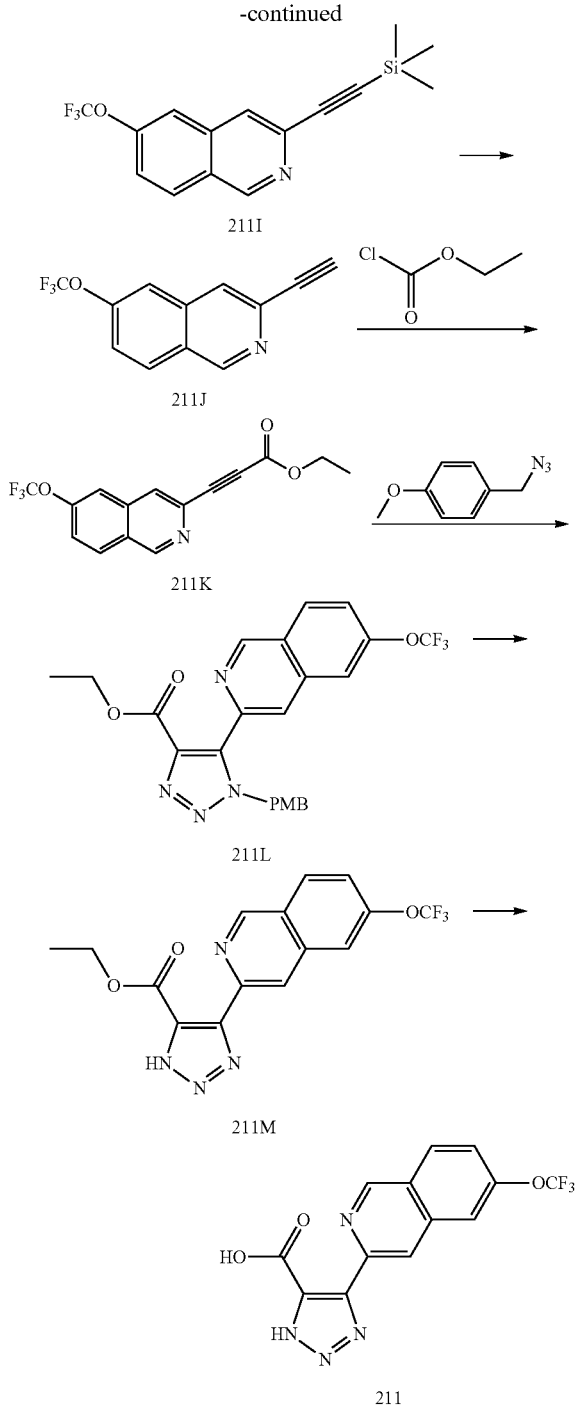

m/z: 261 [M+H]⁺; ¹H-NMR (CDCl₃, 400 MHz): δ (ppm) 1.34 (t, J=7.2 Hz, 3H), 4.27 (q, J=7.2 Hz, 2H), 6.45 (d, J=16.4 Hz, 1H), 7.22-7.24 (m, 1H), 7.36-7.43 (m, 3H), 7.65 (d, J=16.4 Hz, 1H).

To a solution of Compound 211B (6.5 g, 25 mmol) in EtOH (100 mL) was added Pd/C (10%, 1.0 g) and stirred at room temperature under hydrogen (1 atm) for 12 hours. The mixture was filtered through Celite and the filtrate was concentrated to give a crude Compound 211C. LC-MS (ESI) m/z: 263 [M+H]⁺.

Compound 211D was synthesized by employing the procedure described for Compound 2 using Compound 211C with MeOH/H₂O as solvent in lieu of Compound 1 with THF/H₂O as solvent, LC-MS (ESI) m/z: 235 [M+H]⁺; ¹H-NMR (CDCl₃, 400 MHz): δ (ppm) 2.69 (t, J=7.2 Hz, 2H), 2.97 (t, J=7.2 Hz, 2H), 7.06-7.08 (m, 1H), 7.13-7.15 (m, 2H), 7.29-7.33 (m, 1H), 9.93 (s, 1H).

The mixture of Compound 211D (8.5 g, 36 mmol) in PPA (30 mL) was stirred at 80° C. for 12 hours. The mixture was quenched with ice-water (100 mL), adjusted to pH 8 with saturated NaHCO₃ solution, and extracted with ethyl acetate (100 mL×3). The combined organic layers was dried over anhydrous sodium sulfate, filtered, concentrated, and purified with flash column chromatography on silica gel (ethyl acetate in petroleum ether, 20% v/v) to afford Compound 211E. LC-MS (ESI) m/z: 217 [M+H]⁺; ¹H-NMR (CDCl₃, 500 MHz): δ (ppm) 2.73-2.76 (m, 2H), 3.17-3.19 (m, 2H), 7.21 (dd, J=7.2, 2.0 Hz, 1H), 7.28 (d, J=2.0 Hz, 1H), 7.79 (d, J=7.2 Hz, 1H).

Compounds 211F, 211G, and 211H were synthesized by employing the procedures described for Compounds 210B, 210C, and 210D using Compounds 211E, 211F, and 211G in lieu of Compounds 210A, 210B, and 210C. Compound 211F: LC-MS (ESI) m/z: 246 [M+H]⁺. Compound 211G: LC-MS (ESI) m/z: 282 [M+H]⁺. Compound 211H: LC-MS (ESI) m/z: 248 [M+H]⁺; ¹H-NMR (CD₃OD, 400 MHz): δ (ppm) 7.46 (dd, J=8.8, 1.6 Hz, 1H), 7.71 (s, 1H), 7.86 (s, 1H), 8.14 (d, J=8.8 Hz, 1H), 9.04 (s, 1H).

To a mixture of Compound 211H (1.5 g, 6.1 mmol) and bis(triphenylphosphine)palladium(II) chloride (428 mg, 0.61 mmol) in triethylamine (3 mL) was added CuI (116 mg, 0.61 mmol) and heated in a sealed tube at 80° C. under nitrogen for 12 hours. After cooled down to room temperature, the mixture was concentrated under reduced pressure. The residue was diluted with ethyl acetate (50 mL), washed with water (50 mL) and brine (50 mL), dried over anhydrous sodium sulfate, filtered, concentrated, and purified with flash column chromatography on silica gel (ethyl acetate in petroleum ether, 20% v/v) to afford a crude Compound 211I, which was used directly in next step without further purification. LC-MS (ESI) m/z: 310 [M+H]⁺.

To a solution of Compound 211I (1.0 g, 3.2 mmol) in MeOH (20 mL) and water (2 mL) was added KOH (896 mg, 16 mmol) and stirred at room temperature for 4 hours. The reaction mixture was adjusted to pH 6 with diluted aqueous HCl solution and extracted with ethyl acetate (100 mL×3). The combined organic layers was dried over anhydrous sodium sulfate, filtered, concentrated, and purified with flash column chromatography on silica gel (ethyl acetate in petroleum ether, 20% v/v) to afford Compound 211J. LC-MS (ESI) m/z: 238 [M+H]⁺.

To a solution of ethyl 2-(diethoxyphosphoryl)acetate (5.0 g, 26.3 mmol) in THF (50 mL) was added NaH (60% suspension in oil, 1.26 g, 31.6 mmol) at 0° C. After the mixture was stirred at 0° C. for 10 minutes, a solution of 3-(trifluoromethoxy)benzaldehyde (211A) (7.1 g, 31.6 mmol) in THF (30 mL) was added. The resulting mixture was stirred at room temperature for 12 hours, quenched with H₂O (50 mL), and extracted with ethyl acetate (100 mL×3). The combined organic layers was dried over anhydrous sodium sulfate, concentrated, and purified with flash column chromatography on silica gel (ethyl acetate in petroleum ether, 20% v/v) to afford Compound 211B. LC-MS (ESI)

To a solution of Compound 211J (480 mg, 2 mmol) in THF (50 mL) at −78° C. under nitrogen was dropped a solution of n-BuLi in n-hexane (2.5 M, 1.6 mL, 4 mmol) and stirred at −78° C. for 15 minutes, followed by addition of ethyl carbonochloridate (1 mL, 10.5 mmol) dropwise. The mixture was stirred at −78° C. for 1.5 hours, quenched with saturated aqueous NH₄Cl solution (50 mL), and extracted with ethyl acetate (50 mL×3). The combined organic layers was washed with brine (100 mL), dried over anhydrous Na₂SO₄, filtered, concentrated, and purified with flash column chromatography on silica gel (ethyl acetate in petroleum ether, 20% v/v) to furnish Compound 211K. LC-MS (ESI) m/z: 310 [M+H]⁺; ¹H-NMR (CDCl₃, 400 MHz): δ (ppm) 1.29 (t, J=7.2 Hz, 3H), 4.26 (q, J=7.2 Hz, 2H), 7.45-7.57 (m, 2H), 7.96-8.01 (m, 2H), 9.19 (s, 1H).

Compounds 211L, 211M, and 211 were synthesized by employing the procedures described for Mixture of 166E-1 and 166E-2, Compounds 1, and 8F using Compounds 211K with EtOH as solvent at reflux, 211L, and 211M in lieu of Compounds 166D with THF as solvent at 60° C., 1E, and 8E. Compound 211L: LC-MS (ESI) m/z: 473 [M+H]⁺. Compound 211M: LC-MS (ESI) m/z: 353 [M+H]⁺. Compound 211: LC-MS (ESI) m/z: 325 [M+H]⁺; ¹H-NMR (DMSO-d₆, 400 MHz): δ (ppm) 7.82 (d, J=8.8 Hz, 1H), 8.33 (s, 1H), 8.48 (d, J=8.8 Hz, 1H), 8.99 (s, 1H), 9.67 (s, 1H).

Example 212

Synthesis of 4-(5,6,7,8-tetrahydroquinolin-2-yl)-1H-1,2,3-triazole-5-carboxylic acid (212)

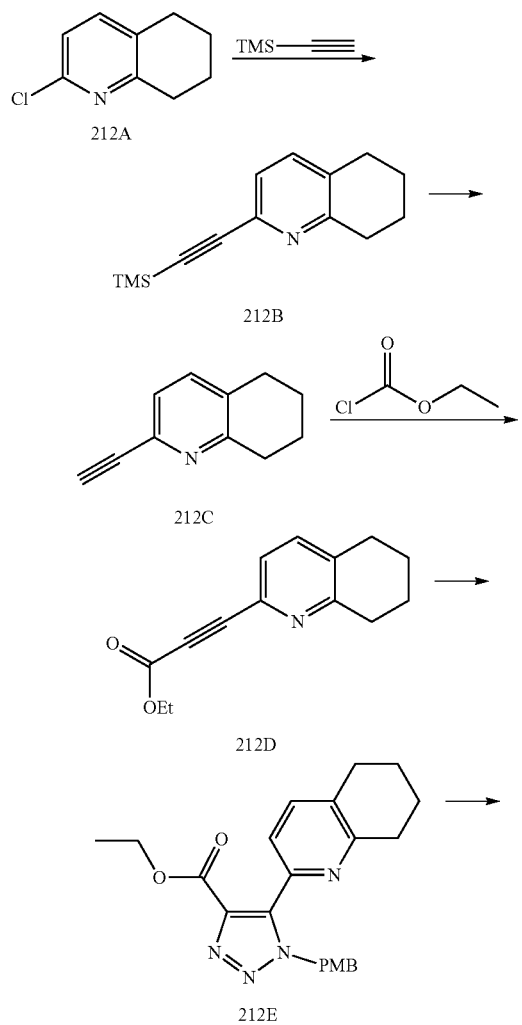

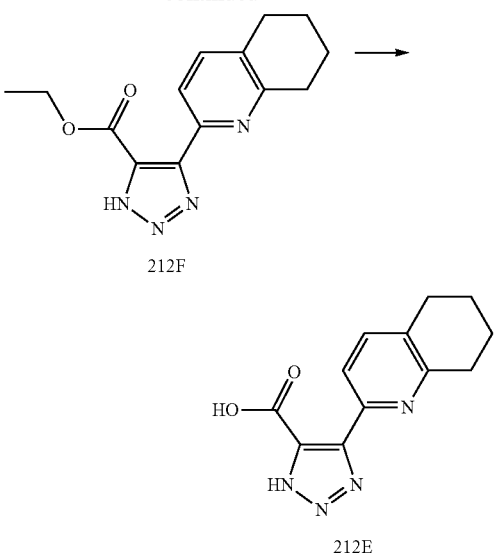

Compounds 212B, 212C, 212D, 212E, 212F, and 212 were synthesized by employing the procedures described for Compounds 211I, 211J, 211K, Mixture of 166E-1 and 166E-2, Compounds 1, and 8F using Compounds 212A, 212B, 212C, 212D with EtOH as solvent at reflux, 212E, and 212F in lieu of Compounds 211H, 211I, 211J, 166D with THF as solvent at 60° C., 1E, and 8E. Compound 212B: LC-MS (ESI) m/z: 230 [M+H]⁺. Compound 212C: LC-MS (ESI) m/z: 158 [M+H]⁺; ¹H-NMR (CDCl₃, 400 MHz): δ (ppm) 1.79-1.90 (m, 4H), 2.77 (t, J=6.4 Hz, 2H), 2.92 (t, J=6.4 Hz, 2H), 3.07 (s, 1H), 7.21 (d, J=8.0 Hz, 1H), 7.31 (d, J=8.0 Hz, 1H). Compound 212D: LC-MS (ESI) m/z: 230 [M+H]⁺. Compound 212E: LC-MS (ESI) m/z: 393 [M+H]⁺. Compound 212F: LC-MS (ESI) m/z: 273 [M+H]⁺. Compound 212: LC-MS (ESI) m/z: 245 [M+H]⁺; ¹H-NMR (DMSO-d₆, 400 MHz): δ (ppm) 1.77-1.88 (m, 4H), 2.77-2.88 (m, 4H), 7.78 (d, J=8.0 Hz, 1H), 8.07 (d, J=8.4 Hz, 1H).

Example 213

Synthesis of 4-(6-fluoroisoquinolin-3-yl)-1H-1,2,3-triazole-5-carboxylic acid 2,2,2-trifluoroacetate (213)

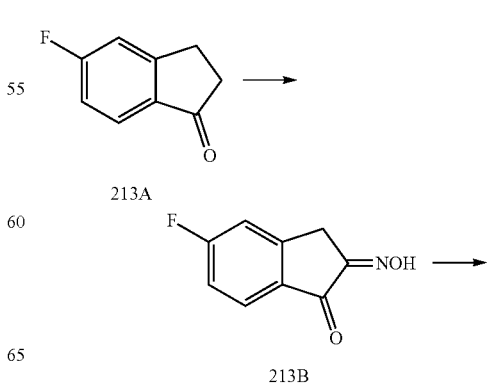

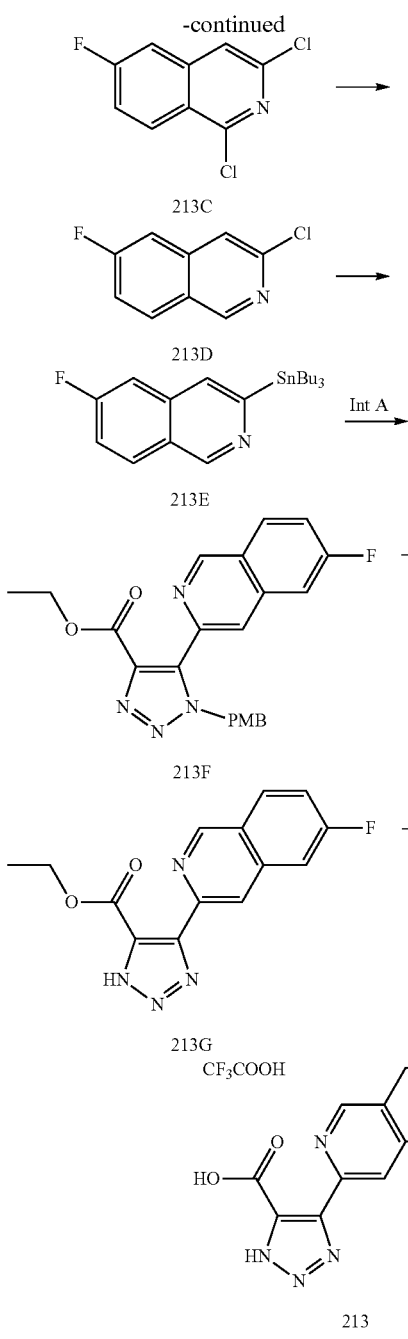

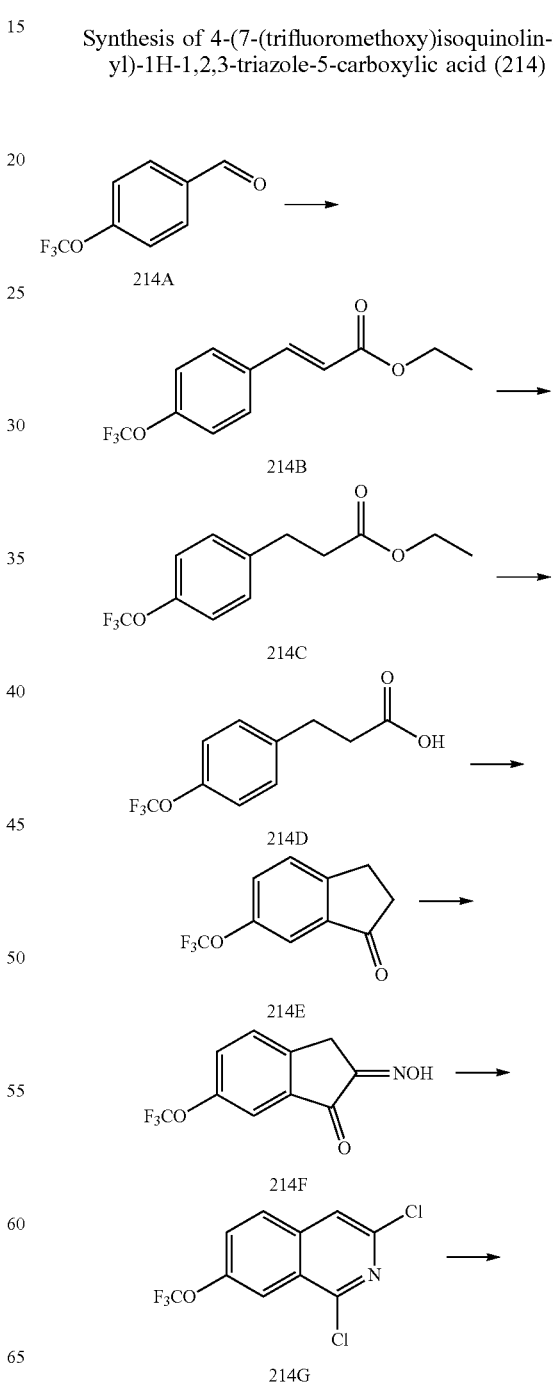

Compounds 213B, 213C, 213D, 213E, 213F, 213G, and 213 were synthesized by employing the procedures described for Compounds 210B, 210C, 210D, 207B, 207C, 1, and 8F using Compounds 213A, 213B, 213C, tributyltin hydride, 213D with xylene as solvent at 135° C., 213E with xylene as solvent, 213F, and 213G in lieu of Compounds 210A, 210B, 210C, 1,1,1,2,2,2-hexamethyldistannane, 207A with 1,4-dioxane as solvent, 207B with DMA as solvent, 8E, and 1E. Compound 210B: LC-MS (ESI) m/z: 180 [M+H]$^+$; $^1$H-NMR (DMSO-d$_6$, 400 MHz): δ (ppm) 3.87 (s, 2H), 7.15-7.22 (m, 2H), 7.91-7.94 (m, 1H), 8.88 (s, 1H). Compound 210C: LC-MS (ESI) m/z: 216 [M+H]$^+$. Compound 210D: LC-MS (ESI) m/z: 182 [M+H]$^+$; $^1$H-NMR (CD$_3$OD, 400 MHz): δ (ppm) 7.48-7.53 (m, 1H), 7.58-7.61 (m, 1H), 7.90 (s, 1H), 8.18-8.22 (m, 1H), 9.09 (s, 1H).

Compound 210E: LC-MS (ESI) m/z: 438 [M+H]$^+$. Compound 210F: LC-MS (ESI) m/z: 407 [M+H]$^+$; $^1$H-NMR (CDCl$_3$, 400 MHz): δ (ppm) 1.33 (t, J=7.2 Hz, 3H), 3.68 (s, 3H), 4.36 (q, J=7.2 Hz, 2H), 5.81 (s, 2H), 6.62-6.64 (m, 2H), 6.91 (d, J=8.8 Hz, 2H), 7.45-7.51 (m, 2H), 7.97 (s, 1H), 8.07-8.11 (m, 1H), 9.35 (s, 1H). Compound 210G: LC-MS (ESI) m/z: 287 [M+H]$^+$. Compound 210: LC-MS (ESI) m/z: 259 [M+H]$^+$; $^1$H-NMR (DMSO-d$_6$, 400 MHz): δ (ppm) 7.61-7.80 (m, 1H), 8.10-8.12 (m, 1H), 8.42-8.46 (m, 1H), 8.95 (s, 1H), 9.63 (s, 1H).

Example 214

Synthesis of 4-(7-(trifluoromethoxy)isoquinolin-3-yl)-1H-1,2,3-triazole-5-carboxylic acid (214)

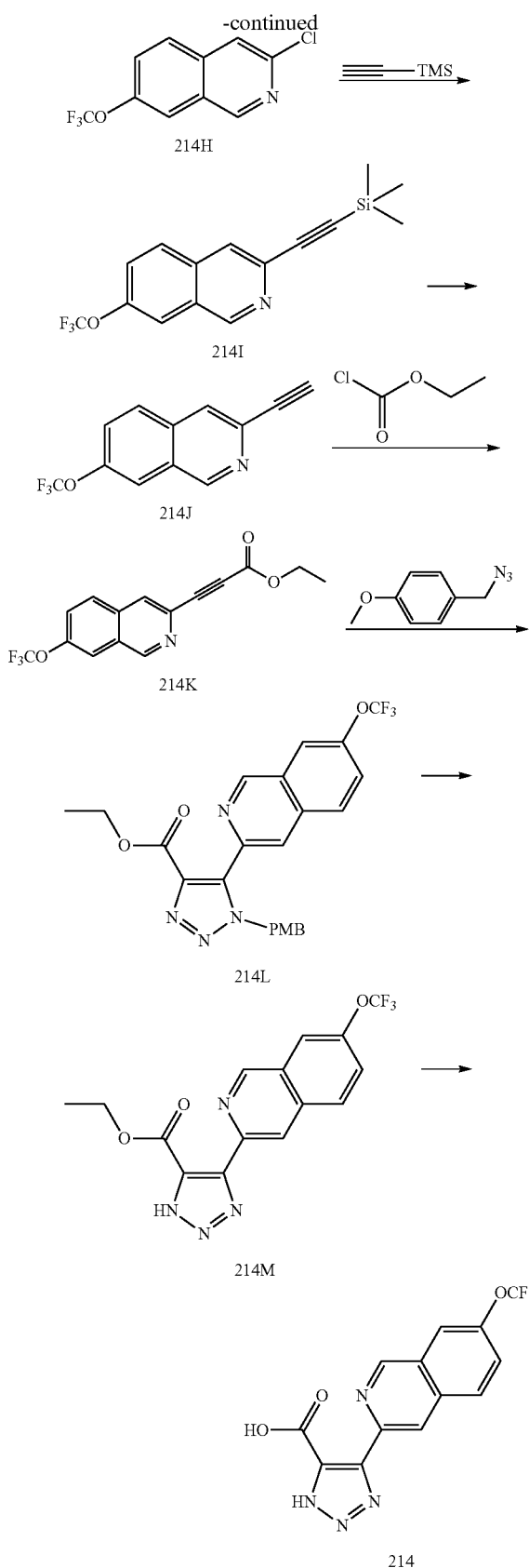

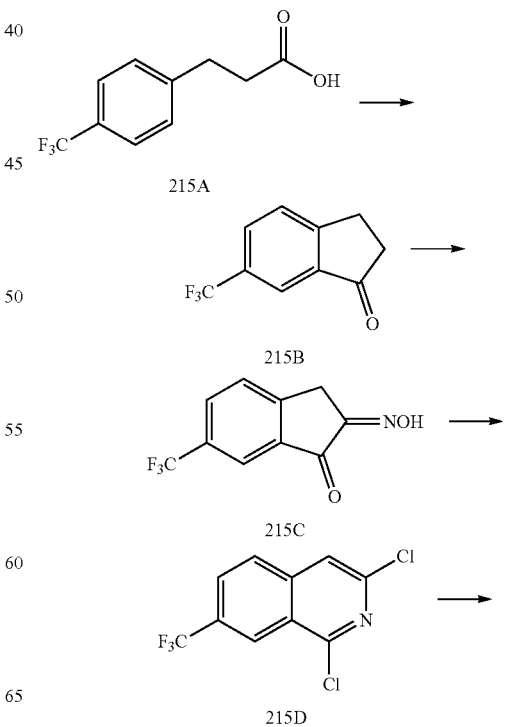

thesized by employing the procedures described for Compounds 211B, 211C, 2, 211E, 210B, 210C, 210D, 211I, 211J, 211K, Mixture of 166E-1 and 166E-2, 1, and 8F using Compounds 214A, 214B, 214C with MeOH/H$_2$O as solvent, 214D, 214E, 214F, 214G, 214H, 214I, 214J, 214K with EtOH as solvent at reflux, 214L, and 214M in lieu of Compounds 211A, 211B, 1 with THF/H$_2$O as solvent, 211D, 210A, 210B, 210C, 211H, 211I, 211J, 166D with THF as solvent at 60° C., 1E, and 8E. Compound 214B: LC-MS (ESI) m/z: 261 [M+H]$^+$; $^1$H-NMR (CDCl$_3$, 400 MHz): δ (ppm) 1.34 (t, J=7.2 Hz, 3H), 4.27 (q, J=7.2 Hz, 2H), 6.41 (d, J=16.0 Hz, 1H), 7.21-7.23 (m, 2H), 7.54-7.56 (m, 2H), 7.65 (d, J=16.0 Hz, 1H). Compound 214C: LC-MS (ESI) m/z: 263 [M+H]$^+$. Compound 214D: LC-MS (ESI) m/z: 235 [M+H]$^+$. Compound 214E: LC-MS (ESI) m/z: 217 [M+H]$^+$; $^1$H-NMR (CDCl$_3$, 400 MHz): δ (ppm) 2.68-2.70 (m, 2H), 3.07-3.10 (m, 2H), 7.34-7.37 (m, 1H), 7.44 (d, J=8.0 Hz, 1H), 7.52 (s, 1H). Compound 214F: LC-MS (ESI) m/z: 246 [M+H]$^+$. Compound 214G: LC-MS (ESI) m/z: 282 [M+H]$^+$. Compound 214H: LC-MS (ESI) m/z: 248 [M+H]$^+$; $^1$H-NMR (CD$_3$OD, 400 MHz): δ (ppm) 7.59-7.61 (m, 1H), 7.85 (s, 1H), 7.90-7.94 (m, 2H), 9.05 (s, 1H). Compound 214I: LC-MS (ESI) m/z: 310 [M+H]$^+$. Compound 214J: LC-MS (ESI) m/z: 238 [M+H]$^+$. Compound 214K: LC-MS (ESI) m/z: 310 [M+H]$^+$. Compound 214L: LC-MS (ESI) m/z: 473 [M+H]$^+$. Compound 214M: LC-MS (ESI) m/z: 353 [M+H]$^+$. Compound 214: LC-MS (ESI) m/z: 325 [M+H]$^+$; $^1$H-NMR (DMSO-d$_6$, 500 MHz): δ (ppm) 7.97 (s, 1H), 8.35-8.43 (m, 2H), 8.97 (s, 1H), 9.65 (s, 1H).

Example 215

Synthesis of 4-(7-(trifluoromethyl)isoquinolin-3-yl)-1H-1,2,3-triazole-5-carboxylic acid (215)

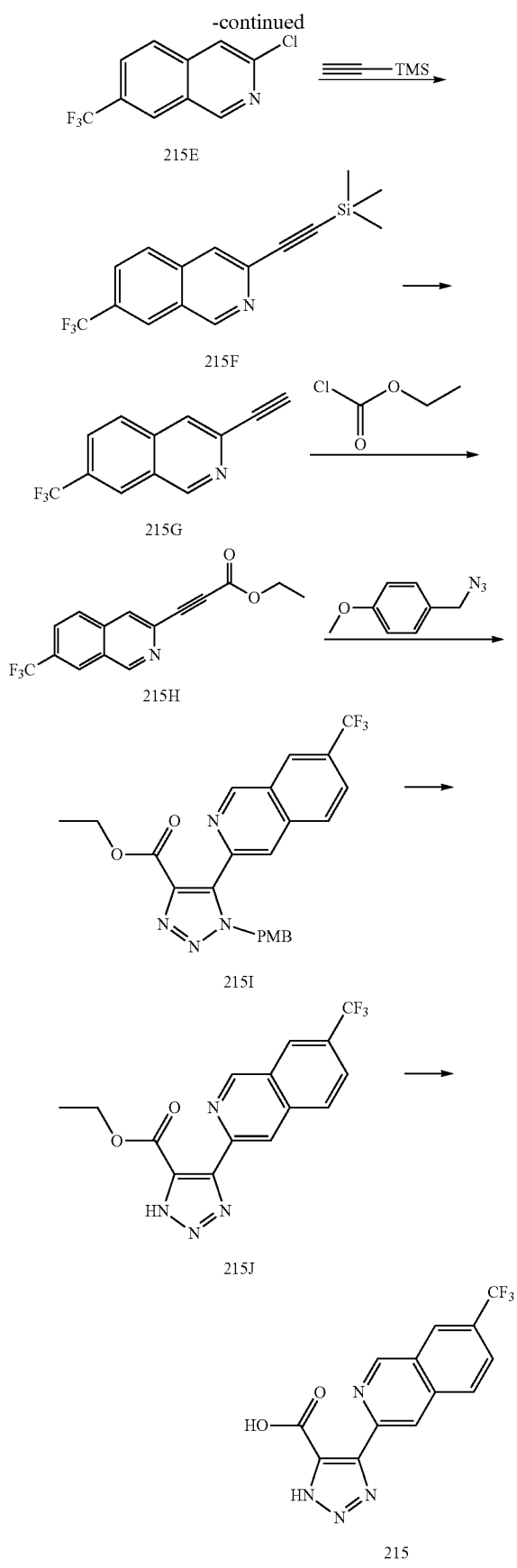

Compounds 215B, 215C, 215D, 215E, 215F, 215G, 215H, 215I, 215J, and 215 were synthesized by employing the procedures described for Compounds 211E, 210B, 210C, 210D, 211I, 211J, 211K, Mixture of 166E-1 and 166E-2, 1, and 8F using Compounds 215A, 215B, 215C, 215D, 215E, 215F, 215G, 215H with EtOH as solvent at reflux, 215I, and 215J in lieu of Compounds 211D, 210A, 210B, 210C, 211H, 211I, 211J, 166D with THF as solvent at 60° C., 1E, and 8E. Compound 215B: LC-MS (ESI) m/z: 201 [M+H]$^+$; $^1$H-NMR (CDCl$_3$, 400 MHz): δ (ppm) 2.77-2.80 (m, 2H), 3.22-3.25 (m, 2H), 7.63 (d, J=8.0 Hz, 1H), 7.84 (dd, J=8.0, 1.2 Hz, 1H), 8.04 (s, 1H). Compound 215C: LC-MS (ESI) m/z: 230 [M+H]$^+$; $^1$H-NMR (CDCl$_3$, 400 MHz): δ (ppm) 3.96 (s, 2H), 7.70 (d, J=8.0 Hz, 1H), 7.93 (d, J=8.0 Hz, 1H), 8.18 (s, 1H). Compound 215D: LC-MS (ESI) m/z: 266 [M+H]$^+$. Compound 215E: LC-MS (ESI) m/z: 232 [M+H]$^+$. Compound 215F: LC-MS (ESI) m/z: 294 [M+H]$^+$; $^1$H-NMR (CDCl$_3$, 500 MHz): δ (ppm) 3.32 (s, 9H), 7.89-7.96 (m, 3H), 8.30 (s, 1H), 9.33 (s, 1H). Compound 215G: LC-MS (ESI) m/z: 222 [M+H]$^+$. Compound 215H: LC-MS (ESI) m/z: 294 [M+H]$^+$; $^1$H-NMR (CDCl$_3$, 400 MHz): δ (ppm) 1.38 (t, J=7.2 Hz, 3H), 4.35 (q, J=7.2 Hz, 2H), 7.91-8.01 (m, 2H), 8.12 (s, 1H), 8.32 (d, J=12 Hz, 1H), 9.35 (d, J=13.6 Hz, 1H). Compound 215I: LC-MS (ESI) m/z: 457 [M+H]$^+$; $^1$H-NMR (CDCl$_3$, 400 MHz): δ (ppm) 1.34 (t, J=7.2 Hz, 3H), 3.68 (s, 3H), 4.38 (q, J=7.2 Hz, 2H), 5.85 (s, 2H), 6.62-6.64 (m, 2H), 6.90-6.94 (m, 2H), 7.92-7.99 (m, 2H), 8.11 (s, 1H), 8.39 (s, 1H), 9.50 (s, 1H). Compound 215J: LC-MS (ESI) m/z: 337 [M+H]$^+$. Compound 215: LC-MS (ESI) m/z: 309 [M+H]$^+$. $^1$H-NMR (DMSO-d$_6$, 400 MHz): δ (ppm) 8.20 (d, J=8.0 Hz, 1H), 8.46 (s, 1H), 8.80 (s, 1H), 8.98 (d, J=11.2 Hz, 1H), 9.74 (s, 1H).

Example 216

Synthesis of 4-(7-chloroquinolin-3-yl)-1H-1,2,3-triazole-5-carboxylic acid 2,2,2-trifluoroacetate (216)

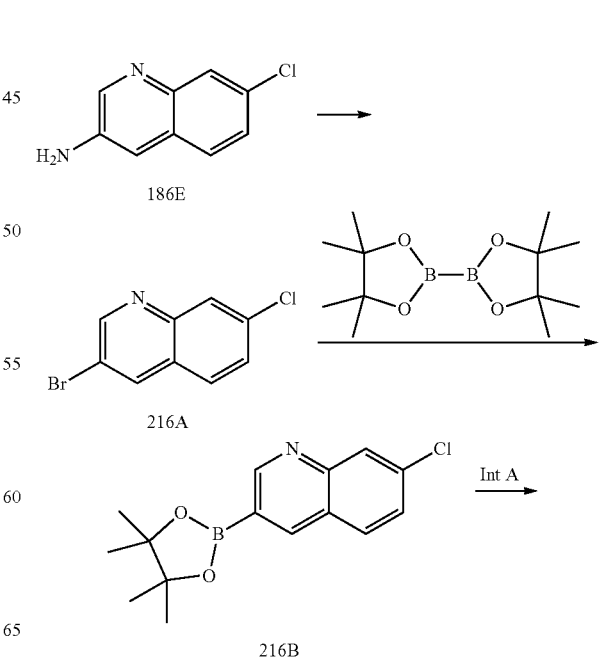

-continued

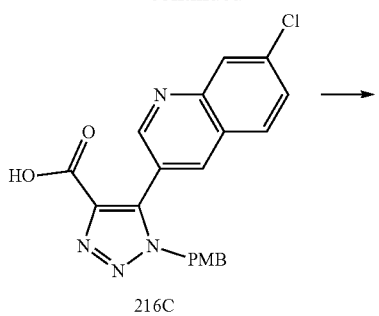
216C

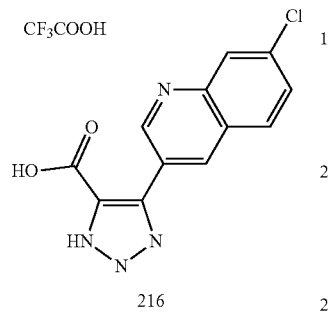
216

Compounds 216A, 216B, 216C, and 216 were synthesized by employing the procedures described for Compounds 30B, 27C, 4B, and 1 using Compounds 186E with tert-butyl nitrite and CuBr₂ and 1,2-dibromoethane as solvent, 216A, Intermediate A, 216B with K₂CO₃ as base and 1,4-dioxane/H₂O as solvent, and 216C in lieu of Compounds 30A with isoamyl nitrite and CuCl₂ and MeCN as solvent, 27B, 4A, (4-bromophenyl)boronic acid with Na₂CO₃ as base and toluene/EtOH/H₂O as solvent, and 1E. Compound 216A: LC-MS (ESI) m/z: 241 [M+H]$^+$; $^1$H-NMR (CDCl₃, 400 MHz): δ (ppm) 7.53-7.56 (m, 1H), 7.69-7.71 (m, 1H), 8.09-8.10 (m, 1H), 8.31 (d, J=2.0 Hz, 1H), 8.92 (d, J=2.0 Hz, 1H). Compound 216B: LC-MS (ESI) m/z: non-ionizable compound under routine conditions used. $^1$H-NMR: (CDCl₃, 400 MHz): δ (ppm) 1.41 (s, 12H), 7.49-7.52 (m, 1H), 7.79 (d, J=8.4 Hz, 1H), 8.12 (d, J=1.6 Hz, 1H), 8.60 (s, 1H), 9.19 (d, J=1.6 Hz, 1H). Compound 216C: LC-MS (ESI) m/z: 395 [M+H]$^+$. Compound 216: LC-MS (ESI) m/z: 275 [M+H]$^+$; $^1$H-NMR (DMSO-d₆, 400 MHz): δ (ppm) 7.70-7.72 (m, 1H), 8.12-8.14 (m, 2H), 8.85 (s, 1H), 9.29 (s, 1H).

Example 217

Synthesis of 4-(3-chloro-5-(cyclopropylmethoxy)phenyl)-1H-1,2,3-triazole-5-carboxylic acid 2,2,2-trifluoroacetate (217)

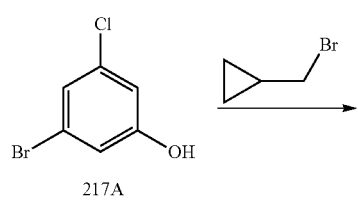
217A

-continued

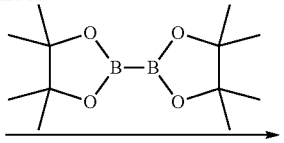

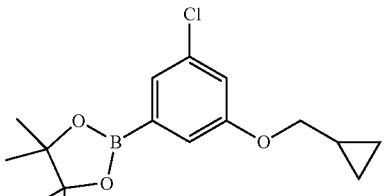
217B

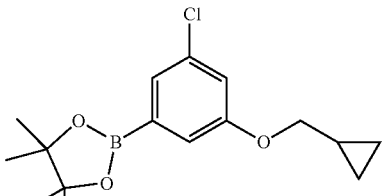
217C

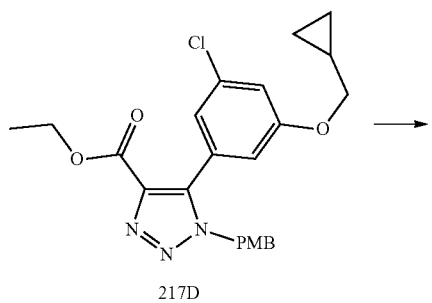
217D

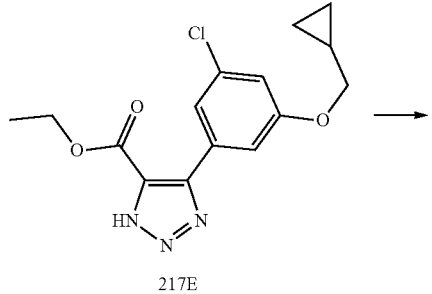
217E

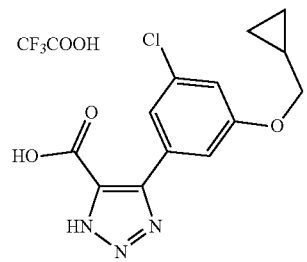
217

Compounds 217B, 217C, and 217D were synthesized by employing the procedures described for Compounds 27B, 27C, and 206C using (bromomethyl)cyclopropane, Compounds 217A with K₂CO₃ as base at 80° C., 217B, and 217C in lieu of 2-bromopropane, Compounds 27A with Cs₂CO₃ as base at 100° C., 27B, and 206B. Compound 217B: LC-MS (ESI) m/z: non-ionizable compound under routine conditions used; $^1$H-NMR (CDCl₃, 400 MHz): δ (ppm) 0.34-0.36 (m, 2H), 0.64-0.67 (m, 2H), 1.25-1.27 (m, 1H), 3.77 (d, J=7.2 Hz, 2H), 6.84 (t, J=1.6 Hz, 1H), 6.95 (t, J=2.4 Hz, 1H), 7.09 (t, J=1.6 Hz, 1H). Compound 217C: %). LC-MS (ESI)

m/z: non-ionizable compound under routine conditions used; ¹H-NMR (CDCl₃, 400 MHz): δ (ppm) 0.32-0.36 (m, 2H), 0.62-0.66 (m, 2H), 1.26 (s, 1H), 1.34 (s, 12H), 3.83 (d, J=6.8 Hz, 2H), 7.01 (t, J=1.6 Hz, 1H), 7.19 (d, J=2.0 Hz, 1H), 7.36 (d, J=1.6 Hz, 1H). Compound 217D: 442 [M+H]⁺.

To a solution of Compound 217D (100 mg, 0.23 mmol) in CH₃CN (3 mL) was added the solution of cerium ammonium nitrate (621 mg, 1.13 mmol) in H₂O (2 mL) and stirred at room temperature for 2 hours. The mixture was extracted with EtOAc (50 mL×3). The combined organic layers was washed with brine (50 mL), dried over anhydrous sodium sulfate, filtered, concentrated, and purified by column chromatography on silica gel (ethyl acetate in petroleum ether, 10% v/v) to afford Compound 217E. LC-MS (ESI) m/z: 322 [M+H]⁺.

Compound 217 was synthesized by employing the procedure described for Compound 8F using Compounds 217E in lieu of Compound 8E, LC-MS (ESI) m/z: 294 [M+H]⁺; ¹H-NMR (DMSO-d₆, 400 MHz): δ (ppm) 0.31 (d, J=4.4 Hz, 2H), 0.57 (d, J=4 Hz, 2H), 1.22-1.25 (m, 1H), 3.87 (d, J=7.2 Hz, 2H), 7.08 (s, 1H), 7.48 (m, 2H).

Example 218

Synthesis of 4-(4-chloro-3-(cyclopropylmethoxy) phenyl)-1H-1,2,3-triazole-5-carboxylic acid (218)

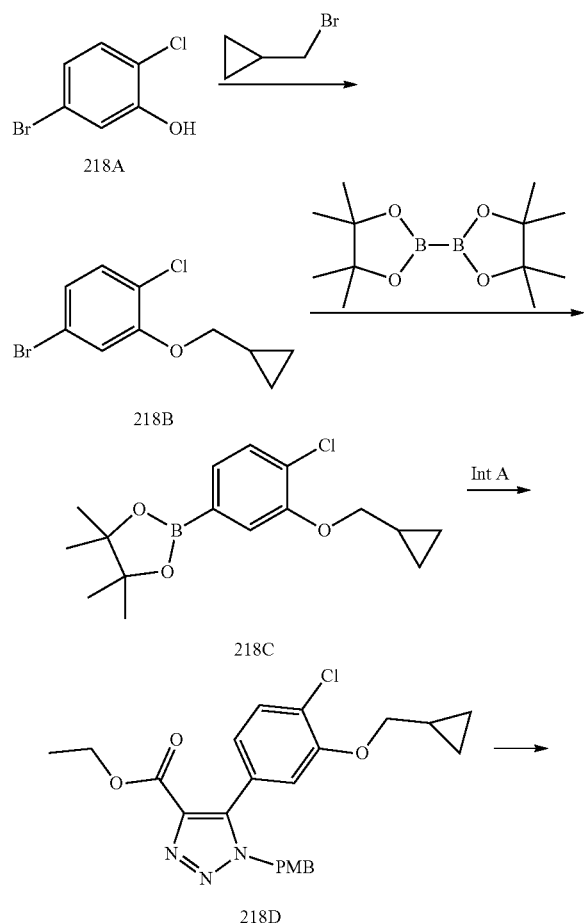

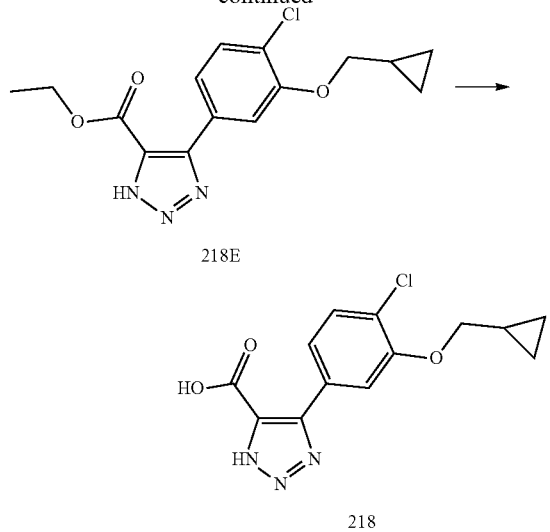

Compounds 218B, 218C, 218D, 218E, and 218 were synthesized by employing the procedures described for Compounds 27B, 27C, 206C, 217E, and 8F using (bromomethyl)cyclopropane, Compounds 218A with K₂CO₃ as base at 90° C., 218B, 218C, 218D, and 218E in lieu of 2-bromopropane, Compounds 27A with Cs₂CO₃ as base at 100° C., 27B, 206B, 217D, and 8E. Compound 218B: LC-MS (ESI) m/z: non-ionizable compound under routine conditions used; ¹H-NMR (CDCl₃, 400 MHz): δ (ppm) 0.38-0.41 (m, 2H), 0.64-0.68 (m, 2H), 1.29-1.34 (m, 1H), 3.86 (d, J=6.8 Hz, 2H), 6.99-7.02 (m, 2H), 7.21 (d, J=8.4 Hz, 1H). Compound 218C: LC-MS (ESI) m/z: non-ionizable compound under routine conditions used; ¹H-NMR (CDCl₃, 400 MHz): δ (ppm) 0.38-0.39 (m, 2H), 0.63-0.63 (m, 2H), 1.33-1.34 (m, 13H), 3.92 (d, J=6.8 Hz, 2H), 7.29-7.35 (m, 3H). Compound 218D: LC-MS (ESI) m/z: 442 [M–H]⁺. Compound 218E: LC-MS (ESI) m/z: 320 [M–H]⁻. Compound 218: LC-MS (ESI) m/z: 294 [M+H]⁺. ¹H-NMR (DMSO-d₆, 400 MHz): δ (ppm) 0.34-0.38 (m, 2H), 0.57-0.62 (m, 2H), 1.29-1.34 (m, 1H), 3.94 (d, J=6.8 Hz, 2H), 7.37-7.64 (m, 3H), 13.22 (s, 1H), 15.66 (s, 1H).

Example 219

Synthesis of 4-(2-chloro-5-(cyclopropylmethoxy) phenyl)-1H-1,2,3-triazole-5-carboxylic acid (219)

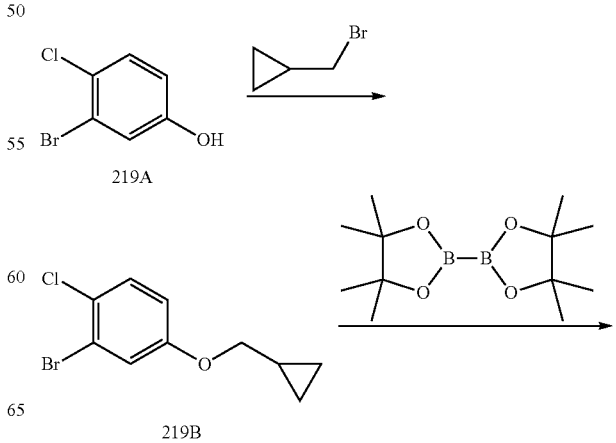

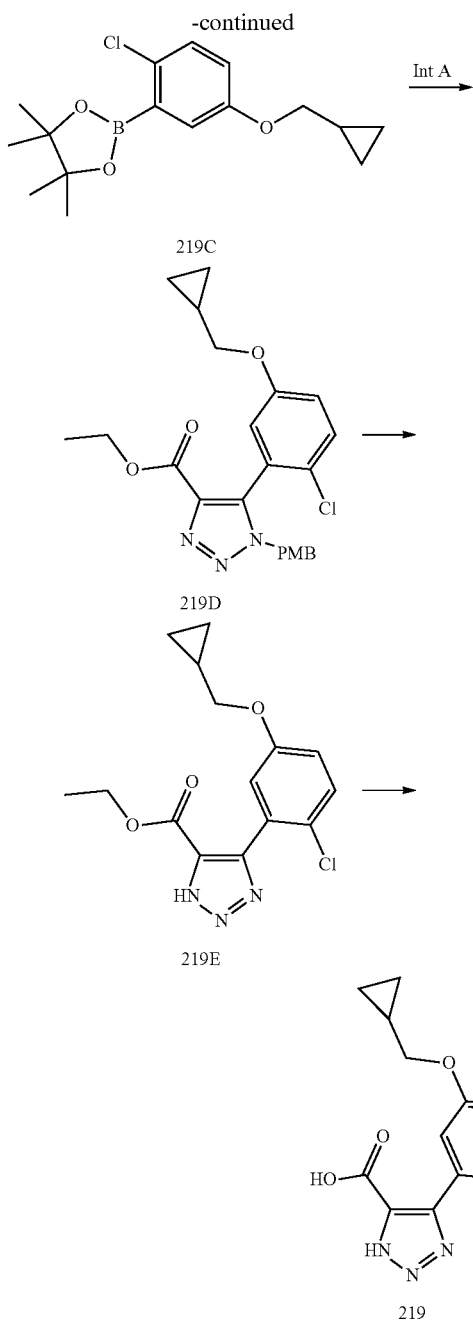

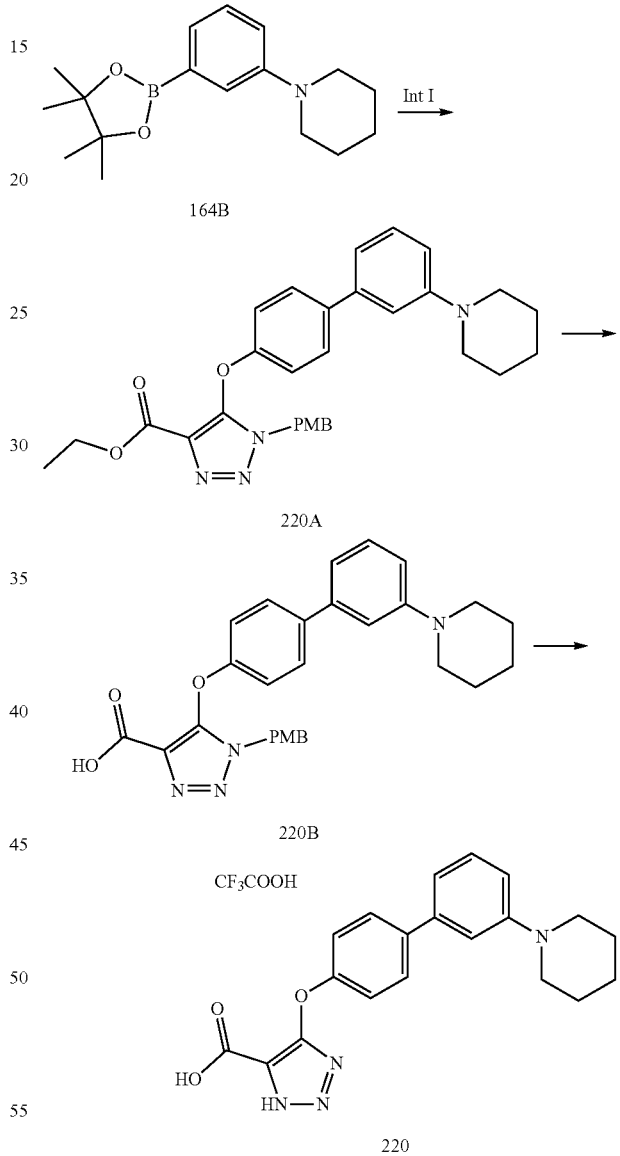

Compounds 219B, 219C, 219D, 219E, and 219 were synthesized by employing the procedures described for Compounds 27B, 27C, 206C, 217E, and 8F using (bromomethyl)cyclopropane, Compounds 219A with $K_2CO_3$ as base at 80° C., 219B, 219C, 219D, and 219E in lieu of 2-bromopropane, Compounds 27A with $Cs_2CO_3$ as base at 100° C., 27B, 206B, 217D, and 8E. Compound 219B: LC-MS (ESI) m/z: non-ionizable compound under routine conditions used; $^1$H-NMR (CDCl$_3$, 400 MHz): δ (ppm) 0.33-0.38 (m, 2H), 0.63-0.69 (m, 2H), 1.20-1.32 (m, 1H), 3.77 (d, J=6.8 Hz, 2H), 6.81 (dd, J=8.8, 2.4 Hz, 1H), 7.16 (d, J=2.4 Hz, 1H), 7.32 (d, J=8.8 Hz, 1H). Compound 219C: LC-MS (ESI) m/z: 309 [M+H]$^+$. Compound 219D: LC-MS (ESI) m/z: 442 [M+H]$^+$. Compound 219E: LC-MS (ESI) m/z: 322 [M+H]$^+$. Compound 219: LC-MS (ESI) m/z: 294 [M+H]$^+$.

$^1$H-NMR (DMSO-d$_6$, 400 MHz): δ (ppm) 0.28-0.33 (m, 2H), 0.52-0.58 (m, 2H), 1.16-1.26 (m, 1H), 3.82 (d, J=7.2 Hz, 2H), 6.95-7.15 (m, 2H), 7.43 (s, 1H), 13.06 (s, 1H), 15.62 (s, 1H).

Example 220

Synthesis of 4-((3'-(piperidin-1-yl)-[1,1'-biphenyl]-4-yl)oxy)-1H-1,2,3-triazole-5-carboxylic acid 2,2,2-trifluoroacetate (220)

Compounds 220A, 220B, and 220 were synthesized by employing the procedures described for Compounds 4B, 8F, and 1 using Intermediate I, Compounds 164B with $K_2CO_3$ as base and DME as solvent, 220A, and 220B in lieu of Compounds 4A, (4-bromophenyl)boronic acid with $Na_2CO_3$ as base and toluene/EtOH/H$_2$O as solvent, 8E, and 1E. Compound 220A: LC-MS (ESI) m/z: 513 [M+H]$^+$. Compound 220B: LC-MS (ESI) m/z: 483 [M−H]$^-$. Compound 220: LC-MS (ESI) m/z: 365 [M+H]$^+$; $^1$H-NMR (DMSO-d$_6$, 400 MHz): δ (ppm) 1.56-1.63 (m, 2H), 1.71-1.77 (m, 4H), 3.30-3.42 (m, 4H), 7.15-7.17 (m, 3H), 7.27-7.58 (m, 3H), 7.68 (d, J=8.4 Hz, 2H).

Example 221

Synthesis of 4-((4'-(piperidin-1-yl)-[1,1'-biphenyl]-4-yl)oxy)-1H-1,2,3-triazole-5-carboxylic acid 2,2,2-trifluoroacetate (221)

Compounds 221A, 221B, and 221 were synthesized by employing the procedures described for Compounds 4B, 1, and 8F using Intermediate I, Compounds 169B with $K_2CO_3$ as base and 1,4-dioxane/$H_2O$ as solvent, 221A, and 221B in lieu of Compounds 4A, (4-bromophenyl)boronic acid with $Na_2CO_3$ as base and toluene/EtOH/$H_2O$ as solvent, 1E, and 8E. Compound 221A: LC-MS (ESI) m/z: 513 [M+H]$^+$; $^1$H-NMR (CDCl$_3$, 400 MHz): δ (ppm) 1.11 (t, J=7.2 Hz, 3H), 1.61-1.64 (m, 2H), 1.70-1.75 (m, 4H), 3.20-3.24 (m, 4H), 3.75 (s, 3H), 4.19 (q, J=7.2 Hz, 2H), 5.37 (s, 2H), 6.77-6.81 (m, 4H), 6.99 (d, J=8.4 Hz, 2H), 7.22 (d, J=8.8 Hz, 2H), 7.41-7.45 (m, 4H). Compound 221B: LC-MS (ESI) m/z: 393 [M+H]$^+$. Compound 221 LC-MS (ESI) m/z: 365 [M+H]$^+$; $^1$H-NMR (CD$_3$OD, 400 MHz): δ (ppm) 1.79-1.83 (m, 2H), 2.02-2.08 (m, 4H), 3.62-2.65 (m, 4H), 7.22 (d, J=8.8 Hz, 2H), 7.65-7.68 (m, 4H), 7.80 (d, J=8.4 Hz, 2H).

Example 222

Synthesis of 4-(4-(1-methyl-1,2,3,4-tetrahydroquinolin-6-yl)phenoxy)-1H-1,2,3-triazole-5-carboxylic acid (222)

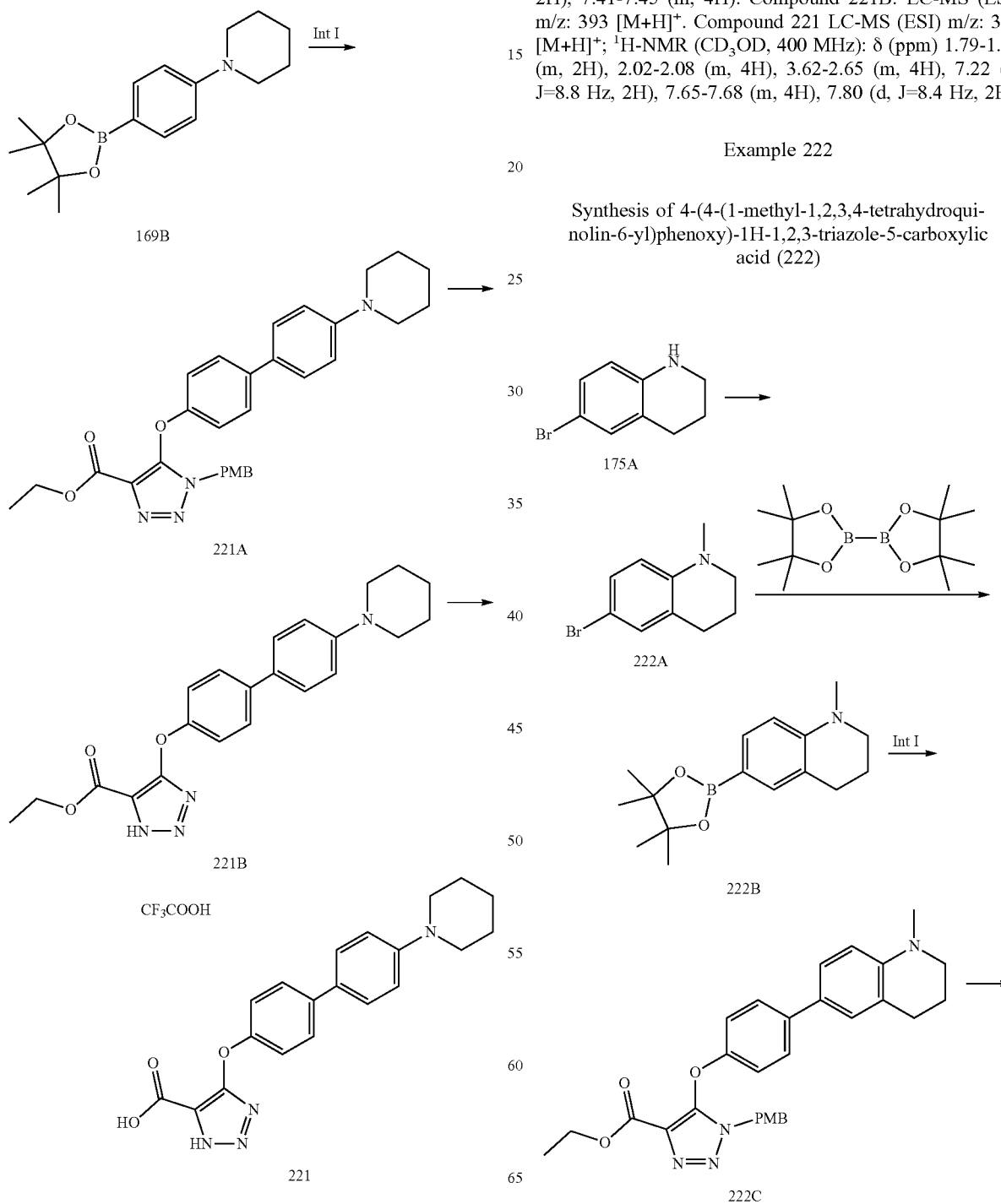

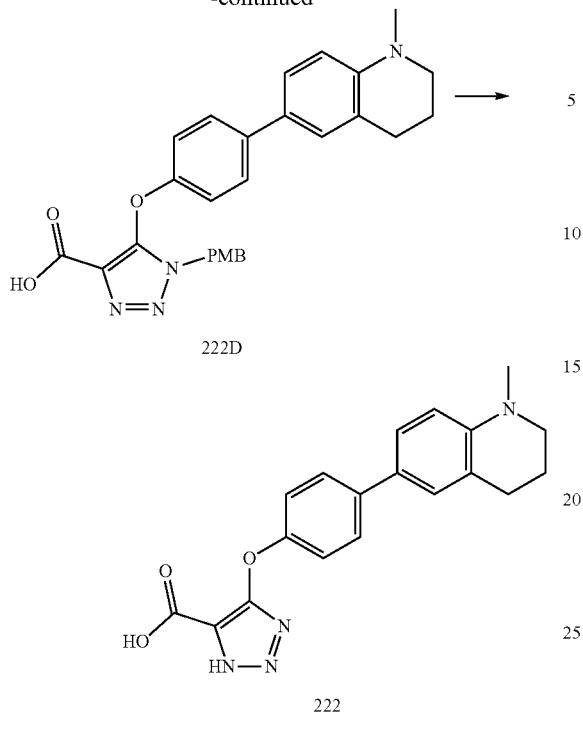

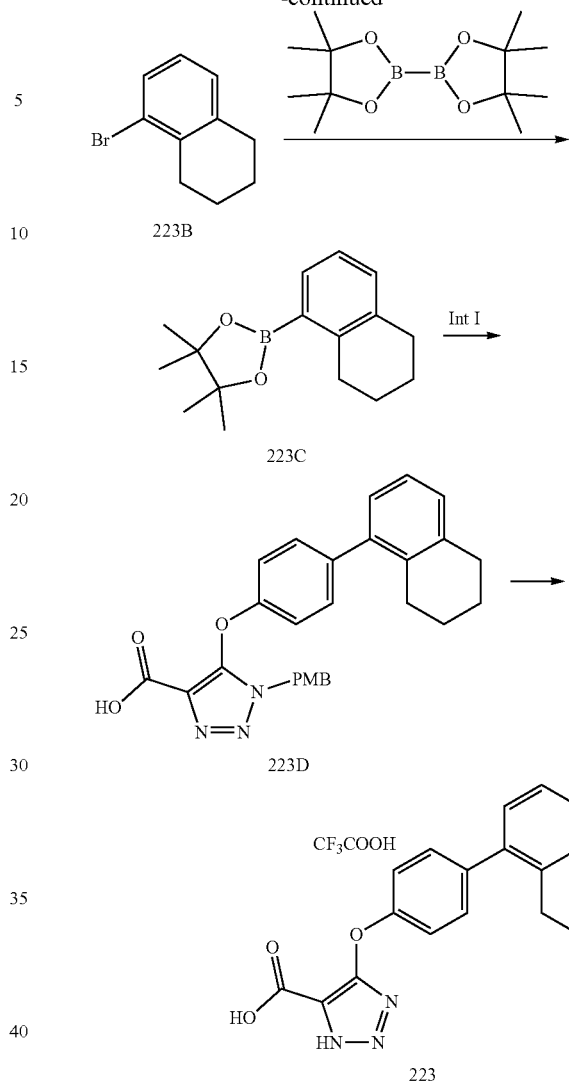

Compounds 222A, 222B, 222C, 222D, and 222 were synthesized by employing the procedures described for Compounds 206A, 27C, 8B, 8F, and 1 using iodomethane with KOtBu as base and DMF as solvent at room temperature, Compounds 222A, Intermediate I, 222B with $Na_2CO_3$ as base and 1,4-dioxane/$H_2O$ as solvent, 222C, and 222D in lieu of 2-iodopropane with $Cs_2CO_3$ as base and DMF as solvent at 60° C., Compounds 27B, 8A, (3,4-dichlorophenyl)boronic acid with $Cs_2CO_3$ as base and DME/$H_2O$ as solvent, 8E, and 1E. Compound 222A: LC-MS (ESI) m/z: 226 [M+H]$^+$. Compound 222B: LC-MS (ESI) m/z: 274 [M+H]$^+$. Compound 222C: LC-MS (ESI) m/z: 499 [M+H]$^+$. Compound 222D: LC-MS (ESI) m/z: 471 [M+H]$^+$. Compound 222: LC-MS (ESI) m/z: 351 [M+H]$^+$; $^1$H-NMR (DMSO-$d_6$, 400 MHz): δ (ppm) 1.89-1.92 (m, 2H), 2.75 (t, J=12.8 Hz, 2H), 2.86 (s, 3H), 3.21 (t, J=10 Hz, 2H), 6.64 (d, J=8.4 Hz, 1H), 7.07 (d, J=8.4 Hz, 2H), 7.20 (s, 1H), 7.27-7.29 (m, 1H), 7.52 (d, J=9.2 Hz, 2H), 15.2 (s, 1H).

Example 223

Synthesis of 4-(4-(5,6,7,8-tetrahydronaphthalen-1-yl)phenoxy)-1H-1,2,3-triazole-5-carboxylic acid 2,2,2-trifluoroacetate (223)

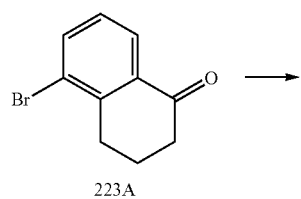

To a stirred solution of 5-bromo-3,4-dihydronaphthalen-1(2H)-one (223A) (225 mg, 1 mmol) in dichloromethane (5 mL) was added $BF_3.Et_2O$ (2 mL) and triethylsilane (2 mL) and stirred at room temperature overnight. The reaction mixture was diluted with $H_2O$ (10 mL) and extracted with dichloromethane (10 mL×2). The combined organic layer was dried over anhydrous $Na_2SO_4$, filtered, concentrated, and purified with flash column chromatography on silica gel (ethyl acetate in petroleum ether, 1% v/v) to afford Compound 223B. LC-MS: (ESI) m/z: non-ionizable compound under routine conditions used; $^1$H-NMR (CDCl$_3$, 400 MHz): δ (ppm) 1.75-1.89 (m, 4H), 2.75-2.81 (m, 4H), 6.94 (t, J=7.2 Hz, 1H), 7.04 (d, J=7.2 Hz, 1H), 7.39 (d, J=8.0 Hz, 1H).

Compounds 223C, 223D, and 223 were synthesized by employing the procedures described for Compounds 27C, 4B, and 1 using Compounds 223B, Intermediate I, 222C with $K_2CO_3$ as base and 1,4-dioxane/$H_2O$ as solvent, and 223D in lieu of Compounds 27B, 4A, (4-bromophenyl)boronic acid with $Na_2CO_3$ as base and toluene/EtOH/$H_2O$ as solvent, and 1E. Compound 223C: LC-MS (ESI) m/z: non-ionizable compound under routine conditions used. $^1$H-NMR (CDCl$_3$, 400 MHz): δ (ppm) 1.33 (s, 12H), 1.76-1.83 (m, 4H), 2.78-2.81 (m, 2H), 3.04-3.08 (m, 2H), 7.08-

7.16 (m, 2H), 7.60-7.63 (m, 1H). Compound 223D: LC-MS (ESI) m/z: 456 [M+H]$^+$; $^1$H-NMR (DMSO-d$_6$, 400 MHz): δ (ppm) 1.63-1.73 (m, 4H), 2.45-2.49 (m, 2H), 2.75-2.79 (m, 2H), 3.67 (s, 3H), 5.35 (s, 2H), 6.79-6.91 (m, 5H), 7.04-7.20 (m, 6H). Compound 223: LC-MS(ESI) m/z: 336 [M+H]$^+$; $^1$H-NMR (DMSO-d$_6$, 400 MHz): δ (ppm) 1.60-1.75 (m, 4H), 2.48-2.53 (m, 2H), 2.76-2.79 (m, 2H), 6.95 (d, J=7.2 Hz, 1H), 7.05-7.15 (m, 4H), 7.26 (d, J=8.8 Hz, 2H).

Example 224

Synthesis of 4-((3'-((2-oxopiperidin-1-yl)methyl)-[1,1'-biphenyl]-4-yl)oxy)-1H-1,2,3-triazole-5-carboxylic acid (224)

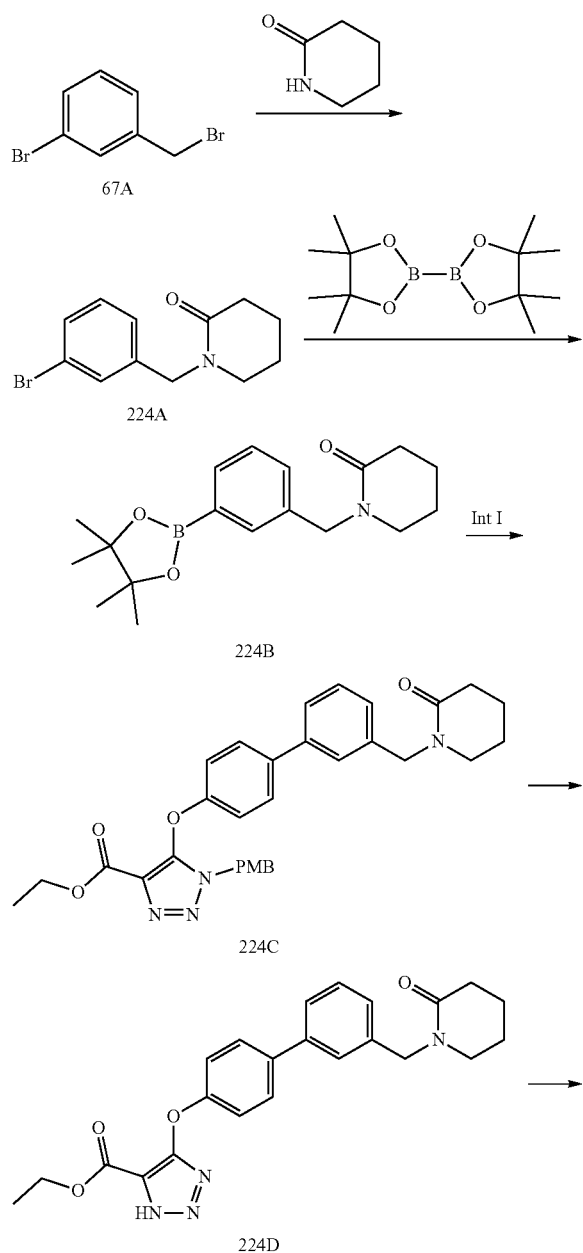

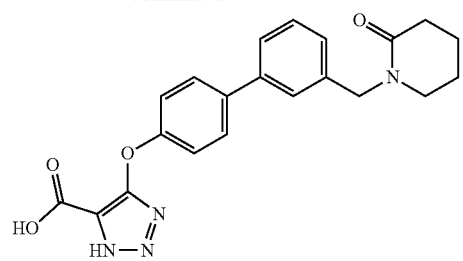

To a solution of piperidin-2-one (396 mg, 4 mmol) in DMF (15 mL) was added NaH (60% suspension in oil, 192 mg, 4.8 mmol) at 0° C. and stirred at 0° C. for 15 minutes, followed by addition of 1-bromo-3-(bromomethyl)benzene (67A) (1000 mg, 4 mmol). The mixture was stirred at room temperature overnight, diluted with ethyl acetate (50 mL) and water (50 mL). The organic layer was separated, dried over anhydrous sodium sulfate, filtered, concentrated, and purified with flash column chromatography on silica gel (ethyl acetate in petroleum ether, 5% v/v) to afford Compound 224A. LC-MS (ESI) m/z: 268 [M+H]$^+$; $^1$H-NMR (CDCl$_3$, 400 MHz): δ (ppm) 1.79-1.84 (m, 4H), 2.46-2.50 (m, 2H), 3.19-3.23 (m, 2H), 4.57 (s, 2H), 7.19-7.28 (m, 2H), 7.39-7.42 (m, 2H).

Compounds 224B, 224C, 224D, and 224 were synthesized by employing the procedures described for Compounds 27C, 4B, 1, and 8F using Compounds 224A, Intermediate I, 224B with K$_2$CO$_3$ as base and 1,4-dioxane/H$_2$O as solvent, 224C, and 224D in lieu of Compounds 27B, 4A, (4-bromophenyl)boronic acid with Na$_2$CO$_3$ as base and toluene/EtOH/H$_2$O as solvent, 1E, and 8E. Compound 224B: LC-MS (ESI) m/z: 316 [M+H]$^+$; $^1$H-NMR (CDCl$_3$, 400 MHz): δ (ppm) 1.25 (s, 12H), 1.73-1.82 (m, 4H), 2.46-12.50 (m, 2H), 3.16-3.20 (m, 2H), 4.62 (s, 2H), 7.32-7.40 (m, 2H), 7.67 (s, 1H), 7.72 (d, J=7.2 Hz, 1H). Compound 224C: LC-MS (ESI) m/z: 541 [M+H]$^+$. Compound 224D: LC-MS (ESI) m/z: 421 [M+H]$^+$. Compound 224: LC-MS (ESI) m/z: 393 [M+H]$^+$; $^1$H-NMR (CD$_3$OD, 400 MHz): δ (ppm) 1.81-1.83 (m, 4H), 2.43-2.46 (m, 2H), 3.31-2.33 (m, 2H), 4.66 (s, 2H), 7.19-7.26 (m, 3H), 7.42 (t, J=7.2 Hz, 1H), 7.51-7.54 (m, 2H), 7.62 (d, J=8.4 Hz, 2H).

Example 225

Synthesis of 4-((4'-cyano-[1,1'-biphenyl]-4-yl)oxy)-1H-1,2,3-triazole-5-carboxylic acid (225)

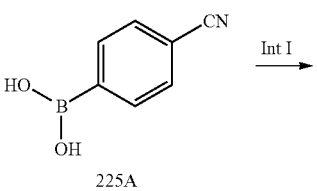

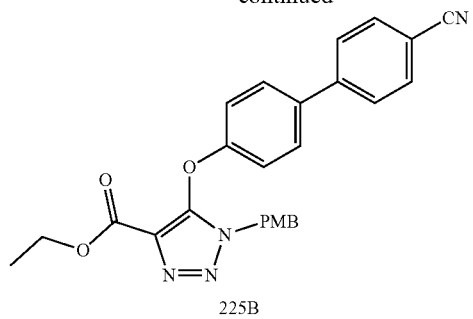

225B

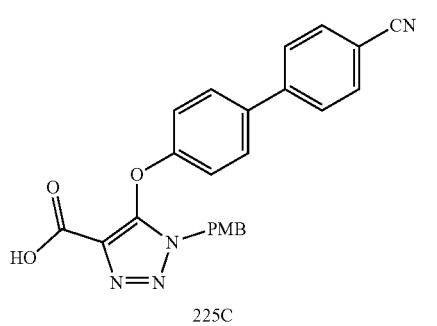

225C

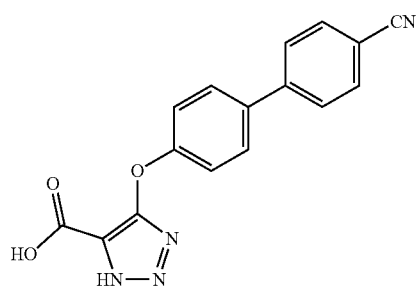

225

Compounds 225B and 225C were synthesized by employing the procedures described for Compounds 8B and 8F using Compounds 225A, Intermediate I with $Na_2CO_3$ as base and 1,4-dioxane/$H_2O$ as solvent, and 225B in lieu of (3,4-dichlorophenyl)boronic acid, Compounds 8A with $Cs_2CO_3$ as base and DME/$H_2O$ as solvent, and 8E. Compound 225B: LC-MS (ESI) m/z: 455 [M+H]⁺. Compound 225C: LC-MS (ESI) m/z: 427 [M+H]⁺.

A mixture of Compound 225C (65 mg, crude) and methyl (phenyl)sulfane (0.5 mL) in TFA (6 mL) was stirred at room temperature for 4 hours. The mixture was concentrated under reduced pressure and the residue was purified with preparative HPLC to afford Compound 225. LC-MS (ESI) m/z: 307 [M+H]⁺; ¹H-NMR (DMSO-$d_6$, 400 MHz): δ (ppm) 7.14 (d, J=8.8 Hz, 2H), 7.75 (d, J=8.8 Hz, 2H), 7.88 (q, J=11.6 Hz, 4H).

Example 226

Synthesis of 4-((2-isopropyl-1,2,3,4-tetrahydroisoquinolin-7-yl)oxy)-1H-1,2,3-triazole-5-carboxylic acid 2,2,2-trifluoroacetate (226)

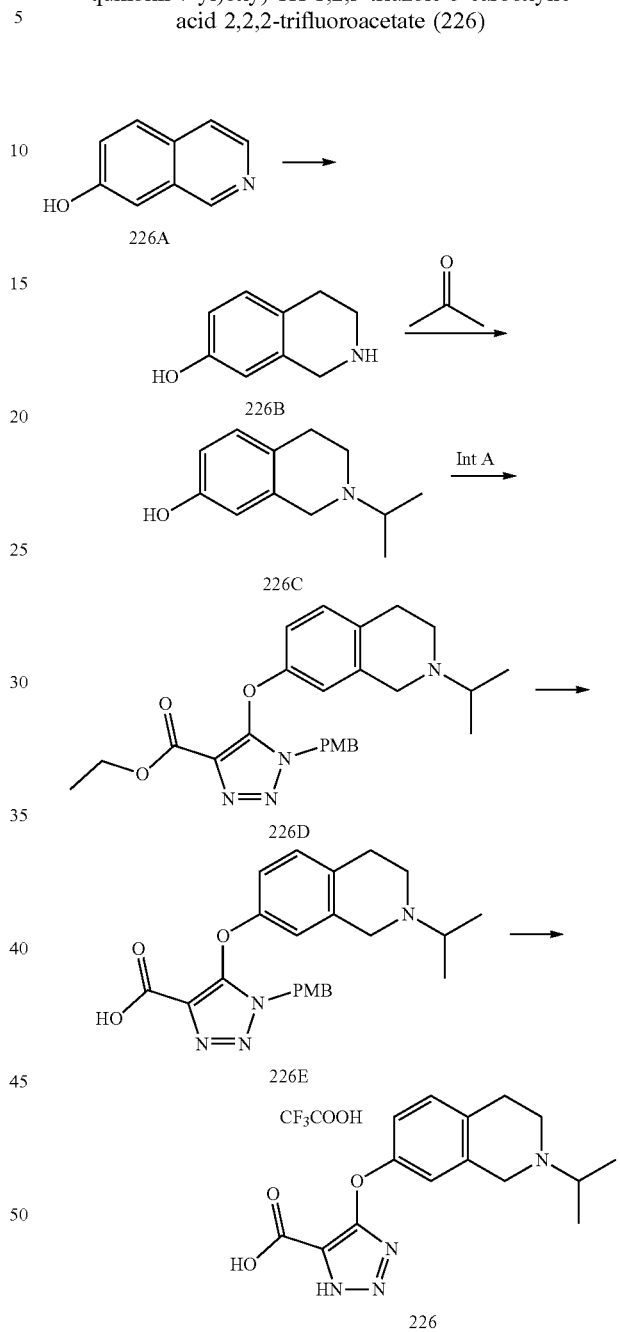

A mixture of isoquinolin-7-ol (226A) (306 mg, 2.11 mmol) and $PtO_2$ (42 mg, 0.19 mmol) in acetic acid (8 mL) was stirred at room temperature under hydrogen (1 atm.) for 40 hours. The mixture was filtered through Celite and the filtrate was concentrated to give a crude Compound 226B. LC-MS (ESI) m/z: 150 [M+H]⁺.

Compounds 226C, 226D, 226E, and 226 were synthesized by employing the procedures described for Compounds 123B, Intermediate I, 8F, and 1 using Compounds 226B, 226C with NMP as solvent, 226D, and 224E in lieu of Compounds 123A, 4-bromophenol with DMF as solvent, 8E, and 1E. Compound 226C: LC-MS (ESI) m/z: 192 [M+H]+. Compound 226D: LC-MS (ESI) m/z: 451 [M+H]+. Compound 226E: LC-MS (ESI) m/z: 423 [M+H]+. Compound 226: LC-MS (ESI) m/z: 303 [M+H]+; $^1$H-NMR (DMSO-$d_6$, 400 MHz): δ (ppm) 1.44 (s, 3H), 1.45 (s, 3H), 3.19 (s, 2H), 3.42 (s, 1H), 3.68-3.75 (m, 2H), 4.43 (s, 2H), 7.02 (s, 1H), 7.09 (dd, =2.4 Hz, $J_1$=8.4 Hz, 1H), 7.28 (d, J=8.4 Hz, 1H).

Example 227

Synthesis of 4-((6-chloronaphthalen-2-yl)methoxy)-1H-1,2,3-triazole-5-carboxylic acid 2,2,2-trifluoroacetate (227)

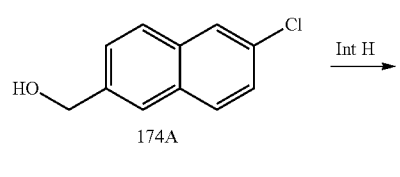

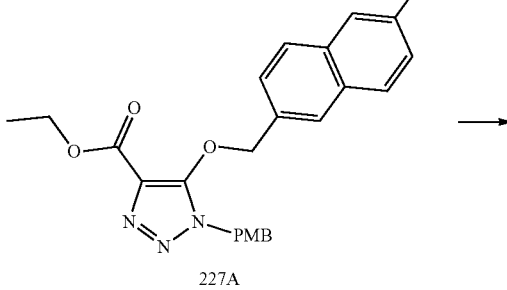

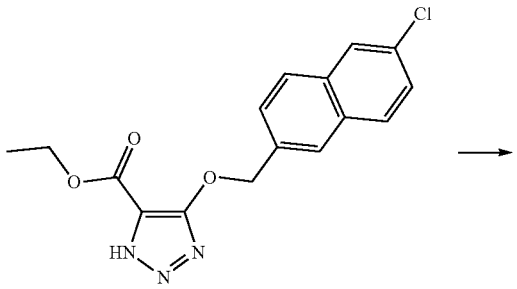

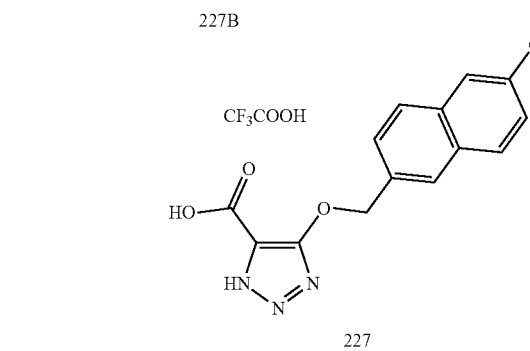

Compounds 227A, 227B, and 227 were synthesized by employing the procedures described for Compounds 90C, 217E, and 1 using Compounds 174A, 227A, and 227B in lieu of Compounds 90B, 217D, and 1E. Compound 227A: LC-MS (ESI) m/z: 452 [M+H]+; $^1$H-NMR (CDCl$_3$, 400 MHz): δ (ppm) 1.44 (t, J=7.2 Hz, 3H), 3.75 (s, 3H), 4.43-4.49 (m, 2H), 5.17 (s, 2H), 5.56 (s, 2H), 7.72 (d, J=8.8 Hz, 2H), 7.05 (d, J=8.4 Hz, 2H), 7.38 (d, J=8.8 Hz, 1H), 7.45 (d, J=8.8 Hz, 1H), 7.64 (s, 1H), 7.71 (d, J=8.4 Hz, 2H), 7.83 (s, 1H). Compound 227B: LC-MS (ESI) m/z: 332 [M+H]+; $^1$H-NMR (CDCl$_3$, 400 MHz): δ (ppm) 1.41 (t, J=7.2 Hz, 3H), 4.40-4.46 (m, 2H), 5.54 (s, 2H), 7.42 (d, J=8.8 Hz, 1H), 7.58 (d, J=8.8 Hz, 1H), 7.75-7.78 (m, 2H), 7.82 (d, J=1.6 Hz, 1H), 7.91 (s, 1H). Compound 227: LC-MS (ESI) m/z: 304 [M+H]+; $^1$H-NMR (DMSO-$d_6$, 400 MHz): δ (ppm) 5.48 (s, 2H), 7.55 (d, J=8.8 Hz, 1H), 7.65 (d, J=8.8 Hz, 1H), 7.94-8.07 (m, 4H), 12.93 (s, 1H), 14.80 (s, 1H).

Example 228

Synthesis of 4-((3'-cyclohexyl-[1,1'-biphenyl]-4-yl)oxy)-1H-1,2,3-triazole-5-carboxylic acid (228)

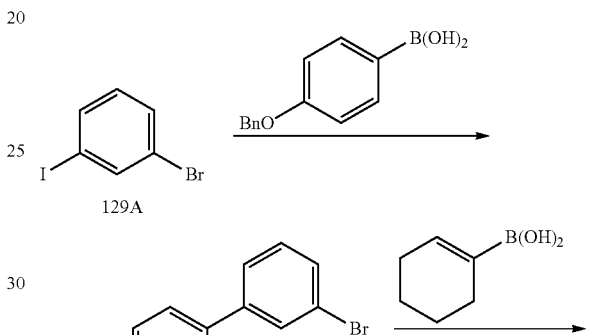

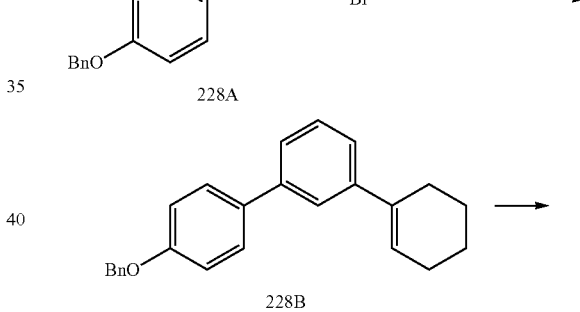

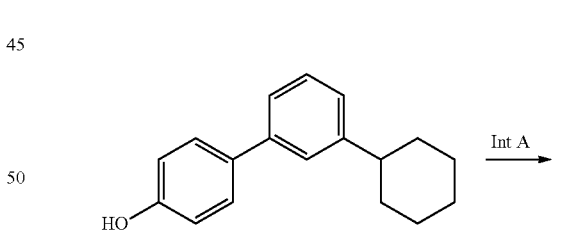

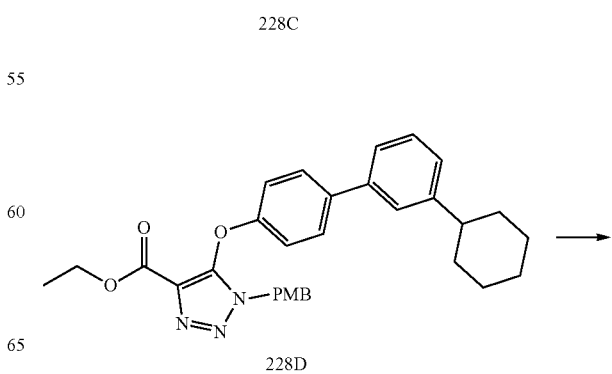

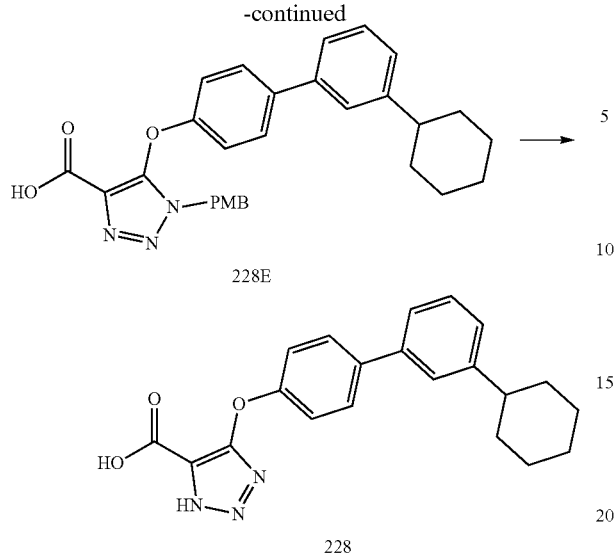

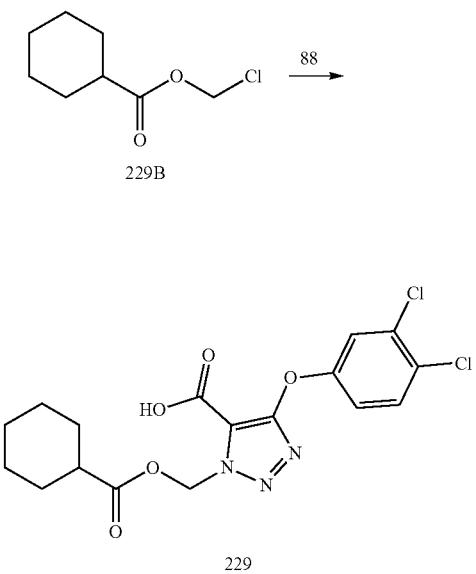

Compounds 228A, 228B, 228C, 228D, 228E, and 228 were synthesized by employing the procedures described for Compounds 8B, 8B, 141, Intermediate I, 8F, and 1 using 4-(benzyloxy)phenylboronic acid, Compounds 129A with Na$_2$CO$_3$ as base and 1,4-dioxane/H$_2$O as solvent, cyclohexenylboronic acid, 228A with Na$_2$CO$_3$ as base and 1,4-dioxane/H$_2$O as solvent, 228B with MeOH as solvent at 50° C., 228C, 228D, and 224E in lieu of (3,4-dichlorophenyl)boronic acid, Compounds 8A with Cs$_2$CO$_3$ as base and DME/H$_2$O as solvent, (3,4-dichlorophenyl)boronic acid, Compounds 8A with Cs$_2$CO$_3$ as base and DME/H$_2$O as solvent, 4-bromophenol with DMF as solvent, 140 with EtOAc as solvent at room temperature, 4-bromophenol, 8E, and 1E. Compound 228A: $^1$H-NMR (DMSO-d$_6$, 400 MHz): δ (ppm) 5.16 (s, 2H), 7.10 (d, J=5.2 Hz, 2H), 7.35 (d, J=9.6 Hz, 1H), 7.41 (t, J=5.2 Hz, 3H), 7.48 (t, J=8.8 Hz, 3H), 7.64 (d, J=4.8 Hz, 3H), 7.80 (t, J=3.6 Hz, 1H). Compound 228B: LC-MS (ESI) m/z: 341 [M+H]$^+$. Compound 228C: LC-MS (ESI) m/z: 253 [M+H]$^+$. Compound 228D: LC-MS (ESI) m/z: 512 [M+H]$^+$. Compound 228E: LC-MS (ESI) m/z: 484 [M+H]$^+$. Compound 228: LC-MS (ESI) m/z: 364 [M+H]$^+$; $^1$H-NMR (DMSO-d$_6$, 400 MHz): δ (ppm) 1.24-1.27 (m, 1H), 1.36-1.49 (m, 4H), 1.72 (d, J=12.4 Hz, 1H), 1.79-1.84 (m, 4H), 2.54-2.60 (m, 1H), 7.13 (d, J=9.2 Hz, 2H), 7.20 (d, J=7.6 Hz, 1H), 7.35 (t, J=7.6 Hz, 1H), 7.44 (t, J=8.4 Hz, 2H), 7.64 (d, J=8.8 Hz, 2H).

Example 229

Synthesis of 1-(((cyclohexanecarbonyl)oxy)methyl)-4-(3,4-dichlorophenoxy)1H-1,2,3-triazole-5-carboxylic acid (229)

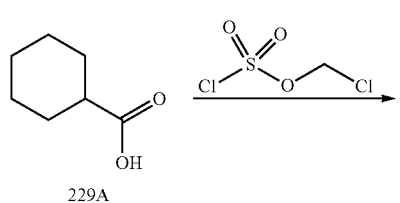

To a suspension of cyclohexanecarboxylic acid (229A) (2.0 g, 15.6 mmol), K$_2$CO$_3$ (8.2 g, 59.4 mmol), and Bn$_4$NHSO$_4$ (0.5 g, 1.5 mmol) in dichloromethane (20 mL) and water (20 mL) at 5° C. was dropped chloromethyl sulfochloridate (3.3 g, 20.3 mmol) and stirred at room temperature for 16 hours. The mixture was diluted with water (30 mL) and extracted with dichlorrmethane (30 mL×3). The combined organic phases was washed with brine (50 mL), dried over anhydrous sodium sulfate, filtered, and evaporated to give Compound 229B. $^1$H-NMR (CDCl$_3$, 400 MHz): δ (ppm) 1.21-1.95 (m, 10H), 2.34-2.41 (m, 1H), 5.71 (s, 2H).

Compound 229 was synthesized by employing the procedure described for Compound 51 using Compounds 229B and 88 in lieu of chloromethyl pivalate and Compound 16, LC-MS (ESI) m/z: 431 [M+18]$^+$; $^1$H-NMR (CD$_3$OD, 400 MHz): δ (ppm) 1.25-1.34 (m, 5H), 1.42-1.44 (m, 1H), 1.65-1.74 (m, 2H), 1.84-1.88 (m, 2H), 2.37-2.42 (m, 1H), 6.20 (s, 2H), 7.13 (dd, J=8.8, 2.8 Hz, 1H), 7.36 (d, J=2.8 Hz, 1H), 7.50 (d, J=8.8 Hz, 1H).

Example 230

Synthesis of 4-((3'-(2-methoxyethoxy)-[1,1'-biphenyl]-4-yl)oxy)-1H-1,2,3-triazole-5-carboxylic acid (230)

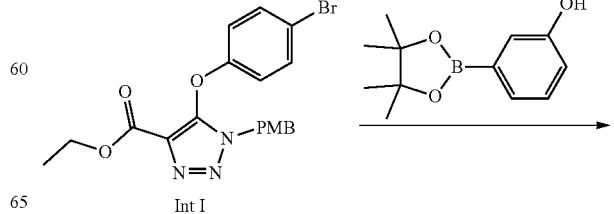

-continued

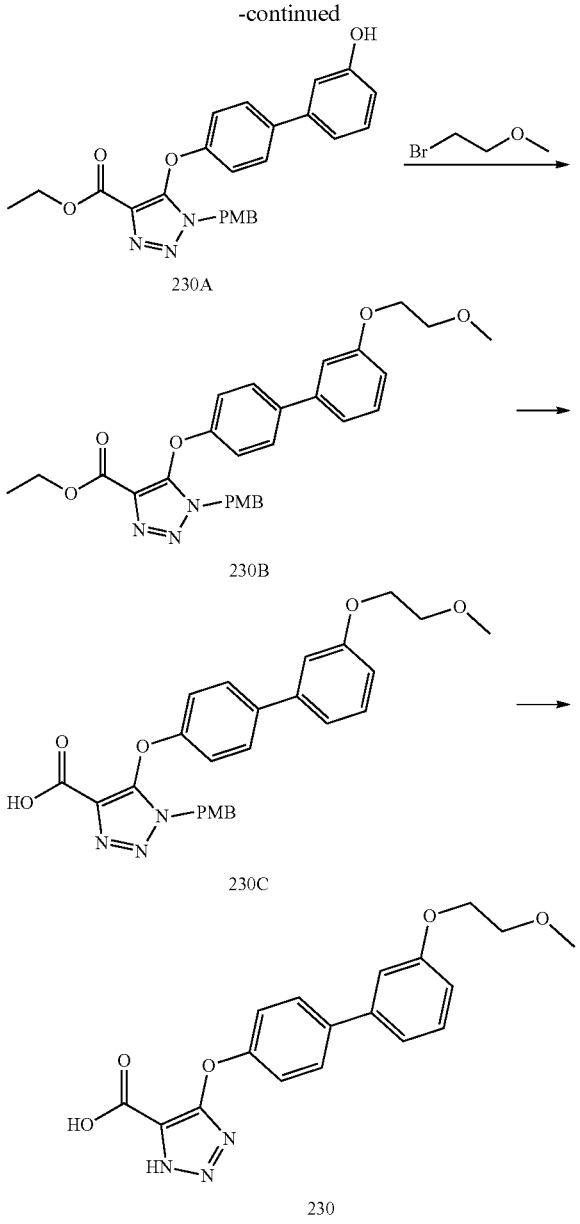

J=8.4 Hz, 2H), 7.17-7.21 (m, 2H), 7.36 (t, J=16 Hz, 1H), 7.67 (d, J=8.8 Hz, 2H), 13.26 (s, 1H), 15.25 (s, 1H).

Example 231

Synthesis of 4-((2,3-dihydrobenzo[b][1,4]dioxin-6-yl)oxy)-1H-1,2,3-triazole-5-carboxylic acid 2,2,2-trifluoroacetate (231)

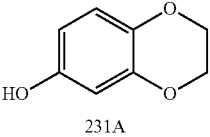

231A

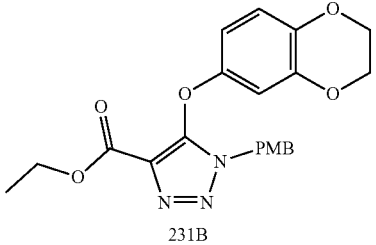

231B

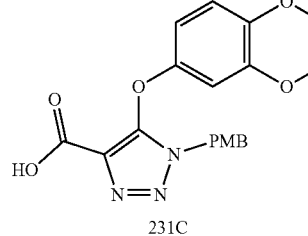

231C

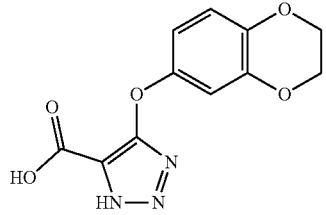

231

Compounds 230A, 230B, 230C, and 230 were synthesized by employing the procedures described for Compounds 8B, 27B, 8F, and 1 using 3-(4,4,5,5-tetramethyl-1,3,2-dioxaborolan-2-yl)phenol, Intermediate I, 1-bromo-2-methoxyethane, Compounds 230A with K$_2$CO$_3$ as base, 230B, and 230C in lieu of (3,4-dichlorophenyl)boronic acid, Compounds 8A with Cs$_2$CO$_3$ as base and DME/H$_2$O as solvent, 2-bromopropane, 27A with Cs$_2$CO$_3$ as base, 8E, and 1E. Compound 230A: LC-MS (ESI) m/z: 446 [M+H]$^+$. Compound 230B: LC-MS (ESI) m/z: 504 [M+H]$^+$. Compound 230C: LC-MS (ESI) m/z: 476 [M+H]$^+$. Compound 230: LC-MS (ESI) m/z: 356 [M+H]$^+$; $^1$H-NMR (DMSO-d$_6$, 400 MHz): δ (ppm) 2.49-2.51 (m, 3H), 3.67-3.69 (m, 2H), 4.16-4.18 (m, 2H), 6.91-6.94 (dd, J=10 Hz, 1H), 7.14 (d, Compounds 231B, 231C, and 231 were synthesized by employing the procedures described for Intermediate I, Compounds 8F, and 1 using Compounds 231A, 231B, and 231C in lieu of 4-bromophenol, Compounds 8E, and 1E. Compound 231B: LC-MS (ESI) m/z: 412 [M+H]$^+$; $^1$H-NMR (CDCl$_3$, 400 MHz): δ (ppm) 1.18 (t, J=7.2 Hz, 3H), 3.77 (s, 3H), 4.20-4.26 (m, 6H), 5.32 (s, 2H), 6.25-6.28 (m, 1H), 6.30-6.31 (m, 1H), 6.72-6.74 (m, 1H), 6.79-6.81 (m, 2H), 7.19-7.27 (m, 2H). Compound 231C: LC-MS (ESI) m/z: 384 [M+H]$^+$; $^1$H-NMR (DMSO-d$_6$, 400 MHz): δ (ppm) 3.70 (s, 3H), 4.17-4.20 (m, 4H), 5.35 (s, 2H), 6.31-6.37 (m, 2H), 6.75-6.77 (m, 1H), 6.83-6.86 (m, 2H), 7.12-7.15 (m, 2H), 13.00 (s, 1H). Compound 231: LC-MS (ESI) m/z: 264 [M+H]$^+$; $^1$H-NMR (DMSO-d$_6$, 400 MHz): δ (ppm) 4.16-4.20 (m, 4H), 6.41-6.43 (m, 2H), 6.73-6.75 (m, 1H).

Example 232

Synthesis of 4-((3'-(cyclopropylmethoxy)-[1,1'-biphenyl]-4-yl)oxy)-1H-1,2,3-triazole-5-carboxylic acid (232)

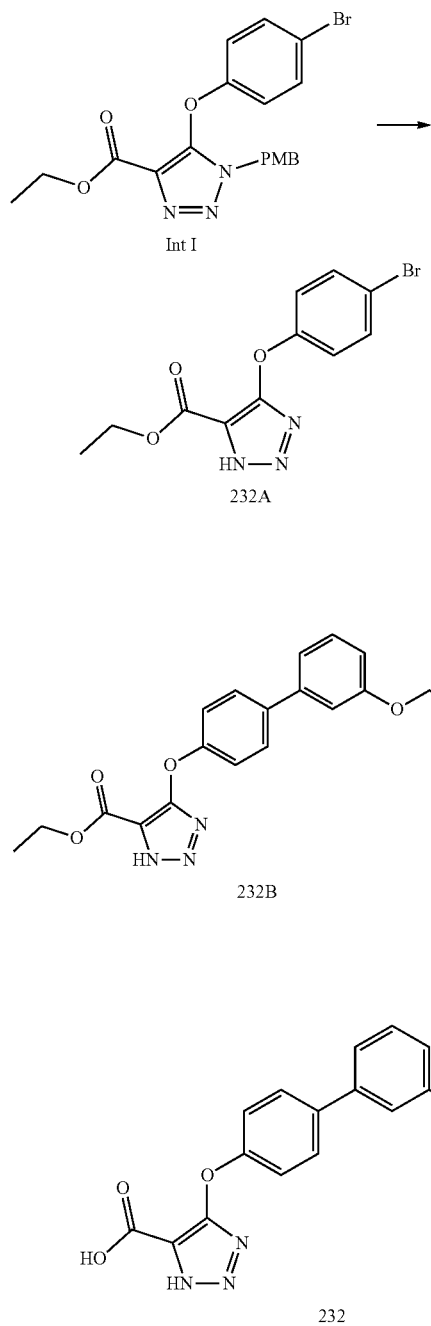

Compounds 232A, 232B, and 232 were synthesized by employing the procedures described for Compounds 8F, 4B, and 1 using Intermediate I, Compounds 232A, 170B with K$_2$CO$_3$ as base and 1,4-dioxane/H$_2$O as solvent, and 232B in lieu of Compounds 8E, 4A, (4-bromophenyl)boronic acid with Na$_2$CO$_3$ as base and toluene/EtOH/H$_2$O as solvent, and 1E. Compound 232A: LC-MS (ESI) m/z: 312 [M+H]$^+$. Compound 232B: LC-MS (ESI) m/z: 380 [M+H]$^+$; $^1$H-NMR (CDCl$_3$, 400 MHz): δ (ppm) 0.37-0.39 (m, 2H), 0.66-0.69 (m, 2H), 1.25-1.28 (m, 1H), 1.36 (t, J=7.6 Hz, 3H), 3.87 (d, J=6.8 Hz, 2H), 4.41 (q, J=7.6 Hz, 2H), 7.09-7.13 (m, 2H), 7.25 (d, J=8.8 Hz, 2H). 7.32-7.36 (m, 2H), 7.59 (d, J=8.8 Hz, 2H). Compound 232: LC-MS (ESI) m/z: 352 [M+H]$^+$; (CD$_3$OD, 400 MHz): δ (ppm) 0.35-0.40 (m, 2H), 0.60-0.66 (m, 2H), 1.26-1.30 (m, 1H), 3.88 (d, J=6.8 Hz, 2H), 6.87-6.90 (m, 1H), 7.11-7.20 (m, 4H), 7.30-7.35 (m, 1H), 7.60-7.63 (m, 2H).

Example 233

Synthesis of 4-((3'-(4-acetylpiperazin-1-yl)-[1,1'-biphenyl]-4-yl)oxy)-1H-1,2,3-triazole-5-carboxylic acid 2,2,2-trifluoroacetate (233)

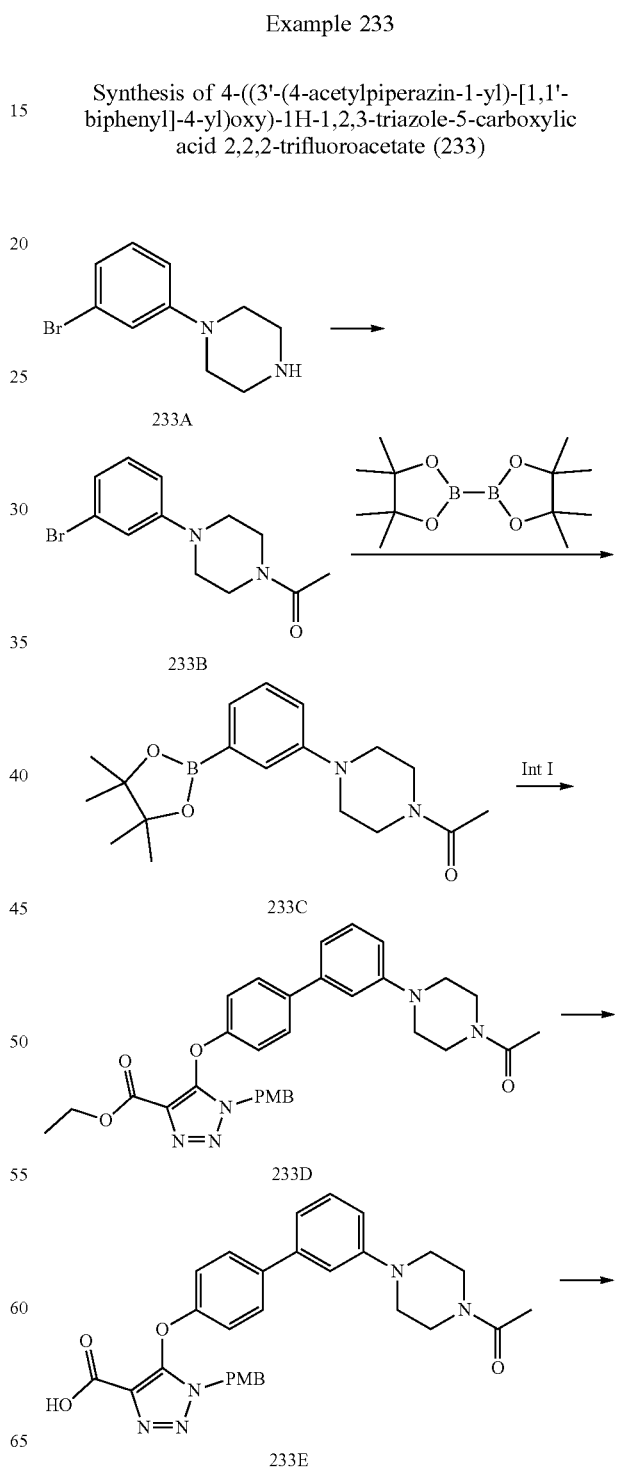

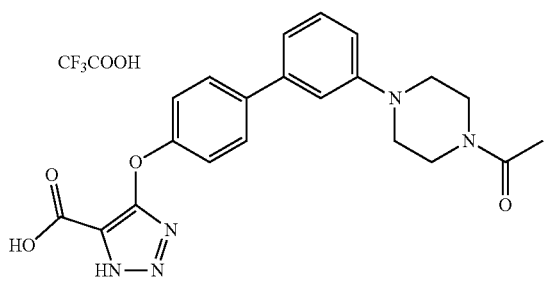

233

A mixture of 1-(3-bromophenyl)piperazine (233A) (480 mg, 2 mmol) and acetic anhydride (2 mL) was stirred at room temperature for 4 hours. The mixture was quenched with saturated NaHCO₃ solution (20 mL) and extracted with ethyl acetate (30 mL×2). The combined organic phases was washed with brine (30 mL), dried over anhydrous sodium sulfate, filtered, and concentrated to yield Compound 233B. LC-MS (ESI) m/z: 283 [M+H]⁺. ¹H-NMR (CDCl₃, 400 MHz): δ (ppm) 2.13 (s, 3H), 3.13-3.19 (m, 4H), 3.60 (t, J=5.6 Hz, 2H), 3.75 (t, J=5.6 Hz, 2H), 6.81-6.84 (m, 1H), 6.99-7.03 (m, 2H), 7.12 (t, J=8.0 Hz, 1H).

Compounds 233C, 233D, 233E, and 233 were synthesized by employing the procedures described for Compounds 27B, 4B, 8F, and 1 using Compounds 233B, 233C, Intermediate I with K₂CO₃ as base and 1,4-dioxane/H₂O as solvent, 233D, and 233E in lieu of Compounds 27A, (4-bromophenyl)boronic acid, 4A with Na₂CO₃ as base and toluene/EtOH/H₂O as solvent, 8E, and 1E. Compound 233C: LC-MS (ESI) m/z: 331 [M+H]⁺. ¹H-NMR (CDCl₃, 400 MHz): δ (ppm) 1.34 (s, 12H), 2.14 (s, 3H), 3.16-3.22 (m, 4H), 3.61 (t, J=5.2 Hz, 2H), 3.76 (t, J=5.2 Hz, 2H), 7.01-7.04 (m, 1H), 7.29 (d, J=8.0 Hz, 1H), 7.35-7.38 (m, 2H). Compound 233D: LC-MS (ESI) m/z: 556 [M+H]⁺. Compound 233E: LC-MS (ESI) m/z: 528 [M+H]⁺. Compound 233: LC-MS (ESI) m/z: 408 [M+H]⁺; ¹H-NMR (DMSO-d₆, 400 MHz): δ (ppm) 2.03 (s, 3H), 3.17 (t, J=5.2 Hz, 2H), 3.23 (t, J=5.2 Hz, 2H), 3.58 (s, 4H), 6.93-6.96 (m, 1H), 7.06 (d, J=8.0 Hz, 1H), 7.14 (t, J=8.8 Hz, 3H), 7.30 (t, J=7.6 Hz, 1H), 7.64 (d, J=8.8 Hz, 2H).

Example 234

Synthesis of 4-((4'-(2-methoxyethoxy)-[1,1'-biphenyl]-4-yl)oxy)-1H-1,2,3-triazole-5-carboxylic acid (234)

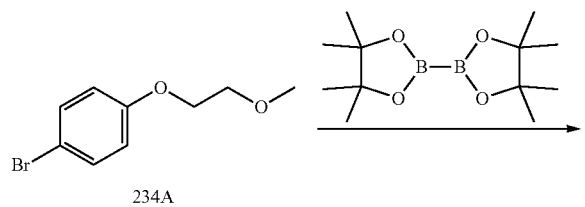

234A

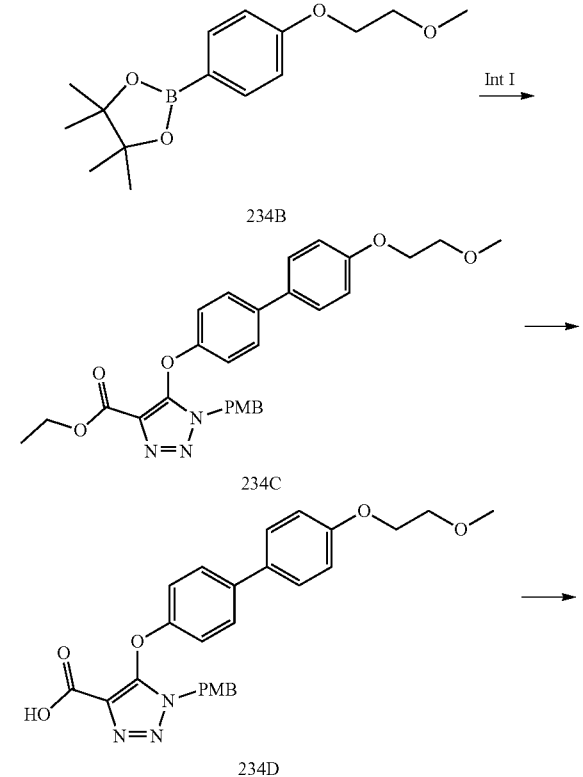

Compounds 234B, 234C, 234D, and 234 were synthesized by employing the procedures described for Compounds 27B, 4B, 8F, and 1 using Compounds 234A, 234B, Intermediate I with K₂CO₃ as base and 1,4-dioxane/H₂O as solvent, 234C, and 234D in lieu of Compounds 27A, (4-bromophenyl)boronic acid, 4A with Na₂CO₃ as base and toluene/EtOH/H₂O as solvent, 8E, and 1E. Compound 234B: LC-MS (ESI) m/z: 279 [M+H]⁺. Compound 234C: LC-MS (ESI) m/z: 504 [M+H]⁺. Compound 234D: LC-MS (ESI) m/z: 476 [M+H]⁺. Compound 234: LC-MS (ESI) m/z: 356 [M+H]⁺; ¹H-NMR (DMSO-d₆, 400 MHz): δ (ppm) 3.32 (s, 3H), 3.67 (d, J=9.2 Hz, 2H), 4.13 (d, J=9.2 Hz, 2H), 7.02 (d, J=8.8 Hz, 2H), 7.12 (d, J=8.8 Hz, 2H), 7.59 (m, 4H), 13.2 (bs, 1H), 15.22 (bs, 1H).

Example 235

Synthesis of acetoxymethyl 4-((6-chloronaphthalen-2-yl)oxy)-1H-1,2,3-triazole-5-carboxylate (235)

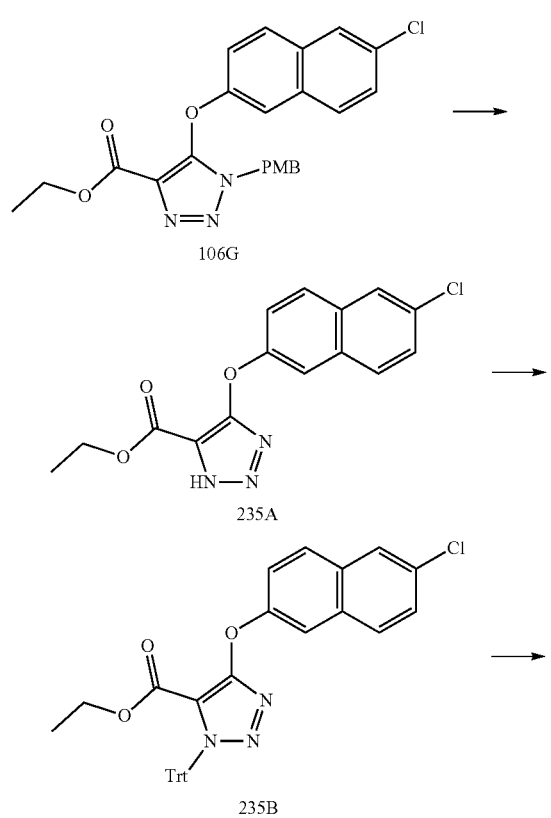

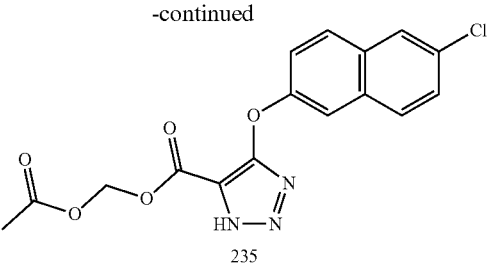

Compounds 235A, 235B, 235C, 235D, and 235 were synthesized by employing the procedures described for Compounds 1, 54A, 8F, 54C, and 54 using Compounds 106G, 235A, 235B, 235C, chloromethyl acetate with Et$_3$N as base and adding NaI, and 235D in lieu of Compounds 1E, 33, 8E, 54B, chloromethyl pivalate with Na$_2$CO$_3$ as base and without NaI, and 54C. Compound 235A: LC-MS (ESI) m/z: 318 [M+H]$^+$. Compound 235B: LC-MS (ESI) m/z: 582 [M+Na]$^+$; (CDCl$_3$, 400 MHz): δ (ppm) 1.20 (t, J=7.6 Hz, 3H), 4.27 (q, J=7.6 Hz, 2H), 7.11-7.19 (m, 6H), 7.28-7.39 (m, 12H), 7.52 (d, J=8.8 Hz, 1H), 7.67 (d, J=8.8 Hz, 1H), 7.76 (d, J=2.0 Hz, 1H). Compound 235C: LC-MS (ESI) m/z: 530 [M−H]; $^1$H-NMR (DMSO-d$_6$, 400 MHz): δ (ppm) 7.11-7.14 (m, 6H), 7.37-7.44 (m, 11H), 7.52 (d, J=8.8 Hz, 1H), 7.82 (d, J=8.8 Hz, 1H), 7.92 (d, J=8.8 Hz, 1H), 8.04 (d, J=2.4 Hz, 1H), 13.42 (s, 1H). Compound 235D: LC-MS (ESI) m/z: 626 [M+Na]$^+$; (CDCl$_3$, 400 MHz): δ (ppm) 2.00 (s, 3H), 5.88 (s, 2H), 7.15-7.18 (m, 6H), 7.25-7.40 (m, 12H), 7.53 (d, J=8.8 Hz, 1H), 7.68 (d, J=8.8 Hz, 1H), 7.77 (d, J=2.0 Hz, 1H). Compound 235: LC-MS (ESI) m/z: 362 [M+H]$^+$; $^1$H-NMR (DMSO-d$_6$, 400 MHz): δ (ppm) 1.95 (s, 3H), 5.81 (s, 2H), 7.43 (d, J=8.8 Hz, 1H), 7.50-7.54 (m, 2H), 7.89 (d, J=8.8 Hz, 1H), 7.96 (d, J=8.8 Hz, 1H), 8.06 (d, J=2.0 Hz, 1H).

Example 236

Synthesis of 4-((6-(difluoromethoxy)naphthalen-2-yl)oxy)-1H-1,2,3-triazole-5-carboxylic acid (236)

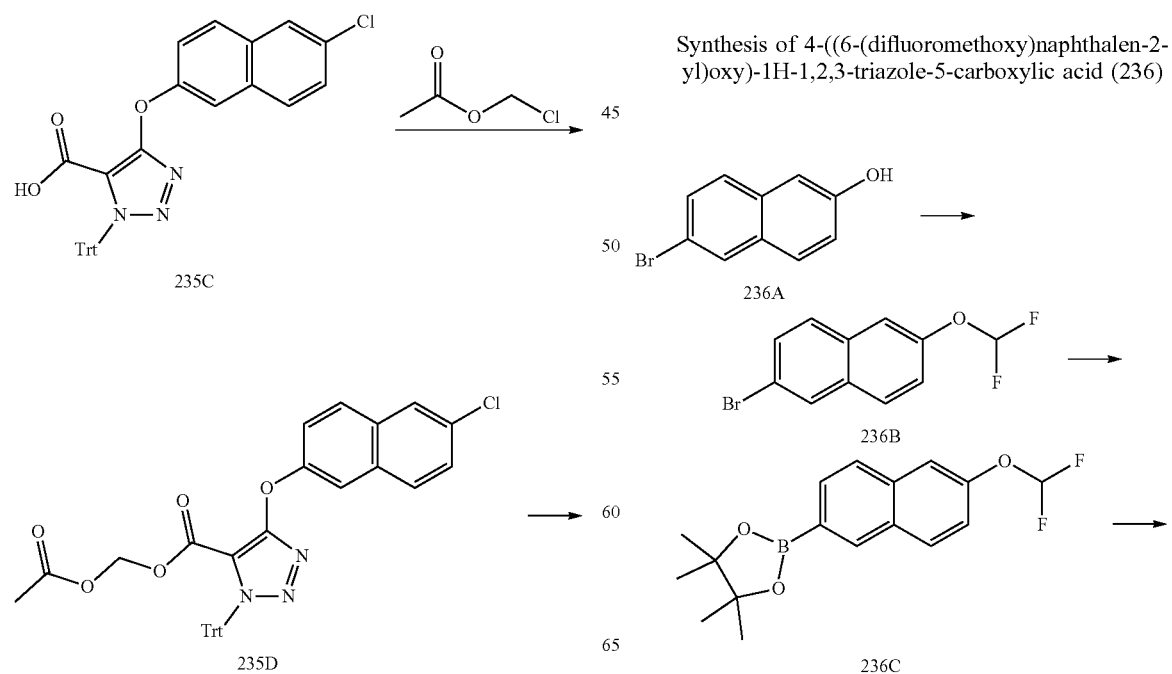

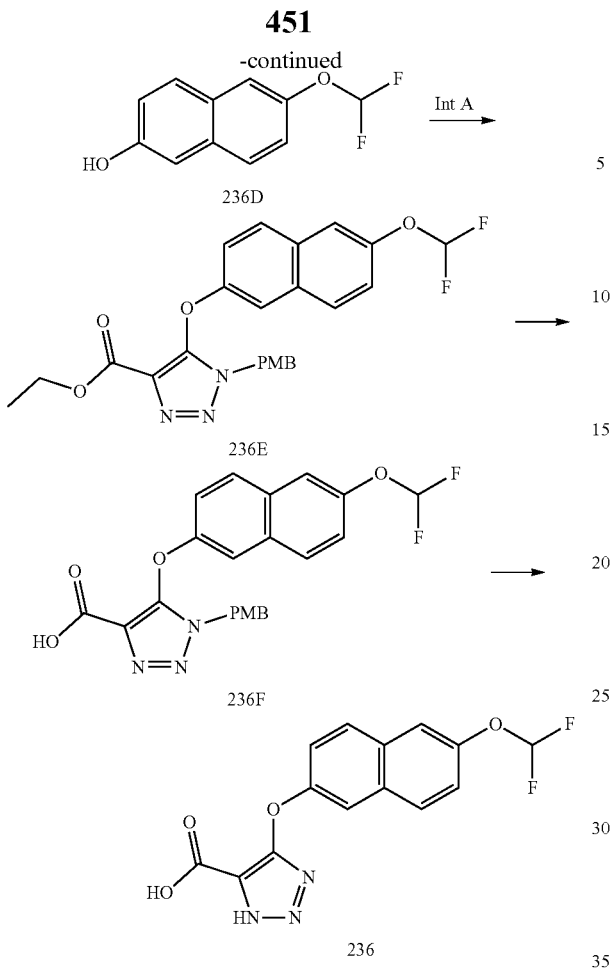

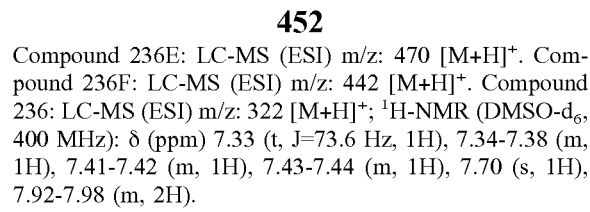

Compound 236E: LC-MS (ESI) m/z: 470 [M+H]$^+$. Compound 236F: LC-MS (ESI) m/z: 442 [M+H]$^+$. Compound 236: LC-MS (ESI) m/z: 322 [M+H]$^+$; $^1$H-NMR (DMSO-d$_6$, 400 MHz): δ (ppm) 7.33 (t, J=73.6 Hz, 1H), 7.34-7.38 (m, 1H), 7.41-7.42 (m, 1H), 7.43-7.44 (m, 1H), 7.70 (s, 1H), 7.92-7.98 (m, 2H).

Example 237

Synthesis of 4-((6,7-difluoro-1,2,3,4-tetrahydronaphthalen-2-yl)oxy)-1H-1,2,3-triazole-5-carboxylic acid (237)

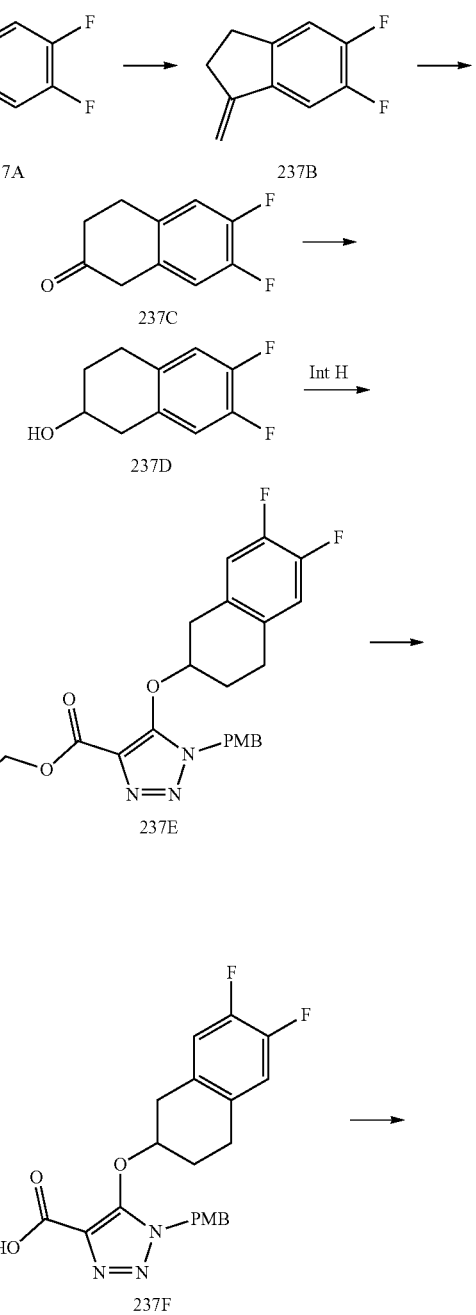

To a stirred mixture of 6-bromonaphthalen-2-ol (236A) (316 mg, 1.42 mmol) and aqueous KOH solution (25%, 1.2 g, 21.32 mmol) in acetonitrile (15 mL) was added 2-chloro-2,2-difluoro-1-phenylethanone (1.35 g, 7.1 mmol) at 0° C. and stirred at 80° C. under nitrogen for 4 hours. After cooled down to room temperature, the mixture was extracted with ethyl acetate (50 mL×3). The combined extracts was washed with brine (50 mL×3), dried over anhydrous sodium sulfate, filtered, concentrated, and purified with flash column chromatography on silica gel (ethyl acetate in petroleum ether, 30% v/v) to afford Compound 236B. LC-MS (ESI) m/z: 273 [M+H]$^+$; $^1$H-NMR (CDCl$_3$, 400 MHz): δ (ppm) 6.39 (t, J=73.6 Hz, 1H), 7.25-7.31 (m, 1H), 7.44-7.47 (m, 1H), 7.55-7.58 (m, 1H), 7.64 (d, J=8.8 Hz, 1H), 7.73 (d, J=8.8 Hz, 1H), 7.98 (s, 1H).

Compound 236C was synthesized by employing the procedure described for Compound 27C using Compound 236B in lieu of Compound 27B, LC-MS (ESI) m/z: 321 [M+H]$^+$.

To a solution of Compound 236C (320 mg, 1.0 mmol) in THF (20 mL) was added NaOH (40 mg, 1 mmol) and H$_2$O$_2$ (30%, 0.1 mL, 1 mmol). The mixture was stirred at room temperature overnight and concentrated under reduced pressure. The residue was purified with flash column chromatography on silica gel (ethyl acetate in petroleum ether, 30% v/v) to afford Compound 236D. LC-MS (ESI) m/z: 209 [M−H]$^-$.

Compounds 236E, 236F, and 236 were synthesized by employing the procedures described for Intermediate I, Compounds 8F, and 1 using Compounds 236D, 236E, and 236F in lieu of 4-bromophenol, Compounds 8E, and 1E.

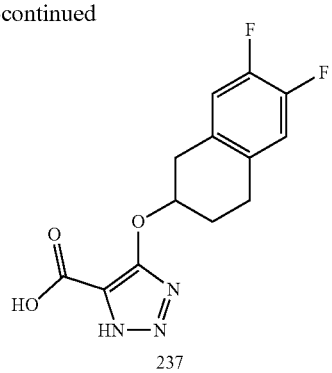

237

Compounds 237B, 237C, 237D, 237E, 237F, and 237 were synthesized by employing the procedures described for Compounds 111B, 111C, 57C, 90C, 8F, and 1 using Compounds 237A, 237B, 237C, 237D, 237E, and 237F in lieu of Compounds 111A, 111B, 57B, 90B, 8E, and 1E. Compound 237B: LC-MS (ESI) m/z: Non-ionizable Compound under routine conditions used; $^1$H-NMR (CDCl$_3$, 400 MHz): δ (ppm) 2.78-2.83 (m, 2H), 2.90-2.94 (m, 2H), 5.02 (t, J=2.4 Hz, 1H), 5.32 (t, J=2.4 Hz, 1H), 7.01 (q, J=7.6, 2.4 Hz, 1H), 7.21 (q, J=7.6, 2.4 Hz, 1H). Compound 237C: LC-MS (ESI) m/z: 183 [M+H]$^+$. Compound 237D: LC-MS (ESI) m/z: 167 [M−OH]$^+$; $^1$H-NMR (CDCl$_3$, 400 MHz): δ (ppm) 1.79-1.95 (m, 1H), 1.99-2.03 (m, 1H), 2.66-2.79 (m, 2H), 2.86-2.91 (m, 1H), 2.97-3.02 (m, 1H), 4.14-4.17 (m, 1H), 6.83-6.89 (m, 2H). Compound 237E: LC-MS (ESI) m/z: 444 [M+H]$^+$; $^1$H-NMR (CDCl$_3$, 400 MHz): δ (ppm) 1.42 (t, J=6.8 Hz, 3H), 1.94-2.07 (m, 2H), 2.73-2.78 (m, 3H), 2.94-2.99 (m, 1H), 3.77 (s, 3H), 4.39 (q, J=7.2 Hz, 2H), 5.0 (d, J=14.8 Hz, 1H), 5.14 (d, J=15.2 Hz, 1H), 5.66-5.71 (m, 1H), 6.73-6.78 (m, 3H), 6.86-6.91 (m, 1H), 7.00 (d, J=1.6 Hz, 2H). Compound 237F: LC-MS (ESI) m/z: 416 [M+H]$^+$. Compound 237: LC-MS (ESI) m/z: 296 [M+H]$^+$; $^1$H-NMR (DMSO-d$_6$, 400 MHz): δ (ppm) 1.99-2.08 (m, 2H), 2.49-2.51 (m, 1H), 2.71-2.97 (m, 2H), 3.15-3.36 (m, 1H), 5.02-5.09 (m, 1H), 7.16-7.21 (m, 2H), 12.81 (s, 1H), 14.76 (s, 1H).

Example 238

Synthesis of 4-((3'-(tetrahydro-2H-pyran-4-yl)-[1,1'-biphenyl]-4-yl)oxy)-1H-1,2,3-triazole-5-carboxylic acid 2,2,2-trifluoroacetate (238)

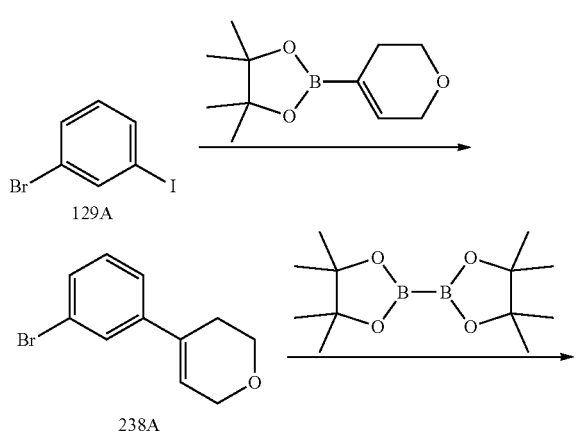

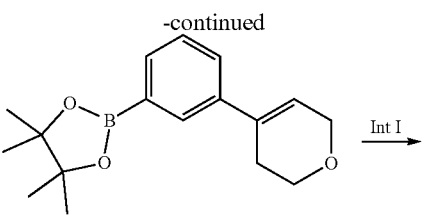

238B

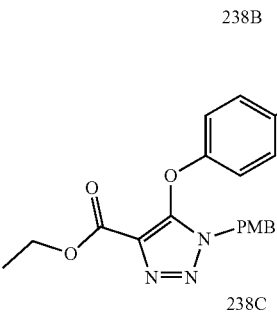

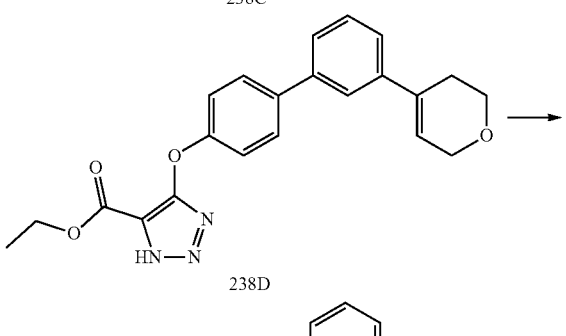

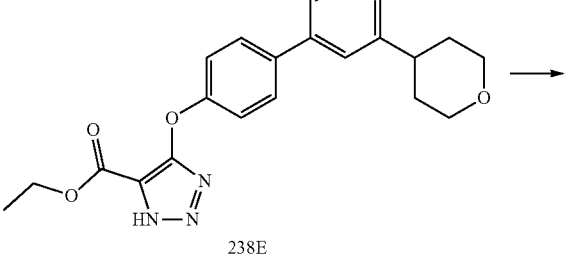

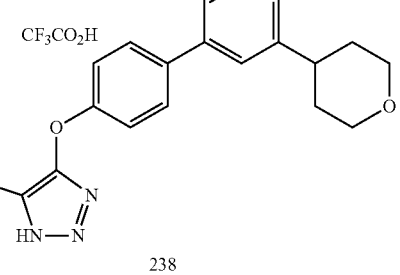

238

Compounds 238A, 238B, 238C, 238D, 238E, and 238 were synthesized by employing the procedures described for Compounds 8B, 27C, 4B, 1, 141, and 8F using 2-(3,6-dihydro-2H-pyran-4-yl)-4,4,5,5-tetramethyl-1,3,2-dioxaborolane, Compounds 129A with Na$_2$CO$_3$ as base and 1,4-dioxane/H$_2$O as solvent, 238A, 238B, Intermediate I with K$_2$CO$_3$ as base and 1,4-dioxane/H$_2$O as solvent, 238C, 238D, and 238E in lieu of (3,4-dichlorophenyl)boronic acid, Compounds 8A with Cs$_2$CO$_3$ as base and DME/H$_2$O as solvent, 27B, (4-bromophenyl)boronic acid, 4A with Na$_2$CO$_3$ as base and toluene/EtOH/H$_2$O as solvent, 1E, 140, and 8E. Compound 238A: LC-MS (ESI) m/z: Non-ionizable compound under routine conditions used; $^1$H-NMR (CDCl$_3$, 400 MHz): δ (ppm) 2.48-2.52 (m, 2H), 3.92-3.96 (m, 2H), 4.32-4.35 (m, 2H), 6.14-6.16 (m, 1H), 7.22 (t, J=8.0 Hz, 1H), 7.33 (d, J=8.0 Hz, 1H), 7.40 (d, J=8.0 Hz, 1H), 7.54 (t, J=2.4 Hz, 1H). Compound 238B: LC-MS (ESI) m/z: 287 [M+H]$^+$. Compound 238C: LC-MS (ESI) m/z: 512 [M+H]$^+$. $^1$H-NMR (CDCl$_3$, 400 MHz): δ (ppm) 1.13 (t, J=7.2 Hz, 3H), 2.57-2.60 (m, 2H), 2.75 (s, 3H), 3.98 (t, J=5.6 Hz, 2H), 4.21 (q, J=7.2 Hz, 2H), 4.35-4.38 (m, 2H), 5.39 (s, 2H), 6.19-6.21 (m, 1H), 6.78-6.85 (m, 4H), 7.23 (d, J=8.4 Hz, 2H), 7.38-7.53 (m, 6H). Compound 238D: LC-MS (ESI) m/z: 392 [M+H]$^+$. Compound 238E: LC-MS (ESI) m/z: 394 [M+H]$^+$. Compound 238: LC-MS (ESI) m/z: 366 [M+H]$^+$; $^1$H-NMR (CD$_3$OD, 400 MHz): δ (ppm) 1.79-1.88 (m, 4H), 2.86-2.91 (m, 1H), 3.56-3.63 (m, 2H), 4.05-4.09 (m, 2H), 7.18-7.25 (m, 3H), 7.35-7.48 (m, 3H), 7.59-7.64 (m, 2H).

Example 239

Synthesis of (isobutyryloxy)methyl 4-((6-chloronaphthalen-2-yl)oxy)-1H-1,2,3-triazole-5-carboxylate (239)

1H), 7.67 (d, J=8.8 Hz, 1H), 7.76 (d, J=2.0 Hz, 1H). Compound 239: LC-MS (ESI) m/z: 390 [M+H]$^+$; $^1$H-NMR (CDCl$_3$, 400 MHz): δ (ppm) 1.12 (d, J=7.2 Hz, 6H), 2.50-2.57 (m, 1H), 5.96 (s, 2H), 7.37-7.41 (m, 2H), 7.52 (s, 1H), 7.66 (d, J=8.8 Hz, 1H), 7.75 (d, J=8.8 Hz, 1H), 7.80 (s, 1H).

Example 240

Synthesis of 1-(((1-(tert-butoxycarbonyl)piperidine-2-carbonyl)oxy)methyl)-4-(3,4-dichlorophenoxy)-1H-1,2,3-triazole-5-carboxylic acid (240)

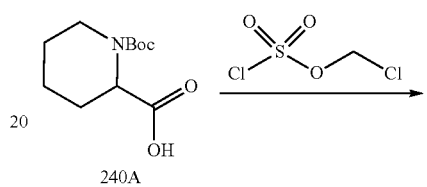

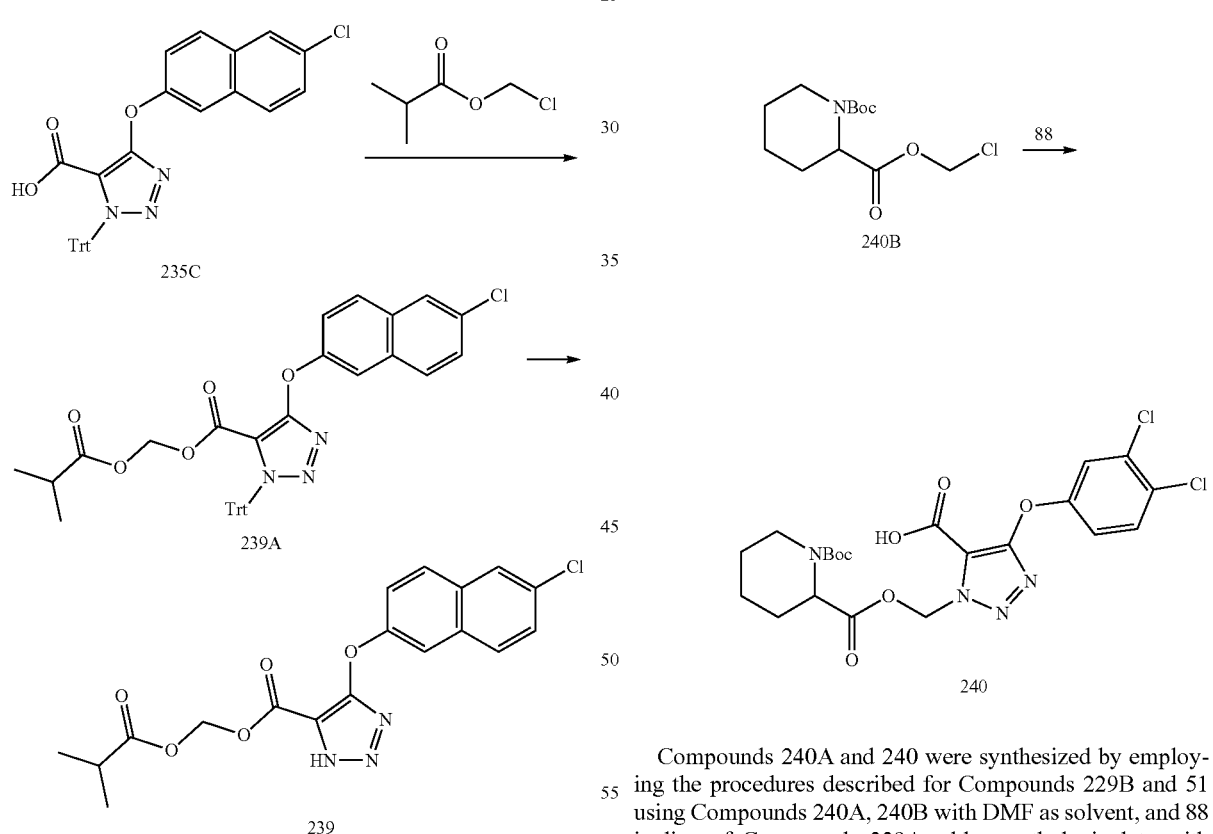

Compounds 239A and 239 were synthesized by employing the procedures described for Compounds 54C and 54 using Compounds 235C, chloromethyl isobutyrate with Et$_3$N as base and adding NaI, and 239A in lieu of Compounds 54B, chloromethyl pivalate with Na$_2$CO$_3$ as base and without NaI, and 54C. Compound 239A: LC-MS (ESI) m/z: 654 [M+Na]$^+$; $^1$H-NMR (CDCl$_3$, 400 MHz): δ (ppm) 1.10 (d, J=7.2 Hz, 6H), 2.46-2.53 (m, 1H), 5.29 (s, 2H), 7.15-7.18 (m, 6H), 7.30-7.40 (m, 12H), 7.53 (d, J=8.8 Hz, Compounds 240A and 240 were synthesized by employing the procedures described for Compounds 229B and 51 using Compounds 240A, 240B with DMF as solvent, and 88 in lieu of Compounds 229A, chloromethyl pivalate with 1,4-dioxane as solvent, and 16. Compound 240A: $^1$H-NMR (CDCl$_3$, 400 MHz): δ (ppm) 1.24-1.27 (m, 1H), 1.30-1.47 (m, 10H), 1.68-1.71 (m, 3H), 2.22-2.24 (m, 1H), 2.90-3.02 (m, 1H), 3.91-4.06 (m, 1H), 4.78-4.94 (m, 1H), 5.66-5.82 (m, 2H). Compound 240: LC-MS (ESI) m/z: 537 [M+Na]$^+$; $^1$H-NMR (CD$_3$OD, 400 MHz): δ (ppm) 1.16-1.23 (m, 1H), 1.37-1.43 (m, 10H), 1.61-1.68 (m, 3H), 2.14-2.17 (m, 1H), 2.84-2.92 (m, 1H), 3.88-3.92 (m, 1H), 4.78-4.80 (m, 1H), 6.22-6.32 (m, 2H), 7.16 (dd, J=9.2, 3.2 Hz, 1H), 7.38 (d, J=2.8 Hz, 1H), 7.50 (d, J=9.2 Hz, 1H).

Example 241

Synthesis of 4-((5,6-dichloro-2,3-dihydro-1H-inden-2-yl)oxy)-1H-1,2,3-triazole-5-carboxylic acid 2,2,2-trifluoroacetate (241)

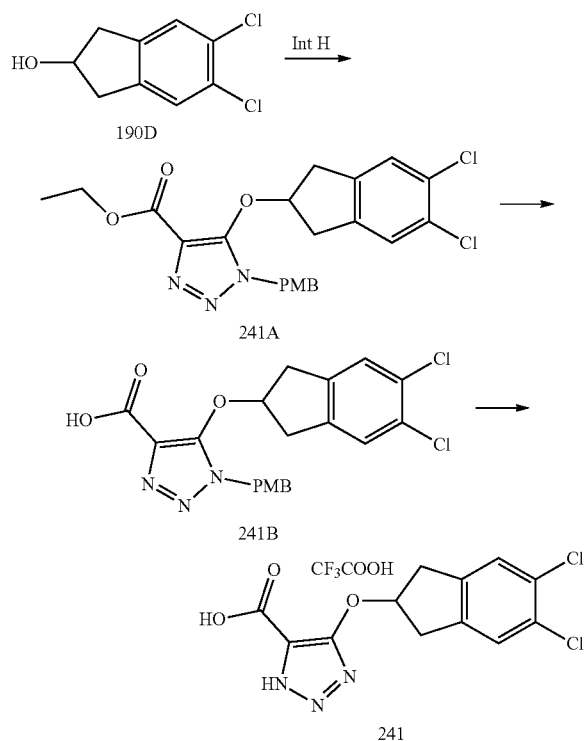

Compounds 241A, 241B, and 241 were synthesized by employing the procedures described for Compounds 90C, 8F, and 1 using Compounds 190D, 241A, and 241B in lieu of Compounds 90B, 8E, and 1E. Compound 241A: LC-MS (ESI) m/z: 462 [M+H]$^+$; $^1$H-NMR (DMSO-d$_6$, 400 MHz): δ (ppm) 1.45 (t, J=7.2 Hz, 3H), 2.95 (d, J=17.6 Hz, 2H), 3.19 (dd, J=17.6, 4.8 Hz, 2H), 3.79 (s, 3H), 4.44 (q, J=7.2 Hz, 2H), 5.06 (s, 2H), 6.19-6.21 (m, 1H), 6.72 (d, J=8.8 Hz, 2H), 6.94 (d, J=8.8 Hz, 2H), 7.26 (s, 2H). Compound 241B: LC-MS (ESI) m/z: 434 [M+H]$^+$. Compound 241: LC-MS (ESI) m/z: 314 [M+H]$^+$; $^1$H-NMR (DMSO-d$_6$, 400 MHz): δ (ppm) 3.12 (d, J=18.8 Hz, 2H), 3.38 (dd, J=18.8, 6.0 Hz, 2H), 5.46 (s, 1H), 7.57 (s, 2H), 12.88 (s, 1H), 14.84 (s, 1H).

Example 242

Synthesis of 4-((4'-(tetrahydro-2H-pyran-4-yl)-[1,1'-biphenyl]-4-yl)oxy)-1H-1,2,3-triazole-5-carboxylic acid (242)

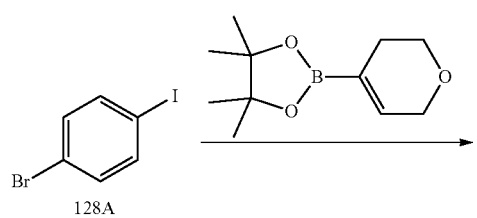

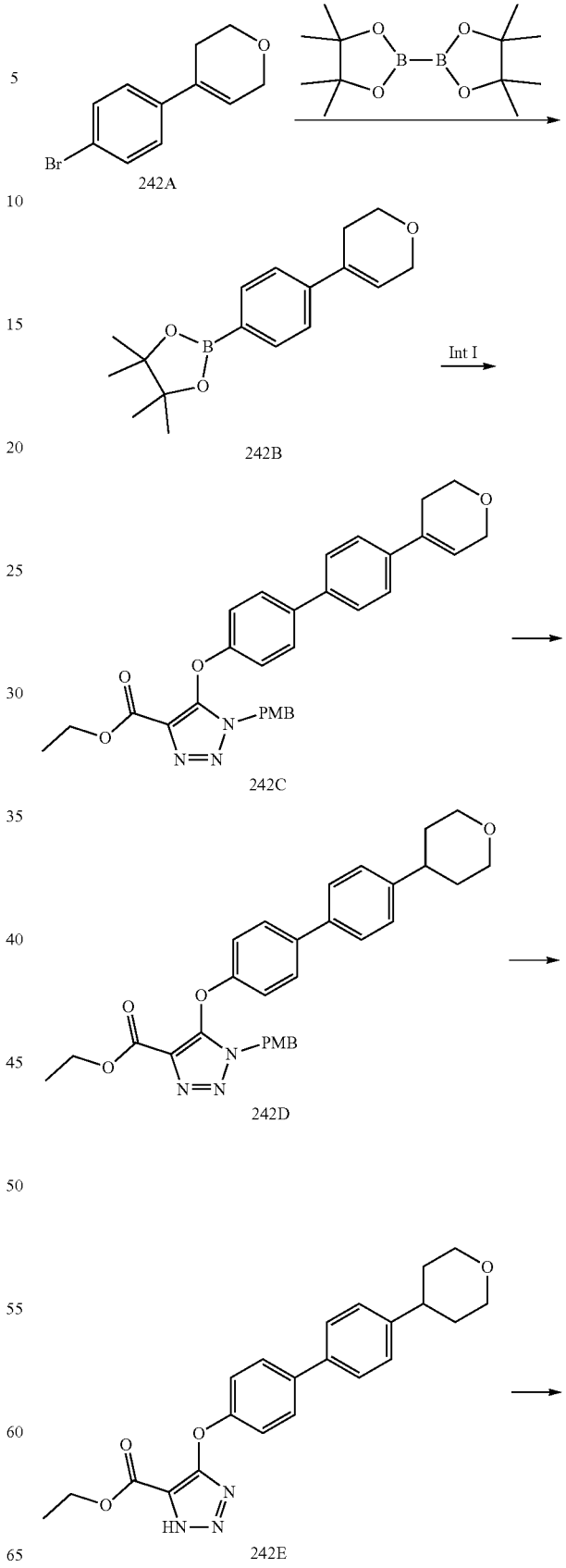

459
-continued

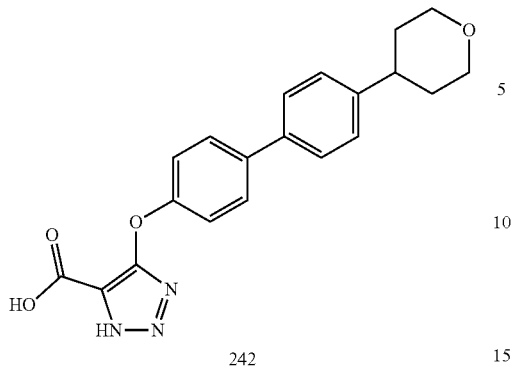

242

Compounds 242A, 242B, 242C, 242D, 242E, and 242 were synthesized by employing the procedures described for Compounds 8B, 27C, 4B, 141, 1, and 8F using 2-(3,6-dihydro-2H-pyran-4-yl)-4,4,5,5-tetramethyl-1,3,2-dioxaborolane, Compounds 128A with Na$_2$CO$_3$ as base and 1,4-dioxane/H$_2$O as solvent, 242A, 242B, Intermediate I with K$_2$CO$_3$ as base and 1,4-dioxane/H$_2$O as solvent, 242C, 242D, and 242E in lieu of (3,4-dichlorophenyl)boronic acid, Compounds 8A with Cs$_2$CO$_3$ as base and DME/H$_2$O as solvent, 27B, (4-bromophenyl)boronic acid, 4A with Na$_2$CO$_3$ as base and toluene/EtOH/H$_2$O as solvent, 140, 1E, and 8E. Compound 242A: LC-MS (ESI) m/z: Non-ionizable compound under routine conditions used; $^1$H-NMR (CDCl$_3$, 400 MHz): δ (ppm) 2.47-2.52 (m, 2H), 3.94 (t, J=5.6 Hz, 2H), 4.31-4.33 (m, 2H), 6.13-6.15 (m, 1H), 7.25-7.28 (m, 2H), 7.345-7.49 (m, 2H). Compound 242B: LC-MS (ESI) m/z: 287 [M+H]$^+$. Compound 242C: LC-MS (ESI) m/z: 512 [M+H]$^+$; $^1$H-NMR (CDCl$_3$, 400 MHz): δ (ppm) 1.12 (t, J=6.8 Hz, 3H), 2.56-2.58 (m, 2H), 3.75 (s, 3H), 3.97 (t, J=5.6 Hz, 2H), 4.21 (q, J=6.8 Hz, 2H), 4.35-4.38 (m, 2H), 5.39 (s, 2H), 6.20 (t, J=1.6 Hz, 1H), 6.78-6.85 (m, 4H), 7.22 (d, J=8.4 Hz, 2H), 7.46-7.53 (m, 6H). Compound 242D: LC-MS (ESI) m/z: Non-ionizable compound under routine conditions used. Compound 242E: LC-MS (ESI) m/z: 394 [M+H]$^+$. Compound 242: LC-MS (ESI) m/z: 366 [M+H]$^+$; $^1$H-NMR (CD$_3$OD, 400 MHz): δ (ppm) 1.79-1.85 (m, 4H), 2.82-2.87 (m, 1H), 3.56-3.63 (m, 2H), 4.05-4.08 (m, 2H), 7.18-7.21 (m, 2H), 7.32 (d, J=8.4 Hz, 2H), 7.56 (dd, J=8.4, 2.0 Hz, 2H), 7.59-7.64 (m, 2H).

Example 243

Synthesis of 4-(((3,4-dichlorophenyl)thio)methyl)-1H-1,2,3-triazole-5-carboxylic acid (243)

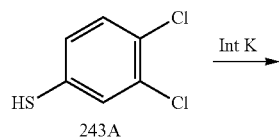

243A

460
-continued

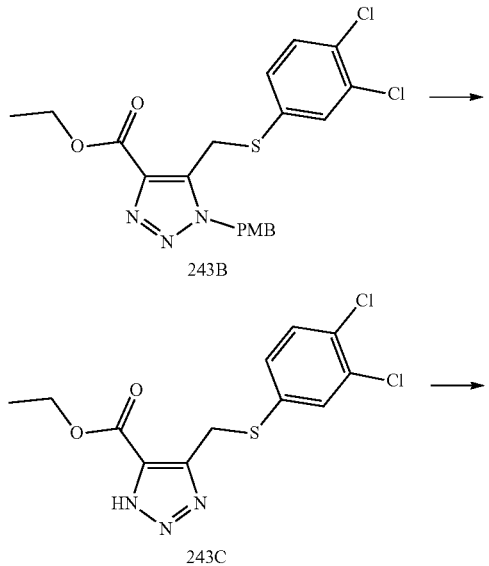

A mixture of Intermediate K (248 mg, 0.7 mmol), 3,4-dichlorobenzenethiol (243A) (126 mg, 0.7 mmol) and sodium carbonate (149 mg, 1.4 mmol) in NMP (10 mL) was stirred at 100° C. overnight. After cooled down to room temperature, the mixture was diluted with EtOAc (50 mL) and washed with brine (50 mL×3). The organic layer was dried over anhydrous sodium sulfate, concentrated, and purified with flash column chromatography on silica gel (ethyl acetate in petroleum ether, 20% v/v) to afford Compound 243B. LC-MS (ESI) m/z: 452 [M+H]$^+$. $^1$H-NMR (CDCl$_3$, 400 MHz): δ (ppm) 1.38 (t, J=6.8 Hz, 3H), 3.81 (s, 3H), 4.27 (s, 2H), 4.34 (q, J=6.8 Hz, 2H), 5.62 (s, 2H), 6.88 (d, J=8.4 Hz, 2H), 7.01-7.07 (m, 1H), 7.15 (d, J=8.4 Hz, 2H), 7.28-7.42 (m, 2H).

Compounds 243C and 243 were synthesized by employing the procedures described for Compounds 1 and 8F using Compounds 243B and 243C in lieu of Compounds 1E and 8E. Compound 243C: LC-MS (ESI) m/z: 332 [M+H]$^+$. Compound 243: LC-MS (ESI) m/z: 304 [M+H]$^+$; $^1$H-NMR (CD$_3$OD, 400 MHz): δ (ppm) 4.52 (s, 2H), 7.27 (dd, J=8.4, 2.0 Hz, 1H), 7.43 (d, J=8.4 Hz, 1H), 7.55 (d, J=2.0 Hz, 1H).

Example 244

Synthesis of (isobutyryloxy)methyl 4-((4'-(piperidin-1-yl)-[1,1'-biphenyl]-4-yl)thio)-1H-1,2,3-triazole-5-carboxylate (244)

Example 245

Synthesis of 4-((1-isopropyl-1,2,3,4-tetrahydroquinolin-7-yl)oxy)-1H-1,2,3-triazole-5-carboxylic acid 2,2,2-trifluoroacetate (245)

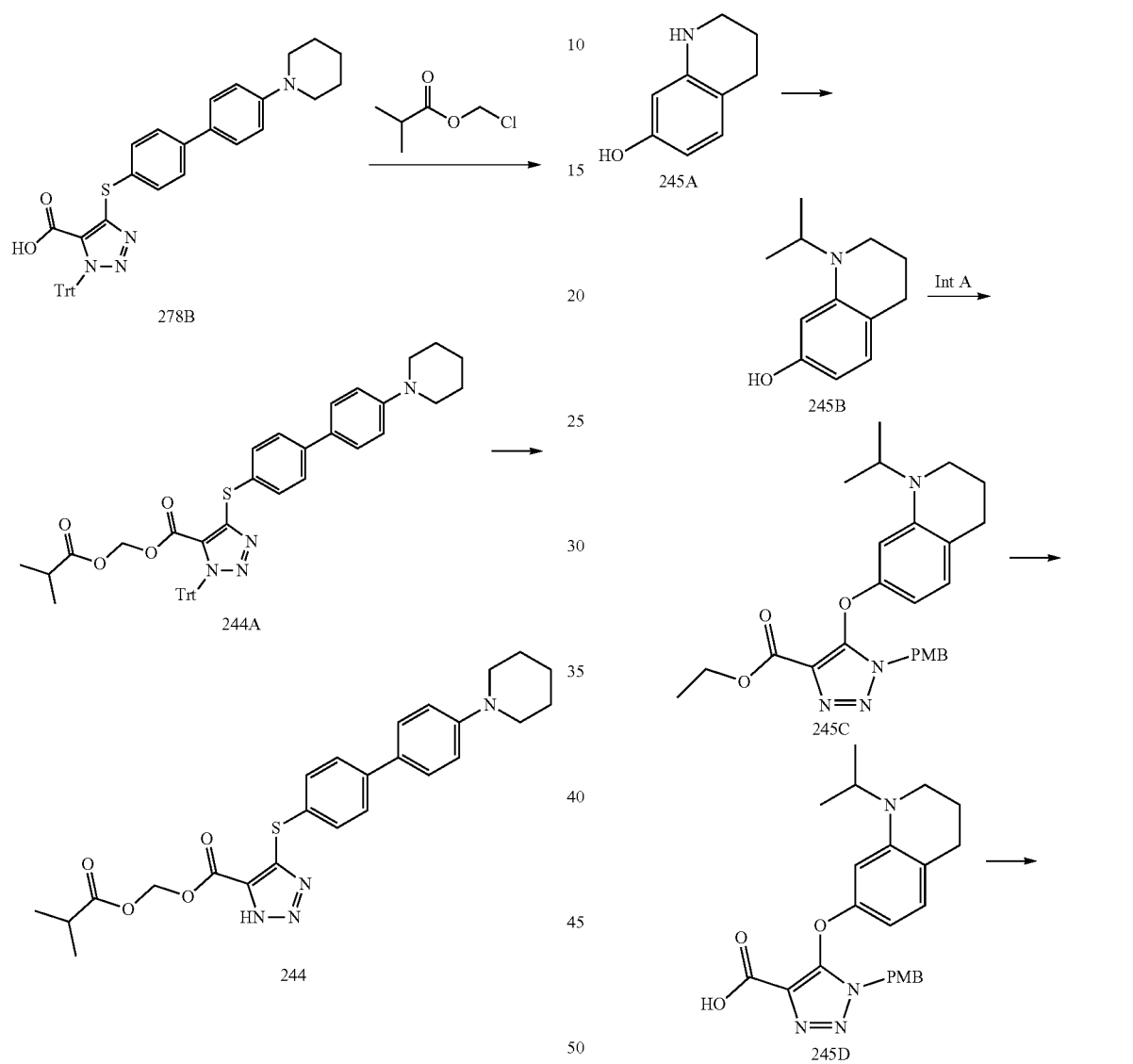

Compounds 244A and 244 were synthesized by employing the procedures described for Compounds 54C and 256 using chloromethyl isobutyrate, Compounds 278B with Na$_2$CO$_3$ as base and DMF/THF as solvent and adding NaI, and 244A in lieu of chloromethyl pivalate, Compounds 54B with Na$_2$CO$_3$ as base and DMF as solvent and without NaI, and 256D. Compound 244A: LC-MS (ESI) m/z: 723 [M+H]$^+$; $^1$H-NMR (CDCl$_3$, 400 MHz): δ (ppm) 1.18 (d, J=6.8 Hz, 6H), 1.59-1.63 (m, 2H), 1.70-1.75 (m, 4H), 2.51-2.60 (m, 1H), 3.22-3.25 (m, 4H), 5.96 (s, 2H), 6.98-7.02 (m, 8H), 7.20-7.25 (m, 5H), 7.28-7.32 (m, 4H), 7.40-7.49 (m, 6H). Compound 244: LC-MS (ESI) m/z: 481 [M+H]$^+$; $^1$H-NMR (DMSO-d$_6$, 400 MHz): δ (ppm) 1.09 (d, J=7.2 Hz, 6H), 1.58-1.70 (m, 6H), 2.57-2.65 (m, 1H), 3.31 (brs, 4H), 5.94 (s, 2H), 7.11-7.275 (m, 2H), 7.51-7.64 (m, 2H), 7.63-7.69 (m, 4H).

To a mixture of Compound 245A (500 mg, 3.36 mmol), acetone (2.12 g, 36.5 mmol) and triethylsilane (4.0 mL) in DCM (15 mL) was added TFA (2.2 mL) and stirred at room temperature for 16 hours. The reaction mixture was concentrated under reduced pressure and the residue was purified with preparative HPLC to afford Compound 245B. LC-MS (ESI) m/z: 192 [M+H]⁺.

Compounds 245C, 245D, and 245 were synthesized by employing the procedures described for Intermediate I, Compounds 8F, and 1 using Compounds 245B, 245C, and 245D in lieu of 4-bromophenol, Compounds 8E, and 1E. Compound 245C: LC-MS (ESI) m/z: 451 [M+H]⁺. Compound 245D: LC-MS (ESI) m/z: 423 [M+H]⁺. Compound 245: LC-MS (ESI) m/z: 303 [M+H]⁺; ¹H-NMR (DMSO-d₆, 400 MHz): δ (ppm) 1.11 (s, 3H), 1.13 (s, 3H), 1.80 (t, J=4.8 Hz, 2H), 2.66 (t, J=6.4 Hz, 2H), 3.08-3.11 (m, 1H), 3.11-3.16 (m, 2H), 4.50-5.50 (br, 1H), 6.18 (s, 1H), 6.90 (s, 1H).

Example 246

Synthesis of 4-((3'-(4-methylpiperazin-1-yl)-[1,1'-biphenyl]-4-yl)oxy)-1H-1,2,3-triazole-5-carboxylic acid 2,2,2-trifluoroacetate (246)

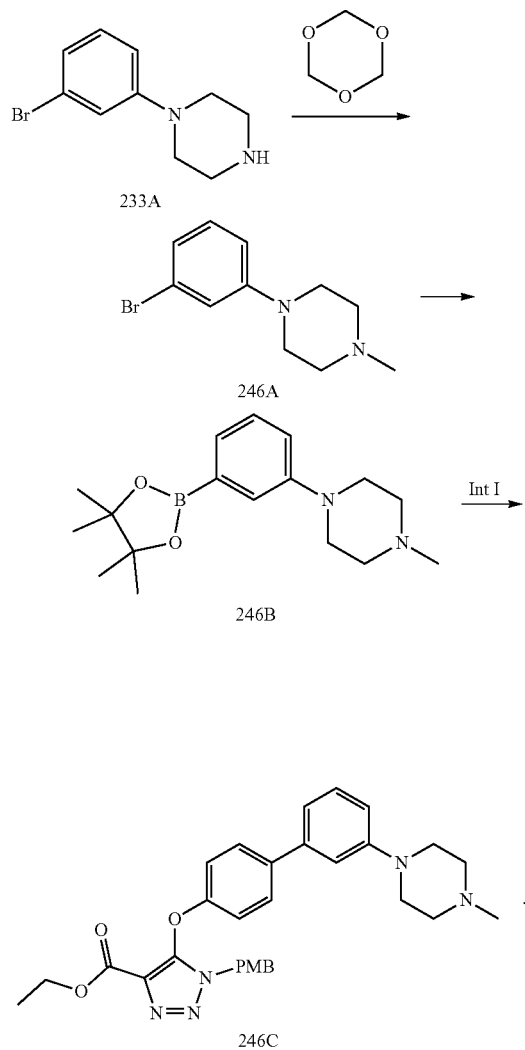

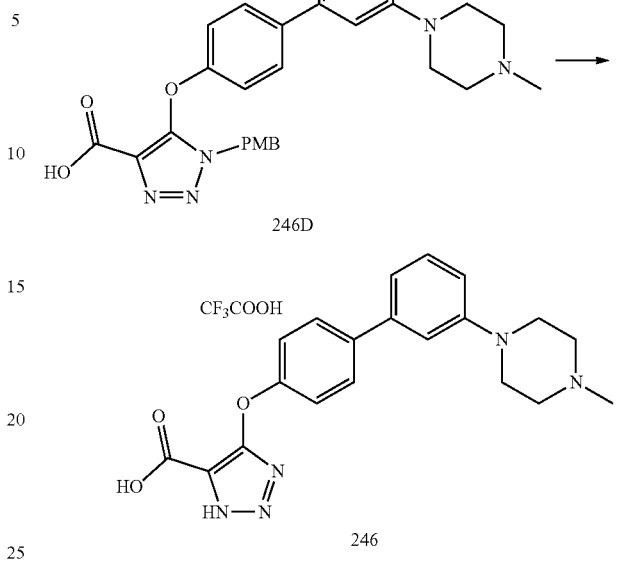

Compounds 246A, 246B, 246C, 246D, and 246 were synthesized by employing the procedures described for Compounds 245B, 27C, 206C, 8F, and 1 using 1,3,5-trioxane, Compounds 233A, 246A, 246B, Intermediate I, 246C, and 246D in lieu of acetone, Compounds 245A, 27B, 206B, Intermediate A, 8E, and 1E. Compound 246A: LC-MS (ESI) m/z: 255 [M+H]⁺. Compound 246C: LC-MS (ESI) m/z: 528 [M+H]⁺. Compound 246D: LC-MS (ESI) m/z: 500 [M+H]⁺. Compound 246: LC-MS (ESI) m/z: 380 [M+H]⁺; ¹H-NMR (DMSO-d₆, 400 MHz): δ (ppm) 2.87 (s, 3H), 3.39 (s, 8H), 6.98-7.00 (m, 1H), 7.12-7.16 (m, 3H), 7.22-7.23 (m, 1H), 7.34 (t, J=15.6 Hz, 1H), 7.66-7.68 (m, 2H).

Example 247

Synthesis of 4-((3'-cyclohexyl-[1,1'-biphenyl]-4-yl)thio)-1H-1,2,3-triazole-5-carboxylic acid (247)

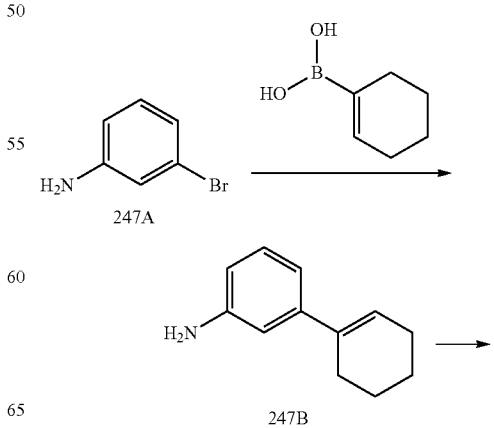

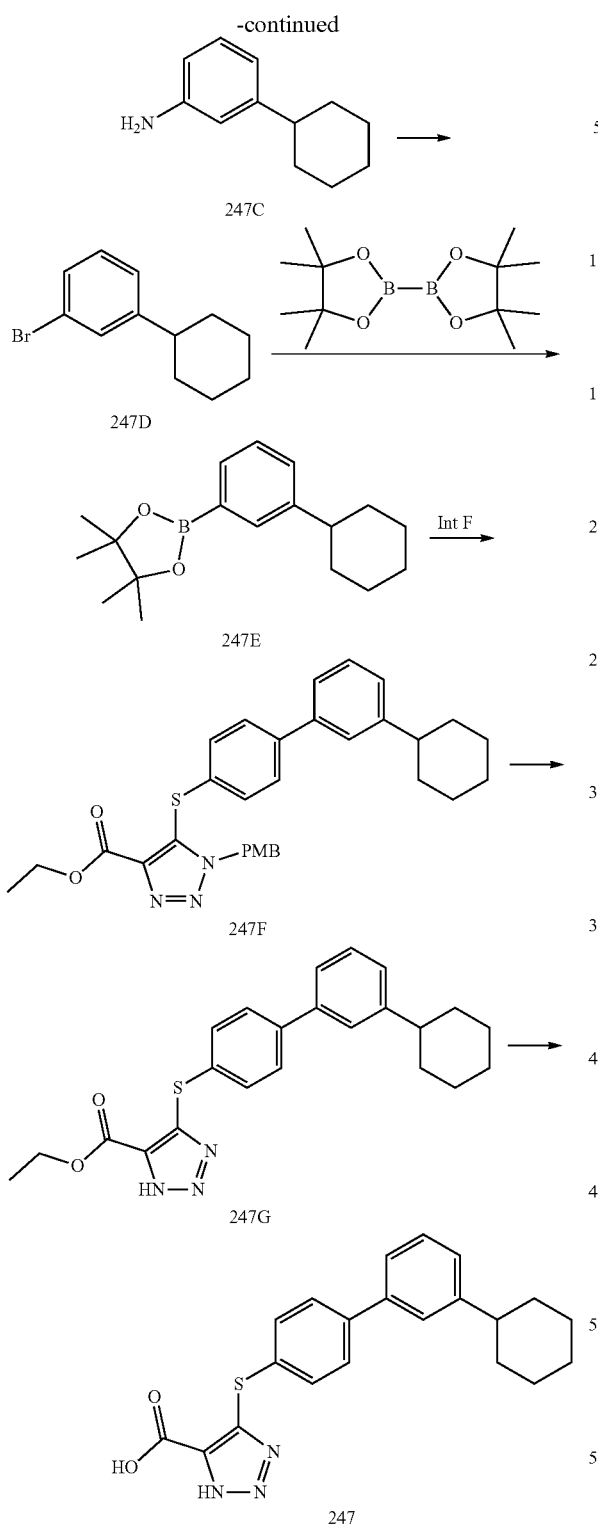

acid, Compounds 4A with Na₂CO₃ as base and toluene/EtOH/H₂O as solvent, 140 with EtOAc as solvent, 30A with isoamyl nitrite/CuCl₂, 27B, 4A with Na₂CO₃ as base and toluene/EtOH/H₂O as solvent, 225C, and 8E. Compound 247B: LC-MS (ESI) m/z: 174 [M+H]⁺; ¹H-NMR (CDCl₃, 400 MHz): δ (ppm) 1.63-1.67 (m, 2H), 1.73-1.77 (m, 2H), 2.16-2.20 (m, 2H), 2.35-2.39 (m, 2H), 3.61 (s, 2H), 6.06-6.08 (m, 1H), 6.55-6.57 (m, 1H), 6.70-6.71 (m, 1H), 6.79-6.80 (m, 1H), 7.07-7.11 (m, 1H). Compound 247C: LC-MS (ESI) m/z: 176 [M+H]⁺. Compound 247D: LC-MS (ESI) m/z: non-ionizable compound under routine conditions used; ¹H-NMR (CDCl₃, 400 MHz): δ (ppm) 1.24-1.44 (m, 5H), 1.72-1.84 (m, 5H), 2.45-2.46 (m, 1H), 7.13-7.17 (m, 2H), 7.28-7.31 (m, 1H), 7.35 (s, 1H). Compound 247E: LC-MS (ESI) m/z: 287 [M+H]⁺; ¹H-NMR (CDCl₃, 400 MHz): δ (ppm) 1.26-1.29 (m, 2H), 1.30-1.32 (m, 12H), 1.36-1.49 (m, 3H), 1.81-1.88 (m, 5H), 2.51-2.53 (m, 1H), 7.29-7.31 (m, 2H), 7.62-7.66 (m, 2H). Compound 247F: LC-MS (ESI) m/z: 528 [M+H]⁺. Compound 247G: LC-MS (ESI) m/z: 408 [M+H]⁺. Compound 247: LC-MS (ESI) m/z: 380 [M+H]⁺; (CD₃OD, 400 MHz): δ (ppm) 1.31-1.34 (m, 1H), 1.45-1.55 (m, 4H), 1.77-1.80 (m, 1H), 1.86-1.92 (m, 4H), 2.58-2.59 (m, 1H), 7.22-7.24 (m, 1H), 7.34-7.36 (m, 1H), 7.42-7.46 (m, 2H), 7.56-7.58 (m, 2H), 7.63-7.65 (m, 2H).

Example 248

Synthesis of 4-(4-(trifluoromethyl)phenoxy)-1H-1,2,3-triazole-5-carboxylic acid (248)

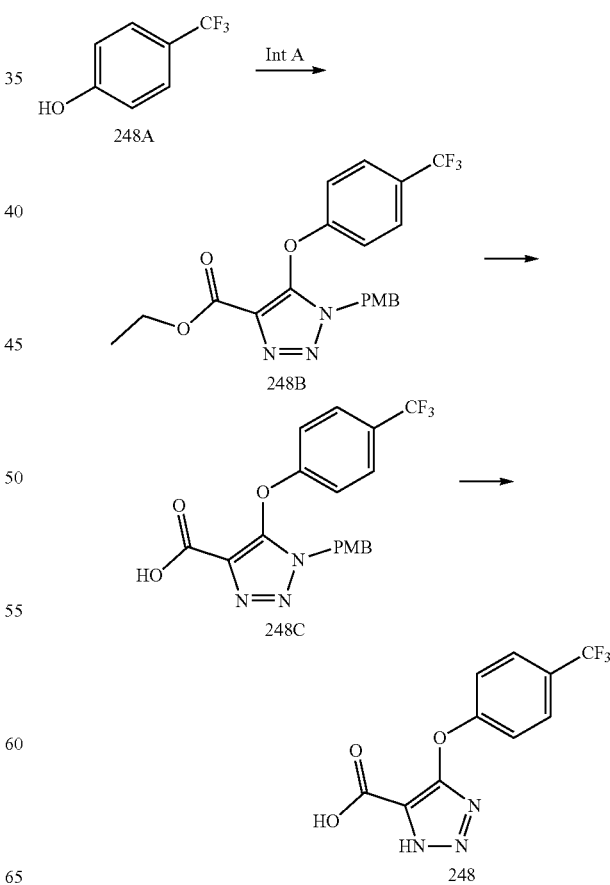

Compounds 247B, 247C, 247D, 247E, 247F, 247G, and 247 were synthesized by employing the procedures described for Compounds 4B, 141, 30B, 27C, 4B, 225, and 8F using cyclohexenylboronic acid, Compounds 247A with K₂CO₃ as base and 1,4-dioxane/H₂O as solvent, 247C with HBr/CuBr/isopentyl nitrite, 247D, 247E with K₂CO₃ as base and 1,4-dioxane/H₂O as solvent, 247F, and 246D in lieu of (4-bromophenyl)boronic Compounds 248B, 248C, and 248 were synthesized by employing the procedures described for Intermediate I, Compounds 8F, and 1 using Compounds 248A, 248B, and 248C in lieu of 4-bromophenol, Compounds 8E, and 1E. Compound 248B: LC-MS (ESI) m/z: 422 [M+H]⁺. Compound 248C: LC-MS (ESI) m/z: 394 [M+H]⁺. Compound 248: LC-MS (ESI) m/z: 274 [M+H]⁺; ¹H-NMR (DMSO-d₆, 400 MHz): δ (ppm) 7.23 (d, J=8.4 Hz, 2H), 7.73 (d, J=8.4 Hz, 2H).

Example 249

Synthesis of (benzoyloxy)methyl 4-((6-chloronaphthalen-2-yl)oxy)-1H-1,2,3-triazole-5-carboxylate (249)

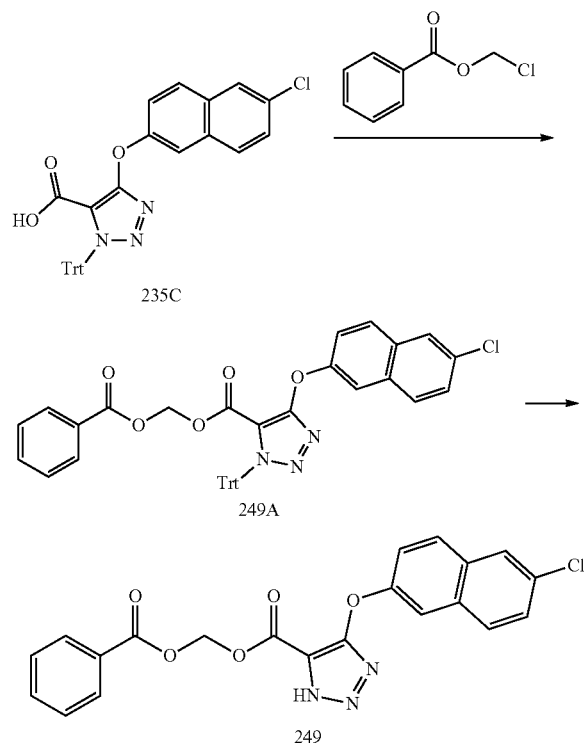

Example 250

Synthesis of 4-(4-(quinolin-7-yl)phenoxy)-1H-1,2,3-triazole-5-carboxylic acid 2,2,2-trifluoroacetate (250)

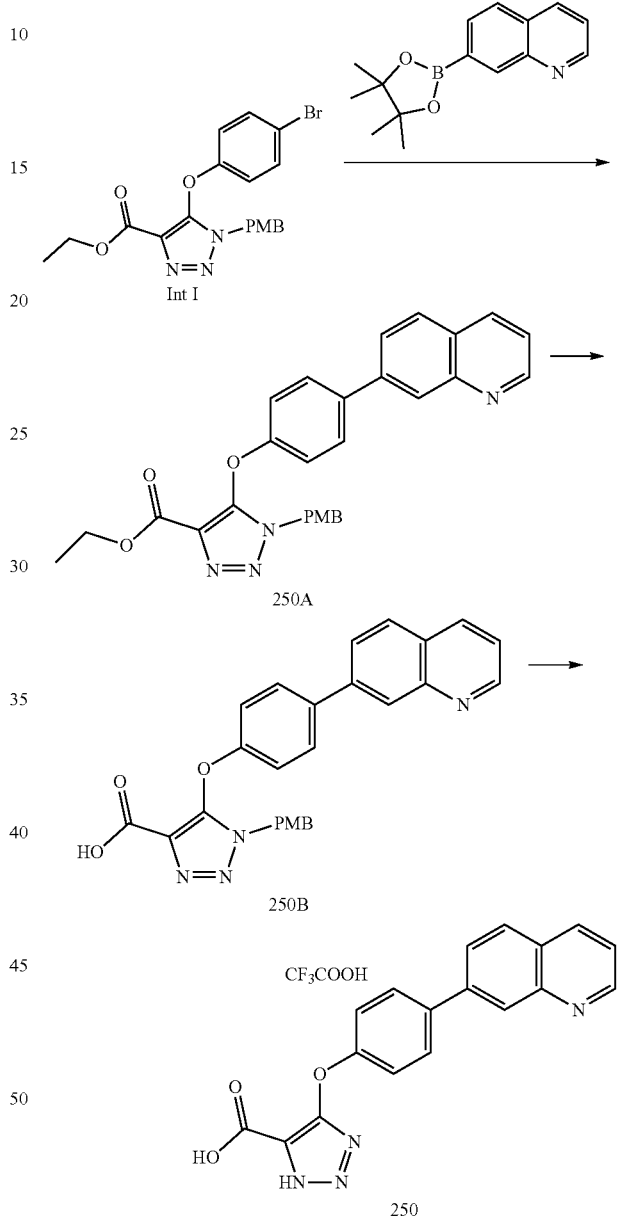

Compounds 249A and 249 were synthesized by employing the procedures described for 54C and 54 using Compounds 235C, chloromethyl benzoate with Et₃N as base and adding NaI, and 249A in lieu of Compounds 54B, chloromethyl pivalate with Na₂CO₃ as base and without NaI, and 54C. Compound 249A: LC-MS (ESI) m/z: 688 [M+Na]⁺; ¹H-NMR (CDCl₃, 400 MHz): δ (ppm) 6.13 (s, 2H), 7.15-7.18 (m, 6H), 7.29-7.41 (m, 14H), 7.46 (d, J=8.8 Hz, 1H), 7.55-7.59 (m, 2H), 7.66 (s, 1H), 7.92 (d, J=8.8 Hz, 2H). Compound 249: LC-MS (ESI) m/z: 424 [M+H]⁺; ¹H-NMR (CD₃OD, 400 MHz): δ (ppm) 6.03 (s, 2H), 7.07 (d, J=2.4 Hz, 1H), 7.23-7.27 (m, 2H), 7.32-7.37 (m, 2H), 7.52-7.7.63 (m, 4H), 7.69-7.72 (m, 2H).

Compounds 250A, 250B, and 250 were synthesized by employing the procedures described for Compounds 8B, 8F, and 1 using 7-(4,4,5,5-tetramethyl-1,3,2-dioxaborolan-2-yl)quinolone, Intermediate I with Na₂CO₃ as base and 1,4-dioxane/H₂O as solvent, Compounds 8E, and 1E in lieu of (3,4-dichlorophenyl)boronic acid, Compounds 8A with Cs₂CO₃ as base and DME/H₂O as solvent, 8E, and 1E. Compound 250A: LC-MS (ESI) m/z: 481 [M+H]⁺. Compound 250B: LC-MS (ESI) m/z: 453 [M+H]⁺. Compound 250: LC-MS (ESI) m/z: 333 [M+H]⁺; ¹H-NMR (DMSO-d₆, 400 MHz): δ (ppm) 7.21-7.25 (m, 2H), 7.55-7.58 (m, 1H), 7.87-7.90 (m, 2H), 7.96-7.99 (m, 1H), 8.10 (d, J=8.4 Hz, 1H), 8.26 (s, 1H), 8.44 (d, J=8.4 Hz, 1H). 8.95-8.97 (m, 1H).

Example 251

Synthesis of (pivaloyloxy)methyl 4-((6-chloronaphthalen-2-yl)oxy)-1H-1,2,3-triazole-5-carboxylate (251)

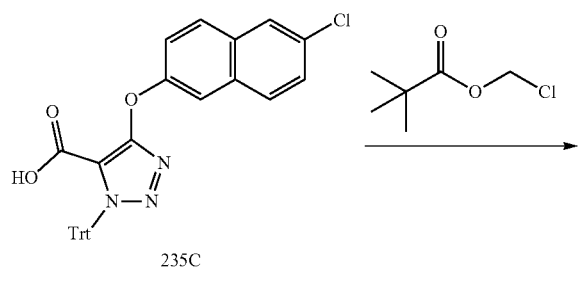
235C

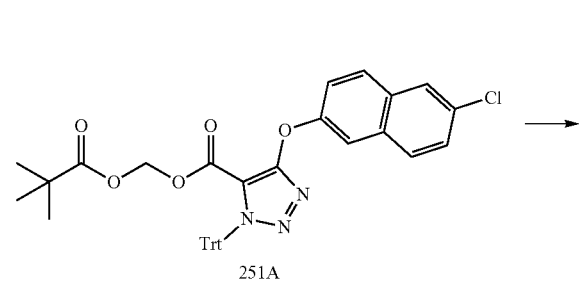
251A

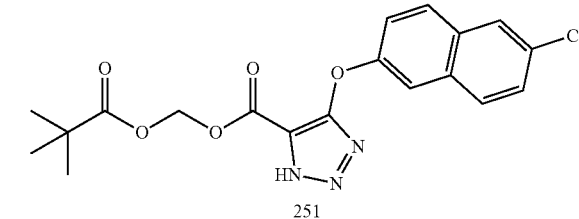
251

Compounds 251A and 251 were synthesized by employing the procedures described for 54C and 54 using Compounds 235C with Et₃N as base and adding NaI, and 251A in lieu of Compounds 54B with Na₂CO₃ as base and without NaI, and 54C. Compound 251A: LC-MS (ESI) m/z: 668 [M+Na]⁺; ¹H-NMR (CDCl₃, 400 MHz): δ (ppm) 1.13 (s, 9H), 5.91 (s, 2H), 7.15-7.18 (m, 6H), 7.29-7.40 (m, 12H), 7.52 (d, J=8.8 Hz, 1H), 7.67 (d, J=8.8 Hz, 1H), 7.60 (s, 1H). Compound 251: LC-MS (ESI) m/z: 426 [M+Na]⁺; ¹H-NMR (CD₃OD, 400 MHz): δ (ppm) 1.02 (s, 9H), 5.84 (s, 2H), 7.23 (d, J=2.4 Hz, 1H), 7.32-7.40 (m, 2H), 7.69 (d, J=8.4 Hz, 1H), 7.81 (d, J=8.8 Hz, 1H), 7.85 (d, J=1.6 Hz, 1H).

Example 252

Synthesis of (isobutyryloxy)methyl 4-((5,6,7,8-tetrahydronaphthalen-2-yl)oxy)-1H-1,2,3-triazole-5-carboxylate (252)

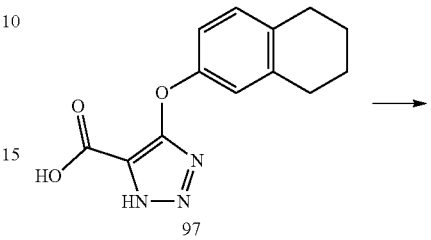
97

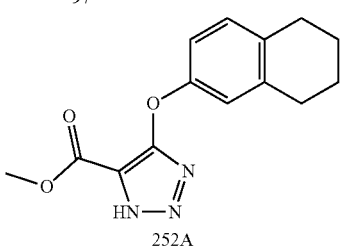
252A

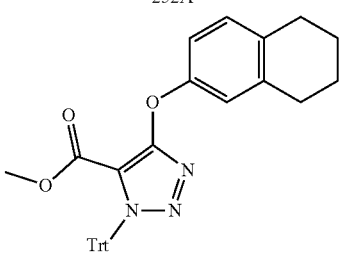
252B

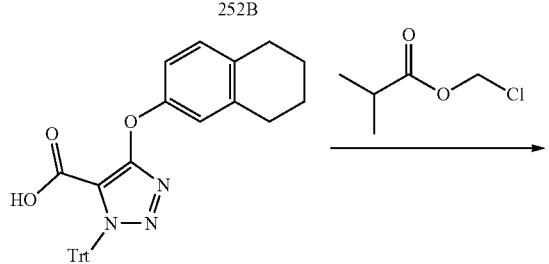
252C

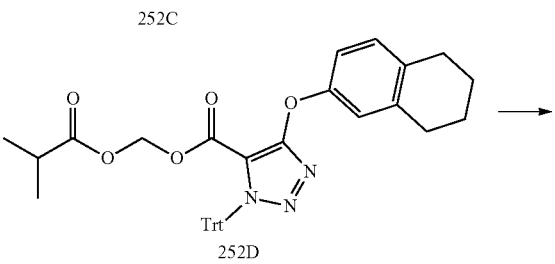
252D

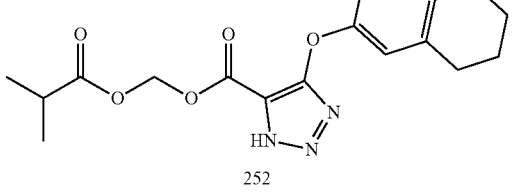
252

To a solution of Compound 97 (180 mg, 0.695 mmol) in MeOH (20 mL) was added oxalyl dichloride (126 mg, 13.9 mmol) and stirred at room temperature under nitrogen overnight. The mixture was diluted with water (100 mL) and extracted with ethyl acetate (20 mL×3). The combined organic phases was washed with brine (50 mL), dried over anhydrous sodium sulfate, filtered, and evaporated to give a crude Compound 252A. LC-MS (ESI) m/z: 274 [M+H]$^+$.

Compounds 252B, 252C, 252D, and 252 were synthesized by employing the procedures described for Compounds 54A, 8F, 54C, and 1 using Compounds 252A, 252B, 252C, chloromethyl isobutyrate with Et$_3$N as base and adding NaI, and 252D in lieu of Compounds 33, 8E, 54B, chloromethyl pivalate with Na$_2$CO$_3$ as base and without NaI, and 1E. Compound 252B: LC-MS (ESI) m/z: non-ionizable compound under routine conditions used. Compound 252C: LC-MS (ESI) m/z: 500 [M−H]$^-$. Compound 252D: LC-MS (ESI) m/z: non-ionizable compound under routine conditions used. Compound 252: LC-MS (ESI) m/z: 360 [M+H]+; $^1$H-NMR (CD$_3$OD, 400 MHz): δ (ppm) 1.10 (s, 3H), 1.11 (s, 3H), 1.76-1.79 (m, 4H), 2.51-2.54 (m, 1H), 2.68-2.70 (m, 4H), 5.88 (s, 2H), 6.66 (d, J=2.8 Hz, 1H), 6.70 (dd, J=2.8, 8.4 Hz, 1H), 6.95 (d, J=8.4 Hz, 1H).

Example 253

Synthesis of 4-(3-cyclopropoxyphenoxy)-1H-1,2,3-triazole-5-carboxylic acid 2,2,2-trifluoroacetate (253)

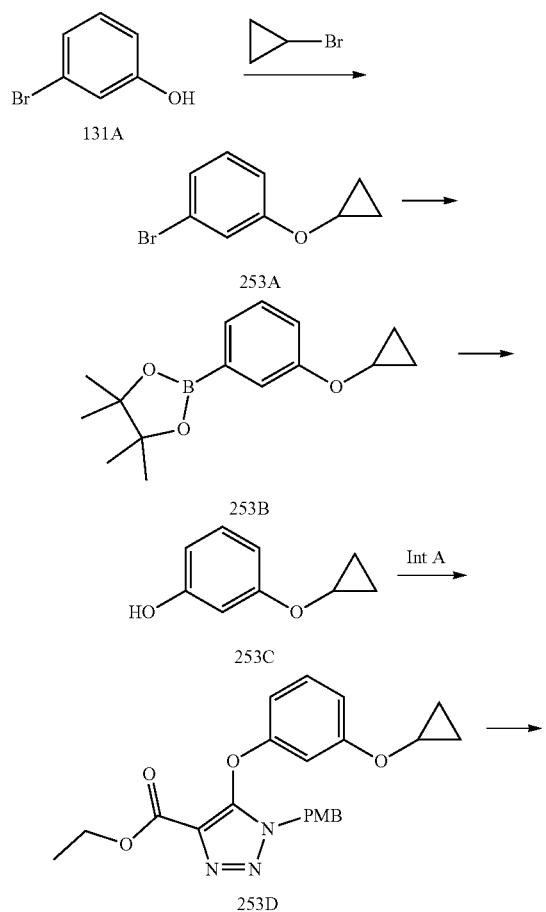

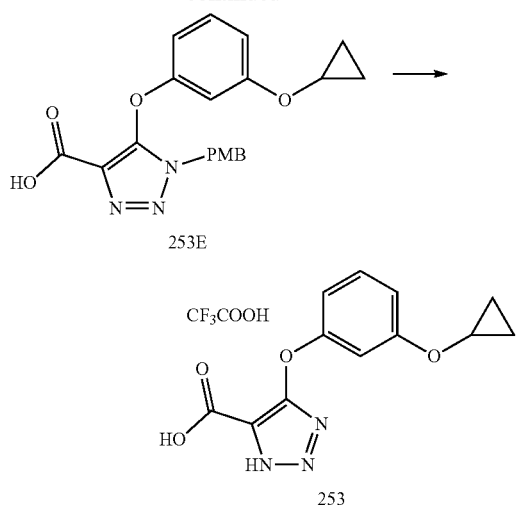

Compounds 253A, 253B, 253C, 253D, 253E, and 253 were synthesized by employing the procedures described for Compounds 27B, 27C, 236D, Intermediate I, 8F, and 1 using bromocyclopropane, Compounds 131A with NMP as solvent at 130° C., 253A, 253B, 253C, 253D, and 253E in lieu of 2-bromopropane, Compounds 27A with DMF as solvent at 100° C., 27B, 236C, 4-bromophenol, 8E, and 1E. Compound 253A: $^1$H-NMR: (CDCl$_3$, 400 MHz): δ (ppm) 0.75-0.79 (m, 4H), 3.68-3.72 (m, 1H), 6.93-6.96 (m, 1H), 7.07-7.10 (m, 1H), 7.12 (d, J=8.0 Hz, 1H), 7.22 (t, J=2.4 Hz, 1H). Compound 253B: LC-MS (ESI) m/z: 261 [M+H]$^+$. Compound 253C: LC-MS (ESI) m/z: 151 [M+H]$^+$. $^1$H-NMR: (CDCl$_3$, 400 MHz): δ (ppm) 0.76 (d, J=4.4 Hz, 4H), 3.68-3.71 (m, 1H), 5.22 (brs, 1H), 6.42-6.45 (m, 1H), 6.56-6.58 (m, 1H), 6.61-6.64 (m, 1H), 7.10 (t, J=8.0 Hz, 1H). Compound 253D: LC-MS (ESI) m/z: 410 [M+H]$^+$. Compound 253E: LC-MS (ESI) m/z: 382 [M+H]$^+$. Compound 253: LC-MS (ESI) m/z: 262 [M+H]$^+$; $^1$H-NMR (DMSO-d$_6$, 400 MHz): δ (ppm) 0.62-0.66 (m, 2H), 0.73-0.78 (m, 2H), 3.81-3.85 (m, 1H), 6.60-6.63 (m, 1H), 6.75-6.85 (m, 2H), 7.24 (t, J=8.0 Hz, 1H), 13.24 (brs, 1H), 15.21 (brs, 1H).

Example 254

Synthesis of 4-(4-chloro-3-(trifluoromethoxy)phenoxy)-1H-1,2,3-triazole-5-carboxylic acid (254)

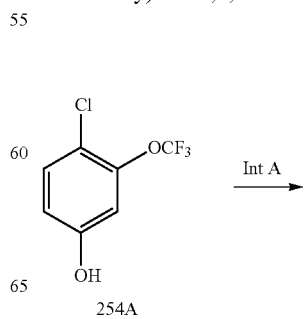

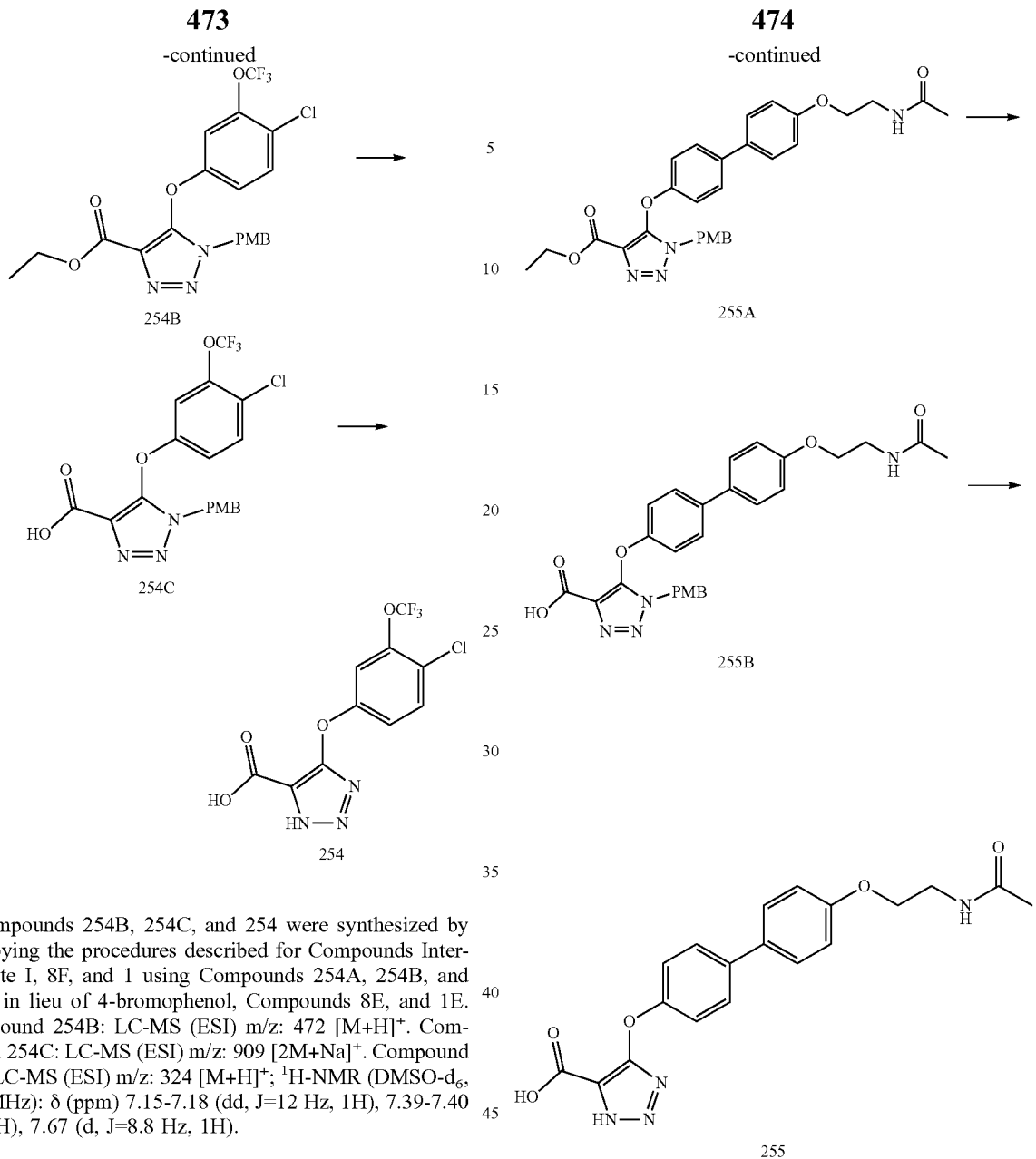

Compounds 254B, 254C, and 254 were synthesized by employing the procedures described for Compounds Intermediate I, 8F, and 1 using Compounds 254A, 254B, and 254C in lieu of 4-bromophenol, Compounds 8E, and 1E. Compound 254B: LC-MS (ESI) m/z: 472 [M+H]+. Compound 254C: LC-MS (ESI) m/z: 909 [2M+Na]+. Compound 254: LC-MS (ESI) m/z: 324 [M+H]+; $^1$H-NMR (DMSO-$d_6$, 400 MHz): δ (ppm) 7.15-7.18 (dd, J=12 Hz, 1H), 7.39-7.40 (m, 1H), 7.67 (d, J=8.8 Hz, 1H).

Example 255

Synthesis of 4-((4'-(2-acetamidoethoxy)-[1,1'-biphenyl]-4-yl)oxy)-1H-1,2,3-triazole-5-carboxylic acid (255)

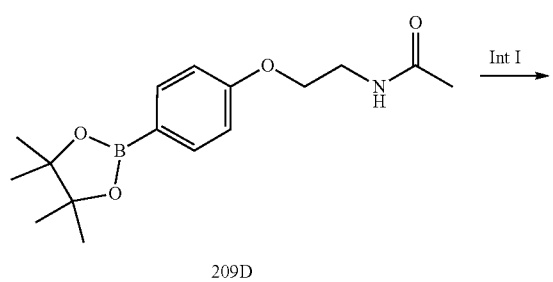

Compounds 255A, 255B, and 255 were synthesized by employing the procedures described for Compounds 4B, 8F, and 1 using Intermediate I, Compounds 209D with $K_3PO_4$ as base and 1,4-dioxane/$H_2O$ as solvent, 255A, and 255B in lieu of Compounds 4A, (4-bromophenyl)boronic acid $Na_2CO_3$ as base and toluene/EtOH/$H_2O$ as solvent, 8E, and 1E. Compound 255A: LC-MS (ESI) m/z: 531 [M+H]+. Compound 255B: LC-MS (ESI) m/z: 503 [M+H]+. Compound 255: LC-MS (ESI) m/z: 383 [M+H]+; $^1$H-NMR (DMSO-$d_6$, 400 MHz): δ (ppm) 1.83 (s, 3H), 3.39-3.44 (m, 2H), 4.01 (t, J=5.6 Hz, 2H), 7.02 (d, J=8.8 Hz, 2H), 7.12 (d, J=8.8 Hz, 2H), 7.56-7.61 (m, 4H), 8.12 (t, J=1.6 Hz, 1H), 13.19 (s, 1H), 15.19 (s, 1H).

Example 256

Synthesis of (isobutyryloxy)methyl 4-((6,7-dichloro-1,2,3,4-tetrahydronaphthalen-2-yl)oxy)-1H-1,2,3-triazole-5-carboxylate (256)

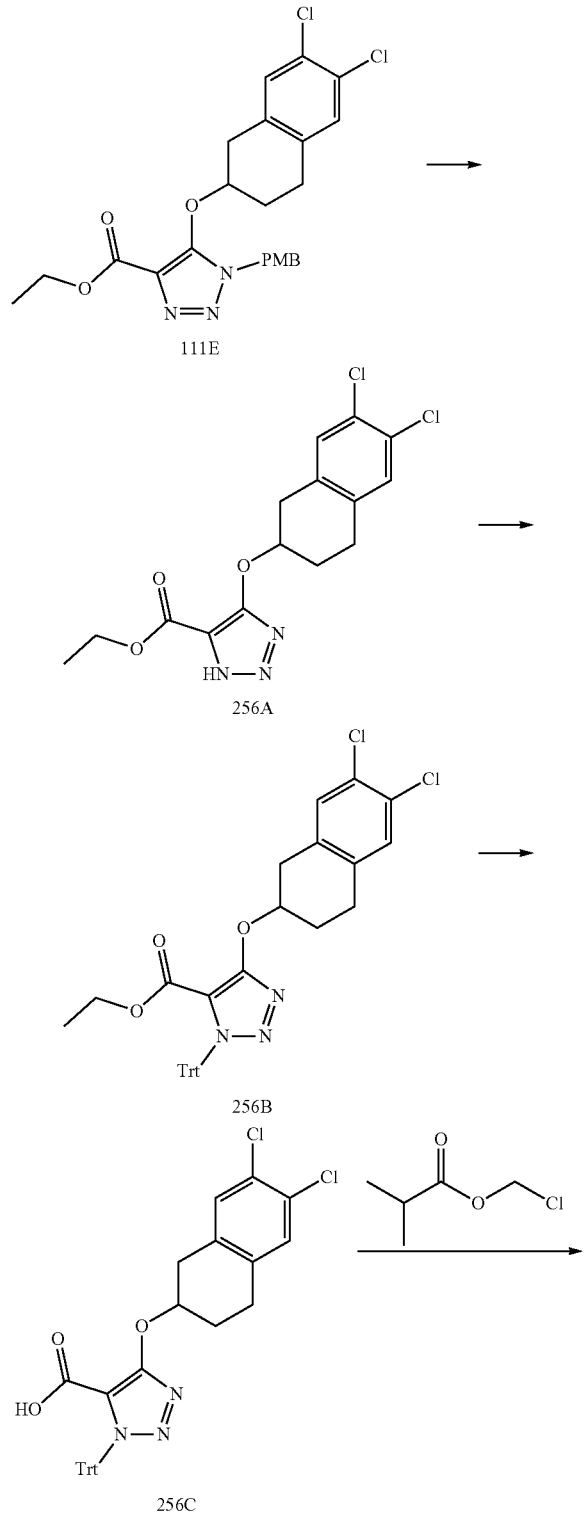

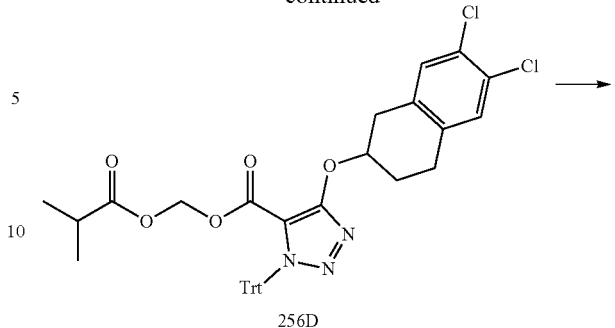

Compounds 256A, 256B, 256C, and 256D were synthesized by employing the procedures described for Compounds 1, 54A, 8F, and 54C using Compounds 111E, 256A, 256B, 256C, and chloromethyl isobutyrate with $Et_3N$ as base and adding NaI, in lieu of Compounds 1E, 33, 8E, 54B, and chloromethyl pivalate with $Na_2CO_3$ as base and without NaI. Compound 256A: LC-MS (ESI) m/z: 356 $[M+H]^+$. Compound 256B: LC-MS (ESI) m/z: 620 $[M+Na]^+$; $^1$H-NMR ($CDCl_3$, 400 MHz): δ (ppm) 1.26 (t, J=7.2 Hz, 3H), 1.98-2.15 (m, 2H), 2.63-2.71 (m, 1H), 2.93-3.00 (m, 3H), 4.27-4.31 (m, 2H), 4.83-4.94 (m, 1H), 7.05 (s, 1H), 7.13-7.16 (m, 6H), 7.28-7.33 (m, 10H). Compound 256C: LC-MS (ESI) m/z: 592 $[M+Na]^+$; $^1$H-NMR (DMSO-$d_6$, 400 MHz): δ (ppm) 1.91-1.96 (m, 2H), 2.63-2.67 (m, 1H), 2.70-2.78 (m, 2H), 3.00-3.07 (m, 1H), 4.83-4.89 (m, 1H), 7.08-7.11 (m, 6H), 7.28 (s, 1H), 7.34-7.40 (m, 10H), 13.02 (s, 1H). Compound 256D: LC-MS (ESI) m/z: 692 $[M+Na]^+$; $^1$H-NMR ($CDCl_3$, 400 MHz): δ (ppm) 1.15 (d, J=7.2 Hz, 6H), 2.01-2.06 (m, 2H), 2.51-2.56 (m, 1H), 2.58-2.70 (m, 1H), 2.87-3.01 (m, 3H), 4.85-4.93 (m, 1H), 5.89 (s, 2H), 7.03 (s, 1H), 7.12-7.17 (m, 7H), 7.28-7.34 (m, 9H).

To a solution of Compound 256D (170 mg, 0.25 mmol) in dichloromethane (5 mL) was added TFA (1.5 mL) and stirred at 20° C. for 16 hours. To the mixture was added triethylsilane (0.3 mL) and stirred at 20° C. for another 1 hour. The reaction mixture was concentrated under reduced pressure and the residue was purified with reverse phase chromatography using eluent (acetonitrile in water, from 0% to 95% v/v) to afford Compound 256. LC-MS (ESI) m/z: 428 $[M+H]^+$; $^1$H-NMR (DMSO-$d_6$, 400 MHz): δ (ppm) 1.05 (d, J=7.2 Hz, 6H), 1.93-1.99 (m, 2H), 2.53-2.56 (m, 1H), 2.68-2.76 (m, 1H), 2.86-2.95 (m, 2H), 3.09-3.15 (m, 1H), 4.95-5.00 (m, 1H), 5.75 (s, 2H), 7.36 (s, 1H), 7.38 (s, 1H).

Example 257

Synthesis of 4-(4-(isoquinolin-6-yl)phenoxy)-1H-1,2,3-triazole-5-carboxylic acid (257)

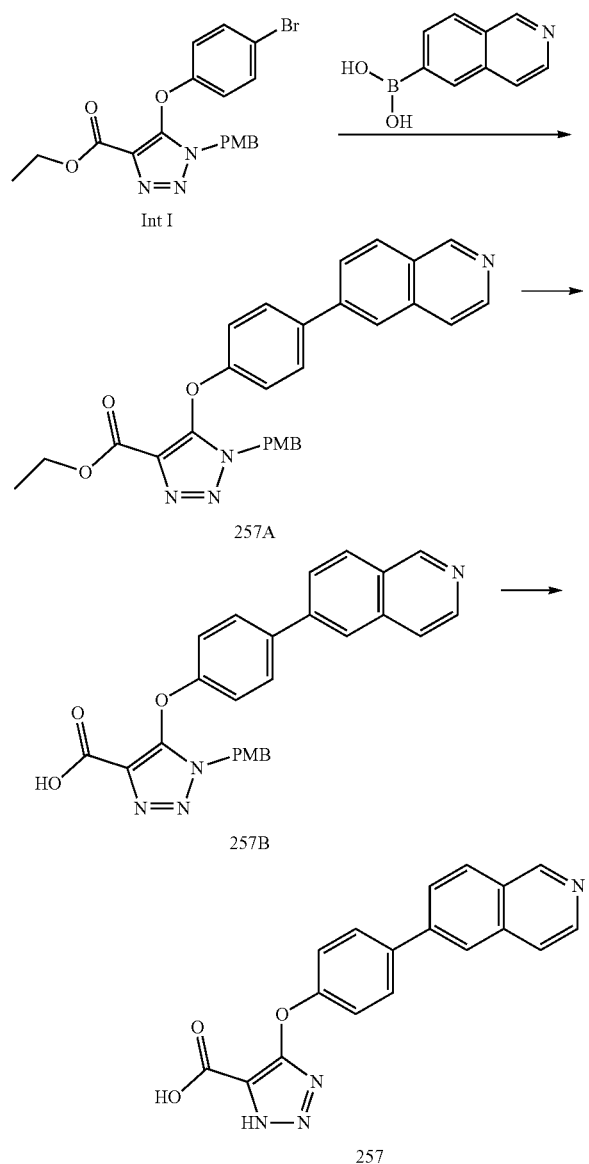

Example 258

Synthesis of (pivaloyloxy)methyl 4-((6,7-dichloro-1,2,3,4-tetrahydronaphthalen-2-yl)oxy)-1H-1,2,3-triazole-5-carboxylate (258)

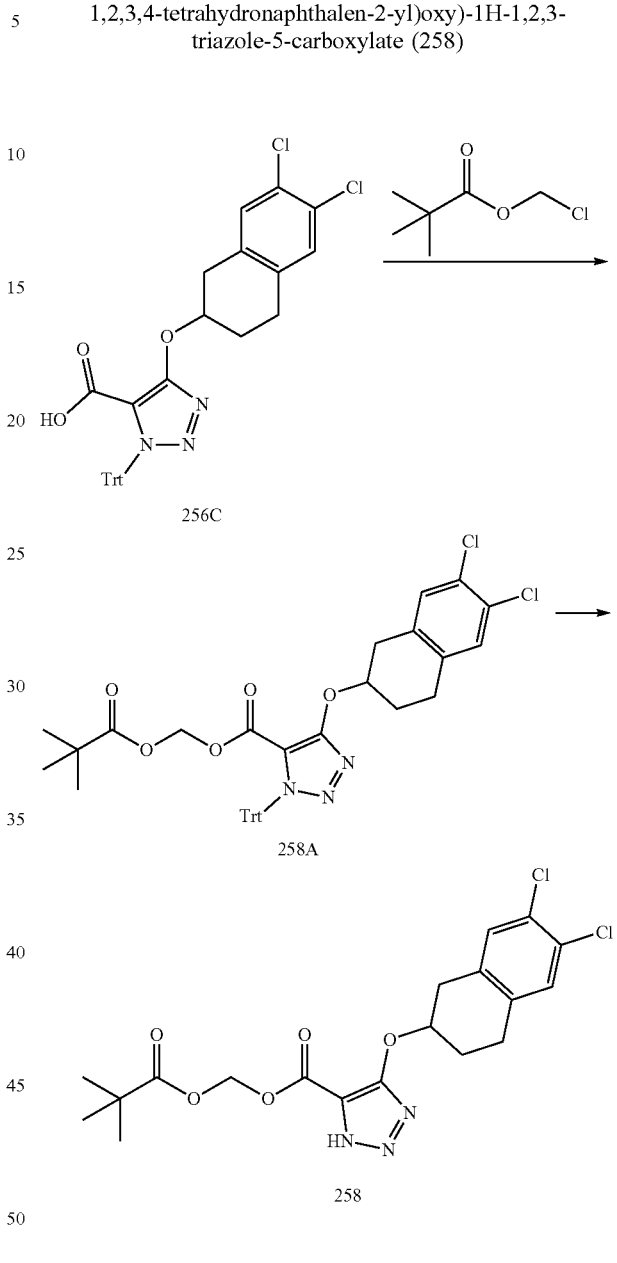

Compounds 257A, 257B, and 257 were synthesized by employing the procedures described for Compounds 4B, 8F, and 1 using isoquinolin-6-ylboronic acid, Intermediate I with $K_3PO_4$ as base and DME/$H_2O$ as solvent, Compounds 25A, and 257B in lieu of (4-bromophenyl)boronic acid, Compounds 4A with $Na_2CO_3$ as base and toluene/EtOH/$H_2O$ as solvent, 8E, and 1E. Compound 257A: LC-MS (ESI) m/z: 481 [M+H]$^+$. Compound 257B: LC-MS (ESI) m/z: 453 [M+H]$^+$. Compound 257: LC-MS (ESI) m/z: 333 [M+H]$^+$; $^1$H-NMR (DMSO-$d_6$, 400 MHz): δ (ppm) 7.24 (d, J=8.8 Hz, 2H), 7.88 (d, J=8.8 Hz, 2H), 7.94 (d, J=6.0 Hz, 1H), 8.05 (d, J=8.8 Hz, 1H), 8.23-8.29 (m, 2H), 8.54 (d, J=6.0 Hz, 1H), 9.38 (s, 1H).

Compounds 258A and 258 were synthesized by employing the procedures described for Compounds 54C and 256 using Compounds 256C with $Et_3N$ as base and adding NaI and 258A in lieu of Compounds 54B with $Na_2CO_3$ as base and without NaI and 256D. Compound 258A: LC-MS (ESI) m/z: 706 [M+Na]$^+$; $^1$H-NMR (CDCl$_3$, 500 MHz): δ (ppm) 1.17 (s, 9H), 2.01-2.05 (m, 2H), 2.63-2.69 (m, 1H), 2.87-3.01 (m, 3H), 4.87-4.92 (m, 1H), 5.89 (s, 2H), 7.03 (s, 1H), 7.12-7.16 (m, 7H), 7.28-7.35 (m, 9H). Compound 258: LC-MS (ESI) m/z: 442 [M+H]$^+$; $^1$H-NMR (CD$_3$OD, 400 MHz): δ (ppm) 1.16 (s, 9H), 2.08-2.13 (m, 2H), 2.75-2.83 (m, 1H), 3.00-3.08 (m, 2H), 3.13-3.19 (m, 1H), 5.04-5.09 (m, 1H), 5.87 (s, 2H), 7.23 (s, 1H), 7.26 (s, 1H).

Example 259

Synthesis of 4-((3'-(2-acetamidoethoxy)-[1,1'-biphenyl]-4-yl)oxy)-1H-1,2,3-triazole-5-carboxylic acid (259)

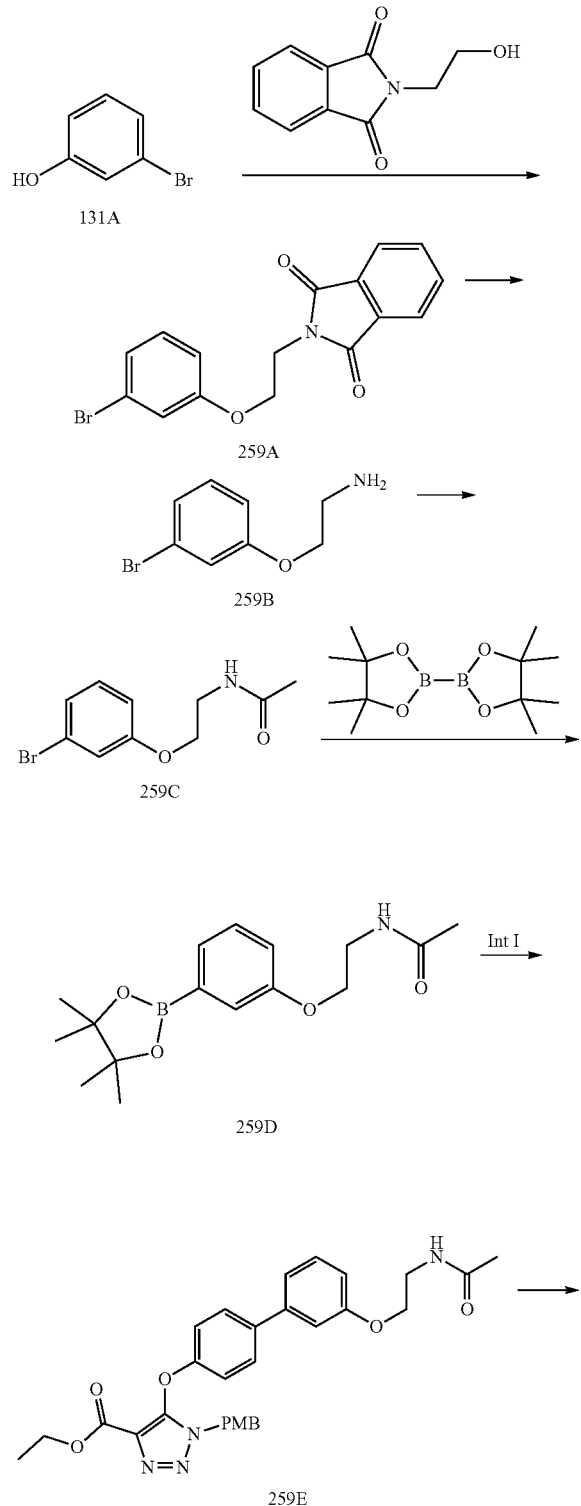

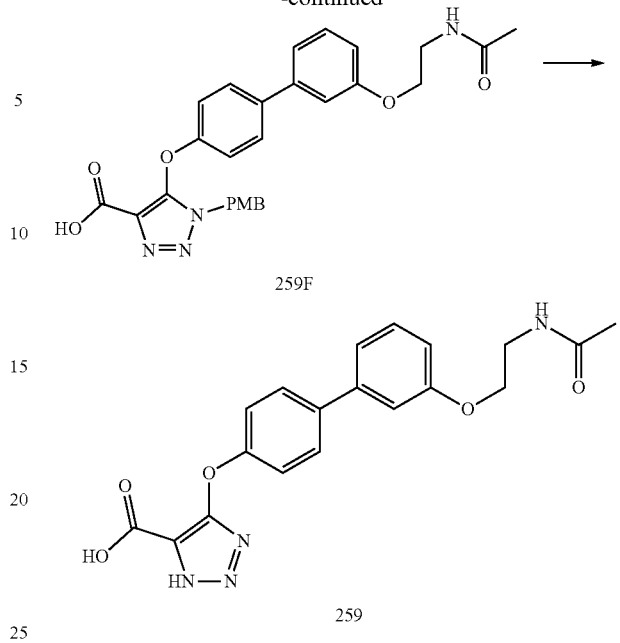

Compounds 259A, 259B, 259C, 259D, 259E, 259F, and 259 were synthesized by employing the procedures described for Compounds 90C, 190F, 209C, 27C, 4B, 8F, and 1 using 2-(2-hydroxyethyl)isoindoline-1,3-dione, Compounds 131A with DEAD as coupling reagent, 259A with EtOH as solvent, 259B, 259C, Intermediate I, 259D with K₃PO₄ as base and 1,4-dioxane/H₂O as solvent, 259E, and 259F in lieu of Compounds 90B, Intermediate H with DIAD as coupling reagent, 190E with MeOH/H₂O as solvent, 209B, 27B, 4A, (4-bromophenyl)boronic acid with Na₂CO₃ as base and toluene/EtOH/H₂O as solvent, 8E, and 1E. Compound 259A: LC-MS (ESI) m/z: 346 [M+H]⁺; ¹H-NMR (CDCl₃, 400 MHz): δ (ppm) 4.11 (t, J=5.6 Hz, 2H), 4.22 (t, J=5.6 Hz, 2H), 6.80-6.83 (m, 1H), 7.05-7.13 (m, 3H), 7.73-7.76 (m, 2H), 7.85-7.90 (m, 2H). Compound 259B: LC-MS (ESI) m/z: 216 [M+H]⁺. Compound 259C: LC-MS (ESI) m/z: 258 [M+H]⁺; ¹H-NMR (CDCl₃, 400 MHz): δ (ppm) 2.02 (s, 3H), 3.64-3.68 (m, 2H), 4.03 (t, J=4.8 Hz, 2H), 5.92 (b, 1H), 6.82-6.85 (m, 1H), 7.06-7.18 (m, 3H). Compound 259D: LC-MS (ESI) m/z: 306 [M+H]⁺. Compound 259E: LC-MS (ESI) m/z: 531 [M+H]⁺. Compound 259F: LC-MS (ESI) m/z: 503 [M+H]⁺. Compound 259: LC-MS (ESI) m/z: 383 [M+H]⁺; ¹H-NMR (DMSO-d₆, 400 MHz): δ (ppm) 1.82 (s, 3H), 3.30-3.41 (m, 2H), 4.04 (t, J=5.6 Hz, 2H), 6.90-6.93 (m, 1H), 7.12-7.21 (m, 4H), 7.35 (t, J=8.0 Hz, 1H), 7.66 (d, J=8.8 Hz, 2H), 8.10 (t, J=5.2 Hz, 1H).

Example 260

Synthesis of 4-((1-(isoquinolin-6-yl)piperidin-4-yl)oxy)-1H-1,2,3-triazole-5-carboxylic acid 2,2,2-trifluoroacetate (260)

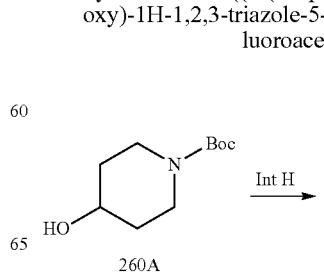

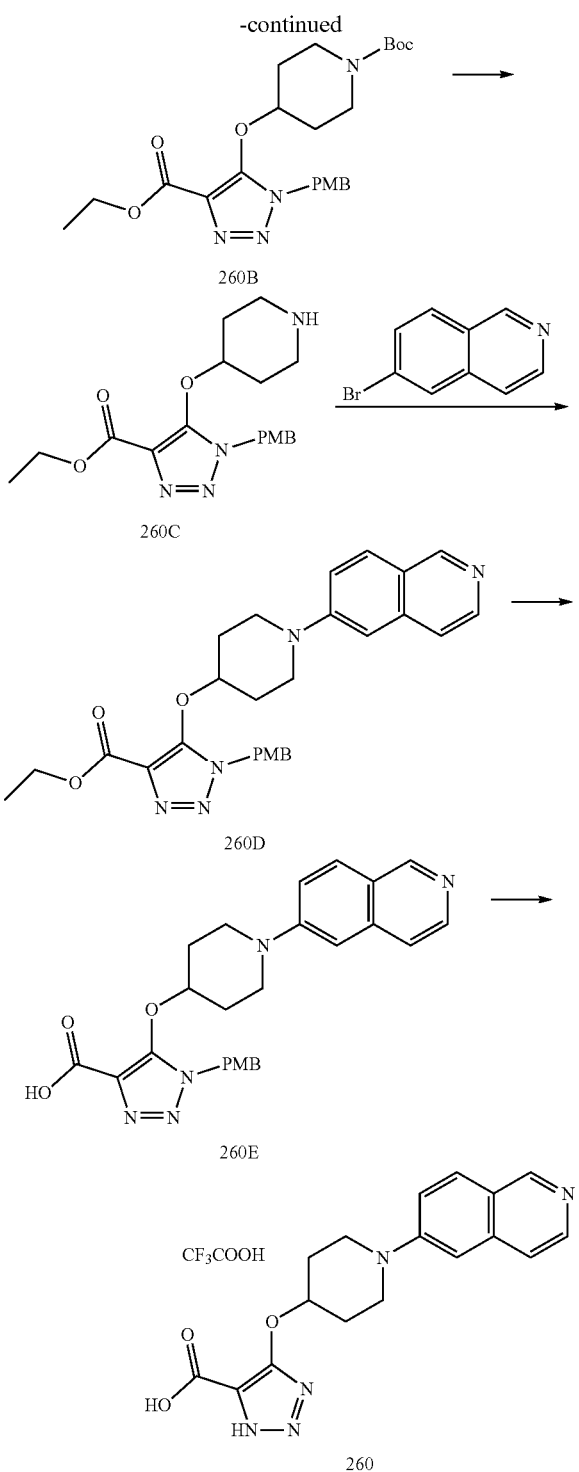

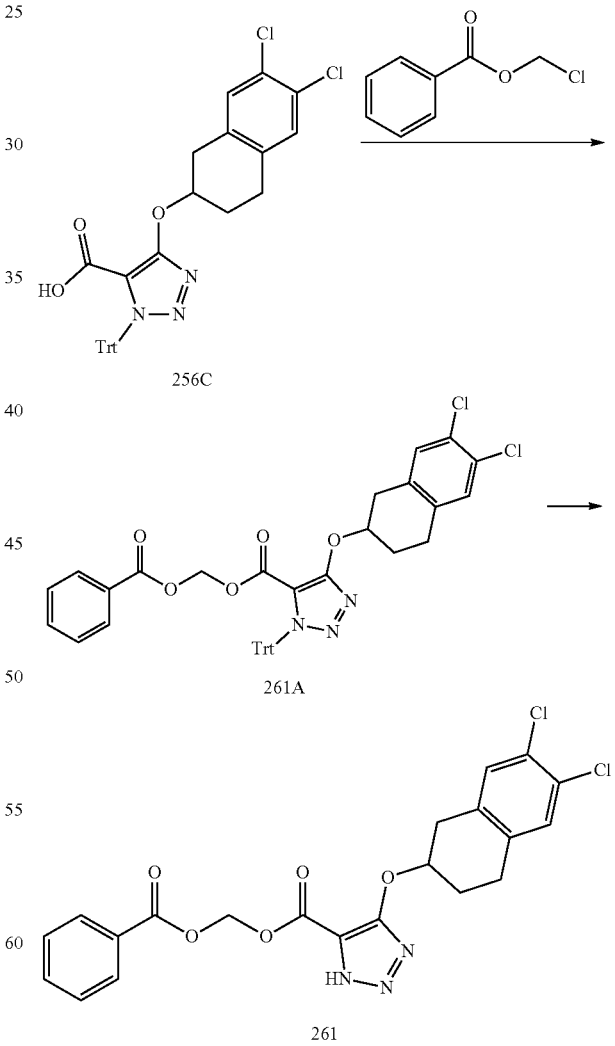

Compounds 260B, 260C, 260D, 260E, and 260 were synthesized by employing the procedures described for Compounds 90C, 175E, 6B, 8F, and 1 using Compounds 260A with DEAD as coupling reagent, 260B, 260C, 6-bromoisoquinoline with $K_3PO_4$ as base, 260D, and 260E in lieu of Compounds 90B with DIAD as coupling reagent, 175D, 1-methylpiperazine, 6A with tBuONa as base, 8E, and 1E. Compound 260B: LC-MS (ESI) m/z: 461 [M+H]$^+$. $^1$H-NMR (DMSO-d$_6$, 400 MHz): δ (ppm) 1.41 (t, J=6.8 Hz, 3H), 1.45 (s, 9H), 1.51-1.60 (m, 2H), 1.82-1.90 (m, 2H), 3.07-3.14 (m, 2H), 3.65-3.75 (m, 2H), 3.78 (s, 3H), 4.39 (q, J=14.4, 7.2 Hz, 2H), 5.20-5.25 (m, 1H), 5.29 (s, 2H), 6.83-6.86 (m, 2H), 7.20-7.22 (m, 2H). Compound 260C: LC-MS (ESI) m/z: 361 [M+H]$^+$. $^1$H-NMR (CDCl$_3$, 400 MHz): δ (ppm) 1.41 (t, J=7.2 Hz, 3H), 1.51-1.55 (m, 2H), 1.92-1.97 (m, 2H), 2.62-2.69 (m, 2H), 3.02-3.08 (m, 2H), 3.78 (s, 3H), 4.39 (q, J=6.8 Hz, 2H), 5.11-5.14 (m, 1H), 5.29 (s, 2H), 6.85 (d, J=8.4 Hz, 2H), 7.23 (d, J=8.8 Hz, 2H). Compound 260D: LC-MS (ESI) m/z: 488 [M+H]$^+$. Compound 260E: LC-MS (ESI) m/z: 460 [M+H]$^+$. Compound 260: LC-MS (ESI) m/z: 340 [M+H]$^+$. $^1$H-NMR (DMSO-d$_6$, 400 MHz): δ (ppm) 1.77-1.80 (m, 2H), 2.06-2.10 (m, 2H), 3.50-3.53 (m, 2H), 3.72-3.76 (m, 2H), 4.85-4.91 (m, 1H), 7.15 (d, J=2.0 Hz, 1H), 7.49-7.53 (m, 2H), 7.88 (d, J=9.2 Hz, 1H), 8.26 (d, J=5.6 Hz, 1H), 8.98 (s, 1H).

Example 261

Synthesis of (benzoyloxy)methyl 4-((6,7-dichloro-1,2,3,4-tetrahydronaphthalen-2-yl)oxy)-1H-1,2,3-triazole-5-carboxylate (261)

Compounds 261A and 261 were synthesized by employing the procedures described for Compounds 54C and 256 using Compounds 256C with Et₃N as base and adding NaI and 261A in lieu of Compounds 54B with Na₂CO₃ as base and without NaI and 256D. Compound 261A: LC-MS (ESI) m/z: 726 [M+Na]⁺; ¹H-NMR (CDCl₃, 500 MHz); δ (ppm) 1.96-2.04 (m, 2H), 2.58-2.63 (m, 1H), 2.95-2.97 (m, 3H), 4.85-4.92 (m, 1H), 6.14 (s, 2H), 6.99 (s, 1H), 7.08 (s, 1H), 7.12-7.15 (m, 6H), 7.28-7.32 (m, 9H), 7.42-7.47 (m, 2H), 7.57-7.61 (m, 1H), 8.05 (d, J=6.5 Hz, 2H). Compound 261: LC-MS (ESI) m/z: 462 [M+H]⁺; ¹H-NMR (CD₃OD, 400 MHz): δ (ppm) 2.04-2.09 (m, 2H), 2.68-2.76 (m, 1H), 2.94-3.03 (m, 2H), 3.09-3.15 (m, 1H), 5.03-5.09 (m, 1H), 6.12 (s, 2H), 7.16 (s, 2H), 7.48 (t, J=8.8 Hz, 2H), 7.63 (t, J=8.0 Hz, 1H), 7.02 (d, J=8.4 Hz, 2H).

Example 262

Synthesis of 4-(3-(cyclopropylmethoxy)phenoxy)-1H-1,2,3-triazole-5-carboxylic acid 2,2,2-trifluoroacetate (262)

Compounds 262A, 262B, 262C, and 262 were synthesized by employing the procedures described for Compounds 236D, Intermediate I, 217E, and 8F using Compounds 170B, 262A with NMP as solvent, 262B, and 262C in lieu of Compounds 236C, 4-bromophenol with DMF as solvent, 217D, and 8E. Compound 262A: LC-MS (ESI) m/z: 165 [M+H]⁺. Compound 262B: LC-MS (ESI) m/z: 424 [M+H]⁺; ¹H-NMR (CDCl₃, 400 MHz): δ (ppm) 0.32-0.34 (m, 2H), 0.63-0.66 (m, 2H), 1.14 (t, J=7.2 Hz, 3H), 1.16-1.26 (m, 1H), 3.66 (d, J=6.8 Hz, 2H), 3.77 (s, 3H), 4.21 (q, J=7.2 Hz, 2H), 5.34 (s, 2H), 6.28 (t, J=2.4 Hz, 1H), 6.35-6.38 (m, 1H), 6.65 (dd, J=8.4, 2.0 Hz, 1H), 6.78-6.80 (m, 2H), 7.13-7.20 (m, 1H), 7.21-7.22 (m, 2H). Compound 262C: LC-MS (ESI) m/z: 304 [M+H]⁺. Compound 262: LC-MS (ESI) m/z: 276 [M+H]⁺; ¹H-NMR (CD₃OD, 400 MHz): δ (ppm) 0.32-0.37 (m, 2H), 0.58-0.63 (m, 2H), 1.21-1.27 (m, 1H), 3.80 (d, J=7.2 Hz, 2H), 6.62-6.72 (m, 3H), 7.23 (t, J=8.0 Hz, 1H).

Example 263

Synthesis of 4-(4-(tetrahydro-2H-pyran-4-yl)phenoxy)-1H-1,2,3-triazole-5-carboxylic acid 2,2,2-trifluoroacetate (263)

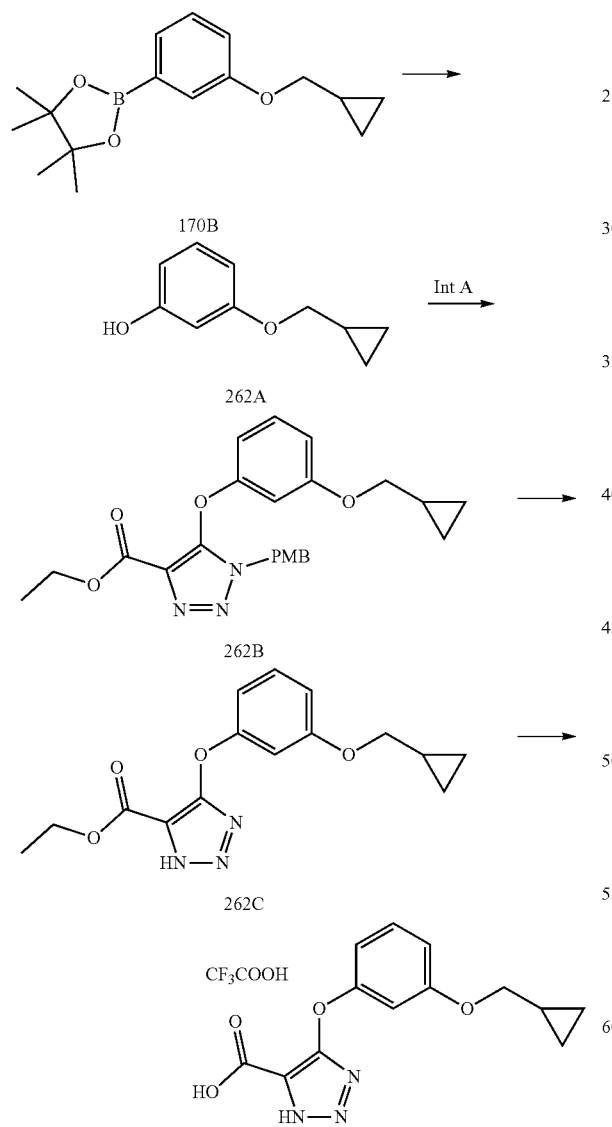

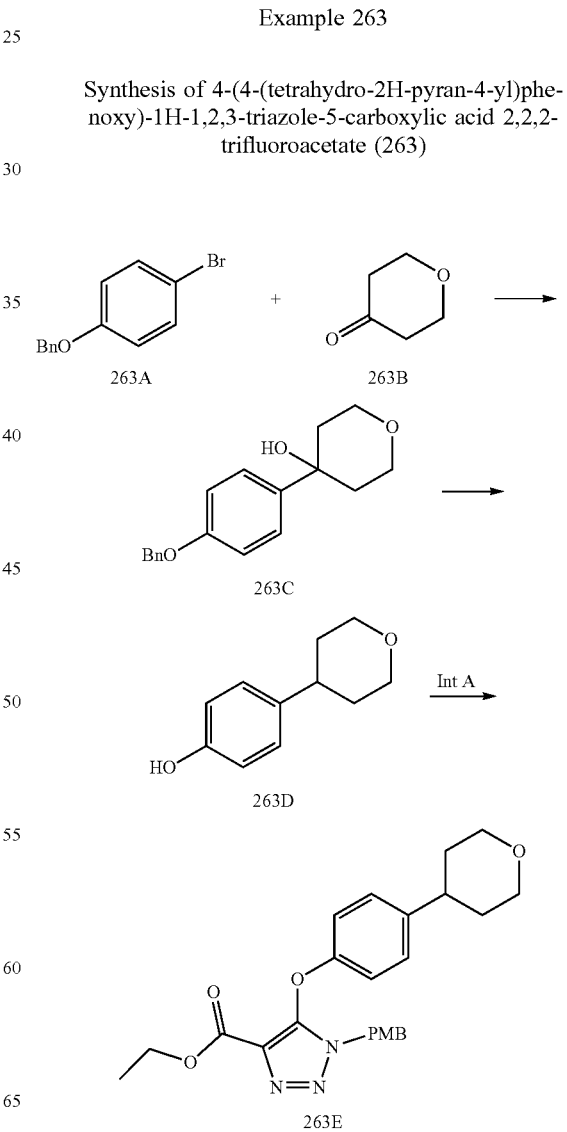

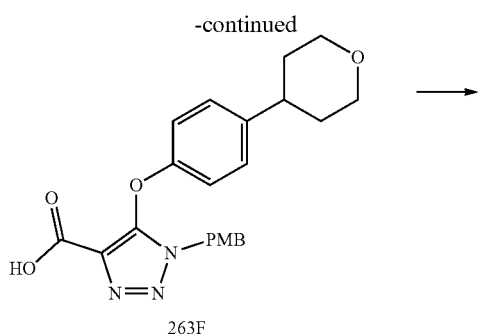

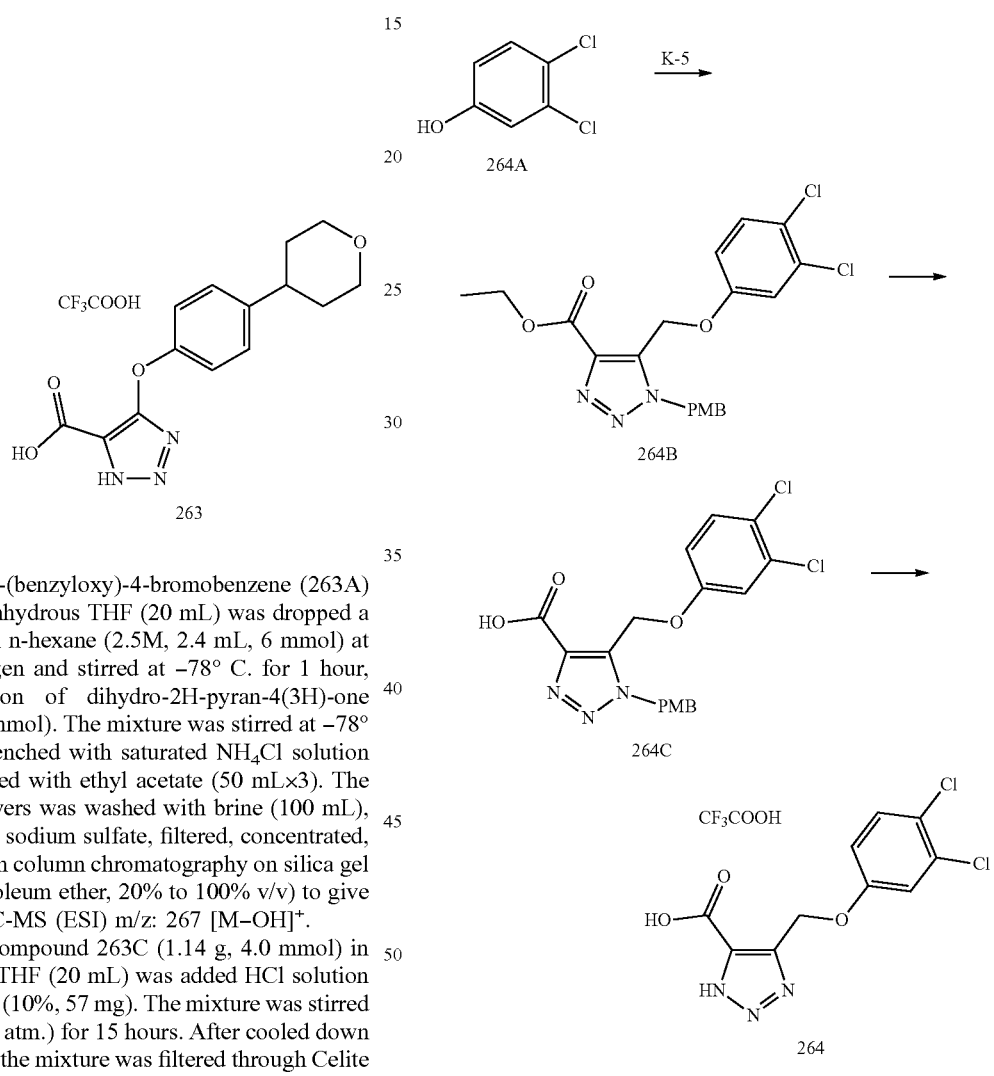

To a solution of 1-(benzyloxy)-4-bromobenzene (263A) (1.3 g, 5 mmol) in anhydrous THF (20 mL) was dropped a solution of n-BuLi in n-hexane (2.5M, 2.4 mL, 6 mmol) at −78° C. under nitrogen and stirred at −78° C. for 1 hour, followed by addition of dihydro-2H-pyran-4(3H)-one (263B) (0.56 mL, 6 mmol). The mixture was stirred at −78° C. for 1.5 hours, quenched with saturated NH$_4$Cl solution (50 mL), and extracted with ethyl acetate (50 mL×3). The combined organic layers was washed with brine (100 mL), dried over anhydrous sodium sulfate, filtered, concentrated, and purified with flash column chromatography on silica gel (ethyl acetate in petroleum ether, 20% to 100% v/v) to give Compound 263C. LC-MS (ESI) m/z: 267 [M−OH]$^+$.

To a solution of Compound 263C (1.14 g, 4.0 mmol) in MeOH (20 mL) and THF (20 mL) was added HCl solution (3M, 2 mL) and Pd/C (10%, 57 mg). The mixture was stirred at 50° C. under H$_2$ (1 atm.) for 15 hours. After cooled down to room temperature, the mixture was filtered through Celite and the filtrate was concentrated to give a crude Compound 263D. LC-MS (ESI) m/z: 179 [M+H]$^+$.

Compounds 263E, 263F, and 263 were synthesized by employing the procedures described for Intermediate I, Compounds 8F, and 1 using Compounds 263D, 263E, and 263F in lieu of 4-bromophenol, Compounds 8E, and 1E. Compound 263E: LC-MS (ESI) m/z: 438 [M+H]$^+$; $^1$H-NMR (CDCl$_3$, 400 MHz): δ (ppm) 1.08 (t, J=7.2 Hz, 3H), 1.72-1.75 (m, 4H), 2.68-2.76 (m, 1H), 3.49-3.55 (m, 2H), 3.77 (s, 3H), 4.06-4.10 (m, 2H), 4.15-4.21 (m, 2H), 5.34 (s, 2H), 6.73 (d, J=8.8 Hz, 2H), 6.78 (d, J=8.8 Hz, 2H), 7.11 (d, J=8.8 Hz, 2H), 7.20 (d, J=8.8 Hz, 2H). Compound 263F: LC-MS (ESI) m/z: 410 [M+H]$^+$. Compound 263: LC-MS (ESI) m/z: 290 [M+H]$^+$; $^1$H-NMR (DMSO-d$_6$, 400 MHz): δ (ppm) 1.57-1.69 (m, 4H), 2.68-2.78 (m, 1H), 3.40-3.44 (m, 2H), 3.91-3.94 (m, 2H), 6.99 (d, J=8.8 Hz, 2H), 7.24 (d, J=8.8 Hz, 2H), 13.14 (s, 1H), 15.16 (s, 1H).

Example 264

Synthesis of 4-((3,4-dichlorophenoxy)methyl)-1H-1,2,3-triazole-5-carboxylic acid 2,2,2-trifluoroacetate (264)

Compounds 264A, 264B, and 264 were synthesized by employing the procedures described for Compounds 90C, 8F, and 1 using Compounds 264A and Intermediate K-5 using DEAD as coupling reagent, 264B, and 264C in lieu of Compounds 90B and Intermediate H using DIAD as coupling reagent, 8E, and 1E. Compound 264A: LC-MS (ESI) m/z: 436 [M+H]$^+$. Compound 264B: LC-MS (ESI) m/z: 408 [M+H]$^+$. Compound 264: LC-MS (ESI) m/z: 288 [M+H]$^+$; $^1$H-NMR (DMSO-d$_6$, 400 MHz): δ (ppm) 5.38 (s, 2H), 7.11 (dd, J$_1$=2.4 Hz, J$_2$=9.2 Hz, 1H), 7.36 (d, J=2.8 Hz, 1H), 7.53 (d, J=9.2 Hz, 1H), 13.55 (s, 1H), 15.81 (s, 1H).

Example 265

Synthesis of 4-(((4'-(trifluoromethoxy)-[1,1'-biphenyl]-4-yl)oxy)methyl)-1H-1,2,3-triazole-5-carboxylic acid (265)

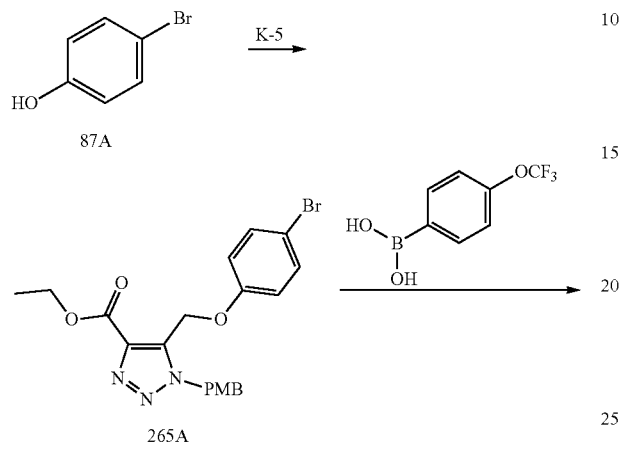

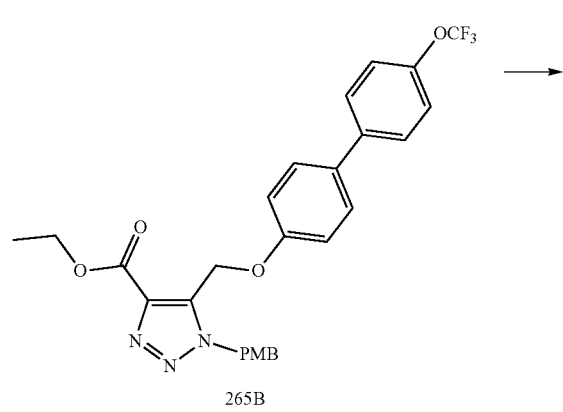

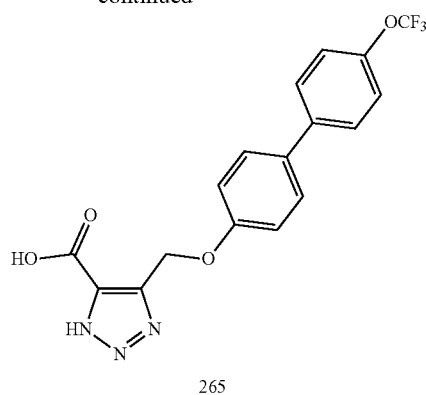

Compounds 265A, 265B, 265C, and 265 were synthesized by employing the procedures described for Compounds 90C, 8B, 8F, and 1 using Compounds 87A and Intermediate K-5 using DEAD as coupling reagent, 4-(trifluoromethoxy)phenylboronic acid, Compounds 265A using Na$_2$CO$_3$ as base and MeCN/H$_2$O as solvent, 265B, and 265C in lieu of Compounds 90B and Intermediate H using DIAD as coupling reagent, (3,4-dichlorophenyl)boronic acid, 8A using t-BuONa as base and DME/H$_2$O as solvent, 8E, and 1E. Compound 265A: LC-MS (ESI) m/z: 446 [M+H]$^+$. Compound 265B: LC-MS (ESI) m/z: 528 [M+H]$^+$. Compound 265C: LC-MS (ESI) m/z: 500 [M+H]$^+$. Compound 265: LC-MS (ESI) m/z: 380 [M+H]$^+$; $^1$H-NMR (DMSO-d$_6$, 400 MHz): δ (ppm) 5.41 (s, 2H), 7.19 (d, J=8.8 Hz, 2H), 7.40 (d, J=8.6 Hz, 2H), 7.58 (d, J=8.8 Hz, 2H), 7.73 (d, J=8.8 Hz, 2H).

Example 266

Synthesis of 4-(((3',4'-dichloro-[1,1'-biphenyl]-4-yl)oxy)methyl)-1H-1,2,3-triazole-5-carboxylic acid 2,2,2-trifluoroacetate (266)

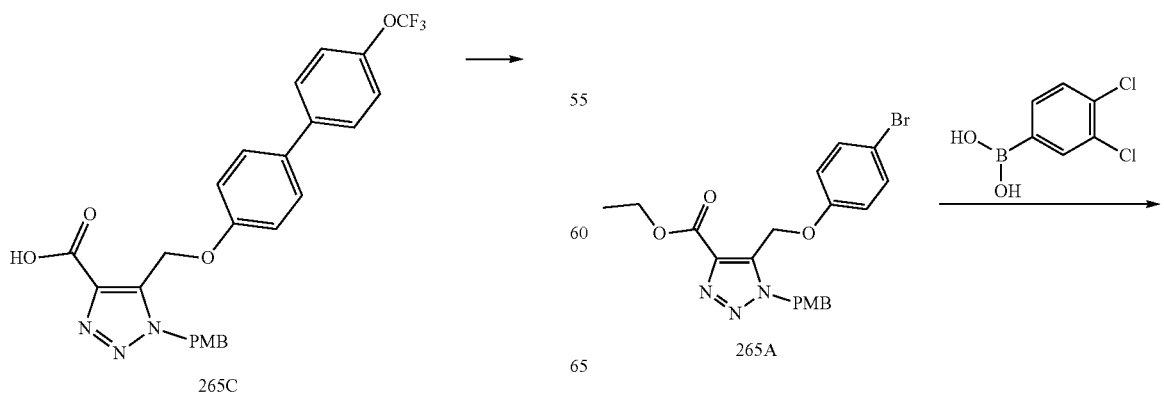

Example 267

Synthesis of (propionyloxy)methyl 4-((6,7-dichloro-1,2,3,4-tetrahydronaphthalen-2-yl)oxy)-1H-1,2,3-triazole-5-carboxylate (267)

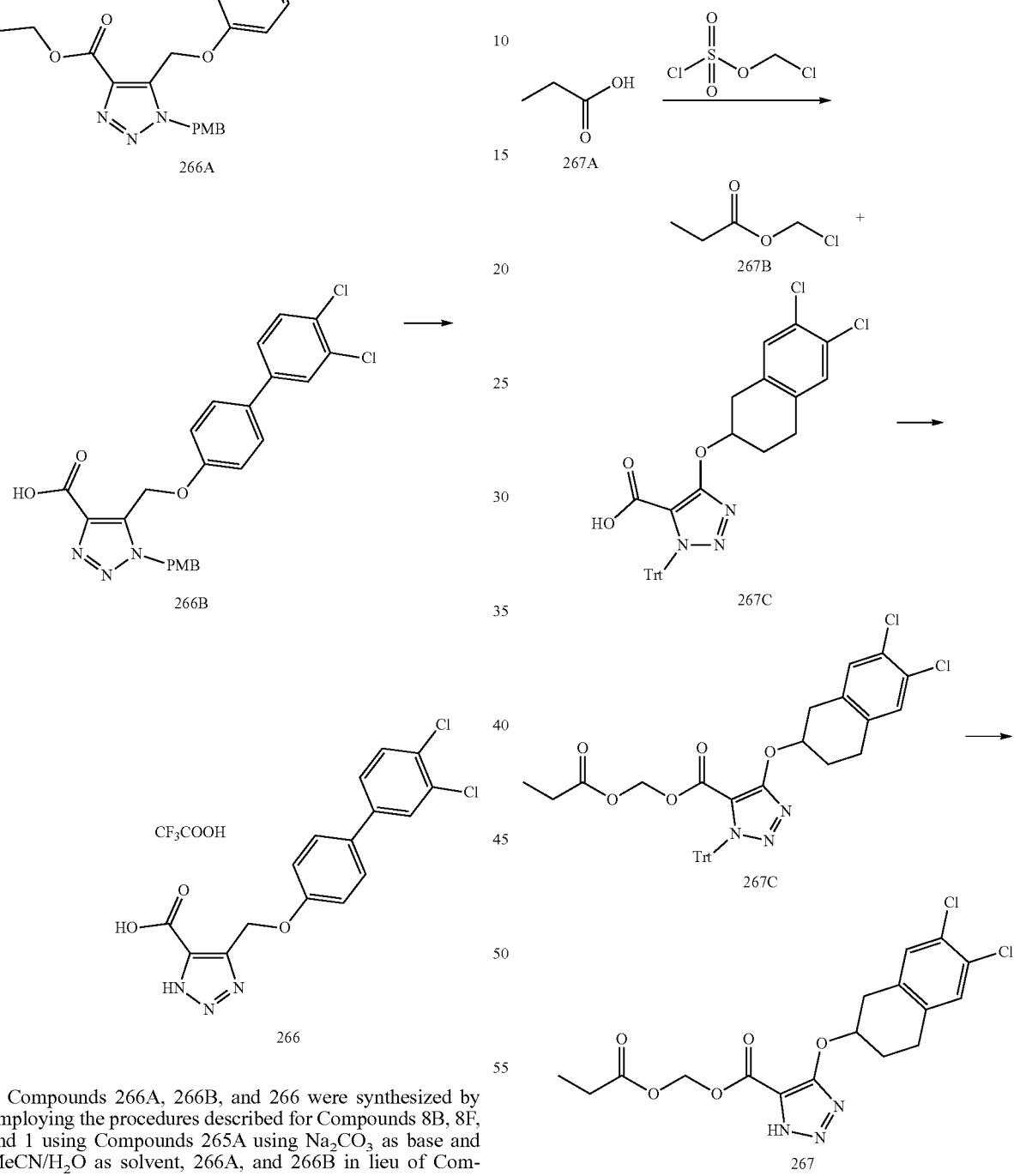

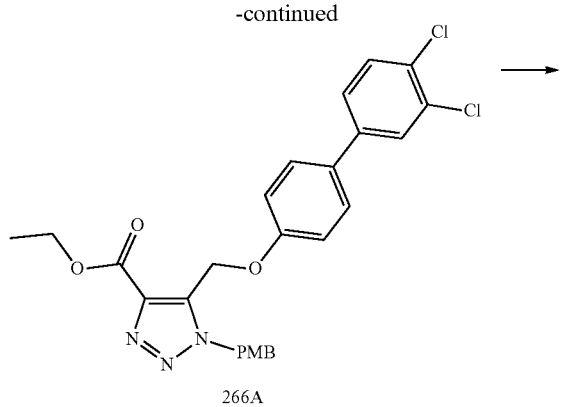

Compounds 266A, 266B, and 266 were synthesized by employing the procedures described for Compounds 8B, 8F, and 1 using Compounds 265A using $Na_2CO_3$ as base and $MeCN/H_2O$ as solvent, 266A, and 266B in lieu of Compounds 8A using t-BuONa as base and $DME/H_2O$ as solvent, 8E, and 1E. Compound 266A: LC-MS (ESI) m/z: 512 $[M+H]^+$. Compound 266B: LC-MS (ESI) m/z: non-ionizable compound under routine conditions used. Compound 266: LC-MS (ESI) m/z: 364 $[M+H]^+$; $^1$H-NMR (DMSO-$d_6$, 400 MHz): δ (ppm) 5.41 (s, 2H), 7.12 (d, J=8.7 Hz, 2H), 7.65-7.66 (m, 4H), 7.90 (d, J=2.0 Hz, 1H), 13.36 (s, 1H), 15.57 (s, 1H).

Compounds 267B, 267C, and 267 were synthesized by employing the procedures described for Compounds 229B, 54C, and 256 using Compounds 267A with $NaHCO_3$ as base, 267B with $Et_3N$ as base and adding NaI, and 267C in lieu of Compounds 229A with $K_2CO_3$ as base, 54B with $Na_2CO_3$ as base and without NaI, and 256D. Compound 267B: ¹H-NMR (CDCl₃, 400 MHz): δ (ppm) 1.18 (t, J=7.6 Hz, 3H), 2.42 (q, J=7.6 Hz, 2H), 5.71 (s, 2H). Compound 267C: LC-MS (ESI) m/z: 678 [M+Na]⁺; ¹H-NMR (CDCl₃, 400 MHz): δ (ppm) 1.12 (t, J=7.6 Hz, 3H), 2.01-2.07 (m, 2H), 2.34 (q, J=7.6 Hz, 2H), 2.63-2.71 (m, 1H), 2.88-3.01 (m, 3H), 4.88-4.94 (m, 1H), 5.30 (s, 2H), 7.04 (s, 1H), 7.12-7.17 (m, 7H), 7.28-7.36 (m, 9H). Compound 267: LC-MS (ESI) m/z: 414 [M+H]⁺; ¹H-NMR (CD₃OD, 400 MHz): δ (ppm) 1.10 (t, J=7.6 Hz, 3H), 2.09-2.14 (m, 2H), 2.35 (q, J=7.6 Hz, 2H), 2.76-2.83 (m, 1H), 3.00-3.08 (m, 2H), 3.14-3.3.20 (m, 1H), 5.06-5.12 (m, 1H), 5.88 (s, 2H), 7.24 (s, 1H), 7.26 (s, 1H).

Example 268

Synthesis of 4-(4-(3,3-difluorocyclobutyl)phenoxy)-1H-1,2,3-triazole-5-carboxylic acid (268)

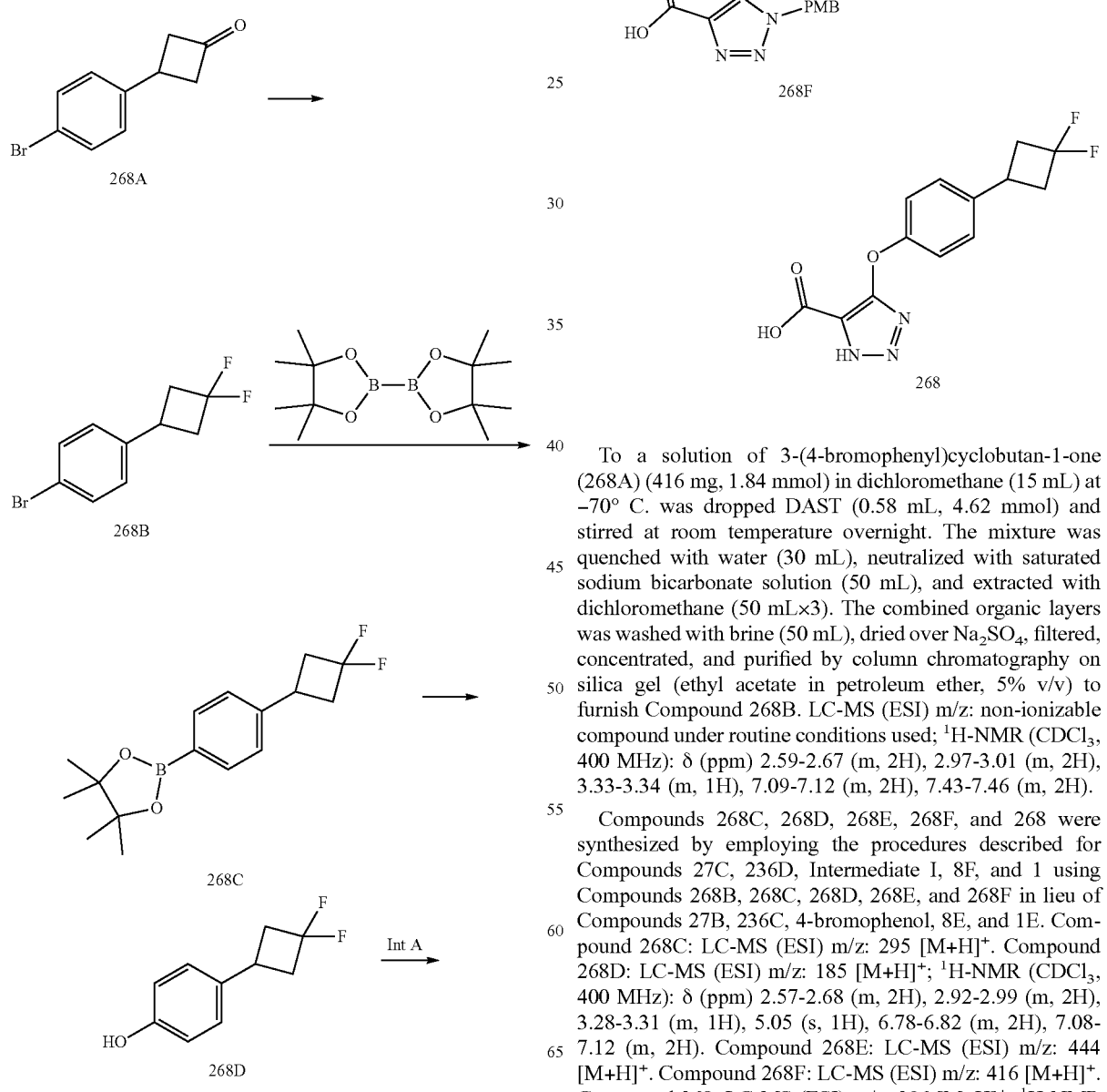

To a solution of 3-(4-bromophenyl)cyclobutan-1-one (268A) (416 mg, 1.84 mmol) in dichloromethane (15 mL) at −70° C. was dropped DAST (0.58 mL, 4.62 mmol) and stirred at room temperature overnight. The mixture was quenched with water (30 mL), neutralized with saturated sodium bicarbonate solution (50 mL), and extracted with dichloromethane (50 mL×3). The combined organic layers was washed with brine (50 mL), dried over Na₂SO₄, filtered, concentrated, and purified by column chromatography on silica gel (ethyl acetate in petroleum ether, 5% v/v) to furnish Compound 268B. LC-MS (ESI) m/z: non-ionizable compound under routine conditions used; ¹H-NMR (CDCl₃, 400 MHz): δ (ppm) 2.59-2.67 (m, 2H), 2.97-3.01 (m, 2H), 3.33-3.34 (m, 1H), 7.09-7.12 (m, 2H), 7.43-7.46 (m, 2H).

Compounds 268C, 268D, 268E, 268F, and 268 were synthesized by employing the procedures described for Compounds 27C, 236D, Intermediate I, 8F, and 1 using Compounds 268B, 268C, 268D, 268E, and 268F in lieu of Compounds 27B, 236C, 4-bromophenol, 8E, and 1E. Compound 268C: LC-MS (ESI) m/z: 295 [M+H]⁺. Compound 268D: LC-MS (ESI) m/z: 185 [M+H]⁺; ¹H-NMR (CDCl₃, 400 MHz): δ (ppm) 2.57-2.68 (m, 2H), 2.92-2.99 (m, 2H), 3.28-3.31 (m, 1H), 5.05 (s, 1H), 6.78-6.82 (m, 2H), 7.08-7.12 (m, 2H). Compound 268E: LC-MS (ESI) m/z: 444 [M+H]⁺. Compound 268F: LC-MS (ESI) m/z: 416 [M+H]⁺. Compound 268: LC-MS (ESI) m/z: 296 [M+H]⁺; ¹H-NMR (DMSO-$d_6$, 400 MHz): δ (ppm) 2.62-2.71 (m, 2H), 2.95-3.01 (m, 2H), 3.28-3.41 (m, 1H), 7.03 (d, J=8.8 Hz, 2H), 7.30 (d, J=9.2 Hz, 2H).

Example 269

Synthesis of 4-((3,4-dichlorobenzyl)oxy)-1H-1,2,3-triazole-5-carboxylic acid (269)

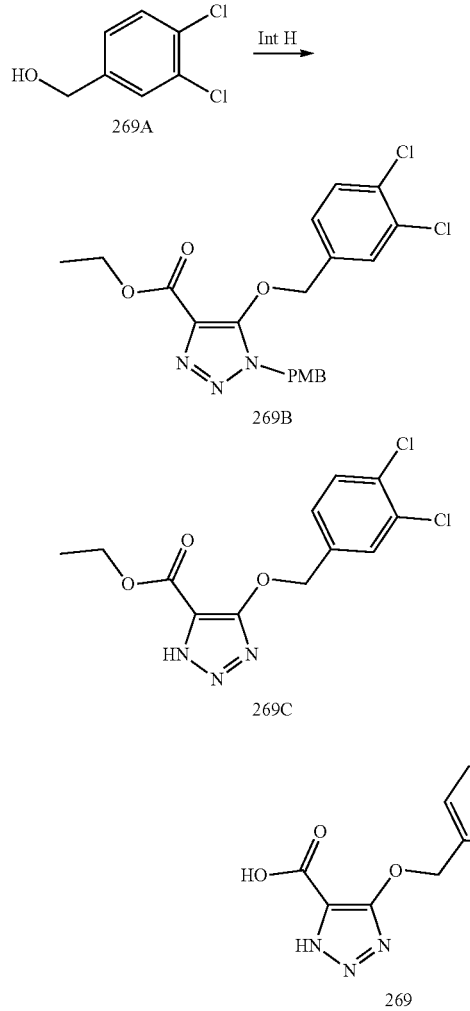

Compounds 269B and 269C were synthesized by employing the procedures described for Compounds 90C and 217E using Compounds 269A with DEAD as coupling reagent and 269B in lieu of Compounds 90B with DIAD as coupling reagent and 217D. Compound 269B: LC-MS (ESI) m/z: 436 [M+H]$^+$. Compound 269C: LC-MS (ESI) m/z: 316 [M+H]$^+$.

A mixture of Compound 269C (253 mg, 0.8 mmol) and KOH (448 mg, 8 mmol) in EtOH (10 ml) and H$_2$O (5 ml) was stirred at 60° C. for 2 hours. The mixture was concentrated under reduced pressure and the residue was purified with preparative HPLC to afford Compound 269. LC-MS (ESI) m/z: 288 [M+H]$^+$; $^1$H-NMR (DMSO-$d_6$, 400 MHz): δ (ppm) 5.34 (s, 2H), 7.45-7.48 (m, 1H), 7.68 (d, J=8 Hz, 1H), 7.74 (d, J=2 Hz, 1H), 13.04 (s, 1H), 14.85 (s, 1H).

Example 270

Synthesis of 4-((1-(4-chlorophenyl)piperidin-4-yl)oxy)-1H-1,2,3-triazole-5-carboxylic acid 2,2,2-trifluoroacetate (270)

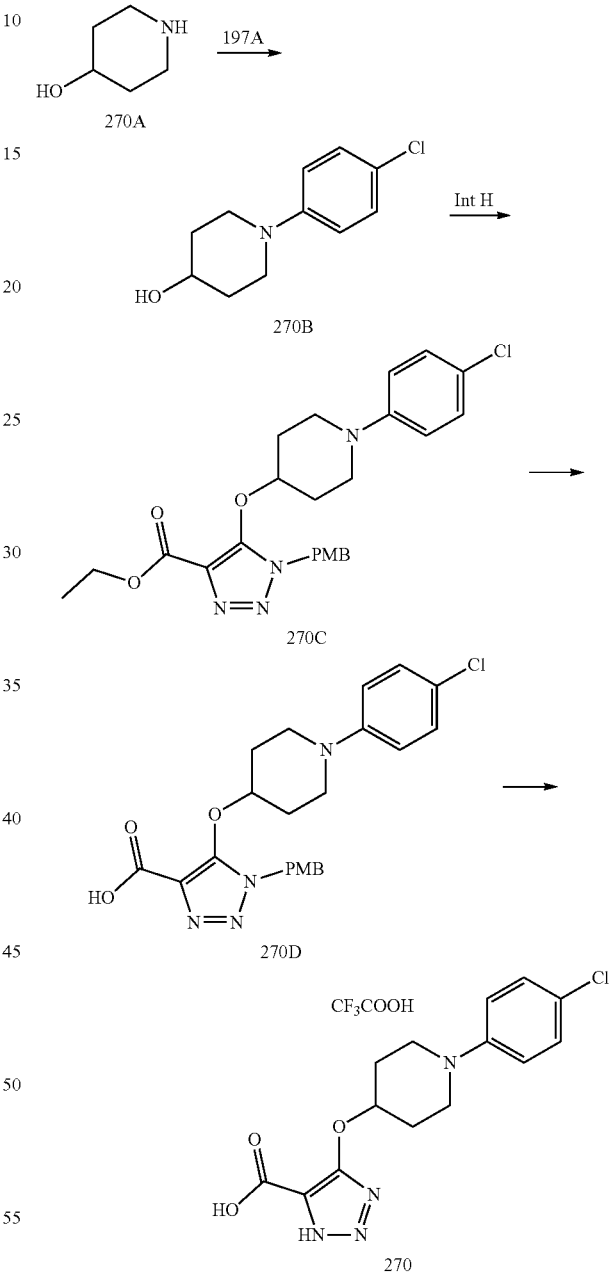

To a solution of piperidin-4-ol (270A) (500 mg, 4.94 mmol) and 1-chloro-4-iodobenzene (197A) (1.18 g, 4.94 mmol) in DMF (25 mL) was added K$_2$CO$_3$ (2.05 g, 14.82 mmol), CuI (94 mg, 0.494 mmol), and L-proline (171 mg, 1.482 mmol). The mixture was stirred at 95° C. for 12 hours. After the reaction mixture was cooled down to room temperature, the precipitate was removed by filtration. The filtrate was concentrated and purified by column chromatography on silica gel (ethyl acetate in petroleum ether, 20% v/v) to furnish Compound 270B. LC-MS (ESI) m/z: 212 [M+H]⁺.

Compounds 270C, 270D, and 270 were synthesized by employing the procedures described for Compounds 90C, 8F, and 1 using Compounds 270B with DEAD as coupling reagent, 270C, and 270D in lieu of Compounds 90B with DIAD as coupling reagent, 8E, and 1E. Compound 270C: LC-MS (ESI) m/z: 471 [M+H]⁺. LC-MS (ESI) m/z: 436 [M+H]⁺. Compound 270D: LC-MS (ESI) m/z: 443 [M+H]⁺. Compound 270: LC-MS (ESI) m/z: 323 [M+H]⁺; ¹H-NMR (DMSO-d₆, 400 MHz): δ (ppm) 1.86 (d, J=8.8 Hz, 2H), 2.12 (t, J=11.2 Hz, 2H), 3.18 (t, J=19.2 Hz, 2H), 3.49-3.54 (m, 2H), 4.86 (s, 1H), 7.13 (d, J=7.2 Hz, 2H), 7.29 (d, J=9.2 Hz, 2H).

Example 271

Synthesis of 4-((5,6-difluoro-2,3-dihydro-1H-inden-2-yl)oxy)-1H-1,2,3-triazole-5-carboxylic acid (271)

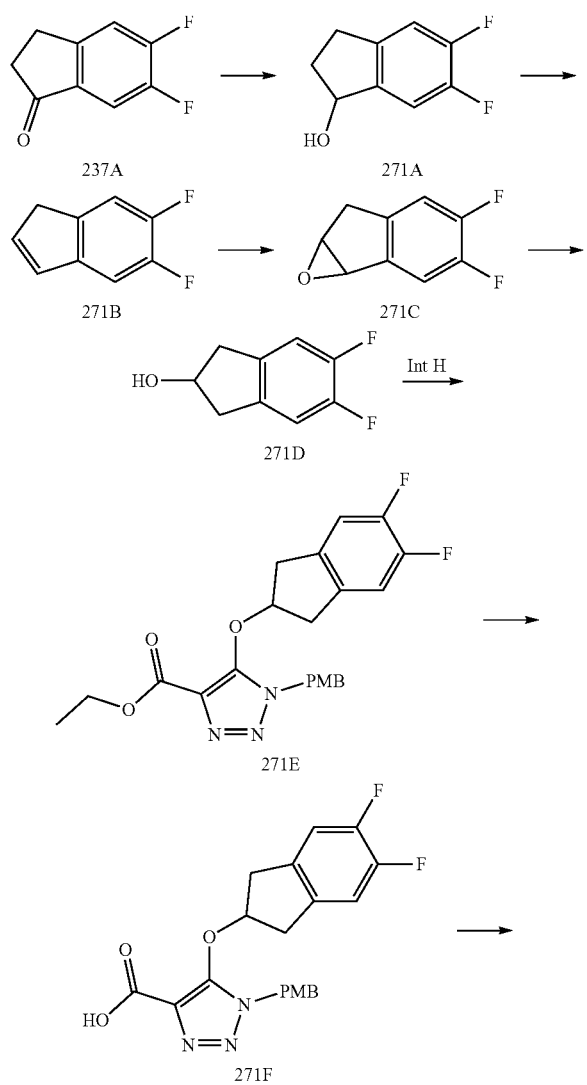

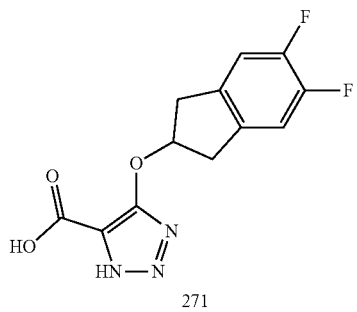

Compounds 271A, 271B, 271C, 271D, 271E, 271F, and 271 were synthesized by employing the procedures described for Compounds 57C, 190B, 190C, 190D, 90C, 8F, and 1 using Compounds 237A, 271A, 271B, 271C, 271D with DEAD as coupling reagent, 271E, and 271F in lieu of Compounds 57B, 190B, 190C, 190D, 90B with DIAD as coupling reagent, 8E, and 1E. Compound 271A: LC-MS (ESI) m/z: 153 [M−OH]⁺; ¹H-NMR (CDCl₃, 400 MHz): δ 1.93-2.01 (m, 1H), 2.49-2.57 (m, 1H), 2.73-2.81 (m, 1H), 2.97-3.04 (m, 1H), 5.19 (t, J=6.0 Hz, 1H), 7.01 (dd, J=7.2, 9.2 Hz, 1H), 7.18 (t, J=8.8 Hz, 1H). Compound 271B: %). LC-MS (ESI) m/z: non-ionizable compound under routine conditions used. ¹H-NMR (CDCl₃, 400 MHz): δ 3.36 (s, 2H), 6.59-6.60 (m, 1H), 6.78-6.79 (m, 1H), 6.59 (dd, J=7.6, 10.4 Hz, 1H), 7.23-7.27 (m, 1H). Compound 271C: LC-MS (ESI) m/z: non-ionizable compound under routine conditions used. ¹H-NMR (CDCl₃, 400 MHz): δ 2.93-2.97 (m, 1H), 3.15-3.19 (m, 1H), 4.14-4.16 (m, 1H), 4.21-4.22 (m, 1H), 7.03 (dd, J=7.2, 10.0 Hz, 1H), 7.30 (dd, J=7.6, 9.2 Hz, 1H). Compound 271D: LC-MS (ESI) m/z: 153 [M−OH]⁺; ¹H-NMR (CDCl₃, 400 MHz): δ 2.86 (dd, J=2.8, 16.0 Hz, 2H), 3.17 (dd, J=6.0, 16.8 Hz, 2H), 4.73 (bs, 1H), 7.02 (t, J=8.8 Hz, 2H). Compound 271E: LC-MS (ESI) m/z: 430 [M+H]⁺; ¹H-NMR (CDCl₃, 400 MHz): δ 1.44 (t, J=7.2 Hz, 3H), 2.89-2.94 (m, 2H), 3.13-3.19 (m, 2H), 3.77 (s, 3H), 4.42 (q, J=7.2 Hz, 2H), 5.04 (s, 2H), 6.13-6.16 (m, 1H), 6.69-6.71 (m, 2H), 6.92-6.97 (m, 4H). Compound 271F: LC-MS (ESI) m/z: 402 [M+H]⁺. Compound 271: LC-MS (ESI) m/z: 282 [M+H]⁺; ¹H-NMR (DMSO-d₆, 400 MHz): δ (ppm) 3.05-3.09 (m, 2H), 3.34-3.39 (m, 2H), 5.44 (bs, 1H), 7.34 (t, J=9.2 Hz, 2H), 12.84 (bs, 1H), 14.79 (bs, 1H).

Example 272

Synthesis of 4-(((trans)-4-(4-(trifluoromethoxy)phenyl)cyclohexyl)oxy)-1H-1,2,3-triazole-5-carboxylic acid and 4-(((cis)-4-(4-(trifluoromethoxy)phenyl)cyclohexyl)oxy)-1H-1,2,3-triazole-5-carboxylic acid (272)

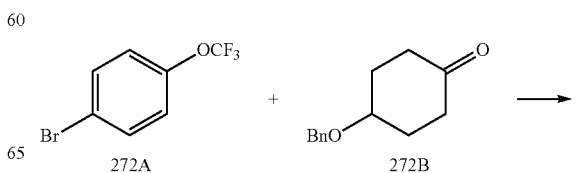

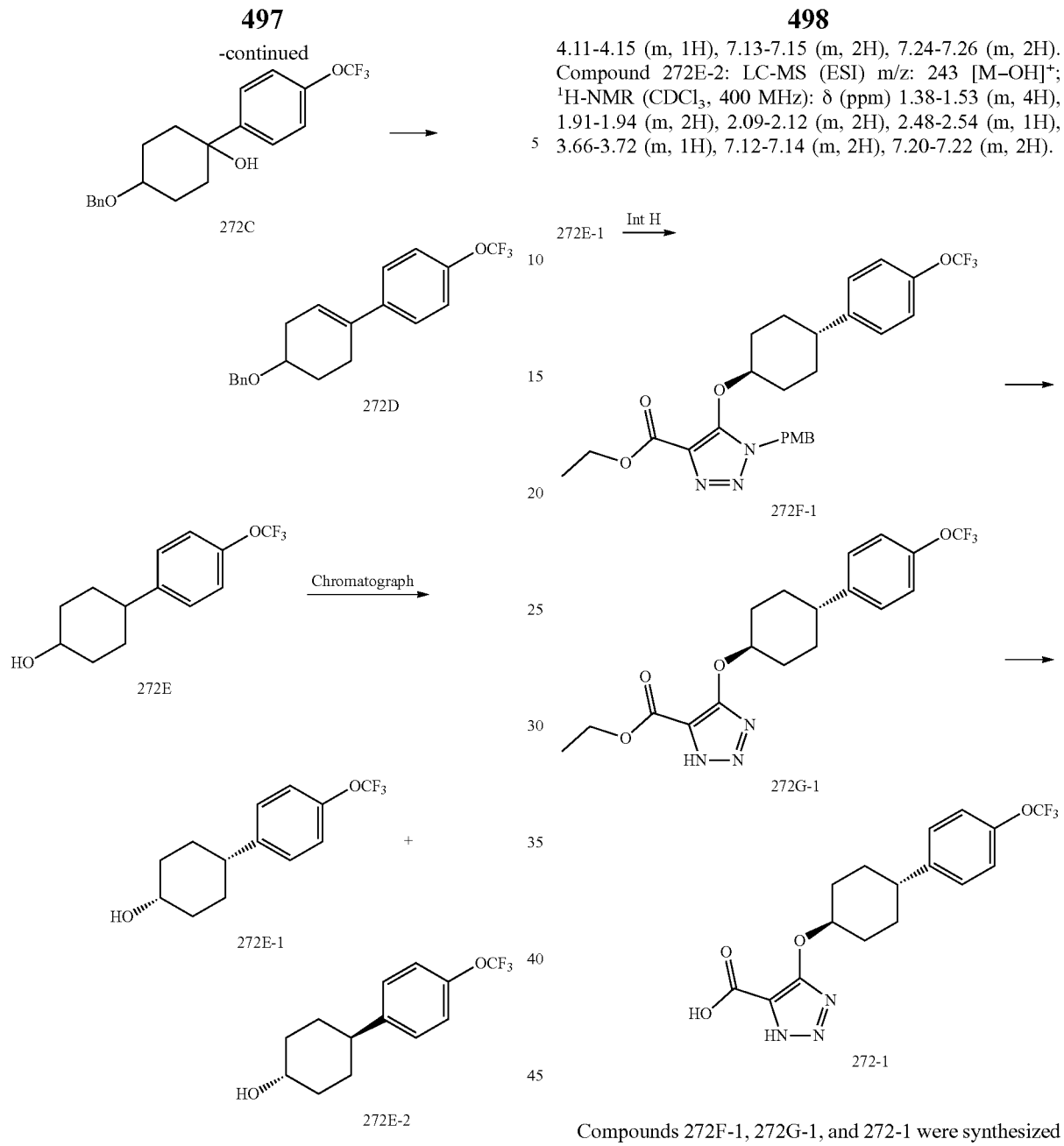

4.11-4.15 (m, 1H), 7.13-7.15 (m, 2H), 7.24-7.26 (m, 2H). Compound 272E-2: LC-MS (ESI) m/z: 243 [M–OH]⁺; ¹H-NMR (CDCl₃, 400 MHz): δ (ppm) 1.38-1.53 (m, 4H), 1.91-1.94 (m, 2H), 2.09-2.12 (m, 2H), 2.48-2.54 (m, 1H), 3.66-3.72 (m, 1H), 7.12-7.14 (m, 2H), 7.20-7.22 (m, 2H).

Compounds 272C, 272D, and 272E were synthesized by employing the procedures described for Compounds 263C, 57E, and 141 using Compounds 272A, 272B, 272C with BF₃·Et₂O as acid, and 272D with MeOH as solvent in lieu of Compounds 263A, 263B, 57D with TFA as acid, and 140 with EtOAc as solvent. Compound 272C: LC-MS (ESI) m/z: non-ionizable compound under routine conditions used; ¹H-NMR (CDCl₃, 400 MHz): δ (ppm) 1.83-1.88 (m, 6H), 2.01-2.04 (m, 2H), 3.44-3.47 (m, 1H), 4.62 (s, 2H), 7.17-7.19 (m, 2H), 7.29-7.34 (m, 1H), 7.34-7.39 (m, 4H), 7.49-7.52 (m, 2H). Compound 272D: LC-MS (ESI) m/z: non-ionizable compound under routine conditions used.

Compound 272E was separated with flash column chromatography on silica gel (ethyl acetate in petroleum ether, from 0% to 30% v/v) to yield Compound 272E-1 and Compound 272E-2. Compound 272E-1: LC-MS (ESI) m/z: 243 [M–OH]⁺; ¹H-NMR (CDCl₃, 400 MHz): δ (ppm) 1.61-1.70 (m, 4H), 1.83-1.93 (m, 4H), 2.52-2.58 (m, 1H), Compounds 272F-1, 272G-1, and 272-1 were synthesized by employing the procedures described for Compounds 90C, 1, and 8F using Compounds 272E-1, 272F-1, and 272G-1 in lieu of Compounds 90B, 1E, and 8E. Compound 272F-1: LC-MS (ESI) m/z: 520 [M+H]⁺; 1.42 (t, J=7.2 Hz, 3H), 1.47-1.54 (m, 4H), 1.91-1.94 (m, 2H), 2.14-2.17 (m, 2H), 2.43-2.47 (m, 1H), 3.79 (s, 3H), 4.41 (q, J=7.2 Hz, 2H), 5.07-5.12 (m, 1H), 5.30 (s, 2H), 6.86-6.88 (m, 2H), 7.12-7.14 (m, 2H), 7.17-7.20 (m, 2H), 7.24-7.26 (m, 2H). Compound 272G-1: LC-MS (ESI) m/z: 400 [M+H]⁺; ¹H-NMR (CD₃OD, 400 MHz): δ (ppm) 1.38 (t, J=7.2 Hz, 3H), 1.66-1.71 (m, 4H), 1.98-2.00 (m, 2H), 2.35-2.38 (m, 2H), 2.66-2.69 (m, 1H), 4.36 (q, J=7.2 Hz, 2H), 4.74-4.76 (m, 1H), 7.18-7.20 (m, 2H), 7.35-7.37 (m, 2H). Compound 272-1: LC-MS (ESI) m/z: 372 [M+H]⁺; ¹H-NMR (CD₃OD, 400 MHz): δ (ppm) 1.63-1.73 (m, 4H), 1.95-1.98 (m, 2H), 2.33-2.36 (m, 2H), 2.66-2.69 (m, 1H), 4.71-4.72 (m, 1H), 7.17-7.19 (m, 2H), 7.34-7.36 (m, 2H).

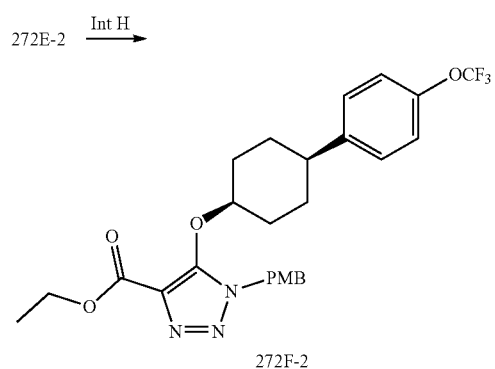

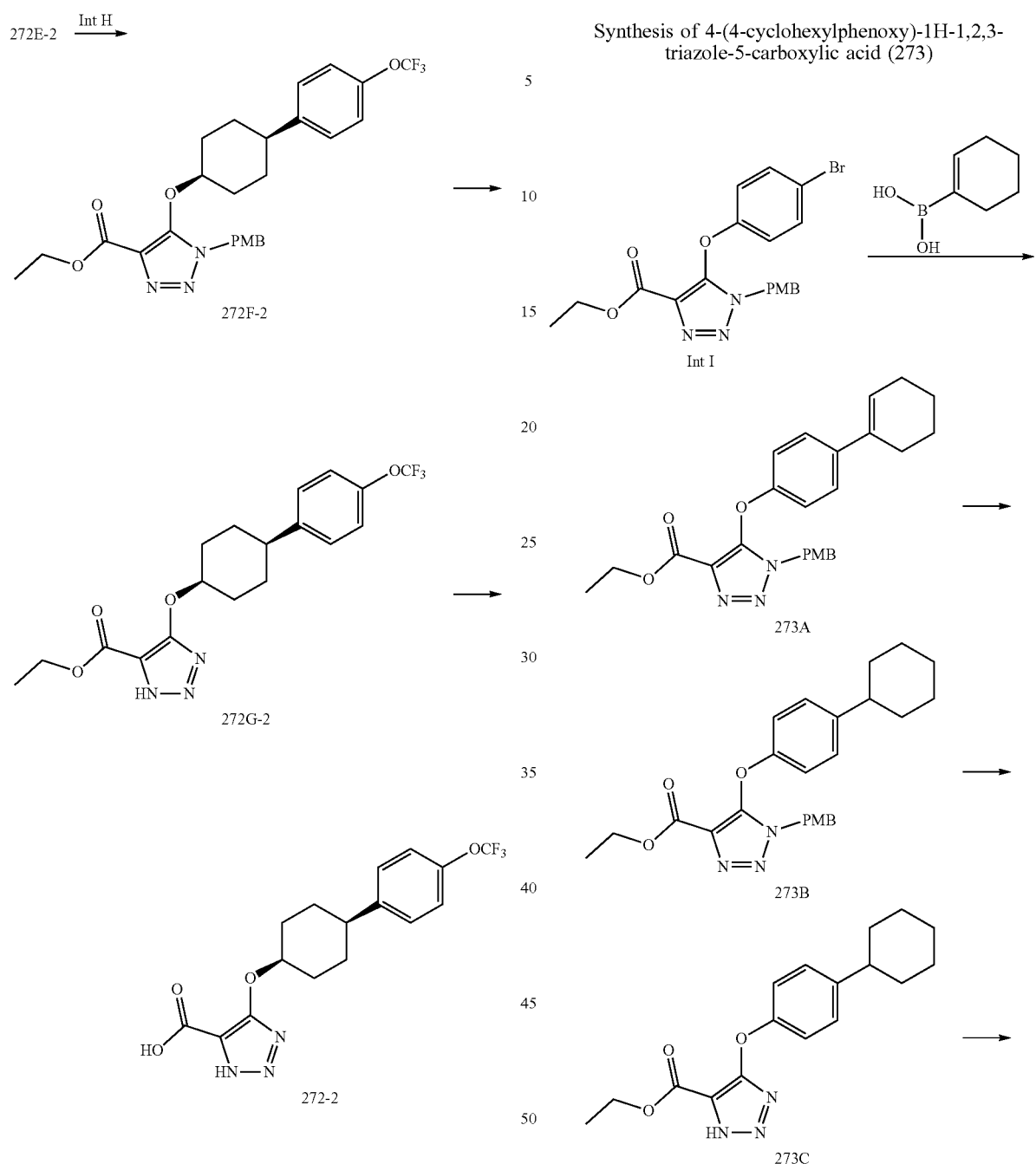

Example 273

Synthesis of 4-(4-cyclohexylphenoxy)-1H-1,2,3-triazole-5-carboxylic acid (273)

Compounds 272F-2, 272G-2, and 272-2 were synthesized by employing the procedures described for Compounds 90C, 1, and 8F using Compounds 272E-2, 272F-2, and 272G-2 in lieu of Compounds 90B, 1E, and 8E. Compound 272F-2: LC-MS (ESI) m/z: 520 [M+H]$^+$; $^1$H-NMR (CDCl$_3$, 400 MHz): δ (ppm) 1.42 (t, J=7.2 Hz, 3H), 1.63-1.73 (m, 6H), 2.10-2.13 (m, 2H), 2.56-2.60 (m, 1H), 3.76 (s, 3H), 4.41 (q, J=7.2 Hz, 2H), 5.37 (s, 2H), 5.48 (s, 1H), 6.82-6.85 (m, 2H), 7.12-7.17 (m, 4H), 7.19-7.22 (m, 2H). Compound 272G-2: LC-MS (ESI) m/z: 400 [M+H]$^+$. Compound 272-2: LC-MS (ESI) m/z: 372 [M+H]$^+$; $^1$H-NMR (CD$_3$OD, 400 MHz): δ (ppm) 1.66-1.79 (m, 4H), 1.97-2.04 (m, 2H), 2.21-2.25 (m, 2H), 2.67-2.71 (m, 1H), 5.06 (s, 1H), 7.17-7.19 (m, 2H), 7.35-7.38 (m, 2H).

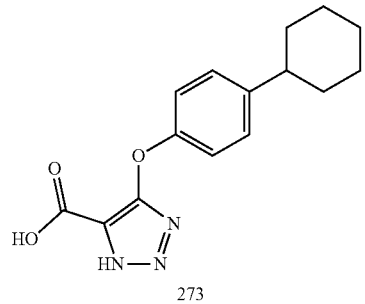

Compounds 273A, 273B, 273C, and 273 were synthesized by employing the procedures described for Compounds 4B, 141, 1, and 8F using cyclohexenylboronic acid, Intermediate I with K₂CO₃ as base and 1,4-dioxane/H₂O as solvent, Compounds 273A, 273B, and 273C in lieu of (4-bromophenyl)boronic acid, Compounds 4A with tBuONa as base and toluene/EtOH/H₂O as solvent, 140, 1E, and 8E. Compound 273A: LC-MS (ESI) m/z: 434 [M+H]⁺; (CDCl₃, 400 MHz): δ (ppm) 1.11 (t, J=7.2 Hz, 3H), 1.64-1.68 (m, 2H), 1.76-1.80 (m, 2H), 2.18-2.22 (m, 2H), 2.33-2.37 (m, 2H), 3.77 (s, 3H), 4.18 (q, J=7.2 Hz, 2H), 5.34 (s, 2H), 6.04-6.07 (m, 1H), 6.69-6.72 (m, 2H), 6.78-6.80 (m, 2H), 7.19-7.22 (m, 2H), 7.26-7.27 (m, 2H). Compound 273B: LC-MS (ESI) m/z: 436 [M+H]⁺; ¹H-NMR (CDCl₃, 400 MHz): δ (ppm) 1.11 (t, J=7.2 Hz, 3H), 1.23-1.26 (m, 4H), 1.82-1.85 (m, 4H), 2.44-2.49 (m, 2H), 2.20-2.28 (m, 1H), 3.77 (s, 3H), 4.18 (q, J=7.2 Hz, 2H), 5.34 (s, 2H), 6.68-6.72 (m, 2H), 6.77-6.81 (m, 2H), 7.08-7.10 (m, 2H), 7.19-7.22 (m, 2H). Compound 273C: LC-MS (ESI) m/z: 316 [M+H]⁺. Compound 273: LC-MS (ESI) m/z: 288 [M+H]⁺; ¹H-NMR (CD₃OD, 400 MHz): δ (ppm) 1.28-1.49 (m, 5H), 1.74-1.87 (m, 5H), 2.49-2.51 (m, 1H), 7.03 (d, J=8.4 Hz, 2H), 7.21 (d, J=8.4 Hz, 2H).

Example 274

Synthesis of 4-((4'-(trifluoromethoxy)-[1,1'-biphenyl]-4-yl)methoxy)-1H-1,2,3-triazole-5-carboxylic acid (274)

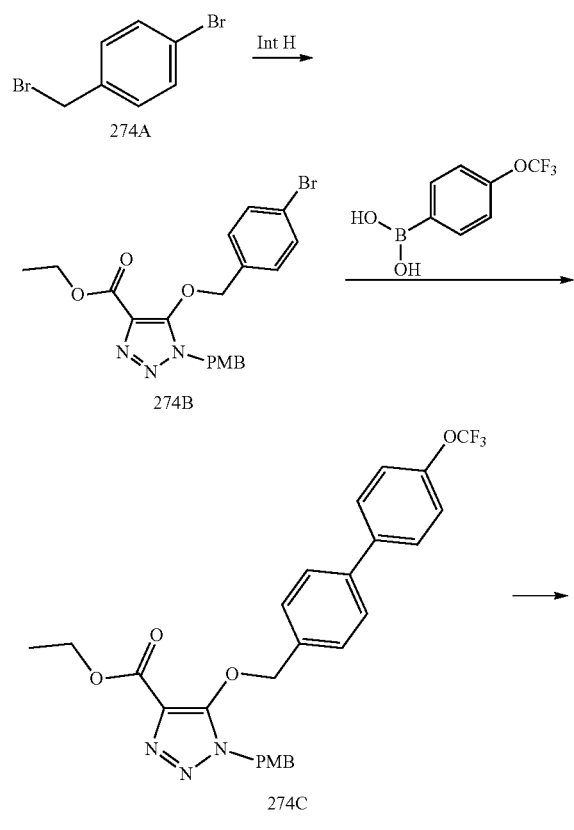

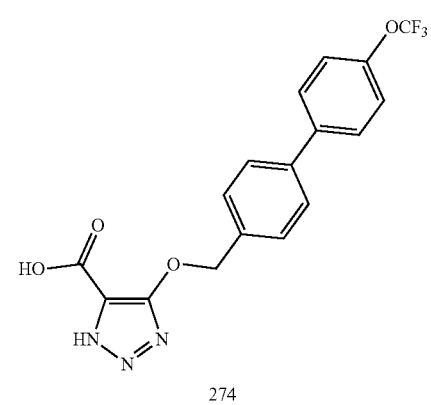

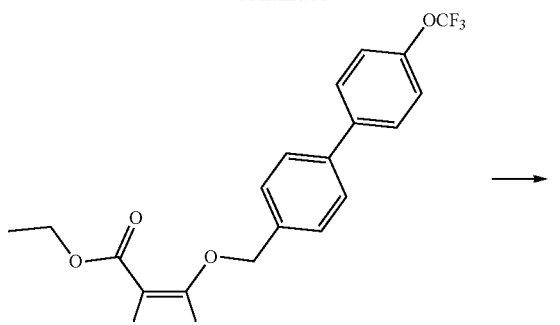

A mixture of Intermediate H (500 mg, 1.8 mmol), 1-bromo-4-(bromomethyl)benzene (274A) (497 mg, 3.6 mmol), and K₂CO₃ (497 mg, 3.6 mmol) in DMF (20 mL) was stirred at room temperature for 12 hours. The mixture was diluted with water (50 mL) and extracted with ethyl acetate (100 mL×3). The combined organic layers was washed with water (100 mL×3) and brine (100 mL), dried over anhydrous sodium sulfate, filtered, concentrated, and purified with flash column chromatography on silica gel (ethyl acetate in petroleum ether, 30% v/v) to furnish Compound 274B. LC-MS (ESI) m/z: 446 [M+H]⁺; ¹H-NMR (CDCl₃, 400 MHz): δ (ppm) 1.35 (t, J=14.4 Hz, 3H), 3.72 (s, 3H), 4.36 (q, J=7.2 Hz, 2H), 5.12 (s, 2H), 5.28 (s, 2H), 6.74 (d, J=8.8 Hz, 2H), 7.00-7.04 (m, 4H), 7.37 (d, J=8.8 Hz, 2H).

Compounds 274C, 274D, and 274 were synthesized by employing the procedures described for Compounds 4B, 217E, and 8F using 4-(trifluoromethoxy)phenylboronic acid, Compounds 274B with K₃PO₄ as base and DME/H₂O as solvent, 274C, and 274D in lieu of (4-bromophenyl)boronic acid, Compounds 4A with Na₂CO₃ as base and toluene/EtOH/H₂O as solvent, 217D, and 8E. Compound 274C: LC-MS (ESI) m/z: 528 [M+H]⁺. Compound 274D: LC-MS (ESI) m/z: 408 [M+H]⁺. Compound 274: LC-MS (ESI) m/z: 402 [M+Na]⁺; ¹H-NMR (DMSO-d₆, 500 MHz): δ (ppm) 5.38 (s, 2H), 7.46 (d, J=8.5 Hz, 2H), 7.57 (d, J=8.5 Hz, 2H), 7.71 (d, J=8.5 Hz, 2H), 7.80 (d, J=8.5 Hz, 2H), 12.93 (s, 1H), 14.84 (s, 1H).

Example 275

Synthesis of 4-((3-(4-(trifluoromethoxy)phenyl)cyclopentyl)oxy)-1H-1,2,3-triazole-5-carboxylic acid (275)

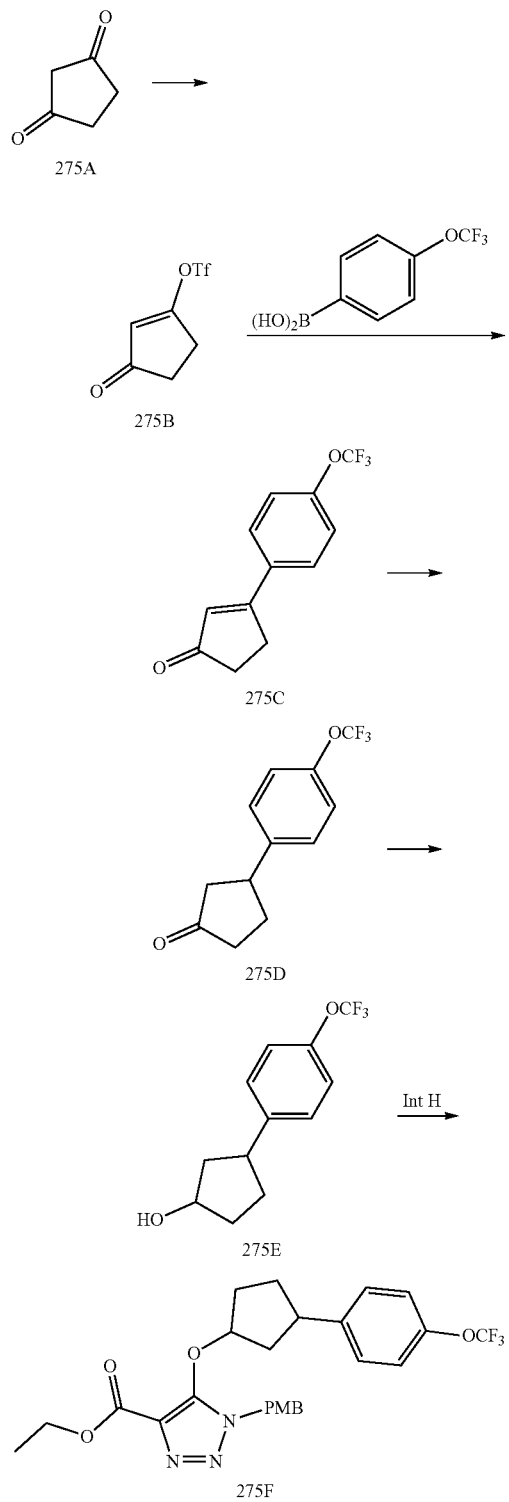

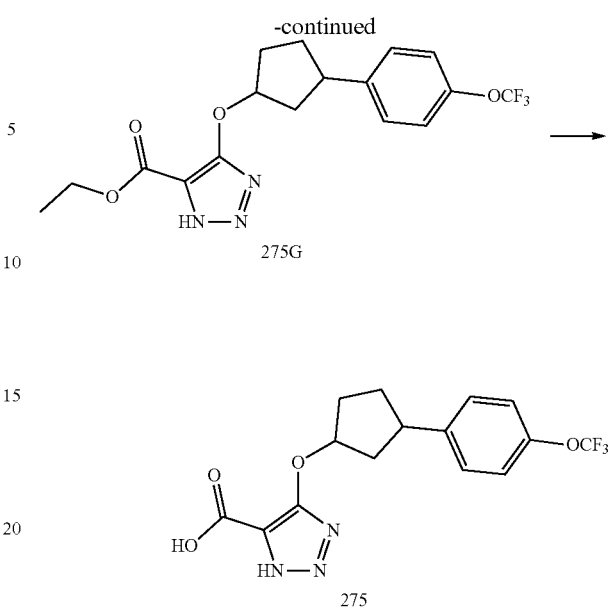

To a solution of cyclopentane-1,3-dione (275A) (300 mg, 3.06 mmol) and 2,6-lutidine (196 mg, 4.59 mmol) in DCM (10 mL) was dropped Tf$_2$O (1.03 g, 3.67 mmol) at −70° C. The mixture was stirred at −70° C. for 1 hour, quenched with water (80 mL), and extracted with dichloromethane (60 mL×3). The combined organic phases was washed with diluted aqueous hydrochloric acid (2M, 80 mL) and water (100 mL) and brine (100 mL), dried over anhydrous sodium sulfate, filtered, and evaporated to give a crude Compound 275B. LC-MS (ESI) m/z: 231 [M+H]$^+$.

Compounds 275C, 275D, 275E, 275F, 275G, and 275 were synthesized by employing the procedures described for Compounds 206C, 141, 57C, 90C, 1, and 8F using 4-(trifluoromethoxy)phenylboronic acid, Compounds 275B with K$_2$CO$_3$ as base, 275C, 275D with EtOH as solvent, 275E, 275F, and 275G in lieu of Compounds 206B, 206A with Na$_2$CO$_3$ as base, 140, 57B with MeOH as solvent, 90B, 1E, and 8E. Compound 275C: LC-MS (ESI) m/z: 243 [M+H]$^+$; $^1$H-NMR (CDCl$_3$, 400 MHz): δ (ppm) 2.60-2.63 (m, 2H), 3.02-3.06 (m, 2H), 6.56-5.57 (m, 1H), 7.30 (d, J=8.8 Hz, 2H), 7.69 (d. J=8.8 Hz, 2H). Compound 275D: LC-MS (ESI) m/z: 245 [M+H]$^+$. Compound 275E: LC-MS (ESI) m/z: 229 [M−OH]$^+$; $^1$H-NMR (CDCl$_3$, 400 MHz): δ (ppm) 1.57-1.93 (m, 4H), 2.08-2.51 (m, 2H), 3.03-3.45 (m, 1H), 4.45-4.56 (m, 1H), 7.12-7.14 (m, 2H), 7.22-7.31 (m, 2H). Compound 275F: LC-MS (ESI) m/z: 506 [M+H]$^+$; $^1$H-NMR (CDCl$_3$, 400 MHz): δ (ppm) 1.42 (t, J=6.8 Hz, 3H), 1.51-1.61 (m, 1H), 1.71-1.91 (m, 2H), 2.01-2.11 (m, 2H), 2.19-2.55 (m, 1H), 2.95-3.08 (m, 1H), 3.73-3.75 (s, 3H), 4.37-4.43 (m, 2H), 5.30-5.37 (m, 2H), 5.76-7.88 (m, 1H), 6.81-6.85 (m, 2H), 7.09-7.14 (m, 4H), 7.16-7.22 (m, 2H). Compound 275G: LC-MS (ESI) m/z: 386 [M+H]$^+$, $^1$H-NMR (CDCl$_3$, 400 MHz): δ (ppm) 1.39-1.43 (m, 3H), 1.61-1.72 (m, 1H), 1.91-2.18 (m, 3H), 2.26-2.72 (m, 2H), 3.11-3.40 (m, 1H), 4.37-7.76 (m, 2H), 5.27-5.36 (m, 1H), 7.13-7.16 (m, 2H), 7.25-7.36 (m, 2H). Compound 275: LC-MS (ESI) m/z: 358 [M+H]$^+$; $^1$H-NMR (CD$_3$OD, 400 MHz): δ (ppm) 1.65-2.70 (m, 1H), 1.90-2.62 (m, 5H), 3.19-3.53 (m, 1H), 5.33 (brs, 1H), 7.16-7.20 (m, 2H), 7.37-7.50 (m, 2H).

Reference Example 276

Synthesis of 4-((4'-fluoro-[1,1'-biphenyl]-4-yl)thio)-1H-1,2,3-triazole-5-carboxylic acid (276)

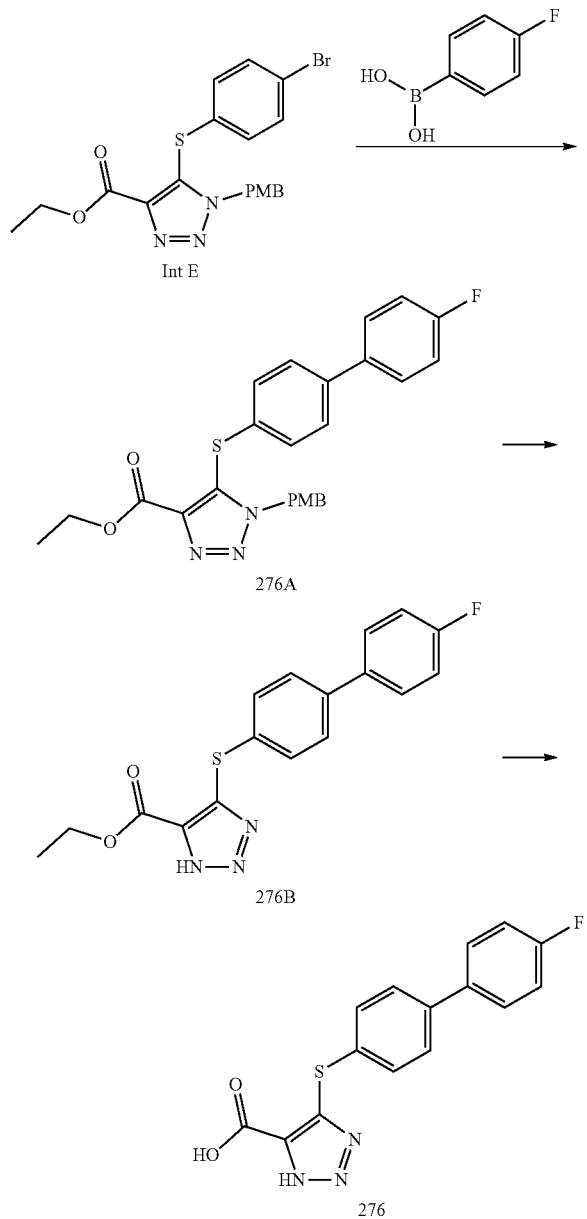

Compounds 276A, 276B, and 276 were synthesized by employing the procedures described for Compounds 4B, 1, and 8F using 4-fluorophenylboronic acid, Intermediate E with $K_2CO_3$ as base and 1,4-dioxane/$H_2O$ as solvent, Compounds 276A, and 276B in lieu of (4-bromophenyl)boronic acid, Compounds 4A with $Na_2CO_3$ as base and toluene/EtOH/$H_2O$ as solvent, 1E, and 8E. Compound 276A: LC-MS (ESI) m/z: 464 [M+H]⁺; ¹H-NMR (CDCl₃, 400 MHz): δ (ppm) 1.33 (t, J=7.2 Hz, 3H), 3.71 (s, 3H), 4.37 (q, J=7.2 Hz, 2H), 5.58 (s, 2H), 6.75 (d, J=8.4 Hz, 2H), 7.05 (d, J=8.4 Hz, 2H), 7.10-7.17 (m, 4H), 7.35 (d, J=8.4 Hz, 2H), 7.45-7.48 (m, 2H). Compound 276B: LC-MS (ESI) m/z: 344 [M+H]⁺. Compound 276: LC-MS (ESI) m/z: 316 [M+H]⁺; ¹H-NMR (CD₃OD, 400 MHz): δ (ppm) 7.19 (d, J=8.8 Hz, 2H), 7.56-7.68 (m, 6H).

Example 277

Synthesis of 4-((6,7-dichloro-1,2,3,4-tetrahydronaphthalen-2-yl)thio)-1H-1,2,3-triazole-5-carboxylic acid (277)

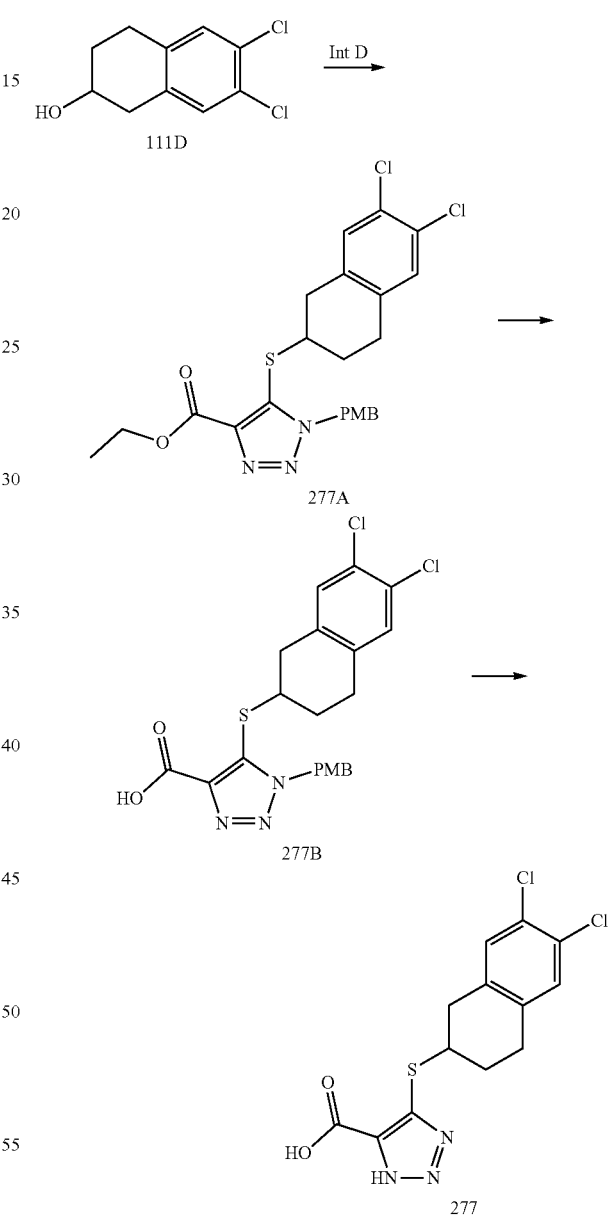

Compounds 277A, 277B, and 277 were synthesized by employing the procedures described for Compounds 90C, 8F, and 1 using Intermediate D, Compounds 111D with DEAD as coupling reagent, 277A, and 277B in lieu of Intermediate H, Compounds 90B with DIAD as coupling reagent, 8E, and 1E. Compound 277A: LC-MS (ESI) m/z: 492 [M+H]⁺. Compound 277B: LC-MS (ESI) m/z: 464 [M+H]⁺. Compound 277: LC-MS (ESI) m/z: 344 [M+H]⁺;

¹H-NMR (DMSO-d₆, 400 MHz): δ (ppm) 1.84-1.89 (m, 1H), 2.15-2.21 (m, 1H), 2.82-2.85 (m, 3H), 3.34-3.41 (m, 1H), 3.96-4.01 (m, 1H), 7.36-7.39 (m, 2H).

Example 278

Synthesis of (benzoyloxy)methyl 4-((4'-(piperidin-1-yl)-[1,1'-biphenyl]-4-yl)thio)-1H-1,2,3-triazole-5-carboxylate (278)

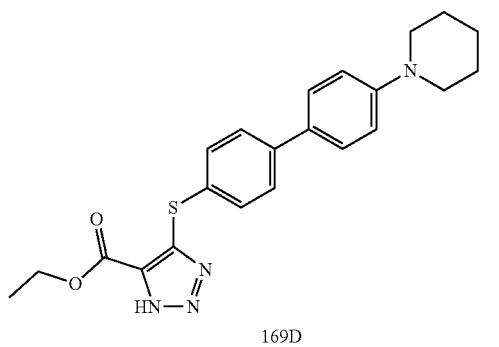

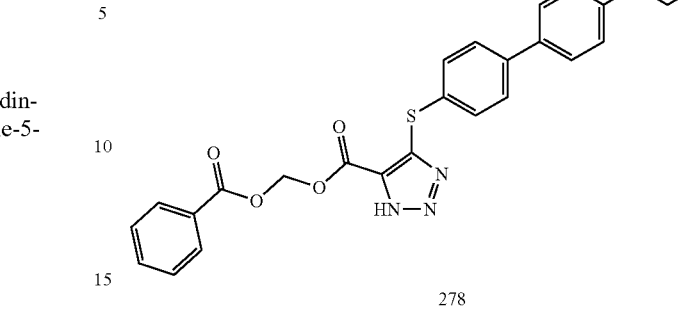

Compounds 278A, 278B, 278C, and 278 were synthesized by employing the procedures described for Compounds 54A, 8F, 54C, and 256 using Compounds 169D, 278A, chloromethyl benzoate, 278B with Et₃N as base and DMF/THF as solvent and adding NaI, and 278C in lieu of Compounds 33, 8E, chloromethyl pivalate, 54B with Na₂CO₃ as base and DMF as solvent and without NaI, and 256D. Compound 278A: LC-MS (ESI) m/z: 651 [M+H]⁺. Compound 278B: LC-MS (ESI) m/z: 623 [M+H]⁺. Compound 278C: LC-MS (ESI) m/z: 757 [M+H]⁺; ¹H-NMR (CDCl₃, 400 MHz): δ (ppm) 1.52-1.64 (m, 6H), 3.73-3.76 (m, 4H), 5.30 (s, 2H), 6.98-7.04 (m, 7H), 7.21-7.30 (m, 9H), 7.36-7.60 (m, 10H), 8.08 (d, J=7.2 Hz, 2H). Compound 278: LC-MS (ESI) m/z: 515 [M+H]⁺; ¹H-NMR (CD₃OD, 400 MHz): δ (ppm) 1.59-1.65 (m, 2H), 1.71-1.76 (m, 4H), 3.18-3.22 (m, 4H), 6.17 (s, 2H), 7.01 (d, J=8.8 Hz, 2H), 7.23 (d, J=8.0 Hz, 2H), 7.37-7.43 (m, 6H), 7.54-7.59 (m, 1H), 7.97 (d, J=7.2 Hz, 2H).

Example 279

Synthesis of 4-(4-(4,4-difluorocyclohexyl)phenoxy)-1H-1,2,3-triazole-5-carboxylic acid (279)

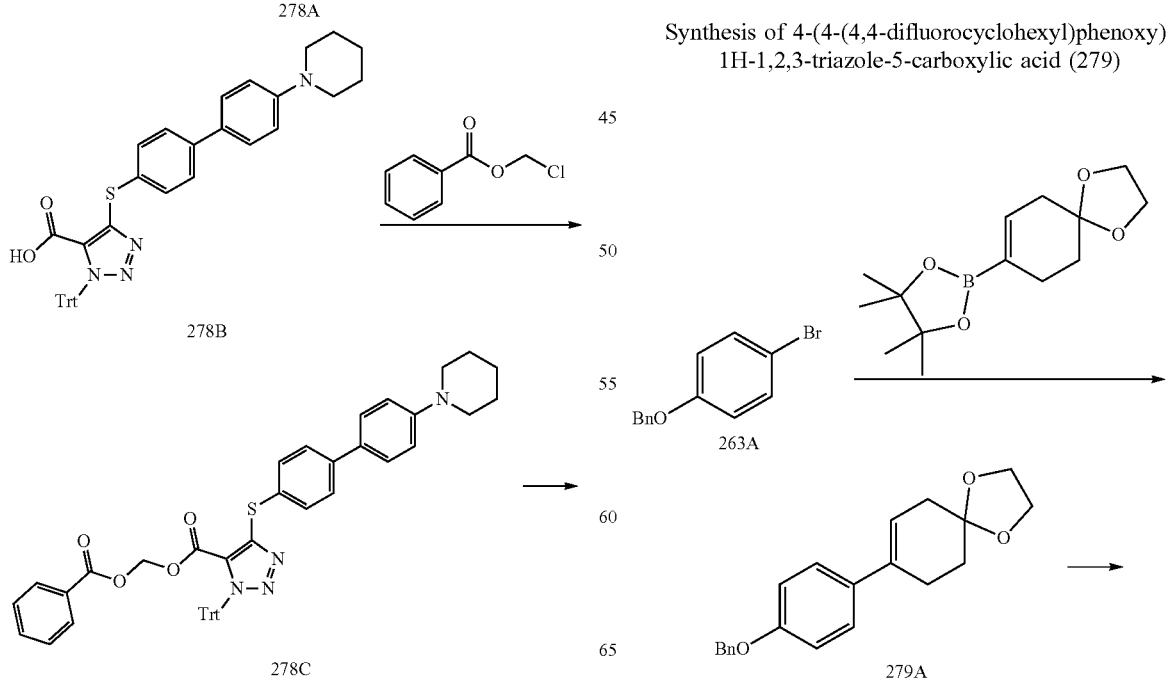

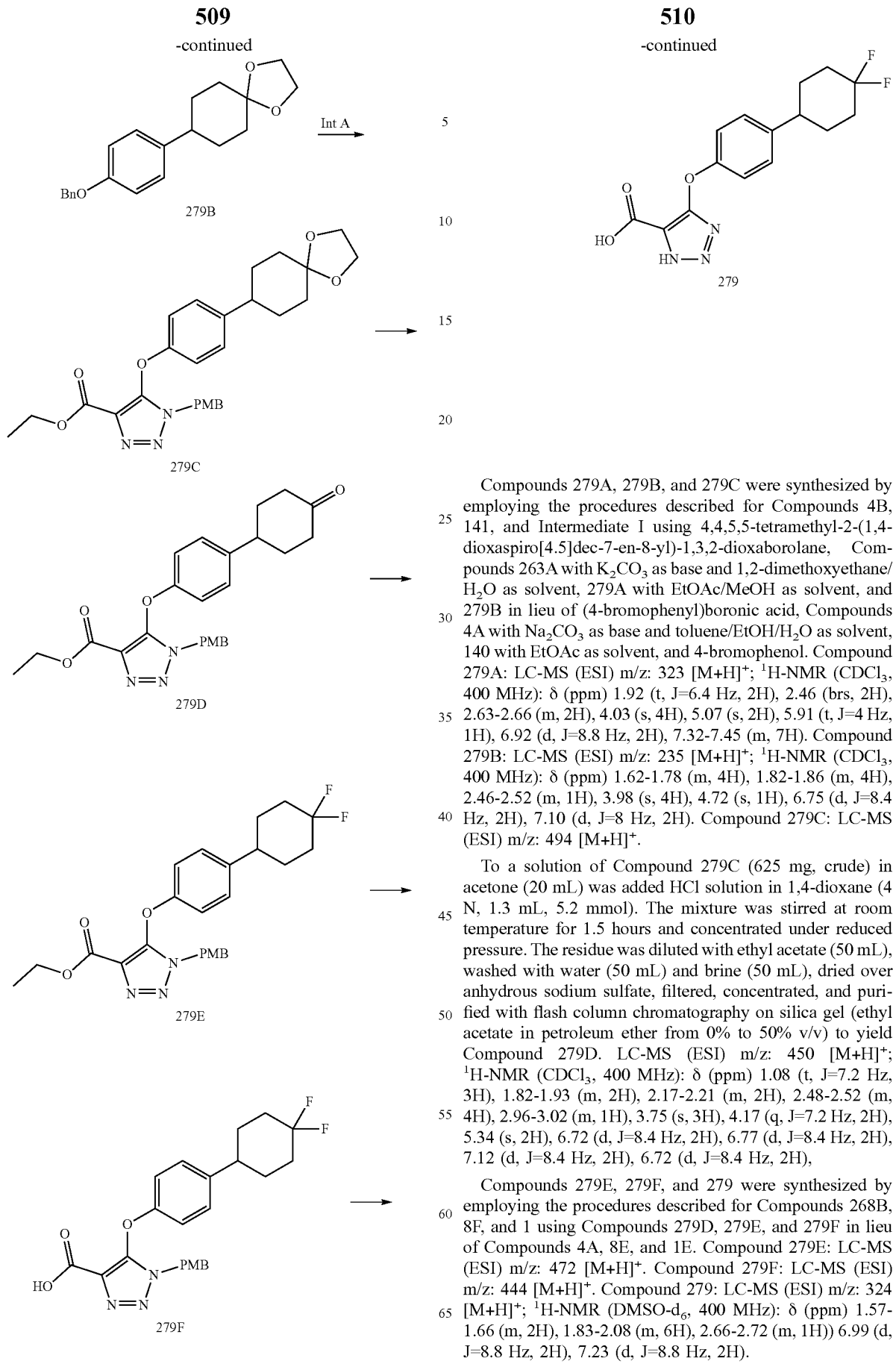

Compounds 279A, 279B, and 279C were synthesized by employing the procedures described for Compounds 4B, 141, and Intermediate I using 4,4,5,5-tetramethyl-2-(1,4-dioxaspiro[4.5]dec-7-en-8-yl)-1,3,2-dioxaborolane, Compounds 263A with $K_2CO_3$ as base and 1,2-dimethoxyethane/$H_2O$ as solvent, 279A with EtOAc/MeOH as solvent, and 279B in lieu of (4-bromophenyl)boronic acid, Compounds 4A with $Na_2CO_3$ as base and toluene/EtOH/$H_2O$ as solvent, 140 with EtOAc as solvent, and 4-bromophenol. Compound 279A: LC-MS (ESI) m/z: 323 [M+H]$^+$; $^1$H-NMR (CDCl$_3$, 400 MHz): δ (ppm) 1.92 (t, J=6.4 Hz, 2H), 2.46 (brs, 2H), 2.63-2.66 (m, 2H), 4.03 (s, 4H), 5.07 (s, 2H), 5.91 (t, J=4 Hz, 1H), 6.92 (d, J=8.8 Hz, 2H), 7.32-7.45 (m, 7H). Compound 279B: LC-MS (ESI) m/z: 235 [M+H]$^+$; $^1$H-NMR (CDCl$_3$, 400 MHz): δ (ppm) 1.62-1.78 (m, 4H), 1.82-1.86 (m, 4H), 2.46-2.52 (m, 1H), 3.98 (s, 4H), 4.72 (s, 1H), 6.75 (d, J=8.4 Hz, 2H), 7.10 (d, J=8 Hz, 2H). Compound 279C: LC-MS (ESI) m/z: 494 [M+H]$^+$.

To a solution of Compound 279C (625 mg, crude) in acetone (20 mL) was added HCl solution in 1,4-dioxane (4 N, 1.3 mL, 5.2 mmol). The mixture was stirred at room temperature for 1.5 hours and concentrated under reduced pressure. The residue was diluted with ethyl acetate (50 mL), washed with water (50 mL) and brine (50 mL), dried over anhydrous sodium sulfate, filtered, concentrated, and purified with flash column chromatography on silica gel (ethyl acetate in petroleum ether from 0% to 50% v/v) to yield Compound 279D. LC-MS (ESI) m/z: 450 [M+H]$^+$; $^1$H-NMR (CDCl$_3$, 400 MHz): δ (ppm) 1.08 (t, J=7.2 Hz, 3H), 1.82-1.93 (m, 2H), 2.17-2.21 (m, 2H), 2.48-2.52 (m, 4H), 2.96-3.02 (m, 1H), 3.75 (s, 3H), 4.17 (q, J=7.2 Hz, 2H), 5.34 (s, 2H), 6.72 (d, J=8.4 Hz, 2H), 6.77 (d, J=8.4 Hz, 2H), 7.12 (d, J=8.4 Hz, 2H), 6.72 (d, J=8.4 Hz, 2H), Compounds 279E, 279F, and 279 were synthesized by employing the procedures described for Compounds 268B, 8F, and 1 using Compounds 279D, 279E, and 279F in lieu of Compounds 4A, 8E, and 1E. Compound 279E: LC-MS (ESI) m/z: 472 [M+H]$^+$. Compound 279F: LC-MS (ESI) m/z: 444 [M+H]$^+$. Compound 279: LC-MS (ESI) m/z: 324 [M+H]$^+$; $^1$H-NMR (DMSO-d$_6$, 400 MHz): δ (ppm) 1.57-1.66 (m, 2H), 1.83-2.08 (m, 6H), 2.66-2.72 (m, 1H)) 6.99 (d, J=8.8 Hz, 2H), 7.23 (d, J=8.8 Hz, 2H).

Example 280

Synthesis of 4-(spiro[2.5]octan-6-yloxy)-1H-1,2,3-triazole-5-carboxylic acid 2,2,2-trifluoroacetate (280)

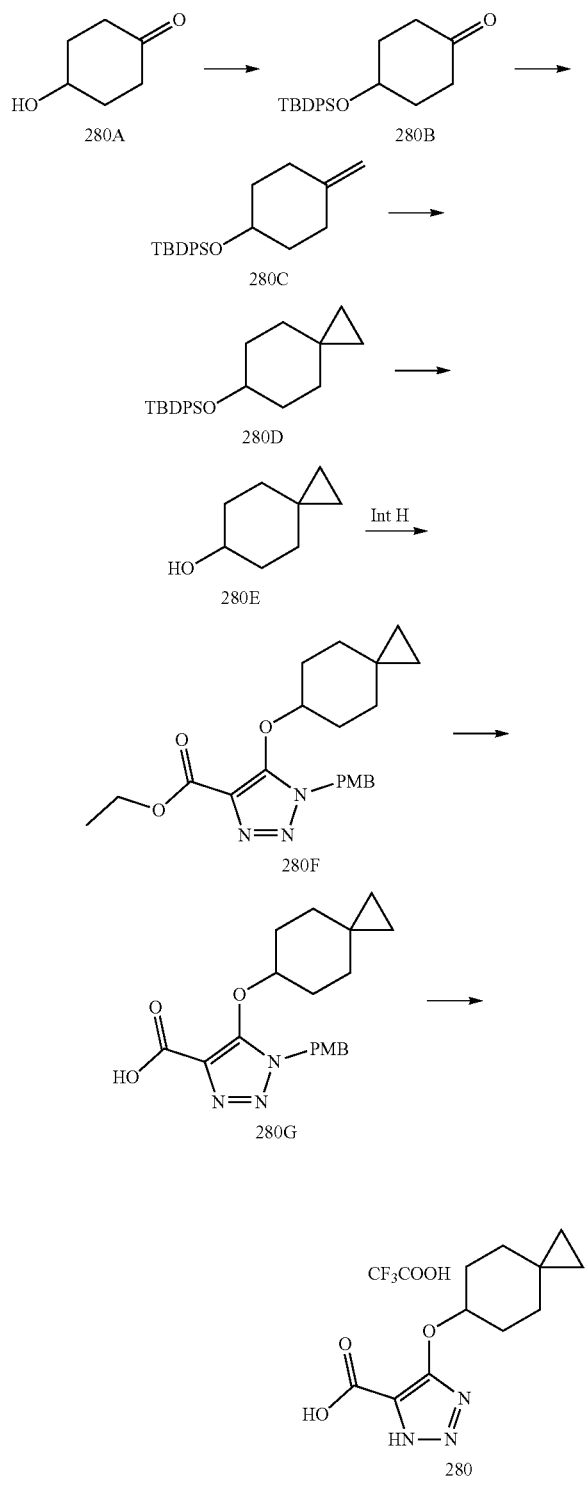

A solution of 4-hydroxycyclohexanone (280A) (3.5 g, 3.07 mmol), TBDPSCl (10 mL, 3.68 mmol), and imidazole (3.13 g, 4.61 mmol) in dry DMF (150 mL) was stirred at 50° C. under nitrogen for 18 hours. It was diluted with water (50 mL) and extracted with ethyl acetate (50 mL×3). The combined organic layers was washed with brine (50 mL), dried over anhydrous sodium sulfate, filtered, concentrated, and purified with flash column chromatography on silica gel (petroleum ether) to afford Compound 280B. LC-MS (ESI) m/z: non-ionizable compound under routine conditions used.

To a solution of methyltriphenylphosphonium bromide (54 g, 153.3 mmol) in dry THF (300 mL) was added t-BuONa (14.67 g, 153.3 mmol) and stirred at room temperature for 1 hour. To the mixture was added Compound 280B (9 g, 25.5 mmol) and stirred at room temperature for 18 hours. It was diluted with water (50 mL) and extracted with ethyl acetate (50 mL×3). The combined organic layers was washed with brine (50 mL), dried over anhydrous sodium sulfate, filtered, concentrated, and purified with flash column chromatography on silica gel (petroleum ether) to afford Compound. LC-MS (ESI) m/z: non-ionizable compound under routine conditions used; $^1$H-NMR (CDCl$_3$, 400 MHz): δ (ppm) 0.97 (s, 9H), 1.50-1.59 (m, 4H), 1.83-1.90 (m, 2H), 2.28-2.33 (m, 2H), 3.81-3.83 (m, 1H), 4.51 (s, 2H), 7.26-7.35 (m, 6H), 7.59-7.61 (m, 4H).

To a solution of trifluoroacetic acid (3.9 g, 34.32 mmol) in dry dichloromethane (100 mL) was slowly dropped diethylzine (37.74 g, 37.74 mmol) at −10° C. After the mixture was stirred at room temperature for 30 minutes, and then Diiodomethane (9 g, 34.32 mmol) was added, followed by Compound 280C (3 g, 8.58 mmol). The resulting mixture was stirred at room temperature for 3 hours, diluted with water (50 mL) and extracted with DCM (50 mL×3). The combined organic layer was washed with brine (50 mL), dried over anhydrous sodium sulfate, concentrated and purified with flash column chromatography on silica gel (petroleum ether) to afford Compound 280D. LC-MS (ESI) m/z: non-ionizable compound under routine conditions used; $^1$H-NMR (CDCl$_3$, 400 MHz): δ (ppm) 0.91-0.95 (m, 4H), 0.97 (s, 9H), 1.55-1.62 (m, 4H), 1.93-1.96 (m, 2H), 2.38-2.43 (m, 2H), 3.87-3.89 (m, 1H), 7.35-7.42 (m, 6H), 7.66-7.69 (m, 4H).

A solution of Compound 280D (1.6 g, 4.39 mmol) and TBAF (8.8 mL, 8.79 mmol) in dry THF (20 mL) was stirred at room temperature under nitrogen for 18 hours. The mixture was diluted with water (50 mL) and extracted with ethyl acetate (50 mL×3). The combined organic layers was washed with brine (50 mL), dried over anhydrous sodium sulfate, filtered, concentrated, and purified with flash column chromatography on silica gel (ethyl acetate in petroleum ether, 20% v/v) to afford Compound. LC-MS (ESI) m/z: non-ionizable compound under routine conditions used; $^1$H-NMR (CDCl$_3$, 400 MHz): δ (ppm) 0.88-0.92 (m, 4H), 1.07-1.42 (m, 8H), 3.55-3.56 (m, 1H).

Compounds 280F, 280G, and 280 were synthesized by employing the procedures described for Compounds 90C, 8F, and 217E using Compounds 280E, 280F, and 280G in lieu of Compounds 90B, 8E, and 217D. Compound 280F: LC-MS (ESI) m/z: 386 [M+H]$^+$. Compound 280G: LC-MS (ESI) m/z: 358 [M+H]$^+$. Compound 280: LC-MS (ESI) m/z: 238 [M+H]$^+$. $^1$H-NMR (DMSO-d$_6$, 400 MHz): δ (ppm) 0.22-0.31 (m, 4H), 1.22-1.49 (m, 4H), 1.61-1.70 (m, 2H), 1.90-1.93 (m, 2H), 4.72 (s, 1H).

Example 281

Synthesis of 4-((5,5-dimethyl-5,6,7,8-tetrahydronaphthalen-2-yl)oxy)-1H-1,2,3-triazole-5-carboxylic acid (281)

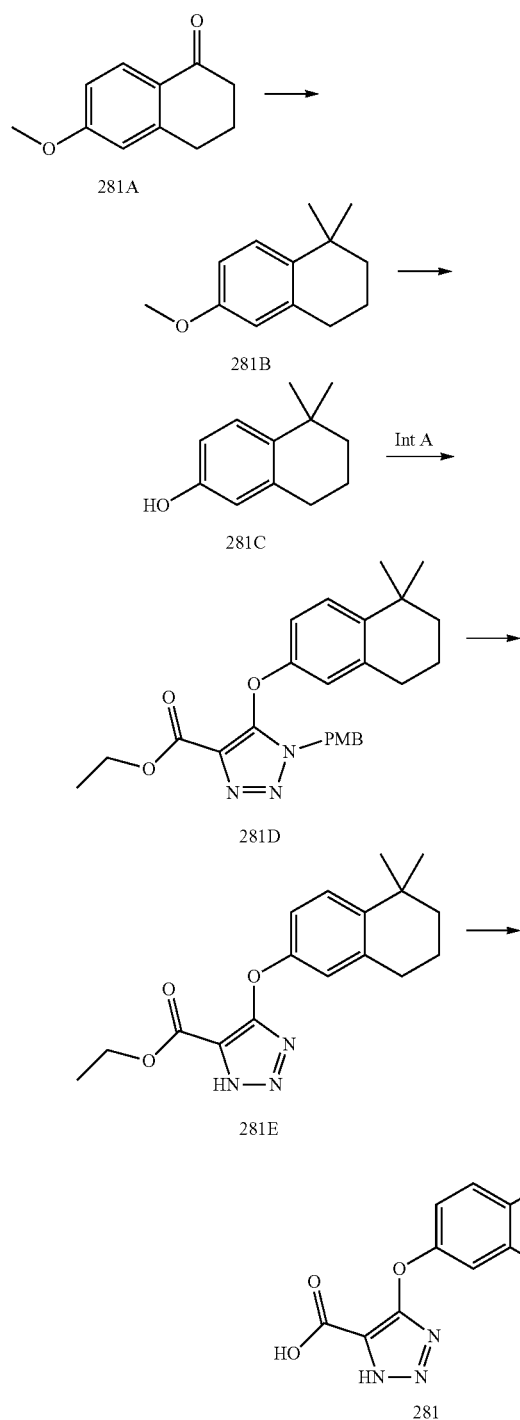

To a solution of TiCl$_4$ (3.76 g, 20 mmol) in dichloromethane (17 mL) was added a solution of Me$_2$Zn in toluene (1.0 M, 20 mL, 20 mmol) at −30° C. and stirred at this temperature for 20 minutes, followed by dropping of a solution of 6-methoxy-3,4-dihydronaphthalen-1(2H)-one (281A) (1.76 g, 10 mmol) in dichloromethane (8 mL). The mixture was stirred at room temperature overnight, poured into ice-water (100 mL), and extracted with ether (40 mL×2). The combined organic layers was washed with brine (50 mL), dried over anhydrous sodium sulfate, filtered, concentrated, and purified with flash column chromatography on silica gel (ethyl acetate in petroleum ether, 10% v/v) to afford Compound. LC-MS (ESI) m/z: 191 [M+H]$^+$. (CDCl$_3$, 400 MHz): δ (ppm) 1.25 (s, 6H), 1.62-1.65 (m, 2H), 1.77-1.80 (m, 2H), 2.73 (t, J=6.4 Hz, 2H), 3.76 (s, 3H), 6.56 (d, J=2.8 Hz, 1H), 6.72 (dd, J=8.8, 2.8 Hz, 1H), 7.22 (d, J=8.8 Hz, 1H).

To a solution of Compound 281B (1.9 g, 10 mmol) in dichloromethane (40 mL) was added a solution of BBr$_3$ in dichloromethane (17%, 3 mL) at 0° C. The mixture was stirred at room temperature overnight, poured into ice water (20 mL), and extracted with ether (40 mL×2). The combined organic layers was washed with brine (50 mL), dried over anhydrous sodium sulfate, filtered, concentrated, and purified with flash column chromatography on silica gel (ethyl acetate in petroleum ether, 20% v/v) to afford Compound 281C. LC-MS (ESI) m/z: 177 [M+H]$^+$.

Compounds 281D, 281E, and 281 were synthesized by employing the procedures described for Intermediate I, Compounds 8F, and 2 using Compounds 281C, 281D, and 281E with EtOH/H$_2$O in lieu of 4-bromophenol, Compounds 8E, and 1. Compound 281D: LC-MS (ESI) m/z: 436 [M+H]$^+$. Compound 281E: LC-MS (ESI) m/z: 316 [M+H]$^+$. Compound 281: LC-MS (ESI) m/z: 288 [M+H]$^+$; $^1$H-NMR (DMSO-d$_6$, 400 MHz): δ (ppm) 1.22 (s, 6H), 1.58-1.62 (m, 2H), 1.69-1.73 (m, 2H), 2.65-2.68 (m, 2H), 6.70 (d, J=2.0 Hz, 1H), 6.82 (dd, J=8.8, 2.0 Hz, 1H), 7.32 (d, J=8.8 Hz, 1H), 13.15 (brs, 1H), 15.15 (brs, 1H).

Example 282

Synthesis of 4-((5-(trifluoromethoxy)-2,3-dihydro-1H-inden-2-yl)oxy)-1H-1,2,3-triazole-5-carboxylic acid (282)

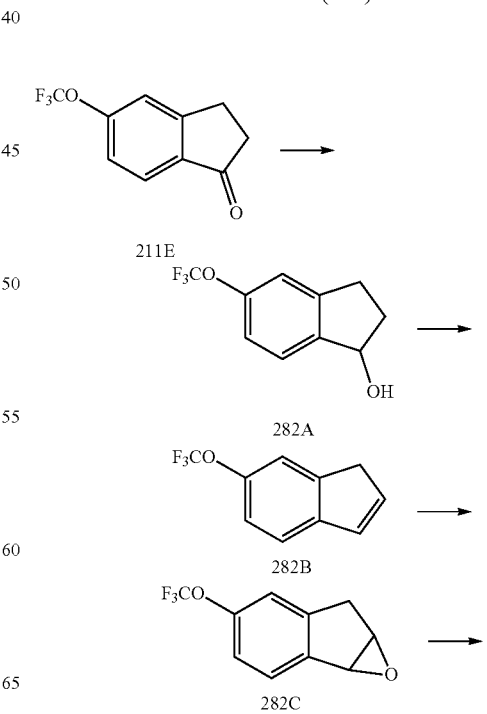

515

-continued

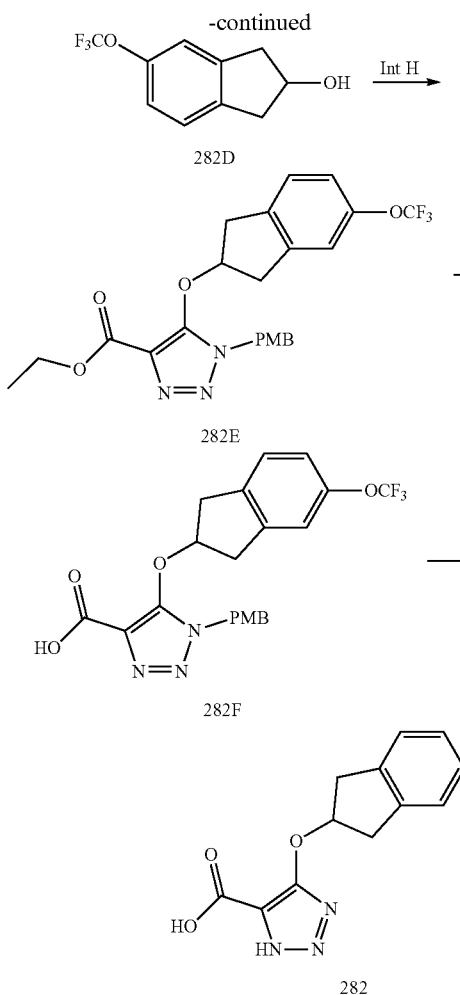

Compounds 282A, 282B, 282C, 282D, 282E, 282F, and 282 were synthesized by employing the procedures described for Compounds 57C, 190B, 190C, 190D, 90C, 8F, and 1 using Compounds 211E, 282A, 282B, 282C, 282D with DEAD as coupling reagent, 282E, and 282F in lieu of Compounds 57B, 190A, 190B, 190C, 90B with DIAD as coupling reagent, 8E, and 1E. Compound 282A: LC-MS (ESI) m/z: 201 [M−OH]+. Compound 282B: LC-MS (ESI) m/z: non-ionizable compound under routine conditions used. $^1$H-NMR (CDCl$_3$, 400 MHz): δ 3.42 (s, 2H), 6.60-6.62 (m, 1H), 6.86-6.88 (m, 1H), 7.13-7.15 (m, 1H), 7.33-7.38 (m, 2H). Compound 282C: LC-MS (ESI) m/z: non-ionizable compound under routine conditions used. Compound 282D: LC-MS (ESI) m/z: non-ionizable compound under routine conditions used; (CDCl$_3$, 400 MHz): δ 1.64 (d, J=4.2 Hz, 1H), 2.88-2.96 (m, 2H), 3.17-3.26 (m, 2H), 4.72-4.78 (m, 1H), 7.02 (d, J=8.0 Hz, 1H), 7.01 (s, 1H), 7.23 (d, J=8.0 Hz, 1H). Compound 282E: LC-MS (ESI) m/z: 478 [M+H]+; (CDCl$_3$, 400 MHz): δ 1.44 (t, J=7.2 Hz, 3H), 2.96-3.03 (m, 2H), 3.18-3.27 (m, 2H), 3.75 (s, 3H), 4.42 (q, J=7.2 Hz, 2H), 5.01 (d, J=3.2 Hz, 2H), 6.12-6.15 (m, 1H), 6.68-6.70 (m, 2H), 6.89-6.92 (m, 2H), 7.08-7.09 (m, 2H), 7.19-7.21 (m, 1H). Compound 282F: LC-MS (ESI) m/z: 450 [M+H]+. Compound 282: LC-MS (ESI) m/z: 330 [M+H]+; $^1$H-NMR (DMSO-d$_6$, 400 MHz): δ (ppm) 3.09-3.17 (m, 2H), 3.36-3.45 (m, 2H), 5.47 (bs, 1H), 7.17 (d, J=8.0 Hz, 1H), 7.30 (s, 1H), 7.39 (d, J=8.8 Hz, 1H), 12.92 (bs, 1H), 14.84 (bs, 1H).

516

Example 283

Synthesis of 4-(spiro[5.5]undecan-3-yloxy)-1H-1,2,3-triazole-5-carboxylic acid (283)

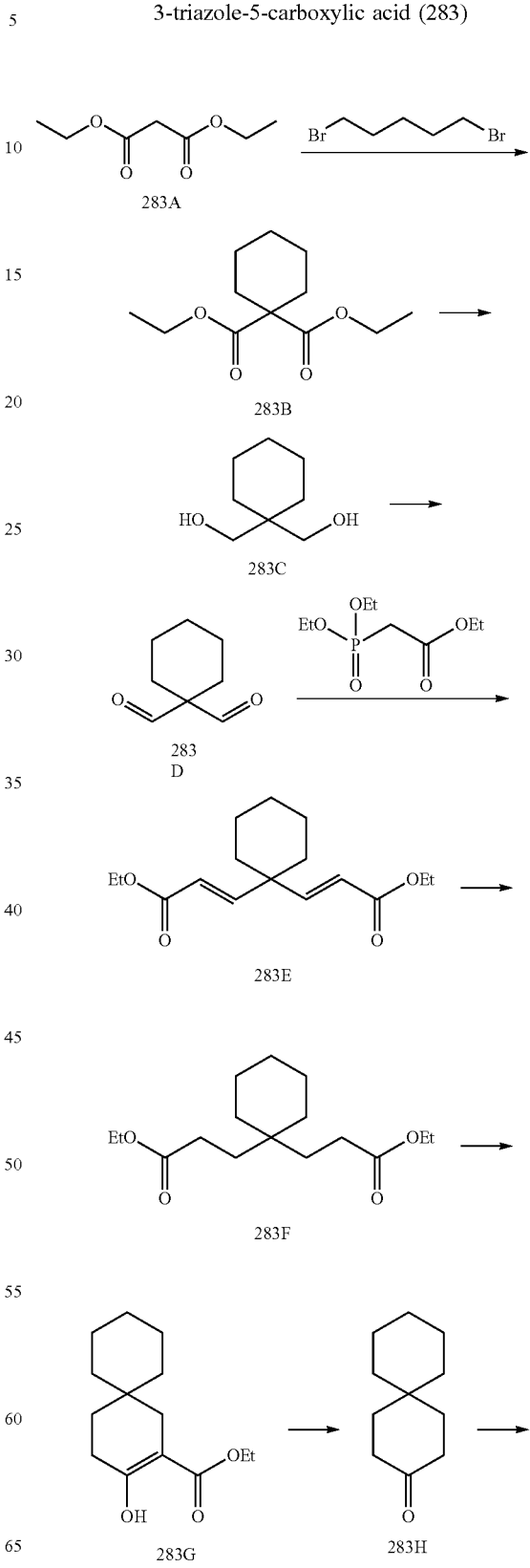

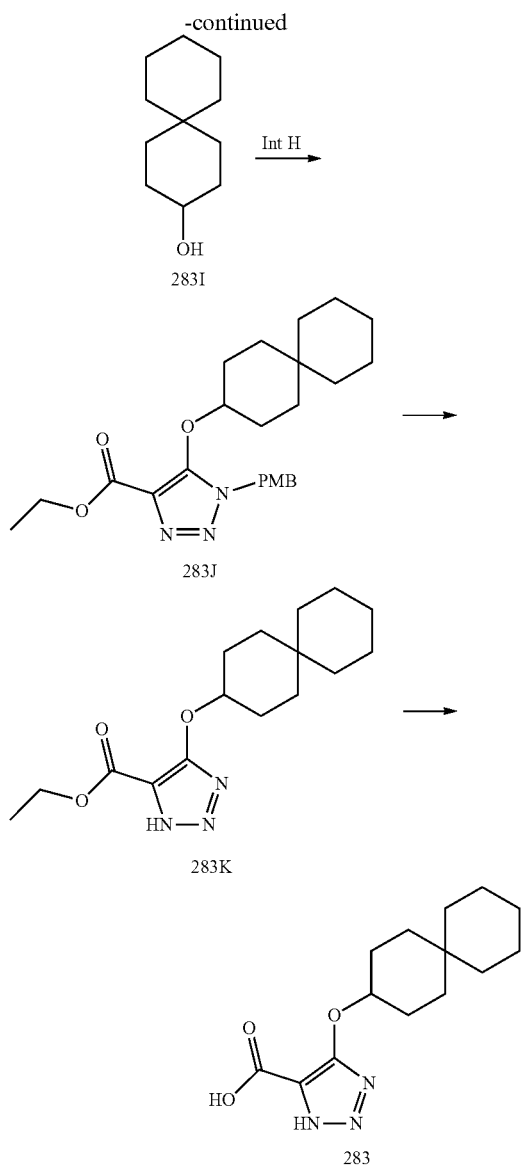

To a sodium ethoxide-ethanol solution, which was prepared by slowly addition sodium (8.625 g, 375 mmol) into ethanol (600 mL) in small pieces, was added diethyl malonate 283A (30 g, 187.5 mmol) at room temperature and stirred at room temperature for 20 minutes. To the solution was added 1,5-dibromopentane (45.29 g, 196.9 mmol) and stirred at reflux for 16 hours. The mixture was concentrated under reduced pressure. The residue was diluted with ethyl acetate (200 mL), washed with water (80 mL) and brine (50 mL×2), dried over anhydrous sodium sulfate, filtered, concentrated, and purified with flash column chromatography on silica gel (ethyl acetate in petroleum ether from 0% to 10% v/v) to yield Compound 283B. LC-MS (ESI) m/z: 229 [M+H]$^+$; $^1$H-NMR (CDCl$_3$, 400 MHz): δ (ppm) 1.25 (t, J=7.2 Hz, 6H), 1.40-1.46 (m, 2H), 1.50-1.55 (m, 4H), 1.96-1.99 (m, 4H), 4.18 (q, J=7.2 Hz, 4H).

To a solution of Compound 283B (16 g, 70.18 mmol) in anhydrous THF (200 mL) was added dropwise LiAlH$_4$ solution (1 Min THF, 210.5 mL, 210.5 mmol) at 0° C. After addition the resulting mixture was stirred at room temperature under nitrogen for 3.5 hours. The mixture was quenched slowly with water (300 mL) at 0° C. and extracted with ethyl acetate (400 mL×4). The combined organic phases were washed with brine (200 mL×2), dried over anhydrous sodium sulfate, filtered and concentrated to yield Compound 283C. LC-MS (ESI) m/z: 167 [M+Na]$^+$; $^1$H-NMR (CDCl$_3$, 400 MHz): δ (ppm) 1.35-1.37 (m, 4H), 1.44-1.48 (m, 6H), 2.28 (s, 2H), 3.64 (s, 4H).

A solution of anhydrous dimethyl sulfoxide (20.6 mL, 290.27 mmol) in anhydrous dichloromethane (48 mL) was dropped to a solution of oxalyl chloride (12.3 mL, 145.13 mmol) in anhydrous dichloromethane (95 mL) at −78° C. under nitrogen and stirred for 30 minutes. To the solution at −78° C. was dropped a solution of Compound 283C (9.5 g, 65.97 mmol) in anhydrous dichloromethane (95 mL) and stirred at −70° C. for 90 minutes. Triethyl amine (65.9 mL, 474.98 mmol) was slowly added and the mixture was stirred at −70° C. for 30 minutes. After it was slowly warmed to room temperature, the mixture was quenched with saturated aqueous NH$_4$Cl solution (178 mL) and extracted with dichloromethane (100 mL×2). The combined organic layers was washed with diluted aqueous HCl solution (2 M, 150 mL×5) and brine (100 mL×2), dried over anhydrous Na$_2$SO$_4$, filtered, and concentrated to give Compound 283D. $^1$H-NMR (CDCl$_3$, 400 MHz): δ (ppm) 1.43-1.47 (m, 2H), 1.50-1.56 (m, 4H), 1.92-1.95 (m, 4H), 9.53 (s, 2H).

To a solution of ethyl 2-(diethoxyphosphoryl)acetate (32.42 g, 145.07 mmol) in anhydrous THF (160 mL) was added NaH (60% suspension in oil, 5.82 g, 145.43 mmol) in four portions at 0° C. and stirred at 0° C. for 15 minutes. To the solution was dropped a solution of Compound 283D (9.15 g, 68.57 mmol) in anhydrous THF (35 mL) and stirred at room temperature for 2 hours. It was quenched with water (60 mL) and extracted with ethyl acetate (150 mL×2). The combined organic layers was washed with brine (100 mL×2), dried over anhydrous Na$_2$SO$_4$, filtered, concentrated, and purified with flash column chromatography on silica gel (ethyl acetate in petroleum ether from 0% to 10% v/v) to yield Compound 283E. LC-MS (ESI) m/z: 281 [M+H]$^+$; $^1$H-NMR (CDCl$_3$, 400 MHz): δ (ppm) 1.29 (t, J=7.2 Hz, 6H), 1.42-1.45 (m, 2H), 1.50-1.54 (m, 4H), 1.65-1.68 (m, 4H), 4.19 (q, J=7.2 Hz, 4H), 5.77 (d, J=16 Hz, 2H), 6.94 (d, J=16 Hz, 2H).

Compound 283F was synthesized by employing the procedure described for Compound 141 using Compound 283E with EtOH as solvent in lieu of Compound 140 with EtOAc as solvent, LC-MS (ESI) m/z: 285 [M+H]$^+$; $^1$H-NMR (CDCl$_3$, 400 MHz): δ (ppm) 1.24-1.27 (m, 10H), 1.38-1.44 (m, 6H), 1.56-1.60 (m, 4H), 2.18-2.22 (m, 4H), 4.12 (q, J=6.8 Hz, 4H).

To a solution of Compound 283F (8.9 g, 31.3 mmol) in anhydrous THF (150 mL) was added NaH (60% suspension in oil, 2.5 g, 62.6 mmol) at 0° C. The solution was stirred at 0° C. for 10 minutes and heated at reflux for 16 hours. The mixture was quenched with water (50 mL), acidified to pH 6 with aqueous HCl solution (4 N), and extracted with ethyl acetate (100 mL×3). The combined organic layers was washed with brine (100 mL), dried over anhydrous sodium sulfate, concentrated, and purified with flash column chromatography on silica gel (ethyl acetate in petroleum ether, from 0% to 10% v/v) to yield Compound 283G. LC-MS (ESI) m/z: 239 [M+H]$^+$; $^1$H-NMR (CDCl$_3$, 400 MHz): δ (ppm) 1.29-1.32 (m, 7H), 1.43-1.57 (m, 8H), 2.06 (s, 2H), 2.25 (t, J=6.4 Hz, 2H), 4.21 (q, J=7.2 Hz, 2H), 12.22 (s, 1H).

To a solution of Compound 283G (5.9 g, 24.79 mmol) in 1,4-dioxane (100 mL) was added a solution of potassium hydroxide (6.94 g, 123.95 mmol) in water (8 mL) and stirred at reflux for 16 hours. It was concentrated under reduced pressure. The residue was diluted with ethyl acetate (100 mL), washed with water (50 mL) and brine (40 mL), dried over anhydrous sodium sulfate, filtered, and concentrated to yield Compound 283H. LC-MS (ESI) m/z: 167 [M+H]$^+$; $^1$H-NMR (CDCl$_3$, 400 MHz): δ (ppm) 1.46-1.47 (m, 10H), 1.70 (t, J=7.2 Hz, 4H), 2.31 (t, J=6.8 Hz, 4H), Compounds 283I, 283J, 283K, and 283 were synthesized by employing the procedures described for Compounds 57C, 90C, 217E, and 8F using Compounds 283H, 283I, 283J, and 283K in lieu of Compounds 57B, 90B, 217D, and 8E. Compound 283I: $^1$H-NMR (CDCl$_3$, 400 MHz): δ (ppm) 1.07-1.14 (m, 2H), 1.20-1.26 (m, 2H), 1.43-1.47 (m, 10H), 1.59-1.63 (m, 2H), 1.69-1.73 (m, 2H), 3.58-3.65 (m, 1H). Compound 283J: LC-MS (ESI) m/z: 428 [M+H]$^+$. Compound 283K: LC-MS (ESI) m/z: 308 [M+H]$^+$. Compound 283: LC-MS (ESI) m/z: 581 [2M+Na]$^+$; $^1$H-NMR (DMSO-d$_6$, 400 MHz): δ (ppm) 1.07-1.22 (m, 4H), 1.36 (brs, 8H), 1.46-1.75 (m, 6H), 4.59-4.64 (m, 1H).

Example 284

Synthesis of 4-(spiro[4.5]decan-8-yloxy)-1H-1,2,3-triazole-5-carboxylic acid (284)

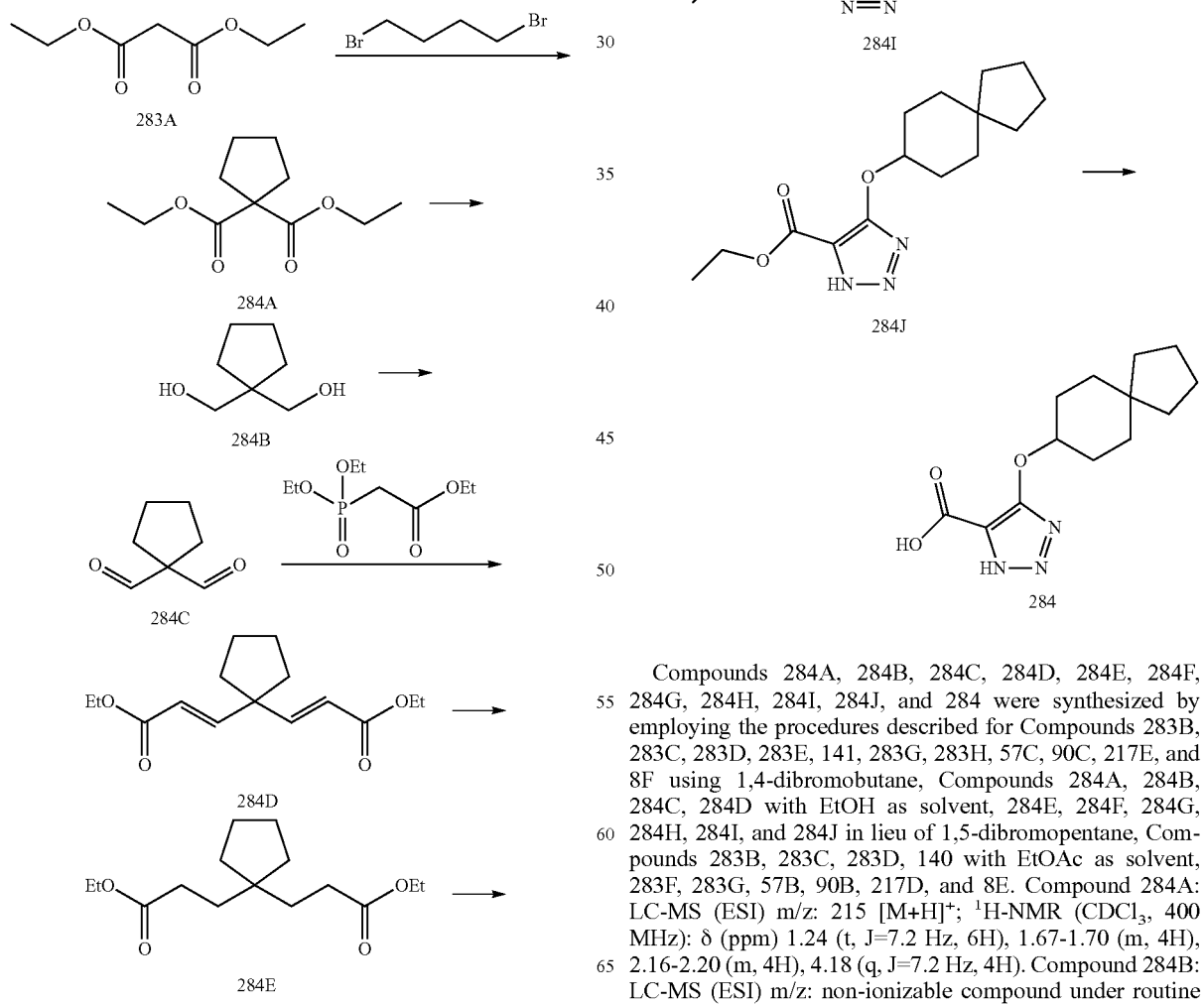

Compounds 284A, 284B, 284C, 284D, 284E, 284F, 284G, 284H, 284I, 284J, and 284 were synthesized by employing the procedures described for Compounds 283B, 283C, 283D, 283E, 141, 283G, 283H, 57C, 90C, 217E, and 8F using 1,4-dibromobutane, Compounds 284A, 284B, 284C, 284D with EtOH as solvent, 284E, 284F, 284G, 284H, 284I, and 284J in lieu of 1,5-dibromopentane, Compounds 283B, 283C, 283D, 140 with EtOAc as solvent, 283F, 283G, 57B, 90B, 217D, and 8E. Compound 284A: LC-MS (ESI) m/z: 215 [M+H]$^+$; $^1$H-NMR (CDCl$_3$, 400 MHz): δ (ppm) 1.24 (t, J=7.2 Hz, 6H), 1.67-1.70 (m, 4H), 2.16-2.20 (m, 4H), 4.18 (q, J=7.2 Hz, 4H). Compound 284B: LC-MS (ESI) m/z: non-ionizable compound under routine conditions used; $^1$H-NMR (CDCl$_3$, 400 MHz): δ (ppm)

1.42-1.45 (m, 4H), 1.60-1.64 (m, 4H), 2.36 (brs, 2H), 3.61 (s, 4H). Compound 284C: LC-MS (ESI) m/z: non-ionizable compound under routine conditions used; ¹H-NMR (CDCl₃, 400 MHz): δ (ppm) 1.69-1.72 (m, 4H), 2.06-2.09 (m, 4H), 9.68 (s, 2H). Compound 284D: LC-MS (ESI) m/z: 267 [M+H]⁺; ¹H-NMR (CDCl₃, 400 MHz): δ (ppm) 1.29 (t, J=7.2 Hz, 6H), 1.70-1.74 (m, 4H), 1.77-1.80 (m, 4H), 4.19 (q, J=7.2 Hz, 4H), 5.77 (d, J=15.6 Hz, 2H), 6.94 (d, J=15.6 Hz, 2H). Compound 284E: LC-MS (ESI) m/z: 271 [M+H]⁺; ¹H-NMR (CDCl₃, 400 MHz): δ (ppm) 1.25 (t, J=7.2 Hz, 6H), 1.36-1.39 (m, 4H), 1.59-1.63 (m, 8H), 2.22-2.27 (m, 4H), 4.11 (q, J=7.2 Hz, 4H). Compound 284F: LC-MS (ESI) m/z: 225 [M+H]⁺; ¹H-NMR (CDCl₃, 400 MHz): δ (ppm) 1.30 (t, J=7.2 Hz, 3H), 1.34-1.47 (m, 4H), 1.53-1.57 (m, 2H), 1.63-1.66 (m, 4H), 2.09 (s, 2H), 2.29-2.32 (m, 2H), 4.20 (q, J=7.2 Hz, 2H), 12.23 (s, 1H). Compound 284G: LC-MS (ESI) m/z: 153 [M+H]⁺; ¹H-NMR (CDCl₃, 400 MHz): δ (ppm) 1.56-1.60 (m, 4H), 1.68-1.71 (m, 4H), 1.75-1.78 (m, 4H), 2.34-2.37 (m, 4H). Compound 284H: LC-MS (ESI) m/z: 177 [M+Na]⁺; ¹H-NMR (CDCl₃, 400 MHz): δ (ppm) 1.24-1.44 (m, 8H), 1.49-1.61 (m, 6H), 1.76-1.81 (m, 2H), 3.60-3.65 (m, 1H). Compound 284I: LC-MS (ESI) m/z: 414 [M+H]⁺. Compound 284J: LC-MS (ESI) m/z: 294 [M+H]⁺. Compound 284: LC-MS (ESI) m/z: 553 [2M+Na]⁺; ¹H-NMR (DMSO-d₆, 400 MHz): δ (ppm) 1.25-1.43 (m, 6H), 1.51-1.56 (m, 8H), 1.85-1.88 (m, 2H), 4.57-4.64 (m, 1H).

Example 285

Synthesis of 4-((1-(3,5-dichlorophenyl)piperidin-4-yl)oxy)-1H-1,2,3-triazole-5-carboxylic acid 2,2,2-trifluoroacetate (285)

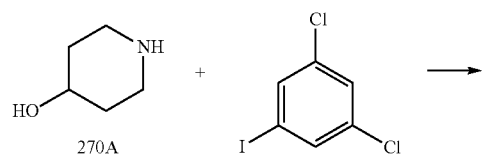

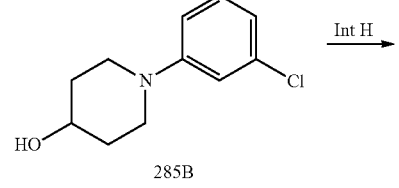

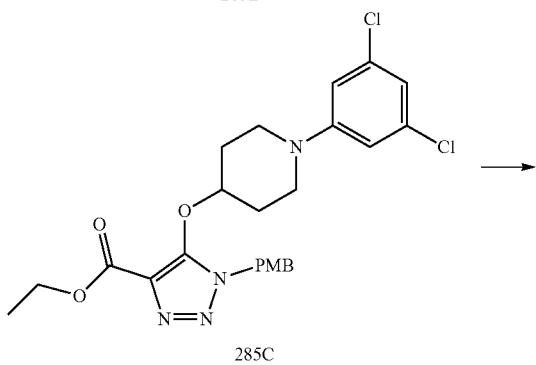

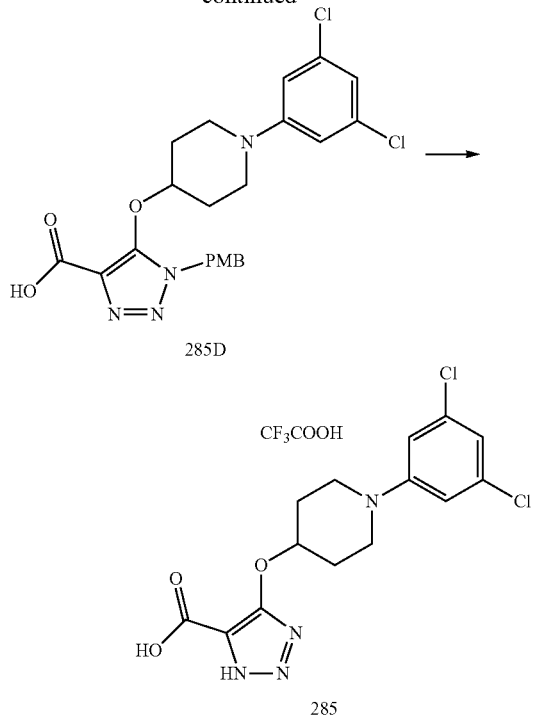

Compounds 285B, 285C, 285D, and 285 were synthesized by employing the procedures described for Compounds 270B, 90C, 8F, and 1 using Compounds 285A, 285B with DEAD as coupling reagent, 285C, and 285D in lieu of Compounds 197A, 90B with DIAD as coupling reagent, 8E, and 1E. Compound 285B: LC-MS (ESI) m/z: 246 [M+H]⁺. Compound 285C: LC-MS (ESI) m/z: 505 [M+H]⁺. Compound 285D: LC-MS (ESI) m/z: 477 [M+H]⁺. Compound 285: LC-MS (ESI) m/z: 357 [M+H]⁺; ¹H-NMR (DMSO-d₆, 400 MHz): δ (ppm) 1.71-1.79 (m, 2H), 2.04-2.08 (m, 2H), 3.18-3.24 (m, 2H), 3.56-3.61 (m, 2H), 4.83-5.00 (m, 1H), 6.84 (s, 1H), 6.98 (s, 2H), 12.94 (s, 1H), 14.80 (s, 1H).

Example 286

Synthesis of 4-((1-(3,4-dichlorophenyl)piperidin-4-yl)oxy)-1H-1,2,3-triazole-5-carboxylic acid 2,2,2-trifluoroacetate (286)

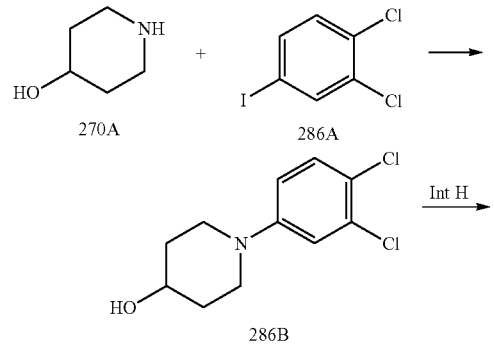

523

-continued

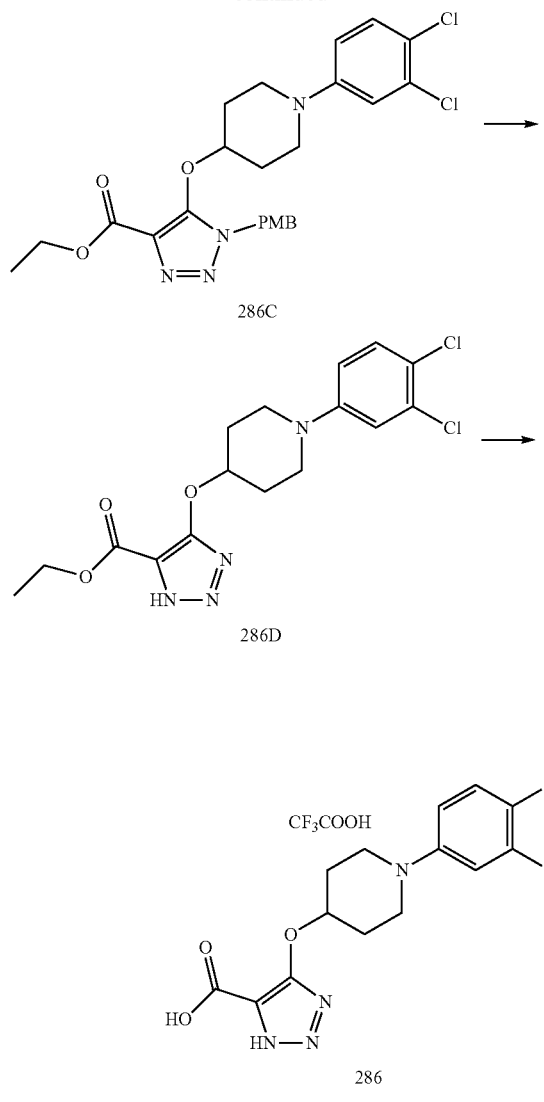

Example 287

Synthesis of 4-((1-(4-(trifluoromethyl)phenyl)piperidin-4-yl)oxy)-1H-1,2,3-triazole-5-carboxylic acid 2,2,2-trifluoroacetate (287)

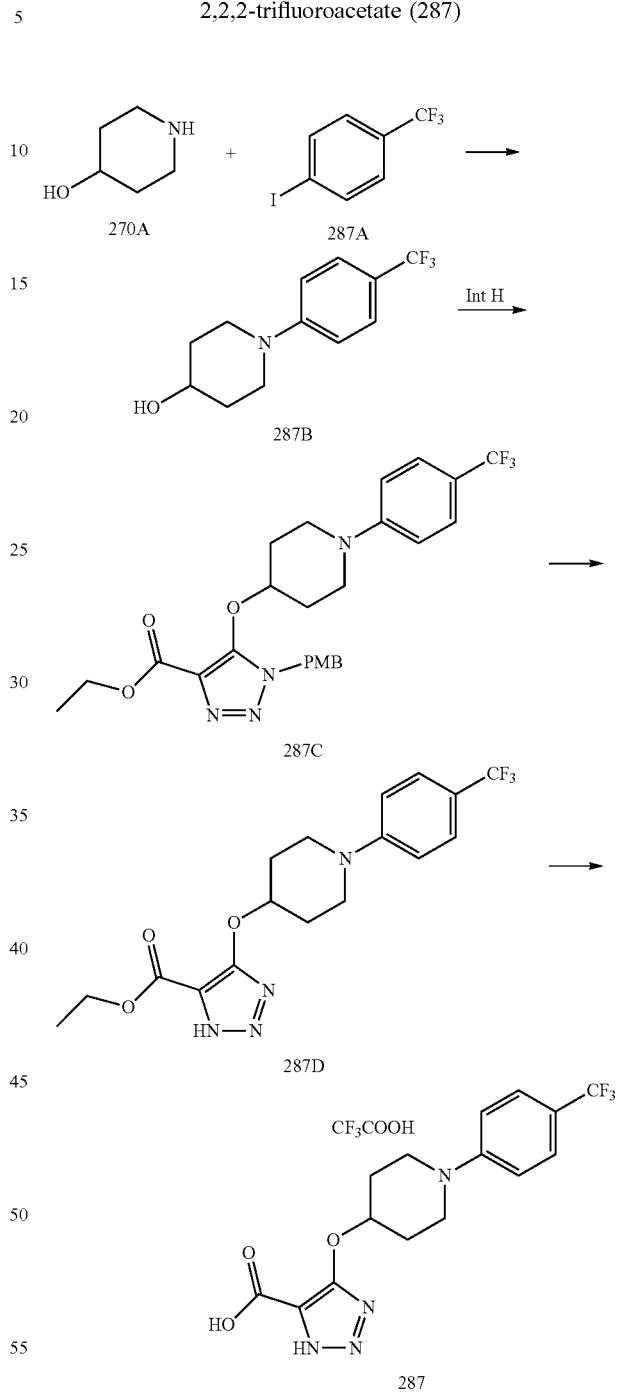

Compounds 286B, 286C, 286D, and 286 were synthesized by employing the procedures described for Compounds 270B, 90C, 1, and 8F using Compounds 286A, 286B with DEAD as coupling reagent, 286C, and 286D in lieu of Compounds 197A, 90B with DIAD as coupling reagent, 1E, and 8E. Compound 286B: LC-MS (ESI) m/z: 246 [M+H]$^+$; $^1$H-NMR (CDCl$_3$, 400 MHz): δ (ppm) 1.49 (d, J=4.4 Hz, 1H), 1.63-1.72 (m, 2H), 1.97-2.03 (m, 2H), 2.93-2.99 (m, 2H), 3.49-3.55 (m, 2H), 3.87-3.91 (m, 1H), 6.76 (dd, J=8.8, 2.8 Hz, 1H), 6.98 (d, J=2.8 Hz, 1H), 7.19 (d, J=8.8 Hz, 1H). Compound 286C: LC-MS (ESI) m/z: 505 [M+H]$^+$; $^1$H-NMR (CDCl$_3$, 500 MHz): δ (ppm) 1.44 (t, J=6.0 Hz, 3H), 1.74-1.77 (m, 2H), 1.99-2.03 (m, 2H), 2.97-3.03 (m, 2H), 3.29-3.34 (m, 2H), 3.77 (s, 3H), 4.42 (q, J=6.0 Hz, 2H), 5.32 (s, 2H), 5.33-5.34 (m, 1H), 6.72 (dd, J=7.2, 2.8 Hz, 1H), 6.82 (dd, J=8.0 Hz, 2H), 6.94 (d, J=2.8 Hz, 1H), 7.21 (d, J=8.0 Hz, 2H), 7.29 (d, J=7.2 Hz, 1H). Compound 286D: LC-MS (ESI) m/z: 385 [M+H]$^+$. Compound 286: LC-MS (ESI) m/z: 357 [M+H]$^+$; $^1$H-NMR (CD$_3$OD, 400 MHz): δ (ppm) 1.97-2.06 (m, 2H), 2.16-2.22 (m, 2H), 3.17-3.24 (m, 2H), 3.56-3.62 (m, 2H), 4.92-4.97 (m, 1H), 6.98 (dd, J=8.8, 2.8 Hz, 1H), 7.16 (d, J=2.8 Hz, 1H), 7.35 (d, J=8.8 Hz, 1H).

Compounds 287B, 287C, 287D, and 287 were synthesized by employing the procedures described for Compounds 270B, 90C, 1, and 2 using Compounds 286A, 286B with DEAD as coupling reagent, 286C, and 286D with EtOH/H$_2$O as solvent in lieu of Compounds 197A, 90B with DIAD as coupling reagent, 1E, and 1 with THF/H$_2$O as solvent. Compound 287B: LC-MS (ESI) m/z: 246 [M+H]$^+$. $^1$H-NMR (CDCl$_3$, 400 MHz): δ (ppm) 2.05-2.15 (m, 4H), 3.14-3.17 (m, 4H), 3.46 (s, 1H), 6.83 (d, J=8.8 Hz, 2H), 6.82

(d, J=8.8 Hz, 2H). Compound 287C: LC-MS (ESI) m/z: 505 [M+H]⁺. Compound 287D: LC-MS (ESI) m/z: 385 [M+H]⁺. Compound 287: LC-MS (ESI) m/z: 357 [M+H]⁺; ¹H-NMR (DMSO-d₆, 400 MHz): δ (ppm) 1.74-1.78 (m, 2H), 2.05-2.09 (m, 2H), 3.22-3.28 (m, 2H), 363-3.67 (m, 2H), 4.88 (s, 1H), 7.08 (d, J=8.8 Hz, 2H), 7.49 (d, J=8.8 Hz, 2H).

Example 288

Synthesis of 4-(3-(cyclopropylmethoxy)-5-(trifluoromethyl)phenoxy)-1H-1,2,3-triazole-5-carboxylic acid (288)

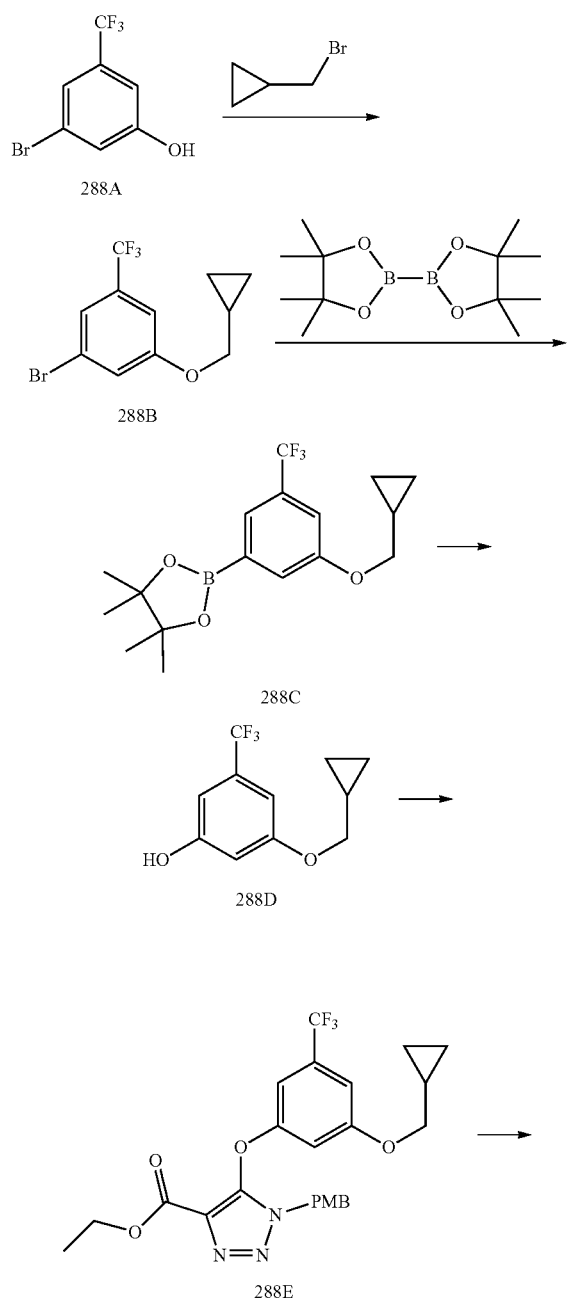

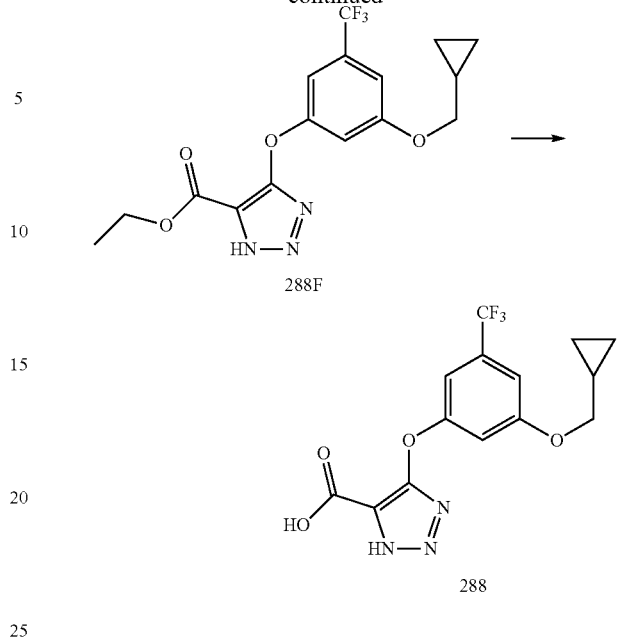

Compounds 288B, 288C, 288D, 288E, 288F, and 288 were synthesized by employing the procedures described for Compounds 27B, 27C, 236D, Intermediate I, 217E, and 8F using (bromomethyl)cyclopropane, Compounds 288A with K₂CO₃ as base, 288B, 288C, 288D, 288E, and 288F in lieu of iodoethane, Compounds 27A with Cs₂CO₃ as base, 27B, 236C, 4-bromophenol, 217D, and 8E. Compound 288B: LC-MS (ESI) m/z: non-ionizable compound under routine conditions used; ¹H-NMR (CDCl₃, 400 MHz): δ (ppm) 0.35-0.37 (m, 2H), 0.66-0.68 (m, 2H), 1.25-1.27 (m, 1H), 3.82 (d, J=7.2 Hz, 2H), 7.06 (s, 1H), 7.20 (d, J=2.0 Hz, 1H), 7.32 (s, 1H). Compound 288C: LC-MS (ESI) m/z: non-ionizable compound under routine conditions used. Compound 288D: LC-MS (ESI) m/z: 231 [M−H]⁻. Compound 288E: LC-MS (ESI) m/z: 492 [M+H]⁺. Compound 288F: LC-MS (ESI) m/z: 372 [M+H]⁺. Compound 288: LC-MS (ESI) m/z: 344 [M+H]⁺. ¹H-NMR (DMSO-d₆, 400 MHz): δ (ppm) 0.30-0.34 (m, 2H), 0.54-0.58 (m, 2H), 1.18-1.22 (m, 1H), 3.89 (d, J=7.2 Hz, 2H), 6.94-6.95 (m, 2H), 7.04 (s, 1H), 13.30 (s, 1H), 15.32 (s, 1H).

Example 289

Synthesis of 4-(3-chloro-5-(cyclopropylmethoxy)phenoxy)-1H-1,2,3-triazole-5-carboxylic acid 2,2,2-trifluoroacetate (289)

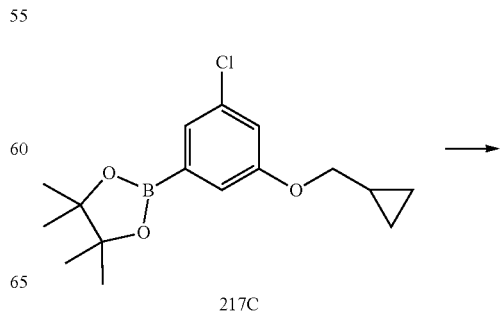

Example 290

Synthesis of 4-(3-(cyclopentylmethoxy)phenoxy)-1H-1,2,3-triazole-5-carboxylic acid 2,2,2-trifluoroacetate (290)


Compounds 289A, 289B, 289C, and 289 were synthesized by employing the procedures described for Compounds 236D, Intermediate I, 217E, and 8F using Compounds 217C, 289B, 289C, and 289D in lieu of Compounds 236C, 4-bromophenol, 217D, and 8E. Compound 289A: LC-MS (ESI) m/z: 197 [M−H]⁻. Compound 289B: LC-MS (ESI) m/z: 458 [M+H]⁺. Compound 289C: LC-MS (ESI) m/z: 338 [M+H]⁺. Compound 289: LC-MS (ESI) m/z: 310 [M+H]⁺. $^1$H-NMR (DMSO-d$_6$, 400 MHz): δ (ppm) 0.28-0.29 (m, 2H), 0.53-0.55 (m, 2H), 1.18-1.22 (m, 1H), 3.80 (d, J=6.8 Hz, 2H), 6.59-6.79 (t, J=8 Hz, 3H), 13.26 (s, 1H), 15.28 (s, 1H).

Compounds 290B, 290C, 290D, and 290 were synthesized by employing the procedures described for Compounds 29B, Intermediate I, 217E, and 8F using (bromomethyl)cyclopentane, Compounds 290A with K$_2$CO$_3$ as base, 290B, 290C, and 290D in lieu of iodoethane, Compounds 29A with Cs$_2$CO$_3$ as base, 4-bromophenol, 217D, and 8E. Compound 290B: LC-MS (ESI) m/z: 193 [M+H]⁺. Compound 290C: LC-MS (ESI) m/z: 452 [M+H]⁺. Compound 290D: LC-MS (ESI) m/z: 332 [M+H]⁺. Compound 290: LC-MS (ESI) m/z: 304 [M+H]⁺. $^1$H-NMR (DMSO-d$_6$, 400

MHz): δ (ppm) 1.28-1.73 (m, 8H), 2.23-2.28 (m, 1H), 3.78-3.80 (m, 2H), 6.52-6.73 (m, 3H) 7.19-7.23 (m, 1H).

Example 291

Synthesis of 4-((1-(2,5-dichlorophenyl)piperidin-4-yl)oxy)-1H-1,2,3-triazole-5-carboxylic acid 2,2,2-trifluoroacetate (291)

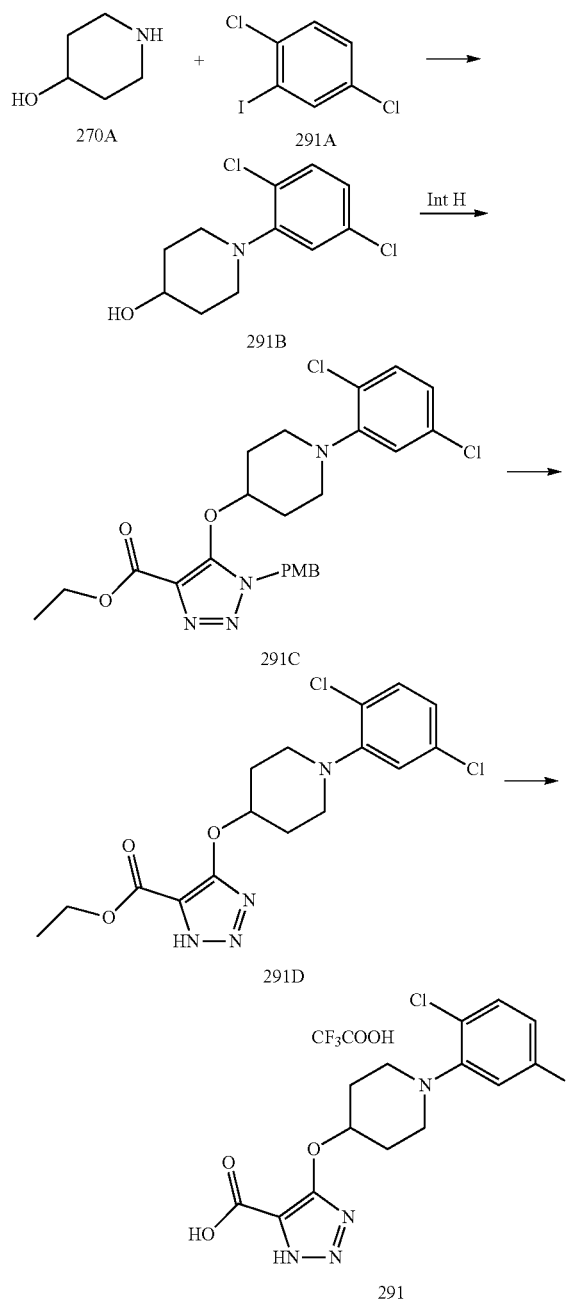

Compounds 291B, 291C, 291D, and 291 were synthesized by employing the procedures described for Compounds 270B, 90C, 57E, and 8F using Compounds 291A, 291B with DEAD as coupling reagent, 291C, and 291D in lieu of Compounds 197A, 90B with DIAD as coupling reagent, 57D, and 8E. Compound 291B: LC-MS (ESI) m/z: 246 [M+H]$^+$; $^1$H-NMR (CDCl$_3$, 500 MHz): δ (ppm) 1.68-1.72 (m, 2H), 1.96-1.99 (m, 2H), 2.71-2.76 (m, 2H), 3.14 (s, 1H), 3.20-3.24 (m, 2H), 3.79-3.81 (m, 1H), 6.68 (dd, J=8.5, 2.5 Hz, 1H), 6.93 (d, J=2.5 Hz, 1H), 7.19 (d, J=8.5 Hz, 1H). Compound 291C: LC-MS (ESI) m/z: 505 [M+H]$^+$. Compound 291D: LC-MS (ESI) m/z: 385 [M+H]$^+$. Compound 291: LC-MS (ESI) m/z: 357 [M+H]$^+$; $^1$H-NMR (DMSO-d$_6$, 400 MHz): δ (ppm) 1.83-1.89 (m, 2H), 2.12-2.15 (m, 2H), 2.91-2.96 (m, 2H), 3.17-3.32 (m, 2H), 4.80 (brs, 1H), 7.09-7.12 (m, 1H), 7.18 (d, J=2.0 Hz, 1H), 7.44 (d, J=8.4 Hz, 1H), 12.88 (brs, 1H), 14.78 (brs, 1H).

Example 292

Synthesis of 4-(4-chloro-3-(cyclopropylmethoxy)phenoxy)-1H-1,2,3-triazole-5-carboxylic acid (292)

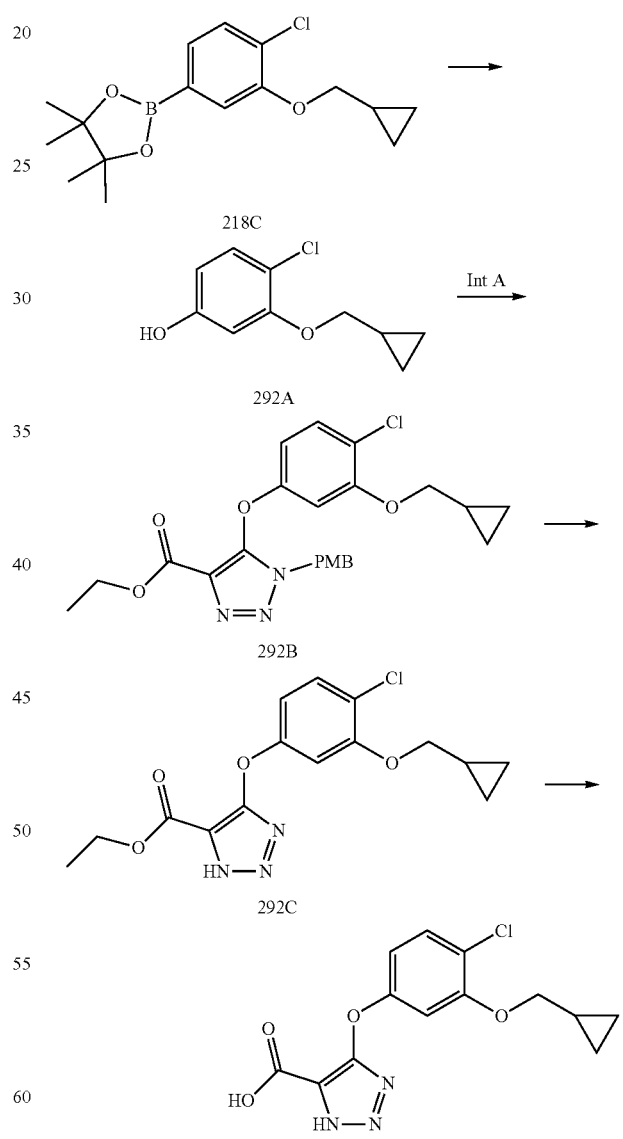

Compounds 292A, 292B, 292C, and 292 were synthesized by employing the procedures described for Compounds 236D, Intermediate I, 217E, and 8F using Compounds 218C, 292A, 292B, and 292C in lieu of Compounds 236C, 4-bromophenol, 217D, and 8E. Compound 292A: LC-MS (ESI) m/z: non-ionizable compound under routine conditions used. Compound 292B: LC-MS (ESI) m/z: 458 [M+H]$^+$. Compound 292C: LC-MS (ESI) m/z: 338 [M+H]$^+$. Compound 292: LC-MS (ESI) m/z: 310 [M+H]$^+$. $^1$H-NMR (DMSO-d$_6$, 400 MHz): δ (ppm) 0.33-0.35 (m, 2H), 0.55-0.59 (m, 2H), 1.19-1.25 (m, 1H), 3.88 (d, J=6.8 Hz, 2H), 6.59 (dd, J=2.4, 8.4 Hz, 1H), 6.92 (d, J=2.8 Hz, 1H), 7.37 (d, J=8.4 Hz, 1H), 13.24 (s, 1H), 15.23 (s, 1H).

236C, 4-bromophenol, 217D, and 8E. Compound 293A: LC-MS (ESI) m/z: 197 [M−H]$^−$. Compound 293B: LC-MS (ESI) m/z: 458 [M+H]$^+$. Compound 293C: LC-MS (ESI) m/z: 338 [M+H]$^+$. Compound 293: LC-MS (ESI) m/z: 310 [M+H]$^+$. $^1$H-NMR (DMSO-d$_6$, 400 MHz): δ (ppm) 0.25-0.30 (m, 2H), 0.49-0.56 (m, 2H), 1.10-1.20 (m, 1H), 3.75 (d, J=6.8 Hz, 2H), 6.70 (s, 1H), 6.76-6.82 (m, 1H), 7.42 (d, J=8.4 Hz, 1H).

Example 293

Synthesis of 4-(2-chloro-5-(cyclopropylmethoxy) phenoxy)-1H-1,2,3-triazole-5-carboxylic acid (293)

Example 294

Synthesis of 4-((1,3-bis(4-chlorophenyl)propan-2-yl)oxy)-1H-1,2,3-triazole-5-carboxylic acid (294)

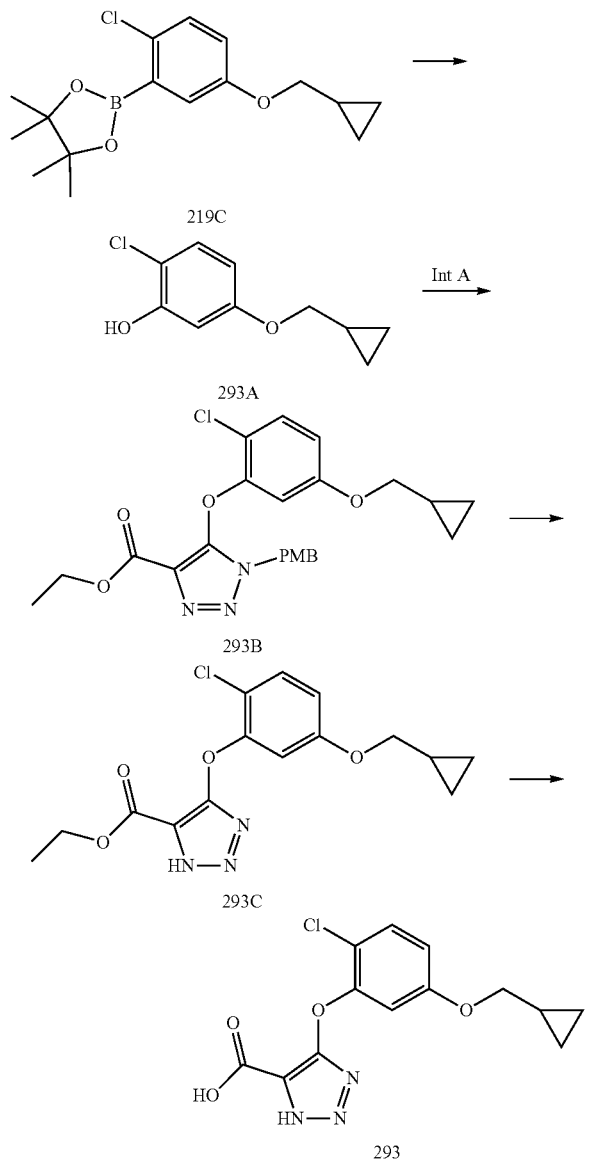

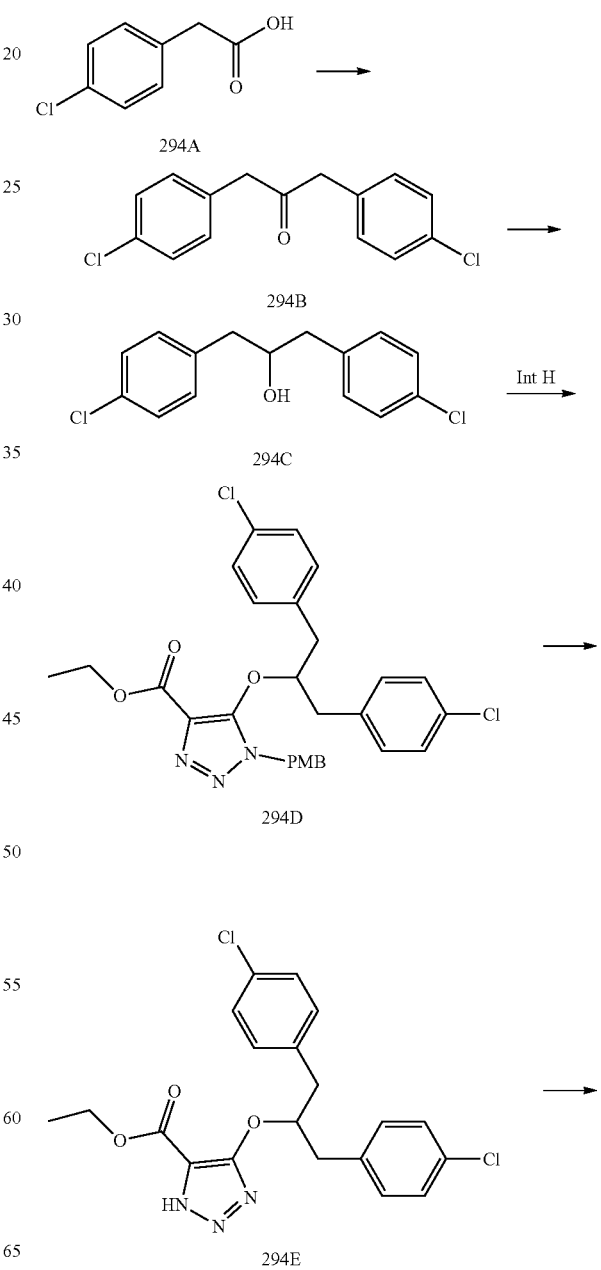

Compounds 293A, 293B, 293C, and 293 were synthesized by employing the procedures described for Compounds 236D, Intermediate I, 217E, and 8F using Compounds 219C, 293A, 293B, and 293C in lieu of Compounds

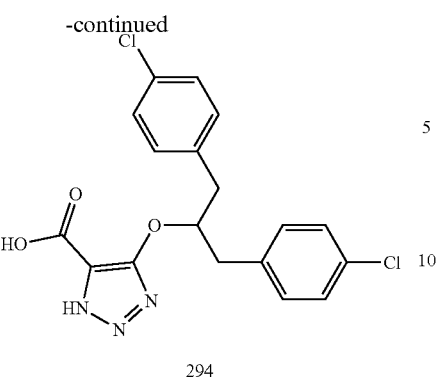

294

To a solution of DCC (2.8 g, 13.6 mmol) and DMAP (0.45 g, 3.69 mmol) in anhydrous dichloromethane was slowly added a solution of 4-chlorophenylacetic acid (294A) (2.0 g, 11.76 mmol) in anhydrous dichloromethane (80 mL). The mixture was stirred at room temperature for 4 hours and concentrated under reduced pressure. The residue was diluted with EtOAc (20 mL), washed with brine (15 mL×3), dried over anhydrous sodium sulfate, concentrated, and purified with flash column chromatography on silica gel (ethyl acetate in petroleum ether, 0% to 25% v/v) to afford Compound 294B. LC-MS (ESI) m/z: 279 [M+H]$^+$. $^1$H-NMR (CDCl$_3$, 400 MHz): δ (ppm) 3.71 (s, 4H), 7.08 (d, J=8.4 Hz, 4H), 7.30 (d, J=8.8 Hz, 4H).

Compounds 294C, 294D, 294E, and 294 were synthesized by employing the procedures described for Compounds 57C, 90C, 57E, and 2 using Compounds 291A, 291B with DEAD as coupling reagent, 291C, and 291D in lieu of Compounds 197A, 90B with DIAD as coupling reagent, 57D, and 1. Compound 294C: 263 [M+H–H$_2$O]$^+$; $^1$H-NMR (CDCl$_3$, 400 MHz): δ (ppm) 2.69-2.85 (m, 4H), 3.99-4.02 (m, 1H), 7.16 (d, J=8.4 Hz, 4H), 7.29 (d, J=8.0 Hz, 4H). Compound 294D: LC-MS (ESI) m/z: 540 [M+H]$^+$. Compound 294E: LC-MS (ESI) m/z: 420 [M+H]$^+$. Compound 294: LC-MS (ESI) m/z: 392 [M+H]$^+$; $^1$H-NMR (DMSO-d$_6$, 400 MHz): δ (ppm) 2.96 (d, J=6 Hz, 4H), 5.05-5.08 (m, 1H), 7.25-7.31 (m, 8H), 12.85 (br, 1H), 14.67 (s, 1H).

Example 295

Synthesis of 4-(3-(cyclopropylmethoxy)-4-(trifluoromethyl)phenoxy)-1H-1,2,3-triazole-5-carboxylic acid (295)

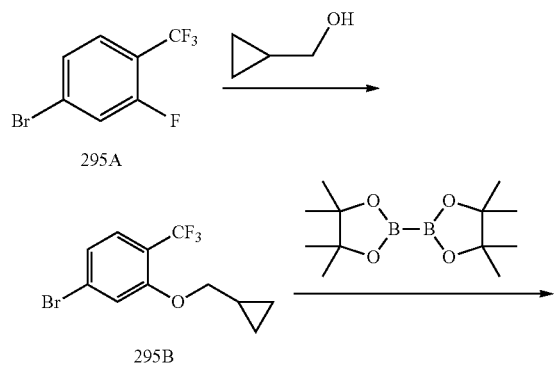

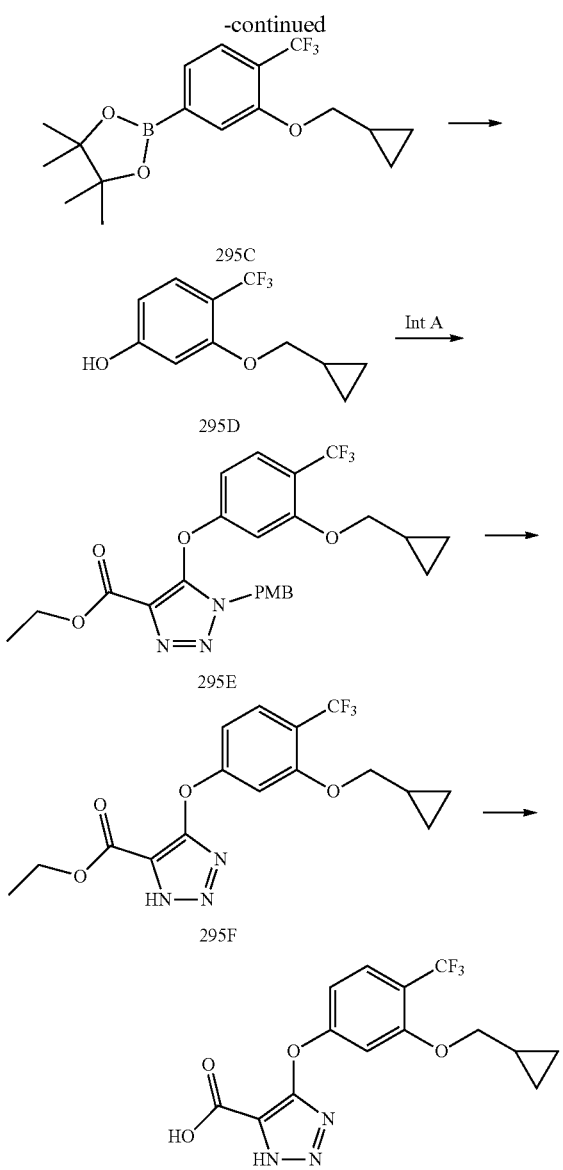

To a solution of cyclopropylmethanol (2.22 g, 31 mmol) in THF (100 mL) at 0° C. was added sodium hydride (60% dispersion in oil, 2.06 g, 51 mmol) in portions and stirred at room temperature for 30 minutes, followed by addition of 4-bromo-2-fluoro-1-(trifluoromethyl)benzeneare (295A) (5.0 g, 20.5 mmol). The mixture was stirred at room temperature for 16 hours, quenched with water (50 mL), and extracted with EtOAc (50 mL×3). The combined organic phases was washed with brine (50 mL), dried over sodium sulphate, concentrated, and purified by column chromatography on silica gel (ethyl acetate in petroleum ether, 10% v/v) to furnish Compound 295B. LC-MS (ESI) m/z: non-ionizable compound under routine conditions used; $^1$H-NMR (CDCl$_3$, 400 MHz): δ (ppm) 0.39 (q, J=4.9 Hz, 2H), 0.64 (q, J=5.9 Hz, 2H), 0.81-0.91 (m, 1H), 3.91 (t, J=8.1 Hz, 2H), 7.03-7.18 (m, 2H), 7.41 (d, J=8.2 Hz, 1H).

Compounds 295C, 295D, 295E, 295F, and 295 were synthesized by employing the procedures described for Compounds 27C, 236D, Intermediate I, 217E, and 8F using Compounds 295B, 295C, 295D, 295E, and 295F in lieu of Compounds 27B, 236C, 4-bromophenol, 217D, and 8E. Compound 295C: LC-MS (ESI) m/z: non-ionizable compound under routine conditions used; $^1$H-NMR (CDCl$_3$, 400 MHz): δ (ppm) 0.39 (q, J=4.9 Hz, 2H), 0.57-0.66 (m, 2H), 0.96-0.77 (m, 1H), 1.35 (s, 12H), 3.98 (d, J=6.5 Hz, 2H), 7.35 (s, 1H), 7.41 (d, J=7.6 Hz, 1H), 7.55 (d, J=7.6 Hz, 1H). Compound 295D: LC-MS (ESI) m/z: 233 [M+H]$^+$. Compound 295E: LC-MS (ESI) m/z: 492 [M+H]$^+$. Compound 295F: LC-MS (ESI) m/z: 372 [M+H]$^+$. Compound 295: LC-MS (ESI) m/z: 344 [M+H]$^+$. $^1$H-NMR (DMSO-d$_6$, 400 MHz): δ (ppm) 0.34 (t, J=5.1 Hz, 2H), 0.46-0.61 (m, 2H), 1.20 (s, 1H), 3.96 (d, J=6.8 Hz, 2H), 6.61 (d, J=8.6 Hz, 1H), 6.98 (s, 1H), 7.56 (d, J=8.8 Hz, 1H).

Example 296

Synthesis of 4-(1,3-diphenylpropoxy)-1H-1,2,3-triazole-5-carboxylic acid (296)

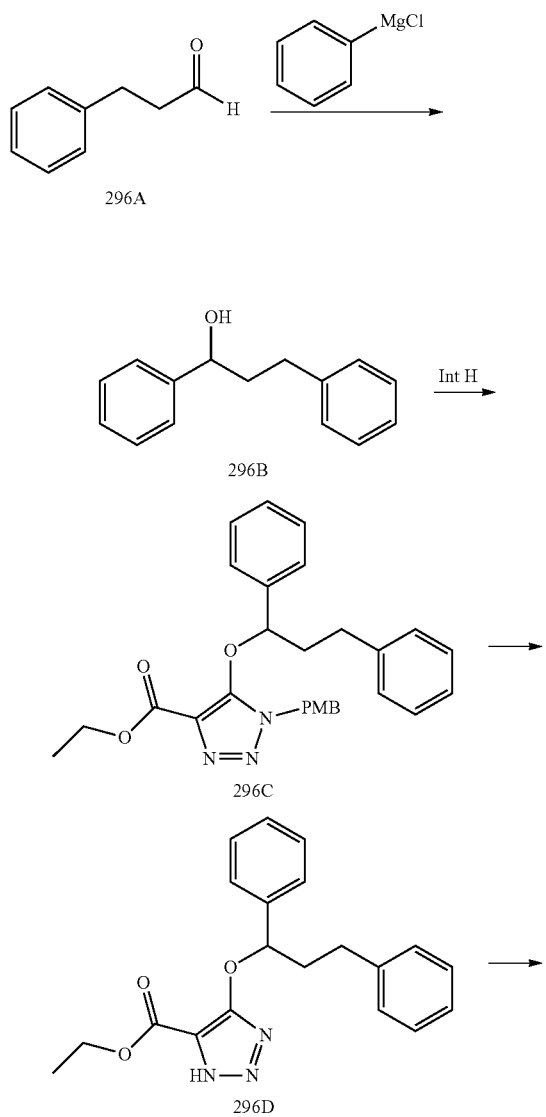

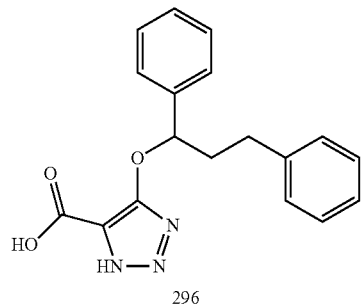

To a solution of 3-phenylpropanal (296A) (1.34 g, 10 mmol) in anhydrous THF (15 mL) was added phenylmagnesium chloride (2.0 M in THF, 5 mL, 10 mmol) at room temperature. The mixture was stirred at room temperature for 2 hours, quenched with saturated NH$_4$Cl solution (50 mL), and extracted with EtOAc (50 mL×3). The combined organic layers was washed with brine (50 mL), dried over anhydrous sodium sulfate, concentrated, and purified by column chromatography on silica gel (ethyl acetate in petroleum ether, 14% v/v) to furnish Compound 296B. LC-MS (ESI) m/z: non-ionizable compound under routine conditions used; $^1$H-NMR (CDCl$_3$, 400 MHz): δ (ppm) 2.02-2.13 (m, 2H), 2.64-2.74 (m, 2H), 4.65-4.68 (m, 1H), 7.15-7.19 (m, 3H), 7.27-7.29 (m, 3H), 7.33-7.34 (m, 4H).

Compounds 296C, 296D, and 296 were synthesized by employing the procedures described for Compounds 90C, 1, and 8F using Compounds 296B, 296C, and 296D in lieu of Compounds 90B, 1E, and 8E. Compound 296C: LC-MS (ESI) m/z: 472 [M+H]$^+$. Compound 296D: LC-MS (ESI) m/z: 352 [M+H]$^+$. Compound 296: LC-MS (ESI) m/z: 324 [M+H]$^+$. $^1$H-NMR (DMSO-d$_6$, 400 MHz): δ (ppm) 1.86-1.99 (m, 1H), 2.18-2.33 (m, 1H), 2.45-2.67 (m, 2H), 4.72-4.76 (m, 1H), 7.17-7.34 (m, 10H).

Example 297

Synthesis of 4-((4'-(4,4-difluoropiperidin-1-yl)-[1,1'-biphenyl]-4-yl)oxy)-1H-1,2,3-triazole-5-carboxylic acid 2,2,2-trifluoroacetate (297)

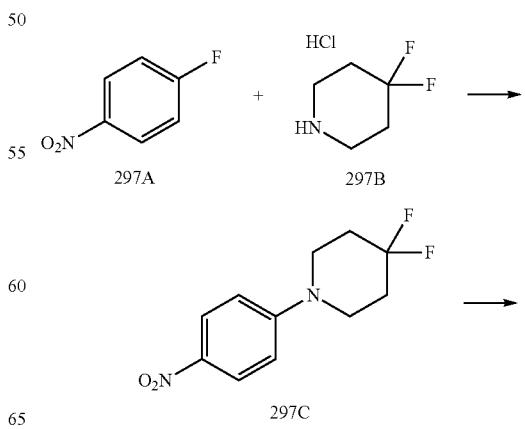

537

-continued

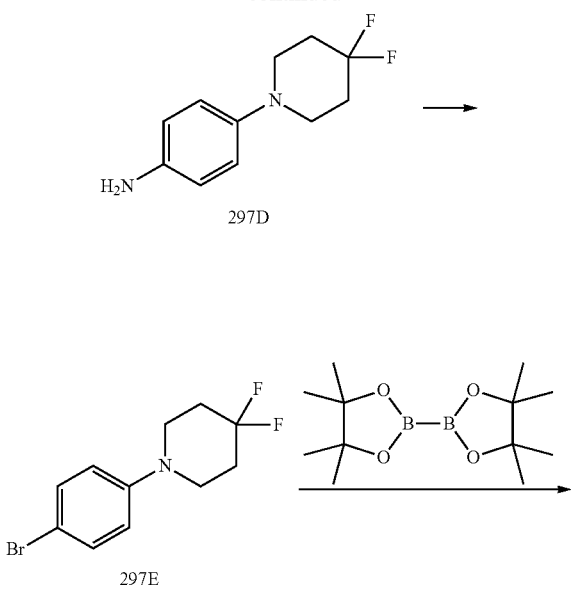

538

-continued

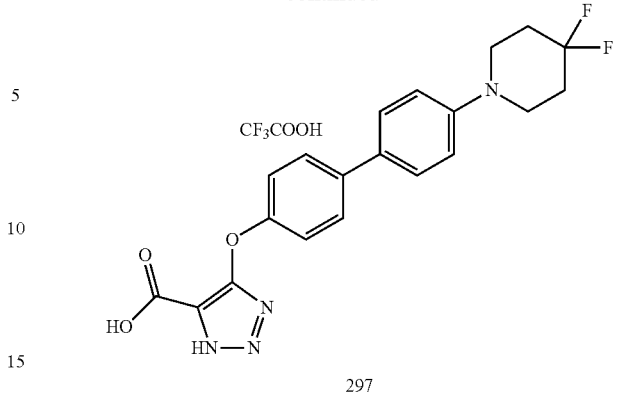

A mixture of 1-fluoro-4-nitrobenzene (297A) (1.42 g, 10 mmol), 4,4-difluoropiperidine hydrochloride (297B) (1.6 g, 10 mmol), and K$_2$CO$_3$ (4.14 g, 30 mmol) in DMF (80 mL) was stirred at 70° C. overnight. After cooled down to room temperature, the mixture was diluted with H$_2$O (200 mL) and extracted with ethyl acetate (80 mL×2). The combined organic layers was washed with brine (200 mL), dried over anhydrous sodium sulfate, concentrated, and purified with flash column chromatography on silica gel (ethyl acetate in petroleum ether, 20% v/v) to afford Compound 297C. LC-MS (ESI) m/z: 243 [M+H]$^+$.

To a mixture of Compound 297C (2.4 g, 10 mmol) and NH$_4$Cl (2.65 g, 50 mmol) in THF/H$_2$O (100 mL/25 mL) was added iron powder (2.8 g, 50 mmol). The mixture was stirred at 70° C. overnight. The mixture was filtered through Celite. The filtrate was concentrated to afford Compound 297D. LC-MS (ESI) m/z: 213 [M+H]$^+$; $^1$H-NMR (CDCl$_3$, 400 MHz): δ (ppm) 2.05-2.15 (m, 4H), 3.15 (t, J=6.0 Hz, 4H), 3.44-3.46 (m, 2H), 6.63-6.66 (m, 2H), 6.81-6.83 (m, 2H).

Compounds 297E, 297F, 297G, 297H, and 297 were synthesized by employing the procedures described for Compounds 56B, 27C, 4B, 1, and 2 using Compounds 297D with HBr/CuBr, 297E, Intermediate I, 297F with K$_2$CO$_3$ as base and 1,4-dioxane/H$_2$O as solvent, 297G, and 297H in lieu of Compounds 56A with HCl/CuCl, 27B, (4-bromophenyl)boronic acid, 4A with Na$_2$CO$_3$ as base and toluene/EtOH/H$_2$O as solvent, 1E, and 1. Compound 297E: LC-MS (ESI) m/z: 276 [M+H]$^+$. Compound 297F: LC-MS (ESI) m/z: 324 [M+H]$^+$. Compound 297G: LC-MS (ESI) m/z: 549 [M+H]$^+$. Compound 297H: LC-MS (ESI) m/z: 429 [M+H]$^+$. Compound 297: LC-MS (ESI) m/z: 401 [M+H]$^+$; $^1$H-NMR (DMSO-d$_6$, 400 MHz): δ (ppm) 1.99-2.12 (m, 4H), 3.37-3.40 (m, 4H), 7.06-7.12 (q, J=9.2 Hz, 4H), 7.51 (d, J=9.2 Hz, 2H), 7.58 (d, J=9.2 Hz, 2H), 13.24 (brs, 1H), 15.20 (brs, 1H).

Example 298

Synthesis of 4-((4-(4-(trifluoromethoxy)phenyl)cyclohexyl)methoxy)-1H-1,2,3-triazole-5-carboxylic acid (298)

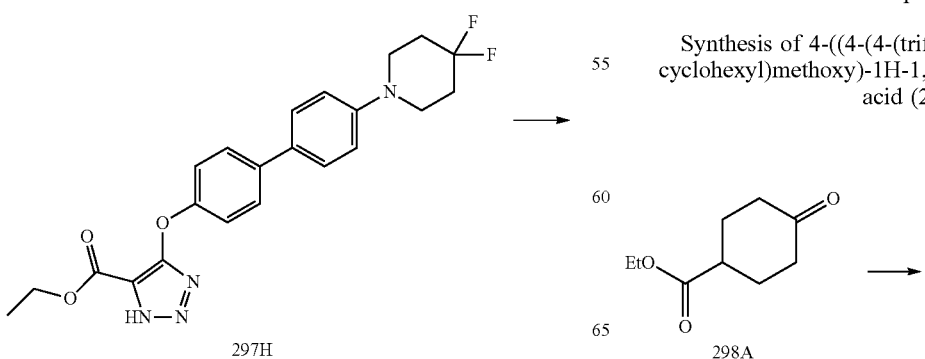

-continued

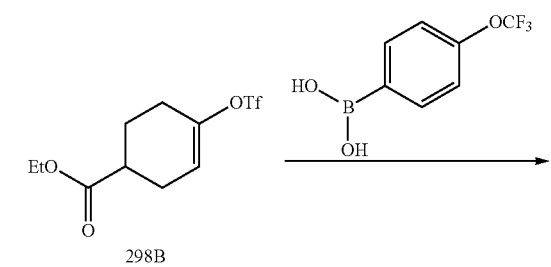

298B

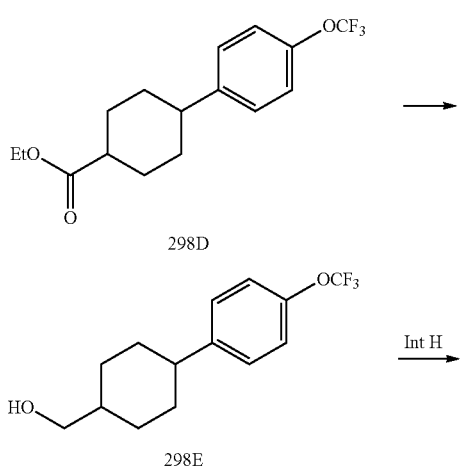

298C

298D

298E

298F

298G

-continued

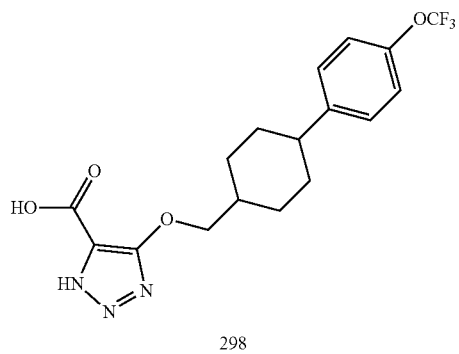 [SMILES: O=C(O)c1[nH]nnc1OCC1CCC(c2ccc(OC(F)(F)F)cc2)CC1]

298

To a solution of LiHMDS (1 M in THF, 13.99 mL, 13.99 mmol) in dry THF (20 mL) was added ethyl 4-oxocyclohexane-1-carboxylate (298A) (2.16 g, 12.72 mmol) at −78° C. and stirred at −78° C. for 30 minutes and, followed by addition of 1,1,1-trifluoro-N-phenyl-N-((trifluoromethyl)sulfonyl)methanesulfonamide (5 g, 13.99 mmol). It was stirred at −78° C. for 30 minutes and at room temperature overnight. The mixture was diluted with EtOAc (100 mL), washed with saturated NaHCO$_3$ solution (100 mL) and brine (100 mL), dried over anhydrous sodium sulfate, concentrated, and purified by column chromatography on silica gel (ethyl acetate in petroleum ether, 20% v/v) to furnish Compound 298B. LC-MS (ESI) m/z: 303 [M+H]$^+$.

A mixture of Compound 298B (1.64 g, 5.43 mmol), (4-(trifluoromethoxy)phenyl) boronic acid (700 mg, 3.39 mmol), Na$_2$CO$_3$ (922 mg, 6.78 mmol), PPh$_3$ (88 mg, 0.339 mmol) and Pd(OAc)$_2$ (76 mg, 0.339 mmol) in toluene/EtOH (15 mL/5 mL) was degassed with N$_2$ for three times and heated to 110° C. for 2 hours. After cooled down to room temperature, the mixture was diluted with H$_2$O (60 mL) and extracted with EtOAc (60 mL×3). The combined organic layers was concentrated and purified by column chromatography on silica gel (ethyl acetate in petroleum ether, 10% v/v) to furnish Compound 298C. LC-MS (ESI) m/z: 315 [M+H]$^+$; $^1$H-NMR (CDCl$_3$, 400 MHz): δ (ppm) 1.16-1.30 (m, 3H), 1.83-1.87 (m, 1H), 2.16-2.20 (m, 1H), 2.41-2.49 (m, 4H), 2.58-2.62 (m, 1H), 4.13-4.18 (m, 2H), 6.08-6.16 (m, 1H), 7.15 (d, J=8.4 Hz, 2H), 7.78 (d, J=6.8 Hz, 2H).

Compounds 298D, 298E, 298F, 298G, and 298 were synthesized by employing the procedures described for Compounds 141, 283B, 90C, 1, and 8E using Compounds 298C, 298D at −30° C., 298E with DEAD as coupling reagent, 298F, and 298G in lieu of Compounds 140, 283B at 0° C. to room temperature, 90C with DIAD as coupling reagent, 1E, and 8E. Compound 298D: LC-MS (ESI) m/z: 317 [M+H]$^+$. Compound 298E: LC-MS (ESI) m/z: 257 [M−OH]$^+$. Compound 298F: LC-MS (ESI) m/z: 534 [M+H]$^+$. Compound 298G: LC-MS (ESI) m/z: 414 [M+H]$^+$. Compound 298: LC-MS (ESI) m/z: 386 [M+H]$^+$. $^1$H-NMR (DMSO-d$_6$, 400 MHz): δ (ppm) 1.61-1.80 (m, 8H), 2.17-2.20 (m, 1H), 2.62-2.64 (m, 1H), 4.31-4.35 (m, 2H), 7.25 (d, J=8 Hz, 2H), 7.41 (d, J=8.4 Hz, 2H), 12.89 (s, 1H), 14.73 (s, 1H).

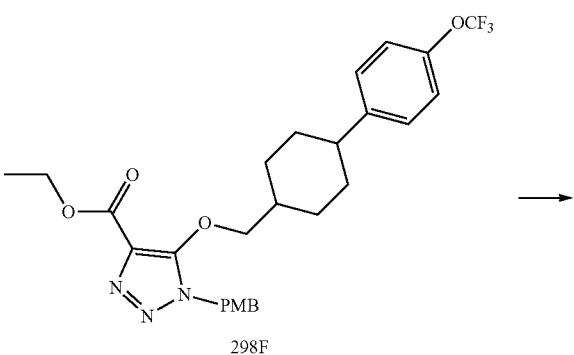

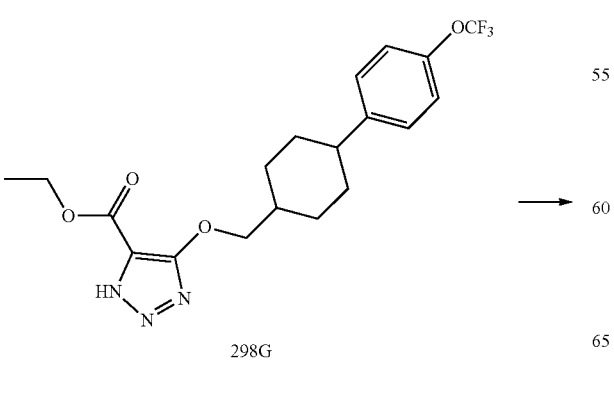

Example 299

Synthesis of 4-(((3',5'-dichloro-[1,1'-biphenyl]-4-yl)oxy)methyl)-1H-1,2,3-triazole-5-carboxylic acid (299)

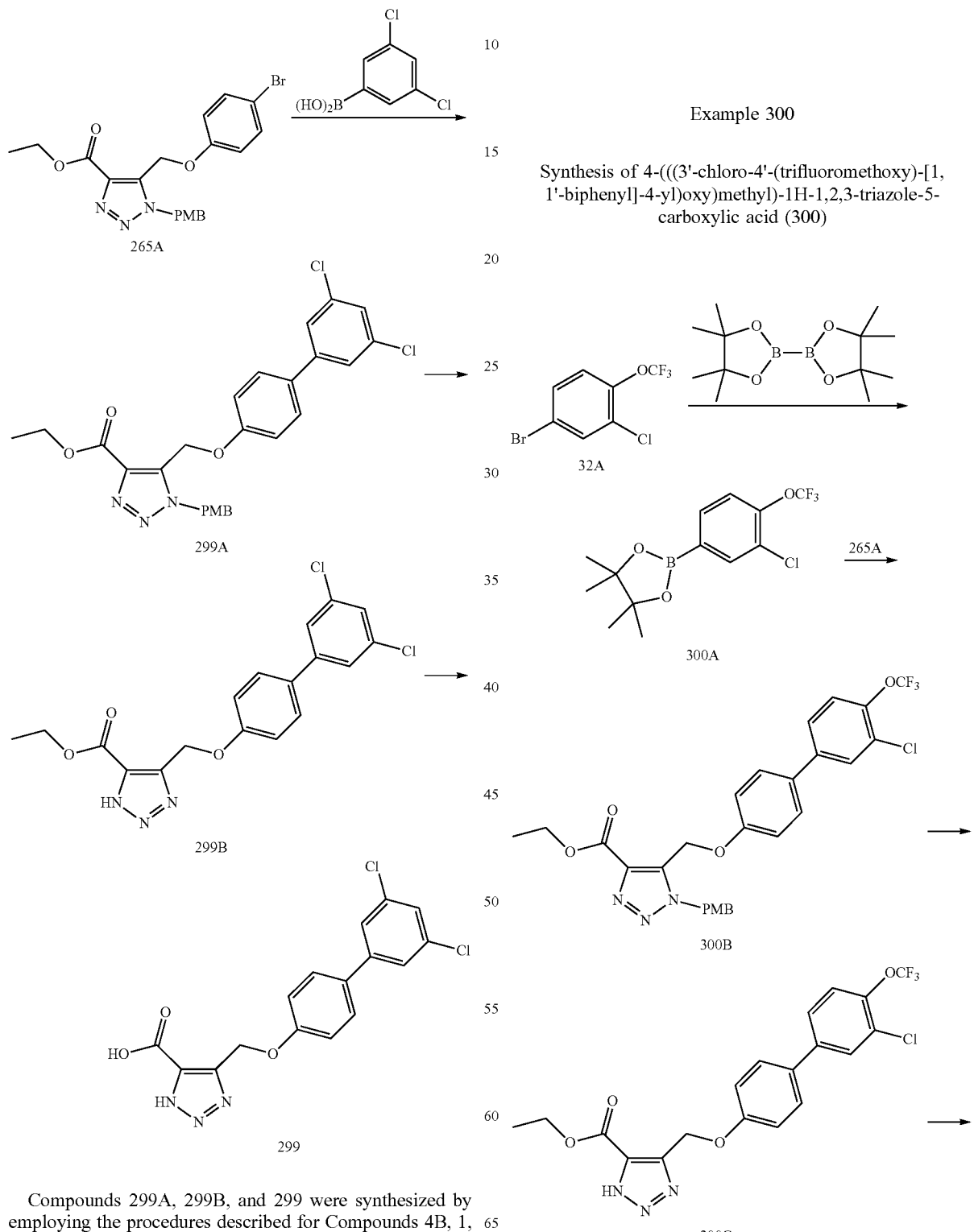

Compounds 299A, 299B, and 299 were synthesized by employing the procedures described for Compounds 4B, 1, and 8E using (3,5-dichlorophenyl)boronic acid, Compounds 265A with 1,4-dioxane/EtOH as solvent, 299A, and 299B in lieu of (4-bromophenyl)boronic acid, Compounds 4A with toluene/EtOH/H$_2$O as solvent, 1E, and 8E. Compound 299A: LC-MS (ESI) m/z: 512 [M+H]$^+$. Compound 299B: LC-MS (ESI) m/z: 392 [M+H]$^+$. Compound 299: LC-MS (ESI) m/z: 364 [M+H]$^+$. $^1$H-NMR (DMSO-d$_6$, 400 MHz): δ (ppm) 5.41 (s, 2H), 7.12 (d, J=8.8 Hz, 2H), 7.53 (s, 1H), 7.69-7.72 (m, 4H), 13.35 (s, 1H), 15.55 (s, 1H).

Example 300

Synthesis of 4-(((3'-chloro-4'-(trifluoromethoxy)-[1,1'-biphenyl]-4-yl)oxy)methyl)-1H-1,2,3-triazole-5-carboxylic acid (300)

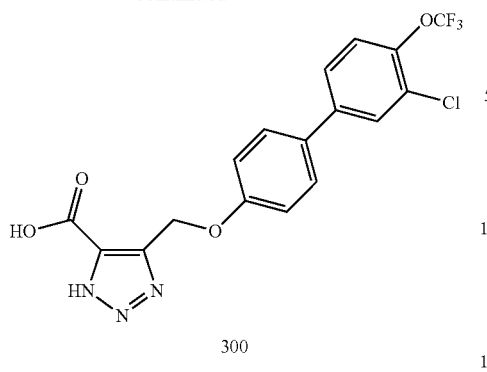

300

Compounds 300A, 300B, 300C, and 300 were synthesized by employing the procedures described for Compounds 27C, 4B, 1, and 8E using Compounds 32A, 300A 265A with 1,4-dioxane/EtOH as solvent, 300B, and 300C in lieu of Compounds 27B, (4-bromophenyl)boronic acid, 4A with toluene/EtOH/H$_2$O as solvent, 1E, and 8E. Compound 300A: LC-MS (ESI) m/z: non-ionizable compound under routine conditions used; $^1$H-NMR (CDCl$_3$, 400 MHz): δ (ppm) 1.34 (s, 12H), 7.31 (dd, J=1.6, 8 Hz, 1H), 7.90 (dd, J=1.6, 8 Hz, 1H), 7.90 (s, 1H). Compound 300B: LC-MS (ESI) m/z: 562 [M+H]$^+$; Compound 300C: LC-MS (ESI) m/z: 442 [M+H]$^+$. Compound 300: LC-MS (ESI) m/z: 414 [M+H]$^+$; $^1$H-NMR (DMSO-d$_6$, 400 MHz): δ (ppm) 5.40 (s, 2H), 7.13 (d, J=8.4 Hz, 2H), 7.60 (d, J=8.8 Hz, 1H), 7.68-7.74 (m, 3H), 7.94 (d, J=2.4 Hz, 1H), 13.39 (s, 1H), 15.56 (s, 1H).

Example 301

Synthesis of 4-(4-(4,4-difluoropiperidin-1-yl)phenoxy)-1H-1,2,3-triazole-5-carboxylic acid 2,2,2-trifluoroacetate (301)

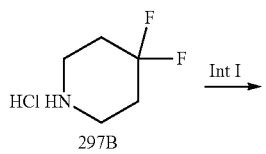

297B

A of Intermediate I (600 mg, 1.39 mmol), 4,4-difluoropiperidine hydrochloride (297B) (439 mg, 2.78 mmol), Pd(OAc)$_2$ (156 mg, 0.695 mmol), X-Phos (331 mg, 0.695 mmol), and Cs$_2$CO$_3$ (1.36 g, 4.17 mmol) in 1,4-dixoane (30 mL) was stirred at 100° C. under nitrogen overnight. The mixture was concentrated under reduced pressure and the residue was purified with flash column chromatography on silica gel (ethyl acetate in petroleum ether, 20% v/v) to afford Compound 301A. LC-MS (ESI) m/z: 473 [M+H]$^+$.

Compounds 301B and 301 were synthesized by employing the procedures described for Compounds 8E and 1 using Compounds 301A and 301B in lieu of Compounds 8E and 1E. Compound 301B: LC-MS (ESI) m/z: 445 [M+H]$^+$. Compound 301: LC-MS (ESI) m/z: 325 [M+H]$^+$; $^1$H-NMR (DMSO-d$_6$, 400 MHz): δ (ppm) 2.03-2.10 (m, 4H), 3.26-3.27 (m, 4H), 7.01 (s, 4H).

Example 302

Synthesis of ((isopropoxycarbonyl)oxy)methyl 4-(((trans)-4-(4-(trifluoromethoxy)phenyl)cyclohexyl)oxy)-1H-1,2,3-triazole-5-carboxylate (302)

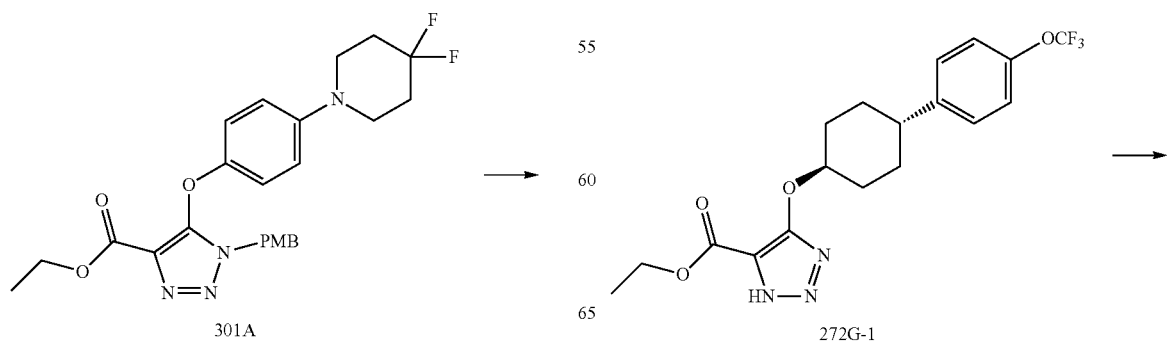

545
-continued

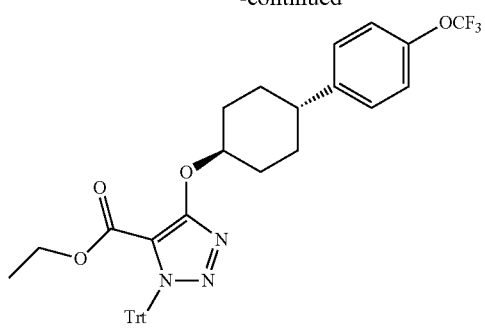

302A

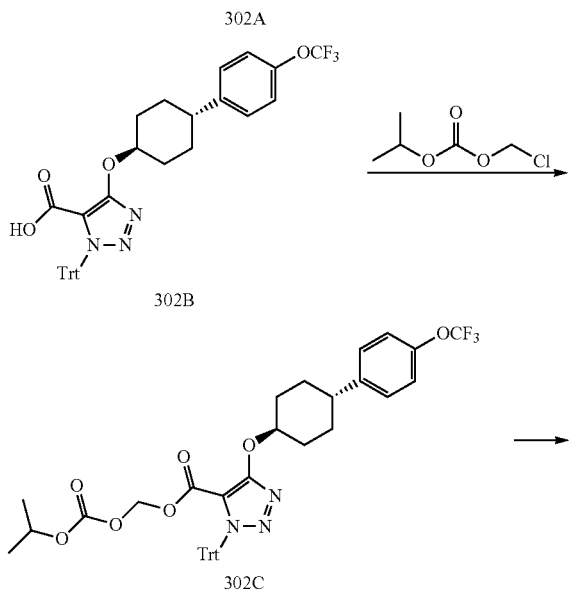

546
-continued

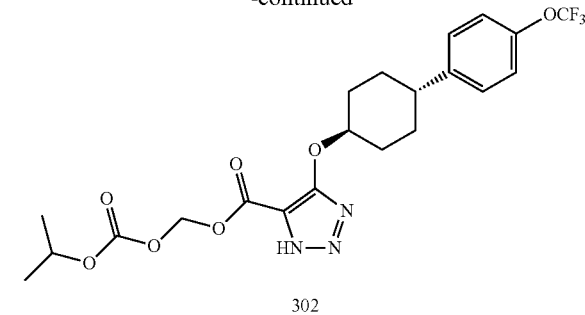

302

Compounds 302A, 302B, 302C, and 302 were synthesized by employing the procedures described for Compounds 54A, 8F, 54C, and 256 using Compounds 271G-1, 302A, 302B, chloromethyl isopropyl carbonate with TEA as base and adding NaI, and 302C in lieu of Compounds 33, 8E, 54B, chloromethyl pivalate with Na$_2$CO$_3$ as base and without NaI, and 256D. Compound 302A: LC-MS (ESI) m/z: 664 [M+Na]$^+$. Compound 302B: LC-MS (ESI) m/z: 636 [M+Na]$^+$; $^1$H-NMR (CD$_3$OD, 400 MHz): δ (ppm) 1.49-1.63 (m, 4H), 1.87-1.90 (m, 2H), 2.22-2.25 (m, 2H), 2.57-2.63 (m, 1H), 4.48-4.55 (m, 1H), 7.15-7.18 (m, 8H), 7.29-7.33 (m, 11H). Compound 302C: LC-MS (ESI) m/z: 752 [M+Na]$^+$. Compound 302: LC-MS (ESI) m/z: 488 [M+H]$^+$; $^1$H-NMR (CD$_3$OD, 400 MHz): δ (ppm) 1.20-1.22 (m, 6H), 1.56-1.61 (m, 4H), 1.87-1.89 (m, 2H), 2.24-2.26 (m, 2H), 2.56-2.58 (m, 1H), 4.66-4.66 (m, 1H), 4.79-4.81 (m, 1H), 5.86 (s, 2H), 7.08-7.10 (m, 2H), 7.25-7.27 (m, 2H).

Example 303

Synthesis of ((cyclohexanecarbonyl)oxy)methyl 4-(((trans)-4-(4-(trifluoromethoxy)phenyl)cyclohexyl)oxy)-1H-1,2,3-triazole-5-carboxylate (303)

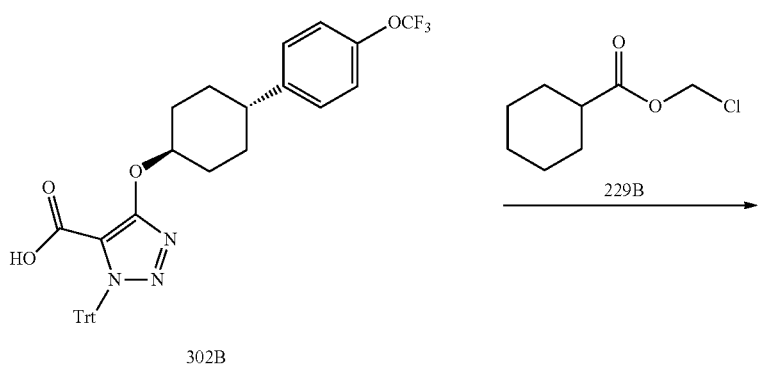

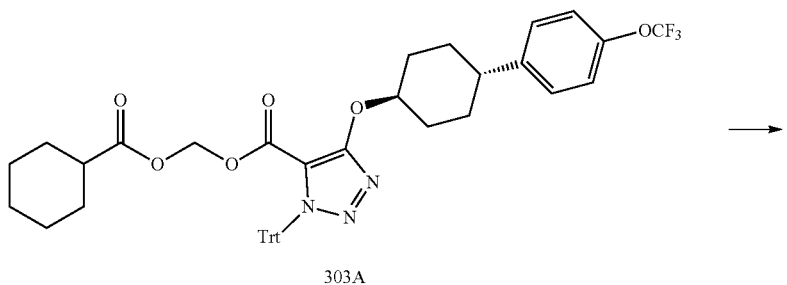

303A

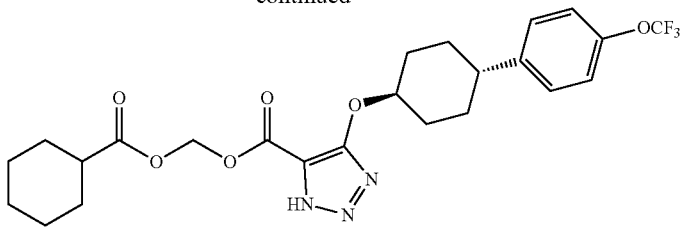

303

Compounds 303A and 303 were synthesized by employing the procedures described for Compounds 54C and 256 using Compounds 302B, 229B with TEA as base and adding NaI, and 303A in lieu of Compounds 54B, chloromethyl pivalate with Na₂CO₃ as base and without NaI, and 256D. Compound 303A: LC-MS (ESI) m/z: 776 [M+Na]⁺. Compound 303: LC-MS (ESI) m/z: 534 [M+Na]⁺; ¹H-NMR (CD₃OD, 400 MHz): δ (ppm) 1.24-1.51 (m, 5H), 1.65-1.77 (m, 7H), 1.90-1.99 (m, 4H), 2.34-2.44 (m, 3H), 2.66-2.68 (m, 1H), 4.74-4.76 (m, 1H), 5.97 (s, 2H), 7.18-7.20 (m, 2H), 7.34-7.37 (m, 2H).

Example 304

Synthesis of 4-(((1s,4s)-4-(3,5-dichlorophenyl)cyclohexyl)oxy)-1H-1,2,3-triazole-5-carboxylic acid (304)

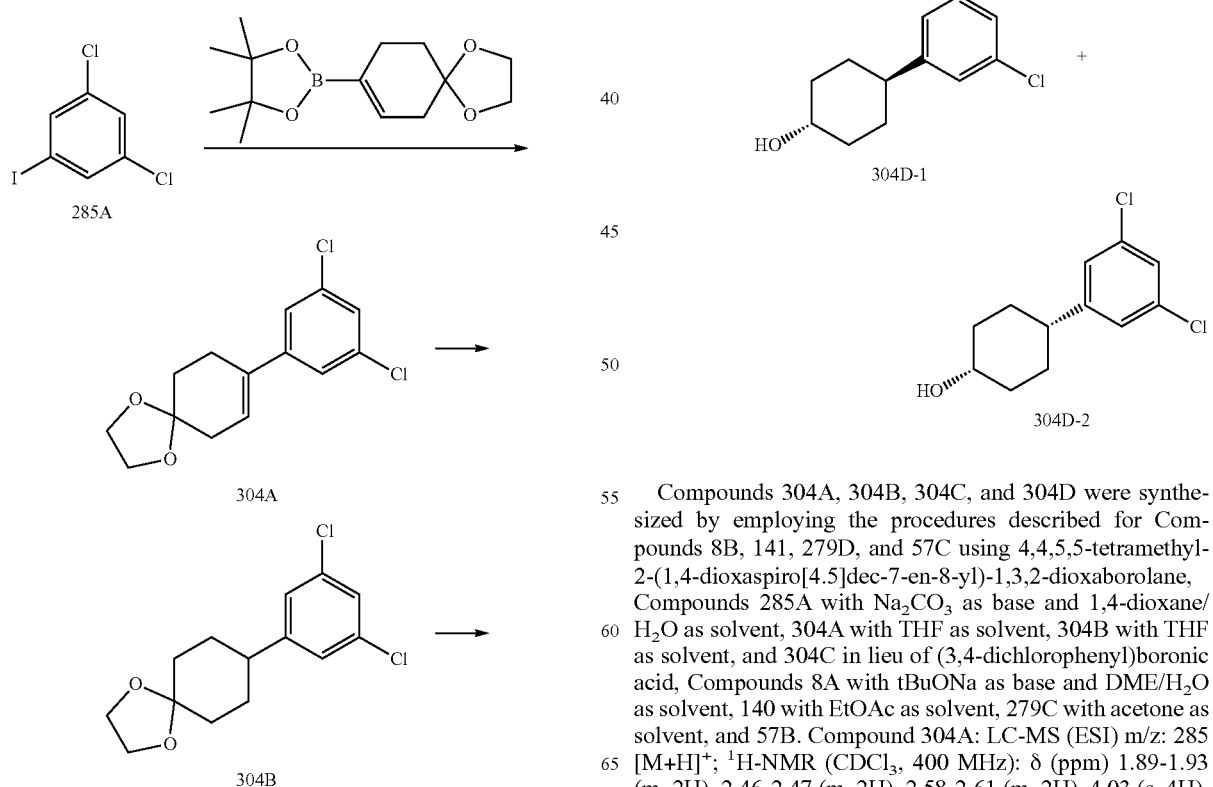

Compounds 304A, 304B, 304C, and 304D were synthesized by employing the procedures described for Compounds 8B, 141, 279D, and 57C using 4,4,5,5-tetramethyl-2-(1,4-dioxaspiro[4.5]dec-7-en-8-yl)-1,3,2-dioxaborolane, Compounds 285A with Na₂CO₃ as base and 1,4-dioxane/H₂O as solvent, 304A with THF as solvent, 304B with THF as solvent, and 304C in lieu of (3,4-dichlorophenyl)boronic acid, Compounds 8A with tBuONa as base and DME/H₂O as solvent, 140 with EtOAc as solvent, 279C with acetone as solvent, and 57B. Compound 304A: LC-MS (ESI) m/z: 285 [M+H]⁺; ¹H-NMR (CDCl₃, 400 MHz): δ (ppm) 1.89-1.93 (m, 2H), 2.46-2.47 (m, 2H), 2.58-2.61 (m, 2H), 4.03 (s, 4H), 6.02 (t, J=2.0 Hz, 1H), 7.20-7.21 (m, 1H), 7.25-7.26 (m, 2H). Compound 304B: LC-MS (ESI) m/z: Non-ionizable compounds under routine condition used; ¹H-NMR (CDCl₃, 400 MHz): δ (ppm) 1.58-1.80 (m, 8H), 2.42-2.45 (m, 1H), 3.91 (s, 4H), 7.04 (d, J=2.0 Hz, 2H), 7.11 (t, J=2.0 Hz, 1H). Compound 304C: LC-MS (ESI) m/z: 243 [M+H]⁺; ¹H-NMR (CDCl₃, 400 MHz): δ (ppm) 1.85-1.95 (m, 2H), 2.20-2.24 (m, 2H), 2.48-2.52 (m, 4H), 2.95-3.02 (m, 1H), 7.13 (d, J=1.2 Hz, 2H), 7.23-7.24 (m, 1H).

Compound 304D was purified with flash column chromatography on silica gel (ethyl acetate in petroleum ether, 5% v/v) to furnish Compound 304D-1 and Compound 304D-2. Compound 304D-1: LC-MS (ESI) m/z: 227 [M−OH]⁺; ¹H-NMR (CD₃OD, 400 MHz): δ (ppm) 1.21-1.44 (m, 4H), 1.74-1.78 (m, 2H), 1.92-1.95 (m, 2H), 2.37-2.41 (m, 1H), 3.48-3.52 (m, 1H), 7.08 (d, J=2.0 Hz, 2H), 7.12-7.13 (m, 1H).

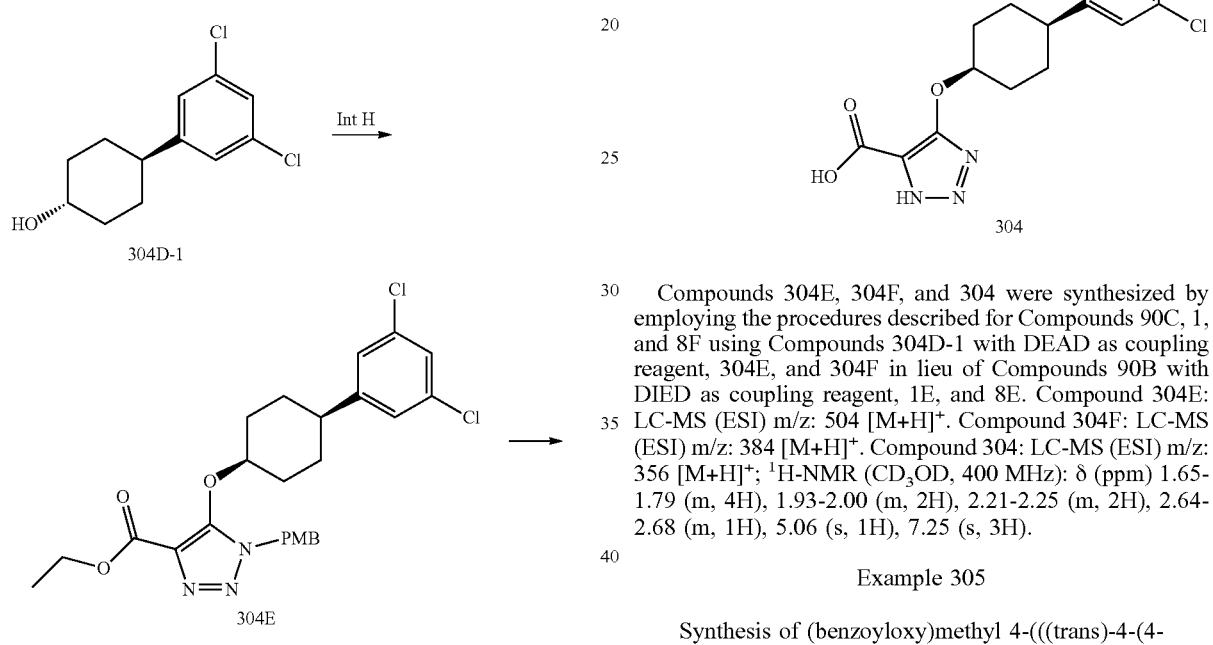

Compounds 304E, 304F, and 304 were synthesized by employing the procedures described for Compounds 90C, 1, and 8F using Compounds 304D-1 with DEAD as coupling reagent, 304E, and 304F in lieu of Compounds 90B with DIED as coupling reagent, 1E, and 8E. Compound 304E: LC-MS (ESI) m/z: 504 [M+H]⁺. Compound 304F: LC-MS (ESI) m/z: 384 [M+H]⁺. Compound 304: LC-MS (ESI) m/z: 356 [M+H]⁺; ¹H-NMR (CD₃OD, 400 MHz): δ (ppm) 1.65-1.79 (m, 4H), 1.93-2.00 (m, 2H), 2.21-2.25 (m, 2H), 2.64-2.68 (m, 1H), 5.06 (s, 1H), 7.25 (s, 3H).

Example 305

Synthesis of (benzoyloxy)methyl 4-(((trans)-4-(4-(trifluoromethoxy)phenyl)cyclohexyl)oxy)-1H-1,2,3-triazole-5-carboxylate (305)

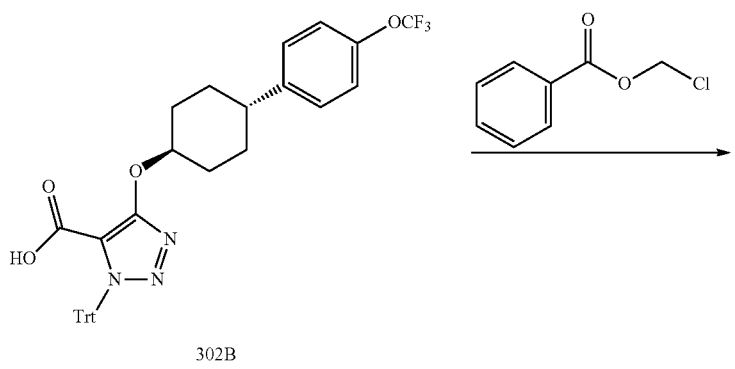

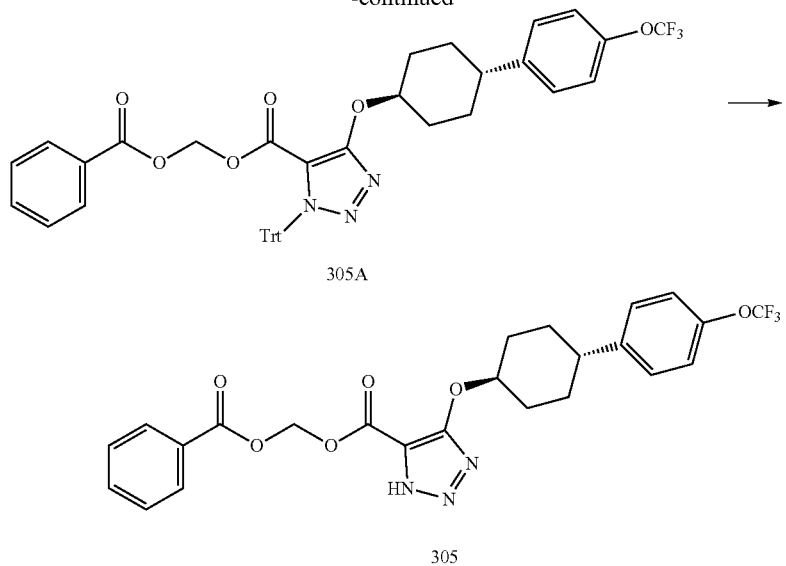

305A

305

Compounds 305A and 305 were synthesized by employing the procedures described for Compounds 54C and 256 using Compounds 302B, chloromethyl benzoate with TEA as base and adding NaI, and 305A in lieu of Compounds 54B, chloromethyl pivalate with $Na_2CO_3$ as base and without NaI, and 256D. Compound 305A: LC-MS (ESI) m/z: 770 [M+Na]$^+$. Compound 305: LC-MS (ESI) m/z: 506 [M+H]$^+$; $^1$H-NMR ($CD_3OD$, 400 MHz): δ (ppm) 1.63-1.65 (m, 4H), 1.93-1.95 (m, 2H), 2.02-2.04 (m, 2H), 2.60-2.61 (m, 1H), 4.70-4.72 (m, 1H), 6.23 (s, 2H), 7.17-7.19 (m, 2H), 7.31-7.33 (m, 2H), 7.49-7.53 (m, 2H), 7.63-7.65 (m, 1H), 8.07-8.09 (m, 2H).

Example 306

Synthesis of 4-(4-(4-(piperidin-1-yl)cyclohexyl)phenoxy)-1H-1,2,3-triazole-5-carboxylic acid 2,2,2-trifluoroacetate (306)

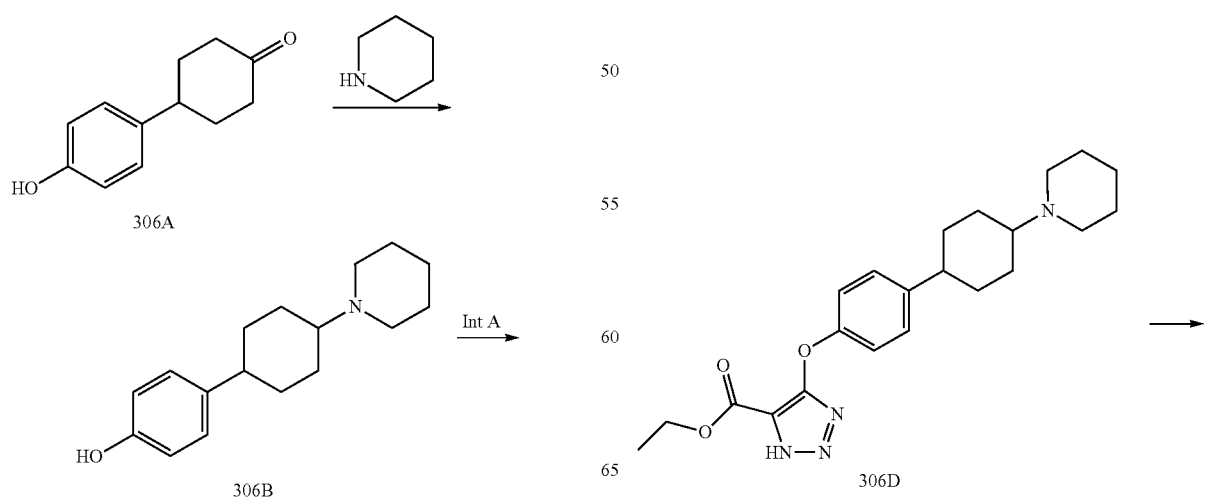

306A

306B

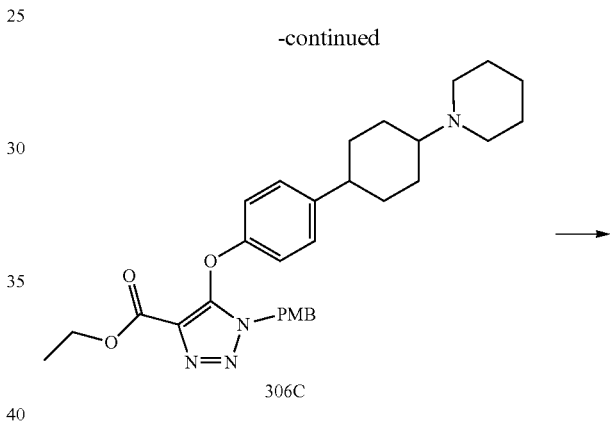

306C

306D

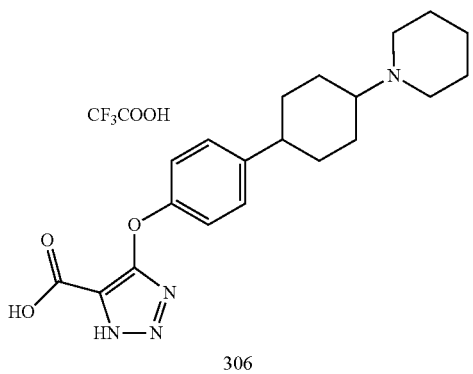

306

Compounds 306B, 306C, 306D, and 306 were synthesized by employing the procedures described for Compounds 160B, Intermediate I, 1, and 2 using Compounds 306A with MeOH as solvent, 306B with Na₂CO₃ as base, 306C, and 306D in lieu of Compounds 160A with dichloromethane as solvent, 4-bromophenol with K₂CO₃ as base, 1E, and 1. Compound 306B: LC-MS (ESI) m/z: 260 [M+H]⁺; ¹H-NMR (DMSO-d₆, 400 MHz): δ (ppm) 1.36-1.50 (m, 10H), 1.74-2.54 (m, 10H), 6.63-6.68 (m, 2H), 6.97-7.02 (m, 2H), 9.08 (s, 1H). Compound 306C: LC-MS (ESI) m/z: 519 [M+H]⁺. Compound 306D: LC-MS (ESI) m/z: 399 [M+H]⁺. Compound 306: LC-MS (ESI) m/z: 371 [M+H]⁺; ¹H-NMR (CD₃OD, 400 MHz): δ (ppm) 1.44-2.06 (m, 12.5H), 2.20-2.33 (m, 2H), 2.58-2.65 (m, 0.5H), 2.96-3.29 (m, 3H), 3.49-3.53 (m, 2H), 7.06-7.12 (m, 2H), 7.23 (d, J=8.4 Hz, 1H), 7.38 (d, J=8.4 Hz, 1H).

Example 307

Synthesis of (isobutyryloxy)methyl 4-(((trans)-4-(4-(trifluoromethoxy)phenyl)cyclohexyl)oxy)-1H-1,2,3-triazole-5-carboxylate (307)

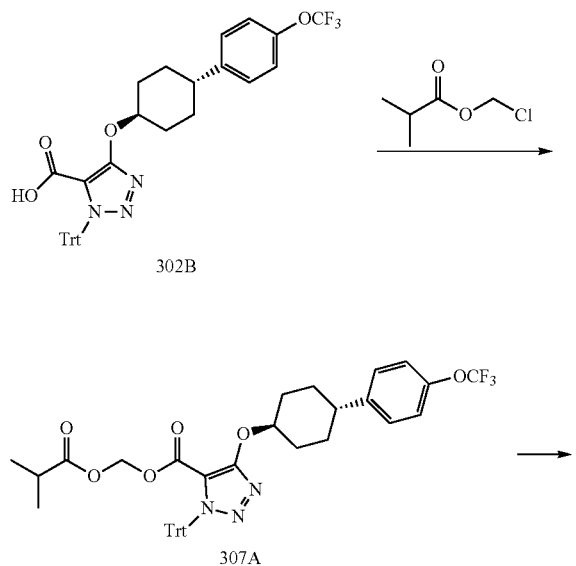

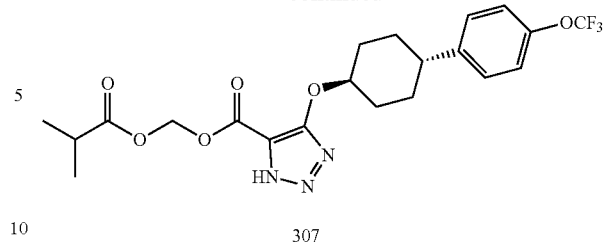

307

Compounds 307A and 307 were synthesized by employing the procedures described for Compounds 54C and 256 using Compounds 302B, chloromethyl isobutyrate with TEA as base and adding NaI, and 307A in lieu of Compounds 54B, chloromethyl pivalate with Na₂CO₃ as base and without NaI, and 256D. Compound 307A: LC-MS (ESI) m/z: 736 [M+Na]⁺. Compound 307: LC-MS (ESI) m/z: 472 [M+H]⁺; ¹H-NMR (CD₃OD, 400 MHz): δ (ppm) 1.18-1.19 (m, 6H), 1.64-1.70 (m, 4H), 1.97-1.99 (m, 2H), 2.33-2.35 (m, 2H), 2.61-2.67 (m, 2H), 4.74-4.75 (m, 1H), 5.97 (s, 2H), 7.17-7.20 (m, 2H), 7.34-7.36 (m, 2H).

Example 308

Synthesis of 4-(((cis)-4-(3,4-dichlorophenyl)cyclohexyl)oxy)-1H-1,2,3-triazole-5-carboxylic acid (308-1) and 4-(((trans)-4-(3,4-dichlorophenyl)cyclohexyl)oxy)-1H-1,2,3-triazole-5-carboxylic acid (308-2)

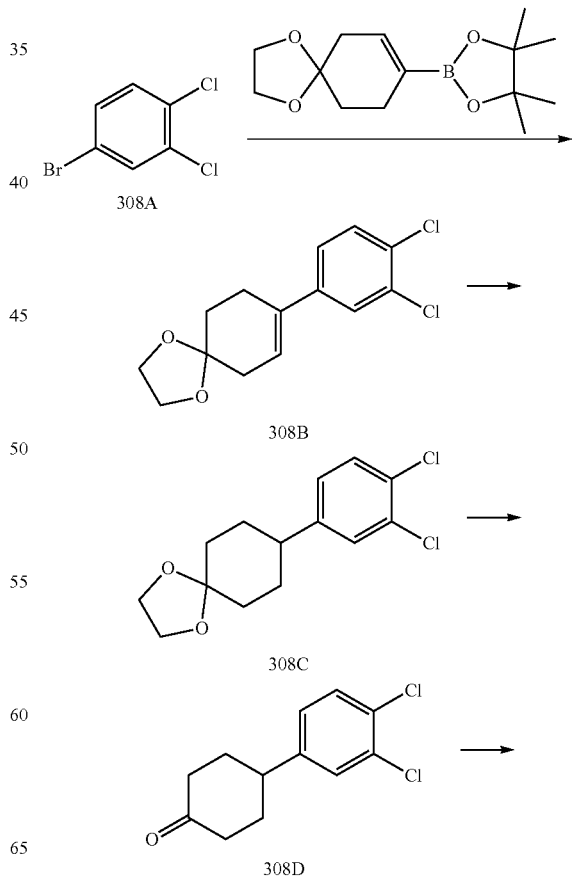

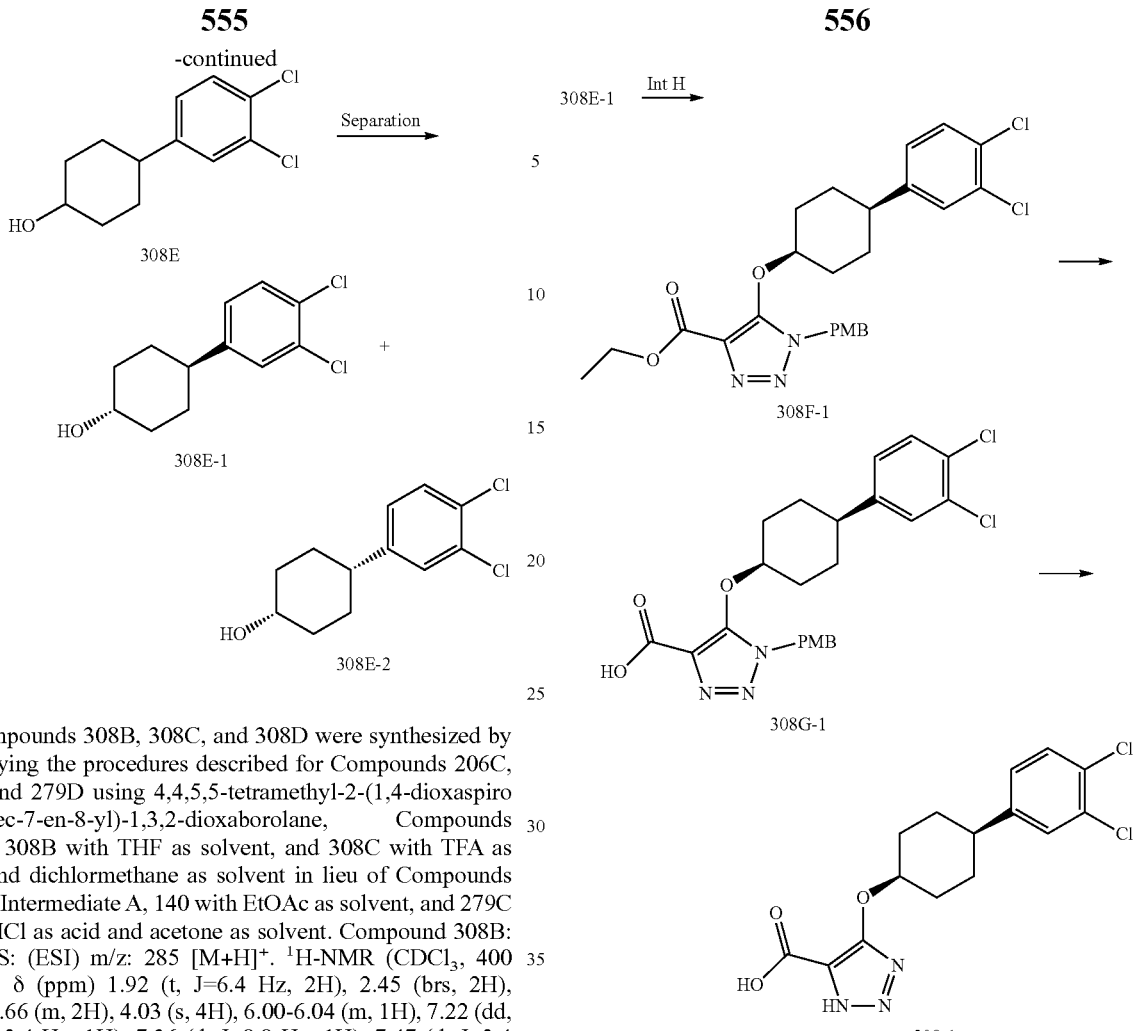

Compounds 308B, 308C, and 308D were synthesized by employing the procedures described for Compounds 206C, 141, and 279D using 4,4,5,5-tetramethyl-2-(1,4-dioxaspiro[4.5]dec-7-en-8-yl)-1,3,2-dioxaborolane, Compounds 308A, 308B with THF as solvent, and 308C with TFA as acid and dichlormethane as solvent in lieu of Compounds 206B, Intermediate A, 140 with EtOAc as solvent, and 279C with HCl as acid and acetone as solvent. Compound 308B: LC-MS: (ESI) m/z: 285 [M+H]$^+$. $^1$H-NMR (CDCl$_3$, 400 MHz): δ (ppm) 1.92 (t, J=6.4 Hz, 2H), 2.45 (brs, 2H), 2.58-2.66 (m, 2H), 4.03 (s, 4H), 6.00-6.04 (m, 1H), 7.22 (dd, J=8.4, 2.4 Hz, 1H), 7.36 (d, J=8.8 Hz, 1H), 7.47 (d, J=2.4 Hz, 1H). Compound 308C: LC-MS: (ESI) m/z: 287 [M+H]$^+$. (CDCl$_3$, 400 MHz): δ (ppm) 1.65-1.90 (m, 8H), 2.48-2.58 (m, 1H), 3.99 (s, 4H), 7.05-7.10 (m, 1H), 7.32-7.37 (m, 2H). Compound 308D: LC-MS (ESI) m/z: 243 [M+H]$^+$. $^1$H-NMR (CDCl$_3$, 400 MHz): δ (ppm) 1.84-1.98 (m, 2H), 2.16-2.28 (m, 2H), 2.48-2.56 (m, 4H), 2.96-3.06 (m, 1H), 7.09 (dd, J=8.4, 2.4 Hz, 1H), 7.34 (d, J=2.0 Hz, 1H), 7.40 (d, J=8.4 Hz, 1H).

To a solution of Compound 308D (1.47 g, 6.05 mmol) in anhydrous THF (20 mL) was added a solution of DIBAL-H in toluene (25%, 6.05 mL) at 0° C. and stirred at room temperature for 2 hours. It was quenched with dilute HCl solution (0.5 M, 50 mL) and extracted with ethyl acetate (50 mL×3). The combined organic layers was washed with brine (50 mL), dried over anhydrous sodium sulfate, and concentrated to give a crude Compound 308E, which was purified with flash column chromatography on silica gel (ethyl acetate in petroleum ether, from 10% to 30% v/v) to yield Compound 308E-1 (trans isomer) and Compound 308E-2 (cis isomer). Compound 308E-1: LC-MS (ESI) m/z: 227 [M−OH]$^+$; retention time: 1.67 min (214 nm). $^1$H-NMR (CDCl$_3$, 400 MHz): δ (ppm) 1.38-1.52 (m, 4H), 1.88-1.96 (m, 2H), 2.06-2.14 (m, 2H), 2.43-2.52 (m, 1H), 3.64-3.73 (m, 1H), 7.04 (dd, J=8.0, 2.0 Hz, 1H), 7.29 (d, J=2.4 Hz, 1H), 7.35 (d, J=8.4 Hz, 1H). Compound 308E-2: LC-MS (ESI) m/z: 227 [M−OH]$^+$; retention time: 1.72 min (214 nm). $^1$H-NMR (CDCl$_3$, 400 MHz): δ (ppm) 1.60-1.72 (m, 4H), 1.80-1.96 (m, 4H), 2.46-2.56 (m, 1H), 4.12-4.18 (m, 1H), 7.08 (dd, J=8.4, 2.0 Hz, 1H), 7.32-7.40 (m, 2H).

Compounds 308F-1, 308G-1, and 308-1 were synthesized by employing the procedures described for Compounds 90C, 8F, and 1 using Compounds 308E-1 with DEAD as coupling reagent, 308F-1, and 308G-1 in lieu of Compounds 90B with DIAD as coupling reagent, 8E, and 1E. Compound 308F-1: LC-MS (ESI) m/z: 504 [M+H]$^+$. Compound 308G-1: LC-MS (ESI) m/z: 476 [M+H]$^+$. Compound 308-1: LC-MS (ESI) m/z: 356 [M+H]$^+$; $^1$H-NMR (DMSO-d$_6$, 400 MHz): 1.58-1.83 (m, 6H), 2.07 (d, J=12.5 Hz, 2H), 2.69 (t, J=11.5 Hz, 1H), 4.91 (s, 1H), 7.25 (d, J=8.4 Hz, 1H), 7.47 (s, 1H), 7.55 (d, J=8.3 Hz, 1H), 12.89 (s, 1H), 14.76 (s, 1H).

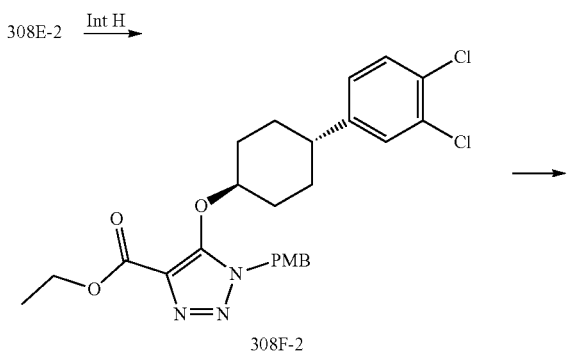

-continued

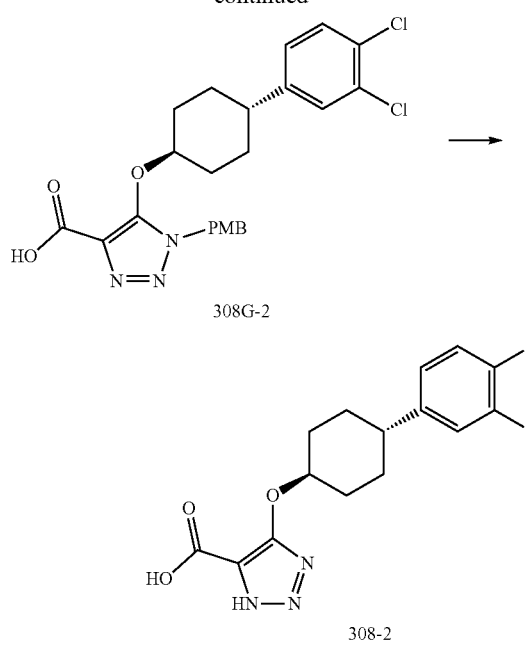

308G-2

308-2

Compounds 308F-2, 308G-2, and 308-2 were synthesized by employing the procedures described for Compounds 90C, 8F, and 1 using Compounds 308E-2 with DEAD as coupling reagent, 308F-2, and 308G-2 in lieu of Compounds 90B with DIAD as coupling reagent, 8E, and 1E. Compound 308F-2: LC-MS (ESI) m/z: 504 [M+H]$^+$. Compound 308G-2: LC-MS (ESI) m/z: 476 [M+H]$^+$. Compound 308-2: LC-MS (ESI) m/z: 356 [M+H]$^+$; $^1$H-NMR (DMSO-$d_6$, 400 MHz): 1.43-1.71 (m, 4H), 1.85 (d, J=12.1 Hz, 2H), 2.23 (d, J=11.2 Hz, 2H), 2.64 (t, J=11.4 Hz, 1H), 4.67 (s, 1H), 7.29 (d, J=8.3 Hz, 1H), 7.55 (d, J=8.2 Hz, 2H), 12.89 (s, 1H), 14.75 (s, 1H).

Example 309

Synthesis of 4-(4-chloro-3-(cyclohexylmethoxy) phenoxy)-1H-1,2,3-triazole-5-carboxylic acid (309)

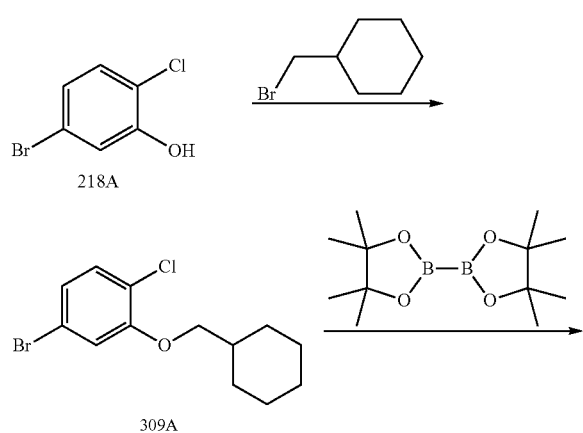

218A

309A

-continued

309B

309C

309D

309E

309

Compounds 309A, 309B, 309C, 309D, 309E, and 309 were synthesized by employing the procedures described for Compounds 27B, 27C, 236D, Intermediate I, 217E, and 8F using Compounds 218A with $K_2CO_3$ as base, 309A, 309B, 309C, 309D, and 309E in lieu of Compounds 27A with $Cs_2CO_3$ as base, 27B, 236C, 4-bromophenol, 217D, and 8E. Compound 309A: LC-MS (ESI) m/z: non-ionizable compound under routine conditions used. Compound 309B: LC-MS (ESI) m/z: non-ionizable compound under routine conditions used; $^1$H-NMR (CDCl$_3$, 400 MHz): δ (ppm) 1.06-1.10 (m, 2H), 1.19-1.22 (m, 1H), 1.29-1.34 (m, 15H), 1.75-1.79 (m, 3H), 1.89-1.93 (m, 2H), 3.86 (d, J=6.0 Hz, 2H), 7.28-7.36 (m, 3H). Compound 309C: LC-MS (ESI) m/z: 241 [M+H]$^+$. Compound 309D: LC-MS (ESI) m/z: 500 [M+H]$^+$. Compound 309E: LC-MS (ESI) m/z: 380 [M+H]$^+$. Compound 309: LC-MS (ESI) m/z: 352 [M+H]$^+$. $^1$H-NMR (DMSO-$d_6$, 400 MHz): δ (ppm) 1.04-1.27 (m, 5H), 1.63-1.82 (m, 6H), 3.83 (d, J=6.4 Hz, 2H), 6.59 (dd, J=2.8, 8.8 Hz, 1H), 6.94 (d, J=2.4 Hz, 1H), 7.36 (d, J=8.8 Hz, 1H), 13.35 (s, 1H), 15.31 (s, 1H).

Example 310

Synthesis of 4-(((cis)-4-(4-(trifluoromethyl)phenyl)cyclohexyl)oxy)-1H-1,2,3-triazole-5-carboxylic acid (310)

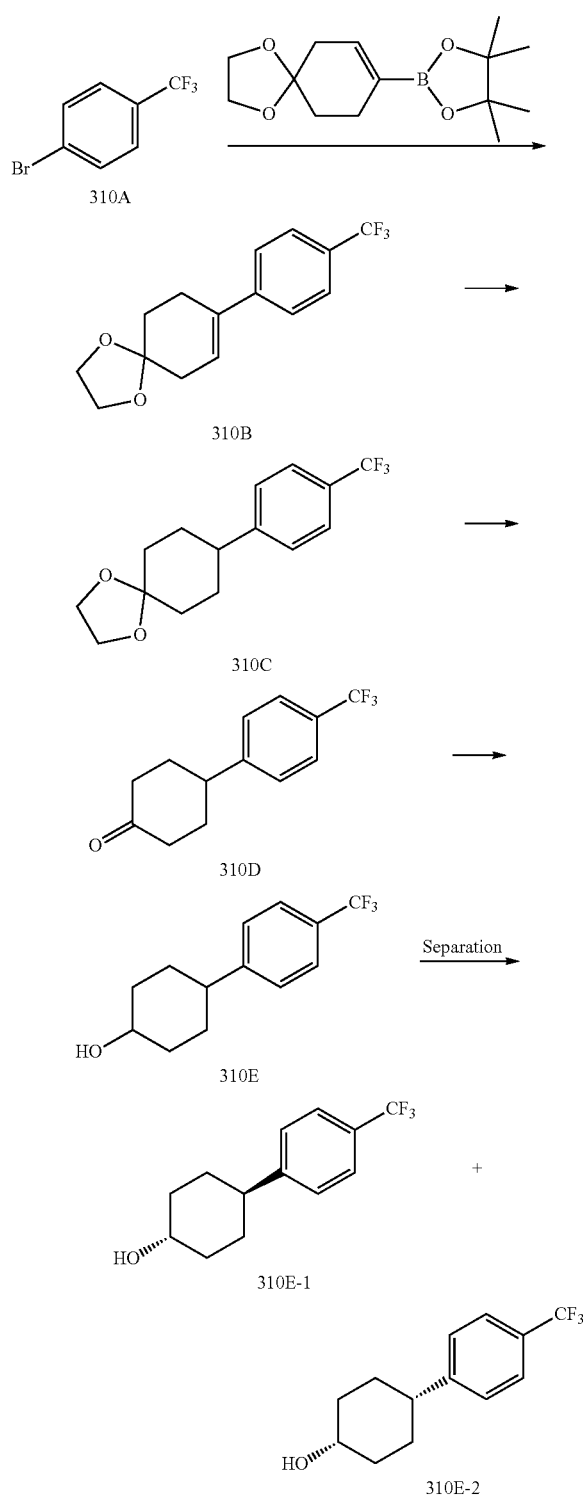

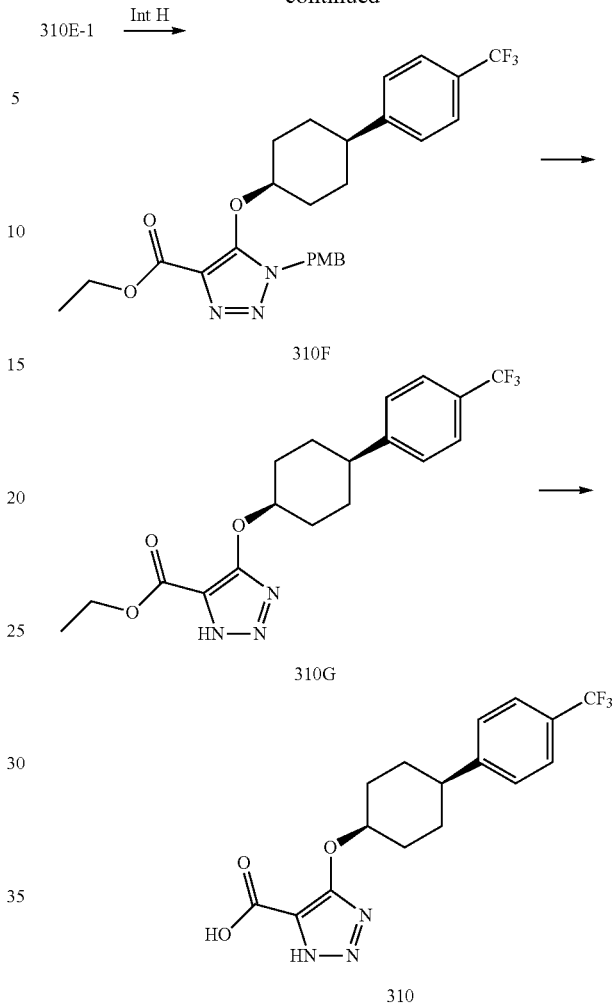

Compounds 310B, 310C, 310D, and 310E were synthesized by employing the procedures described for Compounds 4B, 141, 279D, and 57C using 4,4,5,5-tetramethyl-2-(1,4-dioxaspiro[4.5]dec-7-en-8-yl)-1,3,2-dioxaborolane, Compounds 310A with $K_2CO_3$ as base and 1,4-dioxane/$H_2O$ as solvent, 310B, 310C with 1,4-dioxane as solvent, and 310D in lieu of (4-bromophenyl)boronic acid, Compounds 4A with $Na_2CO_3$ as base and toluene/EtOH/$H_2O$ as solvent, 140, 279C with acetone as solvent, and 57B. Compound 310B: LC-MS (ESI) m/z: 285 [M+H]$^+$; $^1$H-NMR (CDCl$_3$, 400 MHz): δ (ppm) 1.93-1.96 (m, 2H), 2.50 (d, J=2.8 Hz, 2H), 2.66-2.69 (m, 2H), 4.04 (s, 4H), 6.07-6.09 (m, 1H), 7.49 (d, J=8.4 Hz, 2H), 7.56 (d, J=8.4 Hz, 2H). Compound 310C: LC-MS (ESI) m/z: non-ionizable compound under routine conditions used. $^1$H-NMR (CDCl$_3$, 400 MHz): δ (ppm) 1.68-1.90 (m, 8H), 2.60-2.66 (m. 1H), 4.00 (s, 4H), 7.35 (d, J=8.4 Hz, 2H), 7.55 (d, J=8.4 Hz, 2H). Compound 310D: LC-MS (ESI) m/z: 243 [M+H]$^+$; $^1$H-NMR (CDCl$_3$, 400 MHz): δ (ppm) 1.91-2.02 (m, 2H), 2.21-2.26 (m, 2H), 2.52-2.55 (m, 4H), 3.07-3.14 (m, 1H), 7.37 (d, J=8.4 Hz, 2H), 7.59 (d, J=8.4 Hz, 2H).

Compound 310E was purified with flash column chromatography on silica gel (ethyl acetate in petroleum ether, 10% v/v) to afford Compound 310E-1 (trans isomer) and Compound 310E-2 (cis isomer). Compound 310E-1: LC-MS (ESI) m/z: 227 [M−OH]$^+$; $^1$H-NMR (CDCl$_3$, 400 MHz): δ (ppm) 1.39-1.60 (m, 4H), 1.92-1.96 (m, 2H), 2.11-2.15 (m, 2H), 2.53-2.60 (m, 1H), 3.67-3.74 (m, 1H), 7.31 (d, J=8.4

Hz, 2H), 7.55 (d, J=8.4 Hz, 2H). Compound 310E-2: LC-MS (ESI) m/z: 227 [M−OH]⁺; ¹H-NMR (CDCl₃, 400 MHz): δ (ppm) 1.66-1.73 (m, 4H), 1.88-1.98 (m, 4H), 2.58-2.64 (m, 1H), 4.16 (s, 1H), 7.36 (d, J=8.4 Hz, 2H), 7.56 (d, J=8.4 Hz, 2H).

Compounds 310F, 310G, and 310 were synthesized by employing the procedures described for Compounds 90C, 1, and 8F using Compounds 310E-1 with DEAD as coupling reagent, 310F, and 310G in lieu of Compounds 90B with DIAD as coupling reagent, 1E, and 8E. Compound 310F: LC-MS (ESI) m/z: 504 [M+H]⁺; ¹H-NMR (CDCl₃, 400 MHz): 1.24-1.34 (m, 2H), 1.44 (t, J=7.2 Hz, 3H), 1.62-1.71 (m, 4H), 2.12-2.15 (m, 2H), 2.61-2.67 (m, 1H), 3.75 (s, 3H), 4.41 (q, J=7.2 Hz, 2H), 5.38 (s, 2H), 5.49 (s, 1H), 6.84 (d, J=8.4 Hz, 2H), 7.19-7.27 (m, 4H), 7.57 (d, J=8.4 Hz, 2H). Compound 310G: LC-MS (ESI) m/z: 384 [M+H]⁺. Compound 310: LC-MS (ESI) m/z: 356 [M+H]⁺; ¹H-NMR (CD₃OD, 400 MHz): 1.67-1.81 (m, 4H), 2.00-2.11 (m, 2H), 2.24 (d, J=14.4 Hz, 2H), 2.72-2.79 (m, 1H), 5.07 (s, 1H), 7.47 (d, J=8.4 Hz, 2H), 7.58 (d, J=8.4 Hz, 2H).

Example 311

Synthesis of 4-(spiro[4.5]decan-8-ylthio)-1H-1,2,3-triazole-5-carboxylic acid 2,2,2-trifluoroacetate (311)

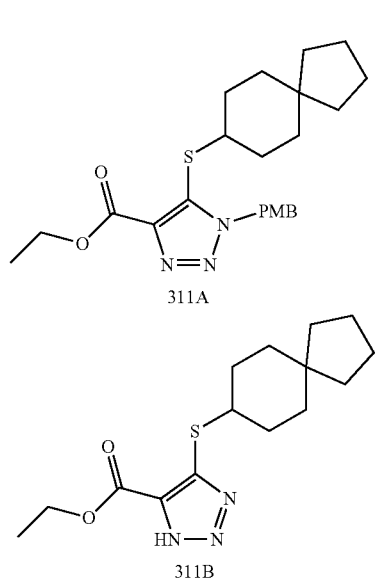

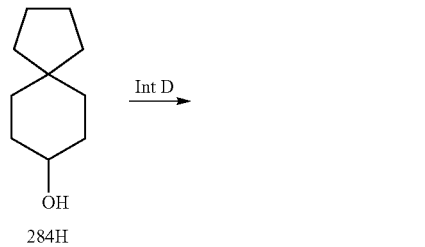

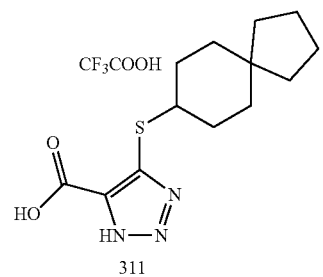

Compounds 311A, 311B, and 311 were synthesized by employing the procedures described for Compounds 90C, 1, and 8F using Intermediate D, Compounds 284H, 311A, and 311B in lieu of Intermediate H, Compounds 90B, 1E, and 8E. Compound 311A: LC-MS (ESI) m/z: 430 [M+H]⁺. Compound 311B: LC-MS (ESI) m/z: 310 [M+H]⁺. Compound 311: LC-MS (ESI) m/z: 282 [M+H]⁺; ¹H-NMR (DMSO-d₆, 400 MHz): δ (ppm) 1.31-1.40 (m, 6H), 1.47-1.55 (m, 8H), 1.91-1.93 (m, 2H), 3.52-3.54 (m, 1H).

Example 312

Synthesis of 4-(((4'-(trifluoromethoxy)-[1,1'-biphenyl]-4-yl)thio)methyl)-1H-1,2,3-triazole-5-carboxylic acid 2,2,2-trifluoroacetate (312)

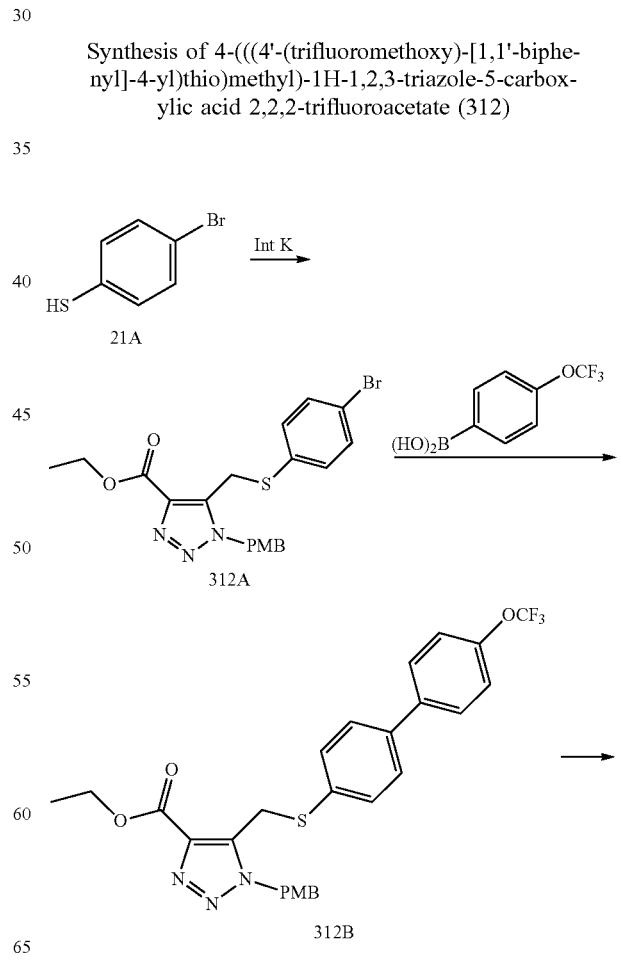

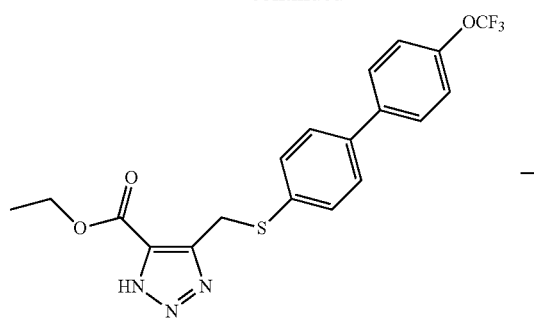

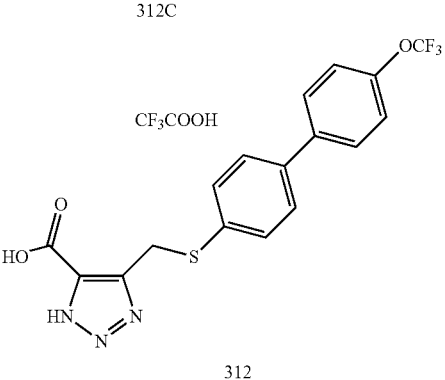

Compounds 312A, 312B, 312C, and 312 were synthesized by employing the procedures described for Compounds 243B, 4B, 1, and 8F using Compounds 21A, 312A with 1,4-dioxane/H₂O as solvent, 312B, and 312C in lieu of Compounds 243A, 4A with toluene/EtOH/H₂O as solvent, 1E, and 8E. Compound 312A: LC-MS (ESI) m/z: 462 [M+H]⁺. Compound 312B: LC-MS (ESI) m/z: 544 [M+H]⁺. Compound 312C: LC-MS (ESI) m/z: 424 [M+H]⁺. Compound 312: LC-MS (ESI) m/z: 396 [M+H]⁺; ¹H-NMR (DMSO-d₆, 400 MHz): δ (ppm) 4.53 (s, 2H), 7.43-7.47 (m, 4H), 7.63 (d, J=8.0 Hz, 2H), 7.78 (d, J=8.0 Hz, 2H).

Example 313

Synthesis of (propionyloxy)methyl 4-((4'-(piperidin-1-yl)-[1,1'-biphenyl]-4-yl)thio)-1H-1,2,3-triazole-5-carboxylate 2,2,2-trifluoroacetate (313)

Compounds 313A and 313 were synthesized by employing the procedures described for Compounds 54C and 256 using Compounds 267B, 278B with Et₃N as base and DMF/THF as solvent and adding NaI, and 313A in lieu of chloromethyl pivalate, Compounds 54B with Na₂CO₃ as base and DMF as solvent and without NaI, and 256D. Compound 313A: LC-MS (ESI) m/z: 709 [M+H]⁺; ¹H-NMR (CDCl₃, 400 MHz): δ (ppm) 1.15 (t, J=7.2 Hz, 3H), 1.59-1.65 (m, 2H), 1.70-1.76 (m, 4H), 2.35-2.42 (m, 2H), 3.22-3.24 (m, 4H), 5.96 (s, 2H), 6.98-7.04 (m, 8H), 7.20-7.30 (m, 9H), 7.40-7.47 (m, 6H). Compound 313: LC-MS (ESI) m/z: 467 [M+H]⁺; (CDCl₃, 400 MHz): δ (ppm) 1.15 (t, J=7.2 Hz, 3H), 1.72 (brs, 2H), 2.05-2.10 (m, 4H), 2.37-7.43 (m, 2H), 3.48 (brs, 4H), 5.99 (s, 2H), 7.41-7.47 (m, 2H), 7.54-7.57 (m, 6H).

Example 314

Synthesis of 4-((3-(4-(trifluoromethoxy)phenyl)cyclopentyl)thio)-1H-1,2,3-triazole-5-carboxylic acid (314)

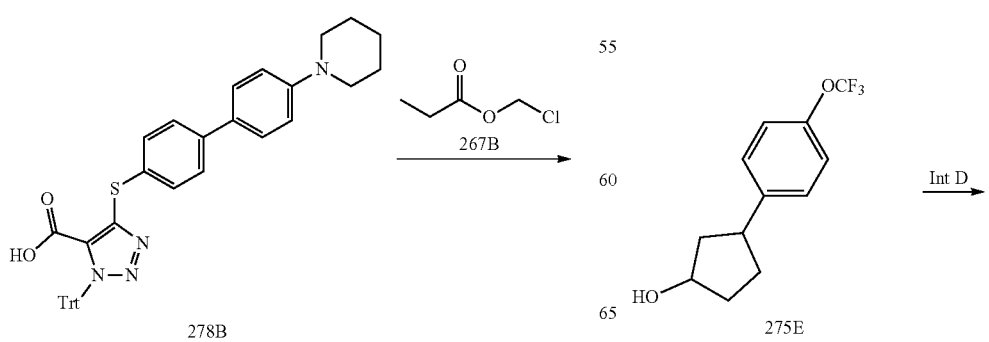

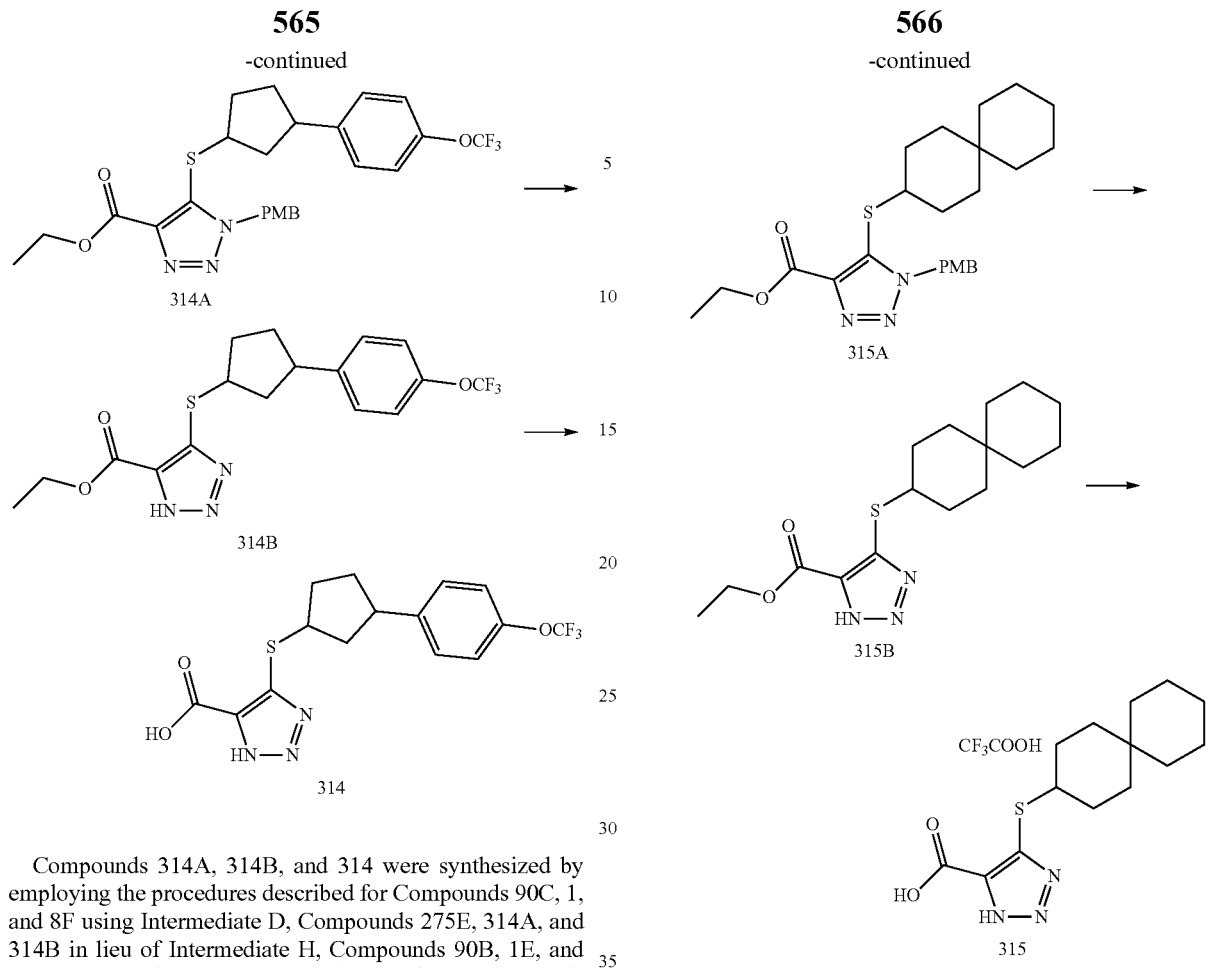

Compounds 314A, 314B, and 314 were synthesized by employing the procedures described for Compounds 90C, 1, and 8F using Intermediate D, Compounds 275E, 314A, and 314B in lieu of Intermediate H, Compounds 90B, 1E, and 8E. Compound 314A: LC-MS (ESI) m/z: 522 [M+H]$^+$. Compound 314B: LC-MS (ESI) m/z: 402 [M+H]$^+$; $^1$H-NMR (CD$_3$OD, 400 MHz): δ (ppm) 1.40 (t, J=7.2 Hz, 3H), 1.59-1.92, 2.11-2.43 (m, 5H), 2.47-2.52, 2.66-2.73 (m, 1H), 3.17-3.23, 3.36-3.42 (m, 1H), 4.04-4.23 (m, 1H), 4.36-4.42 (m, 2H), 7.17-7.20 (m, 2H), 7.36-7.39 (m, 2H). Compound 314: LC-MS (ESI) m/z: 374 [M+H]$^+$; $^1$H-NMR (CD$_3$OD, 400 MHz): δ (ppm) 1.62-1.89, 2.10-2.31 (m, 5H), 2.39-2.48, 2.62-2.70 (m, 1H), 3.14-3.23, 3.37-3.45 (m, 1H), 4.03-4.20 (m, 1H), 7.16-7.19 (m, 2H), 7.35-7.39 (m, 2H).

Example 315

Synthesis of 4-(spiro[5.5]undecan-3-ylthio)-1H-1,2,3-triazole-5-carboxylic acid 2,2,2-trifluoroacetate (315)

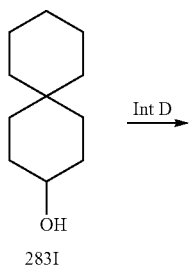

Compounds 315A, 315B, and 315 were synthesized by employing the procedures described for Compounds 90C, 1, and 8F using Intermediate D, Compounds 283I, 315A, and 315B in lieu of Intermediate H, Compounds 90B, 1E, and 8E. Compound 315A: LC-MS (ESI) m/z: 444 [M+H]$^+$. Compound 315B: LC-MS (ESI) m/z: 324 [M+H]$^+$. Compound 315: LC-MS (ESI) m/z: 296 [M+H]$^+$; $^1$H-NMR (DMSO-d$_6$, 400 MHz): δ (ppm) 1.15-1.21 (m, 4H), 1.35 (brs, 8H), 1.47-1.62 (m, 4H), 1.84-1.87 (m, 2H), 3.52 (brs, 1H).

Example 316

Synthesis of 4-(((4-(piperidin-1-yl)naphthalen-1-yl)methyl)thio)-1H-1,2,3-triazole-5-carboxylic acid 2,2,2-trifluoroacetate (316)

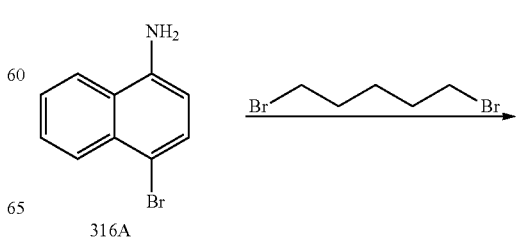

567
-continued

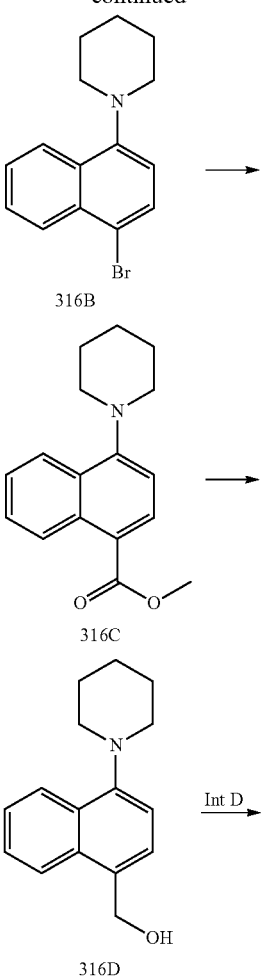

316B

316C

316D

316E

316F

568
-continued

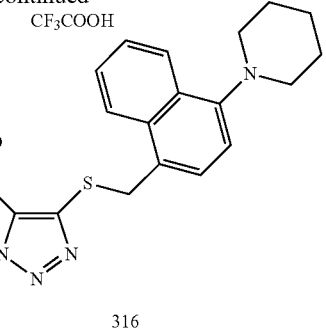

316

A mixture of 4-bromonaphthalen-1-amine (316A) (2.21 g, 10 mmol), 1,5-dibromopentane (2.51 g, 11 mmol), and potassium carbonate (1.52 g, 11 mmol) in DMF (80 mL) was stirred at 120° C. for 16 hours. After cooled down to room temperature, the mixture was diluted with ice-water (90 mL) and extracted with ethyl acetate (80 mL×3). The combined organic phases was washed with water (100 mL) and brine (40 mL), dried over anhydrous sodium sulfate, filtered, concentrated, and purified with flash column chromatography on silica gel (ethyl acetate in petroleum ether, 0% to 20% v/v) to afford Compound 316B. LC-MS (ESI) m/z: 290 [M+H]$^+$. $^1$H-NMR (CDCl$_3$, 400 MHz): δ (ppm) 1.56-1.70 (m, 2H), 1.83-1.88 (m, 4H), 3.03 (s, 4H), 6.92 (d, J=8.4 Hz, 1H), 7.52-7.61 (m, 2H), 7.68 (d, J=8.0 Hz, 1H), 8.23 (t, J=8.0 Hz, 2H).

To a mixture of Compound 316B (1.1 g, 3.8 mmol) and TEA (10 mL) in anhydrous DMF (12 mL) and MeOH (20 mL) was added Pd(OAc)$_2$ (220 mg, 0.98 mmol) and Xantphos (1.15 g, 1.98 mmol) and stirred at 90° C. under CO (5 atm) for 24 hours. The mixture was concentrated under reduced pressure. The residue was diluted with water (50 mL) and extracted with ethyl acetate (50 mL×3). The combined organic layers was washed with brine (100 mL), dried over anhydrous sodium sulfate, concentrated, and purified with flash column chromatography on silica gel (ethyl acetate in petroleum ether, 0% to 15% v/v) to afford Compound 316C. LC-MS (ESI) m/z: 270 [M+H]$^+$.

Compounds 316D, 316E, 316F, and 316 were synthesized by employing the procedures described for Compounds 283C, 90C, 8F, and 57E using Compounds 316C, Intermediate D, 316D with DEAD as coupling reagent, 316E, and 316F in lieu of Compounds 283B, Intermediate H, 90B with DIAD as coupling reagent, 8E, and 57D. Compound 316D: LC-MS (ESI) m/z: 242 [M+H]$^+$. Compound 316E: LC-MS (ESI) m/z: 517 [M+H]$^+$. Compound 316F: LC-MS (ESI) m/z: 489 [M+H]$^+$. Compound 316: LC-MS (ESI) m/z: 369 [M+H]$^+$; $^1$H-NMR (DMSO-d$_6$, 400 MHz): δ (ppm) 1.60 (s, 2H), 1.76-1.79 (m, 4H), 2.97 (br, 4H), 4.78 (s, 2H), 7.03-7.05 (m, 1H), 7.50-7.58 (m, 3H), 8.10-8.17 (m, 2H).

Example 317

Synthesis of ((cyclohexanecarbonyl)oxy)methyl 4-((4'-(piperidin-1-yl)-[1,1'-biphenyl]-4-yl)thio)-1H-1,2,3-triazole-5-carboxylate 2,2,2-trifluoroacetate (317)

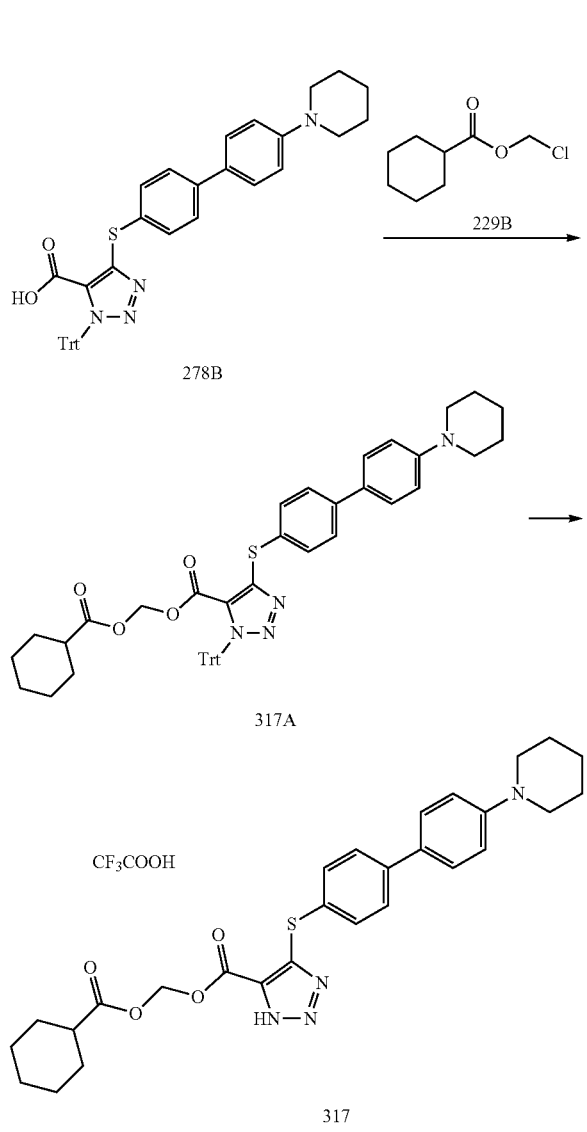

Example 318

Synthesis of 4-((4-chloro-3-(trifluoromethoxy)phenyl)thio)-1H-1,2,3-triazole-5-carboxylic acid (318)

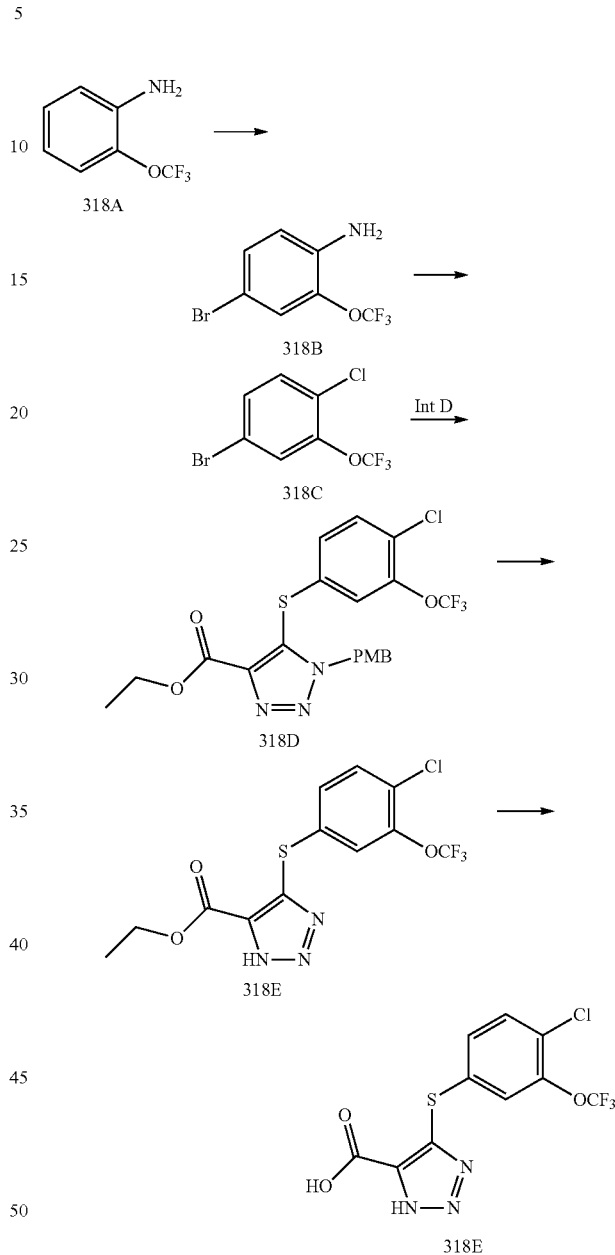

Compounds 317A and 317 were synthesized by employing the procedures described for Compounds 54C and 256 using Compounds 229B, 278B with Et₃N as base and DMF/THF as solvent and adding NaI, and 317A in lieu of chloromethyl pivalate, Compounds 54B with Na₂CO₃ as base and DMF as solvent, and without NaI and 256D. Compound 317A: LC-MS (ESI) m/z: 763 [M+H]⁺; ¹H-NMR (CDCl₃, 400 MHz): δ (ppm) 1.22-1.29 (m, 6H), 1.59-1.63 (m, 2H), 1.70-1.76 (m, 6H), 1.87-1.93 (m, 2H), 2.36-2.38 (m, 1H), 3.21-3.25 (m, 4H), 5.30 (s, 2H), 6.98-7.04 (m, 8H), 7.22-7.30 (m, 9H), 7.40-7.47 (m, 6H). Compound 317: LC-MS (ESI) m/z: 521 [M+H]⁺; ¹H-NMR (DMSO-d₆, 400 MHz): δ (ppm) 1.11-1.35 (m, 5H), 1.55-1.80 (m, 11H), 2.32-2.41 (m, 1H), 3.34 (brs, 4H), 5.94 (s, 2H), 7.24-7.29 (m, 2H), 7.51-7.54 (m, 2H), 7.65-7.70 (m, 4H).

To a solution of 2-(trifluoromethoxy)aniline (318A) (2.655 mg, 15 mmol) in acetic acid (6 mL) was added NBS (2.94 g, 16.5 mmol) at 0° C. and stirred at room temperature overnight. It was concentrated under reduced pressure. The residue was diluted with ethyl acetate (100 mL), washed with water (30 mL) and brine (30 mL), dried over anhydrous sodium sulfate, concentrated, and purified with flash column chromatography on silica gel (ethyl acetate in petroleum ether, 20% v/v) to afford Compound 318B. LC-MS (ESI) m/z: 256 [M+H]⁺; ¹H-NMR (CDCl₃, 400 MHz): δ (ppm) 3.89 (s, 2H), 6.67 (d, J=8.8 Hz, 1H), 7.18 (dd, J=8.8, 2.4 Hz, 1H), 7.28 (d, J=2.4 Hz, 1H).

Compounds 318C, 318D, 318E, and 318 were synthesized by employing the procedures described for Compounds 30B, 35D, 1, and 8F using Compounds 318B with tert-butyl nitrite, 318C with Xantphos as ligand, 318D, and 318E in lieu of Compounds 30A with isoamyl nitrite, 35C with X-phos as ligand, 1E, and 8E. Compound 318C: LC-MS (ESI) m/z: Non-ionizable compound under routine conditions used; ¹H-NMR (CDCl₃, 400 MHz): δ (ppm) 7.34-7.42 (m, 2H), 7.50 (s, 1H). Compound 318D: LC-MS (ESI) m/z: 488 [M+H]⁺; ¹H-NMR (CDCl₃, 400 MHz): δ (ppm) 1.33 (t, J=7.2 Hz, 3H), 3.75 (s, 3H), 4.37 (q, J=7.2 Hz, 2H), 5.62 (s, 2H), 6.66-6.69 (m, 1H), 6.72 (d, J=8.4 Hz, 2H), 6.95 (s, 1H), 7.11 (d, J=8.4 Hz, 2H), 7.19 (d, J=8.4 Hz, 1H). Compound 318E: LC-MS (ESI) m/z: 368 [M+H]⁺. Compound 318: LC-MS (ESI) m/z: 340 [M+H]⁺; ¹H-NMR (CD₃OD, 400 MHz): δ (ppm) 7.45 (dd, J=8.8, 2.0 Hz, 1H), 7.56-7.59 (m, 2H).

Example 319

Synthesis of 4-((4'-(4,4-difluoropiperidin-1-yl)-[1,1'-biphenyl]-4-yl)thio)-1H-1,2,3-triazole-5-carboxylic acid 2,2,2-trifluoroacetate (319)

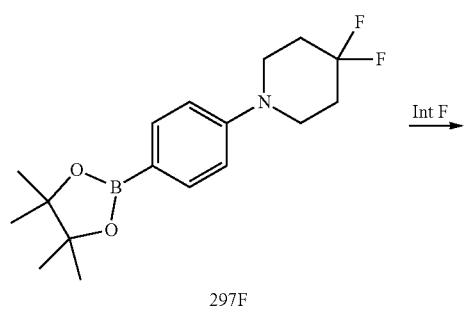

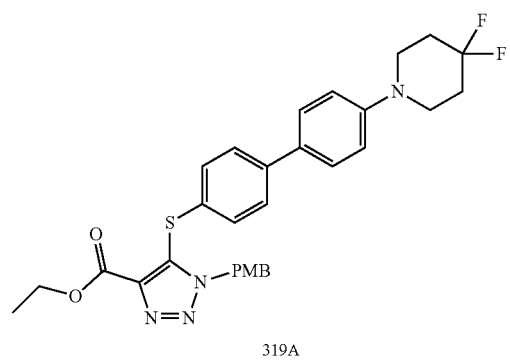

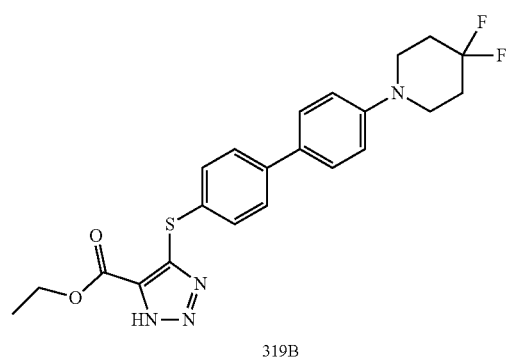

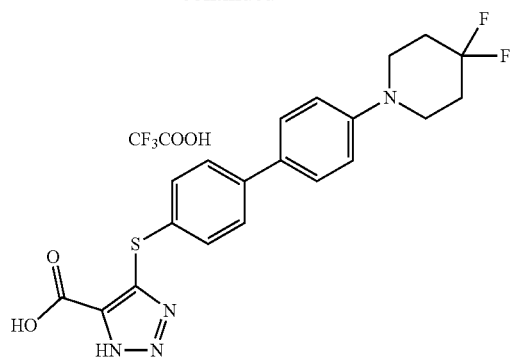

Compounds 319A, 319B, and 319 were synthesized by employing the procedures described for Compounds 4B, 1, and 2 using Intermediate F, Compounds 297F with K₂CO₃ as base and 1,4-dioxane/H₂O as solvent, 319A, and 319B in lieu of Compounds 4A, (4-bromophenyl)boronic acid with Na₂CO₃ as base and toluene/EtOH/H₂O as solvent, 1E, and 1. Compound 319A: LC-MS (ESI) m/z: 565 [M+H]⁺. Compound 319B: LC-MS (ESI) m/z: 445 [M+H]⁺. Compound 319: LC-MS (ESI) m/z: 417 [M+H]⁺; ¹H-NMR (DMSO-d₆, 400 MHz): δ (ppm) 2.00-2.10 (m, 4H), 3.41 (t, J=5.6 Hz, 4H), 7.08 (d, J=8.8 Hz, 2H), 7.49-7.51 (m, 2H), 7.56 (d, J=9.2 Hz, 2H), 7.63 (d, J=9.2 Hz, 2H).

Example 320

Synthesis of 4-((5-(trifluoromethoxy)-2,3-dihydro-1H-inden-2-yl)thio)-1H-1,2,3-triazole-5-carboxylic acid (320)

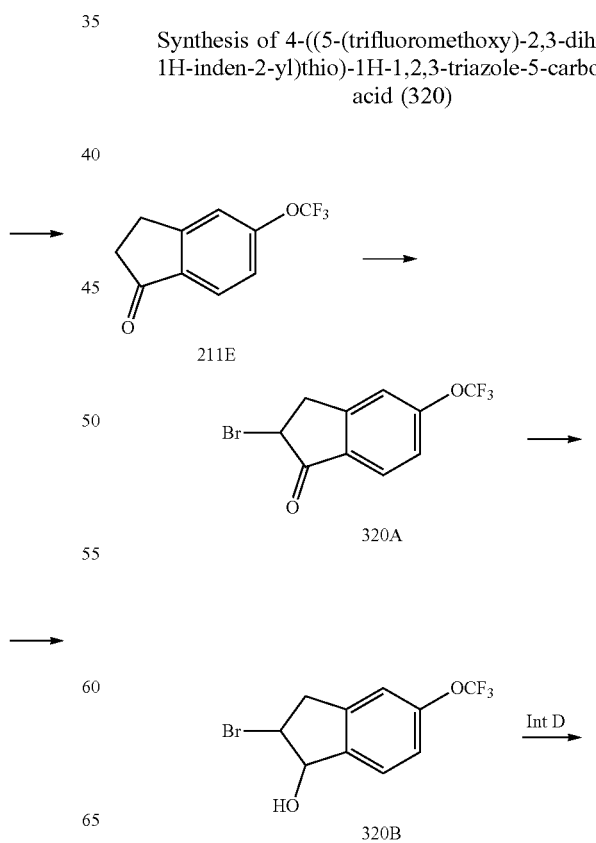

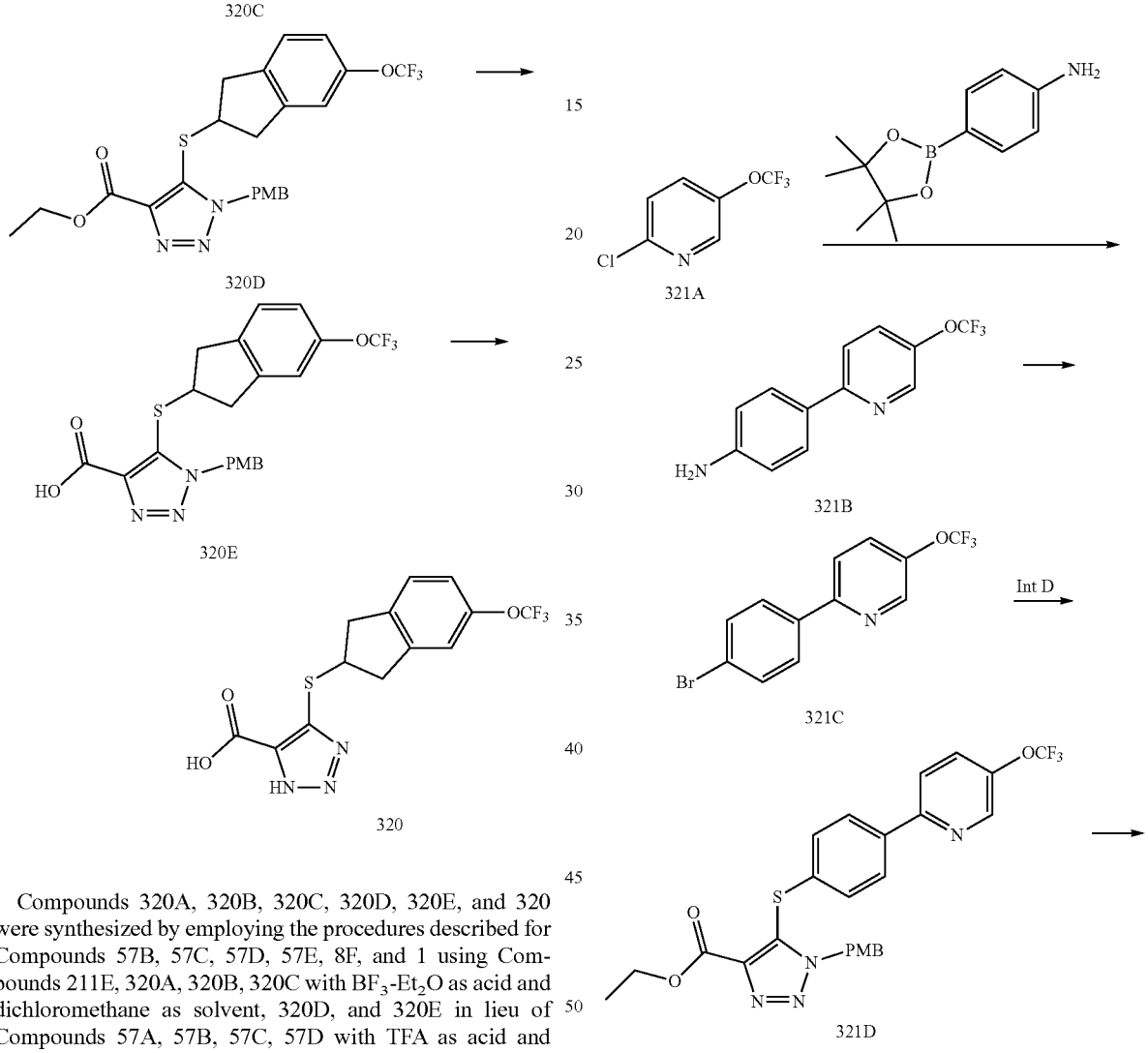

4.41-4.48 (m, 1H), 7.16 (d, J=8.0 Hz, 1H), 7.27 (s, 1H), 7.36 (d, J=8.4 Hz, 1H), 13.33 (bs, 1H), 15.62 (bs, 1H).

Example 321

Synthesis of 4-((4-(5-(trifluoromethoxy)pyridin-2-yl)phenyl)thio)-1H-1,2,3-triazole-5-carboxylic acid 2,2,2-trifluoroacetate (321)

Compounds 320A, 320B, 320C, 320D, 320E, and 320 were synthesized by employing the procedures described for Compounds 57B, 57C, 57D, 57E, 8F, and 1 using Compounds 211E, 320A, 320B, 320C with BF₃-Et₂O as acid and dichloromethane as solvent, 320D, and 320E in lieu of Compounds 57A, 57B, 57C, 57D with TFA as acid and solvent, 8E, and 1E. Compound 320A: LC-MS (ESI) m/z: 295 [M+H]⁺. Compound 320B: LC-MS (ESI) m/z: 279 [M−OH]⁺; ¹H-NMR (CDCl₃, 400 MHz): δ 2.46 (d, J=9.2 Hz, 1H), 3.36-3.49 (m, 2H), 4.93-4.99 (m, 2H), 7.12-7.17 (m, 2H), 7.46 (d, J=8.0 Hz, 1H). Compound 320C: LC-MS (ESI) m/z: 510 [M+H]⁺; ¹H-NMR (CDCl₃, 400 MHz): δ 1.44 (t, J=7.2 Hz, 3H), 2.65-2.71 (m, 1H), 3.08-3.14 (m, 1H), 3.42 (d, J=5.2 Hz, 1H), 3.59-3.65 (m, 1H), 3.77 (s, 3H), 4.47 (q, J=7.2 Hz, 2H), 4.95-4.99 (m, 1H), 5.65 (d, J=2.4 Hz, 2H), 6.85 (d, J=8.8 Hz, 2H), 6.95 (s, 1H), 7.10 (d, J=8.0 Hz, 1H), 7.25 (d, J=8.8 Hz, 2H), 7.33 (d, J=8.0 Hz, 1H). Compound 320D: LC-MS (ESI) m/z: 494 [M+H]⁺ Compound 320E: LC-MS (ESI) m/z: 466 [M+H]⁺. Compound 320: LC-MS (ESI) m/z: 346 [M+H]⁺; ¹H-NMR (DMSO-d₆, 400 MHz): δ (ppm) 2.92-3.01 (m, 2H), 3.48-3.57 (m, 2H),

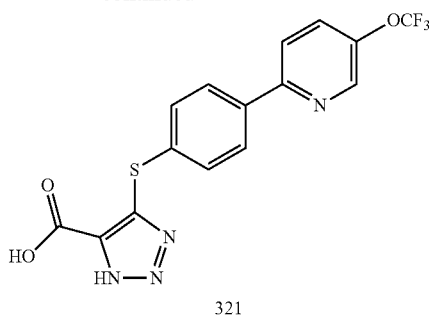

321

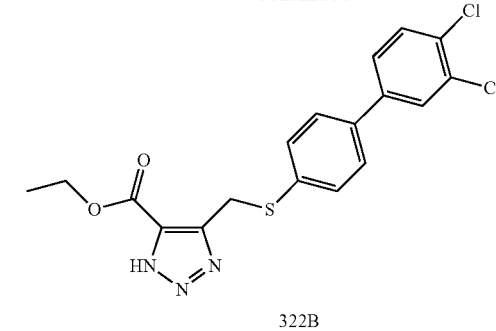

322B

Compounds 321B, 321C, 321D, 321E, and 321 were synthesized by employing the procedures described for Compounds 4B, 30B, 35D, 1, and 8F using 4-(4,4,5,5-tetramethyl-1,3,2-dioxaborolan-2-yl)aniline, Compounds 321A with 1,4-dioxane/H$_2$O as solvent, 321B with isopentyl nitrite and CuBr$_2$, 321C with Xantphos as ligand, 320D, and 320E in lieu of (4-bromophenyl)boronic acid, Compounds 4A with toluene/EtOH/H$_2$O as solvent, 30A with isoamyl nitrite and CuCl$_2$, 35C with X-phos as ligand, 1E, and 8E. Compound 321B: LC-MS (ESI) m/z: 255 [M+H]$^+$. Compound 321C: LC-MS (ESI) m/z: 318 [M+H]$^+$. Compound 321D: LC-MS (ESI) m/z: 531 [M+H]$^+$. Compound 321E: LC-MS (ESI) m/z: 411 [M+H]$^+$. Compound 321: LC-MS (ESI) m/z: 383 [M+H]$^+$; $^1$H-NMR (CD$_3$OD, 400 MHz): δ (ppm) 7.46-7.49 (m, 2H), 7.73-7.76 (m, 1H), 7.90-7.96 (m, 3H), 8.52 (s, 1H).

Example 322

Synthesis of 4-(((3',4'-dichloro-[1,1'-biphenyl]-4-yl)thio)methyl)-1H-1,2,3-triazole-5-carboxylic acid 2,2,2-trifluoroacetate (322)

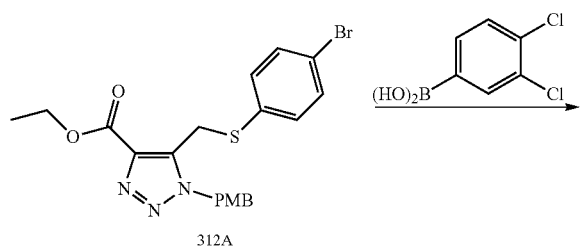

312A

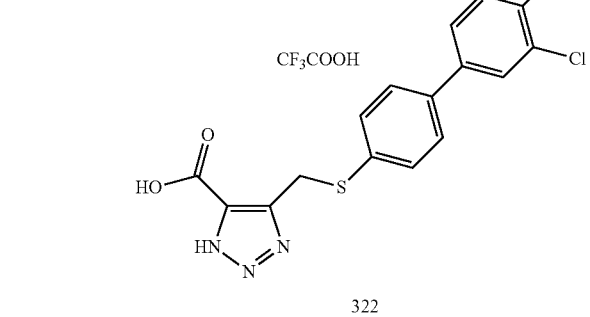

322

Compounds 322A, 322B, and 322 were synthesized by employing the procedures described for Compounds 4B, 57E, and 8F using 3,4-dichlorophenylboronic acid, Compounds 312A with 1,4-dioxane/H$_2$O as solvent, 322A, and 322B in lieu of (4-bromophenyl)boronic acid, Compounds 4A with toluene/EtOH/H$_2$O as solvent, 57D, and 8E. Compound 322A: LC-MS (ESI) m/z: 528 [M+H]$^+$; $^1$H-NMR: (CDCl$_3$, 400 MHz): δ (ppm) 1.31 (t, J=7.2 Hz, 3H), 3.80 (s, 3H), 4.26-4.28 (m, 4H), 5.61 (s, 2H), 6.87 (d, J=8.8 Hz, 2H), 7.14 (d, J=8.8 Hz, 2H), 7.33-7.36 (m, 3H), 7.41-7.44 (m, 2H), 7.49-7.51 (m, 1H), 7.62 (d, J=2.0 Hz, 1H). Compound 322B: LC-MS (ESI) m/z: 408 [M+H]$^+$. Compound 322: LC-MS (ESI) m/z: 380 [M+H]$^+$; $^1$H-NMR (CD$_3$OD, 400 MHz): δ (ppm) 4.62 (s, 2H), 7.43-7.46 (m, 2H), 7.54-7.59 (m, 4H), 7.78 (s, 1H).

Example 323

Synthesis of 4-((1-(3,4-dichlorophenyl)piperidin-4-yl)thio)-1H-1,2,3-triazole-5-carboxylic acid 2,2,2-trifluoroacetate (323)

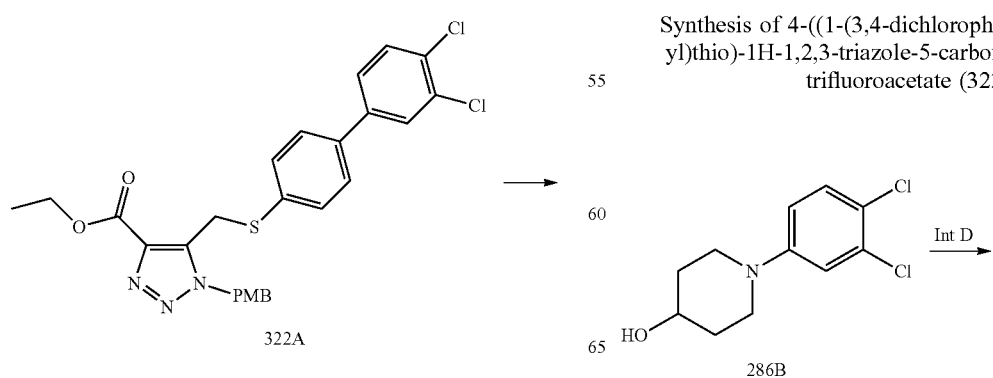

286B

577
-continued

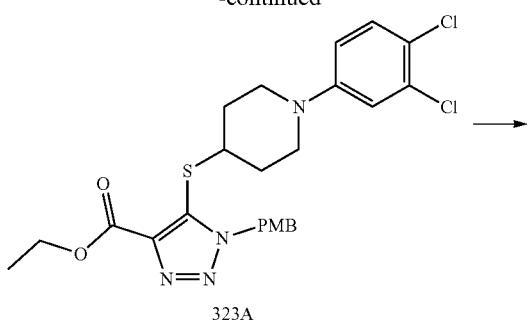
323A

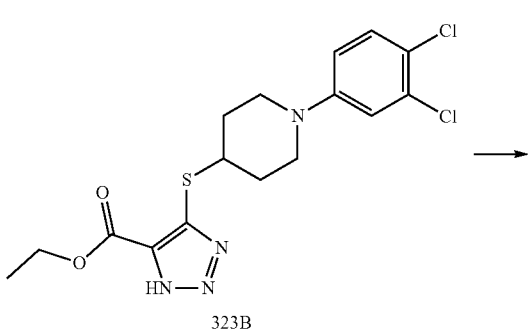
323B

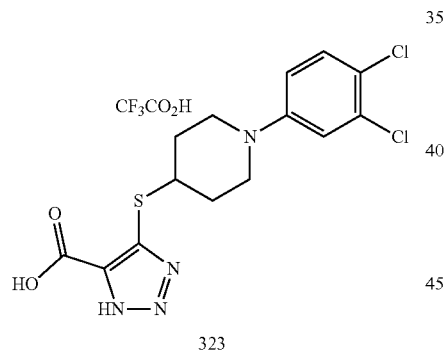
323

Compounds 323A, 323B, and 323 were synthesized by employing the procedures described for Compounds 90C, 1, and 8F using Intermediate D, Compounds 286B with DEAD as coupling reagent, 323A, and 323B in lieu of Intermediate H, Compounds 90B with DIAD as coupling reagent, 1E, and 8E. Compound 323A: LC-MS (ESI) m/z: 521 [M+H]$^+$; $^1$H-NMR (CDCl$_3$, 400 MHz): δ (ppm) 1.44 (t, J=7.2 Hz, 3H), 1.57-1.61 (m, 2H), 1.78-1.83 (m, 2H), 2.70-2.77 (m, 2H), 3.44-3.52 (m, 3H), 3.78 (s, 3H), 4.46 (q, J=6.0 Hz, 2H), 5.62 (s, 2H), 6.68 (dd, J=8.8, 2.8 Hz, 1H), 6.85 (d, J=8.8 Hz, 2H), 6.90 (d, J=2.8 Hz, 1H), 7.26 (d, J=8.8 Hz, 2H), 7.29 (d, J=8.8 Hz, 1H). Compound 323B: LC-MS (ESI) m/z: 401 [M+H]$^+$. Compound 323: LC-MS (ESI) m/z: 373 [M+H]$^+$; $^1$H-NMR (CD$_3$OD, 400 MHz): δ (ppm) 1.77-1.85 (m, 2H), 2.21-2.24 (m, 2H), 2.96-3.02 (m, 2H), 3.65-3.69 (m, 2H), 3.77-3.83 (m, 1H), 6.92 (d, J=8.8 Hz, 1H), 7.11 (s, 1H), 7.32 (d, J=8.8 Hz, 1H).

578
Example 324

Synthesis of 4-((1-(4-(trifluoromethoxy)phenyl)piperidin-4-yl)thio)-1H-1,2,3-triazole-5-carboxylic acid (324)

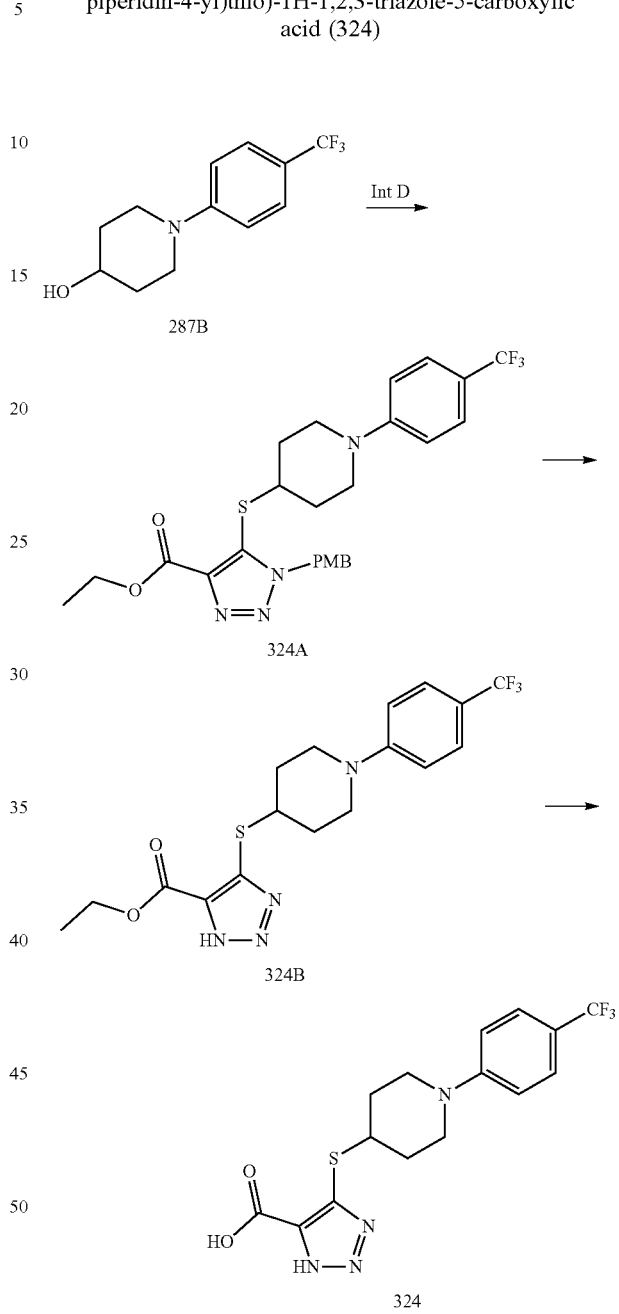

Compounds 324A, 324B, and 324 were synthesized by employing the procedures described for Compounds 90C, 1, and 2 using Intermediate D, Compounds 287B with DEAD as coupling reagent, 324A, and 324B in lieu of Intermediate H, Compounds 90B with DIAD as coupling reagent, 1E, and 1. Compound 324A: LC-MS (ESI) m/z: 521 [M+H]$^+$. Compound 324B: LC-MS (ESI) m/z: 401 [M+H]$^+$. Compound 324: LC-MS (ESI) m/z: 373 [M+H]$^+$; $^1$H-NMR (DMSO-d$_6$, 400 MHz): δ (ppm) 1.65-1.68 (m, 2H), 2.12-2.15 (m, 2H), 3.06 (t, J=10.4 Hz, 2H), 3.79-3.84 (m, 3H), 7.06 (d, J=8.8 Hz, 2H), 7.48 (d, J=8.8 Hz, 2H).

Example 325

Synthesis of 4-((1-(3,5-dichlorophenyl)piperidin-4-yl)thio)-1H-1,2,3-triazole-5-carboxylic acid 2,2,2-trifluoroacetate (325)

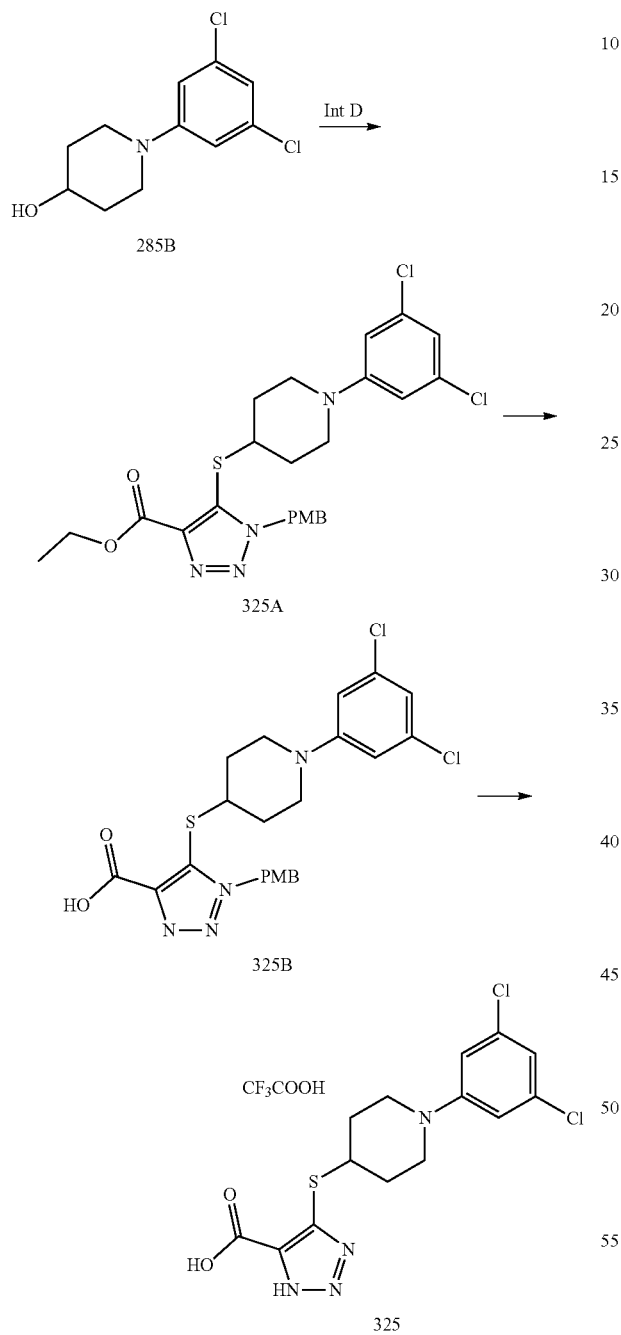

Compounds 325A, 325B, and 325 were synthesized by employing the procedures described for Compounds 90C, 8F, and 1 using Intermediate D, Compounds 285B with DEAD as coupling reagent, 325A, and 325B in lieu of Intermediate H, Compounds 90B with DIAD as coupling reagent, 8E, and 1E. Compound 325A: LC-MS (ESI) m/z: 521 [M+H]$^+$. Compound 325B: LC-MS (ESI) m/z: 493 [M+H]$^+$. Compound 325: LC-MS (ESI) m/z: 373 [M+H]$^+$; $^1$H-NMR (DMSO-d$_6$, 400 MHz): δ (ppm) 1.63-1.68 (m, 2H), 2.08-2.12 (m, 2H), 2.98-3.03 (m, 2H), 3.72-3.75 (m, 3H), 6.84 (s, 1H), 6.95 (s, 2H), 13.34 (s, 1H), 15.52 (s, 1H).

Example 326

Synthesis of 4-((4-(3-(trifluoromethoxy)phenyl)cyclohexyl)thio)-1H-1,2,3-triazole-5-carboxylic acid (326)

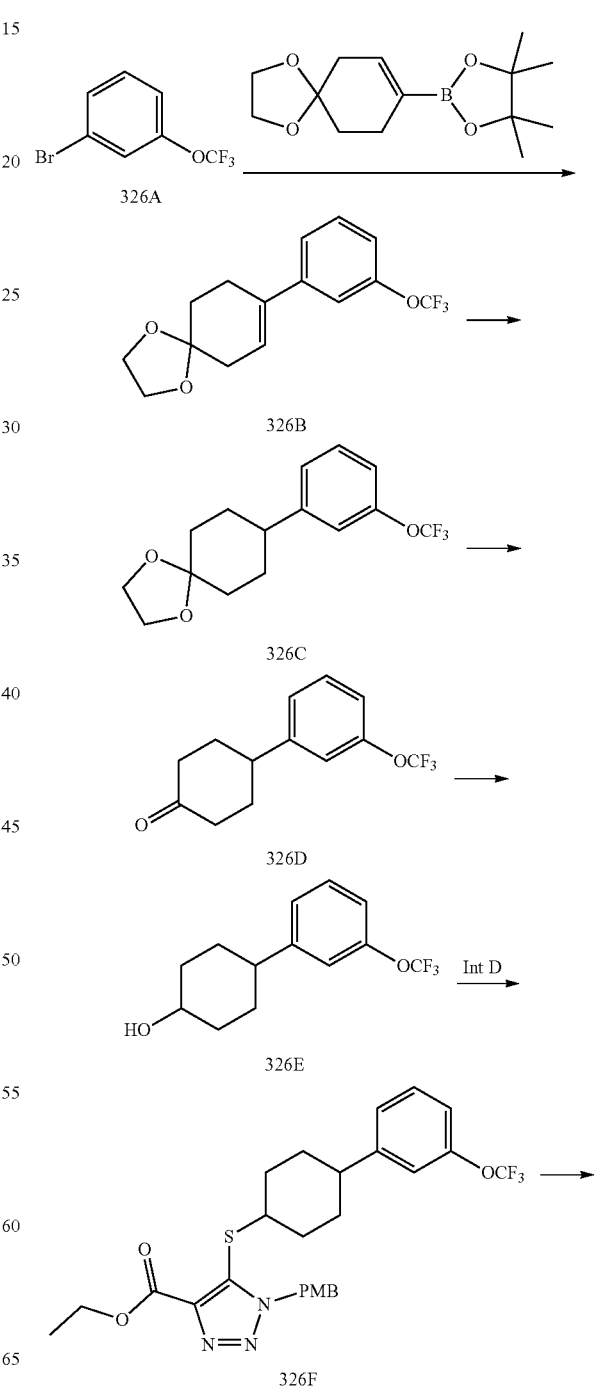

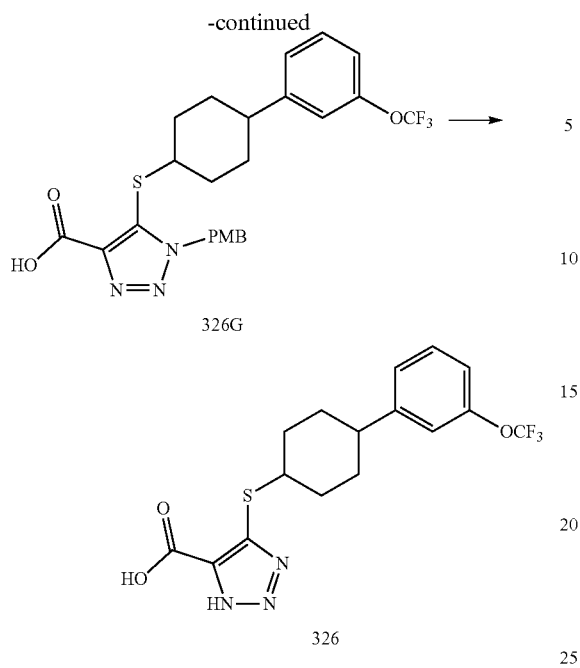

326G

326

Compounds 326B, 326C, 326D, 326E, 326F, 326G, and 326 were synthesized by employing the procedures described for Compounds 4B, 141, 279D, 57C, 90C, 8F, and 1 using 4,4,5,5-tetramethyl-2-(1,4-dioxaspiro[4.5]dec-7-en-8-yl)-1,3,2-dioxaborolane, Compounds 326A with 1,4-dioxane/H₂O as solvent, 326B with MeOH as solvent, 326C with TFA as acid and dichloromethane as solvent, 326D, Intermediate D, 326E, 326F, and 326G in lieu of (4-bromophenyl)boronic acid, Compounds 4A with toluene/EtOH/H₂O as solvent, 140 with EtOAc as solvent, 279C with HCl as acid and acetone as solvent, 57B, Intermediate H, 90B, 8E, and 1E. Compound 326B: LC-MS (ESI) m/z: 301 [M+H]⁺. Compound 326C: LC-MS (ESI) m/z: 303 [M+H]⁺. Compound 326D: LC-MS (ESI) m/z: 259 [M+H]⁺. Compound 326E: LC-MS (ESI) m/z: 243 [M−OH]⁺. ¹H-NMR (CDCl₃, 400 MHz): δ (ppm) 1.42-1.58 (m, 2H), 1.58-1.71 (m, 3H), 1.93-1.97 (m, 2H), 2.10-2.14 (m, 2H), 2.49-2.57 (m, 1H), 3.67-3.74 (m, 1H), 7.04-7.06 (m, 2H), 7.14 (d, J=7.6 Hz, 1H), 7.31 (t, J=8 Hz, 1H). Compound 326F: LC-MS (ESI) m/z: 536 [M+H]⁺. Compound 326G: LC-MS (ESI) m/z: 508 [M+H]⁺. Compound 326: LC-MS (ESI) m/z: 388 [M+H]⁺; ¹H-NMR (DMSO-d₆, 400 MHz): δ (ppm) 1.71-1.80 (m, 4H), 1.98-1.99 (m, 4H), 2.65-2.72 (m, 1H), 4.13 (s, 1H), 7.18 (d, J=7.2 Hz, 2H), 7.29 (d, J=7.6 Hz, 1H), 7.44 (d, J=8 Hz, 1H), 13.25 (s, 1H), 15.52 (s, 1H).

Example 327

Synthesis of 4-((4-(3-(trifluoromethyl)phenyl)cyclohexyl)thio)-1H-1,2,3-triazole-5-carboxylic acid (327)

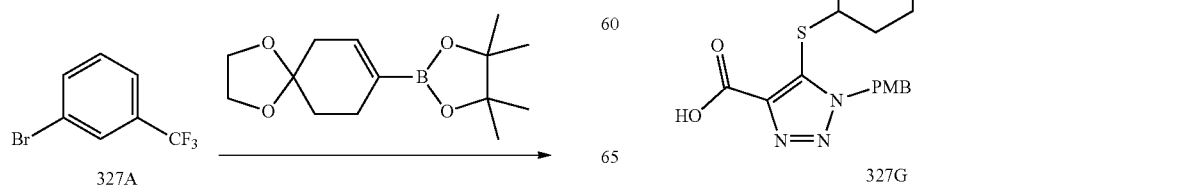

327A

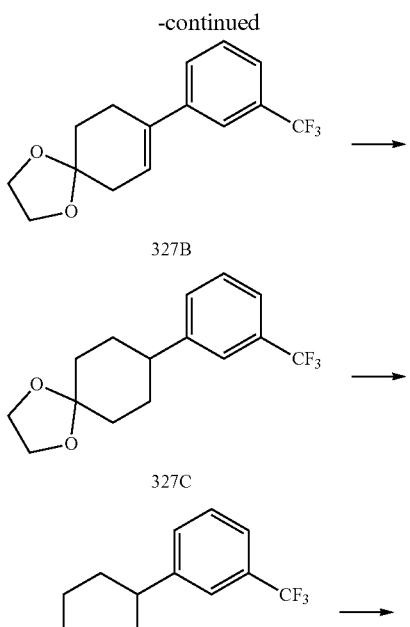

327B

327C

327D

327E

327F

327G

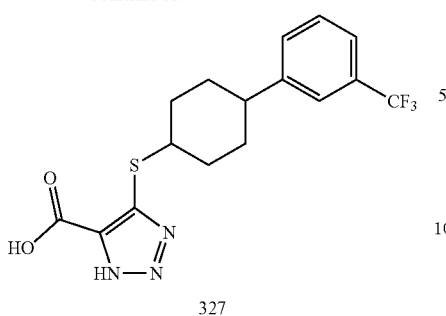

327

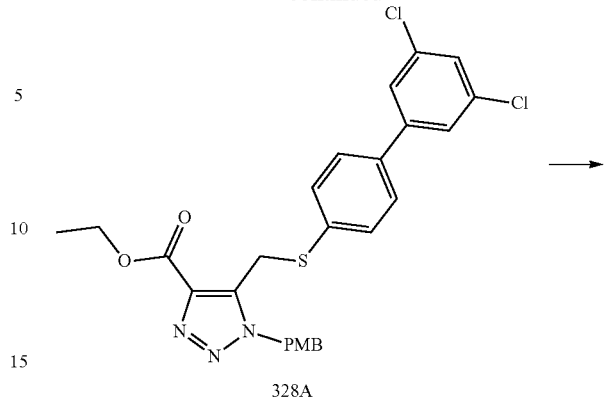

328A

Compounds 327B, 327C, 327D, 327E, 327F, 327G, and 327 were synthesized by employing the procedures described for Compounds 4B, 141, 279D, 57C, 90C, 8F, and 1 using 4,4,5,5-tetramethyl-2-(1,4-dioxaspiro[4.5]dec-7-en-8-yl)-1,3,2-dioxaborolane, Compounds 327A with 1,4-dioxane/H$_2$O as solvent, 327B with MeOH as solvent, 327C, 327D, Intermediate D, 327E with DEAD as coupling reagent, 327F, and 327G in lieu of (4-bromophenyl)boronic acid, Compounds 4A with toluene/EtOH/H$_2$O as solvent, 140 with EtOAc as solvent, 279C, 57B, Intermediate H, 90B with DIAD as coupling reagent, 8E, and 1E. Compound 327B: LC-MS (ESI) m/z: 285 [M+H]$^+$. Compound 327C: LC-MS (ESI) m/z: 287 [M+H]$^+$. Compound 327D: LC-MS (ESI) m/z: 243 [M+H]$^+$. Compound 327E: LC-MS (ESI) m/z: 267 [M+Na]$^+$. Compound 327F: LC-MS (ESI) m/z: 520 [M+H]$^+$. Compound 327G: LC-MS (ESI) m/z: 492 [M+H]$^+$. Compound 327: LC-MS (ESI) m/z: 372 [M+H]$^+$; $^1$H-NMR (DMSO-d$_6$, 400 MHz): δ (ppm) 1.75-1.84 (m, 4H), 1.94-2.08 (m, 4H), 2.73-2.80 (m, 1H), 4.13 (s, 1H), 7.53-7.60 (m, 4H), 13.3 (s, 1H), 15.44-15.47 (m, 1H).

Example 328

Synthesis of 4-(((3',5'-dichloro-[1,1'-biphenyl]-4-yl)thio)methyl)-1H-1,2,3-triazole-5-carboxylic acid (328)

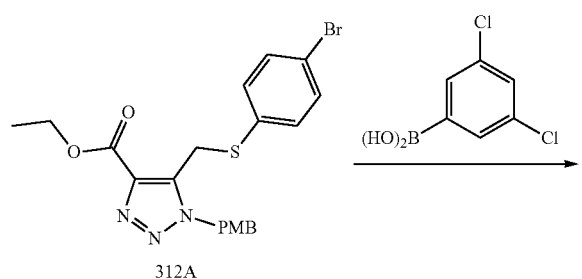

312A

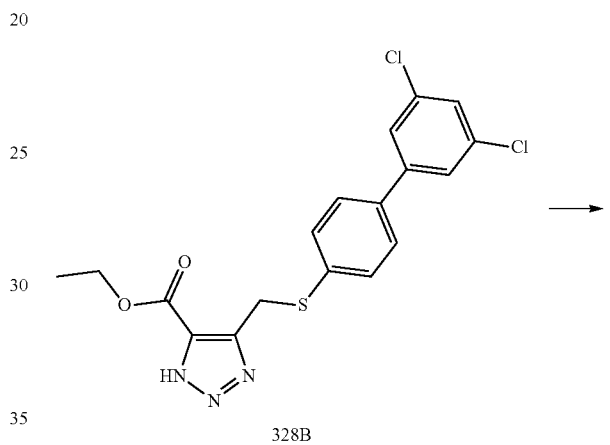

328B

328

Compounds 328A, 328B, and 328 were synthesized by employing the procedures described for Compounds 8B, 1, and 8F using 3,5-dichlorophenylboronic acid, Compounds 312A with Na$_2$CO$_3$ as base and 1,4-dioxane/H$_2$O as solvent, 328A, and 328B in lieu of (3,4-dichlorophenyl)boronic acid, Compounds 8A with Cs$_2$CO$_3$ as base and DME/H$_2$O as solvent, 1E, and 8E. Compound 328A: LC-MS (ESI) m/z: 528 [M+H]$^+$. Compound 328B: LC-MS (ESI) m/z: 408 [M+H]$^+$. Compound 328: LC-MS (ESI) m/z: 380 [M+H]$^+$; $^1$H-NMR (DMSO-d$_6$, 400 MHz): δ (ppm) 4.54 (s, 2H), 7.45 (d, J=7.2 Hz, 2H), 7.59 (t, J=3.6 Hz, 1H), 7.69 (s, 1H), 7.71 (s, 1H), 7.73 (d, J=2.4 Hz, 2H).

Example 329

Synthesis of 4-(((3'-chloro-4'-(trifluoromethoxy)-[1,1'-biphenyl]-4-yl)thio)methyl)-1H-1,2,3-triazole-5-carboxylic acid (329)

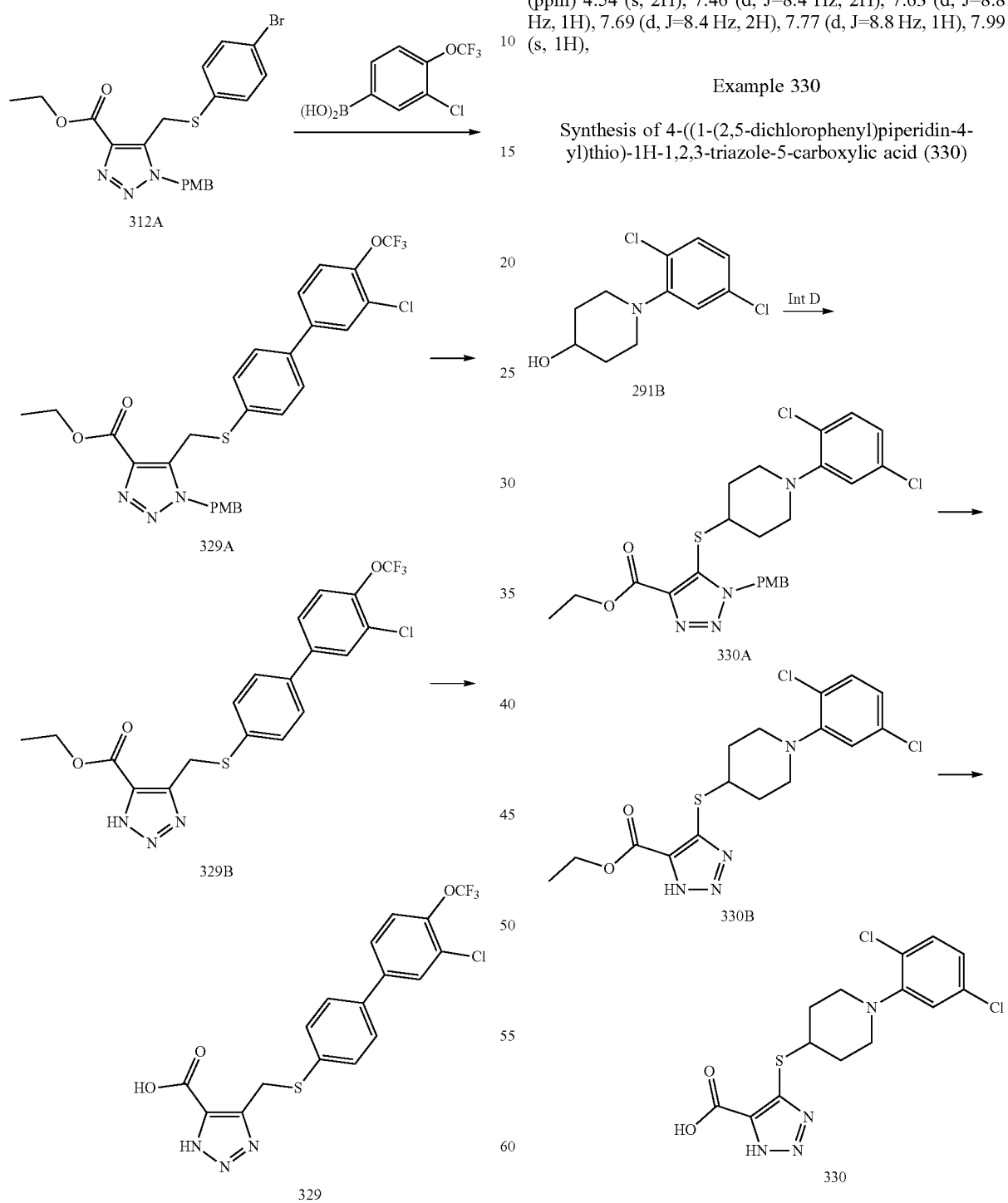

Compounds 329A, 329B, and 329 were synthesized by employing the procedures described for Compounds 8B, 1, and 8F using 3-chloro-4-(trifluoromethoxy)phenylboronic acid, Compounds 312A with Na$_2$CO$_3$ as base and 1,4-dioxane/H$_2$O as solvent, 329A, and 329B in lieu of (3,4-dichlorophenyl)boronic acid, Compounds 8A with Cs$_2$CO$_3$ as base and DME/H$_2$O as solvent, 1E, and 8E. Compound 329A: LC-MS (ESI) m/z: 578 [M+H]$^+$. Compound 329B: LC-MS (ESI) m/z: 458 [M+H]$^+$. Compound 329: LC-MS (ESI) m/z: 430 [M+H]$^+$; $^1$H-NMR (DMSO-d$_6$, 400 MHz): δ (ppm) 4.54 (s, 2H), 7.46 (d, J=8.4 Hz, 2H), 7.63 (d, J=8.8 Hz, 1H), 7.69 (d, J=8.4 Hz, 2H), 7.77 (d, J=8.8 Hz, 1H), 7.99 (s, 1H),

Example 330

Synthesis of 4-((1-(2,5-dichlorophenyl)piperidin-4-yl)thio)-1H-1,2,3-triazole-5-carboxylic acid (330)

Compounds 330A, 330B, and 330 were synthesized by employing the procedures described for Compounds 90C, 57E, and 8F using Intermediate D, Compounds 291B with DEAD as coupling reagent, 330A, and 330B in lieu of Intermediate H, Compounds 90B with DIAD as coupling reagent, 57D, and 8E. Compound 330A: LC-MS (ESI) m/z: 521 [M+H]⁺. Compound 330B: LC-MS (ESI) m/z: 401 [M+H]⁺. Compound 330: LC-MS (ESI) m/z: 373 [M+H]⁺; ¹H-NMR (CD₃OD, 400 MHz): δ (ppm) 1.88-1.93 (m, 2H), 2.23-2.27 (m, 2H), 2.83-2.89 (m, 2H), 3.32-3.38 (m, 2H), 3.77-3.80 (m, 1H), 7.01 (dd, J=8.4, 2.0 Hz, 1H), 7.13 (d, J=2.0 Hz, 1H), 7.34 (d, J=8.4 Hz, 1H).

Example 331

Synthesis of 4-(((cis)-4-(3,5-dichlorophenyl)cyclohexyl)thio)-1H-1,2,3-triazole-5-carboxylic acid (331)

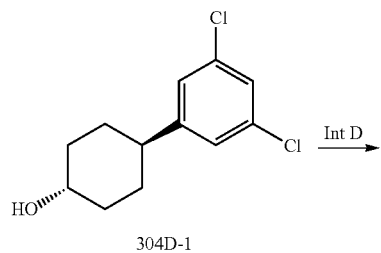

Compounds 331A, 331B, and 331 were synthesized by employing the procedures described for Compounds 90C, 1, and 8F using Intermediate D, Compounds 304D-1 with DEAD as coupling reagent, 331A, and 331B in lieu of Intermediate H, Compounds 90B with DIAD as coupling reagent, 1E, and 8E. Compound 331A: LC-MS (ESI) m/z: 520 [M+H]⁺. Compound 331B: LC-MS (ESI) m/z: 400 [M+H]⁺. Compound 331: LC-MS (ESI) m/z: 372 [M+H]⁺; ¹H-NMR (CD₃OD, 400 MHz): δ (ppm) 1.72-1.75 (m, 2H), 1.90-2.08 (m, 6H), 2.64-2.66 (m, 1H), 4.20 (s, 1H), 7.24 (s, 2H), 7.26 (s, 1H).

Example 332

Synthesis of 4-(((cis)-4-(4-(trifluoromethyl)phenyl)cyclohexyl)thio)-1H-1,2,3-triazole-5-carboxylic acid (332)

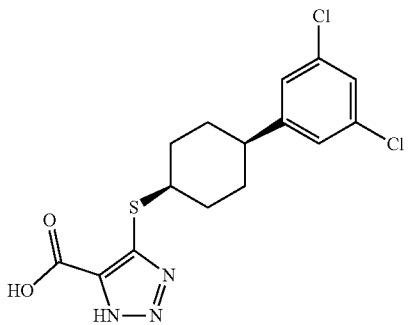
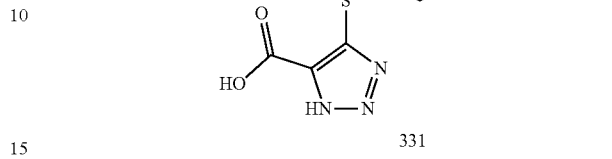
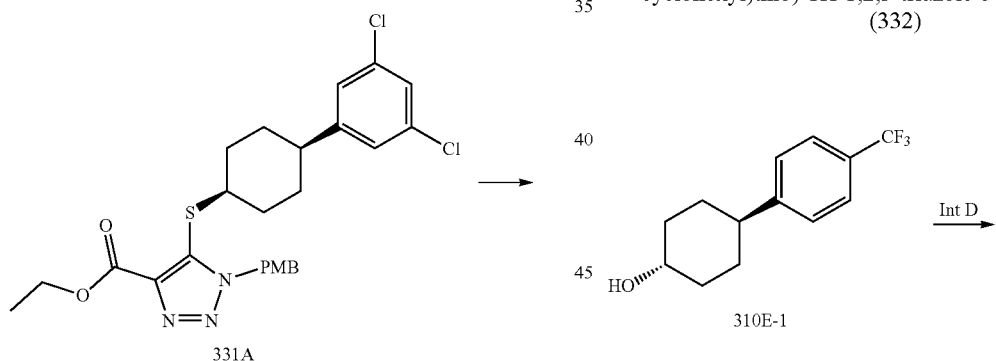
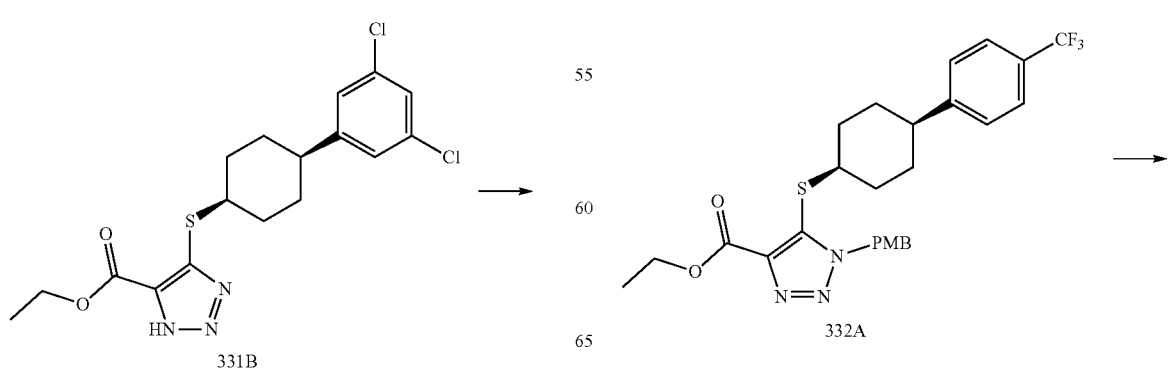

589
-continued

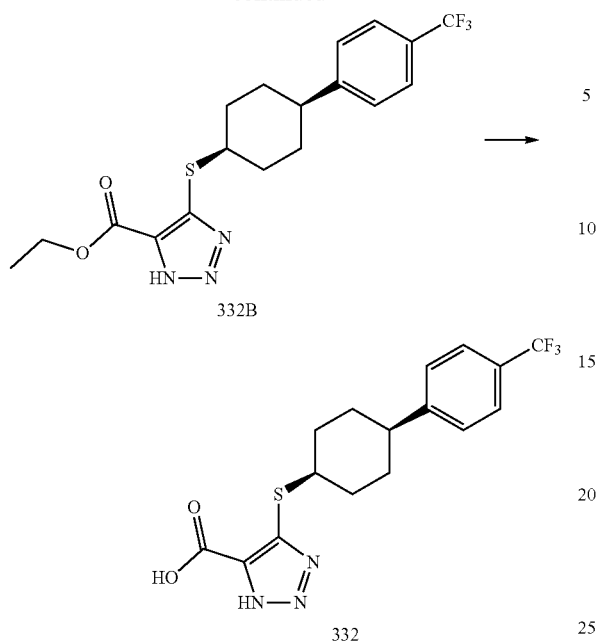

332B

332

Compounds 332A, 332B, and 332 were synthesized by employing the procedures described for Compounds 90C, 1, and 8F using Intermediate D, Compounds 310E-1 with DEAD as coupling reagent, 332A, and 332B in lieu of Intermediate H, Compounds 90B with DIAD as coupling reagent, 1E, and 8E. Compound 332A: LC-MS (ESI) m/z: 520 [M+H]$^+$. Compound 332B: LC-MS (ESI) m/z: 400 [M+H]$^+$. Compound 332: LC-MS (ESI) m/z: 372 [M+H]$^+$; $^1$H-NMR (CD$_3$OD, 400 MHz): 1.75-1.78 (m, 2H), 1.93-2.10 (m, 6H), 2.71-2.76 (m, 1H), 4.21 (s, 1H), 7.46 (d, J=8.4 Hz, 2H), 7.59 (d, J=8.4 Hz, 2H).

Example 333

Synthesis of 4-((methyl(4'-(trifluoromethoxy)-[1,1'-biphenyl]-4-yl)amino)methyl)-1H-1,2,3-triazole-5-carboxylic acid 2,2,2-trifluoroacetate (333)

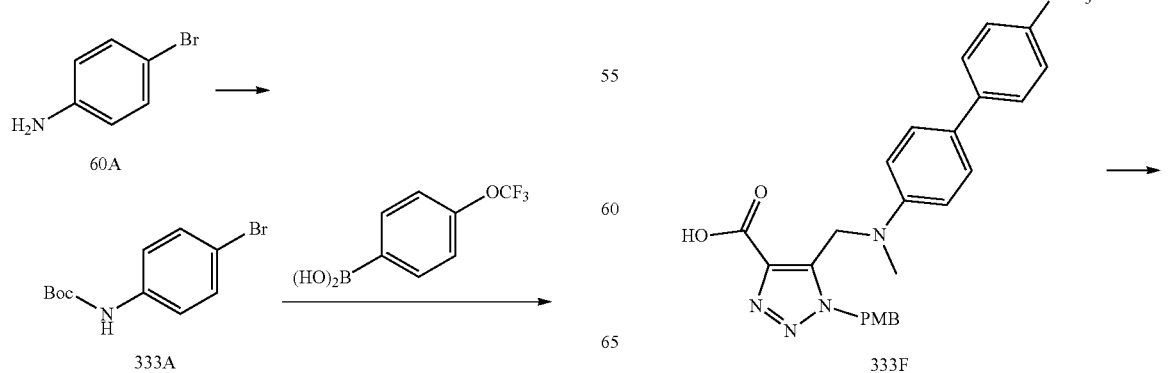

590
-continued

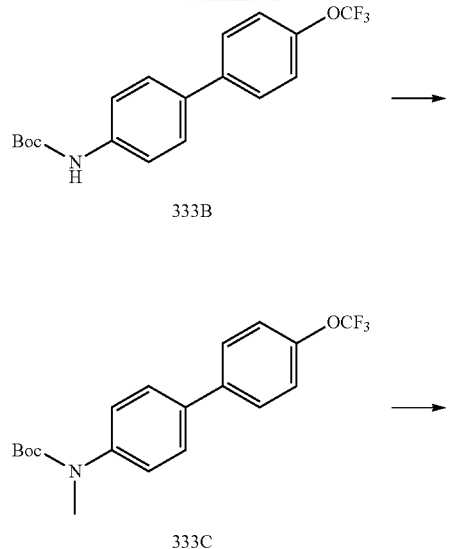

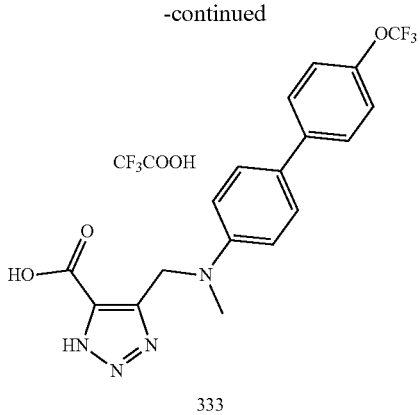

333

To a solution of 4-bromoaniline (60A) (1.71 g, 10.0 mmol) in THF (100 mL) and water (10 mL) was added $K_2CO_3$ (4.14 g, 30.0 mmol) and di-tert-butyl dicarbonate (3.27 g, 15.0 mmol). The mixture was stirred at room temperature overnight, diluted with water (50 mL), and extracted with ethyl acetate (50 mL×3). The combined organic layers was washed with water (100 mL) and brine (100 mL), dried over anhydrous sodium sulfate, concentrated, and purified with flash column chromatography on silica gel (ethyl acetate in petroleum ether, 30% v/v) to afford Compound 333A. LC-MS (ESI) m/z: 216 [M−55]+; $^1$H-NMR (CDCl$_3$, 400 MHz): δ (ppm) 1.52 (s, 9H), 6.48 (brs, 1H), 7.26 (d, J=8.8 Hz, 2H), 7.39 (d, J=8.8 Hz, 2H).

Compounds 333B, 333C, 333D, 333E, 333F, and 333 were synthesized by employing the procedures described for Compounds 4B, 63A, 70C, 178A, 8F, and 1 using 4-(trifluoromethoxy)phenylboronic acid, Compounds 333A with $K_2CO_3$ as base and 1,4-dioxane/H$_2$O as solvent, 333B with $K_2CO_3$ as base at room temperature, 333C, 333D, 333E, and 333F in lieu of (4-bromophenyl)boronic acid, Compounds 4A with Na$_2$CO$_3$ as base and toluene/EtOH/H$_2$O as solvent, 61F with Cs$_2$CO$_3$ as base at 60° C., 70B, 82C, 8E, and 1E. Compound 333B: LC-MS (ESI) m/z: 298 [M−55]+; $^1$H-NMR (CDCl$_3$, 400 MHz): δ (ppm) 1.55 (s, 9H), 6.54 (brs, 1H), 7.27 (d, J=8.8 Hz, 2H), 7.45 (d, J=8.8 Hz, 2H), 7.50 (d, J=8.8 Hz, 2H), 7.57 (d, J=8.8 Hz, 2H). Compound 333C: LC-MS (ESI) m/z: 312 [M−55]+; $^1$H-NMR (CDCl$_3$, 400 MHz): δ (ppm) 1.49 (s, 9H), 3.31 (s, 3H), 7.27 (d, J=8.8 Hz, 2H), 7.34 (d, J=8.8 Hz, 2H), 7.52 (d, J=8.8 Hz, 2H), 7.59 (d, J=8.8 Hz, 2H). Compound 333D: LC-MS (ESI) m/z: 268 [M+H]+; $^1$H-NMR (CDCl$_3$, 400 MHz): δ (ppm) 1.58 (brs, 1H), 2.90 (s, 3H), 6.70 (d, J=8.4 Hz, 2H), 7.24 (d, J=8.4 Hz, 2H), 7.43 (d, J=8.4 Hz, 2H), 7.54 (d, J=8.4 Hz, 2H). Compound 333E: LC-MS (ESI) m/z: 541 [M+H]+. Compound 333F: LC-MS (ESI) m/z: 513 [M+H]+. Compound 333: LC-MS (ESI) m/z: 393 [M+H]+; $^1$H-NMR (DMSO-d$_6$, 400 MHz): δ (ppm) 3.11 (s, 3H), 4.90 (s, 2H), 6.83 (d, J=8.8 Hz, 2H), 7.35 (d, J=8.8 Hz, 2H), 7.50 (d, J=8.8 Hz, 2H), 7.68 (d, J=8.8 Hz, 2H).

Example 334

Synthesis of 4-(3-(cyclopropylmethoxy)-5-(trifluoromethyl)phenyl)-1H-1,2,3-triazole-5-carboxylic acid (334)

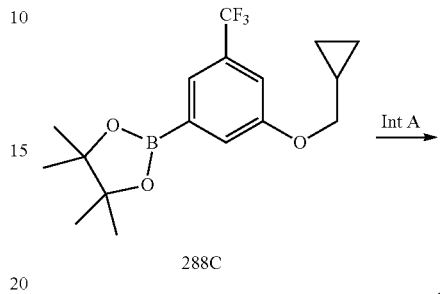

288C

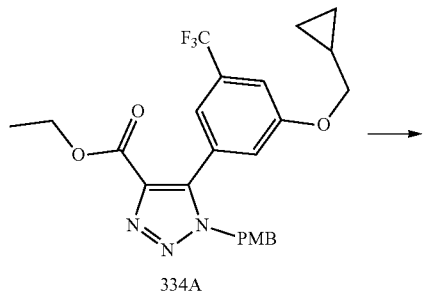

334A

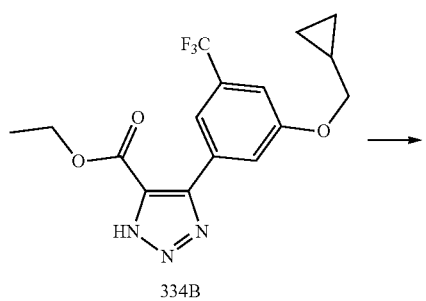

334B

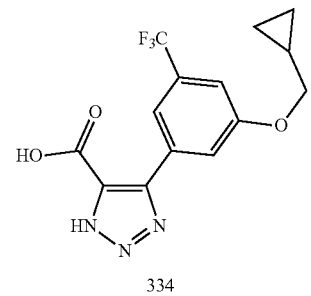

334

Compounds 334A, 334B, and 334 were synthesized by employing the procedures described for Compounds 206C, 217E, and 8F using Compounds 288C, 334A, and 334B in lieu of Compounds 206B, 217D, and 8E. Compound 334A: LC-MS (ESI) m/z: 476 [M+H]+. Compound 334B: LC-MS (ESI) m/z: 356 [M+H]+. Compound 334: LC-MS (ESI) m/z: 328 [M+H]+. $^1$H-NMR (DMSO-d$_6$, 400 MHz): δ (ppm) 0.35-0.37 (m, 2H), 0.57-0.62 (m, 2H), 1.25-1.29 (m, 1H), 3.95 (d, J=7.2 Hz, 2H), 7.30 (s, 1H), 7.74-7.76 (m, 2H), 13.28 (s, 1H), 15.79 (s, 1H).

Example 335

Synthesis of 4-((4-chloro-3-(cyclohexylmethoxy)phenyl)sulfinyl)-1H-1,2,3-triazole-5-carboxylic acid (335)

Example 336

Synthesis of 4-((4-chloro-3-(cyclohexylmethoxy)phenyl)thio)-1H-1,2,3-triazole-5-carboxylic acid (336)

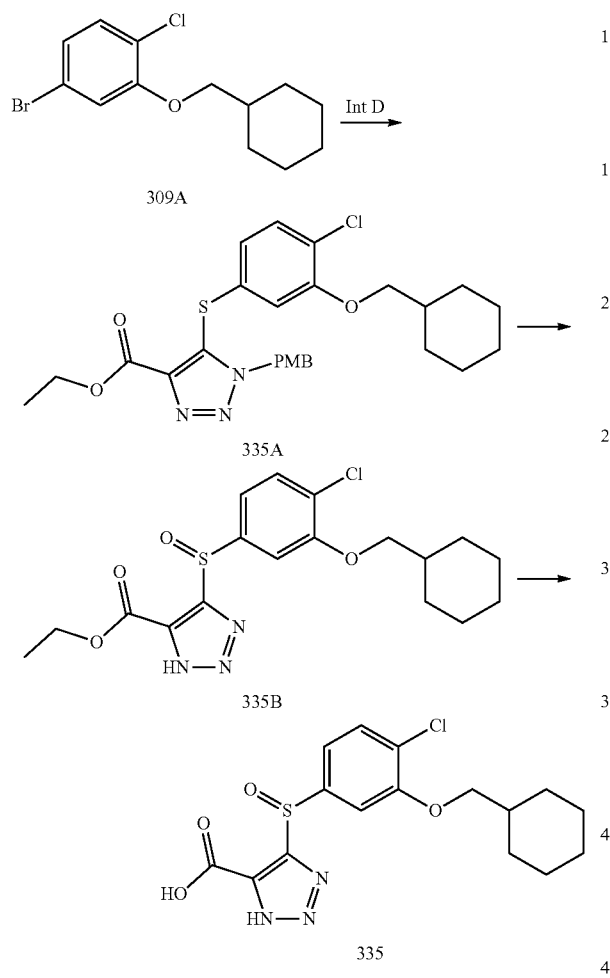

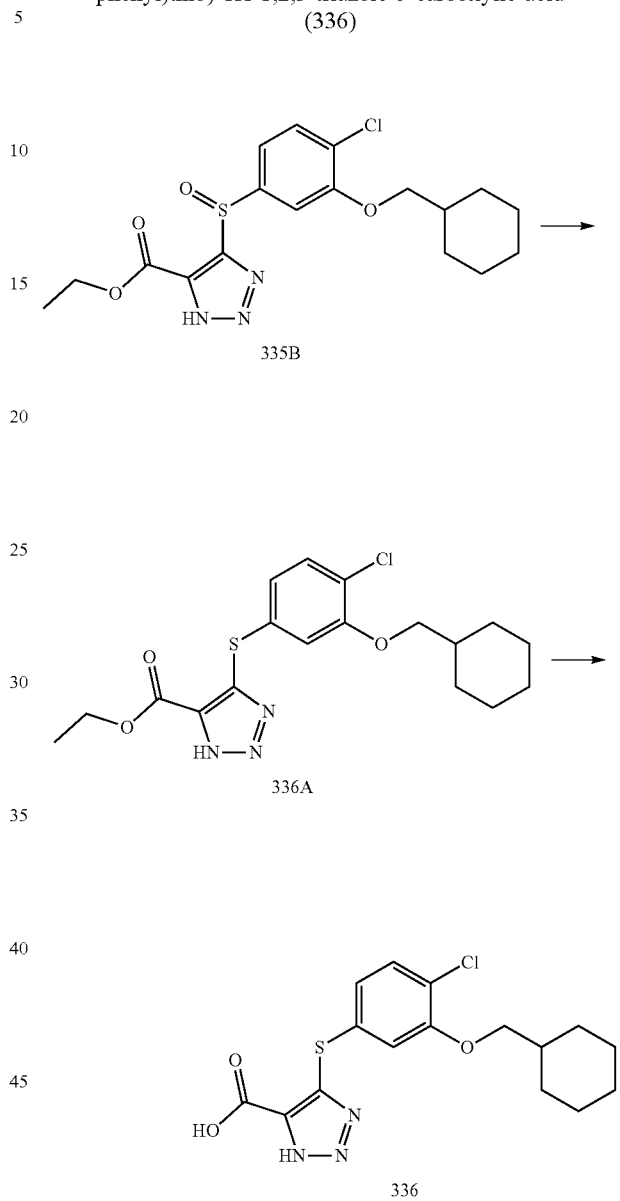

Compound 335A was synthesized by employing the procedure described for Compound 35D using Compound 309A in lieu of Compound 35C, LC-MS (ESI) m/z: 516 [M+H]$^+$.

To a solution of Compound 335A (492 mg, 0.95 mmol) in CH$_3$CN (15 mL) was added a solution of CAN (2.6 g, 6.8 mmol) in H$_2$O (5 mL) and stirred at room temperature overnight. The reaction mixture was diluted with water (50 mL) and extracted with EtOAc (50 mL×3). The combined organic layers was washed with brine (50 mL), dried over anhydrous sodium sulfate, concentrated, and purified by column chromatography on silica gel (ethyl acetate in petroleum ether, 10% v/v) to furnish Compound 335B. LC-MS (ESI) m/z: 412 [M+H]$^+$.

Compound 335 was synthesized by employing the procedure described for Compound 8F using Compound 335B in lieu of Compound 8E, LC-MS (ESI) m/z: 384 [M+H]$^+$; $^1$H-NMR (DMSO-d$_6$, 400 MHz): δ (ppm) 1.04-1.26 (m, 5H), 1.69-1.83 (m, 6H), 3.87-3.90 (m, 2H), 7.27 (dd, J=0.8, 8 Hz, 1H), 7.46 (s, 1H), 7.63 (d, J=8.0 Hz, 1H).

To a mixture of Compound 335B (140 mg, 0.34 mmol) and NaI (255 mg, 1.70 mmol) in CH$_3$CN (15 mL) was dropped neat TiCl$_4$ (0.19 mL, 1.70 mmol) at room temperature and stirred at room temperature for 0.5 hours. The mixture was poured into H$_2$O (50 mL) and extracted with EtOAc (50 mL×3). The combined organic layers was washed with brine (50 mL), dried over anhydrous sodium sulfate, filtered, and concentrated to give a crude Compound 336A. LC-MS (ESI) m/z: 396 [M+H]$^+$.

Compound 336 was synthesized by employing the procedure described for Compound 8F using Compound 336A in lieu of Compound 8E, LC-MS (ESI) m/z: 368 [M+H]$^+$; $^1$H-NMR (DMSO-d$_6$, 400 MHz): δ (ppm) 1.03-1.26 (m, 5H), 1.63-1.81 (m, 6H), 3.84 (d, J=6.4 Hz, 2H), 7.0 (dd, J=1.2, 7.6 Hz, 1H), 7.24 (s, 1H), 7.42 (d, J=8.4 Hz, 1H), 13.46 (s, 1H), 15.60 (s, 1H).

Example 337

Synthesis of 4-(((cis)-4-(3-chloro-5-(trifluoromethoxy)phenyl)cyclohexyl)thio)-1H-1,2,3-triazole-5-carboxylic acid (337)

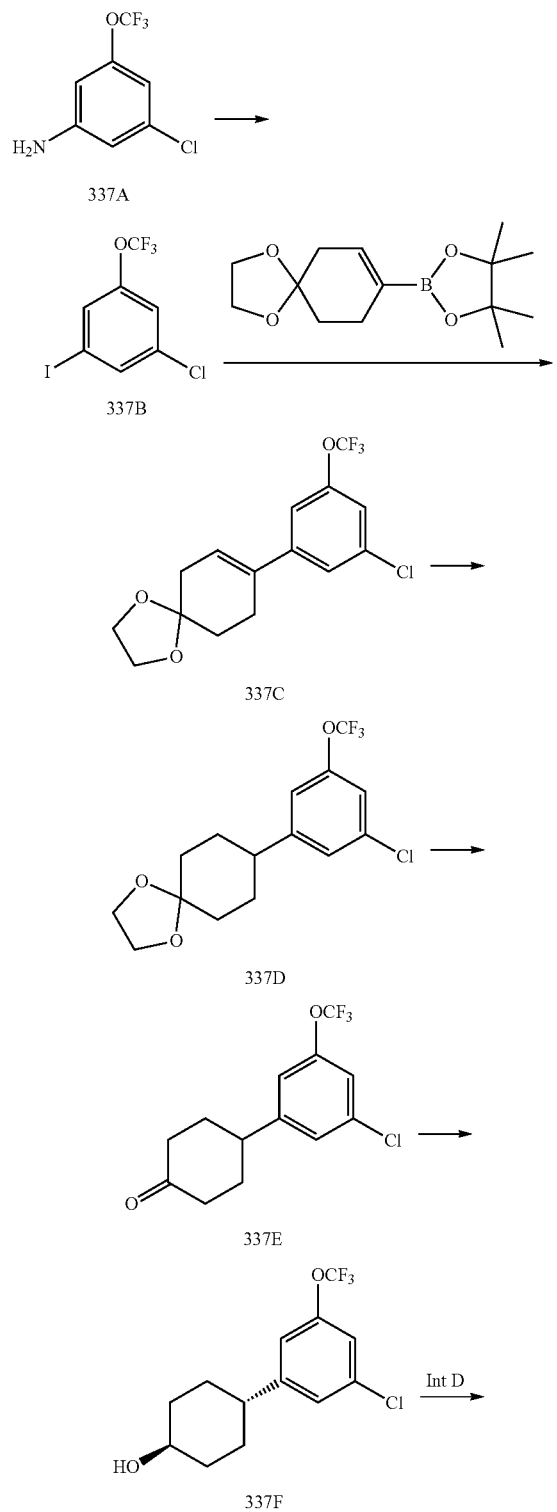

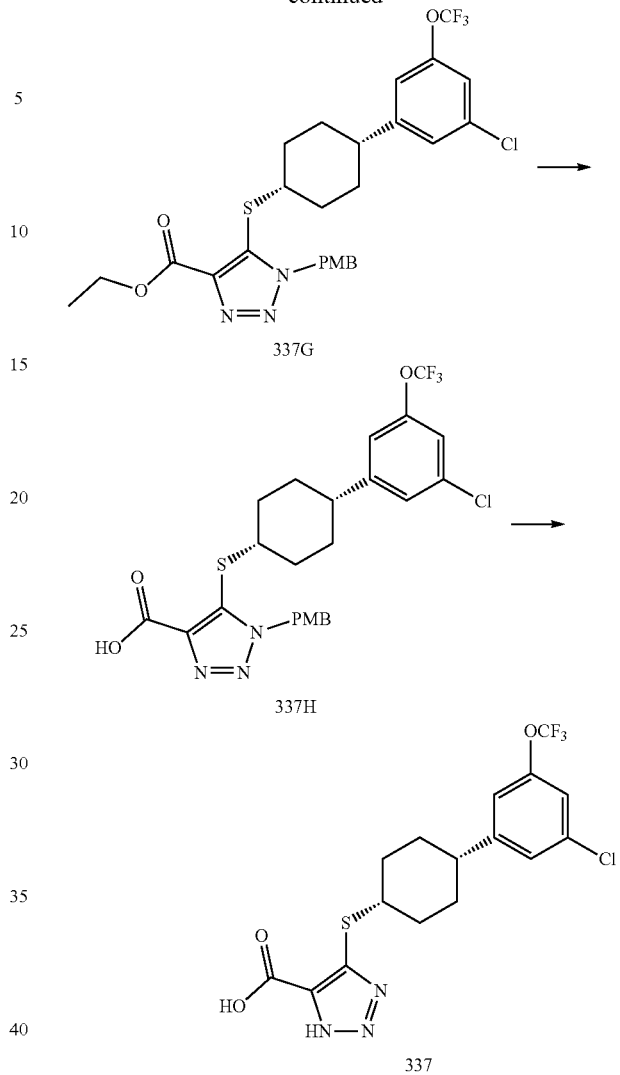

Compounds 337B, 337C, 337D, 337E, 337F, 337G, 337H, and 337 were synthesized by employing the procedures described for Compounds 56B, 8B, 141, 279D, 57C, 90C, 8F, and 1 using Compounds 337A with KI, 4,4,5,5-tetramethyl-2-(1,4-dioxaspiro[4.5]dec-7-en-8-yl)-1,3,2-dioxaborolane, 337B with $Na_2CO_3$ as base and 1,4-dioxane as solvent, 337C with MeOH as solvent, 337D with TFA as acid and dichloromethane as solvent, 337E, Intermediate D, 337F, 337G, and 337H in lieu of Compounds 56A with CuCl, (4-bromophenyl)boronic acid, 8A with $Cs_2CO_3$ as base and DME/$H_2O$ as solvent, 140 with EtOAc as solvent, 279C with HCl as acid and acetone as solvent, 57B, Intermediate H, 90B, 8E, and 1E. Compound 337B: LC-MS (ESI) m/z: non-ionizable compound under routine conditions used. $^1$H-NMR ($CDCl_3$, 400 MHz): δ (ppm) 7.23 (s, 1H), 7.49 (s, 1H), 7.67 (s, 1H). Compound 337C: LC-MS (ESI) m/z: 335 [M+H]$^+$. Compound 337D: LC-MS (ESI) m/z: 337 [M+H]$^+$. Compound 337E: LC-MS (ESI) m/z: 293 [M+H]$^+$. Compound 337F: LC-MS (ESI) m/z: 277 [M−OH]$^+$. ($CDCl_3$, 400 MHz): δ (ppm) 1.40-1.51 (m, 5H), 1.93 (d, J=12.8 Hz, 2H), 2.11 (d, J=11.6 Hz, 2H), 2.46-2.55 (m, 1H), 3.66-3.72 (m, 1H), 6.94 (s, 1H), 7.06 (s, 1H), 7.13 (s, 1H). Compound 337G: LC-MS (ESI) m/z: 570 [M+H]$^+$. Compound 337H: LC-MS (ESI) m/z: 542 [M+H]$^+$. Compound 337: LC-MS (ESI) m/z: 422 [M+H]+; 1H-NMR (DMSO-d6, 400 MHz): δ (ppm) 1.70-1.78 (m, 4H), 1.97 (s, 4H), 2.71-2.76 (m, 1H), 4.11 (s, 1H), 7.23 (s, 1H), 7.37 (d, J=4.8 Hz, 2H), 13.32 (s, 1H), 15.52 (s, 1H).

Example 338

Synthesis of 4-((1-(3-chloro-5-(trifluoromethoxy)phenyl)piperidin-4-yl)thio)-1H-1,2,3-triazole-5-carboxylic acid (338)

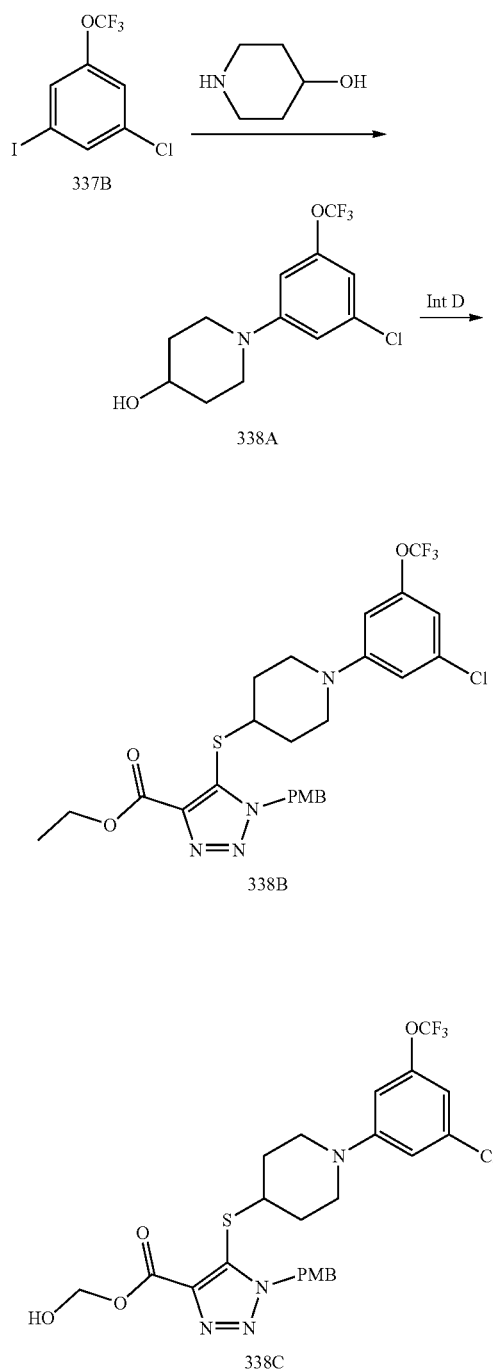

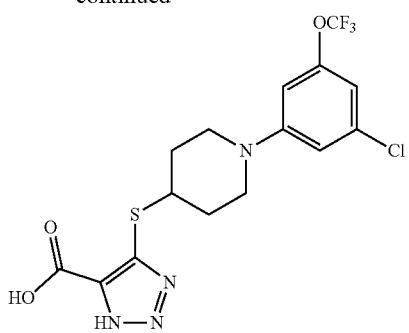

Compounds 338A, 338B, 338C, and 338 were synthesized by employing the procedures described for Compounds 270B, 90C, 8F, and 1 using Compounds 337B with Cs2CO3 as base, Intermediate D, 338A, 338B, and 338C in lieu of Compounds 270A with K2CO3 as base, Intermediate H, 90B, 8E, and 1E. Compound 338A: LC-MS (ESI) m/z: 296 [M+H]+. Compound 338B: LC-MS (ESI) m/z: 571 [M+H]+. Compound 338C: LC-MS (ESI) m/z: 543 [M+H]+. Compound 338: LC-MS (ESI) m/z: 423 [M+H]+; 1H-NMR (DMSO-d6, 400 MHz): δ (ppm) 1.59-1.67 (m, 2H), 2.06-2.12 (m, 2H), 3.02 (t, J=10.8 Hz, 2H), 3.74 (d, J=13.2 Hz, 3H), 6.74 (s, 1H), 6.85 (s, 1H), 7.00 (s, 1H), 13.35 (s, 1H), 15.49 (s, 1H).

Example 339

Synthesis of 4-((4-(4,4-difluoropiperidin-1-yl)phenyl)thio)-1H-1,2,3-triazole-5-carboxylic acid 2,2,2-trifluoroacetate (339)

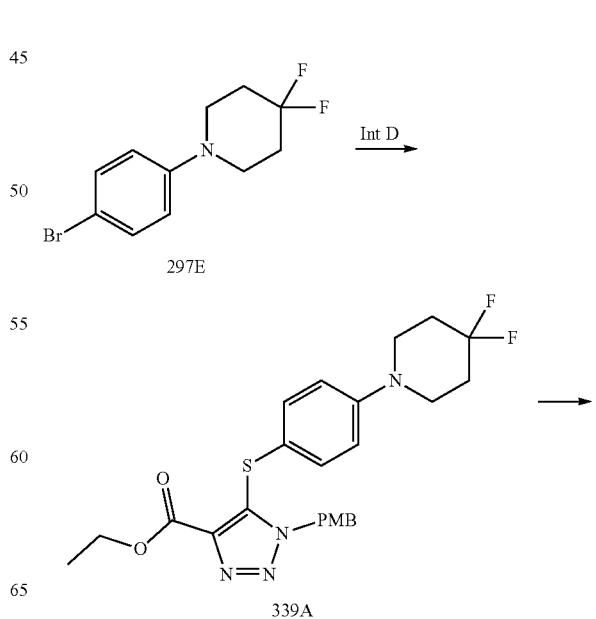

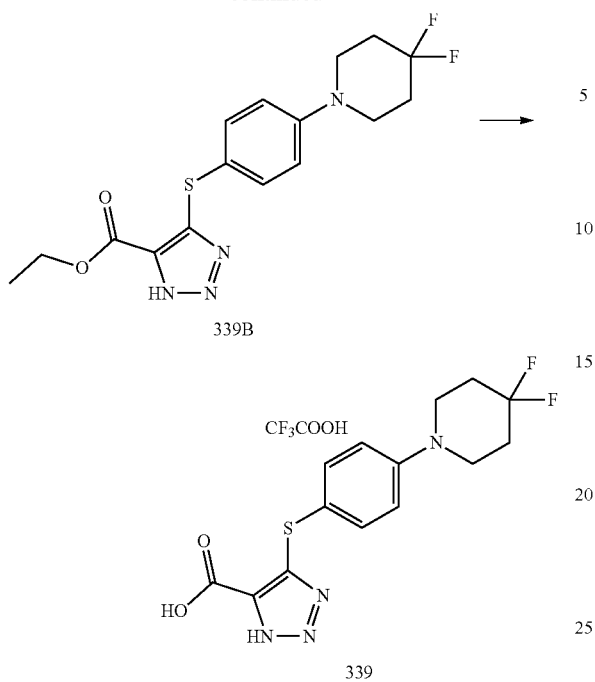

339B

339

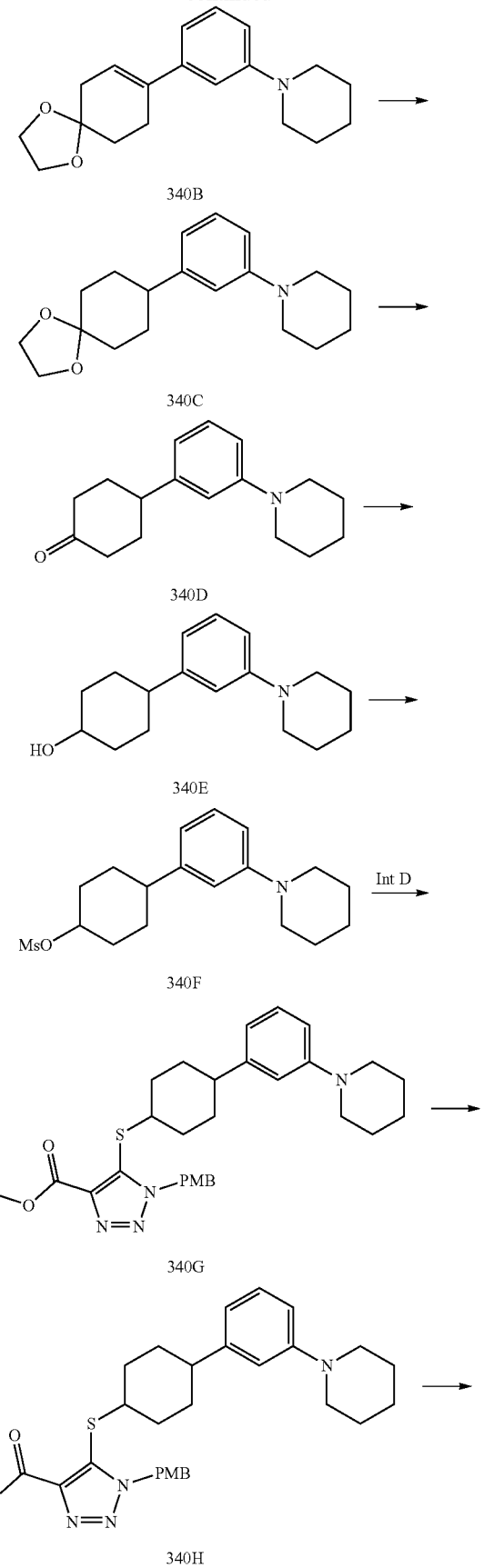

340B

340C

340D

340E

340F

340G

340H

A mixture of Compound 297E (500 mg, 1.82 mmol), Intermediate D (639 mg, 2.18 mmol), L-proline (63 mg, 0.55 mmol), CuI (34 mg, 0.182 mmol), and $K_2CO_3$ (502 mg, 3.64 mmol) in anhydrous DMF (15 mL) was stirred at 110° C. under $N_2$ for 12 hours. After cooled down to room temperature, the mixture was diluted with ethyl acetate (200 mL), washed with water (200 mL) and brine (100 mL), dried over anhydrous sodium sulfate, concentrated, and purified with flash column chromatography on silica gel (ethyl acetate in petroleum ether, 33% v/v) to furnish Compound 339A. LC-MS (ESI) m/z: 489 $[M+H]^+$.

Compounds 339B and 339 were synthesized by employing the procedures described for Compounds 1 and 8F using Compounds 339A and 339B in lieu of Compounds 1E and 8E. Compound 339B: LC-MS (ESI) m/z: 369 $[M+H]^+$. Compound 339: LC-MS (ESI) m/z: 341 $[M+H]^+$; $^1$H-NMR (DMSO-$d_6$, 400 MHz): δ (ppm) 2.00-2.07 (m, 4H), 3.40 (m, 4H), 7.02-7.04 (m, 2H), 7.37-7.40 (m, 2H).

Example 340

Synthesis of 4-((4-(3-(piperidin-1-yl)phenyl)cyclohexyl)thio)-1H-1,2,3-triazole-5-carboxylic acid 2,2,2-trifluoroacetate (340)

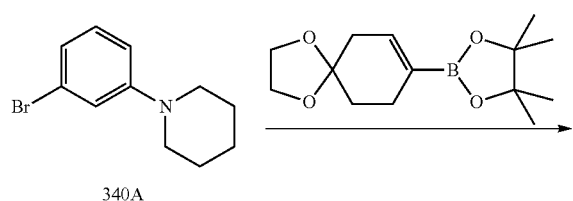

340A

601

-continued

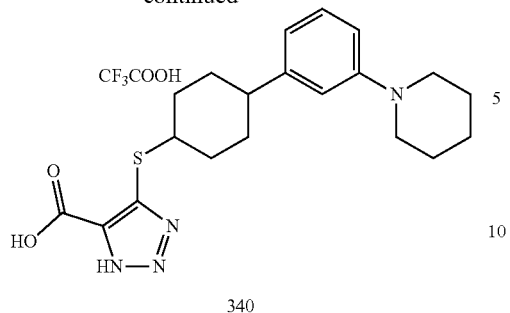

340

Compounds 340B, 340C, 340D, and 340E were synthesized by employing the procedures described for Compounds 8B, 141, 279D, and 57C using 4,4,5,5-tetramethyl-2-(1,4-dioxaspiro[4.5]dec-7-en-8-yl)-1,3,2-dioxaborolane, Compounds 340A with $Na_2CO_3$ as base and 1,4-dioxane as solvent, 340B with MeOH as solvent, 340C with TFA as acid and dichloromethane as solvent, and 340D in lieu of (4-bromophenyl)boronic acid, Compounds 8A with $Cs_2CO_3$ as base and $DME/H_2O$ as solvent, 140 with EtOAc as solvent, 279C with HCl as acid and acetone as solvent, and 57B. Compound 340B: LC-MS (ESI) m/z: 300 $[M+H]^+$. Compound 340C: LC-MS (ESI) m/z: 302 $[M+H]^+$. Compound 340D: LC-MS (ESI) m/z: 258 $[M+H]^+$. Compound 340E: LC-MS (ESI) m/z: 260 $[M+H]^+$.

To a solution of Compound 340E (450 mg, 1.74 mmol) and triethylamine (750 mg, 7.42 mmol) in dichloromethane (40 mL) was added methanesulfonyl chloride (397 mg, 3.46 mmol) and stirred at 30° C. for 3 hours. The mixture was washed with water (50 mL), dried over anhydrous sodium sulfate, filtered, and evaporated to give Compound 340F. LC-MS (ESI) m/z: 338 $[M+H]^+$.

Compounds 340G, 340H, and 340 were synthesized by employing the procedures described for Compounds 1E, 8F, and 1 using Intermediate D, Compounds 340F at 90° C., 340G, and 340H in lieu of Compounds 1D, Intermediate B at 90° C., 8E, and 1E. Compound 340G: LC-MS (ESI) m/z: 535 $[M+H]^+$. Compound 340H: LC-MS (ESI) m/z: 507 $[M+H]^+$. Compound 340: LC-MS (ESI) m/z: 387 $[M+H]^+$; $^1$H-NMR (DMSO-$d_6$, 400 MHz): δ (ppm) 1.60-1.79 (m, 10H), 1.94-2.00 (m, 4H), 2.62-2.65 (m, 1H), 3.63-3.79 (m, 4H), 4.15 (s, 1H), 7.16-7.36 (m, 4H).

Example 341

Synthesis of 4-(((cis)4-(4-(4-methylpiperazin-1-yl)phenyl)cyclohexyl)thio)-1H-1,2,3-triazole-5-carboxylic acid 2,2,2-trifluoroacetate (341)

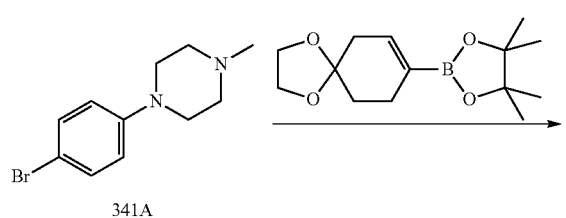

341A

602

-continued

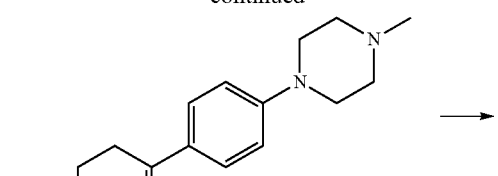

341B

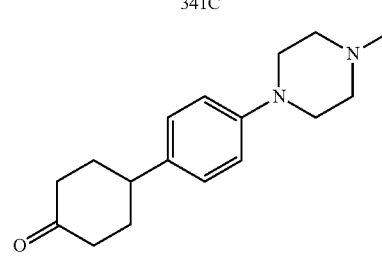

341C

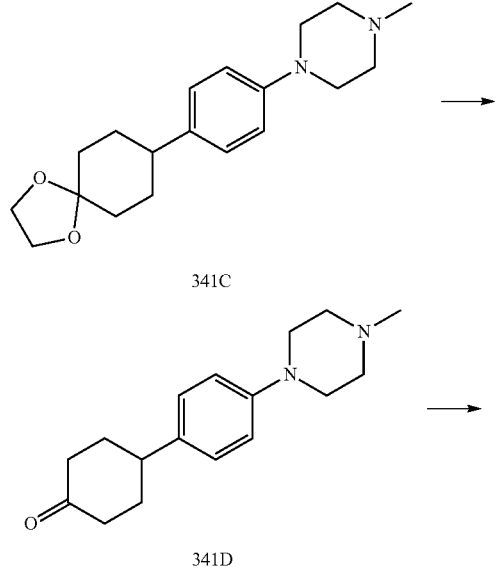

341D

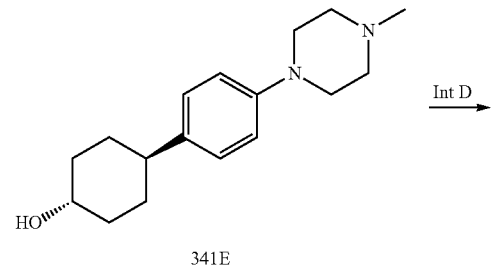

341E

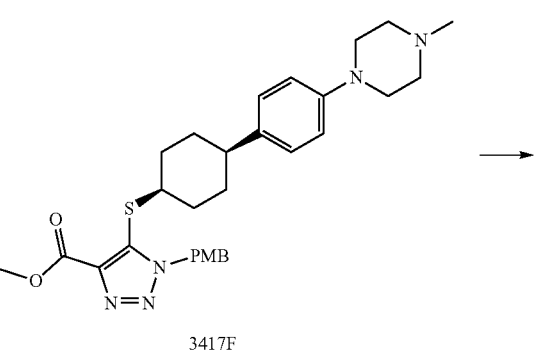

341F

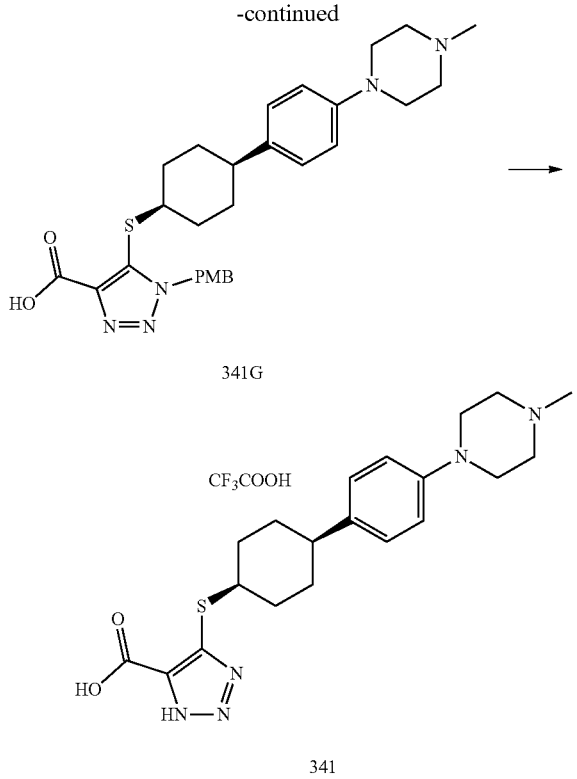

341G

341

Compounds 341B, 341C, 341D, 341E, 341F, 341G, and 341 were synthesized by employing the procedures described for Compounds 8B, 141, 279D, 57C, 90C, 1, and 8F using 4,4,5,5-tetramethyl-2-(1,4-dioxaspiro[4.5]dec-7-en-8-yl)-1,3,2-dioxaborolane, Compounds 341A with $Na_2CO_3$ as base and 1,4-dioxane/$H_2O$ as solvent, 341B with THF/MeOH as solvent, 341C with 1,4-dioxane as solvent, 341D, Intermediate D, 341E with DEAD as coupling reagent, 341F, and 341G in lieu of (4-bromophenyl)boronic acid, Compounds 8A with $Cs_2CO_3$ as base and DME/$H_2O$ as solvent, 140 with EtOAc as solvent, 279C with acetone as solvent, 57B, Intermediate H, 90B with DIAD as coupling reagent, 1E, and 8E. Compound 341B: LC-MS (ESI) m/z: 315 [M+H]$^+$; $^1$H-NMR (CDCl$_3$, 400 MHz): δ (ppm), 1.90-1.97 (m, 2H), 2.38 (s, 3H), 2.46 (s, 2H), 2.60-2.65 (m, 6H), 3.22-3.25 (m, 4H), 4.03 (m, 4H), 5.89-5.91 (m, 1H), 6.87 (d, J=8.8 Hz, 2H), 7.31 (d, J=8.8 Hz, 2H). Compound 341C: LC-MS (ESI) m/z: 317 [M+H]$^+$; $^1$H-NMR (CDCl$_3$, 400 MHz): δ (ppm), 1.68-1.77 (m, 3H), 1.84-1.87 (m, 4H), 2.46 (s, 3H), 2.73-2.76 (m, 6H), 3.26-3.29 (m, 4H), 3.99 (s, 4H), 6.88 (d, J=8.8 Hz, 2H), 7.15 (d, J=8.8 Hz, 2H). Compound 341D: LC-MS (ESI) m/z: 273 [M+H]$^+$. Compound 341E: LC-MS (ESI) m/z: 275 [M+H]$^+$. Compound 341F: LC-MS (ESI) m/z: 550 [M+H]$^+$. $^1$H-NMR (CDCl$_3$, 400 MHz): δ (ppm), 1.44 (t, J=7.2 Hz, 3H), 1.68-1.71 (m, 2H), 1.80-1.83 (m, 4H), 2.36-2.37 (m, 4H), 2.58-2.61 (m, 5H), 3.20-3.23 (m, 5H), 3.77 (s, 3H), 3.92 (s, 1H), 4.42-4.48 (m, 2H), 5.62 (s, 2H), 6.84 (d, J=8.4 Hz, 2H), 6.92 (d, J=8.4 Hz, 2H), 7.14 (d, J=8.0 Hz, 2H), 7.26 (d, J=8.0 Hz, 2H). Compound 341G: LC-MS (ESI) m/z: 430 [M+H]$^+$. Compound 341: LC-MS (ESI) m/z: 402 [M+H]$^+$; $^1$H-NMR (CD$_3$OD, 400 MHz): δ (ppm) 1.69-1.72 (m, 2H), 1.86-2.07 (m, 6H), 2.54-2.60 (m, 1H), 2.97-3.04 (m, 5H), 3.25-3.32 (m, 2H), 3.58-3.62 (s, 2H), 3.78-3.82 (m, 2H), 4.18 (br, 1H), 6.98 (d, J=8.8 Hz, 2H), 7.21 (d, J=8.8 Hz, 2H).

Example 342

Synthesis of 4-((2-chloro-4'-(piperidin-1-yl)-[1,1'-biphenyl]-4-yl)thio)-1H-1,2,3-triazole-5-carboxylic acid 2,2,2-trifluoroacetate (342)

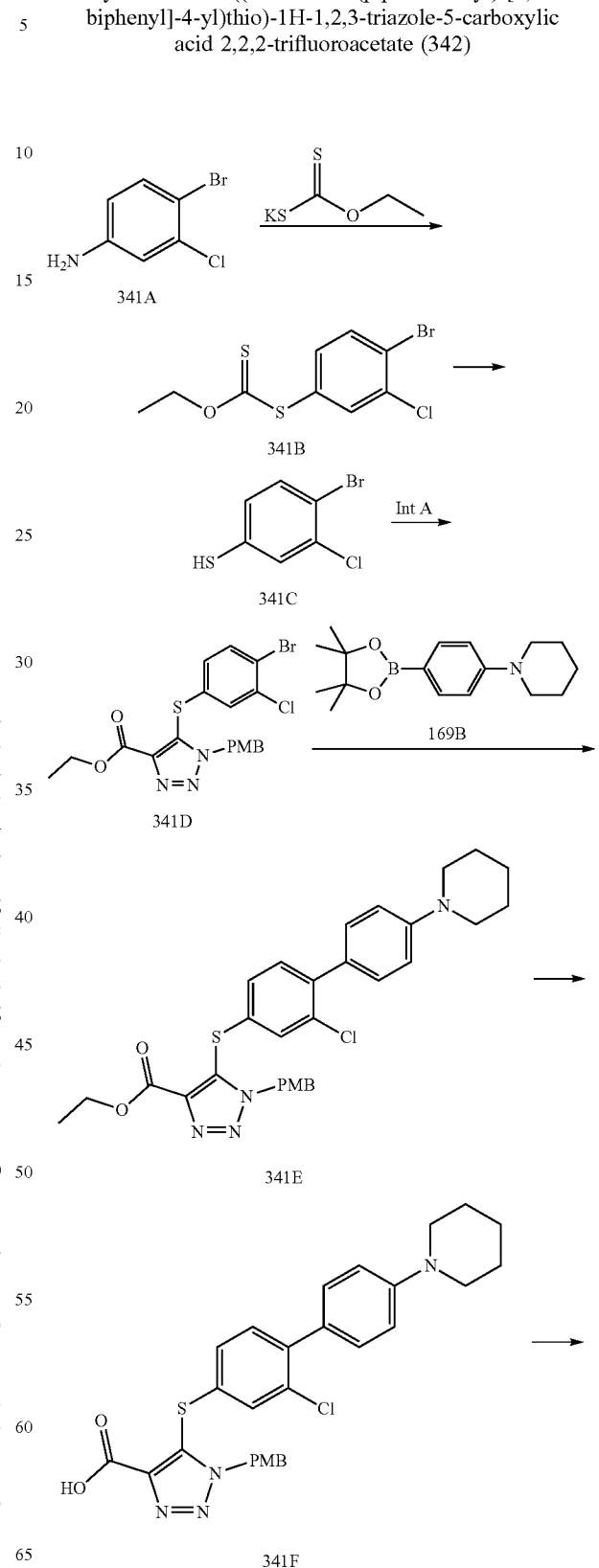

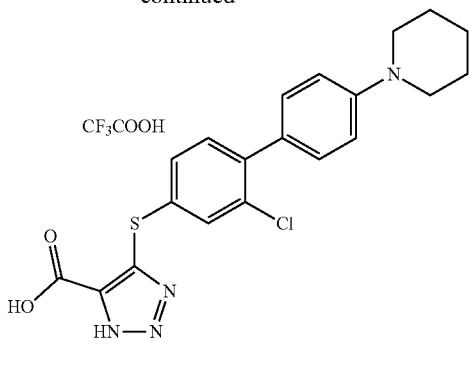

341

To a suspension of 4-bromo-3-chloroaniline (341A) (3.6 g, 14.6 mmol) in aqueous HCl solution (12 N, 4 mL) and ice (7.0 g) was slowly added a solution of NaNO$_2$ (1.0 g, 14.6 mmol) in water (7.0 mL) at 0° C. and stirred at 0° C. for 30 minutes. The diazonium salt solution was dropped into a stirred solution of potassium 0-ethyl carbonodithioate (4.5 g, 28 mmol) in water (7.0 mL). The mixture was carefully warmed to 75° C. and stirred for 1.5 hours. After cooled down to room temperature, the mixture was diluted with saturated aqueous NaHCO$_3$ solution (40 mL) and extracted with ether (50 mL×3). The combined organic layers was washed with water (100 mL) and brine (100 mL), dried over anhydrous sodium sulfate, filtered, and concentrated to give a crude Compound 341B. LC-MS (ESI) m/z: Non-ionizable compound under routine conditions used; $^1$H-NMR (CDCl$_3$, 400 MHz): δ (ppm) 1.37 (t, J=7.2 Hz, 3H), 4.63 (q, J=7.2 Hz, 2H), 7.24-7.25 (m, 1H), 7.60-7.61 (m, 1H), 7.68 (d, J=8.4 Hz, 1H).

To a solution of Compound 341B (3.5 g, 11.3 mmol) in EtOH (25 mL) was added KOH (3.6 g, 64.3 mmol). The mixture was stirred at reflux under nitrogen overnight and concentrated under reduced pressure. The residue was diluted with water (50 mL) and washed with ether (45 mL×3). The aqueous layer was acidified to pH 2 with diluted aqueous H$_2$SO$_4$ solution (2 N) and extracted with CH$_2$Cl$_2$ (50 mL×3). The combined organic layers was washed with water (100 mL) and brine (100 mL), dried over anhydrous sodium sulfate, filtered, and concentrated to give Compound 341C. LC-MS (ESI) m/z: Non-ionizable compound under routine conditions used; $^1$H-NMR (CDCl$_3$, 400 MHz): δ (ppm) 3.51 (s, 1H), 6.94 (dd, J=8.4, 2.4 Hz, 1H), 7.30 (d, J=2.4 Hz, 1H), 7.46 (d, J=8.4 Hz, 1H).

Compounds 341D, 341E, 341F, and 341 were synthesized by employing the procedures described for Compounds 1E, 4B, 8F, and 1 using Compounds 341C with Na$_2$CO$_3$ as base at 80° C., 169B, 341D with K$_2$CO$_3$ as base and 1,4-dioxane/H$_2$O as solvent, 341E, and 341F in lieu of Compounds 1D with K$_2$CO$_3$ as base at 50° C., (4-bromophenyl)boronic acid, 4A with Na$_2$CO$_3$ as base and toluene/EtOH/H$_2$O as solvent, 8E, and 1E. Compound 341D: LC-MS (ESI) m/z: 482 [M+H]$^+$; (CDCl$_3$, 400 MHz): δ (ppm) 1.35 (t, J=7.2 Hz, 3H), 3.77 (s, 3H), 4.38 (q, J=7.2 Hz, 2H), 5.60 (s, 2H), 6.70 (dd, J=8.4, 2.0 Hz, 1H), 6.72 (d, J=8.4 Hz, 2H), 7.80 (d, J=2.0 Hz, 1H), 7.11 (d, J=8.4 Hz, 2H), 7.35 (d, J=8.4 Hz, 1H). Compound 341E: LC-MS (ESI) m/z: 563 [M+H]$^+$. Compound 341F: LC-MS (ESI) m/z: 535 [M+H]$^+$. Compound 341: LC-MS (ESI) m/z: 415 [M+H]$^+$; $^1$H-NMR (DMSO-d$_6$, 400 MHz): δ (ppm) 1.56-1.63 (m, 6H), 3.39-3.46 (m, 4H), 7.07 (d, J=8.4 Hz, 2H), 7.31 (d, J=8.4 Hz, 2H), 7.39 (d, J=8.4 Hz, 1H), 7.44 (d, J=8.4H z, 1H), 7.63 (s, 1H), 13.52 (s, 1H), 15.86 (s, 1H).

Example 343

Synthesis of 4-((2-chloro-5-(cyclopentylmethoxy)phenyl)thio)-1H-1,2,3-triazole-5-carboxylic acid (343)

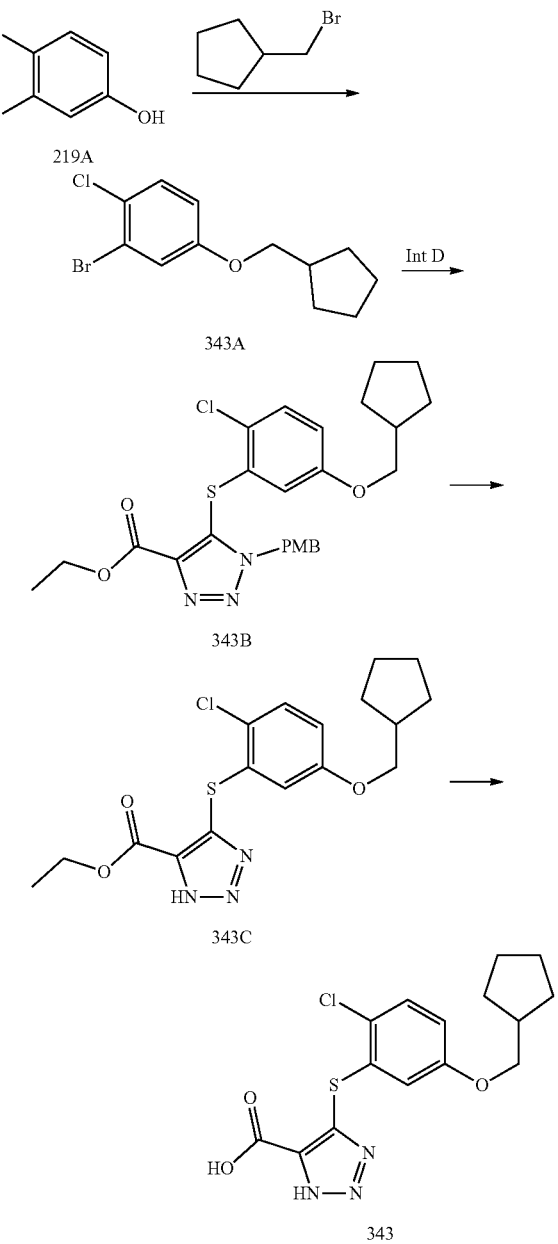

Compounds 343A, 343B, 343C, and 343 were synthesized by employing the procedures described for Compounds 27B, 35D, 217E, and 8F using (bromomethyl)cyclopentane, Compounds 219A with K$_2$CO$_3$ as base, 343A, 343B, and 343C in lieu of 2-bromopropane, Compounds 27A with Cs$_2$CO$_3$ as base, 35C, 217D, and 8E. Compound 343A: LC-MS (ESI) m/z: non-ionizable compound under routine conditions used. Compound 343B: LC-MS (ESI) m/z: 502 [M+H]⁺. Compound 343C: LC-MS (ESI) m/z: 382 [M+H]⁺. Compound 343: LC-MS (ESI) m/z: 354 [M+H]⁺. ¹H-NMR (DMSO-d₆, 400 MHz): δ (ppm) 1.22-1.32 (m, 2H), 1.44-1.60 (m, 4H), 1.66-1.76 (m, 2H), 2.18-2.26 (m, 1H), 3.78 (d, J=6.8 Hz, 2H), 6.92-6.98 (m, 2H), 7.44 (d, J=8.8 Hz, 1H).

Example 344

Synthesis of 4-((1-(4-cyanophenyl)piperidin-4-yl)thio)-1H-1,2,3-triazole-5-carboxylic acid 2,2,2-trifluoroacetate (344)

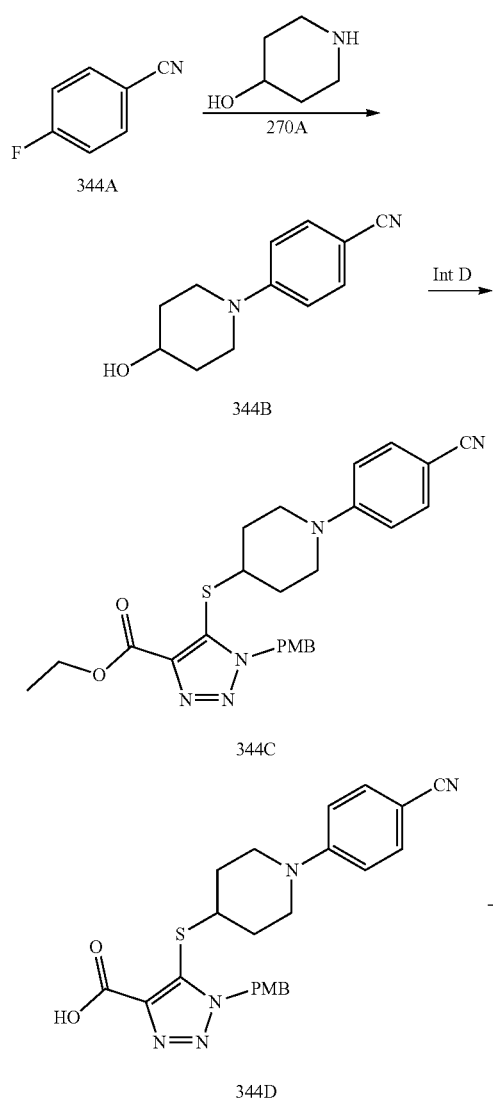

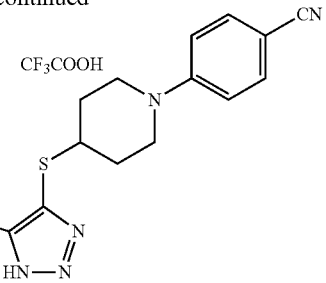

Compounds 344B, 344C, 344D, and 344 were synthesized by employing the procedures described for Compounds 297C, 90C, 8F, and 1 using Compounds 270A, 344A with Cs₂CO₃ as base at 100° C., Intermediate D, 344B, 344C, and 344D in lieu of Compounds 297B, 397A with K₂CO₃ as base as base at 70° C., Intermediate H, 90B, 8E, and 1E. Compound 344B: LC-MS (ESI) m/z: 203 [M+H]⁺; ¹H-NMR (CDCl₃, 400 MHz): δ (ppm) 1.61-1.68 (m, 2H), 1.97-2.03 (m, 2H), 3.10-3.17 (m, 2H), 3.69-3.75 (m, 2H), 3.95-3.98 (m, 1H), 6.88 (d, J=8.4 Hz, 2H), 7.49 (d, J=8.4 Hz, 2H). Compound 344C: LC-MS (ESI) m/z: 478 [M+H]⁺. Compound 344D: LC-MS (ESI) m/z: 550 [M+H]⁺. Compound 344: LC-MS (ESI) m/z: 330 [M+H]⁺; ¹H-NMR (DMSO-d₆, 400 MHz): δ (ppm) 1.60-1.68 (m, 2H), 2.08-2.14 (m, 2H), 3.09-3.15 (m, 2H), 3.81-3.88 (m, 3H), 7.03 (d, J=8.8 Hz, 2H), 7.57 (d, J=8.8 Hz, 2H), 13.29 (s, 1H), 15.52 (s, 1H).

Example 345

Synthesis of 4-(((cis)-4-(3,4-dichlorophenyl)cyclohexyl)thio)-1H-1,2,3-triazole-5-carboxylic acid 2,2,2-trifluoroacetate (345)

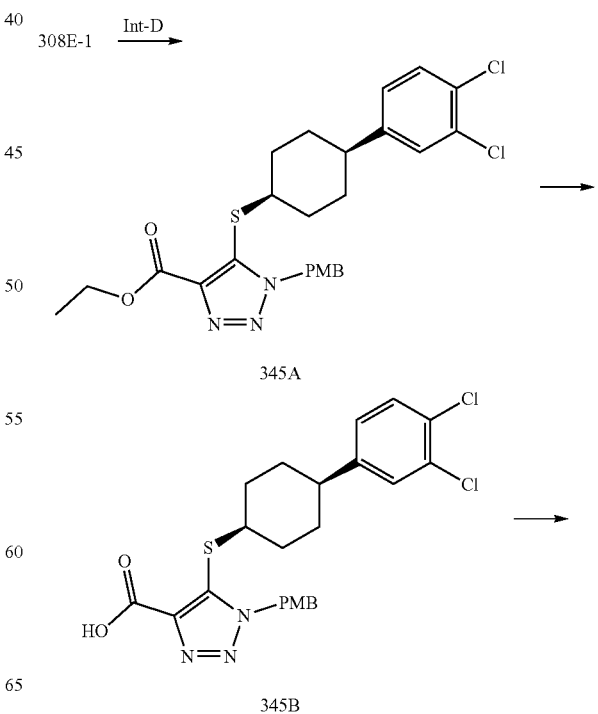

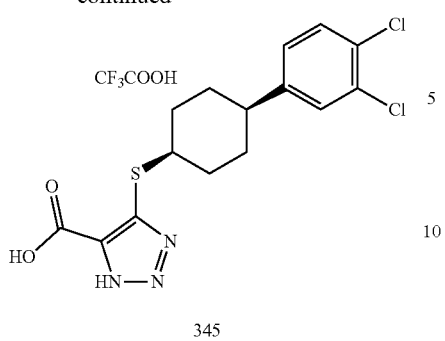

345

Compounds 345A, 345B, and 345 were synthesized by employing the procedures described for Compounds 90C, 8F, and 1 using Intermediate D, Compounds 308E-1 with DEAD as coupling reagent, 345A, and 345B in lieu of Intermediate H, Compounds 90B with DIAD as coupling reagent, 8E, and 1E. Compound 345A: LC-MS (ESI) m/z: 520 [M+H]$^+$. Compound 345B: LC-MS (ESI) m/z: 492 [M+H]$^+$. Compound 345: LC-MS (ESI) m/z: 372 [M+H]$^+$; $^1$H-NMR (DMSO-d$_6$, 400 MHz): δ (ppm) 1.68-1.78 (m, 2H), 1.84-2.14 (m, 6H), 2.58-2.69 (m, 1H), 4.19 (brs, 1H), 7.21 (d, J=8.0 Hz, 1H), 7.39-7.46 (m, 2H).

Example 346

Synthesis of 4-((1-(3-chloro-4-(trifluoromethoxy)phenyl)piperidin-4-yl)thio)-1H-1,2,3-triazole-5-carboxylic acid (346)

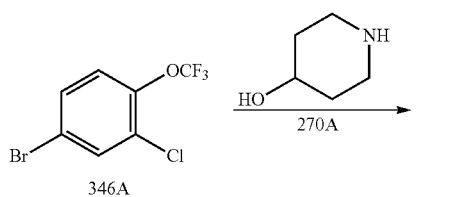

346A

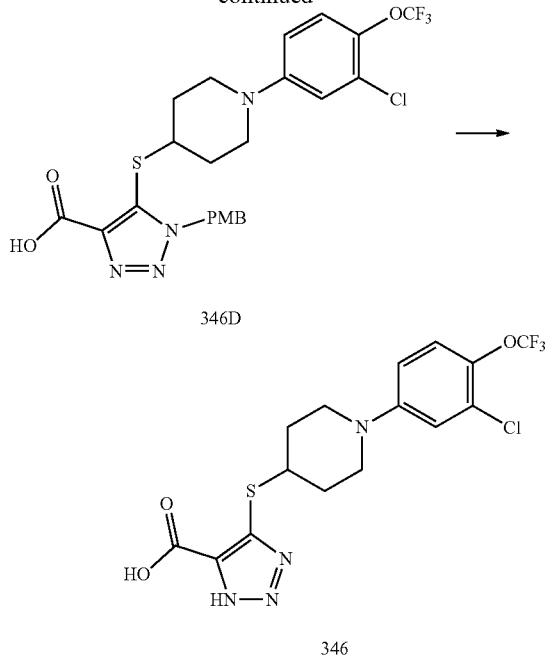

346

Compounds 346B, 346C, 346D, and 346 were synthesized by employing the procedures described for Compounds 6B, 90C, 8F, and 1 using Compounds 270A, 346A with Ruphos as ligand and THF as solvent, Intermediate D, 346B, 346C, and 346D in lieu of 1-methylpiperazine, Compounds 6A with Xantphos as ligand and toluene as solvent, Intermediate H, 90B, 8E, and 1E. Compound 346B: LC-MS (ESI) m/z: 296 [M+H]$^+$. Compound 346C: LC-MS (ESI) m/z: 571 [M+H]$^+$. Compound 346D: LC-MS (ESI) m/z: 543 [M+H]$^+$. Compound 346: LC-MS (ESI) m/z: 423 [M+H]$^+$; $^1$H-NMR (DMSO-d$_6$, 400 MHz): δ (ppm) 1.64-1.67 (m, 2H), 2.10-2.13 (m, 2H), 2.98 (t, J=10.8 Hz, 2H), 3.67-3.75 (m, 3H), 6.96 (d, J=13 Hz, 1H), 7.13 (d, J=2.4 Hz, 1H), 7.32 (d, J=9.2 Hz, 1H), 15.52 (s, 1H).

Example 347

Synthesis of 4-(((cis)-4-(4-(pyrrolidin-1-yl)phenyl)cyclohexyl)thio)-1H-1,2,3-triazole-5-carboxylic acid 2,2,2-trifluoroacetate (347)

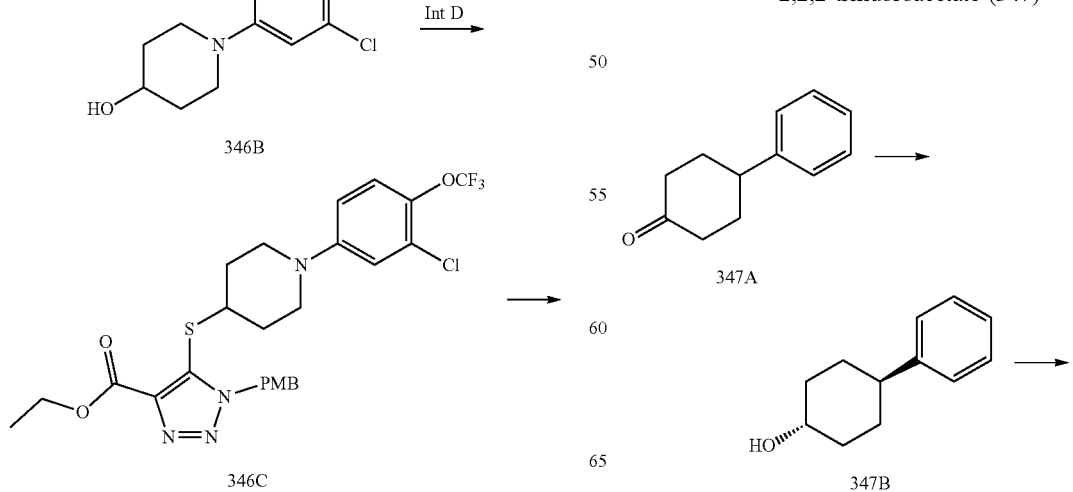

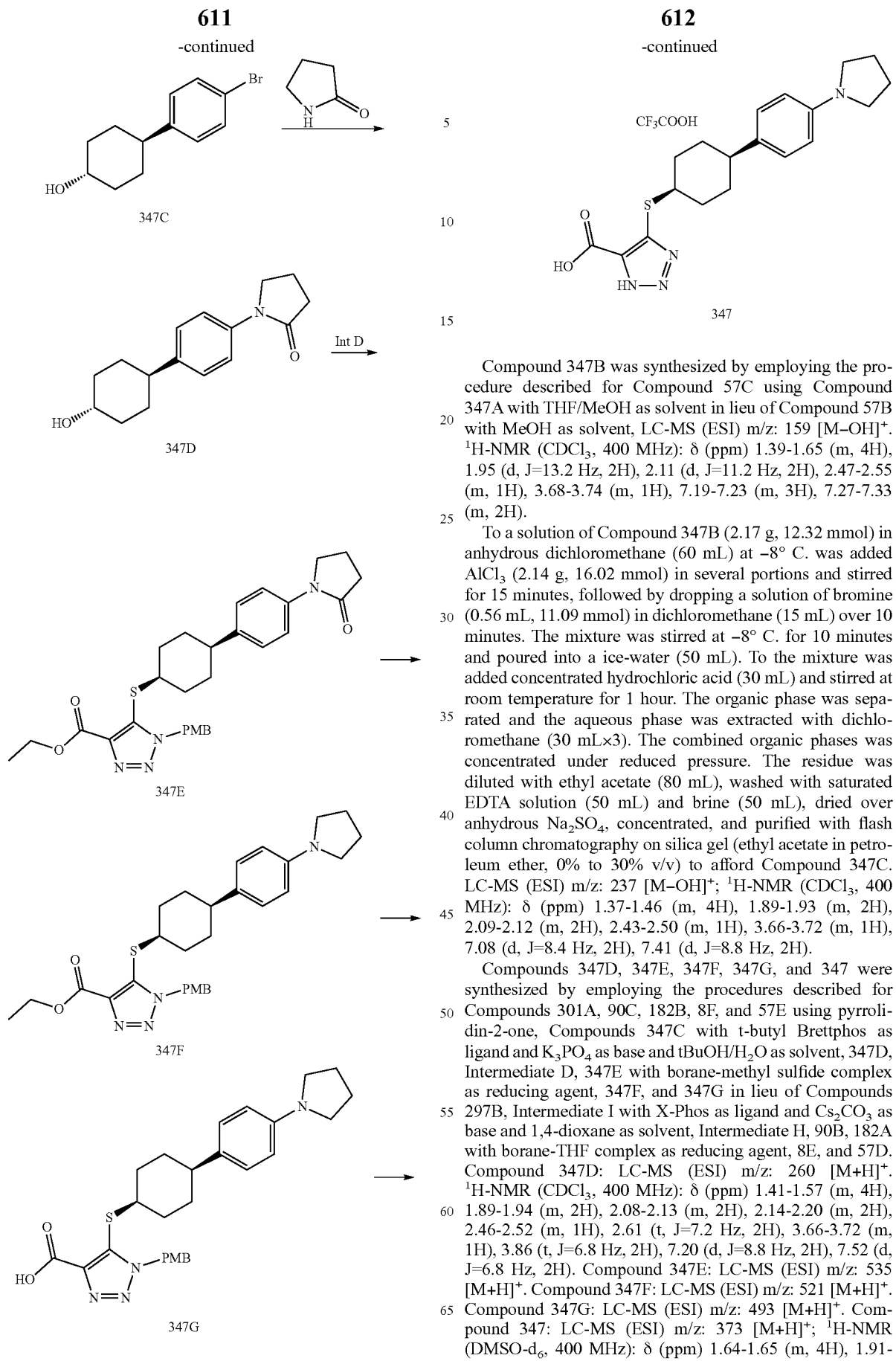

Compound 347B was synthesized by employing the procedure described for Compound 57C using Compound 347A with THF/MeOH as solvent in lieu of Compound 57B with MeOH as solvent, LC-MS (ESI) m/z: 159 [M−OH]$^+$. $^1$H-NMR (CDCl$_3$, 400 MHz): δ (ppm) 1.39-1.65 (m, 4H), 1.95 (d, J=13.2 Hz, 2H), 2.11 (d, J=11.2 Hz, 2H), 2.47-2.55 (m, 1H), 3.68-3.74 (m, 1H), 7.19-7.23 (m, 3H), 7.27-7.33 (m, 2H).

To a solution of Compound 347B (2.17 g, 12.32 mmol) in anhydrous dichloromethane (60 mL) at −8° C. was added AlCl$_3$ (2.14 g, 16.02 mmol) in several portions and stirred for 15 minutes, followed by dropping a solution of bromine (0.56 mL, 11.09 mmol) in dichloromethane (15 mL) over 10 minutes. The mixture was stirred at −8° C. for 10 minutes and poured into a ice-water (50 mL). To the mixture was added concentrated hydrochloric acid (30 mL) and stirred at room temperature for 1 hour. The organic phase was separated and the aqueous phase was extracted with dichloromethane (30 mL×3). The combined organic phases was concentrated under reduced pressure. The residue was diluted with ethyl acetate (80 mL), washed with saturated EDTA solution (50 mL) and brine (50 mL), dried over anhydrous Na$_2$SO$_4$, concentrated, and purified with flash column chromatography on silica gel (ethyl acetate in petroleum ether, 0% to 30% v/v) to afford Compound 347C. LC-MS (ESI) m/z: 237 [M−OH]$^+$; $^1$H-NMR (CDCl$_3$, 400 MHz): δ (ppm) 1.37-1.46 (m, 4H), 1.89-1.93 (m, 2H), 2.09-2.12 (m, 2H), 2.43-2.50 (m, 1H), 3.66-3.72 (m, 1H), 7.08 (d, J=8.4 Hz, 2H), 7.41 (d, J=8.8 Hz, 2H).

Compounds 347D, 347E, 347F, 347G, and 347 were synthesized by employing the procedures described for Compounds 301A, 90C, 182B, 8F, and 57E using pyrrolidin-2-one, Compounds 347C with t-butyl Brettphos as ligand and K$_3$PO$_4$ as base and tBuOH/H$_2$O as solvent, 347D, Intermediate D, 347E with borane-methyl sulfide complex as reducing agent, 347F, and 347G in lieu of Compounds 297B, Intermediate I with X-Phos as ligand and Cs$_2$CO$_3$ as base and 1,4-dioxane as solvent, Intermediate H, 90B, 182A with borane-THF complex as reducing agent, 8E, and 57D. Compound 347D: LC-MS (ESI) m/z: 260 [M+H]$^+$. $^1$H-NMR (CDCl$_3$, 400 MHz): δ (ppm) 1.41-1.57 (m, 4H), 1.89-1.94 (m, 2H), 2.08-2.13 (m, 2H), 2.14-2.20 (m, 2H), 2.46-2.52 (m, 1H), 2.61 (t, J=7.2 Hz, 2H), 3.66-3.72 (m, 1H), 3.86 (t, J=6.8 Hz, 2H), 7.20 (d, J=8.8 Hz, 2H), 7.52 (d, J=6.8 Hz, 2H). Compound 347E: LC-MS (ESI) m/z: 535 [M+H]$^+$. Compound 347F: LC-MS (ESI) m/z: 521 [M+H]$^+$. Compound 347G: LC-MS (ESI) m/z: 493 [M+H]$^+$. Compound 347: LC-MS (ESI) m/z: 373 [M+H]$^+$; $^1$H-NMR (DMSO-d$_6$, 400 MHz): δ (ppm) 1.64-1.65 (m, 4H), 1.91-

1.96 (m, 8H), 2.40 (s, 1H), 3.19 (s, 4H), 4.11 (s, 1H), 6.51 (d, J=7.6 Hz, 2H), 7.03 (d, J=8.0 Hz, 2H).

Example 348

Synthesis of 4-(((cis)-4-(4-(trifluoromethoxy)phenyl)cyclohexyl)thio)-1H-1,2,3-triazole-5-carboxylic acid (348)

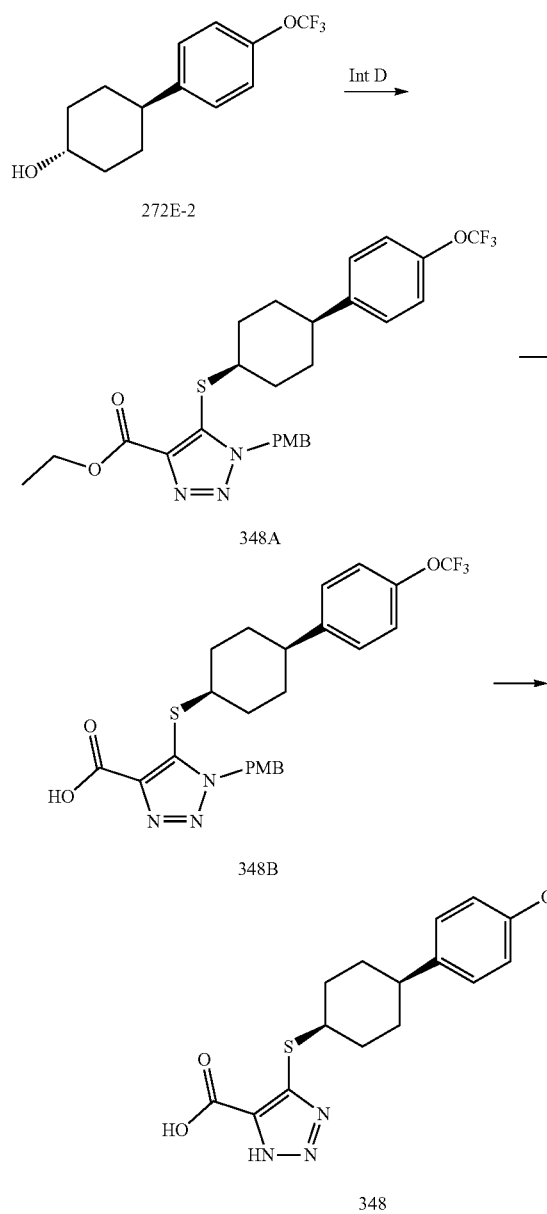

Compounds 348A, 348B, and 348 were synthesized by employing the procedures described for Compounds 90C, 8F, and 1 using Compounds 272E-2, Intermediate D, 348A, and 348B in lieu of Compounds 90B, Intermediate H, 8E, and 1E. Compound 348A: LC-MS (ESI) m/z: 536 [M+H]⁺. Compound 348B: LC-MS (ESI) m/z: 508 [M+H]⁺. Compound 348: LC-MS (ESI) m/z: 388 [M+H]⁺; ¹H-NMR (CD$_3$OD, 400 MHz): δ (ppm) 1.62-1.65 (m, 2H), 1.79-2.02 (m, 6H), 2.54-2.61 (m, 1H), 4.09 (s, 1H), 7.09 (d, J=8.4 Hz, 2H), 7.25 (d, J=8.4 Hz, 2H Example 349

Synthesis of 4-((4'-(2-methylpiperidin-1-yl)-[1,1'-biphenyl]-4-yl)thio)-1H-1,2,3-triazole-5-carboxylic acid 2,2,2-trifluoroacetate (349)

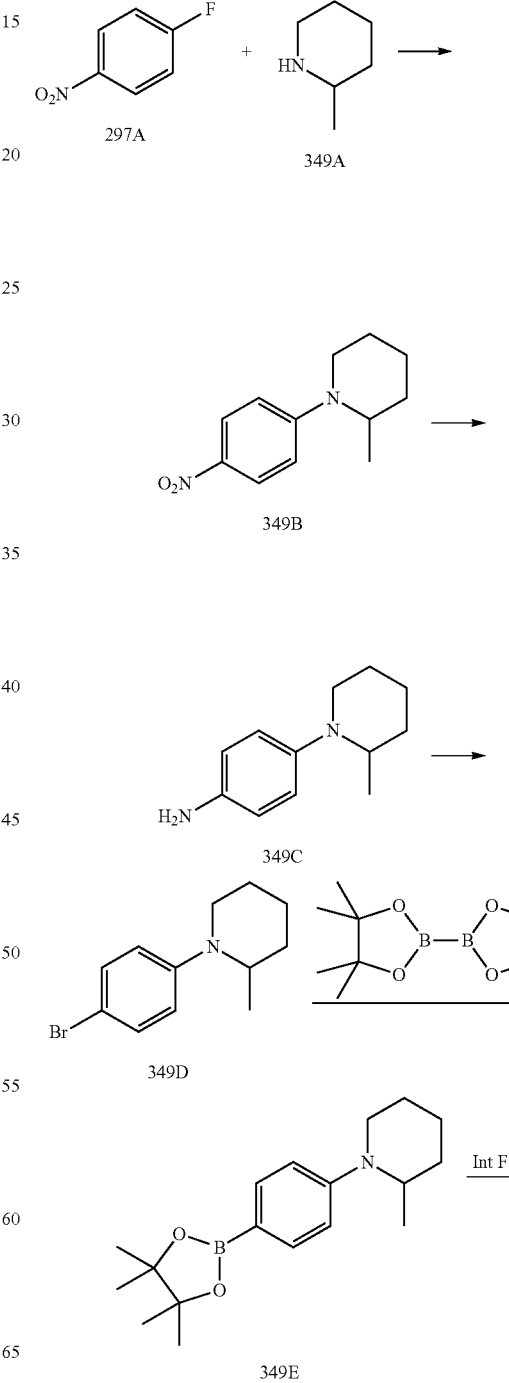

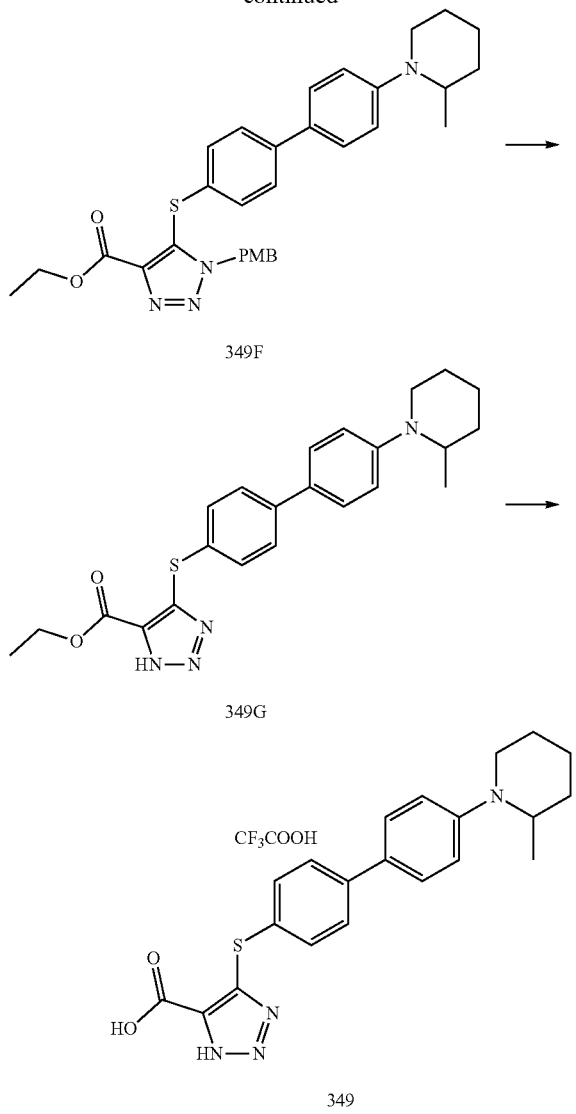

349F

349G

349

Compound 349B was synthesized by employing the procedure described for Compound 297C using Compound 349A with as $Cs_2CO_3$ base and NMP as solvent at 100° C. in lieu of Compound 297B with as $K_2CO_3$ base and DMF as solvent at 70° C., LC-MS (ESI) m/z: 221 [M+H]$^+$.

To a mixture of Compound 349B (2.2 g, 10 mmol) and Ranny-Ni (1.0 g) in EtOH (20 mL) was dropped 85% $N_2H_4 \cdot H_2O$ (3 mL) at 60° C., and stirred at this temperature for 3 hours. The mixture was filtered through Celite and the filtrate was concentrated. The residue was purified with flash column chromatography on silica gel (ethyl acetate in petroleum ether, 35% v/v) to afford Compound. LC-MS (ESI) m/z: 191 [M+H]$^+$; $^1$H-NMR (CDCl$_3$, 400 MHz): δ (ppm) 0.88 (d, J=6.8 Hz, 3H), 1.44-1.48 (m, 2H), 1.64-1.82 (m, 4H), 2.80-2.84 (m, 1H), 2.94-2.96 (m, 1H), 3.21-3.25 (m, 1H), 3.46 (brs, 2H), 6.62-6.65 (m, 2H), 6.86-6.89 (m, 2H)

Compounds 349D, 349E, 349F, 349G, and 349 were synthesized by employing the procedures described for Compounds 30B, 27C, 4B, 57E, and 8F using Compounds 349C with isopentyl nitrite/CuBr$_2$ and THF as solvent, 349D, 349E, Intermediate F with 1,4-dioxane/H$_2$O as solvent, 349F, and 349G in lieu of Compounds 30A with Isoamyl nitrite/CuCl$_2$ and MeCN as solvent, 27B, (4-bromophenyl)boronic acid, 4A with toluene/EtOH/H$_2$O as solvent, 57D, and 8E. Compound 349D: LC-MS (ESI) m/z: 254 [M+H]$^+$. Compound 349E: LC-MS (ESI) m/z: 302 [M+H]$^+$. Compound 349F: LC-MS (ESI) m/z: 543 [M+H]$^+$. Compound 349G: LC-MS (ESI) m/z: 423 [M+H]$^+$. Compound 349: LC-MS (ESI) m/z: 395 [M+H]$^+$; $^1$H-NMR (DMSO-d$_6$, 400 MHz): δ (ppm) 0.99 (d, J=6.8 Hz, 3H), 1.50-1.61 (m, 4H), 1.73-1.75 (m, 2H), 2.88-2.90 (m, 1H), 3.41-3.42 (m, 1H), 4.11-4.15 (m, 1H), 6.97-0.99 (m, 2H), 7.48-7.64 (m, 6H).

Example 350

Synthesis of 4-(((1-(3,5-dichlorophenyl)piperidin-4-yl)thio)methyl)-1H-1,2,3-triazole-5-carboxylic acid 2,2,2-trifluoroacetate (350)

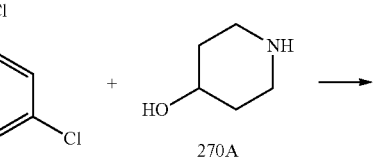

285A     270A

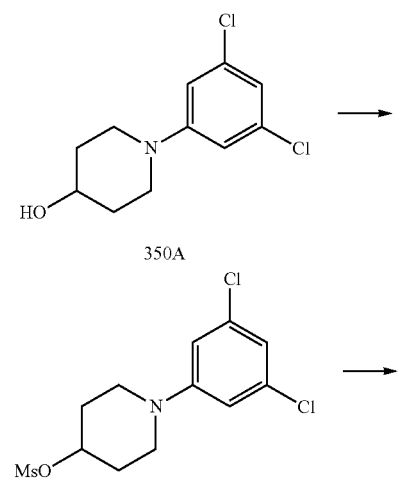

350A

350B

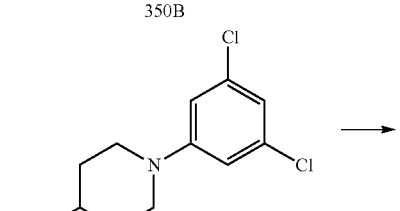

350C

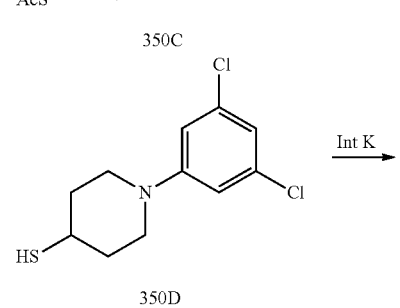

350D

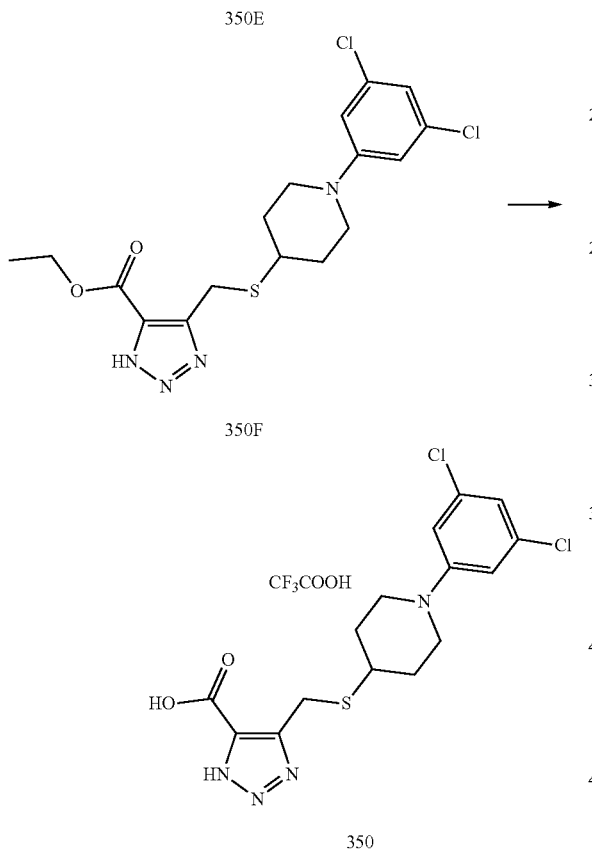

10% aqueous NaOH solution (20 mL) and extracted with EtOAc (30 mL×3). The combined organic layers was washed with brine (50 mL), dried over anhydrous sodium sulfate, filtered, and concentrated to furnish Compound 350D. LC-MS (ESI) m/z: 262 [M+H]$^+$.

Compounds 350E, 350F, and 350 were synthesized by employing the procedures described for Compounds 243B, 57E, and 8F using Compounds 350D with $K_2CO_3$ as base and DMF as solvent, 350E, and 350F in lieu of Compounds 243A with $Na_2CO_3$ as base and NMP as solvent, 57D, and 8E. Compound 350E: LC-MS (ESI) m/z: 535 [M+H]$^+$. Compound 350F: LC-MS (ESI) m/z: 415 [M+H]$^+$. Compound 350: LC-MS (ESI) m/z: 387 [M+H]$^+$; $^1$H-NMR (DMSO-$d_6$, 400 MHz): δ (ppm) 1.44-1.47 (m, 2H), 1.93-1.96 (m, 2H), 2.83-2.89 (m, 3H), 3.67-3.71 (m, 2H), 4.07 (s, 2H), 6.81 (s, 1H), 6.91-6.92 (m, 2H).

Example 351

Synthesis of 4-((3-(cyclopentyloxy)phenyl)thio)-1H-1,2,3-triazole-5-carboxylic acid 2,2,2-trifluoroacetate (351)

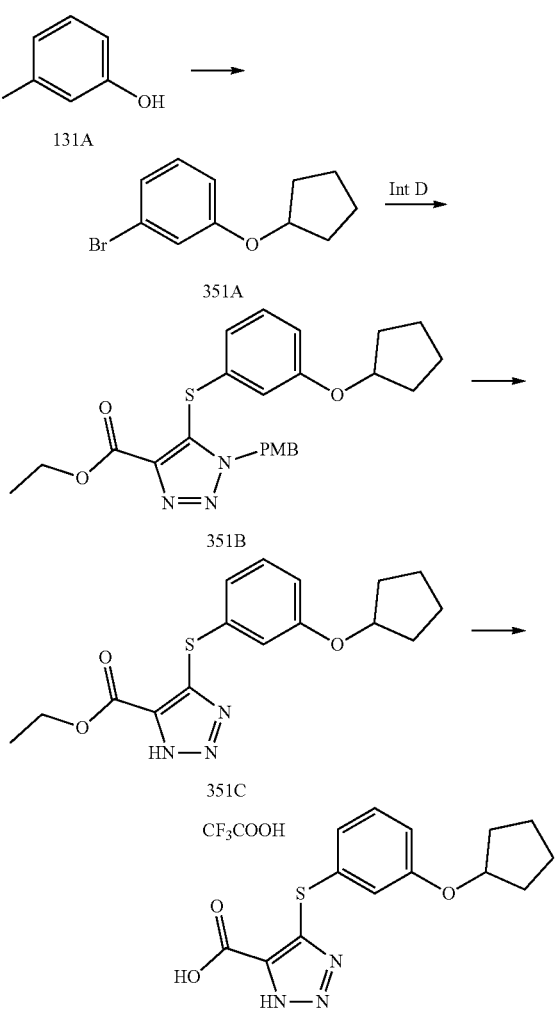

Compounds 350A and 350B were synthesized by employing the procedures described for Compounds 270B and 340F using Compounds 285A and 350A in lieu of Compounds 197A and 340E. Compound 350A: LC-MS (ESI) m/z: 246 [M+H]$^+$. Compound 350B: LC-MS (ESI) m/z: 324 [M+H]$^+$.

To a solution of Compound 350B (0.72 g, 2.22 mmol) in DMF (20 mL) was added KSAc (759 mg, 6.66 mmol) and stirred at 130° C. for 2 hours. The mixture was diluted with $H_2O$ (30 mL) and extracted with EtOAc (50 mL×3). The combined organic layers was washed with brine (50 mL), dried over anhydrous sodium sulfate, concentrated, and purified with flash column chromatography on silica gel (ethyl acetate in petroleum ether, 20% v/v) to furnish Compound 350C. LC-MS (ESI) m/z: 304 [M+H]$^+$.

After a suspension of LiAlH$_4$ (23 mg, 0.2 mmol) in THF (10 mL) was stirred at 0° C. for 10 minutes, to the suspension was added Compound 350C (60 mg, 0.2 mmol) and stirred at room temperature overnight. It was quenched with Compounds 351A, 351B, 351C, and 351 were synthesized by employing the procedures described for Compounds 27B, 35D, 1, and 8F using bromocyclopentane, Compounds 131A, 351A, 351B, and 351C in lieu of 2-bromopropane, Compounds 27A, 35C, 1E, and 8E. Compound 351A: LC-MS (ESI) m/z: non-ionizable compound under routine conditions used; $^1$H-NMR (CDCl$_3$, 400 MHz): δ (ppm) 1.60-1.65 (m, 2H), 1.74-1.93 (m, 6H), 4.70-4.75 (m, 1H), 6.78 (d, J=7.6 Hz, 1H), 7.01-7.06 (m, 2H), 7.11 (t, J=8.0 Hz, 1H). Compound 351B: LC-MS (ESI) m/z: 454 [M+H]$^+$; $^1$H-NMR (CDCl$_3$, 400 MHz): δ (ppm) 1.31 (t, J=7.2 Hz, 3H), 1.41-1.45 (m, 2H), 1.71-1.81 (m, 6H), 3.76 (s, 3H), 4.36 (q, J=7.2 Hz, 2H), 4.53-4.56 (m, 1H), 5.51 (s, 2H), 6.45 (s, 1H), 6.61 (d, J=8.0 Hz, 1H), 6.68 (d, J=8.0 Hz, 1H), 6.76 (d, J=8.4 Hz, 2H), 7.02 (t, J=8.4 Hz, 1H), 7.16 (d, J=8.4 Hz, 2H). Compound 351C: LC-MS (ESI) m/z: 334 [M+H]$^+$. Compound 351: LC-MS (ESI) m/z: 306 [M+H]$^+$; $^1$H-NMR (CD$_3$OD, 400 MHz): δ (ppm) 1.58-1.63 (m, 2H), 1.64-1.82 (m, 4H), 1.86-1.95 (m, 2H), 4.77 (t, J=6.0 Hz, 1H), 6.86-6.88 (m, 1H), 6.98-7.02 (m, 2H), 7.26 (t, J=8.0 Hz, 1H).

Example 352

Synthesis of 4-(((cis)-4-(4-cyanophenyl)cyclohexyl)thio)-1H-1,2,3-triazole-5-carboxylic acid (352)

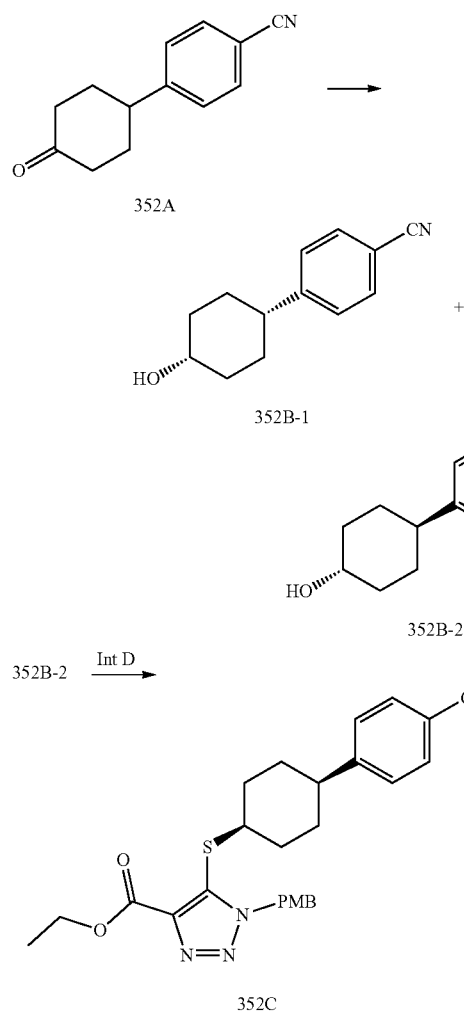

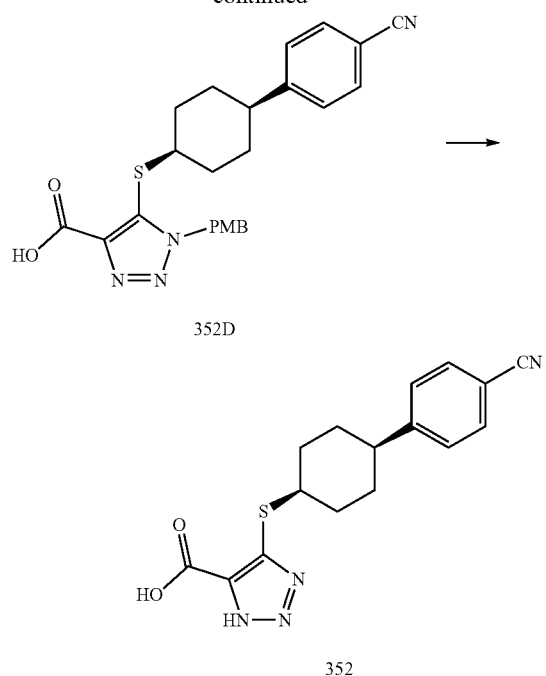

Compounds 352B-1, 352B-2, 352C, 352D, and 352 were synthesized by employing the procedures described for Compounds 57C, 90C, 8F, and 1 using Compounds 352A, Intermediate D, 352B-2, 352C, and 352D in lieu of Compounds 57B, Intermediate H, 90B, 8E, and 1E. Compound 352B-1: LC-MS (ESI) m/z: 202 [M+H]$^+$; $^1$H-NMR (CDCl$_3$, 400 MHz): δ (ppm) 1.64-1.71 (m, 4H), 1.86-1.96 (m, 4H), 2.57-2.63 (m, 1H), 4.16 (s, 1H), 7.34 (d, J=8.2 Hz, 2H), 7.58 (d, J=8.2 Hz, 2H). Compound 352B-2: LC-MS (ESI) m/z: 202 [M+H]$^+$; $^1$H-NMR (CDCl$_3$, 400 MHz): δ (ppm) 1.39-1.58 (m, 4H), 1.91-1.94 (m, 2H), 2.11-2.14 (m, 2H), 2.52-2.59 (m, 1H), 3.67-3.72 (m, 1H), 7.29 (d, J=8.2 Hz, 2H), 7.58 (d, J=8.2 Hz, 2H). Compound 352C: LC-MS (ESI) m/z: 477 [M+H]$^+$. Compound 352D: LC-MS (ESI) m/z: 449 [M+H]$^+$. Compound 352: LC-MS (ESI) m/z: 329 [M+H]$^+$; $^1$H-NMR (CD$_3$OD, 400 MHz): δ (ppm) 1.73-1.77 (m, 2H), 1.92-2.10 (m, 6H), 2.71-2.78 (m, 1H), 4.20 (s, 1H), 7.47 (d, J=8.2 Hz, 2H), 7.66 (d, J=8.1 Hz, 2H).

Example 353

Synthesis of 4-(4-chloro-3-(cyclopentylmethoxy)phenoxy)-1H-1,2,3-triazole-5-carboxylic acid 2,2,2-trifluoroacetate (353)

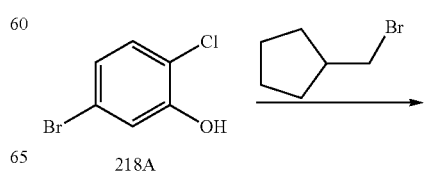

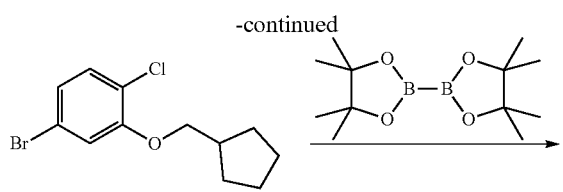

353A

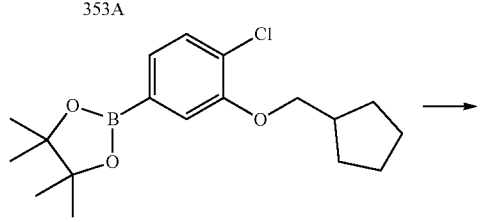

353B

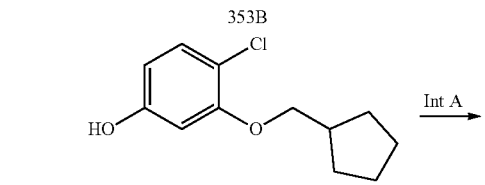

353C

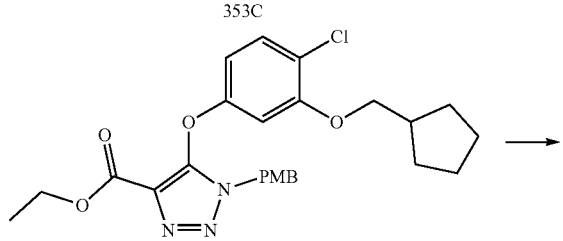

353D

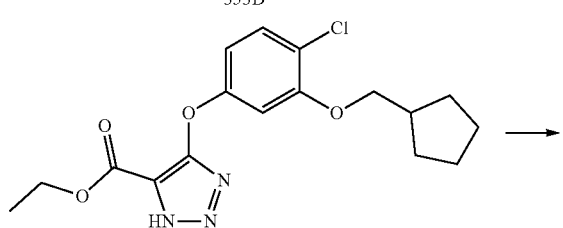

353E

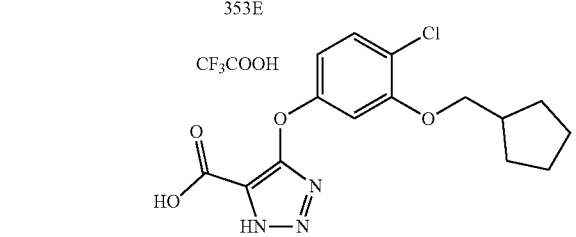

353

Compounds 353A, 353B, 353C, 353D, 353E, and 353 were synthesized by employing the procedures described for Compounds 27B, 27C, 236D, Intermediate I, 217E, and 8F using (bromomethyl)cyclopentane, Compounds 218A with $K_2CO_3$ as base, 353A, 353B, 353C, 353D, and 353E in lieu of 2-bromopropane, Compounds 27A with $Cs_2CO_3$ as base, 27B, 236C, 4-bromophenol, 217D, and 8E. Compound 353A: LC-MS (ESI) m/z: non-ionizable compound under routine conditions used. Compound 353B: LC-MS (ESI) m/z: 337 [M+H]$^+$. Compound 353C: LC-MS (ESI) m/z: 227 [M+H]$^+$. Compound 353D: LC-MS (ESI) m/z: 486 [M+H]$^+$.

Compound 353E: LC-MS (ESI) m/z: 366 [M+H]$^+$. Compound 353: LC-MS (ESI) m/z: 338 [M+H]$^+$; $^1$H-NMR (DMSO-$d_6$, 400 MHz): δ (ppm) 1.31-1.39 (m, 2H), 1.49-1.55 (m, 2H), 1.57-1.65 (m, 2H), 1.72-1.80 (m, 2H), 2.26-2.37 (m, 1H), 3.90 (d, J=6.8 Hz, 2H), 6.59 (d, J=8.4 Hz, 1H), 6.96 (s, 1H), 7.37 (d, J=8.8 Hz, 1H), 13.24 (s, 1H), 15.24 (s, 1H).

Example 354

Synthesis of 4-((1-(3-chloro-5-(trifluoromethoxy) phenyl)piperidin-4-yl)oxy)-1H-1,2,3-triazole-5-carboxylic acid (354)

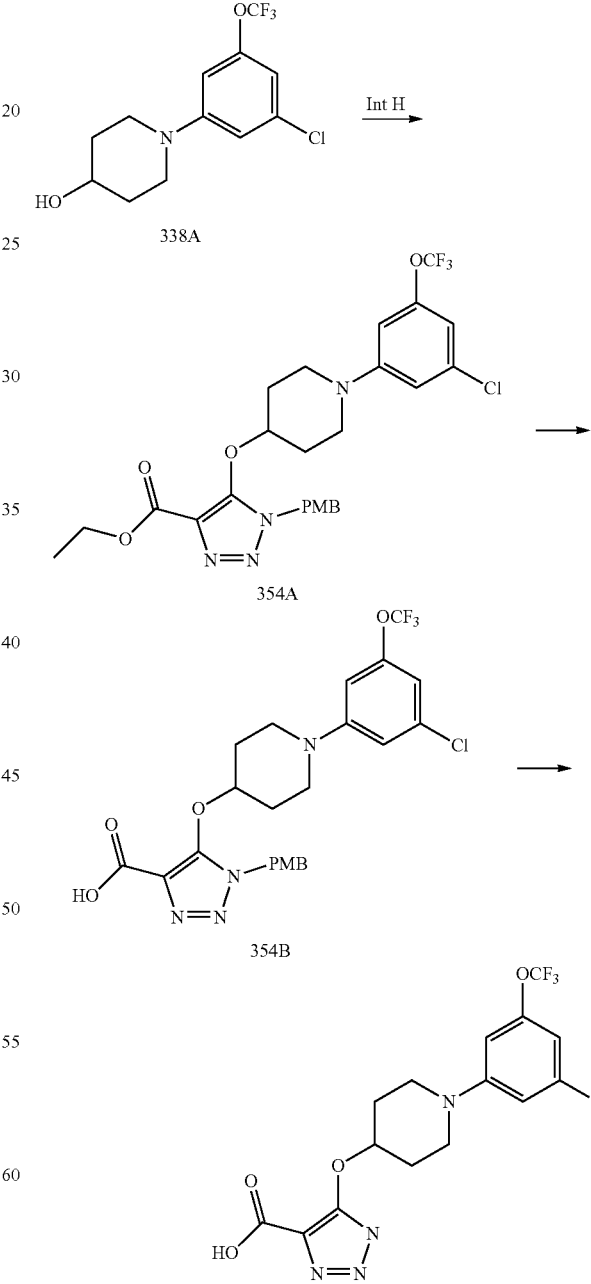

Compounds 354A, 354B, and 354 were synthesized by employing the procedures described for Compounds 90C, 8F, and 1 using Compounds 338A, 354A, and 354B in lieu of Compounds 90B, 8E, and 1E. Compound 354A: LC-MS (ESI) m/z: 555 [M+H]⁺. Compound 354B: LC-MS (ESI) m/z: 527 [M+H]⁺. Compound 354: LC-MS (ESI) m/z: 407 [M+H]⁺; ¹H-NMR (DMSO-d₆, 400 MHz): δ (ppm) 1.69-1.76 (m, 2H), 2.02-2.06 (m, 2H), 3.17-3.25 (m, 2H), 3.55-3.61 (m, 2H), 4.81 (s, 1H), 6.75 (s, 1H), 6.87 (s, 1H), 7.02 (s, 1H), 12.84 (s, 1H), 14.78 (s, 1H).

Example 355

Synthesis of 4-(((cis)-4-(3-chloro-5-(trifluoromethoxy)phenyl)cyclohexyl)oxy)-1H-1,2,3-triazole-5-carboxylic acid (355)

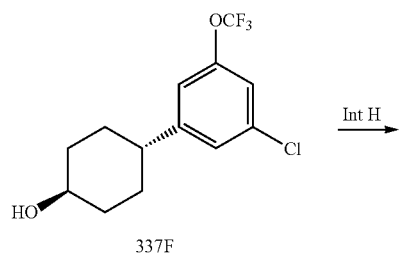

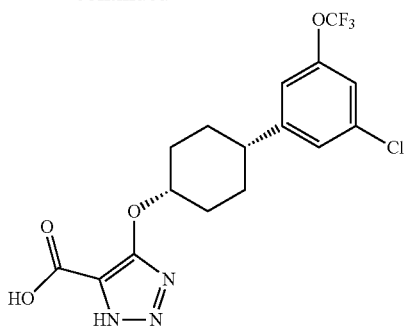

Compounds 355A, 355B, and 355 were synthesized by employing the procedures described for Compounds 90C, 8F, and 1 using Compounds 337F, 355A, and 355B in lieu of Compounds 90B, 8E, and 1E. Compound 354A: LC-MS (ESI) m/z: 554 [M+H]⁺. Compound 354B: LC-MS (ESI) m/z: 526 [M+H]⁺. Compound 354: LC-MS (ESI) m/z: 406 [M+H]⁺; ¹H-NMR (DMSO-d₆, 400 MHz): δ (ppm) 1.60-1.85 (m, 6H), 2.06 (d, J=13.2 Hz, 2H), 2.75 (t, J=12 Hz, 1H), 4.93 (s, 1H), 7.19 (s, 1H), 7.36 (d, J=10.4 Hz, 2H), 12.95 (s, 1H), 14.79 (s, 1H).

Example 356

Synthesis of 4-(((cis)-4-(4-(pyrrolidin-1-yl)phenyl)cyclohexyl)oxy)-1H-1,2,3-triazole-5-carboxylic acid 2,2,2-trifluoroacetate (356)

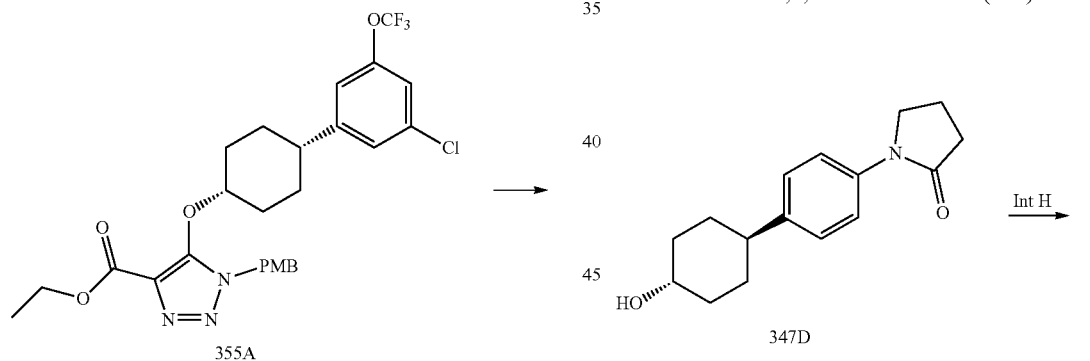

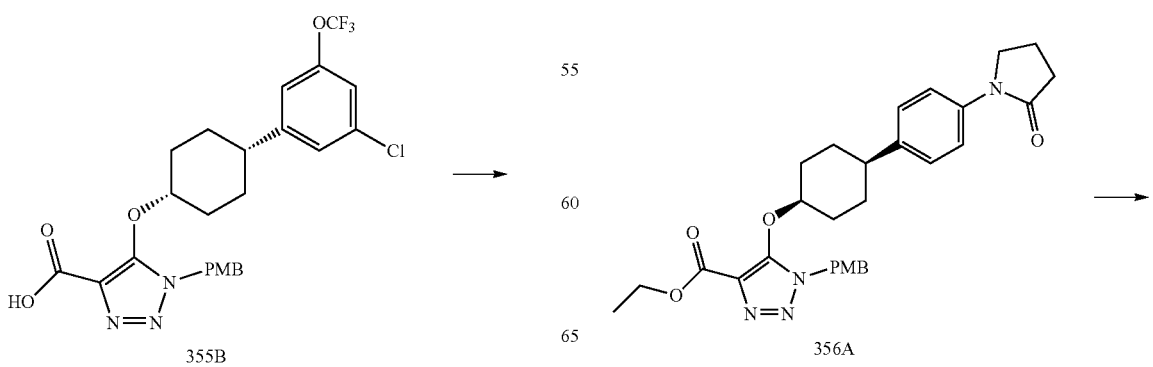

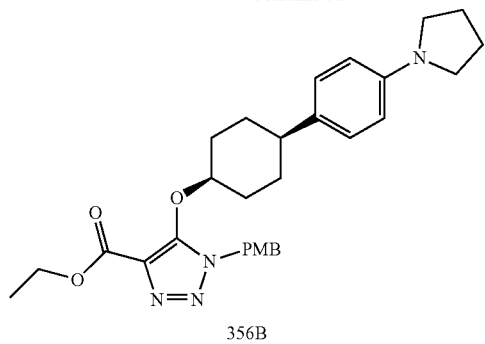

356B

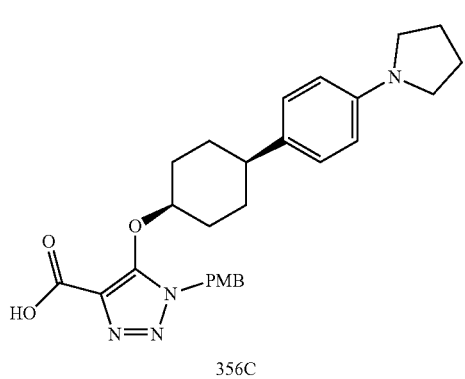

356C

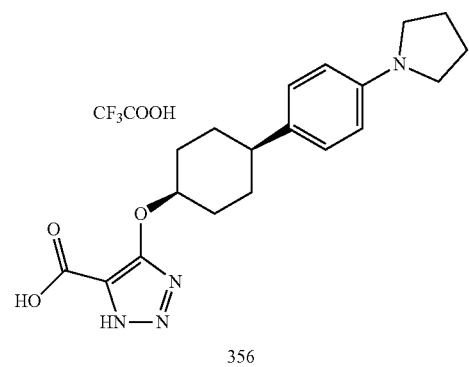 [SMILES: O=C(O)c1[nH]nnc1O[C@H]1CC[C@@H](c2ccc(N3CCCC3)cc2)CC1 ; "CF3COOH"]

356

Compounds 356A, 356B, 356C, and 356 were synthesized by employing the procedures described for Compounds 90C, 182B, 8F, and 57E using Compounds 347D, 356A with borane-methyl sulfide complex as reducing agent, 356B, and 356C in lieu of Compounds 90B, 182A with borane-THF complex as reducing agent, 8E, and 57D. Compound 356A: LC-MS (ESI) m/z: 519 [M+H]$^+$. Compound 356B: LC-MS (ESI) m/z: 505 [M+H]$^+$. Compound 356C: LC-MS (ESI) m/z: 477 [M+H]$^+$. Compound 356: LC-MS (ESI) m/z: 357 [M+H]$^+$; $^1$H-NMR (DMSO-d$_6$, 400 MHz): δ (ppm) 1.52 (d, J=10.4 Hz, 2H), 1.65-1.69 (m, 2H), 1.74-1.81 (m, 2H), 1.91-1.95 (m, 4H), 2.02-2.06 (m, 2H), 2.45 (s, 1H), 3.18-3.21 (m, 4H), 4.92 (s, 1H), 6.54 (d, J=7.6 Hz, 2H), 7.05 (d, J=8.4 Hz, 2H).

Example 357

Synthesis of 4-(2-chloro-5-(cyclopentylmethoxy)phenoxy)-1H-1,2,3-triazole-5-carboxylic acid (357)

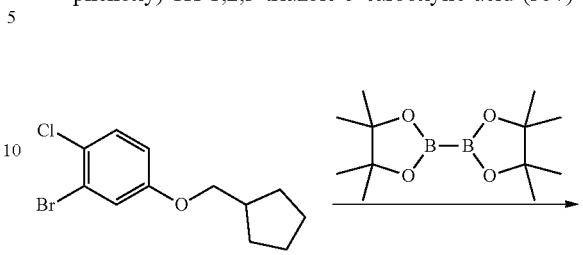

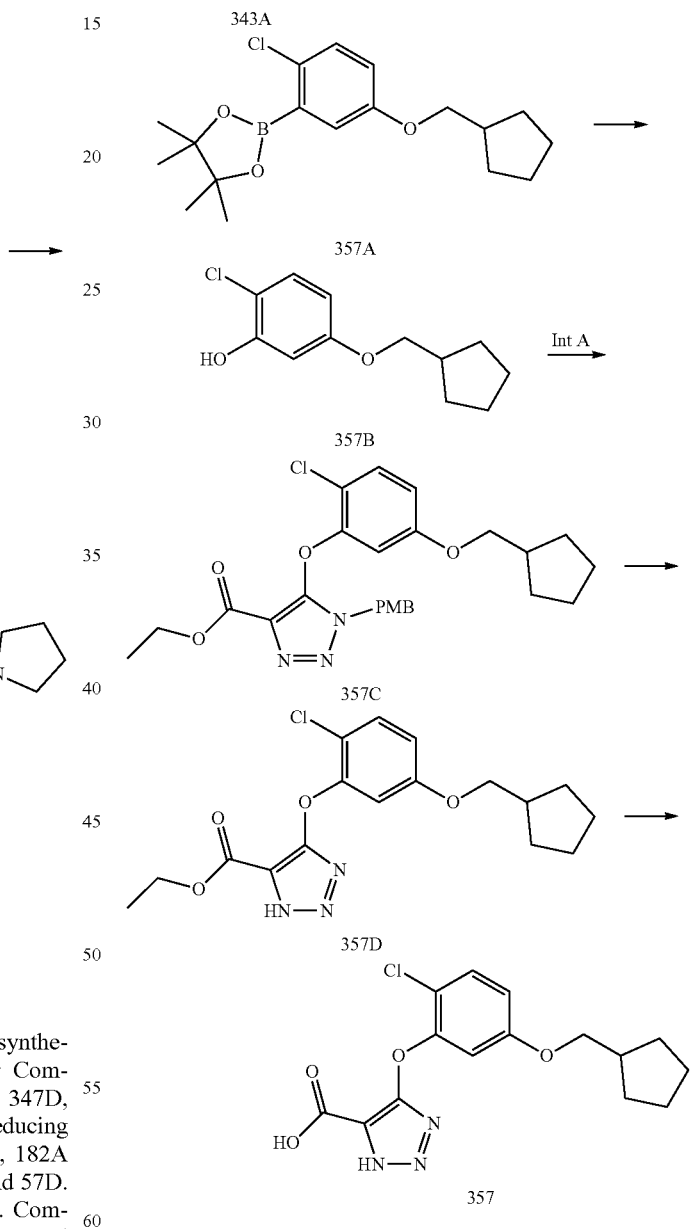

Compounds 357A, 357B, 357C, 357D, and 357 were synthesized by employing the procedures described for Compounds 27C, 236D, Intermediate I, 217E, and 8F using Compounds 343A, 357A, 357B, 357C, and 357D in lieu of Compounds 27B, 236C, 4-bromophenol, 217D, and 8E. Compound 357A: LC-MS (ESI) m/z: non-ionizable compound under routine conditions used. Compound 357B: LC-MS (ESI) m/z: 225 [M–H]⁻. Compound 357C: LC-MS (ESI) m/z: 486 [M+H]⁺. Compound 357D: LC-MS (ESI) m/z: 366 [M+H]⁺. Compound 357: LC-MS (ESI) m/z: 338 [M+H]⁺. ¹H-NMR (DMSO-d₆, 400 MHz): δ (ppm) 1.22-1.32 (m, 2H), 1.46-1.60 (m, 4H), 1.67-1.77 (m, 2H), 2.19-2.23 (m, 1H), 3.80 (d, J=7.2 Hz, 2H), 6.72 (s, 1H), 6.81 (dd, J=8.8, 2.8 Hz, 1H), 7.43 (d, J=8.4 Hz, 1H), 13.21 (s, 1H), 15.14 (s, 1H).

Example 358

Synthesis of 4-(3-chloro-5-(trifluoromethoxy)phenoxy)-1H-1,2,3-triazole-5-carboxylic acid (358)

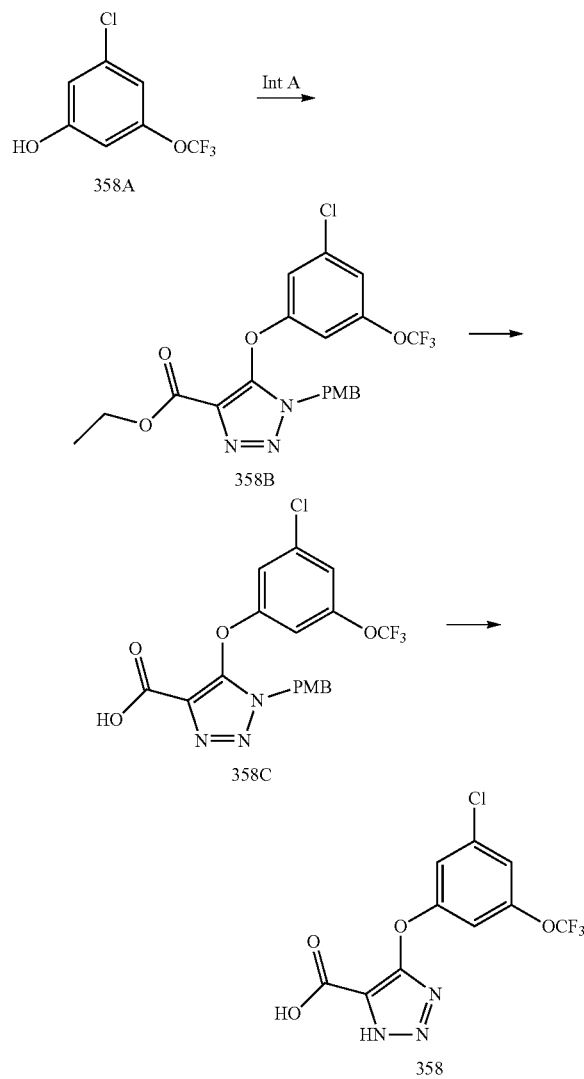

358: LC-MS (ESI) m/z: 324 [M+H]⁺; ¹H-NMR (d-DMSO, 400 MHz): δ (ppm) 7.18 (s, 1H), 7.29 (t, J=2 Hz, 2H), 7.35 (s, 1H).

Example 359

Synthesis of 4-((1-(4-cyanophenyl)piperidin-4-yl)oxy)-1H-1,2,3-triazole-5-carboxylic acid 2,2,2-trifluoroacetate (359)

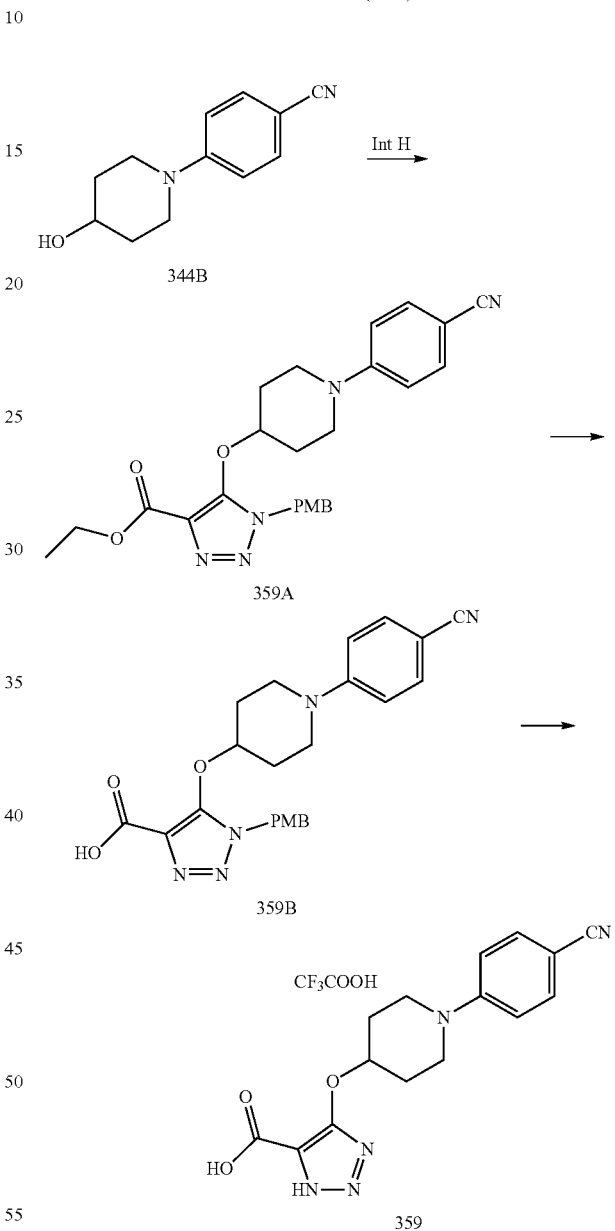

Compounds 358B, 358C, and 358 were synthesized by employing the procedures described for Intermediate I, Compounds 8F, and 1 using Compounds 358A, 358B, and 358C in lieu of 4-bromophenol, Compounds 8E, and 1E. Compound 358B: LC-MS (ESI) m/z: 472 [M+H]⁺. Compound 358C: LC-MS (ESI) m/z: 909 [2M+Na]⁺. Compound Compounds 359A, 359B, and 359 were synthesized by employing the procedures described for Compounds 90C, 8F, and 1 using Compounds 344B, 359A, and 359B in lieu of Compounds 90B, 8E, and 1E. Compound 359A: LC-MS (ESI) m/z: 462 [M+H]⁺. Compound 359B: LC-MS (ESI) m/z: 434 [M+H]⁺. Compound 359: LC-MS (ESI) m/z: 314 [M+H]⁺; ¹H-NMR (DMSO-d₆, 400 MHz): δ (ppm) 1.69-1.78 (m, 2H), 2.03-2.08 (m, 2H), 3.29-3.35 (m, 2H), 3.66-3.71 (m, 2H), 4.86-4.87 (m, 1H), 7.05 (d, J=8.8 Hz, 2H), 7.07 (d, J=8.8 Hz, 2H), 12.79 (s, 1H), 14.79 (s, 1H).

Example 360

Synthesis of 4-(((cis)-4-(3-chloro-4-(trifluoromethoxy)phenyl)cyclohexyl)oxy)-1H-1,2,3-triazole-5-carboxylic acid (360)

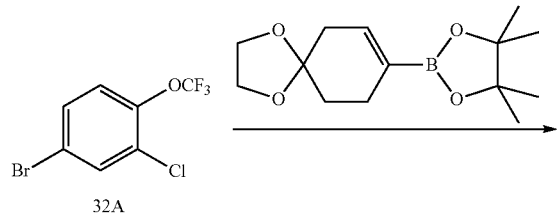

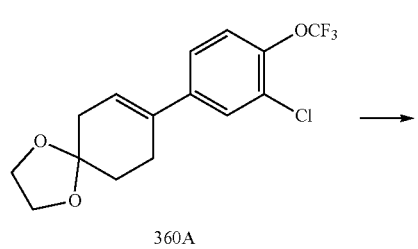

360A

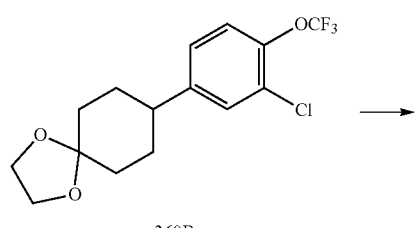

360B

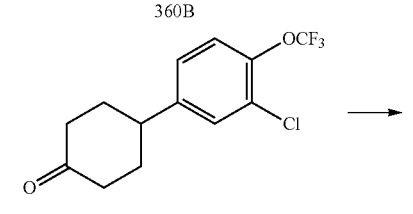

360C

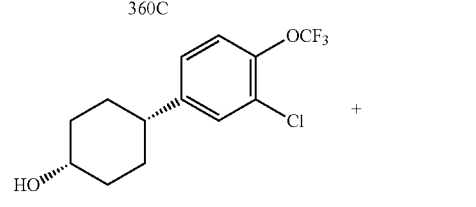

360D-1

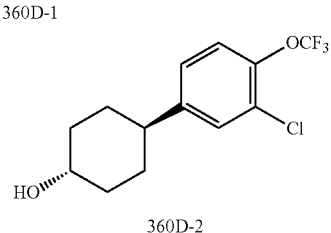

360D-2

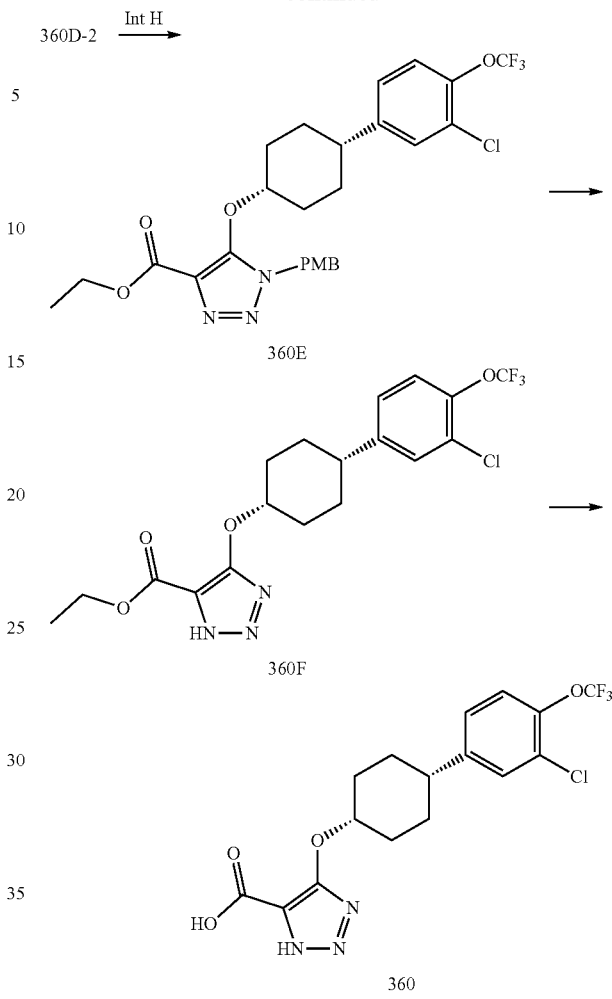

Compounds 360A, 360B, 360C, 360D-1, 360D-2, 360E, 360F, and 360 were synthesized by employing the procedures described for Compounds 4B, 141, 279D, 308E-1, 90C, 1, and 8F using 4,4,5,5-tetramethyl-2-(1,4-dioxaspiro[4.5]dec-7-en-8-yl)-1,3,2-dioxaborolane, Compounds 32A with $K_2CO_3$ as base and 1,4-dioxane as solvent, 360A with MeOH as solvent, 360B with TFA as acid and dichloromethane as solvent, 360C, 360D-2 with DEAD as coupling reagent, 360E, and 360F in lieu of (4-bromophenyl)boronic acid, Compounds 4A with $Na_2CO_3$ as base and toluene/EtOH/$H_2O$ as solvent, 140 with EtOAc as solvent, 279C with HCl as acid and acetone as solvent, 308D, 90B with DIAD as coupling reagent, 1E, and 8E. Compound 360A: LC-MS (ESI) m/z: 335 [M+H]+. Compound 360B: LC-MS (ESI) m/z: 337 [M+H]+. Compound 360C: LC-MS (ESI) m/z: 293 [M+H]+. Compound 360D-1: LC-MS (ESI) m/z: 278 [M+H−OH]+. 1H-NMR (CDCl3, 400 MHz): δ (ppm) 1.64-1.70 (m, 4H), 1.82-1.92 (m, 4H), 2.51-2.56 (m, 1H), 4.15 (s, 1H), 7.14-7.16 (m, 1H), 7.25-7.27 (m, 1H), 7.34 (s, 1H). Compound 360D-2: LC-MS (ESI) m/z: 278 [M+H−OH]+. 1H-NMR (CDCl3, 400 MHz): δ (ppm) 1.41-1.51 (m, 4H), 1.91-1.94 (m, 2H), 2.10-2.13 (m, 2H), 2.48-2.50 (m, 1H), 3.63-3.78 (m, 1H), 7.10-7.12 (m, 1H), 7.22-7.24 (m, 1H), 7.30 (s, 1H). Compound 360E: LC-MS (ESI) m/z: 554 [M+H]+. Compound 360F: LC-MS (ESI) m/z: 434 [M+H]+. Compound 360: LC-MS (ESI) m/z: 406 [M+H]+; 1H-NMR (CD₃OD, 400 MHz): δ (ppm) 1.63-1.75 (m, 4H), 2.04-2.26 (m, 4H), 2.62-2.73 (m, 1H), 5.01 (s, 1H), 7.32-7.40 (m, 2H), 7.53 (s, 1H).

Example 361

Synthesis of 4-((1-(3-chloro-4-(trifluoromethoxy)phenyl)piperidin-4-yl)oxy)-1H-1,2,3-triazole-5-carboxylic acid (361)

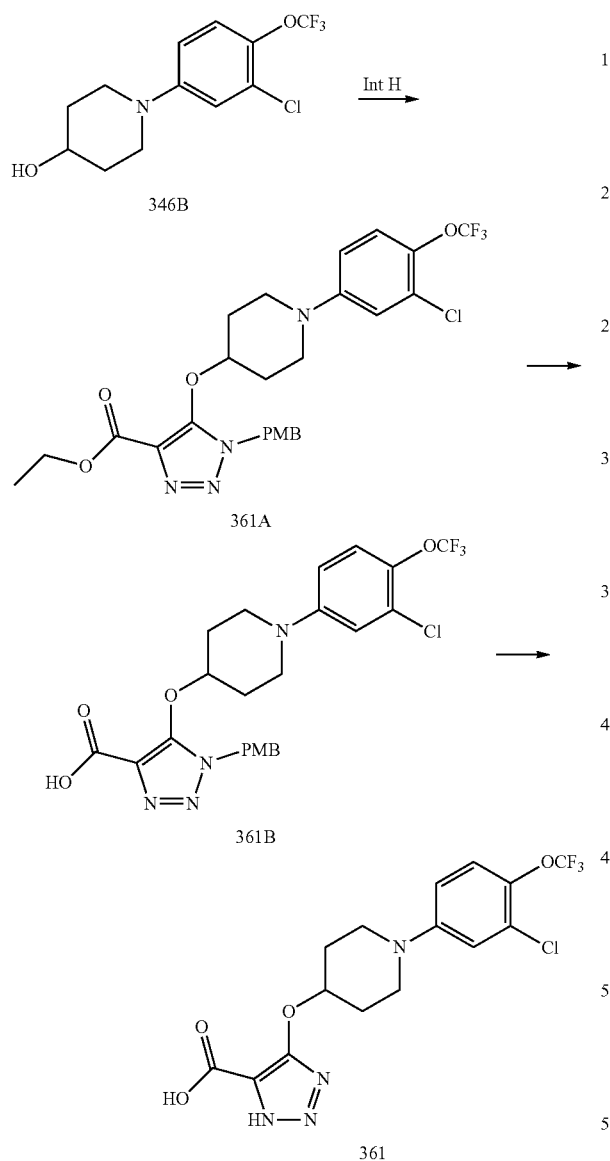

Compounds 361A, 361B, and 361 were synthesized by employing the procedures described for Compounds 90C, 8F, and 1 using Compounds 346B with DEAD as coupling reagent, 361A, and 361B in lieu of Compounds 90B with DIAD as coupling reagent, 8E, and 1E. Compound 361A: LC-MS (ESI) m/z: 555 [M+H]⁺. Compound 361B: LC-MS (ESI) m/z: 527 [M+H]⁺. Compound 361: LC-MS (ESI) m/z: 407 [M+H]⁺; ¹H-NMR (DMSO-d₆, 400 MHz): δ (ppm) 1.69-1.78 (m, 2H), 2.02-2.06 (m, 2H), 3.14-3.19 (m, 2H), 3.51-3.57 (m, 2H), 4.83 (s, 1H), 6.99 (d, J=12.4 Hz, 1H), 7.15 (d, J=3.2 Hz, 1H), 7.32 (d, J=8.8 Hz, 1H), 14.76 (s, 1H).

Example 362

Synthesis of 4-(4-chloro-3-((4-fluorobenzyl)oxy)phenoxy)-1H-1,2,3-triazole-5-carboxylic acid (362)

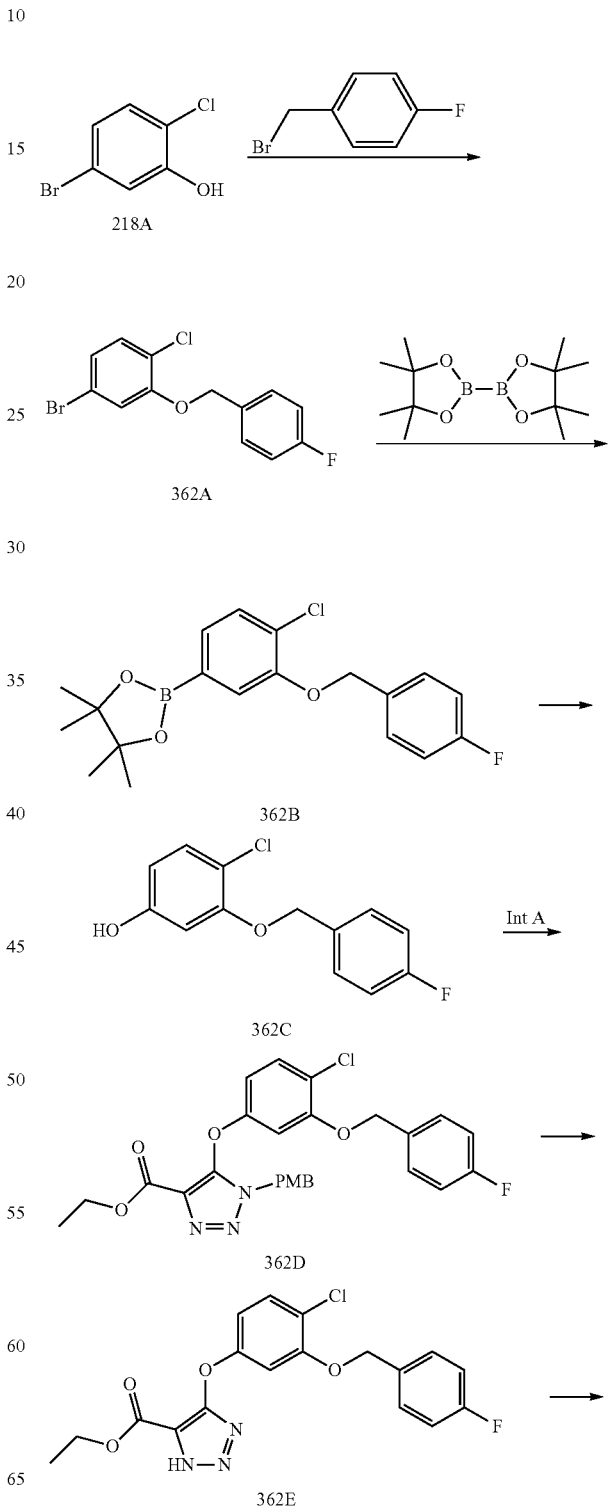

-continued

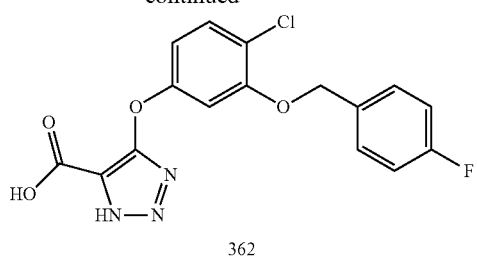

362

Compounds 362A, 362B, 362C, 362D, 362E, and 362 were synthesized by employing the procedures described for Compounds 27B, 27C, 236D, Intermediate I, 217E, and 8F using 1-(bromomethyl)-4-fluorobenzene, Compounds 218A, 362A, 362B, 362C, 362D, and 362E in lieu of 2-bromopropane, Compounds 27A, 27B, 236C, 4-bromophenol, 217D, and 8E. Compound 362A: LC-MS (ESI) m/z: non-ionizable compound under routine conditions used; $^1$H-NMR (CDCl$_3$, 400 MHz): δ (ppm) 5.23 (s, 2H), 7.18 (d, J=8.5 Hz, 1H), 7.26 (t, J=8.8 Hz, 2H), 7.41 (d, J=8.4 Hz, 1H), 7.48 (s, 1H), 7.52 (dd, J=8.0, 5.9 Hz, 2H). Compound 362B: LC-MS (ESI) m/z: 263 [M+H]$^+$. Compound 362C: LC-MS (ESI) m/z: 253 [M+H]$^+$. Compound 362D: LC-MS (ESI) m/z: 512 [M+H]$^+$. Compound 362E: LC-MS (ESI) m/z: 392 [M+H]$^+$. Compound 362: LC-MS (ESI) m/z: 364 [M+H]$^+$. $^1$H-NMR (DMSO-d$_6$, 400 MHz): δ (ppm) 5.16 (s, 2H), 6.62 (dd, J=8.7, 2.5 Hz, 1H), 7.07 (d, J=2.5 Hz, 1H), 7.24 (t, J=8.8 Hz, 2H), 7.40 (d, J=8.7 Hz, 1H), 7.50 (dd, J=8.3, 5.8 Hz, 2H).

Example 363

Synthesis of 4-(((cis)-4-(4-carbamoylphenyl)cyclohexyl)oxy)-1H-1,2,3-triazole-5-carboxylic acid 2,2,2-trifluoroacetate (363)

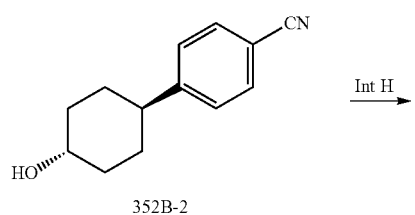

352B-2

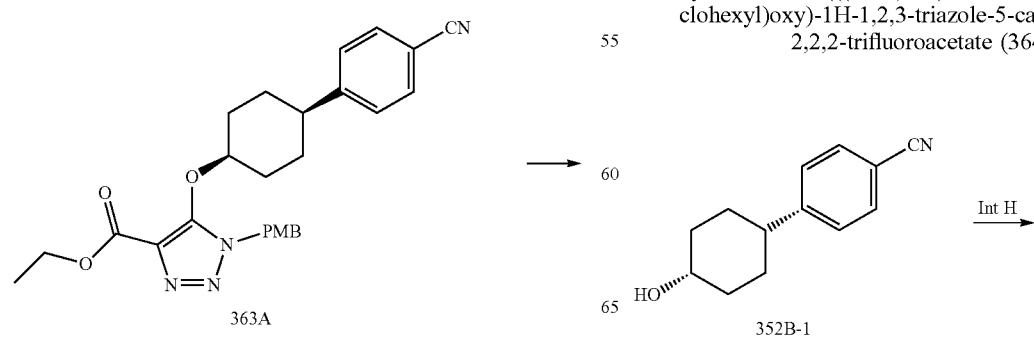

363A

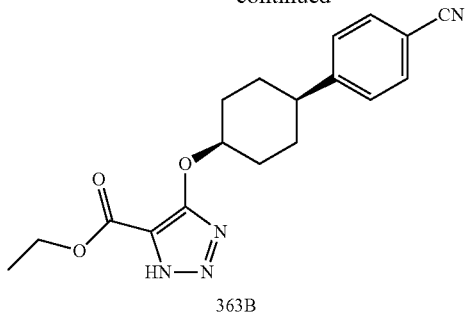

363B

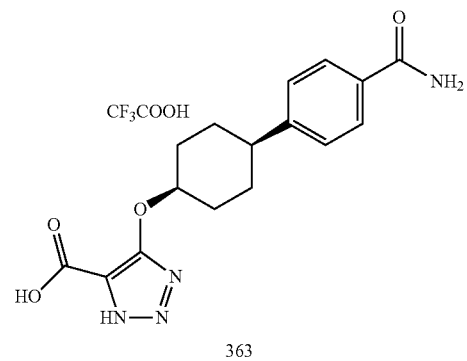

363

Compounds 363A and 363B were synthesized by employing the procedures described for Compounds 90C and 1 using Compounds 352B-2 with DEAD as coupling reagent and 363A in lieu of Compounds 90B with DIAD as coupling reagent and 1E. Compound 363A: LC-MS (ESI) m/z: 461 [M+H]$^+$; $^1$H-NMR (CDCl$_3$, 400 MHz): δ (ppm) 1.26-1.31 (m, 4H), 1.42 (t, J=7.2 Hz, 3H), 1.67-1.73 (m, 2H), 2.05-2.14 (m, 2H), 2.62-2.66 (m, 1H), 3.77 (s, 3H), 4.41 (q, J=7.2 Hz, 2H), 5.36 (s, 2H), 5.47 (s, 1H), 6.83 (d, J=8.7 Hz, 2H), 7.17-7.22 (m, 4H), 7.60 (d, J=8.2 Hz, 2H). Compound 363B: LC-MS (ESI) m/z: 341 [M+H]$^+$.

To a solution of Compound 363B (140 mg, 0.41 mmol) in EtOH (10 mL) and H$_2$O (5 mL) was added LiOH.H$_2$O (86 mg, 2.05 mmol) and stirred at 40° C. overnight. It was concentrated under reduced pressure and the residue was purified with preparative HPLC to afford Compound 363. LC-MS (ESI) m/z: 331 [M+H]$^+$; $^1$H-NMR (DMSO-d$_6$, 400 MHz): δ (ppm) 1.59 (d, J=10.6 Hz, 2H), 1.65-1.72 (m, 2H), 1.81-1.90 (m, 2H), 2.07 (d, J=13.7 Hz, 2H), 2.64-2.70 (m, 1H), 4.94 (s, 1H), 7.29 (d, J=8.2 Hz, 3H), 7.78 (d, J=8.1 Hz, 2H), 7.88 (s, 1H), 12.90 (s, 1H), 14.74 (s, 1H).

Example 364

Synthesis of 4-(((trans)-4-(4-carbamoylphenyl)cyclohexyl)oxy)-1H-1,2,3-triazole-5-carboxylic acid 2,2,2-trifluoroacetate (364)

352B-1

-continued

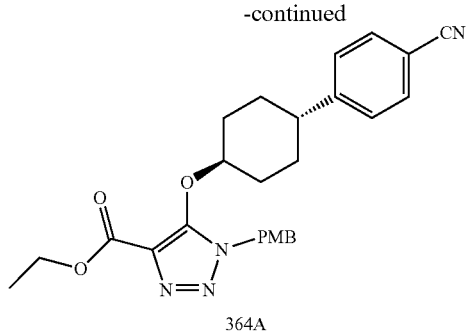

364A

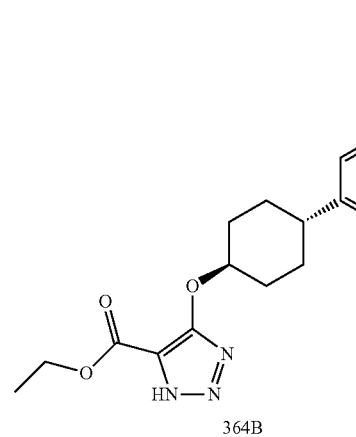

364B

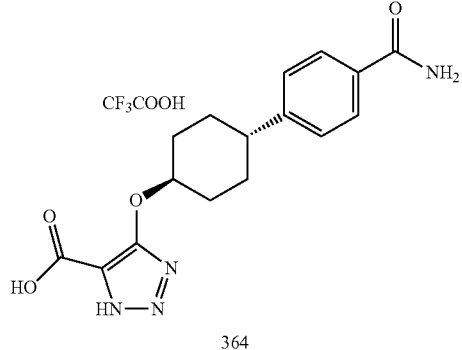

364

Compounds 364A, 364B, and 364 were synthesized by employing the procedures described for Compounds 90C, 1, and 363 using Compounds 352B-1 with DEAD as coupling reagent, 364A, and 364B in lieu of Compounds 90B with DIAD as coupling reagent, 1E, and 363B. Compound 364A: LC-MS (ESI) m/z: 461 [M+H]$^+$; $^1$H-NMR (CDCl$_3$, 400 MHz): δ (ppm) 1.42 (t, J=7.2 Hz, 3H), 1.47-1.59 (m, 4H), 1.91-1.95 (m, 2H), 2.15-2.18 (m, 2H), 2.51-2.57 (m, 1H), 3.79 (s, 3H), 4.41 (q, J=7.2 Hz, 2H), 5.06-5.11 (m, 1H), 5.30 (s, 2H), 6.87 (d, J=8.7 Hz, 2H), 7.24-7.29 (m, 4H), 7.58 (d, J=8.2 Hz, 2H). Compound 364B: LC-MS (ESI) m/z: 341 [M+H]$^+$. Compound 364: LC-MS (ESI) m/z: 331 [M+H]$^+$; $^1$H-NMR (DMSO-d$_6$, 400 MHz): δ (ppm) 1.51-1.66 (m, 4H), 1.86 (d, J=10.8 Hz, 2H), 2.23 (d, J=9.9 Hz, 2H), 2.60-2.65 (m, 1H), 4.67 (s, 1H), 7.26 (s, 1H), 7.32 (d, J=8.0 Hz, 2H), 7.78 (d, J=8.0 Hz, 2H), 7.89 (s, 1H).

Example 365

Synthesis of 4-(((cis)-4-(4-cyanophenyl)cyclohexyl)oxy)-1H-1,2,3-triazole-5-carboxylic acid (365)

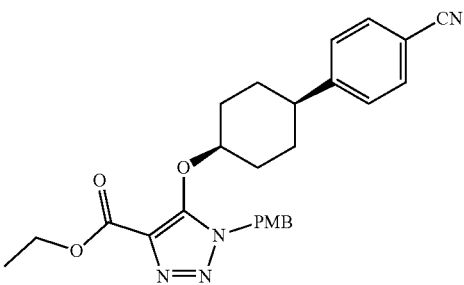

363A

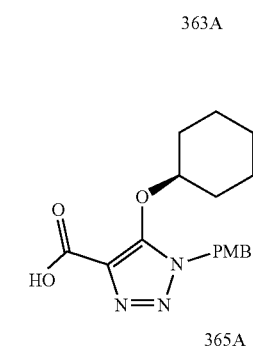

365A

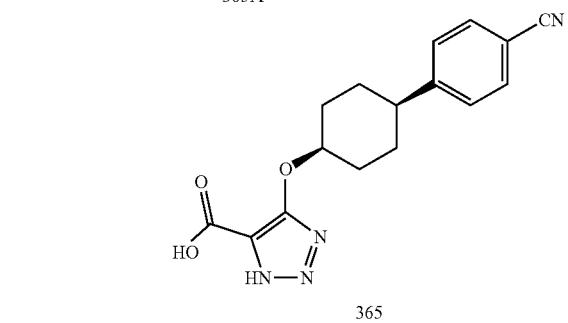

365

Compounds 365A and 365 were synthesized by employing the procedures described for Compounds 8F and 1 using Compounds 353A and 365A in lieu of Compounds 8E and 1E. Compound 365A: LC-MS (ESI) m/z: 433 [M+H]$^+$. Compound 365: LC-MS (ESI) m/z: 313 [M+H]$^+$; $^1$H-NMR (CD$_3$OD, 400 MHz): δ (ppm) 1.66-1.80 (m, 4H), 2.08-2.08 (m, 2H), 2.22-2.26 (m, 2H), 2.73-2.79 (m, 1H), 5.06 (s, 1H), 7.48 (d, J=8.2 Hz, 2H), 7.65 (d, J=8.2 Hz, 2H).

Example 366

Synthesis of 4-((1,3-bis(4'-(trifluoromethoxy)-[1,1'-biphenyl]-4-yl)propan-2-yl)oxy)-1H-1,2,3-triazole-5-carboxylic acid (366)

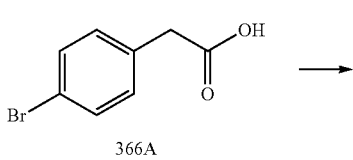

366A

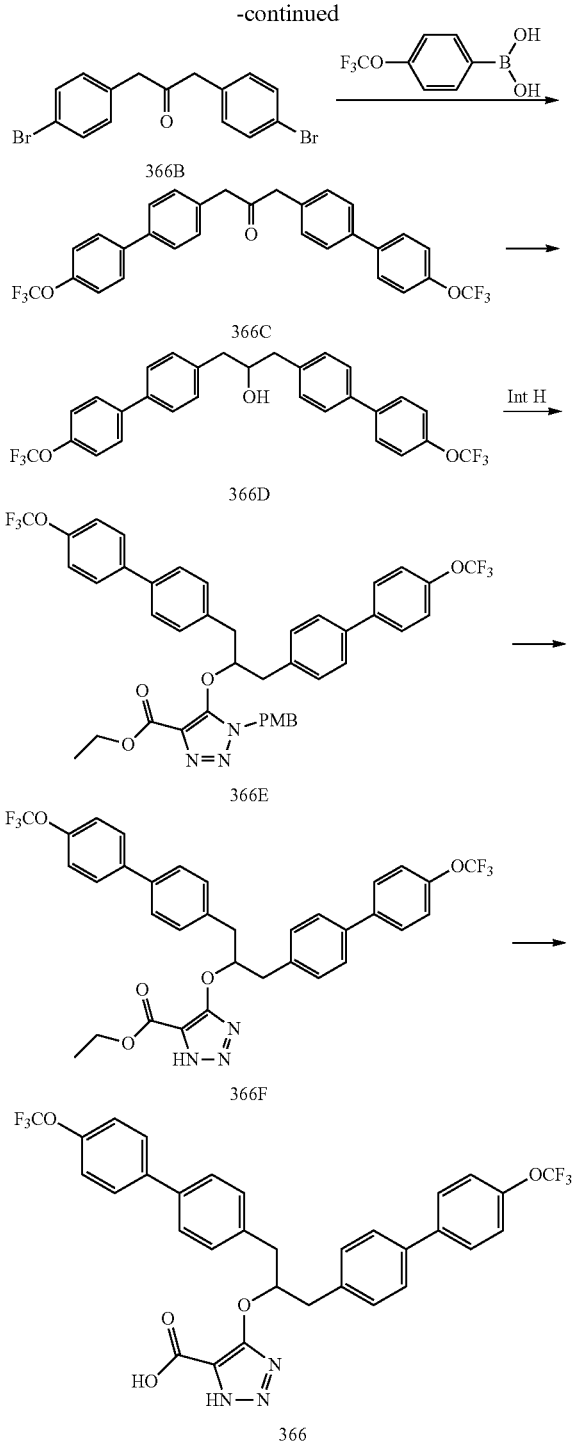

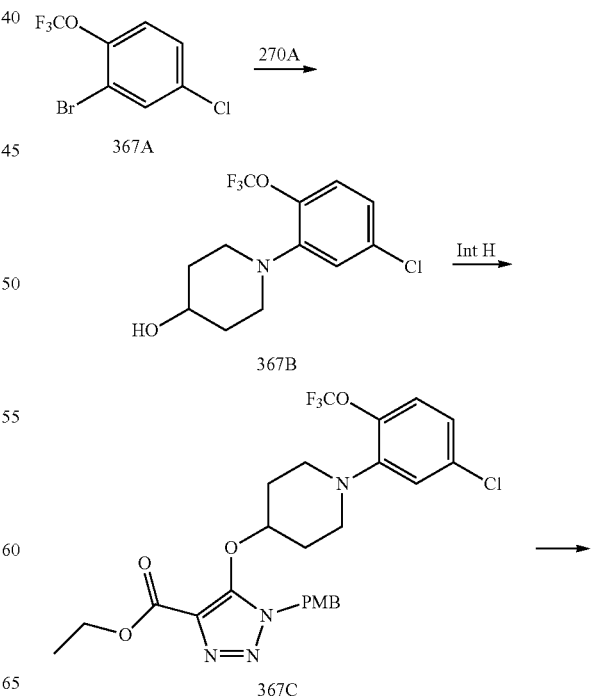

25% v/v) to afford Compound 366B. LC-MS (ESI) m/z: non-ionizable compound under routine conditions used; $^1$H-NMR (DMSO-d$_6$, 400 MHz): δ (ppm) 3.87 (s, 4H), 7.13 (d, J=8.3 Hz, 4H), 7.49 (d, J=8.3 Hz, 4H).

Compounds 366C, 366D, 366E, 366F, and 366 were synthesized by employing the procedures described for Compounds 8B, 57C, 90C, 217E, and 8F using 4-(trifluoromethoxy)phenylboronic acid, Compounds 366B with Na$_2$CO$_3$ as base and 1,4-dioxane/H$_2$O as solvent, 366C, 366D, 366E, and 366F in lieu of (3,4-dichlorophenyl)boronic acid, Compounds 8A with Cs$_2$CO$_3$ as base and DME/H$_2$O as solvent, 57B, 90B, 217D, and 8E. Compound 366C: LC-MS (ESI) m/z: non-ionizable compound under routine conditions used; $^1$H-NMR (DMSO-d$_6$, 400 MHz): δ (ppm) 3.95 (s, 4H), 7.30 (d, J=8.0 Hz, 4H), 7.44 (d, J=8.3 Hz, 4H), 7.63 (d, J=8.0 Hz, 4H), 7.78 (d, J=8.6 Hz, 4H). Compound 366D: LC-MS (ESI) m/z: non-ionizable compound under routine conditions used; $^1$H-NMR (DMSO-d$_6$, 400 MHz): δ (ppm) 2.75 (ddd, J=21.2, 13.6, 6.2 Hz, 4H), 3.90-4.08 (m, 1H), 4.76 (d, J=5.9 Hz, 1H), 7.33 (d, J=8.2 Hz, 4H), 7.43 (d, J=8.2 Hz, 4H), 7.59 (d, J=8.2 Hz, 4H), 7.72-7.83 (m, 4H). Compound 366E: LC-MS (ESI) m/z: 792 [M+H]$^+$. Compound 366F: LC-MS (ESI) m/z: 672 [M+H]$^+$. Compound 366: LC-MS (ESI) m/z: 644 [M+H]$^+$; $^1$H-NMR (DMSO-d$_6$, 400 MHz): δ (ppm) 3.06 (s, 4H), 5.17 (s, 1H), 7.38 (d, J=8.0 Hz, 4H), 7.43 (d, J=8.4 Hz, 4H), 7.59 (d, J=8.0 Hz, 4H), 7.76 (d, J=8.7 Hz, 4H), 12.98 (s, 1H), 14.78 (s, 1H).

Example 367

Synthesis of 4-((1-(5-chloro-2-(trifluoromethoxy)phenyl)piperidin-4-yl)oxy)-1H-1,2,3-triazole-5-carboxylic acid 2,2,2-trifluoroacetate (367)

To a solution of DCC (2.23 g, 10.8 mmol) and DMAP (0.35 g, 2.91 mmol) in anhydrous dichloromethane (50 mL) was slowly added a solution of 2-(4-bromophenyl)acetic acid (366A) (2.0 g, 9.35 mmol) in anhydrous dichloromethane (80 mL). The mixture was stirred at room temperature for 4 hours and concentrated under reduced pressure. The residue was partitioned between EtOAc (50 mL) and water (50 mL). The organic layer was separated, washed with brine (30 mL×3), dried over anhydrous sodium sulfate, concentrated, and purified with flash column chromatography on silica gel (ethyl acetate in petroleum ether, 0% to -continued

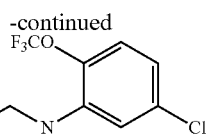

367D

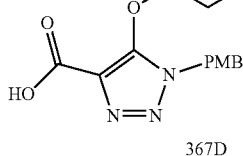

367

A solution of 2-bromo-4-chloro-1-(trifluoromethoxy)benzene (367A) (2 g, 7.3 mmol), Compound 270A (3 g, 29.2 mmol), and Cs₂CO₃ (9.6 g, 29.4 mmol) in DMF (20 mL) were stirred at 180° C. under nitrogen in a microwave oven for 8 hours. After cooled down to room temperature, the mixture was concentrated and purified with flash column chromatography on silica (ethyl acetate in petroleum ether, from 0% to 20% v/v) to give Compound 367B. LC-MS (ESI) m/z: 296 [M+H]⁺; ¹H-NMR (CDCl₃, 400 MHz): δ (ppm) 1.67-1.76 (m, 2H), 1.99-2.05 (m, 2H), 2.80-2.87 (m, 2H), 3.29-3.35 (m, 2H), 3.84-3.88 (m, 1H), 6.89-6.97 (m, 2H), 7.10 (d, J=8.4 Hz, 1H).

Compounds 367C, 367D, and 367 were synthesized by employing the procedures described for Compounds 90C, 8F, and 1 using Compounds 367B, 367C, and 367D in lieu of Compounds 90B, 8E, and 1E. Compound 367C: LC-MS (ESI) m/z: 555 [M+H]⁺; ¹H-NMR (CDCl₃, 400 MHz): δ (ppm) 1.42 (t, J=7.2 Hz, 3H), 1.77-1.80 (m, 2H), 2.00-2.05 (m, 2H), 2.83-2.88 (m, 2H), 3.14-3.18 (m, 2H), 3.76 (s, 3H), 4.41 (q, J=7.2 Hz, 2H), 5.29-5.33 (m, 3H), 6.84-6.97 (m, 4H), 7.11 (d, J=8.8 Hz, 1H), 7.23-7.27 (m, 2H). Compound 367D: LC-MS (ESI) m/z: 527 [M+H]⁺. Compound 367: LC-MS (ESI) m/z: 407 [M+H]⁺; ¹H-NMR (DMSO-d₆, 400 MHz): δ (ppm) 1.82-1.90 (m, 2H), 2.12-2.16 (m, 2H), 2.92-2.98 (m, 2H), 3.22-3.26 (m, 2H), 4.84 (s, 1H), 7.03-7.06 (m, 1H), 7.10 (d, J=2.8 Hz, 1H), 7.55 (d, J=8.8 Hz, 1H).

Example 368

Synthesis of 4-(((cis)-4-(4-(4,4-difluoropiperidin-1-yl)phenyl)cyclohexyl)oxy)-1H-1,2,3-triazole-5-carboxylic acid 2,2,2-trifluoroacetate (368)

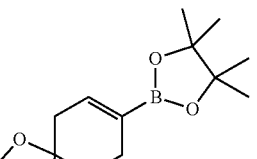

297E

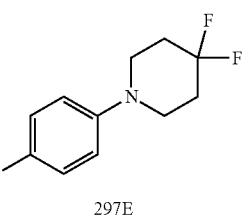

368A

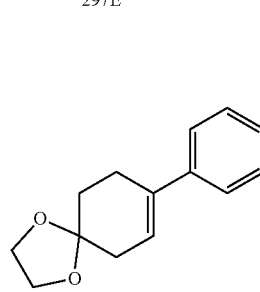

368B

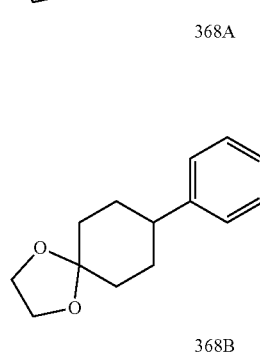

368C

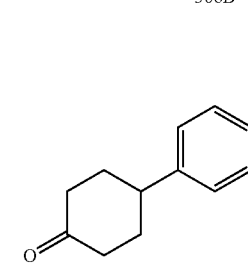

368D-1

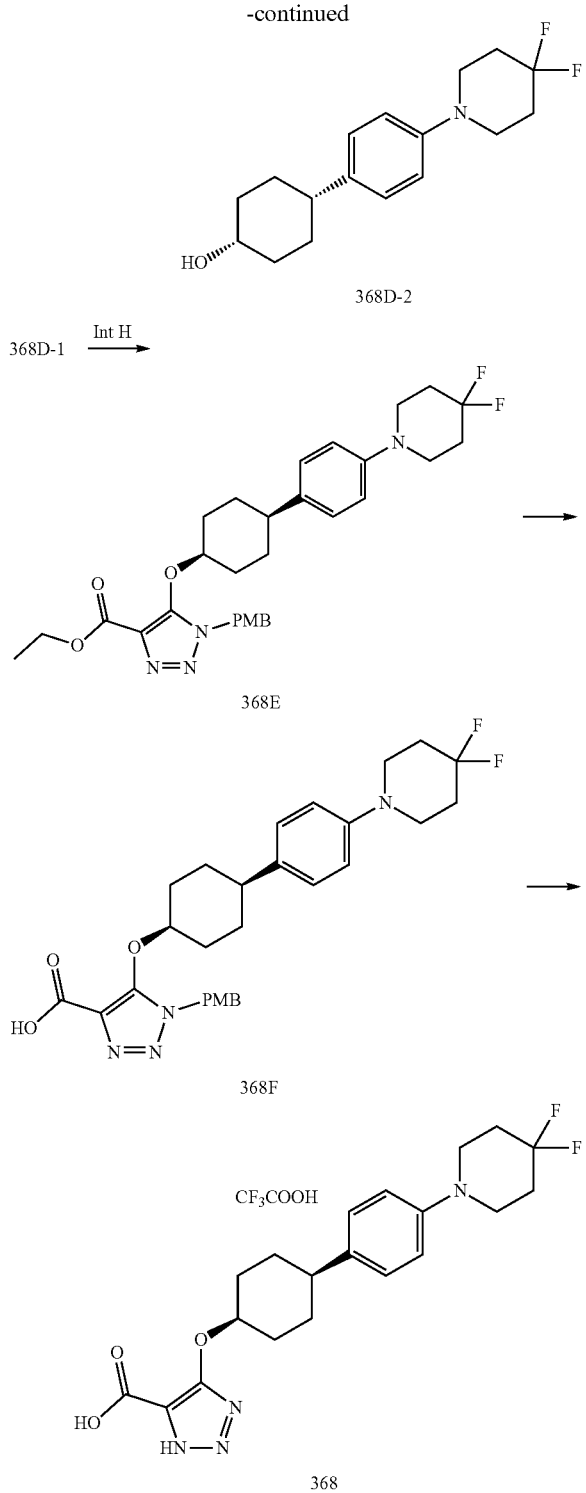

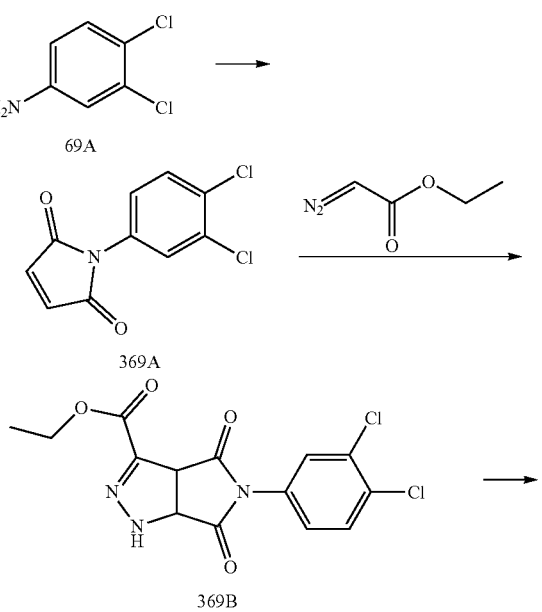

solvent, 279C with acetone as solvent, 57B, 90B, 8E, and 1E. Compound 368A: LC-MS (ESI) m/z: 336 [M+H]$^+$; $^1$H-NMR (CDCl$_3$, 400 MHz): δ (ppm) 1.91 (t, J=6.4 Hz, 2H), 2.01-2.13 (m, 4H), 2.40-2.46 (m, 2H), 2.61-2.67 (m, 2H), 3.34 (t, J=6.0 Hz, 4H), 4.01 (s, 4H), 5.90 (s, 1H), 6.86 (d, J=8.4 Hz, 2H), 7.30 (d, J=8.4 Hz, 2H). Compound 368B: LC-MS (ESI) m/z: 338 [M+H]$^+$; $^1$H-NMR (CDCl$_3$, 400 MHz): δ (ppm) 1.56-1.96 (m, 8H), 2.04-2.14 (m, 4H), 2.46-2.52 (m, 1H), 3.31 (t, J=5.6 Hz, 4H), 3.98 (s, 4H), 6.88 (d, J=8.4 Hz, 2H), 7.14 (d, J=8.4 Hz, 2H). Compound 368C: LC-MS (ESI) m/z: 294 [M+H]$^+$; $^1$H-NMR (CDCl$_3$, 400 MHz): δ (ppm) 1.57-1.96 (m, 2H), 2.05-2.22 (m, 6H), 2.48-2.52 (m, 4H), 2.94-2.99 (m, 1H), 3.33 (t, J=6.0 Hz, 4H), 6.91 (d, J=8.8 Hz, 2H), 7.15 (d, J=8.4 Hz, 2H). Compound 368D-1: LC-MS (ESI) m/z: 296 [M+H]$^+$; $^1$H-NMR (CDCl$_3$, 400 MHz): δ (ppm) 1.36-1.51 (m, 4H), 1.89-1.92 (m, 2H), 2.04-2.14 (m, 6H), 2.40-2.46 (m, 1H), 3.31 (t, J=5.6 Hz, 4H), 3.65-3.70 (m, 1H), 6.88 (d, J=8.8 Hz, 2H), 7.11 (d, J=8.8 Hz, 2H). Compound 368D-2: LC-MS (ESI) m/z: 296 [M+H]$^+$; $^1$H-NMR (CDCl$_3$, 400 MHz): δ (ppm) 1.63-1.70 (m, 4H), 1.80-1.90 (m, 4H), 2.04-2.14 (m, 4H), 2.44-2.51 (m, 1H), 3.29-3.32 (m, 4H), 4.12 (s, 1H), 6.89 (d, J=8.8 Hz, 2H), 7.15 (d, J=8.8 Hz, 2H). Compound 368E: LC-MS (ESI) m/z: 555 [M+H]$^+$; $^1$H-NMR (CDCl$_3$, 400 MHz): δ (ppm) 1.42 (t, J=6.8 Hz, 3H), 1.66-1.74 (m, 6H), 2.06-2.15 (m, 6H), 2.52-2.53 (m, 1H), 3.33 (t, J=5.2 Hz, 4H), 3.77 (s, 3H), 4.40 (q, J=6.8 Hz, 2H), 5.36 (s, 2H), 5.45 (s, 1H), 6.84 (d, J=8.4 Hz, 2H), 6.91 (d, J=8.4 Hz, 2H), 7.07 (d, J=8.4 Hz, 2H), 7.24 (d, J=8.4 Hz, 2H). Compound 368F: LC-MS (ESI) m/z: 527 [M+H]$^+$. Compound 368: LC-MS (ESI) m/z: 407 [M+H]$^+$; $^1$H-NMR (DMSO-d$_6$, 400 MHz): δ (ppm) 1.54-1.57 (m, 2H), 1.67-1.70 (m, 2H), 1.79-1.83 (m, 2H), 2.00-2.10 (m, 6H), 2.49-2.53 (m, 1H), 3.27 (t, J=5.6 Hz, 4H), 4.94 (s, 1H), 6.94 (d, J=8.8 Hz, 2H), 7.11 (d, J=8.8 Hz, 2H).

Example 369

Synthesis of 4-((3-(3,4-dichlorophenyl)-3-azabicyclo[3.1.0]hexan-6-yl)methoxy)-1H-1,2,3-triazole-5-carboxylic acid (369)

Compounds 368A, 368B, 368C, 368D-1, 368D-2, 368E, 368F, and 368 were synthesized by employing the procedures described for Compounds 4B, 141, 279D, 57C, 90C, 8F, and 1 using 4,4,5,5-tetramethyl-2-(1,4-dioxaspiro[4.5]dec-7-en-8-yl)-1,3,2-dioxaborolane, Compounds 297E with 1,4-dioxane/H$_2$O as solvent, 368A with MeOH as solvent, 368B with 1,4-dioxane as solvent, 368C, 368D-1, 368E, and 368F in lieu of (4-bromophenyl)boronic acid, Compounds 4A with toluene/EtOH/H$_2$O as solvent, 140 with EtOAc as

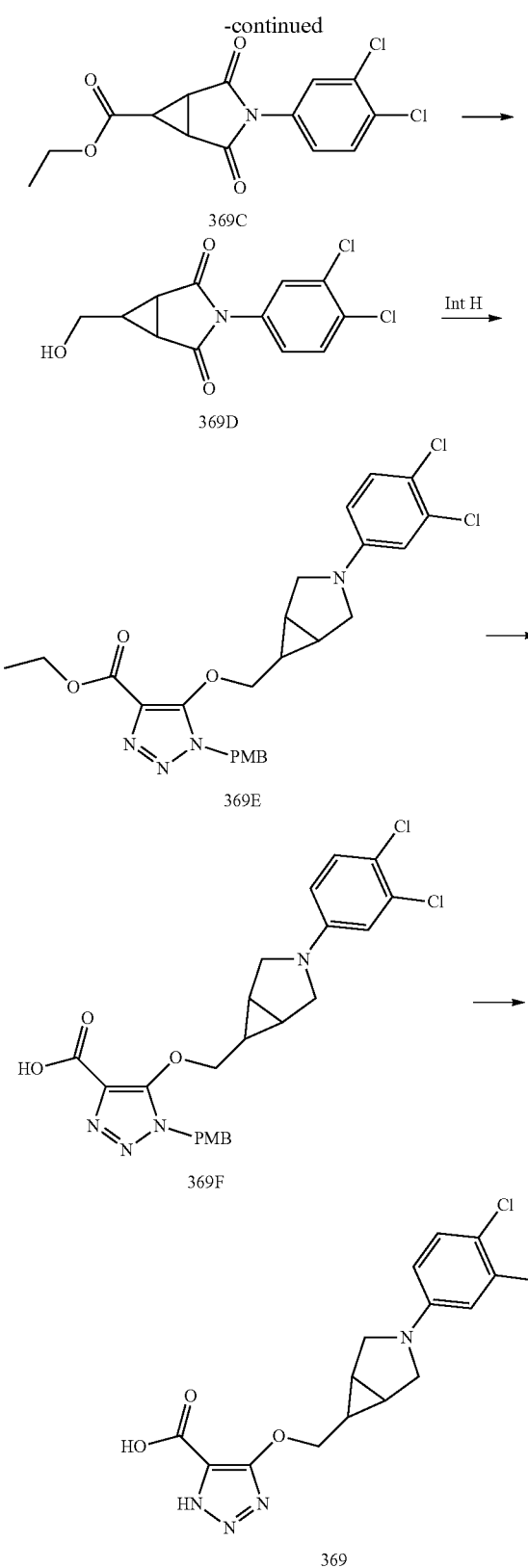

solved in Ac$_2$O (100 mL) and stirred at 100° C. for 4 hours. After cooled down to room temperature, the mixture was filtered, washed with petroleum ether (100 mL), and dried under vacuum to give Compound 369A. LC-MS (ESI) m/z: 242 [M+H]$^+$; $^1$H-NMR (CDCl$_3$, 400 MHz): δ (ppm) 6.88 (s, 2H), 7.28 (dd, J=8.4, 2.4 Hz, 1H), 7.53-7.56 (m, 2H).

To a mixture of Compound 369A (10.7 g, 44.2 mmol) in toluene (130 mL) was dropped a solution of ethyl 2-diazoacetate in dichloromethane (90% wt, 5.04 g, 44.2 mmol) at room temperature and the resulting mixture was stirred at 100° C. for 3 hours. After cooled down to room temperature, the mixture was filtered, washed with petroleum ether (50 mL), and dried under vacuum to afford Compound 369B. LC-MS (ESI) m/z: 356 [M+H]$^+$; $^1$H-NMR (DMSO-d$_6$, 400 MHz): δ (ppm) 1.24 (t, J=7.2 Hz, 3H), 4.13-4.26 (m, 2H), 4.65 (d, J=11.6 Hz, 1H), 5.09 (dd, J=11.6, 2.0 Hz, 1H), 7.35 (dd, J=8.8, 2.0 Hz, 1H), 7.67 (d, J=2.0 Hz, 1H), 7.79 (d, J=8.8 Hz, 1H), 9.71 (d, J=2.0 Hz, 1H).

Compound 369B (1.07 g, 3 mmol) was heated at 190° C. for 1 hour. After cooled down to room temperature, the residue was dissolved in CH$_2$Cl$_2$ (30 mL) and evaporated under reduced pressure and purified with flash column chromatography on silica gel (ethyl acetate in petroleum ether, 20% v/v) to furnish Compound 369C. LC-MS (ESI) m/z: 328 [M+H]$^+$.

To a solution of Compound 369C (2.38 g, 7.25 mmol) in andyrous THF (25 mL) was dropped a solution of BH$_3$-Me$_2$S in THF (2M, 15 mL, 30 mmol) at 0° C. and heated at reflux overnight. After cooled down to 0° C., the mixture was slowly quenched with methanol (25 mL) and heated at reflux for 1 hour. The mixture was evaporated under reduced pressure. The residue was purified with flash column chromatography on silica gel (ethyl acetate in petroleum ether, from 0% to 30% v/v) to afford Compound 369D. LC-MS (ESI) m/z: 258 [M+H]$^+$; $^1$H-NMR (CDCl$_3$, 400 MHz): δ (ppm) 1.06-1.12 (m, 1H), 1.35-1.38 (m, 1H), 1.64-1.65 (m, 2H), 3.24-3.27 (m, 2H), 3.50 (d, J=9.2 Hz, 2H), 3.54-3.57 (m, 2H), 6.35 (dd, J=8.8, 2.4 Hz, 1H), 6.57 (d, J=2.4 Hz, 1H), 7.19 (d, J=8.8 Hz, 1H).

Compounds 369E, 369F, and 369 were synthesized by employing the procedures described for Compounds 90C, 8F, and 1 using Compounds 369D, 369E, and 369F in lieu of Compounds 90B, 8E, and 1E. Compound 369E: LC-MS (ESI) m/z: 517 [M+H]$^+$. Compound 369F: LC-MS (ESI) m/z: 489 [M+H]$^+$. Compound 369: LC-MS (ESI) m/z: 369 [M+H]$^+$; $^1$H-NMR (CD$_3$OD, 400 MHz): δ (ppm) 1.29-1.34 (m, 1H), 1.85-1.87 (m, 2H), 3.23-3.26 (m, 2H), 3.55 (d, J=9.2 Hz, 2H), 4.26 (d, J=7.2 Hz, 2H), 6.49 (dd, J=8.8, 2.4 Hz, 1H), 6.66 (d, J=2.4 Hz, 1H), 7.22 (d, J=8.8 Hz, 1H).

Example 370

Synthesis of ((diethylcarbamoyl)oxy)methyl 4-(((trans)-4-(4-(trifluoromethoxy)phenyl)cyclohexyl)oxy)-1H-1,2,3-triazole-5-carboxylate (370)

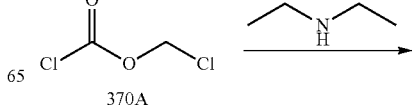

A mixture of 3,4-dichloroaniline (69A) (16.2 g, 0.1 mol) and furan-2,5-dione (9.8 g, 0.1 mmol) in 1,2-dichloroethane (150 mL) was stirred at 80° C. for 3 hours. The mixture was concentrated under reduced pressure. The residue was dis-

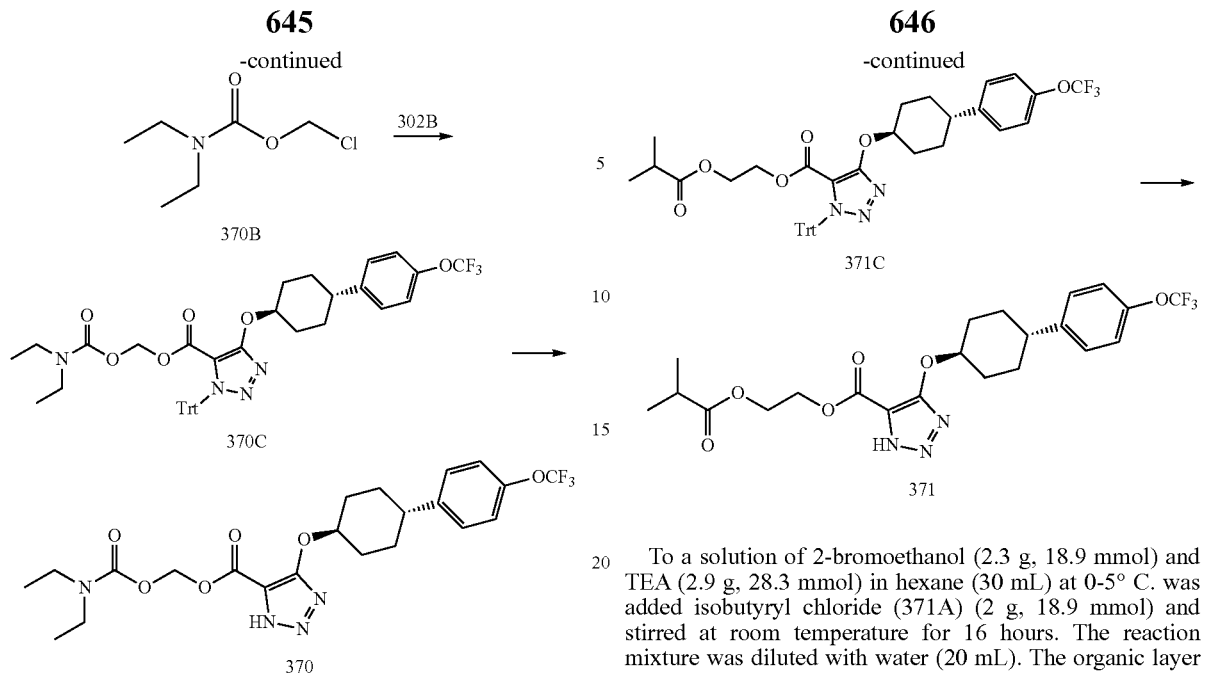

To a solution of diethylamine (3.86 g, 52.9 mmol) in THF (150 mL) was dropped chloromethyl carbonochloridate (370A) (3.38 g, 26.4 mmol) at 0° C. and stirred at room temperature overnight. The mixture was diluted with dichloromethane (100 mL) and washed with H$_2$O (100 mL). The organic layer was washed with HCl solution (1M, 50 mL) and aqueous NaHCO$_3$ solution (100 mL) and brine (50 mL), dried over anhydrous Na$_2$SO$_4$, filtered, and evaporated to give Compound 370B. LC-MS (ESI) m/z: non-ionizable compound under routine conditions used.

Compounds 370C and 370 were synthesized by employing the procedures described for Compounds 54C and 256 using Compounds 370B with TEA as base and adding NaI, 302B, and 370C in lieu of chloromethyl pivalate with Na$_2$CO$_3$ as base and without adding NaI, Compounds 54B, and 256D. Compound 370C: LC-MS (ESI) m/z: 765 [M+Na]$^+$. Compound 370: LC-MS (ESI) m/z: 501 [M+H]$^+$; $^1$H-NMR (CD$_3$OD, 400 MHz): δ (ppm) 1.11-1.16 (m, 6H), 1.62-1.69 (m, 4H), 1.95-1.97 (m, 2H), 2.33-2.35 (m, 2H), 2.64-2.66 (m, 1H), 3.31-3.34 (m, 4H), 4.72-4.74 (m, 1H), 5.98 (s, 2H), 7.17-7.19 (m, 2H), 7.33-7.35 (m, 2H).

Example 371

Synthesis of 2-(isobutyryloxy)ethyl 4-(((trans)-4-(4-(trifluoromethoxy)phenyl)cyclohexyl)oxy)-1H-1,2,3-triazole-5-carboxylate (371)

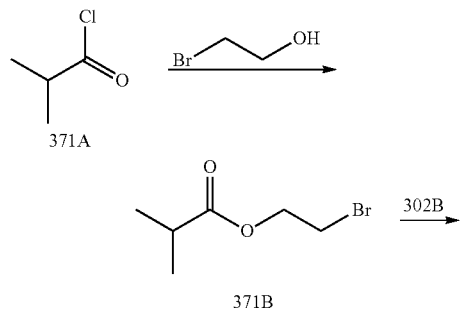

To a solution of 2-bromoethanol (2.3 g, 18.9 mmol) and TEA (2.9 g, 28.3 mmol) in hexane (30 mL) at 0-5° C. was added isobutyryl chloride (371A) (2 g, 18.9 mmol) and stirred at room temperature for 16 hours. The reaction mixture was diluted with water (20 mL). The organic layer was washed with diluted aqueous HCl solution (1 N, 20 mL) and brine (20 mL), dried over anhydrous sodium sulfate, filtered, and concentrated to afford Compound 371B. $^1$H-NMR (CDCl$_3$, 400 MHz): δ (ppm) 1.20 (d, J=6.8 Hz, 6H), 2.58-2.62 (m, 1H), 3.52 (t, J=5.6 Hz, 2H), 4.38 (d, J=6.0 Hz, 2H).

Compounds 371C and 371 were synthesized by employing the procedures described for Compounds 54C and 256 using Compounds 371B with TEA as base and adding NaI, 302B, and 371C in lieu of chloromethyl pivalate with Na$_2$CO$_3$ as base and without adding NaI, Compounds 54B, and 256D. Compound 371C: LC-MS (ESI) m/z: 750 [M+Na]$^+$. Compound 371: LC-MS (ESI) m/z: 486 [M+H]$^+$; $^1$H-NMR (CD$_3$OD, 400 MHz): δ (ppm) 1.15 (d, J=7.2 Hz, 6H), 1.63-1.68 (m, 4H), 1.95-1.97 (m, 2H), 2.33-2.34 (m, 2H), 2.54-2.65 (m, 2H), 4.38-4.41 (m, 2H), 4.52-4.54 (m, 2H), 4.72-4.74 (m, 1H), 7.17-7.19 (m, 2H), 7.32-7.34 (m, 2H).

Example 372

Synthesis of 4-(2-(bis(4-chlorobenzyl)amino)ethyl)-1H-1,2,3-triazole-5-carboxylic acid 2,2,2-trifluoroacetate (372)

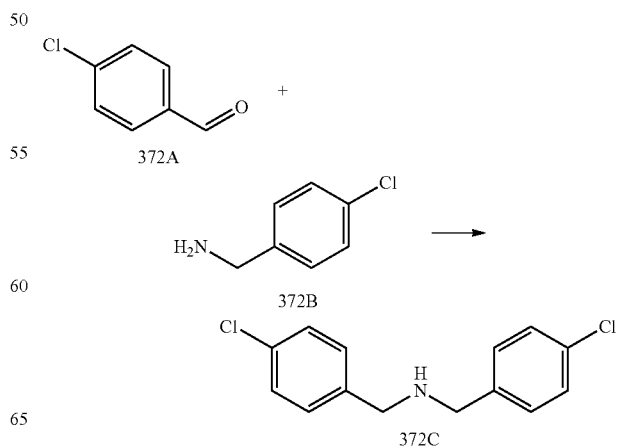

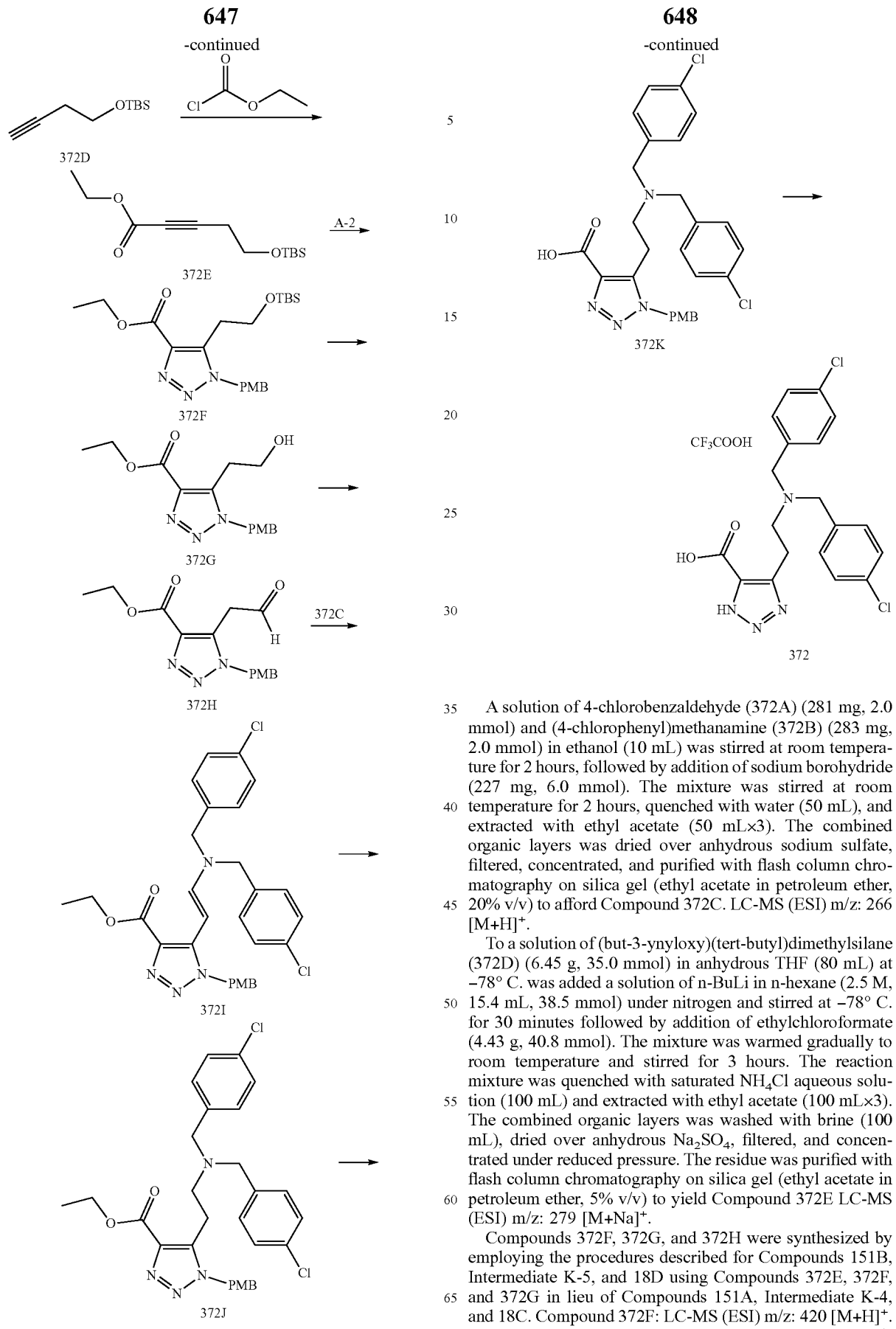

A solution of 4-chlorobenzaldehyde (372A) (281 mg, 2.0 mmol) and (4-chlorophenyl)methanamine (372B) (283 mg, 2.0 mmol) in ethanol (10 mL) was stirred at room temperature for 2 hours, followed by addition of sodium borohydride (227 mg, 6.0 mmol). The mixture was stirred at room temperature for 2 hours, quenched with water (50 mL), and extracted with ethyl acetate (50 mL×3). The combined organic layers was dried over anhydrous sodium sulfate, filtered, concentrated, and purified with flash column chromatography on silica gel (ethyl acetate in petroleum ether, 20% v/v) to afford Compound 372C. LC-MS (ESI) m/z: 266 [M+H]$^+$.

To a solution of (but-3-ynyloxy)(tert-butyl)dimethylsilane (372D) (6.45 g, 35.0 mmol) in anhydrous THF (80 mL) at −78° C. was added a solution of n-BuLi in n-hexane (2.5 M, 15.4 mL, 38.5 mmol) under nitrogen and stirred at −78° C. for 30 minutes followed by addition of ethylchloroformate (4.43 g, 40.8 mmol). The mixture was warmed gradually to room temperature and stirred for 3 hours. The reaction mixture was quenched with saturated NH$_4$Cl aqueous solution (100 mL) and extracted with ethyl acetate (100 mL×3). The combined organic layers was washed with brine (100 mL), dried over anhydrous Na$_2$SO$_4$, filtered, and concentrated under reduced pressure. The residue was purified with flash column chromatography on silica gel (ethyl acetate in petroleum ether, 5% v/v) to yield Compound 372E LC-MS (ESI) m/z: 279 [M+Na]$^+$.

Compounds 372F, 372G, and 372H were synthesized by employing the procedures described for Compounds 151B, Intermediate K-5, and 18D using Compounds 372E, 372F, and 372G in lieu of Compounds 151A, Intermediate K-4, and 18C. Compound 372F: LC-MS (ESI) m/z: 420 [M+H]$^+$. Compound 372G: LC-MS (ESI) m/z: 306 [M+H]$^+$;

$^1$H-NMR (CDCl$_3$, 400 MHz): δ (ppm) 1.37 (t, J=7.2 Hz, 3H), 2.89 (t, J=6.0 Hz, 1H), 3.16 (t, J=6.0 Hz, 2H), 3.79 (s, 3H), 4.00-4.07 (m, 2H), 4.34-4.40 (m, 2H), 5.83 (s, 2H), 6.85 (d, J=8.8 Hz, 2H), 7.30 (d, J=8.8 Hz, 2H). Compound 372H: LC-MS (ESI) m/z: 304 [M+H]$^+$.

A mixture of Compounds 372I1 (607 mg, 2.0 mmol) and 372C (300 mg, 1.13 mmol) in ethanol (10 mL) was stirred at room temperature for 4 hours. The reaction mixture was concentrated under reduced pressure. The residue was diluted with a mixture of ethyl acetate (10 mL) and petroleum ether (80 mL) and stirred at room temperature for 5 minutes. The resulting solid was collected by filtration to give Compound 372I. LC-MS (ESI) m/z: 551 [M+H]$^+$.

Compounds 372J, 372K, and 372 were synthesized by employing the procedures described for Compounds 141, 8F, and 1 using Compounds 372I with dichloromethane as solvent, 372J, and 372K in lieu of Compounds 140 with EtOAc as solvent, 8E, and 1E. Compound 372J: LC-MS (ESI) m/z: 553 [M+H]$^+$. Compound 372K: LC-MS (ESI) m/z: 525 [M+H]$^+$. Compound 372: LC-MS (ESI) m/z: 405 [M+H]$^+$; $^1$H-NMR (DMSO-d$_6$, 400 MHz): δ (ppm) 3.01 (brs, 2H), 3.27 (brs, 2H), 3.71 (brs, 4H), 7.43 (br, 8H).

Example 373

Synthesis of 4-(((3-(3,4-dichlorophenyl)-3-azabicyclo[3.1.0]hexan-6-yl)methyl)thio)-1H-1,2,3-triazole-5-carboxylic acid (373)

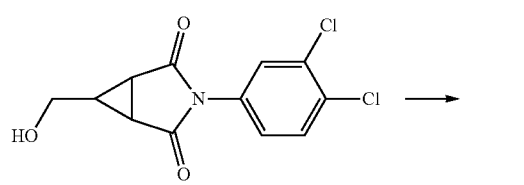

369D

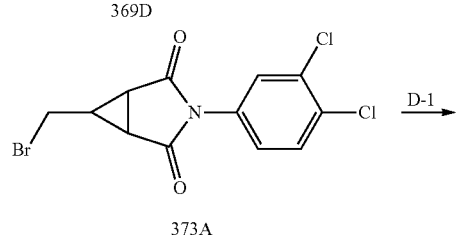

373A

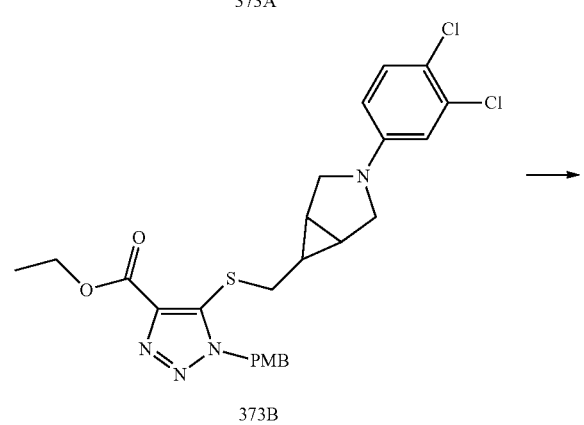

373B

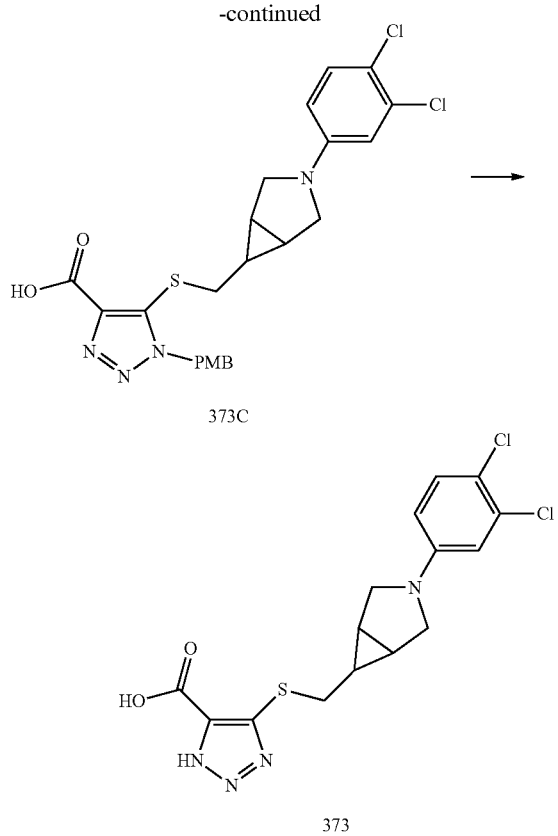

373C

373

Compounds 373A, 373B, 373C, and 373 were synthesized by employing the procedures described for Intermediate K, Compounds 171B, 8F, and 57E using Compounds 369D, 373A, Intermediate D-1, 373B, and 373C in lieu of Intermediates K-5, K, Compounds 171A, 8E, and 57D. Compound 373A: LC-MS (ESI) m/z: 320 [M+H]$^+$; $^1$H-NMR (CDCl$_3$, 400 MHz): δ (ppm) 1.27-133 (m, 1H), 1.72-1.75 (m, 2H), 3.23-3.26 (m, 2H), 3.38 (d, J=11.6 Hz, 2H), 3.52 (d, J=9.2 Hz, 2H), 6.35 (dd, J=8.8, 2.8 Hz, 1H), 6.57 (d, J=2.8 hz, 1H), 7.20 (d, J=8.8 Hz, 1H). Compound 373C: LC-MS (ESI) m/z: 505 [M+H]$^+$. Compound 373: LC-MS (ESI) m/z: 385 [M+H]$^+$; $^1$H-NMR (CD$_3$OD, 400 MHz): δ (ppm) 1.12 (s, 1H), 1.75 (s, 2H), 3.15 (d, J=7.2 Hz, 2H), 3.19-3.21 (m, 2H), 3.49 (d, J=9.2 Hz, 2H), 6.46 (dd, J=8.4, 2.8 Hz, 1H), 6.63 (d, J=2.8 Hz, 1H), 7.20 (d, J=8.4 Hz, 1H).

Example 374

Synthesis of 4-(2-((4-chlorobenzyl)((4'-(trifluoromethoxy)-[1,1'-biphenyl]-4-yl)methyl)amino)ethyl)-1H-1,2,3-triazole-5-carboxylic acid 2,2,2-trifluoroacetate (374)

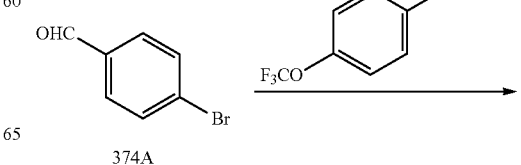

374A

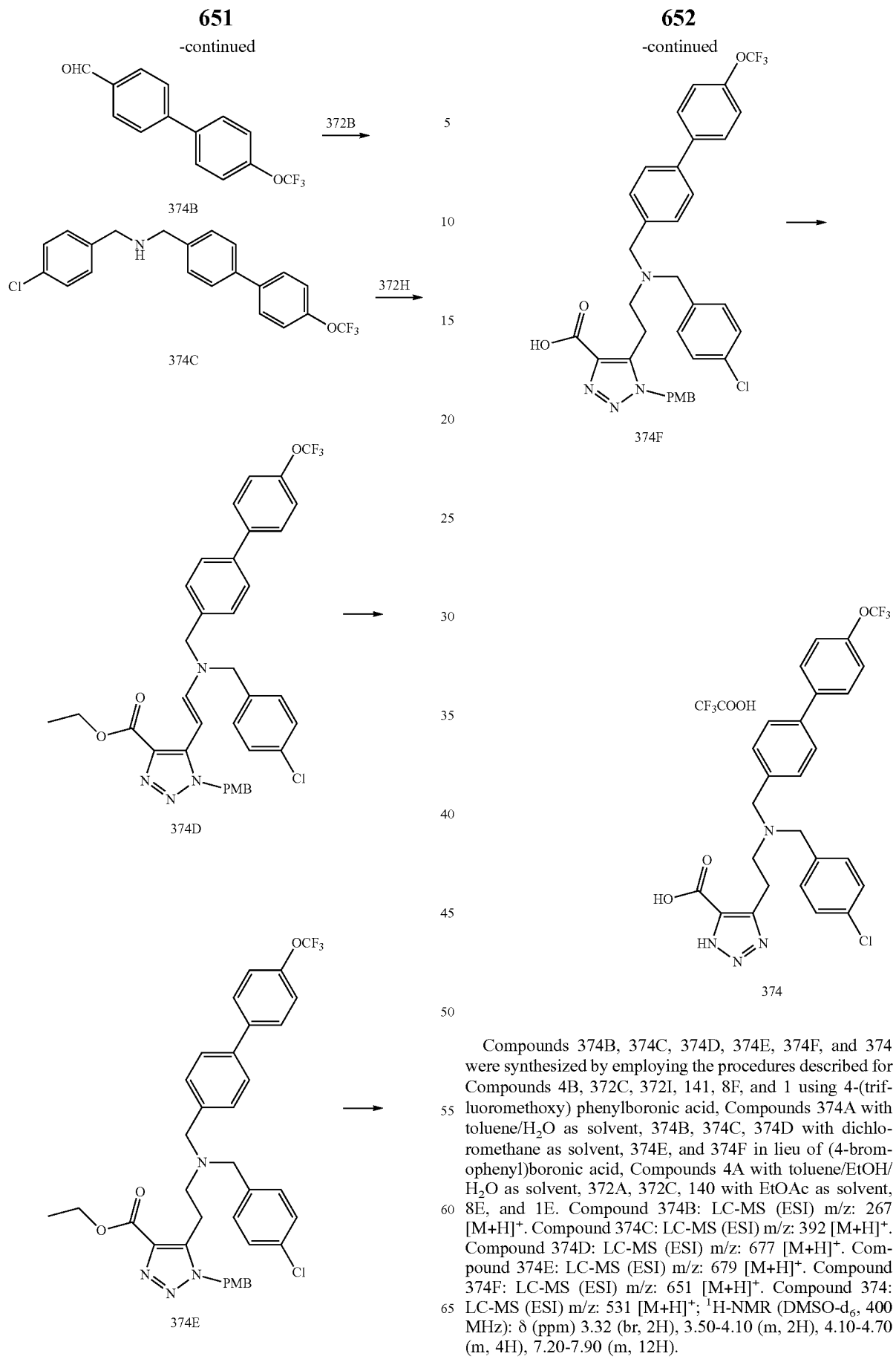

Compounds 374B, 374C, 374D, 374E, 374F, and 374 were synthesized by employing the procedures described for Compounds 4B, 372C, 372I, 141, 8F, and 1 using 4-(trifluoromethoxy) phenylboronic acid, Compounds 374A with toluene/H$_2$O as solvent, 374B, 374C, 374D with dichloromethane as solvent, 374E, and 374F in lieu of (4-bromophenyl)boronic acid, Compounds 4A with toluene/EtOH/H$_2$O as solvent, 372A, 372C, 140 with EtOAc as solvent, 8E, and 1E. Compound 374B: LC-MS (ESI) m/z: 267 [M+H]$^+$. Compound 374C: LC-MS (ESI) m/z: 392 [M+H]$^+$. Compound 374D: LC-MS (ESI) m/z: 677 [M+H]$^+$. Compound 374E: LC-MS (ESI) m/z: 679 [M+H]$^+$. Compound 374F: LC-MS (ESI) m/z: 651 [M+H]$^+$. Compound 374: LC-MS (ESI) m/z: 531 [M+H]$^+$; $^1$H-NMR (DMSO-d$_6$, 400 MHz): δ (ppm) 3.32 (br, 2H), 3.50-4.10 (m, 2H), 4.10-4.70 (m, 4H), 7.20-7.90 (m, 12H).

Example 375

Synthesis of 4-(3-(cyclopentyloxy)phenoxy)-1H-1,2,3-triazole-5-carboxylic acid 2,2,2-trifluoroacetate (375)

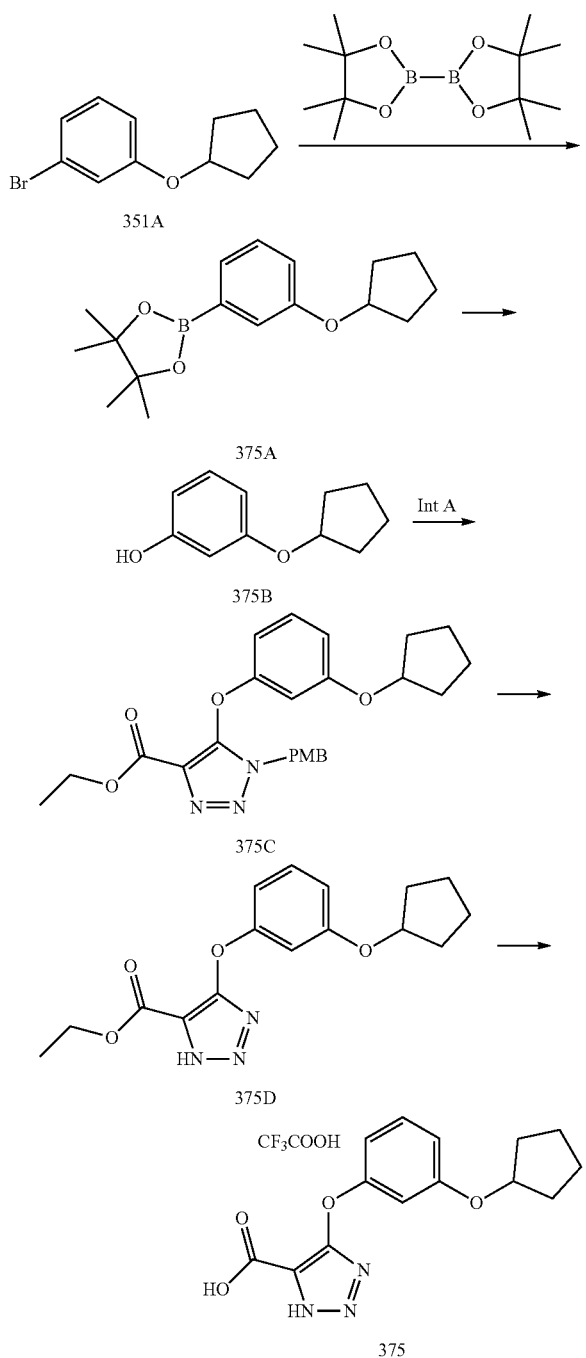

Compounds 375A, 375B, 375C, 375D, and 375 were synthesized by employing the procedures described for Compounds 27C, 336D, Intermediate I, 217E, and 8F using Compounds 351A, 375A, 375B, 375C, and 375D in lieu of Compounds 27B, 336C, 4-bromophenol, 217D, and 8E. Compound 375A: LC-MS (ESI) m/z: non-ionizable compound under routine conditions used; $^1$H-NMR (CDCl$_3$, 400 MHz): δ (ppm) 1.33 (s, 12H), 1.59-1.64 (m, 2H), 1.76-1.93 (m, 6H), 4.79-4.83 (m, 1H), 6.95-6.99 (m, 1H), 7.24-7.36 (m, 3H). Compound 375B: LC-MS (ESI) m/z: 177 [M−H]; $^1$H-NMR (CDCl$_3$, 400 MHz): δ (ppm) 1.58-1.63 (m, 2H), 1.77-1.88 (m, 6H), 4.69-4.74 (m, 1H), 4.90 (s, 1H), 6.37-6.39 (m, 2H), 6.44-6.48 (m, 1H), 7.09 (t, J=8.0 Hz, 1H). Compound 375C: LC-MS (ESI) m/z: 438 [M+H]$^+$. Compound 375D: LC-MS (ESI) m/z: 318 [M+H]$^+$. Compound 375: LC-MS (ESI) m/z: 290 [M+H]$^+$; $^1$H-NMR (CD$_3$OD, 400 MHz): δ (ppm) 1.60-1.66 (m, 2H), 1.68-1.87 (m, 4H), 1.89-1.95 (m, 2H), 4.75-4.80 (m, 1H), 6.60-6.69 (m, 3H), 7.21 (t, J=8.0 Hz, 1H).

Example 376

Synthesis of 4-((3'-chloro-4'-(piperidin-1-yl)-[1,1'-biphenyl]-4-yl)thio)-1H-1,2,3-triazole-5-carboxylic acid 2,2,2-trifluoroacetate (376)

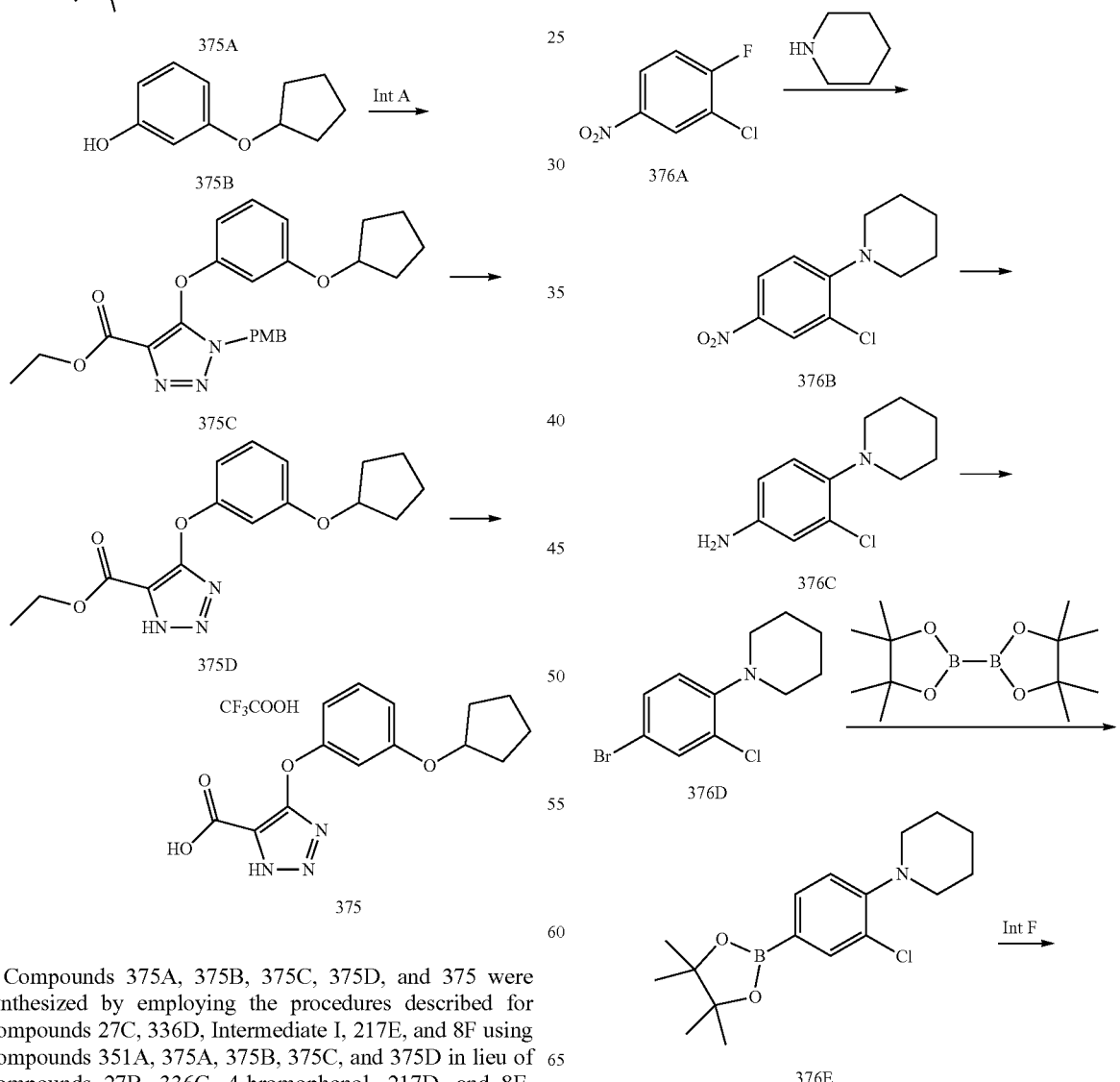

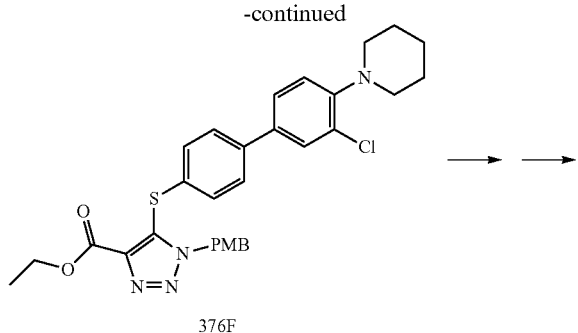

376F

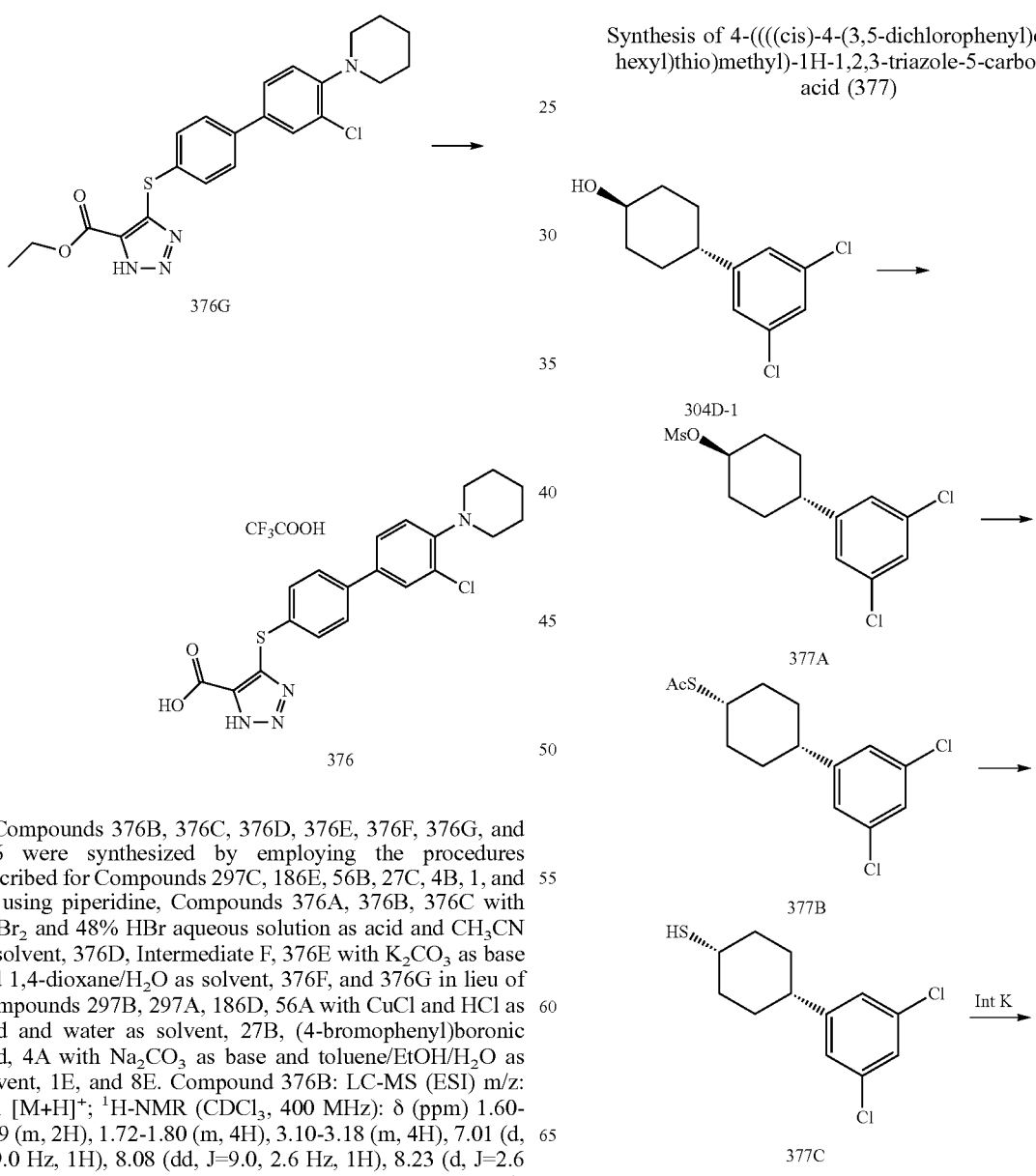

¹H-NMR (CDCl₃, 400 MHz): δ (ppm) 1.53 (m, 2H), 1.71 (m, 4H), 2.66-2.99 (m, 4H), 3.50 (s, 2H), 6.55 (dd, J=8.4, 2.6 Hz, 1H), 6.73 (d, J=2.6 Hz, 1H), 6.87 (d, J=8.4 Hz, 1H). Compound 376D: LC-MS (ESI) m/z: 274 [M+H]⁺; ¹H-NMR (CDCl₃, 400 MHz): δ (ppm) 1.39-1.56 (m, 2H), 1.66 (m, 4H), 2.70-3.16 (m, 4H), 6.81 (d, J=8.6 Hz, 1H), 7.31 (dd, J=8.6, 2.2 Hz, 1H), 7.41 (d, J=2.2 Hz, 1H). Compound 376E: LC-MS (ESI) m/z: 322 [M+H]⁺; ¹H-NMR (CDCl₃, 400 MHz): δ (ppm) 1.33 (s, 12H), 1.53-1.59 (m, 2H), 1.71-1.77 (m, 4H), 2.98-3.03 (m, 4H), 7.00 (d, J=8.0 Hz, 1H), 7.62 (d, J=7.9 Hz, 1H), 7.78 (s, 1H). Compound 376F: LC-MS (ESI) m/z: 563 [M+H]⁺. Compound 376G: LC-MS (ESI) m/z: 443 [M+H]⁺. Compound 376: LC-MS (ESI) m/z: 415 [M+H]⁺; ¹H-NMR (CD₃OD, 400 MHz): δ (ppm) 1.58-1.70 (m, 2H), 1.74-1.85 (m, 4H), 3.01-3.16 (m, 4H), 7.25 (d, J=8.4 Hz, 1H), 7.51-7.60 (m, 3H), 7.63 (d, J=8.5 Hz, 2H), 7.69 (d, J=2.2 Hz, 1H).

Example 377

Synthesis of 4-((((cis)-4-(3,5-dichlorophenyl)cyclohexyl)thio)methyl)-1H-1,2,3-triazole-5-carboxylic acid (377)

Compounds 376B, 376C, 376D, 376E, 376F, 376G, and 376 were synthesized by employing the procedures described for Compounds 297C, 186E, 56B, 27C, 4B, 1, and 8F using piperidine, Compounds 376A, 376B, 376C with CuBr₂ and 48% HBr aqueous solution as acid and CH₃CN as solvent, 376D, Intermediate F, 376E with K₂CO₃ as base and 1,4-dioxane/H₂O as solvent, 376F, and 376G in lieu of Compounds 297B, 297A, 186D, 56A with CuCl and HCl as acid and water as solvent, 27B, (4-bromophenyl)boronic acid, 4A with Na₂CO₃ as base and toluene/EtOH/H₂O as solvent, 1E, and 8E. Compound 376B: LC-MS (ESI) m/z: 241 [M+H]⁺; ¹H-NMR (CDCl₃, 400 MHz): δ (ppm) 1.60-1.69 (m, 2H), 1.72-1.80 (m, 4H), 3.10-3.18 (m, 4H), 7.01 (d, J=9.0 Hz, 1H), 8.08 (dd, J=9.0, 2.6 Hz, 1H), 8.23 (d, J=2.6 Hz, 1H). Compound 376C: LC-MS (ESI) m/z: 211 [M+H]⁺;

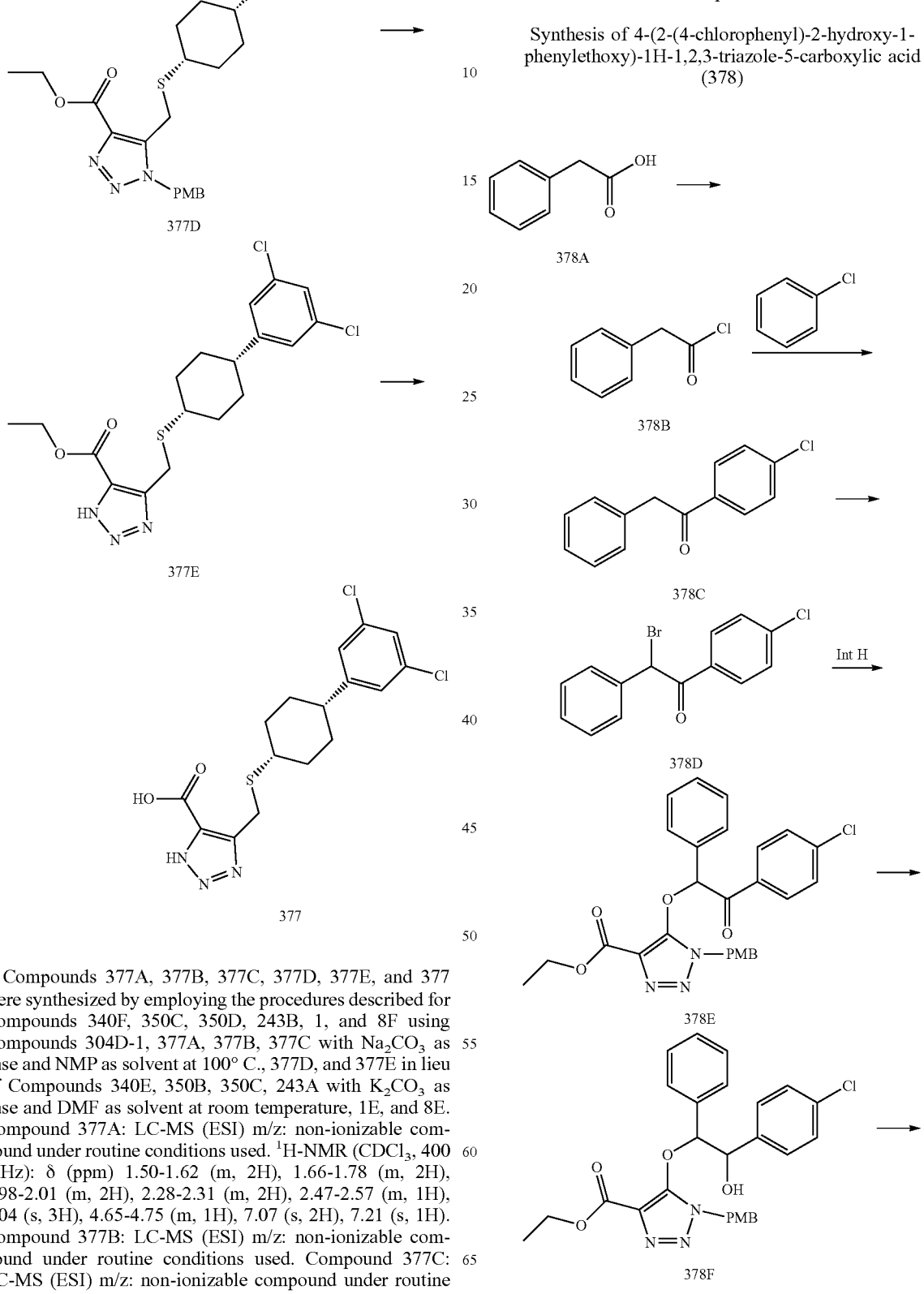

Compounds 377A, 377B, 377C, 377D, 377E, and 377 were synthesized by employing the procedures described for Compounds 340F, 350C, 350D, 243B, 1, and 8F using Compounds 304D-1, 377A, 377B, 377C with Na$_2$CO$_3$ as base and NMP as solvent at 100° C., 377D, and 377E in lieu of Compounds 340E, 350B, 350C, 243A with K$_2$CO$_3$ as base and DMF as solvent at room temperature, 1E, and 8E. Compound 377A: LC-MS (ESI) m/z: non-ionizable compound under routine conditions used. $^1$H-NMR (CDCl$_3$, 400 MHz): δ (ppm) 1.50-1.62 (m, 2H), 1.66-1.78 (m, 2H), 1.98-2.01 (m, 2H), 2.28-2.31 (m, 2H), 2.47-2.57 (m, 1H), 3.04 (s, 3H), 4.65-4.75 (m, 1H), 7.07 (s, 2H), 7.21 (s, 1H). Compound 377B: LC-MS (ESI) m/z: non-ionizable compound under routine conditions used. Compound 377C: LC-MS (ESI) m/z: non-ionizable compound under routine conditions used. Compound 377D: LC-MS (ESI) m/z: 534 [M+H]$^+$. Compound 377E: LC-MS (ESI) m/z: 414 [M+H]$^+$. Compound 377: LC-MS (ESI) m/z: 386 [M+H]$^+$; $^1$H-NMR (DMSO-d$_6$, 400 MHz): δ (ppm) 1.58-1.82 (m, 8H), 2.58-2.63 (m, 1H), 3.17-3.21 (m, 1H), 4.01 (s, 2H), 7.24 (s, 2H), 7.42 (s, 1H), 13.21 (bs, 1H), 15.33 (bs, 1H).

Example 378

Synthesis of 4-(2-(4-chlorophenyl)-2-hydroxy-1-phenylethoxy)-1H-1,2,3-triazole-5-carboxylic acid (378)

Example 379

Synthesis of 4-(((cis)-4-(4-(2-oxopiperidin-1-yl)phenyl)cyclohexyl)oxy)-1H-1,2,3-triazole-5-carboxylic acid (379)

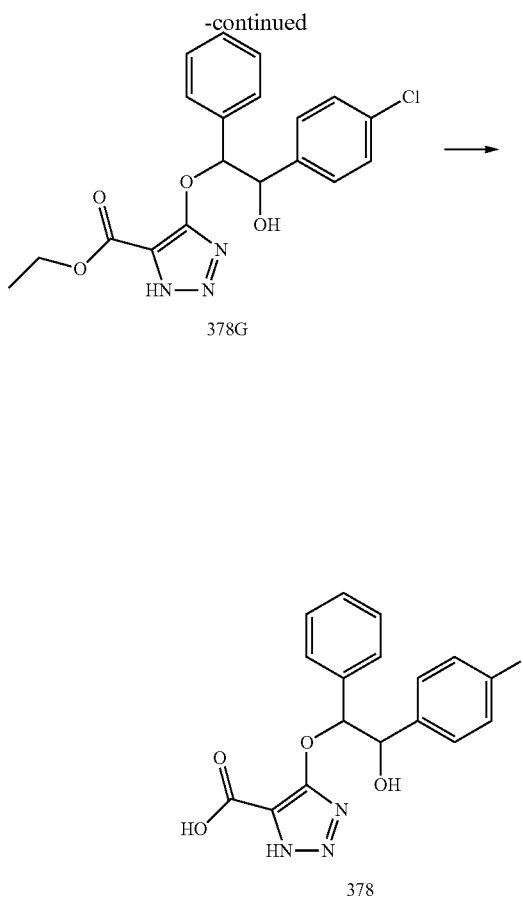

To a solution of 2-phenylacetic acid (378A) (1.36 g, 10 mmol) in dichloromethane (10 mL) was added oxalyl dichloride (1.9 g, 15 mmol). The mixture was stirred at room temperature for 18 hours and concentrated under reduced pressure to give a crude Compound 378B, which was used directly for next step without any purification. LC-MS (ESI) m/z: non-ionizable compound under routine conditions used.

To a mixture of compound 378B (1.54 g, 10 mmol) and chlorobenzene (1.45 g, 13 mmol) in dichloromethane (10 mL) was added $AlCl_3$ (1.73 g, 13 mmol). The mixture was stirred at room temperature for 3 hours, poured into water (100 mL), and extracted with ethyl acetate (50 mL×3). The combined organic layers was washed with brine (50 mL), dried over anhydrous sodium sulfate, concentrated, and purified with flash column chromatography on silica gel (ethyl acetate in petroleum ether, from 10% v/v) to afford Compound 378C. LC-MS (ESI) m/z: 231 [M+H]$^+$.

Compounds 378D, 378E, 378F, 378G, and 378 were synthesized by employing the procedures described for Compounds 43B, 274B, 57C, 217E, and 8F using Compounds 378C, 378D with acetone as solvent at 90° C., 378E, 378F, and 378G in lieu of Compounds 43A, 274A with DMF as solvent at room temperature, 57B, 217D, and 8E. Compound 378D: LC-MS (ESI) m/z: 309 [M+H]$^+$. Compound 378E: LC-MS (ESI) m/z: 506 [M+H]$^+$. Compound 378F: LC-MS (ESI) m/z: 530 [M+Na]$^+$. Compound 378G: LC-MS (ESI) m/z: 410 [M+Na]$^+$. Compound 378: LC-MS (ESI) m/z: 382 [M+Na]$^+$; $^1$H-NMR (DMSO-$d_6$, 400 MHz): δ (ppm) 4.98-5.03 (m, 1H), 5.64-6.03 (brs, 2H), 7.11-7.36 (m, 9H), 13.0-13.2 (brs, 1H), 14.63-14.65 (m, 1H).

-continued

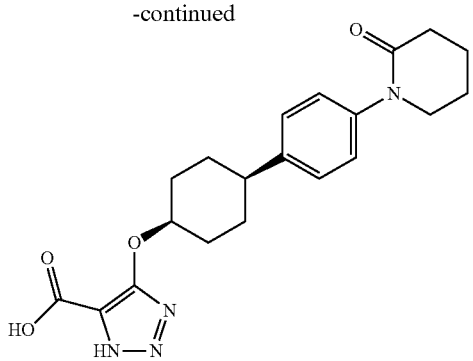

379

Compounds 379A, 379B, 379C, and 379 were synthesized by employing the procedures described for Compounds 301A, 90C, 269, and 256 using piperidin-2-one, Compounds 347C K₃PO₄ as base and t-BuOH/water as solvent and t-butyl Brettphos as ligand, 379A with DEAD as coupling reagent, 379B with EtOH/water as solvent at room temperature, and 379C at room temperature in lieu of Compounds 297B, Intermediate I with Cs₂CO₃ as base and 1,4-dioxane as solvent and X-Phos as ligand, 90B with DIAD as coupling reagent, 269C with MeOH/water as solvent at 60° C., and 256D at 50° C. Compound 379A: LC-MS (ESI) m/z: 274 [M+H]⁺. Compound 379B: LC-MS (ESI) m/z: 533 [M+H]⁺. Compound 379C: LC-MS (ESI) m/z: 505 [M+H]⁺. Compound 379: LC-MS (ESI) m/z: 385 [M+H]⁺. ¹H-NMR (CD₃OD, 400 MHz): δ (ppm) 1.66 (d, J=12 Hz, 2H), 1.75 (t, J=14 Hz, 2H), 1.93-2.00 (m, 4H), 2.04-2.10 (m, 2H), 2.23 (d, J=14 Hz, 2H), 2.51 (t, J=6 Hz, 2H), 2.67 (t, J=15.2 Hz, 1H), 3.65 (t, J=5.2 Hz, 2H), 5.05 (s, 1H), 7.17 (d, J=8.8 Hz, 2H), 7.36 (d, J=8.4 Hz, 2H).

Example 380

Synthesis of 4-(3-(cyclohexyloxy)phenoxy)-1H-1,2,3-triazole-5-carboxylic acid 2,2,2-trifluoroacetate (380)

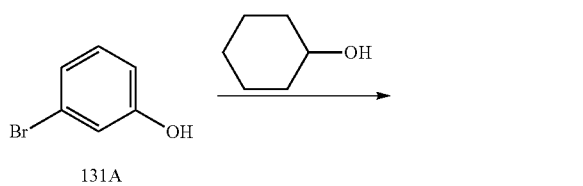

131A

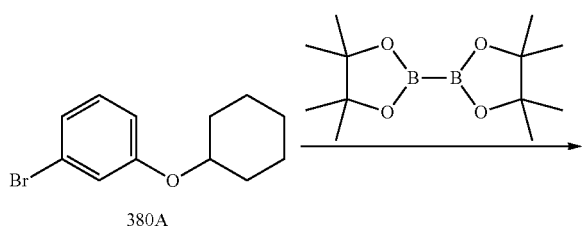

380A

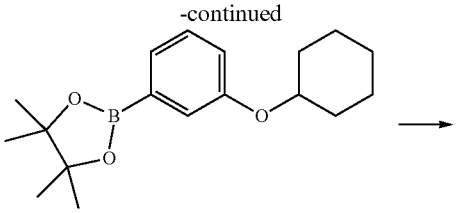

380B

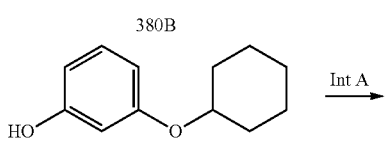

380C

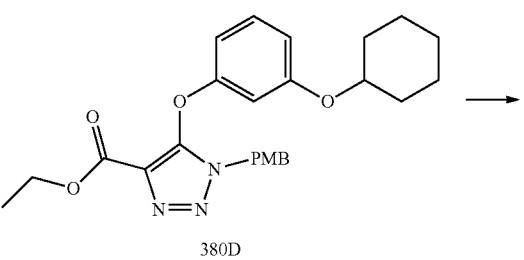

380D

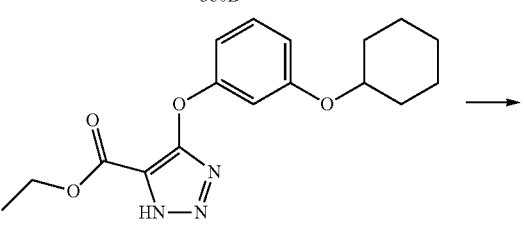

380E

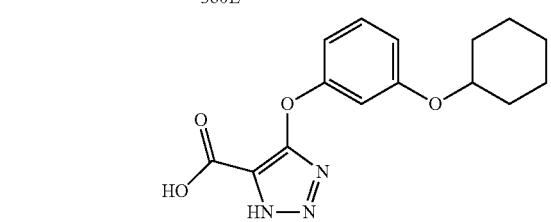

380

Compounds 380A, 380B, 380C, and 380D were synthesized by employing the procedures described for Compounds 90C, 27C, 236D, and Intermediate I using cyclohexanol, Compounds 131A CH₂Cl₂ as solvent and DEAD as coupling reagent, 380A, 380B, and 380C in lieu of Compounds 90B, Intermediate H with THF as solvent and DIAD as coupling reagent, 27B, 236C, and 4-bromophenol. Compound 380A: LC-MS (ESI) m/z: non-ionizable compound under routine conditions used; ¹H-NMR (CDCl₃, 400 MHz): δ (ppm) 1.29-1.38 (m, 3H), 1.40-1.55 (m, 3H), 1.76-1.80 (m, 2H), 1.93-1.98 (m, 2H), 4.18-4.25 (m, 1H), 6.82 (d, J=8.8 Hz, 1H), 7.02-7.07 (m, 2H), 7.11 (t, J=8.0 Hz, 1H). Compound 380B: LC-MS (ESI) m/z: non-ionizable compound under routine conditions used; ¹H-NMR (CDCl₃, 400 MHz): δ (ppm) 1.35-1.40 (m, 15H), 1.51-1.56 (m, 3H), 1.77-1.80 (m, 2H), 1.93-1.97 (m, 2H), 4.26-4.32 (m, 1H), 6.98-7.01 (m, 1H), 7.24-7.28 (m, 1H), 7.33-7.37 (m, 2H). Compound 380C: LC-MS (ESI) m/z: 191 [M−H]⁻; ¹H-NMR (CDCl₃, 400 MHz): δ (ppm) 1.35-1.41 (m, 3H), 1.48-1.58 (m, 3H), 1.77-1.81 (m, 2H), 1.96-2.05 (m, 2H), 4.16-4.23 (m, 1H), 4.98 (s, 1H), 6.37-6.42 (m, 2H), 6.47-6.50 (m, 1H), 7.10 (t, J=8.0 Hz, 1H). Compound 380D: LC-MS (ESI) m/z: 452 [M+H]⁺.

A mixture of Compound 380D (280 mg, 0.62 mmol) and 10% Pd/C (200 mg) in MeOH (20 mL) was stirred at room temperature under H₂ (1 atm.) for 16 hours. The mixture was filtered through Celite and the filtrate was concentrated. The residue was purified with flash column chromatography on silica gel (tetrahydrofuran in petroleum ether, from 0% to 70% v/v) to furnish Compound 380E. LC-MS (ESI) m/z: 332 [M+H]⁺.

Compound 380 was synthesized by employing the procedure described for Compound 8F using Compound 380E in lieu of Compound 8E, LC-MS (ESI) m/z: 304 [M+H]⁺; ¹H-NMR (CD₃OD, 400 MHz): δ (ppm) 1.39-1.53 (m, 6H), 1.79-1.81 (m, 2H), 1.97-2.00 (m, 2H), 4.28-4.33 (m, 1H), 6.63-6.65 (m, 1H), 6.68-6.69 (m, 1H), 6.71-6.73 (m, 1H), 7.23 (t, J=6.8 Hz, 1H).

Example 381

Synthesis of 4-(4-chloro-3-(cyclopentyloxy)phenoxy)-1H-1,2,3-triazole-5-carboxylic acid 2,2,2-trifluoroacetate (381)

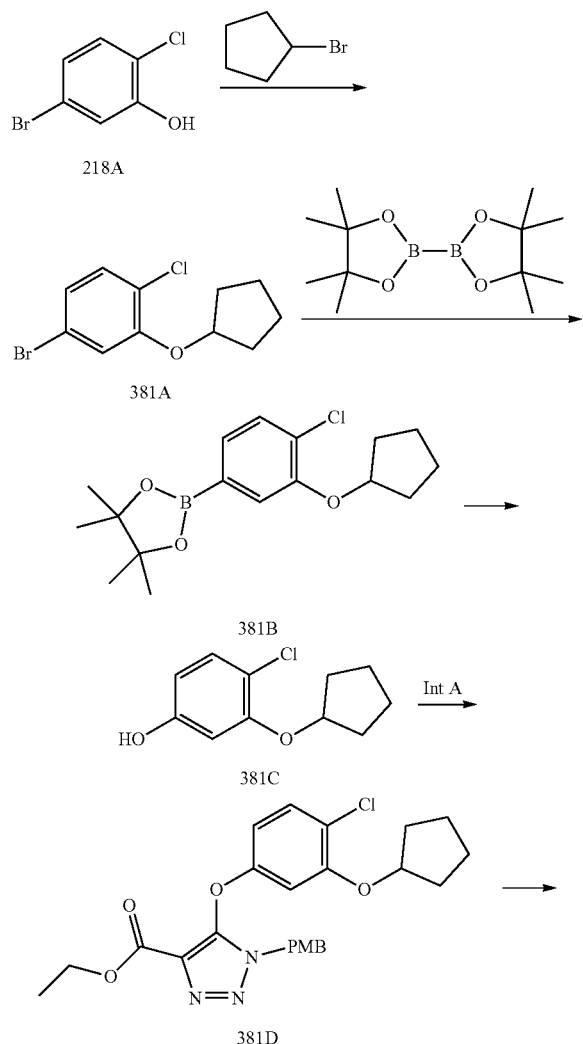

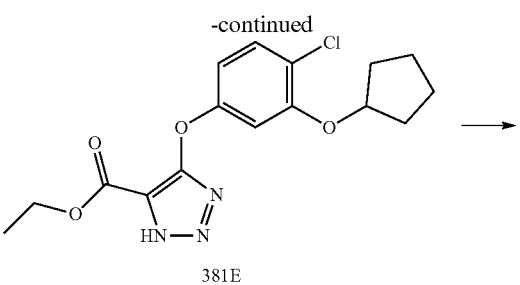

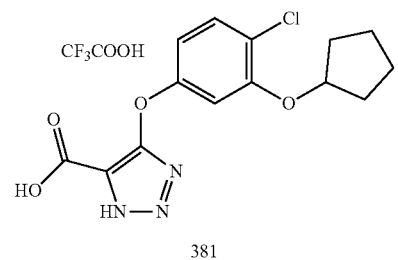

Compounds 381A, 381B, 381C, 381D, 381E, and 381 were synthesized by employing the procedures described for Compounds 27B, 27C, 236D, Intermediate I, 217E, and 8F using bromocyclopentane, Compounds 218A, 381A, 381B, 381C with Cs₂CO₃ as base, 381D, and 381E in lieu of 2-bromopropane, Compounds 27A, 27B, 236C, 4-bromophenol with K₂CO₃ as base, 217D, and 8E. Compound 381A: LC-MS (ESI) m/z: Non-ionzable Compound under routine conditions used; ¹H-NMR (CDCl₃, 400 MHz): δ (ppm) 1.62-1.766 (m, 2H), 1.82-1.91 (m, 6H), 4.78 (t, J=4.0 Hz, 1H), 6.98 (dd, J=8.0, 1.6 Hz, 1H), 7.04 (d, J=1.6 Hz, 1H), 7.19 (d, J=8.0 Hz, 1H). Compound 381B: LC-MS (ESI) m/z: Non-ionzable Compound under routine conditions used; ¹H-NMR (CDCl₃, 400 MHz): δ (ppm) 1.34 (d, J=4.0 Hz, 12H), 1.61-1.64 (m, 2H), 1.83-1.91 (m, 6H), 4.90-4.92 (m, 1H), 7.28-7.37 (m, 3H). Compound 381C: LC-MS (ESI) m/z: 213 [M+H]⁺; ¹H-NMR (CDCl₃, 400 MHz): δ (ppm) 1.60-1.64 (m, 2H), 1.81-1.91 (m, 6H), 4.72-4.74 (m, 1H), 6.33 (dd, J=8.4, 2.4 Hz, 1H), 6.45 (d, J=2.4 Hz, 1H), 7.16 (d, J=8.4 Hz, 1H). Compound 381D: LC-MS (ESI) m/z: 472 [M+H]⁺; ¹H-NMR (CDCl₃, 400 MHz): δ (ppm) 1.15 (t, J=7.2 Hz, 3H), 1.58-1.63 (m, 2H), 1.76-1.81 (m, 6H), 3.76 (s, 3H), 4.21 (q, J=7.2 Hz, 2H), 4.50-4.52 (m, 1H), 5.35 (s, 2H), 6.23 (dd, J=8.4, 2.8 Hz, 1H), 6.29 (d, J=2.8 Hz, 1H), 6.76-6.78 (m, 2H), 7.17-7.20 (m, 3H). Compound 381E: LC-MS (ESI) m/z: 352 [M+H]⁺; ¹H-NMR (CDCl₃, 400 MHz): δ (ppm) 1.34 (t, J=7.2 Hz, 3H), 1.60-1.64 (m, 2H), 1.81-1.91 (m, 6H), 4.10 (q, J=7.2 Hz, 2H), 4.74-4.75 (m, 1H), 6.64 (dd, J=8.8, 2.8 Hz, 1H), 6.81 (d, J=2.8 Hz, 1H), 7.29 (d, J=8.8 Hz, 1H). Compound 381: LC-MS (ESI) m/z: 324 [M+H]⁺; ¹H-NMR (CD₃OD, 400 MHz): δ (ppm) 1.64-1.70 (m, 2H), 1.81-1.93 (m, 6H), 4.81-4.89 (m, 1H), 6.63 (dd, J=8.8, 2.4 Hz, 1H), 6.88 (d, J=2.4 Hz, 1H), 7.31 (d, J=8.8 Hz, 1H).

Example 382

Synthesis of 4-((3-(cyclohexyloxy)phenyl)thio)-1H-1,2,3-triazole-5-carboxylic acid 2,2,2-trifluoroacetate (382)

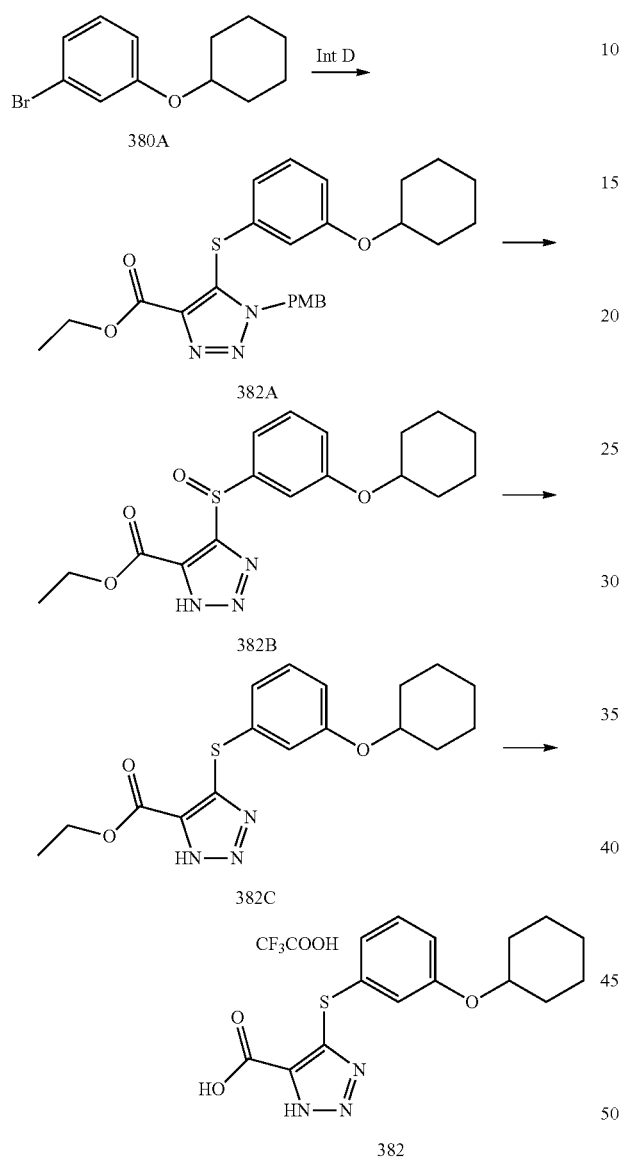

Compound 382A was synthesized by employing the procedure described for Compound 35D using Compound 380A in lieu of Compound 35C, LC-MS (ESI) m/z: 468 [M+H]+; $^1$H-NMR (CDCl$_3$, 400 MHz): δ (ppm) 1.26-1.42 (m, 9H), 1.73-1.78 (m, 2H), 1.83-1.89 (m, 2H), 3.76 (s, 3H), 4.05-4.10 (m, 1H), 4.36 (q, J=7.2 Hz, 2H), 5.51 (s, 2H), 6.53-6.58 (m, 2H), 6.70-6.73 (m, 1H), 7.78 (d, J=8.8 Hz, 2H), 7.09 (t, J=8.0 Hz, 1H), 7.16 (d, J=8.8 Hz, 2H).

To a solution of Compound 382A (600 mg, 1.28 mmol) in CH$_3$CN (15 mL) was added a solution of CAN (3.52 g, 6.42 mmol) in H$_2$O (5 mL). The mixture was stirred at 25° C. for 5 hours, diluted with water (50 mL), and extracted with EtOAc (50 mL×3). The combined organic layers was washed with brine (50 mL), dried over anhydrous sodium sulfate, concentrated, and purified with flash column chromatography on silica gel (ethyl acetate in petroleum ether, 30% v/v) to furnish Compound 382B. LC-MS (ESI) m/z: 364 [M+H]+.

To a solution of Compound 382B (200 mg, 0.55 mmol) and NaI (412 mg, 2.75 mmol) in CH$_3$CN (15 mL) was added dropwise TiCl$_4$ (523 mL, 2.75 mmol) at room temperature. The mixture was stirred at room temperature for 2 hours, quenched with water (2 mL), and concentrated under reduced pressure. The residue was purified with reverse phase chromatography using eluent (acetonitrile in water, from 0% to 70% v/v) to give Compound 382C. LC-MS (ESI) m/z: 348 [M+H]+.

Compound 382 was synthesized by employing the procedure described for Compound 8F using Compound 382C in lieu of Compound 8E, LC-MS (ESI) m/z: 320 [M+H]+; $^1$H-NMR (CD$_3$OD, 400 MHz): δ (ppm) 1.32-1.49 (m, 6H), 1.76-1.81 (m, 2H), 1.94-1.98 (m, 2H), 4.26-4.32 (m, 1H), 6.90 (d, J=7.6 Hz, 1H), 7.00-7.03 (m, 2H), 7.26 (t, J=8.0 Hz, 1H).

Example 383

Synthesis of 4-(((1-(2,5-dichlorophenyl)piperidin-4-yl)thio)methyl)-1H-1,2,3-triazole-5-carboxylic acid 2,2,2-trifluoroacetate (383)

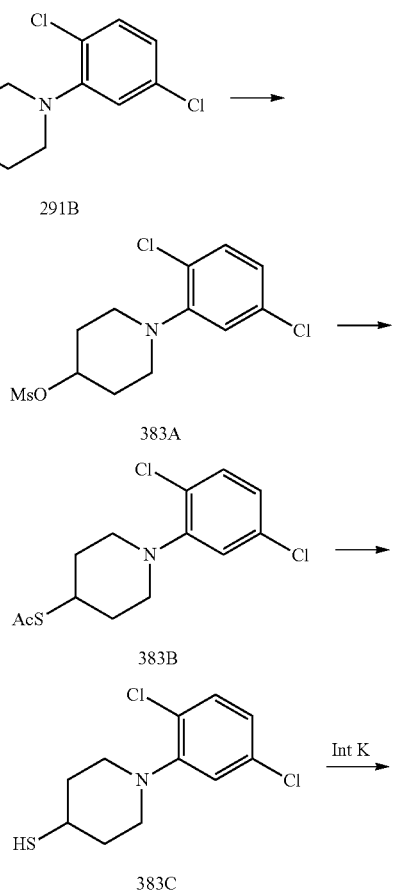

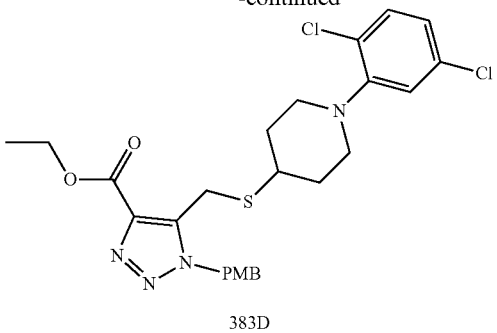

383D

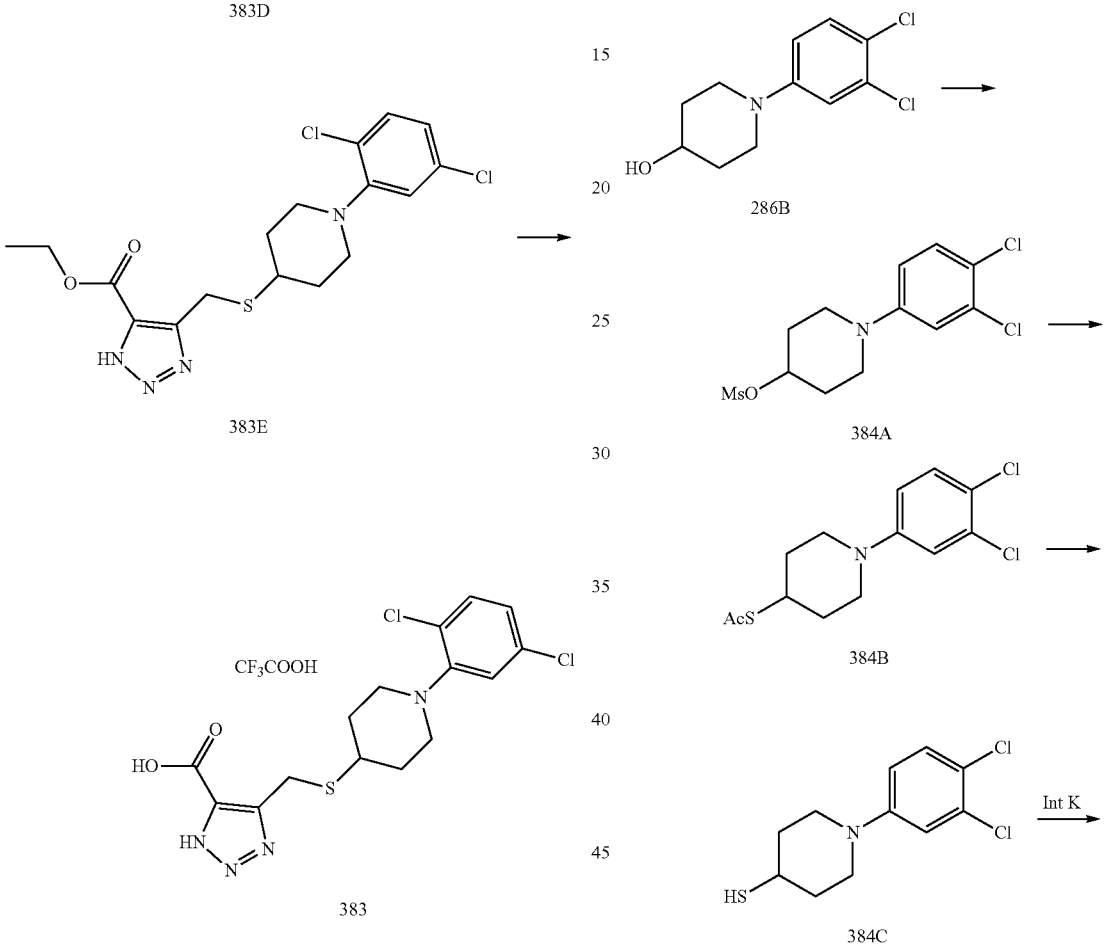

383E

383

3.32-3.34 (m, 2H), 4.17 (s, 2H), 7.00 (dd, J=8.4, 2.4 Hz, 1H), 7.09 (d, J=2.4 Hz, 1H), 7.33 (d, J=8.4 Hz, 1H).

Example 384

Synthesis of 4-(((1-(3,4-dichlorophenyl)piperidin-4-yl)thio)methyl)-1H-1,2,3-triazole-5-carboxylic acid 2,2,2-trifluoroacetate (384)

286B

384A

384B

384C

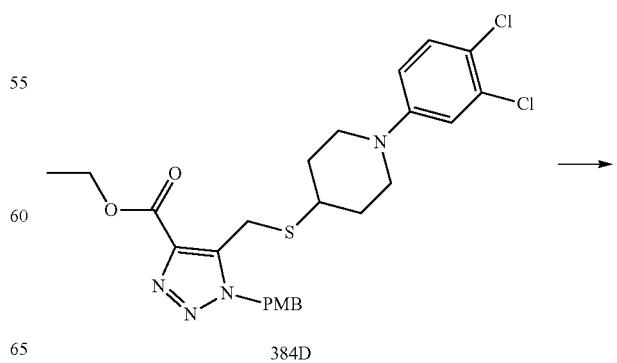

384D

Compounds 383A, 383B, 383C, 383D, 383E, and 383 were synthesized by employing the procedures described for Compounds 340F, 350C, 350D, 243B, 256, and 8F using Compounds 291B, 383A, 383B, 383C, 383D with TFA as acid and solvent, and 383E in lieu of Compounds 340E, 350B, 350C, 243A, 256D with TFA as acid and dichloromethane as solvent, and 8E. Compound 383A: LC-MS (ESI) m/z: 324 [M+H]$^+$. Compound 383B: LC-MS (ESI) m/z: 304 [M+H]$^+$; $^1$H-NMR (CDCl$_3$, 400 MHz): δ (ppm) 1.82-1.88 (m, 2H), 2.07-2.10 (m, 2H), 2.35 (s, 3H), 2.82-2.88 (m, 2H), 3.19-3.28 (m, 2H), 3.57-3.64 (m, 1H), 6.92-7.03 (m, 2H), 7.25-7.28 (m, 1H). Compound 383C: LC-MS (ESI) m/z: 262 [M+H]$^+$. Compound 383D: LC-MS (ESI) m/z: 535 [M+H]$^+$. Compound 383E: LC-MS (ESI) m/z: 415 [M+H]$^+$. Compound 383: LC-MS (ESI) m/z: 387 [M+H]$^+$; $^1$H-NMR (CD$_3$OD, 400 MHz): δ (ppm) 1.70-1.79 (m, 2H), 2.08-2.12 (m, 2H), 2.70-2.76 (m, 2H), 2.81-2.84 (m, 1H),

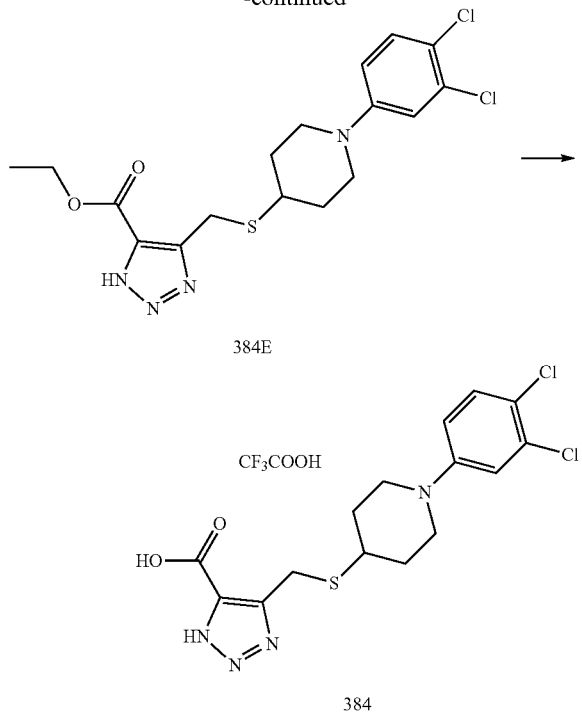

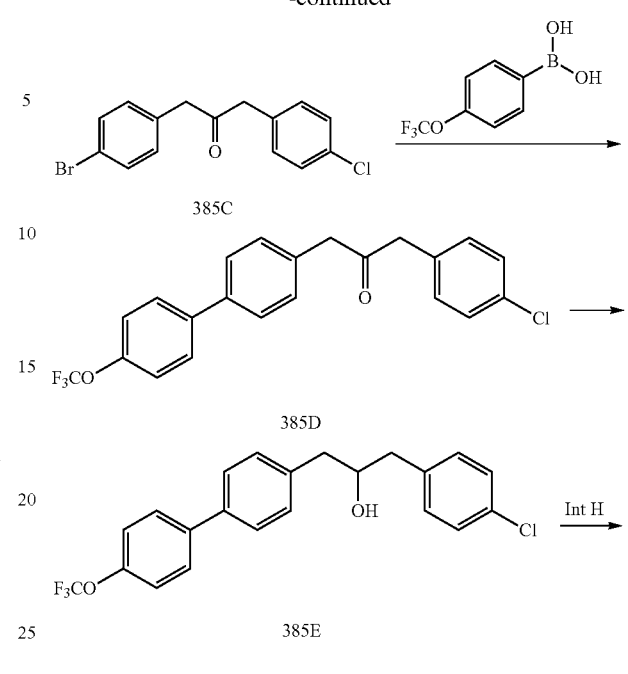

Compounds 384A, 384B, 384C, 384D, 384E, and 384 were synthesized by employing the procedures described for Compounds 340F, 350C, 350D, 243B, 256, and 8F using Compounds 286B, 384A, 384B, 384C, 384D with TFA as both acid and solvent, and 384E in lieu of Compounds 340E, 350B, 350C, 243A, 256D with TFA as acid and dichloromethane as solvent, and 8E. Compound 384A: LC-MS (ESI) m/z: 324 [M+H]$^+$. Compound 384B: LC-MS (ESI) m/z: 304 [M+H]$^+$. Compound 384C: LC-MS (ESI) m/z: 262 [M+H]$^+$. Compound 384D: LC-MS (ESI) m/z: 535 [M+H]$^+$. Compound 384E: LC-MS (ESI) m/z: 415 [M+H]$^+$. Compound 384: LC-MS (ESI) m/z: 387 [M+H]$^+$; $^1$H-NMR (CD$_3$OD, 400 MHz): δ (ppm) 1.52-1.55 (m, 2H), 1.93-1.98 (m, 2H), 2.72-2.78 (m, 3H), 3.49-3.52 (m, 2H), 4.05 (s, 2H), 6.77 (dd, J=9.2, 2.4 Hz, 1H), 6.96 (d, J=2.4 Hz, 1H), 7.19 (d, J=9.2 Hz, 1H).

Example 385

Synthesis of 4-((1-(4-chlorophenyl)-3-(4'-(trifluoromethoxy)-[1,1'-biphenyl]-4-yl)propan-2-yl)oxy)-1H-1,2,3-triazole-5-carboxylic acid 2,2,2-trifluoroacetate (385)

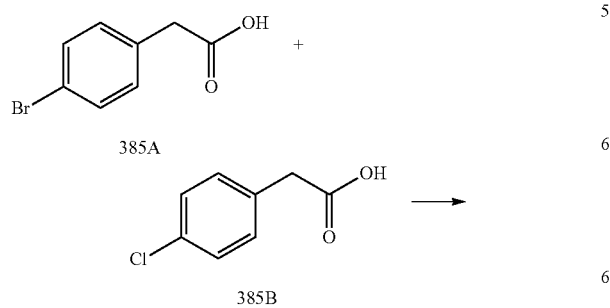

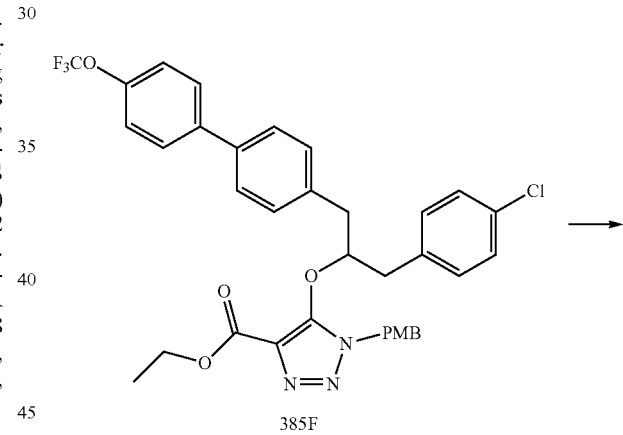

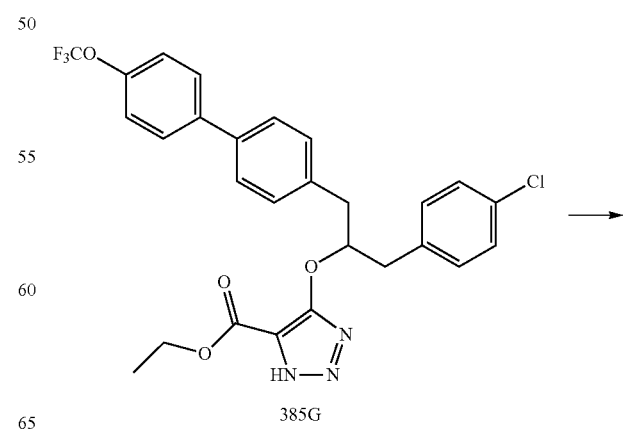

-continued

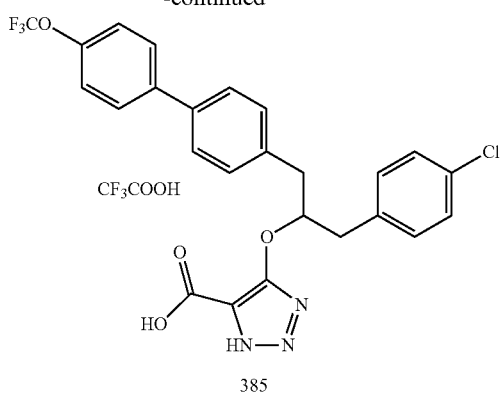

385

To a solution of 2-(4-bromophenyl)acetic acid (385A) (5.1 g, 30 mmol) and 2-(4-chlorophenyl)acetic acid (385B) (6.45 g, 30 mmol) in THF (100 mL) was added DCC (9.27 g, 45 mmol) and catalytic amount of DMAP. The mixture was stirred at room temperature for 18 hours and concentrated under reduced pressure. The residue was purified by column chromatography on silica gel (ethyl acetate in petroleum ether, 10% v/v) to furnish Compound 385C. LC-MS (ESI) m/z: 323 [M+H]$^+$.

Compounds 385D, 385E, 385F, 385G, and 385 were synthesized by employing the procedures described for Compounds 4B, 57C, 90C, 1, and 8F using 4-(trifluoromethoxy)phenylboronic acid, Compounds 385C, 385D, 385E with toluene as solvent, 385F, and 385G in lieu of (4-bromophenyl)boronic acid, Compounds 4A, 57B, 90B with THF as solvent, 1E, and 8E. Compound 385D: LC-MS (ESI) m/z: 405 [M+H]$^+$. Compound 385E: LC-MS (ESI) m/z: non-ionizable compound under routine conditions used. Compound 385F: LC-MS (ESI) m/z: 666 [M+H]$^+$. Compound 385G: LC-MS (ESI) m/z: 546 [M+H]$^+$. Compound 385: LC-MS (ESI) m/z: 518 [M+H]$^+$; $^1$H-NMR (DMSO-d$_6$, 400 MHz): δ (ppm) 2.98-2.99 (m, 4H), 5.14-5.18 (m, 1H), 7.30-7.31 (m, 4H), 7.35-7.44 (m, 4H), 7.57-7.59 (m, 2H), 7.75-7.77 (m, 2H).

Example 386

Synthesis of 4-((1-(5-chloro-2-(trifluoromethoxy)phenyl)piperidin-4-yl)thio)-1H-1,2,3-triazole-5-carboxylic acid 2,2,2-trifluoroacetate (386)

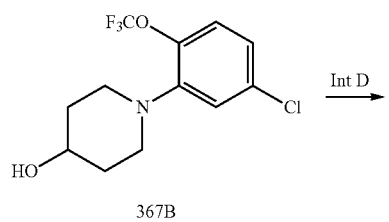

367B

-continued

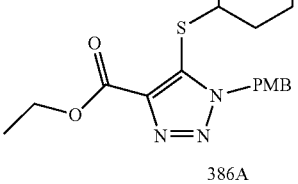

386A

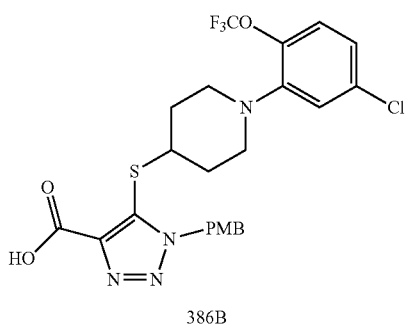

386B

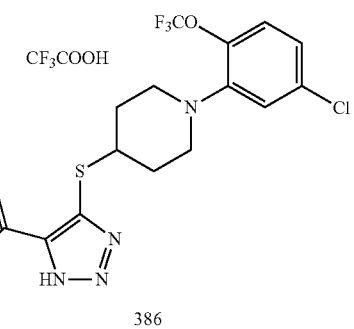

386

Compounds 386A, 386B, and 386 were synthesized by employing the procedures described for Compounds 90C, 8F, and 1 using Intermediate D, Compounds 367B, 386A, and 386B in lieu of Intermediate H, Compounds 90B, 8E, and 1E. Compound 386A: LC-MS (ESI) m/z: 571 [M+H]$^+$; $^1$H-NMR (CDCl$_3$, 400 MHz): δ (ppm) 1.44 (t, J=7.2 Hz, 3H), 1.62-1.71 (m, 2H), 1.80-1.84 (m, 2H), 2.61-2.67 (m, 2H), 3.26-3.30 (m, 2H), 3.46-3.51 (m, 1H), 3.77 (s, 3H), 4.45 (d, J=7.2 Hz, 2H), 5.63 (s, 2H), 6.84-6.96 (m, 4H), 7.08-7.10 (m, 1H), 7.27-7.30 (m, 2H). Compound 386B: LC-MS (ESI) m/z: 543 [M+H]$^+$. Compound 386: LC-MS (ESI) m/z: 423 [M+H]$^+$; $^1$H-NMR (CD$_3$OD, 400 MHz): δ (ppm) 1.79-1.89 (m, 2H), 2.22-2.25 (m, 2H), 2.87-2.93 (m, 2H), 3.38-3.42 (m, 2H), 3.75-3.80 (m, 1H), 7.04 (dd, J=8.8, 2.4 Hz, 1H), 7.12 (d, J=2.4 Hz, 1H), 7.19-7.22 (m, 1H).

Example 387

Synthesis of 4-((4'-chloro-2-(cyclopentylmethoxy)-[1,1'-biphenyl]-4-yl)oxy)-1H-1,2,3-triazole-5-carboxylic acid 2,2,2-trifluoroacetate (387)

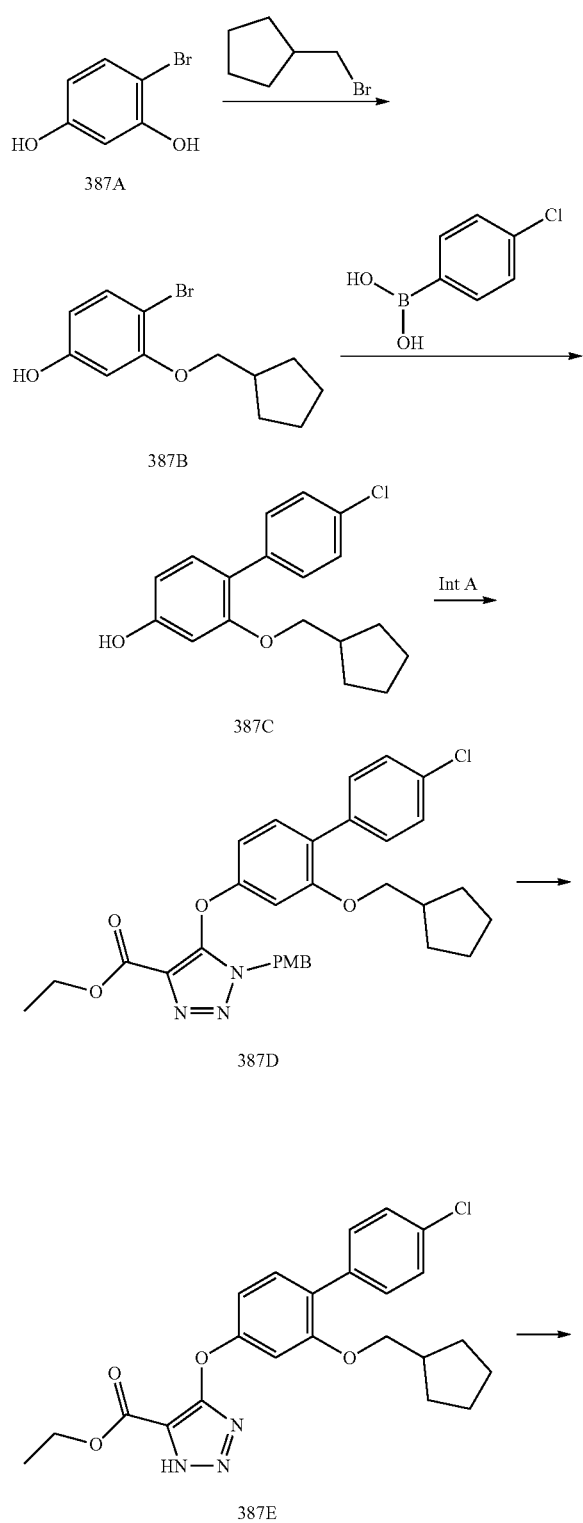
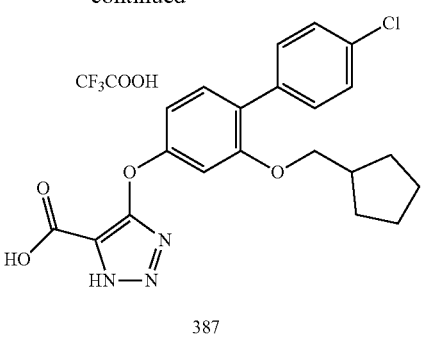

Compounds 387B, 387C, 387D, 387E, and 387 were synthesized by employing the procedures described for Compounds 27B, 4B, Intermediate I, 1, and 8F using (bromomethyl)cyclopentane, Compounds 387A with $K_2CO_3$ as base, (4-chlorophenyl)boronic acid, 387B with $K_2CO_3$ as base and 1,4-dioxane as solvent, 387C, 387D, and 387E in lieu of 2-bromopropane, Compounds 27A with $Cs_2CO_3$ as base, (4-bromophenyl)boronic acid, 4A with $Na_2CO_3$ as base and toluene/EtOH/$H_2O$ as solvent, 4-bromophenol, 1E, and 8E. Compound 387B: LC-MS (ESI) m/z: 254 [M−17+H]+; 1H-NMR (CDCl$_3$, 400 MHz): δ (ppm) 7.33 (d, J=8.4 Hz, 1H), 6.42 (d, J=2.8 Hz, 1H), 6.31-6.28 (m, 1H), 4.93 (s, 1H), 3.84 (d, J=6.8 Hz, 2H), 2.44-2.37 (m, 1H), 1.89-1.81 (m, 2H), 1.69-1.55 (m, 4H), 1.44-1.36 (m, 2H). Compound 387C: LC-MS (ESI) m/z: 286 [M−17+H]+. Compound 387D: LC-MS (ESI) m/z: 562 [M+H]+. Compound 387E: LC-MS (ESI) m/z: 442 [M+H]+. Compound 387: LC-MS (ESI) m/z: 414 [M+H]+; 1H-NMR (DMSO-d$_6$, 400 MHz): δ (ppm) 1.22-1.26 (m, 2H), 1.42-1.54 (m, 4H), 1.64-1.66 (m, 2H), 2.19-2.22 (m, 1H), 3.83 (d, J=6.8 Hz, 2H), 6.59-6.61 (m, 1H), 6.86 (s, 1H), 7.57 (d, J=8.4 Hz, 1H), 7.44-7.51 (m, 4H).

Example 388

Synthesis of 4-(4-(1-cyclohexylpiperidin-4-yl)phenoxy)-1H-1,2,3-triazole-5-carboxylic acid 2,2,2-trifluoroacetate (388)

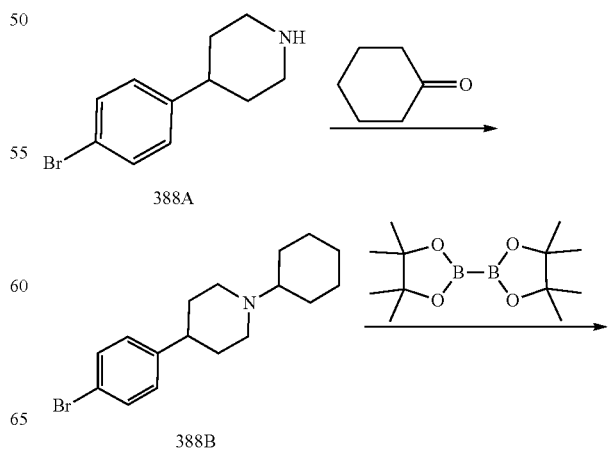

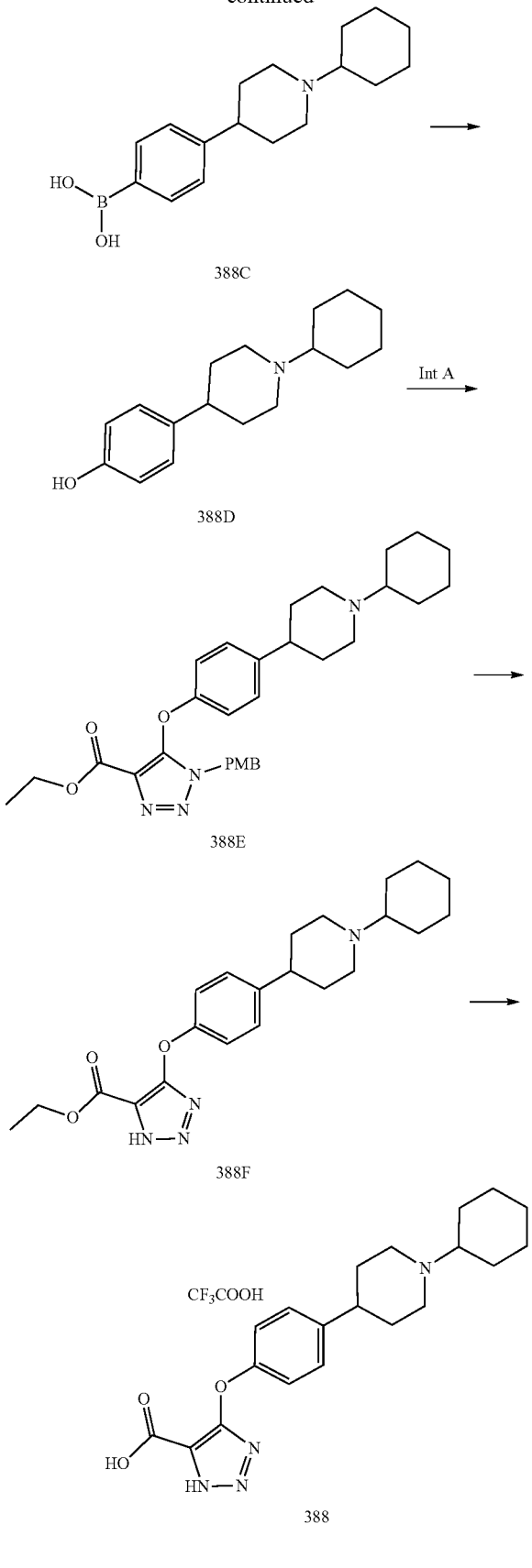

Compounds 388B, 388C, 388D, 388E, 388F, and 388 were synthesized by employing the procedures described for Compounds 160B, 27C, 236D, Intermediate I, 1, and 8F using cyclohexanone, Compounds 388A, 388B, 388C, 388D with $Cs_2CO_3$ as base in a microoven at 120° C., 388E, and 388F in lieu of Compounds 160A, piperidine, 27B, 236C, 4-bromophenol with $K_2CO_3$ as base at 90° C., 1E, and 8E. Compound 388B: LC-MS (ESI) m/z: 322 [M+H]$^+$; $^1$H-NMR (DMSO-$d_6$, 400 MHz): δ (ppm) 1.10-1.31 (m, 4H), 1.36-1.49 (m, 2H), 1.59-1.63 (m, 1H), 1.80-1.84 (m, 2H), 1.95-2.06 (m, 5H), 2.79-2.90 (m, 1H), 3.04-3.23 (m, 3H), 3.45-3.48 (m, 2H), 7.20 (d, J=8.1 Hz, 2H), 7.54 (d, J=8.0 Hz, 2H). Compound 388C: LC-MS (ESI) m/z: 288 [M+H]$^+$; $^1$H-NMR (DMSO-$d_6$, 400 MHz): δ (ppm) 1.05-1.12 (m, 1H), 1.23-1.32 (m, 2H), 1.38-1.47 (m, 2H), 1.60-1.63 (m, 1H), 1.81-2.06 (m, 8H), 2.80-2.86 (m, 1H), 3.07-3.21 (m, 3H), 3.46-3.50 (m, 2H), 7.19 (d, J=7.8 Hz, 2H), 7.74 (d, J=7.8 Hz, 2H), 8.03 (s, 2H). Compound 388D: LC-MS (ESI) m/z: 260 [M+H]$^+$. $^1$H-NMR (DMSO-$d_6$, 400 MHz): δ (ppm) 1.08-1.11 (m, 1H), 1.22-1.31 (m, 2H), 1.37-1.45 (m, 2H), 1.59-1.63 (m, 1H), 1.08-1.97 (m, 6H), 2.01-2.04 (m, 2H), 2.67-2.71 (m, 1H), 3.03-3.18 (m, 3H), 3.42-3.46 (m, 2H), 7.19 (d, J=7.8 Hz, 2H), 7.74 (d, J=7.8 Hz, 2H), 9.31 (d, J=6.3 Hz, 1H). Compound 388E: LC-MS (ESI) m/z: 519 [M+H]$^+$. Compound 388F: LC-MS (ESI) m/z: 399 [M+H]$^+$. Compound 388: LC-MS (ESI) m/z: 371 [M+H]$^+$; $^1$H-NMR (CD$_3$OD, 400 MHz): δ (ppm) 1.22-1.29 (m, 1H), 1.41-1.54 (m, 4H), 1.72-1.76 (m, 1H), 1.95-1.98 (m, 4H), 2.11-2.14 (m, 4H), 2.90 (s, 1H), 3.21 (s, 3H), 3.58-3.60 (m, 2H), 7.09 (d, J=7.8 Hz, 2H), 7.26 (d, J=7.8 Hz, 2H).

Example 389

Synthesis of 4-((4'-cyano-[1,1'-biphenyl]-4-yl)thio)-1H-1,2,3-triazole-5-carboxylic acid 2,2,2-trifluoroacetate (389)

677

-continued

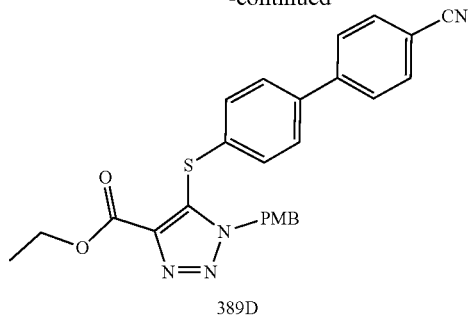

389D

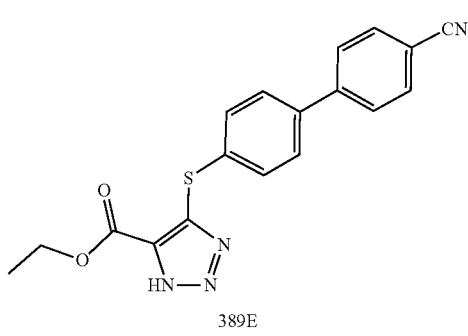

389E

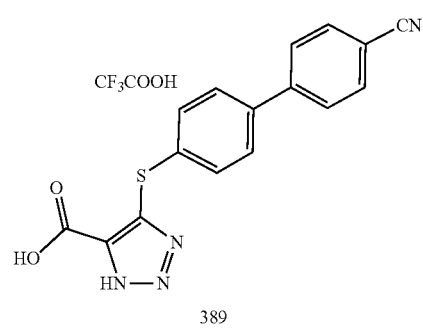

389

Compounds 389B, 389C, 389D, 389E, and 389 were synthesized by employing the procedures described for Compounds 4B, 30B, 35D, 8F, and 1 using 4-(4,4,5,5-tetramethyl-1,3,2-dioxaborolan-2-yl)benzenamine, Compounds 389A with $K_2CO_3$ as base and 1,4-dioxane as solvent, 389B with tert-butyl nitrite and CuBr and dichloromethane as solvent, 389C, 389D, and 389E in lieu of (4-bromophenyl)boronic acid, Compounds 4A with $Na_2CO_3$ as base and toluene/EtOH/$H_2O$ as solvent, 30A with isoamyl nitrite and $CuCl_2$ and MeCN as solvent, 35C, 8E, and 1E. Compound 389B: LC-MS (ESI) m/z: 195 [M+H]$^+$; $^1$H-NMR (CDCl$_3$, 400 MHz): δ (ppm) 3.86 (s, 2H), 6.77-6.79 (m, 2H), 7.43-7.45 (m, 2H), 7.61-7.69 (m, 4H). Compound 389C: LC-MS (ESI) m/z: non-ionizable compound under routine conditions used; $^1$H-NMR (CDCl$_3$, 400 MHz): δ (ppm) 7.44-7.52 (m, 2H), 7.59-7.62 (m, 2H), 7.63-7.76 (m, 4H). Compound 389D: LC-MS (ESI) m/z: 471 [M+H]$^+$. Compound 389E: LC-MS (ESI) m/z: 443 [M+H]$^+$. Compound 389: LC-MS (ESI) m/z: 323 [M+H]$^+$; $^1$H-NMR (CD$_3$OD, 400 MHz): δ (ppm) 7.59 (d, J=8.4 Hz, 2H), 7.71 (d, J=8.4 Hz, 2H), 7.80-7.86 (m, 4H).

678

Example 390

Synthesis of 4-(4-cyano-3-((4-fluorobenzyl)oxy)phenoxy)-1H-1,2,3-triazole-5-carboxylic acid (390)

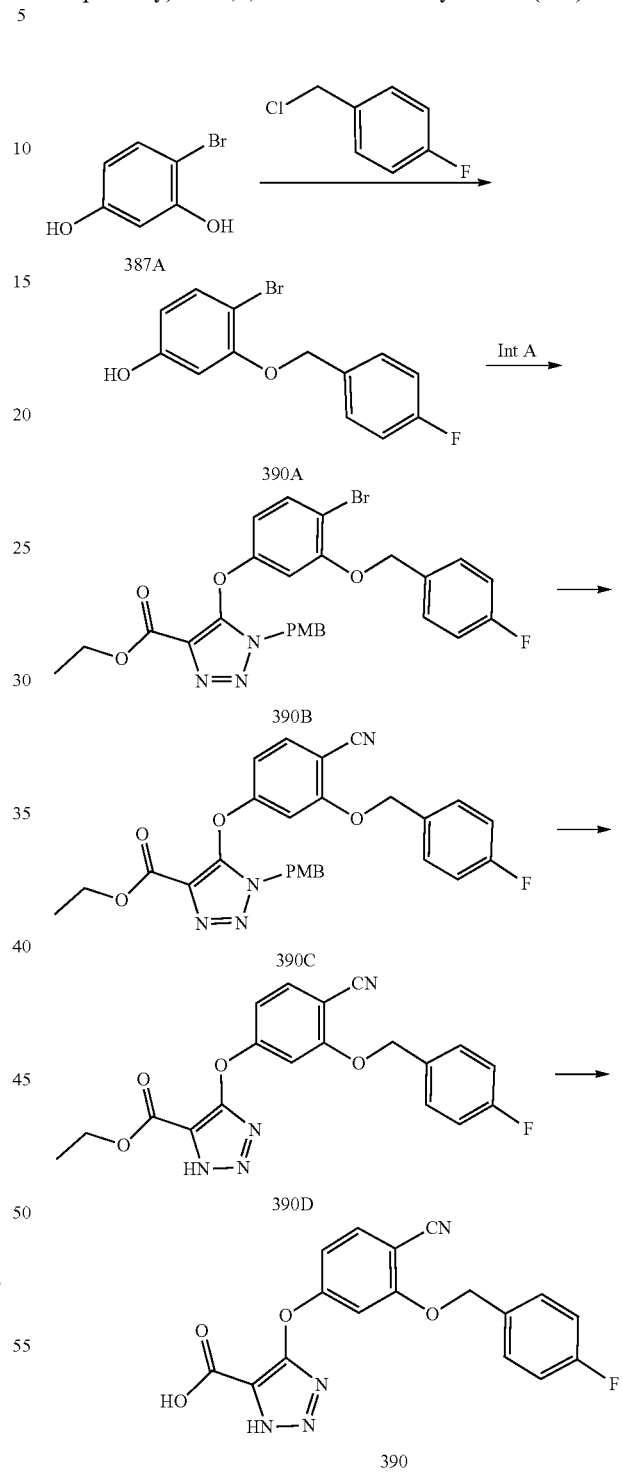

Compounds 390A and 390B were synthesized by employing the procedures described for Compounds 27B and Intermediate I using 1-(chloromethyl)-4-fluorobenzene, Compounds 387A with $K_2CO_3$ as base and acetone as solvent at reflux, and 390A in lieu of 2-bromopropane, Compounds 27A with $Na_2CO_3$ as base and DMF as solvent at 100° C., and 4-bromophenol. Compound 390A: LC-MS (ESI) m/z: non-ionizable compound under routine conditions used; $^1$H-NMR (CDCl$_3$, 400 MHz): δ (ppm) 5.03 (s, 1H), 5.07 (s, 2H), 6.34 (dd, J=2.8, 8.4 Hz, 1H), 6.48 (d, J=2.8 Hz, 1H), 7.08 (t, J=8.4 Hz, 2H), 7.36 (d, J=8.4 Hz, 1H), 7.44 (dd, J=5.2, 8.8 Hz, 2H). Compound 390B: LC-MS (ESI) m/z: 556 [M+H]$^+$.

A mixture of Compound 390B (130 mg, 0.23 mmol), Zn(CN)$_2$ (33 mg, 0.28 mmol), dppf (25 mg, 0.046 mmol), and Pd$_2$(dba)$_3$ (26 mg, 0.023 mmol) in DMF (3 mL) was heated in a microwave reactor at 140° C. under N$_2$ for 1.5 hours. The mixture was diluted with ethyl acetate (100 mL), washed with water (100 mL×3) and brine (50 mL), dried over anhydrous Na$_2$SO$_4$, filtered, and concentrated under reduced pressure. The residue was purified with flash column chromatography on silica gel (ethyl acetate in petroleum ether, from 30% v/v) to afford Compound 390C as a yellow film (59 mg, yield 51%). LC-MS (ESI) m/z: 503 [M+H]$^+$.

Compounds 390D and 390 were synthesized by employing the procedures described for Compounds 217E and 8F using Compounds 390C and 390D in lieu of Compounds 217D and 8E. Compound 390D: LC-MS (ESI) m/z: 383 [M+H]$^+$. Compound 390: LC-MS (ESI) m/z: 355 [M+H]$^+$. $^1$H-NMR (DMSO-d$_6$, 400 MHz): δ (ppm) 5.23 (s, 2H), 6.70 (dd, J=2.0, 8.4 Hz, 1H), 7.09 (d, J=2.0 Hz, 1H), 7.25 (dd, J=8.4, 11.2 Hz, 2H), 7.50 (dd, J=5.6, 8.4 Hz, 2H), 7.72 (d, J=8.4, 1H).

Example 391

Synthesis of 1-((cyclohexanecarbonyl)oxy)ethyl 4-(((trans)-4-(4-(trifluoromethoxy)phenyl)cyclohexyl)oxy)-1H-1,2,3-triazole-5-carboxylate (391)

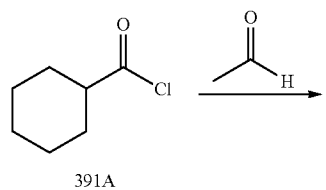

391A

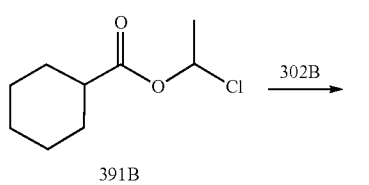

391B

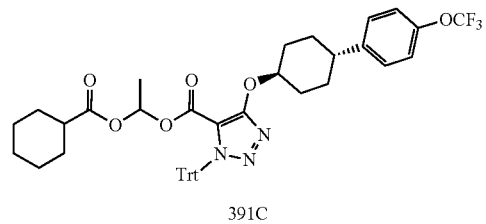

391C

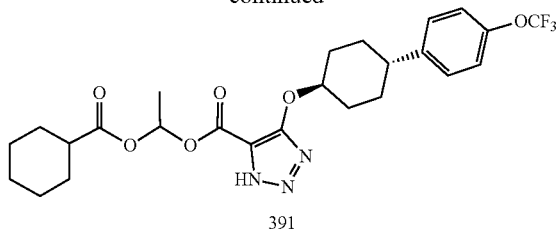

391

To a mixture of cyclohexanecarbonyl chloride (391A) (5.00 g, 34.25 mmol) and anhydrous ZnCl$_2$ (232 mg, 1.72 mmol) was dropped anhydrous acetaldehyde (1.66 g, 37.67 mmol) at −20° C. and stirred at −20° C. for 2 hours. It was warmed gradually to room temperature and stirred for 16 hours. The mixture was concentrated and purified with flash column chromatography on silica gel (ethyl acetate in petroleum ether, from 0% to 10% v/v) to give Compound 391B. $^1$H-NMR (CDCl$_3$, 400 MHz): δ (ppm) 1.23-1.30 (m, 3H), 1.31-1.48 (m, 2H), 1.60-1.65 (m, 1H), 1.74-1.79 (m, 5H), 1.87-1.96 (m, 2H), 2.30-2.37 (m, 1H), 6.54 (q, J=6.0 Hz, 1H).

Compound 391C was synthesized by employing the procedure described for Compound 51 using Compound 391B and Compound 302B with DMF as solvent in lieu of Compound 16 and chloromethyl pivalate with 1,4-dioxane as solvent, LC-MS (ESI) m/z: 790 [M+Na]$^+$.

A suspension of Compound 391C (160 mg, 0.21 mmol), triethylsilane (0.23 mL) and 10% Pd/C (100 mg) in MeOH (20 mL) was stirred at room temperature under H$_2$ (1 atm) for 16 hours. The mixture was filtered through Celite, concentrated, and purified with preparative HPLC to afford Compound 391. LC-MS (ESI) m/z: 1073 [2M+Na]$^+$; $^1$H-NMR (CD$_3$OD, 400 MHz): δ (ppm) 1.24-1.49 (m, 5H), 1.60 (d, J=8.0 Hz, 3H), 1.70-1.79 (m, 7H), 1.91-2.00 (m, 4H), 2.35-2.40 (m, 3H), 2.66-2.70 (m, 1H), 4.72-4.79 (m, 1H), 7.04-7.07 (m, 1H), 7.20 (d, J=6.4 Hz, 2H), 7.37 (d, J=6.4 Hz, 2H).

Example 392

Synthesis of 1-((cyclohexanecarbonyl)oxy)propyl 4-(((trans)-4-(4-(trifluoromethoxy)phenyl)cyclohexyl)oxy)-1H-1,2,3-triazole-5-carboxylate (392)

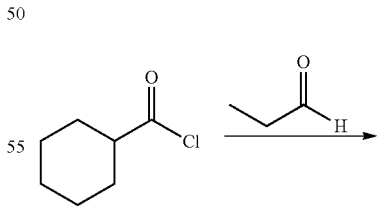

391A

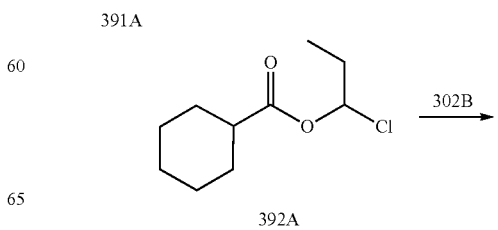

392A

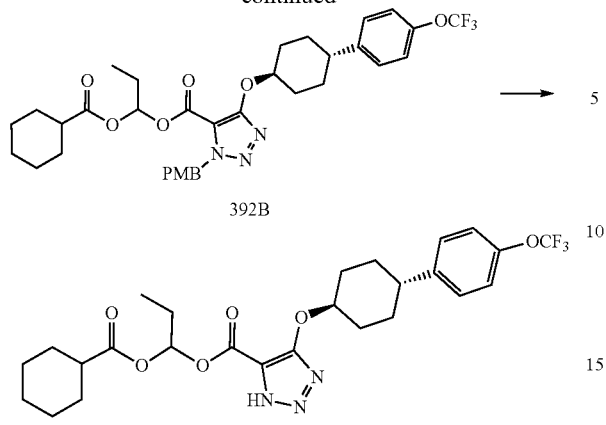

Compounds 392A, 392B, and 392 were synthesized by employing the procedures described for Compounds 391B, 51, and 391 using propionaldehyde, Compounds 392A and Compound 302B with DMF as solvent, and 392B in lieu of acetaldehyde, Compounds 16 and chloromethyl pivalate with 1,4-dioxane as solvent, and 391C. Compound 392A: $^1$H-NMR (CDCl$_3$, 400 MHz): δ (ppm) 1.04 (t, J=7.2 Hz, 3H), 1.23-1.31 (m, 4H), 1.45-1.51 (m, 2H), 1.74-1.77 (m, 2H), 1.89-1.99 (m, 2H), 2.01-2.07 (m, 2H), 2.32-2.38 (m, 1H), 8.38 (t, J=6.0 Hz, 1H). Compound 392B: LC-MS (ESI) m/z: 804 [M+Na]t Compound 392: LC-MS (ESI) m/z: 1101 [2M+Na]$^+$; $^1$H-NMR (CD$_3$OD, 400 MHz): δ (ppm) 1.06 (t, J=6.0 Hz, 3H), 1.26-1.52 (m, 5H), 1.67-1.79 (m, 7H), 1.92-2.01 (m, 6H), 2.37-2.41 (m, 3H), 2365-2.71 (m, 1H), 4.73-7.79 (m, 1H), 6.95 (t, J=6.0 Hz, 1H), 2.20 (d, J=6.4 Hz, 2H), 7.37 (d, J=6.8 Hz, 2H).

Example 393

Synthesis of 4-(((trans)-4-(5-chloro-2-(trifluoromethoxy)phenyl)cyclohexyl)oxy)-1H-1,2,3-triazole-5-carboxylic acid (393)

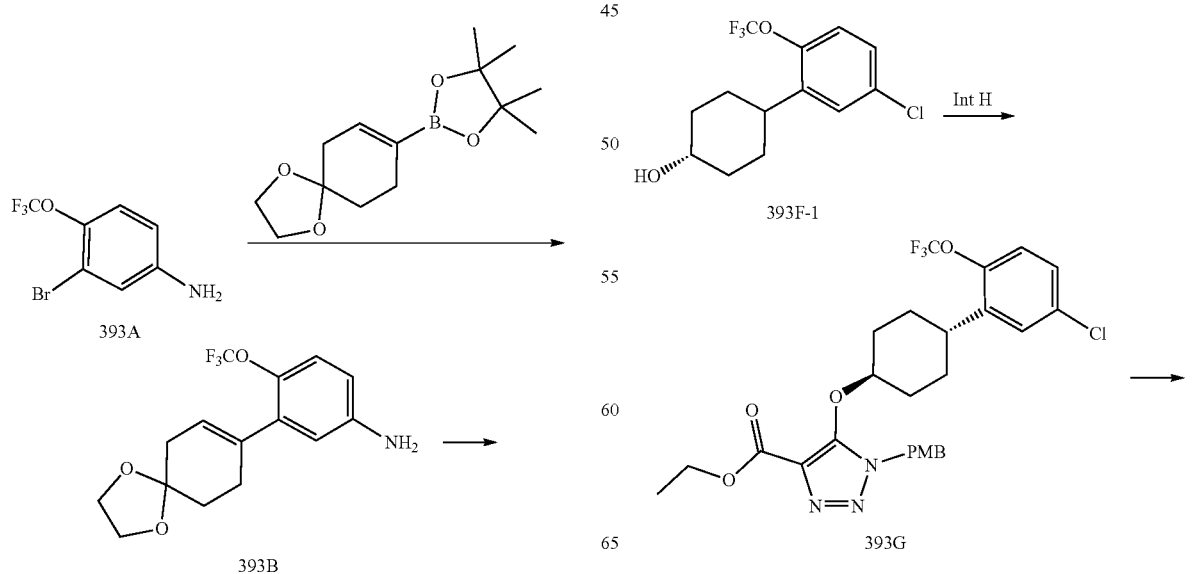

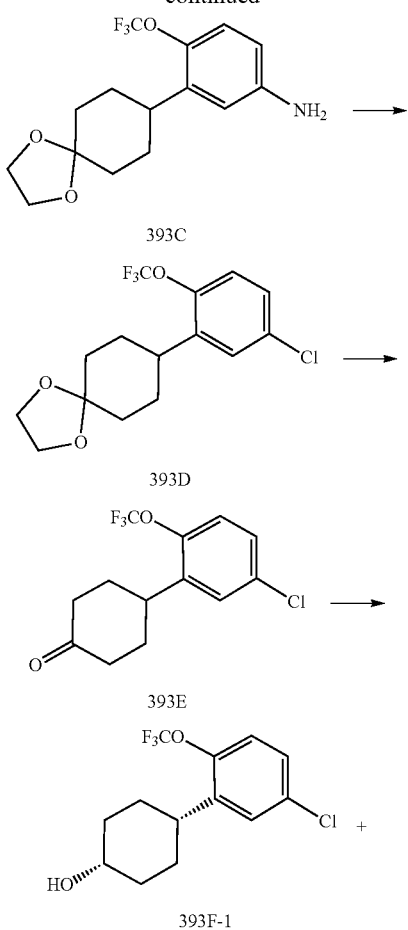

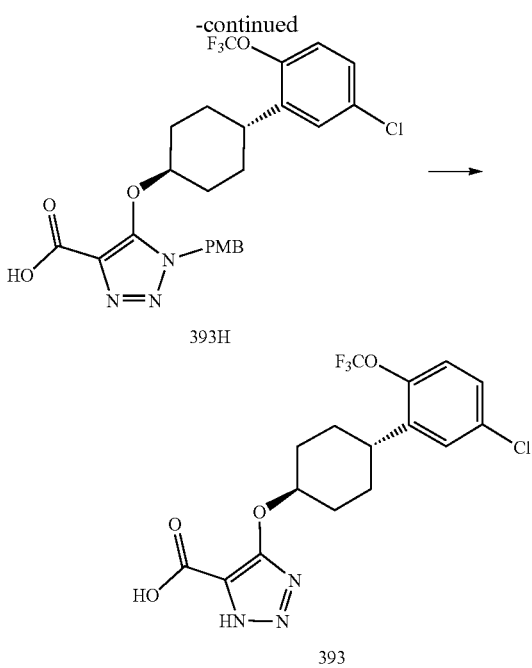

393H

393

Compounds 393B, 393C, 393D, and 393E were synthesized by employing the procedures described for Compounds 8B, 141, 30B, and 279D using 4,4,5,5-tetramethyl-2-(1,4-dioxaspiro[4.5]dec-7-en-8-yl)-1,3,2-dioxaborolane, Compounds 393A with $K_2CO_3$ as base and 1,4-dioxane/$H_2O$ as solvent, 393B, 393C with tert-butyl nitrite, and 393D with TFA as acid and dichloromethane as solvent in lieu of (3,4-dichlorophenyl)boronic acid, Compounds 8A with $Cs_2CO_3$ as base and DME/$H_2O$ as solvent, 140, 30A with isoamyl nitrite, and 279C with HCl as acid and 1,4-dioxane as solvent. Compound 393B: LC-MS (ESI) m/z: 316 [M+H]$^+$; $^1$H-NMR (CDCl$_3$, 400 MHz): δ (ppm) 1.77-1.81 (m, 2H), 2.34-2.36 (m, 2H), 2.43-2.47 (m, 2H), 3.54 (s, 2H), 3.94 (s, 4H), 5.57-5.59 (m, 1H), 6.43-6.49 (m, 2H), 6.90-6.93 (m, 1H). Compound 393C: LC-MS (ESI) m/z: 318 [M+H]$^+$; $^1$H-NMR (CDCl$_3$, 400 MHz): δ (ppm) 1.57-1.79 (m, 8H), 2.79-2.83 (m, 1H), 3.56 (brs, 2H), 3.92 (s, 4H), 6.39-6.42 (m, 1H), 6.55-6.56 (m, 1H), 6.89-6.93 (m, 1H). Compound 393D: LC-MS (ESI) m/z: 337 [M+H]$^+$; $^1$H-NMR (CDCl$_3$, 400 MHz): δ (ppm) 1.53-1.80 (m, 8H), 2.85-2.89 (m, 1H), 3.91 (s, 4H), 7.05-7.12 (m, 2H), 7.26-7.27 (m, 1H). Compound 393E: LC-MS (ESI) m/z: 293 [M+H]$^+$; $^1$H-NMR (CDCl$_3$, 400 MHz): δ (ppm) 1.78-1.83 (m, 2H), 2.06-2.11 (m, 2H), 2.43-2.47 (m, 4H), 3.28-3.34 (m, 1H), 7.13-7.20 (m, 3H).

To a solution of Compound 393E (820 mg, 2.8 mmol) in anhydrous THF (20 mL) was dropped L-Selectride solution of (1 M in THF, 4.2 mL, 4.2 mmol) at −78° C. under nitrogen and stirred at −78° C. for 2 hours. The reaction mixture was quenched with saturated aqueous NH$_4$Cl solution (30 mL), stirred at room temperature for 0.5 hour, and extracted with EtOAc (50 mL×3). The combined organic layer was dried over anhydrous sodium sulfate, concentrated, and purified with flash column chromatography on silica gel (ethyl acetate in petroleum ether, 10% v/v) to furnish Compounds 393F-1 and 393F-2. Compounds 393F-1: LC-MS (ESI) m/z: 277 [M−OH]$^+$; $^1$H-NMR (CDCl$_3$, 400 MHz): δ (ppm) 1.57-1.61 (m, 2H), 1.68-1.73 (m, 2H), 1.82-1.93 (m, 4H), 2.87-2.95 (m, 1H), 4.16-4.17 (m, 2H), 7.14-7.19 (m, 2H), 7.35-7.36 (m, 1H). Compounds 393F-2: LC-MS (ESI) m/z: 277 [M−OH]$^+$; $^1$H-NMR (CDCl$_3$, 400 MHz): δ (ppm) 1.34-1.42 (m, 4H), 1.78-1.82 (m, 2H), 2.03-2.05 (m, 2H), 2.78-2.81 (m, 1H), 3.59-3.63 (m, 1H), 7.08-7.17 (m, 2H), 7.18-7.19 (m, 1H).

Compounds 393G, 393H, and 393 were synthesized by employing the procedures described for Compounds 90C, 8F, and 1 using Compounds 393F-1, 393G, and 393H in lieu of Compounds 90B, 8E, and 1E. Compound 393G: LC-MS (ESI) m/z: 554 [M+H]$^+$; $^1$H-NMR (CDCl$_3$, 400 MHz): δ (ppm) 1.34-1.43 (m, 7H), 1.76-1.79 (m, 2H), 2.08-2.09 (m, 2H), 2.75-2.79 (m, 1H), 3.71 (s, 3H), 4.35 (q, J=7.2 Hz, 2H), 5.00-5.02 (m, 1H), 5.23 (s, 2H), 6.78-6.81 (m, 2H), 7.08-7.20 (m, 5H). Compound 393H: LC-MS (ESI) m/z: 526 [M+H]$^+$. Compound 393: LC-MS (ESI) m/z: 406 [M+H]$^+$; $^1$H-NMR (CD$_3$OD, 400 MHz): δ (ppm) 1.55-1.60 (m, 4H), 1.79 (m, 2H), 2.27-2.28 (m, 2H), 2.83-2.90 (m, 1H), 4.62-4.67 (m, 1H), 7.17-7.20 (m, 2H), 7.36-7.37 (m, 1H).

Example 394

Synthesis of 4-((2-chloro-4'-cyano-[1,1'-biphenyl]-4-yl)oxy)-1H-1,2,3-triazole-5-carboxylic acid (394)

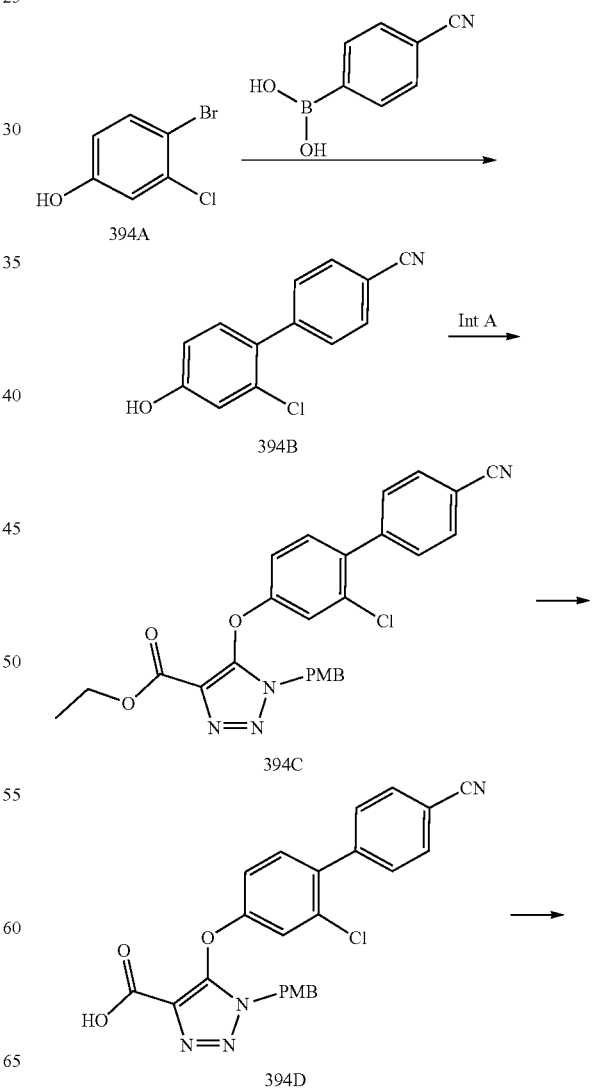

-continued

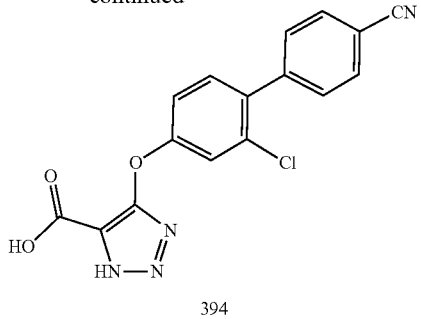

394

Compounds 394B, 394C, 394D, and 394 were synthesized by employing the procedures described for Compounds 4B, Intermediate I, 8F, and 1 using (4-cyanophenyl)boronic acid, Compounds 394A with K$_2$CO$_3$ as base and DME/H$_2$O as solvent, 394B, 394C, and 394D in lieu of (4-bromophenyl)boronic acid, Compounds 4A with Na$_2$CO$_3$ as base and toluene/EtOH/H$_2$O as solvent, 4-bromophenol, 8E, and 1E. Compound 394B: LC-MS (ESI) m/z: 228 [M−H]$^-$. Compound 394C: LC-MS (ESI) m/z: 489 [M+H]$^+$. Compound 394D: LC-MS (ESI) m/z: 459 [M−H]$^-$. Compound 394: LC-MS (ESI) m/z: 341 [M+H]$^+$; $^1$H-NMR (DMSO-d$_6$, 400 MHz): δ (ppm) 7.16 (dd, J=8.4, 2.8 Hz, 1H), 7.39 (d, J=2.8 Hz, 1H), 7.46 (d, J=8.4 Hz, 1H), 7.66 (d, J=8.8 Hz, 2H), 7.94 (d, J=8.8 Hz, 2H).

Example 395

Synthesis of 4-(((trans)-4-(2-chloro-5-(trifluoromethoxy)phenyl)cyclohexyl)oxy)-1H-1,2,3-triazole-5-carboxylic acid (395)

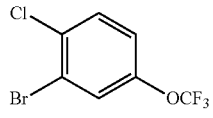

395A

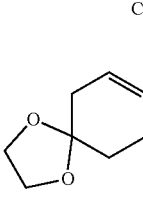

395B

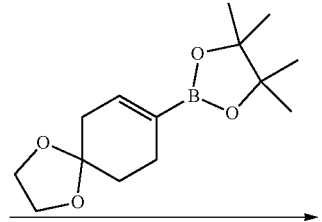

395C

-continued

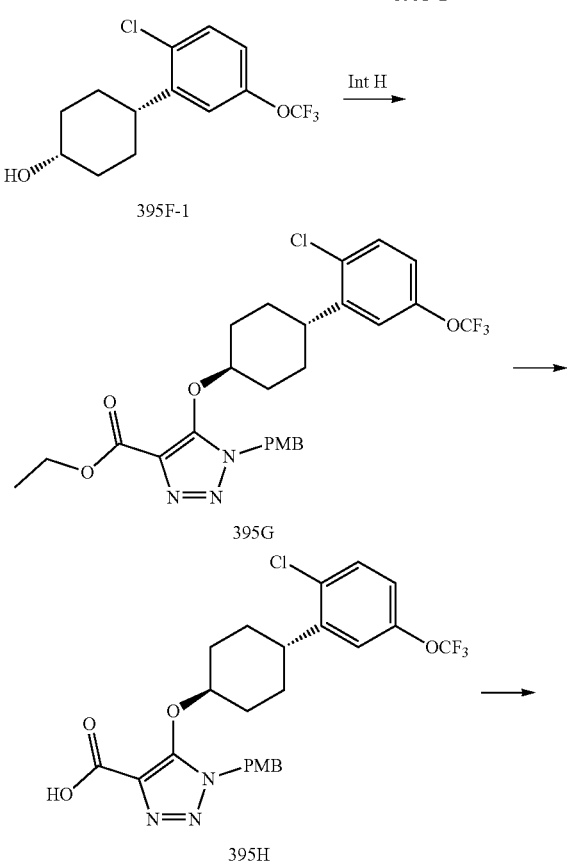

-continued

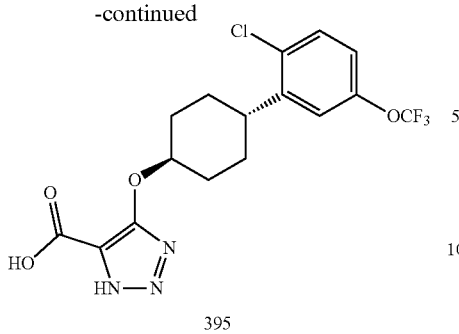

395

Compounds 395B, 395C, 395D, 395E, 395F-1 and 395F-2, 395G, 395H, and 395 were synthesized by employing the procedures described for Compounds 30B, 4B, 141, 279D, 393F-1 and 393F-2, 90C, 8F, and 1 using Compounds 395A with tert-butyl nitrite, 4,4,5,5-tetramethyl-2-(1,4-dioxaspiro[4.5]dec-7-en-8-yl)-1,3,2-dioxaborolane, 395B with $K_2CO_3$ as base and 1,4-dioxane/$H_2O$ as solvent, 395C with MeOH as solvent, 393D with THF/$H_2O$ as solvent, 395E, 395F-1, 395G, and 395H, in lieu of Compounds 30A with isoamyl nitrite, (4-bromophenyl)boronic acid, 4A with $Na_2CO_3$ as base and toluene/EtOH/$H_2O$ as solvent, 140 with EtOAc as solvent, 279C with 1,4-dioxane as a solvent, 393E, 90B, 8E, and 1E. Compound 395B: $^1$H-NMR (CDCl$_3$, 400 MHz): δ (ppm) 7.13-7.15 (m, 1H), 7.47-7.52 (m, 2H). Compound 395C: LC-MS (ESI) m/z: 335 [M+H]$^+$; $^1$H-NMR (CDCl$_3$, 400 MHz): δ (ppm) 1.90 (t, J=6 Hz, 2H), 2.45-2.46 (m, 2H), 2.52-2.56 (m, 2H), 4.00 (s, 4H), 5.62 (brs, 1H), 7.03-7.09 (m, 2H), 7.35 (d, J=8.4 Hz, 1H). Compound 395D: LC-MS (ESI) m/z: 337 [M+H]$^+$; $^1$H-NMR (CDCl$_3$, 400 MHz): δ (ppm) 1.64-1.76 (m, 4H), 1.83-1.90 (m, 4H), 3.01-3.07 (m, 1H), 3.99 (s, 4H), 6.98-7.01 (m, 1H), 7.14 (d, J=2.8 Hz, 1H), 7.36 (d, J=8.8 Hz, 1H). Compound 395E: LC-MS (ESI) m/z: 293 [M+H]$^+$; $^1$H-NMR (CDCl$_3$, 400 MHz): δ (ppm) 1.79-1.90 (m, 2H), 2.24-2.27 (m, 2H), 2.53-2.57 (m, 4H), 3.46-3.54 (m, 1H), 7.05-7.09 (m, 2H), 7.41 (d, J=8.4 Hz, 1H). Compound 395F-1: LC-MS (ESI) m/z: 277 [M–OH]$^+$; $^1$H-NMR (CDCl$_3$, 500 MHz): δ (ppm) 1.67-1.74 (m, 4H), 1.77-1.88 (m, 2H), 1.92-1.95 (m, 2H), 2.98-3.04 (m, 1H), 4.17-4.18 (m, 1H), 6.98-7.01 (m, 1H), 7.16-7.17 (m, 1H), 7.35 (d, J=8 Hz, 1H). Compound 395F-2: LC-MS (ESI) m/z: 277 [M–OH]$^+$; $^1$H-NMR (CDCl$_3$, 500 MHz): δ (ppm) 1.42-1.49 (m, 4H), 1.94-1.96 (m, 2H), 2.12-2.14 (m, 2H), 2.96-3.00 (m, 1H), 3.70 (brs, 1H), 6.99-7.01 (m, 1H), 7.072-7.078 (m, 1H), 7.36 (d, J=7.2 Hz, 1H). Compound 395G: LC-MS (ESI) m/z: 554 [M+H]$^+$. Compound 395H: LC-MS (ESI) m/z: 526 [M+H]$^+$. Compound 395: LC-MS (ESI) m/z: 406 [M+H]$^+$; $^1$H-NMR (CD$_3$OD, 400 MHz): δ (ppm) 1.58-1.78 (m, 4H), 1.98-2.01 (m, 2H), 2.38-2.41 (m, 2H), 3.11-3.17 (m, 1H), 4.74-4.79 (m, 1H), 7.12-7.15 (m, 1H), 7.27-7.28 (m, 1H), 7.49 (d, J=8.8 Hz, 1H).

Example 396

Synthesis of 4-(((cis)-4-(2-chloro-5-(trifluoromethoxy)phenyl)cyclohexyl)oxy)-1H-1,2,3-triazole-5-carboxylic acid (396)

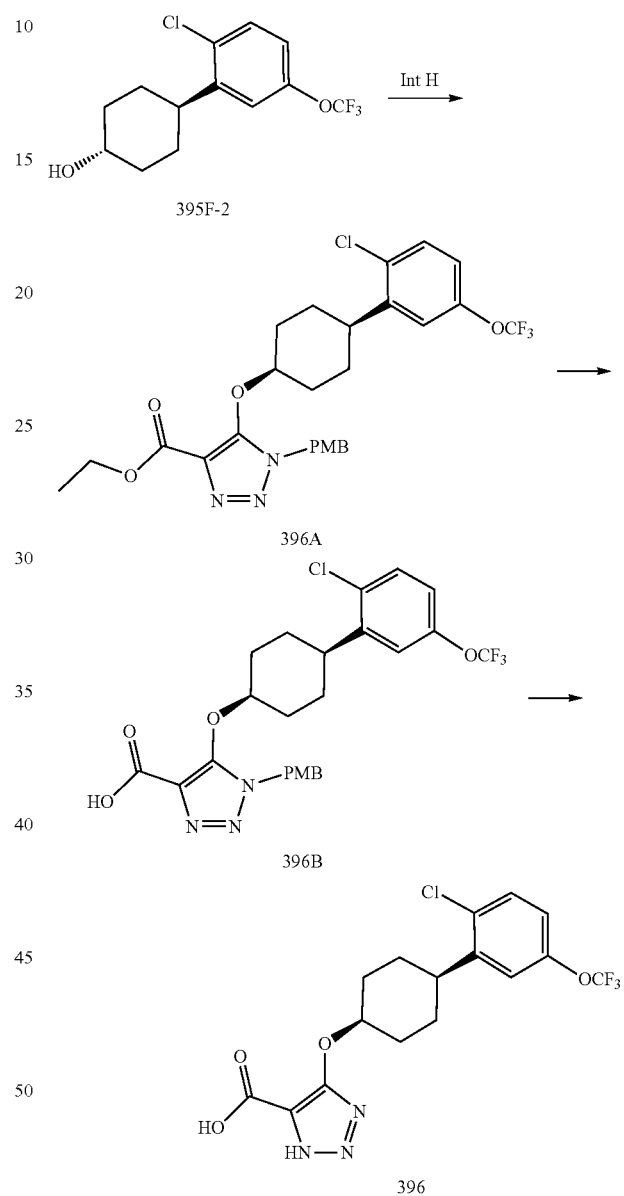

Compounds 396A, 396B, and 396 were synthesized by employing the procedures described for Compounds 90C, 8F, and 1 using Compounds 395F-2, 396A, and 396B in lieu of Compounds 90B, 8E, and 1E. Compound 396A: LC-MS (ESI) m/z: 554 [M+H]$^+$. Compound 396B: LC-MS (ESI) m/z: 526 [M+H]$^+$. Compound 396: LC-MS (ESI) m/z: 406 [M+H]$^+$; $^1$H-NMR (CD$_3$OD, 400 MHz): δ (ppm) 1.67-1.70 (m, 2H), 1.75-1.83 (m, 2H), 1.92-2.03 (m, 2H), 2.25-2.28 (m, 2H), 3.15-3.23 (m, 1H), 5.08 (brs, 1H), 7.10-7.13 (m, 1H), 7.31-7.32 (m, 1H), 7.47 (d, J=8.4 Hz, 1H).

Example 397

Synthesis of 4-((4'-carbamoyl-[1,1'-biphenyl]-4-yl)oxy)-1H-1,2,3-triazole-5-carboxylic acid (397)

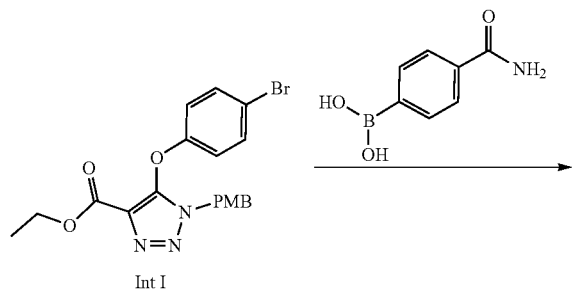

Int I

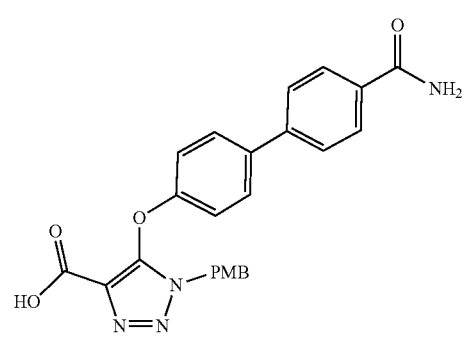

397A

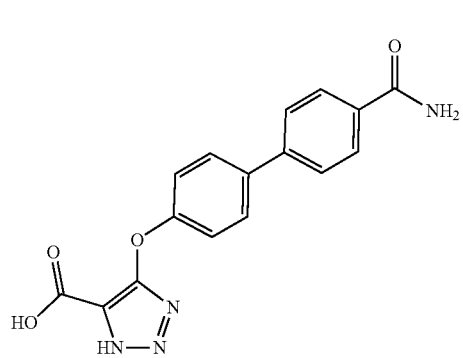

397

Compounds 397A and 397 were synthesized by employing the procedures described for Compounds 4B and 1 using 4-carbamoylphenylboronic acid, Intermediate I, and 397A in lieu of (4-bromophenyl)boronic acid, Compounds 4A, and 1E. Compound 397A: LC-MS (ESI) m/z: 445 [M+H]+; $^1$H-NMR (DMSO-d$_6$, 400 MHz): δ (ppm) 3.68 (s, 3H), 5.43 (s, 2H), 6.85 (d, J=8.7 Hz, 2H), 6.97 (d, J=8.9 Hz, 2H), 7.19 (d, J=8.7 Hz, 2H), 7.39 (s, 1H), 7.60-7.73 (m, 4H), 7.95 (d, J=8.5 Hz, 2H), 8.02 (s, 1H), 13.06 (s, 1H). Compound 397: LC-MS (ESI) m/z: 325 [M+H]+; $^1$H-NMR (DMSO-d$_6$, 400 MHz): δ (ppm) 7.17 (d, J=8.8 Hz, 2H), 7.39 (s, 1H), 7.74 (d, J=8.4 Hz, 4H), 7.95 (d, J=8.8 Hz, 2H), 8.02 (s, 1H).

Example 398

Synthesis of 4-((4'-chloro-2-(cyclopentylmethoxy)-[1,1'-biphenyl]-4-yl)thio)-1H-1,2,3-triazole-5-carboxylic acid 2,2,2-trifluoroacetate (398)

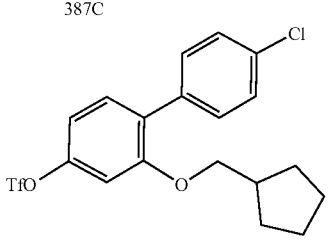

387C

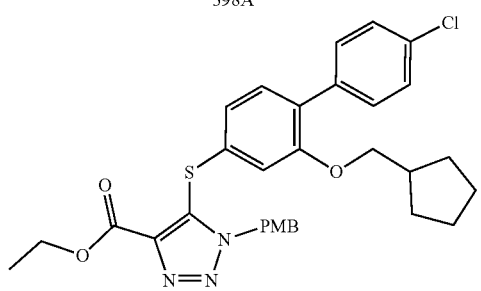

398A

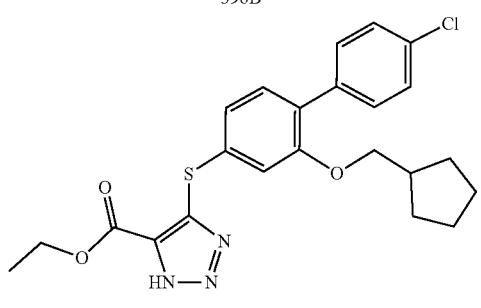

398B

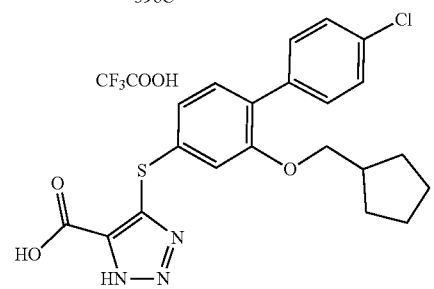

398C

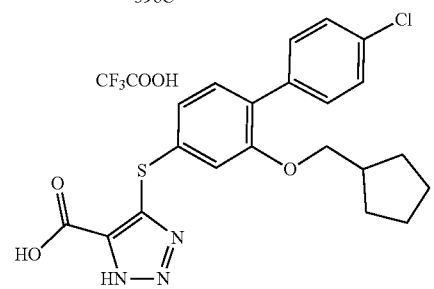

398

To a mixture of Compound 387C (500 mg, 1.66 mmol) and Et$_3$N (251 mg, 2.48 mmol) in CH$_2$Cl$_2$ (20 ml) was added Tf₂O (560 mg, 1.99 mmol) at 0° C. The mixture was stirred at room temperature for 2 hours and concentrated under reduced pressure. The residue was purified with flash column chromatography (ethyl acetate in petroleum ether, from 0% to 3% v/v) to yield Compound 398A. LC-MS (ESI) m/z: non-ionizable compound under routine conditions used.

Compounds 398B, 398C, and 398 were synthesized by employing the procedures described for Compounds 35D, 1, and 8F using Compounds 398A, 398B, and 398C in lieu of Compounds 35C, 1E, and 8E. Compound 398B: LC-MS (ESI) m/z: 578 [M+H]⁺. Compound 398C: LC-MS (ESI) m/z: 458 [M+H]⁺. Compound 398: LC-MS (ESI) m/z: 430 [M+H]⁺; ¹H-NMR (DMSO-d₆, 400 MHz): δ (ppm) 1.23-1.27 (m, 2H), 1.46-1.56 (m, 4H), 1.65-1.69 (m, 2H), 2.18-2.22 (m, 1H), 3.85 (d, J=6.8 Hz, 2H), 7.05-7.07 (m, 1H), 7.21 (s, 1H), 7.31 (d, J=8.0 Hz, 1H), 7.46-7.48 (m, 2H), 7.52-7.55 (m, 2H).

Example 399

Synthesis of 4-(4-chloro-3-(cyclohexyloxy)phenoxy)-1H-1,2,3-triazole-5-carboxylic acid 2,2,2-trifluoroacetate (399)

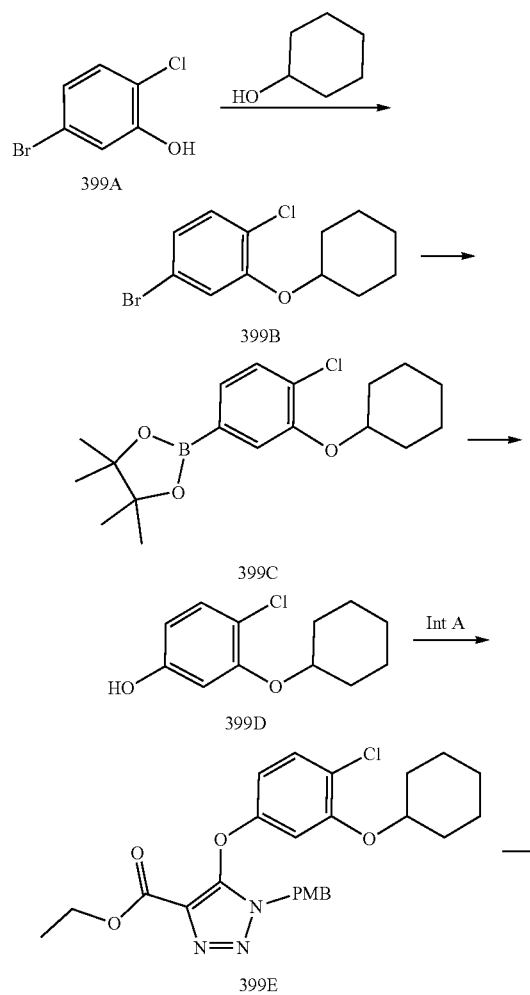

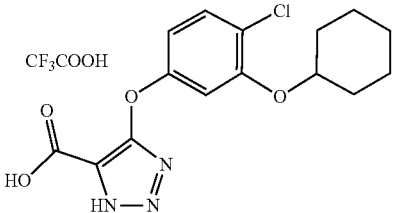

Compounds 399B, 399C, 399D, 399E, 399F, and 399 were synthesized by employing the procedures described for Compounds 90C, 27C, 236D, Intermediate I, 217E, and 8F using cyclohexanol, Compounds 399A, 399B, 399C, 399D, 399E, and 399F in lieu of Compounds 90B, Intermediate H, 27B, 236C, 4-bromophenol, 217D, and 8E. Compound 399B: ¹H-NMR (CDCl₃, 400 MHz): δ (ppm) 1.35-1.55 (m, 3H), 1.64-1.67 (m, 3H), 1.81-1.84 (m, 2H), 1.92-1.95 (m, 2H), 4.26-4.31 (m, 1H), 7.00 (dd, J=8.8, 2.0 Hz, 1H), 7.05 (d, J=2.0 Hz, 1H), 7.21 (d, J=8.8 Hz, 1H). Compound 399C: ¹H-NMR (CDCl₃, 400 MHz): δ (ppm) 1.26-1.41 (m, 16H), 1.62-1.66 (m, 2H), 1.81-1.84 (m, 2H), 1.92-1.95 (m, 2H), 4.38-4.39 (m, 1H), 7.30-7.36 (m, 3H). Compound 399D: LC-MS (ESI) m/z: 227 [M+H]⁺. Compound 399E: LC-MS (ESI) m/z: 486 [M+H]⁺. Compound 399F: LC-MS (ESI) m/z: 366 [M+H]⁺. Compound 399: LC-MS (ESI) m/z: 338 [M+H]⁺; ¹H-NMR (CD₃OD, 400 MHz): δ (ppm) 1.40-1.44 (m, 3H), 1.55-1.65 (m, 3H), 1.78-1.82 (m, 2H), 1.91-1.93 (m, 2H), 4.34-4.38 (m, 1H), 6.64 (dd, J=8.8, 2.4 Hz, 1H), 6.90 (d, J=2.4 Hz, 1H), 7.31 (d, J=8.8 Hz, 1H).

Example 400

Synthesis of 4-(4-fluoro-3-((4-(trifluoromethoxy)benzyl)oxy)phenoxy)-1H-1,2,3-triazole-5-carboxylic acid 2,2,2-trifluoroacetate (400)

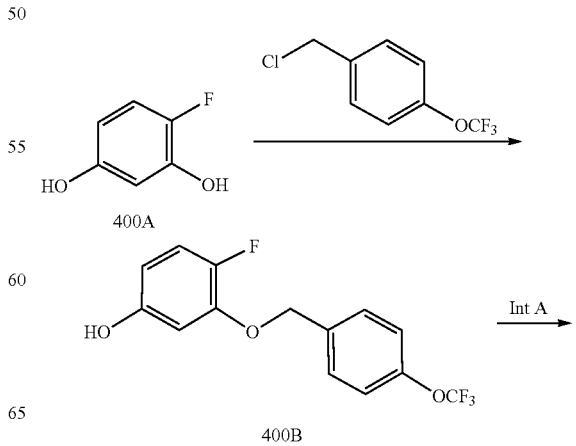

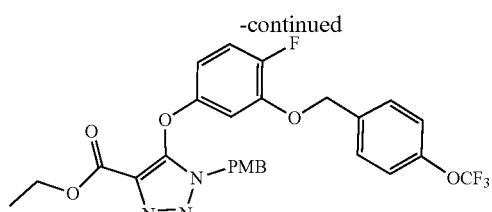

Example 401

Synthesis of 4-((4'-(methylsulfonyl)-[1,1'-biphenyl]-4-yl)oxy)-1H-1,2,3-triazole-5-carboxylic acid 2,2,2-trifluoroacetate (401)

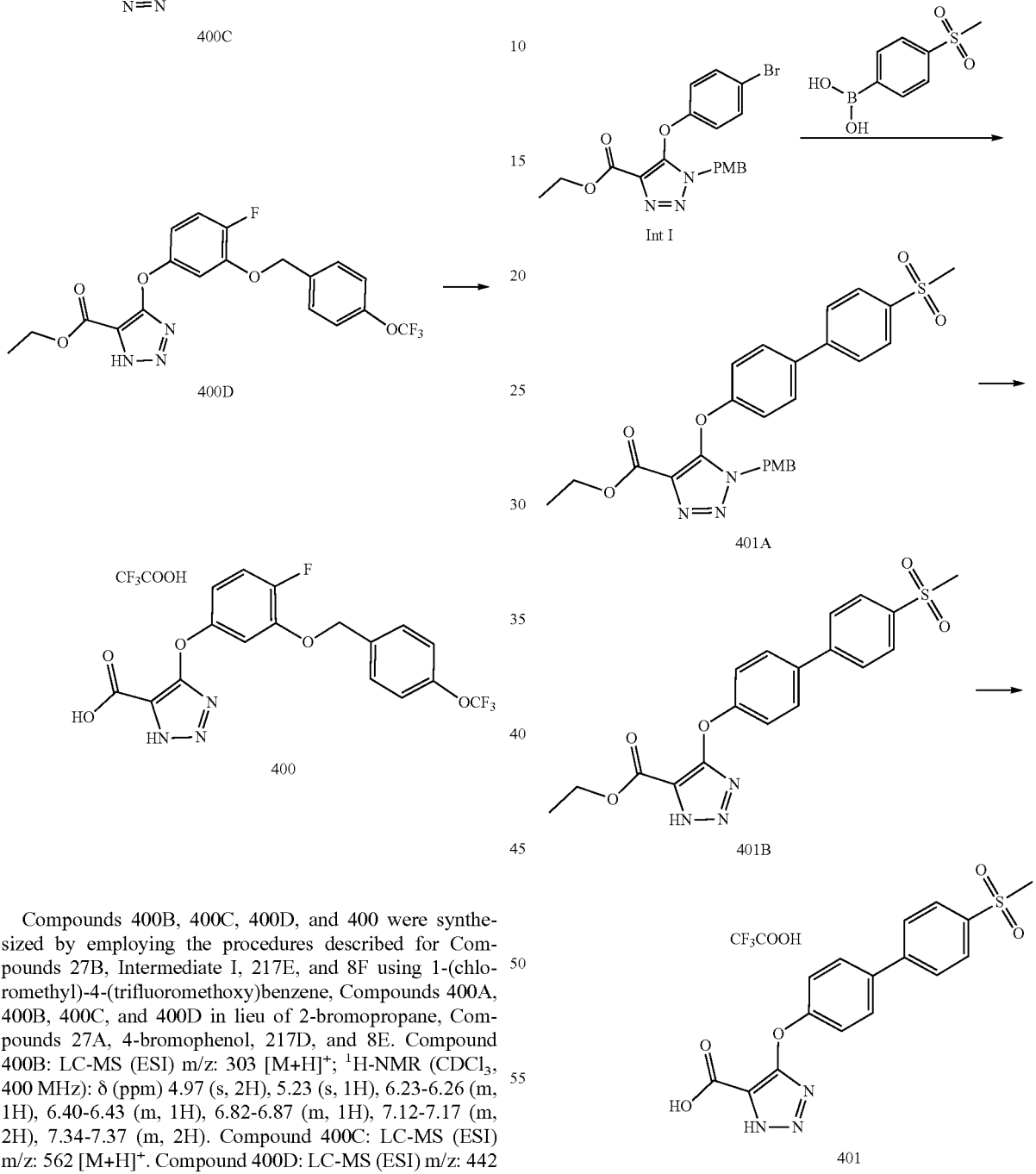

Compounds 400B, 400C, 400D, and 400 were synthesized by employing the procedures described for Compounds 27B, Intermediate I, 217E, and 8F using 1-(chloromethyl)-4-(trifluoromethoxy)benzene, Compounds 400A, 400B, 400C, and 400D in lieu of 2-bromopropane, Compounds 27A, 4-bromophenol, 217D, and 8E. Compound 400B: LC-MS (ESI) m/z: 303 [M+H]$^+$; $^1$H-NMR (CDCl$_3$, 400 MHz): δ (ppm) 4.97 (s, 2H), 5.23 (s, 1H), 6.23-6.26 (m, 1H), 6.40-6.43 (m, 1H), 6.82-6.87 (m, 1H), 7.12-7.17 (m, 2H), 7.34-7.37 (m, 2H). Compound 400C: LC-MS (ESI) m/z: 562 [M+H]$^+$. Compound 400D: LC-MS (ESI) m/z: 442 [M+H]$^+$; $^1$H-NMR (CDCl$_3$, 400 MHz): δ (ppm) 1.21 (t, J=6.8 Hz, 3H), 4.30 (q, J=6.8 Hz, 2H), 4.99 (s, 2H), 6.61-6.63 (m, 1H), 6.79-6.81 (m, 1H), 6.95-7.02 (m, 1H), 7.14-7.16 (m, 2H), 7.36-7.38 (m, 2H). Compound 400: LC-MS (ESI) m/z: 414 [M+H]$^+$; $^1$H-NMR (DMSO-d$_6$, 400 MHz): δ (ppm) 5.18 (s, 2H), 6.61-6.63 (m, 1H), 7.10-7.13 (m, 1H), 7.19-7.24 (m, 1H), 7.39-7.41 (m, 2H), 7.57-7.59 (m, 2H).

Compounds 401A, 401B, and 401 were synthesized by employing the procedures described for Compounds 4B, 1, and 8F using 4-(methylsulfonyl)phenylboronic acid, Intermediate I with K$_2$CO$_3$ as base and 1,4-dioxane/H$_2$O as solvent, Compounds 401A, and 401B in lieu of (4-bromophenyl)boronic acid, Compounds 4A with Na$_2$CO$_3$ as base and toluene/EtOH/H$_2$O as solvent, 1E, and 8E. Compound 401A: LC-MS (ESI) m/z: 508 [M+H]⁺. Compound 401B: LC-MS (ESI) m/z: 388 [M+H]⁺. Compound 401: LC-MS (ESI) m/z: 360 [M+H]⁺; ¹H-NMR (DMSO-d₆, 400 MHz): δ (ppm) 3.26 (s, 3H), 7.20 (d, J=8.8 Hz, 2H), 7.77 (d, J=8.8 Hz, 2H), 7.93 (d, J=8.4 Hz, 2H), 7.99 (d, J=8.4 Hz, 2H).

Example 402

Synthesis of 4-((1-(2-chloro-5-(trifluoromethoxy)phenyl)piperidin-4-yl)thio)-1H-1,2,3-triazole-5-carboxylic acid (402)

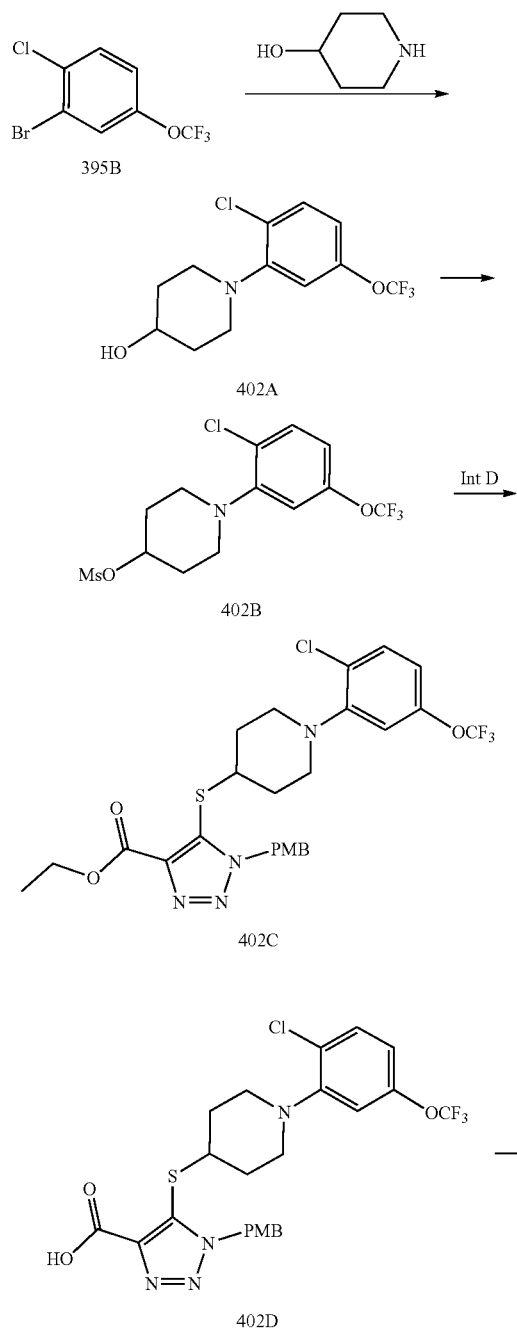

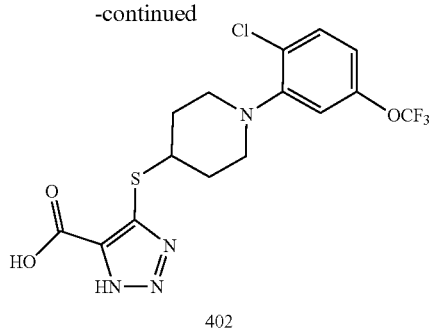

Compounds 402A, 402B, 402C, 402D, and 402 were synthesized by employing the procedures described for Compounds 6B, 340F, 340G, 8F, and 1 using 4-hydroxypiperidine, Compounds 395B with Ruphos as ligand and THF as solvent, 402A, 402B, 402C, and 402D in lieu of 1-methylpiperazine, Compounds 6A with Xantophos as ligand and toluene as solvent, 340E, 340F, 8E, and 1E. Compound 402A: LC-MS (ESI) m/z: 296 [M+H]⁺. Compound 402B: LC-MS (ESI) m/z: 374 [M+H]⁺. Compound 402C: LC-MS (ESI) m/z: 571 [M+H]⁺. Compound 402D: LC-MS (ESI) m/z: 543 [M+H]⁺. Compound 402: LC-MS (ESI) m/z: 423 [M+H]⁺; NMR (DMSO-d₆, 400 MHz): δ (ppm) 1.69-1.72 (m, 2H), 2.11-2.14 (m, 2H), 2.79-2.84 (m, 2H), 3.27 (s, 1H), 3.58-3.71 (m, 2H), 7.02 (d, J=8.8 Hz, 1H), 7.08 (s, 1H), 7.52 (d, J=8.8 Hz, 1H).

Example 403

Synthesis of 4-(((trans)-4-(4-(4H-1,2,4-triazol-4-yl)phenyl)cyclohexyl)oxy)-1H-1,2,3-triazole-5-carboxylic acid (403)

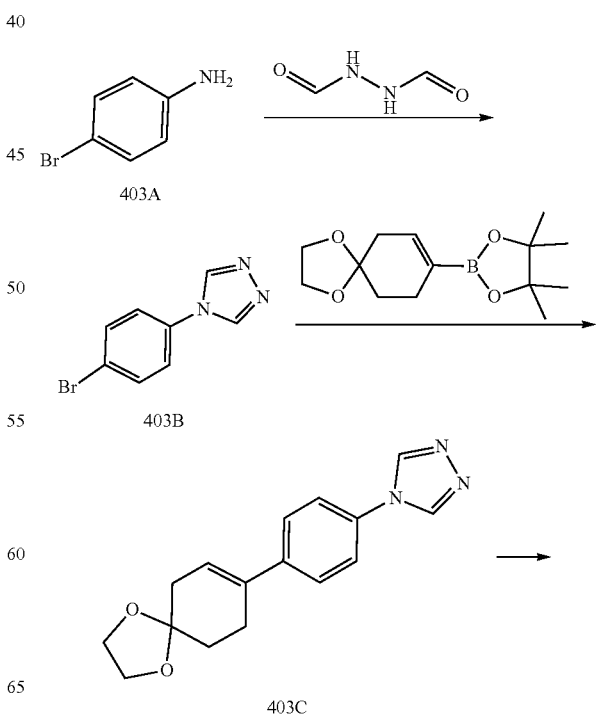

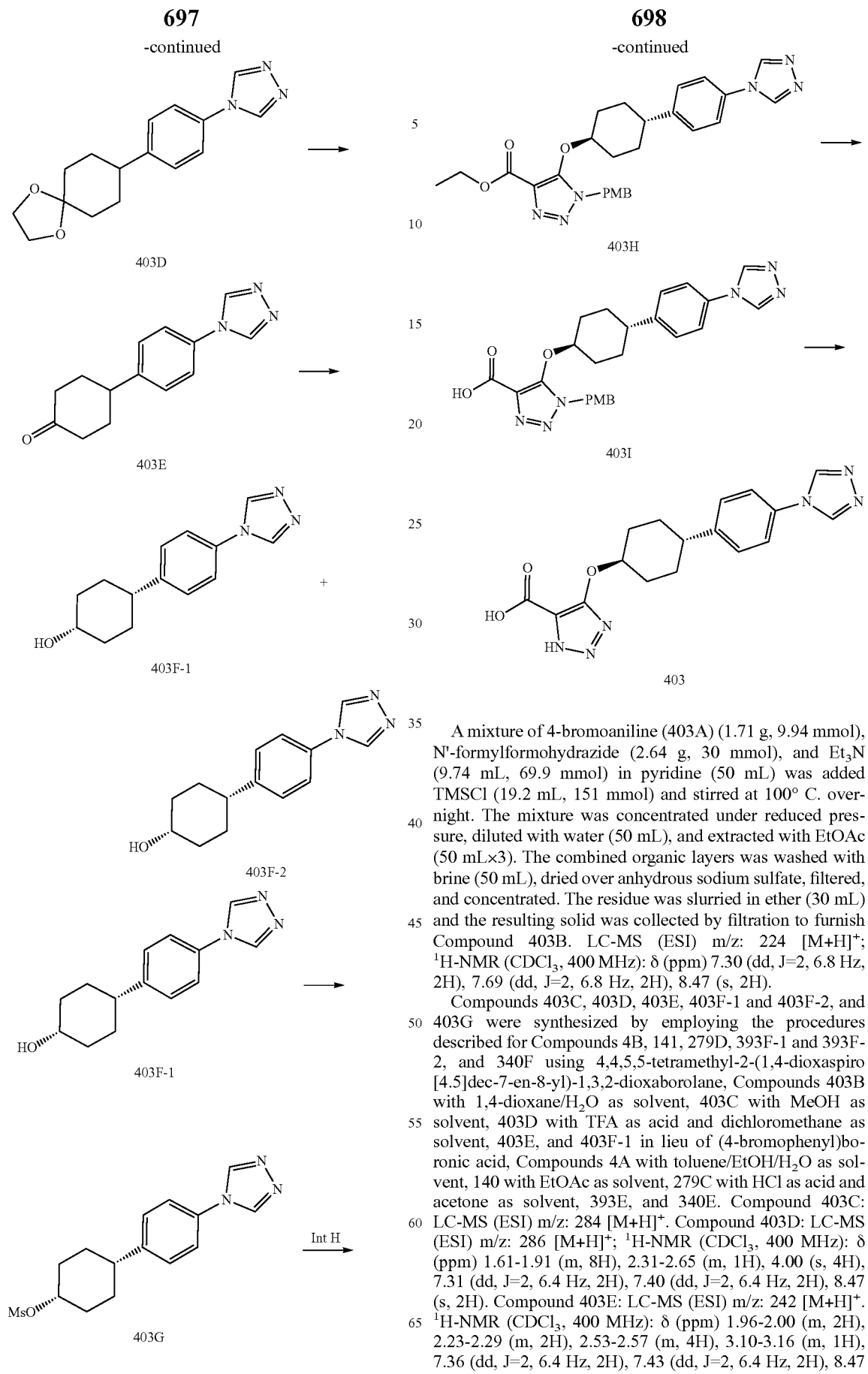

A mixture of 4-bromoaniline (403A) (1.71 g, 9.94 mmol), N'-formylformohydrazide (2.64 g, 30 mmol), and Et₃N (9.74 mL, 69.9 mmol) in pyridine (50 mL) was added TMSCl (19.2 mL, 151 mmol) and stirred at 100° C. overnight. The mixture was concentrated under reduced pressure, diluted with water (50 mL), and extracted with EtOAc (50 mL×3). The combined organic layers was washed with brine (50 mL), dried over anhydrous sodium sulfate, filtered, and concentrated. The residue was slurried in ether (30 mL) and the resulting solid was collected by filtration to furnish Compound 403B. LC-MS (ESI) m/z: 224 [M+H]⁺; ¹H-NMR (CDCl₃, 400 MHz): δ (ppm) 7.30 (dd, J=2, 6.8 Hz, 2H), 7.69 (dd, J=2, 6.8 Hz, 2H), 8.47 (s, 2H).

Compounds 403C, 403D, 403E, 403F-1 and 403F-2, and 403G were synthesized by employing the procedures described for Compounds 4B, 141, 279D, 393F-1 and 393F-2, and 340F using 4,4,5,5-tetramethyl-2-(1,4-dioxaspiro[4.5]dec-7-en-8-yl)-1,3,2-dioxaborolane, Compounds 403B with 1,4-dioxane/H₂O as solvent, 403C with MeOH as solvent, 403D with TFA as acid and dichloromethane as solvent, 403E, and 403F-1 in lieu of (4-bromophenyl)boronic acid, Compounds 4A with toluene/EtOH/H₂O as solvent, 140 with EtOAc as solvent, 279C with HCl as acid and acetone as solvent, 393E, and 340E. Compound 403C: LC-MS (ESI) m/z: 284 [M+H]⁺. Compound 403D: LC-MS (ESI) m/z: 286 [M+H]⁺; ¹H-NMR (CDCl₃, 400 MHz): δ (ppm) 1.61-1.91 (m, 8H), 2.31-2.65 (m, 1H), 4.00 (s, 4H), 7.31 (dd, J=2, 6.4 Hz, 2H), 7.40 (dd, J=2, 6.4 Hz, 2H), 8.47 (s, 2H). Compound 403E: LC-MS (ESI) m/z: 242 [M+H]⁺. ¹H-NMR (CDCl₃, 400 MHz): δ (ppm) 1.96-2.00 (m, 2H), 2.23-2.29 (m, 2H), 2.53-2.57 (m, 4H), 3.10-3.16 (m, 1H), 7.36 (dd, J=2, 6.4 Hz, 2H), 7.43 (dd, J=2, 6.4 Hz, 2H), 8.47

(s, 2H). Compound 403F-1: LC-MS (ESI) m/z: 244 [M+H]⁺; ¹H-NMR: (DMSO-$d_6$, 400 MHz): δ (ppm) 1.49-1.58 (m, 4H), 1.74-1.87 (m, 4H), 2.51-2.59 (m, 1H), 3.89-3.91 (m, 1H), 7.41 (dd, J=1.6, 6.4 Hz, 2H), 7.61 (dd, J=2, 6.8 Hz, 2H), 9.15 (s, 2H). Compound 403F-2: LC-MS (ESI) m/z: 244 [M+H]⁺; ¹H-NMR: (DMSO-$d_6$, 400 MHz): δ (ppm) 1.28-1.31 (m, 2H), 1.49-1.53 (m, 2H), 1.76-1.79 (m, 2H), 1.90-1.95 (m, 2H), 2.50-2.53 (m, 1H), 3.46-3.47 (m, 1H), 5.08 (s, 1H), 7.42 (dd, J=1.6, 6.4 Hz, 2H), 7.59 (dd, J=2, 6.4 Hz, 2H), 9.16 (s, 2H). Compound 403G: LC-MS (ESI) m/z: 322 [M+H]⁺.

To a solution of Compound 403G (290 mg, crude, 0.82 mmol) in DMF (10 ml) was added Intermediate H (263 mg g, 0.82 mmol) and $Cs_2CO_3$ (401 mg, 1.23 mmol). The mixture was stirred at 90° C. overnight. After cooled down to room temperature, the mixture was diluted with $H_2O$ (50 mL) and extracted with ethyl acetate (200 mL). The organic layer was washed with water (200 mL×2) and brine (50 mL), dried over anhydrous sodium sulfate, concentrated, and purified with flash column chromatography on silica gel (methanol in DCM, 10% v/v) to give Compound 403H as a yellow film (190 mg, yield 46%). LC-MS (ESI) m/z: 503 [M+H]⁺.

Compounds 403I and 403 were synthesized by employing the procedures described for Compounds 8F and 1 using Compounds 40311 and 403I in lieu of Compounds 8E and 1E. Compound 403I: LC-MS (ESI) m/z: 475 [M+H]⁺. Compound 403: LC-MS (ESI) m/z: 355 [M+H]⁺; ¹H-NMR (DMSO-$d_6$, 400 MHz): δ (ppm) 1.51-1.59 (m, 4H), 1.85-1.88 (m, 2H), 2.20-2.49 (m, 2H), 2.65-2.67 (m, 1H), 4.70-4.72 (m, 1H), 7.45 (d, J=8.8 Hz, 2H), 7.60 (d, J=8.8 Hz, 2H), 9.07 (s, 2H).

Example 404

Synthesis of 4-((trans)-3-(4-cyanophenyl)cyclobutoxy)-1H-1,2,3-triazole-5-carboxylic acid 2,2,2-trifluoroacetate (404)

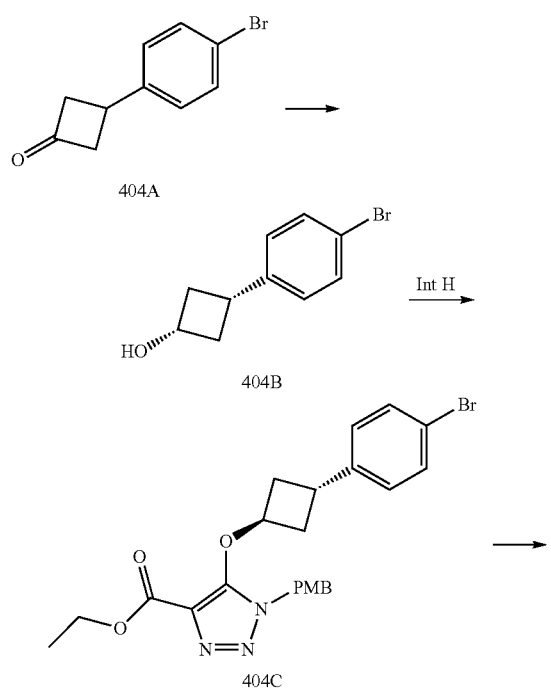

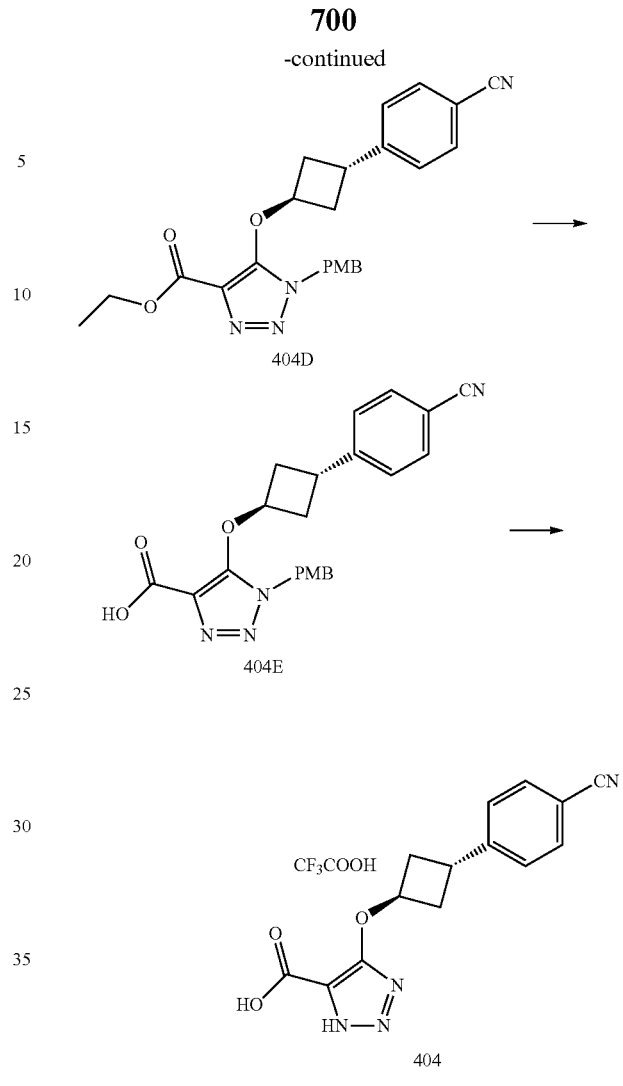

Compounds 404B, 404C, 404D, 404E, and 404 were synthesized by employing the procedures described for Compounds 393F-1, 90C, 390C, 8F, and 1 using Compounds 404A, 404B, 404C with Pd(PPh₃)₄ as catalyst at 140° C., 404D, and 404E in lieu of Compounds 393E, 90B, 390B with Pd₂(dba)₃ as catalyst at 120° C., 8E, and 1E. Compound 404B: LC-MS (ESI) m/z: 209 [M-OH]⁺; ¹H-NMR (CDCl₃, 400 MHz): δ (ppm) 1.77 (d, J=6.4 Hz, 1H), 1.94-2.02 (m, 2H), 2.73-2.81 (m, 2H), 2.88-2.96 (m, 1H), 4.25-4.33 (m, 1H), 7.09 (d, J=8.0 Hz, 2H), 7.41 (d, J=8.0 Hz, 2H). Compound 404C: LC-MS (ESI) m/z: 486 [M+H]⁺. Compound 404D: LC-MS (ESI) m/z: 433 [M+H]⁺; ¹H-NMR (CDCl₃, 400 MHz): δ (ppm) 1.40 (t, J=7.2 Hz, 3H), 2.42-2.46 (m, 4H), 3.39-3.48 (m, 1H), 3.78 (s, 3H), 4.38 (q, J=7.2 Hz, 2H), 4.94-5.01 (m, 1H), 5.38 (s, 2H), 6.88 (d, J=8.4 Hz, 2H), 7.22 (d. J=8.0 Hz, 2H), 7.27 (d, J=8.0 Hz, 2H), 7.69 (d, J=8.4 Hz, 2H). Compound 404E: LC-MS (ESI) m/z: 405 [M+H]⁺; ¹H-NMR (CD₃OD, 400 MHz): δ (ppm) 2.42-2.52 (m, 4H), 3.44-3.52 (m, 1H), 3.76 (s, 3H), 5.40 (s, 2H), 5.70 (brs, 1H), 6.93 (d, J=8.8 Hz, 2H), 7.27 (brs, 2H), 7.37 (d, J=8.8 Hz, 2H), 7.66 (d, J=8.4 Hz, 2H). Compound 404: LC-MS (ESI) m/z: 307 [M+Na]⁺; ¹H-NMR (CD₃OD, 500 MHz): δ (ppm) 2.66-2.71 (m, 2H), 2.76-2.82 (m, 2H), 3.84-3.91 (m, 1H), 5.26 (brs, 1H), 7.53 (d, J=6.8 Hz, 2H), 7.71 (d, J=6.8 Hz, 2H).

Example 405

Synthesis of 4-(((trans)-4-(4-(1H-1,2,4-triazol-1-yl)phenyl)cyclohexyl)oxy)-1H-1,2,3-triazole-5-carboxylic acid (405)

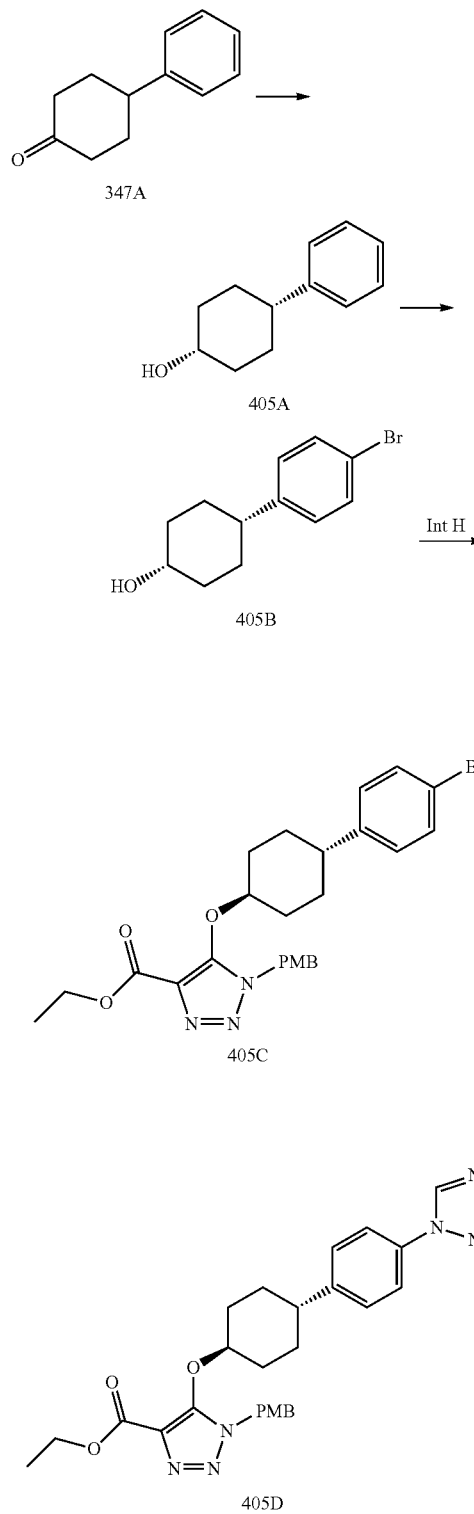

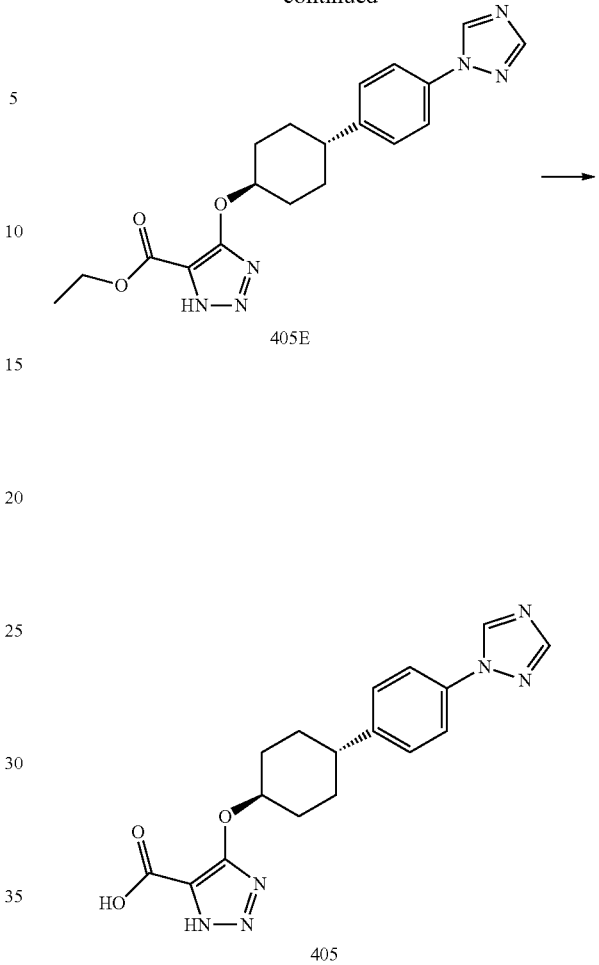

Compounds 405A, 405B, and 405C were synthesized by employing the procedures described for Compounds 393F-1, 347C, and 90C using Compounds 347A, 405A, and 405B in lieu of Compounds 393E, 347B, and 90B. Compound 405A: LC-MS (ESI) m/z: 159 [M−17]$^+$ Compound 405B: LC-MS (ESI) m/z: 237 [M−17]$^+$ Compound 405C: LC-MS (ESI) m/z: 514 [M+H]$^+$.

A mixture of Compound 405C (200 mg, 0.39 mmol), 1H-1,2,4-triazole (40 mg, 0.58 mmol), (1R,3R)—N1,N3-dimethylcyclohexane-1,3-diamine (11 mg, 0.08 mmol), CuI (15 mg, 0.08 mmol), and K$_2$CO$_3$ (74 mg, 0.54 mmol) in DMSO (5 mL) was stirred at 120° C. under nitrogen for 16 hours. The mixture was diluted with EtOAc (20 mL) and H$_2$O (20 mL). The organic layer was separated, dried over anhydrous sodium sulfate, concentrated, and purified with flash column chromatography (MeOH in DCM, from 0% to 6% v/v) to afford Compound 405D. LC-MS (ESI) m/z: 503 [M+H]$^+$.

Compounds 405E and 405 were synthesized by employing the procedures described for Compounds 1 and 8F using Compounds 405D and 405E in lieu of Compounds 1E and 8E. Compound 405E: LC-MS (ESI) m/z: 383 [M+H]$^+$. Compound 405: LC-MS (ESI) m/z: 355 [M+H]$^+$; $^1$H-NMR (DMSO-d$_6$, 400 MHz): δ (ppm) 1.56-1.67 (m, 4H), 1.88-1.92 (m, 2H), 2.24-2.26 (m, 2H), 2.67-2.68 (m, 1H), 4.66-4.68 (m, 1H), 7.46 (d, J=8.4 Hz, 2H), 7.76 (d, J=8.4 Hz, 2H), 8.21 (s, 1H), 9.24 (s, 1H).

Example 406

Synthesis of 4-((2-chloro-4'-(piperidin-1-yl)-[1,1'-biphenyl]-4-yl)oxy)-1H-1,2,3-triazole-5-carboxylic acid 2,2,2-trifluoroacetate (406)

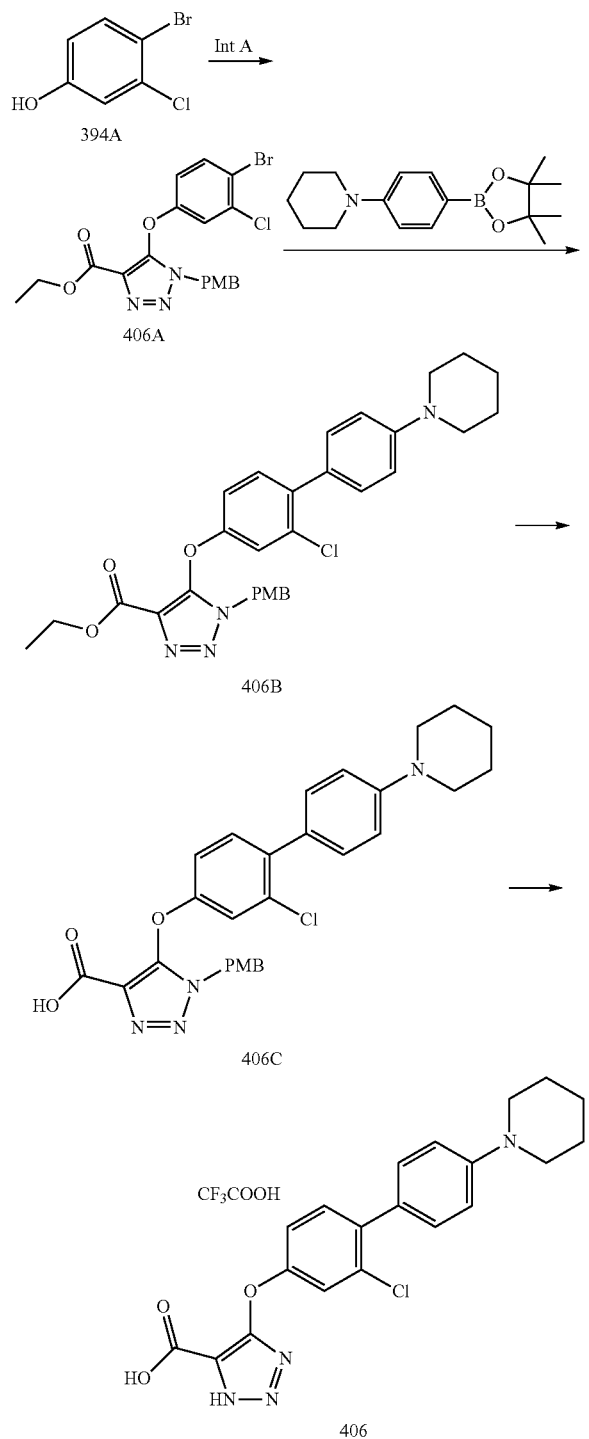

Compounds 406A, 406B, 406C, and 406 were synthesized by employing the procedures described for Intermediate I, Compounds 4B, 8F, and 1 using Compounds 394A with Cs₂CO₃ as base, 1-(4-(4,4,5,5-tetramethyl-1,3,2-dioxaborolan-2-yl)phenyl)piperidine, 406A with K₂CO₃ as base and 1,4-dioxane as solvent, 406B, and 406C in lieu of 4-bromophenol with K₂CO₃ as base, (4-bromophenyl)boronic acid, Compounds 4A with Na₂CO₃ as base and toluene/EtOH/H₂O as solvent, 8E, and 1E. Compound 406A: LC-MS (ESI) m/z: 466 [M+H]⁺. Compound 406B: LC-MS (ESI) m/z: 547 [M+H]⁺. Compound 406C: LC-MS (ESI) m/z: 519 [M+H]⁺. Compound 406: LC-MS (ESI) m/z: 399 [M+H]⁺; ¹H-NMR (CD₃OD, 400 MHz): δ (ppm) 1.69-1.72 (m, 2H), 1.85-1.86 (m, 4H), 3.37-3.39 (m, 4H), 7.11-7.14 (m, 1H), 7.26-7.29 (m, 3H), 7.36 (d, J=8.4 Hz, 1H), 7.43 (d, J=8.8 Hz, 2H).

Example 407

Synthesis of 4-((2'-chloro-4'-(piperidin-1-yl)-[1,1'-biphenyl]-4-yl)oxy)-1H-1,2,3-triazole-5-carboxylic acid (407)

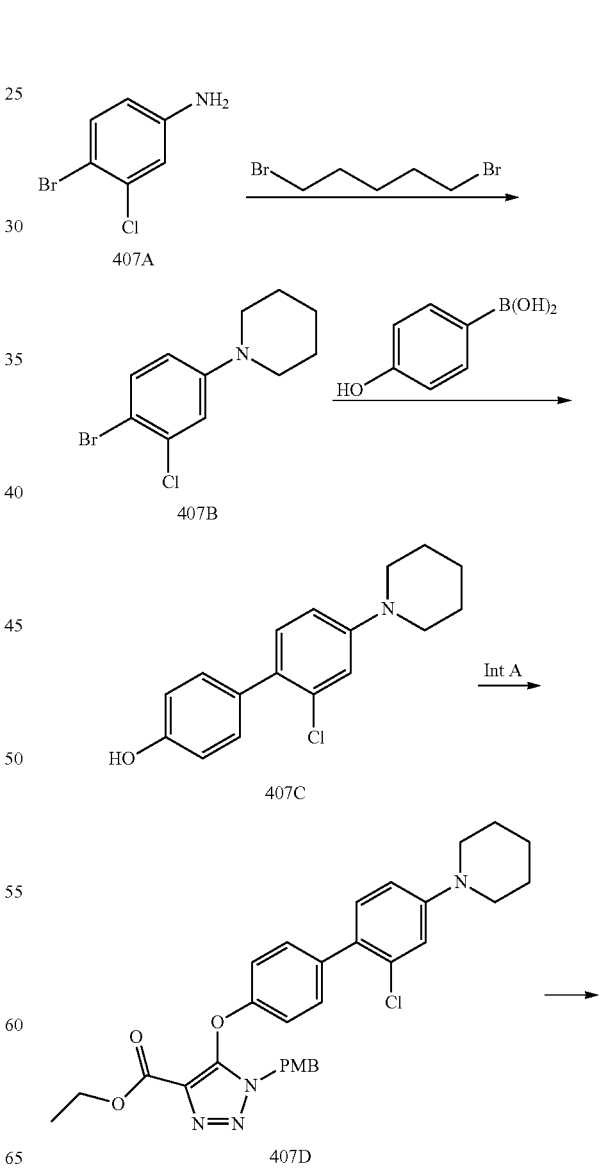

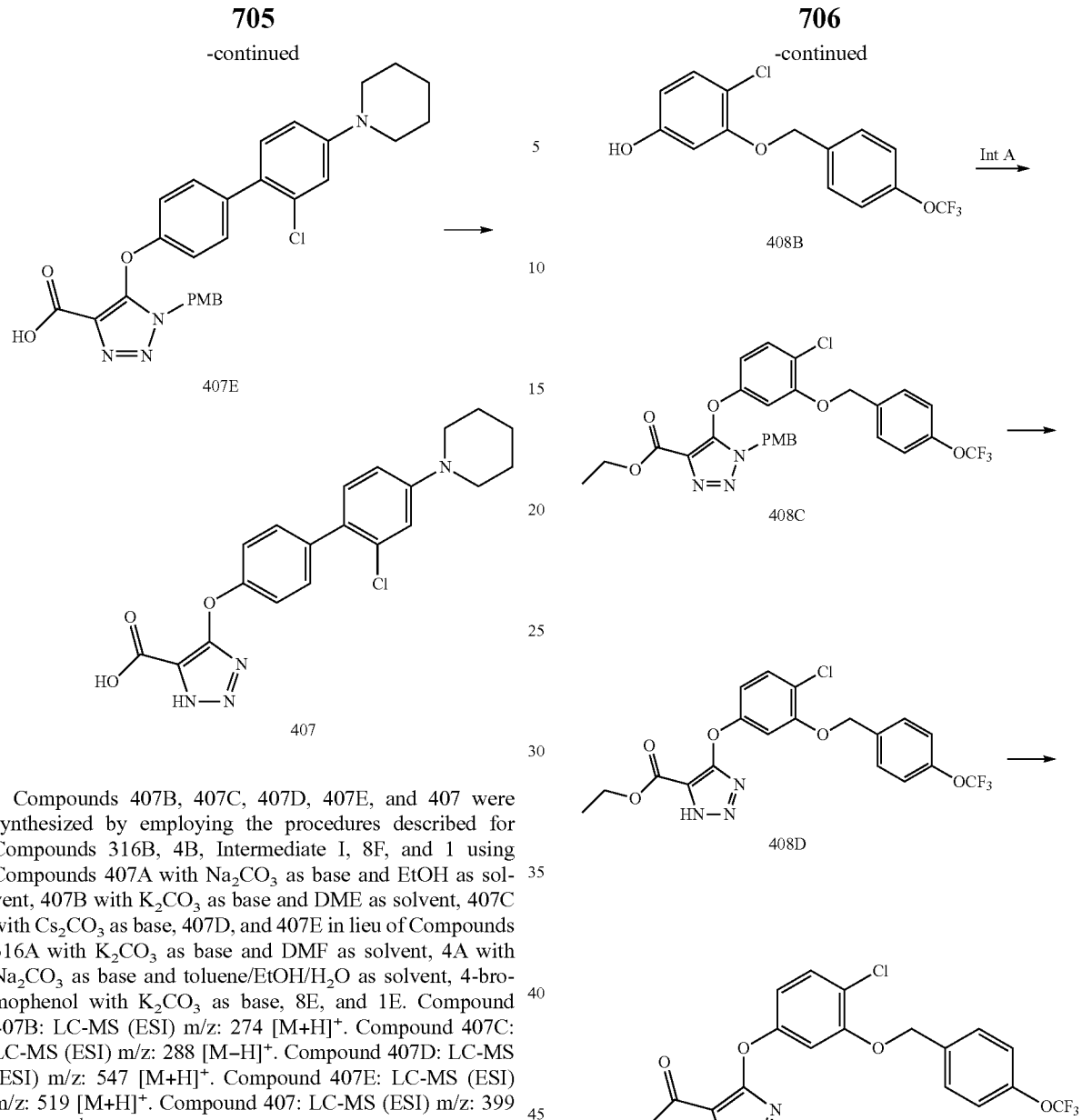

Compounds 407B, 407C, 407D, 407E, and 407 were synthesized by employing the procedures described for Compounds 316B, 4B, Intermediate I, 8F, and 1 using Compounds 407A with Na$_2$CO$_3$ as base and EtOH as solvent, 407B with K$_2$CO$_3$ as base and DME as solvent, 407C with Cs$_2$CO$_3$ as base, 407D, and 407E in lieu of Compounds 316A with K$_2$CO$_3$ as base and DMF as solvent, 4A with Na$_2$CO$_3$ as base and toluene/EtOH/H$_2$O as solvent, 4-bromophenol with K$_2$CO$_3$ as base, 8E, and 1E. Compound 407B: LC-MS (ESI) m/z: 274 [M+H]$^+$. Compound 407C: LC-MS (ESI) m/z: 288 [M−H]$^+$. Compound 407D: LC-MS (ESI) m/z: 547 [M+H]$^+$. Compound 407E: LC-MS (ESI) m/z: 519 [M+H]$^+$. Compound 407: LC-MS (ESI) m/z: 399 [M+H]$^+$; $^1$H-NMR (DMSO-d$_6$, 400 MHz): δ (ppm) 1.52-1.64 (m, 6H), 3.19-3.24 (m, 4H), 6.95-6.99 (m, 1H), 7.02 (s, 1H), 7.08-7.12 (m, 2H), 7.22 (d, J=8.4 Hz, 1H), 7.35-7.39 (m, 2H).

Example 408

Synthesis of 4-(4-chloro-3-((4-(trifluoromethoxy)benzyl)oxy)phenoxy)-1H-1,2,3-triazole-5-carboxylic acid (408)

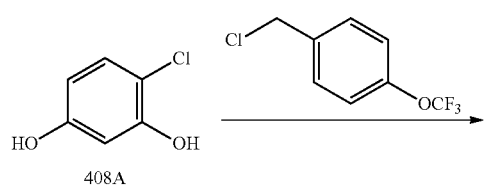

Compounds 408B, 408C, 408D, and 408 were synthesized by employing the procedures described for Compounds 27B, Intermediate I, 217E, and 8F using 1-(chloromethyl)-4-(trifluoromethoxy)benzene, Compounds 408A with K$_2$CO$_3$ as base and acetone as solvent, 408B with NMP as solvent, 408C, and 408D in lieu of 2-bromopropane, Compounds 27A with Cs$_2$CO$_3$ as base and DMF as solvent, 4-bromophenol with DMF as solvent, 217D, and 8E. Compound 408B: LC-MS (ESI) m/z: non-ionizable compound under routine conditions used; $^1$H-NMR (CDCl$_3$, 400 MHz): δ (ppm) 5.10 (s, 2H), 6.40 (dd, J=8.4, 2.4 Hz, 1H), 6.49 (d, J=2.4 Hz, 1H), 7.20-7.26 (m, 3H), 7.47-7.51 (m, 2H). Compound 408C: LC-MS (ESI) m/z: 578 [M+H]$^+$. Compound 408D: LC-MS (ESI) m/z: 458 [M+H]$^+$. Compound 408: LC-MS (ESI) m/z: 430 [M+H]$^+$; $^1$H-NMR (CD$_3$OD, 400 MHz): δ (ppm) 5.17 (s, 2H), 6.70 (dd, J=8.4, 2.4 Hz, 1H), 7.00 (d, J=2.4 Hz, 1H), 7.30 (d, J=8.4 Hz, 2H), 7.36 (d, J=8.4 Hz, 1H), 7.582 (d, J=8.4 Hz, 2H).

Example 409

Synthesis of 4-(((trans)-4-(quinolin-6-yl)cyclohexyl)oxy)-1H-1,2,3-triazole-5-carboxylic acid 2,2,2-trifluoroacetate (409)

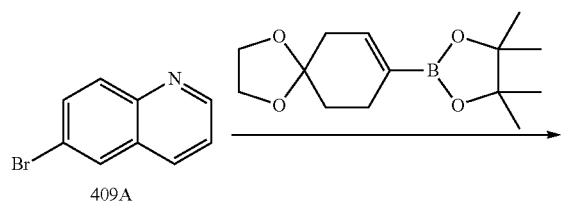

409A

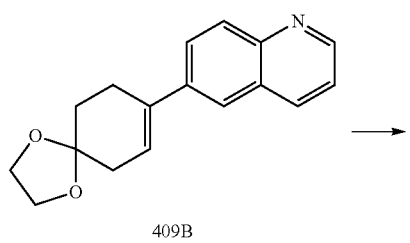

409B

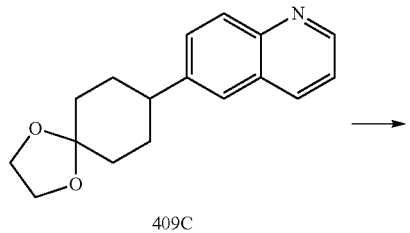

409C

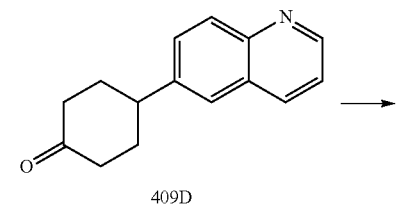

409D

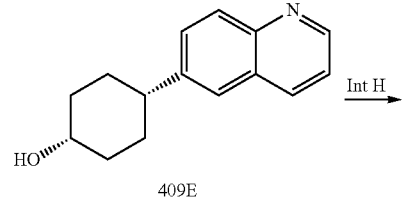

409E

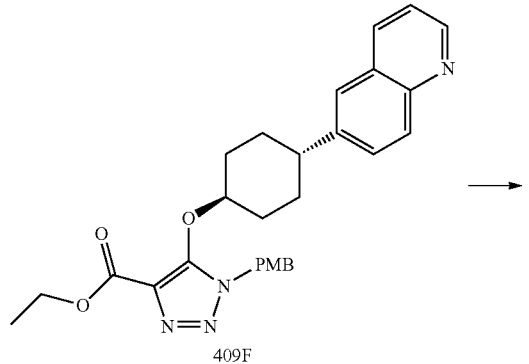

409F

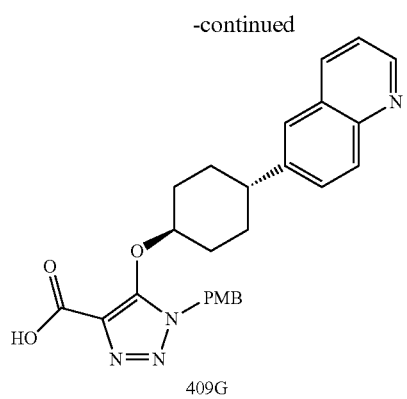

409G

409

Compounds 409B, 409C, 409D, 409E, 409F, 409G, and 409 were synthesized by employing the procedures described for Compounds 4B, 141, 279D, 393F-1, 90C, 8F, and 1 using 4,4,5,5-tetramethyl-2-(1,4-dioxaspiro[4.5]dec-7-en-8-yl)-1,3,2-dioxaborolane, Compounds 409A with $K_2CO_3$ as base and 1,4-dioxane/$H_2O$ as solvent, 409B with THF as solvent, 409C, 409D, 409E, 409F, and 409G in lieu of (4-bromophenyl)boronic acid, Compounds 4A with toluene/EtOH/$H_2O$ as solvent, 140 with EtOAc as solvent, 279C, 393E, 90B, 8E, and 1E. Compound 409B: LC-MS (ESI) m/z: 268 [M+H]$^+$; $^1$H-NMR (CDCl$_3$, 400 MHz): δ (ppm) 1.97-2.00 (m, 2H), 2.53-2.54 (m, 2H), 2.78-2.91 (m, 2H), 4.05 (s, 4H), 6.18-6.20 (m, 1H), 7.35-7.38 (m, 1H), 7.75-7.76 (m, 1H), 7.82-7.85 (m, 1H), 8.01-8.03 (m, 1H), 8.10-8.12 (m, 1H), 8.84-8.86 (m, 1H). Compound 409C: LC-MS (ESI) m/z: 270 [M+H]$^+$; $^1$H-NMR (CDCl$_3$, 400 MHz): δ (ppm) 1.74-1.79 (m, 2H), 1.89-2.00 (m, 6H), 2.75-2.77 (m, 1H), 4.01 (s, 4H), 7.35-7.38 (m, 1H), 7.62-7.63 (m, 2H), 8.03 (d, J=9.6 Hz, 1H), 8.10 (d, J=7.2 Hz, 1H), 8.84-8.86 (m, 1H). Compound 409D: LC-MS (ESI) m/z: 226 [M+H]$^+$; $^1$H-NMR (CDCl$_3$, 400 MHz): δ (ppm) 2.00-2.11 (m, 2H), 2.31-2.35 (m, 2H), 2.55-2.63 (m, 4H), 3.19-3.27 (m, 1H), 7.38-7.42 (m, 1H), 7.62-7.65 (m, 2H), 8.07-8.14 (m, 2H), 8.88-8.89 (m, 1H). Compound 409E: LC-MS (ESI) m/z: 228 [M+H]$^+$; $^1$H-NMR (CDCl$_3$, 500 MHz): δ (ppm) 1.71-1.79 (m, 4H), 1.94-2.04 (m, 4H), 2.70-2.76 (m, 1H), 4.18 (brs, 1H), 7.26-7.38 (m, 1H), 7.63-7.65 (m, 2H), 8.04 (d, J=7.6 Hz, 1H), 8.11 (d, J=6 Hz, 1H), 8.85-8.86 (m, 1H). Compound 409F: LC-MS (ESI) m/z: 487 [M+H]$^+$. Compound 409G: LC-MS (ESI) m/z: 459 [M+H]$^+$. Compound 409: LC-MS (ESI) m/z: 339 [M+H]$^+$; $^1$H-NMR (DMSO-d$_6$, 400 MHz): δ (ppm) 1.58-1.77 (m, 4H), 1.97-1.99 (m, 2H), 2.27-2.30 (m, 2H), 2.82-2.88 (m, 1H), 4.71 (brs, 1H), 7.70-7.73 (m, 1H), 7.86-7.88 (m, 1H), 7.95-7.97 (m, 1H), 8.03-8.05 (m, 1H), 8.59-8.61 (m, 1H), 8.99-9.00 (m, 1H), 14.77 (brs, 1H).

Example 410

Synthesis of 4-(((trans)-4-(quinolin-6-yl)cyclohexyl)thio)-1H-1,2,3-triazole-5-carboxylic acid 2,2,2-trifluoroacetate (410)

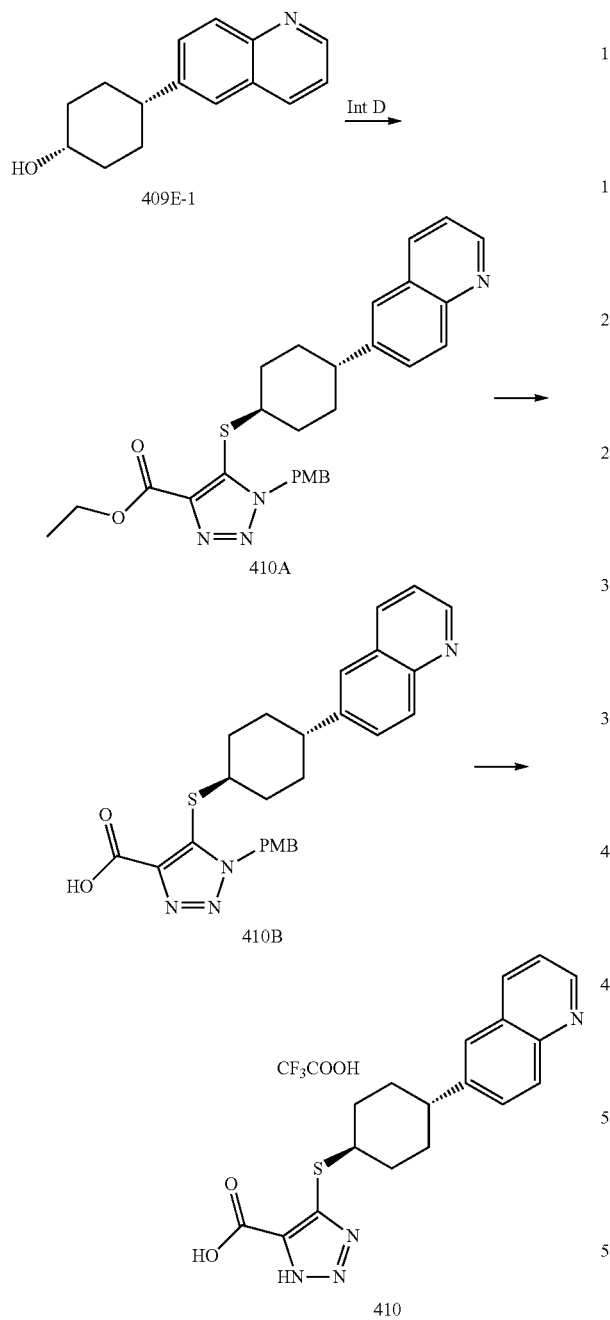

2.06 (m, 2H), 2.23-2.25 (m, 2H), 2.77-2.82 (m, 1H), 3.62 (brs, 1H), 7.50-7.53 (m, 1H), 7.70-7.73 (m, 1H), 7.81 (s, 1H), 7.94-7.96 (m, 1H), 8.33 (d, J=7.6 Hz, 1H), 8.84-8.85 (m, 1H), 15.62 (brs, 1H).

Example 411

Synthesis of 4-(((trans)-4-(2-chloro-5-(trifluoromethoxy)phenyl)cyclohexyl)thio)-1H-1,2,3-triazole-5-carboxylic acid (411)

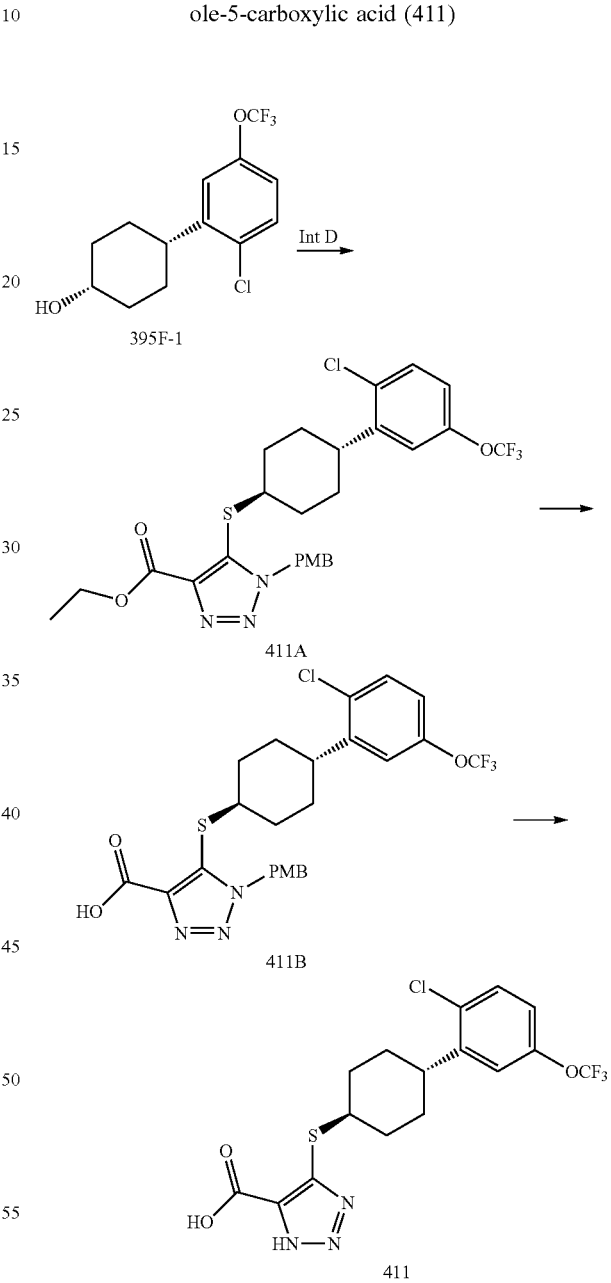

Compounds 410A, 410B, and 410 were synthesized by employing the procedures described for Compounds 90C, 8F, and 1 using Intermediate D, Compounds 409E-1, 410A, and 410B in lieu of Intermediate H, Compounds 90B, 8E, and 1E. Compound 410A: LC-MS (ESI) m/z: 503 [M+H]$^+$. Compound 410B: LC-MS (ESI) m/z: 475 [M+H]$^+$. Compound 410: LC-MS (ESI) m/z: 355 [M+H]$^+$; $^1$H-NMR (DMSO-d$_6$, 400 MHz): δ (ppm) 1.54-1.76 (m, 4H), 1.98-

Compounds 411A, 411B, and 411 were synthesized by employing the procedures described for Compounds 90C, 8F, and 1 using Intermediate D, Compounds 395F-1, 411A, and 411B in lieu of Intermediate H, Compounds 90B, 8E, and 1E. Compound 411A: LC-MS (ESI) m/z: 570 [M+H]$^+$. Compound 411B: LC-MS (ESI) m/z: 542 [M+H]$^+$. Compound 411: LC-MS (ESI) m/z: 422 [M+H]$^+$; $^1$H-NMR (CD$_3$OD, 400 MHz): δ (ppm) 1.59-1.70 (m, 4H), 1.98-2.0

(m, 2H), 2.32 (brs, 2H), 3.10-3.16 (m, 1H), 3.66 (brs, 1H), 7.12-7.15 (m, 1H), 7.271-7.277 (m, 1H), 7.49 (d, J=8.8 Hz, 1H).

Example 412

Synthesis of 4-(((trans)-4-(4-(2-oxopyrrolidin-1-yl)phenyl)cyclohexyl)oxy)-1H-1,2,3-triazole-5-carboxylic acid (412)

Compounds 412A, 412B, and 412 were synthesized by employing the procedures described for Compounds 301A, 8F, and 1 using pyrrolidin-2-one, Compounds 405C with t-butylbrettphos as ligand and $K_3PO_4$ as base and tert-butanol/water as solvent, 412A, and 412B in lieu of Compounds 297B and Intermediate I with X-phos as ligand and $Cs_2CO_3$ as base and 1,4-dioxane as solvent, 8E, and 1E. Compound 412A: LC-MS (ESI) m/z: 519 [M+H]$^+$. Compound 412B: LC-MS (ESI) m/z: 491 [M+H]$^+$. Compound 412: LC-MS (ESI) m/z: 371 [M+H]$^+$; $^1$H-NMR (DMSO-$d_6$, 400 MHz): δ (ppm) 1.30-1.31 (m, 2H), 1.67-1.69 (m, 4H), 1.98-2.0 (m, 2H), 2.16-2.20 (m, 2H), 2.34-2.35 (m, 2H), 2.57-2.61 (m, 3H), 3.89-3.93 (m, 2H), 7.27-7.29 (d, J=8.4 Hz, 2H), 7.49-7.51 (d, J=8.8 Hz, 2H).

Example 413

Synthesis of 4-((4'-sulfamoyl-[1,1'-biphenyl]-4-yl)oxy)-1H-1,2,3-triazole-5-carboxylic acid (413)

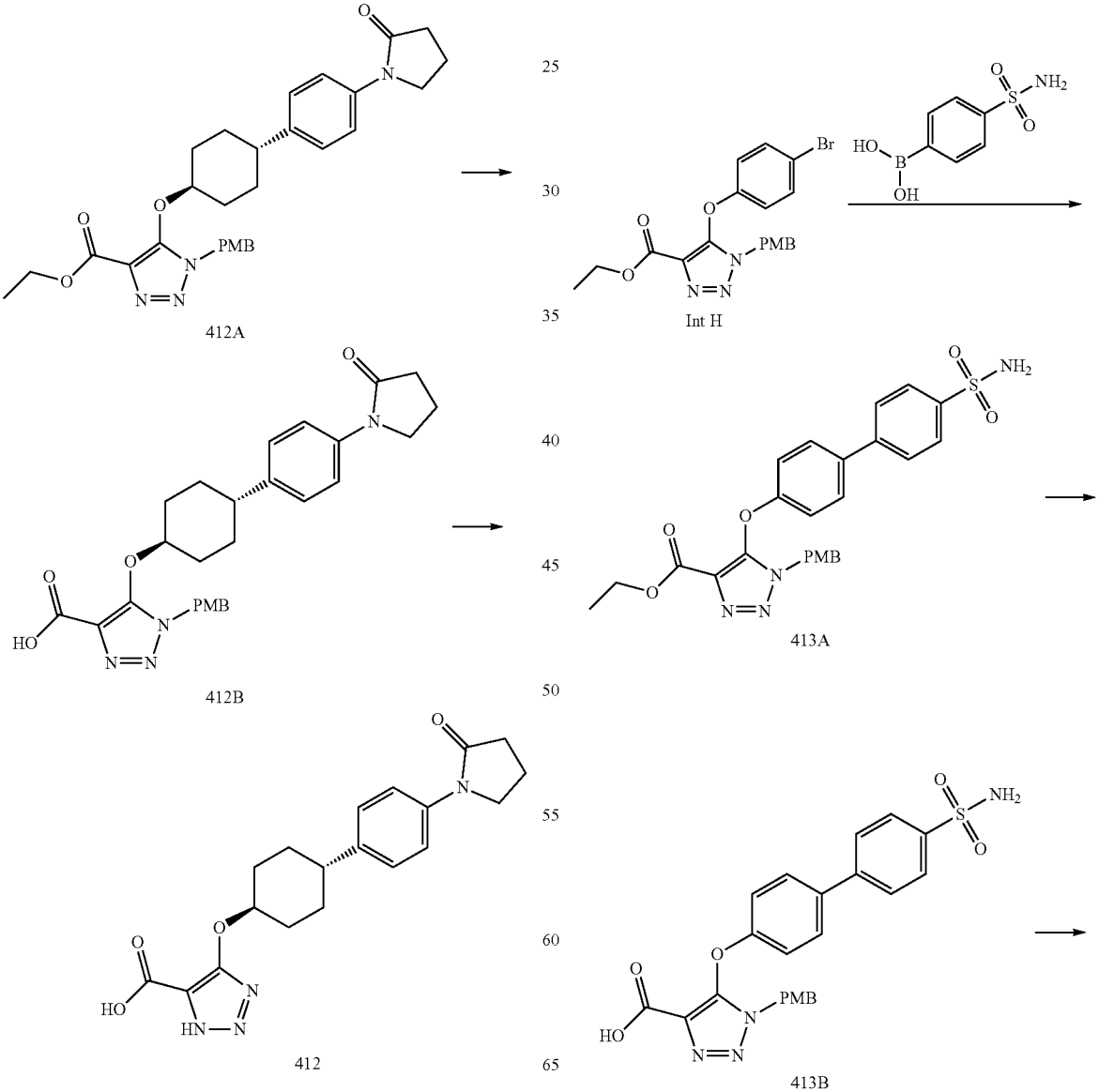

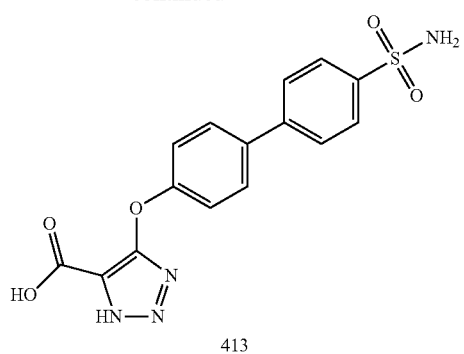

413

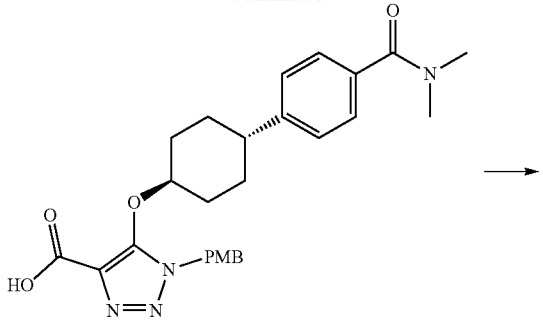

414B

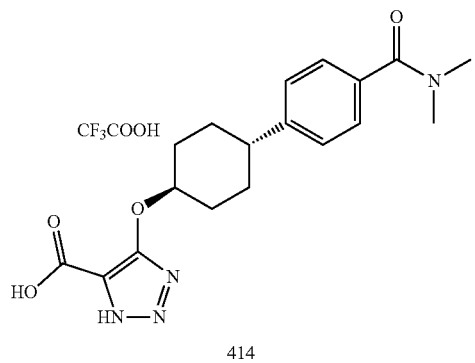

414

Compounds 413A, 413B, and 413 were synthesized by employing the procedures described for Compounds 4B, 8F, and 1 using 4-sulfamoylphenylboronic acid, Intermediate H with $K_2CO_3$ as base and 1,4-dioxane as solvent, Compounds 413A, and 413B in lieu of (4-bromophenyl)boronic acid, Compounds 4A with $Na_2CO_3$ as base and toluene/EtOH/$H_2O$ as solvent, 8E, and 1E. Compound 413A: LC-MS (ESI) m/z: 509 [M+H]$^+$. Compound 413B: LC-MS (ESI) m/z: 983 [2M+Na]t Compound 413: LC-MS (ESI) m/z: 361 [M+H]$^+$; $^1$H-NMR (DMSO-$d_6$, 400 MHz): δ (ppm) 7.04 (d, J=8.8 Hz, 2H), 7.36 (s, 2H), 7.68 (d, J=8.8 Hz, 2H), 7.80-7.87 (m, 4H).

Example 414

Synthesis of 4-(((trans)-4-(4-(dimethylcarbamoyl) phenyl)cyclohexyl)oxy)-1H-1,2,3-triazole-5-carboxylic acid 2,2,2-trifluoroacetate (414)

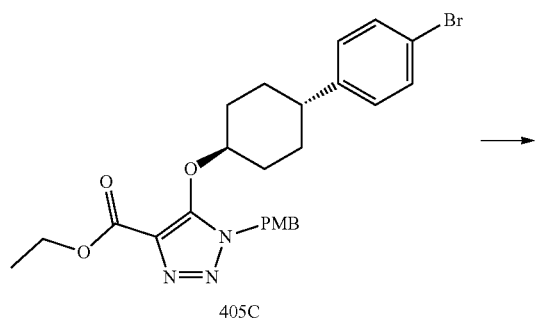

405C

To a solution of Compound 405C (600 mg, 1.17 mmol) in DMF (10 mL) was added dimethylamine (3 mL, 5.83 mmol) and Pd(PPh$_3$)$_2$Cl$_2$ (164 mg, 0.234 mmol) and stirred at 120° C. under CO (4 atm) for 8 hours. After cooled down to room temperature, the mixture was diluted with $H_2O$ (30 mL) and extracted with EtOAc (30 mL×3). The combined organic layers was dried over anhydrous sodium sulfate, concentrated, and purified by column chromatography on silica gel (ethyl acetate in petroleum ether, 20% v/v) to give Compound 414A. LC-MS (ESI) m/z: 507 [M+H]$^+$.

Compounds 414B and 414 were synthesized by employing the procedures described for Compounds 8F and 1 using Compounds 414A and 414B in lieu of Compounds 8E and 1E. Compound 414B: LC-MS (ESI) m/z: 479 [M+H]$^+$. Compound 414: LC-MS (ESI) m/z: 359 [M+H]$^+$. $^1$H-NMR (DMSO-$d_6$, 400 MHz): δ (ppm) 1.56-1.65 (m, 4H), 1.87-1.91 (m, 2H), 2.25 (d, J=8.4 Hz, 2H), 2.64 (s, 1H), 2.92-2.96 (m, 6H), 4.68 (s, 1H), 7.32 (s, 4H).

Example 415

Synthesis of 4-(4-chloro-3-((4-(trifluoromethyl)benzyl)oxy)phenoxy)-1H-1,2,3-triazole-5-carboxylic acid (415)

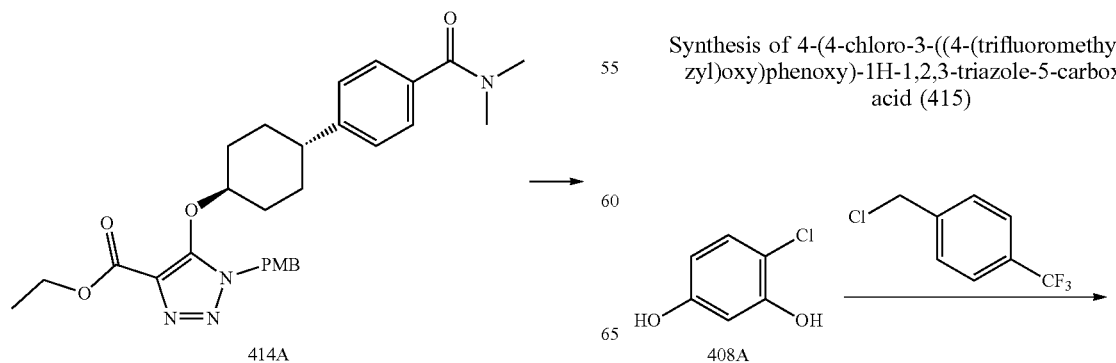

414A

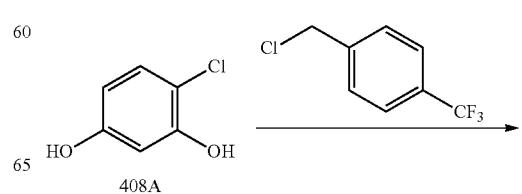

408A

715 -continued

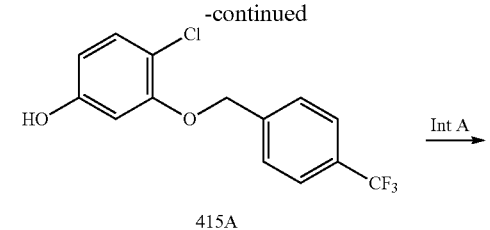

415A

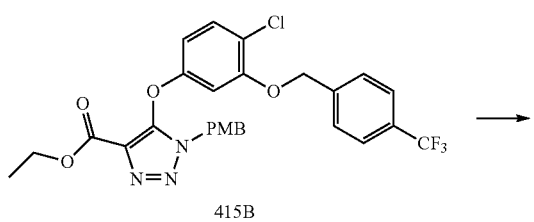

415B

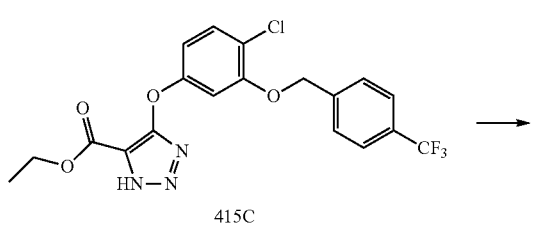

415C

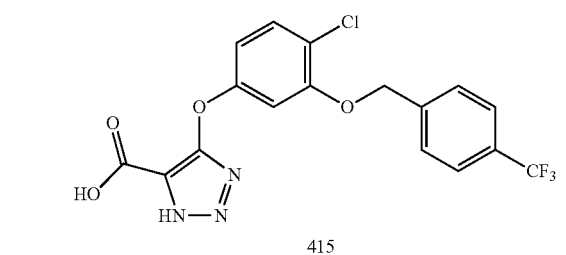

415

Compounds 415A, 415B, 415C, and 415 were synthesized by employing the procedures described for Compounds 27B, Intermediate I, 217E, and 8F using 1-(chloromethyl)-4-(trifluoromethyl)benzene, Compounds 408A with K₂CO₃ as base and acetone as solvent, 415A with NMP as solvent, 415B, and 415C in lieu of 2-bromopropane, Compounds 27A with Cs₂CO₃ as base and DMF as solvent, 4-bromophenol with DMF as solvent, 217D, and 8E. Compound 415A: LC-MS (ESI) m/z: non-ionizable compound under routine conditions used; ¹H-NMR (CDCl₃, 400 MHz): δ (ppm) 5.08 (brs, 1H), 5.17 (s, 2H), 6.40 (dd, J=8.8, 2.8 Hz, 1H), 6.48 (d, J=2.4 Hz, 1H), 7.22 (d, J=8.4 Hz, 1H), 7.58 (d, J=8.0 Hz, 2H), 7.65 (d, J=8.0 Hz, 2H). Compound 415B: LC-MS (ESI) m/z: 562 [M+H]⁺. Compound 415C: LC-MS (ESI) m/z: 442 [M+H]⁺. Compound 415: LC-MS (ESI) m/z: 414 [M+H]⁺; ¹H-NMR (CD₃OD, 400 MHz): δ (ppm) 5.24 (s, 2H), 6.71 (dd, J=8.8, 2.4 Hz, 1H), 7.00 (d, J=2.8 Hz, 1H), 7.37 (d, J=8.8 Hz, 1H), 7.66-7.72 (m, 4H).

716

Example 416

Synthesis of 4-(((trans)-4-(4-(morpholine-4-carbonyl)phenyl)cyclohexyl)oxy)-1H-1,2,3-triazole-5-carboxylic acid 2,2,2-trifluoroacetate (416)

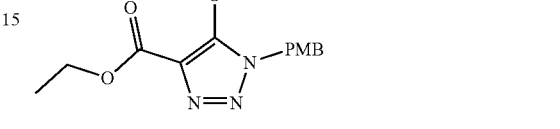

405C

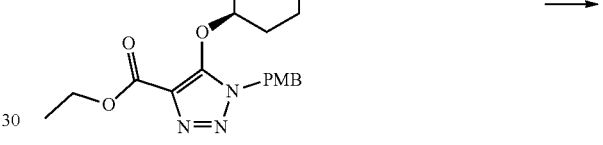

416A

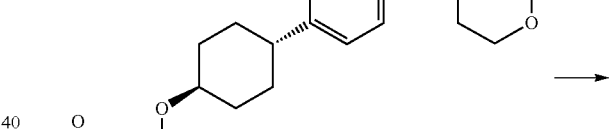

416B

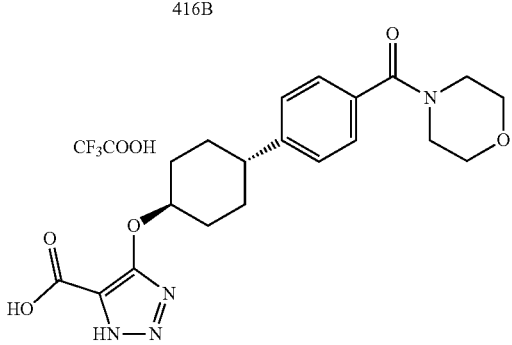

416

Compounds 416A, 416B, and 416 were synthesized by employing the procedures described for Compounds 414A, 8F, and 1 using morpholine, Compounds 416A, and 416B in lieu of dimethylamine, Compounds 8E, and 1E. Compound 416A: LC-MS (ESI) m/z: 549 [M+H]⁺. Compound 416B: LC-MS (ESI) m/z: 521 [M+H]⁺. Compound 416: LC-MS (ESI) m/z: 401 [M+H]⁺. ¹H-NMR (DMSO-d₆, 400 MHz): δ

(ppm) 1.55-1.62 (m, 4H), 1.86-1.90 (m, 2H), 2.23 (d, J=8.8 Hz, 2H), 2.62-2.63 (m, 1H), 3.22-3.44 (m, 4H), 3.51-3.56 (m, 4H), 4.65 (s, 1H), 7.32 (s, 4H), 14.76 (s, 1H).

Example 417

Synthesis of 4-(((trans)-4-(4-(piperidine-1-carbonyl)phenyl)cyclohexyl)oxy)-1H-1,2,3-triazole-5-carboxylic acid 2,2,2-trifluoroacetate (417)

417A: LC-MS (ESI) m/z: 547 [M+H]$^+$. Compound 417B: LC-MS (ESI) m/z: 519 [M+H]$^+$. Compound 417: LC-MS (ESI) m/z: 399 [M+H]$^+$. $^1$H-NMR (DMSO-d$_6$, 400 MHz): δ (ppm) 1.49-1.64 (m, 10H), 1.88 (d, J=10 Hz, 2H), 2.25 (d, J=8.8 Hz, 2H), 2.63-2.64 (m, 1H), 3.25-3.29 (m, 2H), 3.52-3.55 (m, 2H), 4.64 (s, 1H), 7.27-7.33 (m, 4H), 12.85 (s, 1H), 14.72 (s, 1H).

Example 418

Synthesis of 4-(((trans)-4-(4-(1H-pyrazol-1-yl)phenyl)cyclohexyl)oxy)-1H-1,2,3-triazole-5-carboxylic acid (418)

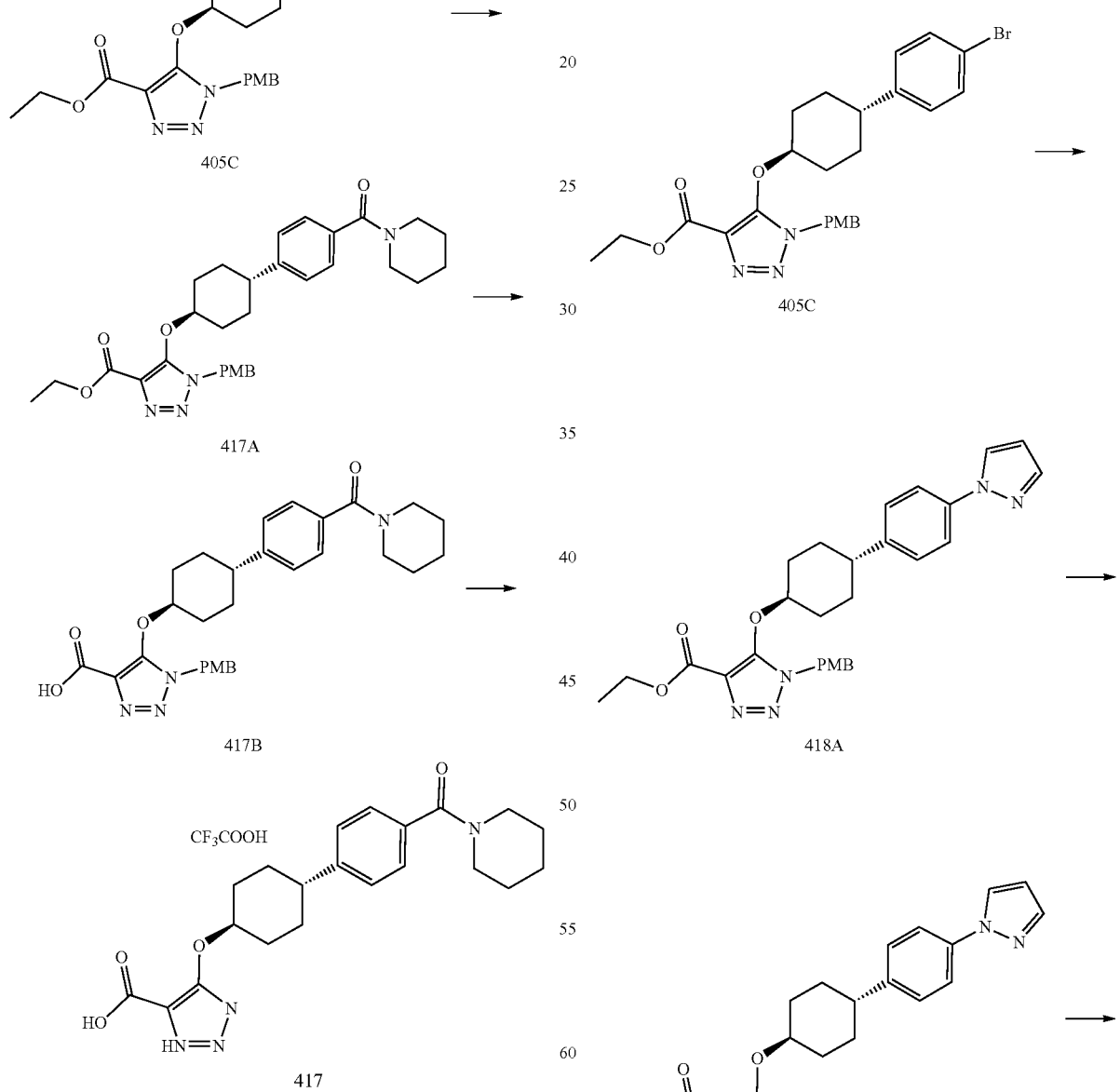

Compounds 417A, 417B, and 417 were synthesized by employing the procedures described for Compounds 414A, 8F, and 1 using piperidine, Compounds 417A, and 417B in lieu of dimethylamine, Compounds 8E, and 1E. Compound -continued

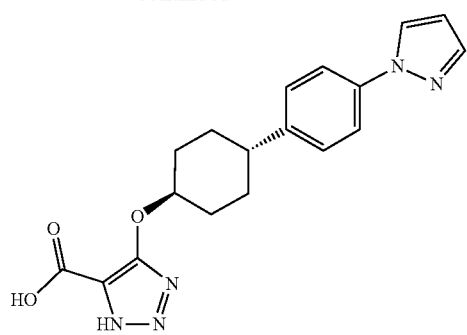

418

Compounds 418A, 418B, and 418 were synthesized by employing the procedures described for Compounds 405D, 8F, and 1 using 1H-pyrazole, Compounds 418A, and 418B in lieu of 1H-1,2,4-triazole, Compounds 8E, and 1E. Compound 418A: LC-MS (ESI) m/z: 502 [M+H]$^+$. Compound 418B: LC-MS (ESI) m/z: 474 [M+H]$^+$. Compound 418: LC-MS (ESI) m/z: 354 [M+H]$^+$; $^1$H-NMR (DMSO-d$_6$, 400 MHz): δ (ppm) 1.51-1.67 (m, 4H), 1.88 (d, J=10 Hz, 2H), 2.24 (d, J=10 Hz, 2H), 2.60-2.66 (m, 1H), 4.63-4.71 (m, 1H), 6.50 (s, 1H), 7.37 (d, J=8.8 Hz, 2H), 7.72 (t, J=8.4 Hz, 3H), 8.42 (d, J=2.8 Hz, 1H).

Example 419

Synthesis of 4-(((trans)-4-(3-chloro-4-(trifluoromethoxy)phenyl)cyclohexyl)oxy)-1H-1,2,3-triazole-5-carboxylic acid (419)

-continued

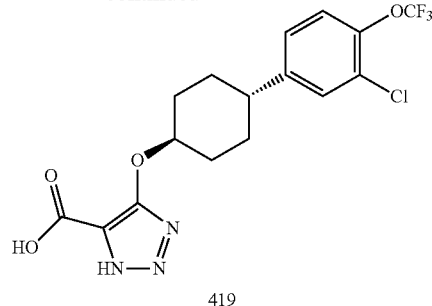

419

Compounds 419A, 419B, and 419 were synthesized by employing the procedures described for Compounds 90C, 8F, and 1 using Compounds 360D-1 with DEAD as coupling reagent, 419A, and 419B in lieu of Compounds 90B with DIAD as coupling reagent, 8E, and 1E. Compound 419A: LC-MS (ESI) m/z: 554 [M+H]$^+$. Compound 419B: LC-MS (ESI) m/z: 526 [M+H]$^+$. Compound 419: LC-MS (ESI) m/z: 406 [M+H]$^+$; $^1$H-NMR (CD$_3$OD, 400 MHz): δ (ppm) 1.48-1.66 (m, 4H), 1.84-1.92 (m, 2H), 2.22-2.30 (m, 2H), 2.52-2.62 (m, 1H), 4.60-4.70 (m, 1H), 7.18-7.26 (m, 2H), 7.37 (s, 1H).

Example 420

Synthesis of 4-(((trans)-3-(4-cyanophenyl)cyclobutyl)thio)-1H-1,2,3-triazole-5-carboxylic acid 2,2,2-trifluoroacetate (420)

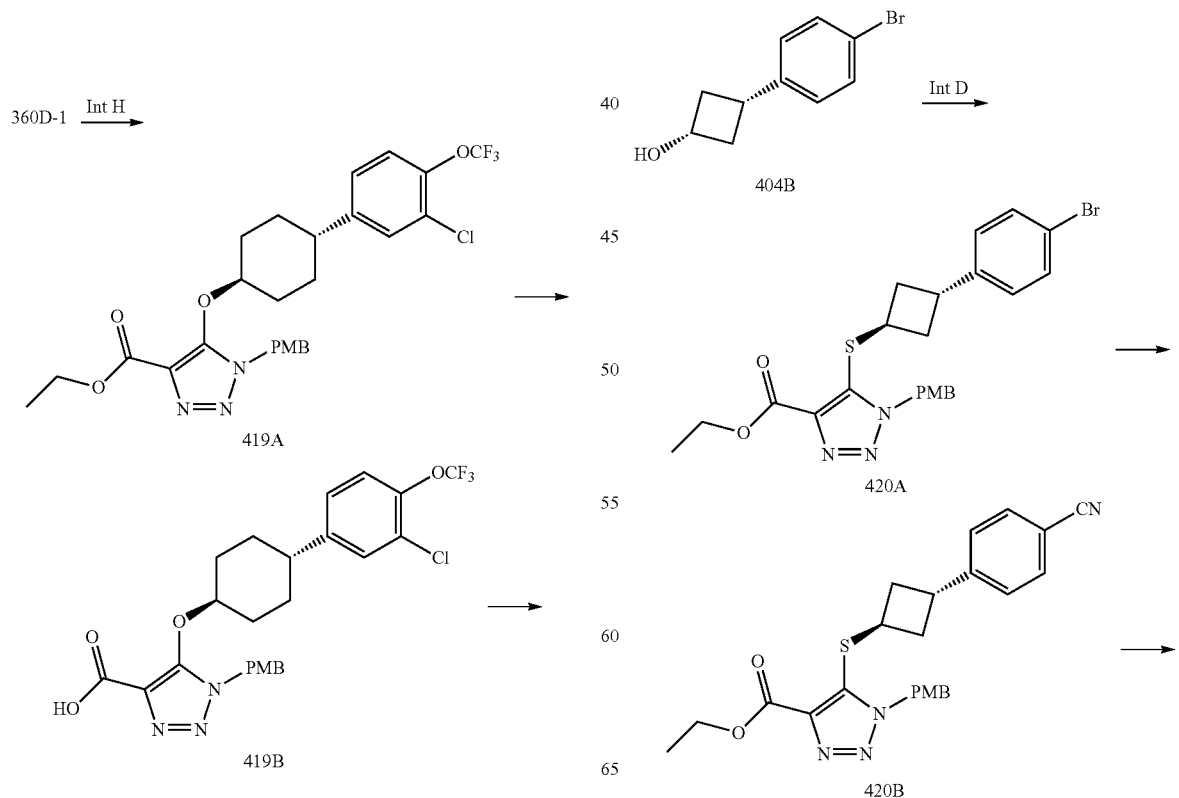

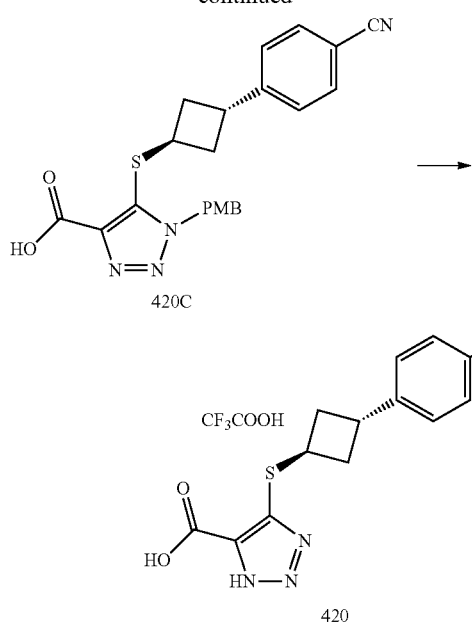

Compounds 420A, 420B, and 420 were synthesized by employing the procedures described for Compounds 90C, 8F, and 1 using Intermediate D, Compounds 304B with dichloromethane as solvent, 420A, and 420B in lieu of Intermediate H, Compounds 90B with THF as solvent, 8E, and 1E. Compound 420A: LC-MS (ESI) m/z: 449 [M+H]$^+$. Compound 420B: LC-MS (ESI) m/z: 419 [M−H]$^-$. Compound 420: LC-MS (ESI) m/z: 301 [M+H]$^+$; $^1$H-NMR (CD$_3$OD, 400 MHz): δ (ppm) 2.48-2.54 (m, 2H), 2.76-2.83 (m, 2H), 3.94-4.01 (m, 1H), 4.24-4.30 (m, 1H), 7.53 (d, J=8.4 Hz, 2H), 7.71 (d, J=8.4 Hz, 2H).

Example 421

Synthesis of 4-(4-cyano-3-((4-(trifluoromethoxy)benzyl)oxy)phenoxy)-1H-1,2,3-triazole-5-carboxylic acid (421)

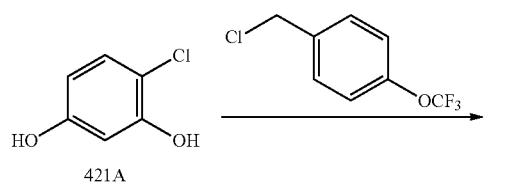

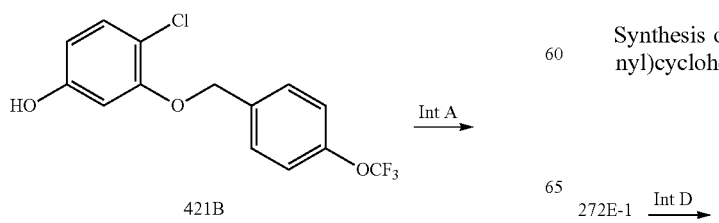

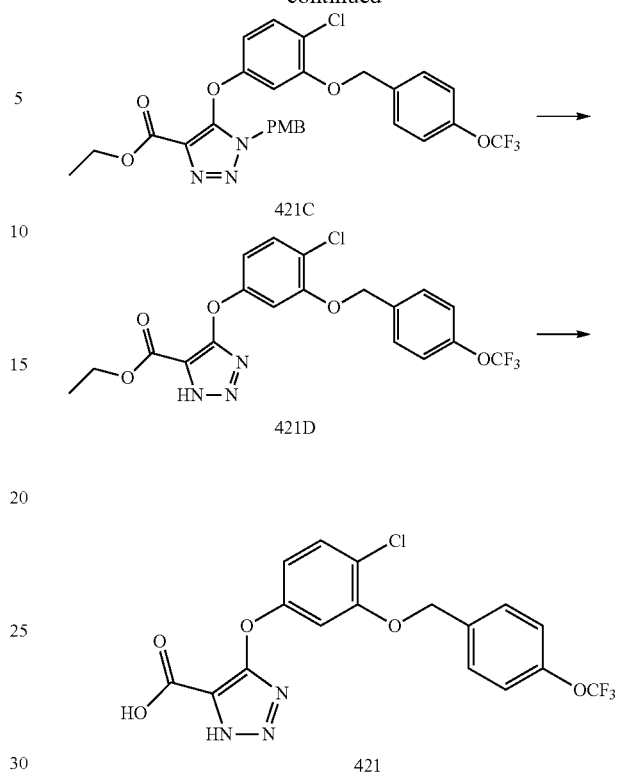

Compounds 421B, 421C, 421D, and 421 were synthesized by employing the procedures described for Compounds 27B, Intermediate I, 217E, and 8F using 1-(chloromethyl)-4-(trifluoromethoxy)benzene, Compounds 421A with K$_2$CO$_3$ as base and acetone as solvent, 421B, 421C, and 421D in lieu of 2-bromopropane, Compounds 27A with Cs$_2$CO$_3$ as base and DMF as solvent, 4-bromophenol, 217D, and 8E. Compound 421B: LC-MS (ESI) m/z: 310 [M+H]$^+$; $^1$H-NMR (DMSO-d$_6$, 400 MHz): δ (ppm) 5.24 (s, 2H), 6.48-6.51 (m, 1H), 6.62 (m, 1H), 7.42-7.44 (m, 2H), 7.51-7.53 (m, 1H), 7.58-7.60 (m, 2H), 10.68 (s, 1H). Compound 421C: LC-MS (ESI) m/z: 569 [M+H]$^+$. (CDCl$_3$, 400 MHz): δ (ppm) 1.14 (t, J=7.2 Hz, 3H), 3.70 (s, 3H), 4.19 (q, J=7.2 Hz, 2H), 4.87 (s, 2H), 5.36 (s, 2H), 6.15-6.16 (m, 1H), 6.37-6.40 (m, 1H), 6.71-6.73 (m, 2H), 7.12-7.14 (m, 2H), 7.24-7.26 (m, 2H), 7.39-7.41 (m, 2H), 7.44-7.46 (m, 1H). Compound 421D: LC-MS (ESI) m/z: 449 [M+H]$^+$. Compound 421: LC-MS (ESI) m/z: 421 [M+H]$^+$; $^1$H-NMR (DMSO-d$_6$, 400 MHz): δ (ppm) 5.29 (s, 2H), 6.70 (dd, J=8.8, 2.0 Hz, 1H), 7.10 (d, J=2.0 Hz, 1H), 7.43 (d, J=8.0 Hz, 2H), 7.59 (d, J=8.0 Hz, 2H), 7.73 (d, J=8.8 Hz, 1H).

Example 422

Synthesis of 4-(((trans)-4-(4-(trifluoromethoxy)phenyl)cyclohexyl)thio)-1H-1,2,3-triazole-5-carboxylic acid (422)

272E-1 $\xrightarrow{\text{Int D}}$

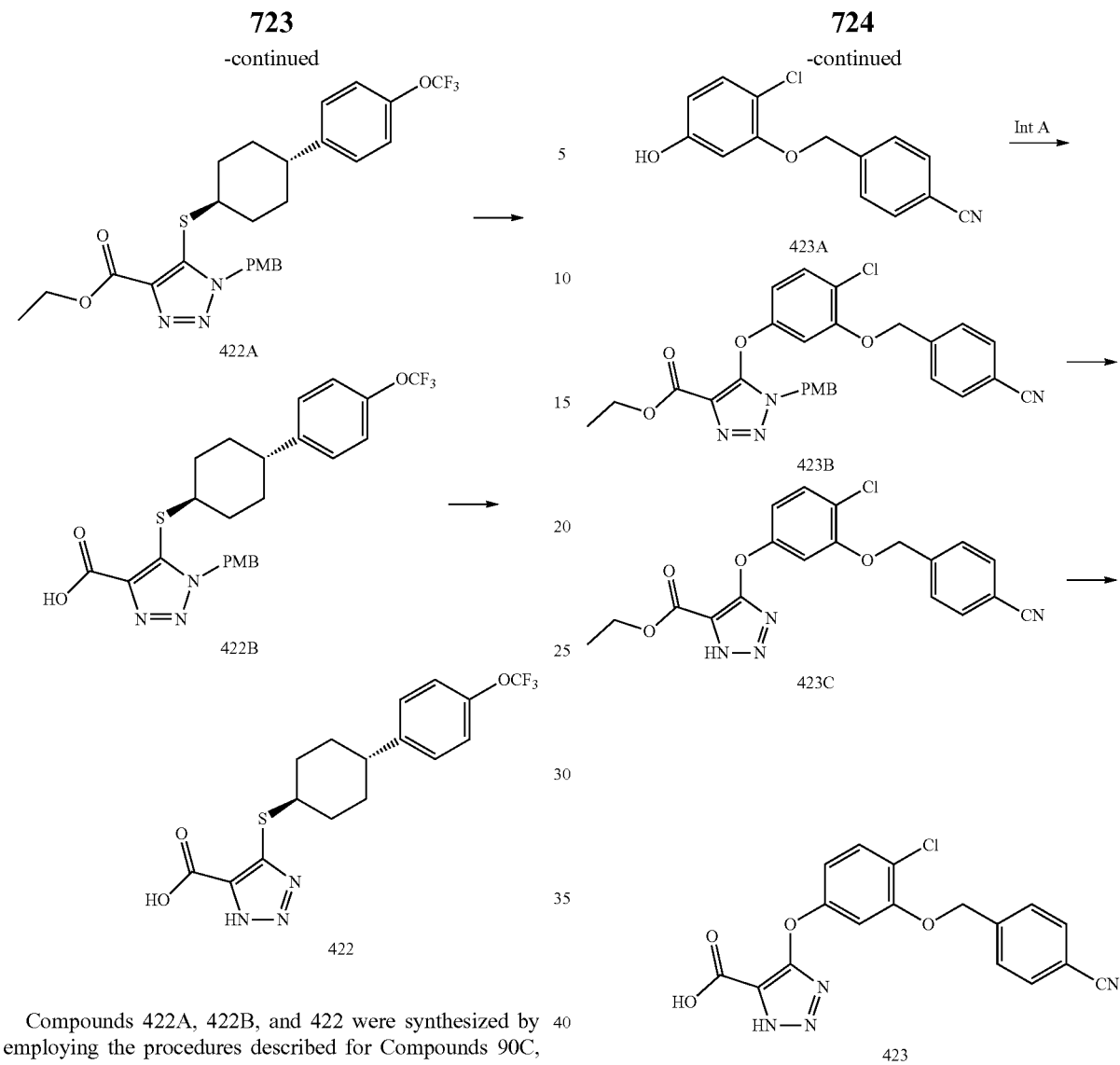

Compounds 422A, 422B, and 422 were synthesized by employing the procedures described for Compounds 90C, 8F, and 1 using Intermediate D, Compounds 272E-1, 422A, and 422B in lieu of Intermediate H, Compounds 90B, 8E, and 1E. Compound 422A: LC-MS (ESI) m/z: 536 [M+H]$^+$. Compound 422B: LC-MS (ESI) m/z: 508 [M+H]$^+$. Compound 422: LC-MS (ESI) m/z: 388 [M+H]$^+$; $^1$H-NMR (CD$_3$OD, 400 MHz): δ (ppm) 1.55-1.72 (m, 4H), 1.95-1.98 (m, 2H), 2.27-2.30 (m, 2H), 2.62-2.68 (m, 1H), 3.60-3.63 (m, 1H), 7.18 (d, J=8 Hz, 2H), 7.34 (d, J=9.2 Hz, 2H).

Example 423

Synthesis of 4-(4-chloro-3-((4-cyanobenzyl)oxy) phenoxy)-1H-1,2,3-triazole-5-carboxylic acid (423)

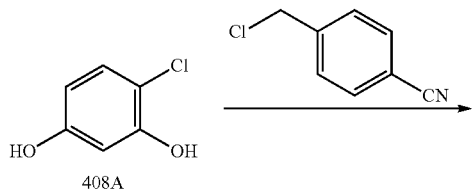

Compounds 423A, 423B, 423C, and 423 were synthesized by employing the procedures described for Compounds 27B, Intermediate I, 217E, and 8F using 4-(chloromethyl)benzonitrile, Compounds 408A with K$_2$CO$_3$ as base and acetone as solvent, 423A with NMP as solvent, 423B, and 423C in lieu of 2-bromopropane, Compounds 27A with Cs$_2$CO$_3$ as base and DMF as solvent, 4-bromophenol with DMF as solvent, 217D, and 8E. Compound 423A: LC-MS (ESI) m/z: 260 [M+H]$^+$; $^1$H-NMR (CDCl$_3$, 400 MHz): δ (ppm) 5.08 (brs, 1H), 5.16 (s, 2H), 6.41 (dd, J=8.4, 2.8 Hz, 1H), 6.47 (d, J=2.8 Hz, 1H), 7.22 (d, J=8.4 Hz, 1H), 7.59 (d, J=8.8 Hz, 2H), 7.69 (d, J=8.4 Hz, 2H). Compound 423B: LC-MS (ESI) m/z: 519 [M+H]$^+$; $^1$H-NMR (CDCl$_3$, 400 MHz): δ (ppm) 1.16 (t, J=7.2 Hz, 3H), 3.71 (s, 3H), 4.20 (q, J=7.2 Hz, 2H), 4.88 (s, 2H), 5.35 (s, 2H), 6.20 (d, J=2.8 Hz, 1H), 6.35-6.37 (m, 1H), 6.75 (d, J=8.8 Hz, 2H), 7.17 (d, J=8.8 Hz, 2H), 7.24-7.27 (m, 1H), 7.52 (d, J=8.0 Hz, 2H), 7.69 (d, J=8.4 Hz, 2H). Compound 423C: LC-MS (ESI) m/z: 399 [M+H]$^+$. Compound 423: LC-MS (ESI) m/z: 371 [M+H]$^+$; $^1$H-NMR (CD$_3$OD, 400 MHz): δ (ppm) 5.25 (s, 2H), 6.71 (dd, J=8.8, 2.4 Hz, 1H), 6.96 (d, J=2.4 Hz, 1H), 7.38 (d, J=8.8 Hz, 1H), 7.66 (d, J=8.4 Hz, 2H), 7.76 (d, J=8.4 Hz, 2H).

Example 424

Synthesis of 4-(((trans)-4-(2,4-difluorophenyl)cyclohexyl)oxy)-1H-1,2,3-triazole-5-carboxylic acid 2,2,2-trifluoroacetate (424)

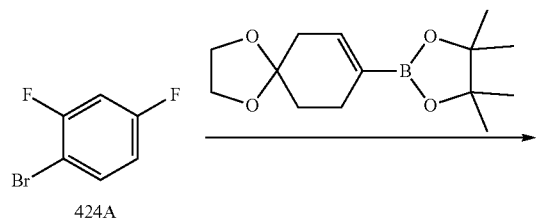

424A

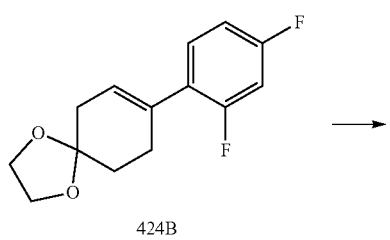

424B

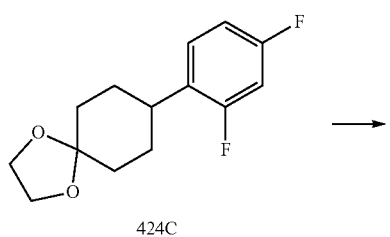

424C

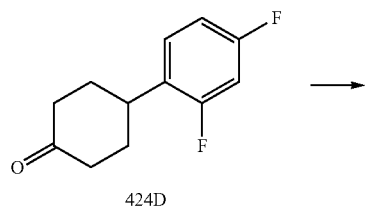

424D

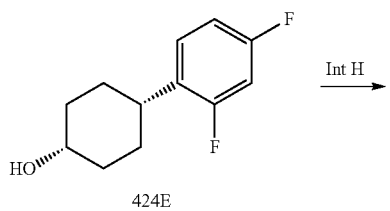

424E

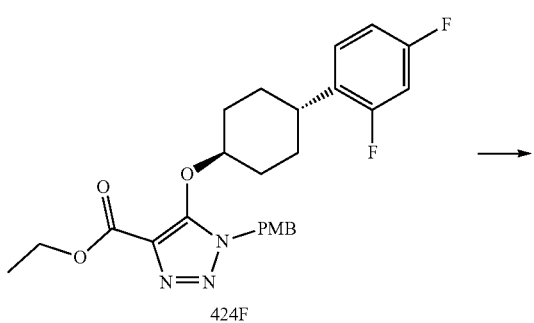

424F

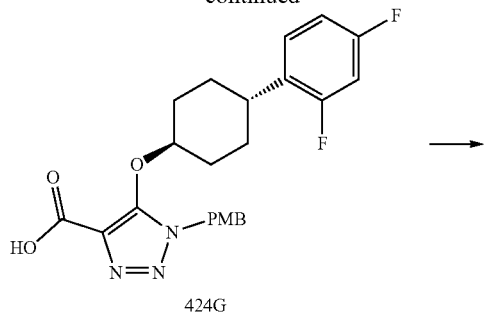

424G

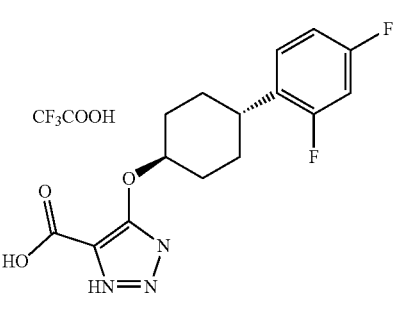

424

Compounds 424B, 424C, 424D, 424E, 424F, 424G, and 424 were synthesized by employing the procedures described for Compounds 4B, 141, 279D, 393F-1, 90C, 8F, and 1 using 4,4,5,5-tetramethyl-2-(1,4-dioxaspiro[4.5]dec-7-en-8-yl)-1,3,2-dioxaborolane, Compounds 424A with $K_3PO_4$ as base and DME as solvent, 424B with MeOH as solvent, 424C with TFA as acid and dichloromethane as solvent, 424D, 424E, 424F, and 424G in lieu of (4-bromophenyl)boronic acid, Compounds 4A with $Na_2CO_3$ as base and toluene/EtOH/$H_2O$ as solvent, 140 with EtOAc as solvent, 279C with HCl as acid and 1,4-dioxane as solvent, 393E, 90B, 8E, and 1E. Compound 424B: LC-MS (ESI) m/z: 253 [M+H]$^+$. $^1$H-NMR (CDCl$_3$, 400 MHz): δ (ppm) 1.90 (t, J=6.8 Hz, 2H), 2.47 (s, 2H), 2.59-2.62 (m, 2H), 4.03 (s, 4H), 5.80-5.82 (m, 1H), 6.75-6.84 (m, 2H), 7.20-7.27 (m, 1H). Compound 424C: LC-MS (ESI) m/z: 255 [M+H]$^+$. Compound 424D: LC-MS (ESI) m/z: 211 [M+H]$^+$. Compound 424E: LC-MS (ESI) m/z: 195 [M–OH]$^+$. $^1$H-NMR (CDCl$_3$, 400 MHz): δ (ppm) 1.57-1.73 (m, 4H), 1.83-1.92 (m, 4H), 2.82-2.89 (m, 1H), 3.73-3.91 (m, 1H), 4.16 (d, J=7.6 Hz, 1H), 6.73-6.85 (m, 2H), 7.20-7.27 (m, 1H). Compound 424F: LC-MS (ESI) m/z: 472 [M+H]$^+$. Compound 424G: LC-MS (ESI) m/z: 444 [M+H]$^+$. Compound 424: LC-MS (ESI) m/z: 324 [M+H]$^+$; $^1$H-NMR (DMSO-d$_6$, 400 MHz): δ (ppm) 1.52-1.68 (m, 4H), 1.80-1.83 (m, 2H), 2.22-2.24 (m, 2H), 2.81-2.87 (m, 1H), 4.62 (s, 1H), 7.00-7.05 (m, 1H), 7.12-7.18 (m, 1H), 7.37-7.43 (m, 1H), 12.81 (s, 1H), 14.70 (s, 1H).

Example 425
Synthesis of 4-(((trans)-4-(4-(4H-1,2,4-triazol-3-yl)phenyl)cyclohexyl)oxy)-1H-1,2,3-triazole-5-carboxylic acid (425)
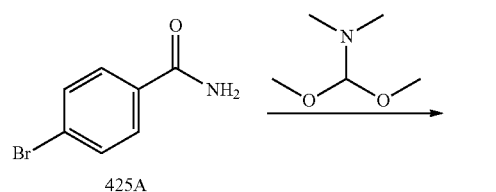
425A
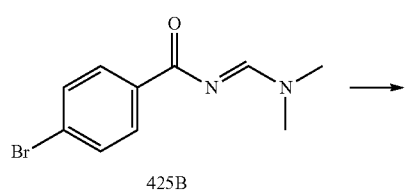
425B
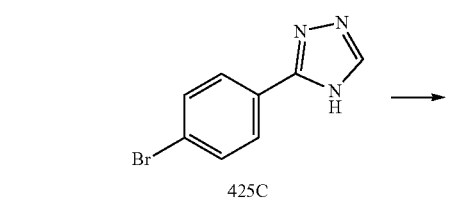
425C
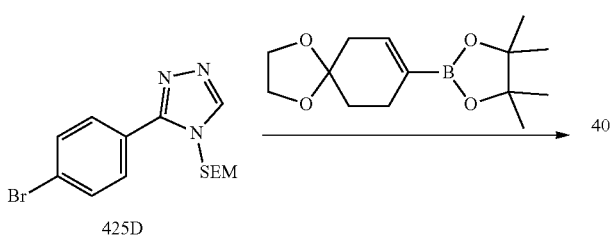
425D
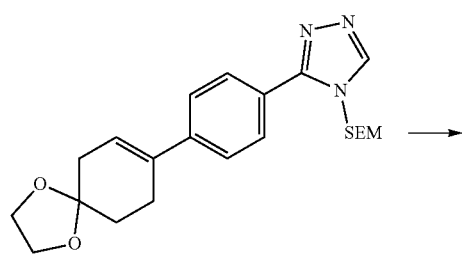
425E
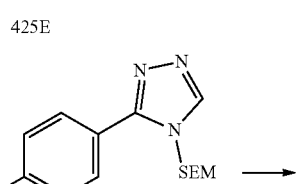
425F
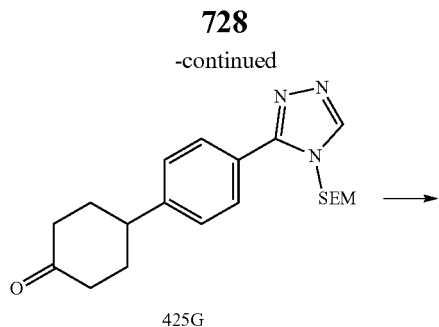
425G
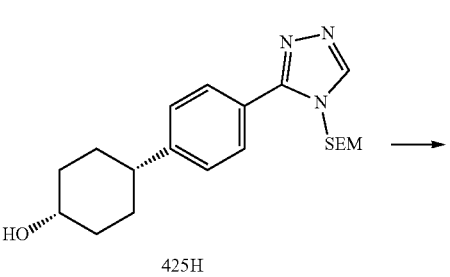
425H
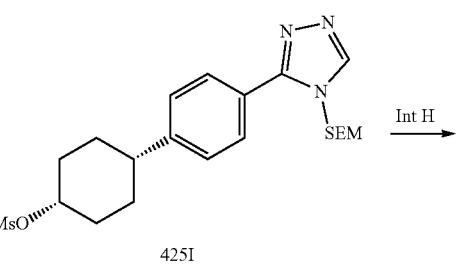
425I
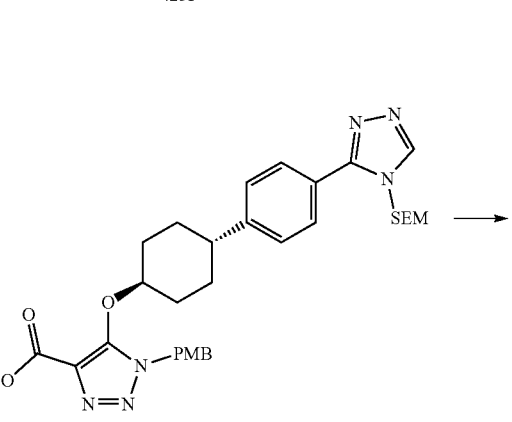
425J
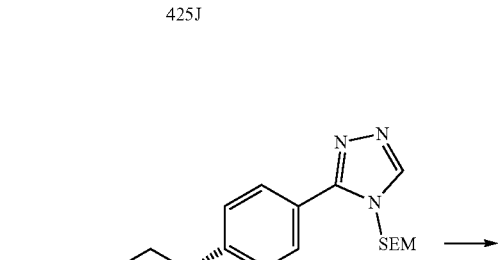
425K
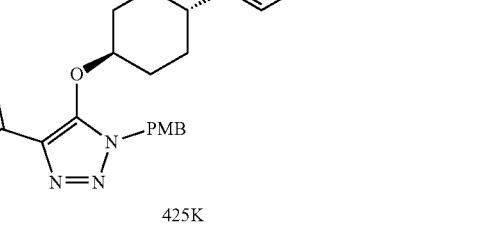

729
-continued

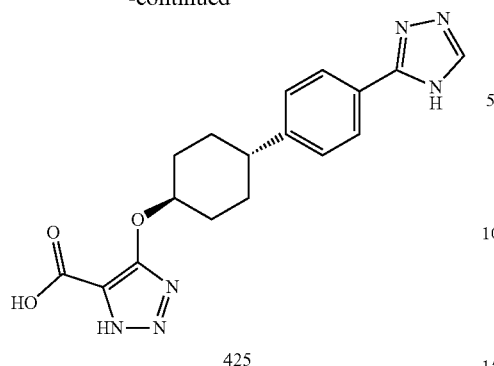

425

A mixture of Compound 425A (4 g, 20 mmol) and 1,1-dimethoxy-N,N-dimethylmethanamine (20 mL) was heated at 100° C. overnight. The mixture was concentrated to give a crude Compound 425B. LC-MS (ESI) m/z: 255 [M+H]$^+$.

To a solution of Compound 425B (5.1 g, 20 mmol) in acetic acid (50 mL) was added hydrazine hydrate (1.2 g, 23.99 mmol). The mixture was stirred at 90° C. for 3 hours and concentrated under reduced pressure. The residue was re-crystallized from ethyl acetate (100 mL) to give Compound 425C. LC-MS (ESI) m/z: 224 [M+H]$^+$; $^1$H-NMR (CDCl$_3$, 400 MHz): δ (ppm) 7.67-7.69 (m, 2H), 7.96-7.98 (m, 2H), 8.49-8.50 (m, 1H).

To a solution of Compound 425C (3.25 g, 14.5 mmol) in DMF (50 mL) was added NaH (696 mg, 17.4 mmol) in portions at 0° C., followed by addition of SEMCl (2.9 g, 17.4 mmol). The mixture was stirred at room temperature for 3 hours, diluted with ethyl acetate (200 mL), washed with water (200 mL×3) and brine (50 mL), dried over anhydrous sodium sulfate, concentrated, and purified with flash column chromatography on silica gel (ethyl acetate in petroleum ether, 20% v/v) to afford Compound 425D. LC-MS (ESI) m/z: 354 [M+H]$^+$.

Compounds 425E, 425F, 425G, 425H, 425I, 425J, 425K, and 425 were synthesized by employing the procedures described for Compounds 8B, 141, 279D, 393F-1, 340F, 403H, 8F, and 1 using 4,4,5,5-tetramethyl-2-(1,4-dioxaspiro[4.5]dec-7-en-8-yl)-1,3,2-dioxaborolane, Compounds 425D with K$_2$CO$_3$ as base and 1,4-dioxane/H$_2$O as solvent, 425E with MeOH as solvent, 425F with TFA as acid and dichloromethane as solvent, 425G, 425H, 425I with K$_2$CO$_3$ as base, 425J, and 425K in lieu of (3,4-dichlorophenyl)boronic acid, Compounds 8A with Cs$_2$CO$_3$ as base and DME/H$_2$O as solvent, 140 with EtOAc as solvent, 279C with HCl as acid and 1,4-dioxane as solvent, 393E, 340E, 403G with Cs$_2$CO$_3$ as base, 8E, and 1E. Compound 425E: LC-MS (ESI) m/z: 414 [M+H]$^+$. Compound 425F: LC-MS (ESI) m/z: 416 [M+H]$^+$. Compound 425G: LC-MS (ESI) m/z: 372 [M+H]$^+$. Compound 425H: LC-MS (ESI) m/z: 374 [M+H]$^+$. Compound 425I: LC-MS (ESI) m/z: 452 [M+H]$^+$. Compound 425J: LC-MS (ESI) m/z: 633 [M+H]$^+$. Compound 425K: LC-MS (ESI) m/z: 605 [M+H]$^+$. Compound 425: LC-MS (ESI) m/z: 355 [M+H]$^+$; $^1$H-NMR (DMSO-d$_6$, 400 MHz): δ (ppm) 1.57-1.66 (m, 4H), 1.89-1.92 (m, 2H), 2.25-2.27 (m, 2H), 2.60-2.70 (m, 1H), 4.61-4.70 (m, 1H), 7.34-7.44 (m, 2H), 7.92-8.01 (m, 2H), 8.58 (s, 1H), 12.80 (bs, 1H), 14.02-14.35 (m, 1H), 14.72 (s, 1H).

730

Example 426

Synthesis of 4-((trans)-3-(4-(piperidin-1-yl)phenyl)cyclobutoxy)-1H-1,2,3-triazole-5-carboxylic acid 2,2,2-trifluoroacetate (426)

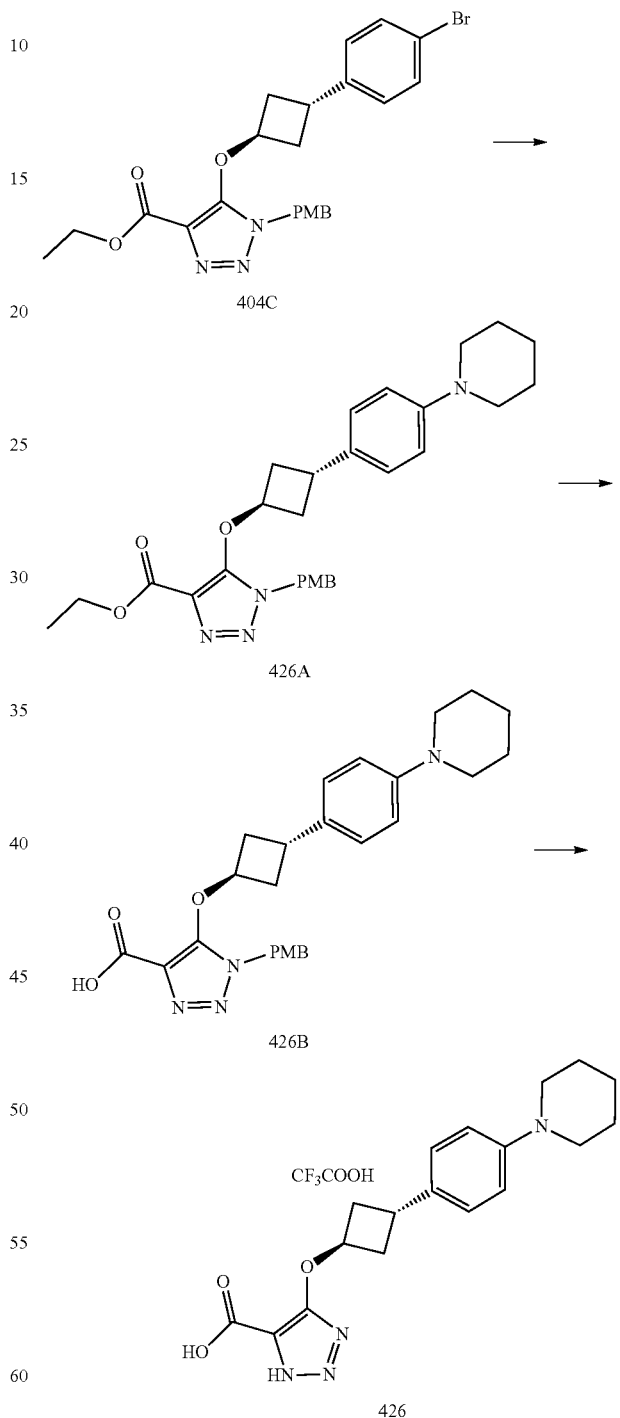

Compounds 426A, 426B, and 426 were synthesized by employing the procedures described for Compounds 6B, 8F, and 1 using piperidine, Compounds 404C with Cs$_2$CO$_3$ as base and 1,4-dioxane as solvent, 426A, and 426B in lieu of 1-methylpiperazine, Compounds 6A with tBuONa as base and toluene as solvent, 8E, and 1E. Compound 426A: LC-MS (ESI) m/z: 491 [M+H]+; 1H-NMR (CDCl3, 400 MHz): δ (ppm) 1.40 (t, J=7.2 Hz, 3H), 1.57-1.71 (m, 8H), 2.38-2.46 (m, 4H), 3.11-3.13 (m, 3H), 3.78 (s, 3H), 4.39 (q, J=7.2 Hz, 2H), 5.38 (s, 2H), 5.61-5.66 (m, 1H), 6.89 (d, J=8.4 Hz, 4H), 7.00-7.04 (m, 2H), 7.24-7.30 (m, 2H). Compound 426B: LC-MS (ESI) m/z: 463 [M+H]+. Compound 426: LC-MS (ESI) m/z: 343 [M+H]+; 1H-NMR (CD3OD, 400 MHz): δ (ppm) 1.81-1.83 (m, 2H), 2.03-2.06 (m, 4H), 2.63-2.69 (m, 2H), 2.74-2.81 (m, 2H), 3.62-3.65 (m, 4H), 3.81-3.89 (m, 1H), 5.22-5.28 (m, 1H), 7.56 (d, J=8.8 Hz, 2H), 7.62 (d, J=8.4 Hz, 2H).

Example 427

Synthesis of 4-(((3aR,5s,6aS)-2-(3,4-dichlorophenyl)octahydrocyclopenta[c]pyrrol-5-yl)oxy)-1H-1,2,3-triazole-5-carboxylic acid (427)

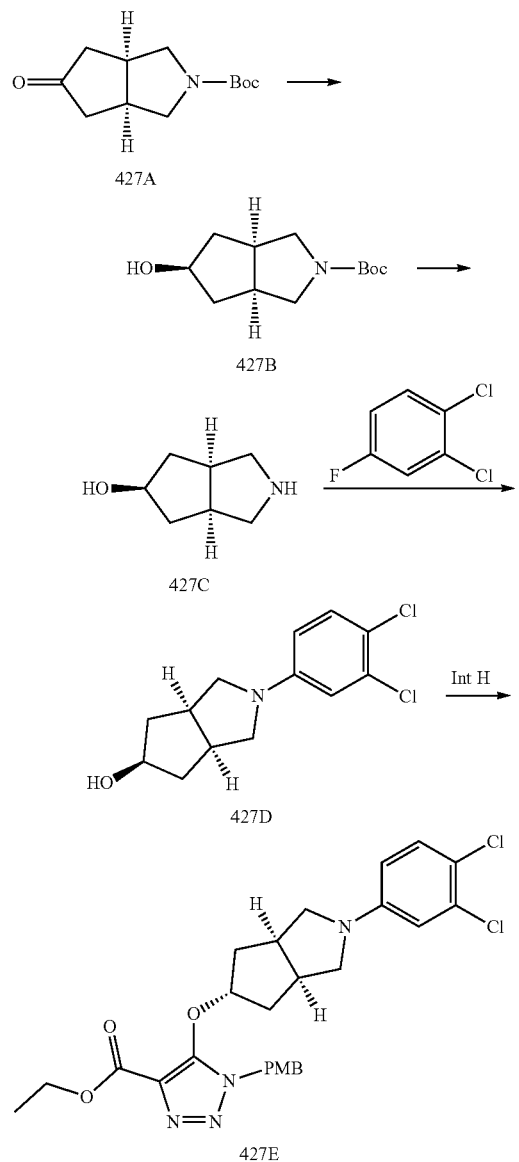

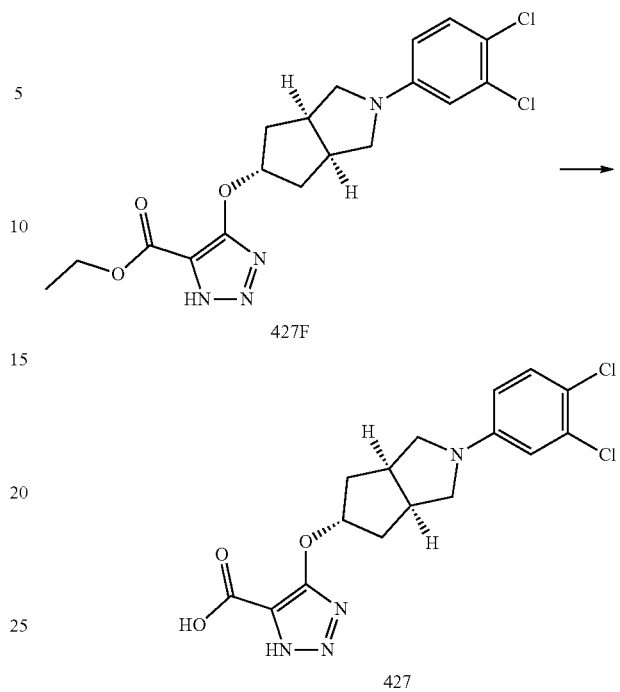

Compounds 427B, 427C, 427D, 427E, 427F, and 427 were synthesized by employing the procedures described for Compounds 57C, 175E, 297C, 90C, 1, and 8F using Compounds 427A, 427B with HCl as acid and 1,4-dioxane as solvent, 1,2-dichloro-4-fluorobenzene, 427C at 100° C., 427D, 427E, and 425F in lieu of Compounds 57B, and 175D with TFA as acid and dichloromethane as solvent, 297A, 297B at 70° C., 90B, 1E, and 8E. Compound 427B: LC-MS (ESI) m/z: 228 [M+H]+. Compound 427C: LC-MS (ESI) m/z: 128 [M+H]+. Compound 427D: LC-MS (ESI) m/z: 272 [M+H]+. Compound 427E: LC-MS (ESI) m/z: 531 [M+H]+. Compound 427F: LC-MS (ESI) m/z: 411 [M+H]+. Compound 427: LC-MS (ESI) m/z: 383 [M+H]+; 1H-NMR (CD3OD, 400 MHz) δ (ppm) 1.90-1.96 (m, 2H), 2.28-2.35 (m, 2H), 3.07-3.08 (m, 2H), 3.19-3.22 (m, 2H), 3.31-3.36 (m, 2H), 5.29-5.30 (m, 1H), 6.55-6.58 (m, 1H), 6.74 (d, J=2.8 Hz, 1H), 7.24 (d, J=8.0 Hz, 1H).

Example 428

Synthesis of 4-(((3aR,5s,6aS)-2-(3,4-dichlorophenyl)octahydrocyclopenta[c]pyrrol-5-yl)thio)-1H-1,2,3-triazole-5-carboxylic acid (428)

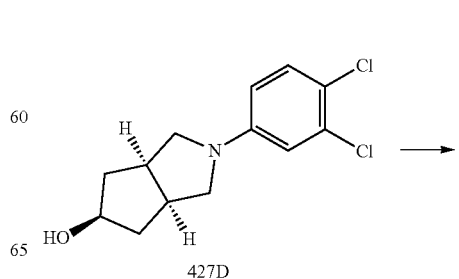

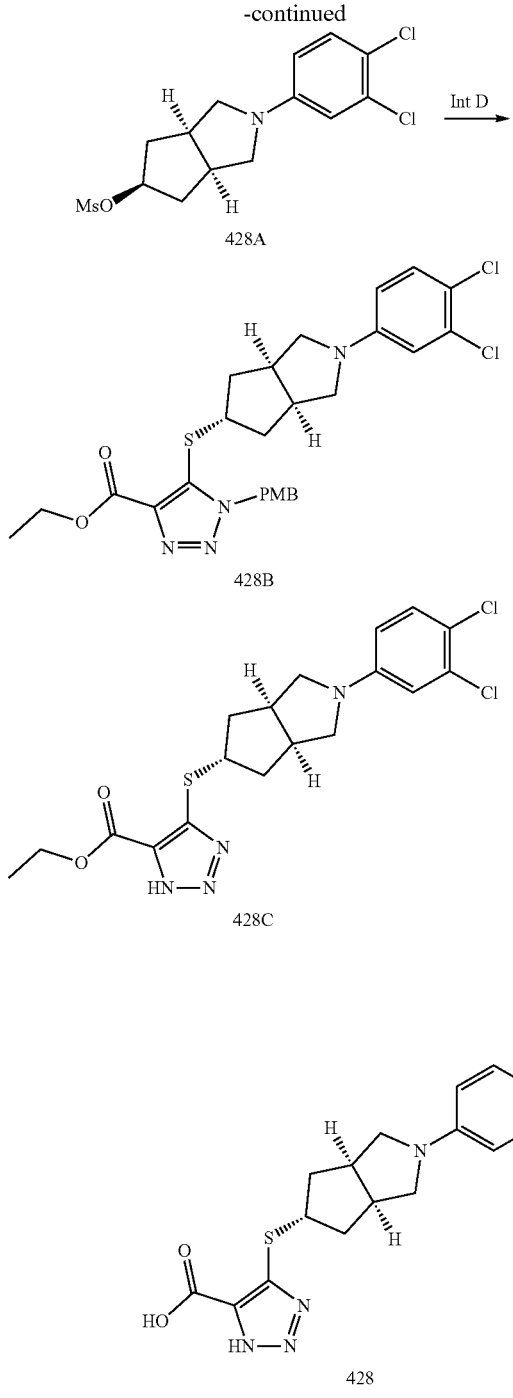

Example 429

Synthesis of 4-((1-(2-chloro-5-(trifluoromethoxy)phenyl)piperidin-4-yl)oxy)-1H-1,2,3-triazole-5-carboxylic acid (429)

Compounds 428A, 428B, 428C, and 428 were synthesized by employing the procedures described for Compounds 340F, 340G, 1, and 8F using Compounds 427D, 428A, 428B, and 428C in lieu of Compounds 340E, 340F, 1E, and 8E. Compound 428A: LC-MS (ESI) m/z: 350 [M+H]⁺. Compound 428B: LC-MS (ESI) m/z: 547 [M+H]⁺. Compound 428C: LC-MS (ESI) m/z: 427 [M+H]⁺. Compound 428: LC-MS (ESI) m/z: 399 [M+H]⁺; ¹H-NMR (CD₃OD, 400 MHz): δ (ppm) 1.98-2.03 (m, 2H), 2.08-2.12 (m, 2H), 3.03-3.06 (m, 2H), 3.14-3.17 (m, 2H), 3.35-3.39 (m, 2H), 4.09-4.13 (m, 1H), 6.55-6.58 (m, 1H), 6.73 (d, J=2.4 Hz, 1H), 7.39 (d, J=8.8 Hz, 1H).

Compounds 429A, 429B, and 429 were synthesized by employing the procedures described for Compounds 403H, 8F, and 1 using Compounds 402B, 428A, and 429B in lieu of Compounds 403G, 8E, and 1E. Compound 429A: LC-MS (ESI) m/z: 555 [M+H]⁺. Compound 429B: LC-MS (ESI) m/z: 527 [M+H]⁺. Compound 429: LC-MS (ESI) m/z: 407 [M+H]+; ¹H-NMR (DMSO-d₆, 400 MHz): δ (ppm) 1.85-1.87 (m, 2H), 2.12-2.15 (m, 2H), 2.90-2.96 (m, 2H), 3.2-3.24 (m, 2H), 4.8 (m, 1H), 7.01 (d, J=12 Hz, 1H), 7.08 (s, 1H), 7.53 (d, J=8.8 Hz, 1H).

Example 430

Synthesis of 4-(((trans)-4-(5-chloro-2-(trifluoromethoxy)phenyl)cyclohexyl)thio)-1H-1,2,3-triazole-5-carboxylic acid (430)

Example 431

Synthesis of 4-(((trans)-4-(4-(1,3,4-thiadiazol-2-yl)phenyl)cyclohexyl)oxy)-1H-1,2,3-triazole-5-carboxylic acid 2,2,2-trifluoroacetate (431)

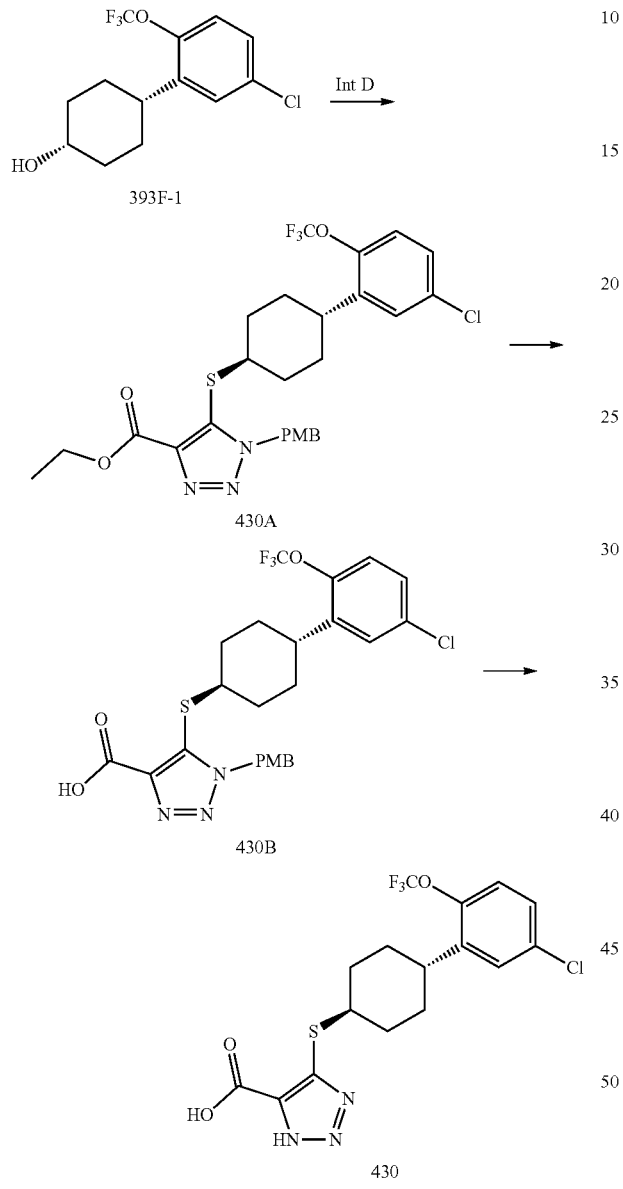

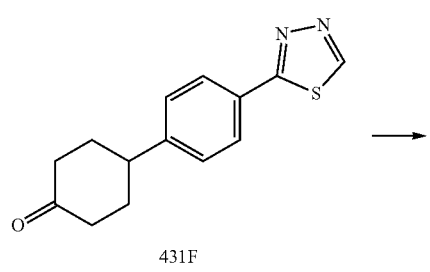

Compounds 430A, 430B, and 430 were synthesized by employing the procedures described for Compounds 90C, 8F, and 1 using Intermediate D, Compounds 393F-1, 430A, and 430B in lieu of Intermediate H, Compounds 90B, 8E, and 1E. Compound 430A: LC-MS (ESI) m/z: 570 [M+H]$^+$. Compound 430B: LC-MS (ESI) m/z: 542 [M+H]$^+$. Compound 430: LC-MS (ESI) m/z: 422 [M+H]$^+$; $^1$H-NMR (DMSO-$d_6$, 400 MHz): δ (ppm) 1.50-1.54 (m, 2H), 1.69-1.75 (m, 4H), 2.20-2.23 (m, 2H), 2.88-2.89 (m, 1H), 3.61-3.63 (m, 1H), 7.35-7.41 (m, 2H), 7.60-7.61 (m, 1H).

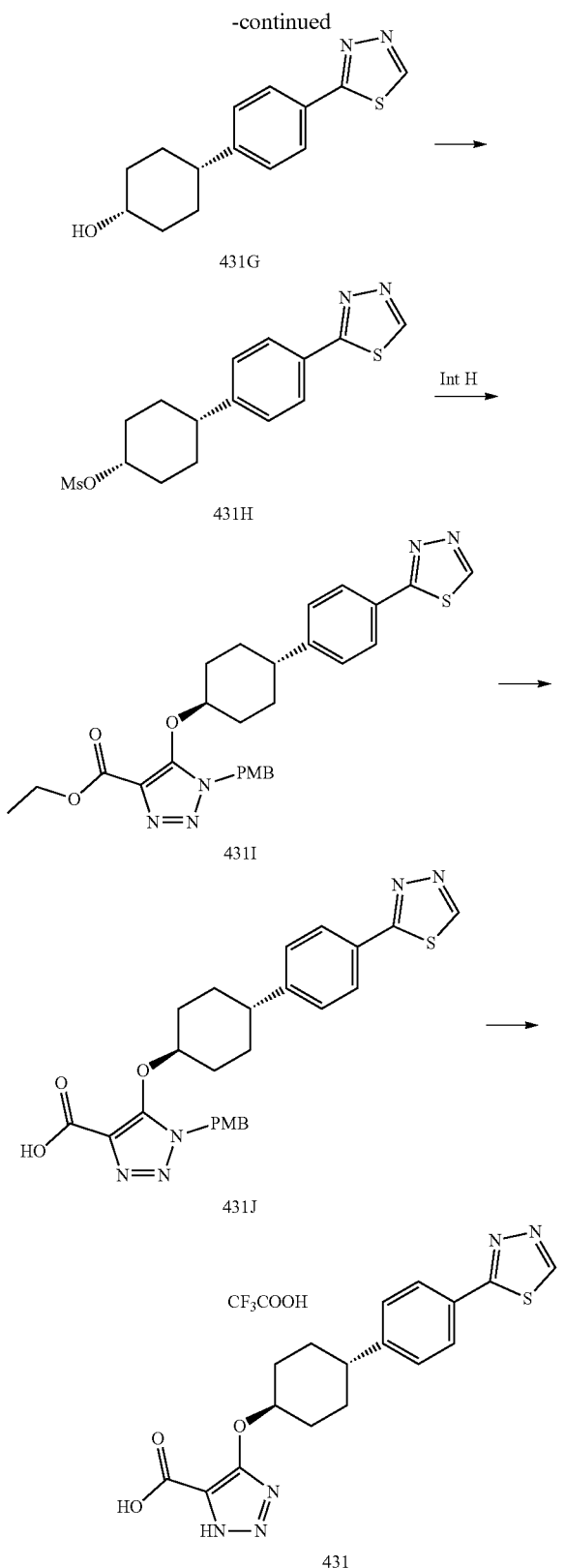

trated under reduced pressure. The residue was purified by column chromatography on silica gel (ethyl acetate in petroleum ether, 50% v/v) to furnish Compound 431B. LC-MS (ESI) m/z: 243 [M+H]$^+$.

To a solution of Compound 431B (400 mg, 1.65 mmol) in toluene (12 mL) was added Lawesson's reagent (1.0 g, 2.47 mmol) and heated in a microwave reactor at 90° C. for 30 minutes and concentrated under reduced pressure. The residue was purified by column chromatography on silica gel (ethyl acetate in petroleum ether, 10% v/v) to furnish Compound 431C. LC-MS (ESI) m/z: 241 [M+H]$^+$.

Compounds 431D, 431E, 431F, 431G, 431H, 431I, 431J, and 431 were synthesized by employing the procedures described for Compounds 8B, 141, 279D, 393F-1 and 393F-2, 340F, 403H, 8F, and 1 using 4,4,5,5-tetramethyl-2-(1,4-dioxaspiro[4.5]dec-7-en-8-yl)-1,3,2-dioxaborolane, Compounds 431C with Na$_2$CO$_3$ as base and 1,4-dioxane/H$_2$O as solvent, 431D with MeOH as solvent, 431E with TFA as acid and dichloromethane as solvent, 431F, 431G, 431H with K$_2$CO$_3$ as base, 431I, and 431J in lieu of (3,4-dichlorophenyl)boronic acid, Compounds 8A with Cs$_2$CO$_3$ as base and DME/H$_2$O as solvent, 140 with EtOAc as solvent, 279C with HCl as acid and 1,4-dioxane as solvent, 393E, 340E, 403G with Cs$_2$CO$_3$ as base, 8E, and 1E. Compound 431D: LC-MS (ESI) m/z: 301 [M+H]$^+$. Compound 431E: LC-MS (ESI) m/z: 303 [M+H]$^+$. Compound 431F: LC-MS (ESI) m/z: 259 [M+H]$^+$. Compound 431G: LC-MS (ESI) m/z: 261 [M+H]$^+$. Compound 431H: LC-MS (ESI) m/z: 339 [M+H]$^+$. Compound 43H: LC-MS (ESI) m/z: 520 [M+H]$^+$. Compound 431J: LC-MS (ESI) m/z: 492 [M+H]$^+$. Compound 431: LC-MS (ESI) m/z: 372 [M+H]$^+$; $^1$H-NMR (DMSO-d$_6$, 400 MHz): δ (ppm) 1.53-1.69 (m, 4H), 1.88-1.91 (m, 2H), 2.23-2.31 (m, 2H), 2.65-2.70 (m, 1H), 4.67-4.69 (m, 1H), 7.45 (d, J=8.4 Hz, 2H), 7.92 (d, J=8.4 Hz, 2H), 9.59 (s, 1H).

Example 432

Synthesis of 4-(((trans)-4-(4-(piperidin-1-yl)phenyl)cyclohexyl)thio)-1H-1,2,3-triazole-5-carboxylic acid 2,2,2-trifluoroacetate (432)

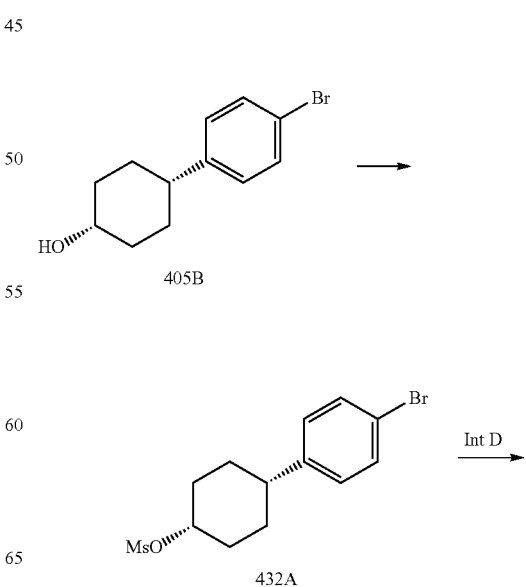

To a solution of 4-bromobenzohydrazide 431A (460 mg, 2.15 mmol) in toluene (12 mL) was dropped neat formic acid (1.5 g, 32.6 mmol) over 10 minute, heated in a microwave reactor at 120° C. for 90 minutes, and concen-

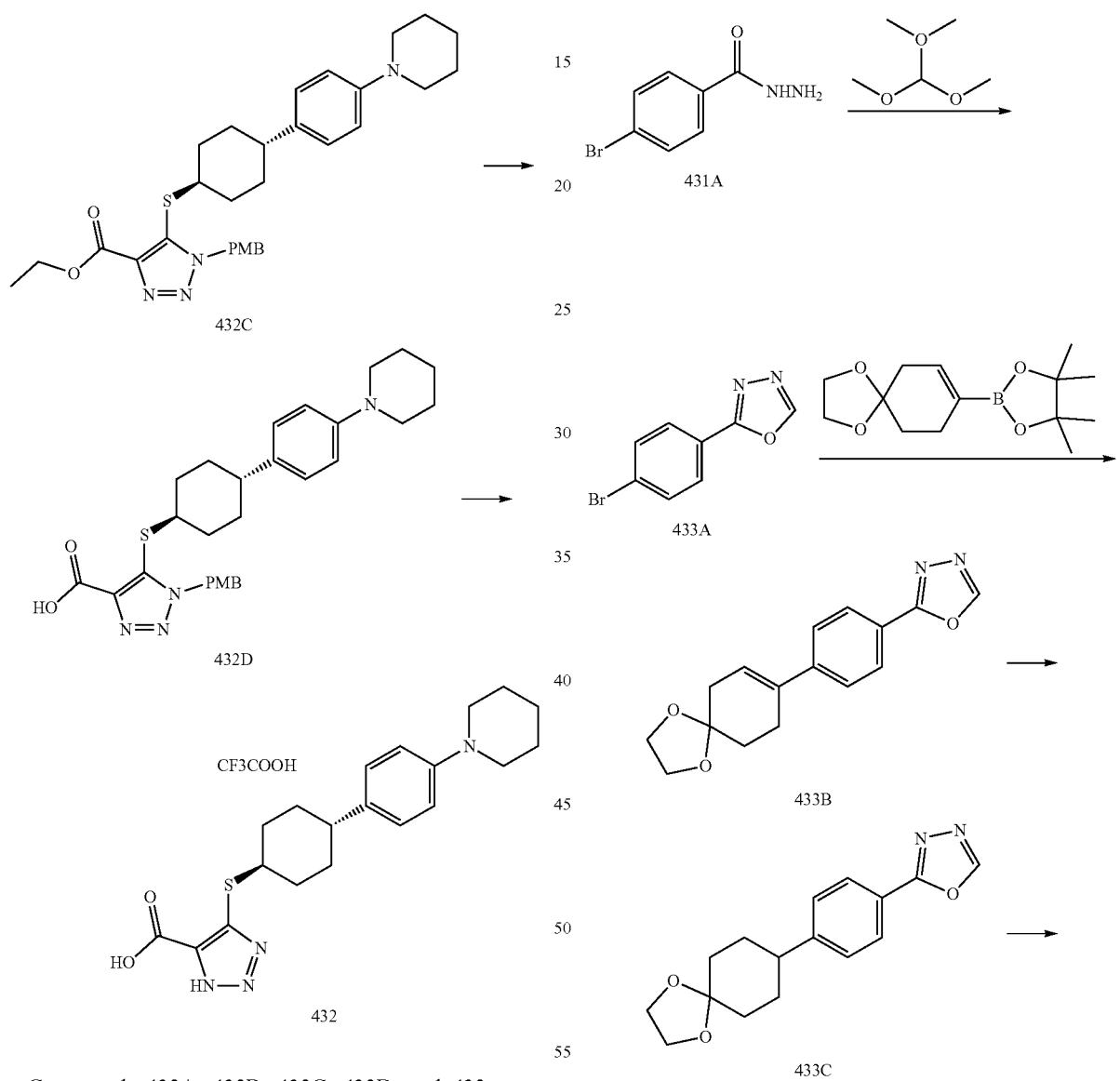

(ppm) 1.50-1.60 (m, 6H), 1.75 (s, 4H), 1.84 (d, J=10.8 Hz, 2H), 2.20 (d, J=8.4 Hz, 2H), 3.42 (s, 6H), 7.25 (s, 4H).

Example 433

Synthesis of 4-(((trans)-4-(4-(1,3,4-oxadiazol-2-yl)phenyl)cyclohexyl)oxy)-1H-1,2,3-triazole-5-carboxylic acid (433)

Compounds 432A, 432B, 432C, 432D, and 432 were synthesized by employing the procedures described for Compounds 340F, 340G, 6B, 8F, and 1 using Compounds 405B, 432A, piperidine, 432B with 1,4-dioxane as solvent, 432C, and 432D in lieu of Compounds 340E, 340F, 1-methylpiperazine, 6A with toluene as solvent, 8E, and 1E. Compound 432A: LC-MS (ESI) m/z: 355 [M+Na]⁺. Compound 432B: LC-MS (ESI) m/z: 530 [M+H]⁺. Compound 432C: LC-MS (ESI) m/z: 535 [M+H]⁺. Compound 432D: LC-MS (ESI) m/z: 507 [M+H]⁺. Compound 432: LC-MS (ESI) m/z: 387 [M+H]⁺. ¹H-NMR (DMSO-d₆, 400 MHz): δ

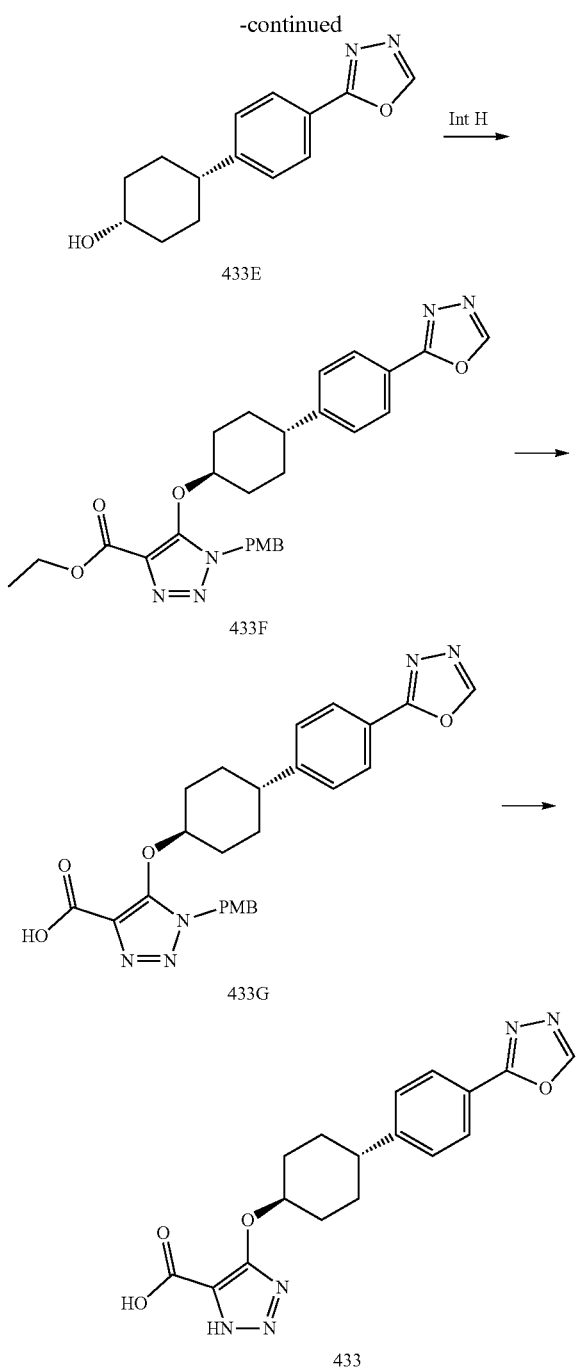

(3,4-dichlorophenyl)boronic acid, Compounds 8A with Cs$_2$CO$_3$ as base and DME/H$_2$O as solvent, 140 with EtOAc as solvent, 279C with HCl as acid and 1,4-dioxane as solvent, 393E, 90B, 8E, and 1E. Compound 433B: LC-MS (ESI) m/z: 285 [M+H]$^+$. Compound 433C: LC-MS (ESI) m/z: 287 [M+H]$^+$. Compound 433D: LC-MS (ESI) m/z: 243 [M+H]$^+$. Compound 433E: LC-MS (ESI) m/z: 245 [M+H]$^+$. Compound 433F: LC-MS (ESI) m/z: 504 [M+H]$^+$. Compound 433G: LC-MS (ESI) m/z: 476 [M+H]$^+$. Compound 433: LC-MS (ESI) m/z: 356 [M+H]$^+$; $^1$H NMR (DMSO-d$_6$, 400 MHz) δ 1.44-1.65 (m, 4H), 1.85-1.89 (s, 2H), 2.18-2.22 (m, 2H), 2.66-2.69 (m, 1H), 4.68-4.72 (m, 1H), 7.51 (d, J=7.9 Hz, 2H), 7.95 (d, J=7.9 Hz, 2H), 9.32 (s, 1H).

Example 434

Synthesis of 4-(((trans)-3-(4-(piperidin-1-yl)phenyl) cyclobutyl)thio)-1H-1,2,3-triazole-5-carboxylic acid 2,2,2-trifluoroacetate (434)

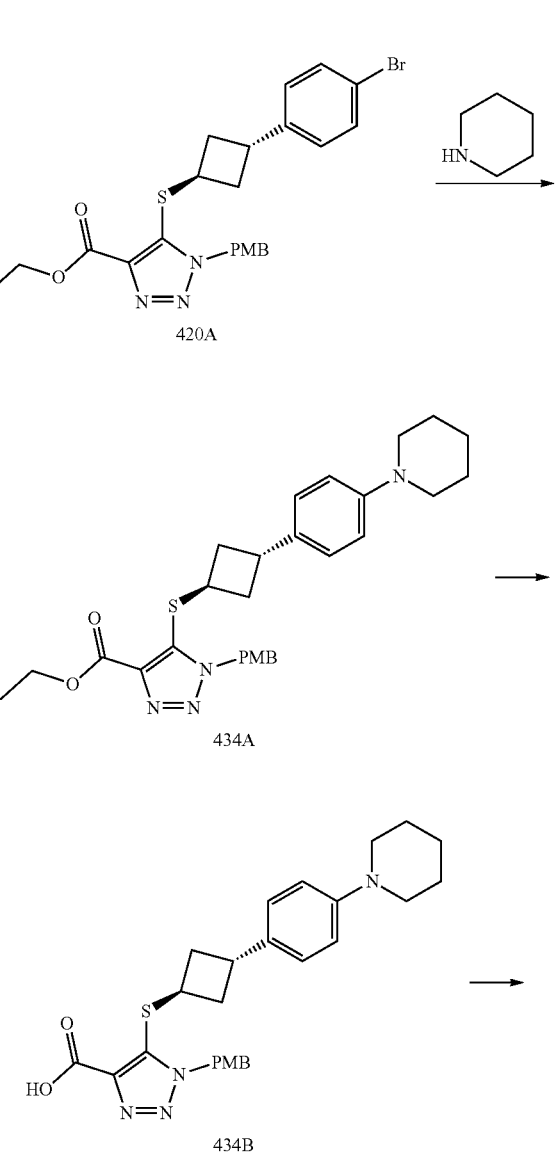

A mixture of 4-bromobenzohydrazide (431A) (5.0 g, 23.36 mmol) and triethoxymethane (50 mL) was stirred at 120° C. for 12 hours and concentrated under reduced pressure. The residue was slurred in petroleum ether (200 mL) for 15 minutes and filtered to afford Compound 433A. LC-MS (ESI) m/z: 225 [M+H]$^+$.

Compounds 433B, 433C, 433D, 433E, 433F, 433G, and 433 were synthesized by employing the procedures described for Compounds 8B, 141, 279D, 393F-1, 90C, 8F, and 1 using 4,4,5,5-tetramethyl-2-(1,4-dioxaspiro[4.5]dec-7-en-8-yl)-1,3,2-dioxaborolane, Compounds 433A with K$_2$CO$_3$ as base and 1,4-dioxane/H$_2$O as solvent, 433B with MeOH as solvent, 433C with TFA as acid and dichloromethane as solvent, 433D, 433E, 433F, and 433G in lieu of

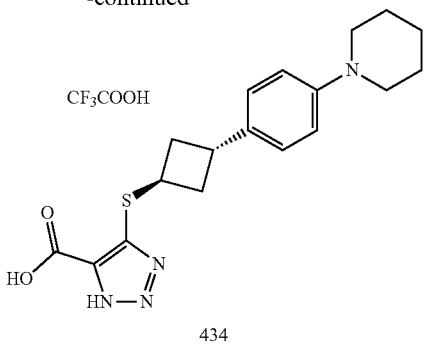

Compounds 434A, 434B, and 434 were synthesized by employing the procedures described for Compounds 6B, 8F, and 1 using piperidine, Compounds 420A with Cs₂CO₃ as base and 1,4-dioxane as solvent, 434A, and 434B in lieu of 1-methylpiperazine, Compounds 6A with t-BuONa as base and toluene as solvent, 8E, and 1E. Compound 434A: LC-MS (ESI) m/z: 507 [M+H]⁺. Compound 434B: LC-MS (ESI) m/z: 479 [M+H]⁺. Compound 434: LC-MS (ESI) m/z: 359 [M+H]⁺; ¹H-NMR (CD₃OD, 400 MHz): δ (ppm) 1.77-1.83 (m, 2H), 2.00-2.06 (m, 4H), 2.48-2.54 (m, 2H), 2.74-2.82 (m, 2H), 3.59-3.62 (m, 4H), 3.93-4.01 (m, 1H), 4.24-4.30 (m, 1H), 7.52 (d, J=8.8 Hz, 2H), 7.58 (d, J=8.8 Hz, 2H).

Example 435

Synthesis of 4-((spiro[4.5]decan-8-ylthio)methyl)-1H-1,2,3-triazole-5-carboxylic acid (435)

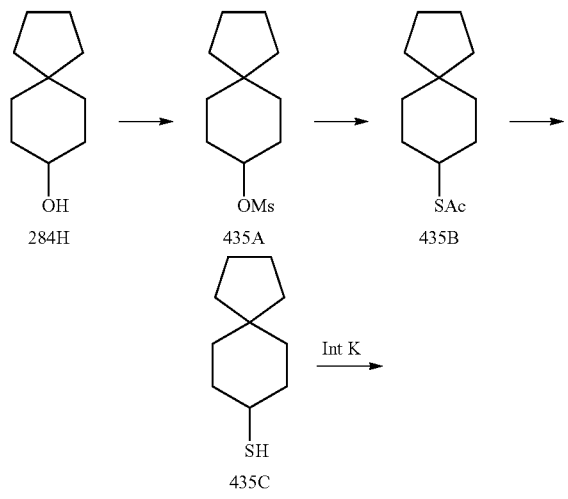

Compounds 435A, 435B, 435C, 435D, 435E, and 435 were synthesized by employing the procedures described for Compounds 340F, 350C, 350D, 243B, 256, and 8F using Compounds 284H, 435A, 435B, 435C with DMF solvent, 435D with TFA as both acid and solvent, and 435E in lieu of Compounds 340E, 350B, 350C, 243A with NMPF solvent, 256D with TFA as acid and dichloromethane as solvent, and 8E. Compound 435A: ¹H-NMR (CDCl₃, 400 MHz): δ (ppm) 1.30-1.45 (m, 6H), 1.55-1.63 (m, 6H), 1.69-1.80 (m, 2H), 1.87-1.96 (m, 2H), 3.00 (s, 3H), 4.67-4.75 (m, 1H). Compound 435B: ¹H-NMR (CDCl₃, 400 MHz): δ (ppm) 1.34-1.52 (m, 10H), 1.55-1.60 (m, 4H), 1.80-1.88 (m, 2H), 2.29 (s, 3H) 3.42-3.52 (m, 1H). Compound 435C: ¹H-NMR (CDCl₃, 400 MHz): δ (ppm) 1.22-1.54 (m, 14H), 1.78-1.85 (m, 2H), 2.66-2.76 (m, 1H). Compound 435D: LC-MS (ESI) m/z: 444 [M+H]⁺. Compound 435E: LC-MS (ESI) m/z: 416 [M+H]⁺. Compound 435: LC-MS (ESI) m/z: 296 [M+H]⁺; ¹H-NMR (DMSO-d₆, 400 MHz): δ (ppm) 1.17-1.37 (m, 8H), 1.41-1.57 (m, 6H), 1.72-1.84 (m, 2H), 2.54-2.68 (m, 1H), 3.97-4.07 (m, 2H), 13.17 (br, 1H), 15.26, 15.64 (brs, 1H).

Example 436

Synthesis of 4-(((trans)-4-(4-(piperidin-1-yl)phenyl)cyclohexyl)oxy)-1H-1,2,3-triazole-5-carboxylic acid 2,2,2-trifluoroacetate (436)

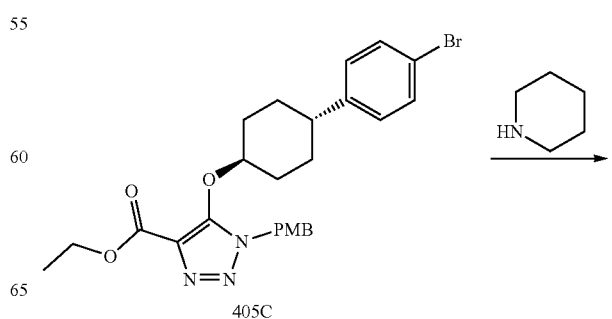

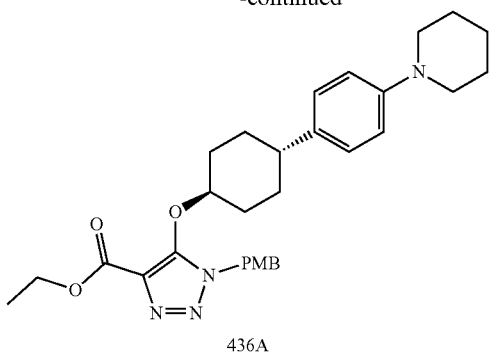

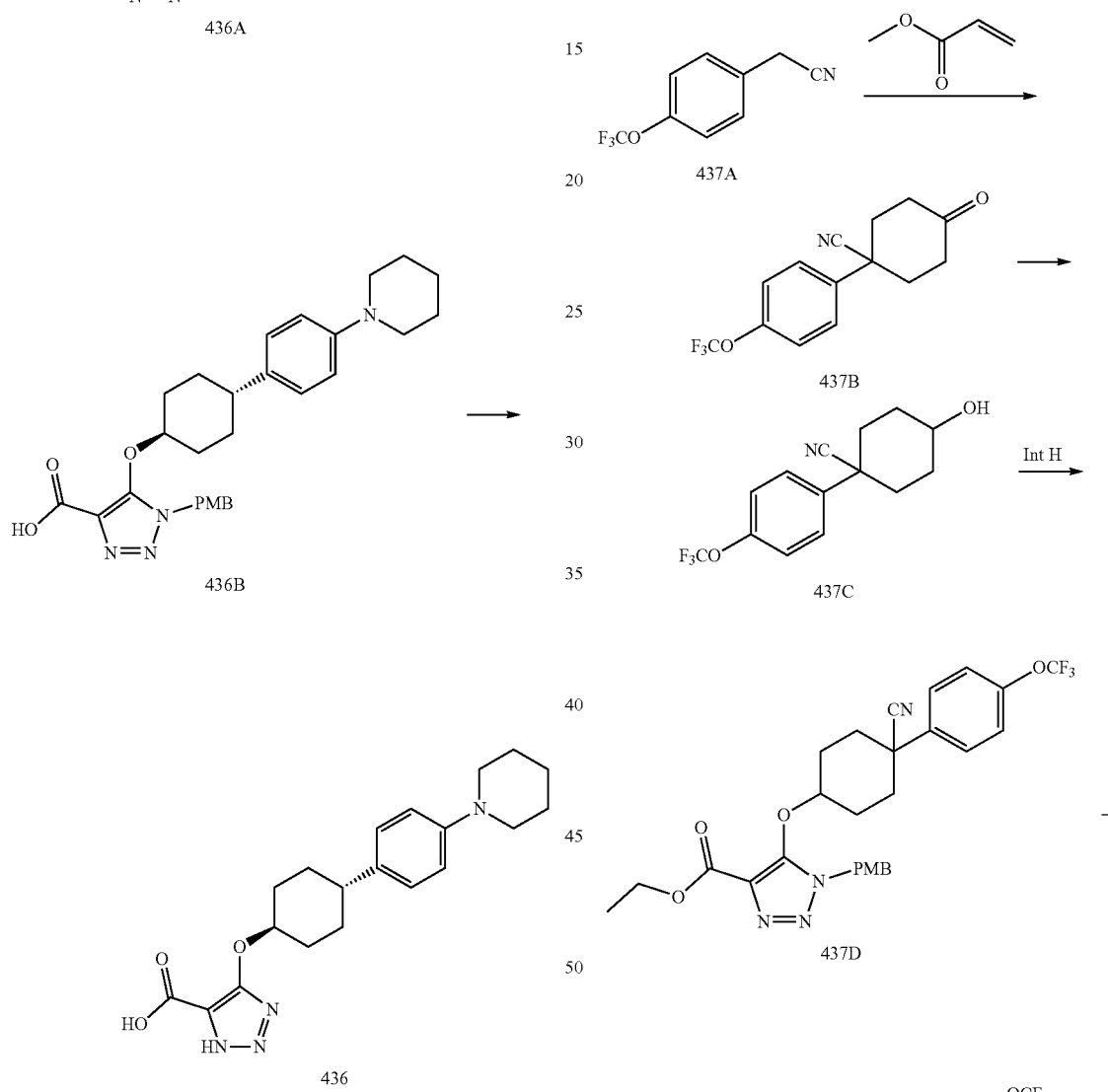

400 MHz): δ (ppm) 1.47-1.64 (m, 6H), 1.76-1.83 (m, 6H), 2.21-2.23 (m, 2H), 2.58-2.66 (m, 1H), 3.11-3.18 (m, 4H), 4.64-4.66 (m, 1H), 7.22-7.50 (m, 4H), 14.71 (s, 1H).

Example 437

Synthesis of 4-((4-cyano-4-(4-(trifluoromethoxy)phenyl)cyclohexyl)oxy)-1H-1,2,3-triazole-5-carboxylic acid (437)

Compounds 436A, 436B, and 436 were synthesized by employing the procedures described for Compounds 6B, 8F, and 256 using piperidine, Compounds 405C with X-phos as ligand and Cs₂CO₃ as base and 1,4-dioxane as solvent, 436A, and 436B with TFA as both base and solvent in lieu of 1-methylpiperazine, Compounds 6A with Xantphos as ligand and t-BuONa as base and toluene as solvent, 8E, and 256D with TFA as base and dichloromethane as solvent. Compound 436A: LC-MS (ESI) m/z: 519 [M+H]⁺. Compound 436B: LC-MS (ESI) m/z: 491 [M+H]⁺. Compound 436: LC-MS (ESI) m/z: 371 [M+H]⁺. ¹H-NMR (DMSO-d₆, -continued

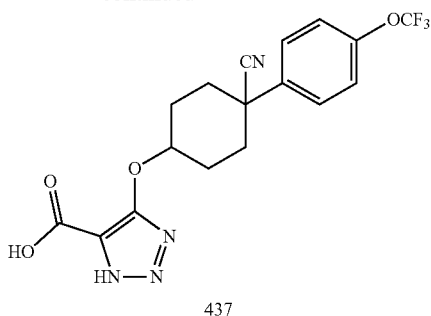

437

To a solution of 2-(4-(trifluoromethoxy)phenyl)acetonitrile (437A, 32.8 g, 163 mmol) and methyl acrylate (28.1 g, 326 mmol) in THF (475 mL) at room temperature was added potassium t-butoxide (55 g, 489 mmol), and stirred at room temperature for one hour, followed by addition of water (2.4 L). The mixture was stirred at 70° C. for 2 hours and extracted with ethyl acetate (500 mL×3). The combined extracts was dried over anhydrous sodium sulphate, filtered, and evaporated under reduced pressure. The residue was purified by column chromatography on silica gel (eluted with ethyl acetate in petroleum ether from 5% to 35%) to afford Compound 437B. LC-MS (ESI) m/z: 284 [M+H]$^+$; $^1$H-NMR (CDCl$_3$, 400 MHz) δ (ppm) 2.19-2.34 (m, 2H), 2.45-2.51 (m, 2H), 2.67-2.56 (m, 2H), 2.89-2.95 (m, 2H), 7.29 (d, J=8.2 Hz, 2H), 7.54-7.61 (m, 2H).

Compounds 437C, 437D, 437E, and 437 were synthesized by employing the procedures described for Compounds 57C, 90C, 8F, and 1 using Compounds 437B, 437C, 437D, and 437E in lieu of Compounds 57B, 90B, 8E, and 1E. Compound 437C: LC-MS (ESI) m/z: 286 [M+H]$^+$; $^1$H-NMR (CDCl$_3$, 400 MHz) δ (ppm) 1.83-1.95 (m, 4H), 2.14-2.26 (m, 4H), 3.61-3.78 (m, 1H), 7.25 (d, J=8.3 Hz, 2H), 7.55-7.49 (m, 2H). Compound 437D: LC-MS (ESI) m/z: 545 [M+H]$^+$; $^1$H-NMR (CDCl$_3$, 400 MHz) δ (ppm) 1.44 (t, J=7.1 Hz, 3H), 1.90-1.99 (m, 4H), 2.08-2.18 (m, 4H), 3.74 (s, 3H), 4.42 (q, J=7.1 Hz, 2H), 5.35 (s, 2H), 5.42-5.49 (m, 1H), 6.80 (d, J=8.6 Hz, 2H), 7.09 (d, J=8.6 Hz, 2H), 7.21-7.27 (m, 2H), 7.37 (d, J=8.8 Hz, 2H). Compound 437E: LC-MS (ESI) m/z: 517 [M+H]$^+$. Compound 437: LC-MS (ESI) m/z: 397 [M+H]$^+$; $^1$H-NMR (DMSO-d$_6$, 400 MHz) δ (ppm) 1.94-1.99 (m, 4H), 2.10-2.33 (m, 4H), 5.04 (s, 1H), 7.46 (d, J=8.3 Hz, 2H), 7.69 (d, J=8.8 Hz, 2H).

Example 438

Synthesis of 4-(((trans)-4-(4-(methylsulfonyl)phenyl)cyclohexyl)oxy)-1H-1,2,3-triazole-5-carboxylic acid (438)

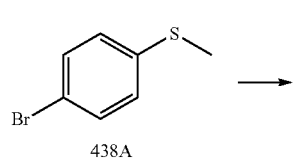

438A

-continued

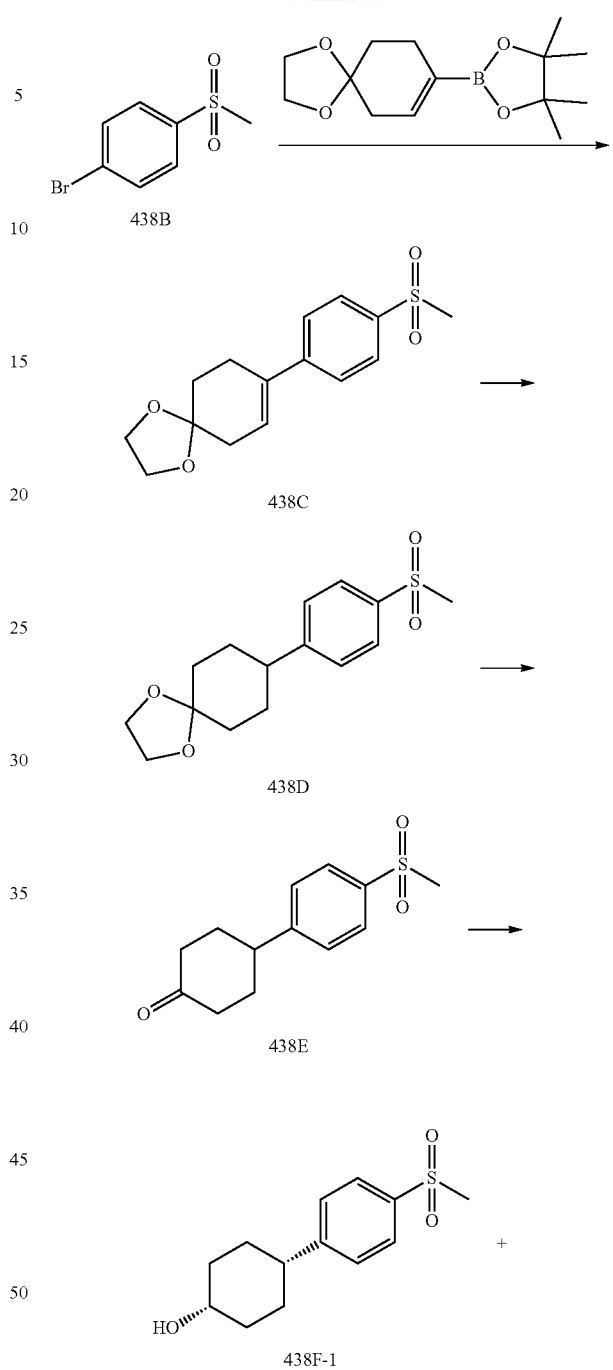

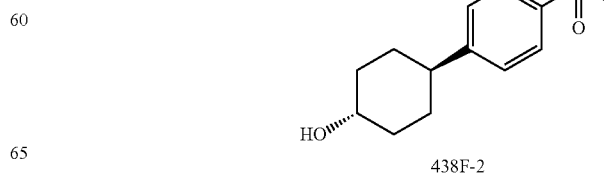

438F-2

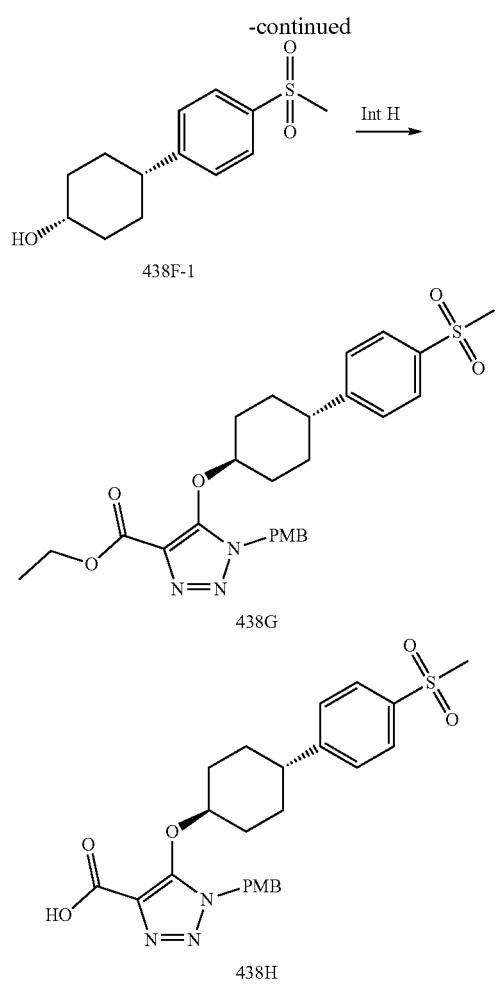

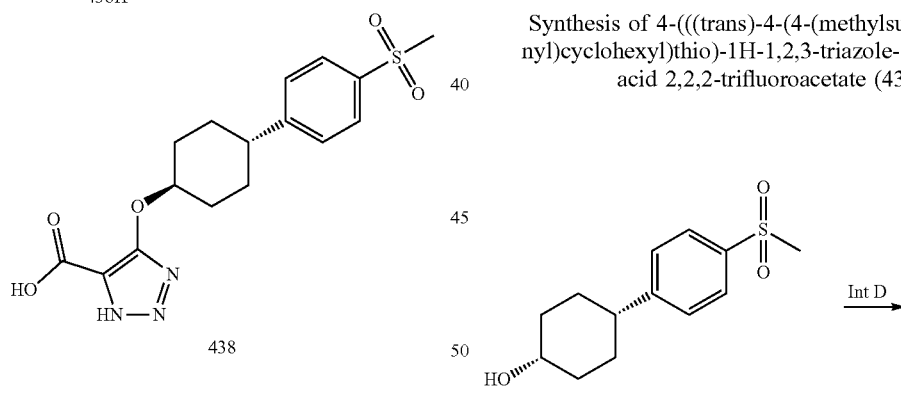

To a solution of (4-bromophenyl)(methyl)sulfane (438A, 4.5 g, 22.17 mmol) in dichloromethane (100 mL) was added m-chlorobenzoperoxoic acid (11.44 g, 66.51 mmol) in several portions at 0° C., stirred at room temperature for 16 hours, and filtered. The filtrate was washed with saturated aqueous NaHCO$_3$ solution (60 mL×2) and brine (60 mL), dried over anhydrous sulfate, filtered, concentrated, and purified with flash column chromatography on silica gel (ethyl acetate in petroleum ether, from 0% to 40% v/v) to furnish Compound 438B. LC-MS (ESI) m/z: 235 [M+H]$^+$; $^1$H-NMR (CDCl$_3$, 400 MHz): δ (ppm) 3.05 (s, 3H), 7.72 (d, J=8.4 Hz, 2H), 7.81 (d, J=8.8 Hz, 2H).

Compounds 438C, 438D, 438E, 438F-1 and 438F-2, 438G, 438H, and 438 were synthesized by employing the procedures described for Compounds 4B, 141, 279D, 393F-1 and 393F-2, 90C, 8F, and 1 using 4,4,5,5-tetramethyl-2-(1,4-dioxaspiro[4.5]dec-7-en-8-yl)-1,3,2-dioxaborolane, Compounds 438B with K$_2$CO$_3$ as base and 1,4-dioxane/H$_2$O as solvent, 438C, 438D with THF/MeOH as solvent, 438E, 438F-1, 438G, and 438H in lieu of (4-bromophenyl)boronic acid, Compounds 4A with Na$_2$CO$_3$ as base and toluene/EtOH/H$_2$O as solvent, 140, 279C with 1,4-dioxane as solvent, 393E, 90B, 8E, and 1E. Compound 438C: LC-MS (ESI) m/z: 295 [M+H]$^+$; $^1$H-NMR (CDCl$_3$, 400 MHz): δ (ppm) 1.94 (t, J=6.8 Hz, 2H), 2.50 (brs, 2H), 2.65-2.69 (m, 2H), 3.04 (s, 3H), 4.03 (s, 4H), 6.13-6.15 (m, 1H), 7.56 (d, J=8.4 Hz, 2H), 7.86 (d, J=8.4 Hz, 2H). Compound 438D: LC-MS (ESI) m/z: 297 [M+H]$^+$. Compound 438E: LC-MS (ESI) m/z: 253 [M+H]$^+$; $^1$H-NMR (CDCl$_3$, 400 MHz): δ (ppm) 1.91-2.02 (m, 2H), 2.23-2.26 (m, 2H), 2.52-2.55 (m, 4H), 3.05 (s, 3H), 3.10-3.17 (m, 1H), 7.45 (d, J=8.4 Hz, 2H), 7.90 (d, J=8.8 Hz, 2H). Compound 438F-1: LC-MS (ESI) m/z: 237 [M−17]$^+$; $^1$H-NMR (CDCl$_3$, 400 MHz): δ (ppm) 1.62-1.72 (m, 4H), 1.88-1.98 (m, 4H), 2.61-2.68 (m, 1H), 3.04 (s, 3H), 4.16 (brs, 1H), 7.43 (d, J=8 Hz, 2H), 7.86 (d, J=8 Hz, 2H). Compound 438F-2: LC-MS (ESI) m/z: 255 [M+H]$^+$; (CDCl$_3$, 400 MHz): δ (ppm) 1.40-1.59 (m, 4H), 1.92-1.96 (m, 2H), 2.11-2.14 (m, 2H), 2.56-2.63 (m, 1H), 3.04 (s, 3H), 3.66-3.74 (m, 1H), 7.39 (d, J=8.4 Hz, 2H), 7.86 (d, J=8.4 Hz, 2H). Compound 438G: LC-MS (ESI) m/z: 514 [M+H]$^+$. Compound 438H: LC-MS (ESI) m/z: 486 [M+H]$^+$. Compound 438: LC-MS (ESI) m/z: 366 [M+H]$^+$; $^1$H-NMR (CD$_3$OD, 400 MHz): δ (ppm) 1.67-1.78 (m, 4H), 2.00-2.02 (m, 2H), 2.38 (brs, 2H), 2.76-2.81 (m, 1H), 3.10 (s, 3H), 4.78 (brs, 1H), 7.55 (d, J=8 Hz, 2H), 7.88 (d, J=8 Hz, 2H).

Example 439

Synthesis of 4-(((trans)-4-(4-(methylsulfonyl)phenyl)cyclohexyl)thio)-1H-1,2,3-triazole-5-carboxylic acid 2,2,2-trifluoroacetate (439)

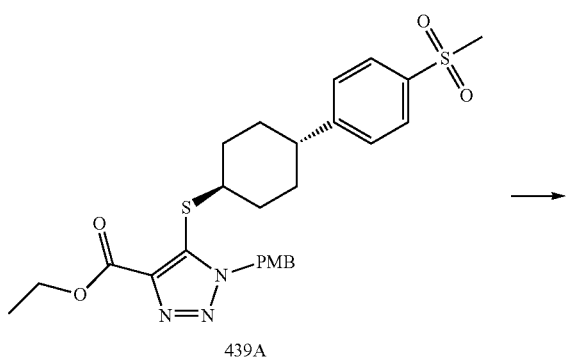

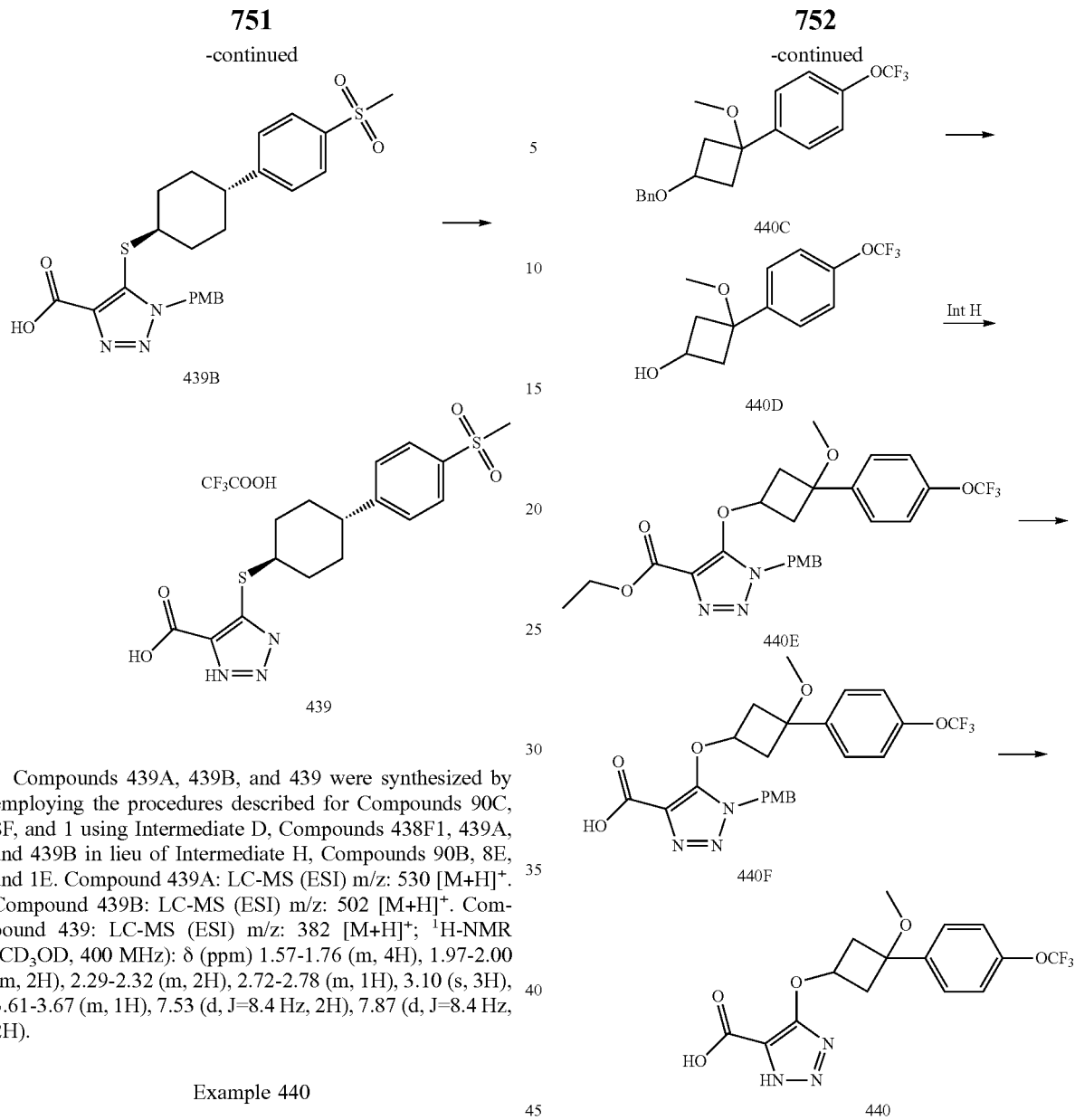

Compounds 439A, 439B, and 439 were synthesized by employing the procedures described for Compounds 90C, 8F, and 1 using Intermediate D, Compounds 438F1, 439A, and 439B in lieu of Intermediate H, Compounds 90B, 8E, and 1E. Compound 439A: LC-MS (ESI) m/z: 530 [M+H]⁺. Compound 439B: LC-MS (ESI) m/z: 502 [M+H]⁺. Compound 439: LC-MS (ESI) m/z: 382 [M+H]⁺; ¹H-NMR (CD₃OD, 400 MHz): δ (ppm) 1.57-1.76 (m, 4H), 1.97-2.00 (m, 2H), 2.29-2.32 (m, 2H), 2.72-2.78 (m, 1H), 3.10 (s, 3H), 3.61-3.67 (m, 1H), 7.53 (d, J=8.4 Hz, 2H), 7.87 (d, J=8.4 Hz, 2H).

Example 440

Synthesis of 4-(3-methoxy-3-(4-(trifluoromethoxy)phenyl)cyclobutoxy)-1H-1,2,3-triazole-5-carboxylic acid (440)

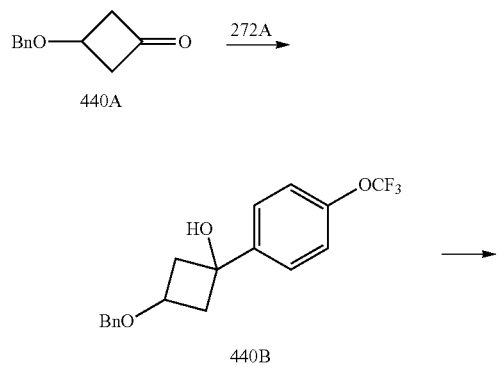

Compound 440B was synthesized by employing the procedure described for Compounds 263C using Compounds 272A and 440A in lieu of Compounds 263A and 263B, LC-MS (ESI) m/z: 361 [M+Na]⁺; ¹H-NMR (CDCl₃, 400 MHz): δ (ppm) 2.44-2.49 (m, 3H), 2.88-2.93 (m, 2H), 3.86-3.89 (m, 1H), 4.47 (s, 2H), 7.20 (d, J=8.4 Hz, 2H), 7.29-7.31 (m, 1H), 7.33-7.35 (m, 4H), 7.48 (dd, J=2.4, 6.8 Hz, 2H).

To a solution of Compound 440B (500 mg, 1.48 mmol) in THF (5 mL) was added NaH (89 mg, 2.2 mmol) at 0° C. After stirred at 0° C. for 10 minutes, to the mixture was added CH₃I (312 mg, 2.2 mmol) and stirred at room temperature overnight. The mixture was quenched with saturated NH₄Cl solution (50 mL) and extracted with EtOAc (50 mL×3). The combined organic layers was washed with brine (50 mL), dried over anhydrous sodium sulfate, concentrated, and purified by column chromatography on silica gel (AcOEt in PE, 17% v/v) to furnish Compound 440C as a colorless film (307 mg, yield 59%). LC-MS (ESI) m/z: 375 [M+Na]⁺.

The mixture of Compound 440C (304 mg, 0.86 mmol) and Pd/C (10%, 150 mg) in MeOH (30 mL) was stirred under hydrogen at room temperature (1 atm.) for 12 hours. The mixture was filtered through Celite, concentrated, and purified by column chromatography on silica gel (AcOEt in PE, 50% v/v) to furnish Compound 440D. LC-MS (ESI) m/z: non-ionizable compound under routine conditions used; $^1$H-NMR (CDCl$_3$, 400 MHz): δ (ppm) 2.01 (d, J=6.0 Hz, 1H), 2.32-2.37 (m, 2H), 2.83-2.88 (m, 2H), 2.95 (s, 3H), 4.09-4.11 (m, 1H), 7.21 (d, J=8 Hz, 2H), 7.40 (dd, J=2.4, 6.8 Hz, 2H).

Compounds 440E, 440F, and 440 were synthesized by employing the procedures described for Compounds 90C, 8F, and 1 using Compounds 440D, 440E, and 440F in lieu of Compounds 90B, 8E, and 1E. Compound 440E: LC-MS (ESI) m/z: 522 [M+H]$^+$. Compound 440F: LC-MS (ESI) m/z: 494 [M+H]$^+$. Compound 440: LC-MS (ESI) m/z: 374 [M+H]$^+$. $^1$H-NMR (DMSO-d$_6$, 400 MHz) δ (ppm) 2.35-2.40 (m, 2H), 2.84-2.89 (m, 2H), 2.90 (s, 3H), 5.15-5.18 (m, 1H), 7.36 (d, J=8 Hz, 2H), 7.48 (d, J=8.4 Hz, 2H).

Example 441

Synthesis of 4-(((trans)-4-(3-chloro-4-(piperidin-1-yl)phenyl)cyclohexyl)oxy)-1H-1,2,3-triazole-5-carboxylic acid 2,2,2-trifluoroacetate (441)

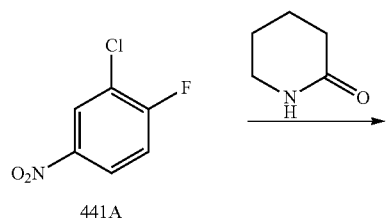

441A

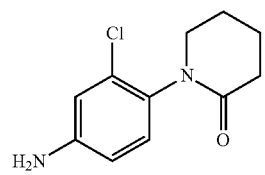

441B

441C

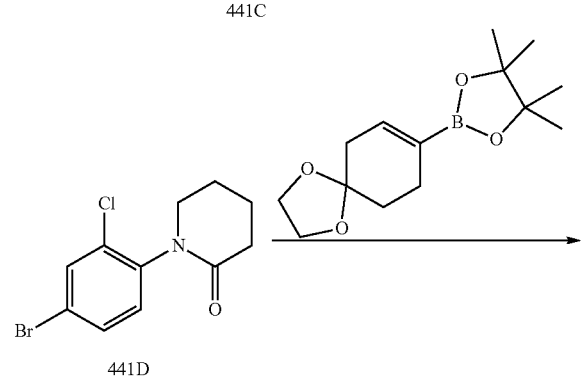

441D

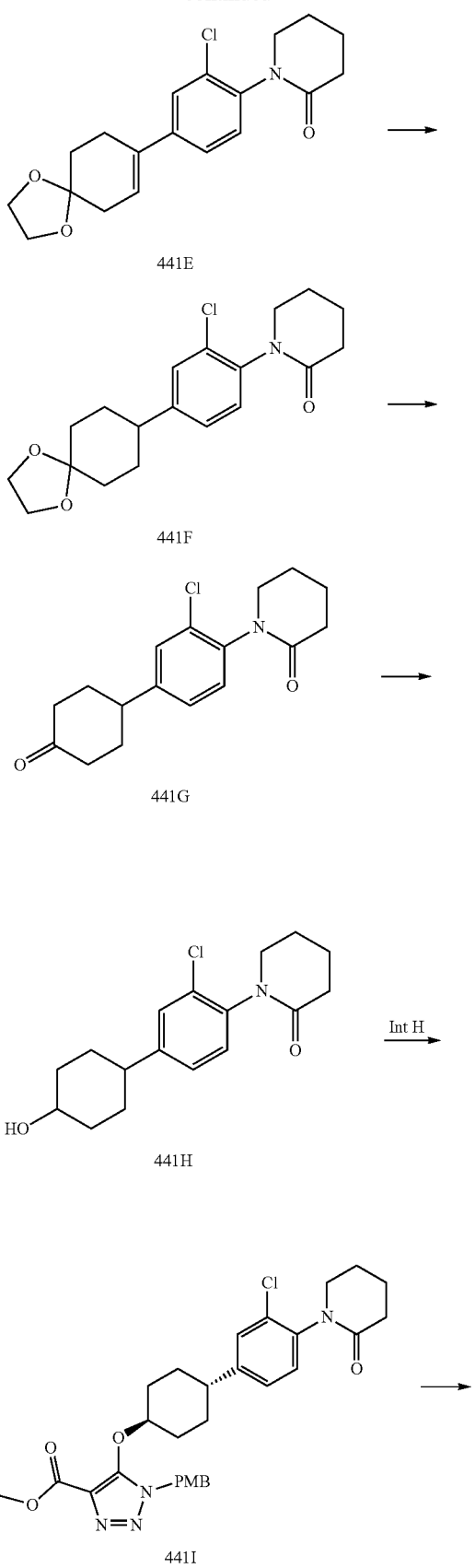

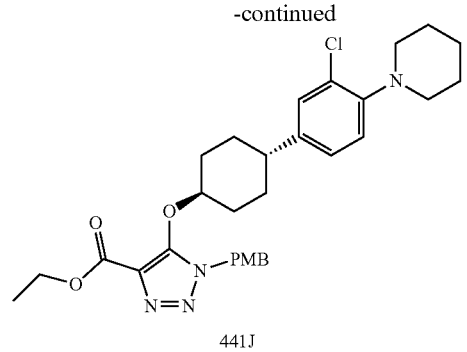

441J

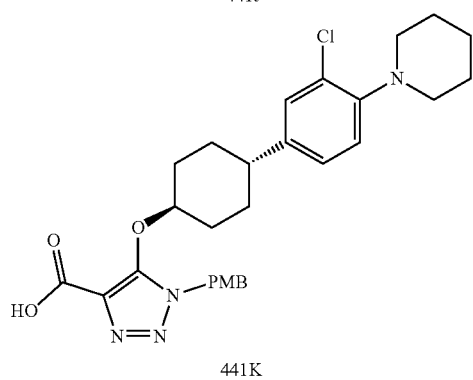

441K

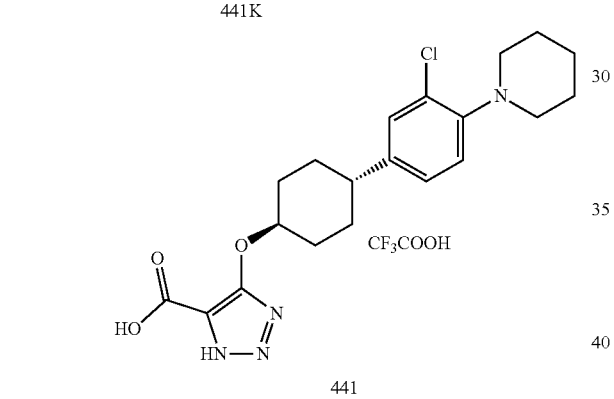

441

To a solution of piperidin-2-one (3.96 g, 40 mmol) in DMF (40 mL) was added NaH (1.6 g, 40 mmol) at 0° C. and stirred at 0° C. under N$_2$ for 5 minutes. To the mixture was added 2-chloro-1-fluoro-4-nitrobenzene (441A, 6.96 g, 40 mmol) was added, stirred at room temperature for 15 hours, diluted with water (40 mL), and extracted with EtOAc (50 mL×3). The combined organic layers was washed with brine (50 mL), dried over anhydrous sodium sulfate, concentrated, and purified by column chromatography on silica gel (ethyl acetate in petroleum ether, from 50% to 80% v/v) to furnish Compound 441B. LC-MS (ESI) m/z: 255 [M+H]$^+$; $^1$H-NMR (CDCl$_3$, 400 MHz): δ (ppm) 2.02 (s, 4H), 2.60 (s, 2H), 3.57 (d, J=20 Hz, 2H), 7.46 (d, J=8.8 Hz, 1H), 8.19 (d, J$_1$=2.8 Hz, J$_2$=8.8 Hz, 1H), 8.38 (d, J=2.4 Hz, 1H).

Compounds 441C, 441D, 441E, 441F, 441G, 441H, 441I, 441J, 441K, and 440 were synthesized by employing the procedures described for Compounds 186E, 56B, 8B, 141, 279D, 393F-1 and 393F-2, 90C, 182B, 8F, and 1 using Compounds 441B, 441C with aqeuous HBr solution (47%) and CuBr$_2$, 4,4,5,5-tetramethyl-2-(1,4-dioxaspiro[4.5]dec-7-en-8-yl)-1,3,2-dioxaborolane and 441D with K$_2$CO$_3$ as base, 441E, 441F with TFA solution (4 M) as acid and dichloromethane as solvent, 441G, 441H, 441I, 441J, and 441K in lieu of Compounds 186D, 56A with aqeuous HCl solution (47%) and CuCl, 3,4-dichlorophenylboronic acid and 8A with Cs$_2$CO$_3$ as base, 140, 279C with HCl as acid and 1,4-dioxane as solvent, 393E, 90B, 182A, 8E, and 1E. Compound 441C: LC-MS (ESI) m/z: 225 [M+H]$^+$. Compound 441D: LC-MS (ESI) m/z: 288 [M+H]$^+$. Compound 441E: LC-MS (ESI) m/z: 348 [M+H]$^+$. Compound 441F: LC-MS (ESI) m/z: 350 [M+H]$^+$. Compound 441G: LC-MS (ESI) m/z: 306 [M+H]$^+$; $^1$H-NMR (CDCl$_3$, 400 MHz): δ (ppm) 1.87-1.96 (m, 6H), 2.21-2.25 (m, 2H), 2.50-2.59 (m, 6H), 2.98-3.05 (m, 1H), 3.44-3.59 (m, 2H), 7.19 (s, 2H), 7.35 (s, 1H). Compound 441H: LC-MS (ESI) m/z: 308 [M+1]$^+$. $^1$H-NMR (CDCl$_3$, 400 MHz): δ (ppm) 1.37-1.54 (m, 1H), 1.65-1.68 (m, 3H), 1.81-1.95 (m, 8H), 2.49-2.58 (m, 3H), 3.44-3.59 (m, 2H), 4.13 (s, 1H), 7.14 (s, 1H), 7.26 (s, 1H), 7.34 (s, 1H). Compound 441I: LC-MS (ESI) m/z: 567 [M+H]$^+$. Compound 441J: LC-MS (ESI) m/z: 553 [M+H]$^+$. Compound 441K: LC-MS (ESI) m/z: 525 [M+H]$^+$. Compound 441: LC-MS (ESI) m/z: 405 [M+H]$^+$; $^1$H-NMR (DMSO-d$_6$, 400 MHz) δ (ppm) 1.51-1.66 (m, 10H), 1.81-1.84 (m, 2H), 2.20-2.21 (m, 2H), 2.53-2.56 (m, 1H), 2.86 (t, J=5.6 Hz, 4H), 4.65 (s, 1H), 7.05 (d, J=8.4 Hz, 1H), 7.16 (dd, J$_1$=1.6 Hz, J$_2$=8.0 Hz, 1H), 7.27 (s, 1H).

Example 442

Synthesis of 4-(((cis)-4-(3-chloro-4-(piperidin-1-yl)phenyl)cyclohexyl)thio)-1H-1,2,3-triazole-5-carboxylic acid 2,2,2-trifluoroacetate (442-1) and 4-(((trans)-4-(3-chloro-4-(piperidin-1-yl)phenyl)cyclohexyl)thio)-1H-1,2,3-triazole-5-carboxylic acid 2,2,2-trifluoroacetate (442-2)

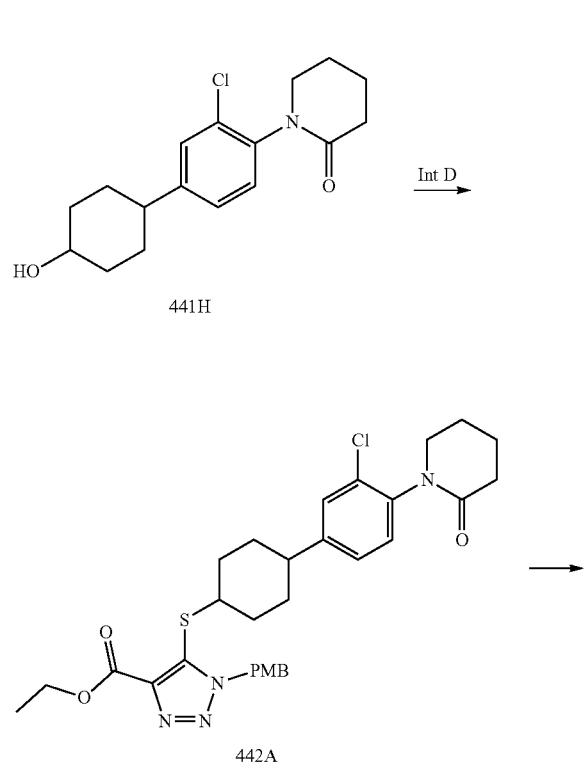

441H

442A

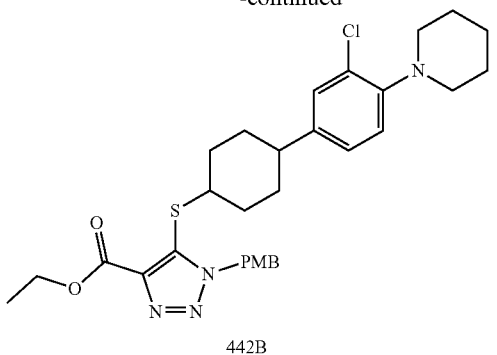

442B

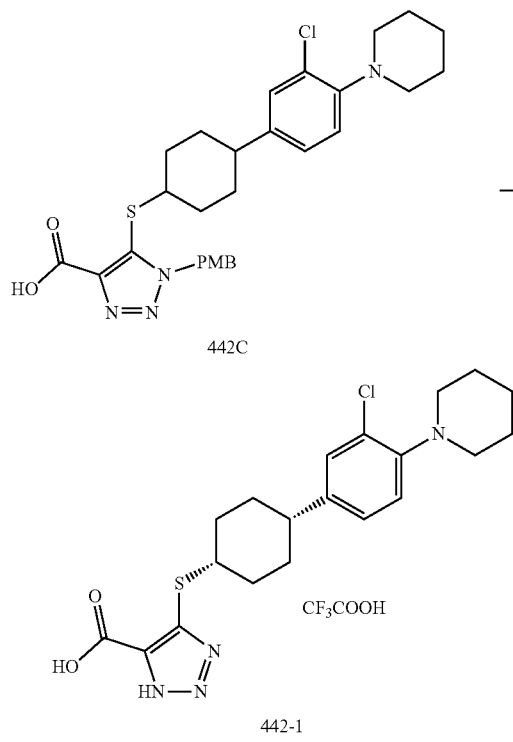

442C 442-1

442-2

Compounds 442A, 442B, 442C, 442-1, and 442-2 were synthesized by employing the procedures described for Compounds 90C, 182B, 8F, and 1 using Compounds 441H, 442A, 442B, and 442C in lieu of Compounds 90B, 182A, 8E, and 1E. Compound 442A: LC-MS (ESI) m/z: 583 [M+H]$^+$. Compound 442B: LC-MS (ESI) m/z: 569 [M+H]$^+$. Compound 442C: LC-MS (ESI) m/z: 541 [M+H]$^+$. Compound 442-1: LC-MS (ESI) m/z: 421 [M+H]$^+$; $^1$H-NMR (DMSO-d$_6$, 400 MHz) δ (ppm) 1.51-1.52 (m, 2H), 1.61-1.68 (m, 8H), 1.95 (s, 4H), 2.53-2.59 (m, 1H), 2.87 (t, J=4.8 Hz, 4H), 4.11 (s, 1H), 7.07 (d, J=8.4 Hz, 1H), 7.15 (dd, J$_1$=2 Hz, J$_2$=8.4 Hz, 1H), 7.22 (s, 1H). Compound 442-2: LC-MS (ESI) m/z: 421 [M+H]$^+$; $^1$H-NMR (DMSO-d$_6$, 400 MHz) δ (ppm) 1.47-1.63 (m, 10H), 1.80-1.83 (m, 2H), 2.18 (s, 2H), 2.49 (s, 1H), 2.86 (s, 4H), 3.55 (s, 1H), 7.04 (d, J=8.0 Hz, 1H), 7.14 (d, J=9.2 Hz, 1H), 7.25 (s, 1H).

Example 443

Synthesis of 4-(((1r,4r)-4-methyl-4-(4-(trifluoromethoxy)phenyl)cyclohexyl)oxy)-1H-1,2,3-triazole-5-carboxylic acid (443)

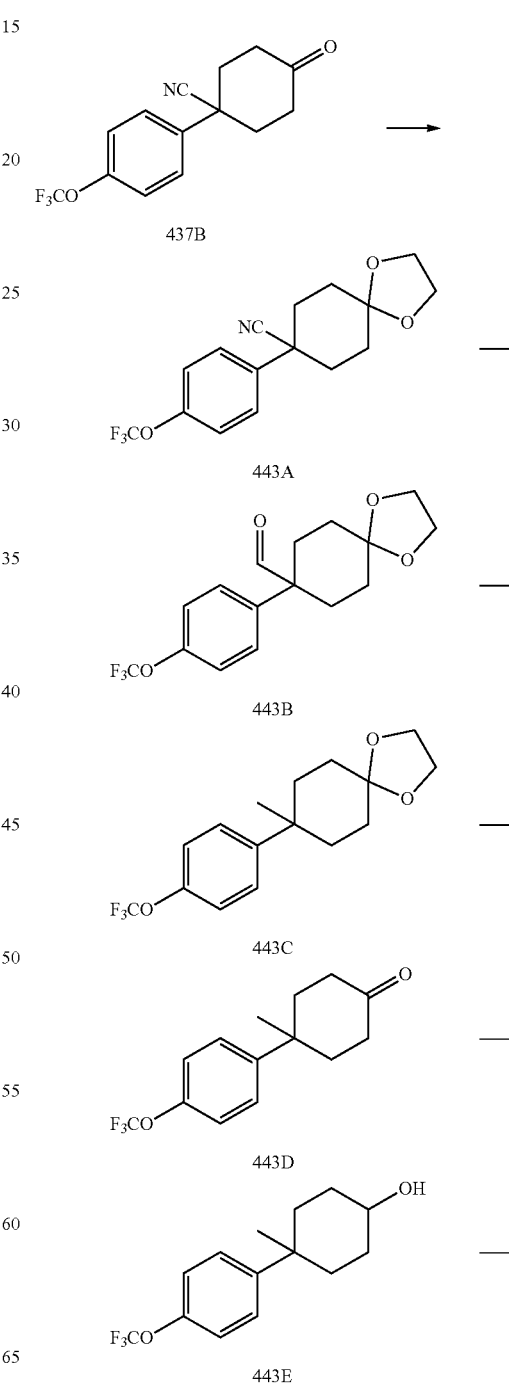

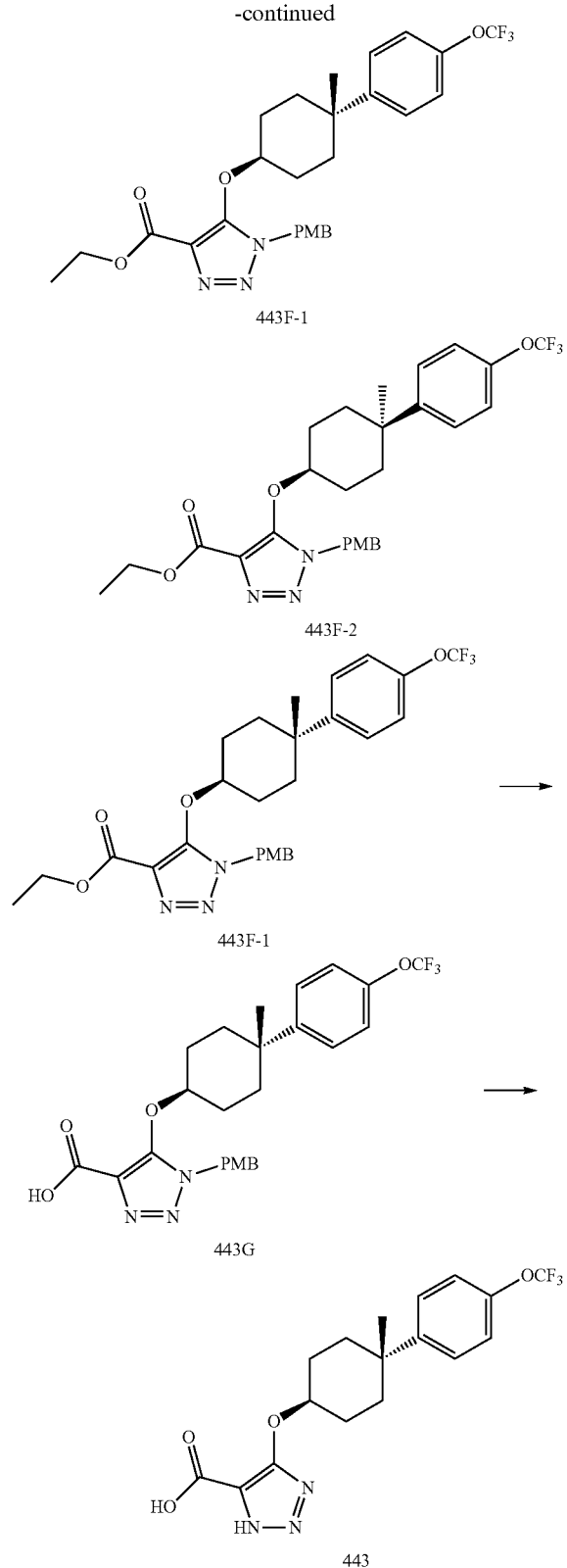

A mixture of Compound 437B (13.0 g, 45.95 mmol), ethylene glycol (2.9 g, 46.85 mol), and p-TSOH (111 mg, 0.643 mmol) in toluene (250 mL) was heated at reflux for 6 hours with continued removal of water by using a Dean-Stark trap. The mixture was concentrated in vacuum and the residue was purified with flash column chromatography on silica gel (ethyl acetate in petroleum ether, 20% v/v) to furnish Compound 443A. LC-MS (ESI) m/z: 328 [M+H]$^+$.

To a solution of Compound 443A (8 g, 24.45 mmol) in toluene (160 mL) was dropped a solution of diisobutylaluminum hydride in toluene (1 M, 37 mL, 37 mmol) at −78° C. and stirred at −78° C. for 2 hours. The mixture was quenched with ethyl acetate (300 mL) and water (10 mL), stirred at room temperature for 20 minutes, washed with diluted HCl solution (2 N, 200 mL) and water (200 mL) and brine (200 mL), dried over anhydrous sodium sulfate, filtered, and concentrated to yield a crude Compound 443B. LC-MS (ESI) m/z: 331 [M+H]$^+$; $^1$H-NMR (CDCl$_3$, 400 MHz) δ (ppm) 1.66-1.77 (m, 4H), 2.08-2.17 (m, 4H), 3.93-3.97 (m, 4H), 7.22 (d, J=8.7 Hz, 2H), 7.32-7.36 (m, 2H), 9.41 (s, 1H).

To a solution of N$_2$H$_4$—H$_2$O (6.54 g, 121.2 mmol) in ethylene glycol (20 mL) was dropped Compound 443B (4 g, 12.12 mmol) and stirred at room temperature for 1 hour followed by addition of powdered KOH (2.71 g, 48.48 mmol). After heated at reflux for 4 hours, the mixture was cool down to room temperature, diluted with H$_2$O (300 mL), and extracted with ethyl acetate (200 mL×2). The combined extracts was washed with brine (200 mL), dried over anhydrous sodium sulfate, concentrated, and purified with flash column chromatography on silica gel (ethyl acetate in petroleum ether, 20% v/v) to furnish Compound 443C. LC-MS (ESI) m/z: 317 [M+H]$^+$; $^1$H-NMR (CDCl$_3$, 400 MHz) δ (ppm) 1.22 (s, 3H), 1.51-1.59 (m, 2H), 1.65-1.83 (m, 4H), 2.10-2.22 (m, 2H), 3.88-4.01 (m, 4H), 7.15 (d, J=8.5 Hz, 2H), 7.33-7.43 (m, 2H).

Compounds 443D, 443E, 443F-1, 443F-2, 443G, and 443 were synthesized by employing the procedures described for Compounds 279D, 57C, 90C, 8F, and 1 using Compounds 443C with TFA as acid and dichloromethane as solvent, 443D with EtOH as solvent, 443E with toluene as solvent, 443F-1, and 443G in lieu of Compounds 279C with HCl as acid and 1,4-dioxane as solvent, 57B with MeOH as solvent, 90B with THF as solvent, 8E, and 1E. Compound 443D: LC-MS (ESI) m/z: 273 [M+H]$^+$; $^1$H-NMR (CDCl$_3$, 400 MHz) δ (ppm) 1.34 (s, 3H), 1.95-1.99 (m, 2H), 2.24-2.35 (m, 2H), 2.40-2.45 (m, 4H), 7.23 (d, J=8.5 Hz, 2H), 7.41-7.48 (m, 2H). Compound 443E: LC-MS (ESI) m/z: 257 [M−OH]$^+$. Compound 443F-1: LC-MS (ESI) m/z: 534 [M+H]$^+$; $^1$H-NMR (CDCl$_3$, 400 MHz) δ (ppm) 1.15 (s, 3H), 1.27 (d, J=6.4 Hz, 3H), 1.42 (t, J=7.1 Hz, 4H), 1.80-1.93 (m, 2H), 2.15-2.29 (m, 2H), 3.76 (s, 3H), 4.40 (q, J=7.1 Hz, 2H), 5.11-5.25 (m, 3H), 6.71 (d, J=8.7 Hz, 2H), 7.09 (d, J=8.7 Hz, 2H), 7.21 (d, J=8.4 Hz, 2H), 7.33 (d, J=8.9 Hz, 2H). Compound 443F-2: LC-MS (ESI) m/z: 534 [M+H]$^+$; $^1$H-NMR (CDCl$_3$, 400 MHz) δ (ppm) 1.19 (s, 3H), 1.39 (t, J=7.1 Hz, 3H), 1.63-1.90 (m, 8H), 3.79 (s, 3H), 4.37 (q, J=7.1 Hz, 2H), 5.34 (s, 2H), 5.09-5.13 (m, 1H), 6.88 (d, J=8.7 Hz, 2H), 7.15 (d, J=8.3 Hz, 2H), 7.27 (t, J=4.3 Hz, 2H), 7.33 (d, J=8.9 Hz, 2H). Compound 443G: LC-MS (ESI) m/z: 506 [M+H]$^+$. Compound 443: LC-MS (ESI) m/z: 386 [M+H]$^+$; $^1$H-NMR (DMSO-d$_6$, 400 MHz) δ (ppm) 1.18 (s, 3H), 1.47-1.55 (m, 4H), 1.85-2.02 (m, 2H), 2.20-2.31 (m, 2H), 4.75 (s, 1H), 7.31 (d, J=8.3 Hz, 2H), 7.55 (d, J=8.8 Hz, 2H), 12.85 (s, 1H), 14.72 (s, 1H).

Example 444

Synthesis of 4-(((1s,4s)-4-methyl-4-(4-(trifluoromethoxy)phenyl)cyclohexyl)oxy)-1H-1,2,3-triazole-5-carboxylic acid (444)

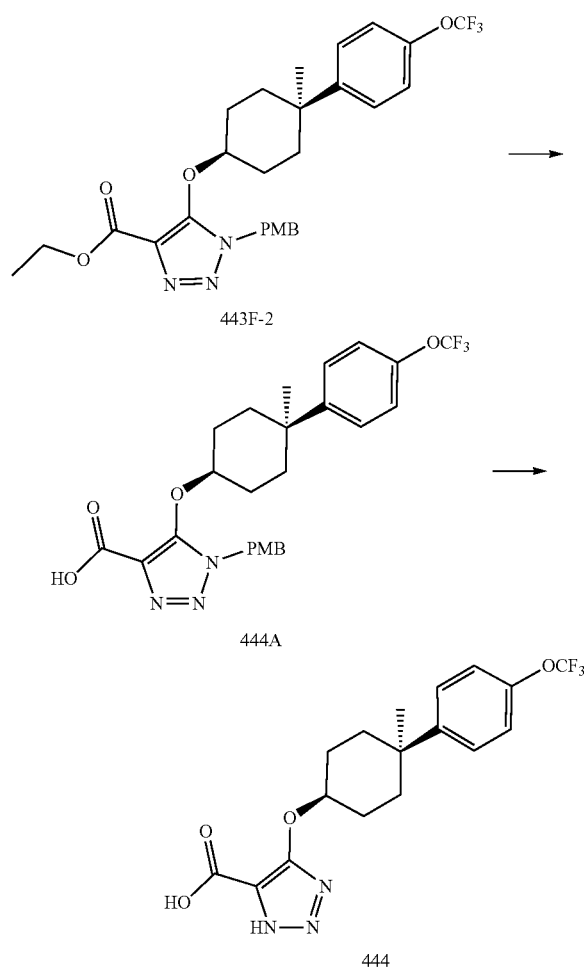

Compounds 444A and 444 were synthesized by employing the procedures described for Compounds 8F and 1 using Compounds 443F-2 and 444A in lieu of Compounds 8E and 1E. Compound 444A: LC-MS (ESI) m/z: 506 [M+H]⁺. Compound 444: LC-MS (ESI) m/z: 386 [M+H]⁺; ¹H-NMR (DMSO-d₆, 400 MHz) δ (ppm) 1.22 (s, 3H), 1.72-2.02 (m, 8H), 4.66 (s, 1H), 7.30 (d, J=8.2 Hz, 2H), 7.55 (d, J=8.9 Hz, 2H), 12.90 (s, 1H), 14.71 (s, 1H).

Example 445

Synthesis of 4-(4-chloro-3-cyclopropoxyphenoxy)-1H-1,2,3-triazole-5-carboxylic acid (445)

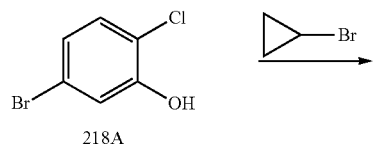

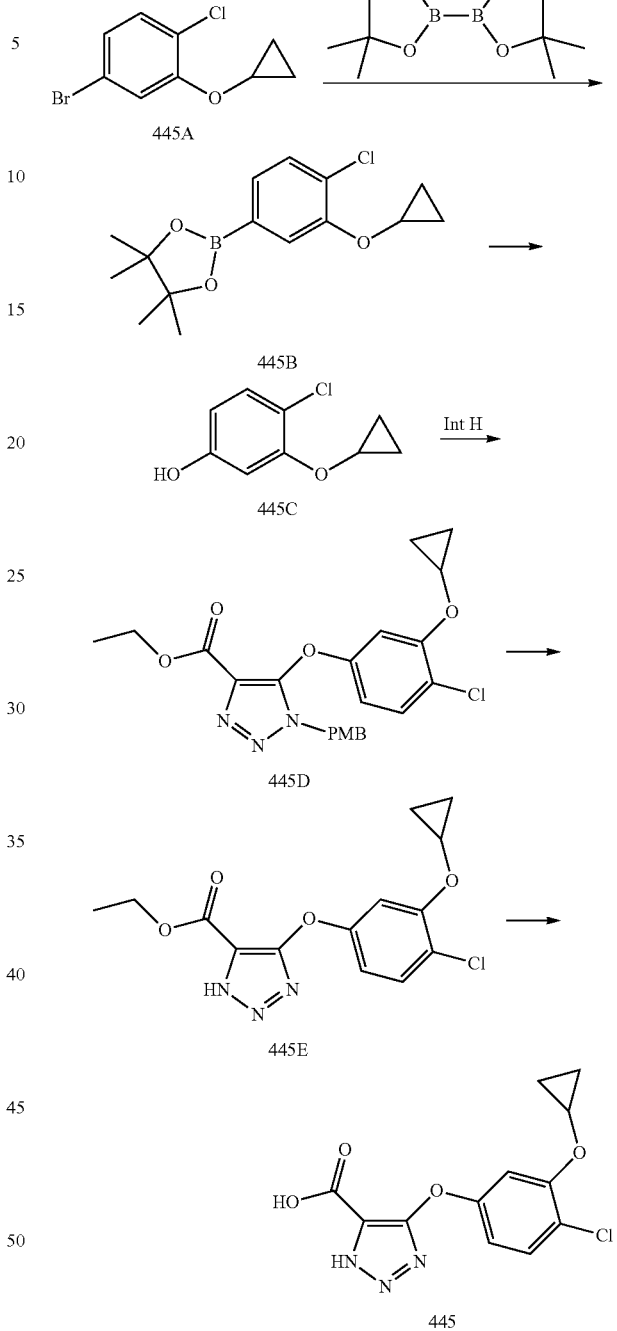

Compounds 445A, 445B, 445C, 445D, 445E, and 445 were synthesized by employing the procedures described for Compounds 27B, 27C, 236D, Intermediate I, 217E, and 8F using bromocyclopropane, Compounds 218A, 445A, 445B, 445C, 445D, and 445E in lieu of 2-bromopropane, Compounds 27A, 27B, 236C, 4-bromophenol, 217D, and 8E. Compound 445A: ¹H-NMR (CDCl₃, 400 MHz): δ (ppm) 0.86-0.87 (m, 4H), 3.78-3.80 (m, 1H), 7.04 (dd, J=8.4, 2.4 Hz, 1H), 7.20 (d, J=8.4 Hz, 1H), 7.42 (d, J=2.4 Hz, 1H). Compound 445B: ¹H-NMR (CDCl₃, 400 MHz): δ (ppm) 0.85-0.87 (m, 4H), 1.36 (s, 12H), 3.89-3.90 (m, 1H), 7.35 (s, 2H), 7.66 (s, 1H). Compound 445C: LC-MS (ESI) m/z: 185

[M+H]⁺. Compound 445D: LC-MS (ESI) m/z: 444 [M+H]⁺. Compound 445E: LC-MS (ESI) m/z: 324 [M+H]⁺. Compound 445: LC-MS (ESI) m/z: 296 [M+H]⁺; ¹H-NMR (CD₃OD, 400 MHz): δ (ppm) 0.73-0.77 (m, 2H), 0.78-0.85 (m, 2H), 3.81-3.86 (m, 1H), 6.67 (dd, J=8.8, 2.8 Hz, 1H), 7.21 (d, J=2.8 Hz, 1H), 7.30 (d, J=8.8 Hz, 1H).

Example 446

Synthesis of 4-(((trans)-4-(4-cyclopropoxyphenyl)cyclohexyl)oxy)-1H-1,2,3-triazole-5-carboxylic acid (446)

Compounds 446B, 446C, 446D, 446E, 446F, 446G, and 446 were synthesized by employing the procedures described for Compounds 8B, 141, 279D, 393F-1 and 393F-2, 90C, 380E, and 8F using 4,4,5,5-tetramethyl-2-(1,4-dioxaspiro[4.5]dec-7-en-8-yl)-1,3,2-dioxaborolane, Compounds 446A with K₂CO₃ as base and 1,4-dioxane/H₂O as solvent, 446B, 446C with TFA as acid and dichloromethane as solvent, 446D, 446E, 446F with THF as solvent, and 446G in lieu of (3,4-dichlorophenyl)boronic acid, Compounds 8A with Cs₂CO₃ as base and DME/H₂O as solvent, 140, 279C with HCl as acid and 1,4-dioxane as solvent, 393E, 90B, 380D with MeOH as solvent, and 8E. Compound 446B: LC-MS (ESI) m/z: 273 [M+H]⁺; ¹H-NMR (CDCl₃, 400 MHz): δ (ppm) 0.76-0.77 (m, 4H), 1.91 (t, J=6.4 Hz, 2H), 2.45-2.46 (m, 2H), 2.62-2.66 (m, 2H), 3.70-3.74 (m, 1H), 4.01-4.02 (m, 4H), 5.88-5.90 (m, 1H), 6.98 (d, J=8.8 Hz, 2H), 7.32 (d, J=8.8 Hz, 2H). Compound 446C: LC-MS (ESI) m/z: 275 [M+H]⁺. Compound 446D: LC-MS (ESI) m/z: 231 [M+H]⁺; ¹H-NMR (CDCl₃, 400 MHz): δ (ppm) 0.76-0.77 (m, 4H), 1.86-1.97 (m, 2H), 2.18-2.23 (m, 2H), 2.48-2.52 (m, 4H), 2.95-3.03 (m, 1H), 3.69-3.74 (m, 1H), 7.01 (d, J=8.4 Hz, 2H), 7.16 (d, J=8.8 Hz, 2H). Compound 446E: LC-MS (ESI) m/z: 215 [M−OH]⁺; ¹H-NMR (CDCl₃, 400 MHz): δ (ppm) 0.75-0.76 (m, 4H), 1.64-1.70 (m, 4H), 1.85-1.91 (m, 4H), 2.47-2.54 (m, 1H), 3.68-3.73 (m, 1H), 4.10-4.15 (m, 1H), 6.98 (d, J=8.4 Hz, 2H), 7.16 (d, J=8.8 Hz, 2H). Compound 446F: LC-MS (ESI) m/z: 492 [M+H]⁺. Compound 446G: LC-MS (ESI) m/z: 372 [M+H]⁺. Compound 446: LC-MS (ESI) m/z: 366 [M+Na]⁺; ¹H-NMR (CD₃OD, 400 MHz): δ (ppm) 0.64-0.79 (m, 4H), 1.58-1.73 (m, 4H), 1.93-1.96 (m, 2H), 2.33-2.35 (m, 2H), 2.53-2.60 (m, 1H), 3.72-3.76 (m, 1H), 4.73-4.75 (m, 1H), 6.96 (d, J=8.4 Hz, 2H), 7.16 (d, J=8.4 Hz, 2H).

Example 447

Synthesis of 4-(((trans)-4-(4-fluorophenyl)cyclohexyl)oxy)-1H-1,2,3-triazole-5-carboxylic acid (447)

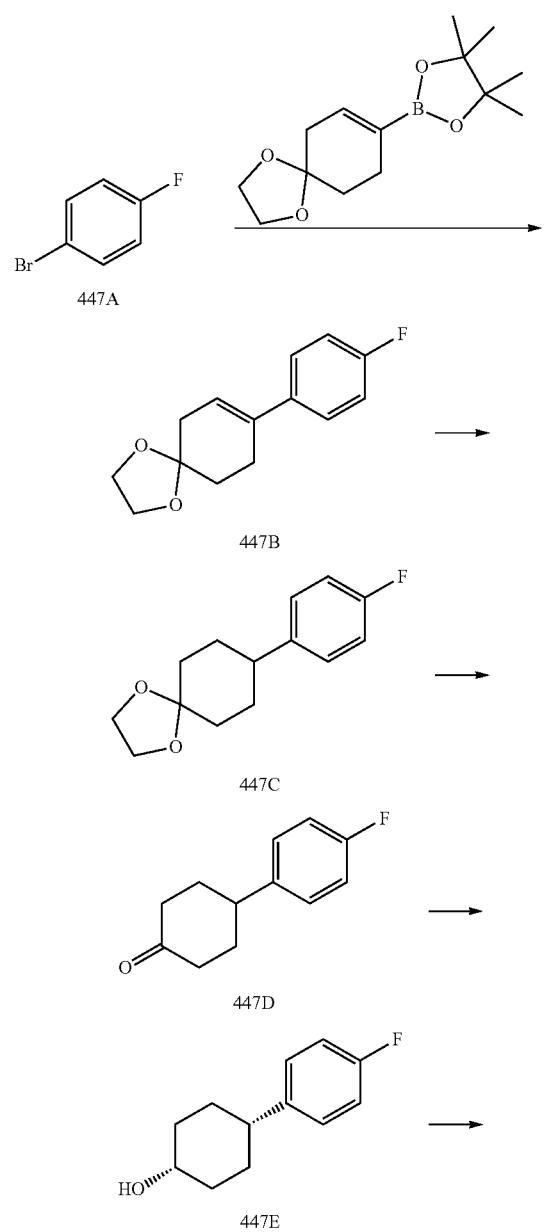

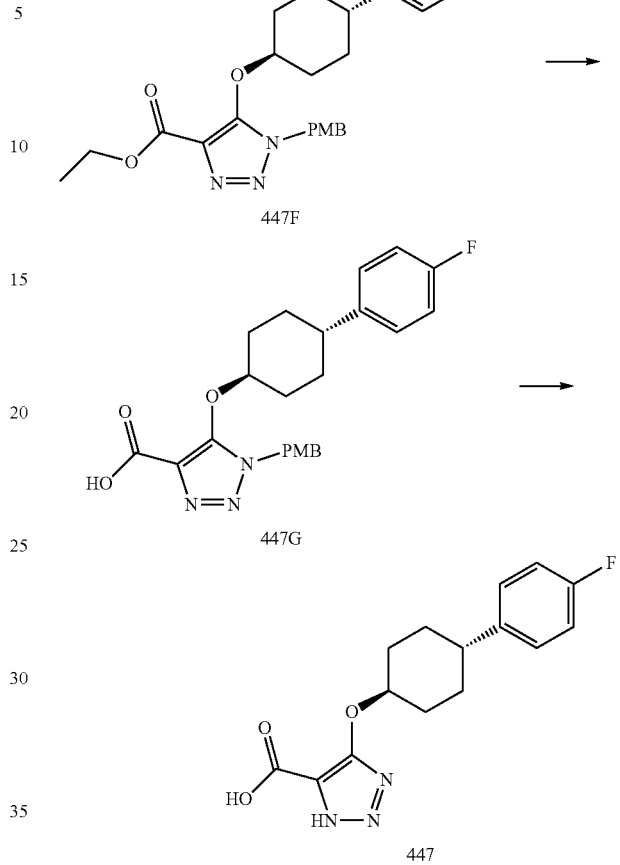

Compounds 447B, 447C, 447D, 447E, 447F, 447G, and 447 were synthesized by employing the procedures described for Compounds 4B, 141, 279D, 393F-1 and 393F-2, 90C, 1, and 8F using 4,4,5,5-tetramethyl-2-(1,4-dioxaspiro[4.5]dec-7-en-8-yl)-1,3,2-dioxaborolane, Compounds 447A with 1,4-dioxane/H$_2$O as solvent, 447B, 447C with TFA as acid and dichloromethane as solvent, 447D, 447E, 447F, and 447G in lieu of (3,4-dichlorophenyl)boronic acid, Compounds 4A with toluene/EtOH/H$_2$O as solvent, 140, 279C with HCl as acid and 1,4-dioxane as solvent, 393E, 90B, 1E, and 8E. Compound 447B: LC-MS (ESI) m/z: 235 [M+H]$^+$; $^1$H-NMR (CDCl$_3$, 400 MHz): δ (ppm) 1.90-1.93 (m, 2H), 2.46 (m, 2H), 2.61-2.65 (m, 2H), 4.02 (s, 4H), 5.91-5.93 (m, 1H), 6.95-7.00 (m, 2H), 7.32-7.36 (m, 2H). Compound 447C: LC-MS (ESI) m/z: 237 [M+H]$^+$; $^1$H-NMR (CDCl$_3$, 400 MHz): δ (ppm) 1.60-1.79 (m, 8H), 2.46-2.47 (m, 1H), 3.91 (s, 4H), 6.87-6.91 (m, 2H), 7.09-7.13 (m, 2H). Compound 447D: LC-MS (ESI) m/z: 193 [M+H]$^+$; $^1$H-NMR (CDCl$_3$, 400 MHz): δ (ppm) 1.81-1.87 (m, 2H), 2.11-2.15 (m, 2H), 2.42-2.46 (m, 4H), 2.92-2.98 (m, 1H), 6.91-6.95 (m, 2H), 7.11-7.14 (m, 2H). Compound 447E: LC-MS (ESI) m/z: 177 [M−OH]$^+$; $^1$H-NMR (CDCl$_3$, 400 MHz): δ (ppm) 1.55-1.63 (m, 4H), 1.74-1.84 (m, 4H), 2.42-2.45 (m, 1H), 4.04-4.06 (m, 1H), 6.88-6.92 (m, 2H), 7.10-7.13 (m, 2H). Compound 447F: LC-MS (ESI) m/z: 454 [M+H]$^+$. Compound 447G: LC-MS (ESI) m/z: 426 [M+H]$^+$. Compound 447: LC-MS (ESI) m/z: 306 [M+H]$^+$; $^1$H-NMR (CD$_3$OD, 400 MHz): δ (ppm) 1.51-1.60 (m, 4H), 1.83-1.86

(m, 2H), 2.22-2.25 (m, 2H), 2.51-2.52 (m, 1H), 4.63 (m, 1H), 6.87-6.91 (m, 2H), 7.13-7.17 (m, 2H).

Example 448

Synthesis of 4-(4-chloro-3-cyclobutoxyphenoxy)-1H-1,2,3-triazole-5-carboxylic acid (448)

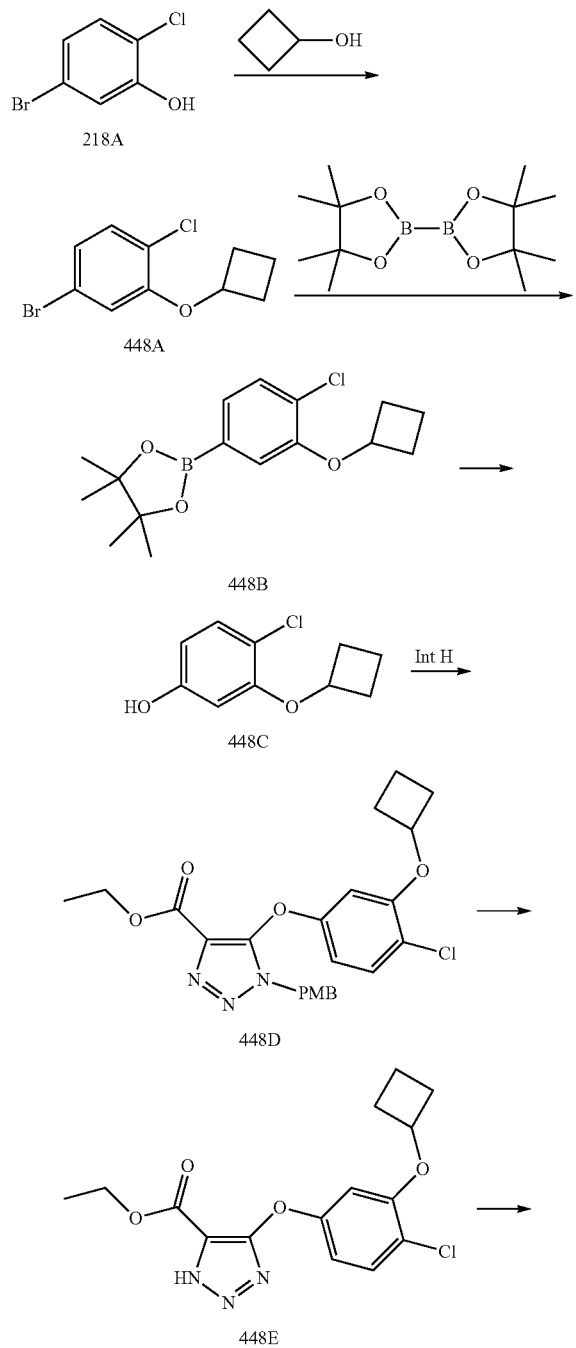

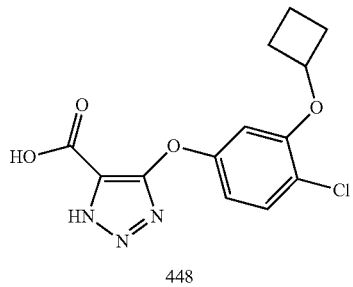

Compounds 448A, 448B, 448C, 448D, 448E, and 448 were synthesized by employing the procedures described for Compounds 90C, 27C, 236D, Intermediate I, 217E, and 8F using cyclobutanol, Compounds 218A, 448A, 448B, 448C, 448D, and 445E in lieu of Compounds 90B, Intermediate H, 27B, 236C, 4-bromophenol, 217D, and 8E. Compound 448A: $^1$H-NMR (CDCl$_3$, 400 MHz): δ (ppm) 1.95-2.01 (m, 1H), 2.14-2.25 (m, 2H), 2.28-2.34 (m, 1H), 3.96-4.01 (m, 1H), 4.06-4.12 (m, 1H), 5.77-5.79 (m, 1H), 7.06 (dd, J=8.4, 2.4 Hz, 1H), 7.20 (d, J=8.4 Hz, 1H), 7.40 (d, J=2.4 Hz, 1H). Compound 448B: $^1$H-NMR (CDCl$_3$, 400 MHz): δ (ppm) 1.33 (s, 12H), 1.92-2.01 (m, 1H), 2.09-2.34 (m, 3H), 3.95-4.01 (m, 2H), 5.90-5.92 (m, 1H), 7.34-7.38 (m, 2H), 7.60 (s, 1H). Compound 448C: LC-MS (ESI) m/z: 199 [M+H]$^+$. Compound 448D: LC-MS (ESI) m/z: 458 [M+H]$^+$. Compound 448E: LC-MS (ESI) m/z: 338 [M+H]$^+$; $^1$H-NMR (CD$_3$OD, 400 MHz): δ (ppm) 1.21-1.26 (m, 3H), 1.68-1.90 (m, 2H), 2.11-2.21 (m, 2H), 2.40-2.48 (m, 2H), 4.28-4.30 (m, 2H), 4.64-4.71 (m, 1H), 6.56-6.59 (m, 1H), 6.66 (d, J=2.4 Hz, 1H), 7.23 (dd, J=8.8, 2.8 Hz, 1H). Compound 448: LC-MS (ESI) m/z: 310 [M+H]$^+$; $^1$H-NMR (CD$_3$OD, 400 MHz): δ (ppm) 1.69-1.79 (m, 1H), 1.83-1.91 (m, 1H), 2.12-2.22 (m, 2H), 2.42-2.49 (m, 2H), 4.66-4.79 (m, 1H), 6.64 (dd, J=8.8, 2.8 Hz, 1H), 7.73 (d, J=2.8 Hz, 1H), 7.31 (d, J=8.8 Hz, 1H).

Example 449

Synthesis of 4-(3-(4-(trifluoromethoxy)phenyl)cyclobutoxy)-1H-1,2,3-triazole-5-carboxylic acid (449)

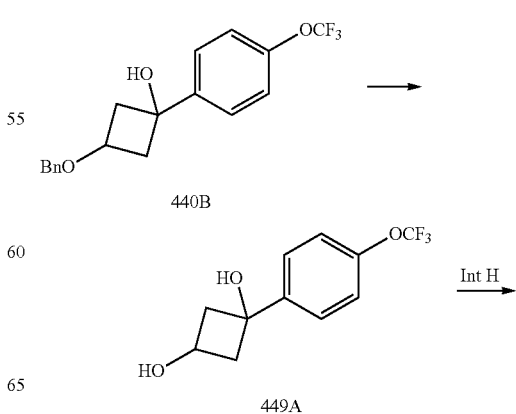

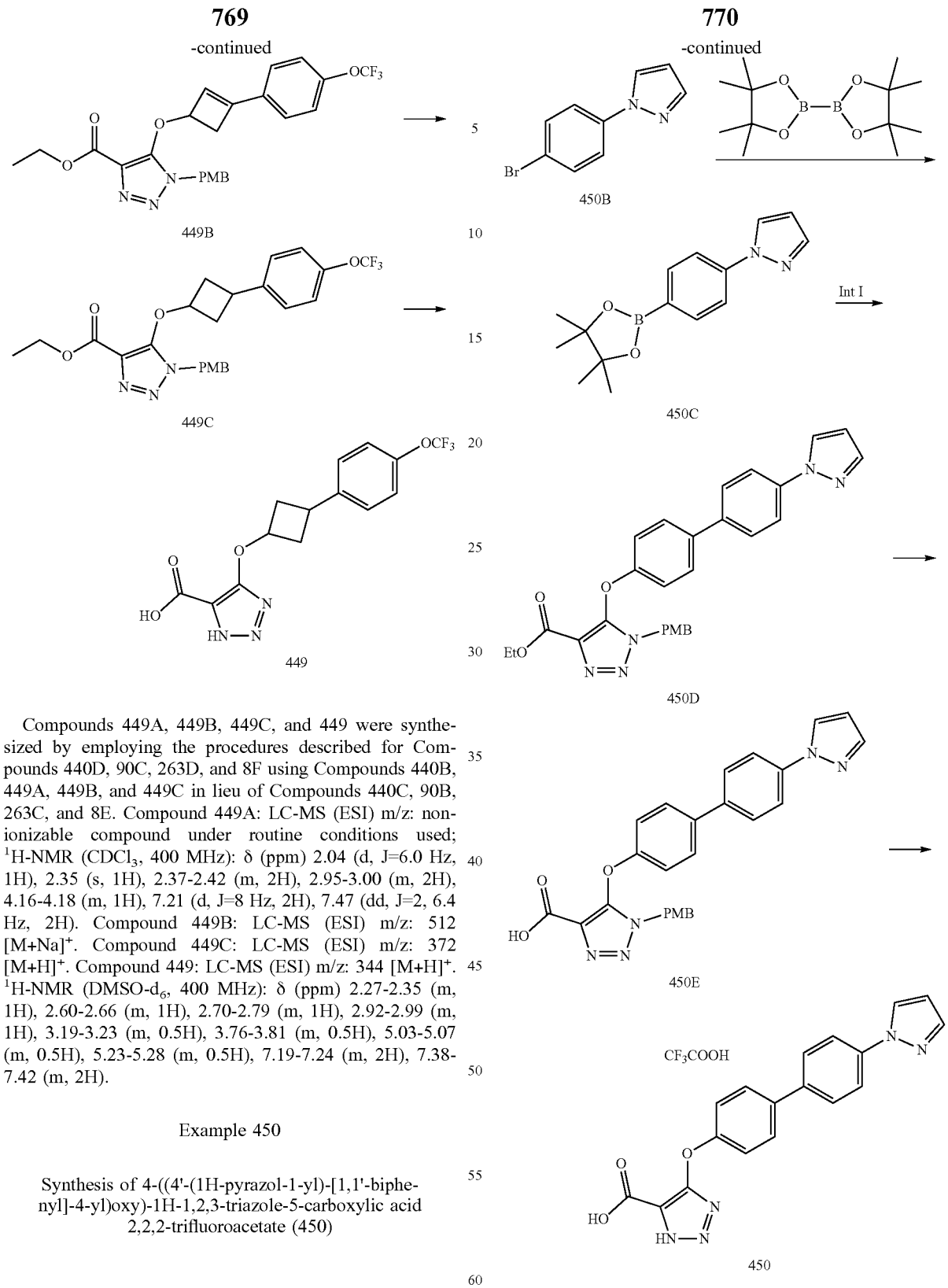

Compounds 449A, 449B, 449C, and 449 were synthesized by employing the procedures described for Compounds 440D, 90C, 263D, and 8F using Compounds 440B, 449A, 449B, and 449C in lieu of Compounds 440C, 90B, 263C, and 8E. Compound 449A: LC-MS (ESI) m/z: non-ionizable compound under routine conditions used; $^1$H-NMR (CDCl$_3$, 400 MHz): δ (ppm) 2.04 (d, J=6.0 Hz, 1H), 2.35 (s, 1H), 2.37-2.42 (m, 2H), 2.95-3.00 (m, 2H), 4.16-4.18 (m, 1H), 7.21 (d, J=8 Hz, 2H), 7.47 (dd, J=2, 6.4 Hz, 2H). Compound 449B: LC-MS (ESI) m/z: 512 [M+Na]$^+$. Compound 449C: LC-MS (ESI) m/z: 372 [M+H]$^+$. Compound 449: LC-MS (ESI) m/z: 344 [M+H]$^+$. $^1$H-NMR (DMSO-d$_6$, 400 MHz): δ (ppm) 2.27-2.35 (m, 1H), 2.60-2.66 (m, 1H), 2.70-2.79 (m, 1H), 2.92-2.99 (m, 1H), 3.19-3.23 (m, 0.5H), 3.76-3.81 (m, 0.5H), 5.03-5.07 (m, 0.5H), 5.23-5.28 (m, 0.5H), 7.19-7.24 (m, 2H), 7.38-7.42 (m, 2H).

Example 450

Synthesis of 4-((4'-(1H-pyrazol-1-yl)-[1,1'-biphenyl]-4-yl)oxy)-1H-1,2,3-triazole-5-carboxylic acid 2,2,2-trifluoroacetate (450)

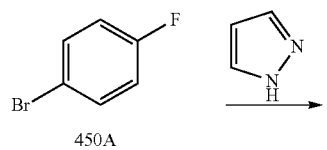

A mixture of 1H-pyrazole (680 mg, 10 mmol), 1-bromo-4-fluorobenzene (450A, 3.50 g, 20 mmol), and K$_3$PO$_4$ (6.37 g, 30 mmol) in NMP (20 mL) was heated in a sealed tube at 200° C. for 2 hours. The mixture was cooled down to room temperature, quenched with water (100 mL), and extracted with ethyl acetate (100 mL×3). The combined organic layers was washed with brine (100 mL), dried over anhydrous sodium sulfate, concentrated, and purified with column chromatography on silica gel (ethyl acetate in petroleum ether, 10%, v/v) to furnish Compound 450B. LC-MS (ESI) m/z: 223 [M+H]$^+$.

Compounds 450C, 450D, 450E, and 450 were synthesized by employing the procedures described for Compounds 27C, 4B, 8F, and 1 using Compounds 450B, 450C, Intermediate I with Na$_2$CO$_3$ as base and 1,4-dioxane as solvent, 450D, and 450E in lieu of 2-bromopropane, Compounds 27B, (3,4-dichlorophenyl)boronic acid, 4-bromophenylboronic acid and 4A with Cs$_2$CO$_3$ as base and DME/H$_2$O as solvent, 8E, and 1E. Compound 450C: LC-MS (ESI) m/z: 271 [M+H]$^+$. Compound 450D: LC-MS (ESI) m/z: 496 [M+H]$^+$. Compound 450E: LC-MS (ESI) m/z: 468 [M+H]$^+$. Compound 450: LC-MS (ESI) m/z: 348 [M+H]$^+$; $^1$H-NMR (DMSO-d$_6$, 400 MHz): δ (ppm) 6.56 (t, J=2.0 Hz, 1H), 7.16 (d, J=8.8 Hz, 2H), 7.71 (d, J=8.8 Hz, 2H), 7.76 (s, 1H), 7.77 (d, J=8.8 Hz, 2H), 7.92 (d, J=8.8 Hz, 2H), 8.54 (t, J=2.0 Hz, 1H).

Example 451

Synthesis of 4-(((trans)-4-(4-(trifluoromethoxy)phenyl)cyclohexyl)amino)-1H-1,2,3-triazole-5-carboxylic acid (451)

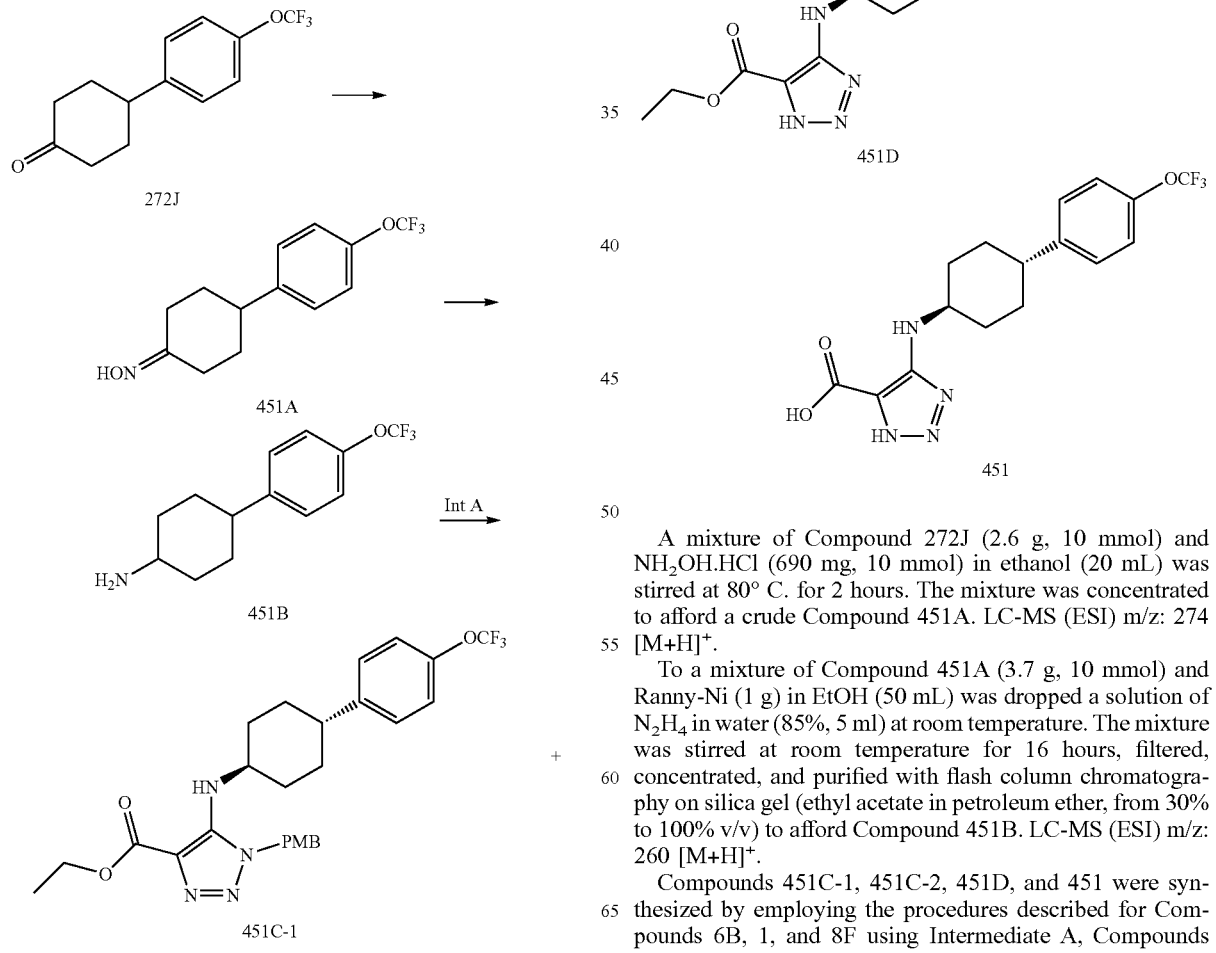

A mixture of Compound 272J (2.6 g, 10 mmol) and NH$_2$OH.HCl (690 mg, 10 mmol) in ethanol (20 mL) was stirred at 80° C. for 2 hours. The mixture was concentrated to afford a crude Compound 451A. LC-MS (ESI) m/z: 274 [M+H]$^+$.

To a mixture of Compound 451A (3.7 g, 10 mmol) and Ranny-Ni (1 g) in EtOH (50 mL) was dropped a solution of N$_2$H$_4$ in water (85%, 5 ml) at room temperature. The mixture was stirred at room temperature for 16 hours, filtered, concentrated, and purified with flash column chromatography on silica gel (ethyl acetate in petroleum ether, from 30% to 100% v/v) to afford Compound 451B. LC-MS (ESI) m/z: 260 [M+H]$^+$.

Compounds 451C-1, 451C-2, 451D, and 451 were synthesized by employing the procedures described for Compounds 6B, 1, and 8F using Intermediate A, Compounds 451B with K$_3$PO$_4$ as base and NMP as solvent, 451C-1, and 451D in lieu of Compounds 6A, 1-methylpiperazine with tBuONa as base and toluene as solvent, 1E, and 8E. Compound 451C-1: LC-MS (ESI) m/z: 519 [M+H]$^+$; $^1$H-NMR (CDCl$_3$, 400 MHz): δ (ppm) 1.09-1.26 (m, 4H), 1.33-1.38 (m, 3H), 1.74-1.82 (m, 4H), 2.33-2.37 (m, 1H), 3.11-3.14 (m, 1H), 3.72 (s, 3H), 4.31-4.35 (m, 2H), 5.39-5.41 (m, 3H), 6.82-6.85 (m, 2H), 7.04-7.19 (m, 6H). Compound 451C-2: LC-MS (ESI) m/z: 519 [M+H]$^+$; $^1$H-NMR (CDCl$_3$, 400 MHz): δ (ppm) 1.42-1.46 (m, 3H), 1.50-1.72 (m, 8H), 2.48-2.52 (m, 1H), 3.79-3.83 (m, 4H), 4.40-4.47 (m, 2H), 5.44 (s, 2H), 6.23-6.26 (m, 1H), 6.87 (d, J=8.8 Hz, 2H), 7.12-7.14 (m, 4H), 7.23-7.26 (m, 2H). Compound 451D: LC-MS (ESI) m/z: 399 [M+H]$^+$. Compound 451: LC-MS (ESI) m/z: 371 [M+H]$^+$; $^1$H-NMR (CD$_3$OD, 400 MHz): δ (ppm) 1.48-1.53 (m, 2H), 1.63-1.72 (m, 2H), 1.96-2.02 (m, 2H), 2.21-2.24 (m, 2H), 2.63-2.69 (m, 1H), 2.31-2.45 (m, 1H), 7.19 (d, J=8.4 Hz, 2H) 7.34-7.38 (m, 2H).

Example 452

Synthesis of 4-(((cis)-4-(4-(trifluoromethoxy)phenyl)cyclohexyl)amino)-1H-1,2,3-triazole-5-carboxylic acid (452)

Compounds 452A, and 452 were synthesized by employing the procedures described for Compounds 1 and 8F using 451C-2 and 452A in lieu of Compounds 1E and 8E. Compound 452A: LC-MS (ESI) m/z: 399 [M+H]$^+$. Compound 452: LC-MS (ESI) m/z: 371 [M+H]$^+$; $^1$H-NMR (CD$_3$OD, 400 MHz): δ (ppm) 1.71-1.87 (m, 6H), 2.01-2.04 (m, 2H), 2.69-2.72 (m, 1H), 3.87 (s, 1H), 7.19 (d, J=8.4 Hz, 2H), 7.36 (d, J=8.4 Hz, 2H).

Example 453

Synthesis of 4-((4-hydroxy-4-(4-(trifluoromethoxy)phenyl)cyclohexyl)oxy)-1H-1,2,3-triazole-5-carboxylic acid (453)

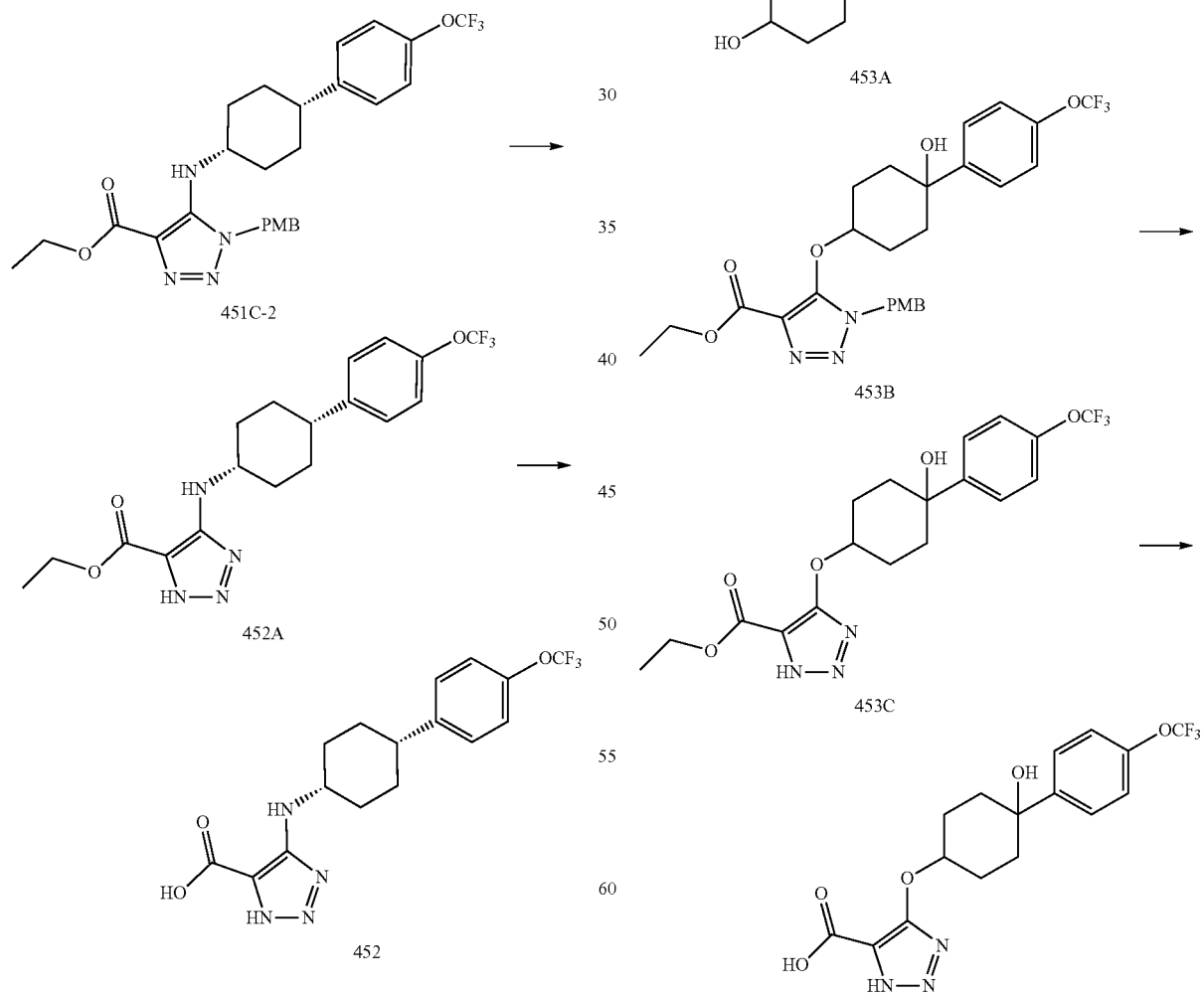

Compounds 453A, 453B, 453C, and 453 were synthesized by employing the procedures described for Compounds 263D, 90C, 380E, and 8F using Compounds 272C, 453A with toluene as solvent, 453B with THF as solvent, and 453C in lieu of Compounds 263C, 90B with THF as solvent, 380D with MeOH as solvent, and 8E. Compound 453A: $^1$H-NMR (DMSO-d$_6$, 400 MHz): δ (ppm) 1.57-1.64 (m, 5H), 1.70-1.74 (m, 3H), 3.90-3.54 (m, 1H), 4.47 (m, 1H), 4.84 (s, 1H), 7.25 (d, J=8 Hz, 2H), 7.57 (d, J=8 Hz, 2H). Compound 453B: LC-MS (ESI) m/z: 536 [M+H]$^+$. Compound 453C: LC-MS (ESI) m/z: 416 [M+H]$^+$. Compound 453: LC-MS (ESI) m/z: 388 [M+H]$^+$. $^1$H-NMR (DMSO-d$_6$, 400 MHz): δ (ppm) 1.44-1.47 (m, 2H), 1.82-1.85 (m, 2H), 1.96-2.02 (m, 2H), 2.07-2.11 (m, 2H), 4.94 (s, 1H), 5.05 (s, 1H), 7.27 (d, J=8.4 Hz, 2H), 7.58 (d, J=8.8 Hz, 2H).

Example 454

Synthesis of 4-((4'-(trifluoromethoxy)-2,3,4,5-tetrahydro-[1,1'-biphenyl]-4-yl)oxy)-1H-1,2,3-triazole-5-carboxylic acid (454)

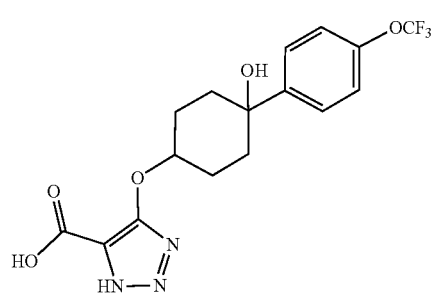

453

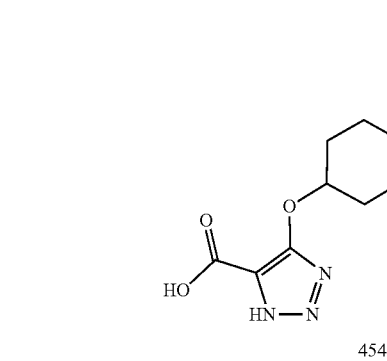

454

A mixture of Compound 453 (0.04 g, 0.103 mmol) and BF$_3$-Et$_2$O (0.035 g, 0.246 mmol) was stirred at room temperature for 16 hours. The mixture was concentrated under reduced pressure. The residue was purified with preparative HPLC to yield Compound 454. LC-MS (ESI) m/z: 370 [M+H]$^+$. $^1$H-NMR (DMSO-d$_6$, 400 MHz): δ (ppm) 1.96-2.00 (m, 1H), 2.06-2.08 (m, 1H), 2.37-2.42 (m, 1H), 2.49-2.55 (m, 2H), 2.69-2.73 (m, 1H), 4.93 (s, 1H), 6.12 (s, 1H), 7.30 (d, J=8 Hz, 2H), 7.54 (d, J=8 Hz, 2H).

Example 455

Synthesis of 4-(((cis-3a,6a)-5-(4-(trifluoromethoxy)phenyl)octahydropentalen-2-yl)oxy)-1H-1,2,3-triazole-5-carboxylic acid (455)

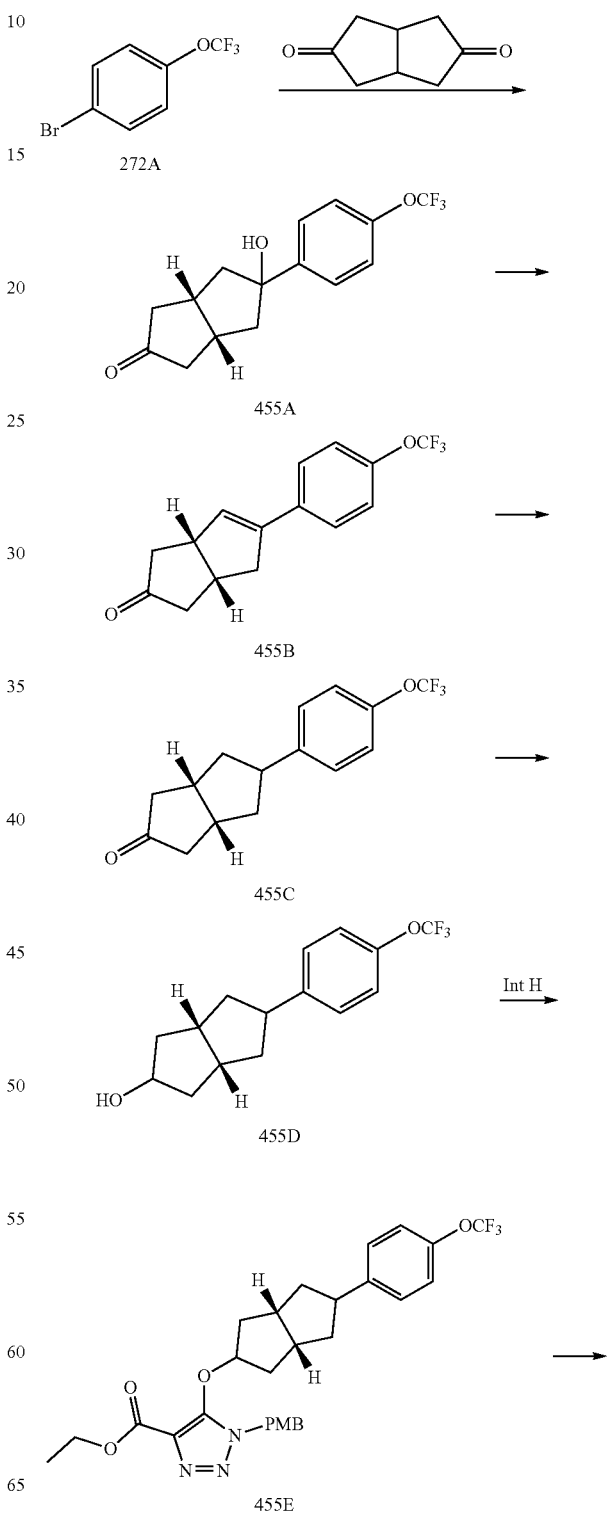

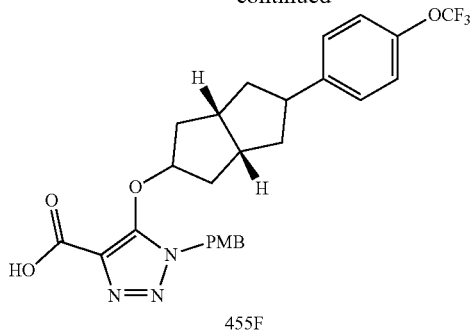

455F

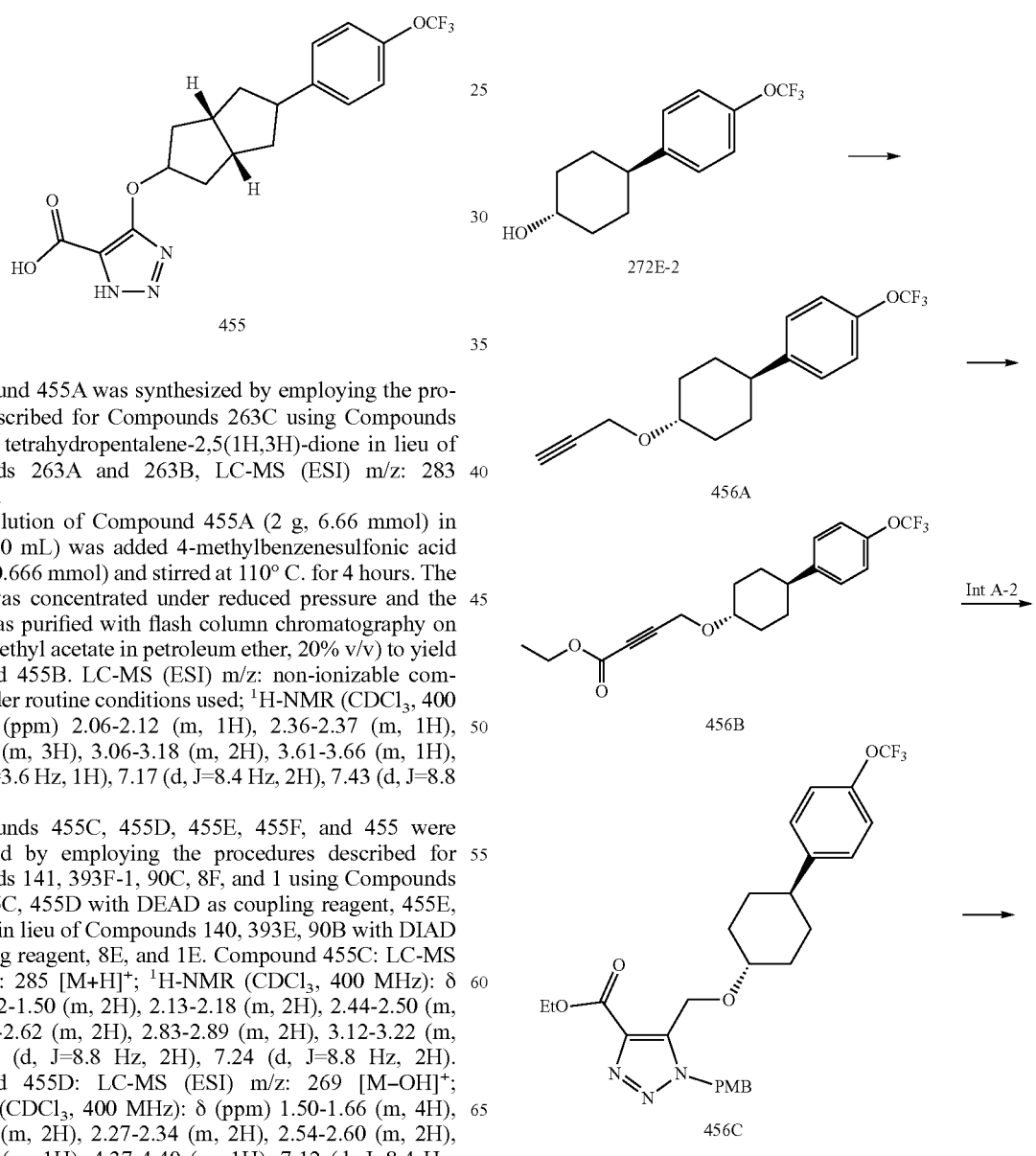

2H), 7.26 (d, J=8.0 Hz, 2H). Compound 455E: LC-MS (ESI) m/z: 546 [M+H]+. 1H-NMR (CDCl3, 400 MHz): δ (ppm) 1.26-1.28 (m, 2H), 1.41 (t, J=7.2 Hz, 3H), 1.65-1.71 (m, 2H), 1.96-2.02 (m, 2H), 2.25-2.32 (m, 2H), 2.59-2.65 (m, 2H), 3.00-3.09 (m, 1H), 3.79 (s, 3H), 4.40 (q, J=7.2 Hz, 2H), 5.27 (s, 2H), 5.75-5.80 (m, 1H), 6.86 (d, J=8.8 Hz, 2H), 7.13 (d, J=8.4 Hz, 2H), 7.20-7.24 (m, 4H). Compound 455F: LC-MS (ESI) m/z: 518 [M+H]+. Compound 455: LC-MS (ESI) m/z: 420 [M+Na]+; 1H-NMR (DMSO-d6, 400 MHz): δ (ppm) 1.28-1.36 (m, 2H), 1.86-1.97 (m, 4H), 2.26-2.29 (m, 2H), 2.67-2.71 (m, 2H), 3.00-3.09 (m, 1H), 5.20-5.26 (m, 1H), 7.26 (d, J=8.0 Hz, 2H), 7.40 (d, J=8.4 Hz, 2H), 12.95 (bs, 1H), 14.74 (bs, 1H).

Example 456

Synthesis of 4-((((trans)-4-(4-(trifluoromethoxy)phenyl)cyclohexyl)oxy)methyl)-1H-1,2,3-triazole-5-carboxylic acid (456)

Compound 455A was synthesized by employing the procedure described for Compounds 263C using Compounds 272A and tetrahydropentalene-2,5(1H,3H)-dione in lieu of Compounds 263A and 263B, LC-MS (ESI) m/z: 283 [M–OH]+.

To a solution of Compound 455A (2 g, 6.66 mmol) in toluene (40 mL) was added 4-methylbenzenesulfonic acid (115 mg, 0.666 mmol) and stirred at 110° C. for 4 hours. The mixture was concentrated under reduced pressure and the residue was purified with flash column chromatography on silica gel (ethyl acetate in petroleum ether, 20% v/v) to yield Compound 455B. LC-MS (ESI) m/z: non-ionizable compound under routine conditions used; 1H-NMR (CDCl3, 400 MHz): δ (ppm) 2.06-2.12 (m, 1H), 2.36-2.37 (m, 1H), 2.50-2.63 (m, 3H), 3.06-3.18 (m, 2H), 3.61-3.66 (m, 1H), 6.04 (d, J=3.6 Hz, 1H), 7.17 (d, J=8.4 Hz, 2H), 7.43 (d, J=8.8 Hz, 2H).

Compounds 455C, 455D, 455E, 455F, and 455 were synthesized by employing the procedures described for Compounds 141, 393F-1, 90C, 8F, and 1 using Compounds 455B, 455C, 455D with DEAD as coupling reagent, 455E, and 455F in lieu of Compounds 140, 393E, 90B with DIAD as coupling reagent, 8E, and 1E. Compound 455C: LC-MS (ESI) m/z: 285 [M+H]+; 1H-NMR (CDCl3, 400 MHz): δ (ppm) 1.42-1.50 (m, 2H), 2.13-2.18 (m, 2H), 2.44-2.50 (m, 2H), 2.55-2.62 (m, 2H), 2.83-2.89 (m, 2H), 3.12-3.22 (m, 1H), 7.14 (d, J=8.8 Hz, 2H), 7.24 (d, J=8.8 Hz, 2H). Compound 455D: LC-MS (ESI) m/z: 269 [M–OH]+; 1H-NMR (CDCl3, 400 MHz): δ (ppm) 1.50-1.66 (m, 4H), 2.05-2.11 (m, 2H), 2.27-2.34 (m, 2H), 2.54-2.60 (m, 2H), 2.97-3.06 (m, 1H), 4.37-4.40 (m, 1H), 7.12 (d, J=8.4 Hz, 2H), 2.53-2.60 (m, 1H), 3.40-3.48 (m, 1H), 4.79, 4.85 (s, 2H), 7.24 (d, J=8.4 Hz, 2H), 7.35 (d, J=8.4 Hz, 2H), 13.20 (s, 1H), 15.37, 15.70 (s, 1H).

Example 457

Synthesis of 4-(((trans)-4-(4-sulfamoylphenyl)cyclohexyl)oxy)-1H-1,2,3-triazole-5-carboxylic acid (457)

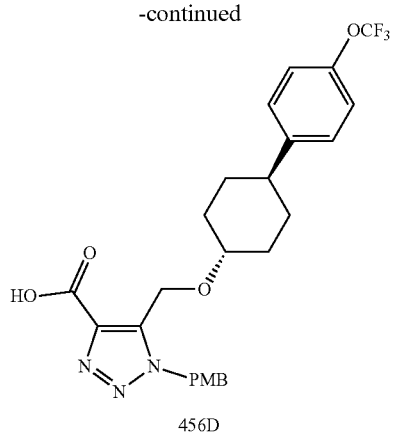

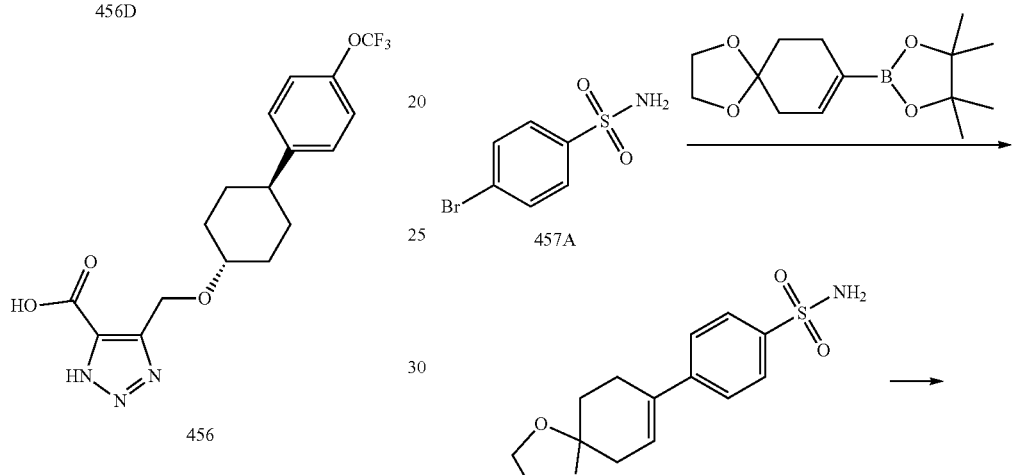

To a solution of compound 272E-2 (3.76 g, 14.45 mmol) in THF (100 mL) was added 18-crown-6 (9.55 g, 36.13 mmol) and NaH (60% oil dispersion, 1.45 g, 36.13 mmol) at 0° C. and stirred at 0° C. for 20 minutes. To the solution was added 3-bromoprop-1-yne (8.59 g, 72.25 mmol) and stirred at room temperature overnight. It was quenched with water (100 mL) and extracted with ethyl acetate (100 mL×3). The combined organic layers was washed with brine (100 mL), dried over anhydrous sodium sulfate, filtered, and concentrated. The residue was purified with column chromatography on silica gel (ethyl acetate in petroleum ether, from 15% to 25%, v/v) to furnish Compound 456A. LC-MS (ESI) m/z: non-ionizable compound under routine conditions used. $^1$H-NMR (CDCl$_3$, 400 MHz): δ (ppm) 1.35-1.56 (m, 4H), 1.92-2.00 (m, 2H), 2.16-2.24 (m, 2H), 2.44 (t, J=2.0 Hz, 1H), 2.50-2.58 (m, 1H), 3.52-3.60 (m, 1H), 4.24 (t, J=2.0 Hz, 2H), 7.14 (d, J=8.4 Hz, 2H), 7.22 (d, J=8.4 Hz, 2H).

Compounds 456B, 456C, 456D, and 456 were synthesized by employing the procedures described for Compounds 372E, 151B, 8F, and 1 using Compounds 456A, 456B, 456C with DEAD as coupling reagent, and 456D in lieu of Compounds 372D, 151A, 8E, and 1E. Compound 456B: LC-MS (ESI) m/z: non-ionizable compound under routine conditions used. $^1$H-NMR (CDCCl$_3$, 400 MHz): δ (ppm) 1.33 (t, J=7.2 Hz, 3H), 1.38-1.58 (m, 4H), 1.93-2.00 (m, 2H), 2.16-2.24 (m, 2H), 2.50-2.58 (m, 1H), 3.50-3.58 (m, 1H), 4.23-4.40 (m, 2H), 4.36 (s, 2H), 7.14 (d, J=8.4 Hz, 2H), 7.21 (d, J=8.4 Hz, 2H). Compound 456C: LC-MS (ESI) m/z: 534 [M+H]$^+$. Compound 456D: LC-MS (ESI) m/z: 504 [M−H]$^−$. Compound 456: LC-MS (ESI) m/z: 386 [M+H]$^+$; $^1$H-NMR (DMSO-d$_6$, 400 MHz): δ (ppm) 1.24-1.38 (m, 2H), 1.39-1.52 (m, 2H), 1.76-1.85 (m, 2H), 2.04-2.14 (m,

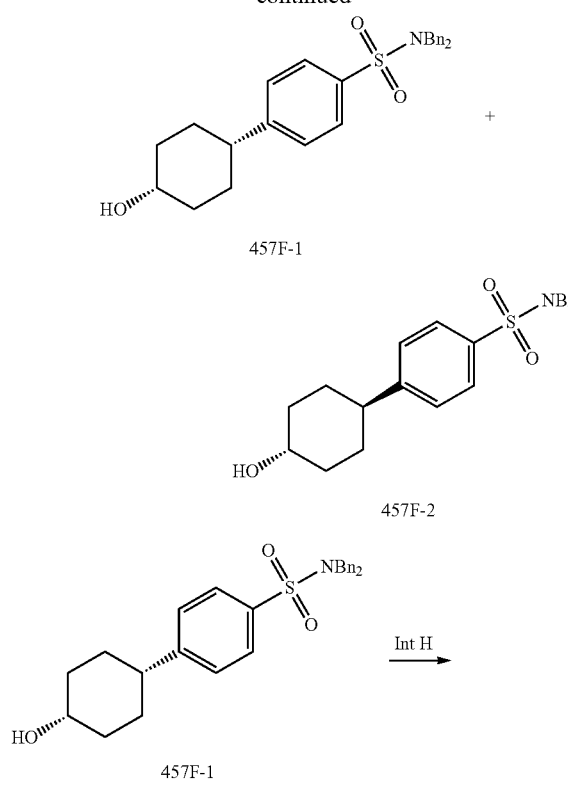

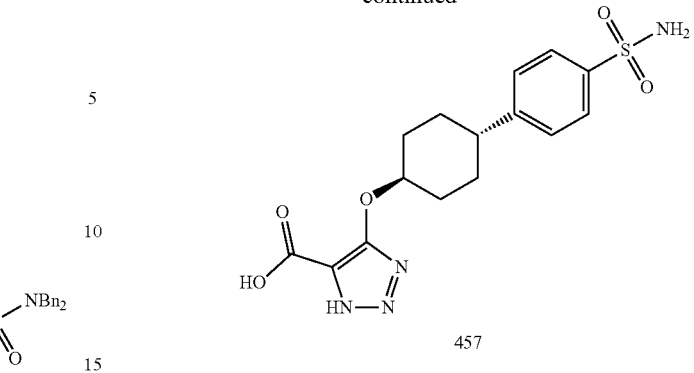

Compounds 457B, 457C, and 457D were synthesized by employing the procedures described for Compounds 4B, 141, and 279D using 4,4,5,5-tetramethyl-2-(1,4-dioxaspiro[4.5]dec-7-en-8-yl)-1,3,2-dioxaborolane, Compounds 457A with $K_2CO_3$ as base and 1,4-dioxane/$H_2O$ as solvent, 457B at reflux, and 457C with THF/methanol as solvent in lieu of (3,4-dichlorophenyl)boronic acid, Compounds 4A with $Na_2CO_3$ as base and toluene/EtOH/$H_2O$ as solvent, 140 at room temperature, and 279C with HCl as acid and 1,4-dioxane as solvent. Compound 457B: LC-MS (ESI) m/z: 296 [M+H]$^+$; $^1$H-NMR (DMSO-$d_6$, 500 MHz): δ (ppm) 1.83 (t, J=6.5 Hz, 2H), 2.40 (brs, 2H), 2.55-2.58 (m, 2H), 3.92 (s, 4H), 6.17 (brs, 1H), 7.32 (s, 2H), 7.59 (d, J=8.5 Hz, 2H), 7.75 (d, J=8.5 Hz, 2H). Compound 457C: LC-MS (ESI) m/z: 298 [M+H]$^+$. Compound 457D: LC-MS (ESI) m/z: 254 [M+H]$^+$; $^1$H-NMR (DMSO-$d_6$, 400 MHz): δ (ppm) 1.85-196 (m, 2H), 2.05-2.09 (m, 2H), 2.26-2.29 (m, 2H), 2.55-2.63 (m, 2H), 3.13-3.19 (m, 1H), 7.28 (brs, 2H), 7.50 (d, J=8.0 Hz, 2H), 7.75 (d, J=8.4 Hz, 2H).

To a mixture of Compound 457D (840 mg, 3.32 mmol), NaOH (664 mg, 16.6 mmol), $K_2CO_3$ (641 mg, 4.64 mmol), and $Bu_4NHSO_4$ (181 g, 0.532 mmol) in toluene (8 mL) was added a solution of (bromomethyl)benzene (1.361 mg, 7.96 mmol) in THF (3 mL) at 45° C. and stirred at 45° C. for 16 hours. The mixture was cooled down to room temperature and filtered. The cake was washed with THF (8 mL). The combined filtrate and washing was washed with brine (20 mL), dried over anhydrous sodium sulfate, filtered, concentrated, and purified with flash column chromatography (ethyl acetate in petroleum ether, from 0% to 50% v/v) to yield Compound 457E. LC-MS (ESI) m/z: 434 [M+H]$^+$; $^1$H-NMR (CDCl$_3$, 400 MHz): δ (ppm) 1.91-2.02 (m, 2H), 2.23-2.27 (m, 2H), 2.53-2.56 (m, 4H), 3.08-3.16 (m, 1H), 4.33 (s, 4H), 7.05-7.05 (m, 4H), 7.19-7.21 (m, 6H), 7.37 (d, J=8.4 Hz, 2H), 7.78 (d, J=8.4 Hz, 2H).

Compounds 457F-1, 457F-2, 457G, 457H, and 457 were synthesized by employing the procedures described for Compounds 393F-1, 90C, 380E, and 8F using Compounds 457E, 457F-1, 457G with MeOH/THF as solvent at reflux, and 457H in lieu of Compounds 393E, 90B, 380D with MeOH as solvent at room temperature, and 8E. Compound 457F-1: LC-MS (ESI) m/z: 436 [M+H]$^+$; $^1$H-NMR (CDCl$_3$, 400 MHz): δ (ppm) 1.57-1.74 (m, 4H), 1.89-1.99 (m, 4H), 2.60-2.68 (m, 1H), 4.17 (brs, 1H), 4.32 (s, 4H), 7.01-7.03 (m, 4H), 7.19-7.21 (m, 6H), 7.36 (d, J=8.8 Hz, 2H), 7.76 (d, J=8.8 Hz, 2H). Compound 457F-2: LC-MS (ESI) m/z: 436 [M+H]$^+$; $^1$H-NMR (CDCl$_3$, 400 MHz): δ (ppm) 1.41-1.55 (m, 4H), 1.94-1.97 (m, 2H), 2.12-2.15 (m, 2H), 2.55-2.63 (m, 1H), 3.69-3.74 (m, 1H), 4.08 (s, 4H), 7.01-7.03 (m, 4H), 7.18-7.21 (m, 6H), 7.32 (d, J=8.0 Hz, 2H), 7.75 (d, J=8.4 Hz, 2H). Compound 457G: LC-MS (ESI) m/z: 695 [M+H]$^+$.

$^1$H-NMR (CDCl$_3$, 400 MHz): δ (ppm) 1.25-1.56 (m, 7H), 1.94-1.97 (m, 2H), 2.17-2.20 (m, 2H), 2.53-2.60 (m, 1H), 3.80 (s, 3H), 4.31 (s, 4H), 4.42 (q, J=7.2 Hz, 2H), 5.06-5.14 (m, 1H), 5.30 (s, 2H), 6.87 (d, J=8.8 Hz, 2H), 7.01-7.03 (m, 4H), 7.18-7.21 (m, 6H), 7.26-7.26 (m, 1H), 7.27-7.30 (m, 3H), 7.75 (d, J=8.4 Hz, 2H). Compound 457H: LC-MS (ESI) m/z: 395 [M+H]$^+$. Compound 457: LC-MS (ESI) m/z: 367 [M+H]$^+$. $^1$H-NMR (CD$_3$OD, 400 MHz): δ (ppm) 1.65-1.76 (m, 4H), 1.98-2.00 (m, 2H), 2.37-2.38 (m, 2H), 2.70-2.76 (m, 1H), 4.74-4.79 (m, 1H), 7.45 (d, J=8.4 Hz, 2H), 7.83 (d, J=8.0 Hz, 2H).
Example 458
Synthesis of 4-(((trans)-4-(4-(1-(2-ethyl-2-hydroxy-pentyl)-1H-pyrazol-3-yl)phenyl)cyclohexyl)oxy)-1H-1,2,3-triazole-5-carboxylic acid (458)
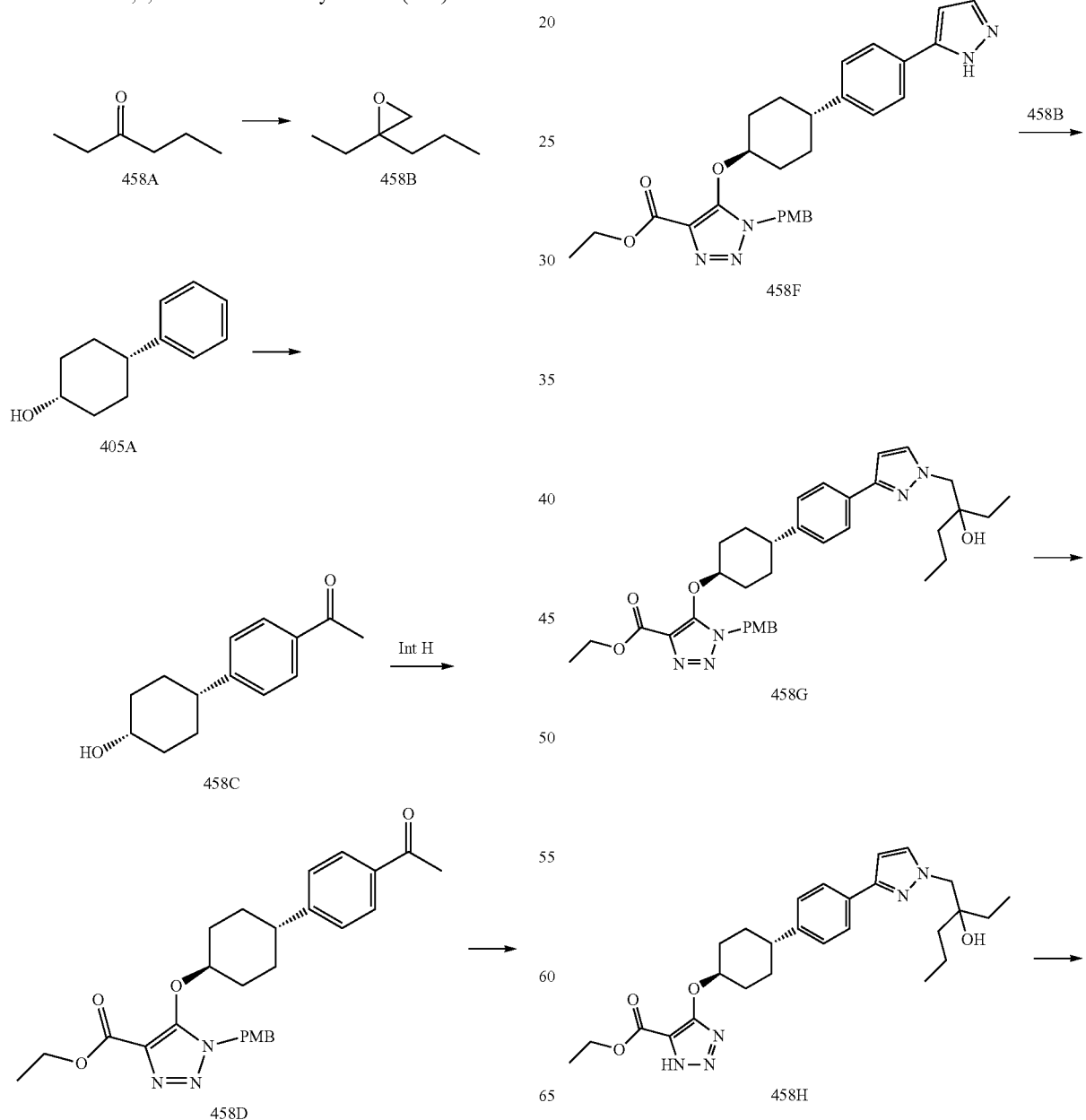

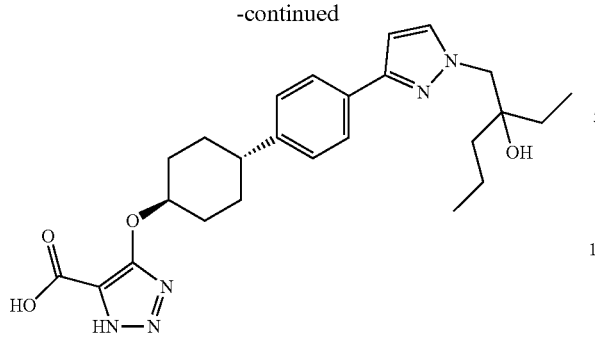

458

To a suspension of hexan-3-one (458A, 3.0 g, 30 mmol) and trimethyl sulfoxonium iodide (7.92 g, 36 mmol) in DMSO (35 mL) was added potassium tert-butoxide solution (1 M solution in THF, 33 mL, 33.0 mmol). The reaction mixture was stirred at room temperature under $N_2$ for 16 hours and concentrated under reduced pressure. The residue was partitioned between $Et_2O$ (50 mL) and brine (50 mL). The organic layer was separated, washed with water (50 mL) and brine (50 mL), dried over $MgSO_4$, filtered, and distillated to afford a crude Compound 458B. $^1$H-NMR (DMSO-$d_6$, 400 MHz): δ (ppm) 0.93 (t, J=7.2 Hz, 6H), 1.36-1.64 (m, 6H), 1.85-2.60 (m, 2H).

To a solution of Compound 405A (500 mg, 2.84 mmol) in dichloromethane (30 mL) was added $AlCl_3$ (1.13 g, 8.52 mmol) at 0° C. and stirred at 0° C. for 20 minutes, followed by addition of acetyl chloride (266 mg, 3.41 mmol). The mixture was stirred at 0° C. for 30 minutes, pour into ice-water (50 mL), and extracted with EtOAc (50 mL×2). The combined extracts was dried over anhydrous $Na_2SO_4$, filtered, and concentrated. The crude product was purified by flash column chromatography (eluting with EA/PE=1:5) to afford Compound 458C. LC-MS (ESI) m/z: 219 [M+H]$^+$.

Compound 458D was synthesized by employing the procedure described for Compound 90C using Compound 458C with toluene as solvent at 70° C. in lieu of Compound 90B with THF as solvent at room temperature, Compound 458D: LC-MS (ESI) m/z: 478 [M+H]$^+$.

A mixture of Compound 458D (800 mg, 1.67 mmol) and DMF-DMA (20 mL) was heated at 110° C. for 48 hours. The mixture was concentrated and purified by flash column chromatography (eluting with MeOH/DCM=1:13) to afford Compound 458E. LC-MS (ESI) m/z: 533 [M+H]$^+$.

A mixture of Compound 458E (1.5 g, 2.81 mmol) and $N_2H_4$—$H_2O$ (3 mL) in EtOH (20 mL) was stirred at 80° C. for 2 hours and concentrated. The residue was purified by flash column chromatography (eluting with MeOH/DCM=1:13) to afford Compound 458F. LC-MS (ESI) m/z: 502 [M+H]$^+$.

A mixture of Compound 458F (200 mg, 0.40 mmol), $Cs_2CO_3$ (261 mg, 0.8 mmol), Compound 458B and DMF (5 mL) was heated in a sealed tube at 60° C. for 16 hours. The mixture was diluted with EtOAc (30 mL), washed with brine (20 mL×2), dried over anhydrous $Na_2SO_4$, concentrated, and purified by flash column chromatography (eluting with MeOH/DCM=1:10) to afford Compound 458G. LC-MS (ESI) m/z: 616 [M+H]$^+$.

Compounds 458H and 458 were synthesized by employing the procedures described for Compounds 1 and 8F using Compounds 458G and 458I1 in lieu of Compounds 1E and 8E. Compound 458H: LC-MS (ESI) m/z: 496 [M+H]$^+$. Compound 458: LC-MS (ESI) m/z: 468 [M+H]$^+$; $^1$H-NMR (CD$_3$OD, 400 MHz): δ (ppm) 0.90-0.97 (m, 6H), 1.35-1.48 (m, 6H), 1.65-1.72 (m, 4H), 1.96-1.99 (m, 2H), 2.33-2.36 (m, 2H), 2.61-2.63 (m, 1H), 4.15 (s, 2H), 4.71-4.74 (m, 1H), 6.60 (d, J=2.0 Hz, 1H), 7.27 (d, J=8.0 Hz, 2H), 7.64 (d, J=2.4 Hz, 1H), 7.69 (d, J=8.4 Hz, 2H).

Example 459

Synthesis of 4-(((trans)-4-(4-(1H-pyrazol-1-yl)phenyl)cyclohexyl)thio)-1H-1,2,3-triazole-5-carboxylic acid 2,2,2-trifluoroacetate (459)

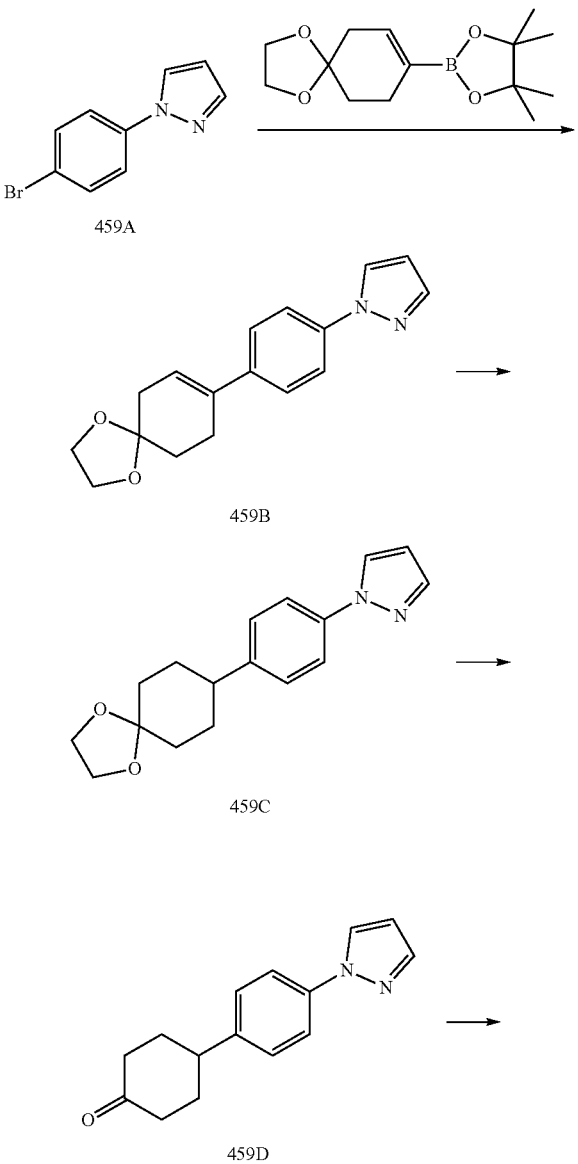

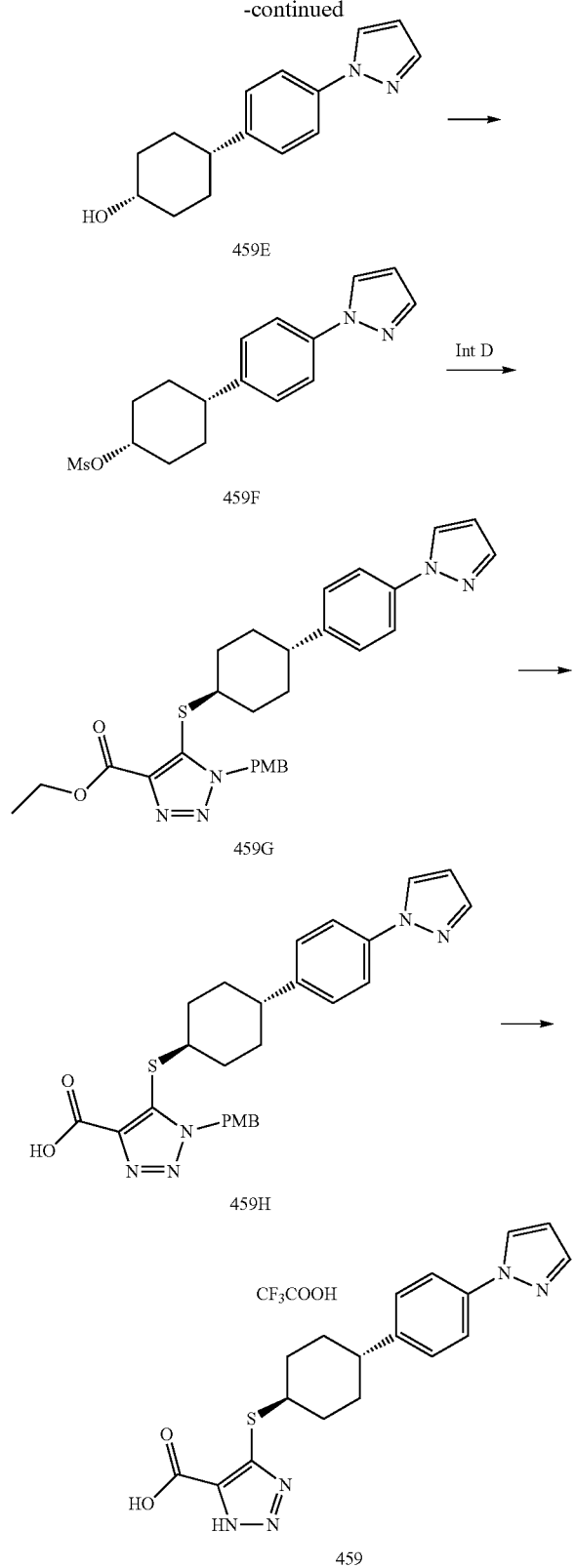

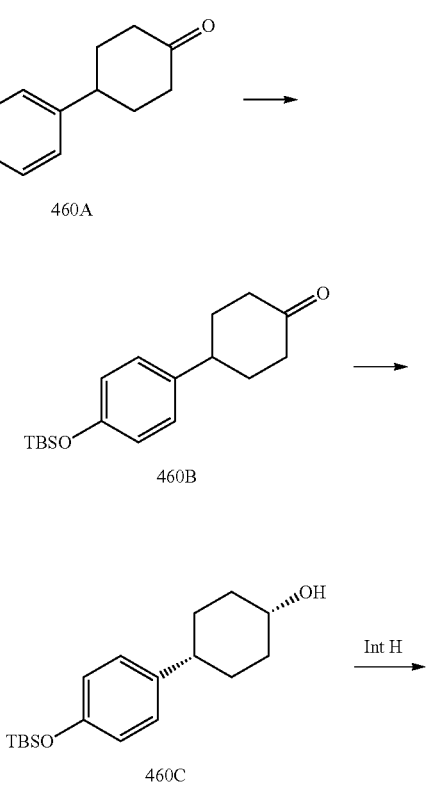

Compounds 459B, 459C, 459D, 459E, 459F, 459G, 459H, and 459 were synthesized by employing the procedures described for Compounds 4B, 141, 279D, 393F-1, 340F, 340G, 8F, and 1 using 4,4,5,5-tetramethyl-2-(1,4-dioxaspiro[4.5]dec-7-en-8-yl)-1,3,2-dioxaborolane, Compounds 459A with $K_3PO_4$ as base and toluene/$H_2O$ as solvent, 459B, 459C with TFA as acid and dichloromethane as solvent, 459D, 459E, 459F, 459G, and 459H in lieu of (3,4-dichlorophenyl)boronic acid, Compounds 4A with $Na_2CO_3$ as base and toluene/EtOH/$H_2O$ as solvent, 140, 279C with HCl as acid and 1,4-dioxane as solvent, 393E, 340E, 340F, 8E, and 1E. Compound 459B: LC-MS (ESI) m/z: 283 [M+H]$^+$. Compound 459C: LC-MS (ESI) m/z: 285 [M+H]$^+$; $^1$H-NMR (CDCl$_3$, 400 MHz): δ (ppm) 1.61-1.90 (m, 8H), 2.58-2.65 (m, 1H), 4.00 (s, 4H), 6.45 (s, 1H), 7.33 (d, J=8.4 Hz, 2H), 7.61 (d, J=8.4 Hz, 2H), 7.71 (s, 1H), 7.89 (s, 1H). Compound 459D: LC-MS (ESI) m/z: 241 [M+H]$^+$; $^1$H-NMR (CDCl$_3$, 400 MHz): δ (ppm) 1.92-2.03 (m, 2H), 2.24-2.30 (m, 2H), 2.52-2.56 (m, 4H), 3.05-3.12 (m, 1H), 6.47 (s, 1H), 7.34 (d, J=8.4 Hz, 2H), 7.65 (d, J=8.4 Hz, 2H), 7.72 (s, 1H), 7.91 (s, 1H). Compound 459E: LC-MS (ESI) m/z: 243 [M+H]$^+$. Compound 459F: LC-MS (ESI) m/z: 321 [M+H]$^+$. Compound 459G: LC-MS (ESI) m/z: 518 [M+H]$^+$. Compound 459H: LC-MS (ESI) m/z: 490 [M+H]$^+$. Compound 459: LC-MS (ESI) m/z: 370 [M+H]$^+$; $^1$H-NMR (DMSO-d$_6$, 400 MHz): δ (ppm) 1.53-1.66 (m, 4H), 1.88-1.90 (m, 2H), 2.21-2.24 (m, 2H), 2.60-2.66 (m, 1H), 3.58-3.59 (m, 1H), 6.51-6.52 (m, 1H), 7.36 (d, J=8.4 Hz, 2H), 7.71-7.75 (m, 3H), 8.43 (s, 1H).

Example 460

Synthesis of 4-(((trans)-4-(4-(cyclohexylmethoxy)phenyl)cyclohexyl)oxy)-1H-1,2,3-triazole-5-carboxylic acid (460)

trated, and purified with flash column chromatography on silica gel (ethyl acetate in petroleum ether, from 0% to 30% v/v) to furnish Compound 460B. LC-MS (ESI) m/z: 305 [M+H]$^+$; $^1$H-NMR (CDCl$_3$, 400 MHz): δ (ppm) 0.19 (s, 6H), 0.98 (m, 9H), 1.83-1.95 (m, 2H), 2.16-2.21 (m, 2H), 2.47-2.51 (m, 4H), 2.92-3.00 (m, 1H), 6.78 (d, J=8.8 Hz, 2H), 7.08 (d, J=8.4 Hz, 2H).

Compounds 460C, 460D, 460E, 460F, 460G, and 460 were synthesized by employing the procedures described for Compounds 393F-1, 90C, 280E, 27B, 380E, and 8F using Compounds 460B, 460C, 460D with THF/H$_2$O as solvent and adding KF, 460E, (bromomethyl)cyclohexane, 460F, and 460G in lieu of Compounds 393E, 90B, 280D with THF as solvent and without KF, 27A, 2-bromopropane, 380D, and 8E. Compound 460C: LC-MS (ESI) m/z: 289 [M−OH]$^+$; $^1$H-NMR (CDCl$_3$, 400 MHz): δ (ppm) 0.19 (s, 6H), 0.98 (m, 9H), 1.63-1.69 (m, 4H), 1.79-1.89 (m, 4H), 2.44-2.51 (m, 1H), 4.05-4.18 (m, 1H), 6.76 (d, J=8.4 Hz, 2H), 7.08 (d, J=8.4 Hz, 2H). Compound 460D: LC-MS (ESI) m/z: 566 [M+H]$^+$. Compound 460E: LC-MS (ESI) m/z: 452 [M+H]$^+$; $^1$H-NMR (DMSO-d$_6$, 400 MHz): δ (ppm) 1.31 (t, J=7.2 Hz, 3H), 1.32-1.39 (m, 2H), 1.44-1.51 (m, 2H), 1.76-1.70 (m, 2H), 2.02-2.05 (m, 2H), 2.37-2.44 (m, 1H), 3.73 (s, 3H), 4.27-4.33 (m, 2H), 4.71-4.91 (m, 1H), 5.35 (s, 2H), 6.65 (d, J=8.4 Hz, 2H), 6.92-7.00 (m, 4H), 7.23 (d, J=8.8 Hz, 2H), 9.13 (s, 1H). Compound 460F: LC-MS (ESI) m/z: 548 [M+H]$^+$. Compound 460G: LC-MS (ESI) m/z: 428 [M+H]$^+$. Compound 460: LC-MS (ESI) m/z: 400 [M+H]$^+$. $^1$H-NMR (DMSO-d$_6$, 400 MHz): δ (ppm) 1.00-1.25 (m, 6H), 1.52-1.81 (m, 12H), 1.21 (m, 2H), 3.71-3.73 (m, 2H), 4.65 (m, 1H), 6.81-6.83 (m, 2H), 7.13-7.15 (m, 2H).

Example 461

Synthesis of 4-(((cis-3a,6a)-5-(4-(trifluoromethoxy)phenyl)octahydropentalen-2-yl)thio)-1H-1,2,3-triazole-5-carboxylic acid (461)

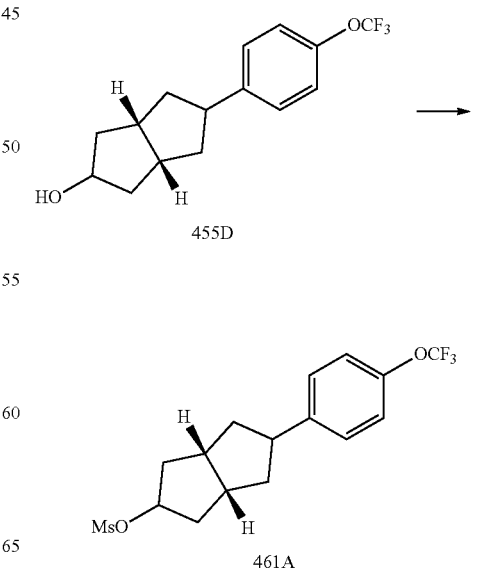

To a solution of 4-(4-hydroxyphenyl)cyclohexanone (460A, 15.00 g, 78.95 mmol) and 1H-imidazole (8.05 g, 118.42 mmol) in dichloromethane (150 mL) was added TBSCl (17.77 g, 118.42 mmol) at room temperature. The mixture was stirred at room temperature for 3 hours, diluted with ethyl acetate (200 mL), washed with water (200 mL) and brine (200 mL), dried over anhydrous Na$_2$SO$_4$, concen- 791
-continued

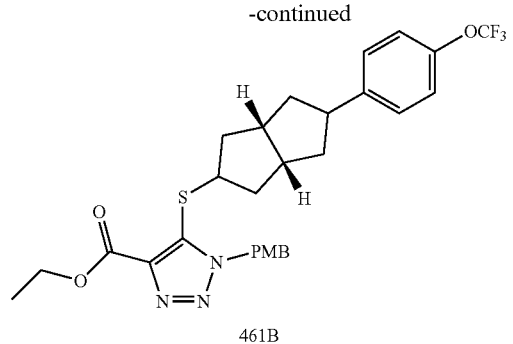
461B

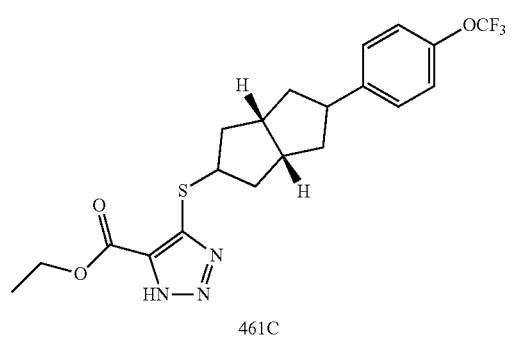
461C

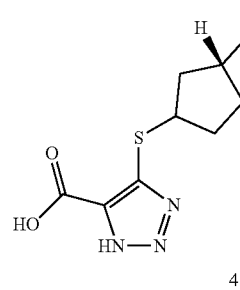
461

Compounds 461A, 461B, 461C, and 461 were synthesized by employing the procedures described for Compounds 340F, 340G, 1, and 8F using Compounds 459A with K₃PO₄ as base and toluene/H₂O as solvent, 455D, 461A, 461B, and 461C in lieu of Compounds 340E, 340F, 1E, and 8E. Compound 461A: LC-MS (ESI) m/z: 382 [M+18]⁺. Compound 461B: LC-MS (ESI) m/z: 562 [M+H]⁺. ¹H-NMR (CDCl₃, 400 MHz): δ (ppm) 0.99-1.07 (m, 2H), 1.42 (t, J=7.2 Hz, 3H), 1.60-1.68 (m, 4H), 2.14-2.22 (m, 2H), 2.60-2.65 (m, 2H), 2.81-2.90 (m, 1H), 3.63-3.69 (m, 4H), 4.45 (q, J=7.2 Hz, 2H), 5.62 (s, 2H), 6.84 (d, J=8.4 Hz, 2H), 7.10-7.17 (m, 4H), 7.27 (d, J=8.8 Hz, 2H). Compound 461C: LC-MS (ESI) m/z: 442 [M+H]⁺. Compound 461: LC-MS (ESI) m/z: 414 [M+H]⁺; ¹H-NMR (DMSO-d₆, 400 MHz): δ (ppm) 1.28-1.36 (m, 2H), 1.62-1.70 (m, 2H), 2.01-2.05 (m, 2H), 2.21-2.28 (m, 2H), 2.65-2.72 (m, 2H), 2.89-2.99 (m, 1H), 4.00-4.05 (m, 1H), 7.27 (d, J=8.8 Hz, 2H), 7.40 (d, J=8.8 Hz, 2H), 13.25 (bs, 1H), 15.43 (bs, 1H).

792

Example 462

Synthesis of 4-(((trans)-4-(4-(2-cyclohexylethoxy)phenyl)cyclohexyl)oxy)-1H-1,2,3-triazole-5-carboxylic acid (462)

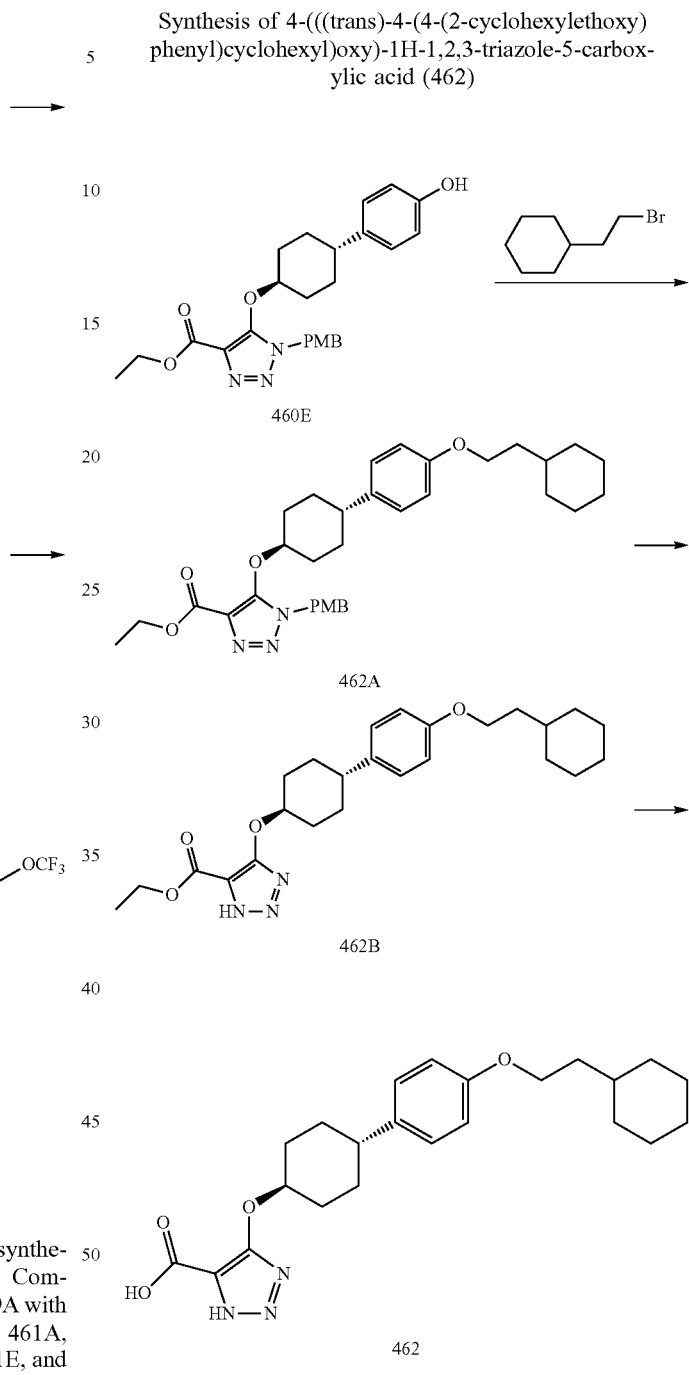

Compounds 462A, 462B, and 462 were synthesized by employing the procedures described for Compounds 27B, 380E, and 8F using Compounds 460E, (2-bromoethyl)cyclohexane, 462A, and 462B in lieu of Compounds 27A, 2-bromopropane, 380D, and 8E. Compound 462A: LC-MS (ESI) m/z: 562 [M+H]⁺. Compound 462B: LC-MS (ESI) m/z: 442 [M+H]⁺. Compound 462: LC-MS (ESI) m/z: 414 [M+H]⁺. ¹H-NMR (DMSO-d₆, 400 MHz): δ (ppm) 0.91-1.22 (m, 5H), 1.52-1.82 (m, 14H), 2.21 (m, 2H), 2.49 (m, 1H), 3.92-3.96 (m, 2H), 4.65 (m, 1H), 6.82-6.84 (m, 2H), 7.13-7.15 (m, 2H).

Example 463

Synthesis of 4-(((trans)-4-(4-(3-hydroxypropoxy)phenyl)cyclohexyl)oxy)-1H-1,2,3-triazole-5-carboxylic acid (463)

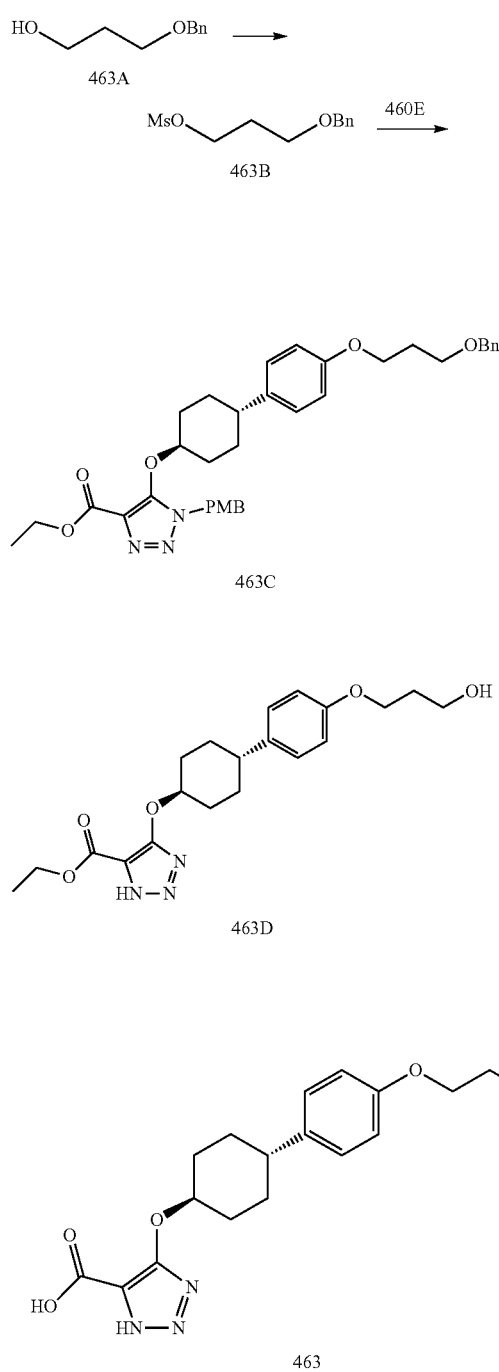

Compounds 463B, 463C, 463D, and 463 were synthesized by employing the procedures described for Compounds 340F, 27B, 380E, and 8F using Compounds 463A, 460E, 463B, 463C, and 463D in lieu of Compounds 340E, 27A, 2-bromopropane, 380D, and 8E. Compound 463B: LC-MS (ESI) m/z: 245 [M+H]+. Compound 463C: LC-MS (ESI) m/z: 600 [M+H]+. Compound 463D: LC-MS (ESI) m/z: 390 [M+H]+. Compound 463: LC-MS (ESI) m/z: 362 [M+H]+. $^1$H-NMR (DMSO-d$_6$, 400 MHz): δ (ppm) 1.52-1.57 (m, 4H), 1.80-1.85 (m, 4H), 2.22 (m, 2H), 3.52-3.56 (m, 2H), 3.97-4.00 (m, 2H), 4.51-4.62 (m, 2H), 6.82-6.84 (m, 2H), 7.13-7.16 (m, 2H), 12.83 (s, 1H), 14.75 (s, 1H).

Example 464

Synthesis of 4-(((trans)-4-(4-(3-isopropyl-1H-pyrazol-5-yl)phenyl)cyclohexyl)oxy)-1H-1,2,3-triazole-5-carboxylic acid 2,2,2-trifluoroacetate (464)

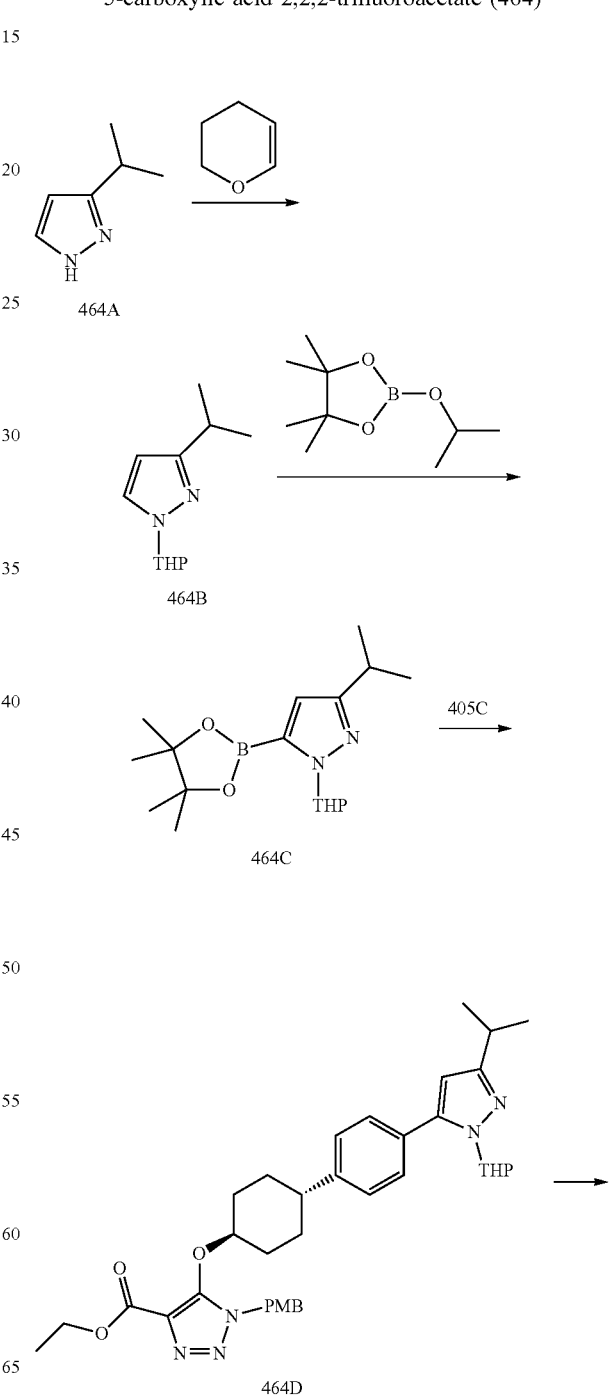

795
-continued

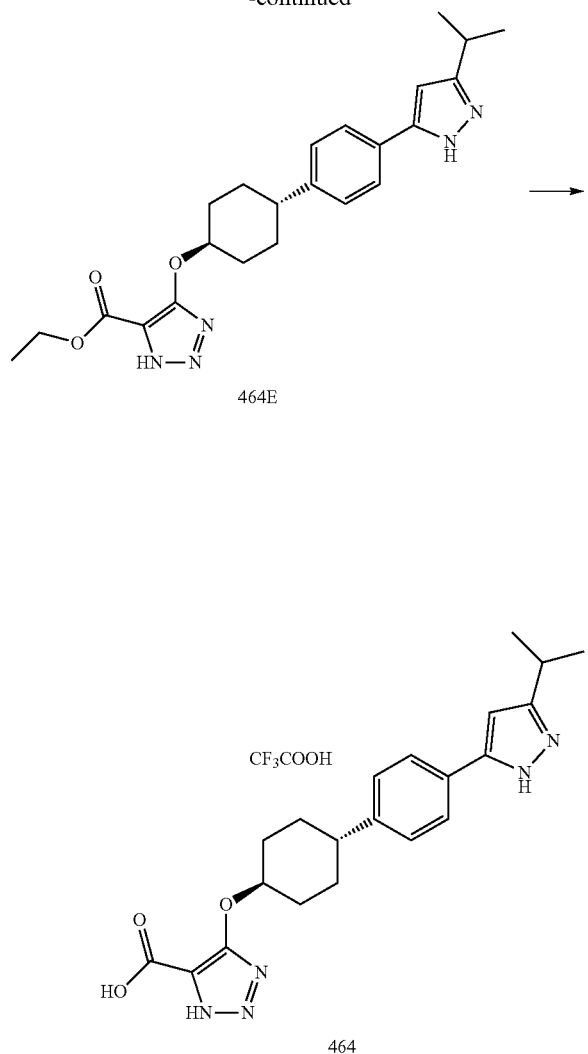

A mixture of 3-isopropyl-1H-pyrazole (464A, 2 g, 18 mmol) and 3,4-dihydro-2H-pyran (3.05 g, 36 mmol) was heated in a seal tube at 120° C. for 12 hours. The reaction mixture was cooled down to room temperature, concentrated, and purified by preparative HPLC to give Compound 464B. LC-MS (ESI) m/z: 195 [M+1]$^+$.

Compounds 464C, 464D, 464E, and 464 were synthesized by employing the procedures described for Compounds 30C-1, 8B, 1, and 8F using 2-isopropoxy-4,4,5,5-tetramethyl-1,3,2-dioxaborolane, Compounds 464B without treatment of HCl, 464C, 405C with Na$_2$CO$_3$ as base and 1,4-dioxane/H$_2$O as solvent, 464D, and 464E in lieu of triisopropyl borate, Compounds 30B with treatment of HCl, (3,4-dichlorophenyl)boronic acid, 8A with Cs$_2$CO$_3$ as base and DME/H$_2$O as solvent, 1E, and 8E. Compound 464C: LC-MS (ESI) m/z: 321 [M+H]$^+$. Compound 464D: LC-MS (ESI) m/z: 628 [M+H]$^+$. Compound 464E: LC-MS (ESI) m/z: 424 [M+H]$^+$. Compound 464: LC-MS (ESI) m/z: 396 [M+H]$^+$. $^1$H-NMR (DMSO-d$_6$, 400 MHz): δ (ppm) 1.23-1.27 (m, 6H), 1.38-1.41 (m, 1H), 1.55-1.65 (m, 3H), 1.80-1.90 (m, 2H), 2.20-2.25 (m, 2H), 2.92-3.00 (m, 1H), 3.16-3.29 (m, 1H), 4.64 (s, 1H), 6.15 (s, 1H), 6.41 (s, 1H), 7.20-7.41 (m, 3H), 7.65 (d, J=8.4 Hz, 1H), 14.71 (s, 1H).

796
Example 465

Synthesis of 4-(methyl((cis)-4-(4-(trifluoromethoxy)phenyl)cyclohexyl)amino)-1H-1,2,3-triazole-5-carboxylic acid (465)

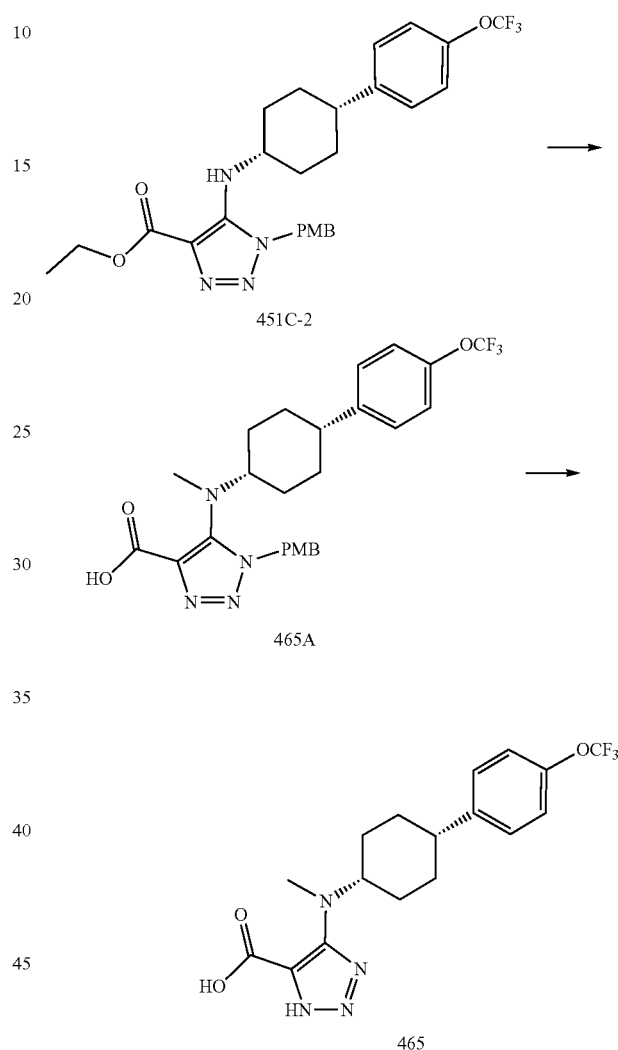

To a solution of Compound 451C-2 (180 mg, 0.35 mmol) in THF (5 mL) was added NaH (60%, 70 mg, 1.7 mmol) and stirred at room temperature for 0.5 hour. To the mixture was added CH$_3$I (241 mg, 1.7 mmol) and stirred at room temperature for 16 hours. It was quenched with water (0.2 mL) and concentrated in vacuum. The residue was purified with flash column chromatography on silica gel (ethyl acetate in petroleum ether, 50% v/v) to furnish Compound 465A. LC-MS (ESI) m/z: 505 [M+H]$^+$.

Compound 465 was synthesized by employing the procedure described for Compound 1 using Compounds 465A in lieu of Compounds 1E, LC-MS (ESI) m/z: 385 [M+H]$^+$; $^1$H-NMR (CD$_3$OD, 400 MHz): δ (ppm) 1.58-1.73 (m, 4H), 1.84-1.90 (m, 2H), 2.10-2.16 (m, 2H), 2.80-2.90 (m, 4H), 3.86 (d, J=2.8 Hz, 1H), 7.19 (d, J=8.0 Hz, 2H), 7.45 (d, J=8.8 Hz, 2H).

Example 466
Synthesis of 4-(((trans)-4-(3-(hydroxymethyl)-4-(1H-pyrazol-5-yl)phenyl)cyclohexyl)oxy)-1H-1,2,3-triazole-5-carboxylic acid (466)
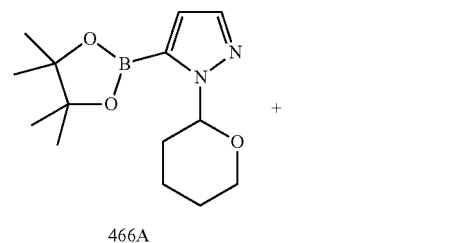
466A
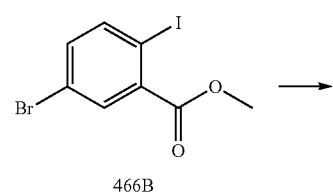
466B
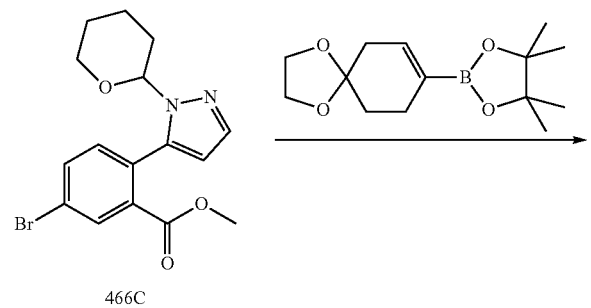
466C
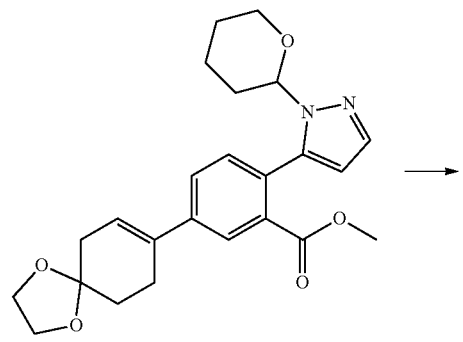
466D
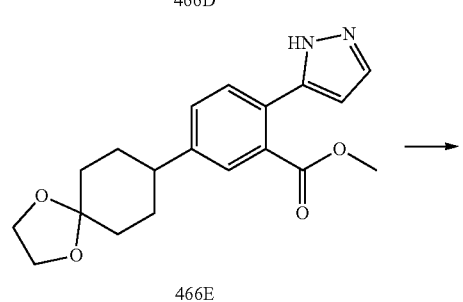
466E
-continued
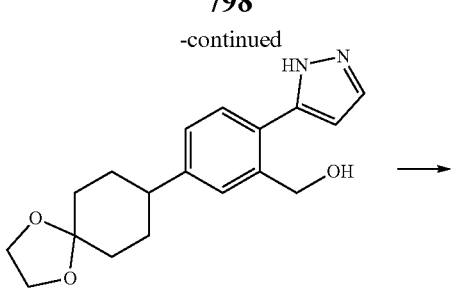
466F
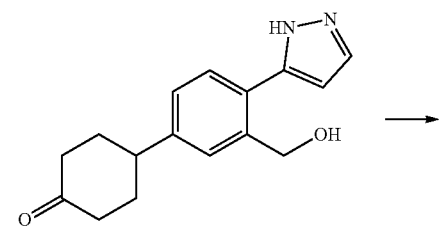
466G
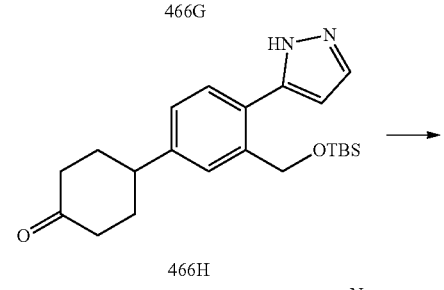
466H
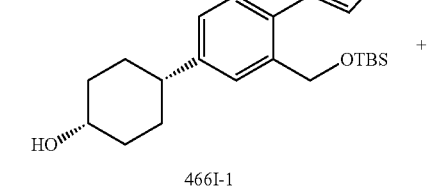
466I-1
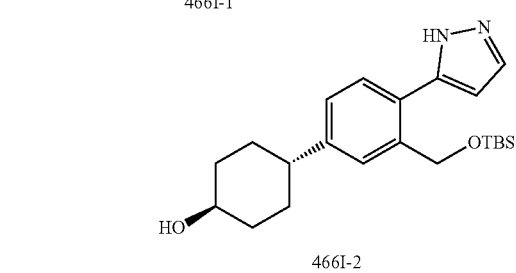
466I-2
466I-1 —Int H→
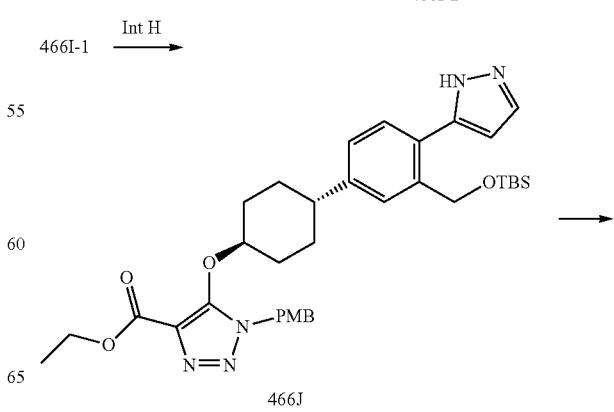
466J -continued

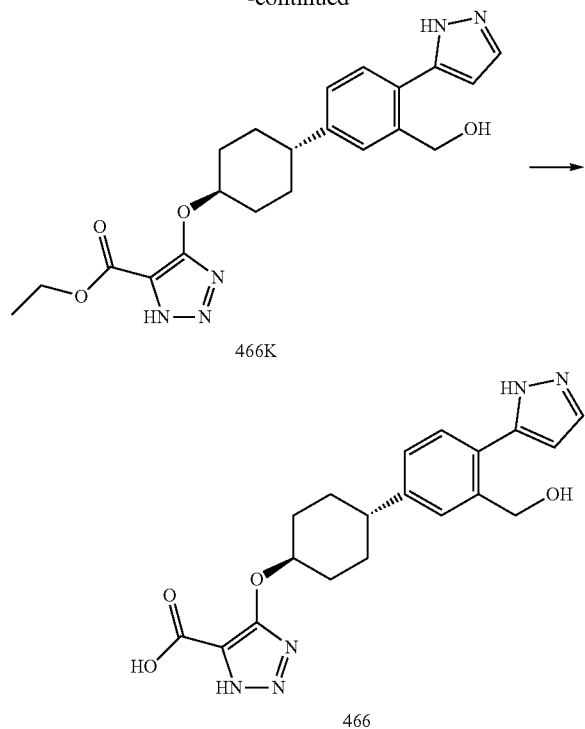

Compounds 466C, 466D, 466E, 466F, 466G, 466H, 466I-1, 466I-2, 466J, 466K, and 466 were synthesized by employing the procedures described for Compounds 8B, 4B, 141, 283C, 279D, 460B, 393F-1, 90C, 1, and 8F using Compounds 466A, 466B with $Na_2CO_3$ as base and 1,4-dioxane/$H_2O$ as solvent, 4,4,5,5-tetramethyl-2-(1,4-dioxaspiro[4.5]dec-7-en-8-yl)-1,3,2-dioxaborolane, 466C with $K_2CO_3$ as base and 1,4-dioxane/$H_2O$ as solvent, 466D, 466E, 466F with TFA as acid and dichloromethane as solvent, 466G, 466H, 466I-1, 466J, and 466K in lieu of (3,4-dichlorophenyl)boronic acid, Compounds 8A with $Cs_2CO_3$ as base and DME/$H_2O$ as solvent, (4-bromophenyl)boronic acid, 4A with $Na_2CO_3$ as base and toluene/EtOH/$H_2O$ as solvent, 140, 283B, 279C with HCl as acid and 1,4-dioxane as solvent, 460A, 393E, 90B, 8E, and 1E. Compound 466C: LC-MS (ESI) m/z: 365 [M+1]⁺. Compound 466D: LC-MS (ESI) m/z: 425 [M+1]⁺. Compound 466E: LC-MS (ESI) m/z: 343 [M+1]⁺. Compound 466F: LC-MS (ESI) m/z: 315 [M+H]⁺. Compound 466G: LC-MS (ESI) m/z: 271 [M+H]⁺. Compound 466H: LC-MS (ESI) m/z: 385 [M+H]⁺. Compound 466I-1: LC-MS (ESI) m/z: 387 [M+H]⁺; ¹H-NMR (DMSO-$d_6$, 400 MHz): δ (ppm) 0.86 (s, 15H), 1.7-1.50 (m, 3H), 1.70-1.73 (m, 2H), 1.80-1.90 (m, 2H), 2.46-2.52 (m, 2H), 3.86 (s, 1H), 4.34 (s, 1H), 4.69 (s, 1H), 4.90 (s, 1H), 6.50 (s, 1H), 7.12 (s, 1H), 7.44-7.51 (m, 2H), 7.73 (s, 1H), 12.89 (s, 1H). Compound 466I-2: LC-MS (ESI) m/z: 387 [M+H]⁺; ¹H-NMR (DMSO-$d_6$, 400 MHz): δ (ppm) 0.86 (s, 9H), 1.26-1.33 (m, 2H), 1.40-1.49 (m, 2H), 1.76 (d, J=12 Hz, 2H), 1.90 (d, J=9.6 Hz, 2H), 2.42-2.48 (m, 1H), 3.43 (br, 8H), 4.63 (s, 1H), 4.89 (s, 1H), 6.50 (s, 1H), 7.13 (s, 1H), 7.42 (s, 2H), 7.74 (s, 1H), 12.89 (s, 1H). Compound 466J: LC-MS (ESI) m/z: 646 [M+1]⁺. Compound 466K: LC-MS (ESI) m/z: 412 [M+1]⁺, Compound 466: LC-MS (ESI) m/z: 384 [M+H]⁺; ¹H-NMR (DMSO-$d_6$, 400 MHz): δ (ppm) 1.64-1.67 (m, 4H), 1.88-1.90 (m, 2H), 2.23-2.32 (m, 2H), 2.53-2.69 (m, 1H), 4.56 (s, 2H), 4.68 (s, 1H), 5.41 (s, 1H), 6.54 (s, 1H), 7.20 (d, J=9.2 Hz, 1H), 7.43-7.48 (m, 2H), 7.72 (s, 1H).

Example 467

Synthesis of 4-(((cis)-4-(3-(hydroxymethyl)-4-(1H-pyrazol-5-yl)phenyl)cyclohexyl)oxy)-1H-1,2,3-triazole-5-carboxylic acid 2,2,2-trifluoroacetate (467)

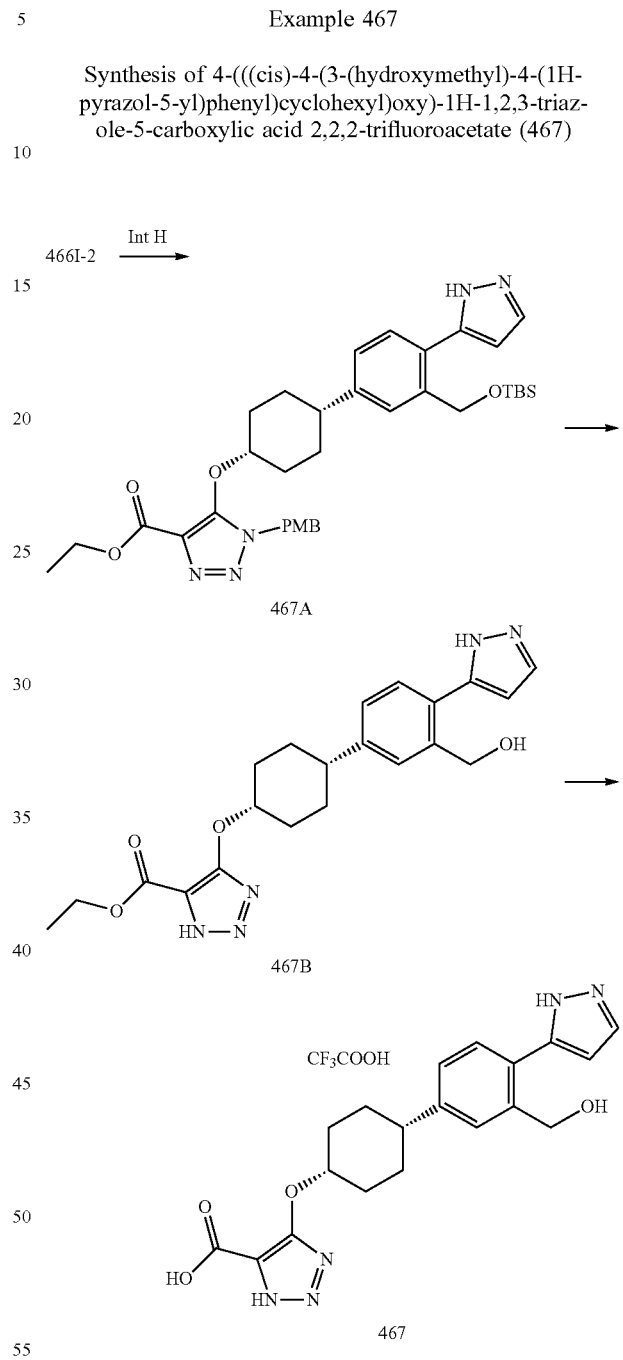

Compounds 467A, 467B, and 467 were synthesized by employing the procedures described for Compounds 90C, 1, and 8F using Compounds 466I-2, 467A, and 467B in lieu of Compounds 90B, 1E, and 8E. Compound 467A: LC-MS (ESI) m/z: 646 [M+H]⁺. Compound 467B: LC-MS (ESI) m/z: 412 [M+H]⁺. Compound 467: LC-MS (ESI) m/z: 384 [M+H]⁺. ¹H-NMR (DMSO-$d_6$, 400 MHz): δ (ppm) 1.62-1.76 (m, 4H), 1.88-1.91 (m, 2H), 2.08-2.12 (m, 2H), 2.67-2.68 (m, 1H), 4.59 (s, 2H), 4.96 (s, 1H), 6.56 (d, J=1.6 Hz, 1H), 7.19-7.21 (m, 1H), 7.42 (s, 1H), 7.49 (d, J=7.6 Hz, 1H), 7.74 (s, 1H).

Example 468

Synthesis of 4-(((trans)-4-(4-(4-methylpiperazin-1-yl)phenyl)cyclohexyl)oxy)-1H-1,2,3-triazole-5-carboxylic acid 2,2,2-trifluoroacetate (468)

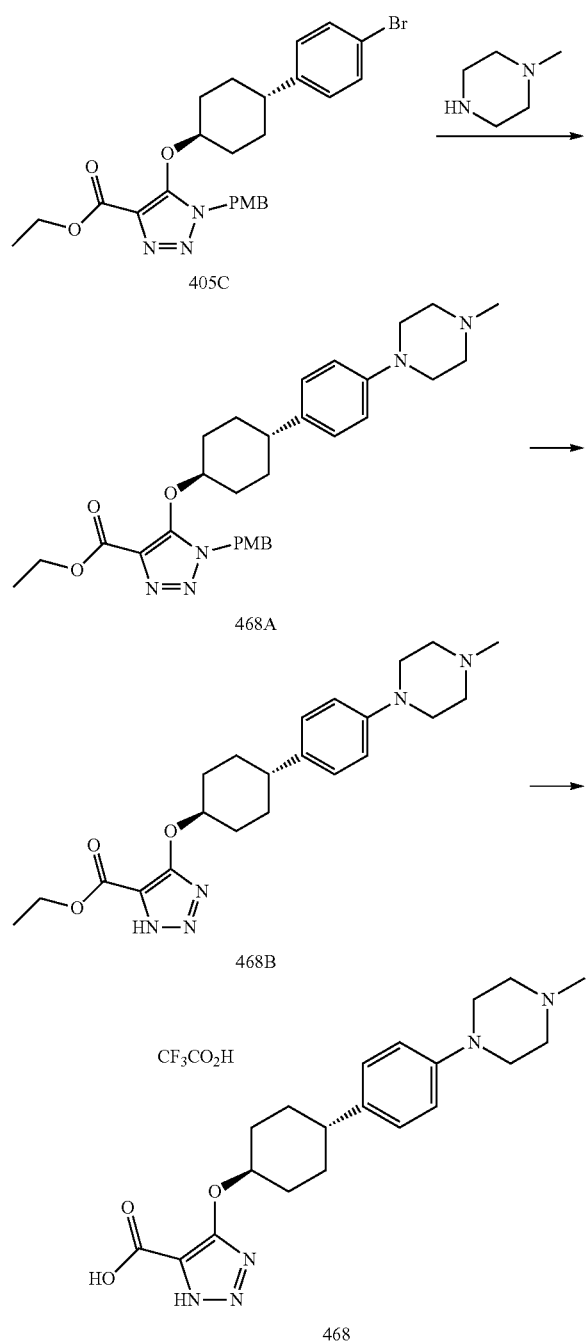

Compounds 468A, 468B, and 468 were synthesized by employing the procedures described for Compounds 6B, 1, and 8F using Compounds 405C with X-phos as ligand and Cs₂CO₃ as base and 1,4-dioxane as solvent, 468A, and 468B in lieu of Compounds 6A with Xantophos as ligand and tBuONa as base and toluene as solvent, 1E, and 8E. Compound 468A: LC-MS (ESI) m/z: 534 [M+H]⁺; ¹H-NMR (CDCl₃, 400 MHz): δ (ppm), 1.24-1.30 (m, 6H), 1.41-4.43 (t, J=7.2 Hz, 3H), 1.70 (s, 3H), 1.89-1.93 (m, 2H), 2.13-2.15 (m, 2H), 2.37-2.43 (m, 3H), 2.56-2.64 (m, 2H), 3.16-3.22 (m, 2H), 3.80 (s, 3H), 4.39-4.45 (m, 2H), 5.01-5.08 (m, 1H), 5.31 (s, 2H), 6.86-6.89 (m, 2H), 7.07-7.09 (m, 1H), 7.17-7.20 (m, 1H), 7.25-7.30 (m, 4H). Compound 468B: LC-MS (ESI) m/z: 414 [M+H]⁺. Compound 468: LC-MS (ESI) m/z: 386 [M+H]⁺; ¹H-NMR (CD₃OD, 400 MHz): δ (ppm) 1.60-1.70 (m, 4H), 1.92-1.95 (m, 2H), 2.32-2.35 (m, 2H), 2.53-2.57 (m, 1H), 3.02-3.04 (m, 5H), 3.26-3.30 (m, 2H), 3.57-3.60 (m, 2H), 3.78-3.80 (m, 2H), 4.73-4.75 (m, 1H), 6.97 (d, J=8.8 Hz, 2H), 7.21 (d, J=8.8 Hz, 2H).

Example 469

Synthesis of 4-(((trans)-4-(4-(1-(2-hydroxy-2-methylpropyl)-1H-pyrazol-3-yl)phenyl)cyclohexyl)oxy)-1H-1,2,3-triazole-5-carboxylic acid 2,2,2-trifluoroacetate (469)

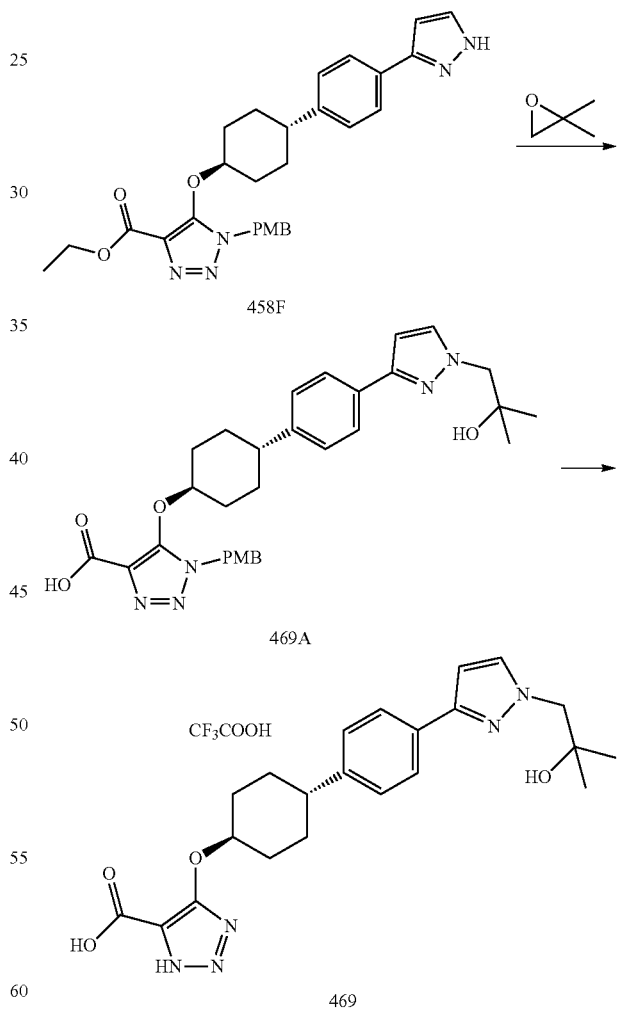

To a solution of Compound 458F (0.3 g, 0.598 mmol) in anhydrous THF (3 mL) was added NaH (60% in mineral oil, 0.03 g, 0.716 mmol) and stirred at 0° C. for 10 minutes, followed by addition of 1,2-epoxy-2-methylpropane (0.129 g, 1.794 mmol). The mixture was stirred at room temperature overnight, quenched with saturated NH₄Cl solution (15 mL), and extracted with ethyl acetate (30 mL×3). The combined organic layers was washed with brine (50 mL), dried over anhydrous Na₂SO₄, filtered, and concentrated under reduced pressure. The residue was purified with flash column chromatography on silica gel (ethyl acetate in petroleum ether, 50%-100% v/v) to give Compound 469A. LC-MS (ESI) m/z: 546 [M+H]⁺.

Compound 469 was synthesized by employing the procedure described for Compound 1 using Compound 469A in lieu of Compound 1E, LC-MS (ESI) m/z: 426 [M+H]⁺.

$^1$H-NMR (DMSO-d$_6$, 400 MHz): δ (ppm) 1.07 (s, 6H), 1.55-1.62 (m, 4H), 1.85-1.88 (m, 2H), 2.23-2.24 (m, 2H), 2.58-2.60 (m, 1H), 4.0 (s, 2H), 4.64-4.73 (m, 2H), 6.30 (d, J=2 Hz, 1H), 7.26 (d, J=8 Hz, 2H), 7.68 (d, J=8 Hz, 3H).

Example 470

Synthesis of 4-(((trans)-4-(4-(1-(2-ethyl-2-hydroxy-pentyl)-1H-pyrazol-5-yl)phenyl)cyclohexyl)oxy)-1H-1,2,3-triazole-5-carboxylic acid (470)

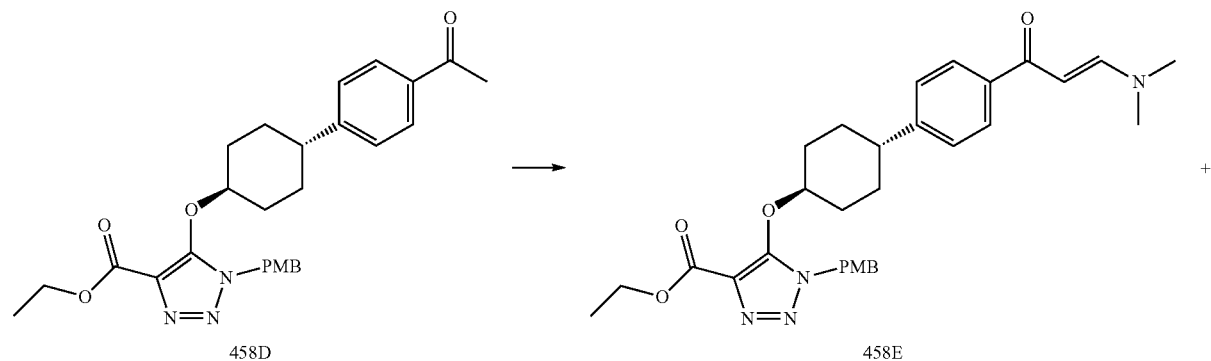

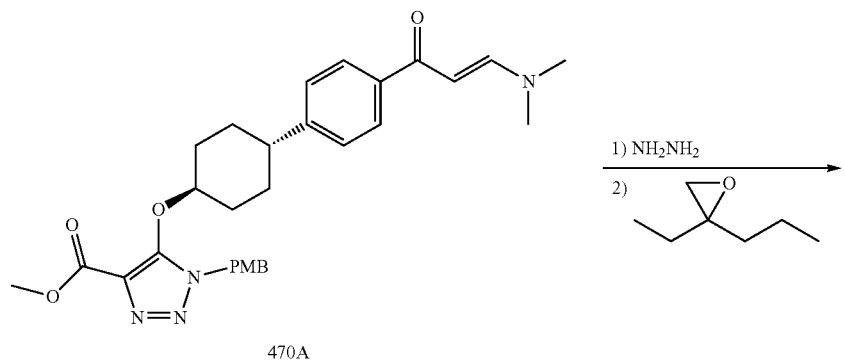

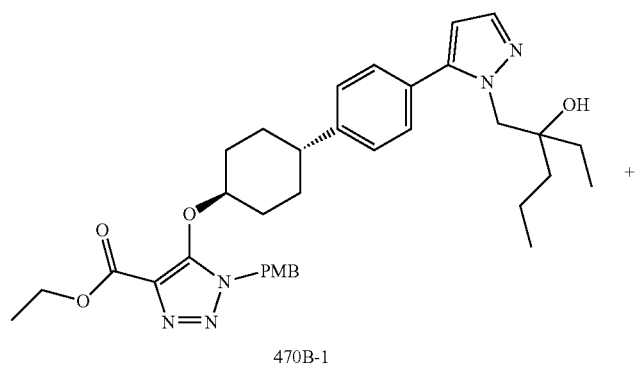

-continued

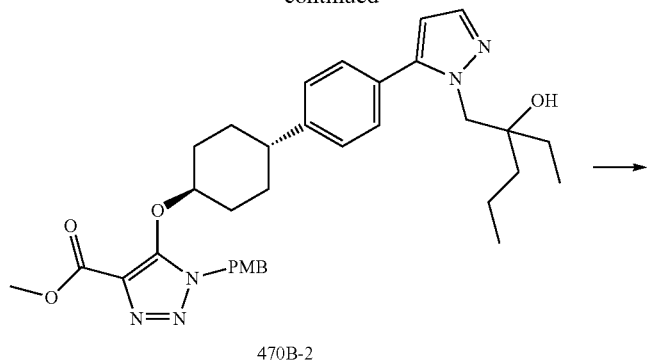
470B-2

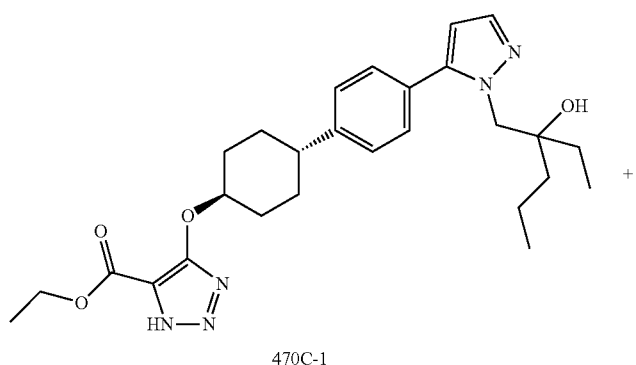
470C-1
+

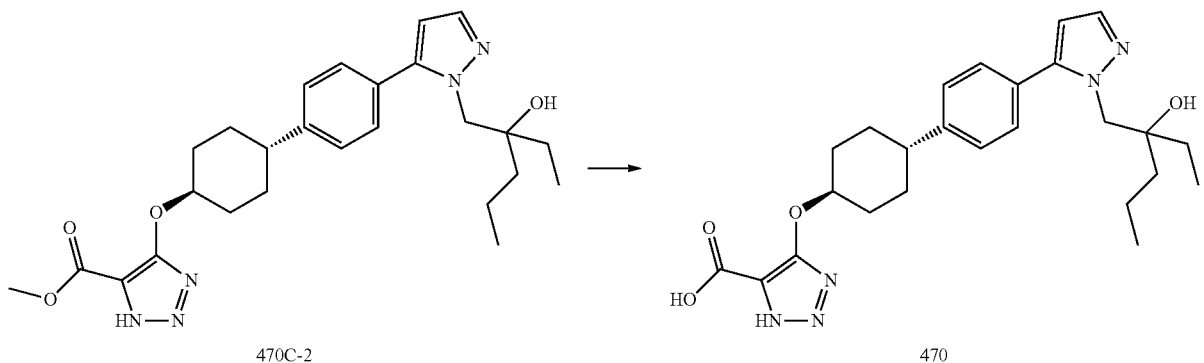
470C-2        470

A mixture of Compound 458D (800 mg, 1.67 mmol) and DMF-DMA (20 ml) was stirred at 110° C. for 72 hours. The mixture was concentrated and purified by flash column chromatography (eluting with MeOH/DCM=1:13) to afford a mixture of Compounds 458E and 470A. LC-MS (ESI) m/z: 533 [M+H]$^+$ and 519 [M+H]$^+$.

A mixture of 2-ethyl-2-propyloxirane (600 mg, 5.3 mmol) and 98% hydrazine monohydrate (45 mg, 1.59 mmol) in EtOH (10 mL) was heated in a sealed tube at 60° C. for 16 hours. After the mixture was cooled down to room temperature, to it was added the Mixture of 458E and 470A (254 mg, 0.47 mmol), stirred at 80° C. for 2 hours, and concentrated under reduced pressure. The residue was purified by flash column chromatography (eluting with EtOAc/PE=4:5) to afford a mixture of Compounds 470B-1 and 470B-2. LC-MS (ESI) m/z: 616 [M+H]$^+$ and 602 [M+H]$^+$.

Mixture of 470C-1 and 470C-2, and Compound 470 were synthesized by employing the procedures described for Compounds 1 and 8F using Mixtures of 470B-1 and 470B-2, and 470C-1 and 470C-2 in lieu of Compounds 1E and 8E. Mixture of 470C-1 and 470C-2: LC-MS (ESI) m/z: 496 [M+H]$^+$ and 482 [M+H]$^+$. Compound 470: LC-MS (ESI) m/z: 468 [M+H]$^+$; $^1$H-NMR (CD$_3$OD, 400 MHz): δ (ppm) 0.71 (t, J=7.6 Hz, 3H), 0.77 (t, J=6.4 Hz, 3H), 1.14-1.34 (m, 6H), 1.70-1.75 (m, 4H), 2.01-2.04 (m, 2H), 2.35-2.38 (m, 2H), 2.70-2.71 (m, 1H), 4.16 (s, 2H), 4.76-4.80 (m, 1H), 6.33 (d, J=1.6 Hz, 1H), 7.40 (s, 4H), 7.56 (d, J=2.0 Hz, 1H).

Example 471

Synthesis of 4-(((trans)-4-(4-(1-((1-hydroxycyclohexyl)methyl)-1H-pyrazol-5-yl)phenyl)cyclohexyl)oxy)-1H-1,2,3-triazole-5-carboxylic acid 2,2,2-trifluoroacetate (471)

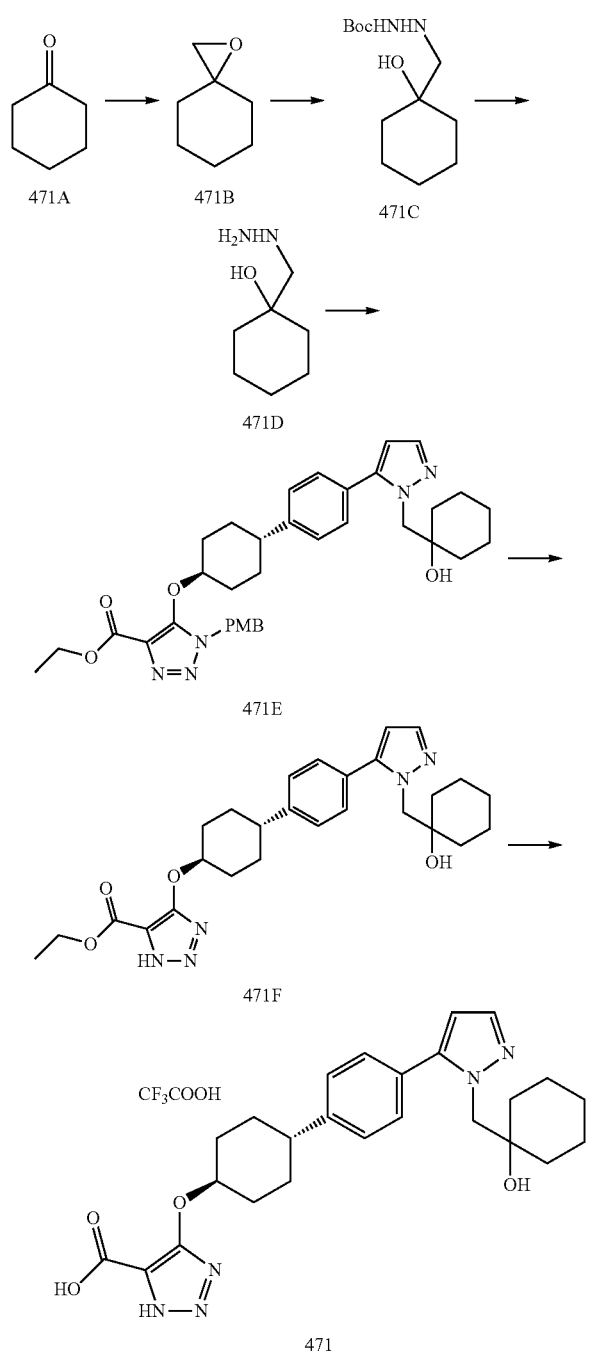

Compound 471B was synthesized by employing the procedure described for Compound 458B using Compound 471A in lieu of Compound 458A, LC-MS (ESI) m/z: non-ionizable compound under routine conditions used; $^1$H-NMR (CDCl$_3$, 400 MHz): δ (ppm) 1.48-1.62 (m, 10H), 2.60 (s, 2H).

A mixture of Compound 471B (720 mg, crude) and tert-butyl hydrazinecarboxylate (800 mg, 6.05 mmol) in ethanol (5 mL) was heated at 80° C. overnight. The reaction mixture was concentrated and purified with flash column chromatography on silica gel (ethyl acetate in petroleum ether, 20% to 50% v/v) to furnish Compound 471C. LC-MS (ESI) m/z: 267 [M+Na]$^+$.

To a solution of Compound 471C (540 mg, 2.21 mmol) in dichloromethane (10 mL) was added 2,2,2-trifluoroacetic acid (1 mL) and stirred at room temperature for 2 hours. The solution was concentrated under reduced pressure to afford Compound 471D. LC-MS (ESI) m/z: 145 [M+H]$^+$.

The mixture of Compound 471D (350 mg, 2.21 mmol) and Compound 458E (150 mg, 0.244 mmol) in ethanol (5 ml) was stirred at 80° C. for 2 hours. The mixture was diluted with ethyl acetate (100 mL), washed with saturated NaHCO$_3$ solution (100 mL) and brine (50 mL), dried over anhydrous sodium sulfate, concentrated, and purified with flash column chromatography on silica gel (ethyl acetate in petroleum ether, 20% to 33% v/v) to give Compound 471E. LC-MS (ESI) m/z: 614 [M+H]$^+$.

Compounds 471F and 471 were synthesized by employing the procedures described for Compounds 1 and 8F using Compounds 471E and 471F in lieu of Compounds 1E and 8E. Compound 471F: LC-MS (ESI) m/z: 494 [M+H]$^+$. Compound 471: LC-MS (ESI) m/z: 466 [M+H]$^+$; $^1$H-NMR (DMSO-d$_6$, 400 MHz): δ (ppm) 1.01-1.28 (m, 7H), 1.39-1.69 (m, 7H), 1.90-1.93 (m, 2H), 2.25-2.27 (m, 2H), 2.63-2.70 (m, 1H), 4.04 (s, 2H), 4.61-4.68 (m, 2H), 6.33 (d, J=1.6 Hz, 1H), 7.38 (d, J=8.4 Hz, 2H), 7.45 (d, J=8.4 Hz, 2H), 7.53 (d, J=1.6 Hz, 1H), 12.96 (bs, 1H), 14.80 (bs, 1H).

Example 472

Synthesis of 4-(((trans)-4-(4-(3-aminopropoxy)phenyl)cyclohexyl)oxy)-1H-1,2,3-triazole-5-carboxylic acid 2,2,2-trifluoroacetate (472)

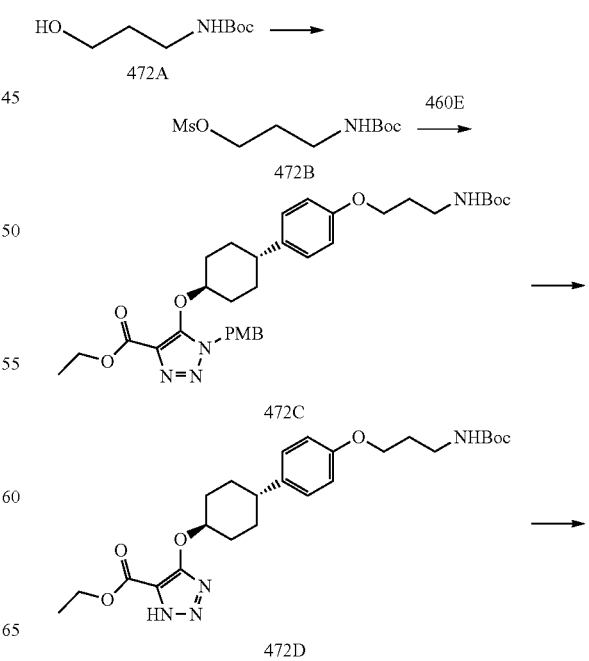

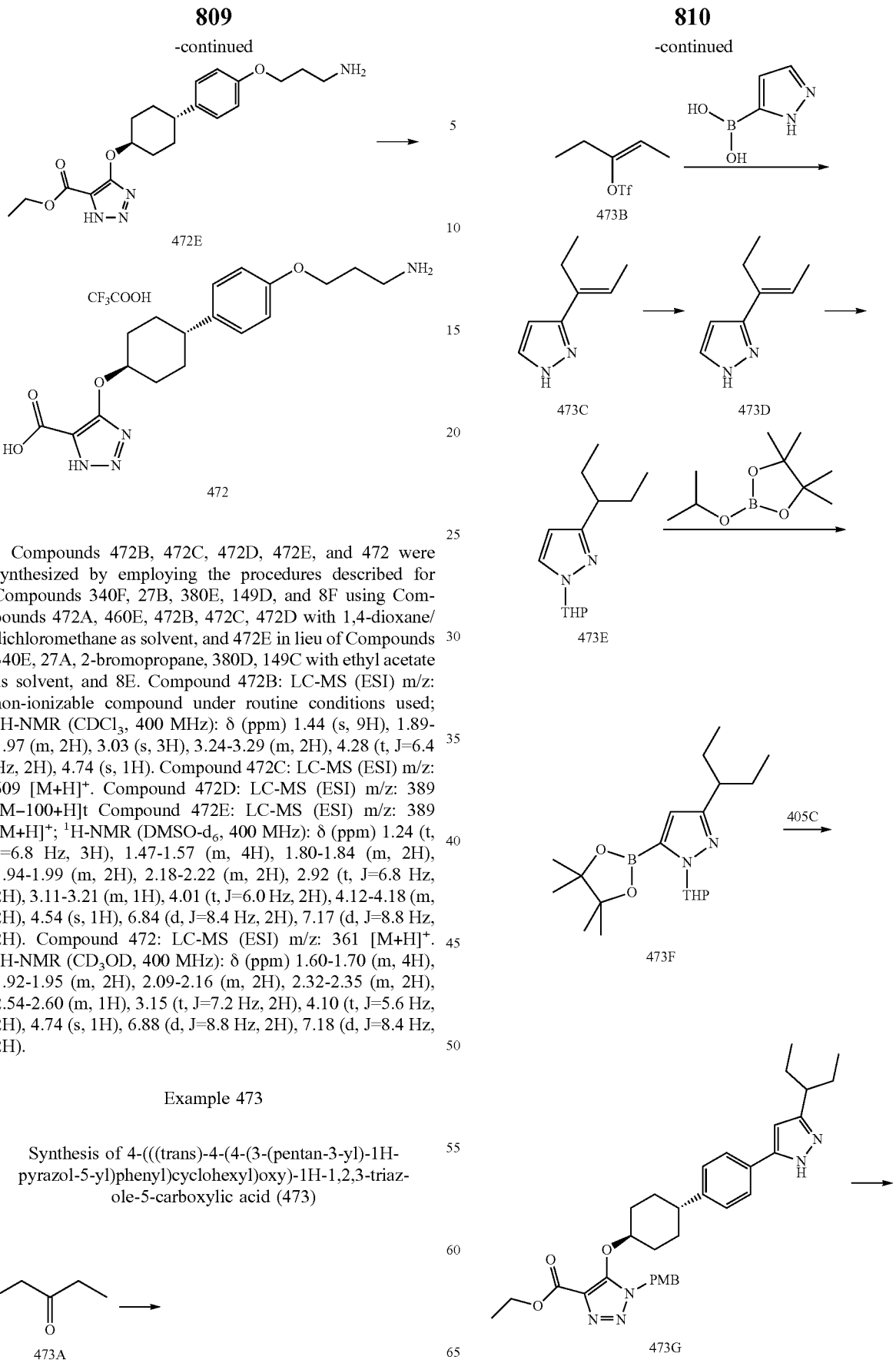

Compounds 472B, 472C, 472D, 472E, and 472 were synthesized by employing the procedures described for Compounds 340F, 27B, 380E, 149D, and 8F using Compounds 472A, 460E, 472B, 472C, 472D with 1,4-dioxane/dichloromethane as solvent, and 472E in lieu of Compounds 340E, 27A, 2-bromopropane, 380D, 149C with ethyl acetate as solvent, and 8E. Compound 472B: LC-MS (ESI) m/z: non-ionizable compound under routine conditions used; $^1$H-NMR (CDCl$_3$, 400 MHz): δ (ppm) 1.44 (s, 9H), 1.89-1.97 (m, 2H), 3.03 (s, 3H), 3.24-3.29 (m, 2H), 4.28 (t, J=6.4 Hz, 2H), 4.74 (s, 1H). Compound 472C: LC-MS (ESI) m/z: 609 [M+H]$^+$. Compound 472D: LC-MS (ESI) m/z: 389 [M−100+H]t Compound 472E: LC-MS (ESI) m/z: 389 [M+H]$^+$; $^1$H-NMR (DMSO-d$_6$, 400 MHz): δ (ppm) 1.24 (t, J=6.8 Hz, 3H), 1.47-1.57 (m, 4H), 1.80-1.84 (m, 2H), 1.94-1.99 (m, 2H), 2.18-2.22 (m, 2H), 2.92 (t, J=6.8 Hz, 2H), 3.11-3.21 (m, 1H), 4.01 (t, J=6.0 Hz, 2H), 4.12-4.18 (m, 2H), 4.54 (s, 1H), 6.84 (d, J=8.4 Hz, 2H), 7.17 (d, J=8.8 Hz, 2H). Compound 472: LC-MS (ESI) m/z: 361 [M+H]$^+$. $^1$H-NMR (CD$_3$OD, 400 MHz): δ (ppm) 1.60-1.70 (m, 4H), 1.92-1.95 (m, 2H), 2.09-2.16 (m, 2H), 2.32-2.35 (m, 2H), 2.54-2.60 (m, 1H), 3.15 (t, J=7.2 Hz, 2H), 4.10 (t, J=5.6 Hz, 2H), 4.74 (s, 1H), 6.88 (d, J=8.8 Hz, 2H), 7.18 (d, J=8.4 Hz, 2H).

Example 473

Synthesis of 4-(((trans)-4-(4-(3-(pentan-3-yl)-1H-pyrazol-5-yl)phenyl)cyclohexyl)oxy)-1H-1,2,3-triazole-5-carboxylic acid (473)

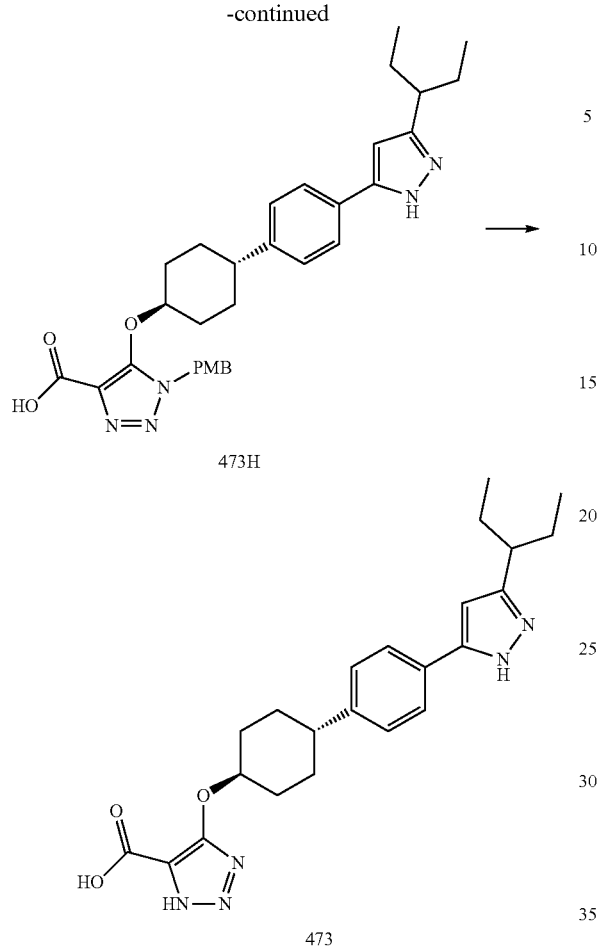

4.59-4.69 (m, 1H), 6.12 (s, 0.5H), 6.40 (s, 0.5H), 7.13-7.46 (m, 3H), 7.67 (d, J=8.2 Hz, 1H).

Example 474

Synthesis of 4-(((trans)-4-(4-(3-(methylamino)propoxy)phenyl)cyclohexyl)oxy)-1H-1,2,3-triazole-5-carboxylic acid 2,2,2-trifluoroacetate (474)

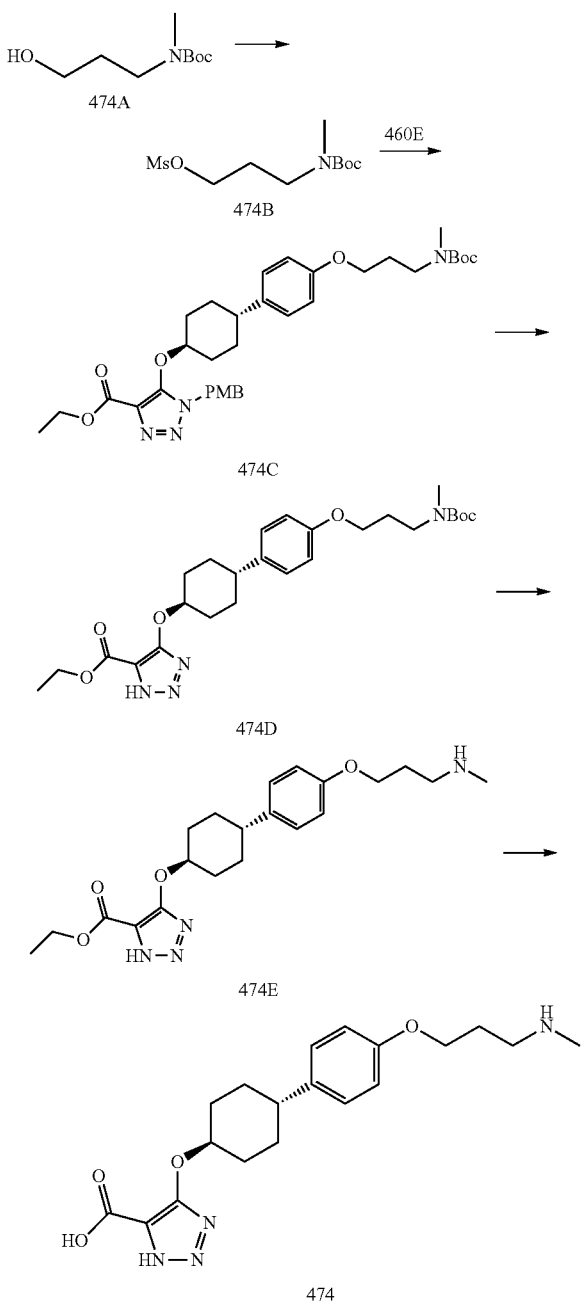

Compounds 473B, 473C, 473D, 473E, 473F, 473G, 473H, and 473 were synthesized by employing the procedures described for Compounds 275B, 8B, 141, 464B, 30C-1, 8B, 8F, and 1 using Compounds 473A with Na$_2$CO$_3$ as base and 1,4-dioxane/H$_2$O as solvent, 1H-pyrazol-5-ylboronic acid, 473B with Na$_2$CO$_3$ as base and 1,4-dioxane/H$_2$O as solvent, 473C, 473D with toluene as solvent and p-TsOH as acidic catalyst, 2-isopropoxy-4,4,5,5-tetramethyl-1,3,2-dioxaborolane, 473E without treatment of HCl, 473F, 405C with Na$_2$CO$_3$ as base and 1,4-dioxane/H$_2$O as solvent, 473G, and 473H in lieu of Compounds 275A with 2,6-lutidine as base, (3,4-dichlorophenyl)boronic acid, 8A with Cs$_2$CO$_3$ as base and DME/H$_2$O as solvent, 140, 464A without acid as acidic catalyst, triisopropyl borate, 30B with treatment of HCl, (3,4-dichlorophenyl)boronic acid, 8A with Cs$_2$CO$_3$ as base and DME/H$_2$O as solvent, 8E, and 1E. Compound 473B: LC-MS (ESI) m/z: non-ionizable compound under routine conditions used; $^1$H-NMR (CDCl$_3$, 400 MHz) δ 1.08-1.18 (m, 3H), 1.66-1.80 (m, 3H), 2.37 (dt, J=14.9, 6.8 Hz, 2H), 5.23-5.38 (m, 1H). Compound 473C: LC-MS (ESI) m/z: 137 [M+H]$^+$. Compound 473D: LC-MS (ESI) m/z: 139 [M+H]$^+$. Compound 473E: LC-MS (ESI) m/z: 223 [M+H]$^+$. Compound 473F: LC-MS (ESI) m/z: 349 [M+H]$^+$. Compound 473G: LC-MS (ESI) m/z: 572 [M+H]$^+$. Compound 473H: LC-MS (ESI) m/z: 544 [M+H]$^+$. Compound 473: LC-MS (ESI) m/z: 424 [M+H]$^+$; $^1$H-NMR (400 MHz, DMSO-d$_6$) δ 0.71-0.87 (m, 6H), 1.18 (d, J=6.2 Hz, 2H), 1.29-1.37 (m, 1H), 1.49-1.71 (m, 5H), 1.79-1.85 (m, 2H), 2.11-2.28 (m, 2H), 2.53-2.63 (m, 1H), 3.08 (s, 1H), Compounds 474B, 474C, 474D, 474E, and 474 were synthesized by employing the procedures described for Compounds 340F, 27B, 380E, 149D, and 8F using Compounds 474A, 460E, 474B, 474C, 474D with 1,4-dioxane/dichloromethane as solvent, and 474E in lieu of Compounds 340E, 27A, 2-bromopropane, 380D, 149C with ethyl acetate as solvent, and 8E. Compound 474B: ¹H-NMR (CDCl₃, 400 MHz): δ (ppm) 1.46 (s, 9H), 1.94-2.01 (m, 2H), 2.87 (s, 3H), 3.03 (s, 3H), 3.35 (t, J=6.4 Hz, 2H), 4.28 (t, J=6.4 Hz, 2H). Compound 474C: LC-MS (ESI) m/z: 623 [M+H]⁺. Compound 474D: LC-MS (ESI) m/z: 403 [M−100+H]⁺. Compound 474E: LC-MS (ESI) m/z: 403 [M+H]⁺. Compound 474: LC-MS (ESI) m/z: 375 [M+H]⁺. ¹H-NMR (CD₃OD, 400 MHz): δ (ppm) 1.55-1.70 (m, 4H), 1.855-1.95, 2.32-2.35 (m, 4H), 2.12-2.19 (m, 2H), 2.50-2.61 (m, 1H), 2.75 (s, 3H), 3.22 (t, J=7.2 Hz, 2H), 4.04, 4.73 (s, 1H), 4.10 (t, J=5.6 Hz, 2H), 6.88 (d, J=8.8 Hz, 2H), 7.18 (d, J=8.8 Hz, 2H).

Example 475

Synthesis of 4-(((trans)-4-(4-(3-(2-methoxybutyl)-1H-pyrazol-5-yl)phenyl)cyclohexyl)oxy)-1H-1,2,3-triazole-5-carboxylic acid (475)

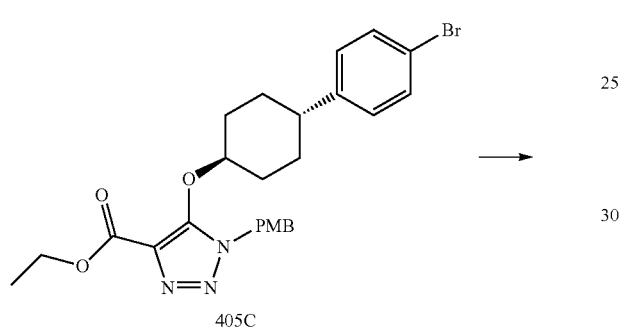

405C

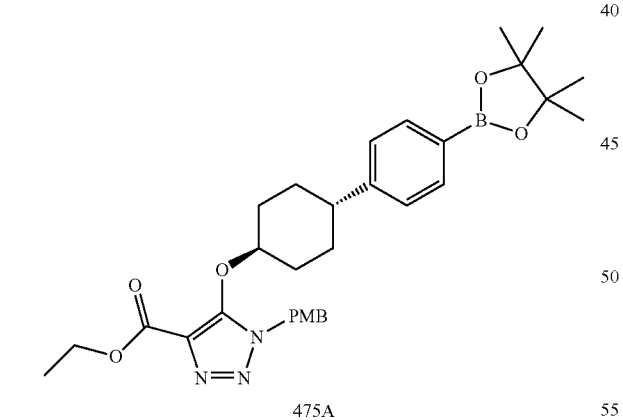

475A

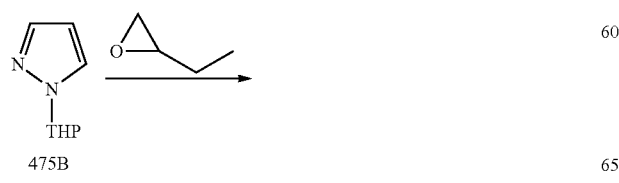

475B

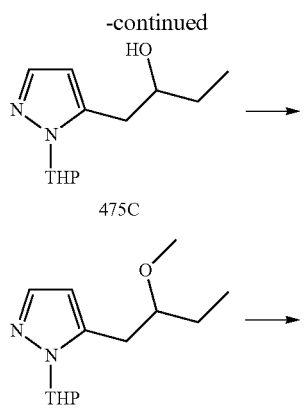

475C

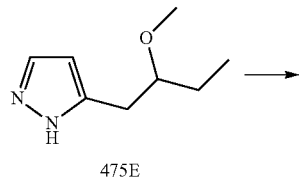

475D

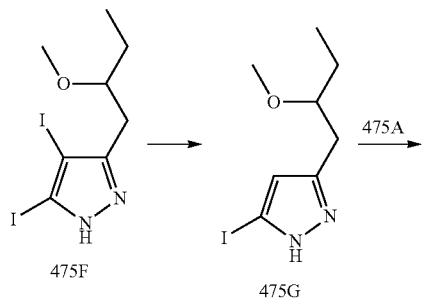

475E

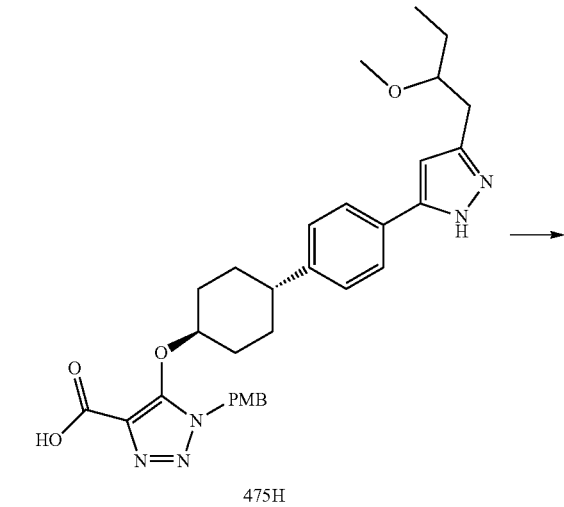

475F, 475G

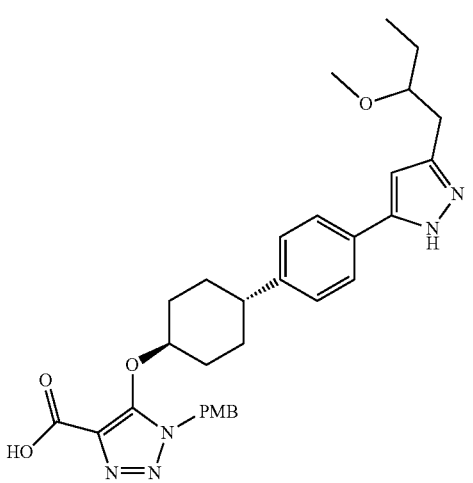

475H

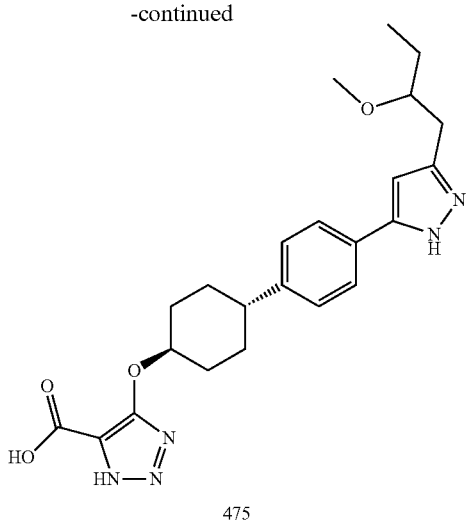

475

Compound 475A was synthesized by employing the procedure described for Compound 27C using Compound 405C in lieu of Compound 27B. LC-MS (ESI) m/z: 562 [M+H]+.

To a solution of 1-(tetrahydro-2H-pyran-2-yl)-1H-pyrazole (475B, 6 g, 39.4 mmol) and N,N,N'N'-tetraethyl-ethylenediamine (6.86 g, 59.1 mmol) in anhydrous THF (60 mL) was dropped a solution of n-BuLi in hexane (2.5 M, 23.6 mL, 59.1 mmoL) at −78° C. under nitrogen and stirred at −78° C. for 30 minutes, followed by addition of 1,2-epoxybutane (4.26 g, 59.1 mmoL). The mixture was stirred at −78° C. for 90 minutes, warmed gradually to room temperature, and stirred overnight. The mixture was quenched with saturated NH₄Cl solution (50 mL) and extracted with ethyl acetate (50 mL×3). The combined organic layers was dried over anhydrous Na₂SO₄, concentrated, and purified by flash column chromatography on silica gel (ethyl acetate in petroleum ether, 50% v/v) to give Compound 475C. LC-MS (ESI) m/z: 225 [M+H]+.

To a stirred solution of Compound 475C (3.3 g, 14.7 mmoL) in anhydrous THF (35 mL) was added NaH (1.18 g, 29.4 mmoL, 60% in mineral oil) at 0° C. and stirred at 0° C. for 10 minutes, followed by addition of iodomethane (8.345 g, 58.8 mmoL) dropwise. The mixture was warmed gradually to room temperature, stirred under nitrogen overnight, quenched with saturated NH₄Cl solution (30 mL), and extracted with ethyl acetate (30 mL×3). The combined organic layers was washed with brine (50 mL), dried over anhydrous Na₂SO₄, concentrated, and purified by flash column chromatography on silica gel (ethyl acetate in petroleum ether, 30% v/v) to afford Compound 475D. LC-MS (ESI) m/z: 239 [M+H]+.

A mixture of Compound 475D (2.9 g, 12.2 mmoL) and TFA (6 mL) in dichloromethane (24 mL) was stirred at room temperature overnight. The mixture was quenched with dichloromethane (30 mL), washed with saturated Na₂CO₃ solution (30 mL×3) and brine (50 mL), dried over anhydrous Na₂SO₄, filtered, and concentrated to give a crude Compound 475E, which was used directly for the next step without further purification. LC-MS (ESI) m/z: 155 [M+H]+.

A mixture of Compound 475E (2.7 g crude, 17.5 mmol) and N-iodosuccinimide (8.27 g, 36.75 mmol) in dichloromethane (48 mL) was heated at reflux under nitrogen overnight. The mixture was diluted with dichloromethane (40 mL), washed with saturated sodium sulfite solution (50 mL) and brine (50 mL), dried over anhydrous Na₂SO₄, concentrated, and purified by flash column chromatography on silica gel (ethyl acetate in petroleum ether, 30% v/v) to give Compound 475F. LC-MS (ESI) m/z: 407 [M+H]+.

A mixture of Compound 475F (1.75 g, 4.3 mmoL) and diluted hydrochloric acid (2 N, 60 mL, 120 mmol) was heated at reflux overnight. The mixture was cooled down to room temperature, adjusted to pH 10 with potassium carbonate, and extracted with ethyl acetate (50 mL×3). The combined organic layers was dried over anhydrous Na₂SO₄, concentrated, and purified by flash column chromatography on silica gel (ethyl acetate in petroleum ether, 30% v/v) to give Compound 475G. LC-MS (ESI) m/z: 281 [M+H]+.

Compounds 475H and 475 were synthesized by employing the procedures described for Compounds 4B and 1 using Compounds 475A with K₂CO₃ as base and 1,4-dioxane as solvent, 475G, and 475II in lieu of (4-bromophenyl)boronic acid, Compounds 4A with Na₂CO₃ as base and toluene/EtOH/H₂O as solvent, and 1E. Compound 475H: LC-MS (ESI) m/z: 560 [M+H]+. Compound 475: LC-MS (ESI) m/z: 440 [M+H]+. $^1$H-NMR (DMSO-d₆, 400 MHz): δ (ppm) 0.86 (t, J=7.6 Hz, 3H), 1.36-1.50 (m, 2H), 1.51-1.65 (m, 4H), 1.86-1.88 (m, 2H), 2.16-2.24 (m, 2H), 2.56-2.61 (m, 1H), 2.66-2.8 (m, 3H), 3.25 (s, 3H), 4.64 (m, 1H), 6.30 (d, J=104.4 Hz, 1H), 7.27 (d, J=8 Hz, 2H), 7.64 (d, J=8 Hz, 2H), 14.72 (s, 1H).

Example 476

Synthesis of 4-(((trans)-4-(4-(1-((1S,2S)-2-hydroxycyclohexyl)-1H-pyrazol-5-yl)phenyl)cyclohexyl)oxy)-1H-1,2,3-triazole-5-carboxylic acid (476)

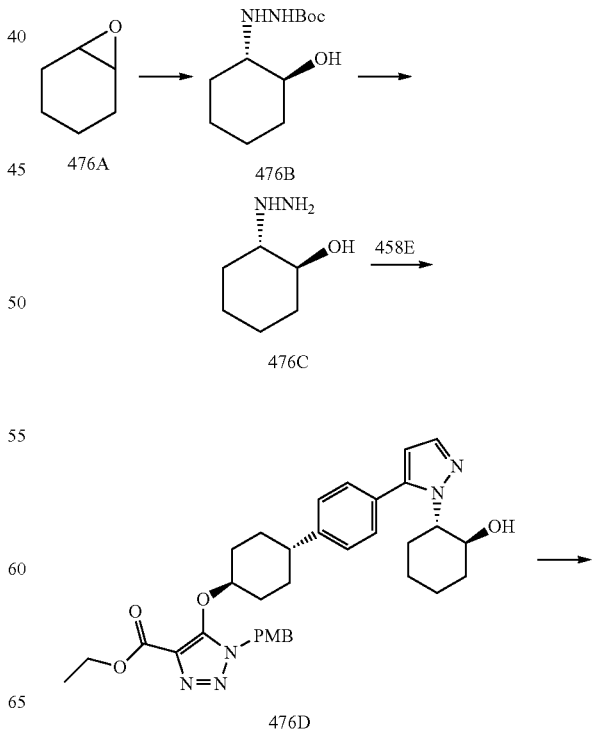

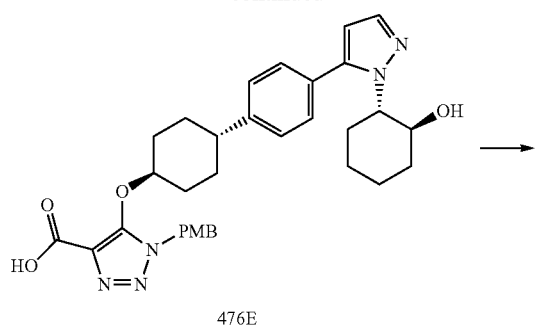

476E

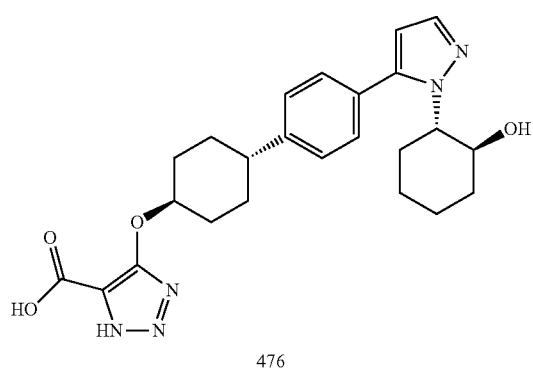

476

Compounds 476B, 476C, 476D, 476E, and 476 were synthesized by employing the procedures described for Compounds 471C, 471D, 471E, 8F, and 1 using Compounds 476A, 476B, 476C, 476D, and 476E in lieu of Compounds 471B, 471C, 471D, 8E, and 1E. Compound 476B: LC-MS (ESI) m/z: 253 [M+Na]⁺. Compound 476C: LC-MS (ESI) m/z: 131 [M+H]⁺. Compound 476D: LC-MS (ESI) m/z: 600 [M+H]⁺. Compound 476E: LC-MS (ESI) m/z: 572 [M+H]⁺. Compound 476: LC-MS (ESI) m/z: 452 [M+H]⁺; ¹H-NMR (DMSO-d₆, 400 MHz) δ 1.20-1.26 (m, 3H), 1.60-1.65 (m, 6H), 1.75 (d, J=12.1 Hz, 1H), 1.83-1.99 (m, 4H), 2.24 (d, J=10.5 Hz, 2H), 2.64 (t, J=11.4 Hz, 1H), 3.92 (d, J=9.7 Hz, 2H), 4.65-4.74 (m, 1H), 6.23 (d, J=1.7 Hz, 1H), 7.37 (d, J=8.2 Hz, 2H), 7.44-7.55 (m, 3H).

Example 477

Synthesis of 4-(((1-(3,5-dichlorophenyl)piperidin-4-yl)oxy)methyl)-1H-1,2,3-triazole-5-carboxylic acid (477)

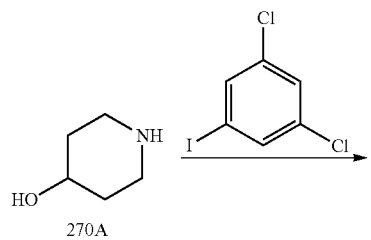

270A

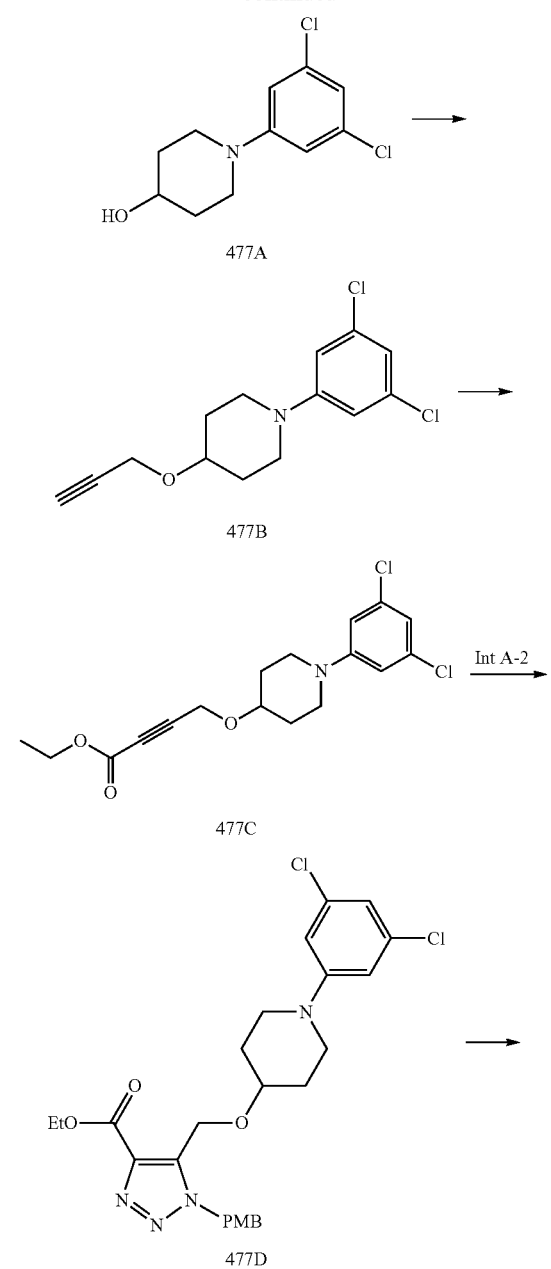

477A

477B

477C

477D

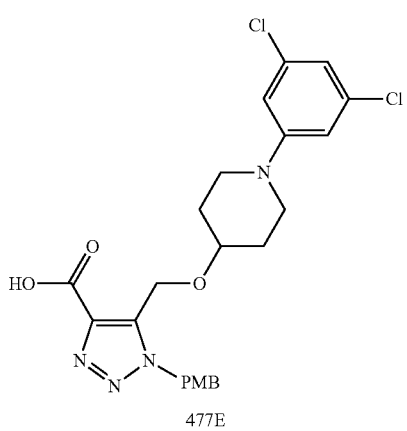

477E

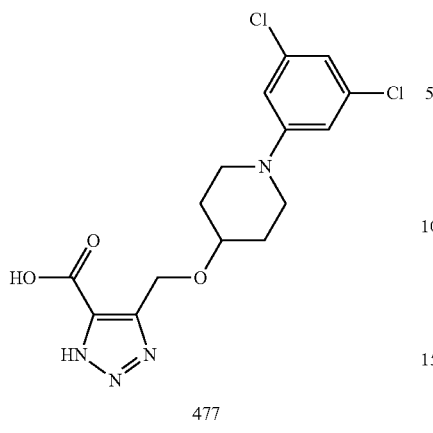

477

Compounds 477A, 477B, 477C, 477D, 477E, and 477 were synthesized by employing the procedures described for Compounds 270B, 456A, 372E, 151B, 8F, and 1 using 1,3-dichloro-5-iodobenzene, Compounds 477A, 477B, 477C, 477D, and 477E in lieu of Compounds 197A, 272E-2, 372D, 151A, 8E, and 1E. Compound 477A: LC-MS (ESI) m/z: 246 [M+H]⁺. Compound 477B: LC-MS (ESI) m/z: 284 [M+H]⁺. Compound 477C: LC-MS (ESI) m/z: 356 [M+H]⁺. Compound 477D: LC-MS (ESI) m/z: 519 [M+H]⁺. Compound 477E: LC-MS (ESI) m/z: 491 [M+H]⁺. Compound 477: LC-MS (ESI) m/z: 371 [M+H]⁺; ¹H-NMR (DMSO-d₆, 400 MHz): δ (ppm) 1.50-1.52 (m, 2H), 1.86-1.89 (m, 2H), 2.97-3.02 (m, 2H), 3.53-3.65 (m, 3H), 4.81 (s, 2H), 6.78 (s, 1H), 6.91 (m, 2H), 13.18 (s, 1H).

Example 478

Synthesis of 4-(((trans)-4-(4-(3-(dimethylamino)propoxy)phenyl)cyclohexyl)oxy)-1H-1,2,3-triazole-5-carboxylic acid 2,2,2-trifluoroacetate (478)

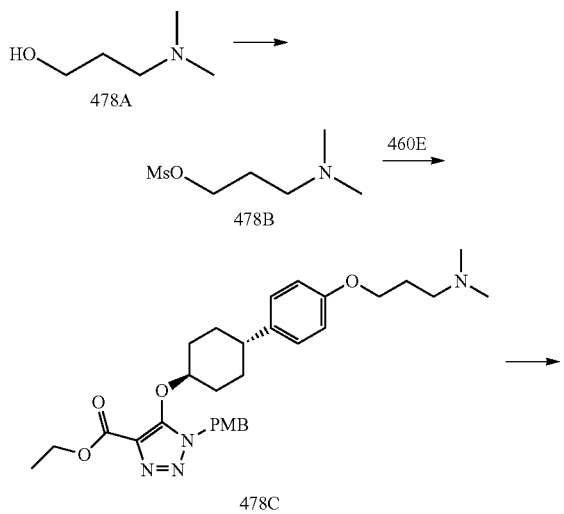

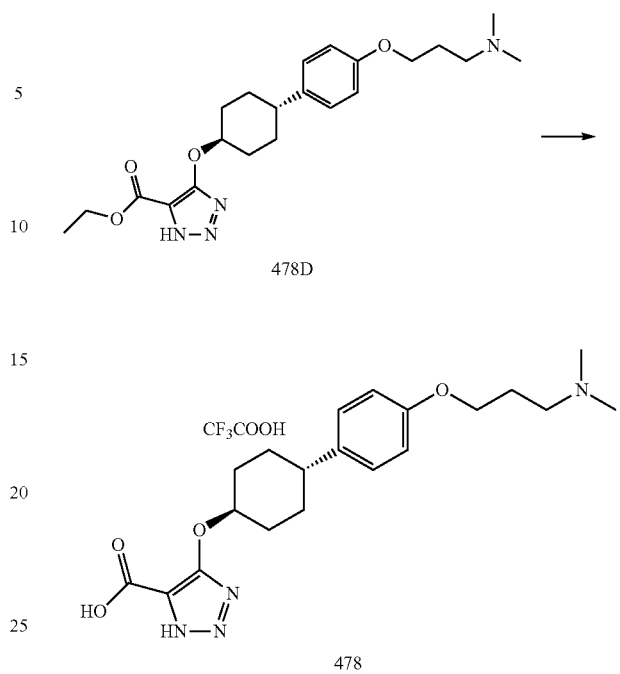

478

Compounds 478B, 478C, 478D, and 478 were synthesized by employing the procedures described for Compounds 340F, 27B, 380E, and 8F using Compounds 478A, 460E, 478B, 478C, and 478D in lieu of Compounds 340E, 27A, 2-bromopropane, 380D, and 8E. Compound 478B: ¹H-NMR (CDCl₃, 400 MHz): δ (ppm) 1.88-1.95 (m, 2H), 2.23 (s, 6H), 2.39 (t, J=6.8 Hz, 2H), 3.02 (s, 3H), 4.30 (t, J=6.4 Hz, 2H). Compound 478C: LC-MS (ESI) m/z: 537 [M+H]⁺; ¹H-NMR (CD₃OD, 400 MHz): δ (ppm) 1.40 (t, J=6.8 Hz, 3H), 1.47-1.61 (m, 4H), 1.85-1.89 (m, 2H), 2.10-2.22 (m, 4H), 2.44-2.51 (m, 1H), 2.95 (s, 6H), 3.33-3.37 (m, 2H), 3.79 (s, 3H), 4.07 (t, J=6.0 Hz, 2H), 4.36-4.42 (m, 2H), 4.94-5.01 (m, 1H), 5.36 (s, 2H), 6.85 (d, J=8.4 Hz, 2H), 6.93 (d, J=8.4 Hz, 2H), 7.12 (d, J=8.8 Hz, 2H), 7.28 (d, J=8.0 Hz, 2H). Compound 478D: LC-MS (ESI) m/z: 417 [M+H]⁺. Compound 478: LC-MS (ESI) m/z: 389 [M+H]⁺; ¹H-NMR (CD₃OD, 400 MHz): δ (ppm) 1.55-1.70 (m, 4H), 1.92-1.96 (m, 2H), 2.16-2.23 (m, 2H), 2.32-2.35 (2H), 2.52-2.61 (m, 1H), 2.95 (s, 6H), 3.32-3.38 (m, 2H), 4.09 (t, J=6.0 Hz, 2H), 4.74 (s, 1H), 6.88 (d, J=8.4 Hz, 2H), 7.18 (d, J=8.4 Hz, 2H).

Example 479

Synthesis of 4-(((trans)-4-(4-(1-(2-ethyl-2-hydroxybutyl)-1H-pyrazol-5-yl)phenyl)cyclohexyl)oxy)-1H-1,2,3-triazole-5-carboxylic acid (479)

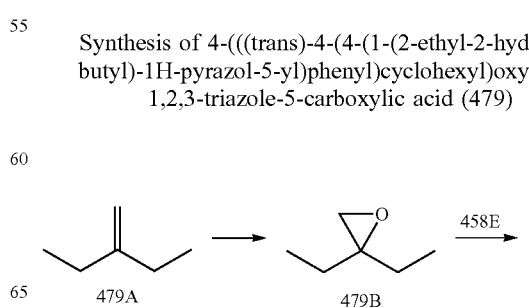

821
-continued

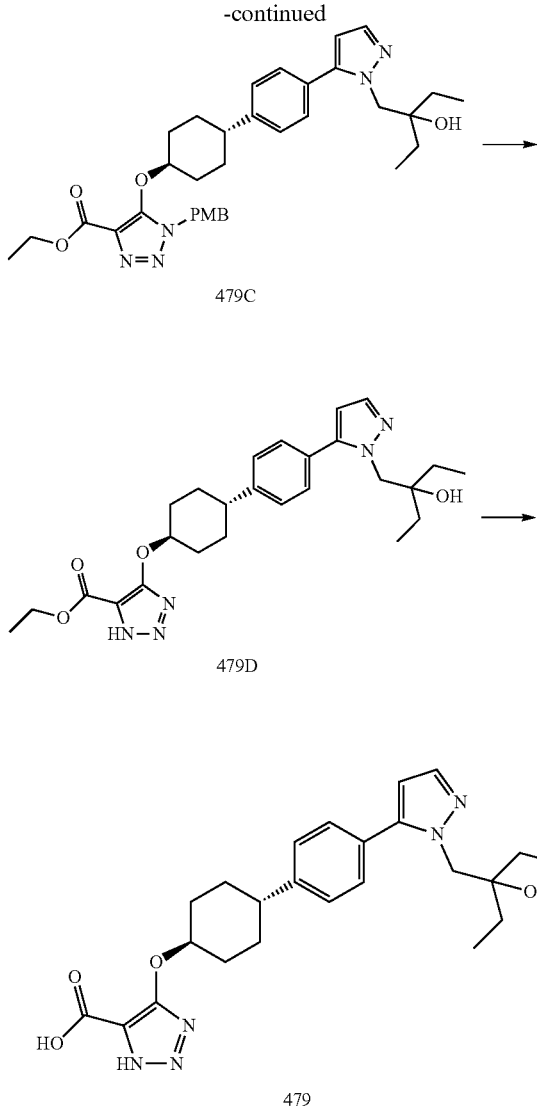

To a solution of 3-methylenepentane (479A, 3.0 g, 35.71 mmol) in dichloromethane (90 mL) was dropped a solution of 3-chloroperbenzoic acid (9.3 g, 53.56 mmol) in dichloromethane (45 ml) over 30 minutes. The reaction mixture was stirred at room temperature for 16 hours, washed with saturated sodium sulfite solution (100 mL) and saturated sodium bicarbonate solution (100 mL), water (100 mL) and brine (100 mL), dried over anhydrous sodium sulfate, and concentrated to give a crude Compound 479B. $^1$H-NMR (CDCl$_3$, 400 MHz): δ (ppm) 0.92 (t, J=7.6 Hz, 6H), 1.54-1.68 (m, 4H), 2.59 (s, 2H).

Compounds 479C, 479D, and 479 were synthesized by employing the procedures described for Compounds 470A, 1, and 8F using Compounds 479B, 479C, and 479D in lieu of 2-ethyl-2-propyloxirane, Compounds 1E, and 8E. Compound 479C: LC-MS (ESI) m/z: 602 [M+H]$^+$. Compound 479D: LC-MS (ESI) m/z: 482 [M+H]$^+$. Compound 479: LC-MS (ESI) m/z: 454 [M+H]$^+$; $^1$H-NMR (CD$_3$OD, 400 MHz): δ (ppm) 0.68 (t, J=7.2 Hz, 6H), 1.21-1.33 (m, 4H), 1.65-1.78 (m, 4H), 1.98-2.04 (m, 2H), 2.34-2.40 (m, 2H), 2.67-2.72 (m, 1H), 4.15 (s, 2H), 4.74-4.80 (m, 1H), 6.33 (d, J=2.0 Hz, 1H), 7.40 (s, 4H), 7.56 (d, J=2.0 Hz, 1H).

822

Example 480

Synthesis of 4-(((trans)-4-(4-(1-(2-hydroxy-2-methylpropyl)-1H-pyrazol-5-yl)phenyl)cyclohexyl)oxy)-1H-1,2,3-triazole-5-carboxylic acid (480)

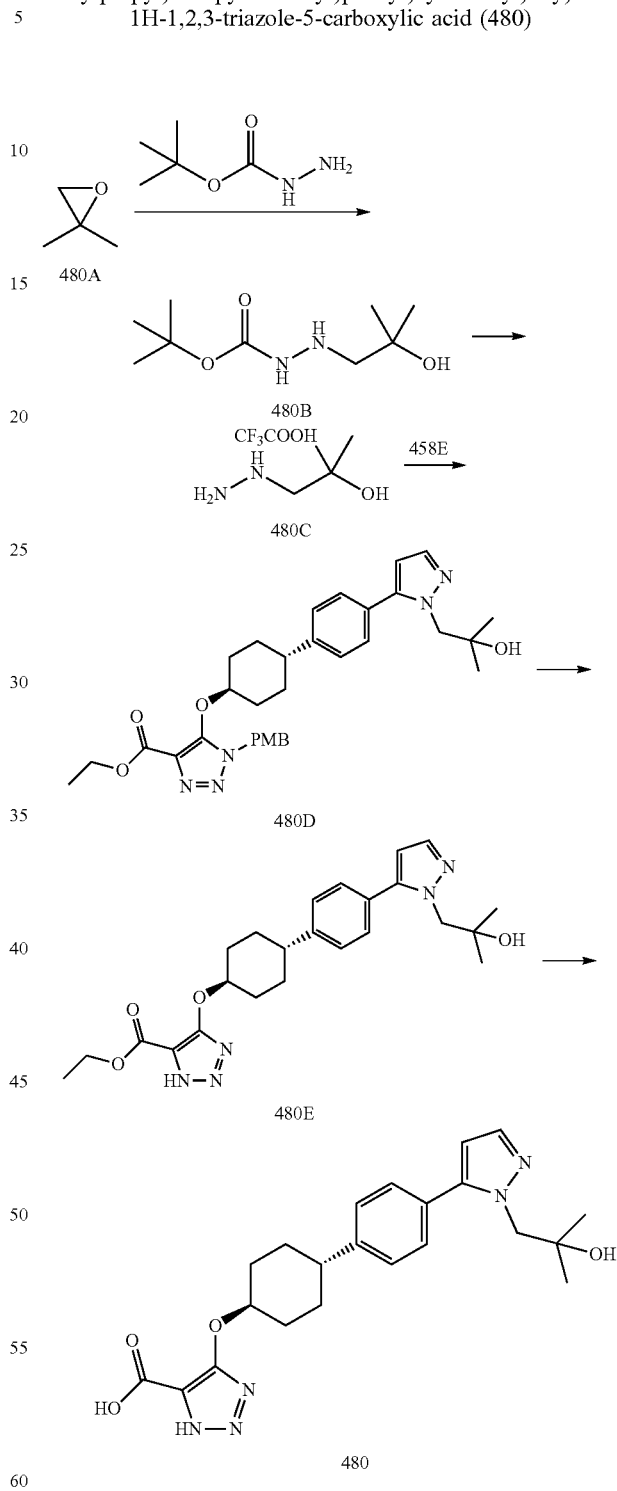

Compounds 480B, 480C, 480D, 480E, and 480 were synthesized by employing the procedures described for Compounds 471C, 471D, 471E, 1, and 8F using Compounds 480A, 480B, 480C, 476D0, and 480E in lieu of Compounds 471B, 471C, 471D, 1E, and 8E. Compound 480B: LC-MS (ESI) m/z: 227 [M+Na]$^+$. $^1$H-NMR (CD$_3$OD, 400 MHz): δ

(ppm) 1.20 (s, 6H), 1.46 (s, 9H), 4.8 (s, 4H). Compound 480C: $^1$H-NMR (DMSO-d$_6$, 400 MHz): δ (ppm) 1.26 (s, 6H), 2.95 (s, 2H). Compound 480D: LC-MS (ESI) m/z: 574 [M+H]$^+$. Compound 480E: LC-MS (ESI) m/z: 454 [M+H]$^+$. Compound 480: LC-MS (ESI) m/z: 426 [M+H]$^+$. $^1$H-NMR (DMSO-d$_6$, 400 MHz): δ (ppm) 0.95 (s, 6H), 1.53-1.65 (m, 4H), 1.88-1.92 (m, 2H), 2.23-2.25 (m, 2H), 2.61-2.66 (m, 1H), 3.96 (s, 2H), 4.64-4.67 (m, 1H), 6.32 (d, J=1.6 Hz, 1H), 7.36 (d, J=8 Hz, 2H), 7.42 (d, J=8 Hz, 2H), 7.52 (d, J=1.6 Hz, 1H).

Example 481

Synthesis of 4-(((1-(2,5-dichlorophenyl)piperidin-4-yl)oxy)methyl)-1H-1,2,3-triazole-5-carboxylic acid 2,2,2-trifluoroacetate (481)

Compounds 481A, 481B, 481C, 481D, and 481 were synthesized by employing the procedures described for Compounds 456A, 372E, 151B, 1, and 8F using Compounds 291A, 481A, 481B, 481C, and 481D in lieu of Compounds 272E-2, 372D, 151A, 1E, and 8E. Compound 481A: LC-MS (ESI) m/z: 284 [M+H]$^+$. Compound 481B: LC-MS (ESI) m/z: 356 [M+H]$^+$. Compound 481C: LC-MS (ESI) m/z: 519 [M+H]$^+$. Compound 481D: LC-MS (ESI) m/z: 399 [M+H]$^+$. Compound 481: LC-MS (ESI) m/z: 371 [M+H]$^+$; $^1$H-NMR (CD$_3$OD, 400 MHz): δ (ppm) 1.84-1.87 (m, 2H), 2.08-2.12 (m, 2H), 2.83-2.88 (m, 2H), 3.27-3.30 (m, 2H), 3.70-3.73 (m, 1H), 4.97 (s, 2H), 6.71 (dd, J=8.4, 2.0 Hz, 1H), 7.13 (d, J=2.4 Hz, 1H), 7.33 (d, J=8.8 Hz, 1H).

Example 482

Synthesis of 4-(((trans)-4-(4-chloro-3-cyclobutylphenyl)cyclohexyl)oxy)-1H-1,2,3-triazole-5-carboxylic acid (482)

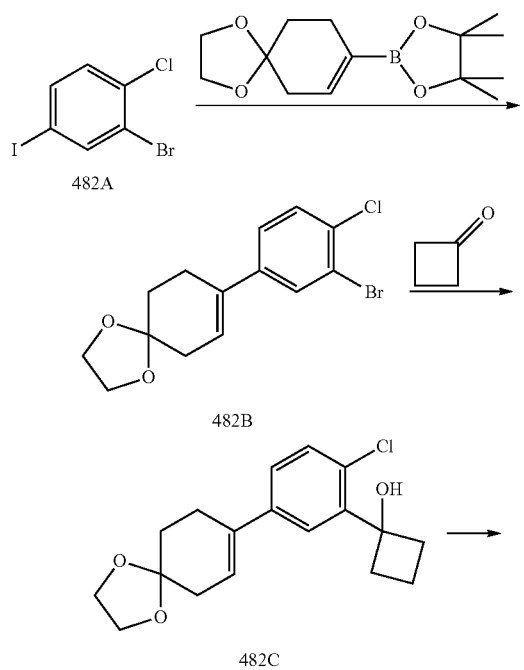

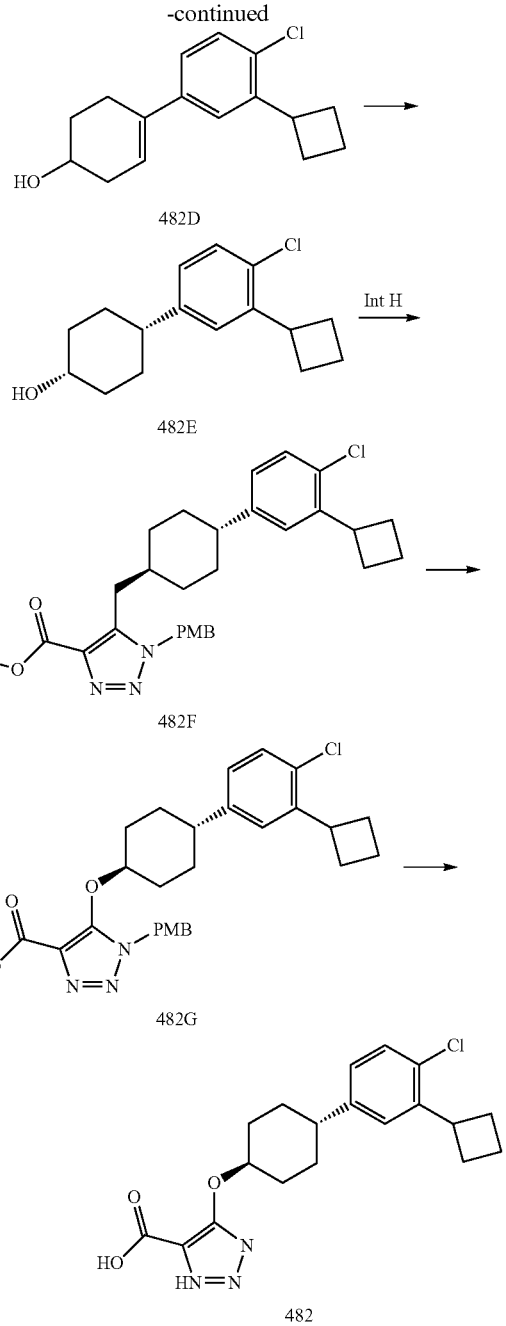

Compounds 482B, 482C, 482D, 482E, 482F, 482G, and 482 were synthesized by employing the procedures described for Compounds 8B, 263C, 57E, 141, 90C, 8F, and 1 using 4,4,5,5-tetramethyl-2-(1,4-dioxaspiro[4.5]dec-7-en-8-yl)-1,3,2-dioxaborolane, Compounds 482A with Na$_2$CO$_3$ as base and 1,4-dioxane/H$_2$O as solvent, 482B, cyclobutanone, 482C with BF$_3$.Et$_2$O as acid, 482D, 482E with diphenyl-2-pyridylphosphine and di-tert-Butyl azodicarboxylate, 482F, and 482G in lieu of (3,4-dichlorophenyl) boronic acid, Compounds 8A with tBuONa as base and toluene as solvent, 263A, 263B, 57D with TFA as acid, 140, 90B with triphenylphosphane and DIAD, 8E, and 1E. Compound 482B: LC-MS (ESI) m/z: 329 [M+H]$^+$; $^1$H-NMR (CDCl$_3$, 400 MHz): δ (ppm) 1.91 (t, J=6.8 Hz, 2H), 2.45-2.46 (m, 2H), 2.58-2.62 (m, 2H), 4.02 (s, 4H), 5.99-6.01 (m, 1H), 7.24-7.27 (m, 1H), 7.35-7.37 (m, 1H), 7.63-7.64 (m, 1H). Compound 482C: LC-MS (ESI) m/z: 303 [M−OH]$^+$; $^1$H-NMR (CDCl$_3$, 400 MHz): δ (ppm) 1.63-1.73 (m, 1H), 1.92 (t, J=6.4 Hz, 2H), 2.04-2.18 (m, 1H), 2.41-2.47 (m, 4H), 2.62-2.69 (m, 4H), 2.77 (s, 1H), 4.01-4.02 (m, 4H), 5.96-5.97 (m, 1H), 7.21-7.23 (m, 1H), 7.26-7.29 (m, 1H), 7.37-7.38 (m, 1H). Compound 482D: LC-MS (ESI) m/z: 263 [M+H]$^+$; $^1$H-NMR (CDCl$_3$, 400 MHz): δ (ppm) 1.77-1.87 (m, 3H), 1.99-2.19 (m, 5H), 2.37-2.44 (m, 2H), 2.51-2.59 (m, 3H), 3.76-3.80 (m, 1H), 4.05-4.07 (m, 1H), 5.97-5.99 (m, 1H), 7.10-7.12 (m, 1H), 7.12-7.26 (m, 1H), 7.29-7.30 (m, 1H). Compound 482E: LC-MS (ESI) m/z: 247 [M−OH]$^+$; $^1$H-NMR (CDCl$_3$, 400 MHz): δ (ppm) 1.48-1.60 (m, 3H), 1.81-2.16 (m, 10H), 2.36-2.43 (m, 2H), 2.50-2.56 (m, 1H), 3.75-3.80 (m, 1H), 4.13-4.14 (m, 1H), 6.98-7.01 (m, 1H), 7.05-7.16 (m, 1H), 7.21-7.23 (m, 1H). Compound 482F: LC-MS (ESI) m/z: 524 [M+H]$^+$. Compound 482G: LC-MS (ESI) m/z: 496 [M+H]$^+$. Compound 482: LC-MS (ESI) m/z: 398 [M+Na]$^+$; $^1$H-NMR (CD$_3$OD, 400 MHz): δ (ppm) 1.63-1.89 (m, 4H), 1.95-2.10 (m, 6H), 2.17-2.44 (m, 4H), 2.60-2.65 (m, 1H), 3.75-3.82 (m, 1H), 4.73-4.78 (m, 1H), 7.04-7.06 (m, 1H), 7.21-7.23 (m, 2H).

Example 483

Synthesis of 4-(((trans)-4-(4-(((trans)-3-(hydroxymethyl)cyclohexyl)methoxy)phenyl)cyclohexyl)oxy)-1H-1,2,3-triazole-5-carboxylic acid (483)

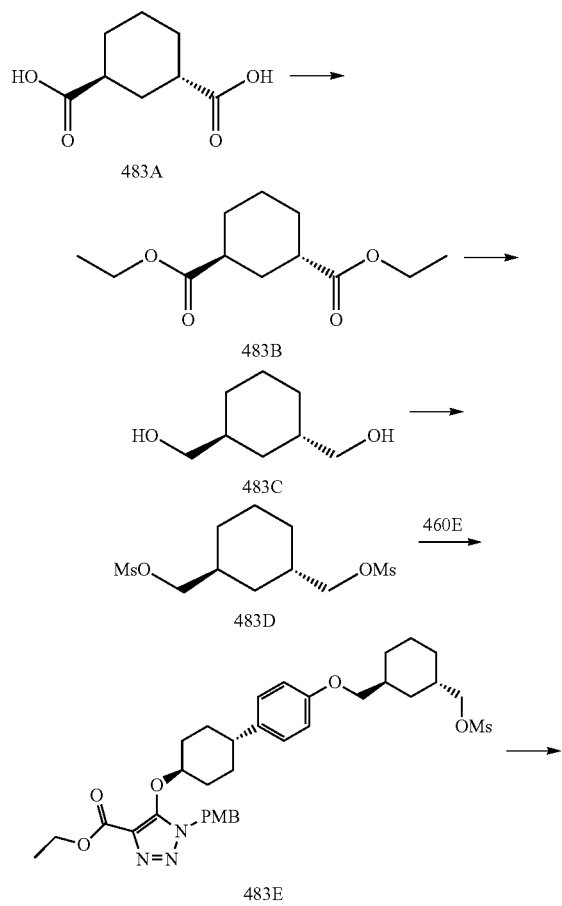

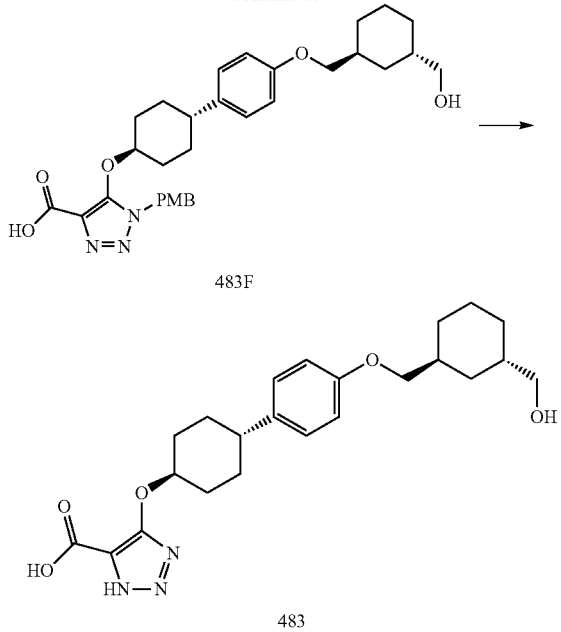

To a solution of (trans)-cyclohexane-1,3-dicarboxylic acid (483A, 3 g, 17.44 mmol) in ethanol (20 mL) was dropped neat sulfurous dichloride (6.2 g, 52.32 mmol) at room temperature, stirred at room temperature for 3 hours, and concentrated under reduced pressure. The residue was diluted with saturated NaHCO$_3$ solution (30 mL) and extracted with ethyl acetate (15 mL×3), the combined organic layers was washed with brine (20 mL×2), dried over anhydrous sodium sulfate, filtered, and concentrated to afford Compound 483B. LC-MS (ESI) m/z: 251 [M+Na]$^+$; $^1$H-NMR (CDCl$_3$, 400 MHz): δ (ppm) 1.26 (t, J=7.6 Hz, 6H), 1.51-1.57 (m, 2H), 1.67-1.77 (m, 4H), 1.95-1.98 (m, 2H), 2.63-2.69 (m, 2H), 4.13 (q, J=7.6 Hz, 4H).

Compounds 483C, 483D, and 483E were synthesized by employing the procedures described for Compounds 283C, 340F, and 27B using Compounds 483B, 483C, 460E, and 483D in lieu of Compounds 283B, 340E, 27A, and 2-bromopropane. Compound 483C: LC-MS (ESI) m/z: 289 [2M+H]$^+$; $^1$H-NMR (CD$_3$OD, 400 MHz): δ (ppm) 1.20-1.28 (m, 2H), 1.34-1.41 (m, 4H), 1.47-1.54 (m, 2H), 1.60-1.67 (m, 2H), 3.45 (d, J=7.2 Hz, 4H). Compound 483D: LC-MS (ESI) m/z: 323 [M+Na]$^+$; $^1$H-NMR (CDCl$_3$, 400 MHz): δ (ppm) 1.34-1.43 (m, 2H), 1.51-1.54 (m, 2H), 1.56-1.59 (m, 2H), 1.62-1.70 (m, 2H), 2.06-2.11 (m, 2H), 3.02 (s, 6H), 4.12-4.14 (m, 4H). Compound 483E: LC-MS (ESI) m/z: 656 [M+H]$^+$.

To a stirred solution of Compound 483E (650 mg, crude) in t-BuOH (16 mL) was added a solution of NaOH (200 mg, 5 mmol) in H$_2$O (2 mL) and stirred at reflux for 16 hours. After cooled down to room temperature, the mixture was acidified to pH 6 with aqueous HCl solution (2 M) and extracted with ethyl acetate (15 mL×2). The combined organic layers was dried over anhydrous sodium sulfate, concentrated, and purified with reversed phase chromatography (elution with MeCN in water, from 15 to 100%) to afford Compound 483F. LC-MS (ESI) m/z: 550 [M+H]$^+$.

Compound 483 was synthesized by employing the procedure described for Compound 380E using Compound 483F in lieu of Compound 380D, LC-MS (ESI) m/z: 430 [M+H]$^+$; $^1$H-NMR (DMSO-d$_6$, 400 MHz): δ (ppm) 1.21-

1.27 (m, 1H), 1.34-1.68 (m, 13H), 1.81-1.83 (m, 2H), 1.96-2.02 (m, 1H), 2.21 (brs, 2H), 3.27-3.29 (m, 2H), 3.80 (d, J=6.8 Hz, 2H), 4.36 (brs, 1H), 4.63 (brs, 1H), 6.83 (d, J=8.4 Hz, 2H), 7.13 (d, J=8.4 Hz, 2H), 12.80 (brs, 1H), 14.72 (brs, 1H).

Example 484

Synthesis of 4-(((trans)-4-(3-cyclobutyl-4-(trifluoromethoxy)phenyl)cyclohexyl)oxy)-1H-1,2,3-triazole-5-carboxylic acid (484)

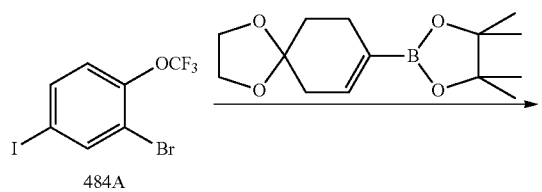

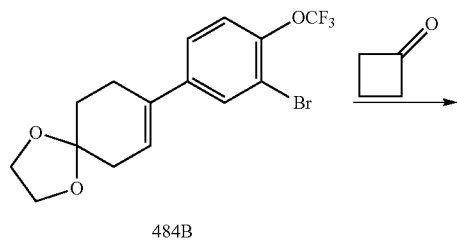

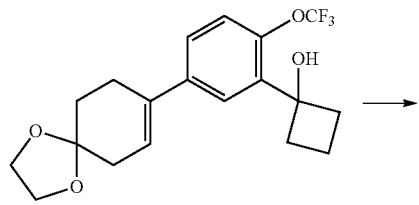

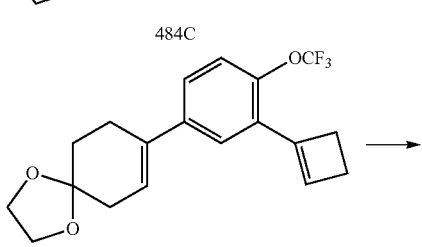

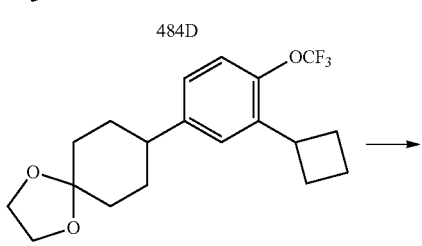

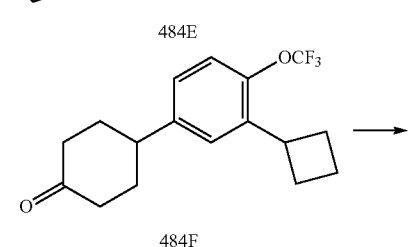

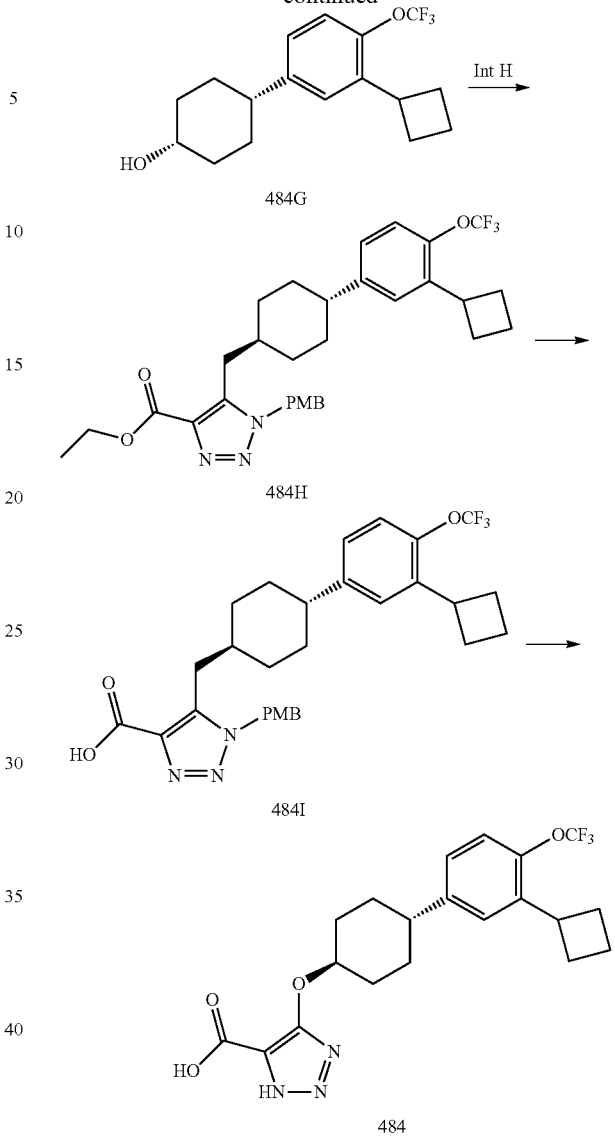

Compounds 484B, 484C, 484D, 484E, 484F, 484G, 484H, 484I, and 484 were synthesized by employing the procedures described for Compounds 8B, 263C, 455B, 141, 279D, 393F-1, 90C, 8F, and 1 using 4,4,5,5-tetramethyl-2-(1,4-dioxaspiro[4.5]dec-7-en-8-yl)-1,3,2-dioxaborolane, Compounds 484A with $Na_2CO_3$ as base and 1,4-dioxane/$H_2O$ as solvent, 484B, cyclobutanone, 484C, 484D, 484E with TFA as acid and dichloromethane as solvent, 484F, 484G with diphenyl-2-pyridylphosphine and di-tert-Butyl azodicarboxylate, 484H, and 484I in lieu of (3,4-dichlorophenyl)boronic acid, Compounds 8A with tBuONa as base and toluene as solvent, 263A, 263B, 455A, 140, 279C with HCl as acid and 1,4-dioxane as solvent, 393E, 90B with triphenylphosphine and DIAD, 8E, and 1E. Compound 484B: LC-MS (ESI) m/z: 379 [M+H]$^+$; $^1$H-NMR (CDCl$_3$, 400 MHz): δ (ppm) 1.92 (t, J=6.4 Hz, 2H), 2.47-2.48 (m, 2H), 2.60-2.64 (m, 2H), 4.03 (s, 4H), 6.00-6.02 (m, 1H), 7.24 (dd, J=8.4 Hz, 1.6 Hz, 1H), 7.34 (dd, J=8.4 Hz, 1.6 Hz, 1H), 7.65 (d, J=1.6 Hz, 1H). Compound 484C: LC-MS (ESI) m/z: 353 [M–OH]$^+$; $^1$H-NMR (CDCl$_3$, 400 MHz): δ (ppm) 1.75-1.83 (m, 1H), 1.93 (t, J=6.4 Hz, 2H), 2.22-2.31 (m, 1H), 2.35-2.41 (m, 3H), 2.47-2.48 (m, 1H), 2.59-2.67 (m, 4H), 4.03 (s, 4H), 5.95-5.98 (m, 1H), 7.19 (dd, J=8.4 Hz, 1.6 Hz, 1H), 7.31 (dd, J=8.4 Hz, 1.6 Hz, 1H), 7.36 (d, J=1.6 Hz, 1H). Compound 484D: LC-MS (ESI) m/z: non-ionizable compound under routine conditions used; $^1$H-NMR (CDCl$_3$, 400 MHz): δ (ppm) 1.94 (t, J=6.4 Hz, 2H), 2.48-2.49 (m, 2H), 2.58-2.59 (m, 2H), 2.63-2.67 (m, 2H), 2.86-2.90 (m, 2H), 4.04 (s, 4H), 5.96-5.99 (m, 1H), 6.42 (s, 1H), 7.15 (d, J=8.4 Hz, 1H), 7.24 (dd, J=8.4 Hz, 2.4 Hz, 1H), 7.30 (d, J=2.4 Hz, 1H). Compound 484E: LC-MS (ESI) m/z: non-ionizable compound under routine conditions used. Compound 484F: LC-MS (ESI) m/z: 313 [M+H]$^+$; $^1$H-NMR (CDCl$_3$, 400 MHz): δ (ppm) 1.84-1.89 (m, 1H), 1.91-2.00 (m, 2H), 2.01-2.16 (m, 3H), 2.20-2.25 (m, 2H), 2.33-2.40 (m, 2H), 2.51-2.54 (m, 4H), 3.01-3.09 (m, 1H), 3.71-3.80 (m, 1H), 7.06 (d, J=9.6 Hz, 1H), 7.12 (d, J=9.6 Hz, 1H), 7.20 (d, J=2.4 Hz, 1H). Compound 484G: LC-MS (ESI) m/z: 297 [M−OH]$^+$. $^1$H-NMR (CDCl$_3$, 400 MHz): δ (ppm) 1.66-1.90 (m, 10H), 2.10-2.20 (m, 2H), 2.32-2.38 (m, 2H), 2.53-2.61 (m, 1H), 3.71-3.80 (m, 1H), 4.12-4.16 (m, 1H), 7.05-7.10 (m, 2H), 7.20 (s, 1H). Compound 484H: LC-MS (ESI) m/z: 574 [M+H]$^+$. $^1$H-NMR (CD$_3$OD, 400 MHz): δ (ppm) 1.26 (t, J=7.2 Hz, 3H), 1.50-1.56 (m, 4H), 1.81-1.95 (m, 4H), 2.09-2.17 (m, 4H), 2.31-2.39 (m, 2H), 2.46-2.52 (m, 1H), 3.70-3.77 (m, 1H), 3.80 (s, 3H), 4.42 (q, J=7.2 Hz, 2H), 5.04-5.12 (m, 1H), 5.30 (s, 2H), 6.87 (d, J=8.4 Hz, 2H), 6.99 (dd, J=8.4 Hz, 2.4 Hz, 1H), 7.08 (dd, J=8.4 Hz, 2.4 Hz, 1H), 7.12 (d, J=8.4 Hz, 1H), 7.26 (d, J=8.4 Hz, 2H). Compound 484I: LC-MS (ESI) m/z: 546 [M+H]$^+$. Compound 484: LC-MS (ESI) m/z: 448 [M+Na]$^+$; $^1$H-NMR (CD$_3$OD, 400 MHz): δ (ppm) 1.52-1.66 (m, 4H), 1.74-1.81 (m, 1H), 1.87-1.89 (m, 2H), 1.93-2.00 (m, 1H), 2.03-2.13 (m, 2H), 2.22-2.28 (m, 4H), 2.55-2.60 (m, 1H), 3.61-3.70 (m, 1H), 4.65-4.69 (m, 1H), 7.00-7.07 (m, 2H), 7.19 (d, J=2.0 Hz, 1H).

Example 485

Synthesis of 4-(((trans)-4-(4-(3-(2-methoxyethyl)-1H-pyrazol-5-yl)phenyl)cyclohexyl)oxy)-1H-1,2,3-triazole-5-carboxylic acid 2,2,2-trifluoroacetate (485)

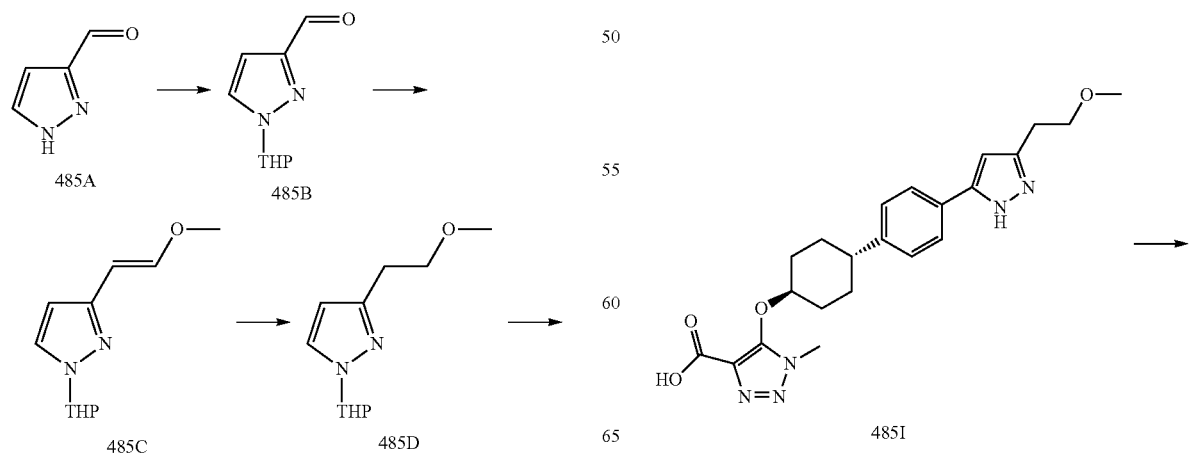

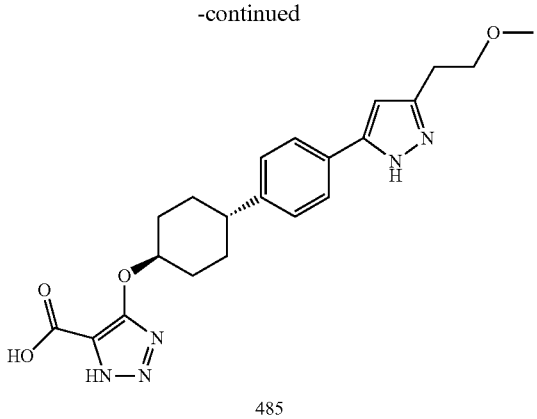

485

Compound 485B was synthesized by employing the procedure described for Compound 464B using Compound 485A with toluene as solvent and p-TsOH as acidic catalyst, in lieu of Compound 464A without acid as acidic catalyst, LC-MS (ESI) m/z: 203 [M+Na]$^+$; $^1$H-NMR (CDCl$_3$, 400 MHz): δ (ppm) 1.60-1.73 (m, 3H), 1.99-2.19 (m, 3H), 3.70-3.77 (m, 1H), 4.06-4.12 (m, 1H), 5.46-5.49 (m, 1H), 6.84 (d, J=2.4 Hz, 1H), 7.68 (d, J=2.0 Hz, 1H), 10.0 (s, 1H).

To the solution of (methoxymethyl)triphenylphosphonium chloride (8.4 g, 24.4 mmol) in THF (20 mL) was dropped a solution of n-BuLi in hexane (2.5 M, 9.76 mL, 24.4 mmol) at 0° C. and stirred at 0° C. for 1 hour. The mixture was cooled down to −78° C. and a solution of Compound 485B (2.2 g, 12.2 mmol) in THF (10 mL) was dropped and stirred at −78° C. for 1 hour. It was warmed gradually to room temperature, stirred overnight, and quenched with saturated NH$_4$Cl solution (20 mL), and extracted with ethyl acetate (20 mL). The organic layer was washed with water (20 mL) and brine (50 mL), dried over anhydrous sodium sulfate, concentrated, and purified with flash column chromatography on silica gel (ethyl acetate in petroleum ether, 20% v/v) to give Compound 485C. LC-MS (ESI) m/z: 209 [M+H]$^+$.

Compounds 485D, 485E, 485F, 485G, 485H, 485I, and 485 were synthesized by employing the procedures described for Compounds 141, 475E, 475F, 475G, 4B, 8F, and 1 using Compounds 485C, 485D with HCl as acid and EtOH as solvent, 485E with TFA as acid and dichloromethane as solvent, 485F, 475A, 485G with K$_2$CO$_3$ as base and 1,4-dioxane/H$_2$O as solvent, 485H, and 485I in lieu of Compounds 140, 475D with TFA as acid and dichloromethane as solvent, 475E, 475F, (4-bromophenyl)boronic acid, 4A with Na$_2$CO$_3$ as base and toluene/EtOH/H$_2$O as solvent, 8E, and 1E. Compound 485D: LC-MS (ESI) m/z: 211 [M+H]$^+$. Compound 485E: LC-MS (ESI) m/z: 127 [M+H]$^+$. Compound 485F: LC-MS (ESI) m/z: 379 [M+H]$^+$. $^1$H-NMR (CDCl$_3$, 400 MHz): δ (ppm) 2.94 (t, J=5.6 Hz, 2H), 3.41 (s, 3H), 3.62 (t, J=5.6 Hz, 2H), 10.82 (s, 1H). Compound 485G: LC-MS (ESI) m/z: 253 [M+H]$^+$; $^1$H-NMR (CDCl$_3$, 400 MHz): δ (ppm) 2.90 (t, J=5.6 Hz, 2H), 3.40 (s, 3H), 3.61 (t, J=5.6 Hz, 2H), 6.22 (s, 1H). Compound 485H: LC-MS (ESI) m/z: 560 [M+H]$^+$. Compound 485I: LC-MS (ESI) m/z: 532 [M+H]$^+$. Compound 485: LC-MS (ESI) m/z: 412 [M+H]$^+$; $^1$H-NMR (DMSO-d$_6$, 400 MHz): δ (ppm) 1.51-1.66 (m, 4H), 1.86-1.90 (m, 2H), 2.22-2.25 (m, 2H), 2.55-2.64 (m, 1H), 2.81 (t, J=7.2 Hz, 2H), 3.25 (s, 3H), 3.57 (t, J=7.2 Hz, 2H), 4.62 (s, 1H), 6.44 (s, 1H), 7.27 (d, J=8.4 Hz, 2H), 7.64 (d, J=8.4 Hz, 2H), 12.73 (s, 2H), 14.71 (s, 1H).

Example 486

Synthesis of 4-(((((trans)-4-(3,5-dichlorophenyl)cyclohexyl)oxy)methyl)-1H-1,2,3-triazole-5-carboxylic acid (486)

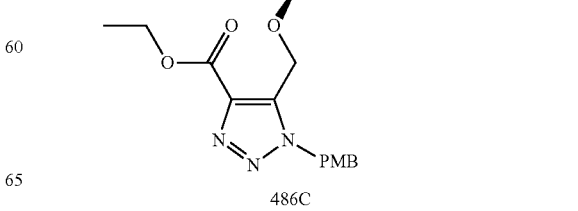

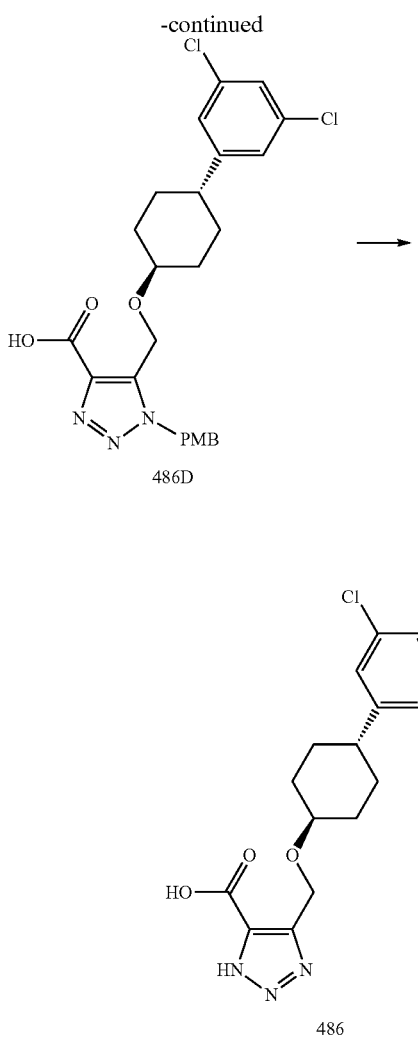

486D

486

Compounds 486A, 486B, 486C, 486D, and 486 were synthesized by employing the procedures described for Compounds 456A, 372E, 151B, 8F, and 1 using Compounds 304D-1, 486A, 486B, 486C, and 486D in lieu of Compounds 272E-2, 372D, 151A, 8E, and 1E. Compound 486A: LC-MS (ESI) m/z: non-ionizable compound under routine conditions used. $^1$H-NMR (CDCl$_3$, 400 MHz): δ (ppm) 1.37-1.53 (m, 4H), 1.93-1.96 (m, 2H), 2.18-2.21 (m, 2H), 2.43-2.44 (m, 1H), 2.47-2.52 (m, 1H), 3.50-3.59 (m, 1H), 4.23 (s, 2H), 7.08-7.09 (m, 2H), 7.19-7.20 (m, 1H). Compound 486B: LC-MS (ESI) m/z: non-ionizable compound under routine conditions used. $^1$H-NMR (CDCCl$_3$, 400 MHz): δ (ppm) 1.33 (t, J=7.2 Hz, 3H), 1.37-1.55 (m, 4H), 1.93-1.96 (m, 2H), 2.17-2.20 (m, 2H), 2.44-2.52 (m, 1H), 3.49-3.56 (m, 1H), 4.26 (q, J=7.2 Hz, 2H), 4.35 (s, 2H), 7.07-7.08 (m, 2H), 7.19-7.20 (m, 1H). Compound 486C: LC-MS (ESI) m/z: 518 [M+H]$^+$; $^1$H-NMR (CDCl$_3$, 400 MHz): δ (ppm) 1.37 (t, J=7.2 Hz, 3H), 1.41-1.51 (m, 4H), 1.92-1.95 (m, 2H), 2.21-2.24 (m, 2H), 2.44-2.51 (m, 1H), 3.46-3.52 (m, 1H), 3.78 (s, 3H), 4.39 (q, J=7.2 Hz, 2H), 4.82 (s, 2H), 5.81 (s, 2H), 6.84 (d, J=9.2 Hz, 2H), 7.07-7.09 (m, 2H), 7.18-7.19 (m, 1H), 7.30 (d, J=9.2 Hz, 2H). Compound 486D: LC-MS (ESI) m/z: 490 [M+H]$^+$. Compound 486: LC-MS (ESI) m/z: 370 [M+H]$^+$; $^1$H-NMR (CD$_3$OD, 400 MHz): δ (ppm) 1.40-1.59 (m, 4H), 1.91-1.94 (m, 2H), 2.23-2.26 (m, 2H), 2.53-2.60 (m, 1H), 3.53-3.58 (m, 1H), 4.98 (s, 2H), 7.21-7.22 (m, 2H), 7.24-7.25 (m, 1H).

BIOLOGICAL EXAMPLES

The following describes ways in which the compounds described herein were tested to measure in vitro activity in enzymatic assays. A person of ordinary skill in the art would know that variations in the assay conditions could be used to determine the activity of the compounds.

Assay 1: GO Enzymatic Assay

Human GO was obtained from Novus Biologicals (NBP1-72412, Novus Biologicals, LLC, 8100 Southpark Way, A-8 Littleton, Colo. 80120, USA). A coupled fluorescence GO enzymatic assay was performed as previously described (Martin-Higueras et al., Mol Ther. 24(4): 719-725). GO was incubated with its substrate, glycolate, in 50 mM potassium phosphate buffer, pH 7. The addition of sulfonated-DCIP and 4-aminoantipyrine (Sigma Aldrich) in a coupled HRP reaction produced a chromogen that was measured at 515 nm. The enzyme assay was linear and sensitive. The enzyme was optimized and the kinetics was determined. The $K_m$ of substrate was determined to be about 50 μM, where the tolerance of DMSO was 0.5% in both compound-treated and mock-treated samples.

Compound inhibition was determined by adding various concentrations of inhibitors in the GO enzyme assay. The IC$_{50}$ value for each measured compound was generated from sigmoidal dose-response (variable slope) curves with GraphPad Prism software (GraphPad Software, Inc., San Diego, Calif.) using the percent inhibition of GO activity relative to DMSO control.

Assay 2: GO Cellular Assay

Primary hepatocytes were used for a GO cellular assay as previously described (Martin-Higueras et al., Mol Ther. 24(4): 719-725). Hepatocytes were isolated using an in situ collagenase perfusion method from male C56BL/6 mice liver. The freshly isolated hepatocytes were cultured in six well plates with Williams E medium supplemented with 5% fetal bovine serum, 2 mM 1-glutamine, 100 U/ml penicillin, 100 μg/ml streptomycin, 2.2 mUI/ml insulin and 0.3 μg/ml hydrocortisone. After 5 hours, the medium was changed to Williams E complete medium (Biochrom, Cambridge, UK) without serum and cells were treated with various concentrations of inhibitors in the presence of 5 mM glycolate. Culture medium was harvested at 72 hours after treatment, and the oxalate was quantified by using an oxalate oxidase assay kit (Trinity Biotech, Co Wicklow, Ireland) following manufacturer's instructions. The oxalate level was also confirmed by LC-MS method. The IC$_{50}$ value for each measured compound was generated from sigmoidal dose-response (variable slope) curves with GraphPad Prism software (GraphPad Software, Inc., San Diego, Calif.) using the percent inhibition of GO activity relative to DMSO control.

Using the above assays, the compounds of Table 1, Table 2, Table 3, Table 4, Table 5, and Table 6 were tested. In Table 1, Table 2, Table 3, Table 4, Table 5, and Table 6 biological data range of IC$_{50}$ values calculated from the enzymatic assays are provided, where:

A is <0.1 μM;

B is 0.1 to 1.0 μM;

C is >1.0 to 10 μM;

D is >10 μM; and

TABLE 1

| Example | Name | Range |
|---|---|---|
| 1 | ethyl 4-((4-(3,4-dichlorophenyl)thiazol-2-yl)thio)-1H-1,2,3-triazole-5-carboxylate | |
| 2 | 4-((4-(3,4-dichlorophenyl)thiazol-2-yl)thio)-1H-1,2,3-triazole-5-carboxylic acid | A |
| 3 | 4-((5-(3,4-dichlorophenyl)thiazol-2-yl)thio)-1H-1,2,3-triazole-5-carboxylic acid | A |
| 5 | 4-((4'-chloro-[1,1'-biphenyl]-4-yl)thio)-1H-1,2,3-triazole-5-carboxylic acid | A |
| 6 | 5-((3-(4-methylpiperazin-1-yl)phenyl)thio)-1H-1,2,3-triazole-4-carboxylic acid | D |
| 7 | 4-((4-(piperidin-1-yl)phenyl)thio)-1H-1,2,3-triazole-5-carboxylic acid | B |
| 8 | 4-((2-(3,4-dichlorophenyl)thiazol-4-yl)thio)-1H-1,2,3-triazole-5-carboxylic acid | A |
| 9 | cyclobutyl 4-((4-(3,4-dichlorophenyl)thiazol-2-yl)thio)-1H-1,2,3-triazole-5-carboxylate | D |
| 10 | 4-((4-(4-methylpiperazin-1-yl)phenyl)thio)-1H-1,2,3-triazole-5-carboxylic acid | C |
| 11 | isopropyl 4-((4-(3,4-dichlorophenyl)thiazol-2-yl)thio)-1H-1,2,3-triazole-5-carboxylate | D |
| 12 | 4-((5-(4-bromophenyl)pyridin-2-yl)thio)-1H-1,2,3-triazole-5-carboxylic acid | B |
| 13 | 4-((5-(3,4-dichlorophenyl)-4H-1,2,4-triazol-3-yl)thio)-1H-1,2,3-triazole-5-carboxylic acid | B |
| 14 | 4-((4'-methoxy-[1,1'-biphenyl]-4-yl)thio)-1H-1,2,3-triazole-5-carboxylic acid | A |
| 15 | 4-((4-(3-chloro-4-methoxyphenyl)thiazol-2-yl)thio)-1H-1,2,3-triazole-5-carboxylic acid | A |
| 16 | 4-((4'-(trifluoromethoxy)-[1,1'-biphenyl]-4-yl)thio)-1H-1,2,3-triazole-5-carboxylic acid | A |
| 17 | methyl 4-((4-(3,4-dichlorophenyl)thiazol-2-yl)thio)-1H-1,2,3-triazole-5-carboxylate | D |
| 18 | 4-((4-(3-chloro-4-cyclopropoxyphenyl)thiazol-2-yl)thio)-1H-1,2,3-triazole-5-carboxylic acid | A |
| 19 | cyclopropyl 4-((4-(3,4-dichlorophenyl)thiazol-2-yl)thio)-1H-1,2,3-triazole-5-carboxylate | D |
| 20 | 4-((6-(3,4-dichlorophenyl)pyridin-2-yl)thio)-1H-1,2,3-triazole-5-carboxylic acid | A |
| 21 | 4-((3',4'-dichloro-[1,1'-biphenyl]-4-yl)thio)-1H-1,2,3-triazole-5-carboxylic acid | A |
| 22 | 4-((2',4'-dichloro-[1,1'-biphenyl]-4-yl)thio)-1H-1,2,3-triazole-5-carboxylic acid | A |
| 23 | 4-((2-(4-chloro-3-methoxyphenyl)thiazol-4-yl)thio)-1H-1,2,3-triazole-5-carboxylic acid | A |
| 24 | 4-((2-(4-chloro-3-isopropoxyphenyl)thiazol-4-yl)thio)-1H-1,2,3-triazole-5-carboxylic acid | A |
| 25-1 | 5-((2-(3-chloro-4-methoxyphenyl)thiazol-4-yl)thio)-1-(4-methoxybenzyl)-1H-1,2,3-triazole-4-carboxylic acid | D |
| 25-2 | 4-((2-(3-chloro-4-methoxyphenyl)thiazol-4-yl)thio)-1H-1,2,3-triazole-5-carboxylic acid | A |
| 26 | 4-((2-(2,4-dichlorophenyl)thiazol-4-yl)thio)-1H-1,2,3-triazole-5-carboxylic acid | A |
| 27 | 4-((2-(3-chloro-4-isopropoxyphenyl)thiazol-4-yl)thio)-1H-1,2,3-triazole-5-carboxylic acid | A |
| 28 | 4-((5-(3,4-dichlorophenyl)-4-methyl-4H-1,2,4-triazol-3-yl)thio)-1H-1,2,3-triazole-5-carboxylic acid • 2,2,2-trifluoroacetate | C |
| 29 | 4-((5-ethoxybenzo[d]thiazol-2-yl)thio)-1H-1,2,3-triazole-5-carboxylic acid | B |
| 30 | 4-((4'-chloro-3'-(trifluoromethoxy)-[1,1'-biphenyl]-4-yl)thio)-1H-1,2,3-triazole-5-carboxylic acid | A |
| 31 | 4-((2'-chloro-3'-(trifluoromethoxy)-[1,1'-biphenyl]-4-yl)thio)-1H-1,2,3-triazole-5-carboxylic acid | A |
| 32 | 4-((3'-chloro-4'-(trifluoromethoxy)-[1,1'-biphenyl]-4-yl)thio)-1H-1,2,3-triazole-5-carboxylic acid | A |
| 33 | methyl 4-((4'-(trifluoromethoxy)-[1,1'-biphenyl]-4-yl)thio)-1H-1,2,3-triazole-5-carboxylate | D |
| 34 | 4-((5-butoxybenzo[d]thiazol-2-yl)thio)-1H-1,2,3-triazole-5-carboxylic acid | B |
| 35 | 4-((2-(3,4-dichlorophenyl)-1-methyl-1H-imidazol-5-yl)thio)-1H-1,2,3-triazole-5-carboxylic acid | B |
| 36 | 4-((5-(3,4-dichlorophenyl)thiophen-3-yl)thio)-1H-1,2,3-triazole-5-carboxylic acid | A |
| 37 | 2-(dimethylamino)ethyl 4-((4'-(trifluoromethoxy)-[1,1'-biphenyl]-4-yl)thio)-1H-1,2,3-triazole-5-carboxylate | D |
| 38 | N,N,N-trimethyl-2-((4-((4'-(trifluoromethoxy)-[1,1'-biphenyl]-4-yl)thio)-1H-1,2,3-triazole-5-carbonyl)oxy)ethan-1-aminium iodide | C |

TABLE 1-continued

| Example | Name | Range |
|---|---|---|
| 39 | 4-((2-(3-chloro-4-(trifluoromethoxy)phenyl)thiazol-4-yl)thio)-1H-1,2,3-triazole-5-carboxylic acid | A |
| 40 | methyl 4-((2-(3-chloro-4-(trifluoromethoxy)phenyl)thiazol-4-yl)thio)-1H-1,2,3-triazole-5-carboxylate | D |
| 41 | 4-((3,4-dichlorophenyl)thio)-1H-1,2,3-triazole-5-carboxylic acid | A |
| 42 | 4-((4'-(trifluoromethoxy)-[1,1'-biphenyl]-3-yl)thio)-1H-1,2,3-triazole-5-carboxylic acid | A |
| 43 | 4-((4-(3-chloro-4-(trifluoromethoxy)phenyl)thiazol-2-yl)thio)-1H-1,2,3-triazole-5-carboxylic acid | A |
| 44 | methyl 4-((4-(3-chloro-4-(trifluoromethoxy)phenyl)thiazol-2-yl)thio)-1H-1,2,3-triazole-5-carboxylate | D |
| 45 | oxetan-3-yl 4-((4'-(trifluoromethoxy)-[1,1'-biphenyl]-4-yl)thio)-1H-1,2,3-triazole-5-carboxylate | C |
| 46 | 4-((6-chloroquinolin-2-yl)thio)-1H-1,2,3-triazole-5-carboxylic acid | B |
| 47 | 4-((2,4'-dichloro-[1,1'-biphenyl]-4-yl)thio)-1H-1,2,3-triazole-5-carboxylic acid | A |
| 48 | 4-((3,4'-dichloro-[1,1'-biphenyl]-4-yl)thio)-1H-1,2,3-triazole-5-carboxylic acid | A |
| 49 | 4-((3,4-difluorophenyl)thio)-1H-1,2,3-triazole-5-carboxylic acid | A |
| 50 | 4-((5,6,7,8-tetrahydronaphthalen-2-yl)thio)-1H-1,2,3-triazole-5-carboxylic acid | A |
| 51 | 1-((pivaloyloxy)methyl)-4-((4'-(trifluoromethoxy)-[1,1'-biphenyl]-4-yl)thio)-1H-1,2,3-triazole-5-carboxylic acid | B |
| 52 | 1-((isobutyryloxy)methyl)-4-((4'-(trifluoromethoxy)-[1,1'-biphenyl]-4-yl)thio)-1H-1,2,3-triazole-5-carboxylic acid | B |
| 53 | 4-(benzo[d]thiazol-6-ylthio)-1H-1,2,3-triazole-5-carboxylic acid | A |
| 54 | (pivaloyloxy)methyl 4-((4'-(trifluoromethoxy)-[1,1'-biphenyl]-4-yl)thio)-1H-1,2,3-triazole-5-carboxylate | C |
| 55 | (isobutyryloxy)methyl 4-((4'-(trifluoromethoxy)-[1,1'-biphenyl]-4-yl)thio)-1H-1,2,3-triazole-5-carboxylate | B |
| 56 | 4-((6-chloronaphthalen-2-yl)thio)-1H-1,2,3-triazole-5-carboxylic acid | A |
| 57 | 4-((5,6-dichloro-2,3-dihydro-1H-inden-2-yl)thio)-1H-1,2,3-triazole-5-carboxylic | A |
| 58-1 | ethyl 4-((4'-chloro-[1,1'-biphenyl]-4-yl)amino)-1H-1,2,3-triazole-5-carboxylate | D |
| 58-2 | 4-((4'-chloro-[1,1'-biphenyl]-4-yl)amino)-1H-1,2,3-triazole-5-carboxylic acid | A |
| 59 | 4-((4-(3,4-dichlorophenyl)thiazol-2-yl)amino)-1H-1,2,3-triazole-5-carboxylic acid | A |
| 60 | 4-((3',4'-dichloro-[1,1'-biphenyl]-4-yl)amino)-1H-1,2,3-triazole-5-carboxylic acid | A |
| 61 | ammonium 4-((2-(3,4-dichlorophenyl)thiazol-4-yl)amino)-1H-1,2,3-triazole-5-carboxylate | A |
| 62 | 4-((4'-(trifluoromethoxy)-[1,1'-biphenyl]-4-yl)amino)-1H-1,2,3-triazole-5-carboxylic acid | A |
| 63 | 4-((2-(3,4-dichlorophenyl)thiazol-4-yl)(methyl)amino)-1H-1,2,3-triazole-5-carboxylic acid | B |
| 64 | 4-((4-(3-chloro-4-(trifluoromethoxy)phenyl)thiazol-2-yl)amino)-1H-1,2,3-triazole-5-carboxylic acid | A |
| 65 | methyl 4-((4'-(trifluoromethoxy)-[1,1'-biphenyl]-4-yl)amino)-1H-1,2,3-triazole-5-carboxylate | D |
| 66 | 4-((carboxymethyl)(4'-chloro-[1,1'-biphenyl]-4-yl)amino)-1H-1,2,3-triazole-5-carboxylic acid | C |
| 67 | 4-(((3',4'-dichloro-[1,1'-biphenyl]-3-yl)methyl)amino)-1H-1,2,3-triazole-5-carboxylic acid | B |
| 68 | 4-(((3',4'-dichloro-[1,1'-biphenyl]-4-yl)methyl)amino)-1H-1,2,3-triazole-5-carboxylic acid | A |
| 69 | 4-((3,4-dichlorophenyl)amino)-1H-1,2,3-triazole-5-carboxylic acid | A |
| 70 | 4-((1-(4-(trifluoromethoxy)phenyl)piperidin-3-yl)amino)-1H-1,2,3-triazole-5-carboxylic acid | B |
| 71 | 4-((1-(4-chlorophenyl)piperidin-4-yl)amino)-1H-1,2,3-triazole-5-carboxylic acid | B |
| 72 | cyclopropyl 4-((4'-(trifluoromethoxy)-[1,1'-biphenyl]-4-yl)amino)-1H-1,2,3-triazole-5-carboxylate | D |
| 73 | 4-((1-(4-(trifluoromethoxy)phenyl)pyrrolidin-3-yl)amino)-1H-1,2,3-triazole-5-carboxylic acid | B |
| 74 | 4-((1-(4-(trifluoromethoxy)phenyl)piperidin-4-yl)amino)-1H-1,2,3-triazole-5-carboxylic acid | B |
| 75 | 4-((4'-chloro-[1,1'-biphenyl]-4-yl)(methyl)amino)-1H-1,2,3-triazole-5-carboxylic acid | B |
| 76 | 4-((6-chloroquinolin-2-yl)amino)-1H-1,2,3-triazole-5-carboxylic acid | A |

TABLE 1-continued

| Example | Name | Range |
|---|---|---|
| 77 | 4-((5,6,7,8-tetrahydronaphthalen-2-yl)amino)-1H-1,2,3-triazole-5-carboxylic acid | C |
| 78 | 4-((4-chloronaphthalen-1-yl)amino)-1H-1,2,3-triazole-5-carboxylic acid | B |
| 79 | 4-(benzo[d]thiazol-6-ylamino)-1H-1,2,3-triazole-5-carboxylic acid | C |
| 80 | 4-((3,4-difluorophenyl)amino)-1H-1,2,3-triazole-5-carboxylic acid | B |
| 81 | (pivaloyloxy)methyl 4-((4'-chloro-[1,1'-biphenyl]-4-yl)amino)-1H-1,2,3-triazole-5-carboxylate | C |
| 82 | 4-((6-chloronaphthalen-2-yl)amino)-1H-1,2,3-triazole-5-carboxylic acid | B |
| 83 | 4-(4-(trifluoromethoxy)phenyl)amino)-1H-1,2,3-triazole-5-carboxylic acid | B |
| 84 | 4-(3,4-dihydroisoquinolin-2(1H)-yl)-1H-1,2,3-triazole-5-carboxylic acid | B |
| 85 | 4-((6-bromonaphthalen-2-yl)amino)-1H-1,2,3-triazole-5-carboxylic acid | A |
| 86 | 4-((4'-chloro-[1,1'-biphenyl]-4-yl)oxy)-1H-1,2,3-triazole-5-carboxylic acid | A |
| 87 | 4-((4'-(trifluoromethoxy)-[1,1'-biphenyl]-4-yl)oxy)-1H-1,2,3-triazole-5-carboxylic acid | A |
| 88 | 4-(3,4-dichlorophenoxy)-1H-1,2,3-triazole-5-carboxylic acid | A |
| 89 | 4-((6-bromonaphthalen-2-yl)oxy)-1H-1,2,3-triazole-5-carboxylic acid | A |
| 90 | 4-((1-(4-(trifluoromethoxy)phenyl)pyrrolidin-3-yl)oxy)-1H-1,2,3-triazole-5-carboxylic acid | A |
| 91 | 4-(3,5-dichlorophenoxy)-1H-1,2,3-triazole-5-carboxylic acid | A |
| 92 | 4-((4-chloronaphthalen-1-yl)oxy)-1H-1,2,3-triazole-5-carboxylic acid | A |
| 93 | methyl 4-((6-bromonaphthalen-2-yl)oxy)-1H-1,2,3-triazole-5-carboxylate | D |
| 94 | 4-(3,4-difluorophenoxy)-1H-1,2,3-triazole-5-carboxylic acid | A |
| 95 | 4-(2,4-dichlorophenoxy)-1H-1,2,3-triazole-5-carboxylic acid | A |
| 96 | 4-(4-(trifluoromethoxy)phenoxy)-1H-1,2,3-triazole-5-carboxylic acid | A |
| 97 | 4-((5,6,7,8-tetrahydronaphthalen-2-yl)oxy)-1H-1,2,3-triazole-5-carboxylic acid | A |
| 98 | methyl 4-(3,4-dichlorophenoxy)-1H-1,2,3-triazole-5-carboxylate | |
| 99 | 4-(benzo[d]thiazol-6-yloxy)-1H-1,2,3-triazole-5-carboxylic acid | A |
| 100 | 4-(2,5-dichlorophenoxy)-1H-1,2,3-triazole-5-carboxylic acid | A |
| 101 | 1-(acetoxymethyl)-4-((6-bromonaphthalen-2-yl)oxy)-1H-1,2,3-triazole-5-carboxylic acid | B |
| 102 | 4-(3,4-dichlorophenoxy)-1-((pivaloyloxy)methyl)-1H-1,2,3-triazole-5-carboxylic acid | B |
| 103 | 4-(3,4-dichlorophenoxy)-1-((isobutyryloxy)methyl)-1H-1,2,3-triazole-5-carboxylic acid | B |
| 104 | 1-(acetoxymethyl)-4-(3,4-dichlorophenoxy)-1H-1,2,3-triazole-5-carboxylic acid | B |
| 105 | acetoxymethyl 4-((6-bromonaphthalen-2-yl)oxy)-1H-1,2,3-triazole-5-carboxylate | C |
| 106 | 4-((6-chloronaphthalen-2-yl)oxy)-1H-1,2,3-triazole-5-carboxylic acid | A |
| 107 | (pivaloyloxy)methyl 4-(3,4-dichlorophenoxy)-1H-1,2,3-triazole-5-carboxylate | C |
| 108 | (isobutyryloxy)methyl 4-(3,4-dichlorophenoxy)-1H-1,2,3-triazole-5-carboxylate | B |
| 109 | acetoxymethyl 4-(3,4-dichlorophenoxy)-1H-1,2,3-triazole-5-carboxylate | A |
| 110 | cyclopropyl 4-((6-bromonaphthalen-2-yl)oxy)-1H-1,2,3-triazole-5-carboxylate | |
| 111 | 4-((6,7-dichloro-1,2,3,4-tetrahydronaphthalen-2-yl)oxy)-1H-1,2,3-triazole-5-carboxylic acid | A |
| 112 | cyclopropyl 4-(3,4-dichlorophenoxy)-1H-1,2,3-triazole-5-carboxylate | D |
| 113 | 4-(quinolin-7-yloxy)-1H-1,2,3-triazole-5-carboxylic acid | A |
| 114 | 4-(3-(trifluoromethoxy)phenoxy)-1H-1,2,3-triazole-5-carboxylic acid | A |
| 115 | 4-(quinolin-3-yloxy)-1H-1,2,3-triazole-5-carboxylic acid | B |
| 116 | cyclopropyl 4-((5,6,7,8-tetrahydronaphthalen-2-yl)oxy)-1H-1,2,3-triazole-5-carboxylate | D |
| 117 | 4-((1,2,3,4-tetrahydronaphthalen-2-yl)oxy)-1H-1,2,3-triazole-5-carboxylic acid | A |
| 118 | 4-(isoquinolin-7-yloxy)-1H-1,2,3-triazole-5-carboxylic acid | A |
| 119 | 4-((2-chloro-4'-(trifluoromethoxy)-[1,1'-biphenyl]-4-yl)oxy)-1H-1,2,3-triazole-5-carboxylic acid | A |

TABLE 1-continued

| Example | Name | Range |
|---|---|---|
| 120 | 4-(quinolin-6-yloxy)-1H-1,2,3-triazole-5-carboxylic acid | B |
| 121 | 4-(isoquinolin-6-yloxy)-1H-1,2,3-triazole-5-carboxylic acid | B |
| 122 | 5-(4-(quinolin-6-yl)phenoxy)-1H-1,2,3-triazole-4-carboxylic acid | A |
| 123 | 4-((2-isopropyl-1,2,3,4-tetrahydroisoquinolin-6-yl)oxy)-1H-1,2,3-triazole-5-carboxylic acid | |
| 124 | 4-(2-(3,4-dichlorophenyl)thiazol-4-yl)-1H-1,2,3-triazole-5-carboxylic acid | A |
| 125 | 4-(3,4-dichlorophenyl)-1H-1,2,3-triazole-5-carboxylic acid | A |
| 126 | 4-(4'-chloro-[1,1'-biphenyl]-4-yl)-1H-1,2,3-triazole-5-carboxylic acid | A |
| 127 | 4-(4-(4-chlorophenoxy)phenyl)-1H-1,2,3-triazole-5-carboxylic acid | A |
| 128 | 4-(4'-(trifluoromethoxy)-[1,1'-biphenyl]-4-yl)-1H-1,2,3-triazole-5-carboxylic acid | B |
| 129 | 4-(3',4'-dichloro-[1,1'-biphenyl]-3-yl)-1H-1,2,3-triazole-5-carboxylic acid | A |
| 130 | 4-(2,4'-dichloro-[1,1'-biphenyl]-4-yl)-1H-1,2,3-triazole-5-carboxylic acid | A |
| 131 | 4-(3-(3,4-dichlorophenoxy)phenyl)-1H-1,2,3-triazole-5-carboxylic acid | A |
| 132 | 4-(6-chloroquinolin-2-yl)-1H-1,2,3-triazole-5-carboxylic acid | A |
| 133 | 4-(6-chloronaphthalen-2-yl)-1H-1,2,3-triazole-5-carboxylic acid | A |
| 134 | 4-(7-chloroisoquinolin-1-yl)-1H-1,2,3-triazole-5-carboxylic acid | D |
| 135 | 4-(3-(trifluoromethoxy)phenyl)-1H-1,2,3-triazole-5-carboxylic acid | A |
| 136 | 4-(4-(trifluoromethoxy)phenyl)-1H-1,2,3-triazole-5-carboxylic acid | B |
| 137 | 4-(4-(cyclopentylmethoxy)phenyl)-1H-1,2,3-triazole-5-carboxylic acid | B |
| 138 | 4-(4-(cyclopentyloxy)phenyl)-1H-1,2,3-triazole-5-carboxylic acid | B |
| 139 | 4-(2-chloro-4'-(trifluoromethoxy)-[1,1'-biphenyl]-4-yl)-1H-1,2,3-triazole-5-carboxylic acid | B |
| 140 | 4-(3,4-dihydronaphthalen-2-yl)-1H-1,2,3-triazole-5-carboxylic acid | A |
| 141 | 4-(1,2,3,4-tetrahydronaphthalen-2-yl)-1H-1,2,3-triazole-5-carboxylic acid | B |
| 142 | 4-(1-isopropyl-1,2,3,4-tetrahydroquinolin-7-yl)-1H-1,2,3-triazole-5-carboxylic acid | |
| 143 | 4-(2-isopropyl-1,2,3,4-tetrahydroisoquinolin-6-yl)-1H-1,2,3-triazole-5-carboxylic acid | D |
| 144 | 4-(2-isopropyl-1,2,3,4-tetrahydroisoquinolin-7-yl)-1H-1,2,3-triazole-5-carboxylic acid | D |
| 145 | 4-(5-(trifluoromethoxy)pyridin-2-yl)-1H-1,2,3-triazole-5-carboxylic acid | C |
| 146 | 4-(3-(4-chlorophenyl)pyrrolidine-1-carbonyl)-1H-1,2,3-triazole-5-carboxylic acid | C |
| 147 | 4-(5-chloroisoindoline-2-carbonyl)-1H-1,2,3-triazole-5-carboxylic acid | C |
| 148 | 4-(5-chloroindoline-1-carbonyl)-1H-1,2,3-triazole-5-carboxylic acid | A |
| 149 | 4-(3-(2,4-dichlorophenyl)pyrrolidine-1-carbonyl)-1H-1,2,3-triazole-5-carboxylic acid | C |
| 150 | 4-(3-(3,4-dichlorophenyl)pyrrolidine-1-carbonyl)-1H-1,2,3-triazole-5-carboxylic acid | C |
| 151 | 4-((5-chloroisoindolin-2-yl)methyl)-1H-1,2,3-triazole-5-carboxylic acid | |
| 152 | 4-(((4-chloronaphthalen-1-yl)methyl)thio)-1H-1,2,3-triazole-5-carboxylic acid | A |
| 153 | 4-((3,5-dichlorophenyl)amino)-1H-1,2,3-triazole-5-carboxylic acid | B |
| 154 | 4-((2,5-dichlorophenyl)amino)-1H-1,2,3-triazole-5-carboxylic acid | C |
| 155 | 4-((3'-chloro-4'-(trifluoromethoxy)-[1,1'-biphenyl]-4-yl)amino)-1H-1,2,3-triazole-5-carboxylic acid | A |
| 156 | 4-((3'-chloro-4'-(trifluoromethoxy)-[1,1'-biphenyl]-4-yl)oxy)-1H-1,2,3-triazole-5-carboxylic acid | A |
| 157 | 4-((3'-(piperidine-1-carbonyl)-[1,1'-biphenyl]-4-yl)oxy)-1H-1,2,3-triazole-5-carboxylic acid | A |
| 158 | 4-(((6-chloronaphthalen-2-yl)oxy)methyl)-1H-1,2,3-triazole-5-carboxylic acid | A |
| 159 | 4-((4-chloronaphthalen-1-yl)methoxy)-1H-1,2,3-triazole-5-carboxylic acid | |
| 160 | 4-((3'-(piperidin-1-ylmethyl)-[1,1'-biphenyl]-4-yl)oxy)-1H-1,2,3-triazole-5-carboxylic acid | B |

TABLE 1-continued

| Example | Name | Range |
|---|---|---|
| 161 | 4-((4'-(trifluoromethyl)-[1,1'-biphenyl]-4-yl)oxy)-1H-1,2,3-triazole-5-carboxylic acid | A |
| 162 | 4-((3'-(cyclopentyloxy)-[1,1'-biphenyl]-4-yl)oxy)-1H-1,2,3-triazole-5-carboxylic acid | A |
| 163 | 4-((4'-chloro-3'-(trifluoromethoxy)-[1,1'-biphenyl]-4-yl)oxy)-1H-1,2,3-triazole-5-carboxylic acid | A |
| 164 | 4-((3'-(piperidin-1-yl)-[1,1'-biphenyl]-4-yl)thio)-1H-1,2,3-triazole-5-carboxylic acid | A |
| 165 | 4-((3',4'-dichloro-[1,1'-biphenyl]-4-yl)oxy)-1H-1,2,3-triazole-5-carboxylic acid | A |
| 166 | 4-((3,4-dichlorophenyl)difluoromethyl)-1H-1,2,3-triazole-5-carboxylic acid | A |
| 167 | 4-((4,4-difluorocyclohexyl)oxy)-1H-1,2,3-triazole-5-carboxylic acid | A |
| 168 | 4-(bicyclo[2.2.1]heptan-2-yloxy)-1H-1,2,3-triazole-5-carboxylic acid | A |

TABLE 2

| Example | Name | Range |
|---|---|---|
| 169 | 4-((4'-(piperidin-1-yl)-[1,1'-biphenyl]-4-yl)thio)-1H-1,2,3-triazole-5-carboxylic acid 2,2,2,-trifluoroacetate | A |
| 170 | 4-((3'-(cyclopropylmethoxy)-[1,1'-biphenyl]-4-yl)thio)-1H-1,2,3-triazole-5-carboxylic acid 2,2,2,-trifluoroacetate | A |
| 171 | 4-(((6-chloronaphthalen-2-yl)thio)methyl)-1H-1,2,3-triazole-5-carboxylic acid 2,2,2,-trifluoroacetate | A |
| 172 | 4-((6,7-difluoro-1,2,3,4-tetrahydronaphthalen-2-yl)thio)-1H-1,2,3-triazole-5-carboxylic acid | A |
| 173 | 4-((5,6-difluoro-2,3-dihydro-1H-inden-2-yl)thio)-1H-1,2,3-triazole-5-carboxylic acid | A |
| 174 | 4-(((6-chloronaphthalen-2-yl)methyl)thio)-1H-1,2,3-triazole-5-carboxylic acid 2,2,2-trifluoroacetate | A |
| 175 | 4-((4-(1-methyl-1,2,3,4-tetrahydroquinolin-6-yl)phenyl)thio)-1H-1,2,3-triazole-5-carboxylic acid 2,2,2-trifluoroacetate | A |
| 176 | 4-((3,4-dichlorobenzyl)thio)-1H-1,2,3-triazole-5-carboxylic acid | A |
| 177 | 4-(((4'-(trifluoromethoxy)-[1,1'-biphenyl]-4-yl)methyl)thio)-1H-1,2,3-triazole-5-carboxylic acid | A |
| 178 | 4-(((6-chloronaphthalen-2-yl)amino)methyl)-1H-1,2,3-triazole-5-carboxylic acid 2,2,2-trifluoroacetate | A |
| 179 | 4-(((3,4-dichlorophenyl)(methyl)amino)methyl)-1H-1,2,3-triazole-5-carboxylic acid 2,2,2-trifluoroacetate | A |
| 180 | 4-(((6-chloronaphthalen-2-yl)(methyl)amino)methyl)-1H-1,2,3-triazole-5-carboxylic acid 2,2,2-trifluoroacetate | A |
| 181 | 4-((2,4'-dichloro-[1,1'-biphenyl]-4-yl)amino)-1H-1,2,3-triazole-5-carboxylic acid | A |
| 182 | 4-(((6-chloronaphthalen-2-yl)methyl)amino)-1H-1,2,3-triazole-5-carboxylic acid | B |
| 183 | 4-((4'-(trifluoromethyl)-[1,1'-biphenyl]-4-yl)amino)-1H-1,2,3-triazole-5-carboxylic acid | A |
| 184 | 4-((4-(4-chlorophenyl)piperidin-1-yl)methyl)-1H-1,2,3-triazole-5-carboxylic acid | |
| 185 | 4-(((3,4-dichlorophenyl)(ethyl)amino)methyl)-1H-1,2,3-triazole-5-carboxylic acid | B |
| 186 | 4-((7-chloroquinolin-3-yl)amino)-1H-1,2,3-triazole-5-carboxylic acid | C |
| 187 | 4-(((6-chloronaphthalen-2-yl)(ethyl)amino)methyl)-1H-1,2,3-triazole-5-carboxylic acid | B |
| 188 | 4-((6-chloro-3,4-dihydroquinolin-1(2H)-yl)methyl)-1H-1,2,3-triazole-5-carboxylic acid | C |
| 189 | 4-((ethyl(4'-(trifluoromethoxy)-[1,1'-biphenyl]-4-yl)amino)methyl)-1H-1,2,3-triazole-5-carboxylic acid | B |
| 190 | 4-((5,6-dichloro-2,3-dihydro-1H-inden-2-yl)amino)-1H-1,2,3-triazole-5-carboxylic acid | B |
| 191 | 4-((6-chloro-3,4-dihydroisoquinolin-2(1H)-yl)methyl)-1H-1,2,3-triazole-5-carboxylic acid | |
| 192 | 4-((4-(4-chlorophenyl)piperazin-1-yl)methyl)-1H-1,2,3-triazole-5-carboxylic acid | |
| 193 | 4-((benzyl(1-(4-chlorophenyl)piperidin-4-yl)amino)methyl)-1H-1,2,3-triazole-5-carboxylic acid 2,2,2-trifluoroacetate | |
| 194 | 4-((benzyl(4-cyclohexylphenyl)amino)methyl)-1H-1,2,3-triazole-5-carboxylic acid | C |

TABLE 2-continued

| Example | Name | Range |
|---|---|---|
| 195 | 4-(((4-chlorophenyl)(4-(trifluoromethoxy)benzyl)amino)methyl)-1H-1,2,3-triazole-5-carboxylic acid | B |
| 196 | 4-((benzyl(4'-(trifluoromethoxy)-[1,1'-biphenyl]-4-yl)amino)methyl)-1H-1,2,3-triazole-5-carboxylic acid 2,2,2-trifluoroacetate | B |
| 197 | 4-((2,4'-dichloro-[1,1'-biphenyl]-4-yl)difluoromethyl)-1H-1,2,3-triazole-5-carboxylic acid 2,2,2-trifluoroacetate | A |
| 198 | 4-(difluoro(4'-(trifluoromethoxy)-[1,1'-biphenyl]-4-yl)methyl)-1H-1,2,3-triazole-5-carboxylic acid 2,2,2-trifluoroacetate | A |
| 199 | 4-((6-chloronaphthalen-2-yl)difluoromethyl)-1H-1,2,3-triazole-5-carboxylic acid | A |
| 200 | 4-((4'-chloro-[1,1'-biphenyl]-4-yl)difluoromethyl)-1H-1,2,3-triazole-5-carboxylic acid 2,2,2-trifluoroacetate | A |
| 201 | 4-((3',4'-dichloro-[1,1'-biphenyl]-4-yl)difluoromethyl)-1H-1,2,3-triazole-5-carboxylic acid 2,2,2-trifluoroacetate | A |
| 203 | 4-(4'-chloro-2-(trifluoromethoxy)-[1,1'-biphenyl]-4-yl)-1H-1,2,3-triazole-5-carboxylic acid | A |
| 204 | (isobutyryloxy)methyl 4-(6-chloroquinolin-2-yl)-1H-1,2,3-triazole-5-carboxylate | C |
| 206 | 4-(1-isopropyl-1,2,3,4-tetrahydroquinolin-6-yl)-1H-1,2,3-triazole-5-carboxylic acid 2,2,2-trifluoroacetate | C |
| 207 | 4-(4,5-dichloropyridin-2-yl)-1H-1,2,3-triazole-5-carboxylic acid | B |
| 208 | 4-(5-chloropyridin-2-yl)-1H-1,2,3-triazole-5-carboxylic acid 2,2,2-trifluoroacetate | B |
| 209 | 4-(4-(2-acetamidoethoxy)phenyl)-1H-1,2,3-triazole-5-carboxylic acid | C |
| 210 | 4-(7-fluoroisoquinolin-3-yl)-1H-1,2,3-triazole-5-carboxylic acid 2,2,2-trifluoroacetate | B |
| 211 | 4-(6-(trifluoromethoxy)isoquinolin-3-yl)-1H-1,2,3-triazole-5-carboxylic acid | C |
| 212 | 4-(5,6,7,8-tetrahydroquinolin-2-yl)-1H-1,2,3-triazole-5-carboxylic acid | C |
| 213 | 4-(6-fluoroisoquinolin-3-yl)-1H-1,2,3-triazole-5-carboxylic acid | C |
| 214 | 4-(7-(trifluoromethoxy)isoquinolin-3-yl)-1H-1,2,3-triazole-5-carboxylic acid | B |
| 215 | 4-(7-(trifluoromethyl)isoquinolin-3-yl)-1H-1,2,3-triazole-5-carboxylic acid | B |
| 216 | 4-(7-chloroquinolin-3-yl)-1H-1,2,3-triazole-5-carboxylic acid 2,2,2-trifluoroacetate | A |
| 217 | 4-(3-chloro-5-(cyclopropylmethoxy)phenyl)-1H-1,2,3-triazole-5-carboxylic acid 2,2,2-trifluoroacetate | A |
| 218 | 4-(4-chloro-3-(cyclopropylmethoxy)phenyl)-1H-1,2,3-triazole-5-carboxylic acid | B |
| 219 | 4-(2-chloro-5-(cyclopropylmethoxy)phenyl)-1H-1,2,3-triazole-5-carboxylic acid | C |
| 220 | 4-((3'-(piperidin-1-yl)-[1,1'-biphenyl]-4-yl)oxy)-1H-1,2,3-triazole-5-carboxylic acid 2,2,2-trifluoroacetate | A |
| 221 | 4-((4'-(piperidin-1-yl)-[1,1'-biphenyl]-4-yl)oxy)-1H-1,2,3-triazole-5-carboxylic acid 2,2,2-trifluoroacetate | A |
| 222 | 4-(4-(1-methyl-1,2,3,4-tetrahydroquinolin-6-yl)phenoxy)-1H-1,2,3-triazole-5-carboxylic acid | A |
| 223 | 4-(4-(5,6,7,8-tetrahydronaphthalen-1-yl)phenoxy)-1H-1,2,3-triazole-5-carboxylic acid 2,2,2-trifluoroacetate | A |
| 224 | 4-((3'-((2-oxopiperidin-1-yl)methyl)-[1,1'-biphenyl]-4-yl)oxy)-1H-1,2,3-triazole-5-carboxylic acid | A |
| 225 | 4-((4'-cyano-[1,1'-biphenyl]-4-yl)oxy)-1H-1,2,3-triazole-5-carboxylic acid | A |
| 226 | 4-((2-isopropyl-1,2,3,4-tetrahydroisoquinolin-7-yl)oxy)-1H-1,2,3-triazole-5-carboxylic acid 2,2,2-trifluoroacetate | C |
| 227 | 4-((6-chloronaphthalen-2-yl)methoxy)-1H-1,2,3-triazole-5-carboxylic acid 2,2,2-trifluoroacetate | A |
| 228 | 4-((3'-cyclohexyl-[1,1'-biphenyl]-4-yl)oxy)-1H-1,2,3-triazole-5-carboxylic acid | A |
| 229 | 1-(((cyclohexanecarbonyl)oxy)methyl)-4-(3,4-dichlorophenoxy)-1H-1,2,3-triazole-5-carboxylic acid | B |
| 230 | 4-((3'-(2-methoxyethoxy)-[1,1'-biphenyl]-4-yl)oxy)-1H-1,2,3-triazole-5-carboxylic acid | A |
| 231 | 4-((2,3-dihydrobenzo[b][1,4]dioxin-6-yl)oxy)-1H-1,2,3-triazole-5-carboxylic acid 2,2,2-trifluoroacetate | A |
| 232 | 4-((3'-(cyclopropylmethoxy)-[1,1'-biphenyl]-4-yl)oxy)-1H-1,2,3-triazole-5-carboxylic acid | A |
| 233 | 4-((3'-(4-acetylpiperazin-1-yl)-[1,1'-biphenyl]-4-yl)oxy)-1H-1,2,3-triazole-5-carboxylic acid 2,2,2-trifluoroacetate | A |

TABLE 2-continued

| Example | Name | Range |
|---|---|---|
| 234 | 4-((4'-(2-methoxyethoxy)-[1,1'-biphenyl]-4-yl)oxy)-1H-1,2,3-triazole-5-carboxylic acid | A |
| 235 | acetoxymethyl 4-((6-chloronaphthalen-2-yl)oxy)-1H-1,2,3-triazole-5-carboxylate | A |
| 236 | 4-((6-(difluoromethoxy)naphthalen-2-yl)oxy)-1H-1,2,3-triazole-5-carboxylic acid | A |
| 237 | 4-((6,7-difluoro-1,2,3,4-tetrahydronaphthalen-2-yl)oxy)-1H-1,2,3-triazole-5-carboxylic acid | A |
| 238 | 4-((3'-(tetrahydro-2H-pyran-4-yl)-[1,1'-biphenyl]-4-yl)oxy)-1H-1,2,3-triazole-5-carboxylic acid 2,2,2-trifluoroacetate | A |
| 239 | (isobutyryloxy)methyl 4-((6-chloronaphthalen-2-yl)oxy)-1H-1,2,3-triazole-5-carboxylate | B |
| 240 | 1-(((1-(tert-butoxycarbonyl)piperidine-2-carbonyl)oxy)methyl)-4-(3,4-dichlorophenoxy)-1H-1,2,3-triazole-5-carboxylic acid | C |
| 241 | 4-((5,6-dichloro-2,3-dihydro-1H-inden-2-yl)oxy)-1H-1,2,3-triazole-5-carboxylic acid 2,2,2-trifluoroacetate | A |
| 242 | 4-((4'-(tetrahydro-2H-pyran-4-yl)-[1,1'-biphenyl]-4-yl)oxy)-1H-1,2,3-triazole-5-carboxylic acid | A |
| 243 | 4-(((3,4-dichlorophenyl)thio)methyl)-1H-1,2,3-triazole-5-carboxylic acid | A |
| 244 | (isobutyryloxy)methyl 4-((4'-(piperidin-1-yl)-[1,1'-biphenyl]-4-yl)thio)-1H-1,2,3-triazole-5-carboxylate | C |
| 245 | 4-((1-isopropyl-1,2,3,4-tetrahydroquinolin-7-yl)oxy)-1H-1,2,3-triazole-5-carboxylic acid 2,2,2-trifluoroacetate | C |
| 246 | 4-((3'-(4-methylpiperazin-1-yl)-[1,1'-biphenyl]-4-yl)oxy)-1H-1,2,3-triazole-5-carboxylic acid 2,2,2-trifluoroacetate | B |
| 247 | 4-((3'-cyclohexyl-[1,1'-biphenyl]-4-yl)thio)-1H-1,2,3-triazole-5-carboxylic acid | A |
| 249 | (benzoyloxy)methyl 4-((6-chloronaphthalen-2-yl)oxy)-1H-1,2,3-triazole-5-carboxylate | C |
| 250 | 4-(4-(quinolin-7-yl)phenoxy)-1H-1,2,3-triazole-5-carboxylic acid 2,2,2-trifluoroacetate | A |
| 251 | (pivaloyloxy)methyl 4-((6-chloronaphthalen-2-yl)oxy)-1H-1,2,3-triazole-5-carboxylate | C |
| 252 | (isobutyryloxy)methyl 4-((5,6,7,8-tetrahydronaphthalen-2-yl)oxy)-1H-1,2,3-triazole-5-carboxylate | B |
| 253 | 4-(3-cyclopropoxyphenoxy)-1H-1,2,3-triazole-5-carboxylic acid 2,2,2-trifluoroacetate | A |
| 254 | 4-(4-chloro-3-(trifluoromethoxy)phenoxy)-1H-1,2,3-triazole-5-carboxylic acid | A |
| 255 | 4-((4'-(2-acetamidoethoxy)-[1,1'-biphenyl]-4-yl)oxy)-1H-1,2,3-triazole-5-carboxylic acid | A |
| 256 | (isobutyryloxy)methyl 4-((6,7-dichloro-1,2,3,4-tetrahydronaphthalen-2-yl)oxy)-1H-1,2,3-triazole-5-carboxylate | B |
| 257 | 4-(4-(isoquinolin-6-yl)phenoxy)-1H-1,2,3-triazole-5-carboxylic acid | A |
| 258 | (pivaloyloxy)methyl 4-((6,7-dichloro-1,2,3,4-tetrahydronaphthalen-2-yl)oxy)-1H-1,2,3-triazole-5-carboxylate | C |
| 259 | 4-((3'-(2-acetamidoethoxy)-[1,1'-biphenyl]-4-yl)oxy)-1H-1,2,3-triazole-5-carboxylic acid | A |
| 260 | 4-((1-(isoquinolin-6-yl)piperidin-4-yl)oxy)-1H-1,2,3-triazole-5-carboxylic acid 2,2,2-trifluoroacetate | B |
| 261 | (benzoyloxy)methyl 4-((6,7-dichloro-1,2,3,4-tetrahydronaphthalen-2-yl)oxy)-1H-1,2,3-triazole-5-carboxylate | C |
| 262 | 4-(3-(cyclopropylmethoxy)phenoxy)-1H-1,2,3-triazole-5-carboxylic acid 2,2,2-trifluoroacetate | A |
| 263 | 4-(4-(tetrahydro-2H-pyran-4-yl)phenoxy)-1H-1,2,3-triazole-5-carboxylic acid 2,2,2-trifluoroacetate | A |
| 264 | 4-((3,4-dichlorophenoxy)methyl)-1H-1,2,3-triazole-5-carboxylic acid 2,2,2-trifluoroacetate | A |
| 265 | 4-(((4'-(trifluoromethoxy)-[1,1'-biphenyl]-4-yl)oxy)methyl)-1H-1,2,3-triazole-5-carboxylic acid | A |
| 266 | 4-(((3',4'-dichloro-[1,1'-biphenyl]-4-yl)oxy)methyl)-1H-1,2,3-triazole-5-carboxylic acid 2,2,2-trifluoroacetate | A |
| 267 | (propionyloxy)methyl 4-((6,7-dichloro-1,2,3,4-tetrahydronaphthalen-2-yl)oxy)-1H-1,2,3-triazole-5-carboxylate | A |
| 268 | 4-(4-(3,3-difluorocyclobutyl)phenoxy)-1H-1,2,3-triazole-5-carboxylic acid | A |
| 269 | 4-((3,4-dichlorobenzyl)oxy)-1H-1,2,3-triazole-5-carboxylic acid | A |
| 270 | 4-((1-(4-chlorophenyl)piperidin-4-yl)oxy)-1H-1,2,3-triazole-5-carboxylic acid 2,2,2-trifluoroacetate | A |

TABLE 2-continued

| Example | Name | Range |
|---|---|---|
| 271 | 4-((5,6-difluoro-2,3-dihydro-1H-inden-2-yl)oxy)-1H-1,2,3-triazole-5-carboxylic acid | A |
| 272-1 | 4-(((trans)4-(4-(trifluoromethoxy)phenyl)cyclohexyl)oxy)-1H-1,2,3-triazole-5-carboxylic acid | A |
| 272-2 | 4-(((cis)-4-(4-(trifluoromethoxy)phenyl)cyclohexyl)oxy)-1H-1,2,3-triazole-5-carboxylic acid | A |
| 273 | 4-(4-cyclohexylphenoxy)-1H-1,2,3-triazole-5-carboxylic acid | A |
| 274 | 4-((4'-(trifluoromethoxy)-[1,1'-biphenyl]-4-yl)methoxy)-1H-1,2,3-triazole-5-carboxylic acid | A |
| 275 | 4-((3-(4-(trifluoromethoxy)phenyl)cyclopentyl)oxy)-1H-1,2,3-triazole-5-carboxylic acid | A |
| 277 | 4-((6,7-dichloro-1,2,3,4-tetrahydronaphthalen-2-yl)thio)-1H-1,2,3-triazole-5-carboxylic acid | A |
| 278 | (benzoyloxy)methyl 4-((4'-(piperidin-1-yl)-[1,1'-biphenyl]-4-yl)thio)-1H-1,2,3-triazole-5-carboxylate | C |
| 279 | 4-(4-(4,4-difluorocyclohexyl)phenoxy)-1H-1,2,3-triazole-5-carboxylic acid | A |
| 280 | 4-(spiro[2.5]octan-6-yloxy)-1H-1,2,3-triazole-5-carboxylic acid 2,2,2-trifluoroacetate | A |
| 281 | 4-((5,5-dimethyl-5,6,7,8-tetrahydronaphthalen-2-yl)oxy)-1H-1,2,3-triazole-5-carboxylic acid | B |
| 282 | 4-((5-(trifluoromethoxy)-2,3-dihydro-1H-inden-2-yl)oxy)-1H-1,2,3-triazole-5-carboxylic acid | A |
| 283 | 4-(spiro[5.5]undecan-3-yloxy)-1H-1,2,3-triazole-5-carboxylic acid | A |
| 284 | 4-(spiro[4.5]decan-8-yloxy)-1H-1,2,3-triazole-5-carboxylic acid | A |
| 285 | 4-((1-(3,5-dichlorophenyl)piperidin-4-yl)oxy)-1H-1,2,3-triazole-5-carboxylic acid 2,2,2-trifluoroacetate | A |
| 286 | 4-((1-(3,4-dichlorophenyl)piperidin-4-yl)oxy)-1H-1,2,3-triazole-5-carboxylic acid 2,2,2-trifluoroacetate | A |
| 287 | 4-((1-(4-(trifluoromethyl)phenyl)piperidin-4-yl)oxy)-1H-1,2,3-triazole-5-carboxylic acid 2,2,2-trifluoroacetate | A |
| 288 | 4-(3-(cyclopropylmethoxy)-5-(trifluoromethyl)phenoxy)-1H-1,2,3-triazole-5-carboxylic acid | B |
| 289 | 4-(3-chloro-5-(cyclopropylmethoxy)phenoxy)-1H-1,2,3-triazole-5-carboxylic acid 2,2,2-trifluoroacetate | A |
| 290 | 4-(3-(cyclopentylmethoxy)phenoxy)-1H-1,2,3-triazole-5-carboxylic acid 2,2,2-trifluoroacetate | A |
| 291 | 4-((1-(2,5-dichlorophenyl)piperidin-4-yl)oxy)-1H-1,2,3-triazole-5-carboxylic acid 2,2,2-trifluoroacetate | A |
| 292 | 4-(4-chloro-3-(cyclopropylmethoxy)phenoxy)-1H-1,2,3-triazole-5-carboxylic acid | A |
| 293 | 4-(2-chloro-5-(cyclopropylmethoxy)phenoxy)-1H-1,2,3-triazole-5-carboxylic acid | A |
| 295 | 4-(3-(cyclopropylmethoxy)-4-(trifluoromethyl)phenoxy)-1H-1,2,3-triazole-5-carboxylic acid | A |
| 297 | 4-((4'-(4,4-difluoropiperidin-1-yl)-[1,1'-biphenyl]-4-yl)oxy)-1H-1,2,3-triazole-5-carboxylic acid 2,2,2-trifluoroacetate | A |
| 298 | 4-((4-(4-(trifluoromethoxy)phenyl)cyclohexyl)methoxy)-1H-1,2,3-triazole-5-carboxylic acid | A |
| 299 | 4-(((3',5'-dichloro-[1,1'-biphenyl]-4-yl)oxy)methyl)-1H-1,2,3-triazole-5-carboxylic acid | A |
| 300 | 4-(((3'-chloro-4'-(trifluoromethoxy)-[1,1'-biphenyl]-4-yl)oxy)methyl)-1H-1,2,3-triazole-5-carboxylic acid | A |
| 301 | 4-(4-(4,4-difluoropiperidin-1-yl)phenoxy)-1H-1,2,3-triazole-5-carboxylic acid | B |
| 302 | ((isopropoxycarbonyl)oxy)methyl 4-(((trans)-4-(4-(trifluoromethoxy)phenyl)cyclohexyl)oxy)-1H-1,2,3-triazole-5-carboxylate | |
| 303 | ((cyclohexanecarbonyl)oxy)methyl 4-(((trans)-4-(4-(trifluoromethoxy)phenyl)cyclohexyl)oxy)-1H-1,2,3-triazole-5-carboxylate | D |
| 304 | 4-(((1s,4s)-4-(3,5-dichlorophenyl)cyclohexyl)oxy)-1H-1,2,3-triazole-5-carboxylic acid | A |
| 305 | (benzoyloxy)methyl 4-(((trans)-4-(4-(trifluoromethoxy)phenyl)cyclohexyl)oxy)-1H-1,2,3-triazole-5-carboxylate | D |
| 306 | 4-(4-(4-(piperidin-1-yl)cyclohexyl)phenoxy)-1H-1,2,3-triazole-5-carboxylic acid | B |
| 307 | (isobutyryloxy)methyl 4-(((trans)-4-(4-(trifluoromethoxy)phenyl)cyclohexyl)oxy)-1H-1,2,3-triazole-5-carboxylate | C |
| 308-1 | 4-(((cis)-4-(3,4-dichlorophenyl)cyclohexyl)oxy)-1H-1,2,3-triazole-5-carboxylic acid | A |

TABLE 2-continued

| Example | Name | Range |
|---|---|---|
| 308-2 | 4-(((trans)-4-(3,4-dichlorophenyl)cyclohexyl)oxy)-1H-1,2,3-triazole-5-carboxylic acid | A |
| 309 | 4-(4-chloro-3-(cyclohexylmethoxy)phenoxy)-1H-1,2,3-triazole-5-carboxylic acid | A |
| 310 | 4-(((cis)-4-(4-(trifluoromethyl)phenyl)cyclohexyl)oxy)-1H-1,2,3-triazole-5-carboxylic acid | A |
| 311 | 4-(spiro[4.5]decan-8-ylthio)-1H-1,2,3-triazole-5-carboxylic acid 2,2,2-trifluoroacetate | A |
| 312 | 4-(((4'-(trifluoromethoxy)-[1,1'-biphenyl]-4-yl)thio)methyl)-1H-1,2,3-triazole-5-carboxylic acid 2,2,2-trifluoroacetate | A |
| 313 | (propionyloxy)methyl 4-((4'-(piperidin-1-yl)-[1,1'-biphenyl]-4-yl)thio)-1H-1,2,3-triazole-5-carboxylate | C |
| 314 | 4-((3-(4-(trifluoromethoxy)phenyl)cyclopentyl)thio)-1H-1,2,3-triazole-5-carboxylic acid | A |
| 315 | 4-(spiro[5.5]undecan-3-ylthio)-1H-1,2,3-triazole-5-carboxylic acid 2,2,2-trifluoroacetate | A |
| 316 | 4-(((4-(piperidin-1-yl)naphthalen-1-yl)methyl)thio)-1H-1,2,3-triazole-5-carboxylic acid 2,2,2-trifluoroacetate | A |
| 317 | ((cyclohexanecarbonyl)oxy)methyl 4-((4'-(piperidin-1-yl)-[1,1'-biphenyl]-4-yl)thio)-1H-1,2,3-triazole-5-carboxylate 2,2,2-trifluoroacetate | D |
| 318 | 4-((4-chloro-3-(trifluoromethoxy)phenyl)thio)-1H-1,2,3-triazole-5-carboxylic acid | A |
| 319 | 4-((4'-(4,4-difluoropiperidin-1-yl)-[1,1'-biphenyl]-4-yl)thio)-1H-1,2,3-triazole-5-carboxylic acid 2,2,2-trifluoroacetate | A |
| 320 | 4-((5-(trifluoromethoxy)-2,3-dihydro-1H-inden-2-yl)thio)-1H-1,2,3-triazole-5-carboxylic acid | A |
| 321 | 4-((4-(5-(trifluoromethoxy)pyridin-2-yl)phenyl)thio)-1H-1,2,3-triazole-5-carboxylic acid 2,2,2-trifluoroacetate | A |
| 322 | 4-(((3',4'-dichloro-[1,1'-biphenyl]-4-yl)thio)methyl)-1H-1,2,3-triazole-5-carboxylic acid 2,2,2-trifluoroacetate | A |
| 323 | 4-((1-(3,4-dichlorophenyl)piperidin-4-yl)thio)-1H-1,2,3-triazole-5-carboxylic acid 2,2,2-trifluoroacetate | A |
| 324 | 4-((1-(4-(trifluoromethyl)phenyl)piperidin-4-yl)thio)-1H-1,2,3-triazole-5-carboxylic acid | A |
| 325 | 4-((1-(3,5-dichlorophenyl)piperidin-4-yl)thio)-1H-1,2,3-triazole-5-carboxylic acid | A |
| 326 | 4-((4-(3-(trifluoromethoxy)phenyl)cyclohexyl)thio)-1H-1,2,3-triazole-5-carboxylic acid | A |
| 327 | 4-((4-(3-(trifluoromethyl)phenyl)cyclohexyl)thio)-1H-1,2,3-triazole-5-carboxylic acid | A |
| 328 | 4-(((3',5'-dichloro-[1,1'-biphenyl]-4-yl)thio)methyl)-1H-1,2,3-triazole-5-carboxylic acid | A |
| 329 | 4-(((3'-chloro-4'-(trifluoromethoxy)-[1,1'-biphenyl]-4-yl)thio)methyl)-1H-1,2,3-triazole-5-carboxylic acid | A |
| 330 | 4-((1-(2,5-dichlorophenyl)piperidin-4-yl)thio)-1H-1,2,3-triazole-5-carboxylic acid | A |
| 331 | 4-(((cis)-4-(3,5-dichlorophenyl)cyclohexyl)thio)-1H-1,2,3-triazole-5-carboxylic acid | A |
| 332 | 4-(((cis)-4-(4-(trifluoromethyl)phenyl)cyclohexyl)thio)-1H-1,2,3-triazole-5-carboxylic acid | A |
| 333 | 4-(((methyl(4'-(trifluoromethoxy)-[1,1'-biphenyl]-4-yl)amino)methyl)-1H-1,2,3-triazole-5-carboxylic acid 2,2,2-trifluoroacetate | A |
| 334 | 4-(3-(cyclopropylmethoxy)-5-(trifluoromethyl)phenyl)-1H-1,2,3-triazole-5-carboxylic acid | A |
| 335 | 4-((4-chloro-3-(cyclohexylmethoxy)phenyl)sulfinyl)-1H-1,2,3-triazole-5-carboxylic acid | C |
| 336 | 4-((4-chloro-3-(cyclohexylmethoxy)phenyl)thio)-1H-1,2,3-triazole-5-carboxylic acid | A |
| 337 | 4-(((cis)-4-(3-chloro-5-(trifluoromethoxy)phenyl)cyclohexyl)thio)-1H-1,2,3-triazole-5-carboxylic acid | A |
| 338 | 4-((1-(3-chloro-5-(trifluoromethoxy)phenyl)piperidin-4-yl)thio)-1H-1,2,3-triazole-5-carboxylic acid | A |
| 339 | 4-((4-(4,4-difluoropiperidin-1-yl)phenyl)thio)-1H-1,2,3-triazole-5-carboxylic acid 2,2,2-trifluoroacetate | A |
| 340 | 4-((4-(3-(piperidin-1-yl)phenyl)cyclohexyl)thio)-1H-1,2,3-triazole-5-carboxylic acid 2,2,2-trifluoroacetate | A |
| 341 | 4-(((cis)4-(4-(4-methylpiperazin-1-yl)phenyl)cyclohexyl)thio)-1H-1,2,3-triazole-5-carboxylic acid | A |
| 342 | 4-((2-chloro-4'-(piperidin-1-yl)-[1,1'-biphenyl]-4-yl)thio)-1H-1,2,3-triazole-5-carboxylic acid | A |
| 343 | 4-((2-chloro-5-(cyclopentylmethoxy)phenyl)thio)-1H-1,2,3-triazole-5-carboxylic acid | A |

TABLE 2-continued

| Example | Name | Range |
|---|---|---|
| 344 | 4-((1-(4-cyanophenyl)piperidin-4-yl)thio)-1H-1,2,3-triazole-5-carboxylic acid 2,2,2-trifluoroacetate | A |
| 345 | 4-(((cis)-4-(3,4-dichlorophenyl)cyclohexyl)thio)-1H-1,2,3-triazole-5-carboxylic acid 2,2,2-trifluoroacetate | A |
| 346 | 4-((1-(3-chloro-4-(trifluoromethoxy)phenyl)piperidin-4-yl)thio)-1H-1,2,3-triazole-5-carboxylic acid | A |
| 347 | 4-(((cis)-4-(4-(pyrrolidin-1-yl)phenyl)cyclohexyl)thio)-1H-1,2,3-triazole-5-carboxylic acid 2,2,2-trifluoroacetate | A |
| 348 | 4-(((cis)-4-(4-(trifluoromethoxy)phenyl)cyclohexyl)thio)-1H-1,2,3-triazole-5-carboxylic acid | A |
| 349 | 4-((4'-(2-methylpiperidin-1-yl)-[1,1'-biphenyl]-4-yl)thio)-1H-1,2,3-triazole-5-carboxylic acid 2,2,2-trifluoroacetate | A |
| 350 | 4-(((1-(3,5-dichlorophenyl)piperidin-4-yl)thio)methyl)-1H-1,2,3-triazole-5-carboxylic acid 2,2,2-trifluoroacetate | A |
| 351 | 4-((3-(cyclopentyloxy)phenyl)thio)-1H-1,2,3-triazole-5-carboxylic acid 2,2,2-trifluoroacetate | B |
| 352 | 4-(((cis)-4-(4-cyanophenyl)cyclohexyl)thio)-1H-1,2,3-triazole-5-carboxylic acid | A |
| 353 | 4-(4-chloro-3-(cyclopentylmethoxy)phenoxy)-1H-1,2,3-triazole-5-carboxylic acid 2,2,2-trifluoroacetate | A |
| 354 | 4-((1-(3-chloro-5-(trifluoromethoxy)phenyl)piperidin-4-yl)oxy)-1H-1,2,3-triazole-5-carboxylic acid | A |
| 355 | 4-(((cis)-4-(3-chloro-5-(trifluoromethoxy)phenyl)cyclohexyl)oxy)-1H-1,2,3-triazole-5-carboxylic acid | A |
| 356 | 4-(((cis)-4-(4-(pyrrolidin-1-yl)phenyl)cyclohexyl)oxy)-1H-1,2,3-triazole-5-carboxylic acid 2,2,2-trifluoroacetate | A |
| 357 | 4-(2-chloro-5-(cyclopentylmethoxy)phenoxy)-1H-1,2,3-triazole-5-carboxylic acid | A |
| 358 | 4-(3-chloro-5-(trifluoromethoxy)phenoxy)-1H-1,2,3-triazole-5-carboxylic acid | A |
| 359 | 4-((1-(4-cyanophenyl)piperidin-4-yl)oxy)-1H-1,2,3-triazole-5-carboxylic acid 2,2,2-trifluoroacetate | A |
| 360 | 4-(((cis)-4-(3-chloro-4-(trifluoromethoxy)phenyl)cyclohexyl)oxy)-1H-1,2,3-triazole-5-carboxylic acid | A |
| 361 | 4-((1-(3-chloro-4-(trifluoromethoxy)phenyl)piperidin-4-yl)oxy)-1H-1,2,3-triazole-5-carboxylic acid | A |
| 362 | 4-(4-chloro-3-((4-fluorobenzyl)oxy)phenoxy)-1H-1,2,3-triazole-5-carboxylic acid | A |
| 363 | 4-(((cis)-4-(4-carbamoylphenyl)cyclohexyl)oxy)-1H-1,2,3-triazole-5-carboxylic acid 2,2,2-trifluoroacetate | A |
| 364 | 4-(((trans)-4-(4-carbamoylphenyl)cyclohexyl)oxy)-1H-1,2,3-triazole-5-carboxylic acid 2,2,2-trifluoroacetate | A |
| 365 | 4-(((cis)-4-(4-cyanophenyl)cyclohexyl)oxy)-1H-1,2,3-triazole-5-carboxylic acid | A |
| 367 | 4-((1-(5-chloro-2-(trifluoromethyl)phenyl)piperidin-4-yl)oxy)-1H-1,2,3-triazole-5-carboxylic acid 2,2,2-trifluoroacetate | A |
| 368 | 4-(((cis)-4-(4-(4,4-difluoropiperidin-1-yl)phenyl)cyclohexyl)oxy)-1H-1,2,3-triazole-5-carboxylic acid 2,2,2-trifluoroacetate | A |
| 369 | 4-((3-(3,4-dichlorophenyl)-3-azabicyclo[3.1.0]hexan-6-yl)methoxy)-1H-1,2,3-triazole-5-carboxylic acid | A |
| 370 | ((diethylcarbamoyl)oxy)methyl 4-(((trans)-4-(4-(trifluoromethoxy)phenyl)cyclohexyl)oxy)-1H-1,2,3-triazole-5-carboxylate | D |
| 371 | 2-(isobutyryloxy)ethyl 4-(((trans)-4-(4-(trifluoromethoxy)phenyl)cyclohexyl)oxy)-1H-1,2,3-triazole-5-carboxylate | |
| 373 | 4-(((3-(3,4-dichlorophenyl)-3-azabicyclo[3.1.0]hexan-6-yl)methyl)thio)-1H-1,2,3-triazole-5-carboxylic acid | A |
| 375 | 4-(3-(cyclopentyloxy)phenoxy)-1H-1,2,3-triazole-5-carboxylic acid | A |

TABLE 3

| Example | Name | Range |
|---|---|---|
| 294 | 4-((1,3-bis(4-chlorophenyl)propan-2-yl)oxy)-1H-1,2,3-triazole-5-carboxylic acid | A |
| 296 | 4-(1,3-diphenylpropoxy)-1H-1,2,3-triazole-5-carboxylic acid | D |
| 366 | 4-((1,3-bis(4'-(trifluoromethoxy)-[1,1'-biphenyl]-4-yl)propan-2-yl)oxy)-1H-1,2,3-triazole-5-carboxylic acid | B |

TABLE 3-continued

| Example | Name | Range |
|---|---|---|
| 372 | 4-(2-(bis(4-chlorobenzyl)amino)ethyl)-1H-1,2,3-triazole-5-carboxylic acid 2,2,2-trifluoroacetate | B |
| 374 | 4-(2-((4-chlorobenzyl)((4'-(trifluoromethoxy)-[1,1'-biphenyl]-4-yl)methyl)amino)ethyl)-1H-1,2,3-triazole-5-carboxylic acid 2,2,2-trifluoroacetate | B |

TABLE 4

| Example | Name | Range |
|---|---|---|
| 376 | 4-((3'-chloro-4'-(piperidin-1-yl)-[1,1'-biphenyl]-4-yl)thio)-1H-1,2,3-triazole-5-carboxylic acid | A |
| 377 | 4-((((cis)-4-(3,5-dichlorophenyl)cyclohexyl)thio)methyl)-1H-1,2,3-triazole-5-carboxylic acid | A |
| 378 | 4-(2-(4-chlorophenyl)-2-hydroxy-1-phenyl ethoxy)-1H-1,2,3-triazole-5-carboxylic acid | B |
| 379 | 4-(((cis)-4-(4-(2-oxopiperidin-1-yl)phenyl)cyclohexyl)oxy)-1H-1,2,3-triazole-5-carboxylic acid | A |
| 380 | 4-(3-(cyclohexyloxy)phenoxy)-1H-1,2,3-triazole-5-carboxylic acid | A |
| 381 | 4-(4-chloro-3-(cyclopentyloxy)phenoxy)-1H-1,2,3-triazole-5-carboxylic acid | A |
| 382 | 4-((3-(cyclohexyloxy)phenyl)thio)-1H-1,2,3-triazole-5-carboxylic acid | B |
| 383 | 4-(((1-(2,5-dichlorophenyl)piperidin-4-yl)thio)methyl)-1H-1,2,3-triazole-5-carboxylic acid | A |
| 384 | 4-(((1-(3,4-dichlorophenyl)piperidin-4-yl)thio)methyl)-1H-1,2,3-triazole-5-carboxylic acid | A |
| 386 | 4-((1-(5-chloro-2-(trifluoromethoxy)phenyl)piperidin-4-yl)thio)-1H-1,2,3-triazole-5-carboxylic acid | A |
| 387 | 4-((4'-chloro-2-(cyclopentylmethoxy)-[1,1'-biphenyl]-4-yl)oxy)-1H-1,2,3-triazole-5-carboxylic acid | A |
| 388 | 4-(4-(1-cyclohexylpiperidin-4-yl)phenoxy)-1H-1,2,3-triazole-5-carboxylic acid | C |
| 389 | 4-((4'-cyano-[1,1'-biphenyl]-4-yl)thio)-1H-1,2,3-triazole-5-carboxylic acid | A |
| 390 | 4-(4-cyano-3-((4-fluorobenzyl)oxy)phenoxy)-1H-1,2,3-triazole-5-carboxylic acid | A |
| 391 | 1-((cyclohexanecarbonyl)oxy)ethyl 4-(((trans)-4-(4-(trifluoromethoxy)phenyl)cyclohexyl)oxy)-1H-1,2,3-triazole-5-carboxylate | B |
| 392 | 1-((cyclohexanecarbonyl)oxy)propyl 4-(((trans)-4-(4-(trifluoromethoxy)phenyl)cyclohexyl)oxy)-1H-1,2,3-triazole-5-carboxylate | B |
| 393 | 4-(((trans)-4-(5-chloro-2-(trifluoromethoxy)phenyl)cyclohexyl)oxy)-1H-1,2,3-triazole-5-carboxylic acid | A |
| 394 | 4-((2-chloro-4'-cyano-[1,1'-biphenyl]-4-yl)oxy)-1H-1,2,3-triazole-5-carboxylic acid | A |
| 395 | 4-(((trans)-4-(2-chloro-5-(trifluoromethoxy)phenyl)cyclohexyl)oxy)-1H-1,2,3-triazole-5-carboxylic acid | A |
| 397 | 4-((4'-carbamoyl-[1,1'-biphenyl]-4-yl)oxy)-1H-1,2,3-triazole-5-carboxylic acid | A |
| 398 | 4-((4'-chloro-2-(cyclopentylmethoxy)-[1,1'-biphenyl]-4-yl)thio)-1H-1,2,3-triazole-5-carboxylic acid | A |
| 399 | 4-(4-chloro-3-(cyclohexyloxy)phenoxy)-1H-1,2,3-triazole-5-carboxylic acid | A |
| 400 | 4-(4-fluoro-3-((4-(trifluoromethoxy)benzyl)oxy)phenoxy)-1H-1,2,3-triazole-5-carboxylic acid | A |
| 401 | 4-((4'-(methylsulfonyl)-[1,1'-biphenyl]-4-yl)oxy)-1H-1,2,3-triazole-5-carboxylic acid | A |
| 402 | 4-((1-(2-chloro-5-(trifluoromethoxy)phenyl)piperidin-4-yl)thio)-1H-1,2,3-triazole-5-carboxylic acid | A |
| 403 | 4-(((trans)-4-(4-(4H-1,2,4-triazol-4-yl)phenyl)cyclohexyl)oxy)-1H-1,2,3-triazole-5-carboxylic acid | A |
| 404 | 4-((trans-3-(4-cyanophenyl)cyclobutoxy)-1H-1,2,3-triazole-5-carboxylic acid 2,2,2-trifluoroacetate | A |
| 405 | 4-(((trans)-4-(4-(1H-1,2,4-triazol-1-yl)phenyl)cyclohexyl)oxy)-1H-1,2,3-triazole-5-carboxylic acid | A |
| 406 | 4-((2-chloro-4'-(piperidin-1-yl)-[1,1'-biphenyl]-4-yl)oxy)-1H-1,2,3-triazole-5-carboxylic acid | A |
| 407 | 4-((2'-chloro-4'-(piperidin-1-yl)-[1,1'-biphenyl]-4-yl)oxy)-1H-1,2,3-triazole-5-carboxylic acid | A |

TABLE 4-continued

| Example | Name | Range |
|---|---|---|
| 408 | 4-(4-chloro-3-((4-(trifluoromethoxy)benzyl)oxy)phenoxy)-1H-1,2,3-triazole-5-carboxylic acid | A |
| 409 | 4-(((trans)-4-(quinolin-6-yl)cyclohexyl)oxy)-1H-1,2,3-triazole-5-carboxylic acid 2,2,2-trifluoroacetate | A |
| 396 | 4-(((cis)-4-(2-chloro-5-(trifluoromethoxy)phenyl)cyclohexyl)oxy)-1H-1,2,3-triazole-5-carboxylic acid | A |
| 410 | 4-(((trans)-4-(quinolin-6-yl)cyclohexyl)thio)-1H-1,2,3-triazole-5-carboxylic acid 2,2,2-trifluoroacetate | A |
| 411 | 4-(((trans)-4-(2-chloro-5-(trifluoromethoxy)phenyl)cyclohexyl)thio)-1H-1,2,3-triazole-5-carboxylic acid | A |
| 412 | 4-(((trans)-4-(4-(2-oxopyrrolidin-1-yl)phenyl)cyclohexyl)oxy)-1H-1,2,3-triazole-5-carboxylic acid | A |
| 413 | 4-((4'-sulfamoyl-[1,1'-biphenyl]-4-yl)oxy)-1H-1,2,3-triazole-5-carboxylic acid | A |
| 414 | 4-(((trans)-4-(4-(dimethylcarbamoyl)phenyl)cyclohexyl)oxy)-1H-1,2,3-triazole-5-carboxylic acid 2,2,2-trifluoroacetate | A |
| 415 | 4-(4-chloro-3-((4-(trifluoromethyl)benzyl)oxy)phenoxy)-1H-1,2,3-triazole-5-carboxylic acid | A |
| 416 | 4-(((trans)-4-(4-(morpholine-4-carbonyl)phenyl)cyclohexyl)oxy)-1H-1,2,3-triazole-5-carboxylic acid 2,2,2-trifluoroacetate | A |
| 417 | 4-(((trans)-4-(4-(piperidine-1-carbonyl)phenyl)cyclohexyl)oxy)-1H-1,2,3-triazole-5-carboxylic acid 2,2,2-trifluoroacetate | A |
| 418 | 4-(((trans)-4-(4-(1H-pyrazol-1-yl)phenyl)cyclohexyl)oxy)-1H-1,2,3-triazole-5-carboxylic acid | A |
| 419 | 4-(((trans)-4-(3-chloro-4-(trifluoromethoxy)phenyl)cyclohexyl)oxy)-1H-1,2,3-triazole-5-carboxylic acid | A |
| 420 | 4-(((trans)-3-(4-cyanophenyl)cyclobutyl)thio)-1H-1,2,3-triazole-5-carboxylic acid 2,2,2-trifluoroacetate | A |
| 421 | 4-(4-cyano-3-((4-(trifluoromethoxy)benzyl)oxy)phenoxy)-1H-1,2,3-triazole-5-carboxylic acid | A |
| 422 | 4-(((trans)-4-(4-(trifluoromethoxy)phenyl)cyclohexyl)thio)-1H-1,2,3-triazole-5-carboxylic acid | A |
| 423 | 4-(4-chloro-3-((4-cyanobenzyl)oxy)phenoxy)-1H-1,2,3-triazole-5-carboxylic acid | A |
| 424 | 4-(((trans)-4-(2,4-difluorophenyl)cyclohexyl)oxy)-1H-1,2,3-triazole-5-carboxylic acid 2,2,2-trifluoroacetate | A |
| 425 | 4-(((trans)-4-(4-(4H-1,2,4-triazol-3-yl)phenyl)cyclohexyl)oxy)-1H-1,2,3-triazole-5-carboxylic acid | A |
| 426 | 4-((trans)-3-(4-(piperidin-1-yl)phenyl)cyclobutoxy)-1H-1,2,3-triazole-5-carboxylic acid 2,2,2-trifluoroacetate | A |
| 427 | 4-(((3aR,5s,6aS)-2-(3,4-dichlorophenyl)octahydrocyclopenta[c]pyrrol-5-yl)oxy)-1H-1,2,3-triazole-5-carboxylic acid | A |
| 428 | 4-(((3aR,5s,6aS)-2-(3,4-dichlorophenyl)octahydrocyclopenta[c]pyrrol-5-yl)thio)-1H-1,2,3-triazole-5-carboxylic acid | A |
| 429 | 4-((1-(2-chloro-5-(trifluoromethoxy)phenyl)piperidin-4-yl)oxy)-1H-1,2,3-triazole-5-carboxylic acid | A |
| 430 | 4-(((trans)-4-(5-chloro-2-(trifluoromethoxy)phenyl)cyclohexyl)thio)-1H-1,2,3-triazole-5-carboxylic acid | A |
| 431 | 4-(((trans)-4-(4-(1,3,4-thiadiazol-2-yl)phenyl)cyclohexyl)oxy)-1H-1,2,3-triazole-5-carboxylic acid 2,2,2-trifluoroacetate | A |
| 432 | 4-(((trans)-4-(4-(piperidin-1-yl)phenyl)cyclohexyl)thio)-1H-1,2,3-triazole-5-carboxylic acid 2,2,2-trifluoroacetate | A |
| 433 | 4-(((trans)-4-(4-(1,3,4-oxadiazol-2-yl)phenyl)cyclohexyl)oxy)-1H-1,2,3-triazole-5-carboxylic acid | A |
| 434 | 4-(((trans)-3-(4-(piperidin-1-yl)phenyl)cyclobutyl)thio)-1H-1,2,3-triazole-5-carboxylic acid 2,2,2-trifluoroacetate | A |
| 435 | 4-((spiro[4.5]decan-8-ylthio)methyl)-1H-1,2,3-triazole-5-carboxylic acid | A |
| 436 | 4-(((trans)-4-(4-(piperidin-1-yl)phenyl)cyclohexyl)oxy)-1H-1,2,3-triazole-5-carboxylic acid 2,2,2-trifluoroacetate | A |
| 437 | 4-((4-cyano-4-(4-(trifluoromethoxy)phenyl)cyclohexyl)oxy)-1H-1,2,3-triazole-5-carboxylic acid | A |
| 438 | 4-(((trans)-4-(4-(methylsulfonyl)phenyl)cyclohexyl)oxy)-1H-1,2,3-triazole-5-carboxylic acid | A |
| 440 | 4-(3-methoxy-3-(4-(trifluoromethoxy)phenyl)cyclobutoxy)-1H-1,2,3-triazole-5-carboxylic acid | B |
| 439 | 4-(((trans)-4-(4-(methylsulfonyl)phenyl)cyclohexyl)thio)-1H-1,2,3-triazole-5-carboxylic acid 2,2,2-trifluoroacetate | A |

TABLE 4-continued

| Example | Name | Range |
|---|---|---|
| 441 | 4-(((trans)-4-(3-chloro-4-(piperidin-1-yl)phenyl)cyclohexyl)oxy)-1H-1,2,3-triazole-5-carboxylic acid 2,2,2-trifluoroacetate | A |
| 442-1 | 4-(((cis)-4-(3-chloro-4-(piperidin-1-yl)phenyl)cyclohexyl)thio)-1H-1,2,3-triazole-5-carboxylic acid 2,2,2-trifluoroacetate | A |
| 442-2 | 4-(((trans)-4-(3-chloro-4-(piperidin-1-yl)phenyl)cyclohexyl)thio)-1H-1,2,3-triazole-5-carboxylic acid 2,2,2-trifluoroacetate | A |
| 443 | 4-(((1r,4r)-4-methyl-4-(4-(trifluoromethoxy)phenyl)cyclohexyl)oxy)-1H-1,2,3-triazole-5-carboxylic acid | A |
| 444 | 4-(((1s,4s)-4-methyl-4-(4-(trifluoromethoxy)phenyl)cyclohexyl)oxy)-1H-1,2,3-triazole-5-carboxylic acid | A |
| 445 | 4-(4-chloro-3-cyclopropoxyphenoxy)-1H-1,2,3-triazole-5-carboxylic acid | A |
| 446 | 4-(((trans)-4-(4-cyclopropoxyphenyl)cyclohexyl)oxy)-1H-1,2,3-triazole-5-carboxylic acid | A |
| 447 | 4-(((trans)-4-(4-fluorophenyl)cyclohexyl)oxy)-1H-1,2,3-triazole-5-carboxylic acid | A |
| 448 | 4-(4-chloro-3-cyclobutoxyphenoxy)-1H-1,2,3-triazole-5-carboxylic acid | A |
| 449 | 4-(3-(4-(trifluoromethoxy)phenyl)cyclobutoxy)-1H-1,2,3-triazole-5-carboxylic acid | A |
| 450 | 4-((4'-(1H-pyrazol-1-yl)-[1,1'-biphenyl]-4-yl)oxy)-1H-1,2,3-triazole-5-carboxylic acid 2,2,2-trifluoroacetate | A |
| 451 | 4-(((trans)-4-(4-(trifluoromethoxy)phenyl)cyclohexyl)amino)-1H-1,2,3-triazole-5-carboxylic acid | A |
| 452 | 4-(((cis)-4-(4-(trifluoromethoxy)phenyl)cyclohexyl)amino)-1H-1,2,3-triazole-5-carboxylic acid | A |
| 453 | 4-((4-hydroxy-4-(4-(trifluoromethoxy)phenyl)cyclohexyl)oxy)-1H-1,2,3-triazole-5-carboxylic acid | B |
| 454 | 4-((4'-(trifluoromethoxy)-2,3,4,5-tetrahydro-[1,1'-biphenyl]-4-yl)oxy)-1H-1,2,3-triazole-5-carboxylic acid | A |
| 455 | 4-(((cis-3a,6a)-5-(4-(trifluoromethoxy)phenyl)octahydropentalen-2-yl)oxy)-1H-1,2,3-triazole-5-carboxylic acid | A |
| 456 | 4-((((trans)-4-(4-(trifluoromethoxy)phenyl)cyclohexyl)oxy)methyl)-1H-1,2,3-triazole-5-carboxylic acid | B |
| 457 | 4-(((trans)-4-(4-sulfamoylphenyl)cyclohexyl)oxy)-1H-1,2,3-triazole-5-carboxylic acid | A |
| 458 | 4-(((trans)-4-(4-(1-(2-ethyl-2-hydroxypentyl)-1H-pyrazol-3-yl)phenyl)cyclohexyl)oxy)-1H-1,2,3-triazole-5-carboxylic acid | A |
| 459 | 4-(((trans)-4-(4-(1H-pyrazol-1-yl)phenyl)cyclohexyl)thio)-1H-1,2,3-triazole-5-carboxylic acid 2,2,2-trifluoroacetate | A |
| 460 | 4-(((trans)-4-(4-(cyclohexylmethoxy)phenyl)cyclohexyl)oxy)-1H-1,2,3-triazole-5-carboxylic acid | A |
| 461 | 4-(((cis-3a,6a)-5-(4-(trifluoromethoxy)phenyl)octahydropentalen-2-yl)thio)-1H-1,2,3-triazole-5-carboxylic acid | A |
| 462 | 4-(((trans)-4-(4-(2-cyclohexylethoxy)phenyl)cyclohexyl)oxy)-1H-1,2,3-triazole-5-carboxylic acid | A |
| 463 | 4-(((trans)-4-(4-(3-hydroxypropoxy)phenyl)cyclohexyl)oxy)-1H-1,2,3-triazole-5-carboxylic acid | A |
| 464 | 4-(((trans)-4-(4-(3-isopropyl-1H-pyrazol-5-yl)phenyl)cyclohexyl)oxy)-1H-1,2,3-triazole-5-carboxylic acid 2,2,2-trifluoroacetate | A |
| 465 | 5-(methyl((1s,4s)-4-(4-(trifluoromethoxy)phenyl)cyclohexyl)amino)-1H-1,2,3-triazole-4-carboxylic acid | B |
| 466 | 4-(((trans)-4-(3-(hydroxymethyl)-4-(1H-pyrazol-5-yl)phenyl)cyclohexyl)oxy)-1H-1,2,3-triazole-5-carboxylic acid | A |
| 467 | 4-(((cis)-4-(3-(hydroxymethyl)-4-(1H-pyrazol-5-yl)phenyl)cyclohexyl)oxy)-1H-1,2,3-triazole-5-carboxylic acid 2,2,2-trifluoroacetate | A |
| 468 | 4-(((trans)-4-(4-(4-methylpiperazin-1-yl)phenyl)cyclohexyl)oxy)-1H-1,2,3-triazole-5-carboxylic acid 2,2,2-trifluoroacetate | A |
| 469 | 4-(((trans)-4-(4-(1-(2-hydroxy-2-methylpropyl)-1H-pyrazol-3-yl)phenyl)cyclohexyl)oxy)-1H-1,2,3-triazole-5-carboxylic acid 2,2,2-trifluoroacetate | A |
| 470 | 4-(((trans)-4-(4-(1-(2-ethyl-2-hydroxypentyl)-1H-pyrazol-5-yl)phenyl)cyclohexyl)oxy)-1H-1,2,3-triazole-5-carboxylic acid | A |

TABLE 4-continued

| Example | Name | Range |
|---|---|---|
| 471 | 4-(((trans)-4-(4-(1-((1-hydroxycyclohexyl)methyl)-1H-pyrazol-5-yl)phenyl)cyclohexyl)oxy)-1H-1,2,3-triazole-5-carboxylic acid 2,2,2-trifluoroacetate | A |
| 472 | 4-(((trans)-4-(4-(3-aminopropoxy)phenyl)cyclohexyl)oxy)-1H-1,2,3-triazole-5-carboxylic acid 2,2,2-trifluoroacetate | A |
| 473 | 4-(((trans1r,4r)-4-(4-(3-(pentan-3-yl)-1H-pyrazol-5-yl)phenyl)cyclohexyl)oxy)-1H-1,2,3-triazole-5-carboxylic acid | A |
| 474 | 4-(((trans)-4-(4-(3-(methylamino)propoxy)phenyl)cyclohexyl)oxy)-1H-1,2,3-triazole-5-carboxylic acid 2,2,2-trifluoroacetate | A |
| 475 | 4-(((trans)-4-(4-(3-(2-methoxybutyl)-1H-pyrazol-5-yl)phenyl)cyclohexyl)oxy)-1H-1,2,3-triazole-5-carboxylic acid | A |
| 476 | 4-(((trans)-4-(4-(1-((trans)-2-hydroxycyclohexyl)-1H-pyrazol-5-yl)phenyl)cyclohexyl)oxy)-1H-1,2,3-triazole-5-carboxylic acid | A |
| 477 | 4-(((1-(3,5-dichlorophenyl)piperidin-4-yl)oxy)methyl)-1H-1,2,3-triazole-5-carboxylic acid | A |
| 478 | 4-(((trans)-4-(4-(3-(dimethylamino)propoxy)phenyl)cyclohexyl)oxy)-1H-1,2,3-triazole-5-carboxylic acid 2,2,2-trifluoroacetate | A |
| 479 | 4-(((trans)-4-(4-(1-(2-ethyl-2-hydroxybutyl)-1H-pyrazol-5-yl)phenyl)cyclohexyl)oxy)-1H-1,2,3-triazole-5-carboxylic acid | A |
| 480 | 4-(((trans)-4-(4-(1-(2-hydroxy-2-methylpropyl)-1H-pyrazol-5-yl)phenyl)cyclohexyl)oxy)-1H-1,2,3-triazole-5-carboxylic acid | A |
| 481 | 4-(((1-(2,5-dichlorophenyl)piperidin-4-yl)oxy)methyl)-1H-1,2,3-triazole-5-carboxylic acid | B |
| 482 | 4-(((trans)-4-(4-chloro-3-cyclobutylphenyl)cyclohexyl)oxy)-1H-1,2,3-triazole-5-carboxylic acid | A |
| 483 | 4-(((trans)-4-(4-(((trans)-3-(hydroxymethyl)cyclohexyl)methoxy)phenyl)cyclohexyl)oxy)-1H-1,2,3-triazole-5-carboxylic acid | A |
| 484 | 4-(((trans)-4-(3-cyclobutyl-4-(trifluoromethoxy)phenyl)cyclohexyl)oxy)-1H-1,2,3-triazole-5-carboxvlic acid | A |
| 485 | 4-(((trans)-4-(4-(3-(2-methoxyethyl)-1H-pyrazol-5-yl)phenyl)cyclohexyl)oxy)-1H-1,2,3-triazole-5-carboxylic acid 2,2,2-trifluoroacetate | A |
| 486 | 4-((((trans)-4-(3,5-dichlorophenyl)cyclohexyl)oxy)methyl)-1H-1,2,3-triazole-5-carboxylic acid | A |

TABLE 5

| Example | Name | Range |
|---|---|---|
| 378 | 4-(2-(4-chlorophenyl)-2-hydroxy-1-phenylethoxy)-1H-1,2,3-triazole-5-carboxylic acid | B |
| 385 | 4-((1-(4-chlorophenyl)-3-(4'-(trifluoromethoxy)-[1,1'-biphenyl]-4-yl)propan-2-yl)oxy)-1H-1,2,3-triazole-5-carboxylic acid | B |

TABLE 6

| Example | Name | Range |
|---|---|---|
| 111-1 | (R)-4-((6,7-dichloro-1,2,3,4-tetrahydronaphthalen-2-yl)oxy)-1H-1,2,3-triazole-5-carboxylic acid | A |
| 111-2 | (S)-4-((6,7-dichloro-1,2,3,4-tetrahydronaphthalen-2-yl)oxy)-1H-1,2,3-triazole-5-carboxylic acid | A |

Primary Hyperoxaluria Type I Mouse Model

PH1 male mice (agxt$^{-/-}$) are obtained from Dr. Salido (Salido et al., *Proc Natl Acad Sci USA.*, 103(48): 18249-18254) and are housed in the "Association for Assessment and Accreditation of Laboratory Animal Care" (AAALAC) in Bulk Institute, Novato, following standards and procedures approved by the local "Institutional Animal Care and Use Committee" for ethical use of animals in experiments. Mice are fed with normal chow and drinking water, and are oral dosed with GO inhibitors at specific time intervals. Mice are individually housed in a metabolic cage for a 5-7 day acclimation period before the first oral dosing and at the time of sample collection.

Urine and plasma samples are collected every 24 hours for biomarker analysis. Biomarkers include glycolate (LC-MS), oxalate (Oxalate kit, Trinity Biotech #591-D), creatinine (Creatinine Urinary Colorimetric Assay Kit, Cayman Chemical #500701), LDH (using LDH Activity Colorimetric Assay Kit, BioVision Inc. #K726), and $Ca^{+2}$.

Urine is collected every 24 hours using the metabolic cage. Urine is collected 3 days before the first oral dosing to establish baseline, and at the end of treatment. For the oxalate measurement, the urine sample is acidified by collection in a tube containing 50 μl of 6N HCl. Any urine samples with volumes less than 1 ml and/or urine samples that are contaminated with food and/or fecal matter are excluded from collection.

Plasma is collected using lithium-heparin as anticoagulant. Plasma is ultrafiltered at 1500×g for 30 min at 4° C. using a Centrisart-Iultrafiltration vial (Sartorius, Type: Vivaspin® 500 μl). Plasma is placed in the inner chamber of the vial and 204, of 2 molar HCl per ml plasma is added into the outer chamber to ensure simultaneous acidification of the ultrafiltrate. The acidified plasma is stored at −80° C. before being delivered on dry ice for oxalate and glycolate measurement.

Other objects, features and advantages of the compounds, methods and compositions described herein will become apparent from the following description. It should be understood, however, that the description and the specific examples, while indicating specific embodiments, are given by way of illustration only, since various changes and modifications within the spirit and scope of the present description will become apparent from this detailed description.

All publications including patents, patent applications and published patent applications cited herein are hereby incorporated by reference for all purposes.

Exemplary Embodiments

1. In one embodiment, disclosed herein is a compound of Formula (I):

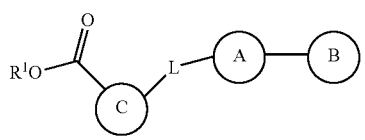

(I)

wherein:
ring C is selected from:

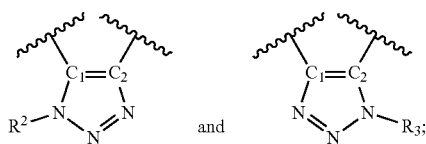

and wherein the wavy lines ($\sim$) indicate the points of attachment of the $C_1$ carbon to the carbonyl of C(O)—$OR^1$, and the $C_2$ carbon to L;
L is a bond, $CH_2$, $CF_2$, O, $NR^L$, S, S(=O), C(=O), $CH_2$-Q, or Q-$CH_2$; wherein Q is O, $NR^L$, or S;
$R^L$ is hydrogen, $C_{1-4}$ alkyl, $C_{3-6}$ cycloalkyl, phenyl, or benzyl; wherein the $C_{1-4}$ alkyl is optionally substituted with hydroxycarbonyl, alkoxycarbonyl, hydroxycarbonylalkyl, or alkylcarbonyloxy; and the phenyl group alone or as a part of the benzyl group is optionally substituted with one or two groups selected from halo and haloalkoxy;
Ring A is $C_{3-8}$ cycloalkyl, $C_{8-11}$ spirocycloalkyl, 5-8 membered heterocycloalkyl, pyrazolyl, imidazolyl, triazolyl, thiazolyl, thienyl, phenyl, naphthyl, indanyl, tetrahydronaphthyl, dihydronaphthyl, pyridyl, indolyl, benzothiazolyl, quinolinyl, isoquinolinyl, indolinyl, isoindolinyl, tetrahydroquinolinyl, dihydroisoquinolinyl, tetrahydroisoquinolinyl, 2,3-dihydrobenzo[b][1,4]dioxinyl, or tetrahydro-methanonaphthalenyl;
Ring B is present or not present; wherein:
when Ring B is present, then Ring A is optionally substituted with one or two groups independently selected from halo, alkyl, alkoxy, cyano, hydroxy, haloalkoxy, (cycloalkyl)alkoxy, and cycloalkyl;
when Ring B is not present and Ring A is phenyl, then Ring A is substituted with:
(i) one or two $R^{AA}$ groups;
(ii) 2 halo groups when L is other than O;
(iii) 2 halo groups when L is O, and $R^2$ and $R^3$ are not hydrogen or alkyl;
(iv) one halo group when L is $CH_2NR^L$;
(v) one halo group and one group selected from the group consisting of haloalkoxy, cycloalkyloxy, (cycloalkyl)alkoxy, and (phenyl)alkoxy, when L is bond, O, S, or S(=O), wherein the phenyl is optionally substituted with halo, cyano, haloalkyl, or haloalkoxy; or
(vi) one cyano group and one (phenyl)alkoxy group, when L is bond or O, wherein the phenyl as part of the (phenyl)alkoxy group is optionally substituted with halo or haloalkoxy;
when Ring B is not present and Ring A is other than phenyl, then
(i) Ring A is substituted with one or two R groups or
(ii) Ring A is unsubstituted, wherein:
1) when Ring A is unsubstituted tetrahydroquinolinyl, then L is a bond;
2) when Ring A is unsubstituted 2,3-dihydrobenzo[b][1,4]dioxinyl, then L is O;
3) when Ring A is unsubstituted tetrahydronaphthyl, then L is O, and $R^1$ is not hydrogen or ethyl; or
4) when Ring A is unsubstituted spirocycloalkyl, then L is O, S, or $CH_2S$;
each $R^{AA}$ is independently alkyl; haloalkyl; haloalkoxy; cycloalkyloxy; (cycloalkyl)alkoxy; phenoxy optionally substituted with one or two halo groups; or alkylcarbonylaminoalkoxy;
each $R^{AB}$ is independently halo; alkyl; hydroxy; alkoxy; haloalkyl; haloalkoxy; cycloalkyloxy; (cycloalkyl)alkoxy; or phenoxy optionally substituted with one or two halo groups;
Ring B, when present, is cycloalkyl, heterocycloalkyl, aryl, or heteroaryl; wherein each is optionally substituted with 1, 2, or 3 $R^B$ groups;
each $R^B$ is independently halo; cyano; alkyl; hydroxyalkyl; alkylsulfonyl; aminosulfonyl; alkylaminosulfonyl; dialkylaminosulfonyl; haloalkyl; alkoxy; aminoalkoxy; alkylaminoalkoxy; dialkylaminoalkoxy; hydroxyalkoxy; haloalkoxy; alkylcarbonyl; alkoxyalkoxy; aminocarbonyl; alkylaminocarbonyl; dialkylaminocarbonyl; alkylcarbonylaminoalkoxy; cycloalkyl; (cycloalkyl)alkyl; cycloalkyloxy; (cycloalkyl)alkoxy wherein the cycloalkyl group is optionally substituted with hydroxyalkyl; cycloalkylcarbonyl; cycloalkylcarbonyloxy; heterocycloalkyl optionally substituted with one or two groups independently selected from halo, alkyl, and alkylcarbonyl; (5-6-membered heterocycloalkyl-one)alkyl; 5-6-membered heterocycloalkyl-one; (heterocycloalkyl)alkyl; heterocycloalkylcarbonyl; or 5-6-membered heteroaryl optionally substituted with one group selected from alkyl, hydroxyalkyl, (hydroxycycloalkyl)alkyl, alkoxyalkyl, and hydroxycycloalkyl;

$R^1$ is hydrogen, alkyl, cycloalkyl, heterocycloalkyl, or W; wherein W is alkyl substituted with amino, alkylamino, dialkylamino, alkylcarbonyloxy, alkoxycarbonyl, phenylcarbonyloxy, aminocarbonyloxy, alkylaminocarbonyloxy, dialkylaminocarbonyloxy, alkoxycarbonyloxy, cycloalkylcarbonyloxy, —N($R^{1A}$)C(O)$R^{1B}$, —N($R^{1A}$)C(O)O$R^{1B}$, or —N($R^{1A}$)C(O)N$R^{1B}R^{1C}$; wherein $R^{1A}$, $R^{1B}$, and $R^{1C}$ are each independently hydrogen or $C_{1-6}$ alkyl;

$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;

provided:
  i. when L is S or $CH_2$, and Ring A is phenyl other than phenyl substituted with (cycloalkyl)alkoxy, then Ring B cannot be halo-substituted phenyl;
  ii. when L is O, Ring A is phenyl, and Ring B is not present, then $R^{AA}$ cannot be alkyl;
  iii. when L is O, Ring A is phenyl substituted with 1 $R^{AA}$, and Ring B is not present, then $R^{AA}$ cannot be meta-substituted trifluoromethyl;
  iv. when L is O, Ring A is phenyl, Ring B is not present, and $R^1$ is ethyl, then $R^{AA}$ cannot be trifluoromethoxy;
  v. when L is bond, Ring A is other than phenyl, Ring B is not present, and $R^1$ is H, then $R^{AB}$ cannot be methyl, and
  vi. when L is NH, Ring A is pyridyl, indolyl, or indolinyl, and Ring B is not present, then $R^{AB}$ cannot be alkyl; and optionally a single stereoisomer or mixture of stereoisomers thereof and additionally optionally a pharmaceutically acceptable salt thereof.

2. In certain embodiments, the compound, single stereoisomer or mixture of stereoisomers or pharmaceutically acceptable salt of the above embodiment is that wherein L is a bond, $CH_2$, $CF_2$, O, $NR^L$, S, C(=O), $CH_2$-Q, or Q-$CH_2$; wherein Q is O, $NR^L$, or S;

$R^L$ is hydrogen or $C_{1-4}$ alkyl optionally substituted with hydroxycarbonyl, alkoxycarbonyl, hydroxycarbonylalkyl, or alkylcarbonyloxy;

Ring A is $C_{5-7}$ cycloalkyl, 5-6 membered heterocycloalkyl, pyrazolyl, imidazolyl, triazolyl, thiazolyl, phenyl, naphthyl, indanyl, tetrahydronaphthalinyl, dihydronaphthalinyl, pyridyl, indolyl, benzothiazolyl, quinolinyl, isoquinolinyl, indolinyl, isoindolinyl, tetrahydroquinolinyl, dihydroisoquinolinyl, or tetrahydro-methanonaphthalenyl;

Ring B is present or not present; wherein:
when Ring B is present, then Ring A is optionally substituted with one or two halo, alkyl, alkoxy, or haloalkoxy;
when Ring B is not present and Ring A is phenyl, then Ring A is substituted with:
  (i) one or two $R^{AA}$ groups, or (ii) 2 halo groups when L is other than O;
when Ring B is not present and Ring A is other than phenyl, then Ring A is substituted with one or two $R^{AB}$ groups;
each $R^{AA}$ is independently alkyl, haloalkyl, haloalkoxy, cycloalkyloxy, (cycloalkyl)alkoxy, or phenoxy optionally substituted with one or two halo;

each $R^{AB}$ is independently halo, alkyl, hydroxy, alkoxy, haloalkyl, haloalkoxy, cycloalkyloxy, (cycloalkyl)alkoxy, or phenoxy optionally substituted with one or two halo;

Ring B, when present, is cycloalkyl, heterocycloalkyl, aryl, or heteroaryl; wherein each is optionally substituted with one or two $R^B$ groups;

each $R^B$ is independently halo, cyano, alkyl, haloalkyl, alkoxy, haloalkoxy, alkylcarbonyl, alkoxyalkoxy, alkylcarbonylaminoalkoxy, cycloalkyl, (cycloalkyl)alkyl, cycloalkyloxy, (cycloalkyl)alkoxy, cycloalkylcarbonyl, cycloalkylcarbonyloxy, heterocycloalkyl optionally substituted with alkyl or alkylcarbonyl, (5-6-membered heterocycloalkyl-one)alkyl, (heterocycloalkyl)alkyl, or heterocycloalkylcarbonyl;

$R^1$ is hydrogen, alkyl, cycloalkyl, heterocycloalkyl, or W; where W is alkyl substituted with amino, alkylamino, dialkylamino, alkylcarbonyloxy, alkoxycarbonyl, or phenylcarbonyloxy; and $R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;

3. In certain embodiments, the compound, single stereoisomer or mixture of stereoisomers or pharmaceutically acceptable salt of any one of the above embodiments is that wherein Ring B is present; wherein Ring B is cycloalkyl, heterocycloalkyl, aryl, or heteroaryl; wherein each is optionally substituted with one or two $R^B$ groups;

each $R^B$ is independently halo, cyano, alkyl, haloalkyl, alkoxy, haloalkoxy, alkylcarbonyl, alkoxyalkoxy, alkylcarbonylaminoalkoxy, cycloalkyl, (cycloalkyl)alkyl, cycloalkyloxy, (cycloalkyl)alkoxy, cycloalkylcarbonyl, cycloalkylcarbonyloxy, heterocycloalkyl optionally substituted with alkyl or alkylcarbonyl, (5-6-membered heterocycloalkyl-one)alkyl, (heterocycloalkyl)alkyl, or heterocycloalkylcarbonyl; provided that when L is S and Ring A is phenyl, then Ring B is not halo-substituted phenyl.

4. In certain embodiments, the compound, single stereoisomer or mixture of stereoisomers or pharmaceutically acceptable salt of any one of the above embodiments is that wherein Ring A is $C_{3-7}$ cycloalkyl, $C_{8-11}$ spirocycloalkyl, 5-8 membered heterocycloalkyl, pyrazolyl, imidazolyl, triazolyl, thiazolyl, thienyl, phenyl, naphthyl, indanyl, tetrahydronaphthyl, dihydronaphthyl, pyridyl, indolyl, benzothiazolyl, quinolinyl, isoquinolinyl, indolinyl, isoindolinyl, tetrahydroquinolinyl, dihydroisoquinolinyl, tetrahydroisoquinolinyl, 2,3-dihydrobenzo[b][1,4]dioxinyl, or tetrahydro-methanonaphthalenyl;

Ring B is present or not present; wherein:
when Ring B is present, then Ring A is optionally substituted with one or two groups selected from halo, alkyl, alkoxy, haloalkoxy, (cycloalkyl)alkoxy, and cycloalkyl;

when Ring B is not present and Ring A is other than phenyl, then
  (i) Ring A is substituted with one or two R groups or
  (ii) Ring A is unsubstituted, wherein:
    1) when Ring A is unsubstituted tetrahydroquinolinyl, then L is bond;
    2) when Ring A is unsubstituted 2,3-dihydrobenzo[b][1,4]dioxinyl, then L is O;
    3) when Ring A is unsubstituted tetrahydronaphthyl, then L is O, and $R^1$ is not hydrogen or ethyl; or 4) when Ring A is unsubstituted spirocycloalkyl, then L is O or S;

each $R^B$ is independently halo; cyano; alkyl; alkylsulfonyl; aminosulfonyl; alkylaminosulfonyl; dialkylaminosulfonyl; haloalkyl; alkoxy; haloalkoxy; alkylcarbonyl; alkoxyalkyl; aminocarbonyl; alkylaminocarbonyl; dialkylaminocarbonyl; alkylcarbonylaminoalkoxy; cycloalkyl; (cycloalkyl)alkyl; cycloalkyloxy; (cycloalkyl)alkoxy; cycloalkylcarbonyl; cycloalkylcarbonyloxy; heterocycloalkyl optionally substituted with one or two groups independently selected from halo, alkyl, and alkylcarbonyl; (5-6-membered heterocycloalkyl-one)alkyl; 5-6-membered heterocycloalkyl-one; (heterocycloalkyl)alkyl; heterocycloalkylcarbonyl; or 5-6 membered heteroaryl.

5. In certain embodiments, the compound, single stereoisomer or mixture of stereoisomers or pharmaceutically acceptable salt of any one of the above embodiments is that wherein Ring B is not present;

L is a bond, $CH_2$, $CF_2$, O, $NR^L$, S, C(=O), $CH_2$-Q, or Q-$CH_2$; wherein Q is O, $NR^L$, or S;

$R^L$ is hydrogen or $C_{1-4}$ alkyl optionally substituted with hydroxycarbonyl, alkoxycarbonyl, hydroxycarbonylalkyl, or alkylcarbonyloxy;

Ring A is $C_{5-7}$ cycloalkyl, 5-6 membered heterocycloalkyl, pyrazolyl, imidazolyl, triazolyl, thiazolyl, phenyl, naphthyl, indanyl, tetrahydronaphthalinyl, dihydronaphthalinyl, pyridyl, indolyl, benzothiazolyl, quinolinyl, isoquinolinyl, indolinyl, isoindolinyl, tetrahydroquinolinyl, dihydroisoquinolinyl, or tetrahydro-methanonaphthalenyl;

wherein:
when Ring A is phenyl, then Ring A is substituted with:
(i) one or two $R^{AA}$ groups, or (ii) 2 halo groups when L is other than O;

when Ring A is other than phenyl, then Ring A is substituted with one or two $R^{AB}$ groups;

each $R^{AA}$ is independently alkyl, haloalkyl, haloalkoxy, cycloalkyloxy, (cycloalkyl)alkoxy, or phenoxy optionally substituted with one or two halo;

each $R^{AB}$ is independently halo, alkyl, hydroxy, alkoxy, haloalkyl, haloalkoxy, cycloalkyloxy, (cycloalkyl)alkoxy, or phenoxy optionally substituted with one or two halo;

$R^1$ is hydrogen, alkyl, cycloalkyl, heterocycloalkyl, or W; where W is alkyl substituted with amino, alkylamino, dialkylamino, alkylcarbonyloxy, alkoxycarbonyl, or phenylcarbonyloxy; and $R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl.

6. In certain embodiments, the compound, single stereoisomer or mixture of stereoisomers or pharmaceutically acceptable salt of any one of the above embodiments is that wherein Ring A is phenyl, naphthyl, indanyl, tetrahydronaphthalinyl, dihydronaphthalinyl, pyridyl, benzothiazolyl, quinolinyl, isoquinolinyl, indolinyl, isoindolinyl, tetrahydroquinolinyl, or dihydroisoquinolinyl;

wherein:
when Ring A is phenyl, then Ring A is substituted with:
(i) one or two $R^{AA}$ groups, or (ii) 2 halo groups when L is other than O;

when Ring A is other than phenyl, then Ring A is substituted with one or two $R^{AB}$ groups;

each $R^{AA}$ is independently haloalkoxy, cycloalkyloxy, or phenoxy optionally substituted with one or two halo;

each $R^{AB}$ is independently halo, alkyl, alkoxy, or haloalkoxy;

$R^1$ is hydrogen, alkyl, cycloalkyl, or W; where W is alkyl substituted with alkylcarbonyloxy; and $R^2$ and $R^3$ are independently hydrogen or alkyl; wherein the alkyl is optionally substituted with alkylcarbonyloxy.

7. In certain embodiments, the compound, single stereoisomer or mixture of stereoisomers or pharmaceutically acceptable salt of any one of the above embodiments is that wherein Ring B is not present;

Ring A is $C_{3-7}$ cycloalkyl, $C_{8-11}$ spirocycloalkyl, 5-6 membered heterocycloalkyl, pyrazolyl, imidazolyl, triazolyl, thiazolyl, phenyl, naphthyl, indanyl, tetrahydronaphthyl, dihydronaphthyl, pyridyl, indolyl, benzothiazolyl, quinolinyl, isoquinolinyl, indolinyl, isoindolinyl, tetrahydroquinolinyl, dihydroisoquinolinyl, tetrahydroisoquinolinyl, 2,3-dihydrobenzo[b][1,4]dioxinyl, or tetrahydromethanonaphthalenyl;

wherein:
when Ring A is phenyl, then Ring A is substituted with:
(i) one or two $R^{AA}$ groups,
(ii) 2 halo groups when L is other than O;
(iii) 2 halo groups when L is O, and $R^2$ and $R^3$ are not hydrogen or alkyl,
(iv) one halo group when L is $CH_2NR^L$, or
(v) one halo group and one group selected from the group consisting of haloalkoxy, (cycloalkyl)alkoxy, and (phenyl)alkoxy, when L is bond, O or S, wherein the phenyl is optionally substituted with halo;

when Ring A is other than phenyl, then
(i) Ring A is substituted with one or two $R^{AB}$ groups; or
(ii) Ring A is unsubstituted, wherein:
1) when Ring A is unsubstituted tetrahydroquinolinyl, then L is bond;
2) when Ring A is unsubstituted 2,3-dihydrobenzo[b][1,4]dioxinyl, then L is O;
3) when Ring A is unsubstituted tetrahydronaphthyl, then L is O, and $R^1$ is not hydrogen or ethyl; or
4) when Ring A is unsubstituted spirocycloalkyl, then L is O or S.

8. In certain embodiments, the compound, single stereoisomer or mixture of stereoisomers or pharmaceutically acceptable salt of any one of the above embodiments is that wherein Ring A is piperidinyl, phenyl, naphthyl, indanyl, tetrahydronaphthyl, 2,3-dihydrobenzo[b][1,4]dioxinyl, pyridyl, quinolinyl, isoquinolinyl, tetrahydroquinolinyl, tetrahydroisoquinolinyl, spiro[2.5]octane, spiro[4.5]decane, or spiro[5.5]undecane;

when Ring A is phenyl, then Ring A is substituted with:
(i) one or two $R^{AA}$ groups,
(ii) 2 halo groups when L is other than O;
(iii) 2 halo groups when L is O, and $R^2$ and $R^3$ are not hydrogen or alkyl,
(iv) one halo group when L is $CH_2NR^L$, or
(v) one halo group and one group selected from the group consisting of haloalkoxy and (cycloalkyl)alkoxy, when L is bond, O or S;

each $R^{AA}$ is independently haloalkyl, cycloalkyloxy, (cycloalkyl)alkoxy, or alkylcarbonylaminoalkoxy;

each $R^{AB}$ is independently halo, alkyl, haloalkyl, or haloalkoxy;

R¹ is hydrogen, alkyl or W; wherein W is alkyl substituted with alkylcarbonyloxy;

R² and R³ are independently hydrogen or alkyl; wherein the alkyl is optionally substituted with cycloalkylcarbonyloxy or heterocycloalkylcarbonyloxy, wherein the heterocycloalkylcarbonyloxy optionally substituted with alkoxycarbonyl.

9. In certain embodiments, the compound, single stereoisomer or mixture of stereoisomers or pharmaceutically acceptable salt of any one of the above embodiments is that wherein Ring B is present;

Ring A is $C_{3-7}$ cycloalkyl, $C_{8-11}$ spirocycloalkyl, 5-6 membered heterocycloalkyl, pyrazolyl, imidazolyl, triazolyl, thiazolyl, thienyl, phenyl, naphthyl, indanyl, tetrahydronaphthyl, dihydronaphthyl, pyridyl, indolyl, benzothiazolyl, quinolinyl, isoquinolinyl, indolinyl, isoindolinyl, tetrahydroquinolinyl, dihydroisoquinolinyl, tetrahydroisoquinolinyl, 2,3-dihydrobenzo[b][1,4]dioxinyl, or tetrahydro-methanonaphthalenyl; wherein Ring A is optionally substituted with one or two groups selected from halo, alkyl, alkoxy, and haloalkoxy;

Ring B is cycloalkyl, heterocycloalkyl, aryl, or heteroaryl; wherein each is optionally substituted with one or two $R^B$ groups;

each $R^B$ is independently halo; cyano; alkyl; haloalkyl; alkoxy; haloalkoxy; alkylcarbonyl; alkoxyalkoxy; aminocarbonyl; alkylcarbonylaminoalkoxy; cycloalkyl; (cycloalkyl)alkyl; cycloalkyloxy; (cycloalkyl)alkoxy; cycloalkylcarbonyl; cycloalkylcarbonyloxy; heterocycloalkyl optionally substituted with 1 or 2 alkyl, alkylcarbonyl or a halo; (5-6-membered heterocycloalkyl-one)alkyl; (heterocycloalkyl)alkyl; or heterocycloalkylcarbonyl.

10. In certain embodiments, the compound, single stereoisomer or mixture of stereoisomers or pharmaceutically acceptable salt of any one of the above embodiments is that wherein L is bond, $CH_2$, $CF_2$, O, $NR^L$, S, $CH_2$-Q, or Q-$CH_2$; wherein Q is O, $NR^L$, or S;

$R^L$ is hydrogen, $C_{1-4}$ alkyl, or benzyl, wherein the phenyl, as part of the benzyl group, is optionally substituted with haloalkoxy;

Ring A is $C_{3-7}$ cycloalkyl, 5-6 membered heterocycloalkyl, phenyl, or naphthyl, wherein Ring A is optionally substituted with halo or haloalkoxy;

Ring B is cycloalkyl, heterocycloalkyl, phenyl, tetrahydronaphthyl, tetrahydroquinolinyl, quinolinyl, or, isoquinolinyl; wherein each Ring B is optionally substituted with one or two $R^B$ groups;

each $R^B$ is independently halo; cyano; haloalkyl; haloalkoxy; alkoxyalkoxy; aminocarbonyl; alkylcarbonylaminoalkoxy; cycloalkyl; (cycloalkyl)alkyl; heterocycloalkyl optionally substituted with 1 or 2 alkyl, alkylcarbonyl or halo; or (5-6-membered heterocycloalkyl-one)alkyl; and R¹ is hydrogen or W; wherein W is alkyl substituted with alkylcarbonyloxy, dialkylaminocarbonyloxy cycloalkylcarbonyloxy, or phenylcarbonyloxy.

11. In certain embodiments, the compound, single stereoisomer or mixture of stereoisomers or pharmaceutically acceptable salt of any one of the above embodiments is that wherein L is a bond, O, S, $NR^L$, $CH_2$-Q, or Q-$CH_2$; wherein Q is O, $NR^L$, or S.

12. In certain embodiments, the compound, single stereoisomer or mixture of stereoisomers or pharmaceutically acceptable salt of any one of the above embodiments is that wherein L is O or S.

13. In another embodiment, disclosed herein is a compound of Formula (IV):

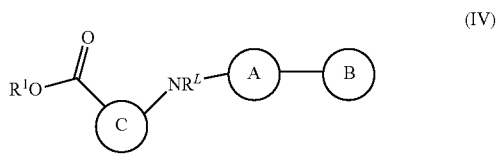

(IV)

wherein:

Ring C is selected from:

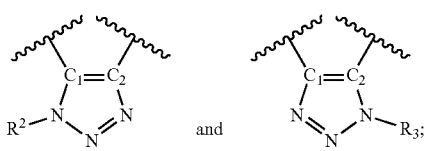

and wherein the wavy lines (~~~) indicate the points of attachment of the $C_1$ carbon to the carbonyl of C(O)—OR¹, and the $C_2$ carbon to N of $NR^L$;

$R^L$ is hydrogen or $C_{1-4}$ alkyl optionally substituted with hydroxycarbonyl, alkoxycarbonyl, hydroxycarbonylalkyl, or alkylcarbonyloxy;

Ring A is $C_{5-7}$ cycloalkyl, 5-6 membered heterocycloalkyl, pyrazolyl, imidazolyl, triazolyl, thiazolyl, phenyl, naphthyl, indanyl, tetrahydronaphthalinyl, dihydronaphthalinyl, pyridyl, indolyl, benzothiazolyl, quinolinyl, isoquinolinyl, indolinyl, isoindolinyl, tetrahydroquinolinyl, dihydroisoquinolinyl, or tetrahydro-methanonaphthalenyl;

Ring B is present or not present; wherein:

when Ring B is present, then Ring A is optionally substituted with one or two halo, alkyl, alkoxy, or haloalkoxy;

when Ring B is not present and Ring A is phenyl, then Ring A is substituted with:
(i) one or two $R^{AA}$ groups, or (ii) 2 halo groups;

when Ring B is not present and Ring A is 5-6 membered heterocycloalkyl, pyrazolyl, imidazolyl, triazolyl, thiazolyl, naphthyl, indanyl, tetrahydronaphthalinyl, dihydronaphthalinyl, benzothiazolyl, quinolinyl, isoquinolinyl, isoindolinyl, tetrahydroquinolinyl, or dihydroisoquinolinyl, then Ring A is substituted with one or two $R^{AB}$ groups;

when Ring B is not present and Ring A is pyridyl, indolyl, or indolinyl, then Ring A is substituted with one or two $R^{AC}$ groups;

each $R^{AA}$ is independently alkyl, haloalkyl, haloalkoxy, cycloalkyloxy, (cycloalkyl)alkoxy, or phenoxy optionally substituted with one or two halo;

each $R^{AB}$ is independently halo, alkyl, hydroxy, alkoxy, haloalkyl, haloalkoxy, cycloalkyloxy, (cycloalkyl)alkoxy, or phenoxy optionally substituted with one or two halo;

each $R^{AC}$ is independently halo, hydroxy, alkoxy, haloalkyl, haloalkoxy, cycloalkyloxy, (cycloalkyl)alkoxy, or phenoxy optionally substituted with one or two halo;

Ring B, when present, is cycloalkyl, heterocycloalkyl, aryl, or heteroaryl; wherein each is optionally substituted with one or two $R^B$ groups;

each $R^B$ is independently halo, cyano, alkyl, haloalkyl, alkoxy, haloalkoxy, alkylcarbonyl, alkoxyalkoxy, alkylcarbonylaminoalkoxy, cycloalkyl, (cycloalkyl)alkyl, cycloalkyloxy, (cycloalkyl)alkoxy, cycloalkylcarbonyl, cycloalkylcarbonyloxy, heterocycloalkyl optionally substituted with alkyl or alkylcarbonyl, (5-6-membered heterocycloalkyl-one)alkyl, (heterocycloalkyl)alkyl, or heterocycloalkylcarbonyl;

$R^1$ is hydrogen, alkyl, cycloalkyl, heterocycloalkyl, or W; where W is alkyl substituted with amino, alkylamino, dialkylamino, alkylcarbonyloxy, alkoxycarbonyl, or phenylcarbonyloxy;

$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl; and optionally a single stereoisomer or mixture of stereoisomers thereof and additionally optionally a pharmaceutically acceptable salt thereof.

14. In another embodiment, disclosed herein is a compound of Formula (IV):

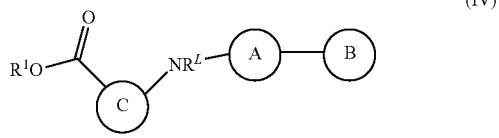

(IV)

wherein:

Ring C is selected from:

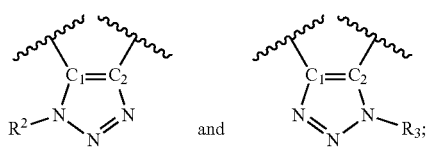

and wherein the wavy lines (∿) indicate the points of attachment of the $C_1$ carbon to the carbonyl of $C(O)$—$OR^1$, and the $C_2$ carbon to N of $NR^L$;

$R^L$ is hydrogen, $C_{1-4}$ alkyl, $C_{3-6}$ cycloalkyl, phenyl, or benzyl; wherein the $C_{1-4}$ alkyl is optionally substituted with hydroxycarbonyl, alkoxycarbonyl, hydroxycarbonylalkyl, or alkylcarbonyloxy; and the phenyl group alone or as a part of the benzyl group is optionally substituted with one or two groups selected from halo and haloalkoxy;

Ring A is $C_{3-7}$ cycloalkyl, $C_{8-11}$ spirocycloalkyl, 5-6 membered heterocycloalkyl, pyrazolyl, imidazolyl, triazolyl, thiazolyl, phenyl, naphthyl, indanyl, tetrahydronaphthyl, dihydronaphthyl, pyridyl, indolyl, benzothiazolyl, quinolinyl, isoquinolinyl, indolinyl, isoindolinyl, tetrahydroquinolinyl, dihydroisoquinolinyl, tetrahydroisoquinolinyl, 2,3-dihydrobenzo[b][1,4]dioxinyl, or tetrahydromethanonaphthalenyl;

Ring B is present or not present; wherein:

when Ring B is present, then Ring A is optionally substituted with one or two groups selected from halo, alkyl, alkoxy, and haloalkoxy;

when Ring B is not present and Ring A is phenyl, then Ring A is substituted with:
  (i) one or two $R^{AA}$ groups, or
  (ii) 2 halo groups;

when Ring B is not present and Ring A is 5-6 membered heterocycloalkyl, pyrazolyl, imidazolyl, triazolyl, thiazolyl, naphthyl, indanyl, tetrahydronaphthyl, dihydronaphthyl, benzothiazolyl, quinolinyl, isoquinolinyl, isoindolinyl, tetrahydroquinolinyl, dihydroisoquinolinyl, tetrahydroisoquinolinyl, or 2,3-dihydrobenzo[b][1,4]dioxinyl, then Ring A is substituted with one or two $R^{AB}$ groups;

when Ring B is not present and Ring A is $C_{3-7}$ cycloalkyl or $C_{8-11}$ spirocycloalkyl, then Ring A is optionally substituted with one or two $R^{AB}$ groups;

when Ring B is not present and Ring A is pyridyl, indolyl, or indolinyl, then Ring A is substituted with one or two $R^{AC}$ groups;

each $R^{AA}$ is independently alkyl; haloalkyl; haloalkoxy; cycloalkyloxy; (cycloalkyl)alkoxy; phenoxy optionally substituted with one or two halo; or alkylcarbonylaminoalkoxy;

each $R^{AB}$ is independently halo; alkyl; hydroxy; alkoxy; haloalkyl; haloalkoxy; cycloalkyloxy; (cycloalkyl)alkoxy; or phenoxy optionally substituted with one or two halo;

each $R^{AC}$ is independently halo; hydroxy; alkoxy; haloalkyl; haloalkoxy; cycloalkyloxy; (cycloalkyl)alkoxy; or phenoxy optionally substituted with one or two halo;

Ring B, when present, is cycloalkyl, heterocycloalkyl, aryl, or heteroaryl; wherein each is optionally substituted with one or two $R^B$ groups;

each $R^B$ is independently halo; cyano; alkyl; haloalkyl; alkoxy; haloalkoxy; alkylcarbonyl; alkoxyalkoxy; aminocarbonyl; alkylcarbonylaminoalkoxy; cycloalkyl; (cycloalkyl)alkyl; cycloalkyloxy; (cycloalkyl)alkoxy; cycloalkylcarbonyl; cycloalkylcarbonyloxy; heterocycloalkyl optionally substituted with 1 or 2 alkyl, alkylcarbonyl or halo; (5-6-membered heterocycloalkyl-one)alkyl; (heterocycloalkyl)alkyl; or heterocycloalkylcarbonyl;

$R^1$ is hydrogen, alkyl, cycloalkyl, heterocycloalkyl, or W; wherein W is alkyl substituted with amino, alkylamino, dialkylamino, alkylcarbonyloxy, alkoxycarbonyl, phenylcarbonyloxy, aminocarbonyloxy, alkylaminocarbonyloxy, dialkylaminocarbonyloxy, alkoxycarbonyloxy, cycloalkylcarbonyloxy, —N($R^{1A}$)C(O)$R^{1B}$, —N($R^{1A}$)C(O)O$R^{1B}$, or —N($R^{1A}$)C(O)N$R^{1B}R^{1C}$; wherein $R^{1A}$, $R^{1B}$, and $R^{1C}$ are each independently hydrogen or $C_{1-6}$ alkyl;

$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl; and optionally a single stereoisomer or mixture of stereoisomers thereof and additionally optionally a pharmaceutically acceptable salt thereof.

15. In certain embodiments, the compound, single stereoisomer or mixture of stereoisomers or pharmaceutically acceptable salt of any one of the above embodiments is that wherein $R^L$ is hydrogen or $C_{1-4}$ alkyl.

16. In certain embodiments, the compound, single stereoisomer or mixture of stereoisomers or pharmaceutically acceptable salt of any one of the above embodiments is that wherein $R^L$ is hydrogen.

17. In another embodiment, disclosed herein is a compound of Formula (V):

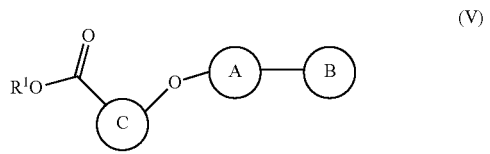

wherein:
Ring C is selected from:

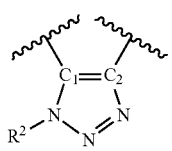 and 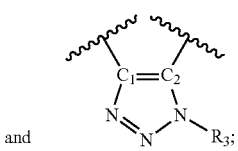

wherein the wavy lines (∿) indicate the points of attachment of the $C_1$ carbon to the carbonyl of C(O)—OR$^1$, and the $C_2$ carbon to O;

Ring A is cycloalkyl, heterocycloalkyl, aryl, or heteroaryl; each is substituted with one or two $R^{AB}$ groups; provided when Ring B is present, then Ring A is optionally substituted with one halo or alkyl;

when Ring B is not present and Ring A is phenyl, then Ring A is substituted with:
(i) one or two $R^{AD}$ groups, or (ii) two groups selected from chloro or bromo;

each $R^{AB}$ is independently halo, alkyl, hydroxy, alkoxy, haloalkyl, haloalkoxy, cycloalkyloxy, (cycloalkyl)alkoxy, or phenoxy optionally substituted with one or two halo;

each $R^{AD}$ is independently hydroxy, alkoxy, haloalkyl, cycloalkyloxy, (cycloalkyl)alkoxy, or phenoxy optionally substituted with one or two halo;

Ring B is present or not present; wherein:
Ring B, when present, is cycloalkyl, heterocycloalkyl, aryl, or heteroaryl; wherein each is optionally substituted with one or two $R^B$ groups;

each $R^B$ is independently halo, cyano, alkyl, haloalkyl, alkoxy, haloalkoxy, alkylcarbonyl, alkoxyalkoxy, alkylcarbonylaminoalkoxy, cycloalkyl, (cycloalkyl)alkyl, cycloalkyloxy, (cycloalkyl)alkoxy, cycloalkylcarbonyl, cycloalkylcarbonyloxy, heterocycloalkyl optionally substituted with alkyl or alkylcarbonyl, (5-6-membered heterocycloalkyl-one)alkyl, (heterocycloalkyl)alkyl, or heterocycloalkylcarbonyl;

$R^1$ is hydrogen, alkyl, cycloalkyl, heterocycloalkyl, or W; where W is alkyl substituted with amino, alkylamino, dialkylamino, alkylcarbonyloxy, alkoxycarbonyl, or phenylcarbonyloxy;

$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;

provided that when Ring A is phenyl, Ring B is not present, and $R^1$ is ethyl, then Ring A cannot be substituted with trifluoromethoxy; and optionally a single stereoisomer or mixture of stereoisomers thereof and additionally optionally a pharmaceutically acceptable salt thereof.

18. In another embodiment, disclosed herein is a compound of Formula (V):

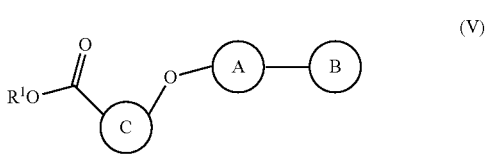

wherein:
Ring C is selected from:

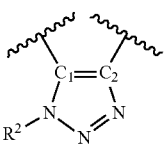 and 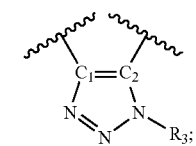

wherein the wavy lines (∿) indicate the points of attachment of the $C_1$ carbon to the carbonyl of C(O)—OR$^1$, and the $C_2$ carbon to O;

Ring A is cycloalkyl, $C_{8-11}$ spirocycloalkyl, heterocycloalkyl, aryl, or heteroaryl; each is substituted with one or two $R^{AB}$ groups;

Ring B is present or not present; wherein
when Ring B is present, then Ring A is optionally substituted with one halo or alkyl;

when Ring B is not present and Ring A is phenyl, then Ring A is substituted with:
(i) one or two $R^{AD}$ groups;
(ii) two groups selected from chloro or bromo; or
(iii) one halo group and one group selected from the group consisting of haloalkoxy, (cycloalkyl)alkoxy, and (phenyl)alkoxy, wherein the phenyl is optionally substituted with halo;

or Ring A is unsubstituted $C_{8-11}$ spirocycloalkyl; unsubstituted dihydroxybenzodioxynyl; or unsubstituted tetrahydronaphthalene when $R^1$ is not hydrogen or ethyl;

each R is independently halo; alkyl; hydroxy; alkoxy; haloalkyl; haloalkoxy; cycloalkyloxy; (cycloalkyl)alkoxy; phenoxy optionally substituted with one or two halo; or (phenyl)alkoxy, wherein the phenyl is optionally substituted with halo;

each $R^{AD}$ is independently hydroxy; alkoxy; haloalkyl; cycloalkyloxy; (cycloalkyl)alkoxy; or phenoxy optionally substituted with one or two halo;

Ring B, when present, is cycloalkyl, heterocycloalkyl, aryl, or heteroaryl; wherein each is optionally substituted with one or two $R^B$ groups;

each $R^B$ is independently halo; cyano; alkyl; haloalkyl; alkoxy; haloalkoxy; alkylcarbonyl; alkoxyalkoxy; aminocarbonyl; alkylcarbonylaminoalkoxy; cycloalkyl; (cycloalkyl)alkyl; cycloalkyloxy; (cycloalkyl)alkoxy; cycloalkylcarbonyl; cycloalkylcarbonyloxy; heterocycloalkyl optionally substituted with 1 or 2 alkyl, alkylcarbonyl or halo; (5-6-membered heterocycloalkyl-one)alkyl; (heterocycloalkyl)alkyl; or heterocycloalkylcarbonyl;

R$^1$ is hydrogen, alkyl, cycloalkyl, heterocycloalkyl, or W; wherein W is alkyl substituted with amino, alkylamino, dialkylamino, alkylcarbonyloxy, alkoxycarbonyl, phenylcarbonyloxy, aminocarbonyloxy, alkylaminocarbonyloxy, dialkylaminocarbonyloxy, alkoxycarbonyloxy, cycloalkylcarbonyloxy, —N(R$^{1A}$)C(O)R$^{1B}$, —N(R$^{1B}$)C(O)OR$^{1B}$, or —N(R$^{1A}$)C(O)NR$^{1B}$R$^{1C}$; wherein R$^{1A}$, R$^{1B}$, and R$^{1C}$ are each independently hydrogen or C$_{1-6}$ alkyl;

R$^2$ and R$^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;

provided:
(i) when Ring A is phenyl, Ring B is not present, and R$^1$ is ethyl, then Ring A cannot be substituted with trifluoromethoxy; and
(ii) when Ring A is phenyl substituted with 1 R$^{AD}$, then R$^{AD}$ cannot be meta-substituted trifluoromethyl; and optionally a single stereoisomer or mixture of stereoisomers thereof and additionally optionally a pharmaceutically acceptable salt thereof.

19. In another embodiment, disclosed herein is a compound of Formula (V):

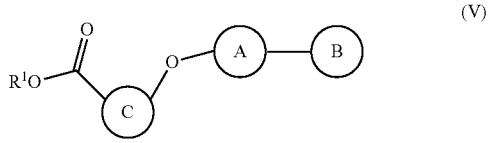

wherein:
Ring C is selected from:

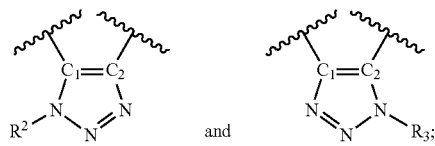

wherein the wavy lines (∿) indicate the points of attachment of the C$_1$ carbon to the carbonyl of C(O)—OR$^1$, and the C$_2$ carbon to O;

Ring A is cycloalkyl, C$_{8-11}$ spirocycloalkyl, heterocycloalkyl, aryl, or heteroaryl; each is substituted with one or two R groups;

Ring B is present or not present; wherein
when Ring B is present, then Ring A is optionally substituted with a group selected from halo, alkyl, alkoxy, cyano, hydroxy, and (cycloalkyl)alkyl;
when Ring B is not present and Ring A is phenyl, then Ring A is substituted with:
(i) one or two R$^{AD}$ groups;
(ii) two groups selected from chloro or bromo; or
(iii) one halo group and one group selected from the group consisting of haloalkoxy, (cycloalkyl)alkoxy, and (phenyl)alkoxy, wherein the phenyl is optionally substituted with halo;
(iv) one cyano group and one (phenyl)alkoxy group, wherein the phenyl as part of the (phenyl)alkoxy group is optionally substituted with halo or haloalkoxy;

or Ring A is unsubstituted C$_{8-11}$ spirocycloalkyl; unsubstituted dihydroxybenzodioxynyl; or unsubstituted tetrahydronaphthalene when R$^1$ is not hydrogen or ethyl;

each R$^{AB}$ is independently halo; alkyl; hydroxy; alkoxy; haloalkyl; haloalkoxy; cycloalkyloxy; (cycloalkyl)alkoxy; phenoxy optionally substituted with one or two halo; or (phenyl)alkoxy, wherein the phenyl is optionally substituted with halo;

each R$^{AD}$ is independently hydroxy; alkoxy; haloalkyl; cycloalkyloxy; (cycloalkyl)alkoxy; or phenoxy optionally substituted with one or two halo;

Ring B, when present, is cycloalkyl, heterocycloalkyl, aryl, or heteroaryl; wherein each is optionally substituted with one or two R$^B$ groups;

each R$^B$ is independently halo; cyano; alkyl; hydroxyalkyl; alkylsulfonyl; aminosulfonyl; alkylaminosulfonyl; dialkylaminosulfonyl; haloalkyl; alkoxy; aminoalkoxy; alkylaminoalkoxy; dialkylaminoalkoxy; hydroxyalkoxy; haloalkoxy; alkylcarbonyl; alkoxyalkoxy; aminocarbonyl; alkylcarbonylaminoalkoxy; cycloalkyl; (cycloalkyl)alkyl; cycloalkyloxy; (cycloalkyl)alkoxy wherein cycloalkyl group is optionally substituted with hydroxyalkyl; cycloalkylcarbonyl; cycloalkylcarbonyloxy; heterocycloalkyl optionally substituted with 1 or 2 alkyl, alkylcarbonyl or halo; (5-6-membered heterocycloalkyl-one)alkyl; (heterocycloalkyl)alkyl; or heterocycloalkylcarbonyl; or 5-6 membered heteroaryl optionally substituted with alkyl wherein alkyl is optionally substituted with 1 or 2 groups independently selected from cycloalkyl and hydroxy; alkoxyalkyl; hydroxyalkyl; or hydroxycycloalkyl;

R$^1$ is hydrogen, alkyl, cycloalkyl, heterocycloalkyl, or W; wherein W is alkyl substituted with amino, alkylamino, dialkylamino, alkylcarbonyloxy, alkoxycarbonyl, phenylcarbonyloxy, aminocarbonyloxy, alkylaminocarbonyloxy, dialkylaminocarbonyloxy, alkoxycarbonyloxy, cycloalkylcarbonyloxy, —N(R$^{1A}$)C(O)R$^{1B}$, —N(R$^{1A}$)C(O)OR$^{1B}$, or —N(R$^{1A}$)C(O)NR$^{1B}$R$^{1C}$, wherein R$^{1A}$, R$^{1B}$, and R$^{1C}$ are each independently hydrogen or C$_{1-6}$ alkyl;

R$^2$ and R$^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;

provided:
(i) when Ring A is phenyl, Ring B is not present, and R$^1$ is ethyl, then Ring A cannot be substituted with trifluoromethoxy; and
(ii) when Ring A is phenyl substituted with 1 R$^{AD}$, then R$^{AD}$ cannot be meta-substituted trifluoromethyl; and optionally a single stereoisomer or mixture of stereoisomers thereof and additionally optionally a pharmaceutically acceptable salt thereof.

20. In another embodiment, disclosed herein is a compound of Formula (VI):

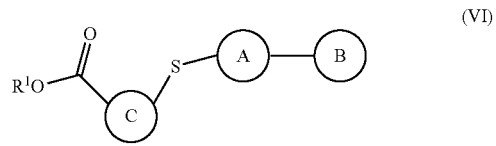

wherein:
Ring C is selected from:

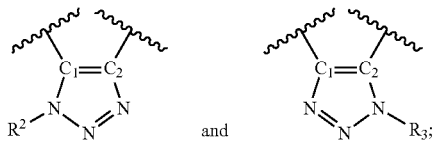

and wherein the wavy lines (⌇) indicate the points of attachment of the C₁ carbon to the carbonyl of C(O)—OR¹, and the C₂ carbon to S;
wherein:
Ring A is cycloalkyl, heterocycloalkyl, aryl, or heteroaryl other than thienyl or benzothiophenyl; each is substituted with one or two $R^{AB}$ groups;
provided when Ring A is phenyl and Ring B is not present, then Ring A is substituted with one or two $R^{AE}$;
each $R^{AB}$ is independently halo, alkyl, hydroxy, alkoxy, haloalkyl, haloalkoxy, cycloalkyloxy, (cycloalkyl)alkoxy, or phenoxy optionally substituted with one or two halo;
each $R^{AE}$ is independently halo, alkyl, haloalkyl, haloalkoxy, cycloalkyloxy, or (cycloalkyl)alkoxy;
Ring B is present or not present; wherein:
Ring B, when present, is cycloalkyl, heterocycloalkyl, aryl, or heteroaryl; wherein each is optionally substituted with one or two $R^B$ groups;
each $R^B$ is independently halo, cyano, alkyl, haloalkyl, alkoxy, haloalkoxy, alkylcarbonyl, alkoxyalkoxy, alkylcarbonylaminoalkoxy, cycloalkyl, (cycloalkyl)alkyl, cycloalkyloxy, (cycloalkyl)alkoxy, cycloalkylcarbonyl, cycloalkylcarbonyloxy, heterocycloalkyl optionally substituted with alkyl or alkylcarbonyl, (5-6-membered heterocycloalkyl-one)alkyl, (heterocycloalkyl)alkyl, or heterocycloalkylcarbonyl;
R¹ is hydrogen, alkyl, cycloalkyl, heterocycloalkyl, or W; where W is alkyl substituted with amino, alkylamino, dialkylamino, alkylcarbonyloxy, alkoxycarbonyl, or phenylcarbonyloxy;
R² and R³ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;
provided that when Ring A is phenyl, then Ring B cannot be halo-substituted phenyl; and
optionally a single stereoisomer or mixture of stereoisomers thereof and additionally optionally a pharmaceutically acceptable salt thereof.
21. In another embodiment, disclosed herein is a compound of Formula (VI):

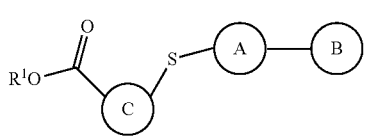

(VI)

wherein:
Ring C is selected from:

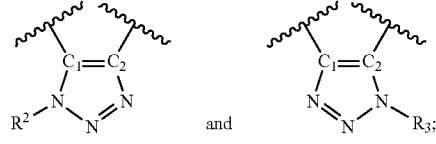

and wherein the wavy lines (⌇) indicate the points of attachment of the C₁ carbon to the carbonyl of C(O)—OR¹, and the C₂ carbon to S;
Ring A is cycloalkyl, $C_{8-11}$ spirocycloalkyl, heterocycloalkyl, aryl, or heteroaryl other than thienyl or benzothiophenyl; each is substituted with one or two $R^{AB}$ groups;
provided when Ring A is phenyl and Ring B is not present, then Ring A is substituted with one or two $R^{AE}$;
Ring B is present or not present; wherein:
each R is independently halo; alkyl; hydroxy; alkoxy; haloalkyl; haloalkoxy; cycloalkyloxy; (cycloalkyl)alkoxy; phenoxy optionally substituted with one or two halo; or (phenyl)alkoxy, wherein the phenyl is optionally substituted with halo;
each $R^{AE}$ is independently halo; haloalkyl; haloalkoxy; cycloalkyloxy; (cycloalkyl)alkoxy; or (phenyl)alkoxy, wherein the phenyl is optionally substituted with halo;
Ring B, when present, is cycloalkyl, heterocycloalkyl, aryl, or heteroaryl; wherein each is optionally substituted with one or two $R^B$ groups;
each $R^B$ is independently halo; cyano; alkyl; haloalkyl; alkoxy; haloalkoxy; alkylcarbonyl; alkoxyalkoxy; aminocarbonyl; alkylcarbonylaminoalkoxy; cycloalkyl; (cycloalkyl)alkyl; cycloalkyloxy; (cycloalkyl)alkoxy; cycloalkylcarbonyl; cycloalkylcarbonyloxy; heterocycloalkyl optionally substituted with 1 or 2 alkyl, alkylcarbonyl or halo; (5-6-membered heterocycloalkyl-one)alkyl; (heterocycloalkyl)alkyl; or heterocycloalkylcarbonyl;
R¹ is hydrogen, alkyl, cycloalkyl, heterocycloalkyl, or W; wherein W is alkyl substituted with amino, alkylamino, dialkylamino, alkylcarbonyloxy, alkoxycarbonyl, phenylcarbonyloxy, aminocarbonyloxy, alkylaminocarbonyloxy, dialkylaminocarbonyloxy, alkoxycarbonyloxy, cycloalkylcarbonyloxy, —N($R^{1A}$)C(O)$R^{1B}$, —N($R^{1A}$)C(O)O$R^{1B}$, or —N($R^{1A}$)C(O)NR$^{1B}$R$^{1C}$, wherein $R^{1A}$, $R^{1B}$, and $R^{1C}$ are each independently hydrogen or $C_{1-6}$ alkyl;
R² and R³ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;
provided when Ring A is phenyl, then Ring B cannot be halo-substituted phenyl; and
optionally a single stereoisomer or mixture of stereoisomers thereof and additionally optionally a pharmaceutically acceptable salt thereof.
22. In another embodiment, disclosed herein is a compound of Formula (VI):

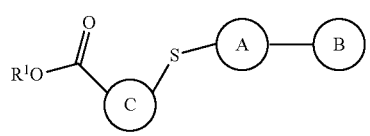

(VI)

wherein:
Ring C is selected from:

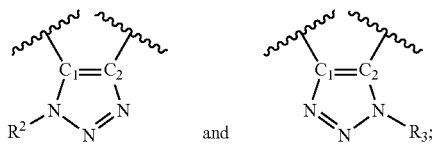

wherein the wavy lines (⁓) indicate the points of attachment of the $C_1$ carbon to the carbonyl of C(O)—OR$^1$, and the $C_2$ carbon to S;

Ring A is cycloalkyl, $C_{8-11}$ spirocycloalkyl, heterocycloalkyl, aryl, or heteroaryl other than thienyl or benzothiophenyl; each is substituted with one or two $R^{AB}$ groups; provided when Ring A is phenyl and Ring B is not present, then Ring A is substituted with one or two $R^{AE}$;

Ring B is present or not present; wherein:

each $R^{AB}$ is independently halo; alkyl; hydroxy; alkoxy; haloalkyl; haloalkoxy; cycloalkyloxy; (cycloalkyl)alkoxy; phenoxy optionally substituted with one or two halo; or (phenyl)alkoxy, wherein the phenyl is optionally substituted with halo;

each $R^{AE}$ is independently halo; haloalkyl; haloalkoxy; cycloalkyloxy; (cycloalkyl)alkoxy; or (phenyl)alkoxy, wherein the phenyl is optionally substituted with halo;

Ring B, when present, is cycloalkyl, heterocycloalkyl, aryl, or heteroaryl; wherein each is optionally substituted with one or two $R^B$ groups;

each $R^B$ is independently halo; cyano; alkyl; alkylsulfonyl; haloalkyl; alkoxy; haloalkoxy; alkylcarbonyl; alkoxyalkoxy; aminocarbonyl; alkylcarbonylaminoalkoxy; cycloalkyl; (cycloalkyl)alkyl; cycloalkyloxy; (cycloalkyl)alkoxy; cycloalkylcarbonyl; cycloalkylcarbonyloxy; heterocycloalkyl optionally substituted with 1 or 2 alkyl, alkylcarbonyl or halo; (5-6-membered heterocycloalkylone)alkyl; (heterocycloalkyl)alkyl; heterocycloalkylcarbonyl; or 5-6 membered heteroaryl;

$R^1$ is hydrogen, alkyl, cycloalkyl, heterocycloalkyl, or W; wherein W is alkyl substituted with amino, alkylamino, dialkylamino, alkylcarbonyloxy, alkoxycarbonyl, phenylcarbonyloxy, aminocarbonyloxy, alkylaminocarbonyloxy, dialkylaminocarbonyloxy, alkoxycarbonyloxy, cycloalkylcarbonyloxy, —N(R$^{1A}$)C(O)R$^{1B}$, —N(R$^{1A}$)C(O)OR$^{1B}$, or —N(R$^{1A}$)C(O)NR$^{1B}$R$^{1C}$, wherein R$^{1A}$, R$^{1B}$, and R$^{1C}$ are each independently hydrogen or $C_{1-6}$ alkyl;

$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;

provided when Ring A is phenyl, then Ring B cannot be halo-substituted phenyl; and optionally a single stereoisomer or mixture of stereoisomers thereof and additionally optionally a pharmaceutically acceptable salt thereof.

23. In certain embodiments, the compound, single stereoisomer or mixture of stereoisomers or pharmaceutically acceptable salt of any one of the above embodiments is that wherein Ring A is $C_{3-7}$ cycloalkyl, 5-6 membered heterocycloalkyl, or phenyl.

24. In certain embodiments, the compound, single stereoisomer or mixture of stereoisomers or pharmaceutically acceptable salt of any one of the above embodiments is that wherein Ring A is $C_{3-7}$ cycloalkyl.

25. In certain embodiments, the compound, single stereoisomer or mixture of stereoisomers or pharmaceutically acceptable salt of any one of the above embodiments is that wherein Ring A is 5-6 membered heterocycloalkyl.

26. In certain embodiments, the compound, single stereoisomer or mixture of stereoisomers or pharmaceutically acceptable salt of any one of the above embodiments is that wherein Ring A is phenyl.

27. In certain embodiments, the compound, single stereoisomer or mixture of stereoisomers or pharmaceutically acceptable salt of any one of the above embodiments is that wherein $R^1$ is hydrogen or W.

28. In certain embodiments, the compound, single stereoisomer or mixture of stereoisomers or pharmaceutically acceptable salt of any one of the above embodiments is that wherein $R^1$ is hydrogen.

29. In certain embodiments, the compound, single stereoisomer or mixture of stereoisomers or pharmaceutically acceptable salt of any one of the above embodiments is that wherein $R^1$ is W.

30. In certain embodiments, the compound, single stereoisomer or mixture of stereoisomers or pharmaceutically acceptable salt of any one of the above embodiments is that wherein $R^2$ and $R^3$ are independently hydrogen.

31. In certain embodiments, the compound, single stereoisomer or mixture of stereoisomers or pharmaceutically acceptable salt of any one of the above embodiments is that wherein ring C is:

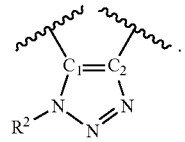

32. In certain embodiments, the compound, single stereoisomer or mixture of stereoisomers or pharmaceutically acceptable salt of any one of the above embodiments is that wherein ring C is:

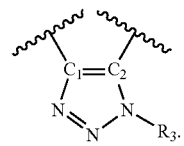

33. In another embodiment, disclosed herein is a compound selected from the group consisting of compounds in Table 1, Table 2, and Table 4; optionally as a tautomer, a single stereoisomer or mixture of stereoisomers thereof and additionally optionally as a pharmaceutically acceptable salt thereof.

34. In another embodiment, disclosed herein is a compound selected from Compounds 1-168, or a single stereoisomer or mixture of stereoisomers thereof and additionally optionally as a pharmaceutically acceptable salt thereof.

35. In another embodiment, disclosed herein is a compound selected from the group consisting of Compounds 169-375, or a single stereoisomer or mixture of stereoisomers thereof and additionally optionally as a pharmaceutically acceptable salt thereof.

36. In another embodiment, disclosed herein is a compound selected from the group consisting of Compounds 376-486, or a single stereoisomer or mixture of stereoisomers thereof and additionally optionally as a pharmaceutically acceptable salt thereof.

37. In another embodiment, disclosed herein is a compound selected from the group consisting of compounds 169, 170, 171, 172, 173, 174, 175, 176, 177, 178, 179, 180, 181, 182, 183, 185, 186, 187, 188, 189, 190, 194, 195, 196, 197, 198, 199, 200, 201, 203, 204, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 249, 250, 251, 252, 253, 254, 255, 256, 257, 258, 259, 260, 261, 262, 263, 264, 265, 266, 267, 268, 269, 270, 271, 272-1, 272-2, 273, 274, 275, 277, 278, 279, 280, 281, 282, 283, 284, 285, 286, 287, 288, 289, 290, 291, 292, 293, 295, 297, 298, 299, 300, 301, 303, 304, 305, 306, 307, 308-1, 308-2, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 367, 368, 369, 370, 373, and 375, or a single stereoisomer or mixture of stereoisomers thereof and additionally optionally as a pharmaceutically acceptable salt thereof.

38. In another embodiment, disclosed herein is a compound selected from the group consisting of compounds 376, 377, 379, 380, 381, 382, 383, 384, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442-1, 442-2, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, and 486, or a single stereoisomer or mixture of stereoisomers thereof and additionally optionally as a pharmaceutically acceptable salt thereof.

39. In another embodiment, disclosed herein is a compound of Formula (VIII):

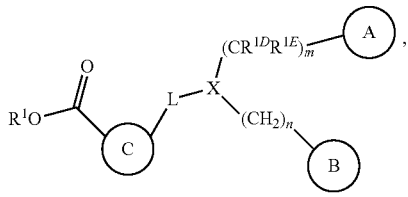

wherein:
ring C is selected from:

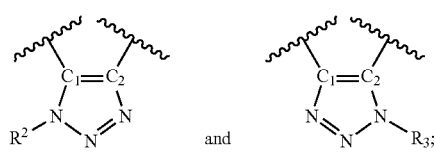

wherein the wavy lines (∿) indicate the points of attachment of the $C_1$ carbon to the carbonyl of $C(O)OR^1$, and the $C_2$ carbon to L;

L is a bond, $CH_2$, $CH_2CH_2$, O, or $CH_2O$;
X is N or CH;
$R^{1D}$ and $R^{1E}$ are each independently H or hydroxy;
m is 1, 2, or 3;
n is 0, 1, 2, or 3;
Ring A and Ring B are each independently $C_{3-7}$ cycloalkyl, 5-6 membered heterocycloalkyl, aryl or heteroaryl, optionally substituted with halo, haloalkyl or phenyl; wherein phenyl is optionally substituted with halo, haloalkyl, or haloalkoxy; and
optionally a single stereoisomer or mixture of stereoisomers thereof and additionally optionally a pharmaceutically acceptable salt thereof.

40. In certain embodiments, the compound of any one of the above embodiments is selected from the group consisting of compounds 294, 296, 366, 372, 374, 378, and 385, or optionally as a tautomer, a single stereoisomer or mixture of stereoisomers thereof and additionally optionally as a pharmaceutically acceptable salt thereof.

41. In another embodiment, disclosed herein is a pharmaceutical composition comprising a compound of any one of the above embodiments, optionally as a single stereoisomer, or mixtures of stereoisomers, and additionally optionally as a pharmaceutically acceptable excipient.

42. In another embodiment, disclosed herein a method of treating a disease or disorder associated with a defect in glyoxylate metabolism comprising administering to a patient suffering from such disease or disorder a compound or pharmaceutically acceptable salt thereof and/or a pharmaceutical composition of any one the above embodiments.

43. In certain embodiments of the embodiment directly above, the disease or disorder is a primary hyperoxaluria.

44. In another embodiment, disclosed herein is a compound or pharmaceutically acceptable salt thereof and/or a pharmaceutical composition of any one the above embodiments, for use as a medicament.

45. In another embodiment, disclosed herein is a compound or pharmaceutically acceptable salt thereof and/or a pharmaceutical composition of any one the above embodiments, for use in a method of treating a disease or disorder associated with a defect in glyoxylate metabolism.

46. In certain embodiments of the two embodiments directly above, the disease of disorder is primary hyperoxaluria.

47. In certain embodiments, the compound of any one of the above embodiments is that wherein Ring B cannot be mono or di-substituted halo.

48. In certain embodiments, the compound of any one of the above embodiments is that wherein Ring B cannot be unsubstituted phenyl or phenyl substituted with one or two groups independently selected from alkyl, halo, or haloalkyl.

49. In certain embodiments, the compound of any one of the above embodiments is that wherein Ring A cannot be unsubstituted phenyl or phenyl substituted with one or two groups independently selected from alkyl, halo, or haloalkyl, and Ring B cannot be unsubstituted phenyl or phenyl substituted with one or two groups independently selected from alkyl, halo, or haloalkyl.

50. In certain embodiments, the compound of any one of the above embodiments is that wherein, when L is S or $CH_2$, Ring B cannot be mono or di-substituted halo.

51. In certain embodiments, the compound of any one of the above embodiments is that wherein, when L is S or $CH_2$, Ring B cannot be unsubstituted phenyl or phenyl substituted with one or two groups independently selected from alkyl, halo, or haloalkyl.

52. In certain embodiments, the compound of any one of the above embodiments is that wherein, when L is S or $CH_2$, Ring A cannot be unsubstituted phenyl or phenyl substituted with one or two groups independently selected from alkyl, halo, or haloalkyl, and Ring B cannot be unsubstituted phenyl or phenyl substituted with one or two groups independently selected from alkyl, halo, or haloalkyl.

We claim:

1. A compound of Formula (I):

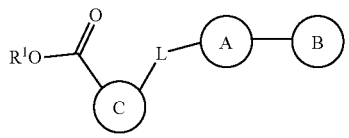

(I)

wherein:

ring C is selected from:

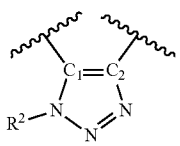 and 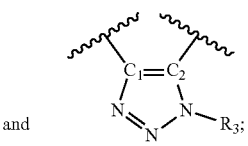;

wherein the wavy lines ( ) indicate the points of attachment of the $C_1$ carbon to the carbonyl of C(O)—$OR^1$, and the $C_2$ carbon to L;

L is S;

Ring A is $C_{3-8}$ cycloalkyl, $C_{8-11}$ spirocycloalkyl, 5-8 membered heterocycloalkyl, pyrazolyl, imidazolyl, triazolyl, thiazolyl, thienyl, phenyl, naphthyl, indanyl, tetrahydronaphthyl, dihydronaphthyl, pyridyl, indolyl, benzothiazolyl, quinolinyl, isoquinolinyl, indolinyl, isoindolinyl, tetrahydroquinolinyl, dihydroisoquinolinyl, tetrahydroisoquinolinyl, 2,3-dihydrobenzo[b][1,4]dioxinyl, or tetrahydro-methanonaphthalenyl;

wherein
Ring A is optionally substituted with one or two groups independently selected from halo, alkyl, alkoxy, cyano, hydroxy, haloalkoxy, (cycloalkyl)alkoxy, and cycloalkyl;

Ring B is cycloalkyl, heterocycloalkyl, aryl, or heteroaryl; wherein each is optionally substituted with one or two $R^B$ groups;

each $R^B$ is independently halo; cyano; alkyl; haloalkyl; alkoxy; haloalkoxy; alkylcarbonyl; alkoxyalkyl; aminocarbonyl; alkylcarbonylaminoalkoxy; cycloalkyl; (cycloalkyl)alkyl; cycloalkyloxy; (cycloalkyl)alkoxy; cycloalkylcarbonyl; cycloalkylcarbonyloxy; heterocycloalkyl optionally substituted with 1 or 2 alkyl, alkylcarbonyl or a halo; (5-6-membered heterocycloalkyl-one)alkyl; (heterocycloalkyl)alkyl; or heterocycloalkylcarbonyl;

$R^1$ is hydrogen, alkyl, cycloalkyl, heterocycloalkyl, or W; wherein W is alkyl substituted with amino, alkylamino, dialkylamino, alkylcarbonyloxy, alkoxycarbonyl, phenylcarbonyloxy, aminocarbonyloxy, alkylaminocarbonyloxy, dialkylaminocarbonyloxy, alkoxycarbonyloxy, cycloalkylcarbonyloxy, —N($R^{1A}$)C(O)$R^{1B}$, —N($R^{1A}$)C(O)O$R^{1B}$, or —N($R^{1A}$)C(O)NR$^{1B}$R$^{1C}$; wherein $R^{1A}$, $R^{1B}$, and $R^{1C}$ are each independently hydrogen or $C_{1-6}$ alkyl;

$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;

provided when Ring A is phenyl, then Ring B cannot be halo-substituted phenyl; and optionally a single stereoisomer or mixture of stereoisomers thereof and additionally optionally a pharmaceutically acceptable salt thereof.

2. The compound, single stereoisomer or mixture of stereoisomers or pharmaceutically acceptable salt of claim 1, wherein Ring A is $C_3$-7 cycloalkyl, 5-6 membered heterocycloalkyl, phenyl, or naphthyl, wherein Ring A is optionally substituted with halo or haloalkoxy;

Ring B is cycloalkyl, heterocycloalkyl, phenyl, tetrahydronaphthyl, tetrahydroquinolinyl, quinolinyl, or, isoquinolinyl; wherein each Ring B is optionally substituted with one or two $R^B$ groups;

each $R^B$ is independently halo; cyano; haloalkyl; haloalkoxy; alkoxyalkoxy; aminocarbonyl; alkylcarbonylaminoalkoxy; cycloalkyl; (cycloalkyl)alkoxy; heterocycloalkyl optionally substituted with 1 or 2 alkyl, alkylcarbonyl or halo; or (5-6-membered heterocycloalkyl-one)alkyl; and $R^1$ is hydrogen or W; wherein W is alkyl substituted with alkylcarbonyloxy, dialkylaminocarbonyloxy, cycloalkylcarbonyloxy, or phenylcarbonyloxy.

3. The compound, single stereoisomer or mixture of stereoisomers or pharmaceutically acceptable salt of claim 1, wherein the compound is a compound of Formula (VI):

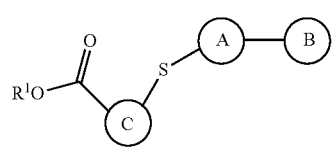

(VI)

wherein:

Ring C is selected from:

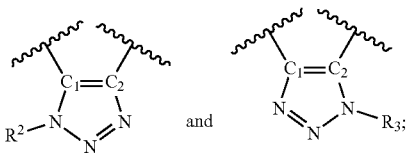 and 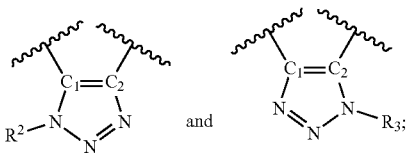;

wherein the wavy lines ( ) indicate the points of attachment of the $C_1$ carbon to the carbonyl of C(O)—$OR^1$, and the $C_2$ carbon to S;

Ring A is $C_{3-8}$ cycloalkyl, $C_{8-11}$ spirocycloalkyl, 5-8 membered heterocycloalkyl, phenyl, naphthyl, pyrazolyl, imidazolyl, triazolyl, thiazolyl, pyridyl, indolyl, quinolinyl, isoquinolinyl, indolinyl, isoindolinyl, dihydroisoquinolinyl, tetrahydroisoquinolinyl, or 2,3-dihydrobenzo[b][1,4]dioxinyl; each is substituted with one or two $R^{AB}$ groups;

Ring B is present; wherein:

each $R^{AB}$ is independently halo; alkyl; hydroxy; alkoxy; haloalkoxy; (cycloalkyl)alkoxy;

Ring B, is cycloalkyl, heterocycloalkyl, aryl, or heteroaryl; wherein each is optionally substituted with one or two $R^B$ groups;

each $R^B$ is independently halo; cyano; alkyl; haloalkyl; alkoxy; haloalkoxy; alkylcarbonyl; alkoxyalkoxy; aminocarbonyl; alkylcarbonylaminoalkoxy; cycloalkyl; (cycloalkyl)alkyl; cycloalkyloxy; (cycloalkyl)alkoxy; cycloalkylcarbonyl; cycloalkylcarbonyloxy; heterocycloalkyl optionally substituted with 1 or 2 alkyl, alkylcarbonyl or halo; (5-6-membered heterocycloalkyl-one)alkyl; (heterocycloalkyl)alkyl; or heterocycloalkylcarbonyl;

$R^1$ is hydrogen, alkyl, cycloalkyl, heterocycloalkyl, or W; wherein W is alkyl substituted with amino, alkylamino, dialkylamino, alkylcarbonyloxy, alkoxycarbonyl, phenylcarbonyloxy, aminocarbonyloxy, alkylaminocarbonyloxy, dialkylaminocarbonyloxy, alkoxycarbonyloxy, cycloalkylcarbonyloxy, —N($R^{1A}$)C(O)$R^{1B}$, —N($R^{1A}$)C(O)O$R^{1B}$, or —N($R^{1A}$)C(O)N$R^{1B}R^{1C}$; wherein $R^{1A}$, $R^{1B}$, and $R^{1C}$ are each independently hydrogen or $C_{1-6}$ alkyl;

$R^2$ and $R^3$ are independently hydrogen, alkyl, phenyl, benzyl, or alkoxy-substituted benzyl; wherein the alkyl is optionally substituted with halo, alkoxy, haloalkoxy, alkylcarbonyloxy, cycloalkylcarbonyloxy, or heterocycloalkylcarbonyloxy optionally substituted with alkoxycarbonyl;

provided when Ring A is phenyl, then Ring B cannot be halo-substituted phenyl.

4. The compound, single stereoisomer or mixture of stereoisomers or pharmaceutically acceptable salt of claim 1, wherein Ring A is $C_{3-7}$ cycloalkyl, 5-6 membered heterocycloalkyl, or phenyl.

5. The compound, single stereoisomer or mixture of stereoisomers or pharmaceutically acceptable salt of claim 4, wherein Ring A is $C_{3-7}$ cycloalkyl.

6. The compound, single stereoisomer or mixture of stereoisomers or pharmaceutically acceptable salt of claim 4, wherein Ring A is 5-6 membered heterocycloalkyl.

7. The compound, single stereoisomer or mixture of stereoisomers or pharmaceutically acceptable salt of claim 4, wherein Ring A is phenyl.

8. The compound, single stereoisomer or mixture of stereoisomers or pharmaceutically acceptable salt of claim 1, wherein $R^1$ is hydrogen or W.

9. The compound, single stereoisomer or mixture of stereoisomers or pharmaceutically acceptable salt of claim 1, wherein $R^2$ and $R^3$ are independently hydrogen.

10. The compound, single stereoisomer or mixture of stereoisomers or pharmaceutically acceptable salt of claim 1, wherein Ring B is cycloalkyl.

11. The compound, single stereoisomer or mixture of stereoisomers or pharmaceutically acceptable salt of claim 1, wherein Ring B is heterocycloalkyl.

12. The compound, single stereoisomer or mixture of stereoisomers or pharmaceutically acceptable salt of claim 1, wherein Ring B is heteroaryl.

13. A compound, single stereoisomer or mixture of stereoisomers or pharmaceutically acceptable salt thereof, wherein the compound is selected from the group consisting of compounds ethyl 4-((4-(3,4-dichlorophenyl)thiazol-2-yl)thio)-1H-1,2,3-triazole-5-carboxylate,
4-((4-(3,4-dichlorophenyl)thiazol-2-yl)thio)-1H-1,2,3-triazole-5-carboxylic acid,
4-((5-(3,4-dichlorophenyl)thiazol-2-yl)thio)-1H-1,2,3-triazole-5-carboxylic acid,
5-((3-(4-methylpiperazin-1-yl)phenyl)thio)-1H-1,2,3-triazole-4-carboxylic acid,
4-((4-(piperidin-1-yl)phenyl)thio)-1H-1,2,3-triazole-5-carboxylic acid,
4-((2-(3,4-dichlorophenyl)thiazol-4-yl)thio)-1H-1,2,3-triazole-5-carboxylic acid,
cyclobutyl 4-((4-(3,4-dichlorophenyl)thiazol-2-yl)thio)-1H-1,2,3-triazole-5-carboxylate,
4-((4-(4-methylpiperazin-1-yl)phenyl)thio)-1H-1,2,3-triazole-5-carboxylic acid,
isopropyl 4-((4-(3,4-dichlorophenyl)thiazol-2-yl)thio)-1H-1,2,3-triazole-5-carboxylate,
4-((5-(4-bromophenyl)pyridin-2-yl)thio)-1H-1,2,3-triazole-5-carboxylic acid,
4-((5-(3,4-dichlorophenyl)-4H-1,2,4-triazol-3-yl)thio)-1H-1,2,3-triazole-5-carboxylic acid,
4-((4'-methoxy-[1,1'-biphenyl]-4-yl)thio)-1H-1,2,3-triazole-5-carboxylic acid,
4-((4-(3-chloro-4-methoxyphenyl)thiazol-2-yl)thio)-1H-1,2,3-triazole-5-carboxylic acid,
4-((4'-(trifluoromethoxy)-[1,1'-biphenyl]-4-yl)thio)-1H-1,2,3-triazole-5-carboxylic acid,
methyl 4-((4-(3,4-dichlorophenyl)thiazol-2-yl)thio)-1H-1,2,3-triazole-5-carboxylate,
4-((4-(3-chloro-4-cyclopropoxyphenyl)thiazol-2-yl)thio)-1H-1,2,3-triazole-5-carboxylic acid,
cyclopropyl 4-((4-(3,4-dichlorophenyl)thiazol-2-yl)thio)-1H-1,2,3-triazole-5-carboxylate,
4-((6-(3,4-dichlorophenyl)pyridin-2-yl)thio)-1H-1,2,3-triazole-5-carboxylic acid,
4-((2-(4-chloro-3-methoxyphenyl)thiazol-4-yl)thio)-1H-1,2,3-triazole-5-carboxylic acid,
4-((2-(4-chloro-3-isopropoxyphenyl)thiazol-4-yl)thio)-1H-1,2,3-triazole-5-carboxylic acid,
5-((2-(3-chloro-4-methoxyphenyl)thiazol-4-yl)thio)-1-(4-methoxybenzyl)-1H-1,2,3-triazole-4-carboxylic acid,
4-((2-(3-chloro-4-methoxyphenyl)thiazol-4-yl)thio)-1H-1,2,3-triazole-5-carboxylic acid,
4-((2-(2,4-dichlorophenyl)thiazol-4-yl)thio)-1H-1,2,3-triazole-5-carboxylic acid,
4-((2-(3-chloro-4-isopropoxyphenyl)thiazol-4-yl)thio)-1H-1,2,3-triazole-5-carboxylic acid,
4-((5-(3,4-dichlorophenyl)-4-methyl-4H-1,2,4-triazol-3-yl)thio)-1H-1,2,3-triazole-5-carboxylic acid.2,2,2-trifluoroacetate,
4-((4'-chloro-3'-(trifluoromethoxy)-[1,1'-biphenyl]-4-yl)thio)-1H-1,2,3-triazole-5-carboxylic acid,
4-((2'-chloro-3'-(trifluoromethoxy)-[1,1'-biphenyl]-4-yl)thio)-1H-1,2,3-triazole-5-carboxylic acid,
4-((3'-chloro-4'-(trifluoromethoxy)-[1,1'-biphenyl]-4-yl)thio)-1H-1,2,3-triazole-5-carboxylic acid,
methyl 4-((4'-(trifluoromethoxy)-[1,1'-biphenyl]-4-yl)thio)-1H-1,2,3-triazole-5-carboxylate,
4-((2-(3,4-dichlorophenyl)-1-methyl-1H-imidazol-5-yl)thio)-1H-1,2,3-triazole-5-carboxylic acid,
4-((5-(3,4-dichlorophenyl)thiophen-3-yl)thio)-1H-1,2,3-triazole-5-carboxylic acid,
2-(dimethylamino)ethyl 4-((4'-(trifluoromethoxy)-[1,1'-biphenyl]-4-yl)thio)-1H-1,2,3-triazole-5-carboxylate,
N,N,N-trimethyl-2-((4-((4'-(trifluoromethoxy)-[1,1'-biphenyl]-4-yl)thio)-1H-1,2,3-triazole-5-carbonyl)oxy)ethan-1-aminium iodide,
4-((2-(3-chloro-4-(trifluoromethoxy)phenyl)thiazol-4-yl)thio)-1H-1,2,3-triazole-5-carboxylic acid,
methyl 4-((2-(3-chloro-4-(trifluoromethoxy)phenyl)thiazol-4-yl)thio)-1H-1,2,3-triazole-5-carboxylate,
4-((4'-(trifluoromethoxy)-[1,1'-biphenyl]-3-yl)thio)-1H-1,2,3-triazole-5-carboxylic acid, 4-((4-(3-chloro-4-(trifluoromethoxy)phenyl)thiazol-2-yl)thio)-1H-1,2,3-triazole-5-carboxylic acid,
methyl 4-((4-(3-chloro-4-(trifluoromethoxy)phenyl)thiazol-2-yl)thio)-1H-1,2,3-triazole-5-carboxylate,
oxetan-3-yl 4-((4'-(trifluoromethoxy)-[1,1'-biphenyl]-4-yl)thio)-1H-1,2,3-triazole-5-carboxylate,
1-((pivaloyloxy)methyl)-4-((4'-(trifluoromethoxy)-[1,1'-biphenyl]-4-yl)thio)-1H-1,2,3-triazole-5-carboxylic acid,
1-((isobutyryloxy)methyl)-4-((4'-(trifluoromethoxy)-[1,1'-biphenyl]-4-yl)thio)-1H-1,2,3-triazole-5-carboxylic acid,
(pivaloyloxy)methyl 4-((4'-(trifluoromethoxy)-[1,1'-biphenyl]-4-yl)thio)-1H-1,2,3-triazole-5-carboxylate,
(isobutyryloxy)methyl 4-((4'-(trifluoromethoxy)-[1,1'-biphenyl]-4-yl)thio)-1H-1,2,3-triazole-5-carboxylate,
4-((3'-(piperidin-1-yl)-[1,1'-biphenyl]-4-yl)thio)-1H-1,2,3-triazole-5-carboxylic acid,
4-((4'-(piperidin-1-yl)-[1,1'-biphenyl]-4-yl)thio)-1H-1,2,3-triazole-5-carboxylic acid 2,2,2-trifluoroacetate,
4-((3'-(cyclopropylmethoxy)-[1,1'-biphenyl]-4-yl)thio)-1H-1,2,3-triazole-5-carboxylic acid 2,2,2-trifluoroacetate,
4-((4-(1-methyl-1,2,3,4-tetrahydroquinolin-6-yl)phenyl)thio)-1H-1,2,3-triazole-5-carboxylic acid 2,2,2-trifluoroacetate,
(isobutyryloxy)methyl 4-((4'-(piperidin-1-yl)-[1,1'-biphenyl]-4-yl)thio)-1H-1,2,3-triazole-5-carboxylate,
4-((3'-cyclohexyl-[1,1'-biphenyl]-4-yl)thio)-1H-1,2,3-triazole-5-carboxylic acid,
(benzoyloxy)methyl 4-((4'-(piperidin-1-yl)-[1,1'-biphenyl]-4-yl)thio)-1H-1,2,3-triazole-5-carboxylate,
(propionyloxy)methyl 4-((4'-(piperidin-1-yl)-[1,1'-biphenyl]-4-yl)thio)-1H-1,2,3-triazole-5-carboxylate,
4-((3-(4-(trifluoromethoxy)phenyl)cyclopentyl)thio)-1H-1,2,3-triazole-5-carboxylic acid,
((cyclohexanecarbonyl)oxy)methyl 4-((4'-(piperidin-1-yl)-[1,1'-biphenyl]-4-yl)thio)-1H-1,2,3-triazole-5-carboxylate 2,2,2-trifluoroacetate,
4-((4'-(4,4-difluoropiperidin-1-yl)-[1,1'-biphenyl]-4-yl)thio)-1H-1,2,3-triazole-5-carboxylic acid 2,2,2-trifluoroacetate,
4-((5-(trifluoromethoxy)-2,3-dihydro-1H-inden-2-yl)thio)-1H-1,2,3-triazole-5-carboxylic acid,
4-((4-(5-(trifluoromethoxy)pyridin-2-yl)phenyl)thio)-1H-1,2,3-triazole-5-carboxylic acid 2,2,2-trifluoroacetate,
4-((1-(3,4-dichlorophenyl)piperidin-4-yl)thio)-1H-1,2,3-triazole-5-carboxylic acid 2,2,2-trifluoroacetate,
4-((1-(4-(trifluoromethyl)phenyl)piperidin-4-yl)thio)-1H-1,2,3-triazole-5-carboxylic acid,
4-((1-(3,5-dichlorophenyl)piperidin-4-yl)thio)-1H-1,2,3-triazole-5-carboxylic acid,
4-((4-(3-(trifluoromethoxy)phenyl)cyclohexyl)thio)-1H-1,2,3-triazole-5-carboxylic acid,
4-((4-(3-(trifluoromethyl)phenyl)cyclohexyl)thio)-1H-1,2,3-triazole-5-carboxylic acid,
4-((1-(2,5-dichlorophenyl)piperidin-4-yl)thio)-1H-1,2,3-triazole-5-carboxylic acid,
4-(((cis)-4-(3,5-dichlorophenyl)cyclohexyl)thio)-1H-1,2,3-triazole-5-carboxylic acid,
4-(((cis)-4-(4-(trifluoromethyl)phenyl)cyclohexyl)thio)-1H-1,2,3-triazole-5-carboxylic acid,
4-(((cis)-4-(3-chloro-5-(trifluoromethoxy)phenyl)cyclohexyl)thio)-1H-1,2,3-triazole-5-carboxylic acid,
4-((1-(3-chloro-5-(trifluoromethoxy)phenyl)piperidin-4-yl)thio)-1H-1,2,3-triazole-5-carboxylic acid,
4-((4-(4,4-difluoropiperidin-1-yl)phenyl)thio)-1H-1,2,3-triazole-5-carboxylic acid 2,2,2-trifluoroacetate,
4-((4-(3-(piperidin-1-yl)phenyl)cyclohexyl)thio)-1H-1,2,3-triazole-5-carboxylic acid 2,2,2-trifluoroacetate,
4-(((cis)4-(4-(4-methylpiperazin-1-yl)phenyl)cyclohexyl)thio)-1H-1,2,3-triazole-5-carboxylic acid,
4-((2-chloro-4'-(piperidin-1-yl)-[1,1'-biphenyl]-4-yl)thio)-1H-1,2,3-triazole-5-carboxylic acid,
4-((1-(4-cyanophenyl)piperidin-4-yl)thio)-1H-1,2,3-triazole-5-carboxylic acid 2,2,2-trifluoroacetate,
4-(((cis)-4-(3,4-dichlorophenyl)cyclohexyl)thio)-1H-1,2,3-triazole-5-carboxylic acid 2,2,2-trifluoroacetate,
4-((1-(3-chloro-4-(trifluoromethoxy)phenyl)piperidin-4-yl)thio)-1H-1,2,3-triazole-5-carboxylic acid,
4-(((cis)-4-(4-(pyrrolidin-1-yl)phenyl)cyclohexyl)thio)-1H-1,2,3-triazole-5-carboxylic acid 2,2,2-trifluoroacetate,
4-(((cis)-4-(4-(trifluoromethoxy)phenyl)cyclohexyl)thio)-1H-1,2,3-triazole-5-carboxylic acid,
4-((4'-(2-methylpiperidin-1-yl)-[1,1'-biphenyl]-4-yl)thio)-1H-1,2,3-triazole-5-carboxylic acid 2,2,2-trifluoroacetate,
4-(((cis)-4-(4-cyanophenyl)cyclohexyl)thio)-1H-1,2,3-triazole-5-carboxylic acid,
4-((3'-chloro-4'-(piperidin-1-yl)-[1,1'-biphenyl]-4-yl)thio)-1H-1,2,3-triazole-5-carboxylic acid,
4-((1-(5-chloro-2-(trifluoromethoxy)phenyl)piperidin-4-yl)thio)-1H-1,2,3-triazole-5-carboxylic acid,
4-((4'-cyano-[1,1'-biphenyl]-4-yl)thio)-1H-1,2,3-triazole-5-carboxylic acid,
4-((4'-chloro-2-(cyclopentylmethoxy)-[1,1'-biphenyl]-4-yl)thio)-1H-1,2,3-triazole-5-carboxylic acid,
4-((1-(2-chloro-5-(trifluoromethoxy)phenyl)piperidin-4-yl)thio)-1H-1,2,3-triazole-5-carboxylic acid,
4-(((trans)-4-(quinolin-6-yl)cyclohexyl)thio)-1H-1,2,3-triazole-5-carboxylic acid 2,2,2-trifluoroacetate,
4-(((trans)-4-(2-chloro-5-(trifluoromethoxy)phenyl)cyclohexyl)thio)-1H-1,2,3-triazole-5-carboxylic acid,
4-(((trans)-3-(4-cyanophenyl)cyclobutyl)thio)-1H-1,2,3-triazole-5-carboxylic acid 2,2,2-trifluoroacetate,
4-(((trans)-4-(4-(trifluoromethoxy)phenyl)cyclohexyl)thio)-1H-1,2,3-triazole-5-carboxylic acid,
4-(((3aR,5s,6aS)-2-(3,4-dichlorophenyl)octahydrocyclopenta[c]pyrrol-5-yl)thio)-1H-1,2,3-triazole-5-carboxylic acid,
4-(((trans)-4-(5-chloro-2-(trifluoromethoxy)phenyl)cyclohexyl)thio)-1H-1,2,3-triazole-5-carboxylic acid,
4-(((trans)-4-(4-(piperidin-1-yl)phenyl)cyclohexyl)thio)-1H-1,2,3-triazole-5-carboxylic acid 2,2,2-trifluoroacetate,
4-(((trans)-3-(4-(piperidin-1-yl)phenyl)cyclobutyl)thio)-1H-1,2,3-triazole-5-carboxylic acid 2,2,2-trifluoroacetate,
4-(((trans)-4-(4-(methylsulfonyl)phenyl)cyclohexyl)thio)-1H-1,2,3-triazole-5-carboxylic acid 2,2,2-trifluoroacetate,
4-(((cis)-4-(3-chloro-4-(piperidin-1-yl)phenyl)cyclohexyl)thio)-1H-1,2,3-triazole-5-carboxylic acid 2,2,2-trifluoroacetate,
4-(((trans)-4-(3-chloro-4-(piperidin-1-yl)phenyl)cyclohexyl)thio)-1H-1,2,3-triazole-5-carboxylic acid 2,2,2-trifluoroacetate,
4-(((trans)-4-(4-(1H-pyrazol-1-yl)phenyl)cyclohexyl)thio)-1H-1,2,3-triazole-5-carboxylic acid 2,2,2-trifluoroacetate, and 4-(((cis-3a,6a)-5-(4-(trifluoromethoxy)phenyl)octahydropentalen-2-yl)thio)-1H-1,2,3-triazole-5-carboxylic acid.

14. A pharmaceutical composition comprising the compound, single stereoisomer or mixture of stereoisomers or pharmaceutically acceptable salt of claim 1 and a pharmaceutically acceptable excipient.

\* \* \* \* \*